US008987195B2

(12) United States Patent
Bara et al.

(10) Patent No.: US 8,987,195 B2
(45) Date of Patent: Mar. 24, 2015

(54) HCV NS3 PROTEASE INHIBITORS

(71) Applicants: Merck Sharp & Dohme Corp., Rahway, NJ (US); Merck Canada Inc., Kirkland, Quebec (CA)

(72) Inventors: Thomas Bara, Scotch Plains, NJ (US); Sathesh Bhat, Hoboken, NJ (US); Dipshikha Biswas, Woodbridge, NJ (US); Linda Brockunier, Orange, NJ (US); Duane A. Burnett, Wayland, MA (US); Samuel Chackalamannil, Califon, NJ (US); Mariappan V. Chelliah, Edison, NJ (US); Austin Chen, San Marcos, CA (US); Martin Clasby, Plainsboro, NJ (US); Vince J. Colandrea, North Brunswick, NJ (US); Zhuyan Guo, Scotch Plains, NJ (US); Yongxin Han, Montreal (CA); Charles Jayne, Staten Island, NY (US); Hubert Josien, Jersey City, NJ (US); Karen Marcantonio, New York, NY (US); Shouwu Miao, Edison, NJ (US); Santhosh Neelamkavil, Edison, NJ (US); Patrick Pinto, Morris Plains, NJ (US); Murali Rajagopalan, Edison, NJ (US); Unmesh Shah, Neshanic Station, NJ (US); Francisco Velazquez, Clinton, NJ (US); Srikanth Venkatraman, Edison, NJ (US); Yan Xia, Edison, NJ (US)

(73) Assignees: Merck Sharp & Dohme Corp., Rahway, NJ (US); Merck Canada Inc., Kirkland, Quebec (CA)

( * ) Notice: Subject to any disclaimer, the term of this patent is extended or adjusted under 35 U.S.C. 154(b) by 0 days.

(21) Appl. No.: 13/960,343

(22) Filed: Aug. 6, 2013

(65) Prior Publication Data

US 2014/0057836 A1 Feb. 27, 2014

Related U.S. Application Data

(60) Provisional application No. 61/680,889, filed on Aug. 8, 2012, provisional application No. 61/739,345, filed on Dec. 19, 2012.

(51) Int. Cl.

| | |
|---|---|
| ***A61K 38/00*** | (2006.01) |
| ***C07K 5/08*** | (2006.01) |
| ***A61K 38/06*** | (2006.01) |
| ***A61K 45/06*** | (2006.01) |
| ***C07D 491/22*** | (2006.01) |
| ***C07D 419/00*** | (2006.01) |

(52) U.S. Cl.

CPC . *C07K 5/08* (2013.01); *A61K 38/06* (2013.01); *A61K 45/06* (2013.01); *C07D 491/22* (2013.01); *C07D 419/00* (2013.01)

USPC .......................................................... 514/3.7

(58) Field of Classification Search

None

See application file for complete search history.

(56) References Cited

U.S. PATENT DOCUMENTS

| | | | |
|---|---|---|---|
| 2007/0027071 | A1 | 2/2007 | Holloway et al. |
| 2008/0108632 | A1 | 5/2008 | Lin et al. |

FOREIGN PATENT DOCUMENTS

| | | | |
|---|---|---|---|
| WO | WO2006102087 | A2 | 9/2006 |
| WO | WO2007025307 | A2 | 3/2007 |
| WO | WO2008106139 | A1 | 9/2008 |
| WO | WO2009047264 | A1 | 4/2009 |
| WO | WO2010030359 | A2 | 3/2010 |
| WO | WO2010115981 | A1 | 10/2010 |
| WO | WO2012048235 | A1 | 4/2012 |

OTHER PUBLICATIONS

Balsano, Recent Advances in Antiviral Agents: Established and Innovative Therapies for Viral Hepatitis, Mini-Reviews in Medicinal Chemistry, 2008, 8(4):307-318.

Carroll et al., Inhibition of Hepatitis C Virus RNA Replication by 2'-Modified Nucleoside Analogs, J Biol Chem 2003, 278(14):11979-84.

De Francesco et al., Approaching a new era for hepatitis C virus therapy: inhibitors of the NS3-4A serine protease and the NS5B RNA-dependent RNA polymerase, Antiviral Research, 2003, 58:1-16.

Faucher et al., Synthesis of BILN 2061, an HCV NS3 Protease Inhibitor with Proven Antival Effects in Humans, Organic Letters, 2004, 6(17):2901-2904.

Mao et al., A time-resolved, internally quenched fluorescence assay to characterize inhibition of hepatitis C virus nonstructural protein 3-4A protease of low enzyme concentrations, Analytical Biochemistry, 2008, 373:1-8.

Ronn et al., New Developments in the Discovery of Agents to Treat Hepatitis C, Current Topics in Medicinal Chemistry, 2008, 8:533-562.

Sheldon et al., Novel protease and polymerase inhibitors for the treatment of hepatitis C virus infection, Expert Opinion Investig. Drugs, 2007, 16(8):1171-1181.

Vrolijk et al., A replicon-based bioassay for the measurement of interferons in patients with chronic hepatitis C, J. Virological Methods, 2003, 110:201-209.

*Primary Examiner* — Thomas S Heard

(74) *Attorney, Agent, or Firm* — Anna Cocuzzo; Henry P. Wu

(57) ABSTRACT

The present invention relates to hepatitis C virus (HCV) NS3 protease inhibitors containing a spirocyclic moeity, uses of such compounds, and synthesis of such compounds.

27 Claims, No Drawings

HCV NS3 PROTEASE INHIBITORS

FIELD OF THE INVENTION

The present invention relates to hepatitis C virus (HCV) NS3 protease inhibitors containing a spirocyclic moiety, uses of such compounds, and synthesis of such compounds.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS4A) and an RNA-dependent RNA polymerase (NS5B).

Potential treatments for HCV infection has been discussed in the different references including Balsano, *Mini Rev. Med. Chem.* 8(4):307-318, 2008, Rönn et al., *Current Topics in Medicinal Chemistry* 8:533-562, 2008, Sheldon et al., *Expert Opin. Investig. Drugs* 16(8):1171-1181, 2007, and De Francesco et al., *Antiviral Research* 58:1-16, 2003.

SUMMARY OF THE INVENTION

The present invention relates to compounds of formula I or II, and pharmaceutically acceptable salts thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts, or as pharmaceutical composition ingredients. As pharmaceutical composition ingredients, these compounds may be the primary active therapeutic agent, and, when appropriate, may be combined with other therapeutic agents including but not limited to other HCV antivirals, anti-infectives, immunomodulators, antibiotics or vaccines.

In a first aspect, the present invention relates to a compound of general Formula I:

(I)

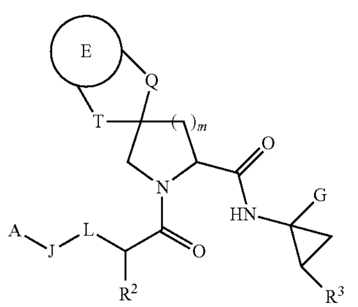

or a pharmaceutically acceptable salt thereof, wherein

A is selected from the group consisting of $C_1$-$C_8$ alkyl, $C_2$-$C_8$ alkenyl, $C_2$-$C_8$ alkynyl, $C_1$-$C_8$ internally substituted alkyl, $C_2$-$C_8$ internally substituted alkenyl, $C_2$-$C_8$ internally substituted alkynyl, $C_3$-$C_8$ cycloalkyl, $C_3$-$C_8$ internally substituted cycloalkyl, $Si(R^A)_3$, $Si(R^A)_2(CH_3)$, $Si(R^A)(CH_3)_2$, $Si(CH_3)_3$, aryl and 7-, 8-, 9- and 10-membered bicyclic groups, wherein said A $Si(R^A)_3$, $Si(R^A)_2(CH_3)$, $Si(R^A)(CH_3)_2$, $Si(CH_3)_3$, $C_1$-$C_8$ internally substituted alkyl, $C_2$-$C_8$ internally substituted alkenyl, $C_2$-$C_8$ internally substituted alkynyl, $C_3$-$C_8$ internally substituted cycloalkyl, aryl and bicyclic groups contain 0, 1, 2 or 3 heteroatoms independently selected from the group consisting of B, O, S and N, each A aryl is independently selected from the group consisting of 5- and 6-membered aromatic rings and 7-, 8-, 9- and 10-membered bicyclic aromatic rings, said A is substituted with 0, 1, 2, 3 or 4 substituents $R^A$;

each $R^A$ is independently selected from the group consisting of H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), phenyl, naphthyl, $C_3$-$C_8$ cycloalkyl, halo($C_1$-$C_6$ alkoxy), —O($C_1$-$C_6$ alkyl), SH, S($C_1$-$C_6$ alkyl), $NH_2$, —NH($C_1$-$C_6$ alkyl), —N($C_1$-$C_6$ alkyl)$_2$, —C(O)($C_1$-$C_6$ alkyl), —$CONH_2$, —$SO_2NH_2$, $NO_2$, CN, —$CF_3$, —$CHF_2$, —$CH_2F$, —$OCHF_2$, —$OCF_3$, —$OCH_2F$, —$SO_2$($C_1$-$C_6$ alkyl), —S(O)($C_1$-$C_6$ alkyl), —($C_1$-$C_6$ alkyl)S(O)($C_1$-$C_6$ alkyl), —S(O)$_2$($C_1$-$C_6$ alkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), —N($C_1$-$C_6$ alkyl)$SO_2$($C_1$-$C_6$ alkyl), —$SO_2$N($C_1$-$C_6$ alkyl)$_2$, —($C_1$-$C_6$ alkyl)$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), —C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), —($C_0$-$C_5$ alkyl)-S(O)$_2$—($C_0$-$C_5$ alkyl)-($C_3$-$C_8$ cycloalkyl), $C_1$-$C_6$ internally substituted alkyl, $C_1$-$C_6$ internally substituted haloalkyl, $C_1$-$C_6$ internally substituted alkyl($NH_2$), $C_3$-$C_8$ internally substituted cycloalkyl, halo($C_1$-$C_6$ internally substituted alkoxy), —O($C_1$-$C_6$ internally substituted alkyl), S($C_1$-$C_6$ internally substituted alkyl), —NH($C_1$-$C_6$ internally substituted alkyl), —N($C_1$-$C_6$ internally substituted alkyl)$_2$, —C(O)($C_1$-$C_6$ internally substituted alkyl), —$SO_2$($C_1$-$C_6$ internally substituted alkyl), —S(O)($C_1$-$C_6$ internally substituted alkyl), —($C_1$-$C_6$ internally substituted alkyl)S(O)($C_1$-$C_6$ internally substituted alkyl), —S(O)$_2$($C_1$-$C_6$ internally substituted alkyl), —($C_1$-$C_6$ internally substituted alkyl)S(O)$_2$($C_1$-$C_6$ internally substituted alkyl), —($C_1$-$C_6$ internally substituted alkyl)N($C_1$-$C_6$ internally substituted alkyl)$SO_2$($C_1$-$C_6$ internally substituted alkyl), —N($C_1$-$C_6$ internally substituted alkyl)$SO_2$($C_1$-$C_6$ internally substituted alkyl), —$SO_2$N($C_1$-$C_6$ internally substituted alkyl)$_2$, —($C_1$-$C_6$ internally substituted alkyl)$SO_2$N($C_1$-$C_6$ internally substituted alkyl)$_2$, —NHCOO($C_1$-$C_6$ internally substituted alkyl), —NHCO($C_1$-$C_6$ internally substituted alkyl), —NHCONH($C_1$-$C_6$ internally substituted alkyl), —$CO_2$($C_1$-$C_6$ internally substituted alkyl), —C(O)N($C_1$-$C_6$ internally substituted alkyl)$_2$, —($C_0$-$C_5$ internally substituted alkyl)-($C_3$-$C_8$ internally substituted cycloalkyl), —($C_0$-$C_5$ internally substituted alkyl)-O—($C_0$-$C_5$ internally substituted alkyl)-($C_3$-$C_8$ internally substituted cycloalkyl), —($C_0$-$C_5$ internally substituted alkyl)-S—($C_0$-$C_5$ internally substituted alkyl)-($C_3$-$C_8$ internally substituted cycloalkyl), and —($C_0$-$C_5$ internally substituted alkyl)-S(O)$_2$—($C_0$-$C_5$ internally substituted alkyl)-($C_3$-$C_8$ internally substituted cycloalkyl), wherein said $R^A$ $C_1$-$C_6$ internally substituted alkyl, $C_1$-$C_6$ internally substituted haloalkyl, $C_1$-$C_6$ internally substituted alkyl ($NH_2$), $C_3$-$C_8$ internally substituted cycloalkyl, halo($C_1$-$C_6$ internally substituted alkoxy), —O($C_1$-$C_6$ internally substituted alkyl), S($C_1$-$C_6$ internally substituted alkyl), —NH($C_1$-$C_6$ internally substituted alkyl), —N($C_1$-$C_6$ internally substituted alkyl)$_2$, —C(O)($C_1$-$C_6$ internally substituted alkyl), —$SO_2$($C_1$-$C_6$ internally substituted alkyl), —S(O)($C_1$-$C_6$ internally substituted alkyl), —($C_1$-$C_6$ internally substituted alkyl)S(O)($C_1$-$C_6$ internally substituted alkyl), —S(O)$_2$($C_1$-$C_6$ internally substituted alkyl), —($C_1$-$C_6$ internally substituted alkyl)S(O)$_2$($C_1$-$C_6$ internally substituted alkyl), —($C_1$-$C_6$ internally substituted alkyl)N($C_1$-$C_6$ internally substituted alkyl)$SO_2$($C_1$-$C_6$ internally substituted alkyl), —N($C_1$-$C_6$ internally substituted alkyl)$SO_2$($C_1$-$C_6$ internally substituted alkyl), —$SO_2$N($C_1$-$C_6$ internally substituted alkyl)$_2$, —($C_1$-$C_6$ internally substituted alkyl)$SO_2$N($C_1$-$C_6$ internally substituted alkyl)$_2$, —NHCOO($C_1$-$C_6$ internally substituted alkyl), —NHCO($C_1$-$C_6$ internally substituted alkyl), —NHCONH($C_1$-$C_6$ internally substituted alkyl), —$CO_2$($C_1$-$C_6$ internally substituted alkyl), —C(O)N($C_1$-$C_6$ internally substituted alkyl)$_2$, —($C_0$-$C_5$ internally substituted alkyl)-($C_3$-$C_8$ internally substituted cycloalkyl), —($C_0$-$C_5$ internally substituted alkyl)-O—($C_0$-$C_5$ internally substituted alkyl)-($C_3$-$C_8$ internally substituted cycloalkyl), —($C_0$-$C_5$ internally substituted alkyl) -S—($C_0$-$C_5$ internally substituted alkyl)-($C_3$-$C_8$ internally substituted cycloalkyl), and —($C_0$-$C_5$ internally substituted alkyl)-S(O)$_2$—($C_0$-$C_5$ internally substituted alkyl)-($C_3$-$C_8$ internally substituted cycloalkyl) groups contain 0, 1, 2 or 3 heteroatoms independently selected from the group consisting of B, O, S and N, two $R^A$ may be taken, together with the atoms to which they are bound, to form a ring having from three to fifteen ring atoms;

$R^A$ and $R^2$ may be taken, together with the atoms to which they are bound, to form a ring having from sixteen to twenty-one ring atoms;

$R^A$ and $R^1$ or $R^4$ may be taken, together with the atoms to which they are bound, to form a ring having from sixteen to twenty-one ring atoms;

J is selected from the group consisting of a direct bond, $C_1$-$C_8$ alkylene,

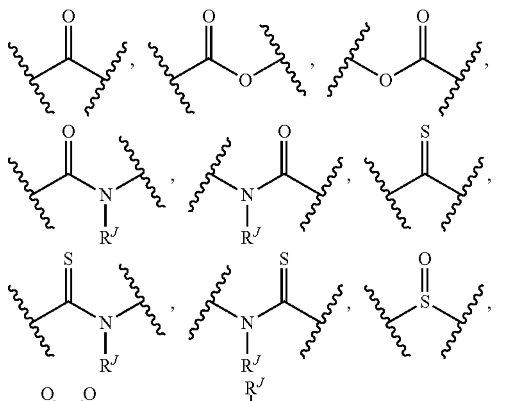

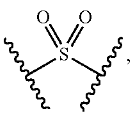

, and

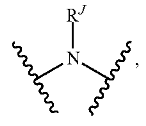

, wherein said $C_1$-$C_8$ alkylene are substituted by 0, 1, 2 or 3 substituents $R^J$;

$R^J$ is selected from the group consisting of H, $C_1$-$C_6$alkyl, $C_1$-$C_6$ internally substituted alkyl, Si($R^A$)$_3$, Si($R^A$)$_2$($CH_3$), Si($R^A$)($CH_3$)$^2$, Si($CH_3$)$_3$, $C_3$-$C_6$cycloalkyl, $C_3$-$C_6$ internally substituted cycloalkyl and aryl, wherein said $R^J$ Si($R^A$)$_3$, Si($R^A$)$_2$($CH_3$), Si($R^A$)($CH_3$)$^2$, Si($CH_3$)$_3$, $C_1$-$C_6$ internally substituted alkyl, $C_3$-$C_6$ internally substituted cycloalkyl and aryl contain 0, 1, 2 or 3 heteroatoms independently selected from the group consisting of B, O, S and N, each $R^J$ aryl is independently selected from the group consisting of 5- and 6-membered aromatic rings, said $R^J$ is substituted with 0, 1, 2, 3 or 4 substituents $R^A$;

L is selected from the group consisting of ($CH_2$)$_{0-4}$, N($R^L$), and O;

each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), Si($R^A$)$_3$, Si($R^A$)$_2$($CH_3$), Si($R^A$)($CH_3$)$_2$, Si($CH_3$)$_3$, $C_1$-$C_6$ alkyl (aryl) groups, $C_1$-$C_6$ internally substituted alkyl, $C_1$-$C_6$ internally substituted haloalkyl, $C_1$-$C_6$ internally substituted alkoxy, $C_1$-$C_6$ internally substituted alkyl($NH_2$), aryl, $C_3$-$C_8$ internally substituted cycloalkyl, halo($C_1$-$C_6$ internally substituted alkoxy), and $C_1$-$C_6$ internally substituted alkyl(aryl), wherein said $R^L$ Si($R^A$)$_3$, Si($R^A$)$_2$($CH_3$), Si($R^A$)($CH_3$)$_2$, Si($CH_3$)$_3$, $C_1$-$C_6$ internally substituted alkyl, $C_1$-$C_6$ internally substituted haloalkyl, $C_1$-$C_6$ internally substituted alkoxy, $C_1$-$C_6$ internally substituted alkyl($NH_2$), aryl, $C_3$-$C_8$ internally substituted cycloalkyl, halo($C_1$-$C_6$ internally substituted alkoxy), and $C_1$-$C_6$ internally substituted alkyl(aryl) groups contain 0, 1, 2 or 3 heteroatoms independently selected from the group consisting of B, O, S and N, each $R^L$ aryl group is independently selected from the group consisting of 5- and 6-membered aromatic rings, G is selected from the group consisting of

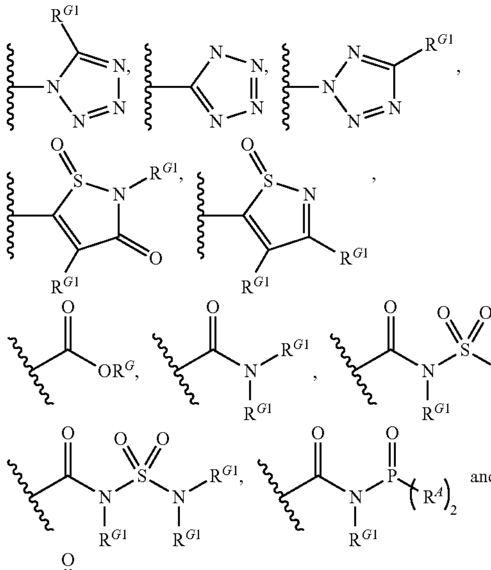

and

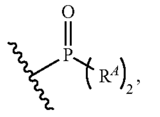

, wherein $R^G$ is selected from the group consisting of H, $C_1$-$C_6$ alkyl, $C_3$-$C_6$ cycloalkyl, $C_3$-$C_6$ cycloalkyl($C_1$-$C_5$)alkyl, Si($R^A$)$_3$, Si($R^A$)$_2$($CH_3$), Si($R^A$)($CH_3$)$_2$, Si($CH_3$)$_3$, aryl, aryl($C_1$-$C_4$)alkyl, $C_1$-$C_6$ internally substituted alkyl, $C_3$-$C_6$ internally substituted cycloalkyl, internally substituted $C_3$-$C_6$ cycloalkyl($C_1$-$C_5$)alkyl, and internally substituted aryl($C_1$-$C_4$)alkyl groups, wherein said $R^G$ $Si(R^A)_3$, $Si(R^A)_2(CH_3)$, $Si(R^A)(CH_3)^2$, $Si(CH_3)_3$, $C_1$-$C_6$ internally substituted alkyl, $C_3$-$C_6$ internally substituted cycloalkyl, internally substituted $C_3$-$C_6$ cycloalkyl($C_1$-$C_5$)alkyl, aryl, and internally substituted aryl($C_1$-$C_4$)alkyl groups contain 0, 1, 2 or 3 heteroatoms independently selected from the group consisting of B, O, S and N, each $R^G$ aryl is independently selected from the group consisting of 5- and 6-membered aromatic rings, said $R^G$ is substituted with 0, 1 or 2 independently selected $R^A$ substituents, each $R^{G1}$ is independently selected from the group consisting of H, $C_1$-$C_6$ alkyl, $C_3$-$C_7$ cycloalkyl, $Si(R^A)_3$, $Si(R^A)_2(CH_3)$, $Si(R^A)(CH_3)^2$, $Si(CH_3)_3$, and benzyl, wherein each $R^{G1}$ is independently substituted with 0 to 4 substituents $R^A$, Ⓔ is selected from the group consisting of:

1) aryl rings in which the aryl ring system attaches to Q and T at points that are two independently selected carbon ring atoms, 2) $C_3$-$C_8$ cycloalkyl rings in which the $C_3$-$C_8$ cycloalkyl ring system attaches to Q and T at points that are two independently selected carbon ring atoms, and 3) heterocyclic rings in which the heterocyclic ring system attaches to Q and T at points that are two independently selected ring atoms that are either two carbon ring atoms or one carbon ring atom and one nitrogen ring atom, and the heterocyclic ring system is selected from the group consisting of:

a) 5- or 6-membered saturated or unsaturated monocyclic rings with 1, 2, 3, or 4 heteroatom ring atoms independently selected from the group consisting of N, O and S, b) 8-, 9- or 10-membered saturated or unsaturated bicyclic rings with 1, 2, 3, 4, or 5 heteroatom ring atoms independently selected from the group consisting of N, O and S, and c) 11- to 15-membered saturated or unsaturated tricyclic rings with 1, 2, 3, 4, or 5 heteroatom ring atoms independently selected from the group consisting of N, O and S, wherein Ⓔ is substituted with 1 substituent $R^1$ and with 0, 1, 2, 3, 4 or 5 independently selected substituents $R^4$;

$R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —$C(O)CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl)-($C_3$-$C_8$ cycloalkyl), —($C_0$-$C_3$ alkyl) -S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —$N(R^A)_2$, $C_1$-$C_9$ alkyl-$N(R^A)_2$, $Si(R^A)_3$, $Si(R^A)_2(CH_3)$, $Si(R^A)(CH_3)_2$, $Si(CH_3)_3$, $C_1$-$C_9$ internally substituted alkyl, $C_1$-$C_9$ internally substituted alkoxy, $C_1$-$C_9$ internally substituted alkyl-$C_1$-$C_9$ internally substituted alkoxy, —$SO_2$($C_1$-$C_9$ internally substituted alkyl), $C_3$-$C_8$ internally substituted cycloalkyl, $C_1$-$C_9$ internally substituted alkyl-$C_3$-$C_8$ internally substituted cycloalkyl, $C_3$-$C_8$ internally substituted cycloalkoxy, $C_1$-$C_9$ alkyl-$C_3$-$C_8$ internally substituted cycloalkoxy, $C_1$-$C_9$ internally substituted haloalkyl, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl) -S—($C_0$-$C_3$ internally substituted alkyl)-($C_3$-$C_8$ internally substituted cycloalkyl), —($C_0$-$C_3$ internally substituted alkyl)-$S(O)_2$—($C_0$-$C_3$ internally substituted alkyl)-($C_3$-$C_8$ internally substituted cycloalkyl), $C_1$-$C_9$ internally substituted alkyl-$N(R^A)_2$, aryl, naphthyl, —O-aryl and —O-naphthyl groups; wherein:

said $R^1$ $C_1$-$C_9$ internally substituted alkyl, $C_1$-$C_9$ internally substituted alkoxy, $C_1$-$C_9$ internally substituted alkyl-$C_1$-$C_9$ internally substituted alkoxy, —$SO_2$($C_1$-$C_9$ internally substituted alkyl), $C_3$-$C_8$ internally substituted cycloalkyl, $C_1$-$C_9$ internally substituted alkyl-$C_3$-$C_8$ internally substituted cycloalkyl, $C_3$-$C_8$ internally substituted cycloalkoxy, $C_1$-$C_9$ alkyl-$C_3$-$C_8$ internally substituted cycloalkoxy, $C_1$-$C_9$ internally substituted haloalkyl, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl)-$S(O)_2$—($C_0$-$C_3$ internally substituted alkyl)-($C_3$-$C_8$ internally substituted cycloalkyl), $C_1$-$C_9$ internally substituted alkyl -$N(R^A)_2$, aryl, naphthyl, —O-aryl and —O-naphthyl groups contain 0, 1, 2 or 3 heteroatoms independently selected from the group consisting of B, O, S and N, each $R^1$ aryl is independently selected from the group consisting of 5- and 6-membered aromatic rings, said $R^1$ groups are substituted with 0 to 4 substituents $R^A$;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, $Si(R^A)_3$, $Si(R^A)_2(CH_3)$, $Si(R^A)(CH_3)_2$, $Si(CH_3)_3$, $C_1$-$C_9$ internally substituted alkyl, $C_2$-$C_9$ internally substituted alkenyl, $C_2$-$C_9$ internally substituted alkynyl, $C_3$-$C_8$ internally substituted cycloalkyl and aryl groups, wherein said $R^2$$Si(R^A)_3$, $Si(R^A)_2(CH_3)$, $Si(R^A)(CH_3)_2$, $C_1$-$C_9$ internally substituted alkyl, $C_2$-$C_9$ internally substituted alkenyl, $C_2$-$C_9$ internally substituted alkynyl, $C_3$-$C_8$ internally substituted cycloalkyl and aryl groups contain 0, 1, 2 or 3 heteroatoms independently selected from the group consisting of B, O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents, $R^3$ is selected from the group consisting of —$CH_2CH_3$, —CH═$CH_2$, $Si(R^A)_3$, $Si(R^A)_2(CH_3)$, $Si(R^A)(CH_3)_2$, $Si(CH_3)_3$, —$CH_2CH_2$-(bond to $R^2$), —CH═CH-(bond to $R^2$) and a direct bond to $R^2$, wherein when $R^3$ is selected from the group consisting of —$CH_2CH_2$-(bond to $R^2$), —CH═CH-(bond to $R^2$) and a direct bond to $R^2$, $R^2$ and $R^3$, together with the atoms to which they are bound, form a ring having from fifteen to twenty-one ring atoms and containing 0, 1, 2 or 3 double bonds and 0, 1, 2 or 3 triple bonds;

T is selected from the group consisting of —$(CH_2)_q$—, —$(CH_2)_q$—O—$(CH_2)_{q1}$—, —$(CH_2)_q$—$N(R^A)$—$(CH_2)_{q1}$—, —$(CH_2)_q$—S—$(CH_2)_{q1}$—, —$(CH_2)_q$—C(O)—$(CH_2)_{q1}$—, —$(CH_2)_q$—S(O)—$(CH_2)_{q1}$—, and —$(CH_2)_q$—$S(O)_2$—$(CH_2)_{q1}$—, where q and q1 are each independently selected from the group consisting of 0, 1 or 2, and each T is substituted by 0, 1 or 2 groups selected from $R^A$;

Q is selected from the group consisting of —$(CR^A{}_2)_p$—, —$(CR^A{}_2)_p$—$CR^A$═$CR^A$—$(CR^A{}_2)_{p1}$, —$(CR^A{}_2)_p$—O—$(CR^A{}_2)_p$—, —$(CR^A{}_2)_p$—$N(R^A)$—$(CR^A{}_2)_{p1}$—, —$(CR^A{}_2)_p$—S—$(CR^A{}_2)_{p1}$—, —$(CR^A{}_2)_p$—S(O)—$(CR^A{}_2)_{p1}$—, and —$(CR^A{}_2)_p$—$S(O)_2$—$(CR^A{}_2)_{p1}$—, where p and p1 are independently selected from 0, 1, 2, 3 or 4;

each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —$C(O)N(R^A)_2$, —$OC(O)N(R^A)_2$, $Si(R^A)_3$, $Si(R^A)_2(CH_3)$, $Si(R^A)(CH_3)_2$, $Si(CH_3)_3$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —$SO(R^A)$, —$SO_2(R^A)$, $C_3$-$C_8$ cycloalkyl, $C_1$-$C_6$ internally substituted alkyl, $C_1$-$C_6$ internally substituted alkoxy, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl)-$S(O)_2$—($C_0$-$C_3$ internally substituted alkyl)-($C_3$-$C_8$ internally substituted cycloalkyl), $C_3$-$C_8$ internally substituted cycloalkyl and aryl, wherein said $R^4$ $C_1$-$C_6$ internally substituted alkyl, $C_1$-$C_6$ internally substituted alkoxy, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl) -$S(O)_2$—($C_0$-$C_3$ internally substituted alkyl)-($C_3$-$C_8$ internally substituted cycloalkyl), $C_3$-$C_8$ internally substituted cycloalkyl and aryl groups contain 0, 1, 2 or 3 heteroatoms independently selected from the group consisting of B, O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$;

two $R^4$ may be taken, together with the atoms to which they are bound, to form a ring; and m is 0, 1, 2 or 3.

In a second aspect, the present invention relates to a compound of general Formula II:

(II)

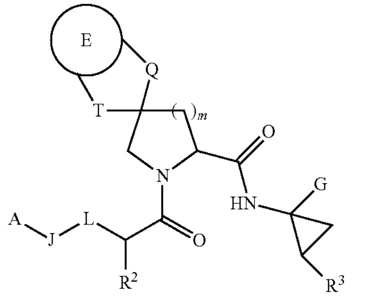

or a pharmaceutically acceptable salt thereof, wherein

A is a selected from the group consisting of a) $C_1$-$C_8$ alkyl, $C_2$-$C_8$ alkenyl, $C_2$-$C_8$ alkynyl, $C_3$-$C_8$ cycloalkyl, $C_6$-$C_8$ bridged cycloalkyl, or $C_6$-$C_8$ bridged cycloalkenyl, b) substituted $C_1$-$C_8$ alkyl, substituted $C_2$-$C_8$ alkenyl, substituted $C_2$-$C_8$ alkynyl, substituted $C_3$-$C_8$ cycloalkyl, substituted $C_6$-$C_8$ bridged cycloalkyl, or substituted $C_6$-$C_8$ bridged cycloalkenyl, each of which is substituted with 0, 1, 2, 3 or 4 independently selected $R^A$, and 0 or 1 $R^B$, provided that at least one $R^A$ substituent, other than H, or an $R^B$ substituent is present;

c) $C_1$-$C_8$ haloalkyl, $C_3$-$C_8$ halocycloalkyl, or $C_1$-$C_8$ haloalkyl substituted with $R^B$, d) Aryl, and e) Het;

J is selected from the group consisting of a direct bond, $C_1$-$C_8$ alkylene,

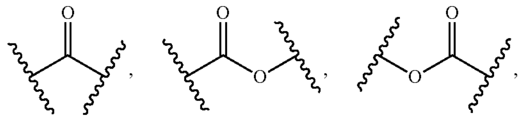

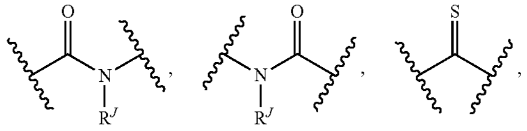

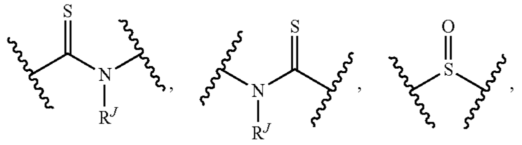

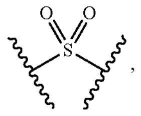, and 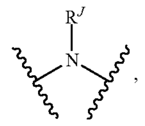, wherein said $C_1$-$C_8$ alkylene is optionally substituted by 0, 1, 2 or 3 substituents independently selected from the group consisting of $C_1$-$C_6$ alkyl, $C_1$-$C_6$ alkyl-$R^B$, $C_3$-$C_6$ cycloalkyl, $C_1$-$C_6$ alkyl-$C_3$-$C_6$ cycloalkyl, Aryl, and Het;

each $R^J$ is selected from the group consisting of hydrogen, $C_1$-$C_6$ alkyl, $C_1$-$C_6$ alkyl-$R^B$, $C_3$-$C_6$ cycloalkyl, $C_1$-$C_6$ alkyl-$C_3$-$C_6$ cycloalkyl, Aryl, and Het;

L is selected from the group consisting of $(CH_2)_{0-4}$, $N(R^L)$, and O;

$R^L$ is selected from the group consisting of H and $C_1$-$C_3$ alkyl;

G is selected from the group consisting of

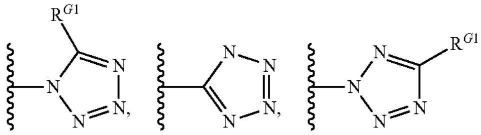

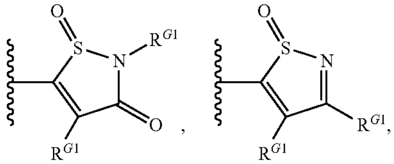

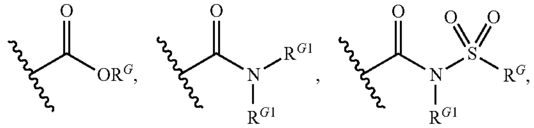

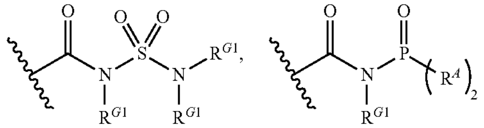 and

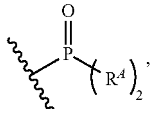

wherein $R^G$ is selected from the group consisting of H, $C_1$-$C_6$ alkyl, $C_3$-$C_6$ cycloalkyl, $C_3$-$C_6$ cycloalkyl-$C_1$-$C_5$ alkyl, $C_1$-$C_6$ alkyl substituted with $R^A$, $C_3$-$C_6$ cycloalkyl substituted with $R^A$, or $C_3$-$C_6$ cycloalkyl-$C_1$-$C_5$ alkyl substituted with $R^A$;

each $R^{G1}$ is independently selected from the group consisting of H, $C_1$-$C_6$ alkyl, $C_3$-$C_7$ cycloalkyl, and benzyl;

Ⓔ is selected from the group consisting of:

1) an aryl ring attached to Q and T at two independently selected carbon ring atoms, wherein the aryl ring is phenyl or naphthyl, 2) a $C_3$-$C_8$ cycloalkyl attached to Q and T at two independently selected carbon ring atoms, and 3) a heterocyclic ring attached to Q and T at two independently selected ring atoms that are either two carbon ring atoms or one carbon ring atom and one nitrogen ring atom, wherein the heterocyclic ring is selected from the group consisting of:

a) a 5- or 6-membered saturated or unsaturated monocyclic ring with 1, 2, 3, or 4 heteroatom ring atoms independently selected from the group consisting of N, O and S, b) a 8-, 9- or 10-membered saturated or unsaturated bicyclic ring with 1, 2, 3, 4, or 5 heteroatom ring atoms independently selected from the group consisting of N, O and S, and c) a 11- to 15-membered saturated or unsaturated tricyclic ring with 1, 2, 3, 4, or 5 heteroatom ring atoms independently selected from the group consisting of N, O and S, wherein Ⓔ further contains 1 $R^1$ substituent and 0, 1, 2, 3, 4 or 5 independently selected $R^4$ substituents;

each $R^1$ is selected from the group consisting of hydrogen, halogen, OH, $C_1$-$C_9$ alkyl, $C_1$-$C_6$ alkyl-$R^B$, $C_1$-$C_9$ hydroxyalkyl, $C_1$-$C_9$ alkoxy, $C_1$-$C_9$ alkyl-$C_1$-$C_9$ alkoxy, CN, C(O)OH, $C(O)CH_3$, $SR^S$, $SO_2$($C_1$-$C_9$ alkyl), $C_3$-$C_8$ cycloalkyl, $C_3$-$C_8$ cycloalkyl-$C_1$-$C_9$ alkyl, $C_1$-$C_9$ alkyl-$C_3$-$C_8$ cycloalkyl, $C_1$-$C_9$ alkyl-O—$C_3$-$C_8$ cycloalkyl, $C_1$-$C_4$ haloalkyl, $C_1$-$C_5$ haloalkoxy, —($C_0$-$C_3$ alkyl)-O—($C_0$-$C_3$ alkyl)-($C_3$-$C_8$ cycloalkyl), —($C_0$-$C_3$ alkyl) -S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), $N(R^5)_2$, $C_1$-$C_9$ alkyl-$N(R^5)_2$, Aryl, and Het;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, Het, and Aryl;

$R^3$ is selected from the group consisting of $C_1$-$C_9$ alkyl, $C_2$-$C_9$ alkenyl, and $C_2$-$C_9$ alkynyl;

T is selected from the group consisting of O, $(CH_2)_{q2}$, NH, $SO_2$ and S, wherein $q_2$ is 0, 1, 2, 3 or 4;

Q is selected from the group consisting of $—(CR^A{}_2)_p—$, $—(CR^A{}_2)_p—CR^A{=}CR^A—(CR^A{}_2)_{p1}$, $—(CR^A{}_2)_p—O—(CR^A{}_2)_{p1}—$, $—(CR^A{}_2)_p—N(R^A)—(CR^A{}_2)_{p1}—$, $—(CR^A{}_2)_p—S—(CR^A{}_2)_{p1}—$, $—(CR^A{}_2)_p—S(O)—(CR^A{}_2)_{p1}—$, and $—(CR^A{}_2)_p—S(O)_2—(CR^A{}_2)_{p1}—$, where p and p1 are independently selected from 0, 1, 2, 3 or 4;

provided that $p+p_1+q_2$ equals 0, 1, 2, 3, or 4;

each $R^4$ is independently selected from the group consisting of: hydrogen, halogen, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkyl-$R^B$, $C_1$-$C_6$ haloalkyl-$R^B$, $C_1$-$C_6$ alkoxy-$R^B$, $C_1$-$C_6$ haloalkoxy —$R^B$, $C_3$-$C_8$ cycloalkyl, $C_3$-$C_8$ cycloalkyl-$C_1$-$C_9$ alkyl, $C_1$-$C_6$ hydroxyalkyl, O—$C_1$-$C_6$ hydroxyalkyl, O—$C_1$-$C_6$ alkyl-$R^B$, CN, $SR^5$, $CO_2R^5$, $C(O)N(R^5)_2$, $OC(O)N(R^5)_2$, O—($C_1$-$C_6$) alkyl-$OR^5$, O—($C_1$-$C_5$ alkyl)-O—($C_1$-$C_3$ alkyl), O—($C_1$-$C_5$ alkyl)-O—($C_1$-$C_3$ alkyl)-$R^B$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), $SO(R^5)$, $SO_2(R^5)$, Het, Aryl, and

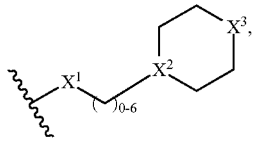

wherein $X^1$ is either $CH_2$, NH, O, or S; $X^2$ is either CH or N; and $X^3$ is either NH, N—$R^5$, $CH_2$, CH—$R^5$, O, or S; provided that two $R^4$ groups can join together to form methylene dioxy;

each $R^5$ is independently selected from the group consisting of: hydrogen, $C_1$-$C_6$ alkyl, $C_1$-$C_6$ haloalkyl, $C_1$-$C_6$ alkyl ($NH_2$), $C_6$-$C_8$ bridged cycloalkyl, $C_3$-$C_8$ cycloalkyl, and $C_3$-$C_8$ halocycloalkyl;

each Aryl is independently phenyl or naphthyl optionally substituted with 1, 2, 3 or 4 $R^C$ substituents;

each Het is independently either (a) 4-, 5- or 6-membered saturated or unsaturated monocyclic ring with 1, 2, 3, or 4 heteroatom ring atoms independently selected from the group consisting of N, O and S; (b) 8-, 9- or 10-membered saturated or unsaturated bicyclic ring with 1, 2, 3, 4, or 5 heteroatom ring atoms independently selected from the group consisting of N, O and S, or (c) 11- to 15-membered saturated or unsaturated tricyclic ring with 1, 2, 3, 4, or 5 heteroatom ring atoms independently selected from the group consisting of N, O and S; provided that said Het is optionally substituted with 1, 2, 3 or 4 $R^C$ substituents;

each $R^A$ is independently selected from the group consisting of: H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), $C_6$-$C_8$ bridged cycloalkyl, $C_3$-$C_8$ cycloalkyl, $C_1$-$C_6$ haloalkoxy, $C_3$-$C_8$ halocycloalkyl, SH, S($C_1$-$C_6$ alkyl), $NH_2$, NH($C_1$-$C_6$ alkyl), N($C_1$-$C_6$ alkyl)$_2$, C(O)($C_1$-$C_6$ alkyl), C(O)($C_3$-$C_8$ cycloalkyl), $CONH_2$, $SO_2NH_2$, $NO_2$, CN, $CF_3$, $CHF_2$, $CH_2F$, $OCHF_2$, $OCF_3$, $OCH_2F$, $SO_2$($C_1$-$C_6$ alkyl), S(O)($C_1$-$C_6$ alkyl), —($C_1$-$C_6$ alkyl)S(O)($C_1$-$C_6$ alkyl), $SO_2$($C_3$-$C_6$ cycloalkyl), —($C_1$-$C_6$ alkyl)$S(O)_2$($C_1$-$C_6$ alkyl), —($C_1$-$C_6$ alkyl)N($C_1$-$C_6$ alkyl)$SO_2$($C_1$-$C_6$ alkyl), N($C_1$-$C_6$ alkyl)$SO_2$($C_1$-$C_6$ alkyl), $SO_2$N($C_1$-$C_6$ alkyl)$_2$, —($C_1$-$C_6$ alkyl)$SO_2$N($C_1$-$C_6$ alkyl)$_2$, NHCOO($C_1$-$C_6$ alkyl), NHCO($C_1$-$C_6$ alkyl), NHCONH($C_1$-$C_6$ alkyl), $CO_2$($C_1$-$C_6$ alkyl), C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), —($C_0$-$C_5$ alkyl)-$S(O)_2$—($C_0$-$C_5$ alkyl)-($C_3$-$C_8$ cycloalkyl), Aryl, and Het; provided that two $R^A$ groups present on adjacent carbon atoms can together with the adjacent carbon atoms form a $C_3$-$C_6$ cycloalkyl;

each $R^B$ is independently either Het or Aryl;

each $R^C$ is independently either hydrogen, halogen, $C_1$-$C_6$ alkyl, $C_1$-$C_6$ alkoxy, $C_3$-$C_6$ cycloalkyl or $C_1$-$C_6$ haloalkyl;

alternatively, with respect to A and $R^1$, A is either $C_1$-$C_4$ alkyl, $C_2$-$C_4$ alkenyl, $C_2$-$C_4$ alkynyl, or $C_3$-$C_8$ cycloalkyl, each of which is substituted with $R^{A1}$, and $R^{A1}$ in combination with $R^1$ forms a $C_3$-$C_8$ alkylene, a $C_3$-$C_8$ alkenylene, or a $C_3$-$C_8$ alkynylene, each of which may be substituted with 1 or 2 independently selected $R^C$;

alternatively, with respect to A and $R^2$, A is either $C_1$-$C_4$ alkyl, $C_2$-$C_4$ alkenyl, $C_2$-$C_4$ alkynyl, or $C_3$-$C_8$ cycloalkyl, each of which is substituted with $R^{A1}$, and $R^{A1}$ in combination with $R^2$ form a $C_3$-$C_8$ alkylene, a $C_3$-$C_8$ alkenylene, or a $C_3$-$C_8$ alkynylene, each of which may be substituted 1 or 2 independently selected $R^C$;

alternatively, with respect to $R^2$ and $R^3$, $R^2$ and $R^3$ form a $C_3$-$C_8$ alkylene, $C_3$-$C_8$ alkenylene, or $C_3$-$C_8$ alkynylene, each of which may be substituted with 1 or 2 independently selected $R^C$; and m is 0, 1, 2 or 3.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

For the first aspect, wherein the compound is compound of General Formula I:

In a first embodiment of the invention, the compound is a compound of Formula I or a pharmaceutically acceptable salt thereof, wherein A is selected from the group consisting of $C_1$-$C_8$ alkyl, $C_2$-$C_8$ alkenyl, $C_2$-$C_8$ alkynyl, $C_3$-$C_8$ cycloalkyl, $Si(R^A)_3$, $Si(R^A)_2(CH_3)$, $Si(R^A)(CH_3)_2$, $Si(CH_3)_3$, aryl and 7-, 8-, 9- and 10-membered bicyclic groups, wherein said A $Si(R^A)_3$, $Si(R^A)_2(CH_3)$, $Si(R^A)(CH_3)_2$, $Si(CH_3)_3$, aryl and bicyclic groups contain 0, 1, 2 or 3 heteroatoms independently selected from the group consisting of O, S and N, each A aryl is independently selected from the group consisting of 5- and 6-membered aromatic rings and 7-, 8-, 9- and 10-membered bicyclic aromatic rings, said A is substituted with 0, 1, 2, 3 or 4 substituents $R^A$;

each $R^A$ is independently selected from the group consisting of H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), phenyl, naphthyl, $C_3$-$C_8$ cycloalkyl, halo($C_1$-$C_6$ alkoxy), —O($C_1$-$C_6$ alkyl), SH, S($C_1$-$C_6$ alkyl), $NH_2$, —NH($C_1$-$C_6$ alkyl), —N($C_1$-$C_6$ alkyl)$_2$, —C(O)($C_1$-$C_6$ alkyl), —$CONH_2$, —$SO_2NH_2$, $NO_2$, CN, —$CF_3$, —$CHF_2$, —$CH_2F$, —$OCHF_2$, —$OCF_3$, —$OCH_2F$, —$SO_2$($C_1$-$C_6$ alkyl), —S(O)($C_1$-$C_6$ alkyl), —($C_1$-$C_6$ alkyl)S(O)($C_1$-$C_6$ alkyl), —S(O)$_2$($C_1$-$C_6$ alkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), —N($C_1$-$C_6$ alkyl)$SO_2$($C_1$-$C_6$ alkyl), —$SO_2$N($C_1$-$C_6$ alkyl)$_2$, —($C_1$-$C_6$ alkyl)$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), —C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), and —($C_0$-$C_5$ alkyl)-S(O)$_2$—($C_0$-$C_5$ alkyl)-($C_3$-$C_8$ cycloalkyl), wherein two $R^A$ may be taken, together with the atoms to which they are bound, to form a ring having from three to fifteen ring atoms;

$R^A$ and $R^2$ may be taken, together with the atoms to which they are bound, to form a ring having from sixteen to twenty-one ring atoms;

$R^A$ and $R^1$ or $R^4$ may be taken, together with the atoms to which they are bound, to form a ring having from sixteen to twenty-one ring atoms;

J is selected from the group consisting of a direct bond, $C_1$-$C_8$ alkylene,

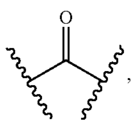, 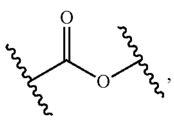, 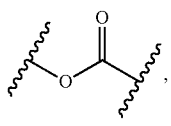,

-continued

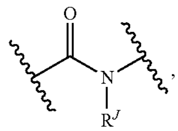, 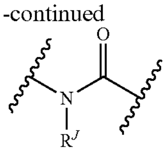, 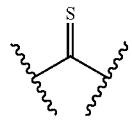,

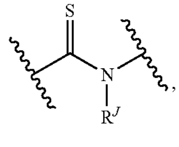, 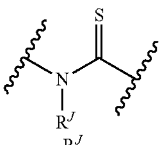, 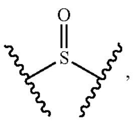,

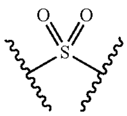, and 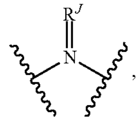, wherein said $C_1$-$C_8$ alkylene are substituted by 0, 1, 2 or 3 substituents $R^J$;

$R^J$ is selected from the group consisting of H, $C_1$-$C_6$alkyl, $Si(R^A)_3$, $Si(R^A)_2(CH_3)$, $Si(R^A)(CH_3)_2$, $Si(CH_3)_3$, $C_3$-$C_6$cycloalkyl, and aryl, wherein said $R^J$ $Si(R^A)_3$, $Si(R^A)_2(CH_3)$, $Si(R^A)(CH_3)_2$, $Si(CH_3)_3$, and aryl contain 0, 1, 2 or 3 heteroatoms independently selected from the group consisting of B, O, S and N, each $R^J$ aryl is independently selected from the group consisting of 5- and 6-membered aromatic rings, said $R^J$ is substituted with 0, 1, 2, 3 or 4 substituents $R^A$;

L is selected from the group consisting of $(CH_2)_{0-4}$, N($R^L$), and O;

each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), $Si(R^A)_3$, $Si(R^A)_2(CH_3)$, $Si(R^A)(CH_3)_2$, $Si(CH_3)_3$, and $C_1$-$C_6$ alkyl(aryl) groups, wherein said $R^L$ $Si(R^A)_3$, $Si(R^A)_2(CH_3)$, $Si(R^A)(CH_3)_2$, and $Si(CH_3)_3$ groups contain 0, 1, 2 or 3 heteroatoms independently selected from the group consisting of O, S and N, each $R^L$ aryl group is independently selected from the group consisting of 5- and 6-membered aromatic rings, G is selected from the group consisting of

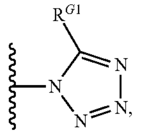 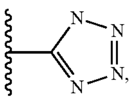 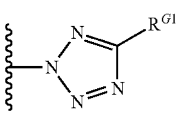,

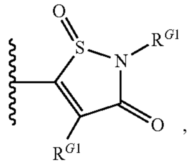, 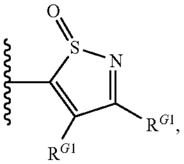

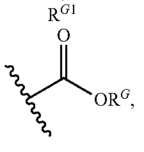 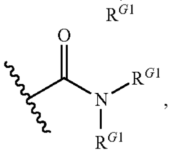, 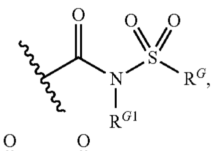

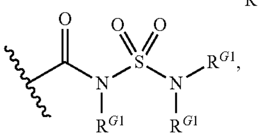 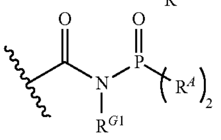 and

-continued

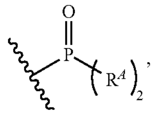

wherein $R^G$ is selected from the group consisting of H, $C_1$-$C_6$ alkyl, $C_3$-$C_6$ cycloalkyl, $C_3$-$C_6$ cycloalkyl($C_1$-$C_5$)alkyl, $Si(R^A)_3$, $Si(R^A)_2(CH_3)$, $Si(R^A)(CH_3)_2$, $Si(CH_3)_3$, aryl, and aryl($C_1$-$C_4$)alkyl groups, wherein said $R^G$ $Si(R^A)_3$, $Si(R^A)_2(CH_3)$, $Si(R^A)(CH_3)_2$, $Si(CH_3)_3$, and aryl groups contain 0, 1, 2 or 3 heteroatoms independently selected from the group consisting of O, S and N, each $R^G$ aryl is independently selected from the group consisting of 5- and 6-membered aromatic rings, said $R^G$ is substituted with 0, 1 or 2 independently selected $R^A$ substituents, each $R^{G1}$ is independently selected from the group consisting of H, $C_1$-$C_6$ alkyl, $C_3$-$C_7$ cycloalkyl, $Si(R^A)_3$, $Si(R^A)_2(CH_3)$, $Si(R^A)(CH_3)^2$, $Si(CH_3)_3$, and benzyl, wherein each $R^{G1}$ is independently substituted with 0 to 4 substituents $R^A$, Ⓔ is selected from the group consisting of:

1) aryl rings in which the aryl ring system attaches to Q and T at points that are two independently selected carbon ring atoms, 2) $C_3$-$C_8$ cycloalkyl rings in which the $C_3$-$C_8$ cycloalkyl ring system attaches to Q and T at points that are two independently selected carbon ring atoms, and 3) heterocyclic rings in which the heterocyclic ring system attaches to Q and T at points that are two independently selected ring atoms that are either two carbon ring atoms or one carbon ring atom and one nitrogen ring atom, and the heterocyclic ring system is selected from the group consisting of:

a) 5- or 6-membered saturated or unsaturated monocyclic rings with 1, 2, 3, or 4 heteroatom ring atoms independently selected from the group consisting of N, O and S, b) 8-, 9- or 10-membered saturated or unsaturated bicyclic rings with 1, 2, 3, 4, or 5 heteroatom ring atoms independently selected from the group consisting of N, O and S, and c) 11- to 15-membered saturated or unsaturated tricyclic rings with 1, 2, 3, 4, or 5 heteroatom ring atoms independently selected from the group consisting of N, O and S, wherein Ⓔ is substituted with 1 substituent $R^1$ and with 0, 1, 2, 3, 4 or 5 independently selected substituents $R^4$;

$R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —C(O)$CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl)-($C_3$-$C_8$ cycloalkyl), —($C_0$-$C_3$ alkyl) -S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —$N(R^A)_2$, $C_1$-$C_9$ alkyl-$N(R^A)_2$, $Si(R^A)_3$, $Si(R^A)_2(CH_3)$, $Si(R^A)(CH_3)_2$, $Si(CH_3)_3$, aryl, naphthyl, —O-aryl and —O-naphthyl groups; wherein:

said $R^1$ aryl, naphthyl, —O-aryl and —O-naphthyl groups contain 0, 1, 2 or 3 heteroatoms independently selected from the group consisting of O, S and N, each $R^1$ aryl is independently selected from the group consisting of 5- and 6-membered aromatic rings, said $R^1$ groups are substituted with 0 to 4 substituents $R^A$;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, $Si(R^A)_3$, $Si(R^A)_2(CH_3)$, $Si(R^A)(CH_3)_2$, $Si(CH_3)_3$, and aryl groups, wherein said $R^2Si(R^A)_3$, $Si(R^A)_2(CH_3)$, $Si(R^A)(CH_3)_2$, and aryl groups contain 0, 1, 2 or 3 heteroatoms independently selected from the group consisting of O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents, $R^3$ is selected from the group consisting of —$CH_2CH_3$, —CH═$CH_2$, $Si(R^A)_3$, $Si(R^A)_2(CH_3)$, $Si(R^A)(CH_3)_2$, $Si(CH_3)_3$, —$CH_2CH_2$-(bond to $R^2$), —CH═CH-(bond to $R^2$) and a direct bond to $R^2$, wherein when $R^3$ is selected from the group consisting of —$CH_2CH_2$-(bond to $R^2$), —CH═CH-(bond to $R^2$) and a direct bond to $R^2$, $R^2$ and $R^3$, together with the atoms to which they are bound, form a ring having from fifteen to twenty-one ring atoms and containing 0, 1, 2 or 3 double bonds and 0, 1, 2 or 3 triple bonds;

T is selected from the group consisting of —$(CH_2)_q$—, —$(CH_2)_q$—O—$(CH_2)_{q1}$—, —$(CH_2)_q$—$N(R^A)$—$(CH_2)_{q1}$—, —$(CH_2)_q$—S—$(CH_2)_{q1}$—, —$(CH_2)_q$—C(O)—$(CH_2)_{q1}$—, —$(CH_2)_q$—S(O)—$(CH_2)_{q1}$—, and —$(CH_2)_q$—$S(O)_2$—$(CH_2)_{q1}$—, where q and q1 are each independently selected from the group consisting of 0, 1 or 2, and each T is substituted by 0, 1 or 2 groups selected from $R^A$;

Q is selected from the group consisting of —$(CR^A{}_2)_p$—, —$(CR^A{}_2)_p$—$CR^A$═$CR^A$—$(CR^A{}_2)_{p1}$, —$(CR^A{}_2)_p$—O—$(CR^A{}_2)_{p1}$—, —$(CR^A{}_2)_p$—$N(R^A)$—$(CR^A{}_2)_{p1}$—, —$(CR^A{}_2)_p$—S—$(CR^A{}_2)_{p1}$—, —$(CR^A{}_2)_p$—S(O)—$(CR^A{}_2)_{p1}$—, and —$(CR^A{}_2)_p$—$S(O)_2$—$(CR^A{}_2)_{p1}$—, where p and p1 are independently selected from 0, 1, 2, 3 or 4;

each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —C(O)$N(R^A)_2$, —OC(O)$N(R^A)_2$, $Si(R^A)_3$, $Si(R^A)_2(CH_3)$, $Si(R^A)(CH_3)_2$, $Si(CH_3)_3$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —SO($R^A$), —$SO_2(R^A)$, $C_3$-$C_8$ cycloalkyl, and aryl, wherein said $R^4$ aryl groups contain 0, 1, 2 or 3 heteroatoms independently selected from the group consisting of O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$;

two $R^4$ may be taken, together with the atoms to which they are bound, to form a ring; and m is 0, 1, 2 or 3.

In a second embodiment of the invention, the compound is a compound of formula I or a pharmaceutically acceptable salt thereof, wherein A is selected from the group consisting of $C_1$-$C_8$ alkyl, $C_2$-$C_8$ alkenyl, $C_2$-$C_8$ alkynyl, $C_3$-$C_8$ cycloalkyl, aryl and 7-, 8-, 9- and 10-membered bicyclic groups, wherein said A aryl and bicyclic groups contain 0, 1, 2 or 3 heteroatoms independently selected from the group consisting of O, S and N, each A aryl is independently selected from the group consisting of 5- and 6-membered aromatic rings and 7-, 8-, 9- and 10-membered bicyclic aromatic rings, said A is substituted with 0, 1, 2, 3 or 4 substituents $R^A$;

each $R^A$ is independently selected from the group consisting of H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), phenyl, naphthyl, $C_3$-$C_8$ cycloalkyl, halo($C_1$-$C_6$ alkoxy), —O($C_1$-$C_6$ alkyl), SH, S($C_1$-$C_6$ alkyl), $NH_2$, —NH($C_1$-$C_6$ alkyl), —N($C_1$-$C_6$ alkyl)$_2$, —C(O)($C_1$-$C_6$ alkyl), —$CONH_2$, —$SO_2NH_2$, $NO_2$, CN, —$CF_3$, —$CHF_2$, —$CH_2F$, —$OCHF_2$, —$OCF_3$, —$OCH_2F$, —$SO_2$($C_1$-$C_6$ alkyl), —S(O)($C_1$-$C_6$ alkyl), —($C_1$-$C_6$ alkyl)S(O)($C_1$-$C_6$ alkyl), —S(O)$_2$($C_1$-$C_6$ alkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), —N($C_1$-$C_6$ alkyl)$SO_2$($C_1$-$C_6$ alkyl), —$SO_2$N($C_1$-$C_6$ alkyl)$_2$, —($C_1$-$C_6$ alkyl)$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), —C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), and —($C_0$-$C_5$ alkyl)-S(O)$_2$—($C_0$-$C_5$ alkyl)-($C_3$-$C_8$ cycloalkyl), wherein two $R^A$ may be taken, together with the atoms to which they are bound, to form a ring having from three to fifteen ring atoms;

$R^A$ and $R^2$ may be taken, together with the atoms to which they are bound, to form a ring having from sixteen to twenty-one ring atoms;

$R^A$ and $R^1$ or $R^4$ may be taken, together with the atoms to which they are bound, to form a ring having from sixteen to twenty-one ring atoms;

J is selected from the group consisting of a direct bond, $C_1$-$C_8$ alkylene,

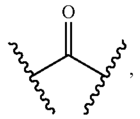, 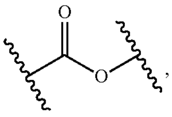, 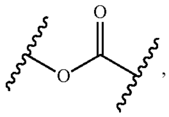, 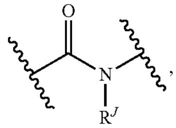, 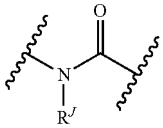, 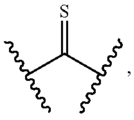, 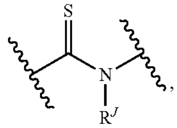, 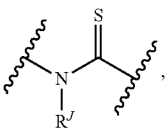, 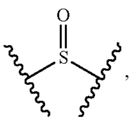, 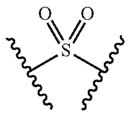, and 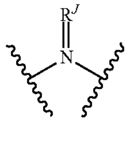, wherein said $C_1$-$C_8$ alkylene are substituted by 0, 1, 2 or 3 substituents $R^J$;

$R^J$ is selected from the group consisting of H, $C_1$-$C_6$alkyl, $C_3$-$C_6$cycloalkyl, and aryl, wherein said $R^J$ aryl contain 0, 1, 2 or 3 heteroatoms independently selected from the group consisting of B, O, S and N, each $R^J$ aryl is independently selected from the group consisting of 5- and 6-membered aromatic rings, said $R^J$ is substituted with 0, 1, 2, 3 or 4 substituents $R^A$;

L is selected from the group consisting of $(CH_2)_{0-4}$ and N($R^L$);

each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), and $C_1$-$C_6$ alkyl(aryl) groups, wherein each $R^L$ aryl group is independently selected from the group consisting of 5- and 6-membered aromatic rings, G is selected from the group consisting of

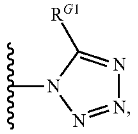 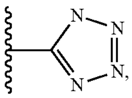 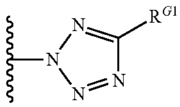, 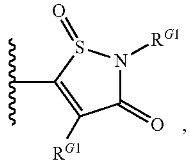, 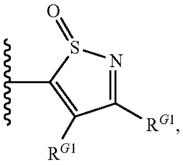 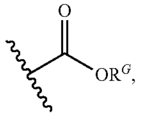 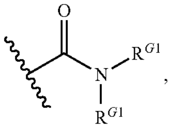, 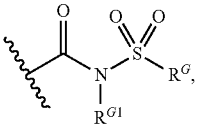 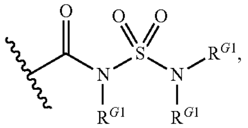 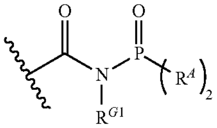 and 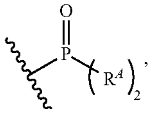, wherein $R^G$ is selected from the group consisting of H, $C_1$-$C_6$ alkyl, $C_3$-$C_6$ cycloalkyl, $C_3$-$C_6$ cycloalkyl($C_1$-$C_5$)alkyl, aryl, and aryl($C_1$-$C_4$)alkyl groups, wherein said $R^G$ aryl groups contain 0, 1, 2 or 3 heteroatoms independently selected from the group consisting of O, S and N, each $R^G$ aryl is independently selected from the group consisting of 5- and 6-membered aromatic rings, said $R^G$ is substituted with 0, 1 or 2 independently selected $R^A$ substituents, each $R^{G1}$ is independently selected from the group consisting of H, $C_1$-$C_6$ alkyl, $C_3$-$C_7$ cycloalkyl, and benzyl, wherein each $R_{G1}$ is independently substituted with 0 to 4 substituents $R^A$, (E) is selected from the group consisting of:

1) aryl rings in which the aryl ring system attaches to Q and T at points that are two independently selected carbon ring atoms, 2) $C_3$-$C_8$ cycloalkyl rings in which the $C_3$-$C_8$ cycloalkyl ring system attaches to Q and T at points that are two independently selected carbon ring atoms, and 3) heterocyclic rings in which the heterocyclic ring system attaches to Q and T at points that are two independently selected ring atoms that are either two carbon ring atoms or one carbon ring atom and one nitrogen ring atom, and the heterocyclic ring system is selected from the group consisting of:

a) 5- or 6-membered saturated or unsaturated monocyclic rings with 1, 2, 3, or 4 heteroatom ring atoms independently selected from the group consisting of N, O and S, b) 8-, 9- or 10-membered saturated or unsaturated bicyclic rings with 1, 2, 3, 4, or 5 heteroatom ring atoms independently selected from the group consisting of N, O and S, and c) 11- to 15-membered saturated or unsaturated tricyclic rings with 1, 2, 3, 4, or 5 heteroatom ring atoms independently selected from the group consisting of N, O and S, wherein Ⓔ is substituted with 1 substituent $R^1$ and with 0, 1, 2, 3, 4 or 5 independently selected substituents $R^4$;

$R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —C(O)$CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl)-($C_3$-$C_8$ cycloalkyl), —($C_0$-$C_3$ alkyl) -S—($C_0$-$C_3$ alkyl)-($C_3$-$C_8$ cycloalkyl), —($C_0$-$C_3$ alkyl)-S(O)$_2$—($C_0$-$C_3$ alkyl)-($C_3$-$C_8$ cycloalkyl), —N($R^A$)$_2$, $C_1$-$C_9$ alkyl-N($R^A$)$_2$, aryl, naphthyl, —O-aryl and —O-naphthyl groups; wherein:

said $R^1$ aryl, naphthyl, —O-aryl and —O-naphthyl groups contain 0, 1, 2 or 3 heteroatoms independently selected from the group consisting of O, S and N, each $R^1$ aryl is independently selected from the group consisting of 5- and 6-membered aromatic rings, said $R^1$ groups are substituted with 0 to 4 substituents $R^A$;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, and aryl groups, wherein said $R^2$ aryl groups contain 0, 1, 2 or 3 heteroatoms independently selected from the group consisting of O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents, $R^3$ is selected from the group consisting of —$CH_2CH_3$, —CH═$CH_2$, —$CH_2CH_2$-(bond to $R^2$), —CH═CH-(bond to $R^2$) and a direct bond to $R^2$, wherein when $R^3$ is selected from the group consisting of —$CH_2CH_2$-(bond to $R^2$), —CH═CH-(bond to $R^2$) and a direct bond to $R^2$, $R^2$ and $R^3$, together with the atoms to which they are bound, form a ring having from fifteen to twenty-one ring atoms and containing 0, 1, 2 or 3 double bonds and 0, 1, 2 or 3 triple bonds;

T is selected from the group consisting of —$(CH_2)_q$—, —$(CH_2)_q$—O—$(CH_2)_{q1}$—, —$(CH_2)_q$—N($R^A$)—$(CH_2)_{q1}$—, —$(CH_2)_q$—S—$(CH_2)_{q1}$—, —$(CH_2)_q$—C(O)—$(CH_2)_{q1}$—, —$(CH_2)_q$—S(O)—$(CH_2)_{q1}$—, and —$(CH_2)_q$—S(O)$_2$—$(CH_2)_{q1}$—, where q and q1 are each independently selected from the group consisting of 0, 1 or 2, and each T is substituted by 0, 1 or 2 groups selected from $R^A$;

Q is selected from the group consisting of —$(CR^A{}_2)_p$—, —$(CR^A{}_2)_p$—$CR^A$═$CR^A$—$(CR^A{}_2)_{p1}$, —$(CR^A{}_2)_p$—O—$(CR^A{}_2)_{p1}$—, —$(CR^A{}_2)_p$—N($R^A$)—$(CR^A{}_2)_{p1}$—, $(CR^A{}_2)_p$—S—$(CR^A{}_2)_{p1}$, $(CR^A{}_2)_p$—, S(O)—$(CR^A{}_2)_{p1}$—, and —$(CR^A{}_2)_p$—S(O)$_2$—$(CR^A{}_2)_{p1}$—, where p and p1 are independently selected from 0, 1, 2, 3 or 4;

each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —C(O)N($R^A$)$_2$, —OC(O)N($R^A$)$_2$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S(O)$_2$—($C_0$-$C_3$ alkyl)-($C_3$-$C_8$ cycloalkyl), —SO($R^A$), —$SO_2$($R^A$), $C_3$-$C_8$ cycloalkyl, and aryl, wherein said $R^4$ aryl groups contain 0, 1, 2 or 3 heteroatoms independently selected from the group consisting of O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$;

two $R^4$ may be taken, together with the atoms to which they are bound, to form a ring; and m is 0, 1, 2 or 3.

In a third embodiment of the invention, the compound is a compound of formula I or a pharmaceutically acceptable salt thereof, wherein $R^A$ and $R^2$ are taken, together with the atoms to which they are bound, to form a ring wherein the $R^A$ to $R^2$ linkage contains from six to nine atoms. In all aspects of this embodiment, all other groups are as provided in the general formula above or in the first through second embodiments.

In a fourth embodiment of the invention, the compound is a compound of formula I or a pharmaceutically acceptable salt thereof, wherein said $R^A$ present on A and $R^4$ are taken, together with the atoms to which they are bound, to form a ring wherein the $R^A$ to $R^4$ linkage contains from six to nine atoms. In all aspects of this embodiment, all other groups are as provided in the general formula above or in the first through third embodiments.

In a fifth embodiment of the invention, the compound is a compound of formula I or a pharmaceutically acceptable salt thereof, wherein $R^3$ is selected from the group consisting of —$CH_2CH_2$-(bond to $R^2$), —CH═CH-(bond to $R^2$) and a direct bond to $R^2$, and wherein $R^2$ and $R^3$, together with the atoms to which they are bound, form a ring having from fifteen to twenty-one ring atoms and containing 0, 1, 2 or 3 double bonds and 0, 1, 2 or 3 triple bonds. In a first aspect of this embodiment, $R^A$ and $R^1$ are taken, together with the atoms to which they are bound, to form a ring wherein the $R^A$ to $R^1$ linkage contains from six to nine atoms; and $R^3$ is selected from the group consisting of —$CH_2CH_2$-(bond to $R^2$), —CH═CH-(bond to $R^2$) and a direct bond to $R^2$, and wherein $R^2$ and $R^3$, together with the atoms to which they are bound, form a ring having from fifteen to twenty-one ring atoms and containing 0, 1, 2 or 3 double bonds and 0, 1, 2 or 3 triple bonds. In a second aspect of this embodiment, $R^A$ and $R^4$ are taken, together with the atoms to which they are bound, to form a ring wherein the $R^A$ to $R^4$ linkage contains from six to nine atoms; and $R^3$ is selected from the group consisting of —$CH_2CH_2$-(bond to $R^2$), —CH═CH-(bond to $R^2$) and a direct bond to $R^2$, and wherein $R^2$ and $R^3$, together with the atoms to which they are bound, form a ring having from fifteen to twenty-one ring atoms and containing 0, 1, 2 or 3 double bonds and 0, 1, 2 or 3 triple bonds. In all aspects of this embodiment, all other groups are as provided in the general formula above or in the first through fourth embodiments.

In a sixth embodiment of the invention, the compound is a compound of formula Ia:

(Ia)

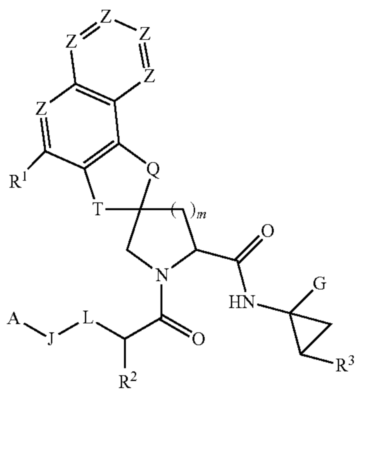

or a pharmaceutically acceptable salt thereof, wherein each Z is independently selected from the group consisting of N and $C(R^4)$. In a first aspect of this embodiment, the compound of formula Ia is a compound of formula Ia1:

(Ia1)

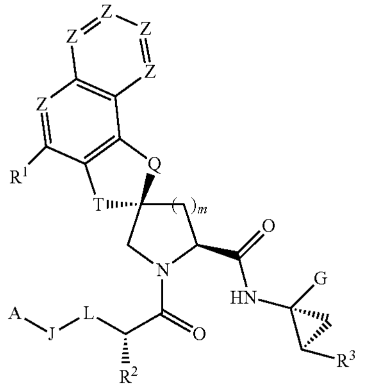

or a pharmaceutically acceptable salt thereof. In a second aspect of this embodiment, the compound of formula Ia is a compound of formula Ia2:

(Ia2)

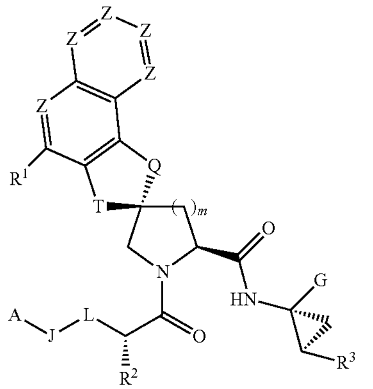

or a pharmaceutically acceptable salt thereof. In all aspects of this embodiment, all groups are as provided in the general formula above or in the first through fifth embodiments.

In a seventh embodiment of the invention, Ⓔ is selected from the group consisting of 1) aryl rings in which the aryl ring system attaches to Q and T at points that are two independently selected carbon ring atoms, 2) $C_3$-$C_8$ cycloalkyl rings in which the $C_3$-$C_8$ cycloalkyl ring system attaches to Q and T at points that are two independently selected carbon ring atoms, and 3) heterocyclic rings in which the heterocyclic ring system attaches to Q and T at points that are two independently selected ring atoms that are either two carbon ring atoms or one carbon ring atom and one nitrogen ring atom, and the heterocyclic ring system is selected from the group consisting of a) 5- or 6-membered saturated or unsaturated monocyclic rings with 1, 2, 3, or 4 heteroatom ring atoms independently selected from the group consisting of N, O and S, b) 8-, 9- or 10-membered saturated or unsaturated bicyclic rings with 1, 2, 3, 4, or 5 heteroatom ring atoms independently selected from the group consisting of N, O and S, and c) 11- to 15-membered saturated or unsaturated tricyclic rings with 1, 2, 3, 4, or 5 heteroatom ring atoms independently selected from the group consisting of N, O and S, wherein Ⓔ is substituted with 1 substituent $R^1$ and with 0, 1, 2, 3, 4 or 5 independently selected substituents $R^4$. In aspects of this embodiment, Ⓔ is selected from the group consisting of heterocyclic rings in which the heterocyclic ring system attaches to Q and T at points that are two independently selected ring atoms that are two carbon ring atoms, and the heterocyclic ring system is selected from the group consisting of 8-, 9- or 10-membered saturated or unsaturated bicyclic rings with 1, 2, 3, 4, or 5 heteroatom ring atoms independently selected from the group consisting of N, O and S, wherein Ⓔ is substituted with 1 substituent $R^1$ and with 0, 1, 2, 3, 4 or 5 independently selected substituents $R^4$.

In aspects of this embodiment, Ⓔ is

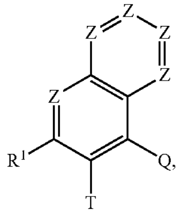

wherein each Z is independently selected from the group consisting of N and CH, substituted by 0, 1, 2, or 3 substituents $R^4$. In instances of these aspects,

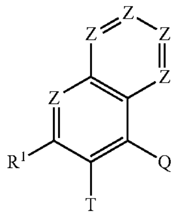

is selected from the group consisting of

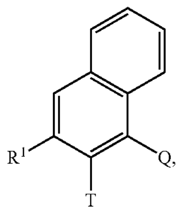

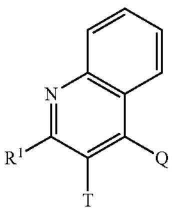

and

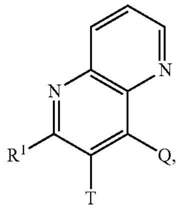

substituted by 0, 1, 2 or 3 substituents $R^4$.

In specific instances of these aspects,

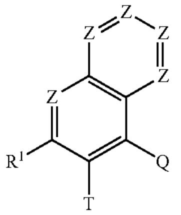

is selected from the group consisting of

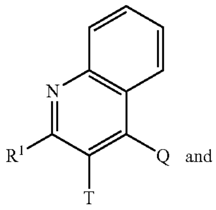

and

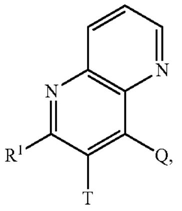

substituted by 0, 1, 2 or 3 substituents $R^4$. In this embodiment, all other groups are as provided in the general formula above or in the first through sixth embodiments.

In an eighth embodiment of the invention, each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —C(O)N$(R^A)_2$, —OC(O)N$(R^A)_2$, Si$(R^A)_3$, Si$(R^A)_2(CH_3)$, Si$(R^A)(CH_3)_2$, Si$(CH_3)_3$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S$(O)_2$—($C_0$-$C_3$ alkyl)-($C_3$-$C_8$ cycloalkyl), —SO$(R^A)$, —$SO_2(R^A)$, $C_3$-$C_8$ cycloalkyl, $C_1$-$C_6$ internally substituted alkyl, $C_1$-$C_6$ internally substituted alkoxy, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl)-S$(O)_2$—($C_0$-$C_3$ internally substituted alkyl)-($C_3$-$C_8$ internally substituted cycloalkyl), $C_3$-$C_8$ internally substituted cycloalkyl and aryl, wherein said $R^4$ $C_1$-$C_6$ internally substituted alkyl, $C_1$-$C_6$ internally substituted alkoxy, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl)-S$(O)_2$—($C_0$-$C_3$ internally substituted alkyl)-($C_3$-$C_8$ internally substituted cycloalkyl), $C_3$-$C_8$ internally substituted cycloalkyl and aryl groups contain 0, 1, 2 or 3 heteroatoms independently selected from the group consisting of B, O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$; two $R^4$ may be taken, together with the atoms to which they are bound, to form a ring. In aspects of this embodiment, each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —C(O)N$(R^A)_2$, —OC(O)N$(R^A)_2$, Si$(R^A)_3$, Si$(R^A)_2(CH_3)$, Si$(R^A)(CH_3)_2$, Si$(CH_3)_3$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S$(O)_2$—($C_0$-$C_3$ alkyl)-($C_3$-$C_8$ cycloalkyl), —SO$(R^A)$, —$SO_2(R^A)$, $C_3$-$C_8$ cycloalkyl, and aryl, wherein said $R^4$ aryl groups contain 0, 1, 2 or 3 heteroatoms independently selected from the group consisting of O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$; two $R^4$ may be taken, together with the atoms to which they are bound, to form a ring. In aspects of this embodiment, each $R^4$ is independently selected from the group consisting of H, halogen atoms, —$OR^A$, $C_1$-$C_6$ alkyl, $C_1$-$C_6$ alkoxy, —CN, —$SR^A$, —$CO_2R^A$, —C(O)N$(R^A)_2$, —OC(O)N$(R^A)_2$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S$(O)_2$—($C_0$-$C_3$ alkyl)-($C_3$-$C_8$ cycloalkyl), —SO$(R^A)$, —$SO_2(R^A)$, $C_3$-$C_8$ cycloalkyl, and aryl, wherein said $R^4$ aryl groups contain 0, 1, 2 or 3 heteroatoms independently selected from the group consisting of O, S and N, each $R^4$ aryl is independently selected from the group consisting of 5- and 6-membered aromatic rings, said $R^4$ $C_1$-$C_6$ alkyl, $C_1$-$C_6$ alkoxy, $C_3$-$C_8$ cycloalkyl and aryl groups are substituted with 0 to 4 substituents $R^A$; two $R^4$ may be taken, together with the atoms to which they are bound, to form a ring. In particular aspects of this embodiment, wherein each $R^4$ is independently selected from the group consisting of H, F, Cl, Br, OH, CN, $C_1$-$C_5$ alkyl, $C_1$-$C_5$ alkoxy, substituted by 0, 1, 2, or 3 $R^A$. In aspects of this embodiment, each $R^4$ is independently selected from the group consisting of H, F, Cl, Br, OH, CN, $C_1$-$C_5$ alkyl, $OCH_3$, $OCH_2CH_3$, $OCF_3$, $OCHF_2$, $OCH_2F$,

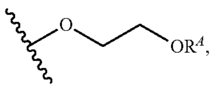

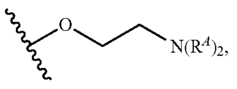

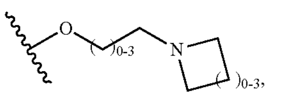

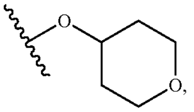

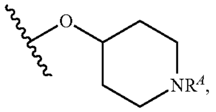

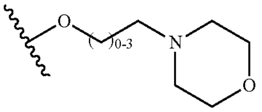

and

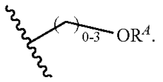

In additional aspects of this embodiment, each $R^4$ is selected from the group consisting of H, Cl, $OCH_3$, $OCF_3$ and

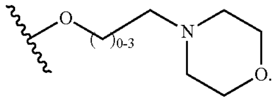

In all aspects of this embodiment, all other groups are as provided in the general formula above or in the first through seventh embodiments.

In a ninth embodiment of the invention, $R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —C(O)$CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl) -($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S$(O)_2$—($C_0$-$C_3$ alkyl)-($C_3$-$C_8$ cycloalkyl), —N$(R^4)_2$, $C_1$-$C_9$ alkyl-N $(R^A)_2$, $Si(R^A)_3$, $Si(R^A)_2(CH_3)$, $Si(R^A)(CH_3)_2$, $Si(CH_3)_3$, $C_1$-$C_9$ internally substituted alkyl, $C_1$-$C_9$ internally substituted alkoxy, $C_1$-$C_9$ internally substituted alkyl-$C_1$-$C_9$ internally substituted alkoxy, —$SO_2$($C_1$-$C_9$ internally substituted alkyl), $C_3$-$C_8$ internally substituted cycloalkyl, $C_1$-$C_9$ internally substituted alkyl-$C_3$-$C_8$ internally substituted cycloalkyl, $C_3$-$C_8$ internally substituted cycloalkoxy, $C_1$-$C_9$ alkyl-$C_3$-$C_8$ internally substituted cycloalkoxy, $C_1$-$C_9$ internally substituted haloalkyl, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl)-$S(O)_2$—($C_0$-$C_3$ internally substituted alkyl)-($C_3$-$C_8$ internally substituted cycloalkyl), $C_1$-$C_9$ internally substituted alkyl-$N(R^A)_2$, aryl, naphthyl, —O-aryl and —O-naphthyl groups; wherein said $R^1$ $C_1$-$C_9$ internally substituted alkyl, $C_1$-$C_9$ internally substituted alkoxy, $C_1$-$C_9$ internally substituted alkyl-$C_1$-$C_9$ internally substituted alkoxy, —$SO_2$ ($C_1$-$C_9$ internally substituted alkyl), $C_3$-$C_8$ internally substituted cycloalkyl, $C_1$-$C_9$ internally substituted alkyl-$C_3$-$C_8$ internally substituted cycloalkyl, $C_3$-$C_8$ internally substituted cycloalkoxy, $C_1$-$C_9$ alkyl-$C_3$-$C_8$ internally substituted cycloalkoxy, $C_1$-$C_9$ internally substituted haloalkyl, —($C_0$-$C_3$ internally substituted alkyl)-O—($C_0$-$C_3$ internally substituted alkyl)-($C_3$-$C_8$ internally substituted cycloalkyl), —($C_0$-$C_3$ internally substituted alkyl)-S—($C_0$-$C_3$ internally substituted alkyl)-($C_3$-$C_8$ internally substituted cycloalkyl), —($C_0$-$C_3$ internally substituted alkyl) -$S(O)_2$—($C_0$-$C_3$ internally substituted alkyl)-($C_3$-$C_8$ internally substituted cycloalkyl), $C_1$-$C_9$ internally substituted alkyl-$N(R^A)_2$, aryl, naphthyl, —O-aryl and —O-naphthyl groups contain 0, 1, 2 or 3 heteroatoms independently selected from the group consisting of B, O, S and N, each $R^1$ aryl is independently selected from the group consisting of 5- and 6-membered aromatic rings, said $R^1$ groups are substituted with 0 to 4 substituents $R^A$. In aspects of this embodiment, $R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —$C(O)CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —$N(R^A)_2$, $C_1$-$C_9$ alkyl-$N(R^A)_2$, $Si(R^A)_3$, $Si(R^A)_2(CH_3)$, $Si(R^A)(CH_3)_2$, $Si(CH_3)_3$, aryl, naphthyl, —O-aryl and —O-naphthyl groups; wherein said $R^1$ aryl, naphthyl, —O-aryl and —O-naphthyl groups contain 0, 1, 2 or 3 heteroatoms independently selected from the group consisting of O, S and N, each $R^1$ aryl is independently selected from the group consisting of 5- and 6-membered aromatic rings, said $R^1$ groups are substituted with 0 to 4 substituents $R^A$. In aspects of this embodiment, $R^1$ is selected from the group consisting of H, halogen atoms, —OH, $C_1$-$C_9$ alkyl, $C_1$-$C_9$ alkoxy, $C_1$-$C_9$ alkyl-$C_1$-$C_9$ alkoxy, —CN, —C(O)OH, —$C(O)CH_3$, —$SR^A$, —$SO_2$($C_1$-$C_9$ alkyl), $C_3$-$C_8$ cycloalkyl, $C_1$-$C_9$ alkyl-$C_3$-$C_8$ cycloalkyl, $C_3$-$C_8$ cycloalkoxy, $C_1$-$C_9$ alkyl-$C_3$-$C_8$ cycloalkoxy, $C_1$-$C_9$ haloalkyl, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), —$N(R^A)_2$, $C_1$-$C_9$ alkyl-N $(R^A)_2$, aryl, naphthyl, —O-aryl and —O-naphthyl groups; wherein said $R^1$ aryl, naphthyl, —O-aryl and —O-naphthyl groups contain 0, 1, 2 or 3 heteroatoms independently selected from the group consisting of O, S and N, each $R^1$ aryl is independently selected from the group consisting of S— and 6-membered aromatic rings, said $R^1$ groups are substituted with 0 to 4 substituents $R^A$. In particular aspects of this embodiment, $R^1$ is selected from the group consisting of H, $C_1$-$C_5$ alkyl, $C_3$-$C_6$ cycloalkyl,

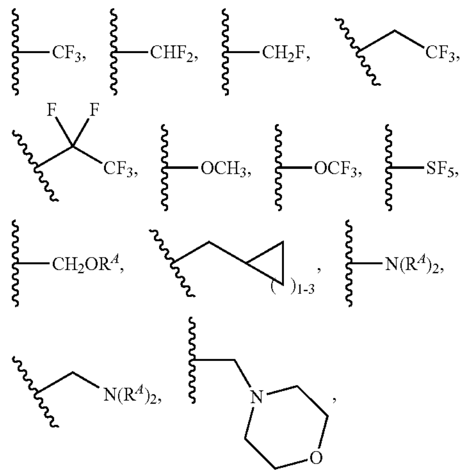

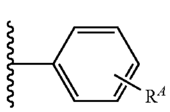

and

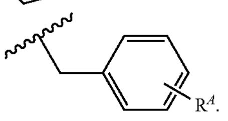

In additional aspects of this embodiment, $R^1$ is selected from the group consisting of H, $C_1$-$C_9$ alkyl, and aryl groups; wherein said $R^1$ aryl groups contain 0 or 1 heteroatoms independently selected from the group consisting of O, S and N, each $R^1$ aryl is independently selected from the group consisting of 5- and 6-membered aromatic rings, said $R^1$ groups are substituted with 0 to 4 substituents $R^A$. In all aspects of this embodiment, all other groups are as provided in the general formula above or in the first through eighth embodiments.

In a tenth embodiment of the invention, T is selected from the group consisting of —$(CH_2)_q$—, —$(CH_2)_q$—O—$(CH_2)_{q1}$—, —$(CH_2)_q$—$N(R^A)$—$(CH_2)_{q1}$—, —$(CH_2)_q$—S—$(CH_2)_{q1}$—, —$(CH_2)_q$—C(O)—$(CH_2)_{q1}$—, —$(CH_2)_q$—S(O)—$(CH_2)_{q1}$—, and —$(CH_2)_q$—$S(O)_2$—$(CH_2)_{q1}$—, where q and q1 are each independently selected from the group consisting of 0, 1 or 2, and T is substituted by 0, 1 or 2 groups selected from $R^A$. In aspects of this embodiment, T is selected from —$(CH_2)_{0-3}$—,

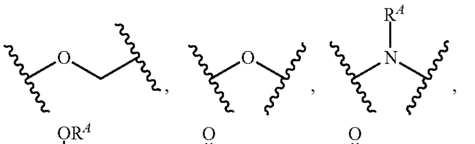

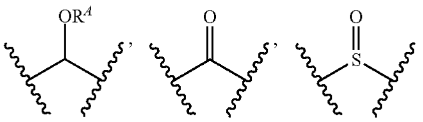

and

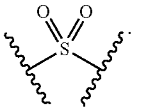

In particular aspects of this embodiment, T is —O—. In all aspects of this embodiment, all groups are as provided in the general formula above or in the first through ninth embodiments.

In an eleventh embodiment of the invention, Q is selected from the group consisting of $-(CR^A{}_2)_p-$, $-(CR^A{}_2)_p-CR^A{=}CR^A-(CR^A{}_2)_{p1}$, $-(CR^A{}_2)_p-O-(CR^A{}_2)_{p1}-$, $-(CR^A{}_2)_p-N(R^A)-(CR^A{}_2)_{p1}-$, $-(CR^A{}_2)_p-S-(CR^A{}_2)_{p1}-$, $-(CR^A{}_2)_p-S(O)-(CR^A{}_2)_{p1}-$, and $-(CR^A{}_2)_p-S(O)_2-(CR^A{}_2)_{p1}-$, where p and p1 are independently selected from 0, 1, 2, 3 or 4. In aspects of this embodiment, Q is selected from $-(CH_2)_{0\text{-}3}-$,

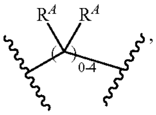, 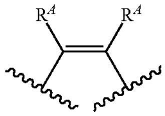,

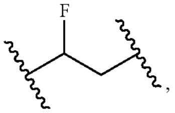, 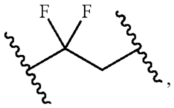,

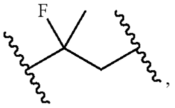, 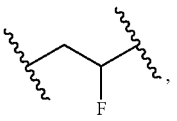,

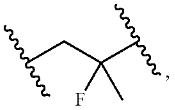, 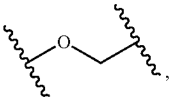,

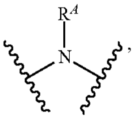, 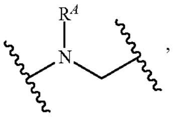,

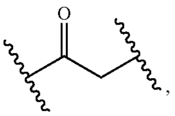, 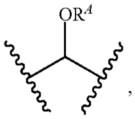,

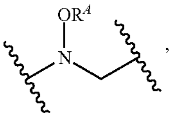, 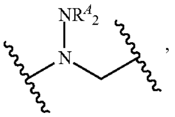,

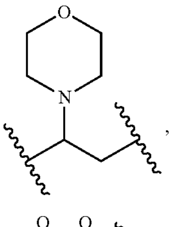, 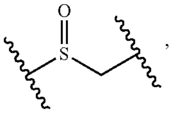,

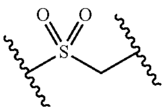 and 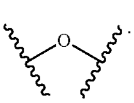.

In particular aspects of this embodiment, Q is selected from the group consisting of selected from $-(CH_2)_2-$,

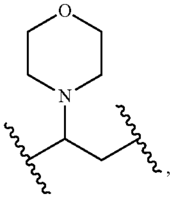, 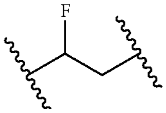 and

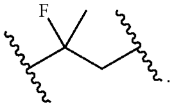.

In all aspects of this embodiment, all other groups are as provided in the general formula above or in the first through tenth embodiments.

In a twelfth embodiment of the invention, m is 0, 1, 2 or 3. In aspects of this embodiment, m is 1. In all aspects of this embodiment, all other groups are as provided in the general formula above or in the first through eleventh embodiments.

In a thirteenth embodiment of the invention, G is selected from the group consisting of

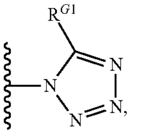, 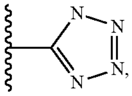, 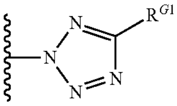,

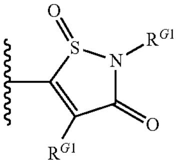, 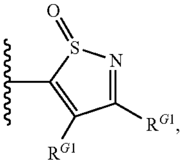,

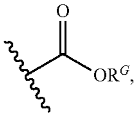, 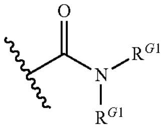, 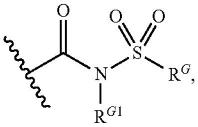,

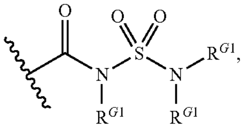, 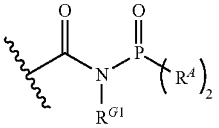 and

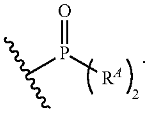.

In aspects of the embodiment, G is selected from the group consisting of

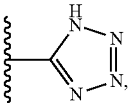, 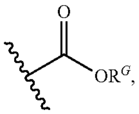, 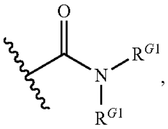,

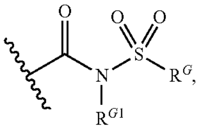, 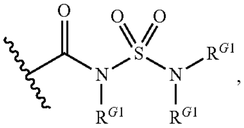,

-continued

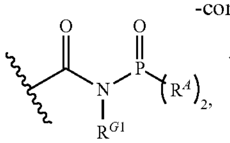

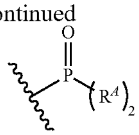

and

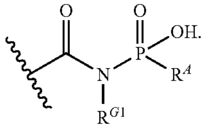

In particular aspects of this embodiment, G is selected from the group consisting of

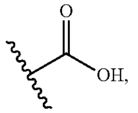

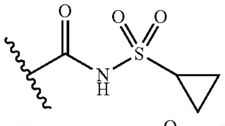

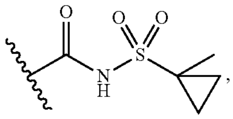

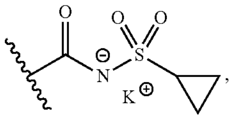

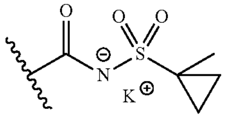

and

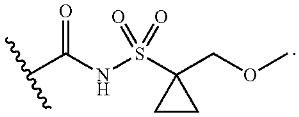

In particular aspects of this embodiment, G is selected from the group consisting of

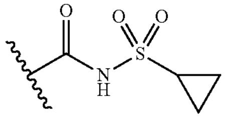

and

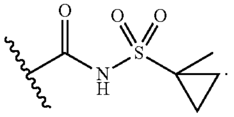

In even more particular embodiments, G is

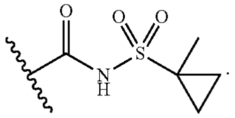 [SMILES: *C(=O)NS(=O)(=O)C1(C)CC1]

In all aspects of this embodiment, all other groups are as provided in the general formula above or in the first through twelfth embodiments.

In a fourteenth embodiment of the invention, $R^G$ is selected from the group consisting of H, $C_1$-$C_6$ alkyl, $C_3$-$C_6$ cycloalkyl, $C_3$-$C_6$ cycloalkyl($C_1$-$C_5$)alkyl, $Si(R^A)_3$, $Si(R^A)_2(CH_3)$, $Si(R^A)(CH_3)_2$, $Si(CH_3)_3$, aryl, aryl($C_1$-$C_4$)alkyl, $C_1$-$C_6$ internally substituted alkyl, $C_3$-$C_6$ internally substituted cycloalkyl, internally substituted $C_3$-$C_6$ cycloalkyl($C_1$-$C_5$)alkyl, and internally substituted aryl($C_1$-$C_4$)alkyl groups, wherein said $R^G$ $Si(R^A)_3$, $Si(R^A)_2(CH_3)$, $Si(R^A)(CH_3)_2$, $Si(CH_3)_3$, $C_1$-$C_6$ internally substituted alkyl, $C_3$-$C_6$ internally substituted cycloalkyl, internally substituted $C_3$-$C_6$ cycloalkyl($C_1$-$C_5$)alkyl, aryl, and internally substituted aryl ($C_1$-$C_4$)alkyl groups contain 0, 1, 2 or 3 heteroatoms independently selected from the group consisting of B, O, S and N, each $R^G$ aryl is independently selected from the group consisting of 5- and 6-membered aromatic rings, said $R^G$ is substituted with 0, 1 or 2 independently selected $R^A$ substituents. In aspects of this embodiment, $R^G$ is selected from the group consisting of H, $C_1$-$C_6$ alkyl, $C_3$-$C_6$ cycloalkyl, $C_3$-$C_6$ cycloalkyl($C_1$-$C_5$)alkyl, $Si(R^A)_3$, $Si(R^A)_2(CH_3)$, $Si(R^A)(CH_3)_2$, $Si(CH_3)_3$, aryl, and aryl($C_1$-$C_4$)alkyl groups, wherein said $R^G$ $Si(R^A)_3$, $Si(R^A)_2(CH_3)$, $Si(R^A)(CH_3)^2$, $Si(CH_3)_3$, and aryl groups contain 0, 1, 2 or 3 heteroatoms independently selected from the group consisting of O, S and N, each $R^G$ aryl is independently selected from the group consisting of 5- and 6-membered aromatic rings, said $R^G$ is substituted with 0, 1 or 2 independently selected $R^A$ substituents. In aspects of this embodiment, $R^G$ is selected from the group consisting of H, $C_1$-$C_6$ alkyl, $C_3$-$C_6$ cycloalkyl, $C_3$-$C_6$ cycloalkyl($C_1$-$C_5$) alkyl, aryl, and aryl($C_1$-$C_4$)alkyl groups, wherein said $R^G$ aryl groups contain 0, 1, 2 or 3 heteroatoms independently selected from the group consisting of O, S and N, each $R^G$ aryl is independently selected from the group consisting of 5- and 6-membered aromatic rings, said $R^G$ is substituted with 0, 1 or 2 independently selected $R^A$ substituents. $R^G$ is selected from the group consisting of $C_1$-$C_5$ alkyl,

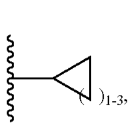

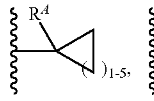

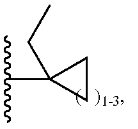

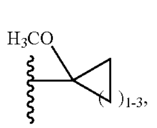

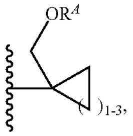

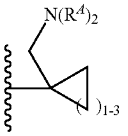

and

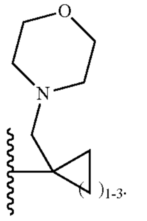

In particular embodiments, $R^G$ is selected from the group consisting of

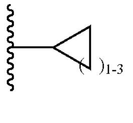

and

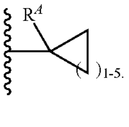

In more particular embodiments, $R^G$ is selected from the group consisting of

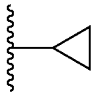

and

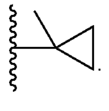

In still more particular embodiments, $R^G$ is

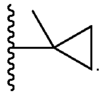.

In all aspects of this embodiment, all other groups are as provided in the general formula above or in the first through thirteenth embodiments.

In a fifteenth embodiment of the invention, each $R^{G1}$ is independently selected from the group consisting of H, $C_1$-$C_6$ alkyl, $C_3$-$C_7$ cycloalkyl, $Si(R^A)_3$, $Si(R^A)_2(CH_3)$, $Si(R^A)(CH_3)_2$, $Si(CH_3)_3$, and benzyl, wherein each $R^{G1}$ is independently substituted with 0 to 4 substituents $R^A$. In particular aspects of this embodiment, each $R^{G1}$ is independently selected from the group consisting of H, $C_1$-$C_6$ alkyl, $C_3$-$C_7$ cycloalkyl, and benzyl, wherein each $R^{G1}$ is independently substituted with 0 to 4 substituents $R^A$. In all aspects of this embodiment, all other groups are as provided in the general formula above or in the first through fourteenth embodiments.

In a sixteenth embodiment of the invention, $R^2$ is selected from the group consisting of $C_1$-$C_9$ alkyl, $C_2$-$C_9$ alkenyl, $C_2$-$C_9$ alkynyl, $C_3$-$C_8$ cycloalkyl, $Si(R^A)_3$, $Si(R^A)_2(CH_3)$, $Si(R^A)(CH_3)_2$, $Si(CH_3)_3$, $C_1$-$C_9$ internally substituted alkyl, $C_2$-$C_9$ internally substituted alkenyl, $C_2$-$C_9$ internally substituted alkynyl, $C_3$-$C_8$ internally substituted cycloalkyl and aryl groups, wherein said $R^2$ $Si(R^A)_3$, $Si(R^A)_2(CH_3)$, $Si(R^A)(CH_3)_2$, $C_1$-$C_9$ internally substituted alkyl, $C_2$-$C_9$ internally substituted alkenyl, $C_2$-$C_9$ internally substituted alkynyl, $C_3$-$C_8$ internally substituted cycloalkyl and aryl groups contain 0, 1, 2 or 3 heteroatoms independently selected from the group consisting of B, O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents. In aspects of the embodiments, $R^2$ is selected from the group consisting of $C_1$-$C_9$ alkyl, $C_2$-$C_9$ alkenyl, $C_2$-$C_9$ alkynyl, $C_3$-$C_8$ cycloalkyl, $Si(R^A)_3$, $Si(R^A)_2(CH_3)$, $Si(R^A)(CH_3)_2$, $Si(CH_3)_3$, and aryl groups, wherein said $R^2$ $Si(R^A)_3$, $Si(R^A)_2(CH_3)$, $Si(R^A)(CH_3)_2$, and aryl groups contain 0, 1, 2 or 3 heteroatoms independently selected from the group consisting of O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents. In aspects of this embodiment, $R^2$ is selected from the group consisting of $C_1$-$C_9$ alkyl, $C_2$-$C_9$ alkenyl, $C_2$-$C_9$ alkynyl, $C_3$-$C_8$ cycloalkyl, and aryl groups, wherein said $R^2$ aryl groups contain 0, 1, 2 or 3 heteroatoms independently selected from the group consisting of O, S and N, and is attached through an atom selected from C and N, said $R^2$ aryl is independently selected from the group consisting of 5- and 6-membered aromatic rings, said $R^2$ is substituted with 0, 1 or 2 independently selected $R^A$ substituents. In particular embodiments, $R^2$ is selected from the group consisting of $C_4$-$C_9$ alkyl. $R^2$ is $C_5$ alkyl. In all aspects of this embodiment, all other groups are as provided in the general formula above or in the first through fifteenth embodiments.

In a seventeenth embodiment of the invention, $R^3$ is selected from the group consisting of —$CH_2CH_3$, —CH═$CH_2$, $Si(R^A)_3$, $Si(R^A)_2(CH_3)$, $Si(R^A)(CH_3)_2$, $Si(CH_3)_3$, —$CH_2CH_2$-(bond to $R^2$), —CH═CH-(bond to $R^2$) and a direct bond to $R^2$, wherein when $R^3$ is selected from the group consisting of —$CH_2CH_2$-(bond to $R^2$), —CH═CH-(bond to $R^2$) and a direct bond to $R^2$, $R^2$ and $R^3$, together with the atoms to which they are bound, form a ring having from fifteen to twenty-one ring atoms and containing 0, 1, 2 or 3 double bonds and 0, 1, 2 or 3 triple bonds. In aspects of the embodiment, $R^3$ is selected from the group consisting of —$CH_2CH_3$, —CH═$CH_2$, —$CH_2CH_2$-(bond to $R^2$), —CH═CH-(bond to $R^2$) and a direct bond to $R^2$, wherein when $R^3$ is selected from the group consisting of —$CH_2CH_2$-(bond to $R^2$), —CH═CH-(bond to $R^2$) and a direct bond to $R^2$, $R^2$ and $R^3$, together with the atoms to which they are bound, form a ring having from fifteen to twenty-one ring atoms and containing 0, 1, 2 or 3 double bonds and 0, 1, 2 or 3 triple bonds. In aspects of this embodiment, $R^3$ is selected from the group consisting of —CH═CH-(bond to $R^2$) and —CH—CH-(bond to $R^2$). In particular embodiments, $R^3$ is —CH═CH-(bond to $R^2$), wherein $R^2$ and $R^3$ form a macrocyclic linkage that contains 1 double bonds. In all aspects of this embodiment, all other groups are as provided in the general formula above or in the first through sixteenth embodiments.

In an eighteenth embodiment of the invention, A is selected from the group consisting of $C_1$-$C_8$ alkyl, $C_2$-$C_8$ alkenyl, $C_2$-$C_8$ alkynyl, $C_1$-$C_8$ internally substituted alkyl, $C_2$-$C_8$ internally substituted alkenyl, $C_2$-$C_8$ internally substituted alkynyl, $C_3$-$C_8$ cycloalkyl, $C_3$-$C_8$ internally substituted cycloalkyl, $Si(R^A)_3$, $Si(R^A)_2(CH_3)$, $Si(R^A)(CH_3)_2$, $Si(CH_3)_3$, aryl and 7-, 8-, 9- and 10-membered bicyclic groups, wherein said A $Si(R^A)_3$, $Si(R^A)_2(CH_3)$, $Si(R^A)(CH_3)_2$, $Si(CH_3)_3$, $C_1$-$C_8$ internally substituted alkyl, $C_2$-$C_8$ internally substituted alkenyl, $C_2$-$C_8$ internally substituted alkynyl, $C_3$-$C_8$ internally substituted cycloalkyl, aryl and bicyclic groups contain 0, 1, 2 or 3 heteroatoms independently selected from the group consisting of B, O, S and N, each A aryl is independently selected from the group consisting of 5- and 6-membered aromatic rings and 7-, 8-, 9- and 10-membered bicyclic aromatic rings, said A is substituted with 0, 1, 2, 3 or 4 substituents $R^A$. In aspects of this embodiment, A is selected from the group consisting of

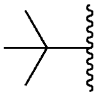, 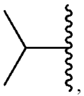, 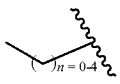, 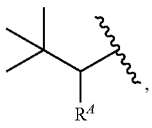,

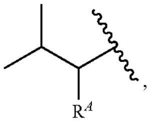, 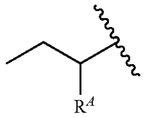,

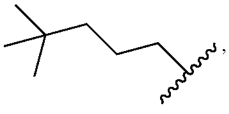, 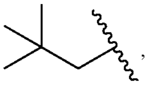,

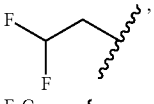, 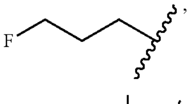,

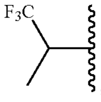, 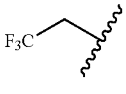, 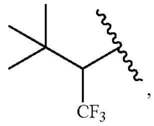,

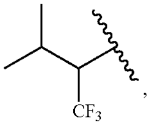, 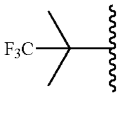, 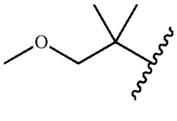,

-continued

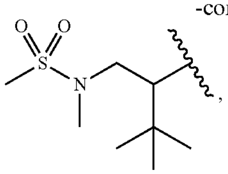, 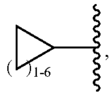, 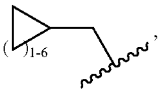,

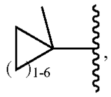, 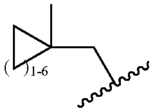, 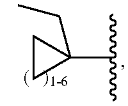,

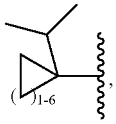, 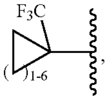, 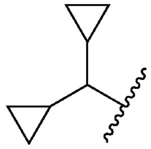,

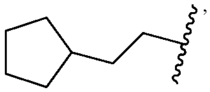, 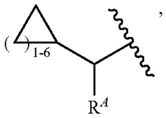,

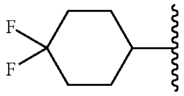, 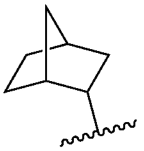,

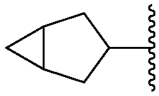, 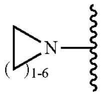,

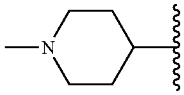, 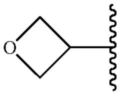, 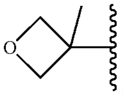,

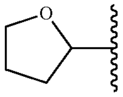, 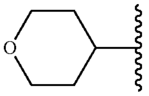 and

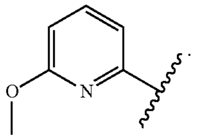.

In particular aspects of this embodiment, A is selected from the group consisting of $C_1$-$C_8$ alkyl and aryl, wherein said A aryl groups contain 0, 1 or 2 heteroatoms independently selected from the group consisting of O, S and N, each A aryl is independently selected from the group consisting of 5-and 6-membered aromatic rings, said A is substituted with 0, 1 or 2 substituents $R^A$. In all aspects of this embodiment, all other groups are as provided in the general formula above or in the first through seventeenth embodiments.

In nineteenth embodiment of the invention, each $R^A$ is independently selected from the group consisting of H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), phenyl, naphthyl, $C_3$-$C_8$ cycloalkyl, halo($C_1$-$C_6$ alkoxy), —O($C_1$-$C_6$ alkyl), SH, S($C_1$-$C_6$ alkyl), $NH_2$, —NH($C_1$-$C_6$ alkyl), —N($C_1$-$C_6$ alkyl)$_2$, —C(O)($C_1$-$C_6$ alkyl), —$CONH_2$, —$SO_2NH_2$, $NO_2$, CN, —$CF_3$, —$CHF_2$, —$CH_2F$, —$OCHF_2$, —$OCF_3$, —$OCH_2F$, —$SO_2$($C_1$-$C_6$ alkyl), —S(O)($C_1$-$C_6$ alkyl), —($C_1$-$C_6$ alkyl)S(O)($C_1$-$C_6$ alkyl), —S(O)$_2$($C_1$-$C_6$ alkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), —N($C_1$-$C_6$ alkyl)$SO_2$($C_1$-$C_6$ alkyl), —$SO_2$N($C_1$-$C_6$ alkyl)$_2$, —($C_1$-$C_6$ alkyl)$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), —C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl) -S—($C_0$-$C_5$ alkyl)-($C_3$-$C_8$ cycloalkyl), —($C_0$-$C_5$ alkyl)-S(O)$_2$—($C_0$-$C_5$ alkyl)-($C_3$-$C_8$ cycloalkyl), $C_1$-$C_6$ internally substituted alkyl, $C_1$-$C_6$ internally substituted haloalkyl, $C_1$-$C_6$ internally substituted alkyl ($NH_2$), $C_3$-$C_8$ internally substituted cycloalkyl, halo($C_1$-$C_6$ internally substituted alkoxy), —O($C_1$-$C_6$ internally substituted alkyl), S($C_1$-$C_6$ internally substituted alkyl), —NH($C_1$-$C_6$ internally substituted alkyl), —N($C_1$-$C_6$ internally substituted alkyl)$_2$, —C(O)($C_1$-$C_6$ internally substituted alkyl), —$SO_2$($C_1$-$C_6$ internally substituted alkyl), —S(O)($C_1$-$C_6$ internally substituted alkyl), —($C_1$-$C_6$ internally substituted alkyl)S(O)($C_1$-$C_6$ internally substituted alkyl), —S(O)$_2$($C_1$-$C_6$ internally substituted alkyl), —($C_1$-$C_6$ internally substituted alkyl)S(O)$_2$($C_1$-$C_6$ internally substituted alkyl), —($C_1$-$C_6$ internally substituted alkyl)N($C_1$-$C_6$ internally substituted alkyl)$SO_2$($C_1$-$C_6$ internally substituted alkyl), —N($C_1$-$C_6$ internally substituted alkyl)$SO_2$($C_1$-$C_6$ internally substituted alkyl), —$SO_2$N($C_1$-$C_6$ internally substituted alkyl)$_2$, —($C_1$-$C_6$ internally substituted alkyl)$SO_2$N($C_1$-$C_6$ internally substituted alkyl)$_2$, —NHCOO($C_1$-$C_6$ internally substituted alkyl), —NHCO($C_1$-$C_6$ internally substituted alkyl), —NHCONH ($C_1$-$C_6$ internally substituted alkyl), —$CO_2$($C_1$-$C_6$ internally substituted alkyl), —C(O)N($C_1$-$C_6$ internally substituted alkyl)$_2$, —($C_0$-$C_5$ internally substituted alkyl)-($C_3$-$C_8$ internally substituted cycloalkyl), —($C_0$-$C_5$ internally substituted alkyl) -O—($C_0$-$C_5$ internally substituted alkyl)-($C_3$-$C_8$ internally substituted cycloalkyl), —($C_0$-$C_5$ internally substituted alkyl)-S—($C_0$-$C_5$ internally substituted alkyl)-($C_3$-$C_8$ internally substituted cycloalkyl), and —($C_0$-$C_5$ internally substituted alkyl)-S(O)$_2$—($C_0$-$C_5$ internally substituted alkyl)-($C_3$-$C_8$ internally substituted cycloalkyl), wherein said $R^A$ $C_1$-$C_6$ internally substituted alkyl, $C_1$-$C_6$ internally substituted haloalkyl, $C_1$-$C_6$ internally substituted alkyl($NH_2$), $C_3$-$C_8$ internally substituted cycloalkyl, halo($C_1$-$C_6$ internally substituted alkoxy), —O($C_1$-$C_6$ internally substituted alkyl), S($C_1$-$C_6$ internally substituted alkyl), —NH($C_1$-$C_6$ internally substituted alkyl), —N($C_1$-$C_6$ internally substituted alkyl)$_2$, —C(O)($C_1$-$C_6$ internally substituted alkyl), —$SO_2$($C_1$-$C_6$ internally substituted alkyl), —S(O)($C_1$-$C_6$ internally substituted alkyl), —($C_1$-$C_6$ internally substituted alkyl)S(O)($C_1$-$C_6$ internally substituted alkyl), —S(O)$_2$($C_1$-$C_6$ internally substituted alkyl), —($C_1$-$C_6$ internally substituted alkyl) S(O)$_2$($C_1$-$C_6$ internally substituted alkyl), —($C_1$-$C_6$ internally substituted alkyl)N($C_1$-$C_6$ internally substituted alkyl) $SO_2$($C_1$-$C_6$ internally substituted alkyl), —N($C_1$-$C_6$ internally substituted alkyl)$SO_2$($C_1$-$C_6$ internally substituted alkyl), —$SO_2$N($C_1$-$C_6$ internally substituted alkyl)$_2$, —($C_1$-$C_6$ internally substituted alkyl)$SO_2$N($C_1$-$C_6$ internally substituted alkyl)$_2$, —NHCOO($C_1$-$C_6$ internally substituted alkyl), —NHCO($C_1$-$C_6$ internally substituted alkyl), —NHCONH ($C_1$-$C_6$ internally substituted alkyl), —$CO_2$($C_1$-$C_6$ internally substituted alkyl), —C(O)N($C_1$-$C_6$ internally substituted alkyl)$_2$, —($C_0$-$C_5$ internally substituted alkyl)-($C_3$-$C_8$ internally substituted cycloalkyl), —($C_0$-$C_5$ internally substituted alkyl)-O—($C_0$-$C_5$ internally substituted alkyl)-($C_3$-$C_8$ internally substituted cycloalkyl), —($C_0$-$C_5$ internally substituted alkyl)-S—($C_0$-$C_5$ internally substituted alkyl)-($C_3$-$C_8$ internally substituted cycloalkyl), and —($C_0$-$C_5$ internally substituted alkyl)-S(O)$_2$—($C_0$-$C_5$ internally substituted alkyl)-($C_3$-$C_8$ internally substituted cycloalkyl) groups contain 0, 1, 2 or 3 heteroatoms independently selected from the group consisting of B, O, S and N, two $R^A$ may be taken, together with the atoms to which they are bound, to form a ring having from three to fifteen ring atoms. In aspects of this embodiment, each $R^A$ is independently selected from the group consisting of H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), phenyl, naphthyl, $C_3$-$C_8$ cycloalkyl, halo($C_1$-$C_6$ alkoxy), —O($C_1$-$C_6$ alkyl), SH, S($C_1$-$C_6$ alkyl), $NH_2$, —NH($C_1$-$C_6$ alkyl), —N($C_1$-$C_6$ alkyl)$_2$, —C(O)($C_1$-$C_6$ alkyl), —$CONH_2$, —$SO_2NH_2$, $NO_2$, CN, —$CF_3$, —$CHF_2$, —$CH_2F$, —$OCHF_2$, —$OCF_3$, —$OCH_2F$, —$SO_2$($C_1$-$C_6$ alkyl), —S(O)($C_1$-$C_6$ alkyl), —($C_1$-$C_6$ alkyl)S(O)($C_1$-$C_6$ alkyl), —S(O)$_2$($C_1$-$C_6$ alkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), —N($C_1$-$C_6$ alkyl)$SO_2$($C_1$-$C_6$ alkyl), —$SO_2$N($C_1$-$C_6$ alkyl)$_2$, —($C_1$-$C_6$ alkyl)$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), —C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), and —($C_0$-$C_5$ alkyl)-S(O)$_2$—($C_0$-$C_5$ alkyl)-($C_3$-$C_8$ cycloalkyl), wherein two $R^A$ may be taken, together with the atoms to which they are bound, to form a ring having from three to fifteen ring atoms. In all aspects of this embodiment, all other groups are as provided in the general formula above or in the first through eighteenth embodiments.

In a twentieth embodiment of the invention, L is selected from the group consisting of $(CH_2)_{0-4}$ and N($R^L$). In aspects of the embodiment, L is NH. In all aspects of this embodiment, all other groups are as provided in the general formula above or in the first through nineteenth embodiments.

In a twenty-first embodiment of the invention, each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), Si($R^A$)$_3$, Si($R^A$)$_2$($CH_3$), Si($R^A$)($CH_3$)$_2$, Si($CH_3$)$_3$, $C_1$-$C_6$ alkyl(aryl) groups, $C_1$-$C_6$ internally substituted alkyl, $C_1$-$C_6$ internally substituted haloalkyl, $C_1$-$C_6$ internally substituted alkoxy, $C_1$-$C_6$ internally substituted alkyl($NH_2$), aryl, $C_3$-$C_8$ internally substituted cycloalkyl, halo($C_1$-$C_6$ internally substituted alkoxy), and $C_1$-$C_6$ internally substituted alkyl(aryl), wherein said $R^L$ Si($R^A$)$_3$, Si($R^A$)$_2$($CH_3$), Si($R^A$)($CH_3$)$_2$, Si($CH_3$)$_3$, $C_1$-$C_6$ internally substituted alkyl, $C_1$-$C_6$ internally substituted haloalkyl, $C_1$-$C_6$ internally substituted alkoxy, $C_1$-$C_6$ internally substituted alkyl($NH_2$), aryl, $C_3$-$C_8$ internally substituted cycloalkyl, halo($C_1$-$C_6$ internally substituted alkoxy), and $C_1$-$C_6$ internally substituted alkyl(aryl) groups contain 0, 1, 2 or 3 heteroatoms independently selected from the group consisting of B, O, S and N, each $R^L$ aryl group is independently selected from the group consisting of 5- and 6-membered aromatic rings. In aspects of the embodiment, each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), Si($R^A$)$_3$, Si($R^A$)$_2$($CH_3$), Si($R^A$)($CH_3$)$_2$, Si($CH_3$)$_3$, and $C_1$-$C_6$ alkyl(aryl) groups, wherein said $R^L$ Si($R^A$)$_3$, Si($R^A$)$_2$($CH_3$), Si($R^A$)($CH_3$)$_2$, and Si($CH_3$)$_3$ groups contain 0, 1, 2 or 3 heteroatoms independently selected from the group consisting of O, S and N, each $R^L$ aryl group is independently selected from the group consisting of 5- and 6-membered aromatic rings. In particular aspects of this embodiment, each $R^L$ is independently selected from the group consisting of H, $C_1$-$C_6$ alkyl, $C_1$-$C_6$ haloalkyl, $C_1$-$C_6$ alkoxy, $C_1$-$C_6$ alkyl($NH_2$), aryl, $C_3$-$C_8$ cycloalkyl, halo($C_1$-$C_6$ alkoxy), and $C_1$-$C_6$ alkyl(aryl) groups, wherein each $R^L$ aryl group is independently selected from the group consisting of 5- and 6-membered aromatic rings. In all aspects of this embodiment, all other groups are as provided in the general formula above or in the first through twentieth embodiments.

In a twenty-second embodiment of the invention,

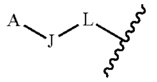 is 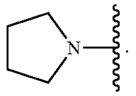.

In all aspects of this embodiment, all other groups are as provided in the general formula above or in the first through twenty-first embodiments.

In another embodiment, for the compounds of formula I, each instance of variables ⓔ A, J, L, G, T, Q, Z, $R^1$, $R^2$, $R^3$, $R^4$, $R^A$, $R^J$, $R^L$, $R^G$, $R^{G1}$ and m are each selected independently from each other.

For the second aspect, wherein the compound is compound of General Formula II:

In a first (1) embodiment, the compound of Formula II is a compound of Formula IIa:

(IIa)

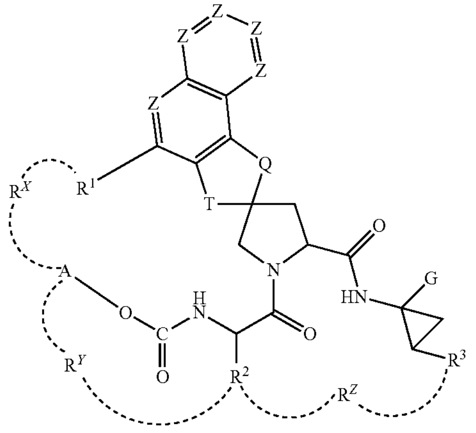

or a pharmaceutically acceptable salt thereof, wherein each Z is independently either N or C—$R^4$;

A is a selected from the group consisting of:

a) $C_1$-$C_6$ alkyl, $C_2$-$C_6$ alkenyl, $C_2$-$C_6$ alkynyl, $C_3$-$C_6$ cycloalkyl, $C_6$-$C_8$ bridged cycloalkyl, or $C_6$-$C_8$ bridged cycloalkenyl, b) substituted $C_1$-$C_8$ alkyl, substituted $C_2$-$C_8$ alkenyl, substituted $C_2$-$C_8$ alkynyl, substituted $C_3$-$C_8$ cycloalkyl, substituted $C_6$-$C_8$ bridged cycloalkyl, or substituted $C_6$-$C_8$ bridged cycloalkenyl, each of which is substituted with 0, 1, 2, 3 or 4 $R^A$, and 0 or 1 $R^B$, provided that at least one $R^A$ or $R^B$ substituent is present;

c) $C_1$-$C_8$ haloalkyl, $C_3$-$C_8$ halocycloalkyl, or $C_1$-$C_8$ haloalkyl substituted with $R^B$, d) Aryl, and e) Het;

Q is selected from the group consisting of —$(CH_2)_2$—,

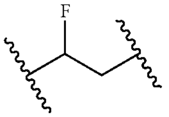 and 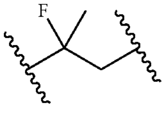

-continued

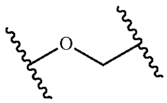
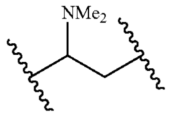
and
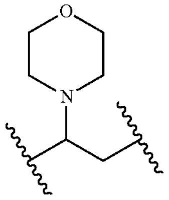
;

T is selected from the group consisting of O, —$(CH_2)_{q2}$—, NH, $SO_2$ and S, wherein $q_2$ is 1 or 2;

G is

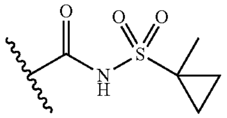
or
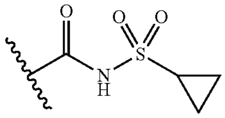
;

$R^1$ is hydrogen, $C_1$-$C_6$ alkyl, $C_3$-$C_8$ cycloalkyl, $C_1$-$C_6$ alkyl-$R^B$, Aryl, or Het;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, Het, and Aryl;

$R^3$ is selected from the group consisting of $C_1$-$C_9$ alkyl, $C_2$-$C_9$ alkenyl, and $C_2$-$C_9$ alkynyl:

each $R^4$ is independently selected from the group consisting of: hydrogen, halogen, OH, $C_1$-$C_6$ alkyl, $C_1$-$C_4$ haloalkyl, $C_1$-$C_6$ alkoxy, $C_1$-$C_6$ haloalkoxy, $C_1$-$C_6$ alkyl-$R^B$, $C_1$-$C_6$ haloalkyl-$R^B$, $C_1$-$C_6$ alkoxy-$R^B$, $C_1$-$C_6$ haloalkoxy —$R^B$, $C_3$-$C_8$ cycloalkyl, $C_3$-$C_8$ cycloalkoxy, $C_3$-$C_8$ cycloalkyl-$C_1$-$C_9$ alkyl, $C_1$-$C_6$ hydroxyalkyl, O—$C_1$-$C_6$ hydroxyalkyl, O—$C_1$-$C_6$ alkyl-$R^B$, CN, O—($C_1$-$C_5$ alkyl)-O—($C_1$-$C_3$ alkyl), O—($C_1$-$C_5$ alkyl)-O—($C_1$-$C_3$ alkyl)-$R^B$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), Het, Aryl, and

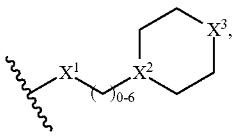
, wherein $X^1$ is either $CH_2$, NH, O, or S; $X^2$ is either CH or N; and $X^3$ is either NH, N—$R^5$, $CH_2$, CH—$R^5$, O, or S;

provided that two $R^4$ groups can join together form methylene dioxy;

each $R^A$ is independently selected from the group consisting of: F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), $C_6$-$C_8$ bridged cycloalkyl, $C_3$-$C_8$ cycloalkyl, $C_1$-$C_6$ haloalkoxy, $C_3$-$C_8$ halocycloalkyl, SH, S($C_1$-$C_6$ alkyl), $NH_2$, NH($C_1$-$C_6$ alkyl), N($C_1$-$C_6$ alkyl)$_2$, C(O)($C_1$-$C_6$ alkyl), C(O)($C_3$-$C_8$ cycloalkyl), $CONH_2$, $SO_2NH_2$, $NO_2$, CN, $CF_3$, $CHF_2$, $CH_2F$, $OCHF_2$, $OCF_3$, $OCH_2F$, $SO_2$($C_1$-$C_6$ alkyl), S(O)($C_1$-$C_6$ alkyl), —($C_1$-$C_6$ alkyl)S(O)($C_1$-$C_6$ alkyl), $SO_2$($C_3$-$C_6$ cycloalkyl), —($C_1$-$C_6$ alkyl)$S(O)_2$($C_1$-$C_6$ alkyl), —($C_1$-$C_6$ alkyl)N($C_1$-$C_6$ alkyl) $SO_2$($C_1$-$C_6$ alkyl), N($C_1$-$C_6$ alkyl)$SO_2$($C_1$-$C_6$ alkyl), $SO_2$N ($C_1$-$C_6$ alkyl)$_2$, —($C_1$-$C_6$ alkyl)$SO_2$N($C_1$-$C_6$ alkyl)$_2$, NHCOO($C_1$-$C_6$ alkyl), NHCO($C_1$-$C_6$ alkyl), NHCONH($C_1$-$C_6$ alkyl), $CO_2$($C_1$-$C_6$ alkyl), C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), —($C_0$-$C_5$ alkyl)-$S(O)_2$—($C_0$-$C_5$ alkyl)-($C_3$-$C_8$ cycloalkyl), Aryl, and Het; provided that two $R^A$ groups present on adjacent carbon atoms can together with the adjacent carbon atoms form a $C_3$-$C_6$cycloalkyl;

each $R^B$ is independently either phenyl or a 5- or 6-membered saturated or unsaturated monocyclic ring with 1, or 2 heteroatom ring atoms independently selected from the group consisting of N, O and S, $R^B$ may be substituted with 1 or 2 independently selected $R^C$;

each $R^C$ is independently either halo, $C_1$-$C_6$ alkyl, $C_1$-$C_6$ alkoxy, $C_3$-$C_6$ cycloalkyl, or $C_1$-$C_6$ haloalkyl;

each Aryl is independently phenyl optionally substituted with 1 or 2 independently selected $R^C$;

each Het is independently a 4-, 5- or 6-membered saturated or unsaturated monocyclic rings with 1 or 2 heteroatom ring atoms independently selected from the group consisting of N, O and S; provided that said Het is optionally substituted with 1 or 2 independently selected $R^C$ substituents;

$R^X$ if present, is a $C_3$-$C_8$ alkylene, $C_3$-$C_8$ alkenylene, or $C_3$-$C_8$ alkynylene, formed between A and $R^1$, $R^Y$ if present, is a $C_3$-$C_8$ alkylene, $C_3$-$C_8$ alkenylene, $C_3$-$C_8$ alkynylene, formed between A and $R^2$, $R^Z$ if present, is a $C_3$-$C_8$ alkylene, $C_3$-$C_8$ alkenylene, or $C_3$-$C_8$ alkynylene, formed between $R^2$ and $R^3$, provided that either (a) $R^X$ is present, $R^Y$ is not present and $R^Z$ is not present; (b) $R^Y$ is present, $R^X$ is not present and $R^Z$ is not present; (c) $R^Z$ is present, $R^X$ is not present and $R^Y$ is not present; or (d) $R^X$ and $R^Z$ are present, and $R^Y$ is not present.

In a second (2) embodiment Rx is present, $R^Y$ is not present and $R^Z$ is not present, and the other variables are as provided in the first embodiment.

In a third (3) embodiment $R^Y$ is present, $R^X$ is not present and $R^Z$ is not present, and the other variables are as provided in the first embodiment.

In a fourth (4) embodiment $R^Z$ is present, $R^X$ is not present and $R^Y$ is not present; and the other variables are as provided in the first embodiment.

In a fifth (5) embodiment $R^X$ and $R^Z$ are present, and $R^Y$ is not present. and the other variables are as provided in the first embodiment.

In a sixth (6) embodiment T is O and the other variables are as provided in general Formula II, or any of embodiments 1 to 5.

In a seventh (7) embodiment Q is either —$(CH_2)_2$—,

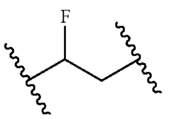
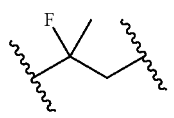
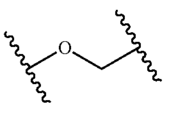
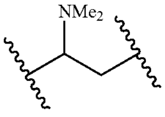
or

-continued

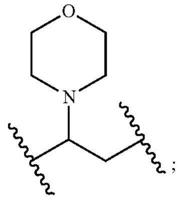

and the other variables are as provided in general Formula II, or any of embodiments 1 to 6.

In an eight (8) embodiment A is a selected from the group consisting of a) $C_1$-$C_6$ alkyl, $C_3$-$C_8$ cycloalkyl, or $C_6$-$C_8$ bridged cycloalkyl, b) substituted $C_1$-$C_6$ alkyl, substituted $C_3$-$C_8$ cycloalkyl, or substituted $C_6$-$C_8$ bridged cycloalkyl, each of which contains 0 or 1 $R^A$ and 0 or 1 $R^B$, provided that at least one $R^A$ or $R^B$ substituent is present;

c) Aryl; and d) Het; and the other variables are as provided in general Formula II, or any of embodiments 1 to 7.

In ninth (9) embodiment G is

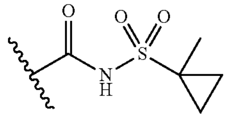 [SMILES: *C(=O)NS(=O)(=O)C1(C)CC1]

and the other variables are as provided in general Formula II, or any of embodiments 1 to 8.

In a tenth (10) embodiment G is

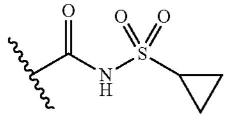 [SMILES: *C(=O)NS(=O)(=O)C1CC1]

and the other variables are as provided in general Formula II, or any of embodiments 1 to 8.

In an eleventh (11) embodiment $R^1$ is either hydrogen, $C_1$-$C_6$ alkyl, $C_3$-$C_8$ cycloalkyl, $C_1$-$C_4$ haloalkyl, $CF_3$, $CH_2CF_3$, $CF_2$, $CH_3$, cyclopropyl, Aryl, or Het; and the other variables are as provided in general Formula II, or any of embodiments 1 to 10.

In a twelfth (12) embodiment each $R^4$ is independently selected from the group consisting of: hydrogen, F, Cl, OH, $C_1$-$C_6$ alkyl, $C_1$-$C_2$ haloalkyl, $CF_3$, $CH_2$—$CF_3$, $CF_2$—$CH_3$, $CF_3$, $C_1$-$C_6$ alkoxy, $C_1$-$C_4$ haloalkoxy, $C_1$-$C_6$ alkyl-$R^B$, $C_3$-$C_8$ cycloalkyl, Het, Aryl and

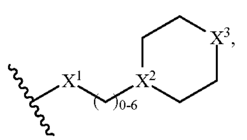

wherein $X^1$ is either $CH_2$, NH, O, or S; $X^2$ is either CH or N; and $X^3$ is either NH, N—$R^5$, $CH_2$, CH—$R^5$, O, or S; and the other variables are as provided in general Formula II, or any of embodiments 1 to 11.

In a thirteenth (13) embodiment, each Aryl is independently phenyl optionally substituted with 1 or 2 independently selected $R^C$; and the other variables are as provided in general Formula II, or any of embodiments 1 to 12

In a fourteenth (14) embodiment, each Het is independently a 4-, 5- or 6-membered saturated or unsaturated monocyclic ring with 1 or 2 heteroatom ring atoms independently selected from the group consisting of N, O and S; provided that said Het is optionally substituted with 1 or 2 independently selected $R^C$; and the other variables are as provided in general Formula II, or any of embodiments 1 to 13.

In a fifteenth (15) embodiment each $R^A$ is independently selected from the group consisting of: F, Cl, OH, $C_1$-$C_6$ alkyl, $C_1$-$C_6$ haloalkyl, $C_1$-$C_6$ alkoxy, $C_3$-$C_8$ halocycloalkyl, and $C_1$-$C_6$ haloalkoxy; and the other variables are as provided for in any of embodiments 1 to 14.

In a sixteenth (16) embodiment each $R^B$ is independently either phenyl or 5- or 6-membered saturated or a unsaturated monocyclic ring with 1, or 2 heteroatom ring atoms independently selected from the group consisting of N, O and S, $R^B$ may be substituted with 1 or 2 independently selected $R^C$; and the other variables are as provided in general Formula II, or any of embodiments 1 to 15.

In a seventieth (17) embodiment each $R^C$ is independently either halo, $C_1$-$C_6$ alkyl, $C_1$-$C_6$ alkoxy, $C_3$-$C_6$ cycloalkyl or $C_1$-$C_6$ haloalkyl and the other variables are as provided in general Formula II, or any of embodiments 1 to 16.

In an eighteenth (18) embodiment, the compound is a compound of Formula IIa is a compound of Formula IIb:

(Formula IIb)

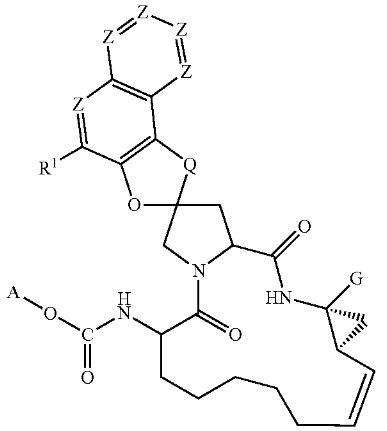

or a pharmaceutically acceptable salt thereof, wherein each Z is independently either N or C—$R^4$;

A is a selected from the group consisting of a) $C_1$-$C_6$ alkyl, $C_3$-$C_8$ cycloalkyl, or $C_6$-$C_8$ bridged cycloalkyl, b) substituted $C_1$-$C_6$ alkyl, substituted $C_3$-$C_8$ cycloalkyl, or substituted $C_6$-$C_8$ bridged cycloalkyl, each of which contains 0 or 1 $R^A$ and 0 or 1 $R^B$, provided that at least one $R^A$ or $R^B$ substituent is present;

c) Aryl; and d) Het;

Q is selected from the group consisting of selected from $-(CH_2)_2-$,

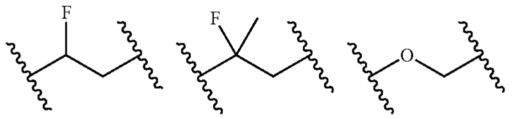

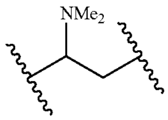
and
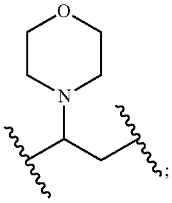
;

G is

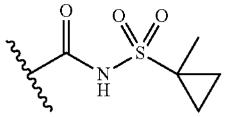
or
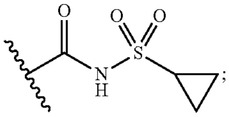
;

$R^1$ is either hydrogen, $C_1$-$C_6$ alkyl, $C_3$-$C_8$ cycloalkyl, $C_1$-$C_4$ haloalkyl, $CF_3$, $CH_2CF_3$, $CF_2$, $CH_3$, cyclopropyl, Aryl, or Het;

each $R^4$ is independently selected from the group consisting of: hydrogen, F, Cl, OH, $C_1$-$C_6$ alkyl, $C_1$-$C_2$ haloalkyl, $CF_3$, $CH_2$—$CF_3$, $CF_2$—$CH_3$, $CF_3$, $C_1$-$C_6$ alkoxy, $C_1$-$C_4$ haloalkoxy, $C_1$-$C_6$ alkyl-$R^B$, $C_3$-$C_8$ cycloalkyl, Het, Aryl and

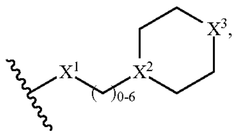
, wherein $X^1$ is either $CH_2$, NH, O, or S; $X^2$ is either CH or N; and $X^3$ is either NH, N—$R^5$, $CH_2$, CH—$R^5$, O, or S;

each Aryl is independently phenyl optionally substituted with 1 or 2 independently selected $R^C$, each Het is independently a 4-, 5- or 6-membered saturated or unsaturated monocyclic ring with 1 or 2 heteroatom ring atoms independently selected from the group consisting of N, O and S; provided that said Het is optionally substituted with 1 or 2 independently selected $R^C$, each $R^A$ is independently selected from the group consisting of: F, Cl, OH, $C_1$-$C_6$ alkyl, $C_1$-$C_6$ haloalkyl, $C_1$-$C_6$ alkoxy, $C_3$-$C_8$ halocycloalkyl, and $C_1$-$C_6$ haloalkoxy;

each $R^B$ is independently either phenyl or 5- or 6-membered saturated or a unsaturated monocyclic ring with 1, or 2 heteroatom ring atoms independently selected from the group consisting of N, O and S, $R^B$ may be substituted with 1 or 2 independently selected $R^C$;

each $R^C$ is independently either halo, $C_1$-$C_6$ alkyl, $C_1$-$C_6$ alkoxy, $C_3$-$C_6$ cycloalkyl or $C_1$-$C_6$ haloalkyl.

In a ninetieth (19) embodiment,

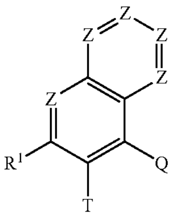

is selected from the group consisting of;

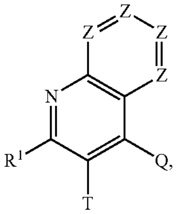
,
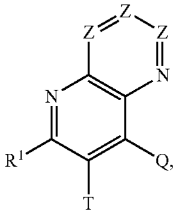
, and

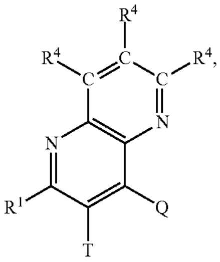
, wherein each Z is independently either N or C—$R^4$, each $R^4$ is independently selected from the group consisting of: hydrogen, F, Cl, OH, $C_1$-$C_6$ alkyl, $C_1$-$C_2$ haloalkyl, $CF_3$, $CH_2$—$CF_3$, $CF_2$—$CH_3$, $CF_3$, $C_1$-$C_6$ alkoxy, $C_1$-$C_4$ haloalkoxy, $C_1$-$C_6$ alkyl-$R^B$, $C_3$-$C_8$ cycloalkyl Het, Aryl, and

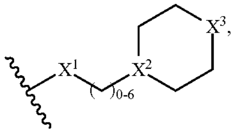
, wherein $X^1$ is either $CH_2$, NH, O, or S; $X^2$ is either CH or N; and $X^3$ is either NH, N—$R^5$, $CH_2$, CH—$R^5$, O, or S;

each Aryl is independently phenyl optionally substituted with 1 or 2 independently selected $R^C$;

each Het is independently a 4-, 5- or 6-membered saturated or unsaturated monocyclic ring with 1 or 2 heteroatom ring atoms independently selected from the group consisting of N, O and S; provided that said Het is optionally substituted with 1 or 2 independently selected $R^C$;

each $R^A$ is independently selected from the group consisting of F, Cl, OH, $C_1$-$C_6$ alkyl, $C_1$-$C_6$ haloalkyl, $C_1$-$C_6$ alkoxy, $C_3$-$C_8$ halocycloalkyl, and $C_1$-$C_6$ haloalkoxy;

each $R^B$ is independently either phenyl or a 5- or 6-membered saturated or unsaturated monocyclic ring with 1, or 2 heteroatom ring atoms independently selected from the group consisting of N, O and S, wherein $R^B$ may be substituted with 1 or 2 independently selected $R^C$; and each $R^C$ is independently either halo, $C_1$-$C_6$ alkyl, $C_1$-$C_6$ alkoxy, $C_3$-$C_6$ cycloalkyl or $C_1$-$C_6$ haloalkyl; and the other variables are as provided in any of embodiments 1 to 18.

In a twentieth (20) embodiment,

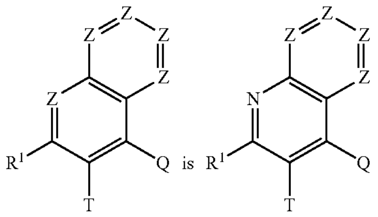

and the other variables are as provided for in any of embodiments 1 to 19.

In a twenty first (21) embodiment,

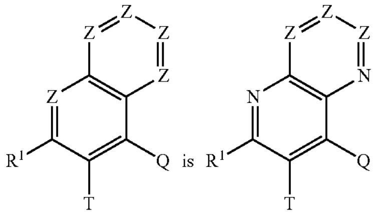

and the other variables are as provided for in any of embodiments 1 to 19.

In a twenty second embodiment,

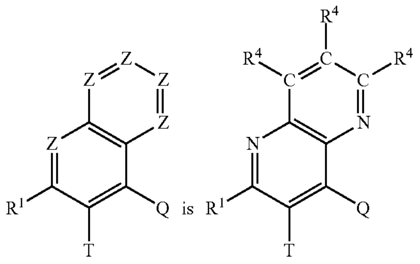

and the other variables are as provided for in any of embodiments 1 to 19.

A particular embodiment referring to a prior embodiment further incorporates all applicable embodiments referred to in the prior embodiment. Applicable embodiments are those consistent with the groups specified in the particular embodiment.

In another embodiment, for the compounds of Formula II, each instance of variables Ⓔ A, J, L, G, T, Q, Z, $R^1$, $R^2$, $R^3$, $R^4$, $R^A$, $R^J$, $R^L$, $R^G$, $R^{G1}$ and m are each selected independently from each other.

In another embodiment of the invention, the compound of the invention is selected from the exemplary species depicted in Examples 1 through 527 shown below as I-1 through I-527, and pharmaceutically acceptable salts thereof. In particular aspects of this embodiment, the compound is selected from the group consisting of I-5, I-6, I-12, I-13, I-16, I-33, I-50, I-63, I-66, I-94, I-124, I-161, I-189, I-359 and I-509 and pharmaceutically acceptable salts thereof.

Other embodiments of the present invention include the following:

(a) A pharmaceutical composition comprising an effective amount of a compound of Formula I or II and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, inhibitors of HCV NS4A, inhibitors of HCV NS4B, inhibitors of HCV NS5A and inhibitors of HCV NS5B.

(d) A pharmaceutical combination that is (i) a compound of Formula I or II and (ii) a second therapeutic agent selected from the group consisting of HCV antiviral agents, immunomodulators, and anti-infective agents; wherein the compound of Formula I or II and the second therapeutic agent are each employed in an amount that renders the combination effective for inhibiting HCV NS3 protease, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof which comprises administering to the subject an effective amount of a compound of Formula I or II.

(g) A method of treating HCV infection and/or reducing the likelihood or severity of symptoms of HCV infection in a subject in need thereof which comprises administering to the subject an effective amount of a compound of Formula I or II.

(h) The method of (g), wherein the compound of Formula I or II is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The compound may be present in different forms including forms having one of more of the following attributes: salt, hydrate, solvate, crystal structure, and amorphous structure.

Specific embodiments of the present invention include a compound of the Examples or made according to the methods therein and pharmaceutically acceptable salts thereof and individual enantiomers and diastereomers thereof.

When any variable (e.g. aryl, heterocycle, R etc.) occurs more than one time in any constituent, its definition on each occurrence is independent at every other occurrence. Also, combinations of substituents or variables are permissible only if such combinations result in stable compounds.

Unless otherwise indicated, or clear from the context in which they appear, the following definitions providing below apply.

As used herein, the term "alkyl" refers to any linear or branched chain alkyl group having a number of carbon atoms in the specified range. The term "$C_{1-6}$" includes alkyls containing 6, 5, 4, 3, 2, or 1 carbon atoms. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl. Alkyl groups may be substituted as indicated.

As used herein, the term "alkenyl" refers to any linear or branched chain alkyl group having a number of carbon atoms in the specified range and including at least one double bond. Alkenyl groups may be substituted as indicated.

As used herein, the term "alkynyl" refers to any linear or branched chain alkyl group having a number of carbon atoms in the specified range and including at least one triple bond. Alkynyl groups may be substituted as indicated.

As used herein, the term "internally substituted alkyl" refers to any alkyl group containing at least one carbon atom and in which 0, 1, 2 or 3 additional carbon atoms are replaced by heteroatoms independently selected from the group consisting of B, O, S and N. The terms "internally substituted alkenyl" and "internally substituted aklynyl" refer respectively to alkenyl and alkynyl groups containing at least two carbon atoms and in which 0, 1, 2 or 3 additional carbon atoms are replaced by heteroatoms independently selected from the group consisting of B, O, S and N. For example, "$C_{1-6}$ internally substituted alkyl" (or "$C_1$-$C_6$ internally substituted alkyl") includes such groups as $-(CH_2)_4BHCH_3$, $-(CH_2)_3BHCH_2CH_3$, $-(CH_2)_2BH(CH_2)_2CH_3$, $-CH_2BH(CH_2)_3CH_3$, $-(CH_2)_4OCH_3$, $-(CH_2)_3OCH_2CH_3$, $-(CH_2)_2-O-(CH_2)_2CH_3$, $-CH_2-O-(CH_2)_3CH_3$, $-(CH_2)_4SCH_3$, $-(CH_2)_3SCH_2CH_3$, $-(CH_2)_2S(CH_2)_2CH_3$, $-CH_2S(CH_2)_3CH_3$, $-(CH_2)_4NHCH_3$, $-(CH_2)_3NHCH_2CH_3$, $-(CH_2)_2NH(CH_2)_2CH_3$, and $-CH_2NH(CH_2)_3CH_3$, as well as groups having additional internal substitutions, branched groups and groups containing fewer carbon atoms. Internally substituted alkyl, internally substituted alkenyl and internally substituted alkynyl groups may be substituted as indicated.

The term "alkylene" refers to any linear or branched chain alkylene group (or alternatively "alkanediyl") having a number of carbon atoms in the specified range. Thus, for example, "$-C_{1-6}$ alkylene" refers to any of the $C_1$ to $C_6$ linear or branched alkylenes. Examples of alkylenes include $-(CH_2)_6-$, $-(CH_2)_5-$, $-(CH_2)_4-$, $-(CH_2)_3-$, $-(CH_2)_2-$, $-CH_2-$ and $-CH(CH_3)-$. Alkylene groups may be substituted as indicated.

The term "alkenylene" refers to any linear or branched chain alkenylene group containing a double bond and having a number of carbon atoms in the specified range. The term "alkynylene" refers to any linear or branched chain alkenylene group containing a triple bond and having a number of carbon atoms in the specified range. Thus, for example, "$C_{2-6}$ alkenylene" refers to any of the $C_2$ to $C_6$ linear or branched alkenylene and "$C_{2-6}$ alkynylene" refers to any of the $C_2$ to $C_6$ linear or branched alkynylene. Alkenylene and alkynylene groups may be substituted as indicated.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "internally substituted cycloalkyl" refers to a saturated hydrocarbon containing one ring having a specified number of ring atoms and in which 0, 1, 2 or 3 carbon ring atoms are replaced by heteroatoms independently selected from the group consisting of B, O, S and N.

The term "alkoxy" as used herein, alone or in combination, includes an alkyl (alkoxy) or cycloalkyl (cycloalkylalkoxy) group connected to the oxy connecting atom. The term "alkoxy" also includes alkyl ether groups, where the term "alkyl" is defined above, and "ether" means two alkyl groups with an oxygen atom between them. Examples of suitable alkoxy groups include methoxy, ethoxy, n-propoxy, iso-propoxy, n-butoxy, sec-butoxy, tert-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "bridged cycloakyl" refers to a cycloakyl containing the indicated number of ring hydrocarbons and a $C_3$-$C_5$ alkenylene linker joining two non-adjacent carbon atoms of the cycloakyl ring.

The term "halo" or halogen refers to F, Cl, Br or I. A preferred halogen is F.

The term "haloalkyl," refers an alkyl group wherein one or more of the alkyl group's hydrogen atoms has been replaced with a halogen atom. In one embodiment, a haloalkyl group has from 1 to 6 carbon atoms. In another embodiment, a haloalkyl group is substituted with from 1 to 3 F atoms. Non-limiting examples of haloalkyl groups include $-CH_2F$, $-CHF_2$, $-CF_3$, $-CH_2Cl$ and $-CCl_3$. The term "$C_1$-$C_6$ haloalkyl" refers to a haloalkyl group having from 1 to 6 carbon atoms and at least halogen atom.

The term "haloalkoxy" refers to an alkoxy wherein one or more hydrogen is replaced with halogen.

The term "halocycloalkyl" refers to a cycloakyl wherein one or more hydrogen is replaced with a halogen.

The term "hydroxyalkyl" refers to an alkyl group wherein one or more of the alkyl group's hydrogen atoms have been replaced with an $-OH$ group. Non-limiting examples of hydroxyalkyl groups include $-CH_2OH$, $-CH_2CH_2OH$, $-CH_2CH_2CH_2OH$ and $-CH_2CH(OH)CH_3$.

The term heterocycle, heterocyclyl, or heterocyclic, as used herein, represents a stable 4- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. In certain embodiments, the heterocyclic group is a heteroaryl group. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

The term "Het" refers to either (a) 4-, 5- or 6-membered saturated or unsaturated monocyclic ring with 1, 2, 3, or 4 heteroatom ring atoms independently selected from the group consisting of N, O and S; (b) 8-, 9- or 10-membered saturated or unsaturated bicyclic ring with 1, 2, 3, 4, or 5 heteroatom ring atoms independently selected from the group consisting of N, O and S, or (c) 11- to 15-membered saturated or unsaturated tricyclic ring with 1, 2, 3, 4, or 5 heteroatom ring atoms independently selected from the group consisting of N, O and S. In one embodiment the Het is an hetereoaryl in another embodiment the Het is a heteroalkyl. The Het may be substituted as indicated.

The term "heteroaryl," as used herein, refers to an aromatic monocyclic or multicyclic ring system comprising 5 to 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. In an embodiment, any available nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl" refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine. Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

Reference to "saturated" with a respect to a ring, includes fully and partially saturated. Thus a saturated ring includes an aromatic ring and a ring with one or more doubles bonds.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4 dimethyl-5-ethyl-octyl and 3-cyclopentyloctyl. Included within this definition are methylenes ($—CH_2—$) substituted with oxygen to form carbonyl (—CO—).

Unless otherwise stated, as employed herein, when a moiety is described as "optionally substituted" it is meant that the group optionally has from one or more hydrogens atoms replaced with an indicated substituent. In a general embodiment one to four, one to three, one or two, non-hydrogen substituents are provided. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Additional substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" and "stable structure" are meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

The compounds of the present invention may be administered in the form of a pharmaceutically acceptable salt. The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, its corresponding salt may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like. It will be understood that, as used herein, references to the compounds of the present invention are meant to also include the pharmaceutically acceptable salts.

In the compounds of generic Formula I or II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I or II. For example, different isotopic forms of hydrogen (H) include protium ($^1$H), deuterium ($^2$H or D) and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I or II can be prepared without undue experimentation by conventional techniques well known to those skilled in the art or by processes analogous to those described in the Schemes and Examples herein using appropriate isotopically-enriched reagents and/or intermediates. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

The term "composition" as used herein is intended to encompass a product comprising specified ingredients and may provide for predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

Accordingly, the pharmaceutical compositions of the present invention encompass any composition made by combining a compound of the present invention and a pharmaceutically acceptable carrier. By "pharmaceutically acceptable" it is meant the carrier, diluent or excipient must be compatible with the other ingredients of the formulation and not deleterious to the recipient thereof.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. Exemplary additional therapeutic agents are discussed below. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The term "pharmaceutical composition" is also intended to encompass both the bulk composition and individual dosage units comprised of one or more pharmaceutically active agents. More than one active agent can be provided by, for example, a compound of the present invention and an additional agent selected from the lists of the additional agents described herein, along with any pharmaceutically inactive excipients. The bulk composition and each individual dosage unit can contain fixed amounts of one or more pharmaceutically active agents. The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

In general, pharmaceutical compositions can be prepared by uniformly and intimately bringing the active ingredient into association with a liquid carrier or a finely divided solid carrier or both, and then, if necessary, shaping the product into the desired formulation. In the pharmaceutical composition the active compound, which is a compound of general Formula I or II, is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to methods known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated". For example, exemplary additional therapeutic agents include, but are not limited to: interferon, pegylated interferon, α-interferon, pegylated α-interferon, ribaviron, inhibitors of HCV NS5A, inhibitors of HCV NS5B and inhibitors of HCV NS4B. Additional appropriate therapeutic agents or approaches are described generally in The Merck Manual, Seventeenth Edition, Ed. Mark H. Beers and Robert Berkow, Merck Research Laboratories, 1999.

The amount of additional therapeutic agent present in the compositions of this invention will be no more than the amount that would normally be administered in a composition comprising that therapeutic agent as the only active agent. Preferably, the amount of additional therapeutic agent in the presently disclosed compositions will range from about 50% to 100% of the amount normally present in a composition comprising that agent as the only therapeutically active agent.

Accordingly, the present invention additionally provides any one of the aforementioned methods further comprising administering to said patient an amount effective to treat said disease or disorder of at least one additional therapeutic agent, wherein the additional therapeutic agent(s) is/are selected from the group consisting of therapeutic agents known to be useful to treat said disease or disorder.

In one embodiment of this combination therapy method, the additional therapeutic agent(s) is/are selected from the group consisting of interferon, pegylated interferon, α-interferon, pegylated α-interferon, ribaviron, inhibitors of HCV NS5A, inhibitors of HCV NS5B and inhibitors of HCV NS4B.

The terms "administration of" or "administering" a compound should be understood to mean providing a compound of the invention to the individual in need of treatment in a form that can be introduced into that individual's body in a therapeutically useful form and therapeutically useful amount. Examples of different routes of administration include one or more of the following: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound sufficient to inhibit HCV replication. Preferably the amount is sufficient to elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The inventive compounds and pharmaceutical compositions of the invention have been found to inhibit the HCV NS3 viral protease. Accordingly, an aspect of this invention is the treatment of HCV infection in vitro and of in vivo HCV infection in mammals by administering an effective amount of a compound of this invention. The term "mammal" includes humans, as well as other animals, such as, for example, dogs, cats, horses, pigs and cattle. Accordingly, it is understood that the treatment of mammals other than humans refers to the treatment of clinical conditions in non-human mammals that correlate to the above recited conditions.

In another aspect, this invention provides a method of treating a disease or disorder, including those disorders and conditions listed above, in a patient in need of such treating, wherein the method comprises administering to said patient an amount effective to treat said disease or disorder of a compound of this invention, or a pharmaceutically acceptable salt, solvate or hydrate thereof, or a pharmaceutically acceptable salt or solvate of said prodrug.

The present invention is further directed to a method for that manufacture of a medicament for treating a disease or disorder, including those disorders and conditions listed above, in humans and animals comprising combining a compound of the present invention with one or more additional therapeutic agents, carriers, or diluents.

Compounds of the invention, such as those disclosed below, may be converted to pharamceutically acceptable salts by suitable methods. For instance, compounds of the Examples described below may be converted to potassium or sodium salts by treatment with stoichiometric amounts of 1M solutions of aqueous potassium hydroxide or sodium hydroxide in acetonitrile, followed by in vacuo concentration. Alternatively, compounds of the Examples bearing basic groups, such as amines, may be converted to acid salts by treatment with stoichiometric amounts of mineral or organic acids.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Several methods for preparing the compounds of this invention are illustrated in the schemes and examples herein. The following examples are provided so that the invention might be more fully understood.

Abbreviations $^1H$ NMR Proton Nuclear Magnetic Resonance spectroscopy
atm Atmospheres
AcOH Acetic acid
$AlCl_3$ Aluminum chloride
aq Aqueous
BINAP 2,2'-bis(diphenylphosphino)-1,1'-binaphthyl
BnBr Benzyl bromide
$BBr_3$ Boron tribromide
BOC Tert-Butyloxycarbonyl, Boc
$BOC_2O$ Di-tert-butyloxycarbonyl
Boc-4-Oxo-PRO-OMe Boc-4-oxo-L-proline methyl ester
Brosyl 4-bromo benzene sulfonyl
Bu Butyl, $C_4H_9$
$Bu_4NI$ Tetra-n-butyl ammonium iodide
BzOH Benzoic acid
$Ca(OH)_2$ Calcium hydroxide
$CHCl_3$ Chloroform
$CDCl_3$ Deuterated chloroform
$CaCO_3$ Calcium carbonate
CDI Carbonyl diimidazole
$CO_2$ Carbon dioxide
$Cs_2CO_3$ Cesium carbonate
Cu—I Copper (I) iodide
d Days
δ Delta (chemical shift)
DBU Diazabicycloundecane DCE Dichloroethane
DCM Dichloromethane, methylene chloride
DeoxoFluor Bis(2-methoxyethyl)aminosulfur trifluoride, oxy-DAST
DIAD Diisopropyl azodicarboxylate
DIBAL-H Diisobutylalumnium hydride
DIPA Diisopropyl amine
DIPEA, DIE Diisopropyl ethyl amine (Hunig's base)
DMAP 4-dimethyl amino pyridine
DMF Dimethyl formamide
DMP Dess Martin periodinane
EDC 1-Ethyl-3-(3-dimethylaminopropyl) carbodiimide
Et Ethyl, $C_2H_5$
$Et_2O$ Diethylether
EtOAc Ethyl acetate
EtOH Ethanol
g Grams
gt Genotype
h Hours
$H_2$ Hydrogen gas or atmosphere
HATU (2-(7-Aza-1H-benzotriazole-1-yl)-1,1,3,3-tetramethyluronium hexafluorophosphate)
HCl Hydrochloric acid
HBr Hydrobromic acid
HPLC High performance liquid chromatography
Hz Hertz
MHz Megahertz
$K_2CO_3$ Potassium carbonate
KOH Potassium hydroxide
KOtBu Potassium tert-butoxide
L Liter
LC-MS Liquid chromatography—mass spectroscopy
LDA Lithium diisopropyl amide
LiCl Lithium chloride
$LiOH.H_2O$ Lithium hydroxide monohydrate
M Molar
MCPBA, mCPBA Meta-chloro-peroxybenzoic acid
Me Methyl, $CH_3$
MeCN, $CH_3CN$ Acetonitrile
MeMgBr Methylmagnesium bromide
MeOH Methanol, $CH_3OH$
MeSNa Sodium methanethiolate, sodium thiomethoxide, $CH_3SNa$
MFSDA Methyl 2,2-difluoro-2-(fluorosulfonyl)acetate
mg milligram
$MgSO_4$ Magnesium sulfate
MHz Megahertz
min Minutes
μl microliter
mL, ml milliliter
mmole millimole
MsCl Methane sulfonyl chloride, mesyl chloride
N Normal
$N_2$ Nitrogen gas
$NaBH_4$ Sodium borohydride
$Na_2S_2O_3$Sodium thiosulfate
$Na_2SO_4$ Sodium sulfate
$Na_2SO_3$ Sodium sulfite
$NaHSO_3$ Sodium bisulfite
$NaBH_4$ Sodium borohydride
$NaCO_3$ Sodium carbonate
$NaHCO_3$ Sodium bicarbonate
$NaKC_4H_4O_6$Sodium potassium tartrate
NBS N-bromosuccinimide
NCS N-chlorosuccinimide
$NH_4Cl$ Ammonium chloride
$NiCl_2.6H_2O$ Nickel(II) chloride hexahydrate
$Pd(OAc)_2$ Palladium acetate
$Pd(PPh_3)_2Cl_2$ Tetrakistriphenylphosphine Palladium(0) Chloride
$Pd(PPh_3)_4$, Tetrakis Tetrakistriphenylphosphine Palladium (0)
Pd/C Palladium on Carbon
Ph Phenyl
PMB p-methoxybenzyl
PMB-Cl p-methoxybenzyl chloride
$Pd_2(dba)_3$ Tris(dibenzylideneacetone)dipalladium(0)
$POBr_3$ Phosphorous oxybromide
$PPh_3$ Triphenyl phosphine
PPA Polyphosphroic acid
RB Round bottom
RT, rt Room temperature, approximately 25° C.
SCF chromatography Supercritical fluid chromatography, SCF
$SeO_2$Selenium dioxide
TBAF Tetrabutyl ammonium fluoride
TBDMS Tert-butyldimethyl silyl
TBS-OTf Trifluoromethane sulfonic acid tert-butyldimethylsilyl ester
TBTU 0-(Benzotriazol-1-yl)-N,N,N',N'-tetramethyluronium tetrafluoroborate
TEA, $Et_3N$ Triethylamine, $N(C_2H_5)_3$
TFAA Trifluoroacetic anhydride
THF Tetrahydrofuran
TLC Thin layer chromatography
TsCl Toluene sulfonyl chloride, tosyl chloride
Zhan Catalyst 1,3-Bis(2,4,6-trimethylphenyl)-4,5-dihydroimidazol-2-yledine[2-isopropoxy)-5-N,N-dimethylaminosulfonyl)phenyl]methylene ruthenium(II)dichloride
sat. Saturated
$SeO_2$Selenium dioxide
$SiO_2$ Silicon dioxide
$TMSCF_3$ (Trifluoromethyl)trimethylsilane
TBAF Tetrabutylammonium fluoride
x Refers to the number of times a process is iterated (e.g., "washed 3x"="washed three times")

INTERMEDIATES

Intermediate 1

2-Methyl-4-(methylsulfonyl)butan-2-yl 4-nitrophenyl carbonate

Step 1

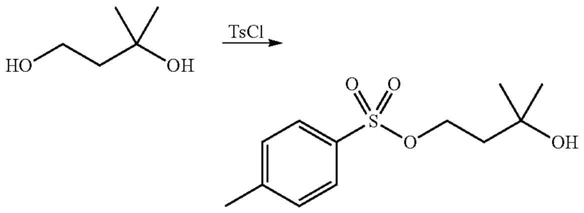

To a solution of 3-methyl-1,3-butanediol (3.72 ml, 35 mmol) in pyridine (30 ml) at 0° C. was added TsCl (6.67 g, 35.0 mmol) in pyridine (10 ml) slowly over 10 min, and the mixture was allowed to warm to RT overnight. The mixture was quenched with water and extracted with EtOAc. The combined organic fractions were washed with half brine, dried over $Na_2SO_4$, filtered and concentrated in vacuo to give the product (6.01 g, 67% yield) as oil.

Step 2

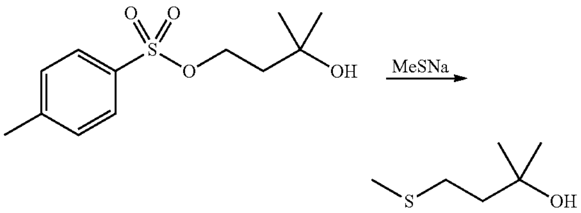

To a solution of the product of Step 1 (1.03 g, 4.00 mmol) in EtOH (10 ml) at RT was added MeSNa (561 mg, 8.00 mmol), and the mixture was warmed to 50° C. and stirred for 72 h. The mixture was quenched at RT with water and extracted with DCM. The combined organic fractions were dried over $Na_2SO_4$, filtered and concentrated in vacuo to afford the product (510 mg, 95% yield).

Step 3

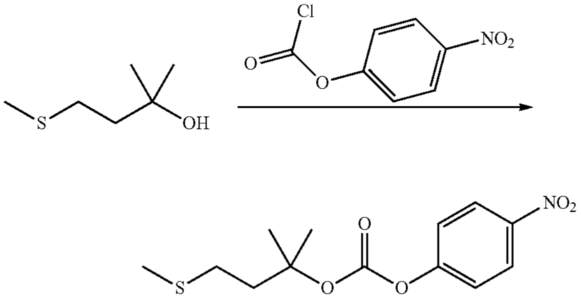

To a solution of the product of Step 2 (510 mg, 3.80 mmol) and pyridine (0.32 ml, 3.99 mmol) in DCE (12 ml) at 0° C. was added 4-nitrophenyl chloroformate (766 mg, 3.80 mmol), and the mixture was warmed to 40° C. and stirred overnight. The final mixture was diluted at RT with DCM, washed with 1N aq. HCl, saturated $NaHCO_3$, and brine, dried over $Na_2SO_4$, filtered and concentrated in vacuo. The residue was purified by column chromatography over silica gel (eluting with Hexanes/DCM 85:15 to 30:70) to give product (902 mg, 79% yield).

Step 4

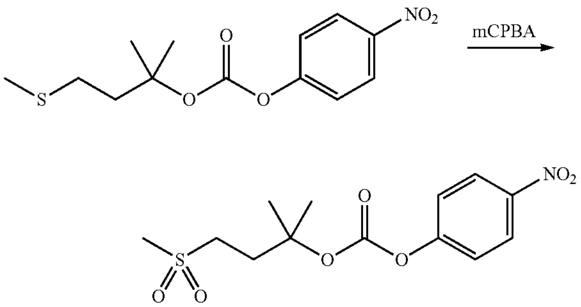

To a solution of the product of Step 3 (300 mg, 1.00 mmol) in DCM (20 ml) at 0° C. was added 3-chloroperoxybenzoic acid (618 mg, 2.51 mmol), and the mixture was stirred for 1 h at 0° C. then 15 min at RT. The mixture was quenched with sat. aq. $NaHCO_3$ and extracted with DCM then EtOAc. The combined organic fractions were dried over $Na_2SO_4$, filtered and concentrated in vacuo. The residue was purified by column chromatography over silica gel (eluting with Hexanes/EtOAc 99:1 to 20:80) to afford 2-methyl-4-(methylsulfonyl)butan-2-yl-4-nitrophenyl carbonate (305 mg, 92% yield) as a white solid. $^1$H-NMR (300 MHz, $CDCl_3$) δ 8.27 (d, J=9.2 Hz, 2H), 7.36 (d, J=9.2 Hz, 2H), 3.15-3.21 (m, 2H), 2.96 (s, 3H), 2.32-2.38 (m, 2H), 1.63 (s, 6H).

Intermediate 2

4-methoxy-2-methylbutan-2-yl 4-nitrophenyl carbonate

Step 1

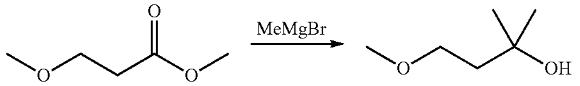

To a solution of 3N MeMgBr in $Et_2O$ (41.7 ml, 125 mmol) and lithium iodide (1.34 g, 10.00 mmol) at 0° C. was added methyl 3-methoxypropionate (5.85 ml, 50 mmol) in $Et_2O$ (40 ml), and the mixture was allowed to warm to RT and stirred overnight. The mixture was slowly poured into ice then diluted with sat. aq. $NH_4Cl$ and extracted with $Et_2O$. The combined organic fractions were washed with sat. aq. $NaHCO_3$, water, dried over $Na_2SO_4$, filtered and concentrated in vacuo at 0.12 atm and 35° C. to give the product (1.46 g, 25% yield) as colorless oil.

Step 2

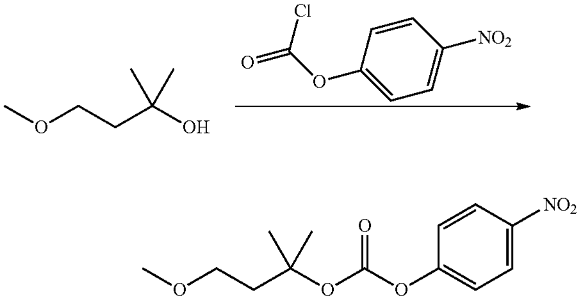

To a solution of the product of Step 1 (1.46 g, 12.3 mmol) and pyridine (1.05 ml, 13.0 mmol) in DCM (40 ml) at 0° C. was added 4-nitrophenyl chloroformate (2.49 g, 12.3 mmol), and the mixture was allowed to warm to RT and stirred for 72 h. The final mixture was diluted at RT with DCM, washed with 1N aq. HCl, saturated $NaHCO_3$, and brine, dried over $Na_2SO_4$, filtered and concentrated in vacuo. The residue was purified by column chromatography over silica gel (eluting with Hexanes/EtOAc 99:1 to 70:30 then hexanes/DCM 80:20 to DCM) to give 4-methoxy-2-methylbutan-2-yl 4-nitrophenyl carbonate (982 mg, 28% yield). $^1$H-NMR (300 MHz, $CDCl_3$) δ 8.26 (d, J=9.2 Hz, 2H), 7.35 (d, J=9.2 Hz, 2H), 3.55 (t, J=6.4 Hz, 2H), 3.34 (s, 3H), 2.16 (t, J=6.4 Hz, 2H), 1.58 (s, 6H).

Intermediate 3

1-methoxy-2-methylpropan-2-yl 4-nitrophenyl carbonate

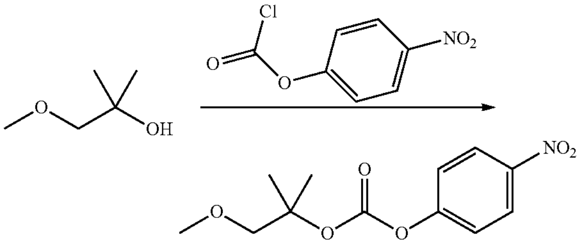

1-Methoxy-2-methyl-2-propanol (3.50 ml, 30 mmol) was treated with 4-nitrophenyl chloroformate according to conditions similar to the ones described above with respect to Intermediate 2, Step 2 to provide, after purification by column chromatography over silica gel (eluting with Hexanes/EtOAc 99:1 to 70:30), 1-methoxy-2-methylpropan-2-yl 4-nitrophenyl carbonate (7.02 g, 87% yield) as a colorless oil. $^1$H-NMR (300 MHz, $CDCl_3$) δ 8.26 (d, J=9.2 Hz, 2H), 7.36 (d, J=9.2 Hz, 2H), 3.56 (s, 3H), 3.43 (s, 3H), 1.57 (s, 6H).

Intermediate 4

Methoxy-2-methylbutan-2-yl 4-nitrophenyl carbonate

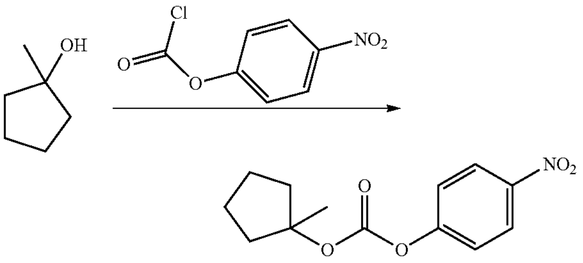

1-Methylcyclopentanol (0.60 ml, 6.00 mmol) was treated with 4-nitrophenyl chloroformate according to conditions similar to the ones described in Intermediate 2, Step 2 to provide, after purification by column chromatography over silica gel (eluting with Hexanes/DCM 85:15 to DCM), methoxy-2-methylbutan-2-yl 4-nitrophenyl carbonate (1.03 g, 65% yield) as colorless oil. $^1$H-NMR (300 MHz, $CDCl_3$) δ 8.26 (d, J=9.2 Hz, 2H), 7.36 (d, J=9.2 Hz, 2H), 2.19-2.26 (m, 2H), 1.65-1.85 (m, 6H), 1.67 (s, 3H)

Intermediate 5

N-cyclohexylcyclohexanaminium (2S)-2-[(tert-butoxycarbonyl)amino]non -8-eonate

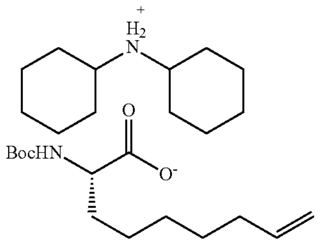

Intermediate 5 was obtained from Synth Tech, and Intermediate 5 can be synthesized by known, published procedures, such as those disclosed in Anne-Marie Faucher et al., "*Synthesis of BILN* 2061, *an HCV NS*3 *Protease Inhibitor with Proven Antiviral Effect in Humans,*" 6(17) Org. Lett. 2901-2904 (2004). The dicyclohexylamine salt can be readily converted into free acid by treatment with aq. HCl and extraction of the mixture with EtOAc (3×). Subsequently, the organic layers are washed with aq. HCl and brine, dried over $MgSO_4$, filtered and concentrated.

Intermediate 6

(2R,6S,13aS,14aR,16aS,Z)-methyl 6-((tert-butoxycarbonyl)amino)-2-hydroxy-5,16-dioxo-1,2,3,5,6,7,8,9,10,11,13a,14,14a,15,16,16a -hexadecahydrocyclopropa[e]pyrrolo[1,2-a][1,4] diazacyclopentadecine-14a-carboxylate Step 1

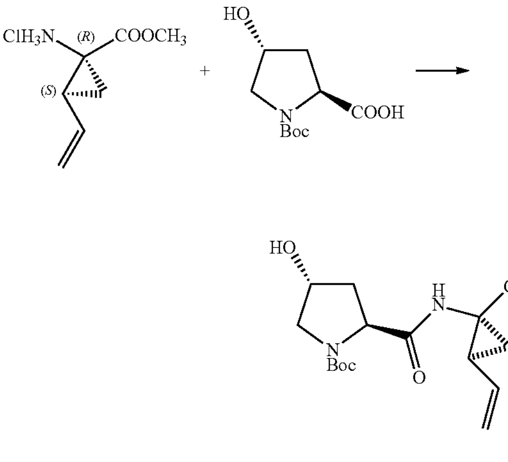

EDC (8.08 g, 42.2 mmol) and pyridine (5.25 ml, 64.9 mmol) were added to a stirred, RT mixture of the HCl salt of amino ester (6.05 g, 34.1 mmol) and carboxylic acid (7.5 g, 32.4 mmol) in MeCN (75 ml), and the resulting mixture was stirred at RT for 24 h. After the completion of the reaction, the mixture was concentrated under reduced pressure. The residue was diluted with EtOAc (100 ml) and quenched with half-saturated brine (100 ml), and then extracted with EtOAc (3×75 ml). The combined organic fractions were dried ($MgSO_4$), filtered, and the solvent was evaporated under reduced pressure. The product amide was obtained as yellow foam (10.5 g, 91%) and used directly in Step 2.

Step 2

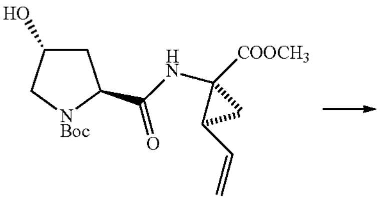

-continued

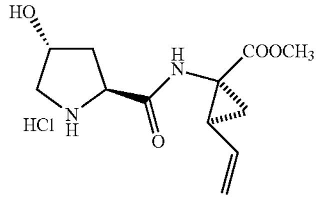

HCl in dioxane 4 N (254 ml, 1016 mmol) was added to a stirred, RT mixture of amide of Step 1 (12.0 g, 33.9 mmol) in DCM (24.0 ml), and the mixture was stirred at RT for 2 h. The reaction mixture was concentrated under reduced pressure to afford a brown solid (10.5 g, ~95 wt % purity, 99%). The product (95 wt %—by $^{1}$H NMR-containing traces of pyridine), was used directly in next step without further purification.

Step 3

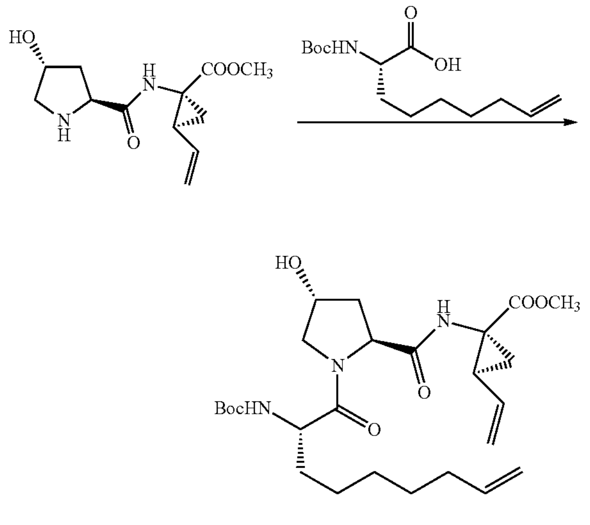

A 1-L RB flask was charged with DCM (163 ml), the product of Step 2 (7.10 g, 22.7 mmol) and Hunig's base (3.77 ml, 21.6 mmol) and then allowed to stir 30 min at RT. This solution was designated "Solution A".

Separately, a 500-mL flask under $N_2$ sweep was charged with DCM (213 ml), (S) -2-((tert-butoxycarbonyl)amino) non-8-enoic acid (6.16 g, 22.7 mmol), TBTU (8.00 g, 24.9 mmol) and Hunig's Base (3.97 ml, 22.7 mmol) and then allowed to stir 30 min at RT. This solution was designated "Solution B".

Solution B was added to Solution A via cannula over 15 min. The resulting solution was stirred 24 h at RT under a $N_2$ sweep. The reaction was quenched with 0.5 N HCl (350 ml), then extracted with DCM (100 ml). The combined organic layers washed with saturated $NaHCO_3$ (250 ml) water (2×250 ml) and then brine (100 ml). The organic layers were dried over $MgSO_4$, then concentrated. The residue was purified by column chromatography on silica gel column (Isco 220 gram), eluting with 80-100% EtOAc/hexanes to give the product bis-olefin as colorless foam (9.90 g, 86%).

Step 4

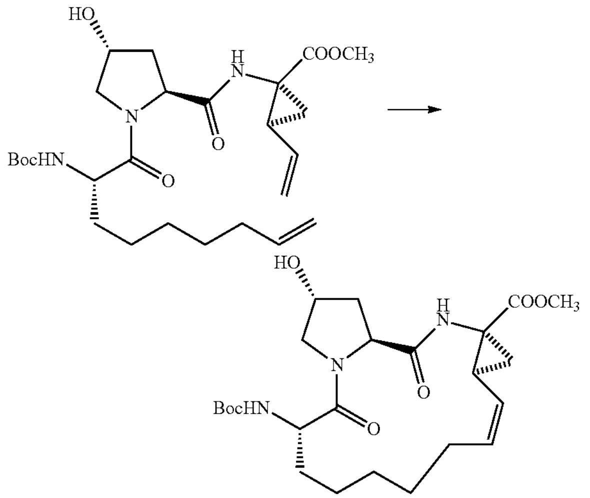

Grubbs-Hoveyda 1st generation catalyst (0.592 g, 0.985 mmol) was added in one portion to a stirred, RT mixture of DCM (2000 ml) and bis-olefin product of Step 3 (10.0 g, 19.7 mmol) in a 3-necked 5-L flask (equipped with condenser and thermocouple) that had been degassed by bubbling with $N_2$ for 30 min. The flask was vacuum-purged and backfilled with $N_2$. The mixture was then heated at 40° C. for 40 h (monitoring by TLC) until completion. The crude reaction mixture was concentrated. The brown residue was purified by column chromatography on silica gel column (Isco 220 g), eluting with 50-100% EtOAc/hexanes to give (2R,6S,13aS,14aR,16aS,Z)-methyl 6-((tert-butoxycarbonyl)amino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate as brown foam (7.05 g, 74%).

Intermediate 7

Ethyl (6S,12Z,13aS,14aR,16aS)-6-[(tert-butoxycarbonyl)amino]-2,5,16-trioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate Step 1

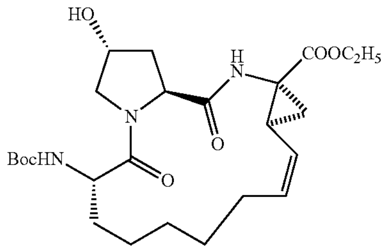

The product alcohol was synthesized using similar procedure described for the synthesis of Intermediate 6, except ethyl ester was used instead of methyl ester.

Step 2

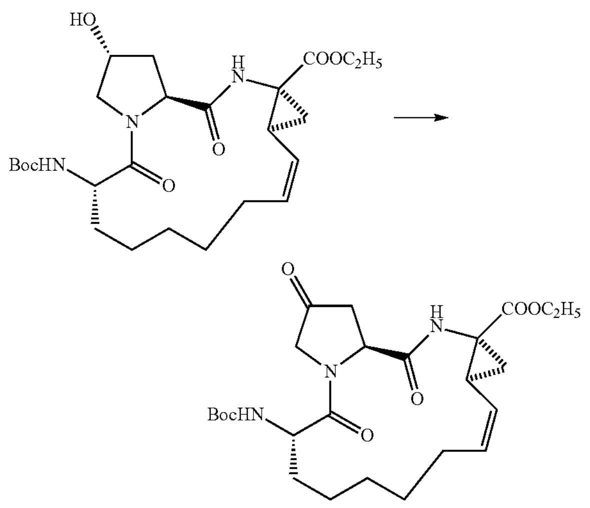

A solution of alcohol product of Step 1 (6.00 g, 12.16 mmol) was taken up in DCM (60 ml) and treated with Dess-Martin reagent (5.42 g, 12.4 mmol). The resulting solution was aged at RT for 1 h, until HPLC showed complete conversion of starting material to product. The reaction mixture was quenched with half-sat. $NaHCO_3$ (120 mL) and stirred for 30 min. The reaction mixture was transferred to a separatory funnel, and the aq. layer was extracted once with 50 mL DCM, and then the combined organic layers were washed with 10% $Na_2S_2O_3$ (100 mL) 2× and brine. The combined organic layers were concentrated, and the crude mixture was purified by silica gel chromatography (EtOAc/hexanes) to yield the Intermediate 7 macrocyclic ketone.

EXAMPLES

Example 1 tert-butyl (2R,6S,13aS,14aR,16aS,Z)-5'-methyl-14a-(1-methylcyclopropyl sulfonylcarbamoyl)-5,16-dioxo-9'-(trifluoromethoxy)-1',2',3,5,6,7,8,9,10,11,13a, 14,14a,15, 16,16a-hexadecahydro-1H-spiro [cyclopropa[e]pyrrolo[1,2-a][1,4] diazacyclopentadecine -2,3'-pyrano[2,3-c]quinoline]-6-ylcarbamate (I-1)

Step 1

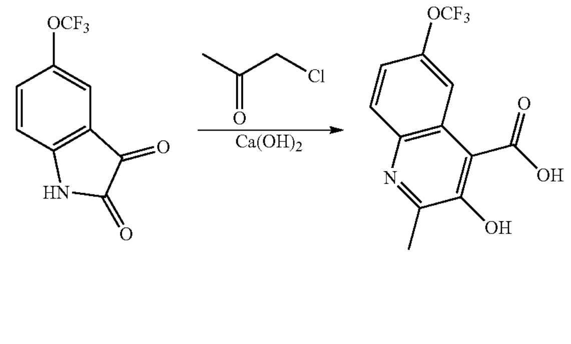

A solution of $Ca(OH)_2$ (38.5 g, 519 mmol) and 5-(trifluoromethoxy)isatin (40 g, 173 mmol) in water (150 ml) was heated at 80° C. for 1 h. The heating bath was removed followed by slow addition of chloroacetone (34.5 ml, 433 mmol). The reaction was then heated at 80° C. for another 5 h then cooled to RT and quenched with 1N aq. HCl until pH=2. The solid was filtered over fitted disk, washed with water and dried overnight at 50° C. under high vacuum to afford the product intermediate (47.0 g, 95% yield) as a slightly yellow solid.

Step 2

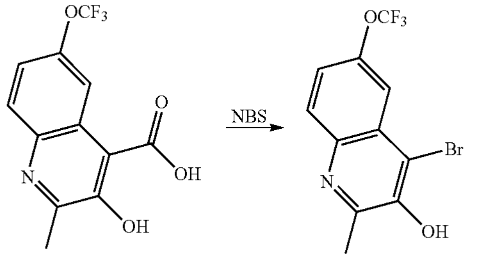

To a solution of the product from Step 1 (40 g, 139 mmol) in THF (1000 ml) at RT was added NBS (29.7 g, 167 mmol), and the mixture was stirred for 4 h. The mixture was quenched with saturated brine and extracted with EtOAc. The combined organic fractions were dried over $Na_2SO_4$, filtered and concentrated in vacuo. The residue was purified by column chromatography over silica gel (eluting with DCM/EtOAc 99:1 to 60:40) to give the product intermediate (25.0 g, 56% yield) as a red solid.

Step 3

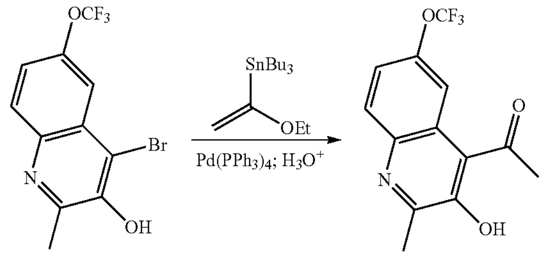

To a solution of the product from Step 2 (20.0 g, 62.1 mmol) and $Pd(PPh_3)_4$ (7.18 g, 6.21 mmol) in dioxane (240 ml) was added tributyl(1-ethoxyvinyl)tin (52.4 ml, 155 mmol) and the mixture was warmed to 110° C. and stirred for 3 h. The reaction was cooled to RT, diluted with 1N aq. HCl (240 ml) and stirred for 90 min. The mixture was then quenched with saturated aq. $NaHCO_3$ and extracted with EtOAc. The combined organic fractions were washed with saturated brine, dried over $Na_2SO_4$, filtered and concentrated in vacuo. The residue was purified by column chromatography over silica gel (eluting with Hexanes/EtOAc 99:1 to 60:40) to give the product intermediate (3.40 g, 19%) as a yellow solid.

Step 4

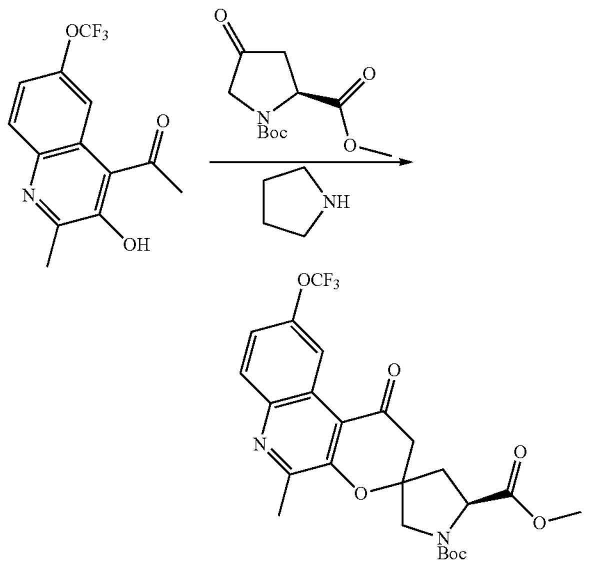

To a solution of the product from Step 3 (2.0 g, 7.01 mmol) in MeOH (30 ml) was added N-Boc-4-oxo-L-proline methyl ester (3.41 g, 14.02 mmol), pyrrolidine (0.58 ml, 7.01 mmol), followed by molecular sieves (4 A powder, 2.0 g), and the mixture was heated in a microwave at 105° C. for 30 min. The cooled mixture was filtered over fritted disk, washing with MeOH, and then concentrated. The residue was purified by column chromatography over silica gel (eluting with Hexanes/EtOAc 99:1 to EtOAc) to afford the product intermediate (2.73 g, 76% yield) as a mixture of diastereoisomers.

Step 5

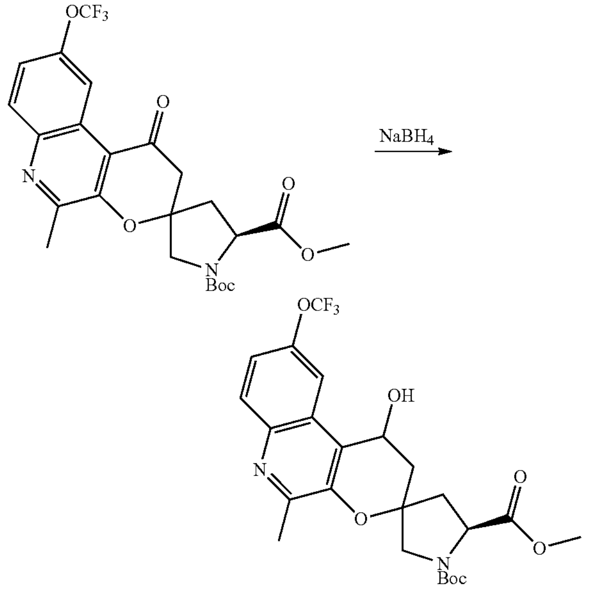

To a solution of the product from Step 4 (2.20 g, 4.31 mmol) in THF (20 ml) and MeOH (20 ml) at 0° C. was added $NaBH_4$ (196 mg, 5.17 mmol), and the mixture was stirred for 30 min. The mixture was quenched at 0° C. with sat. aq. $NH_4Cl$ and extracted with EtOAc. The combined organic fractions were washed with brine, dried over $Na_2SO_4$, filtered and concentrated in vacuo to provide the product intermediate (2.20 g, 100% yield) as a mixture of diastereoisomers.

Step 6

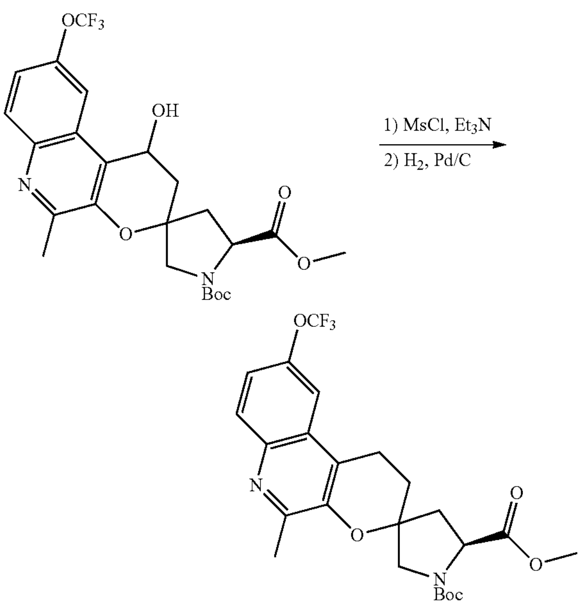

To a solution of the product from Step 5 (2.20 g, 4.29 mmol) in DCM (40 ml) at 0° C. was added TEA (2.094 ml, 15.03 mmol) followed by MsCl (0.67 ml, 8.59 mmol), and the mixture was allowed to warm to RT and stirred overnight. More TEA (0.60 ml, 4.29 mmol) and MsCl (0.16 ml, 2.14 mmol) were then added at 0° C., and the reaction was allowed to warm to RT and stirred for 2 h. The mixture was quenched with sat. aq. $NaHCO_3$ and extracted with DCM. The combined organic fractions were dried over $Na_2SO_4$, filtered and concentrated in vacuo. The residue was purified by column chromatography over silica gel (eluting with Hexanes/EtOAc 99:1 to EtOAc) to give a crude chloro intermediate (2.20 g, 97% yield) as yellow oil. To a solution of this crude chloro intermediate (2.20 g, 4.15 mmol) in EtOAc (90 ml) at RT was added 10% Pd/C (0.440 g, 0.415 mmol) and the mixture was hydrogenated at 1 atm and RT for 3 h. The mixture was filtered over Celite, washing with EtOAc and MeOH. The residue was purified by column chromatography over silica gel (eluting with DCM/MeOH 99:1 to 80:20) to give the product intermediate (1.89 g, 92% yield) as a mixture of diastereoisomers.

Step 7

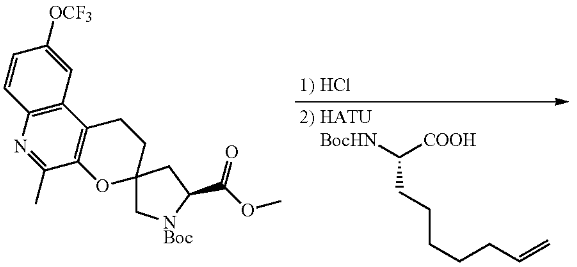

-continued

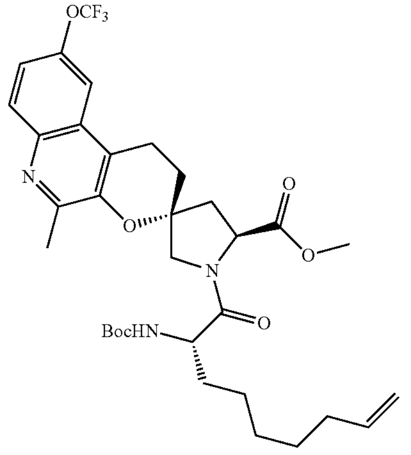

1-7A

+

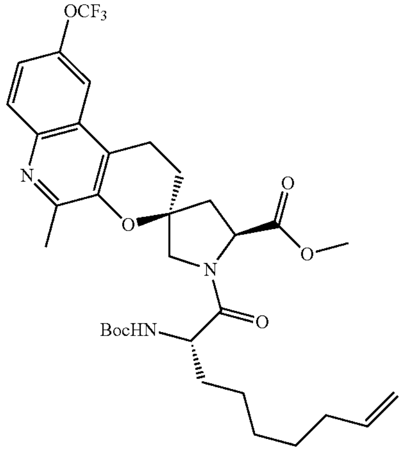

1-7B

The product from Step 6 (1.10 g, 2.22 mmol) was diluted with 4N HCl in dioxane (22.2 ml, 89 mmol), and the mixture was stirred for 2 h at RT then concentrated in vacuo to provide a deprotected amine as HCl salt (1.00 g, 100% yield). To a solution of this deprotected amine as HCl salt (1.00 g, 2.22 mmol), (S)-2-(tert-butoxycarbonylamino)non-8-enoic acid (1.71 g, 3.78 mmol) and HATU (1.44 g, 3.78 mmol) in DMF (20 ml) at RT was added DIPEA (1.72 ml, 10.1 mmol), and the mixture was stirred at RT overnight. The reaction was further diluted with DMF (5 ml), DCM (20 ml), treated with DIPEA (0.40 ml, 2.3 mmol) and stirred at RT overnight. The final mixture was diluted with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to EtOAc) to provide, in order of elution, diastereoisomer 1-7A (660 mg, 40% yield) then diastereoisomer 1-7B (520 mg, 32% yield).

Step 8

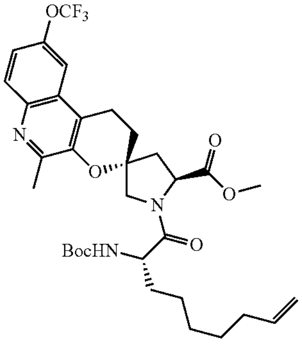

1-7A

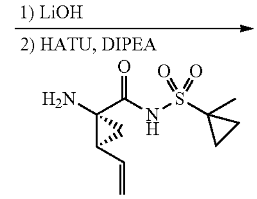

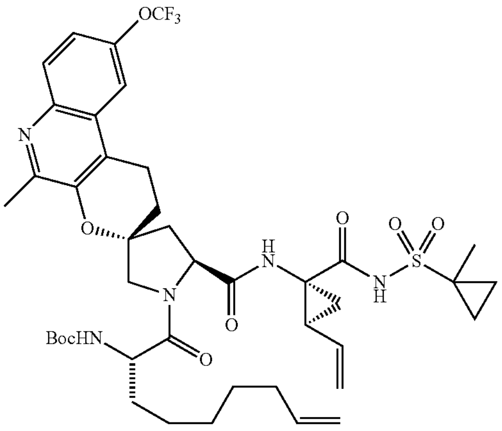

To a solution of diastereoisomer 1-7A from Step 7 (660 mg, 1.02 mmol) in THF (12 ml), MeOH (12.00 ml) and water (8 ml) at RT was added $LiOH.H_2O$ (73.0 mg, 3.05 mmol), and the mixture was warmed to 50° C. and stirred for 2 h. MeOH and THF were concentrated in vacuo, then the mixture was diluted with 0.5M aq. HCl until pH=2 and extracted with EtOAc. The combined organic fractions were dried over $Na_2SO_4$, filtered and concentrated in vacuo to provide a crude acid intermediate (640 mg, 99% yield). To a solution of this crude acid intermediate (640 mg, 1.01 mmol) and (1R,2S)-1-amino-N-(1-methylcyclopropylsulfonyl)-2-vinylcyclopropanecarboxamide (369 mg, 1.51 mmol) in DMF (10 ml) at RT was added HATU (574 mg, 1.51 mmol) followed by DIPEA (0.514 ml, 3.02 mmol), and the mixture was stirred at RT overnight. The mixture was quenched with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to EtOAc) to give the product intermediate (770 mg, 79% yield).

Step 9

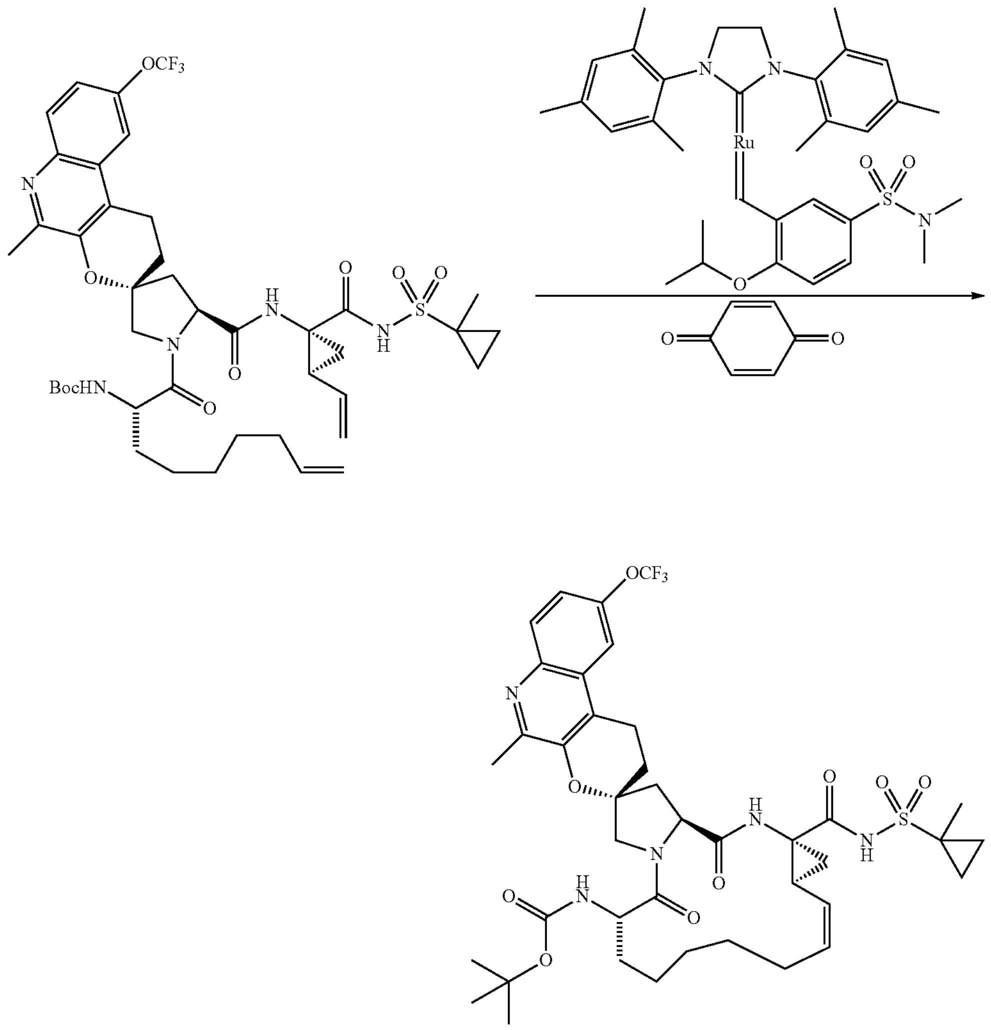

A solution of the product from Step 8 (300 mg, 0.348 mmol), 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II)dichloride (63.8 mg, 0.087 mmol) and 1,4-benzoquinone (11.29 mg, 0.104 mmol) in DCE (150 ml) was degassed, put under $N_2$, then warmed to 70° C. and stirred 4 h. The mixture was quenched at RT with n-butyl vinyl ether (1 ml) and concentrated to dryness. The residue was purified by column chromatography over silica gel (eluting with Hexanes/EtOAc 99:1 to EtOAc) to give I-1 (205 mg, 71% yield). $^1$H-NMR (400 MHz, $CDCl_3$) δ 10.10 (s, 1H), 7.96 (d, J=9.0 Hz, 1H), 7.54 (s, 1H), 7.38 (d, J=9.0 Hz, 1H), 6.89 (s, 1H), 5.71 (m, 1H), 4.95-5.05 (m, 2H), 4.63 (m, 1H), 4.44 (d, J=10.8 Hz, 1H), 4.12 (m, 1H), 3.69 (d, J=10.8 Hz, 1H), 3.00-3.17 (m, 2H), 2.48-2.62 (m, 2H), 2.51 (s, 3H), 2.23-2.44 (m, 4H), 1.72-1.93 (m, 5H), 1.23-1.57 (m, 8H), 1.46 (m, 3H), 1.29 (s, 9H), 0.80 (br s, 2H); LC-MS ($M^+$) Calc. for $C_{40}H_{50}F_3N_5O_9S$ 833.9. Found 833.6.

Example 2 tert-Butyl (2R,6S,13aS,14aR,16aS,Z)-5'-isopropyl-9'-methoxy-14a-(1-methyl cyclopropylsulfonylcarbamoyl)-5,16-dioxo-1',2',3,5,6,7,8,9,10,11,13a,14,14a,15,16,16a-hexadecahydro-1H-spiro[cyclopropa[e]pyrrolo[1,2-a][1,4]diazacyclopentadecine-2,3'-pyrano[2,3-c]quinoline]-6-ylcarbamate (I-2)

Step 1

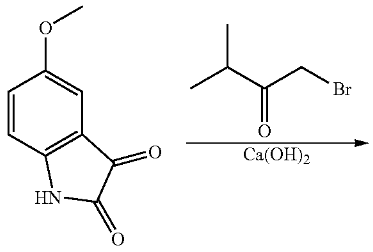

-continued

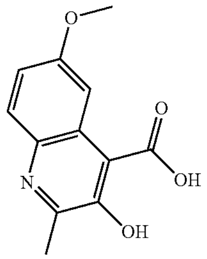

A mixture of 5-methoxyisatin (18 g, 102 mmol) and $Ca(OH)_2$ (22.6 g, 305 mmol) in water (300 ml) was warmed to 80° C. and stirred for 1 h. 1-Bromo-3-methylbutan-2-one (33.5 g, 203 mmol) was then added slowly at 60° C., and the reaction was warmed to 80° C. and stirred for 2 h. The mixture was cooled to RT, then diluted with 1M aq. HCl until pH=2, filtered, rinsing with water then dried under high vacuum at 95° C. overnight to give product (20.41 g, 77% yield) as a yellow solid.

Step 2

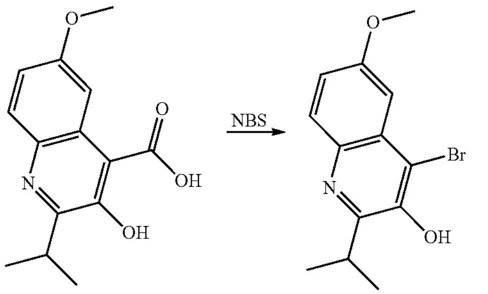

To a suspension of the product from Step 1 (20.4 g, 78 mmol) in THF (250 ml) at RT was added NBS (15.29 g, 86 mmol) portion wise, and the mixture was stirred for 45 min. The mixture was quenched at RT with 5% aq. $Na_2S_2O_3$ and extracted with EtOAc. The combined organic fractions were washed with brine, dried over $Na_2SO_4$, filtered and concentrated in vacuo. The residue was taken up in DCM (100 ml) and filtered to give a first crop. The filtrate was concentrated in vacuo then purified by column chromatography over silica gel (eluting with Hexanes/DCM 80:20 to DCM/EtOAc 95:5) to give a second crop. Both crops were combined to provide intermediate product (20.6 g, 89% yield).

Step 3

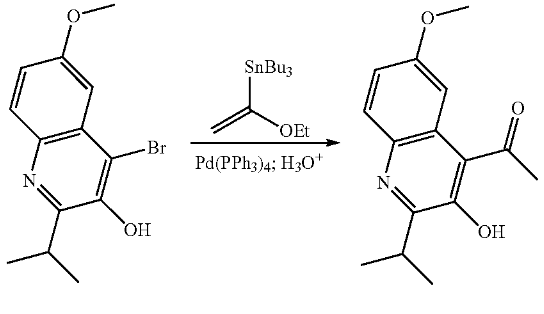

To a solution of the product from Step 2 (20.6 g, 69.5 mmol) and $Pd(PPh_3)_4$ (4.01 g, 3.47 mmol) in dioxane (300 ml) at RT was added tributyl(1-ethoxyvinyl)tin (46.9 ml, 139 mmol), and the mixture was warmed to reflux and stirred overnight. The mixture was quenched at RT with 1 N aq. HCl and stirred for 90 min. The reaction was then diluted with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to 50:50) to give intermediate product (10.53 g, 59% yield) as yellow solid.

Step 4

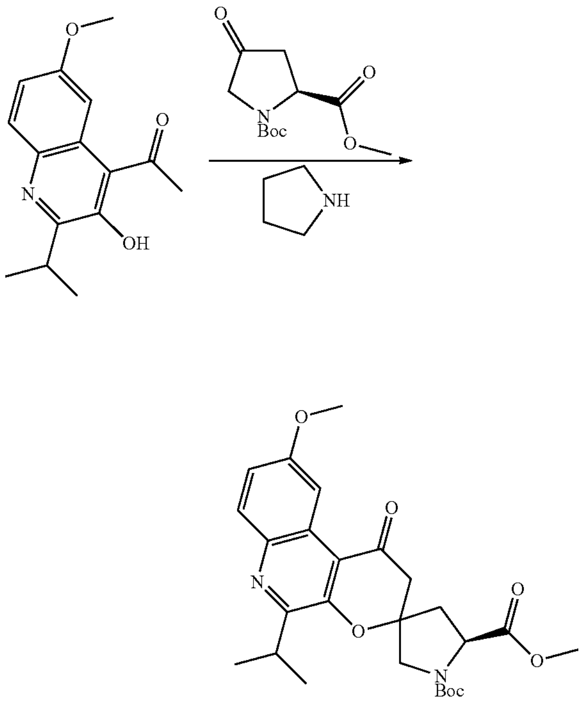

A solution of product from Step 3 (4.30 g, 16.6 mmol), N-Boc-4-oxo-L-proline methyl ester (8.07 g, 33.2 mmol) and pyrrolidine (1.33 ml, 16.6 mmol) in MeOH (60 ml) with molecular sieves (4 A powder, 8 g) in a sealed tube was heated in a microwave reactor at 105° C. for 90 min. The mixture was cooled, filtered over Celite and concentrated in vacuo. The residue was purified by column chromatography over silica gel (eluting with Hexanes/EtOAc 99:1 to 30:70) to give a crop of intermediate product (10.53 g) as a mixture of diastereoisomers.

Step 5

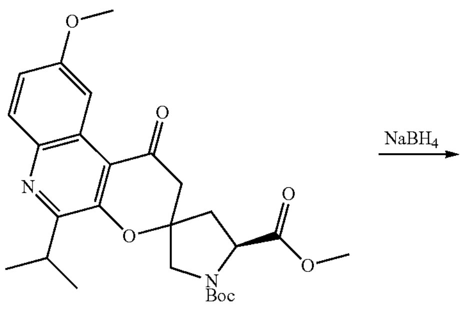

-continued

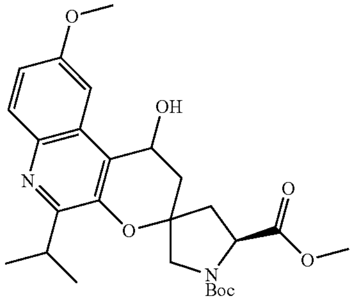

To a solution of product from Step 4 (5.26 g, 10.9 mmol) in THF (40 ml) and MeOH (40 ml) at 0° C. was added $NaBH_4$ (0.616 g, 16.3 mmol), and the mixture was allowed to warm to RT and stirred for 1 h. The mixture was quenched at RT with sat. aq. $NH_4Cl$ and extracted with EtOAc. The combined organic fractions were washed with sat. brine then water, dried over $Na_2SO_4$, filtered and concentrated in vacuo to give intermediate product (5.27 g, 100% yield) as a mixture of diastereoisomers.

Step 6

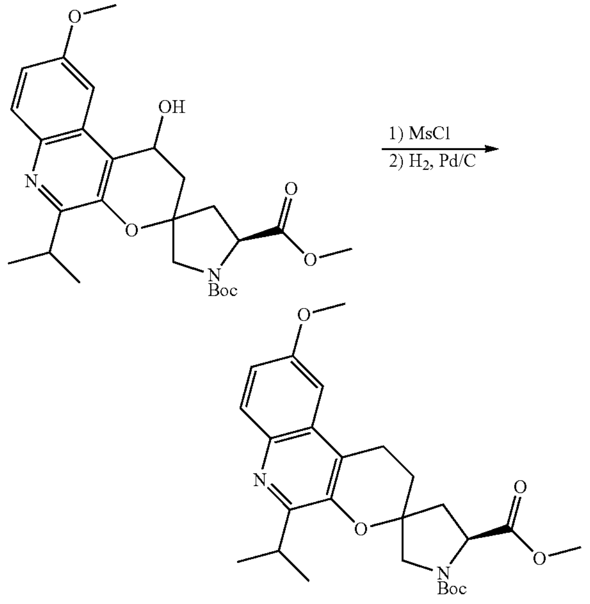

To a solution of intermediate product from Step 5 (5.27 g, 10.83 mmol) in DCM (100 ml) at 0° C. was added TEA (5.28 ml, 37.9 mmol) then MsCl (1.69 ml, 21.7 mmol), and the mixture was allowed to warm to RT and stirred overnight. The final mixture was diluted with EtOAc, washed with sat. aq. $NaHCO_3$, dried over $Na_2SO_4$, filtered and concentrated in vacuo to give a crude chloro intermediate (5.82 g) as yellow foam. A mixture of this crude chloro intermediate (5.82 g, 11.5 mmol) and 10% Pd/C (1.05 g, 0.99 mmol) in EtOAc (100 ml) was hydrogenated at 1 atm for 3 h. The mixture was filtered over Celite, washing with DCM and MeOH then concentrated in vacuo. The residue was purified by column chromatography over silica gel (eluting with DCM/MeOH 99:1 to 90:10) to afford intermediate product (5.27 g, 97% yield) as a mixture of diastereoisomers.

Step 7

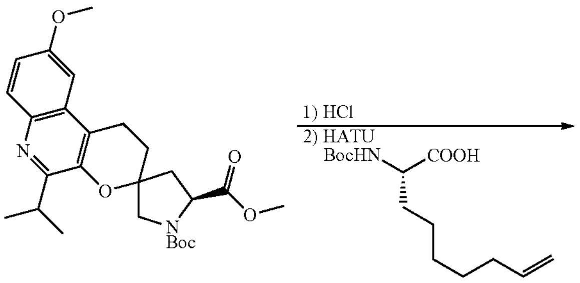

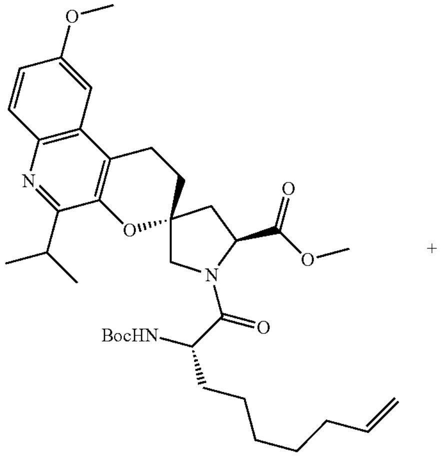

2-7A

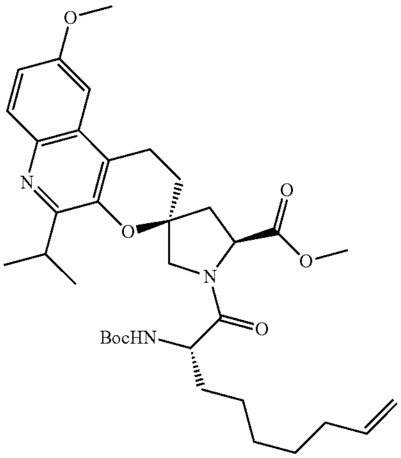

2-7B

Intermediate product from Step 6 (5.27 g, 11.2 mmol) was diluted with 4N HCl in dioxane (60 ml, 240 mmol), and the mixture was stirred at RT for 2 h. The mixture was concentrated in vacuo to give a deprotected amine as HCl salt (5.06 g, 100% yield). To a solution of this deprotected amine as HCl salt (1.20 g, 2.95 mmol) and (S)-2-(tert -butoxycarbonylamino)non-8-enoic acid (1.12 g, 4.13 mmol) in DMF (25 ml) at RT was added HATU (1.57 g, 4.13 mmol) followed by DIPEA (2.01 ml, 11.8 mmol), and the mixture was stirred for 1 h. More DIPEA (0.5 ml) in DCM (15 ml) was then added, and the reaction was stirred at RT overnight. The final mixture was quenched with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to 30:70) to provide, in order of elution, diastereoisomer 2-7A (662 mg, 36% yield) followed by diastereoisomer 2-7B (397 mg, 22% yield).

Step 8

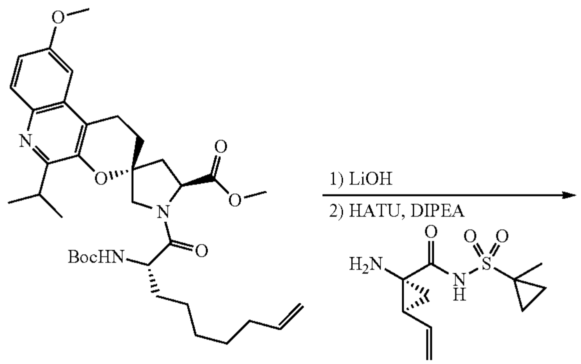

2-7A

-continued

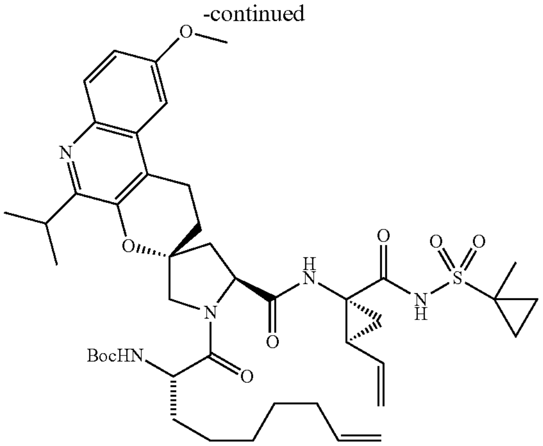

To a solution of diastereoisomer 2-7A from Step 7 (662 mg, 1.06 mmol) in THF (30 ml), MeOH (30 ml) and water (20 ml) at RT was added $LiOH.H_2O$ (134 mg, 3.18 mmol), and the mixture was warmed to 50° C. and stirred for 2 h. MeOH and THF were concentrated in vacuo, then the mixture was diluted with 0.5M aq. HCl until pH=2 and extracted with EtOAc. The combined organic fractions were dried over $Na_2SO_4$, filtered and concentrated in vacuo to provide a crude acid intermediate (570 mg, 88% yield). To a solution of this crude acid intermediate (570 mg, 0.935 mmol) and (1R,2S)-1-amino-N-(1-methylcyclopropylsulfonyl)-2-vinylcyclopropanecarboxamide (297 mg, 1.22 mmol) in DMF (10 ml) at RT was added HATU (462 mg, 1.22 mmol) followed by DIPEA (0.49 ml, 2.80 mmol), and the mixture was stirred 48 h at RT. The final mixture was quenched with water and extracted with EtOAc. The combined organic fractions were washed with brine, dried over $Na_2SO_4$ filtered and concentrated in vacuo. The residue was purified by column chromatography over silica gel (Hexanes/EtOAc 99:1 to EtOAc) to provide intermediate product (660 mg, 84% yield).

Step 9

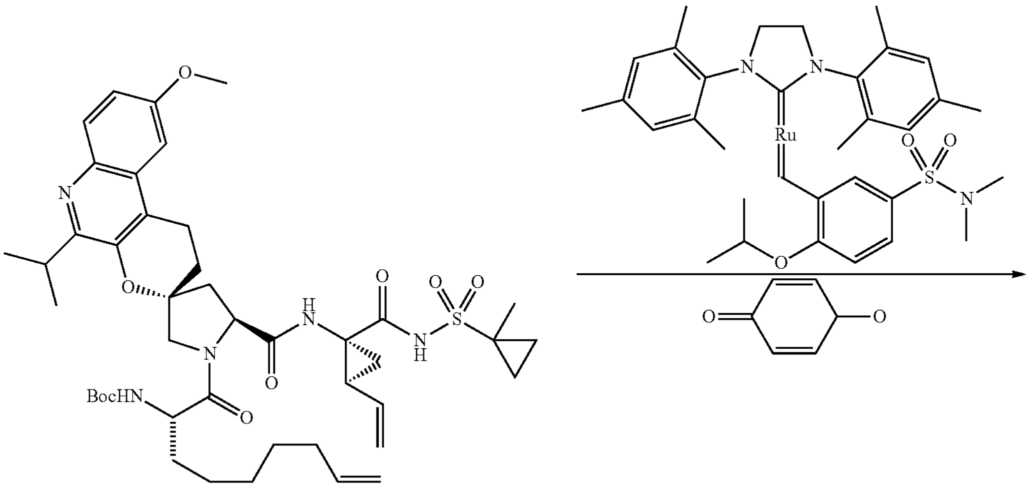

-continued

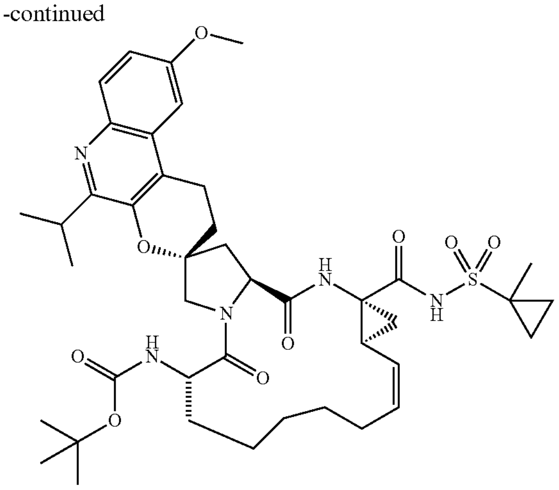

A solution of intermediate product from Step 8 (660 mg, 0.789 mmol), 1,3-bis(2,4,6-trimethylphenyl)-4,5-dihydroimidazol-2-ylidene[2-(isopropoxy)-5-(N,N -dimethylaminosulfonyl)phenyl]methyleneruthenium(II)dichloride (145 mg, 0.197 mmol) and 1,4-benzoquinone (25.6 mg, 0.237 mmol) in DCE (300 ml) was degassed, put under $N_2$, then warmed to 75° C. and stirred for 5 h. The mixture was quenched at RT with n-butyl vinyl ether (1 ml) and concentrated to dryness. The residue was purified by column chromatography over silica gel (eluting with Hexanes/EtOAc 99:1 to EtOAc) to afford I-2 (550 mg, 86% yield). $^1$H-NMR (300 MHz, $CDCl_3$) δ 10.10 (s, 1H), 7.87 (d, J=9.0 Hz, 1H), 7.17 (d, J=9.0 Hz, 1H), 6.94-7.00 (m, 2H), 5.71 (m, 1H), 5.16 (d, J=7.6 Hz, 1H), 4.99 (m, 1H), 4.59 (m, 1H), 4.36 (d, J=11.2 Hz, 1H), 4.28 (m, 1H), 3.92 (s, 3H), 3.74 (d, J=11.2 Hz, 1H), 3.41 (m, 1H), 3.00-3.12 (m, 2H), 2.50-2.60 (m, 2H), 2.21-2.40 (m, 4H), 1.72-2.06 (m, 8H), 1.10-1.55 (m, 11H), 1.47 (s, 3H), 1.31 (s, 9H), 0.80 (br s, 2H); LC-MS ($M^+$) Calc. for $C_{42}H_{57}NO_9S$ 808.0. Found 808.2.

Example 3 tert-Butyl (2S,6S,13aS,14aR,16aS,Z)-1',1'-difluoro-5'-isopropyl-9'-methoxy -14a-(1-methylcyclopropylsulfonylcarbamoyl)-5,16-dioxo-1',2',3,5,6,7,8,9,10,11,13a,14,14a, 15,16,16a-hexadecahydro-1H-spiro[cyclopropa[e]pyrrolo[1,2-a][1,4]diazacyclopentadecine -2,3'-pyrano[2,3-c]quinoline]-6-ylcarbamate (I-3)

Step 1

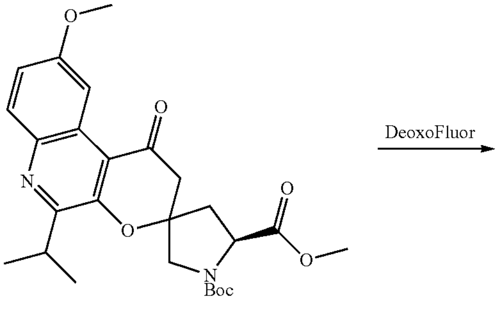

-continued

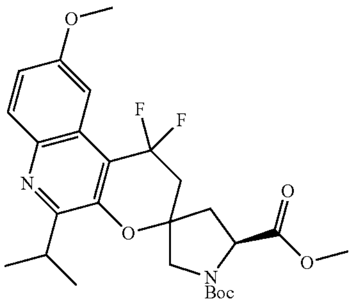

To a solution of the intermediate product of Example 2, Step 4 (1.41 g, 2.91 mmol) in DCM (10 ml) was added DeoxoFluor (2.68 ml, 14.5 mmol) then EtOH (0.017 ml, 0.29 mmol), and the mixture was warmed to 40° C. and stirred overnight. More DeoxoFluor (1.10 ml, 5.95 mmol) and EtOH (0.017 ml, 0.29 mmol) were added, and the reaction was stirred at 50° C. for 48 h. The mixture was poured into sat. aq. $NaHCO_3$ and DCM, stirred for 60 min, and extracted with DCM and EtOAc. The combined organic fractions were dried over $Na_2SO_4$, filtered and concentrated in vacuo. The residue was purified by column chromatography over silica gel (eluting with Hexanes/EtOAc 99:1 to 30:70) to give intermediate product (462 mg, 31% yield) as a mixture of diastereoisomers.

Step 2

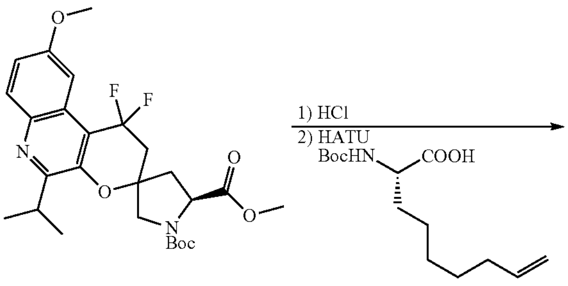

-continued

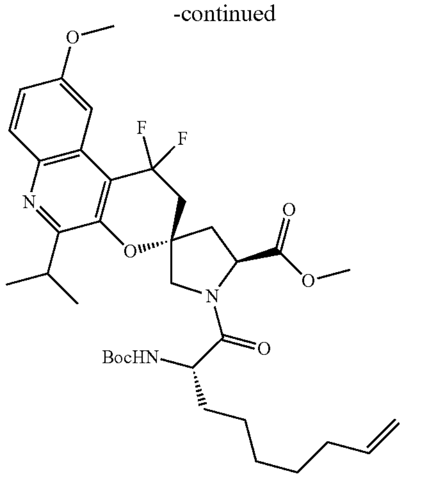

3-2A

+

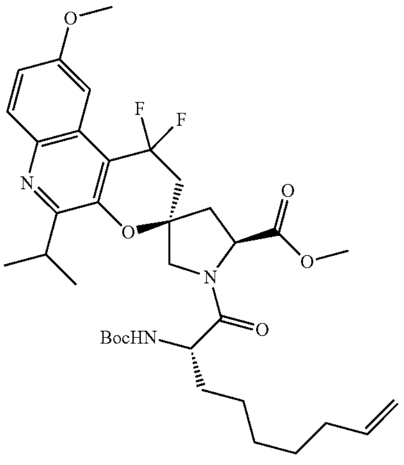

3-2B

Intermediate product from Step 1 (462 mg, 0.912 mmol) was diluted with 4N HCl in dioxane (10 ml, 40.0 mmol), and the mixture was stirred at RT for 2 h. The mixture was concentrated in vacuo to give a deprotected amine as HCl salt (449 mg, 100% yield). To a solution of this deprotected amine as HCl salt (449 mg, 1.01 mmol) and (S)-2-(tert -butoxycarbonylamino)non-8-enoic acid (344 mg, 1.27 mmol) in DMF (10 ml) at RT was added HATU (482 mg, 1.267 mmol) followed by DIPEA (0.69 ml, 4.06 mmol) and DCM (5 ml) and the mixture was stirred at RT overnight. The mixture was quenched with water and extracted with EtOAc. The combined organic fractions were washed with brine, dried over $Na_2SO_4$ filtered and concentrated in vacuo. The residue was purified by column chromatography over silica gel (eluting with Hexanes/EtOAc 99:1 to 40:60) to give, in order of elution, diastereoisomer 3-2A (418 mg) then diastereoisomer 3-2B (328 mg).

Step 3

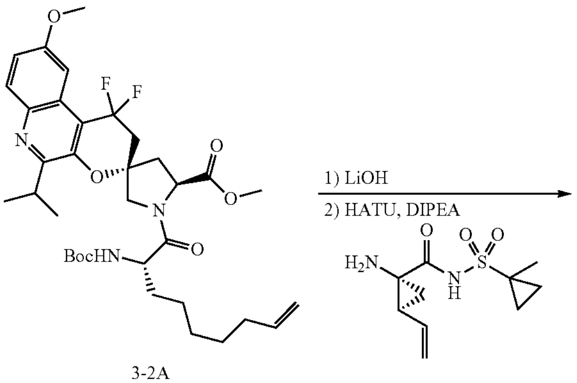

3-2A

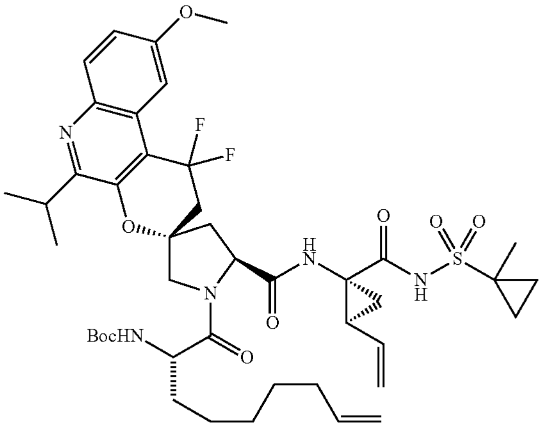

To a solution of diastereoisomer 3-2A from Step 2 (418 mg, 0.63 mmol) in THF (10 ml), MeOH (10 ml) and water (7 ml) at RT was added $LiOH.H_2O$ (80 mg, 1.90 mmol), and the mixture was warmed to 50° C. and stirred for 2 h. MeOH and THF were concentrated in vacuo, then the mixture was diluted with 0.5M aq. HCl until pH=2 and extracted with EtOAc. The combined organic fractions were dried over $Na_2SO_4$ filtered and concentrated in vacuo to give a crude acid intermediate (386 mg, 94% yield). To a solution of this crude acid intermediate (267 mg, 0.413 mmol) and (1R,2S)-1-amino-N-(1-methylcyclopropylsulfonyl)-2-vinylcyclopropanecarboxamide (121 mg, 0.496 mmol) in DMF (7 ml) at RT was added HATU (189 mg, 0.496 mmol) followed by DIPEA (0.21 ml, 1.24 mmol), and the mixture was stirred overnight. The mixture was quenched at RT with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to 30:70) to afford intermediate product (289 mg, 80% yield).

Step 4

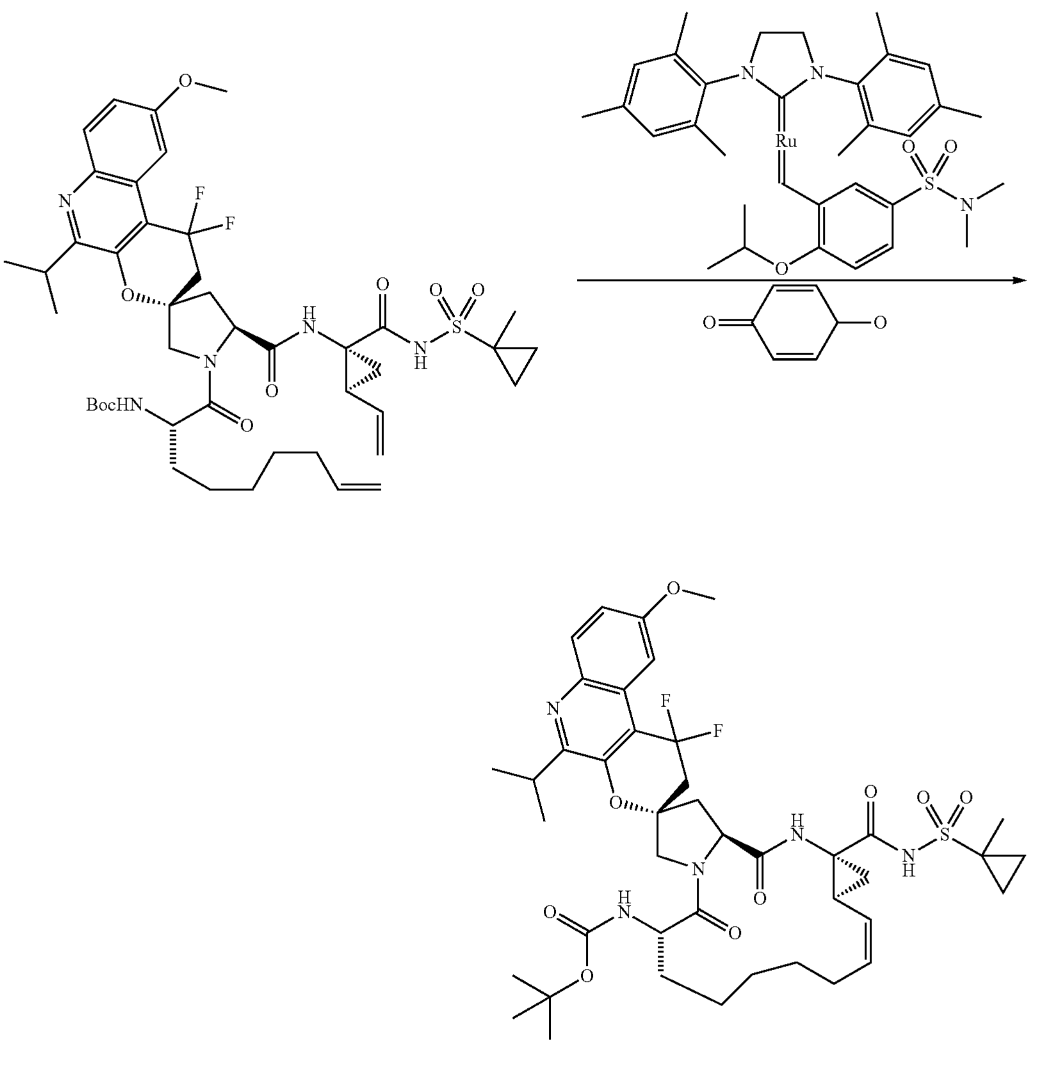

A solution of intermediate product from Step 3 (289 mg, 0.331 mmol), 1,4-benzoquinone (10.75 mg, 0.099 mmol) and 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II)dichloride (60.8 mg, 0.083 mmol) in DCE (120 ml) at RT was degassed, put under $N_2$, then warmed to 75° C. and stirred 3 h. The reaction was quenched at RT with ethyl vinyl ether (1 ml), concentrated in vacuo, then purified by column chromatography over silica gel (eluting with Hexanes/EtOAc 99:1 to 30:70) to give I-3 (256 mg, 92% yield). $^1$H-NMR (300 MHz, $CDCl_3$) δ 10.06 (s, 1H), 7.88 (d, J=9.0 Hz, 1H), 7.49 (s, 1H), 7.22 (d, J=9.0 Hz, 1H), 6.87 (s, 1H), 5.72 (m, 1H), 4.94-5.05 (m, 2H), 4.59 (m, 1H), 4.50 (d, J=11.4 Hz, 1H), 4.19 (m, 1H), 3.94 (s, 3H), 3.79 (d, J=11.4 Hz, 1H), 3.39 (m, 1H), 2.79-2.89 (m, 2H), 2.71 (m, 1H), 2.44-2.58 (m, 2H), 2.31 (m, 1H), 1.72-1.94 (m, 4H), 1.60-1.67 (m, 3H), 1.16-1.50 (m, 12H), 1.47 (s, 3H), 1.28 (s, 9H), 0.81 (br s, 2H); LC-MS ($M^+$) Calc. for $C_{42}H_{55}F_2N_5O_9S$ 844.0. Found 844.2.

Example 4 tert-Butyl (2R,6S,13aS,14aR,16aS,Z)-14a-(1-methylcyclopropylsulfonyl carbamoyl)-5,16-dioxo-5'-(trifluoromethyl)-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-6-ylcarbamate (I-4)

Step 1

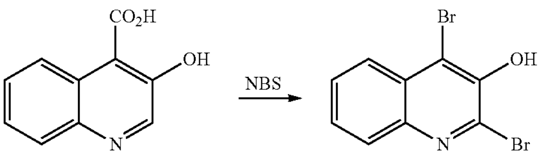

A solution of 3-hydroxyquinoline-4-carboxylic acid (10 g, 52.9 mmol) in THF (320 ml) was treated with NBS (17.88 g, 100 mmol) and stirred at RT for 2.5 h. The reaction mixture was then extracted with EtOAc and washed with water followed by aq. $Na_2S_2O_3$ solution. The combined organic layers were dried with $Na_2SO_4$ and concentrated to afford the intermediate product.

Step 2

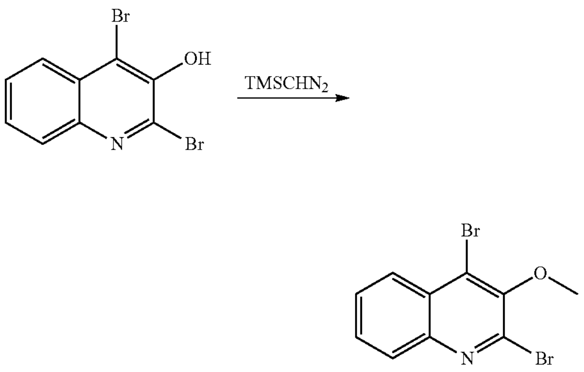

To a solution of crude product of Step 1 (18.5 g, 61.1 mmol) in MeOH (40 ml). Toluene (200 ml) and (trimethylsilyl) diazomethane ($TMSCHN_2$; 61.1 ml, 122 mmol) were added at 0° C. and stirred. The reaction mixture was warmed to RT and stirred for 30 min. Crude LC-MS showed total consumption of starting material. AcOH (3 ml) was added to the reaction mixture until bubbling stopped. The organics were evaporated, and the crude residue was dissolved in toluene and evaporated to get the crude product as brown solid, which was purified by silica gel column chromatography using (0-5) % EtOAc-Hexanes as mobile phase to get the pure intermediate product (12 g, 37.9 mmol, 62.0% yield).

Step 3

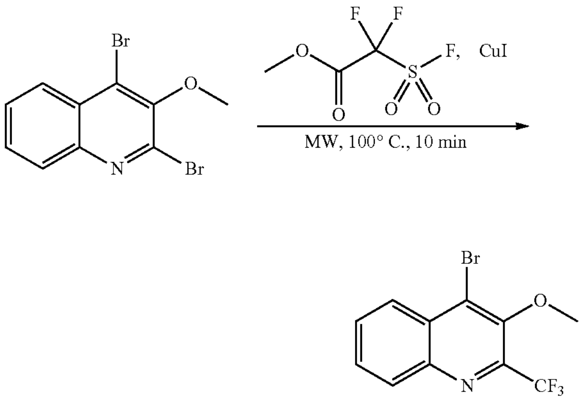

To a solution of the product of Step 2 (6 g, 18.93 mmol) in DMF (32 ml) was added Cu—I (1.803 g, 9.46 mmol) followed by MFSDA (7.22 ml, 56.8 mmol). The reaction mixture was then heated in microwave at 100° C. for 30 min at high absorbance. The reaction was diluted with EtOAc and washed with brine and water. The organics were dried with $Na_2SO_4$ concentrated and purification with 40% hexanes/EtOAc gave intermediate product (2.72 g, 8.89 mmol, 46.9% yield).

Step 4

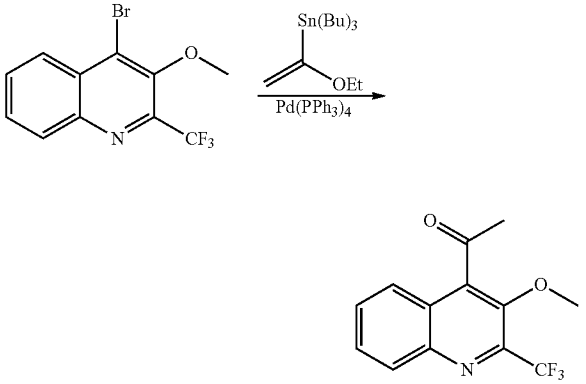

A mixture of the product of Step 3 (2.72 g, 8.89 mmol), tributyl(1-ethoxyvinyl)tin (6.00 ml, 17.77 mmol) and $Pd(PPh_3)_4$ (0.513 g, 0.444 mmol) in dioxane (40 ml) was heated at reflux overnight. The reaction mixture was cooled to RT, added ~10 ml of 1N HCl and stirred at RT for 90 min. The reaction mixture was then diluted with water, extracted 3× with DCM. The combined organic layers were washed with brine, dried over $MgSO_4$, filtered, concentrated and chromatography eluting with 0-15% EtOAc-hexanes to give product (1.3 g, 4.83 mmol, 54.3% yield).

Step 5

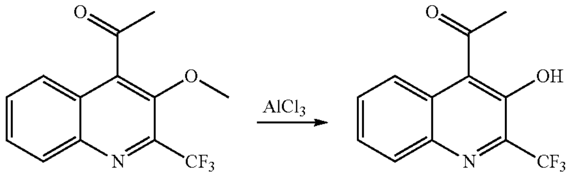

To a solution of the product of Step 5 (1.3 g, 4.83 mmol) in DCM (50 ml) at 0° C. was added $AlCl_3$ (5.79 g, 43.5 mmol) in one rapid portion, and the resulting mixture was allowed to stir at RT overnight. The reaction mixture was quenched with sat. solution of Rochelle's salt (aq.), and the biphasic reaction mixture was stirred at RT for 1H. The organic phase was separated, and the aq. layer was extracted 3× with DCM. The combined organic layers were then washed with water and brine, filtered, and concentrated. The residue was then purified by column chromatography over silica gel (eluting with Hexanes/EtOAc 99:1 to 60:40) to give the product (310 mg, 1.215 mmol, 25.2% yield).

Step 6

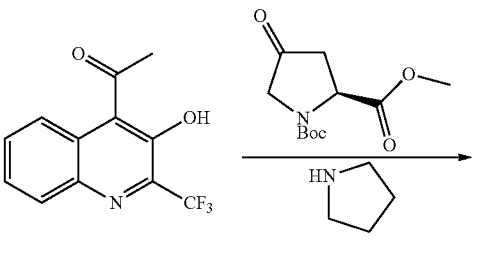

-continued

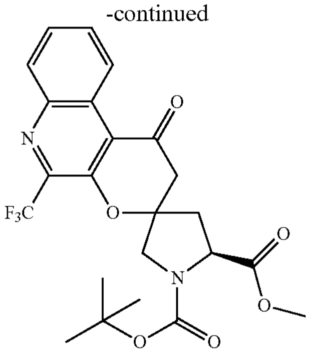

To a solution of the product of Step 5 (0.310 g, 1.215 mmol) in MeOH (4 ml) in a microwave vial was added N-Boc-4-oxo-L-proline methyl ester (0.591 g, 2.430 mmol), and pyrrolidine (0.039 ml, 0.486 mmol). To this was then added molecular sieves (4A beads), and the reaction was heated to 105° C. and stirred for 30 min in the Biotope Initiator microwave reactor on very high absorbance. The reaction was cooled to RT, and the molecular sieves were filtered off The solvent was evaporated under reduced pressure. The crude orange oil was purified by column chromatography using a silica gel column on an Ana-logix, eluting with hexanes/acetone (0-50%) over the course of 30 min to give the product (565 mg, 1.176 mmol, 97% yield) as a mixture of diastereomers.

Step 7

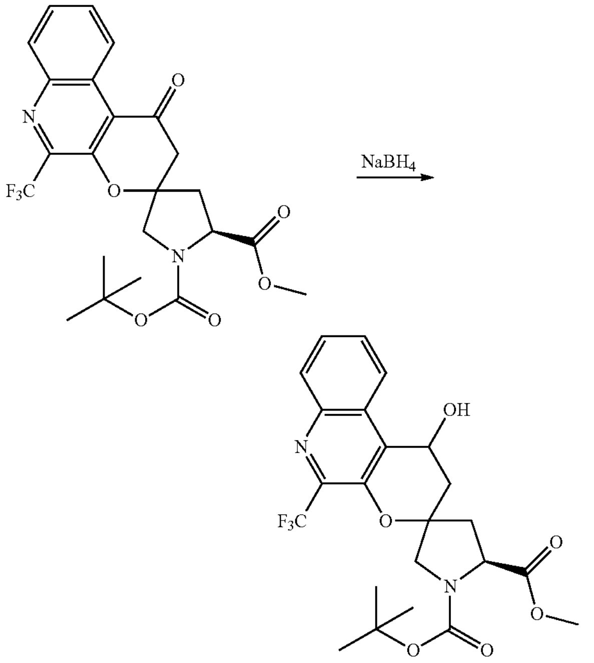

A solution of the product of Step 6 (565 mg, 1.176 mmol) was dissolved in a mixture of THF (10 ml) and MeOH (10 ml). The mixture was cooled to 0° C. and stirred for 15 min. $NaBH_4$ (57.8 mg, 1.529 mmol) was then added to the reaction, and mixture was stirred for 30 min at 0° C. The reaction was then stirred at RT for 1 h. The solvent was diluted with EtOAc and quenched with aq. $NH_4Cl$ at RT. The organic fraction was washed with 1M NaOH, brine, water, dried ($Na_2SO_4$), filtered, and the solvent was evaporated under reduced pressure. The crude yellow solid product (567 mg, 1.175 mmol, 100% yield) was taken to the next step.

Step 8

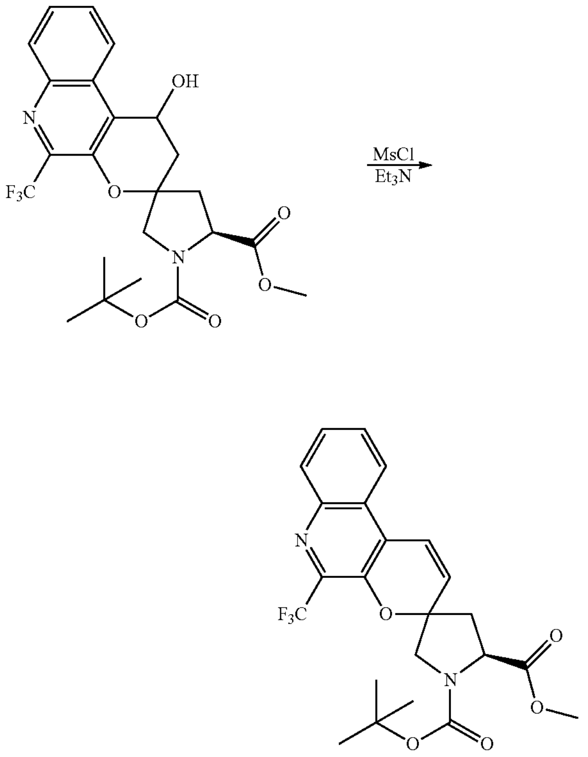

The product of Step 7 (567 mg, 1.175 mmol) and TEA (0.490 ml, 3.53 mmol) were added to DCM (6 ml). MsCl (0.136 ml, 1.763 mmol) was then added to the solution and allowed to stir overnight under $N_2$. The reaction was then quenched with sat. $NH_4Cl$, and the mixture were extracted with DCM (3×10 mL). The combined organic fractions were washed with water and dried ($Na_2SO_4$), filtered, and the solvent was evaporated under reduced pressure to obtain the product (282 mg, 0.607 mmol, 51.7% yield).

Step 9

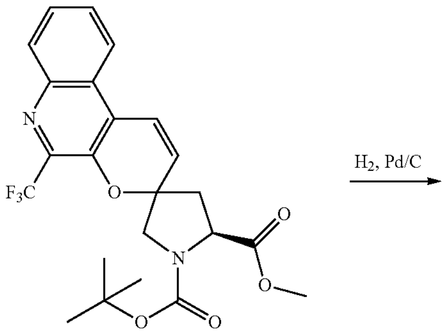

-continued

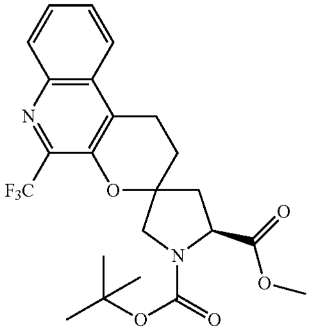

The product of Step 8 (282 mg, 0.607 mmol) was added to a stirred, cooled RT solution of EtOAc (8 ml). Pd/C (36 mg, 0.034 mmol) was added and after evacuating and back-filling with $H_2$, the reaction was allowed to stir at RT attached to a $H_2$-filled balloon for 30 min. The reaction mixture was diluted with DCM (15 mL), and the suspension was filtered through a pad of CELITE. The insoluble's were washed further with DCM, and the filtrate was concentrated in vacuo to afford product (280 mg, 0.600 mmol, 99% yield).

Step 10

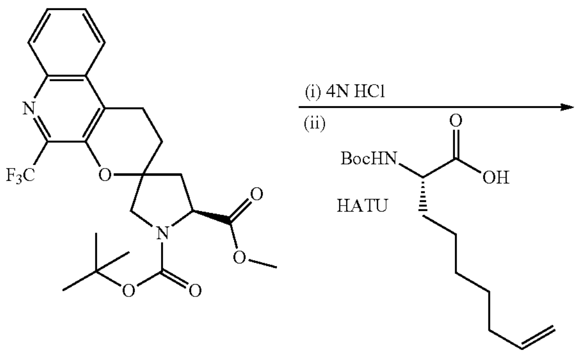

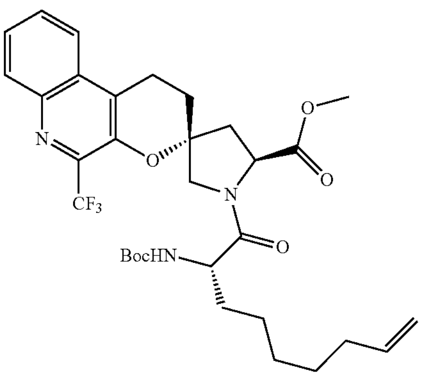

4-10A

+

-continued

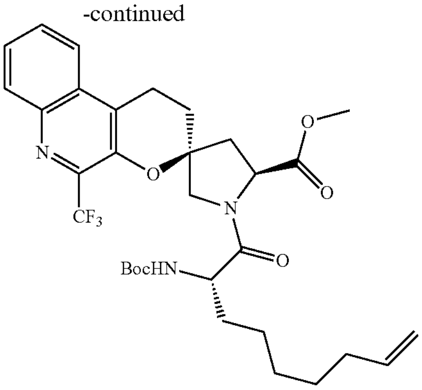

4-10B

A solution of the product of Step 9 (280 mg, 0.600 mmol) in 4N HCl in dioxane (30 ml) was stirred at RT for 1 h, evaporated 2× with toluene, 2× with ether to give the amine hydrochloride salt (230 mg, 0.571 mmol, 95% yield) and used as such for the next step. A slurry of amine salt (230 mg, 0.571 mmol), (S)-2-(tert-butoxycarbonylamino)non-8-enoic acid (388 mg, 0.857 mmol), HATU (326 mg, 0.857 mmol) and TEA (0.239 ml, 1.713 mmol) in DMF (7 ml) was stirred at RT overnight. The reaction mixture was diluted with water, and extracted 3× with EtOAc. The combined organic layers were washed with brine, dried over $MgSO_4$, filtered, concentrated and chromatographed with 0-50-100% EtOAc-hexanes to give product 4-10A (156 mg, 0.252 mmol, 44.1% yield) and 4-10B (45 mg, 0.073 mmol, 12.72% yield).

Step 11

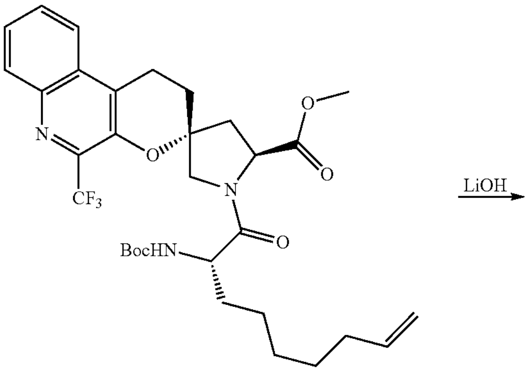

4-10A

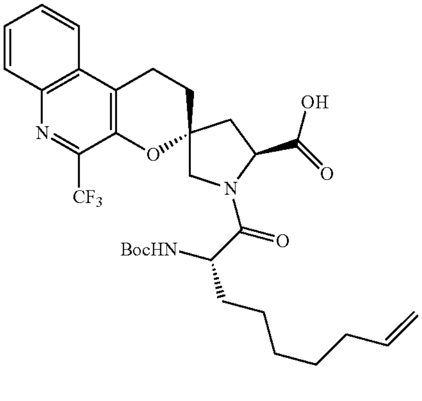

A mixture of 4-10A (156 mg, 0.252 mmol) and $LiOH.H_2O$ (42.3 mg, 1.007 mmol) in THF (1 ml), MeOH (1 ml) and water (0.7 ml) was stirred at 60° C. for 1 h. The reaction was then cooled diluted with water, acidified with 1N HCl, extracted 3× with EtOAc. The combined organic layers were washed with brine, dried over $MgSO_4$, filtered and evaporated to dryness to give the crude acid product (130 mg, 0.215 mmol, 85% yield).

Step 12

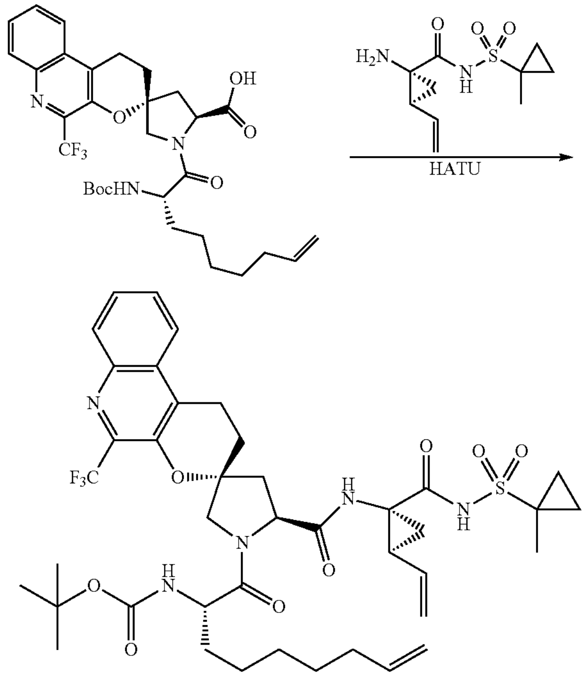

-continued

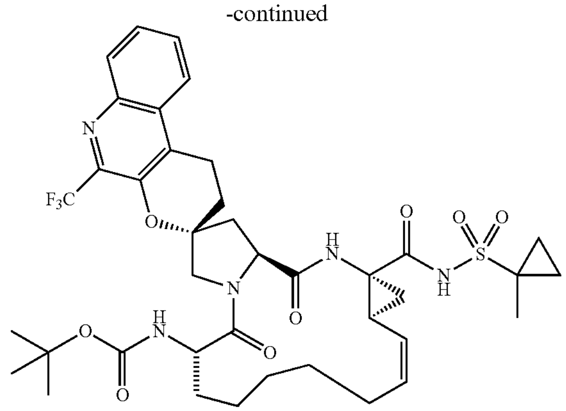

A solution of the product of Step 12 (86 mg, 0.103 mmol), Zhan's catalyst (18.96 mg, 0.026 mmol) and 1,4-benzoquinone (3.35 mg, 0.031 mmol) in DCE (35 ml) was stirred in an oil-bath kept at ~75° C. After the reaction mixture was cooled to RT and quenched with the addition of butyl vinyl ether (0.5 ml), the volatiles were removed in vacuo, and the resulting dark green/brown residue was directly purified by column 30% acetone/hexanes (ANALOGIX) to give I-4 (61 mg, 0.076 mmol, 73.4% yield). $^1$H-NMR (400 MHz, $CDCl_3$) δ 10.06 (s, 1H), 8.13-8.11 (m, 1H), 7.86-7.83 (m, 1H), 7.68-7.63 (m, 2H), 6.68 (br s, 1H), 5.76-5.69 (m, 1H), 5.05-4.99 (m, 2H), 4.60 (dd, J=10.0 Hz, 7 Hz, 1H), 4.44 (d, J=13.0 Hz, 1H), 4.21-4.16 (m, 1H), 3.71 (d, J=11 Hz, 1H), 3.32-3.15 (m, 2H), 2.58-2.33 (m, 6H), 1.95-1.76 (m, 4H), 1.6-0.8 (m, 23H). MS m/e=804.2 ($MH^+$).

To a stirred solution of the product of Step 11 (130 mg, 0.215 mmol), (1R,2S)-1-amino-N-(1-methylcyclopropylsulfonyl)-2-vinylcyclopropanecarboxamide (79 mg, 0.322 mmol), and HATU (122 mg, 0.322 mmol) in DMF (2.5 ml) was added TEA (0.09 ml, 0.64 mmol) and stirred. The mixture was stirred at RT overnight. The mixture was diluted with $Et_2O$ (20 mL), washed with water (15 ml), and back extracted with $Et_2O$ (20 ml). The combined organics were dried ($Na_2SO_4$), filtered, and the solvent was evaporated under reduced pressure. The crude yellow oil was purified by column chromatography eluting with hexanes/EtOAc (0% to 95%) to give the product (82 mg, 0.099 mmol, 45.9% yield) as yellow solid.

Step 13

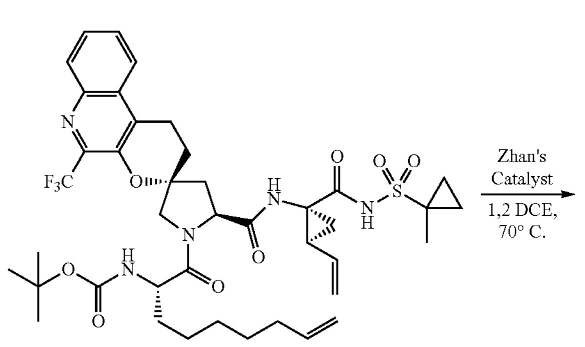

Example 5 tert-Butyl (2R,6S,13aS,14aR,16aS,Z)-9'-methoxy-14a-(1-methylcyclopropyl sulfonylcarbamoyl)-5,16-dioxo-5'-(trifluoromethyl)-1',2',3,5,6,7,8,9,10,11,13a,14,14a,15,16, 16a-hexadecahydro-1H-spiro [cyclopropa[e]pyrrolo[1,2-a][1,4] diazacyclopentadecine-2,3'-pyrano[2,3-c]quinoline]-6-ylcarbamate (I-5)

Step 1

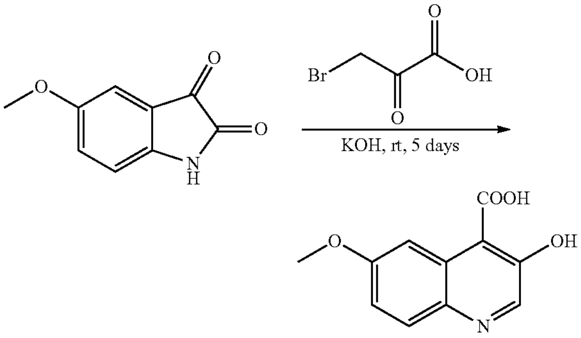

A solution of 5-methoxyindoline-2,3-dione (15 g, 85 mmol) in water (150 ml) was treated with KOH (38.0 g, 677 mmol) and heated at 80° C. until it completely dissolved. The reaction mixture was cooled and treated with bromopyruvic acid (18.94 g, 113 mmol) and stirred at RT for 5 d. The reaction mixture was treated with $NaHSO_3$ (3.0 g) and slowly acidified with concentrated HCl. The solid product (9.8 g, 44.7 mmol, 52.8% yield) separating out was filtered washed thoroughly with water, dried in the oven at 70° C. under vacuum overnight and used in the next step.

Step 2

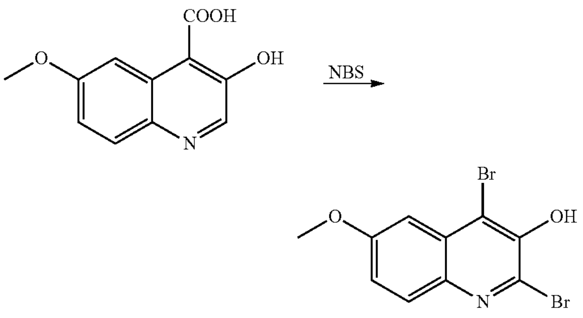

A solution of the product of Step 1 (5 g, 22.81 mmol) in THF (200 ml) was treated with NBS (8.94 g, 50.2 mmol) and stirred at RT for 2.5 h. The solution was extracted with EtOAc and washed with water and aq. $Na_2S_2O_3$ solution. The combined organic layers were dried over anhydrous $Na_2SO_4$ to obtain product (3 g, 9.01 mmol, 39.5% yield).

Step 3

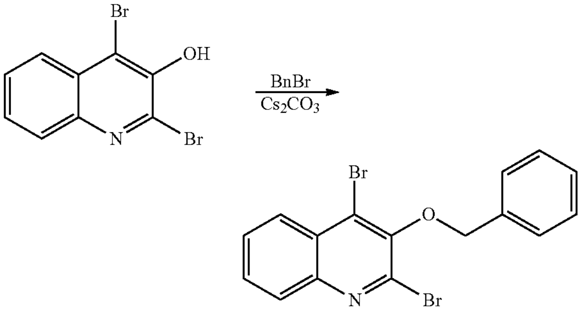

The product of Step 2 (3 g, 9.01 mmol)dissolved in DMF (25 ml) in a $N_2$-evacuated flask. BnBr (1.393 ml, 11.71 mmol) and $Cs_2CO_3$ (5.87 g, 18.02 mmol) was added. The reaction was stirred for 2 h. The reaction mixture was added to a separatory funnel containing aq. $NaHCO_3$. The reaction product was extracted with EtOAc. The combined organic fractions were dried ($Na_2SO_4$) and filtered, and the solvent was evaporated under reduced pressure. The residue was purified by column chromatography on silica gel, eluting with 0% to 30% EtOAc in hexanes over ten column volumes to give the pure product (1.48 g, 38.8% yield).

Step 4

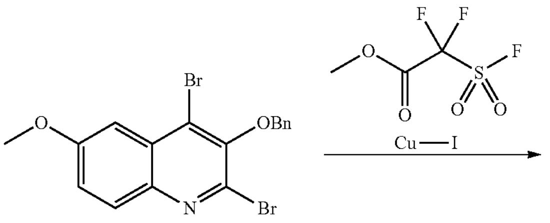

-continued

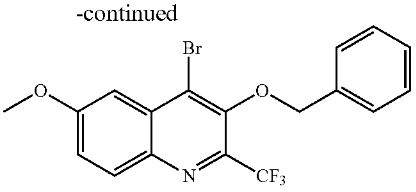

To the product of Step 3 (1.48 g, 3.50 mmol) in DMF (32 ml) was added Cu—I (0.333 g, 1.749 mmol) followed by (MFSDA) methyl 2,2-difluoro-2-(fluorosulfonyl)acetate (1.335 ml, 10.49 mmol). The solution was heated in microwave at 100° C. for 30 min at high absorbance. The solution was diluted with EtOAc and washed with brine and water. The solution was then dried with $Na_2SO_4$ concentrated and purification with chromatography eluting with 0-50% hexanes/DCM gave product (0.48 g, 1.164 mmol, 33.3% yield).

Step 5

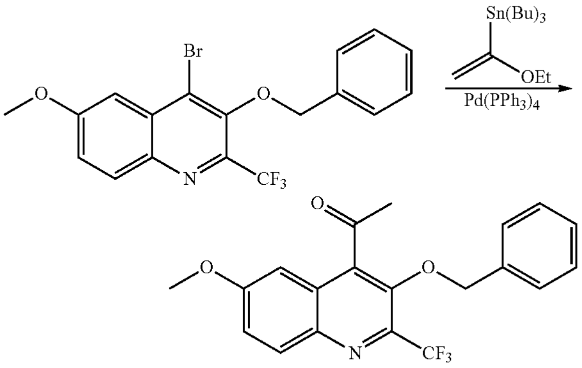

A mixture of the product of Step 4 (0.48 g, 1.164 mmol), tributyl(1-ethoxyvinyl)tin (0.787 ml, 2.329 mmol) and $Pd(PPh_3)_4$ (0.067 g, 0.058 mmol) in dioxane (5 ml) was heated at reflux overnight (oil bath temperature: 119° C.). The reaction mixture was cooled, ~10 ml of 1N HCl was added, and the reaction mixture was stirred at RT. The reaction mixture was diluted with water, extracted 3× with DCM. The combined organic layers washed with brine, dried over $MgSO_4$, filtered, concentrated and chromatographed with 0-15% EtOAc-hexanes to give product (336 mg, 0.895 mmol, 77% yield).

Step 6

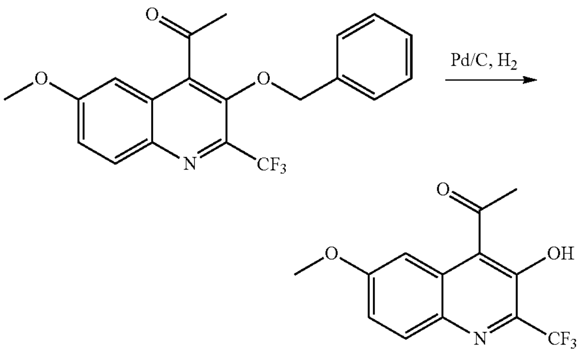

To activated Pd/C (33.3 mg, 0.313 mmol) was added the product of Step 5 (336 mg, 0.895 mmol) in THF (4 ml). A $H_2$ balloon was attached, and the reaction mixture was stirred at RT overnight. The reaction mixture was filtered through CELITE and washed with MeOH to obtain the product (225 mg, 0.789 mmol, 88% yield) contaminated with unreacted starting material.

Step 7-14

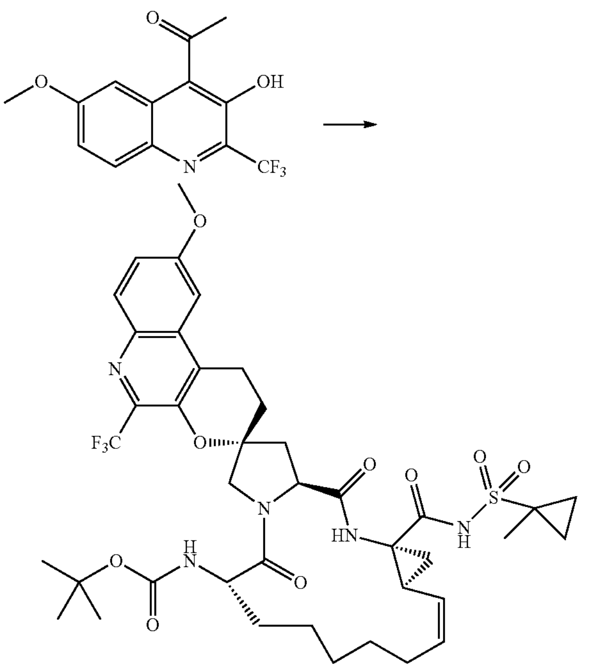

The ketone was treated under the same conditions as used in Example 4 (Steps 6 to 13) to obtain I-5. $^{1}$H-NMR (400 MHz, $CDCl_3$) δ 10.11 (s, 1H), 8.01-7.99 (d, J=9.2 Hz, 1H), 7.29-7.26 (m, 1H), 6.99 (d, J=2.6 Hz, 1H), 6.89 (br s, 1H), 5.74-5.67 (m, 1H), 5.18 (d, J=8.7 Hz, 1H), 4.99 (t, J=10.0 Hz, 1H), 4.61-4.57 (m, 1H), 4.43 (d, J=11.0 Hz, 1H), 4.23-4.17 (m, 1H), 3.96 (s, 3H), 3.71 (d, J=11.0 Hz, 1H), 3.21-3.09 (m, 2H), 2.61-2.53 (m, 2H), 2.44-2.32 (m, 4H), 1.92-0.8 (m, 27H). $^{19}$F-NMR (400 MHz, $CDCl_3$) δ −70.14. MS m/e=834.2 ($MH^+$).

Alternate Procedure for the Preparation of the Compound of Example 5 (I-5)

Step 1

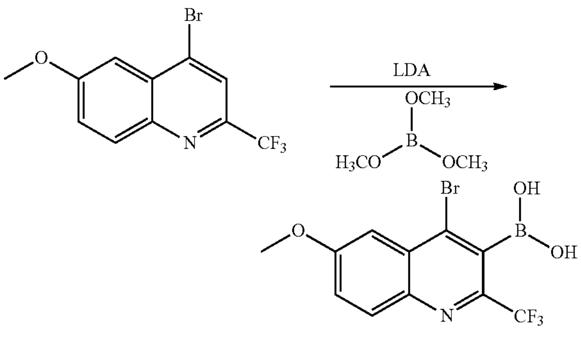

A solution of DIPA (7.16 ml, 50.6 mmol) in 35 mL of THF at −20° C. was treated with n-butyl lithium (19.60 ml, 49.0 mmol) and was stirred at −20° C. for 20 min and at 0° C. for 10 min. The reaction mixture was cooled to −78° C. (30 mins) and was treated dropwise with 2-trifluoromethyl-4-bromo-6-methoxy quinoline (5.0 g, 16.34 mmol) in THF (20.00 mL). The reaction mixture was stirred at −78° C. for 1 h. The reaction mixture was treated with trimethyl borate (14.57 ml, 131 mmol) and stirred at −78° C. for 3 h. The color of the reaction mixture changed from brown to very dark green (almost black) to green to light green to yellow over 3 h. The reaction mixture was quenched with 1N HCl until the system was acidic. The aq. solution was extracted with EtOAc (2×), combined organic layers were washed with water, dried ($Na_2SO_4$), filtered, concentrated in vacuo to obtain the product (5.3 g, 93%) and used in next step. MS m/e=350.0 ($MH^+$).

Step 2

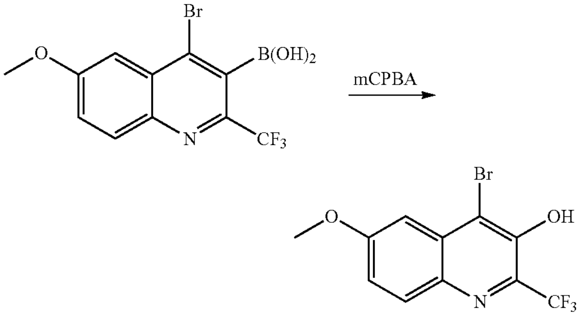

To the product from Step 1 (1 g, 2.8 mmol)dissolved in MeCN (5 ml) was added mCPBA (0.773 g, 3.36 mmol), and the reaction mixture was stirred at RT for 1 h. The reaction mixture was almost homogeneous after addition of mCPBA and then turned to a slurry. LC-MS after 1 h showed ~10% product formation and rest was starting material. Solid $NaHCO_3$ (0.282 g, 3.36 mmol) was added to the mixture, and the resulting mixture was stirred overnight at RT. LC-MS after over night stirring showed ~90% of product formation with very little starting material. $NaHSO_3$ (2.040 ml, 1.961 mmol) was added to the mixture and stirred for 1 min. The solid obtained was filtered and washed with 1:1 ACN/$H_2O$, dried in vacuum to get the product (453 mg, 1.406 mmol, 50.2% yield), which was used in the next step. MS m/e=322, 324 ($MH^+$).

Step 3

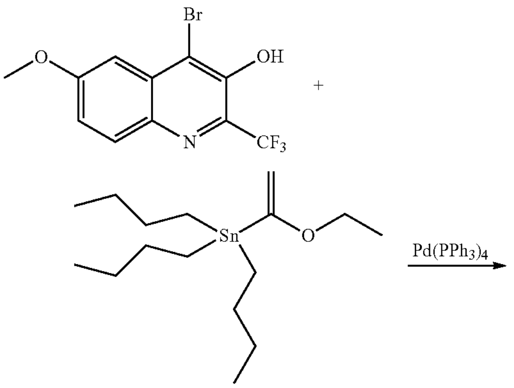

-continued

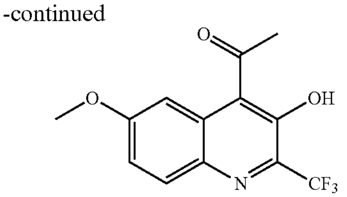

A mixture of product from Step 2 (4.42 g, 13.72 mmol), tributyl(1-ethoxyvinyl)tin (9.27 ml, 27.4 mmol) and Tetrakis (1.586 g, 1.372 mmol) in dioxane (46.5 ml) was heated at reflux overnight at 119° C. The reaction mixture was then cooled to RT, and ~35 mL of 1N HCl was added, and the reaction mixture was stirred at RT for ~30 min. LC-MS indicated hydrolysis of vinyl ether. The reaction mixture was diluted with water, extracted 3× with EtOAc, combined organic layer washed with brine, dried over $MgSO_4$, filtered and concentrated. A lot of solid was obtained. 20 ml of 10% DCM/Hexanes was added to the solid, filtered to get yellow solid, which was the desired product (2.79 g, 9.78 mmol, 71.3% yield). MS m/e=286.1 ($MH^+$).

Step 4

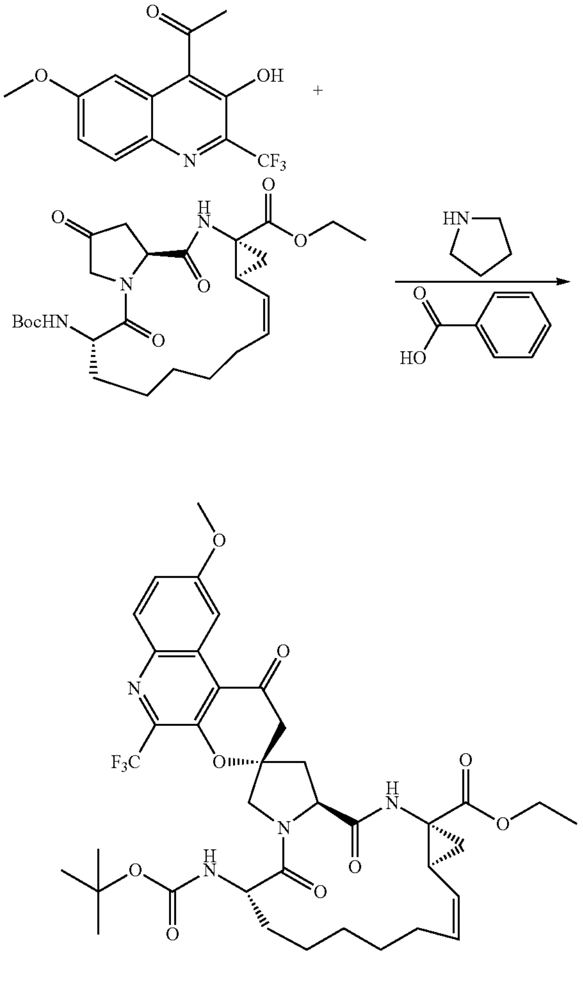

The product from Step 3 (5.25 g, 18.41 mmol), macrocyclic ketone (10 g, 20.34 mmol), benzoic acid (4.5 g, 36.8 mmol), pyrrolidine (0.61 mL, 7.36 mmol) and powdered 4A molecular sieves (1.7 g) were added in dry 2-propanol (108 mL). The reaction mixture was purged with $N_2$ and heated to 75° C. for 20 h. LC-MS shows complete consumption of starting quinoline. The reaction mixture was cooled and filtered through a minimum amount of Celite, and the filter cake was washed well with MeOH and $CH_2Cl_2$. The wash was concentrated in vacuo and purified by silica gel column chromatography using a gradient of 0-100% EtOAc/Hexanes. Further impurtites after the column purification were removed by triturating the product with acetone. The solid was collected by filtration and dried under vacuum to provide the product as a free-flowing tan solid (7.0 g, 50% yield). MS m/e=759.3 ($MH^+$).

Step 5

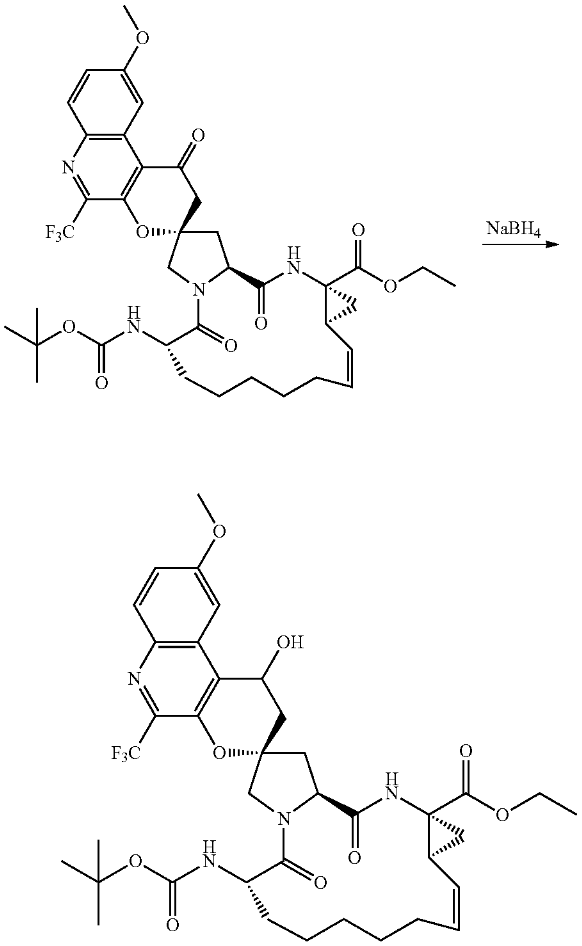

The ketone from Step 4 (5 g, 6.59 mmol) was taken up in MeOH (50 ml)/THF (17 ml) and cooled to 0° C. under $N_2$. $NaBH_4$ (0.374 g, 9.88 mmol) was then added, and the mixture stirred for 15 min. Upon completion, the reaction was quenched with sat. $NH_4Cl$ solution and diluted with EtOAc. The aq. layer was extracted with EtOAc (3×), and the combined organic extracts were washed with brine, dried over $MgSO_4$ and concentrated in vacuo to obtain the product (5.01 g, 100%). MS m/e=761.3 ($MH^+$).

Step 6

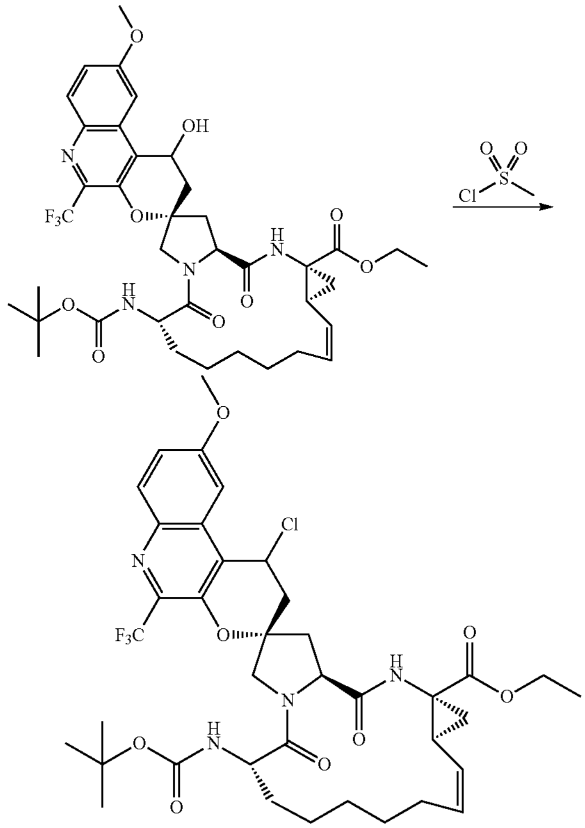

The alcohol from Step 5 (5.01 g, 6.59 mmol) was suspended in DCM (65 ml) and cooled to 0° C. under $N_2$. After 15 min, MsCl (1.284 ml, 16.48 mmol) was added, and the reaction mixture was stirred at 0° C. for 15 min. TEA (2.76 ml, 19.77 mmol) was added and the resultant mixture was allowed to warm to ambient temperature overnight. LC-MS indicated only about 20% conversion to chloride, so the reaction mixture was cooled to 0° C., and additional MsCl (1.284 ml, 16.48 mmol) and 3 eq. of TEA (2.76 ml, 19.77 mmol) were added. LC-MS showed reaction complete. The reaction mixture was diluted with EtOAc, washed with sat. $NaHCO_3$ solution (2×) and brine. The reaction mixture was dried over $MgSO_4$, concentrated in vacuo, and purified by column chromatography (ISCO system, 50% EtOAC/hexanes) to give product (3.9 g, 5.00 mmol, 76% yield). MS m/e=779.3 ($MH^+$).

Step 7

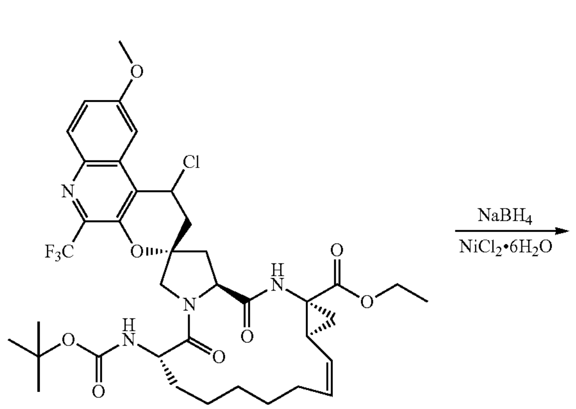

-continued

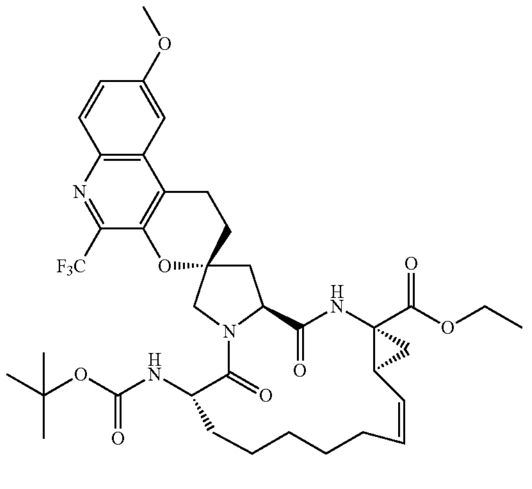

The chloride from Step 6 (3.9 g, 5.00 mmol) was suspended in MeOH, and $NiCl_2.6H_2O$ (3.57 g, 15.01 mmol) was added. The reaction mixture was allowed for the Ni catalyst to fully dissolve (light green color). The mixture was then cooled to −78° C., and $NaBH_4$ (0.473 g, 12.51 mmol) was added in one portion. After stirring the light green solution at −78° C. for 1 h, an aliquot was taken and quenched into HCl—$CH_3CN$ for LC-MS. The LC-MS showed completion. The reaction mixture was quenched by dumping the cold mixture into a stirring mixture of saturated $NaHCO_3$ (aq) solution (200 mL) and EtOAc (100 mL). The mixture was diluted with EtOAc, and the aq. layer was extracted with EtOAc (3×). The combined organic extracts were washed with sat. $NaHCO_3$ solution (3×) and brine (1×). The solution was dried over $MgSO_4$, filtered, and concentrated in vacuo to give the product (3.5 g, 4.70 mmol, 94% yield). MS m/e=745.4 ($MH^+$).

Step 8

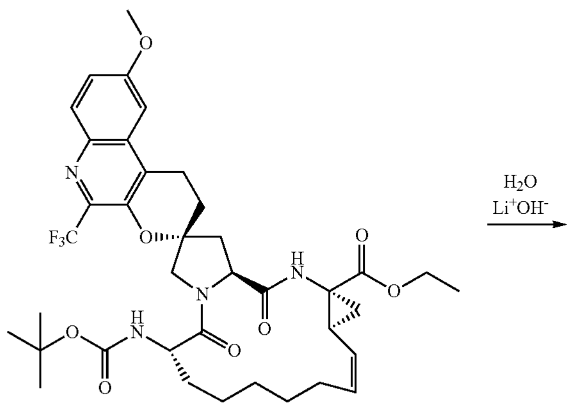

-continued

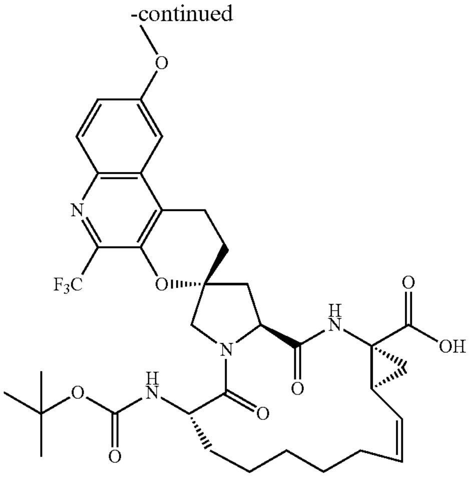

The ester from Step 7 (3.5 g, 4.70 mmol) was suspended in MeOH (20 mL)/THF (72 mL), and $LiOH.H_2O$ (1.18 g, 28.2 mmol) was added. The yellow solution was heated to 60° C. LC-MS after 1.5 h showed hydrolysis complete, so the solution was acidified to pH 2 with 1N HCl. The reaction mixture was diluted with EtOAC and $H_2O$. The layers were separated, and the aq. layer was extracted with EtOAc. The organic layers were combined and washed with brine (4×), ensuring that last brine wash was not acidic. The solution was dried over $MgSO_4$, concentrated in vacuo, and azeotroped with toluene (4×). The resulting white solid was placed under high vacuum and dried to obtain the product (3.37 g, 4.70 mmol, 100% yield). MS m/e=717.4 ($MH^+$).

Step 9

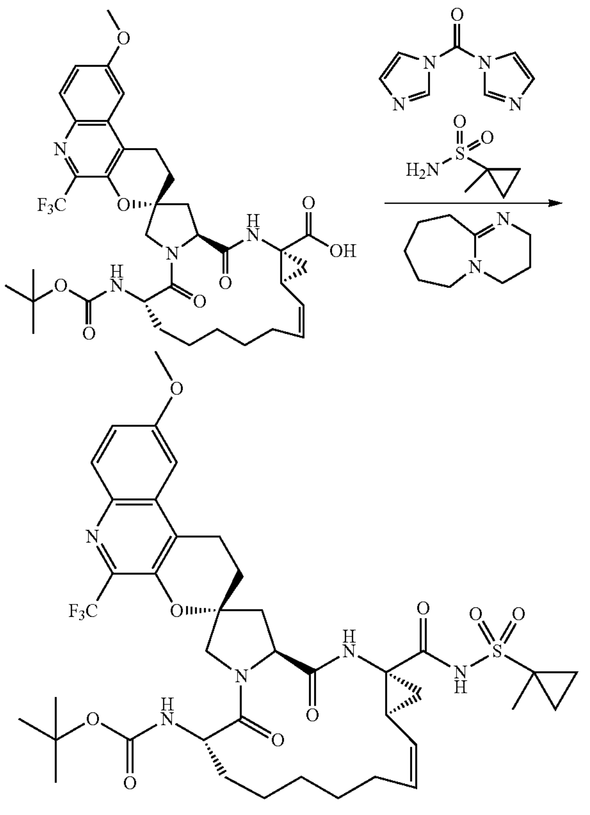

A solution of product from Step 8 (3.37 g, 4.70 mmol) and CDI (1.32 g, 8.14 mmol) in THF (64 ml) was stirred in an oil-bath kept at 70° C. for 3 h, then cooled to RT. To this was added 1-methylcyclopropane-1-sulfonamide (1.589 g, 11.75 mmol) and DBU (11.75 ml, 11.75 mmol) in THF(1M), and the mixture was stirred in an oil-bath kept at 50° C. for overnight. LC-MS indicated that the major peak is desired product. The reaction mixture was diluted with EtOAc (200 ml), washed with aq. $NH_4Cl$ (2×50 ml), brine, water (2×50 mL) dried over $MgSO_4$, filtered and concentrated. The residue was first purified by 30% EtOAc/DCM, and then clean fractions were further purified (dry loading with silica gel) with 0-30% EtOAc/hexanes 10 min to 30% hexanes/EtOAc over 20 min 30-75% EtOAc/hexanes over 20 min to give I-5 (2.2 g, 2.64 mmol, 56.1% yield). MS m/e=834.4 ($MH^+$).

Example 6

Isobutyl ((2R,6S,13aS,14aR,16aS,Z)-9'-methoxy-14a-(((1-methylcyclopropyl) sulfonyl)carbamoyl)-5,16-dioxo-5'-(trifluoromethyl)-1',2',3,5,6,7,8,9,10,11,13a,14,14a, 15,16,16a-hexadecahydro-1H-spiro [cyclopropa[e]pyrrolo[1,2-a][1,4] diazacyclopentadecine -2,3'-pyrano[2,3-c]quinolin]-6-yl)carbamate (I-6) Step 1

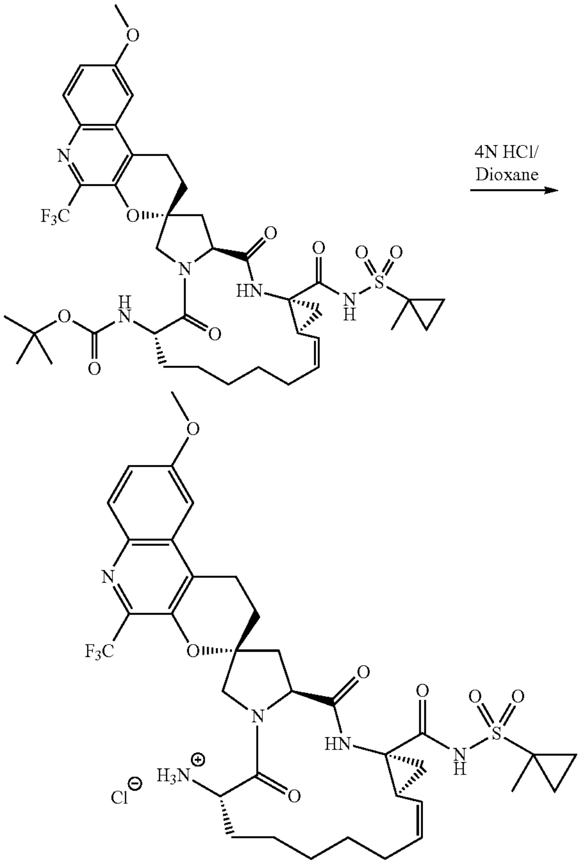

To a solution of I-5 (70 mg, 0.080 mmol) in DCM (1 ml) was added 4M HCl in dioxane (0.020 ml, 0.080 mmol). The resulting mixture was allowed to stir at RT for 3 h. The volatiles were then removed in vacuo to furnish crude product as a white solid (62 mg, 0.080 mmol, 100% yield). MS m/e=734.2 ($MH^+$). This material was used without further purification in the next step.

Step 2

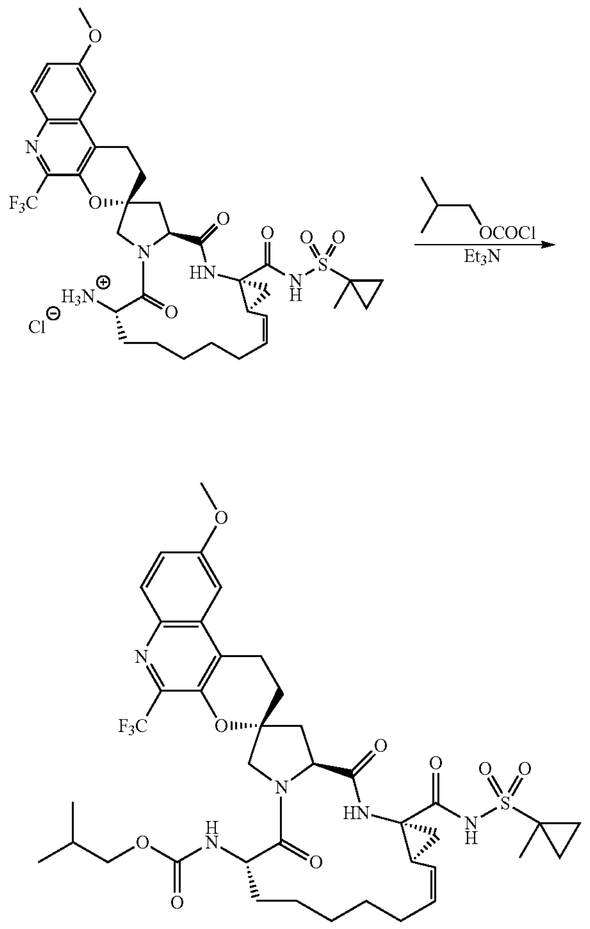

A solution of the product of Step 1 (35 mg, 0.045 mmol), TEA (0.019 ml, 0.136 mmol) and isobutyl chloroformate (0.012 ml, 0.091 mmol) in DCM (2 ml) was stirred at RT for 1 h. The reaction was then quenched with $NH_4Cl$ and extracted with DCM. The organics were washed 2× with water, brine and dried over $Na_2SO_4$. It was then filtered, concentrated and chromatographed with 0-40% acetone-hexanes to give I-6 (25 mg, 0.030 mmol, 66%). MS m/e=834.2 ($MH^+$). $^1H$ NMR δ (ppm)($CHCl_3$-d): 10.17 (1 H, s), 8.03 (1 H, d, J=9.21 Hz), 7.33-7.28 (2 H, m), 7.04 (1 H, d, J=2.66 Hz), 6.89 (1 H, s), 5.74 (1 H, q, J=8.88 Hz), 5.28 (1 H, d, J=8.78 Hz), 5.03 (1 H, t, J=9.45 Hz), 4.65 (1 H, dd, J=9.65, 7.08 Hz), 4.55 (1 H, d, J=11.06 Hz), 4.22 (1 H, t, J=9.47 Hz), 3.99 (3 H, s), 3.70 (1 H, d, J=10.94 Hz), 3.65-3.55 (2 H, m), 3.24-3.19 (1 H, m), 3.15 (1 H, t, J=8.26 Hz), 2.60 (2 H, dd, J=13.53, 7.08 Hz), 2.49-2.33 (5 H, m), 2.20 (1 H, s), 1.94 (1 H, t, J=7.11 Hz), 1.89-1.72 (4 H, m), 1.42-1.25 (7 H, m), 0.93-0.78 (10 H, m).

Example 7 tert-Butyl ((2R,6S,13aS,14aR,16aS,Z)-14a-(((1-methylcyclopropyl)sulfonyl) carbamoyl)-9'-(2-morpholinoethoxy)-5,16-dioxo-5'-(trifluoromethyl)-1',2',3,5,6,7,8,9,10, 11,13a,14,14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I-7)

Step 1

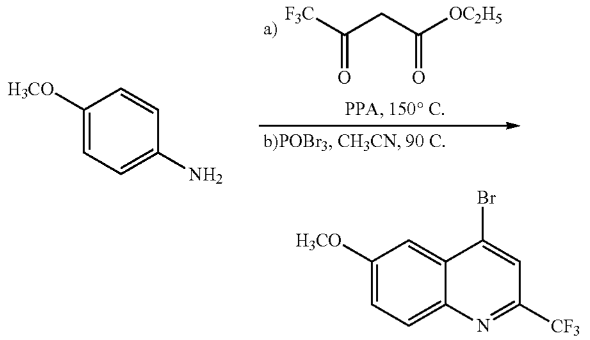

A solution of trifluoro-3-oxa-butyrate (14.95 g, 81 mmol) and PPA (72 ml) was heated at 100° C. and then treated with p-anisidine (10 g, 81 mmol) portion wise. The reaction mixture was further heated to 150° C. and stirred for 2 h at 150° C. After cooling to RT, the reaction mixture was poured into a beaker containing ice water. After stirring for 20 min, the mixture was filtered, and the resulting solid was washed with water (~3 L). The resulting pinkish-purple solid was dried under vacuum to provide 6-methoxy-2-(trifluoromethyl) quinolin -4-ol (11.58 g, 47.6 mmol, 58.6% yield), which was used without purification.

To a solution of above prepared 6-methoxy-2-(trifluoromethyl)quinolin-4-ol (11.55 g, 47.5 mmol) in MeCN (50 ml) was added $POBr_3$ (16.34 g, 57.0 mmol), and the reaction was stirred at 90° C. for 2 h. After bringing to RT, the reaction mixture was slowly poured into aq. sat. $NaHCO_3$ and extracted with EtOAc (200 mL×2). The aq. fraction was back extracted once with EtOAc, and then the combined organic fractions were washed with brine, dried ($MgSO_4$), filtered and concentrated under reduced pressure to give 13.6 g crude material. Purification by column chromatography (0-10% EtOAc in hexane) provided intermediate (12.9 g, 42.1 mmol, 89% yield).

Step 2

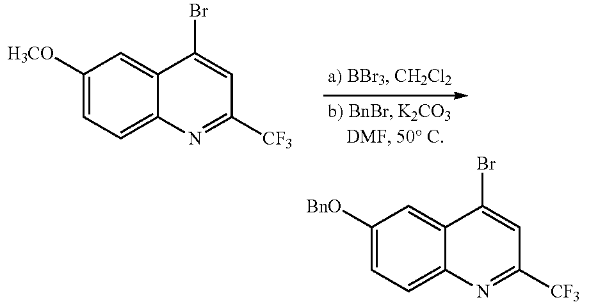

To a solution of the product of Step 1 (12.9 g, 42.1 mmol) in DCM (281 ml) was added $BBr_3$ (8.12 ml, 84 mmol) at 0° C., and the reaction was stirred for 1 h at 0° C. and then at RT for 1 h. TLC (20% EtOAc in hexane) indicated complete consumption of the starting material. The reaction was carefully poured onto ice-cold solution of sat. $NaHCO_3$. The $NaHCO_3$ layer was extracted with EtOAc (600 mL), and the organic layer was washed with brine, dried ($MgSO_4$), filtered, concentrated in vacuo and purified by silica gel chromatography (0-20% EtOAc in hexane) to provide 4-bromo-2-(trifluoromethyl)quinolin-6-ol (11.65 g, 39.9 mmol, 95% yield).

To a solution of 4-bromo-2-(trifluoromethyl)quinolin-6-ol (11.6 g, 39.7 mmol) in DMF (200 ml) was added $K_2CO_3$ (8.23 g, 59.6 mmol) followed by benzyl bromide (5.91 ml, 49.6 mmol). The reaction was stirred under $N_2$ at 50° C. overnight. After cooling to RT, the reaction mixture was diluted with water and extracted with EtOAc. The combined organic layers were dried ($MgSO_4$), filtered, concentrated in vacuo and purified by silica gel chromaography (0-5% EtOAc in hexane) to yield product intermediate (12.0 g, 31.4 mmol, 79% yield) as a white solid.

Step 3

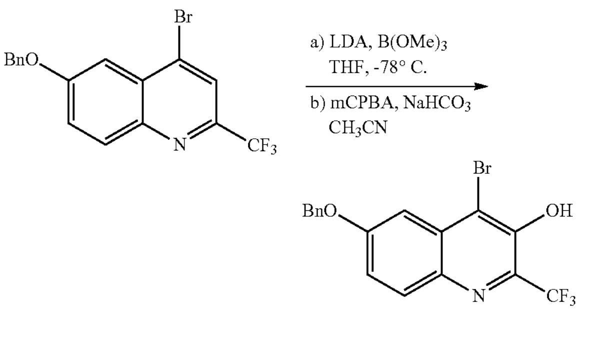

To solution of DIPA (13.76 ml, 97 mmol) in THF (70 ml) at −20° C. was added nBuLi (37.7 ml, 94 mmol) under $N_2$, and the solution was stirred at −20° C. for 20 min and at 0° C. for 10 min. The reaction mixture was cooled to −78° C. and treated with the product of Step 2 (12.00 g, 31.4 mmol) in THF (40.0 ml) dropwise (15-20 min) and stirred at −78° C. for 1.5 h. The reaction mixture was then treated with trimethyl borate (28.0 ml, 251 mmol) and stirred at −78° C. for an additional 3 h. LC-MS at this stage indicated complete consumption of the starting material to a peak with desired mass. The reaction mixture was quenched carefully at −78° C. with 1N HCl until acidic. The aq. solution was extracted with EtOAc (2×), and the combined organic layers were washed with water, dried ($MgSO_4$), filtered and concentrated in vacuo to provide (6-(benzyloxy)-4-bromo-2-(trifluoromethyl)quinolin-3-yl)boronic acid (13.8 g, 32.4 mmol, 103% yield), which was used without purification.

(6-(Benzyloxy)-4-bromo-2-(trifluoromethyl)quinolin-3-yl)boronic acid (13.8 g, 32.4 mmol) was taken in MeCN (70 ml), and to this mixture was added mCPBA (8.94 g, 38.9 mmol) followed by $NaHCO_3$ (3.27 g, 38.9 mmol). The reaction was stirred overnight at RT, at which stage LC-MS indicated complete consumption of the starting material. A solution of $NaHSO_3$ (23.60 ml, 22.68 mmol) in 70 mL water was added, and the reaction was stirred for 10-15 min after which the solid was filtered off and washed once with 40 mL MeCN and then several times with water. The solid was collected and dried under vacuum to provide product (9.0 g, 22.60 mmol, 69.8% yield) as a white solid.

Step 4

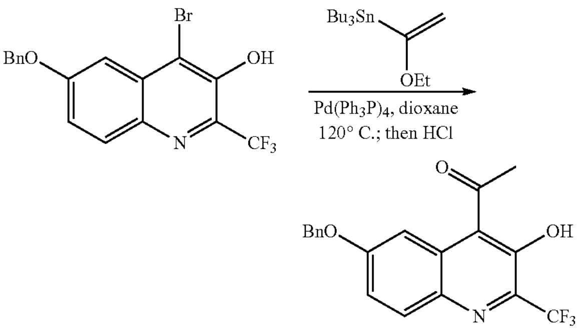

A mixture of the product of Step 3 (9.0 g, 22.60 mmol), tributyl(1-ethoxyvinyl)tin (15.27 ml, 45.2 mmol) and $Pd(PPh_3)_4$ (2.61 g, 2.260 mmol) in dioxane (75 ml) was heated at 120° C. after purging with $N_2$ for 5 min. Upon complete consumption of the starting material, the reaction was cooled to RT and quenched with ~130 mL 1M aq. HCl. The reaction was left stirring overnight at RT and then extracted with EtOAc. The combined organic fractions were washed with water and brine, dried ($MgSO_4$) and concentrated. Purification by column chromatography (0-30% EtOAc in hexane) provided the product of Step 4 (6.9 g, 19.10 mmol, 84% yield).

Step 5

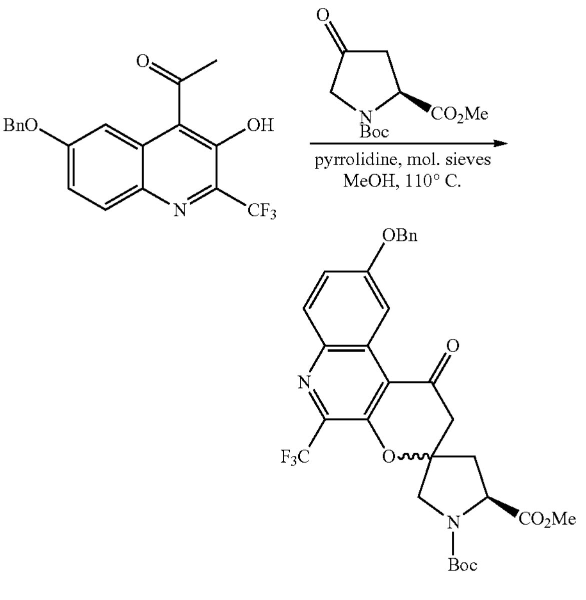

The product of Step 4 (6.9 g, 19.10 mmol), commercially available (S)-1-tert-butyl 2-methyl 4-oxopyrrolidine-1,2-dicarboxylate (9.29 g, 38.2 mmol) and pyrrolidine (0.610 ml, 7.64 mmol) were combined in MeOH (40 ml) in a microwave vial. Molecular sieves (4A beads, 6-7 pieces) were added to the reaction mixture, and the resulting mixture was heated at 105° C. for 30 min in a Biotage Initiator microwave reactor. After cooling to RT, the reaction was filtered, and the residue was washed with MeOH. The filtrate was concentrated, and the residue was purified by silica gel column chromatography (0-60% EtOAc in hexane) to provide the product of Step 5 (8.8 g, 15.00 mmol, 79% yield) as a mixture of two diastereomers that were not separated at this stage.

Step 6

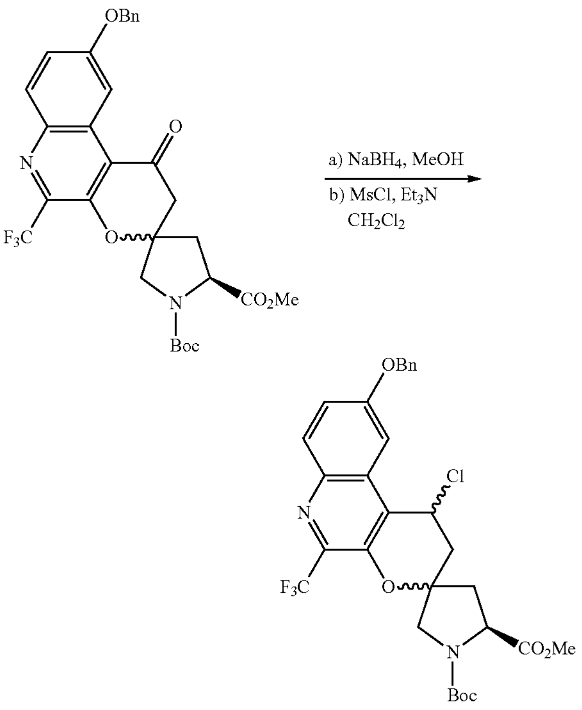

A solution of the product of Step 5 (2.28 g) in MeOH (40.0 mL) was cooled to 0° C. and treated with $NaBH_4$ (0.57 g, 15.0 mmol). After stirring at 0° C. for 1 h, the reaction was quenched with aq. $NaHCO_3$ and extracted with EtOAc. The combined organic layers were washed with brine, dried ($MgSO_4$), filtered, and concentrated under reduced pressure to provide the corresponding hydroxyl compound (8.73 g, 14.83 mmol, 99% yield), which was used without further purification.

To a solution of the above prepared hydroxyl compound (8.73 g, 14.83 mmol) in $CH_2C_{12}$ (124 ml) was added TEA (5.17 ml, 37.1 mmol) followed by MsCl (2.296 ml, 29.7 mmol) at 0° C. The reaction was allowed to warm to RT and stirred overnight. The reaction was diluted with EtOAc and washed with water and brine. The organic layer was dried ($MgSO_4$), filtered, and concentrated to give the product of Step 6 in quantitative yield, which was used further without purification.

Step 7

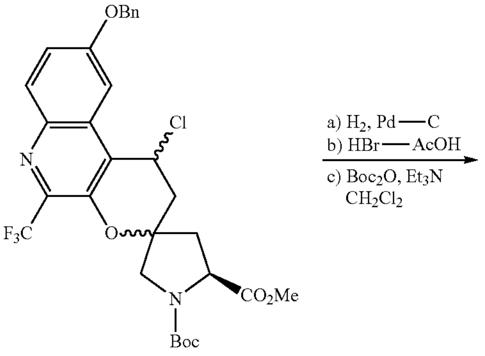

-continued

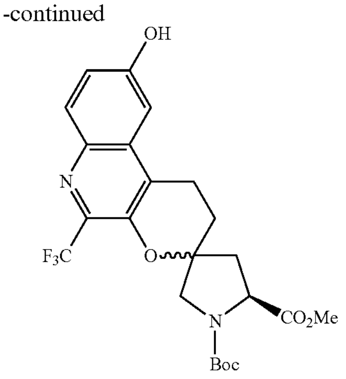

To a solution of the product of Step 6 (9.60 g, 15.82 mmol) in EtOAc (600 mL) was added 10% Pd/C (1.515 g, 1.423 mmol), and the reaction was hydrogenated under a balloon atmosphere for 30 min, at which stage LC-MS indicated complete conversion to the dechlorination product (no debenzylation was observed). The reaction was filtered through CELITE, and the cake was washed with EtOAc. After removing the solvent under reduced pressure, the resulting orange solid was purified by column chromatography (220 g column, 0-60% EtOAc in hexane) to provide the corresponding dechlorinated product (5'S)-1'-tert-butyl 5'-methyl 9-(benzyloxy)-5-(trifluoromethyl)-1,2-dihydrospiro[pyrano[2,3-c]quinoline-3,3'-pyrrolidine]-1',5'-dicarboxylate (6.56 g, 11.46 mmol, 72.4% yield).

A solution of (5'S)-1'-tert-butyl 5'-methyl 9-(benzyloxy)-5-(trifluoromethyl)-1,2-dihydrospiro[pyrano[2,3-c]quinoline-3,3'-pyrrolidine]-1',5'-dicarboxylate (2 g, 3.49 mmol) and HBr in glacial AcOH (20 mL, 177 mmol) was stirred at RT for 4 h. After removing the solvent under reduced pressure, the residue was azeotroped 3x with toluene and then dried under vacuum before using the crude.

To the crude from above in DCM (34.5 ml) was added TEA (0.626 ml, 4.49 mmol), and the reaction was stirred for 15 min at RT during which a homogeneous solution was obtained. $BOC_2O$ (1.203 ml, 5.18 mmol) was added, and the reaction was stirred at RT under $N_2$ for 1 h. The reaction was treated with sat. aq. $NH_4Cl$ solution and extracted with DCM. The organic fraction was washed with sat. aq. $NH_4Cl$ solution, water and brine and then dried ($MgSO_4$), filtered and concentrated to give a brown oily residue. Purification by column chromatography (0-60% acetone in hexane) gave the product of Step 7 (0.95 g, 1.969 mmol, 57.0% yield).

Step 8

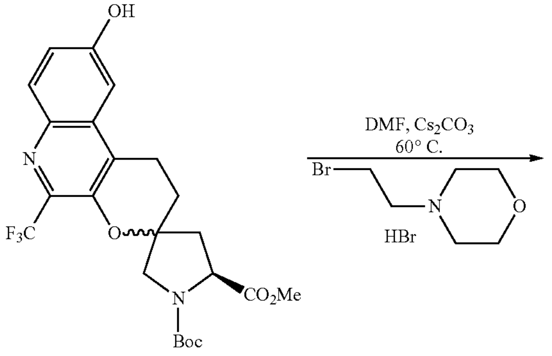

-continued

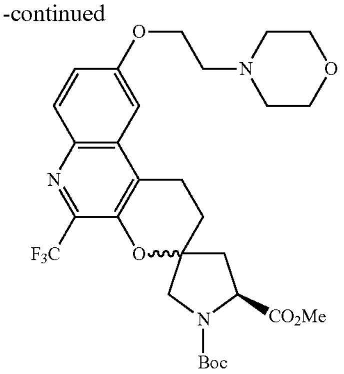

A suspension of the product of Step 7 (440 mg, 0.912 mmol), 4-(2-bromoethyl)morpholine HBr salt (502 mg, 1.824 mmol) and $Cs_2CO_3$ (891 mg, 2.74 mmol) in DMF (9120 µl) was stirred at 55° C. for 2 h. After bringing to RT, the reaction was diluted with EtOAc and washed with water. The organic fractions were washed with water and brine, dried with $Na_2SO_4$ and concentrated. The resulting residue was purified by column chromatography (0-60% acetone in hexane) to afford the product of Step 8 (470 mg, 0.789 mmol, 87% yield) as a mixture of diastereomers.

Step 9

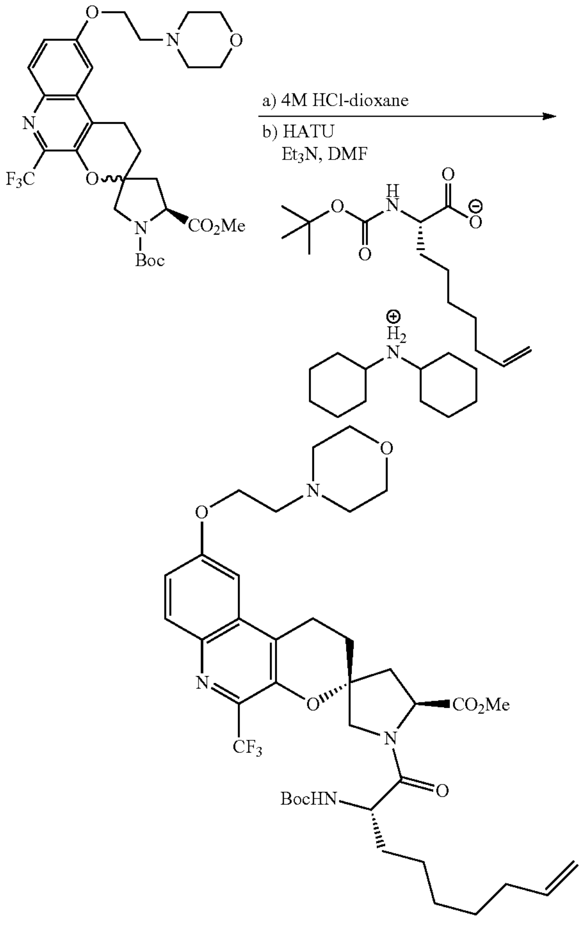

A solution of the product of Step 8 (470 mg, 0.789 mmol) and 4M HCl in dioxane (3 mL, 36.5 mmol) was stirred at RT for 2 h. The volatiles were removed under reduced pressure, and the residue was azeotroped 3× with toluene. The solid thus obtained was taken in DMF (7.90 mL) and treated with TEA (0.451 mL, 3.24 mmol), dicyclohexylammonium (S)-2-((tert -butoxycarbonyl)amino)non-8-enoate (715 mg, 1.579 mmol) followed by HATU (600 mg, 1.579 mmol) at RT under $N_2$. The reaction was stirred at RT overnight and then diluted with EtOAc and washed with water and brine. The organic fraction was dried ($MgSO_4$), concentrated and purified by silica gel column chromatography (0-50-80% acetone in DCM) to provide the product of Step 9 (385 mg, 0.514 mmol, 65.1% yield) and its diasteromer.

Step 10

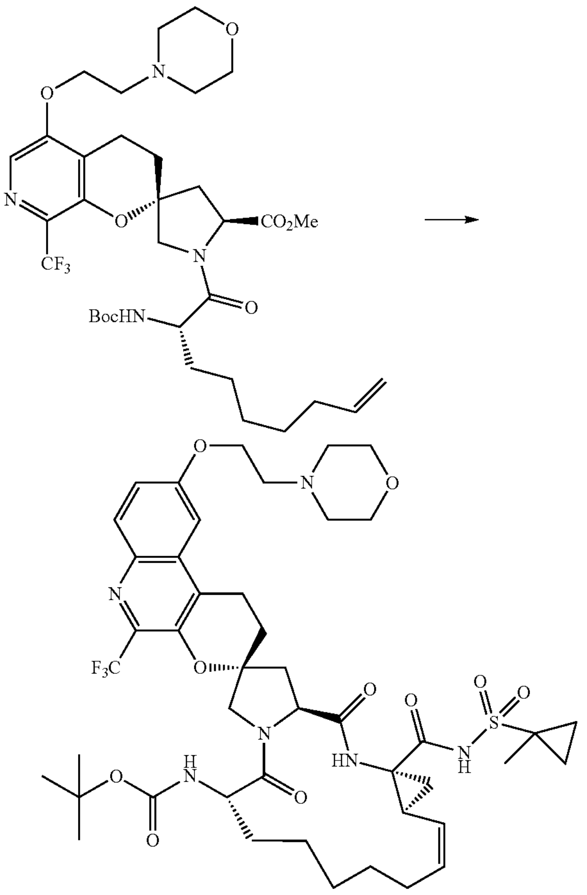

The product of Step 9 was converted to I-7 using the procedures as described in Example 1, Steps 8 and 9.

Example 8 tert-Butyl ((2'R,6'S,13a'S,14a'R,16a'S,Z)-9-methoxy-14a'-(((1-methyl cyclopropyl)sulfonyl)carbamoyl)-5',16'-dioxo-5-(trifluoromethyl)-3',5',6',7',8',9',10',11',13a',14',14a',15',16',16a'-tetradecahydro-1H,2H-spiro[[1,4]dioxino[2,3-c]quinoline-3,2'-cyclopropa[e]pyrrolo[1,2-a][1,4]diazacyclopentadecin]-6'-yl)carbamate (I-8)

Step 1

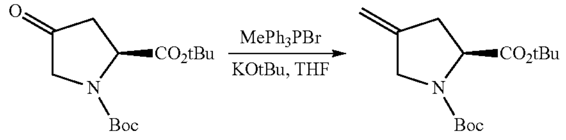 [SMILES: CC(C)(C)OC(=O)[C@@H]1CC(=O)CN1C(=O)OC(C)(C)C ; "MePh3PBr" ; C=C1C[C@@H](C(=O)OC(C)(C)C)N(C(=O)OC(C)(C)C)C1]

To a suspension of methyltriphenylphosphonium bromide (16.90 g, 47.3 mmol) in THF (315 ml) was added 1.7M KOtBu in THF (24.12 ml, 41.0 mmol) in one portion at 0° C. under $N_2$. After the addition, the reaction was removed from the ice bath and stirred at RT for 30 min. The suspension was then cooled to 0° C., and a solution of commercially available (S)-di-tert-butyl 4-oxopyrrolidine-1,2-dicarboxylate (9 g, 31.5 mmol) in 20 ml THF was dropwise over 5 min. The reaction was stirred at 0° C. for 1 h and then at RT for 3 h. TLC (10% EtOAc in hexanes; CMA stain) showed complete conversion of the starting material to a less polar spot. The reaction was added to a sat. aq. solution of $NH_4Cl$ and then extracted with EtOAc. The combined organics were dried ($MgSO_4$), filtered and concentrated to furnish yellow oil, which was purified by silica gel column chromatography on an ISCO (RediSep 120 g, 0-20% EtOAc in hexanes) to provide the product of Step 1 (7.75 g, 27.4 mmol, 87% yield) as colorless oil.

Step 2

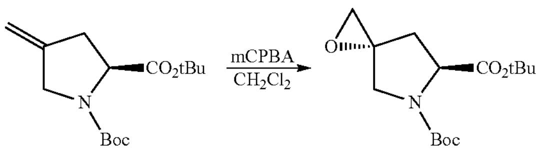 [SMILES: C=C1C[C@@H](C(=O)OC(C)(C)C)N(C(=O)OC(C)(C)C)C1 ; "CH2Cl2" ; "mCPBA" ; CC(C)(C)OC(=O)[C@@H]1C[C@]2(CO2)CN1C(=O)OC(C)(C)C]

To a solution of the product of Step 1 (7.75 g, 27.4 mmol) in $CH_2Cl_2$ (91 ml) at 0° C. was added mCPBA (15.32 g, 68.4 mmol). The reaction was stirred at 0° C. while being warmed up to RT. TLC (10% EtOAc in hexane) after 2 h showed two more polar spots and some unreacted starting material. The reaction was quenched with 10% aq. $Na_2SO_3$ solution, stirred for 15 min and then extracted with EtOAc. The organic fraction was washed with sat. aq. $NaHCO_3$ and water. The aq. $Na_2SO_3$ and $NaHCO_3$ fractions were combined and extracted once with EtOAc. The combined organics were washed with brine, dried ($MgSO_4$) and concentrated to provide a residue, which was purified by silica gel chromatography (ISCO, 220 g RediSep column, 0-50% EtOAc in hexane) to provide the product of Step 2 (2.63 g, 32% yield) as the non-polar diastereomer.

Step 3

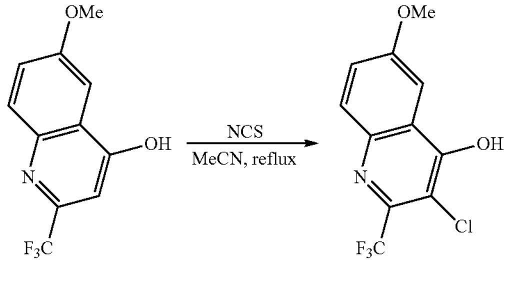 [SMILES: COc1ccc2nc(C(F)(F)F)cc(O)c2c1 ; "NCS" ; COc1ccc2nc(C(F)(F)F)c(Cl)c(O)c2c1]

To a 1 L RB flask fitted with a reflux condenser was taken 6-methoxy-2-(trifluoromethyl)quinolin-4-ol (10 g, 41.1 mmol) and MeCN (400 ml) [0.15M concentration]. This mixture was treated with NCS (6.04 g, 45.2 mmol), and the reaction was stirred at 80° C. for 1 h. The solvent was removed under reduced pressure, and the residue was taken up in MeCN and filtered. The solid was washed with ether and then with DCM and dried under vacuum to provide the product of Step 3 (3-chloro-6-methoxy-2-(trifluoromethyl)quinolin-4-ol, 5.0 g).

Step 4

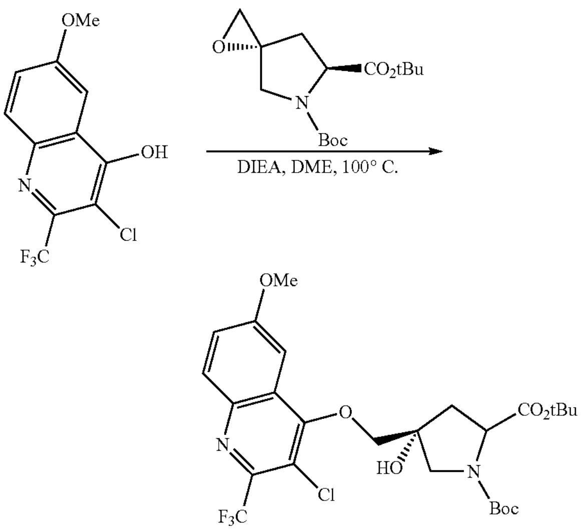

To a solution of the product of Step 2 (1.37 g, 4.58 mmol) in DME (45.8 ml) was added the product of Step 3 (1.525 g, 5.49 mmol) and DIEA (4.00 ml, 22.88 mmol) at RT. The flask was degassed (vacuum/$N_2$—3×) and then stirred at 100° C. under $N_2$ over the weekend. The volatiles were removed under reduced pressure, and the resulting residue was purified by silica gel column chromatography (80 g RediSep column, 0-40% EtOAc/Hexane) to provide the product of Step 4 (2.3 g, 3.99 mmol, 87% yield).

Step 5

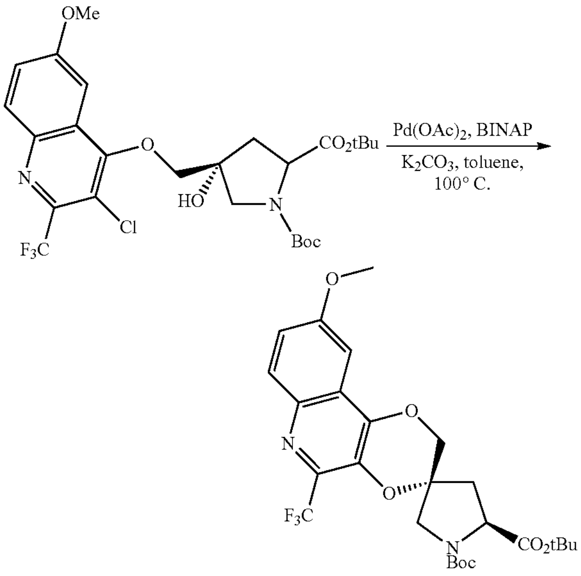

A solution of the product of Step 4 (3.21 g, 5.56 mmol), $Pd(OAc)_2$ (0.187 g, 0.835 mmol), BINAP (0.624 g, 1.001 mmol), and $K_2CO_3$ (1.153 g, 8.35 mmol) in toluene (27.8 ml) was degassed ($N_2$/vacuum) for 5 min and then stirred at 105° C. (using a reflux condenser) for 16 h under $N_2$. After bringing to RT, the reaction was diluted with EtOAc, and the insolubles were filtered off The filtrate was concentrated under reduced pressure, and the residue was purified by silica gel column chromatography (ISCO, 120 g RediSep column, 0-40% EtOAc in hexane) to provide the product of Step 5 (2.08 g, 3.85 mmol, 69.2% yield).

Step 6

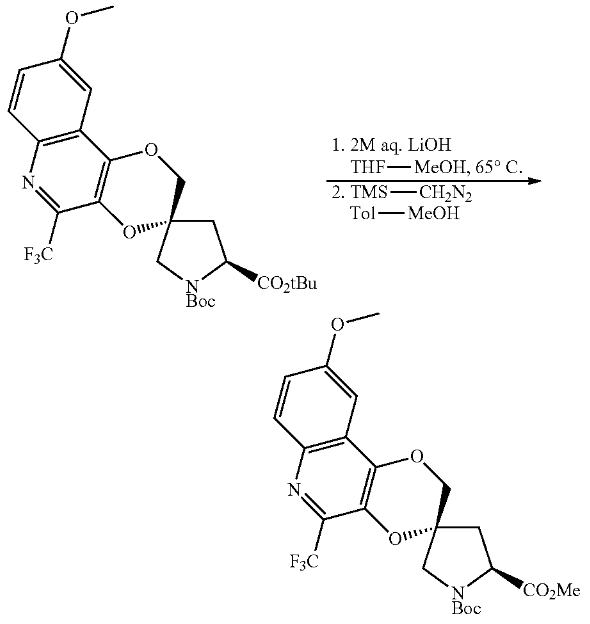

To a solution of the product of Step 5 (2.85 g, 5.27 mmol) in a mixture of THF (26.4 ml) and MeOH (26.4 ml) was added 2M aq. LiOH (26.4 ml, 52.7 mmol), and the reaction was stirred at 65° C. for 90 min. The reaction was allowed to come to RT and was quenched with 2M aq. HCl until pH ~3 and diluted with DCM. The organic layer was separated, washed with brine and then filtered ($MgSO_4$) and concentrated to provide (3R,5'S)-1'-(tert-butoxycarbonyl)-9-methoxy-5-(trifluoromethyl)-2H-spiro[[1,4]dioxino[2,3-c]quinoline-3,3'-pyrrolidine]-5'-carboxylic acid, which was used without purification.

To a solution of (3R,5'S)-1'-(tert-butoxycarbonyl)-9-methoxy-5-(trifluoromethyl) -2H-spiro[[1,4]dioxino[2,3-c]quinoline-3,3'-pyrrolidine]-5'-carboxylic acid (2.55 g, 5.26 mmol) in toluene (80 ml) and MeOH (20.00 ml) was added a 2M solution of trimethylsilyl)diazomethane in hexanes, (5.26 ml, 10.53 mmol) at RT. After 10 min of stirring, the volatiles were removed under reduced pressure to provide the product of Step 6 (2.5 g, 5.02 mmol, 95% yield), which was used without purification.

Step 7

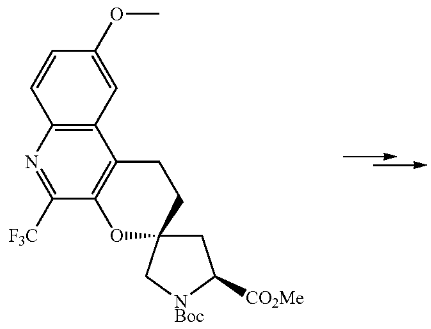

-continued

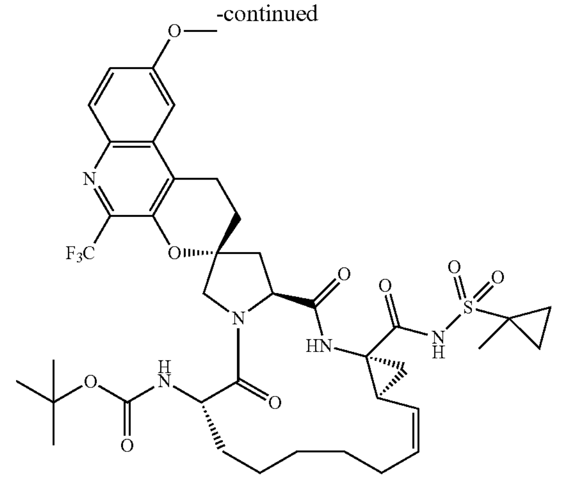

I-8 was prepared from the product of Step 6 by using the procedures described in Example 7, Steps 9-10.

Example 9 tert-Butyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15, 16,16a-hexadecahydrospiro[cyclopropa[e]pyrrolo[1,2-a][1,4]diazacyclopentadecine-2,3'-pyrano[2,3-c]quinolin]-6-yl]carbamate (I-9)

Step 1

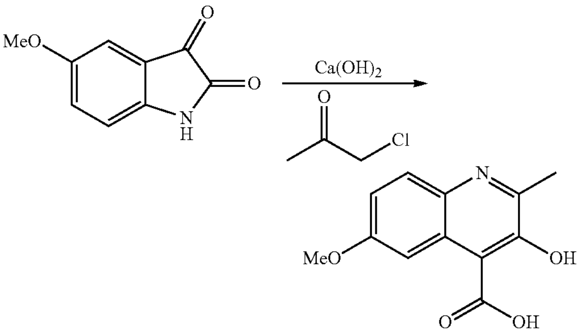

A suspension of 5-methoxyisatin (15 g, 85 mmol) and $Ca(OH)_2$ (18.82 g, 254 mmol) in water (600 ml) was stirred in an oil-bath kept at 80° C. for 1 h, added chloroacetone (10.81 ml, 169 mmol), and the thick slurry was stirred for another 4 h at 80° C. The mixture was cooled to RT, acidified with concentrated HCl, and the solid was filtered, washed several times with water and finally with ether. The solid was dried in vacuum oven to give 17.7 g of the product of Step 1 as a solid. MS m/e=234.2 (MH+).

Step 2

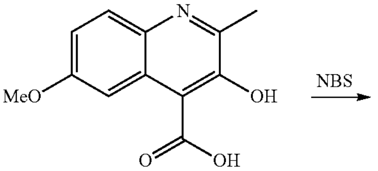

-continued

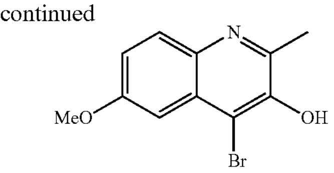

To a suspension of the product of Step 1 (17.6 g, 75 mmol) in DMF (300 ml) at RT was added NBS (13.43 g, 75 mmol) in-portions over a period of 30 min. The mixture was stirred at RT for 3 h. The reaction mixture was diluted with aq. $Na_2S_2O_3$ and extracted 3× with EtOAc. The combined organic layer was washed with brine, dried over $MgSO_4$, filtered and dried to give a solid. The precipitate remaining in the aq. phase was filtered and dried in vacuum oven. Both solids were combined and taken in about 200 ml of 1:1 MeOH-DCM, and to this was added about 60 g of silica gel. The solvent was evaporated to dryness and the adsorbed crude product was chromatographed eluting with 0-30-100% EtOAc-DCM to give 13.02 g of the product of Step 2 as yellow colored solid. MS m/e=270.0 (MH+).

Step 3

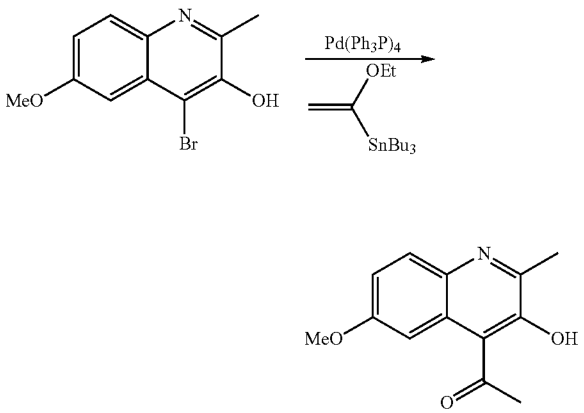

A mixture of the product of Step 2 (13.0 g, 48.5 mmol), tributyl(1-ethoxyvinyl)tin (23.39 ml, 69.2 mmol) and $Pd(PPh_3)_4$ (2.80 g, 2.424 mmol) in dioxane (200 ml) was heated overnight at reflux. The solution was cooled to RT and stirred with 50 ml of 1N HCl for 1.5 h. The reaction mixture was diluted with aq. $NaHCO_3$ and extracted 3× with DCM. The combined organic layer was washed with brine, dried over $MgSO_4$, filtered, concentrated and chromatographed with 0-40-100% EtOAc-hexanes to give 7.19 g of the product of Step 3 as a solid. MS m/e=232.0 ($MH^+$)

Step 4

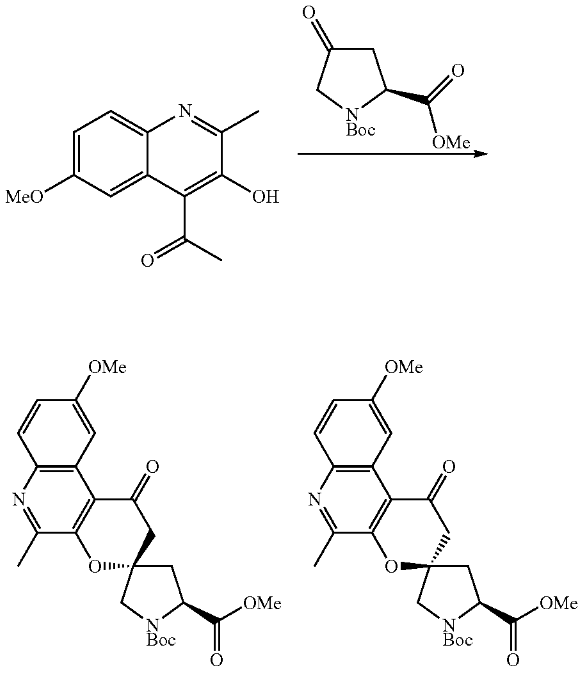

9-4A 9-4B

A mixture of Boc-4-oxo-Pro-OMe (15.13 g, 62.2 mmol), the product of Step 3 (7.19 g, 31.1 mmol) and pyrrolidine (1.029 ml, 12.44 mmol) in MeOH (200 ml) and 3A molecular sieves (~25 g, 4-8 mesh) in a sealed tube was stirred in an oil bath kept at 100° C. for 1 h. The suspension was filtered through a CELITE pad, concentrated and chromatographed with 0-40-100% EtOAc-hexanes to give 4.28 g of 9-4A and 2.87 g of 9-4B. MS for 9-4A m/e=457.0 (MH+). MS for 9-4B m/e=457.0 (MH+).

Step 5

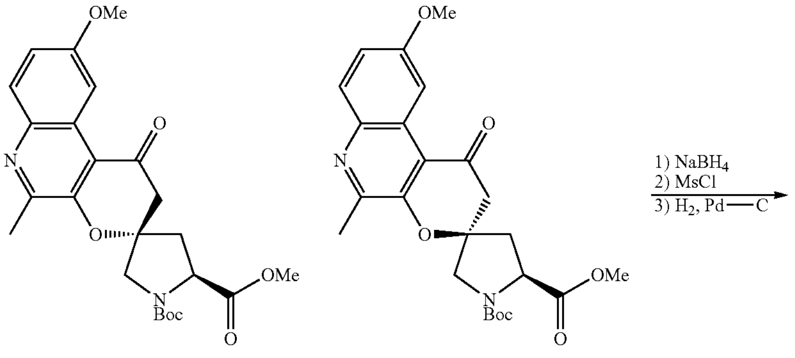

9-4A 9-4B

-continued

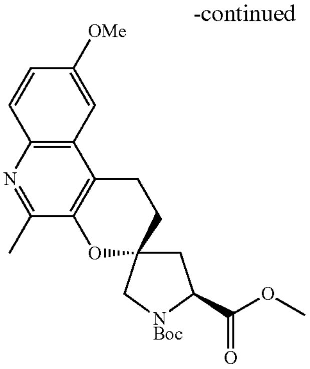

9-5A

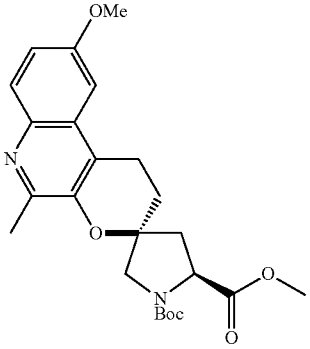

9-5B

To a solution of 9-4A and 9-4B (3.2 g, 7.01 mmol) in THF (20 ml) and MeOH (20 ml) at 0° C. was added $NaBH_4$ (0.265 g, 7.01 mmol) and stirred for 10 min at 0° C. It was quenched by the addition of acetone followed by aq. $NH_4Cl$ and extracted 3× with EtOAc. The combined organic layer was washed with brine, dried over $MgSO_4$, filtered, concentrated and evaporated to dryness to give the crude alcohol, which was used as such.

To a solution of the above product (3.21 g, 7.01 mmol) in DCM (40 ml) at 0° C. was added $Et_3N$ (2.93 ml, 21.03 mmol) followed by MsCl (1.093 ml, 14.02 mmol). The mixture was stirred overnight while allowing it to warm to RT. The reaction mixture was diluted with EtOAc, washed 2× with aq. $NaHCO_3$, brine, dried over $MgSO_4$, filtered and evaporated to dryness to give the crude product, which was used as such.

A suspension of the above product (3343 mg, 7.01 mmol) and 10% Pd—C (600 mg) in EtOAc (60 ml) was stirred under a $H_2$ balloon for 3 h. The suspension was filtered through a CELITE pad, washed with MeOH and EtOAc. The filtrate was washed with aq. $NaHCO_3$, brine, dried over $MgSO_4$, filtered, concentrated and chromatographed with 0-40-100% EtOAc-hexanes to provide 1.64 g of 9-5A and 9-5B as solid. MS m/e=443.2 ($MH^+$).

-continued

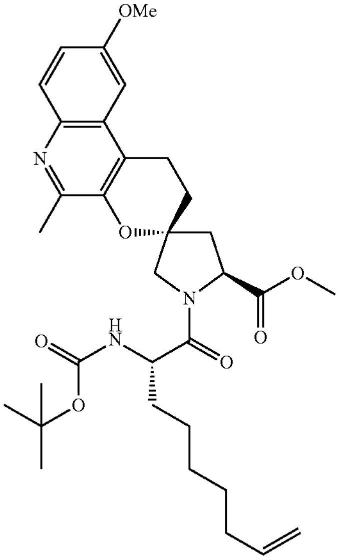

Step 6

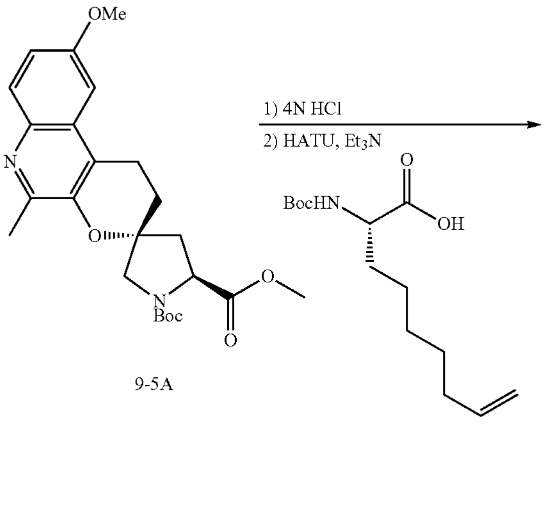

9-5A

A solution of 9-5A (1.60 g, 3.62 mmol) in 4N HCl dioxane (20 ml) and MeOH (5 ml) was stirred at RT for 2 h. The solvent was co-evaporated 2× with toluene and 2× with ether to give the amine as the HCl salt, which was used as such. MS m/e=343.2 ($MH^+$).

To a slurry of the above product (1.371 g, 3.62 mmol) and (S)-2-(tert -butoxycarbonylamino)non-8-enoic acid—dicyclohexylamine salt (2.458 g, 5.43 mmol) in DMF (40 ml) at RT was added HATU (2.065 g, 5.43 mmol) followed by TEA (1.514 ml, 10.86 mmol). The mixture was stirred overnight at RT then diluted with water and extracted 3× with EtOAc. The combined organic layer was washed with water, brine, dried over $MgSO_4$, filtered, concentrated and chromatographed with 0-50-100% EtOAc-hexanes to give 1.57 g of the product of Step 6 as solid. MS m/e=596.2 ($MH^+$).

Step 7

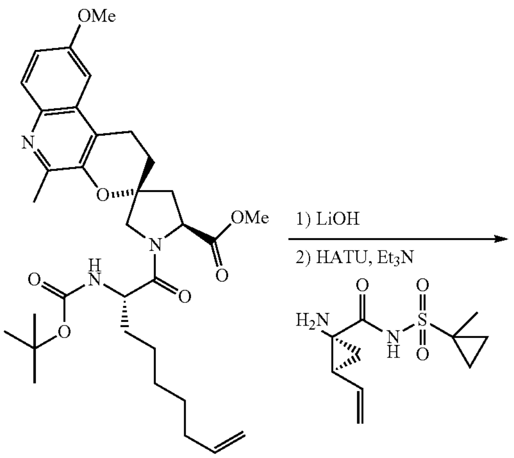

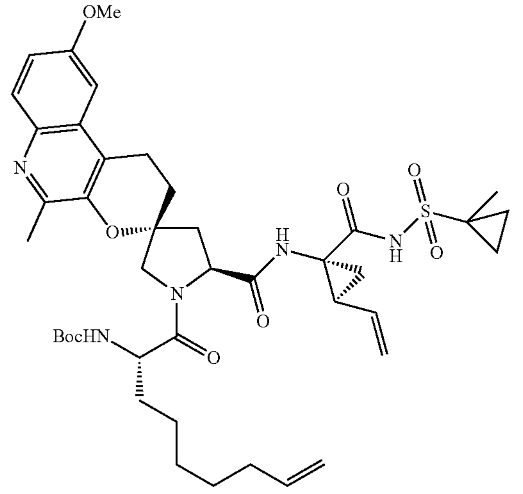

Step 8

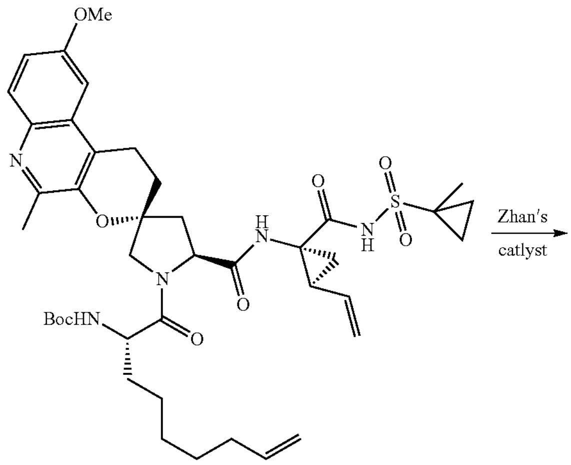

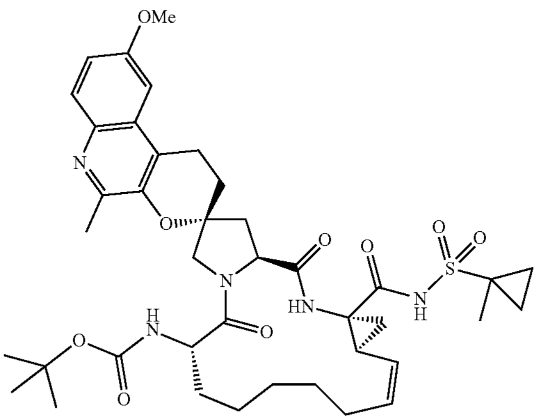

A solution of the product of Step 6 (1.55 g, 2.60 mmol) and $LiOH.H_2O$ (0.437 g, 10.41 mmol) in THF (10 ml), MeOH (10.00 ml) and water (10.00 ml) was stirred in an oil bath kept at 60° C. for 1.5 h. The solution was diluted with water, acidified with 1N HCl and extracted 3× with EtOAc. The combined organic layer was washed with brine, dried over $MgSO_4$, filtered and evaporated to dryness to give the crude acid, which was used as such. MS m/e=582.2 ($MH^+$).

A mixture of the above acid (1.512 g, 2.60 mmol), (1R, 2S)-1-amino-N-(1-methylcyclopropylsulfonyl)-2-vinylcyclopropanecarboxamide tosylate salt (1.624 g, 3.90 mmol), HATU (1.483 g, 3.90 mmol) and TEA (1.087 ml, 7.80 mmol) in DMF (20 ml) was stirred overnight at RT. The reaction mixture was diluted with water and extracted 3× with EtOAc. The combined organic layer was washed with brine, dried over $MgSO_4$, filtered, concentrated and chromatographed with 0-30-100% acetone-hexanes to give 2.14 g of the product of Step 7 as solid. MS m/e=808.4 ($MH^+$).

A solution of the product of Step 7 (1.07 g, 1.324 mmol), 1,3-bis(2,4,6-trimethylphenyl)-4,5-dihydroimidazol-2-ylidene[2-(i-propoxy)-5-(N,N dimethylaminosulfonyl)phenyl]methylene ruthenium(II)dichloride (0.243 g, 0.331 mmol) and 1,4-benzoquinone (0.043 g, 0.397 mmol) in DCE (600 ml) was degassed under vacuum and filled with argon. The mixture was stirred in an oil bath kept at 75° C. (bath temp) for 4 h then stirred with 0.5 ml of n-butylvinyl ether for 30 min. The solvent was evaporated to dryness, and the residue was chromatographed with 0-40-100% acetone-hexanes to give 800 mg of I-9 as a solid.

$^1$H-NMR (400 MHz, acetone-$d_6$) 10.56 (br s, 1H), 8.42 (s, 1H), 7.75 (d, J=838 Hz, 1H), 7.16-7.13 (m, 2H), 6.04 (d, J=7.1 Hz, 1H), 5.72-5.66 (m, 1H), 4.99 (t, J=9.5 Hz, 1H), 4.71 (dd, J=10.2, 6.9 Hz, 1H), 4.50 (d, J=11.3 Hz, 1H), 4.11-4.07 (m, 1H), 3.94 (s, 3H), 3.79 (d, J=10.9 Hz, 1H), 3.77 (s, 1H), 3.20-3.07 (m, 2H), 2.60-2.26 (m, 3H), 2.08-2.04 (m), 1.93-1.86 (m), 1.73 (dd, J=5.5, 8.1 Hz, 1H), 1.65-1.61 (m, 1H), 1.58-1.54 (m, 2H), 1.48 (s, 9H), 1.46-1.26 (m), 0.89-0.820 (m). MS m/e=780.2 (MH+).

Example 10 tert-butyl ((2R,6S,13aS,14aR,16aS,Z)-5'-(difluoromethyl)-9'-methoxy-14a -(((1-methylcyclopropyl)sulfonyl)carbamoyl)-5,16-dioxo-1',2',3,5,6,7,8,9,10,11, 13a,14,14a,15, 16,16a-hexadecahydro-1H-spiro [cyclopropa[e]pyrrolo[1,2-a][1,4] diazacyclopentadecine-2,3'-pyrano[2,3-c]quinolin]-6-yl)carbamate (I-10)

Step 1

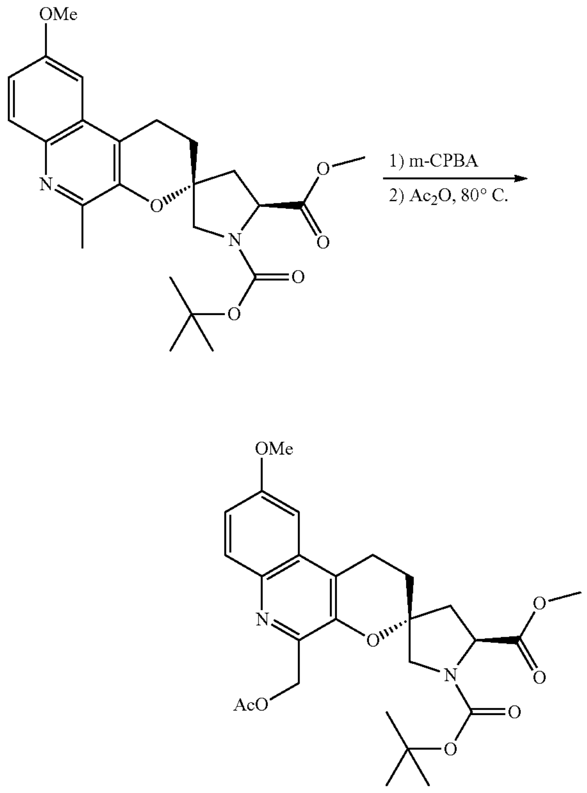

To a solution of intermediate 9-5A (the product of Example 9, Step 5) (6.6 g, 14.92 mmol) in DCM (100 ml) at RT was added MCPBA (6.69 g, 29.8 mmol), and the mixture was stirred overnight at RT. The reaction mixture was diluted with aq. $K_2CO_3$ and aq. $Na_2S_2O_3$. The DCM was concentrated to about a third volume, and the slurry was extracted 3× with EtOAc. The combined organic layer was washed with brine, dried over $MgSO_4$, filtered and evaporated to dryness to give 6.74 g of the N-oxide intermediate as foam. LC-MS me/=459.2 (MH+). The crude product was used as such.

A solution of the crude N-oxide (6.74 g, 14.70 mmol) in acetic anhydride (100 ml, 14.70 mmol) was stirred in an oil-bath kept at 80° C. (bath temperature). After stirring for a total of 1.5 h, the reaction mixture was cooled to RT then poured into ice-cold water. The slurry was extracted 3× with EtOAc, and the combined organic layer was washed with brine, dried over $MgSO_4$, filtered, concentrated and purified by chromatography eluting with 0-50% EtOAc-hexanes to give 5.2 g of the product of Step 1 as a solid: LC-MS m/e=501.2 ($MH^+$).

Step 2

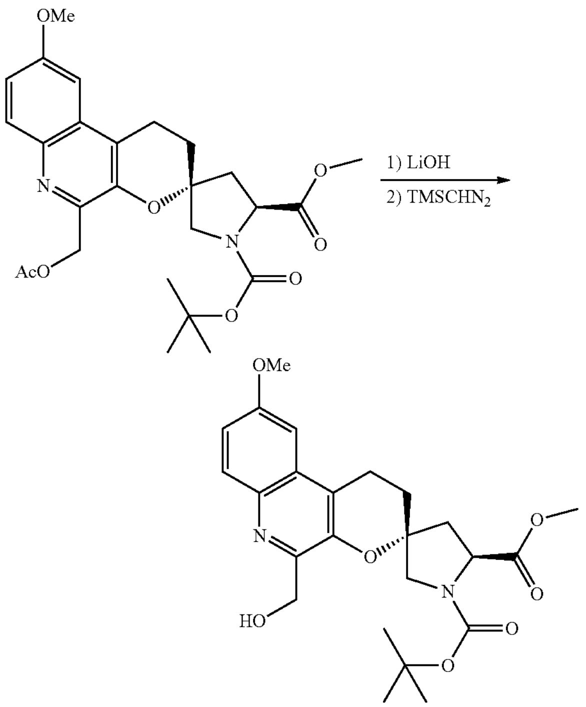

A solution of the product of Step 1 (5.2 g, 10.39 mmol) and $LiOH.H_2O$ (0.785 g, 18.70 mmol) in THF (30 ml), MeOH (30.0 ml) and water (30.0 ml) was stirred at 0° C. The mixture was stirred for 2 h at 0° C. and 1 h at RT, then another 300 mg of $LiOH.H_2O$ (~0.7 eq.) was added. After stirring for additional 1 h at RT, the reaction mixture was diluted with water and acidified with 1N HCl to pH ~3. The mixture was extracted 3× with EtOAc, the combined organic layer washed with brine, dried over $MgSO_4$, filtered and evaporated to dryness to give 4.98 g of product where both the acetate and the methyl ester were hydrolyzed. LC-MS m/e=445.2 (MH+).

To a solution of the acid (1.9 g, 4.27 mmol) in toluene (20 ml) and MeOH (5 ml) at RT was added a 2M hexane solution of trimethylsilyl diazomethane (4.27 ml, 8.55 mmol). The mixture was stirred at RT for 1 h, evaporated to dryness, and the residue was purified by chromatography eluting with 0-60% EtOAc-hexanes to give 1.56 g of the product of Step 2 as a solid. LC-MS m/e=459.2 (MH+).

Step 3

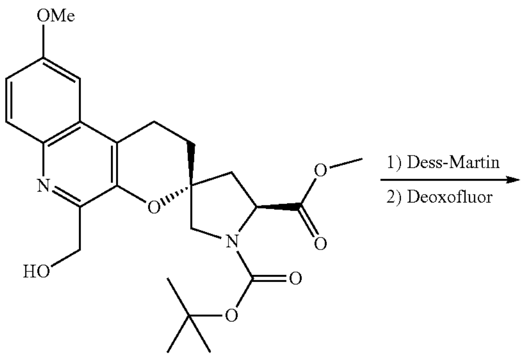

-continued

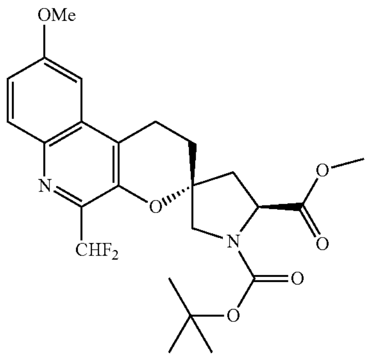

A solution of the product of Step 2 (1.56 g, 3.40 mmol) and Dess Martin periodinane (2.165 g, 5.10 mmol) in DCM (30 ml) was stirred at RT for 1 h, then diluted with ether followed by aq. $NaHCO_3$ and aq. $Na_2S_2O_3$. The mixture was stirred for 10 min, and the organic layer was separated. The aq. phase was extracted 2× with EtOAc, and the combined organic layer was washed with brine, dried over $MgSO_4$, filtered and evaporated to dryness. The product was purified by chromatography eluting with 0-60% EtOAc-hexanes to give 1.45 g of aldehyde intermediate as a solid. LC-MS m/e=475.2 (MNa+).

To a solution of the aldehyde (1.45 g, 3.18 mmol) in DCM (30 ml) was added bis (2-methoxyethyl)aminosulfur trifluoride (1.757 ml, 9.53 mmol) followed by EtOH (0.037 ml, 0.635 mmol), and the mixture was heated at reflux overnight. LC-MS indicated small amount of unreacted starting material. To the reaction mixture was added another 1 eq. of DeoxoFluor, and reaction was heated at reflux for another 4 h. The reaction mixture was cooled to RT, stirred with aq. $NaHCO_3$, and the organic layer was separated. The aq. phase was extracted 2× with EtOAc, and the combined organic layer was washed with brine, dried over $MgSO_4$, filtered and evaporated to dryness. The crude product was purified by chromatography eluting with 0-60% EtOAc-hexanes to give 1.21 g of the product of Step 3. LC-MS m/e=501.2 $(M+Na)^+$.

Step 4

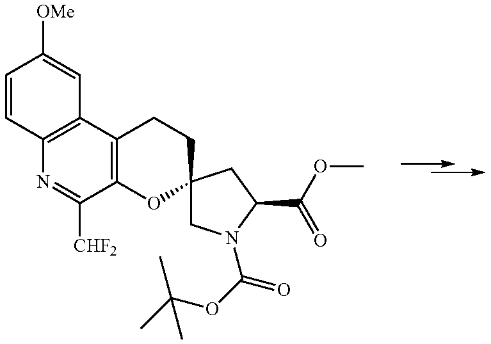

-continued

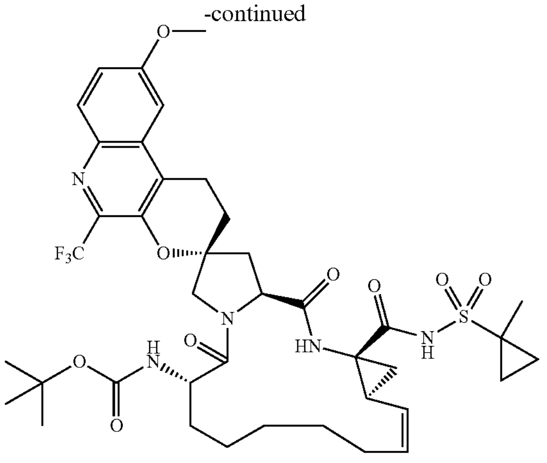

The product of Step 3 was converted to I-10 using a procedure similar to the preparation of Example 9 from the product of Step 5. LC-MS m/e=m/e=816.4 (MH+). $^1H$ NMR ($CDCl_3$, 400 MHz) δ (ppm) 8.49 (1H, d, J=3.6 Hz), 7.90 (1H, d, J=8.8 Hz), 7.29-7.26 (m, 2H), 6.96 (1H, t, J=54.6 Hz), 6.01 (1H, d, J=6.8 Hz), 5.69 (1H, q, J=8.9 Hz), 5.00 (1H, t, J=9.6 Hz), 4.67 (1H, t, J=8.4 Hz), 4.51 (1H, d, J=11.2 Hz), 4.10 (1H, t, J=9.0 Hz), 4.00 (3H, s), 3.84 (1H, d, J=11.2), 3.76 (3H, s), 3.40 (1H, q, J=6.9 Hz), 3.3-3.20 (2H, m), 2.82 (s, 2H), 2.78 (s, 2H), 2.62-2.41 (m), 2.33 (1H, t, J=11.6 Hz), 2.21-2.20 (1H, m), 2.14-2.04 (m), 1.90-1.86b (2H, m), 1.74-1.71 (2H, m), 1.65-1.55 (2H, m), 1.49-1.41 (m), 1.37-1.27 (m), 1.13-1.09 (m).

Example 11 tert-butyl (2R,6S,13aS,14aR,16aS,Z)-2'-methoxy-6'-methyl-14a-(1-methyl cyclopropylsulfonylcarbamoyl)-5,16-dioxo-3,5,6,7,8,9,9',10,10',11,13a,14,14a,15,16,16a -hexadecahydro-1H-spiro[cyclopropa[e]pyrrolo[1,2-a][1,4]diazacyclopentadecine-2,8'-pyrano[2,3-c][1,5]naphthyridine]-6-ylcarbamate (I-11)

Step 1

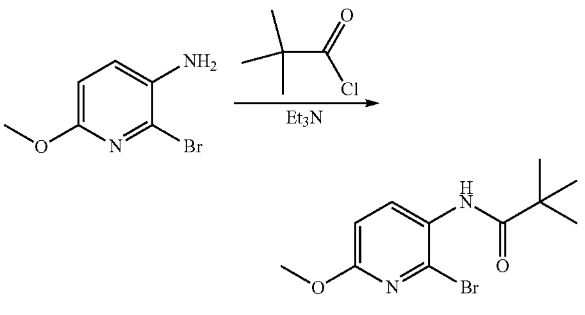

To a solution of 3-amino-2-bromo-6-methoxypyridine (10.0 g, 49.3 mmol) in DCM (200 ml) at 0° C. was added TEA (11.0 ml, 79 mmol) followed by pivaloyl chloride (6.67 ml, 54.2 mmol), and the mixture was allowed to warm to RT and stirred overnight. The mixture was quenched at RT with sat. aq. $NH_4Cl$ and extracted with DCM. The combined organic fractions were washed with sat. aq. $NaHCO_3$ and brine, dried over $Na_2SO_4$, filtered and concentrated in vacuo. The residue was purified by column chromatography over silica gel (eluting with Hexanes/EtOAc 99:1 to 20:80) to give the product of Step 1 (13.3 g, 94% yield) as a white solid.

Step 2

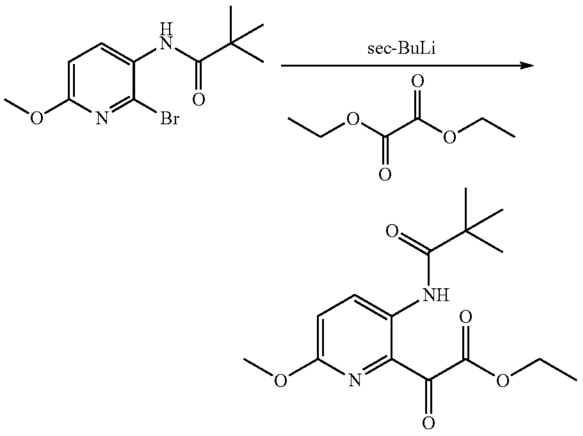

To a solution of the product of Step 1 (13.9 g, 48.3 mmol) in THF (175 ml) at −78° C. was added sec-butyl lithium 1.4N in hexanes (83 ml, 116 mmol) over 15 min. The mixture was allowed to warm to 0° C. after 30 min at −78° C. and stirred for 90 min at 0° C. Diethyl oxalate (7.87 ml, 57.9 mmol) was then added to the reaction at −78° C., and the reaction was slowly allowed to warm to RT overnight. The mixture was poured at RT into sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/DCM 80:20 to DCM) to give the product of Step 2 (6.99 g, 47% yield) as yellow oil.

Step 3

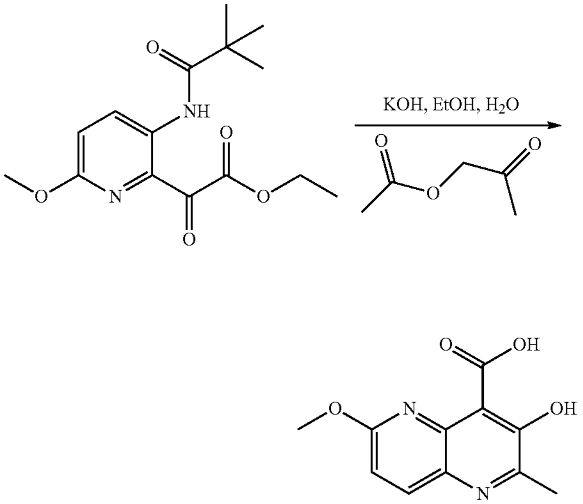

To a solution of the product of Step 2 (10.5 g, 34.1 mmol) in EtOH (70 ml) and water (70 ml) at RT was added 6N KOH (79 ml, 477 mmol), and the mixture was warmed to 90° C. and stirred for 1 h. Acetoxy-2-propanone (4.05 ml, 37.5 mmol) was then added at 90° C. over 3 min, and the reaction was stirred for 1 h. The operation was repeated 2×. The mixture was concentrated from EtOH then slowly quenched at 0° C. with 1N aq. HCl until pH ~4, then filtered and dried in vacuo to provide the product of Step 3 (4.81 g, 60% yield).

Step 4

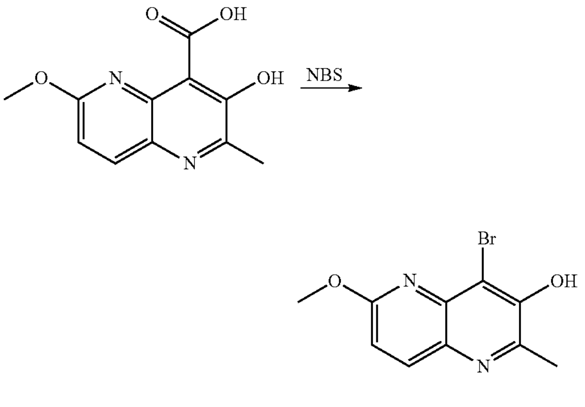

To a solution of the product of Step 3 (5.20 g, 22.2 mmol) in THF (100 ml) at 0° C. was added a solution of NBS (3.36 g, 18.9 mmol) in THF (10 ml), and the mixture was stirred for 1 h at 0° C. then 30 min at RT. The mixture was quenched with 50% brine and extracted with EtOAc. The combined organic fractions were dried over $Na_2SO_4$, filtered and concentrated in vacuo. The residue was purified by column chromatography over silica gel (eluting with Hexanes/EtOAc 99:1 to 40:60) to afford the product of Step 4 (5.50 g, 81% yield).

Step 5

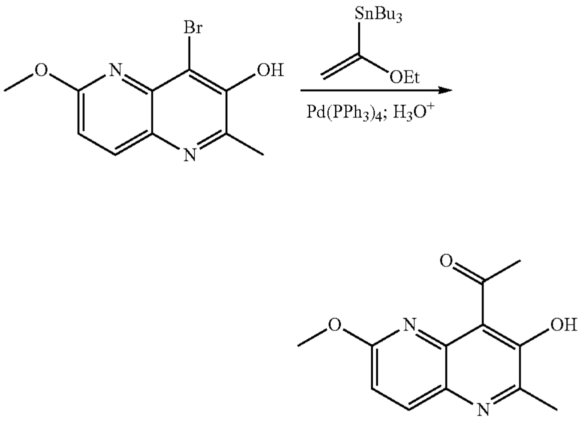

To a solution of the product of Step 4 (5.40 g, 20.1 mmol) and $Pd(PPh_3)_4$ (0) (1.62 g, 1.40 mmol) in 1,4-dioxane (55 ml) in a sealed tube was added tributyl(1-ethoxyvinyl)tin (17.0 ml, 50.2 mmol), and the mixture was warmed to 110° C. and stirred for 3 h. More $Pd(PPh_3)_4$ (400 mg) and tributyl(1-ethoxyvinyl)tin (6 ml) were added, and the reaction was stirred at 110° C. for an additional 4 h. The final mixture was quenched at 0° C. with 1N aq. HCl (60 ml) then stirred at RT for 60 min. The mixture was neutralized at RT with sat. aq. $NaHCO_3$ (100 ml) and extracted with EtOAc. The combined organic fractions were dried over $Na_2SO_4$, filtered and concentrated in vacuo. The residue was purified by column chromatography over silica gel (eluting with Hexanes/EtOAc 99:1 to 60:40) to give the product of Step 5 (2.64 g, purity 70%) as yellow solid.

Step 6

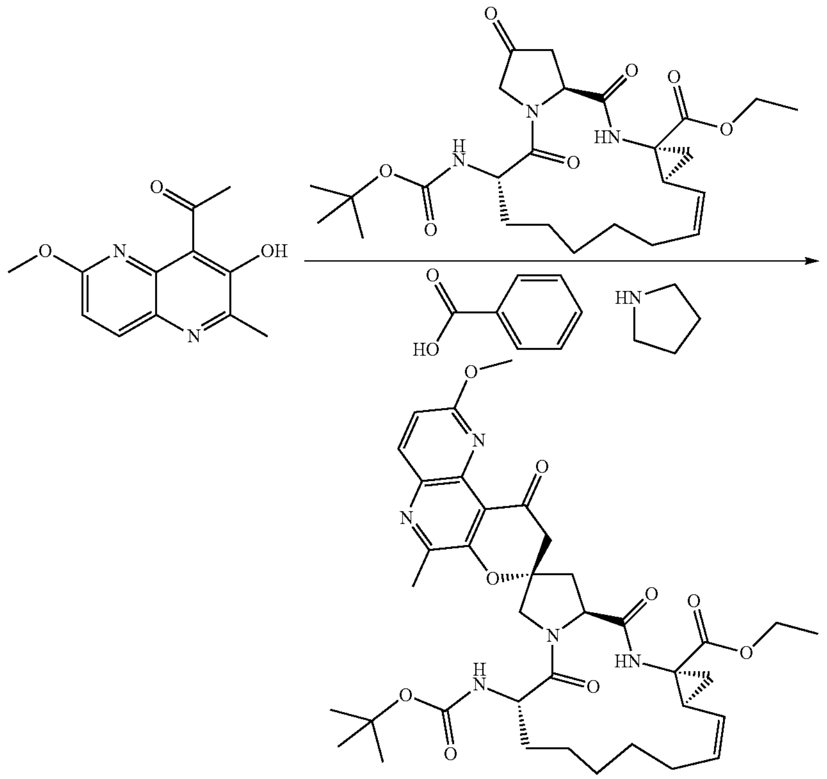

To a solution of the product of Step 5 (500 mg, 2.15 mmol), macrocyclic ketone (1.058 g, 2.153 mmol) and benzoic acid (263 mg, 2.15 mmol) in MeOH (15 ml) was added pyrrolidine (0.069 ml, 0.861 mmol) and 4A molecular sieves (1.0 g), and the mixture was warmed to 55° C. and stirred for 72 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give, in order of elution, the product of Step 6 (820 mg, 54% yield), followed by starting intermediate (100 mg).

Step 7

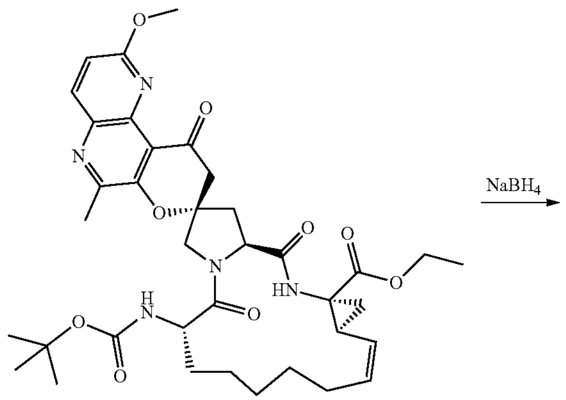

-continued

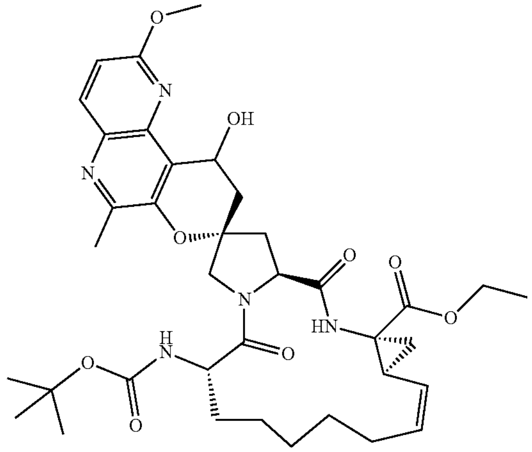

To a solution of the product of Step 6 (540 mg, 0.765 mmol) in THF (6 ml) and MeOH (6 ml) at 0° C. was added $NaBH_4$ (34.7 mg, 0.918 mmol), and the mixture was stirred for 45 min. The mixture was quenched at 0° C. with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give the product of Step 7 (460 mg, 85% yield).

Step 8

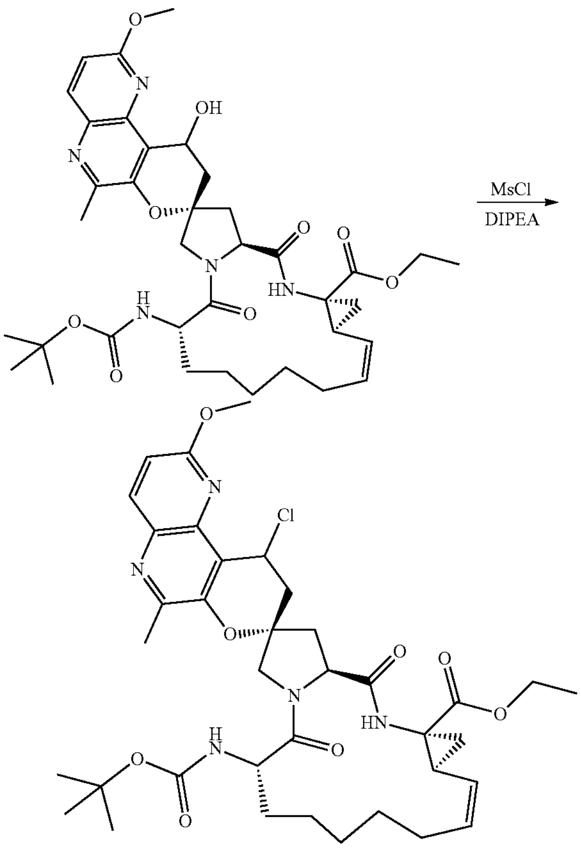

To a solution of the product of Step 7 (460 mg, 0.650 mmol) in DCM (15 ml) was added DIPEA (0.45 ml, 2.60 mmol) followed by MsCl (0.101 ml, 1.300 mmol), and the mixture was stirred at RT overnight. The mixture was quenched at RT with aq. $NH_4Cl$ and extracted with DCM. The combined organic fractions were dried over $Na_2SO_4$, filtered and concentrated in vacuo. A solution of the residue (650 mg) in DMF (5 ml) was treated with LiCl(100 mg, 2.36 mmol), and the mixture was stirred for 1 h. The mixture was diluted with 90% brine and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give the product of Step 8 (398 mg, 80% purity).

Step 9

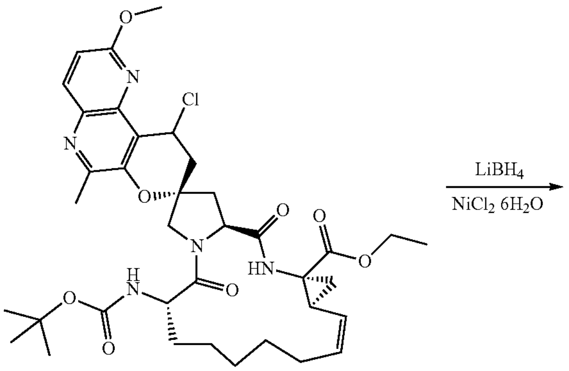

-continued

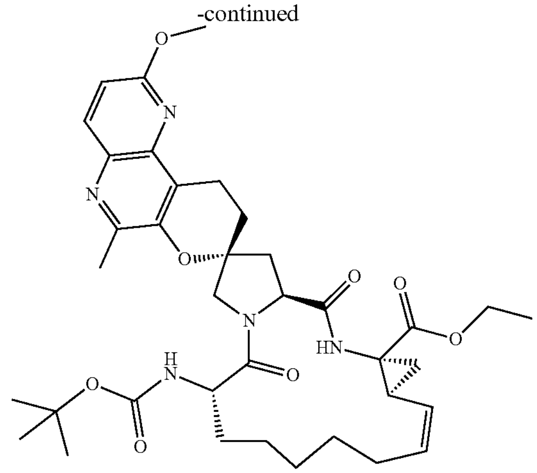

To a solution of the product of Step 8 (420 mg, 0.579 mmol) in MeOH (28 ml) at −78° C. was added $NiCl_2.6H_2O$ (124 mg, 0.521 mmol) then $LiBH_4$ 2N in THF (0.867 ml, 1.74 mmol), and the reaction was stirred for 10 min at −78° C. then allowed to warm to 0° C. over 1 h. The reaction was quenched at 0° C. with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 20:80) to give the product of Step 9 (210 mg, 52% yield).

Step 10

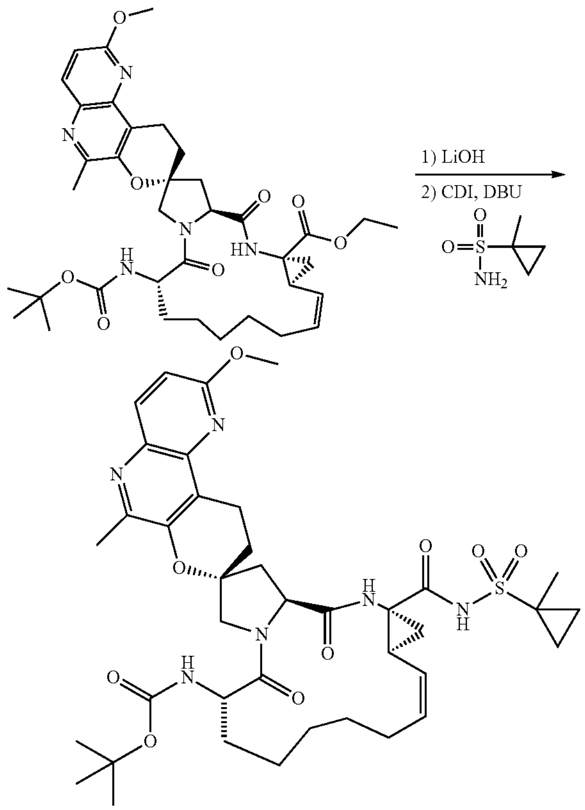

To a solution of the product of Step 9 (210 mg, 0.304 mmol) in THF (3 ml), MeOH (3) and water (2.5 ml) was added LiOH.$H_2O$ (21.8 mg, 0.911 mmol), and the reaction was stirred at 50° C. for 4 h. The mixture was quenched at RT with ice cold 0.3M aq. HCl until pH ~3, and extracted with EtOAc. The combined organic fractions were dried over $Na_2SO_4$, filtered and concentrated in vacuo to give an intermediate acid (190 mg, 94% yield). To a solution of this intermediate acid (190 mg, 0.286 mmol) in THF (12 ml) was added 1,1'-carbonyldiimidazole (139 mg, 0.859 mmol), and the mixture was warmed to 70° C. and stirred for 4 h. 1-Methylcyclopropane-1-sulfonamide (193 mg, 1.431 mmol) and DBU (0.216 ml, 1.431 mmol) were then added at RT, and the reaction was warmed to 50° C. and stirred for 8 h. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give I-11 (130 mg, 58% yield). $^1$H-NMR (400 MHz, $CDCl_3$) δ 10.11 (s, 1H), 8.03 (d, J=8.8 Hz, 1H), 6.90-6.95 (m, 3H), 5.72 (m, 1H), 4.95-5.10 (m, 2H), 4.64 (m, 1H), 4.44 (d, J=10.8 Hz, 1H), 4.18 (m, 1H), 4.03 (s, 3H), 4.00-4.10 (m, 1H), 3.41 (d, 1H), 3.20-3.30 (m, 2H), 2.30-2.65 (m, 3H), 2.48 (s, 3H), 2.21 (m, 2H), 1.72-2.00 (m, 5H), 1.15-1.55 (m, 8H), 1.44 (m, 3H), 1.27 (s, 9H), 0.80 (br s, 2H); LC-MS ($M^+$) Calc. for $C_{39}H_{52}N_6O_9S$: 780.9. Found 781.2 $(M+H)^+$.

Example 12 tert-Butyl ((2R,6S,13aS,14aR,16aS,Z)-6'-(difluoromethyl)-2'-methoxy-14a -(((1-methylcyclopropyl) sulfonyl)carbamoyl)-5,16-dioxo-3,5,6,7,8,9,9',10,10', 11,13a,14,14a, 15,16,16a-hexadecahydro-1H-spiro [cyclopropa[e]pyrrolo[1,2-a][1,4] diazacyclopentadecine -2,8'-pyrano[2,3-c][1,5] naphthyridin]-6-yl)carbamate (I-12)

Step 1

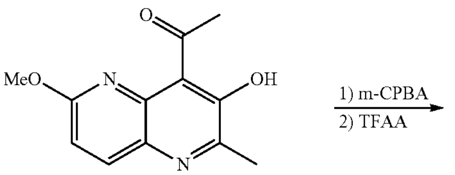

-continued

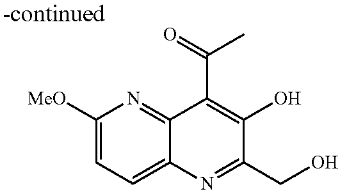

A mixture of 1-(3-hydroxy-6-methoxy-2-methyl-1,5-naphthyridin-4-yl)ethanone (the product of Example 11, Step 5; 10 g, 43.1 mmol), mCPBA (12.55 g, 56.0 mmol) in DCM (200 ml) was stirred at RT for 3 d. The thick slurry was stirred with aq. $NaHCO_3$ and aq. $Na_2S_2O_3$. The solvent was gently evaporated from the aq. slurry, and the resultant solid was filtered, washed with water followed by ether and dried overnight in a vacuum overnight to give 6.8 g of the N-oxide intermediate as a solid.

To a flask containing the above solid (6.3 g, 25.4 mmol) was added trifluoracetic anhydride (100 ml, 708 mmol), and the mixture was heated at reflux. After leaving overnight at RT, the mixture was heated at reflux for another 1 h. The reaction mixture was evaporated to dryness. The residue was dissolved in minimum MeOH and diluted with aq. $NaHCO_3$. The slurry was filtered and washed with water. The solid was suspended in about 100 ml of 1:1 MeOH-DCM, and to this was added about 30 g of silica gel. The solvent was evaporated to dryness, and the adsorbed crude product was purified by chromatography eluting with 0-3%-5% MeOH-DCM to give 3.35 g of product as a dark solid. LC-MS m/e=249.16 (MH+).

Step 2

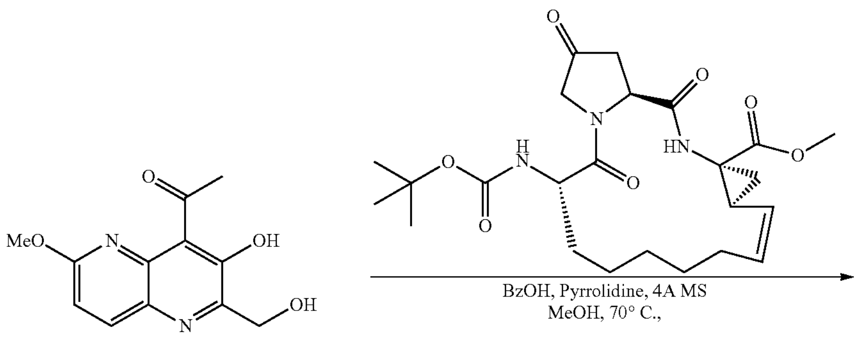

-continued

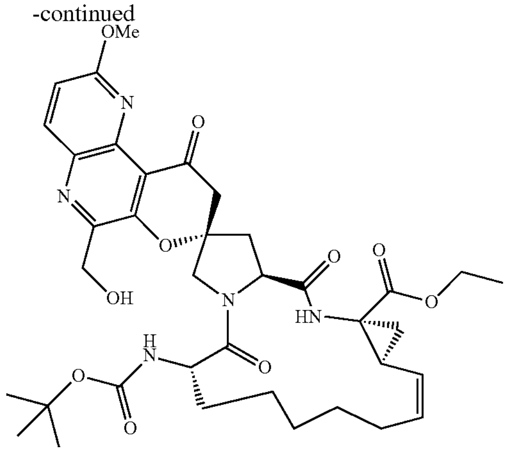

A mixture of the product of Step 1 (500 mg, 2.014 mmol), (6S,13aS,14aR,16aS,Z) -ethyl 6-((tert-butoxycarbonyl) amino)-2,5,16-trioxo 1,2,3,5,6,7,8,9,10,11,13a,14,14a,15,16,16a -hexadecahydrocyclopropa[e]pyrrolo[1,2-a][1,4]diazacyclopentadecine-14a-carboxylate (990 mg, 2.014 mmol), pyrrolidine (0.080 ml, 1.007 mmol), benzoic acid (246 mg, 2.014 mmol), 4A molecular sieves (~1 g) in MeOH (10 ml) in a sealed tube was stirred overnight in an oil-bath kept at ~70° C. (bath temperature). The reaction mixture was filtered through a Celite pad and rinsed with MeOH. The filtrate was concentrated and poured into aq. $NaHCO_3$. The slurry was extracted 3× with EtOAc, the combined organic layer was washed with brine, dried over $MgSO_4$, filtered and evaporated to dryness. The crude product was purified by chromatography eluting with acetone-hexanes to give 340 mg of product as a solid. Mass spec. m/e observed=722.36 $(M+H)^+$.

Step 3

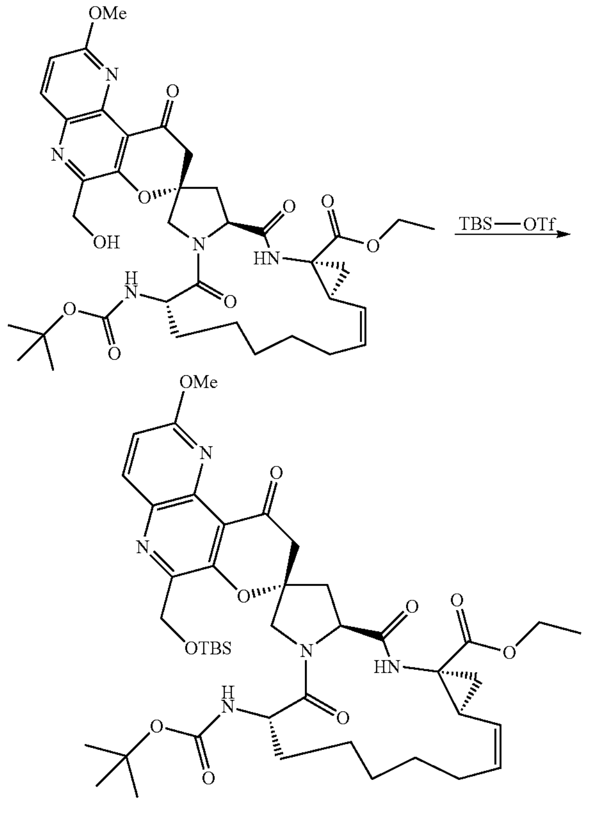

To a solution of the product of Step 2 (860 mg, 1.191 mmol) in DCM (10 ml) at 0° C. was added $Et_3N$ (0.332 ml, 2.383 mmol) followed by TBS-OTf (0.356 ml, 1.549 mmol), and the mixture was stirred at 0° C. After 2 h, added another 0.3 eq. of TBS-OTf. The mixture was stirred for additional 30 min then diluted with aq. $NaHCO_3$. The slurry was extracted 3× with EtOAc, the combined organic layer was washed with brine, dried over $MgSO_4$, filtered and evaporated to dryness. The crude product was purified by chromatography eluting with 0-30% acetone-hexanes to give 570 mg of the product of Step 3 as a solid. LC-MS m/e=836.38 (MH+).

Step 4

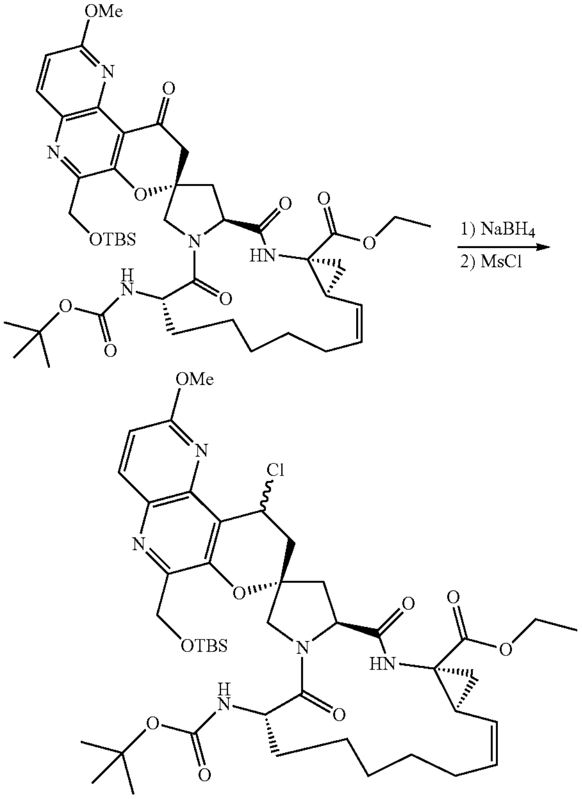

To a solution of the product of Step 3 (550 mg, 0.658 mmol) in MeOH (4 ml) and THF (1 ml) at 0° C. was added $NaBH_4$ (24.89 mg, 0.658 mmol). The mixture was stirred for 10 min then quenched by the addition of acetone followed by aq. $NH_4Cl$. The slurry was extracted 3× with EtOAc, and the combined organic layer was washed with brine, dried over $MgSO_4$, filtered and evaporated to dryness to give the crude alcohol, which was used as such.

To a solution of the alcohol (551 mg, 0.658 mmol) in DCM (7 ml) at 0° C. was added $Et_3N$ (0.275 ml, 1.974 mmol) followed by MsCl (0.103 ml, 1.316 mmol) and the mixture was stirred overnight while being allowed to warm to RT. Because LC-MS indicated unreacted starting material, the reaction was cooled again to 0° C., and TEA (0.275 ml, 1.974 mmol) was added, followed by MsCl (0.103 ml, 1.316 mmol) and stirred overnight. The mixture was diluted with EtOAc, washed 2× with aq. $NaHCO_3$, brine, dried over $MgSO_4$, filtered and evaporated to dryness to give the crude product. The crude product was purified by chromatography eluting with 0-30% acetone-hexanes to give 328 mg of the product of Step 4 as foam. LC-MS m/e=856.35 $(M+H)^+$.

Step 5

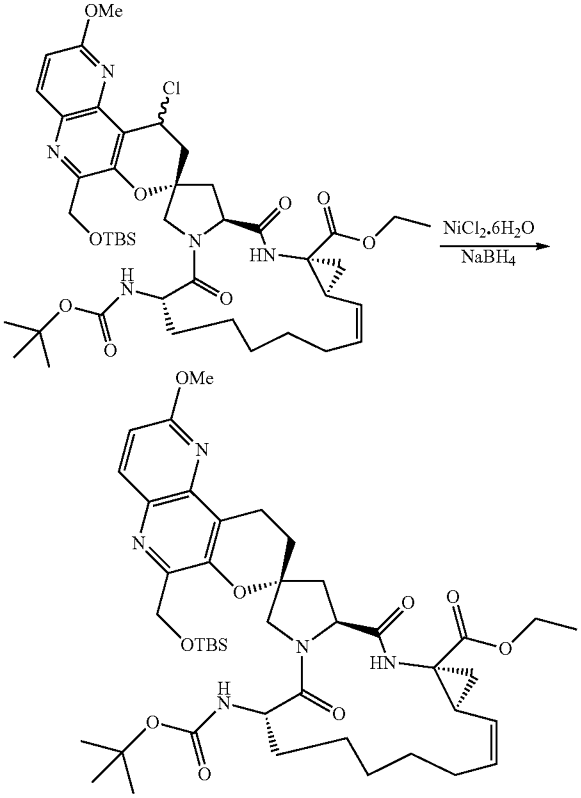

A mixture of the product of Step 4 (320 mg, 0.374 mmol) and $NiCl_2.6H_2O$ (266 mg, 1.121 mmol) in MeOH (5 ml) was stirred at RT until the solids dissolved to give a clear solution (~10 min.). The solution was cooled to −78° C., and $NaBH_4$ (21.20 mg, 0.560 mmol) was added in one portion, and the mixture was stirred at −78° C. for 1 h then another portion of $NaBH_4$ (21.20 mg, 0.560 mmol) was added. The mixture was stirred for another 1 h at −78° C., then quenched by the addition of aq. $NH_4Cl$ and warmed to RT. The slurry was extracted 3× with EtOAc, the combined organic layer was washed with brine, dried over $MgSO_4$, filtered and evaporated to dryness. The crude product was purified by chromatography eluting with 0-40% acetone-hexanes (24 g RediSep cartridge) to give 128 mg of the product of Step 5 as a solid. LC-MS m/e=822.51 $(M+H)^+$.

Step 6

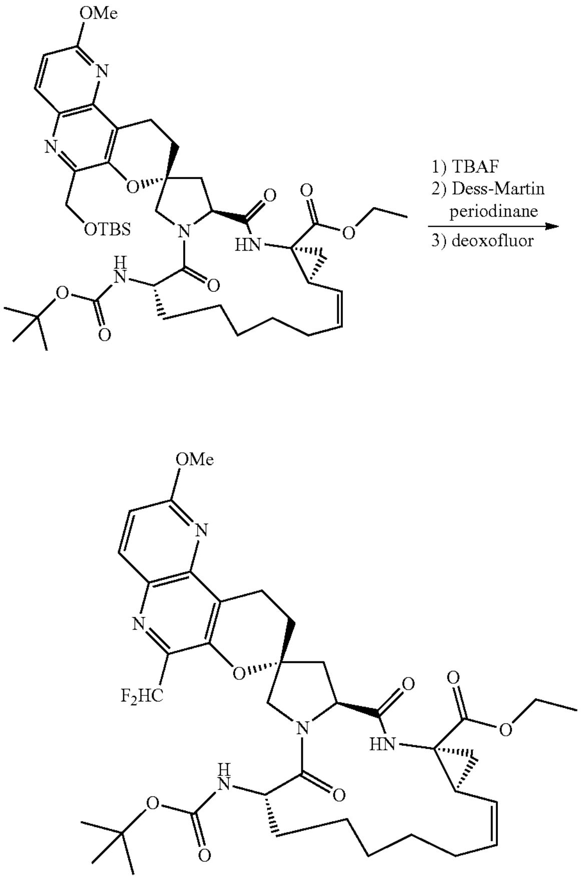

To a solution of the product of Step 5 (128 mg, 0.156 mmol) in THF (2 ml) was added 1M solution of TBAF (0.311 ml, 0.311 mmol) in THF, and the mixture was stirred at RT for 2 h. The reaction mixture was diluted with EtOAc, washed 2× with aq. $NH_4Cl$, brine, dried over $MgSO_4$, filtered and evaporated to dryness. The residue was purified by chromatography eluting with 0-40% acetone-hexanes (4 g RediSep cartridge) to give 98 mg of alcohol intermediate as a solid. LC-MS m/e=708.37 $(MH^+)$.

A solution of the above product (98 mg, 0.138 mmol) and Dess-Martin periodinane (88 mg, 0.208 mmol) in DCM (2 ml) was stirred at RT for 1 h. The reaction mixture was diluted with aq. $Na_2S_2O_3$ and aq. $NaHCO_3$, stirred for few minutes then extracted 3× with EtOAc. The combined organic layer was washed with brine, dried over $MgSO_4$, filtered and evaporated to dryness to give the aldehyde intermediate, which was used as such.

To a solution of the aldehyde (98 mg, 0.139 mmol) in DCM (2 ml) in a sealed tube was added DeoxoFluor (0.102 ml, 0.555 mmol) followed by EtOH (1.621 μl, 0.028 mmol), and the mixture was stirred overnight in an oil bath kept at 40° C. The mixture was diluted with EtOAc, washed 2× with aq. $NaHCO_3$, brine, dried over $MgSO_4$, filtered and evaporated to dryness. The residue was purified by chromatography (4 g RediSep cartridge) eluting with 0-40% acetone-hexanes to give 64 mg of the product of Step 6 as a white solid. LC-MS m/e=728.42 (MH+).

Step 7

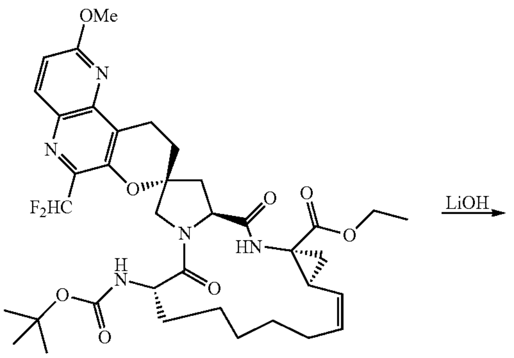

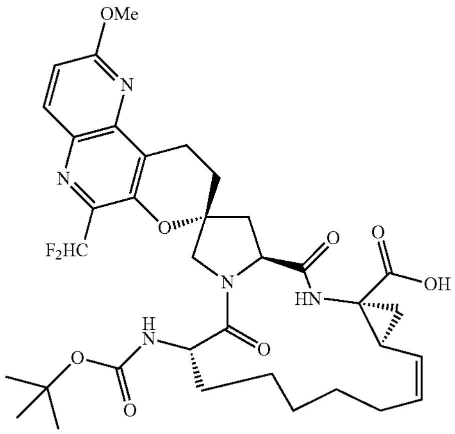

A solution of the product of Step 6 (64 mg, 0.088 mmol), $LiOH.H_2O$ (14.76 mg, 0.352 mmol) in THF (0.5 ml), MeOH (0.5 ml) and water (0.5 ml) was stirred in an oil-bath kept at 60° C. for 1 h then cooled to RT. The reaction mixture was diluted with water, acidified with 1N HCl to pH ~2 and extracted 3× with EtOAc. The combined organic layer was washed with brine, dried over $MgSO_4$, filtered and evaporated to dryness to give 61 mg of the product of Step 7 as a solid. LC-MS m/e=644.31 $(M+H)^+$.

Step 8

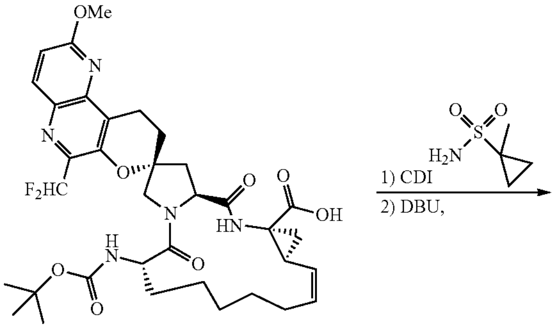

-continued

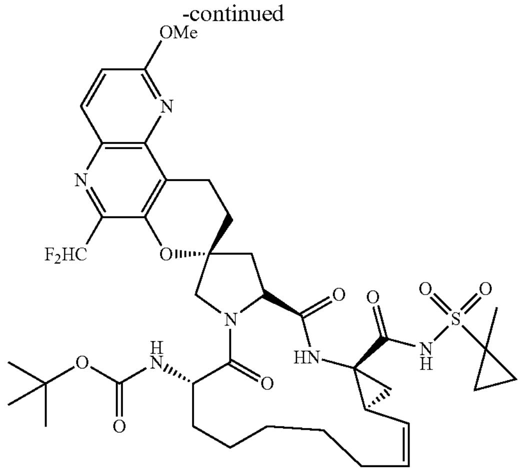

A mixture of the product of Step 7 (40 mg, 0.057 mmol) and CDI (18.54 mg, 0.114 mmol) in THF (2 ml) was stirred in an oil bath kept at 70° C. for 2 h then cooled to RT. To this was added 1-methylcyclopropane-1-sulfonamide (23.18 mg, 0.171 mmol) followed by DBU (0.026 ml, 0.171 mmol), and the mixture was stirred at 50° C. for 3 h. Then the reaction mixture was left overnight at RT. The reaction mixture was diluted with water, acidified with 1N HCl and extracted with EtOAc. The combined organic layer was washed with brine, dried over $MgSO_4$, filtered and evaporated to dryness. The crude product was purified by chromatography (4 g REDISEP cartridge) eluting with 0-40% acetone-hexanes to give 38 mg of I-12 as a solid. LC-MS m/e=817.46 $(M+H)^+$. $^1H$ NMR ($CDCl_3$, 500 MHz) δ (ppm) 8.17 (1 H, d, J=9.03 Hz), 7.07 (1 H, s), 7.02 (1 H, d, J=9.02 Hz), 6.85 (1 H, t, J=54.04 Hz), 5.71 (1 H, q, J=8.98 Hz), 5.09-4.98 (2 H, m), 4.70-4.63 (1 H, m), 4.60 (6 H, s), 4.43 (1 H, d, J=11.01 Hz), 4.19-4.13 (1 H, m), 4.08 (3 H, m), 3.73 (1 H, d, J=10.98 Hz), 3.31-3.27 (2 H, m), 2.57 (2 H, dd, J=13.60, 7.19 Hz), 2.41 (1 H, dd, J=13.48, 9.62 Hz), 2.36-2.25 (3 H, m), 2.17 (1 H, s), 1.94-1.71 (4 H, m), 1.38-1.19 (m), 0.90-0.78 (m).

Example 13 tert-Butyl (2R,6S,13aS,14aR,16aS,Z)-5'-(3-fluorophenyl)-14a-(1-methyl cyclopropylsulfonylcarbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline-]-6-ylcarbamate (I-13)

Step 1

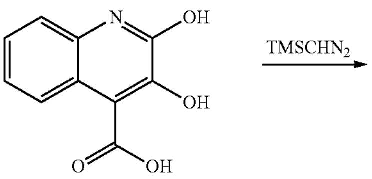

-continued

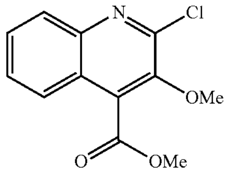

To 2-chloro-3-hydroxy-4-quinolinecarboxylic acid (5 g, 22.36 mmol) in toluene (93 mL)/MeOH (19 mL) was added TMS-diazomethane (33.5 ml, 67.1 mmol) dropwise. Vigorous bubbling occurred, and the mixture began to warm. An ice bath was used to cool the reaction until addition was complete. After 15 min, reaction was complete by LC-MS. AcOH was then added dropwise until bubbling stopped. The mixture was evaporated to dryness yielding a residue, which was purified by column chromatography on silica gel eluting with EtOAc/Hexanes to give the product of Step 1 (5.21 g, 20.70 mmol, 93% yield) as a colorless liquid. MS m/e=252 ($MH^+$).

Step 2

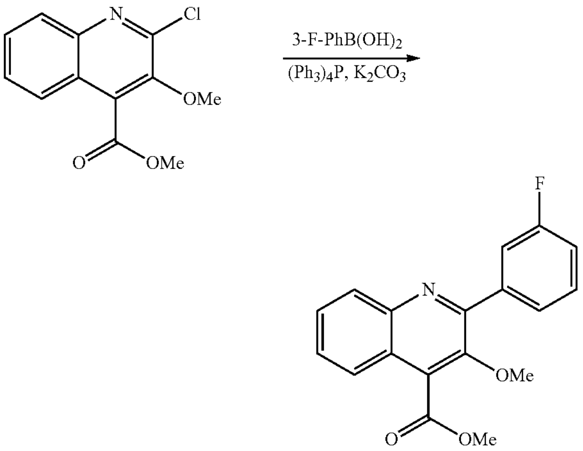

A solution of the product of Step 1 (2 g, 7.95 mmol), $Pd(PPh_3)_4$ (459 mg, 0.05 eq.), 3-fluorophenylboronic acid (1.67 g, 11.92 mmol, 1.5 eq.) and $K_2CO_3$ (4.39 g, 31.8 mmol) in toluene (20 ml), EtOH (10 ml) and water (5 ml) in a sealed tube was bubbled with argon, and the mixture was stirred in an oil bath kept at ~100° C. (bath temperature) for 6 h. The reaction mixture was diluted with water and extracted 3× with EtOAc. The combined organic layer was washed with brine, dried over $MgSO_4$, filtered, concentrated and evaporated to dryness.

The residue was purified by column chromatography on silica gel eluting with 100% hexanes to 15% EtOAc in hexanes to give 2.3 g of the product of Step 2 as a resin. MS m/e=312.2 (MH+).

Step 3

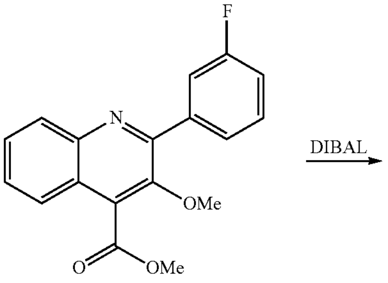

-continued

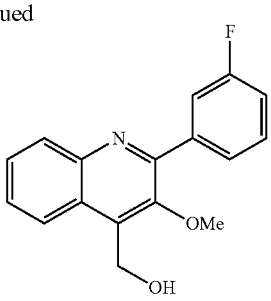

To a solution of the product of Step 2 (3.95 g, 12.69 mmol) in 40 ml DCM at −78° C. was slowly added 1M solution of DIBAL-H (30.5 ml, 30.5 mmol) in toluene, then the cooling bath was removed. After stirring at RT for 2.5 h, the reaction mixture was quenched by the addition of saturated Na—K-tartrate solution, stirred vigorously for 10 min, added some brine, and the organic layer was separated. The aq. phase was extracted 2× with EtOAc, the combined organic layer was washed with brine, dried over $MgSO_4$, filtered and concentrated to provide the 3.96 g of crude product, which was carried to the next step without any purification. MS: m/e=284.2 (MH+).

Step 4

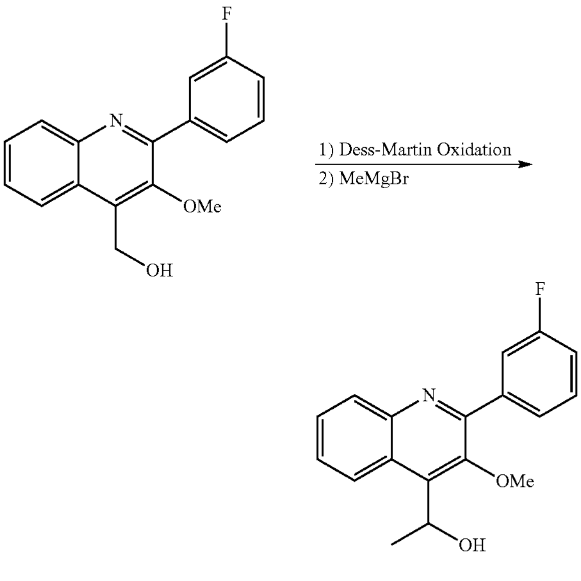

To a suspension of the product of Step 3 (3.60 g, 12.69 mmol) and $NaHCO_3$ (3.20 g, 38.1 mmol) in 60 ml DCM at RT was added Dess-Martin periodinane (8.07 g, 19.04 mmol) in one-portion, and the mixture was stirred at RT. TLC at 1 h in 30% EtOAc-hexanes indicated some unreacted starting alcohol. To the mixture was added another 1 eq. of Dess-Martin reagent, and the stirring was continued at RT. TLC after further 30 min of stirring indicated that the reaction was complete. The reaction mixture was diluted with ether and aq. $Na_2S_2O_3$ and stirred vigorously for 10 min, and the layers separated. The aq. phase was extracted 2× with ether. The combined organic layers was washed with brine, dried over $MgSO_4$, filtered and concentrated to provide the crude aldehyde.

To a solution of the above product (3.57 g, 12.69 mmol) in 60 ml THF at 0° C. (the solution appeared cloudy) was added slowly 3M ether solution of MeMgBr (8.46 ml, 25.4 mmol).

The mixture was stirred at 0° C. After 1 h of stirring, another 0.5 eq. of MeMgBr was added, and the stirring was continued. The reaction mixture was quenched with aq. $NH_4Cl$, extracted 3× with EtOAc, combined organic layer washed with brine, dried over $MgSO_4$ to give the crude product. The crude product was chromatographed with 100% hexanes to 30% EtOAc-hexanes to provide 2.21 g of the product of Step 4 as a solid. MS m/e=298.2 ($MH^+$).

Step 5

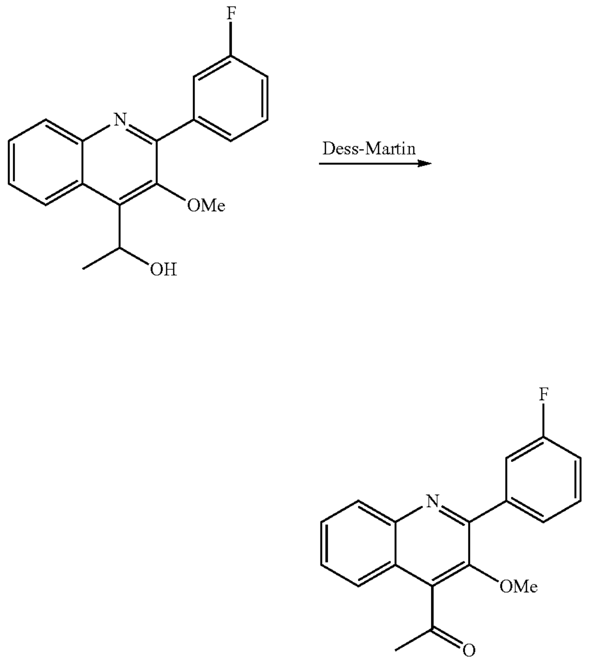

To a mixture of the product of Step 4, $NaHCO_3$ (3.27 g, 38.9 mmol) in DCM (50 ml) at RT was added Dess-Martin periodinane (8.25 g, 19.44 mmol), and the mixture was stirred overnight at RT. TLC after overnight reaction indicated that the reaction is complete. The reaction mixture was diluted with aq. $Na_2S_2O_3$ and stirred vigorously for about 10 min, and the DCM layer was separated. The aq. phase was extracted 3× with ether, and the combined organic layer was washed with aq. $NaHCO_3$ followed by brine, dried over $MgSO_4$, filtered concentrated and purified by chromatography eluting with 0-10% EtOAc-hexanes to provide 2.75 g of the product of Step 5 as yellow colored crystalline solid. MS m/e=296.2 ($MH^+$).

Step 6

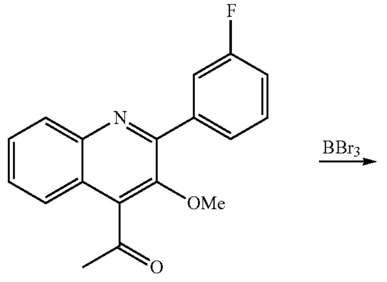

-continued

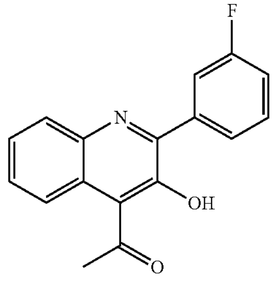

To solution of the product of Step 5 (2.75 g, 9.31 mmol) in DCM (50 ml) at 0° C. was added $BBr_3$ (3.52 ml, 37.2 mmol), and the mixture was stirred at RT. LC-MS at 1 h indicated that the reaction was complete. The solution was cooled in an ice bath and carefully quenched by the addition of water, and the organic layer was separated. The aq. phase was extracted 3× with DCM, the combined organic layer was washed with brine, dried over $MgSO_4$, filtered, concentrated and purified by chromatography eluting with 0-10% EtOAc in hexanes to provide 1.56 g of the product of Step 6 yellow colored solid. MS m/e=282.2 ($MH^+$).

Step 7

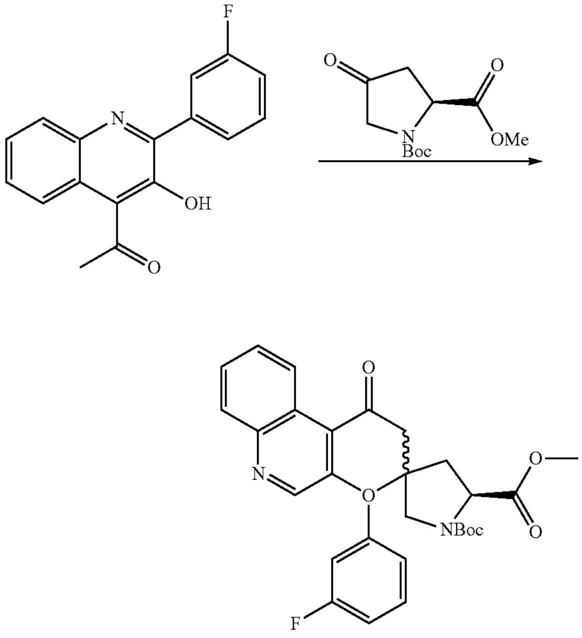

A mixture of the product of Step 6 (1.55 g, 5.51 mmol), Boc-4-Oxo-PRO-OMe (2.68 g, 11.02 mmol), pyrrolidine (0.182 ml, 2.204 mmol) and 3A molecular sieves (4 g, 4-8 mesh) in MeOH (40 ml) in a sealed tube was stirred in an oil-bath kept at 100° C. for 8 h. The mixture was cooled to RT, filtered through a Celite pad and evaporated to dryness. The resultant crude product was purified by chromatography eluting with 0-30% EtOAc in hexanes to provide 2.2 g of the product of Step 7 as a mixture of diastereomers. MS m/e=507.2 ($MH^+$).

Step 8

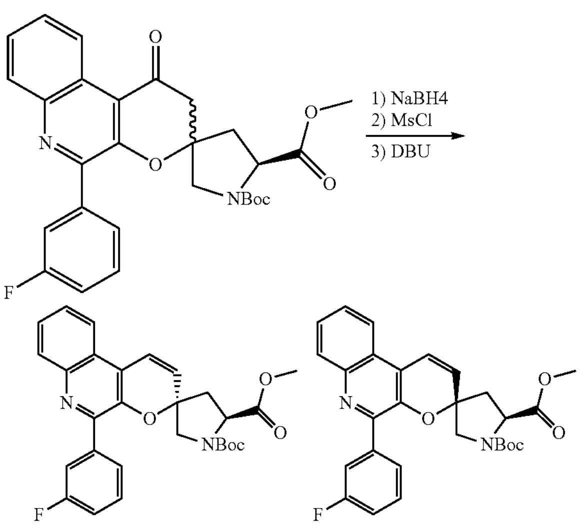

13-8A 13-8B

To a solution of the product of Step 7 (2.2 g, 4.34 mmol) in MeOH (10 ml) and THF (10 ml) at RT was added $NaBH_4$ (0.493 g, 13.03 mmol), and the mixture stirred at RT for 45 min. The reaction mixture poured into aq. $NH_4Cl$ solution and extracted 3× with EtOAc. The combined organic layer was washed with brine, dried over $MgSO_4$, filtered and evaporated to dryness to give the 2.25 g of crude alcohol.

To a solution of the above alcohol (1.8 g, 3.54 mmol) in 20 ml DCM at 0° C. was added $Et_3N$ (1.973 ml, 14.16 mmol) and MsCl (0.552 ml, 7.08 mmol). The reaction mixture was stirred for 1 h at 0° C., then overnight at RT. The reaction mixture was diluted with EtOAc, washed 2× with aq. $NaHCO_3$, brine, dried over $MgSO_4$, filtered and evaporated to dryness to give mixture of mesylate and chloride.

To a solution of the above product in DCM (20 ml) at RT was added DBU (1.067 ml, 7.08 mmol), and the mixture was stirred at RT for 36 h. The reaction mixture was diluted with EtOAc, washed 2× with water, brine, dried over $MgSO_4$, filtered, concentrated and purified by chromatography eluting with 0-30-40% EtOAc-hexanes to give 315 mg of 13-8A and 698 mg of 13-8B. MS for 13-8A m/e=491.0 ($MH^+$). MS for 13-8B m/e=491.0 ($MH^+$).

Step 9

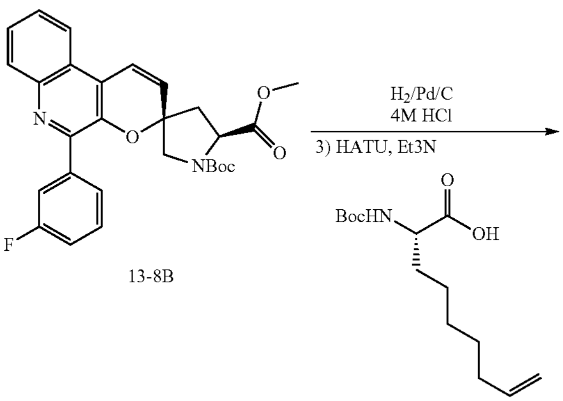

13-8B

-continued

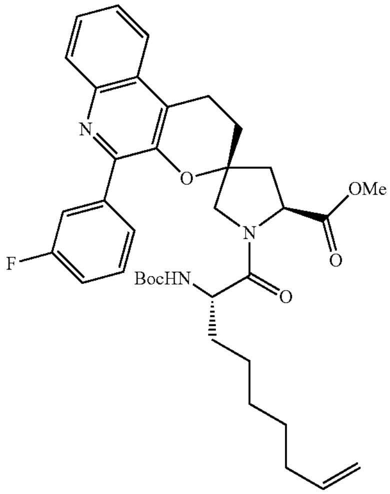

A suspension of 13-8B (730 mg, 1.488 mmol) and 10% Pd—C (140 mg) in EtOAc (10 ml) was stirred overnight under a $H_2$ balloon. The suspension was filtered through a Celite pad and evaporated to dryness. The residue was chromatographed with 0-40% EtOAc-hexanes to give 630 mg of the reduction product.

A solution of above product (630 mg, 1.279 mmol) in 10 ml of 4N HCl/dioxane and 2 ml of MeOH was stirred at RT for 3 h, the solvent was evaporated to dryness, and the residue was co-evaporated with toluene and ether to give crude amine as the HCl salt.

To a mixture of the above product (502 mg, 1.279 mmol), (S)-2-(tert -butoxycarbonylamino)non-8-enoic acid-dicyclohexyl amine salt (868 mg, 1.919 mmol) and DIPEA (0.670 ml, 3.84 mmol) in DMF (3 ml) at RT was added HATU (729 mg, 1.919 mmol), and the mixture was stirred at RT. After stirring overnight, the reaction mixture was diluted with EtOAc. The solution was washed 2× with water, brine, dried over $MgSO_4$, filtered, concentrated and chromatographed with 0-50% EtOAc-hexanes to provide 650 mg of the product of Step 9. MS m/e=646.4 ($MH^+$).

Step 10

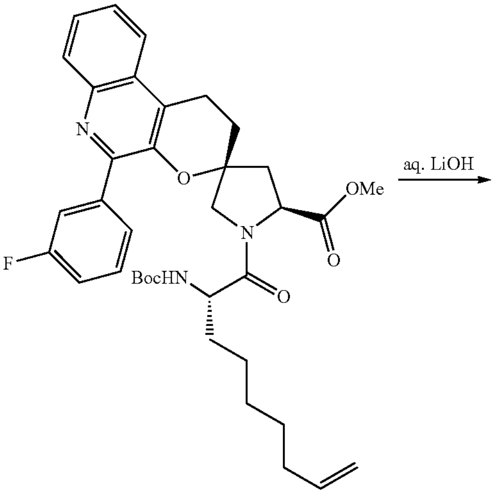

-continued

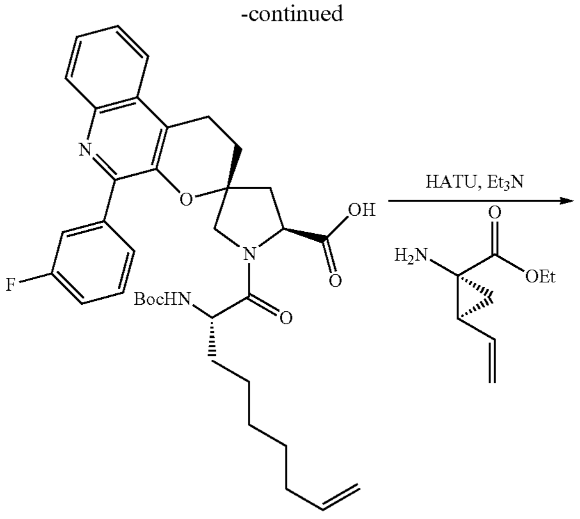

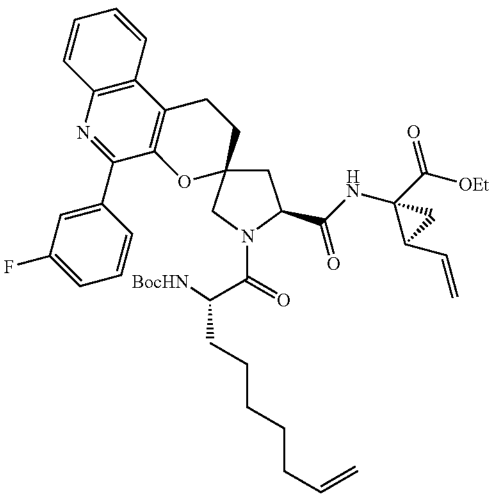

A solution of the product of Step 9 (650 mg, 1.007 mmol) and $LiOH.H_2O$ (169 mg, 4.03 mmol) in THF (3 ml), MeOH (3 ml) and water (3 ml) in an RB flask fitted with a condenser was stirred in an oil-bath kept at 60° C. TLC at 1 h indicated that the reaction was complete. The reaction mixture was diluted with water, acidified with 1N HCl, and extracted 3× with EtOAc. The combined organic layer was washed with brine, dried over $MgSO_4$, filtered and evaporated to dryness to give 610 mg of the acid intermediate.

To a solution of the acid intermediate (610 mg, 0.966 mmol) and (1R,2S)-ethyl 1-amino-2-vinylcyclopropanecarboxylate-hydrochloride salt (278 mg, 1.448 mmol) in DMF (10 ml) at RT was added DIPEA (0.675 ml, 3.86 mmol) followed by HATU (551 mg, 1.448 mmol), and the mixture was stirred at RT for 2 days. The reaction mixture was diluted with EtOAc, washed 2× with water followed by brine. It was dried over $MgSO_4$, filtered, concentrated and chromatographed with 0-60% EtOAc-hexanes to provide 630 mg of the product of Step 10 as resin. MS m/e=769.4 ($MH^+$).

Step 11

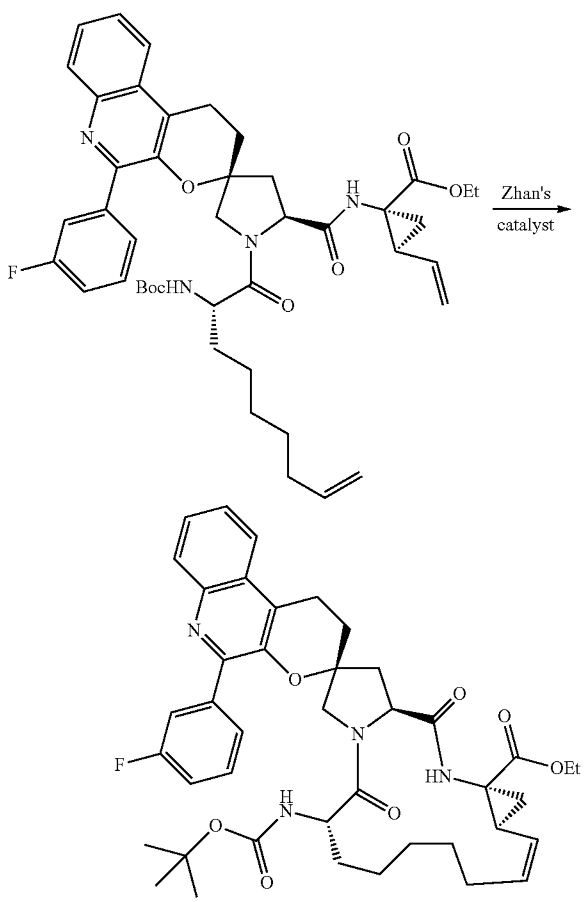

To a solution of the product of Step 10 (220 mg, 0.286 mmol) in DCE (100 ml) at RT was added 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II)dichloride (52.5 mg, 0.072 mmol) followed by p-benzoquinone (9.28 mg, 0.086 mmol). The reaction flask was fitted with a condenser, degassed under vacuum and stirred in an oil-bath kept at 65° C. for 3 h. To the reaction mixture was added 0.5 ml of n-butyl-vinyl ether; the solvent was evaporated to dryness and chromatographed with 0-60% EtOAc-hexanes to provide 123 mg of the product of Step 11 as a resin. MS m/e=741.4 (MH+).

Step 12

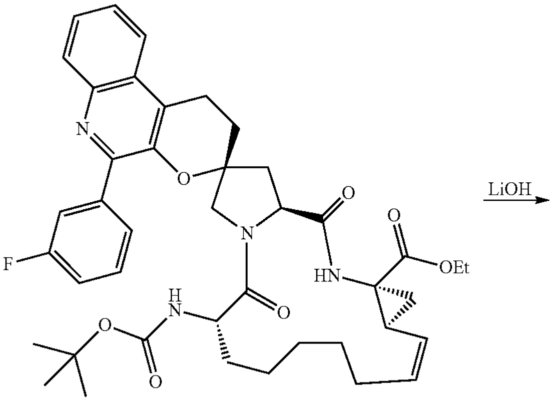

-continued

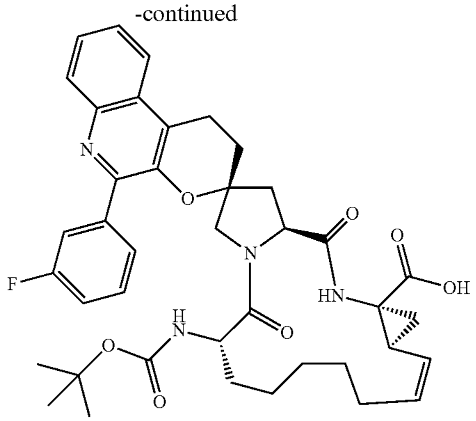

A solution of the product of Step 11 (570 mg, 0.769 mmol) and $LiOH.H_2O$ (129 mg, 3.08 mmol) in THF (2 ml), MeOH (2 ml) and water (2 ml) in an RB flask was stirred in an oil-bath kept at 60° C. for 1 h, poured into water, acidified with 1N HCl and extracted 3× with EtOAc. The combined organic layer was washed with brine, dried over $MgSO_4$, filtered, concentrated and evaporated to dryness to give 480 mg of the product of Step 12 as a solid. MS m/e=713.4 (MH+).

Step 13

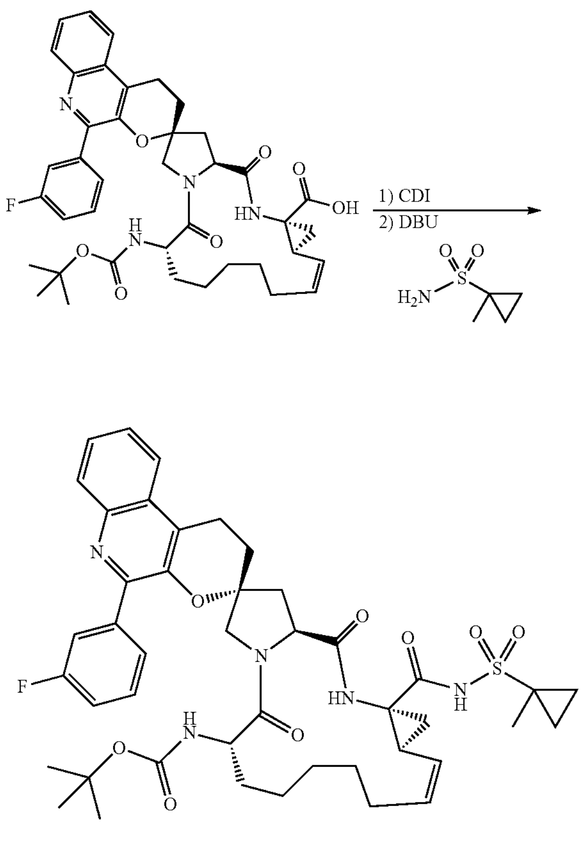

A solution of the product of Step 12 (340 mg, 0.477 mmol) and CDI (155 mg, 0.954 mmol) in THF (5 ml) was heated at reflux for 2 h. The solution was cooled to RT, added 1-methylcyclopropane-1-sulfonamide (258 mg, 1.908 mmol) followed by DBU (0.288 ml, 1.908 mmol), and the mixture was stirred at 50° C. for 10 h then left at RT for 2 d. To the reaction mixture was added few drops of AcOH and diluted with EtOAc. The solution was washed 3× with water, brine, dried over $MgSO_4$, filtered, concentrated and chromatographed with 100% hexanes to 5% MeOH-DCM to provide 390 mg of I-13as a foam. $^1$H-NMR (400 MHz, acetone -d6) 8.01-7.95 (m, 2H), 7.82 (dt, J=8.1, 1.2 Hz, 1H), 7.78-7.75 (m, 1H), 7.63-7.57 (m, 2H), 7.38 (dt, J=6.1, 8.1 Hz, 1H), 7.16 (ddt, J=1.0, 2.7, 8.7 Hz, 1H), 6.0 (d, J=7.6 Hz, 1H), 5.72-5.65 (m, 1H), 5.0 (t, J=9.5 Hz, 1H), 4.68-4.64 (m, 2H), 4.19 (t, J=9.3 Hz, 1H), 3.87 (d, J=11.1 Hz, 1H), 3.40-3.26 (m, 3H), 2.61-2.49 (m, 5H), 2.41-2.33 (m, 2H), 2.08-2.04 (m), 1.96-1.86 (m), 1.71 (dd, J=5.5, 8.0 Hz, 1H), 1.64-1.20 (m), 1.05 (s, 9H), 0.89-0.82 (m). MS m/e=830.4 (MH$^+$).

Example 14 tert-Butyl (2S,6S,13aS,14aR,16aS,Z)-5'-(3-fluorophenyl)-14a-(1-methyl cyclopropylsulfonylcarbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-6-ylcarbamate (I-14)

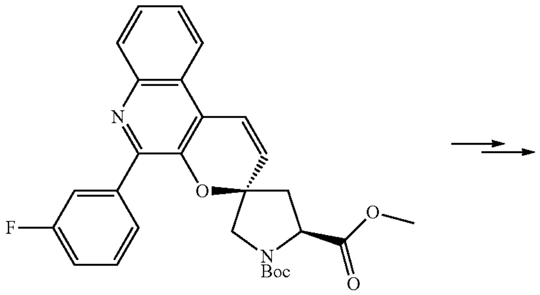

13-8A

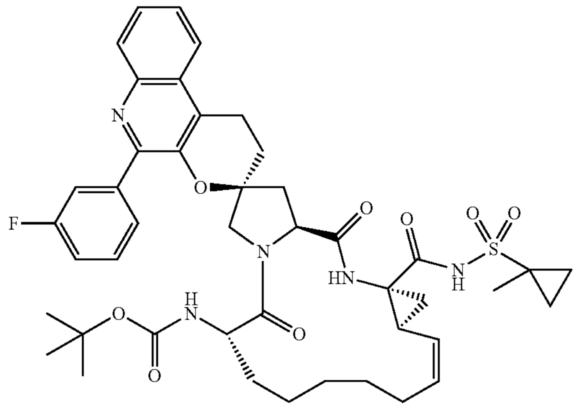

I-14 was prepared using a procedure similar to the preparation of I-13 from the procedures of Example 13, Steps 9-13. MS m/e=830.4 ($MH^+$).

Example 15 tert-Butyl (2R,6S,13aS,14aR,16aS,Z)-14a-(cyclopropylsulfonylcarbamoyl)-5'-(3-fluorophenyl)-5,16-dioxo-1',2',3,5,6,7,8,9,10,11,13a,14,14a,15,16,16a-hexadecahydro-1H -spiro[cyclopropa[e]pyrrolo[1,2-a][1,4]diazacyclopentadecine-2,3'-pyrano[2,3-c]quinoline]-6-ylcarbamate (I-15)

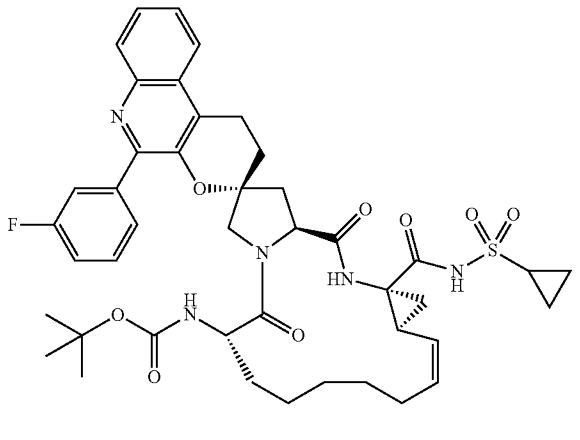 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@]3(CCc4c(c(-c5cccc(F)c5)nc5ccccc45)O3)CN2C1=O]

I-15 was prepared from the product of Example 13, Step 12 and cyclopropanesulfonamide using a procedure similar to Example 13, Step 13. MS m/e=816.4 (MH+).

Example 16 tert-Butyl (2R,6S,13aS,14aR,16aS,Z)-5'-cyclopropyl-9'-methoxy-14a-(1-methylcyclopropylsulfonylcarbamoyl)-5,16-dioxo-1',2',3,5,6,7,8,9,10,11,13a,14,14a,15,16, 16a-hexadecahydro-1H-spiro[cyclopropa[e]pyrrolo[1,2-a][1,4]diazacyclopentadecine-2,3'-pyrano[2,3-c]quinoline]-6-ylcarbamate (I-16)

Step 1

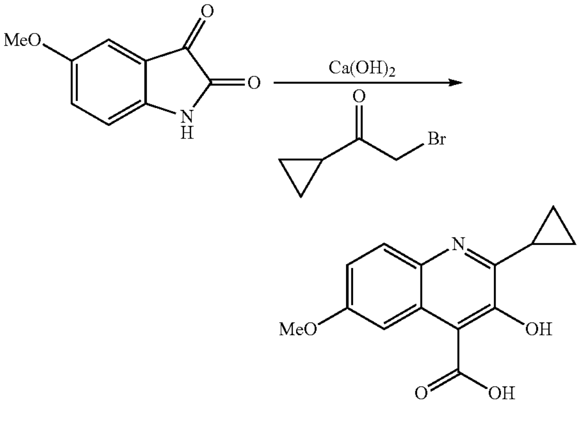

A mixture of 5-methoxyisatin (10 g, 56.4 mmol) and $Ca(OH)_2$ (12.55 g, 169 mmol) in water (150 ml) was stirred in an oil-bath kept at 80° C. for 1 h. Then 2-bromo-1-cyclopropylethan-1-one (18.40 g, 113 mmol) was added through the condenser, while the reaction mixture is still being stirred in the oil-bath. The slurry was stirred for 4 h, diluted with water and acidified with concentrated HCl. The precipitate was filtered, washed with water, ether and dried overnight in vacuum oven to give 10.54 g of the product of Step 1 as yellow colored solid. MS m/e=260.2 (MH+).

Step 2

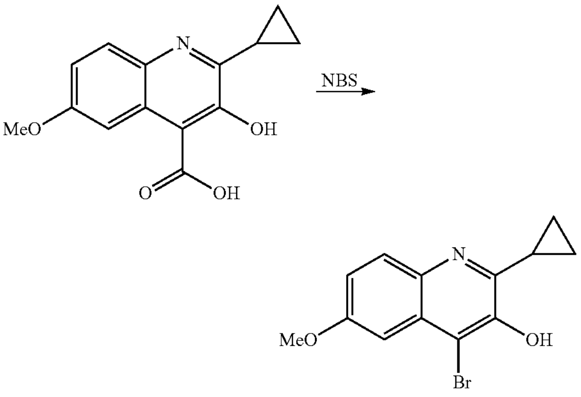

A mixture of the product of Step 1 (10.5 g, 40.5 mmol) and NBS (7.93 g, 44.6 mmol) in THF (150 ml) was stirred at RT for 1 h. The reaction mixture was diluted with aq. $Na_2S_2O_3$ and extracted 3× with EtOAc. The combined organic layer was washed with brine, dried over $MgSO_4$, filtered, concentrated and chromatographed with 100% hexanes to 100% DCM to provide 9.0 g of the product of Step 2 as yellow colored solid. MS m/e=296 (MH+).

Step 3

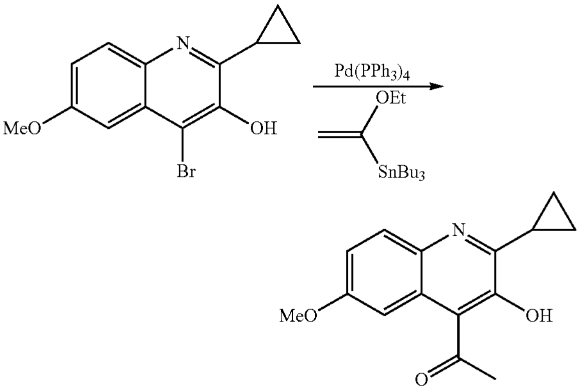

A mixture of the product of Step 2 (9 g, 30.6 mmol), tributyl(1-ethoxyvinyl)tin (20 ml, 59.2 mmol) and $Pd(PPh_3)_4$ (1.768 g, 1.530 mmol) in dioxane (170 ml) was heated at reflux overnight. The reaction mixture was cooled to RT, added ~200 ml of 1N HCl, and the mixture was stirred at RT for 30 min. The solution was diluted with water and extracted 3× with DCM. The combined organic layer was washed with brine, dried over $MgSO_4$, filtered, concentrated and chromatographed with 0-10% EtOAc-hexanes to give 5.74 g of the product of Step 3 as solid. MS m/e=258.2 ($MH^+$).

Step 4

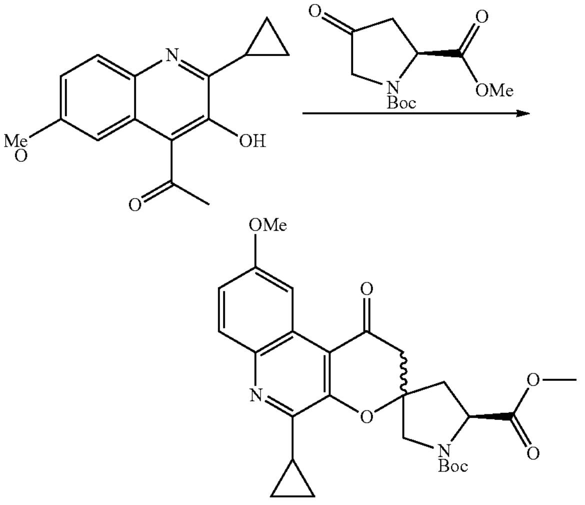

A mixture of the product of Step 3 (3.5 g, 13.60 mmol), Boc-4-oxo-Pro-OMe (6.62 g, 27.2 mmol), pyrrolidine (0.450 ml, 5.44 mmol) and 3A molecular sieves (~15 g, 4-8 mesh) in MeOH (70 ml) in a sealed tube was stirred in an oil-bath kept at 100° C. for 2 h. The mixture was filtered through a Celite pad, rinsed with MeOH, concentrated and chromatographed with 0-30% EtOAc-hexane to provide 3.31 g of the product of Step 4 as a mixture of diastereomers. MS m/e=483.2 (MH+).

Step 5

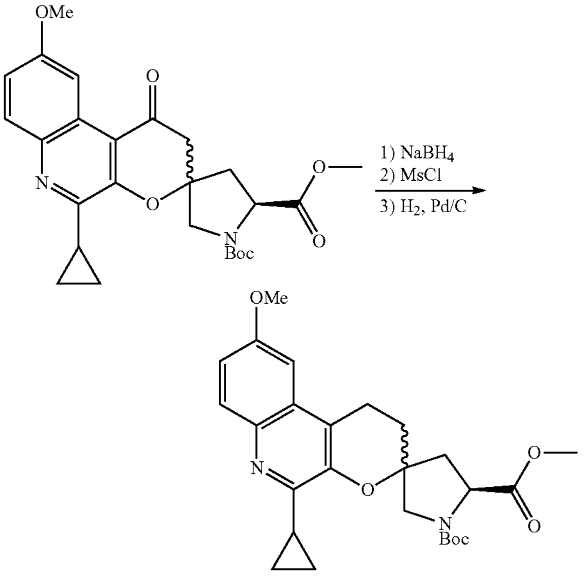

To a solution of the product of Step 4 (3.3 g, 6.84 mmol) in THF (15 ml) and MeOH (15.00 ml) was added $NaBH_4$ (0.776 g, 20.52 mmol), and the mixture was stirred at RT for 45 min, poured into aq. $NH_4Cl$ and extracted 3× with EtOAc. The combined organic layer was washed with brine, dried over $MgSO_4$, filtered and evaporated to dryness to give 2.95 g of the crude alcohol as a mixture of diastereomers.

To a solution of the above alcohol (2.97 g, 6.13 mmol) in DCM (40 ml) at 0° C. was added TEA (3.42 ml, 24.52 mmol)

and MsCl (0.955 ml, 12.26 mmol). The solution was stirred at 0° C. for 1 h then overnight at RT. The reaction mixture was diluted with ether, washed 2× with water, aq. $NaHCO_3$ and brine. It was dried over $MgSO_4$, filtered and evaporated to dryness to give the crude chloride intermediate, which was used as such.

The above product was stirred with activated carbon in EtOAc for about 15 min, filtered through a Celite pad, concentrated and immediately used for this reaction. A suspension of the above product (3.08 g, 6.13 mmol) and 10% Pd/C (500 mg) in EtOAc (50 ml) was stirred under $H_2$ balloon for 3 h. The reaction mixture was filtered through a Celite pad, rinsed with MeOH and EtOAc. The filtrate was washed 2× with aq. $NaHCO_3$, brine, dried over $MgSO_4$, filtered, concentrated and chromatographed with 0-50% EtOAc-hexanes to provide 1.72 g of the product of Step 5 as a resin. MS m/e=469.2 ($MH^+$).

Step 6

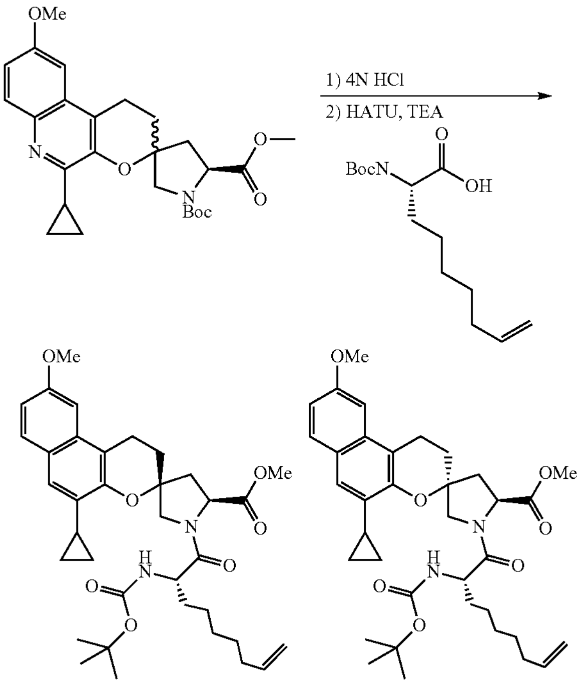

16-6A 16-6B

A solution of the product of Step 5 (1.65 g, 3.52 mmol) in 4N HCl in dioxane (30 ml) was stirred at RT for 1 h, co-evaporated 2× with toluene and 2× with ether to give the crude amine as the hydrochloride, which was used as such.

A slurry of the above product (1425 mg, 3.52 mmol), (S)-2-(tert -butoxycarbonylamino)non-8-enoic acid-dicyclohexylamine salt (2390 mg, 5.28 mmol), HATU (2008 mg, 5.28 mmol) and TEA (1.472 ml, 10.56 mmol) in DMF (40 ml) was stirred at RT for 2 d. The reaction mixture was diluted with water and extracted 3× with EtOAc. The combined organic layer was washed with brine, dried over $MgSO_4$, filtered, concentrated and chromatographed with 0-50-100% EtOAc-hexanes to give 980 mg of 16-6A and 700 mg of 16-6B. MS for 16-6A m/e=621.8 ($MH^+$). MS for 16-6B m/e=621.8 ($MH^+$).

Step 7

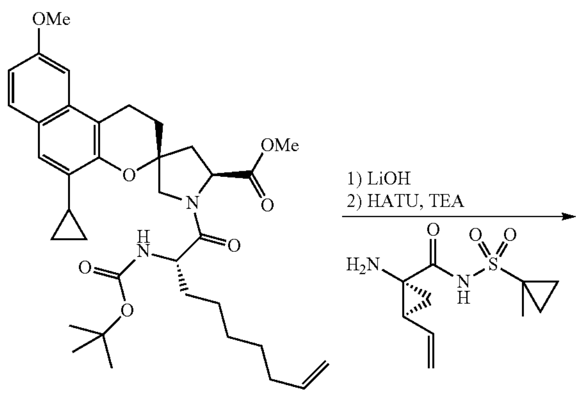

Step 8

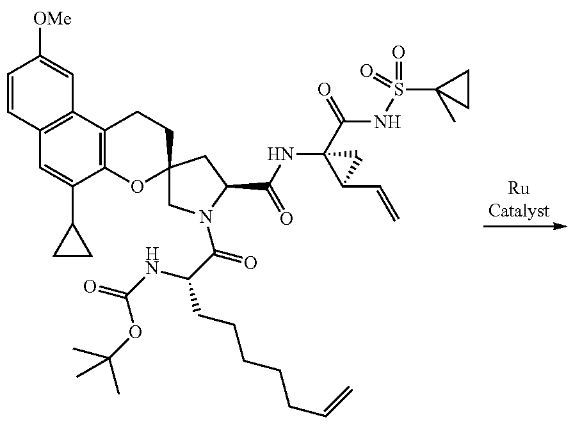

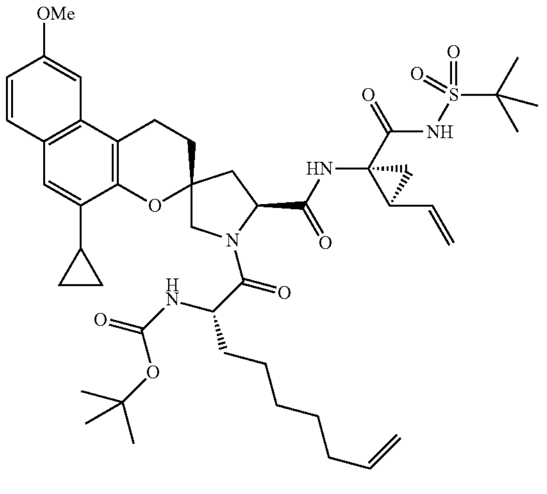

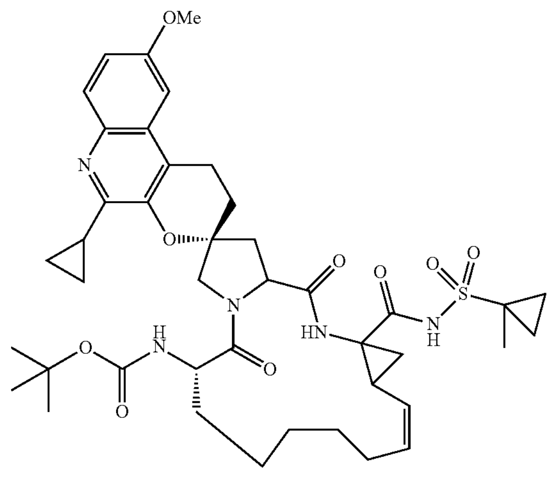

A solution of 16-6A (960 mg, 1.544 mmol) and $LiOH.H_2O$ (259 mg, 6.18 mmol) in THF (5 ml), MeOH (5.00 ml) and water (5.00 ml) was stirred in an oil-bath kept at 60° C. for 1 h. The reaction mixture was cooled to RT, diluted with water, acidified with 1N HCl and extracted 3× with EtOAc. The combined organic layer was washed with brine, dried over $MgSO_4$, filtered, concentrated and evaporated with toluene to give the acid.

A mixture of the above acid (930 mg, 1.530 mmol), (1R, 2S)-1-amino-N-(1-methylcyclopropylsulfonyl)-2-vinylcyclopropanecarboxamide (561 mg, 2.295 mmol) HATU (873 mg, 2.295 mmol) and TEA (0.640 ml, 4.59 mmol) in DMF (15 ml) was stirred overnight at RT. The reaction mixture was diluted with water and extracted 3× with EtOAc. The combined organic layer was washed with brine, dried over $MgSO_4$, filtered, concentrated and chromatographed with 0-30% acetone-hexanes to give 1.24 g of the product of Step 7. MS m/e=833.6 ($MH^+$).

A solution of the product of Step 7 (1.24 g, 1.487 mmol), Zhan's catalyst (0.273 g, 0.372 mmol) and 1,4-benzoquinone (0.048 g, 0.446 mmol) in DCE (600 ml) was degassed under vacuum and filled under argon atmosphere. The mixture was stirred in an oil-bath kept at 75° C. for 4 h. To the reaction mixture was added 1 mL of n-butylvinyl ether and stirred at RT for 30 min. The solvent was evaporated to dryness, and the residue was chromatographed with 0-30% acetone-hexanes to give 990 mg of the compound of I-16 as solid. $^1H$-NMR (400 MHz, $CDCl_3$): 10.09 (s, 1H), 7.73 (d, J=9.0 Hz, 1H), 7.12 (dd, J=2.4, 9.1 Hz, 1H), 6.94 (d, J=2.7 Hz, 1H), 6.92 (s, 1H), 5.72-5.65 (m, 1H), 5.16 (d, J=8.0 Hz, 1H), 4.97 (t, J=9.5 Hz, 1H), 4.59 (t, J=8.1 Hz, 1H), 4.45 (d, J=11.3 Hz, 1H), 4.30-4.24 (m, 1H), 3.90 (s, 3H), 3.75 (d, J=10.8 Hz, 1H), 3.07-3.03 (m, 2H), 2.57-2.52 (m, 2H), 2.43-2.19 (m), 1.86-1.82 (m), 1.74-1.67 (m), 1.40 (s, 9H), 1.42-1.10 (m), 0.89-0.74 (m). MS m/e=805.6 ($MH^+$).

Example 17 tert-Butyl (2S,6S,13aS,14aR,16aS,Z)-5'-cyclopropyl-9'-methoxy-14a-(1-methylcyclopropylsulfonylcarbamoyl)-5,16-dioxo-1',2',3,5,6,7,8,9,10,11,13a,14,14a,15, 16,16a-hexadecahydro-1H-spiro[cyclopropa[e]pyrrolo[1,2-a][1,4]diazacyclopentadecine -2,3'-pyrano[2,3-c]quinoline]-6-ylcarbamate (I-17)

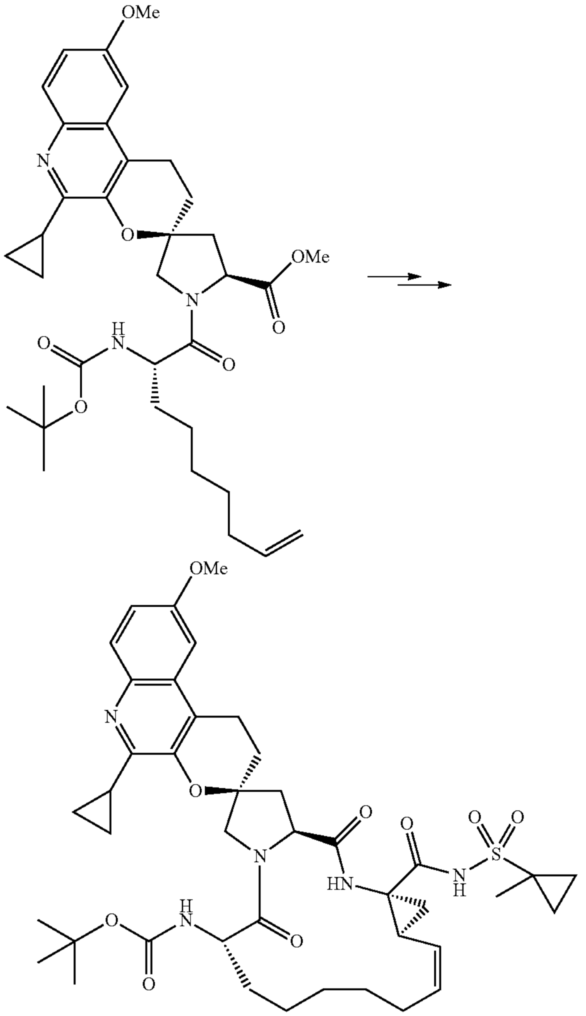

Intermediate 16-6B (the product of Example 16, Step 6) was converted to I-17 using procedures similar to Example 16, Steps 7-8. MS m/e=806.4 (MH+).

Example 18 tert-Butyl (2R,6S,13aS,14aR,16aS,Z)-5'-cyclopropyl-14a-(1-methyl cyclopropylsulfonylcarbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline-]-6-ylcarbamate (I-18)

Step 1

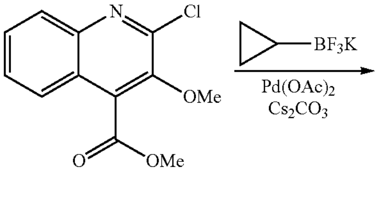

-continued

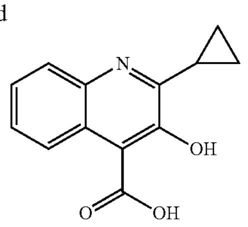

To a pressure vessel with a stir bar was added $Cs_2CO_3$ (7.77 g, 23.84 mmol), palladium(II) acetate (0.089 g, 0.397 mmol), di(1-adamantyl)-n-butylphosphine (available as CataCXium A,0.285 g, 0.795 mmol), cyclopropyl potassiumtetrafluoroborate (1.764 g, 11.92 mmol) and a solution of the product of Example 13, Step 1 (2 g, 7.95 mmol) in toluene (28.9 ml) and water (2.89 ml). After bubbling with argon for about 2 min, the vessel was sealed and heated to 100° C. After 16 h, the mixture was cooled, water (100 ml) was added, and the mixture was extracted with EtOAc (3×75 ml). The combined organic fractions were washed with brine (1×75 mL), dried with $MgSO_4$, filtered, and the solvent was evaporated under reduced pressure. The residue was purified by column chromatography on silica gel, eluting with EtOAc/hexanes to give the product of Step 1 (1.9 g, 7.38 mmol, 93% yield) as an amber oil. MS m/e=258 (MH+).

Step 2

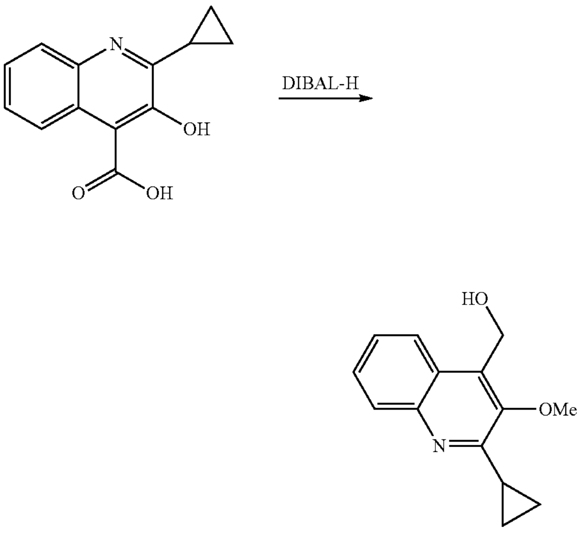

DIBAL-H (15.55 ml, 46.6 mmol) was added to a stirred, cooled −78° C. mixture of the product of Step 1 (4 g, 15.55 mmol) in DCM (78 mL), and the mixture was stirred for 3 h under $N_2$. The reaction mixture was quenched with aq. sodium potassium tartrate, while stirring vigorously. The phases were separated and the aq. phase extracted with EtOAc (3×). The combined organic phases were washed with brine, dried with $MgSO_4$, filtered and evaporated to dryness yielding the product of Step 2 (3.31 g, 14.44 mmol, 93% yield). MS m/e=230 ($MH^+$).

Step 3

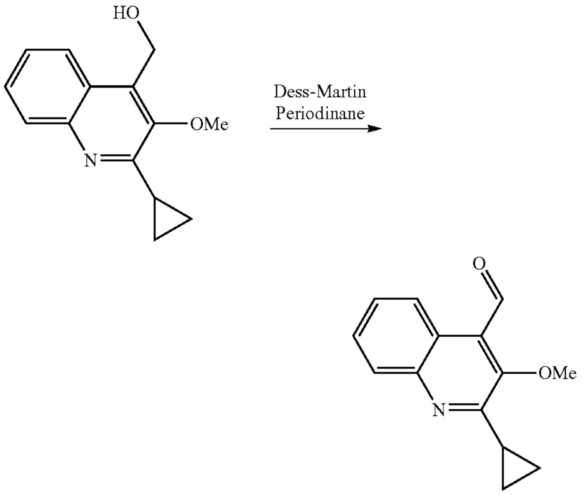

$NaHCO_3$ (1.21 g, 14.4 mmol) and Dess-Martin periodinane (12.25 g, 28.9 mmol) were added to the product of Step 2 (3.31 g, 14.44 mmol) in DCM (72.2 ml), and the mixture was stirred overnight under $N_2$. When the reaction was complete (by LC-MS), the reaction mixture was poured onto aq. $Na_2S_2O_3$ and aq. 1N NaOH solution and extracted (3×) with DCM. The combined extracts were washed with brine, dried with $MgSO_4$, filtered and evaporated to dryness yielding a residue. The residue was purified by column chromatography on silica gel eluting with EtOAc/Hexanes to give 3.38 g of the product of Step 3 as a yellow oil. MS m/e=228 (MH+).

Step 4

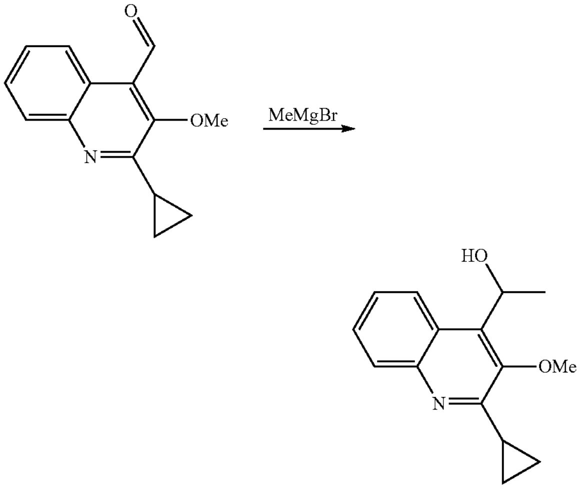

MeMgBr (9.92 ml, 29.7 mmol) was added to a stirred, cooled (−10° C.) mixture of the product of Step 3 (3.38 g, 14.87 mmol) in THF, and the mixture was stirred for about 90 min under $N_2$. The reaction mixture was quenched with aq. $NH_4Cl$ and extracted with EtOAc (3×). The combined extracts were washed with brine, dried with $MgSO_4$, filtered and evaporated to dryness yielding the product of Step 4 (3.82 g, 15.70 mmol, 106% yield). MS m/e=244 (MH+).

Step 5

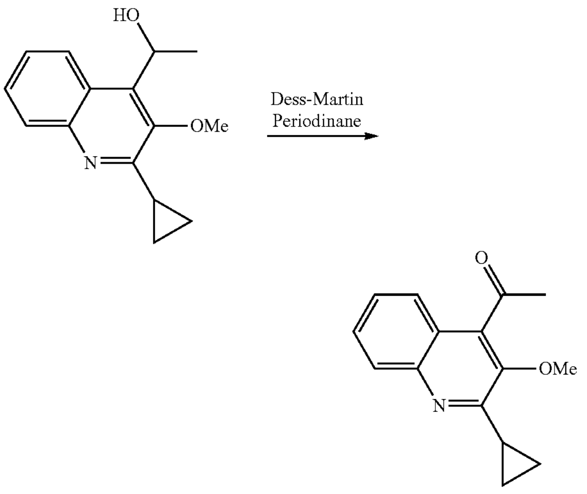

$NaHCO_3$ (2.67 g, 31.7 mmol) and Dess-Martin periodinane (13.46 g, 31.7 mmol) were added to a stirred mixture of the product of Step 4 (3.86 g, 15.87 mmol) in DCM, and the mixture was stirred overnight under $N_2$. The reaction mixture was poured onto aq. $Na_2S_2O_3$ followed by aq. 1N NaOH, which formed a heavy white precipitate. The heavy emulsion was separated from the small amount of clear aq. phase, and the white gloppy mixture was vacuum filtered, and the filtrate (two phases) was partitioned. The aq. part of the filtrate was combined with the aq. phase collected earlier and was extracted (3×) with DCM. The combined organic phases were dried with $MgSO_4$, filtered and evaporated to dryness. 4.48 g of orange oil was obtained. The residue was purified by column chromatography on silica gel eluting with EtOAc/Hexanes to give the product of Step 5 (2.87 g, 11.89 mmol, 75.0% yield) as a light amber oil. MS m/e=242 ($MH^+$).

Step 6

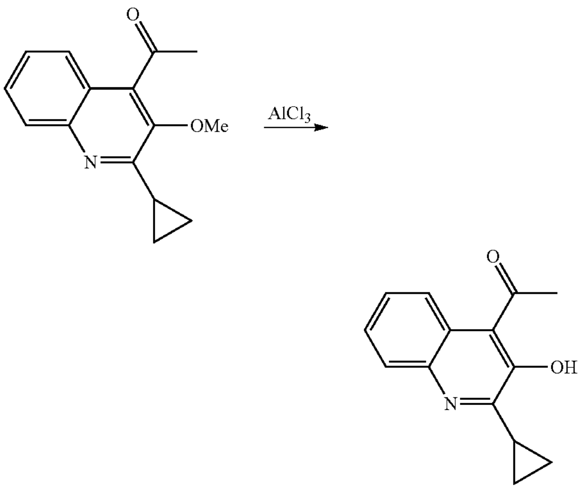

$AlCl_3$ (15.64 g, 117 mmol) was added to a stirred, cooled −10° C. solution of the product of Step 5 (2.83 g, 11.73 mmol) in DCM (58.6 ml), and the mixture was stirred under $N_2$ and warmed to RT. After stirring overnight, the reaction mixture was cooled to −10° C. then quenched with aq. Na—K-tartrate. The layers were separated, and the aq. phase was extracted with EtOAc (3×). The combined organic phases were washed with brine, dried with $MgSO_4$, filtered and evaporated to dryness yielding the product of Step 6 (2.56 g, 11.26 mmol, 96% yield).

Step 7

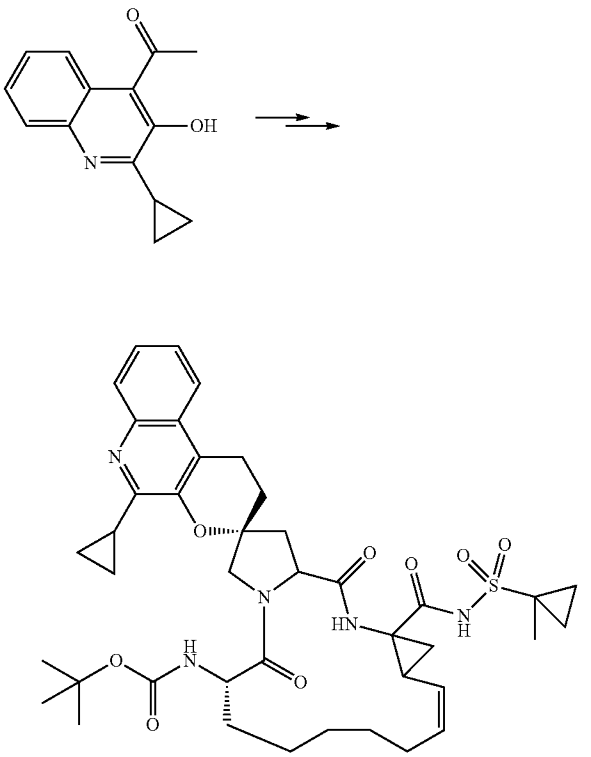 [SMILES: CC(=O)c1c(O)c(C2CC2)nc2ccccc12 ; CC(C)(C)OC(=O)N[C@H]1CCCCC/C=C\C2CC2(C(=O)NS(=O)(=O)C2(C)CC2)NC(=O)C2C[C@]3(CCc4c(c(C5CC5)nc5ccccc45)O3)CN2C1=O]

The product of Step 6 was converted to I-18 using a procedure similar to Example 16, Steps 4-8. MS m/e=776 (MH+).

Example 19 tert-Butyl (2S,6S,13aS,14aR,16aS,Z)-5'-cyclopropyl-1',1'-difluoro-9'-methoxy -14a-(1-methylcyclopropylsulfonylcarbamoyl)-5,16-dioxo-1',2',3,5,6,7,8,9,10,11,13a,14,14a, 15,16,16a-hexadecahydro-1H-spiro[cyclopropa[e]pyrrolo[1,2-a][1,4]diazacyclopentadecine -2,3'-pyrano[2,3-c]quinoline]-6-ylcarbamate (I-19)

Step 1

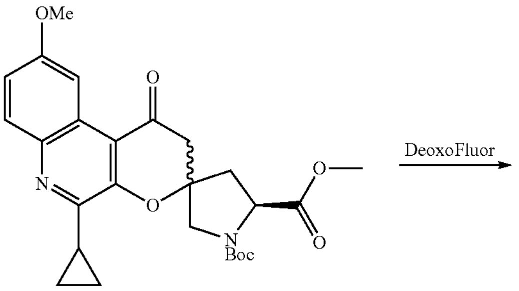

-continued

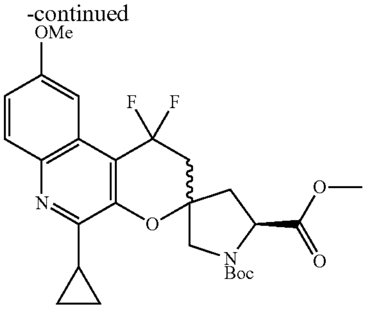

To a solution of the product of Example 16, Step 4 (3 g, 6.22 mmol) in DCM (30 ml) at RT was added DeoxoFluor (5.73 ml, 31.1 mmol) followed by EtOH (0.109 ml, 1.865 mmol), and the mixture was heated at reflux overnight. LC-MS indicated mostly unreacted starting material. To the reaction mixture was added another 10 eq. of DeoxoFluor and 0.3 eq. of EtOH, and the reaction continued. The reaction continued at reflux for 3 d. The reaction mixture was slowly poured in to aq. $NaHCO_3$ and extracted 3× with DCM. The combined organic layer was washed with brine, dried over $MgSO_4$, filtered, concentrated and chromatographed with 0-30-40% EtOAc-hexanes to provide 1.08 g of the product of Step 1 as solid. MS m/e=505.2 (MH+).

Step 2

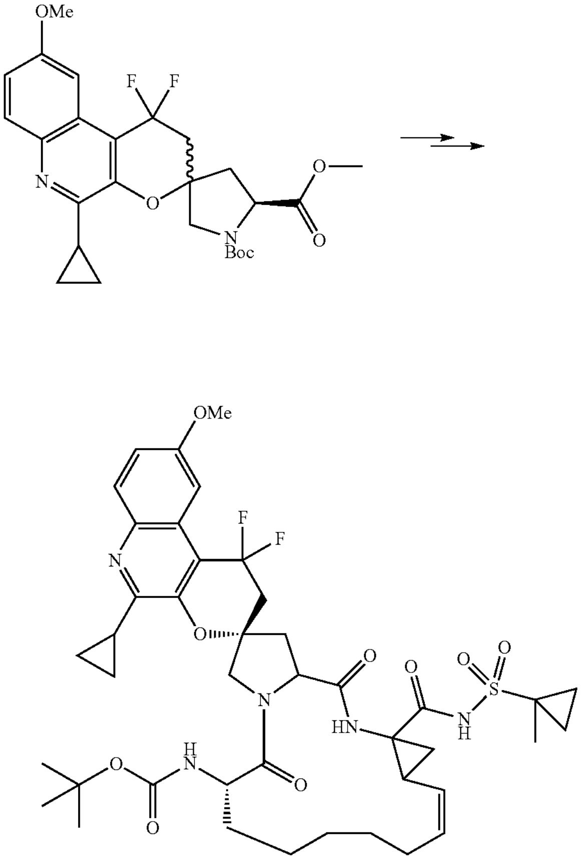

The product of Step 1 was converted to I-19 using a procedure similar to Example 16, Steps 6-8.

Example 20 tert-Butyl (2S,6S,13aS,14aR,16aS,Z)-1',1'-difluoro-9'-methoxy-5'-methyl-14a -(1-methylcyclopropylsulfonylcarbamoyl)-5,16-dioxo-1',2',3,5,6,7,8,9,10,11,13a,14,14a,15, 16,16a-hexadecahydro-1H-spiro[cyclopropa[e]pyrrolo[1,2-a][1,4]diazacyclopentadecine -2,3'-pyrano[2,3-c]quinoline]-6-ylcarbamate (I-20)

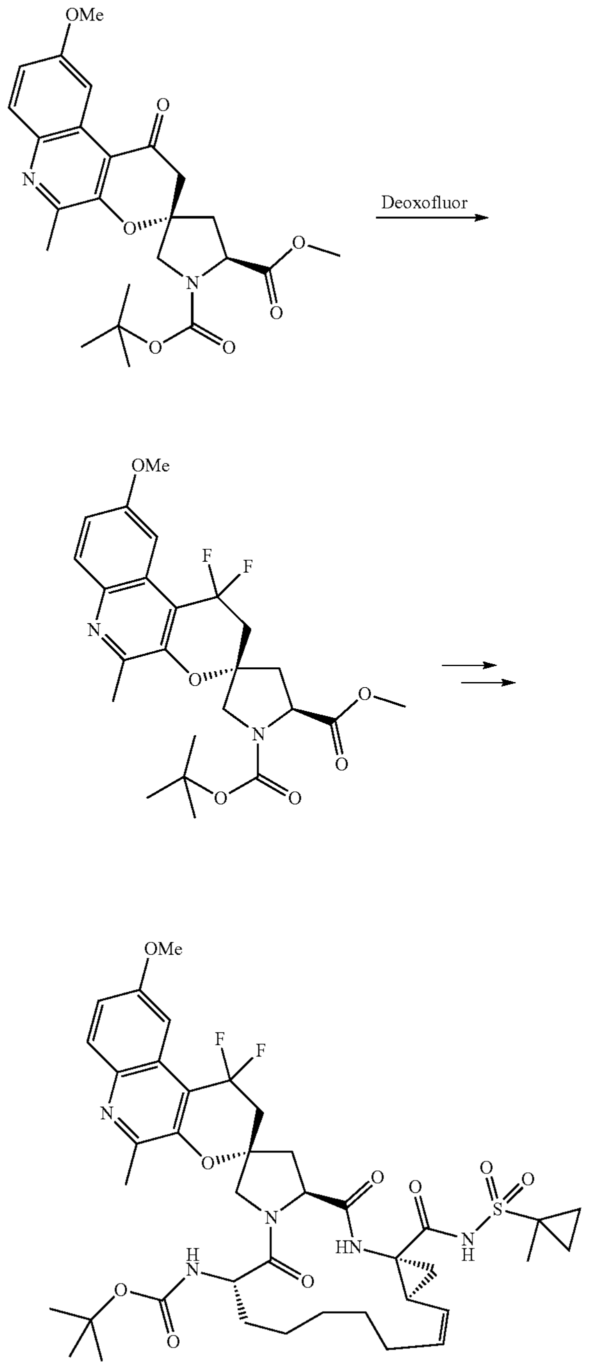

Intermediate 9-4A (the product of Example 9, Step 4) was converted to I-20 using procedures similar to Example 19. MS m/e=806.4 (MH+).

Example 21

Isobutyl (2R,6S,13aS,14aR,16aS,Z)-5'-(3-fluorophenyl)-14a-(1-methyl cyclopropylsulfonylcarbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-6-ylcarbamate (I-21)

Step 1

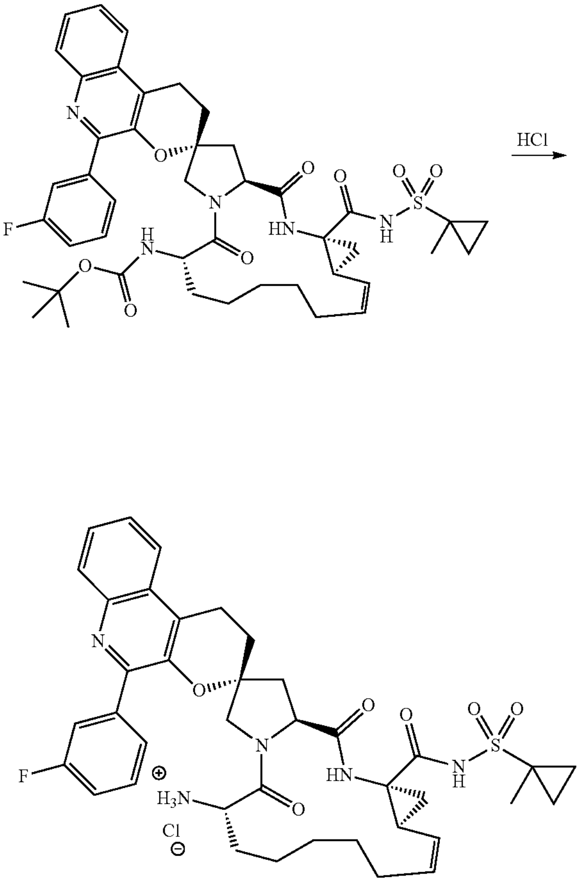

To a flask containing I-13 (200 mg, 0.241 mmol) was added 4 ml of 4N HCl/dioxane solution and 1 ml of MeOH, and the mixture was stirred at RT for 2 h. The solvent was co-evaporated 2× with toluene and 2× with ether to give 180 mg of the product of Step 1 as HCl salt. MS m/e=730.2 ($MH^+$).

Step 2

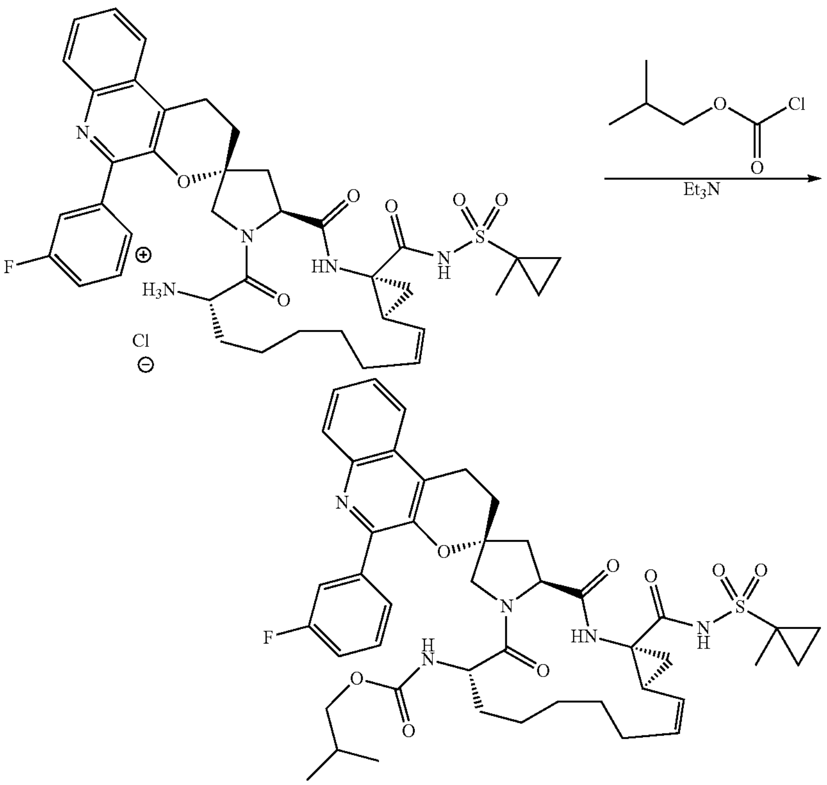

A mixture of the product of Step 1 (50 mg, 0.069 mmol), isobutyl chloroformate (0.018 ml, 0.137 mmol) and TEA (0.038 ml, 0.274 mmol) in DCM (1 ml) was stirred at RT for 2 h then diluted with EtOAc. The solution was washed 2× with water, brine, dried over $MgSO_4$, filtered, concentrated and purified by preparative TLC eluting with 5% MeOH-DCM to give 28 mg of I-21. MS me/=830.4 ($MH^+$).

Example 22

1-Methylcyclopropyl (2R,6S,13aS,14aR,16aS,Z)-5'-(3-fluorophenyl)-14a-(1-methylcyclopropylsulfonyl-carbamoyl)-5,16-dioxo-1',2',3,5,6,7,8,9,10,11,13a, 14,14a,15,16, 16a-hexadecahydro-1H-spiro [cyclopropa[e]pyrrolo[1,2-a][1,4] diazacyclopentadecine-2,3'-pyrano[2,3-c]quinoline]-6-ylcarbamate (I-22)

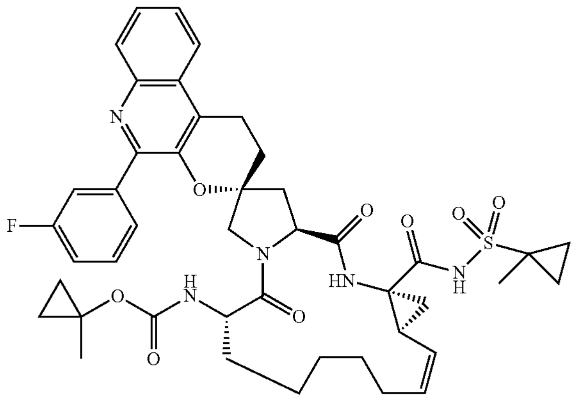 [SMILES: CC1(OC(=O)N[C@H]2CCCCC/C=C\[C@@H]3C[C@@]3(C(=O)NS(=O)(=O)C3(C)CC3)NC(=O)[C@@H]3C[C@]4(CCc5c(c(-c6cccc(F)c6)nc6ccccc56)O4)CN3C2=O)CC1]

A mixture of the product of Example 21, Step 1 (20 mg, 0.026 mmol), 2,5-dioxopyrrolidin-1-yl 1-methylcyclopropyl carbonate (8.35 mg, 0.039 mmol) and $Et_3N$ (10.91 μl, 0.078 mmol) in DCM (1 ml) was stirred at RT for 4 h, then diluted with EtOAc. The solution was washed 2× with water, brine, concentrated and purified by preparative TLC eluting with 5% MeOH-DCM to give 15 mg of I-22. MS m/e=828.4 ($MH^+$).

Example 23

(2R,6S,13aS,14aR,16aS,Z)-6-(3-tert-Butylureido)-5'-(3-fluorophenyl)-N-(1-methylcyclopropylsulfonyl)-5,16-dioxo-1',2',3,5,6,7,8,9,10,11,13a,14,14a,15,16, 16a -hexadecahydro-1H-spiro[cyclopropa[e]pyrrolo [1,2-a][1,4]diazacyclopentadecine-2,3'-pyrano[2,3-c] quinoline]-14a-carboxamide (I-23)

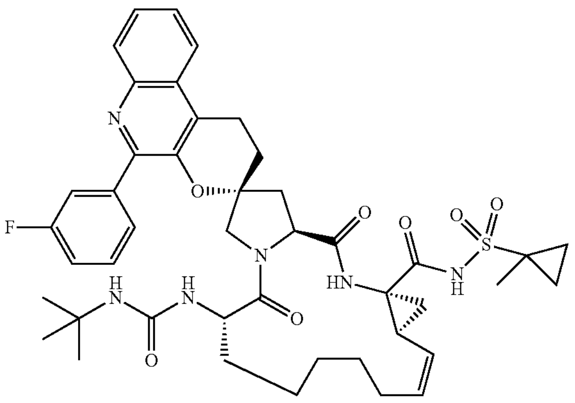 [SMILES: CC(C)(C)NC(=O)N[C@H]1CCCCC/C=C\[C@@H]2C[C@@]2(C(=O)NS(=O)(=O)C2(C)CC2)NC(=O)[C@@H]2C[C@]3(CCc4c(c(-c5cccc(F)c5)nc5ccccc45)O3)CN2C1=O]

To a solution of the product of Example 21, Step 1 (32.2 mg, 0.042 mmol) in DCM (2 ml) at RT was added $Et_3N$ (0.029 ml, 0.210 mmol) and tert-butyl isocyanate (12.49 mg, 0.126 mmol), and the mixture was stirred at RT for 3.5 h. To the reaction mixture was added few drops of AcOH, then diluted with EtOAc. The solution was washed 3× with water, brine, dried over $MgSO_4$, filtered, concentrated and chromatographed with 100% hexanes to 5% MeOH-DCM to provide 34 mg of I-23. MS m/e=829.4 ($MH^+$).

Example 24

(2R,6S,13aS,14aR,16aS,Z)-5'-(3-Fluorophenyl)-N-(1-methylcyclopropyl sulfonyl)-5,16-dioxo-6-(3,3,3-trifluoropropanamido)-1',2',3,5,6,7,8,9,10,11,13a,14,14a,15,16, 16a-hexadecahydro-1H-spiro[cyclopropa[e]pyrrolo[1,2-a][1,4]diazacyclopentadecine-2,3'-pyrano[2,3-c]quinoline]-14a-carboxamide (I-24)

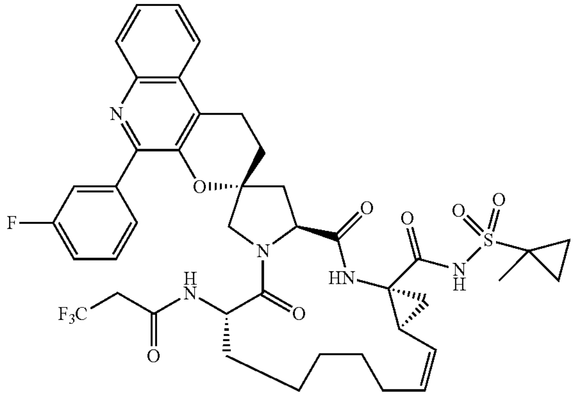 [SMILES: CC1(S(=O)(=O)NC(=O)[C@@]23C[C@H]2/C=C\CCCCC[C@H](NC(=O)CC(F)(F)F)C(=O)N2C[C@@]4(CCc5c(c(-c6cccc(F)c6)nc6ccccc56)O4)C[C@H]2C(=O)N3)CC1]

A mixture of the product of Example 21, Step 1 (20 mg, 0.026 mmol), 3,3,3-trifluoropropionyl chloride (5.38 μl, 0.052 mmol) and $Et_3N$ (10.91 μl, 0.078 mmol) in DCM (1 ml) was stirred at RT for 4 h. The solution was diluted with EtOAc, washed 2× with water, brine, concentrated and purified by preparative TLC eluting with 5% MeOH-DCM to give 8 mg of I-24. MS m/e=840.2 ($MH^+$).

Example 25 tert-Butyl (2S,6S,13aS,14aR,16aS,Z)-1',1'-difluoro-5'-methyl-14a-(1-methyl cyclopropylsulfonylcarbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-6-ylcarbamate (I-25)

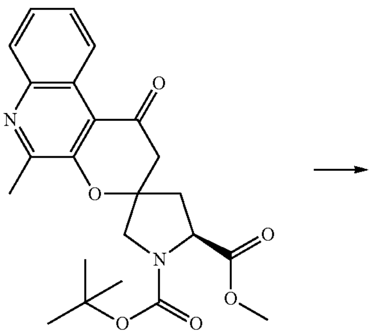

-continued

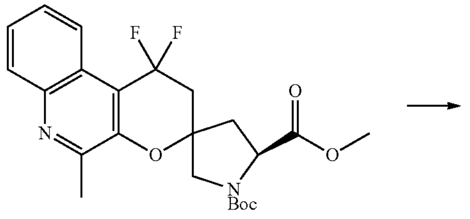

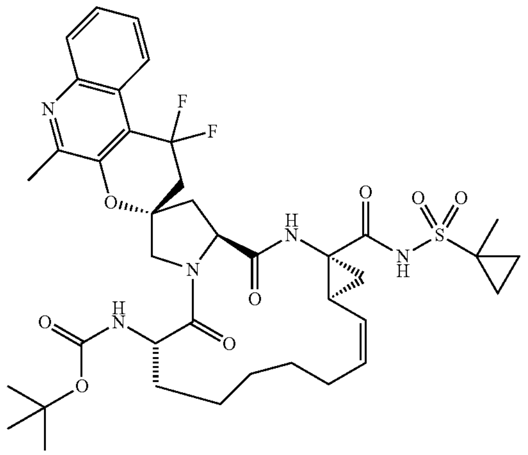

To 1'-tert-butyl 5'-methyl (5'S)-5-methyl-1-oxo-1,2-dihydro-1'H -spiro[pyrano[2,3-c]quinoline-3,3'-pyrrolidine]-1',5'-dicarboxylate (180 mg, 0.422 mmol) in DCM (3 ml) was treated with a solution of DeoxoFluor (0.233 ml, 1.266 mmol) (0.233 ml, 1.266 mmol) in DCM (1 ml) and EtOH (0.084 mmol, 4.9 μL) and heated at 50° C. Another 1.8 eq. of oxy-DAST and 0.2 eq. of EtOH were added and stirred for further 5 h. On completion, the solution was poured into saturated $NaHCO_3$ and after $CO_2$ evolution ceased, extracted with DCM and dried. The crude reaction mixture was purified by column chromatography with 50% hexanes/EtOAc to give the intermediate as a mixture of diastereomers (50 mg, 0.111 mmol, 26.4% yield). This intermediate was treated with conditions similar to Example 4 (steps 10-13) to give I-25. $^1H$ -NMR (400 MHz, $CDCl_3$) δ 10.11 (s, 1H), 8.21 (d, J=6.66 Hz, 1H), 8.00-7.96 (m, 1H), 7.60-7.53 (m, 2H), 7.02 (br s, 1H), 5.73-5.67 (m, 1H), 5.02-4.98 (m, 1H), 4.91-4.89 (m, 1H), 4.69-4.64 (m, 1H), 4.57 (d, J=11.0 Hz, 1H), 4.03-3.98 (m, 1H), 3.73 (d, J=12.0 Hz, 1H), 2.90-0.80 (m, 36H). MS m/e=786.4 ($MH^+$).

Example 26 tert-Butyl (2S,6S,13aS,14aR,16aS,Z)-14a-(cyclopropylsulfonylcarbamoyl)-5'-methyl-5,16-dioxo-3,5,6,7,8,9,10,11,13a,14,14a,15,16,16a-tetradecahydro-1H-spiro [cyclopropa[e]pyrrolo[1,2-a][1,4] diazacyclopentadecine-2,3'-pyrano[2,3-c] quinoline-]-6-ylcarbamate (I-26)

Step 1

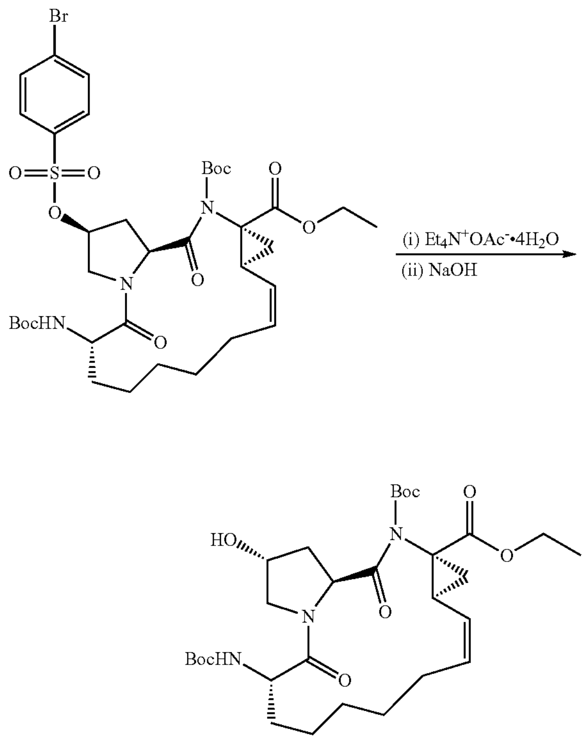

Tetraethylammonium acetate tetrahydrate (1.29 g, 4.92 mmol) was dissolved in benzene (20 ml) equipped with a Dean-Stark trap and heated to reflux overnight. A solution of 15-tert-butyl 14a-ethyl (2S,6S,12Z,13aS,14aR,16aS)-2-{[(4-bromophenyl)sulfonyl]oxy}-6-[(tert -butoxycarbonyl) amino]-5,16-dioxo-2,3,6,7,8,9,10,11,13a,14,16,16a-dodecahydrocyclopropa[e]pyrrolo[1,2-a][1,4] diazacyclopentadecine-14a,15(1H,5H)-dicarboxylate (2.0 g, 2.461 mmol) in benzene (20 ml) was added to the mixture of tetraethylammonium acetate solution, and the resulting solution was refluxed for 1.5 h. The reaction mixture was cooled to the RT, and a solid was formed, which was filtered. The filtrate was evaporated to dryness, and the residue was taken up in MeOH (7 ml) and cooled to 0° C. 1N NaOH solution (6 ml) was slowly added to the mixture, and the resulting mixture was stirred at 0° C. for 2 h. The reaction mixture was neutralized with 2N HCl (aq.) and extracted with DCM. The combined organic layers were dried over anhydrous $Na_2SO_4$, filtered, concentrated, purified by silica gel column chromatography using (0-75%) EtOAc-hexanes as mobile phase, and the product of Step 1 was isolated as white solid.

Step 2

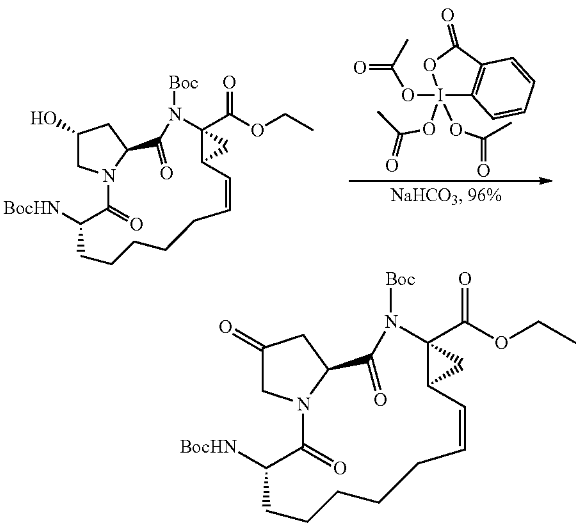

To a suspension of the product of Step 1 (0.76 g, 1.28 mmol) and $NaHCO_3$ (0.108 g, 1.28 mmol) in DCM (10 ml) at 0° C. was added DMP (1.5 eq., Aldrich) in one rapid portion. The resulting suspension was stirred for 1 h at RT. LC-MS showed only starting alcohol. A second 1.5 eq. of DMP (2.17 g, 5.12 mmol) was added at 0° C. and left to stir at RT for 1.0 h. LC-MS showed product formation. After 3.0 h, LC-MS showed starting material to product in 3:2 ratio. To this was added more DMP (1 eq.) and left stirring overnight at RT. The crude reaction mixture was then diluted with ether and quenched with 1N aq. NaOH. The aq. layer was then back extracted with ether. The combined organic layers were washed with 1N HCl, water, brine and dried with $Na_2SO_4$, filtered, and the filtrate was concentrated in vacuo to afford the product of Step 2 (0.728 g, 96%) as white foam.

Step 3

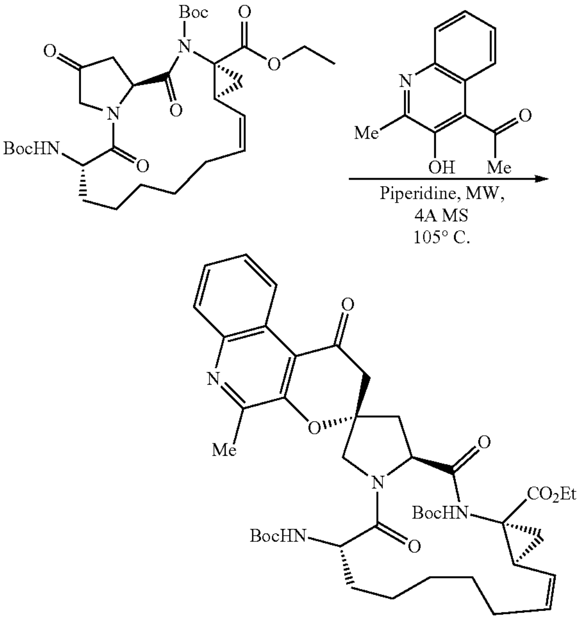

The product of Step 2 (272 mg, 0.460 mmol), 2-methyl-3-hydroxy-4-acylquinoline (143 mg, 0.713 mmol) and piperidine (0.027 ml, 0.276 mmol) were combined in MeOH (4 ml) in a microwave vial. To this was then added molecular sieve (250 mg, 4A, powder), and the mixture was heated at 105° C. for 30 min at high absorbance. The insoluble were removed via filtration, and the insolubles were rinsed further with ether. The combined organic extracts were then washed further with water, 1N aq. NaOH (×2), and brine, dried over $Na_2SO_4$, filtered and the filtrate concentrated in vacuo. Purification by way of column chromatography silica gel (AnaLoGix) using hexanes:EtOAc (2:1) afforded the product of Step 3 (52 mg, 0.067 mmol, 14.60% yield) was obtained. $^1H$ NMR indicated a 5:1 mixture of diastereomer with the product shown above being the major isomer.

Step 4

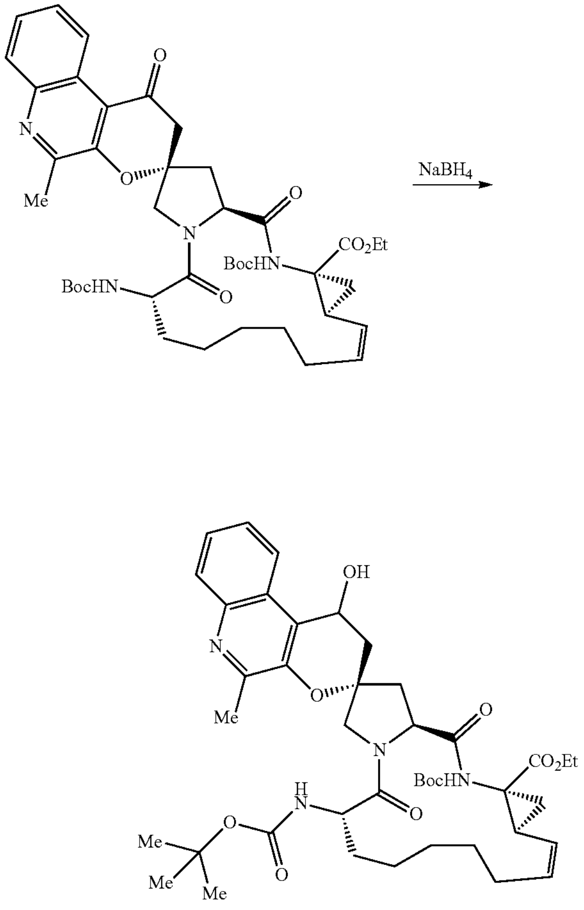

To solution of the major product of Step 3 (50 mg, 0.065 mmol) in MeOH (4 ml) was added $NaBH_4$ (4.88 mg, 0.129 mmol) in one rapid portion. The resulting mixture was then stirred at RT for 1.5 h. The volatiles were then removed, and the resulting mixture was partitioned between EtOAc and 1N aq. NaOH. The organic layer was separated and washed further with 10% aq. HCl, 1 N aq. NaOH, water and brine. This was dried over $Na_2SO_4$, filtered, and the filtrate concentrated in vacuo to furnish the product of Step 4 (0.05 g, 100%).

Step 5

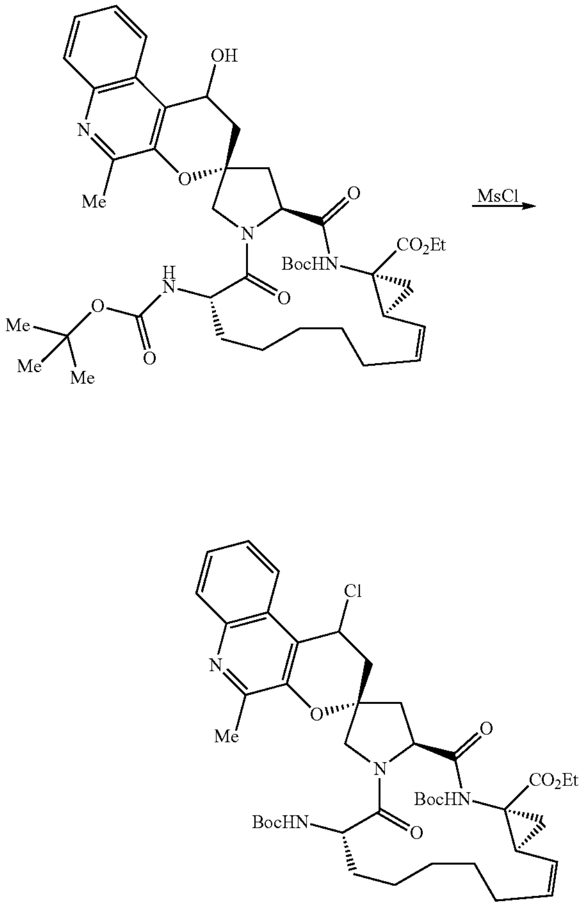

To the product of Step 4 (140 mg, 0.180 mmol) in $CH_2Cl_2$ (4 ml) was added Hunig's base (0.094 ml, 0.541 mmol). MsCl (0.021 ml, 0.270 mmol) was then added dropwise to the reaction mixture. This was then stirred at RT overnight. A small aliquot was withdrawn and analyzed by LC-MS showed formation of the desired product but also the unreacted alcohol. Consequently, another 0.04 mL of MsCl and 0.2 mL of Hunig's base were added, and the mixture was stirred for another 6 h. LC-MS of the resulting red solution revealed no more alcohol. Consequently, the volatiles were removed in vacuo, and the residue was partitioned between ether and water. The aq. layer was separated and back-extracted with ether. The combined organic extracts were washed further with 1N aq. NaOH, water and brine, dried over $Na_2SO_4$, filtered, and the filtrate was concentrated in vacuo to afford viscous oil. Purification by way of column chromatography (RS-24, 9:1 Hexanes:EtOAc, 2 min to 25 min→7:3 EtOAc:Hexanes, 5 min) afforded the desired product (105 mg, 0.132 mmol, 73.3% yield) as white foam.

Step 6

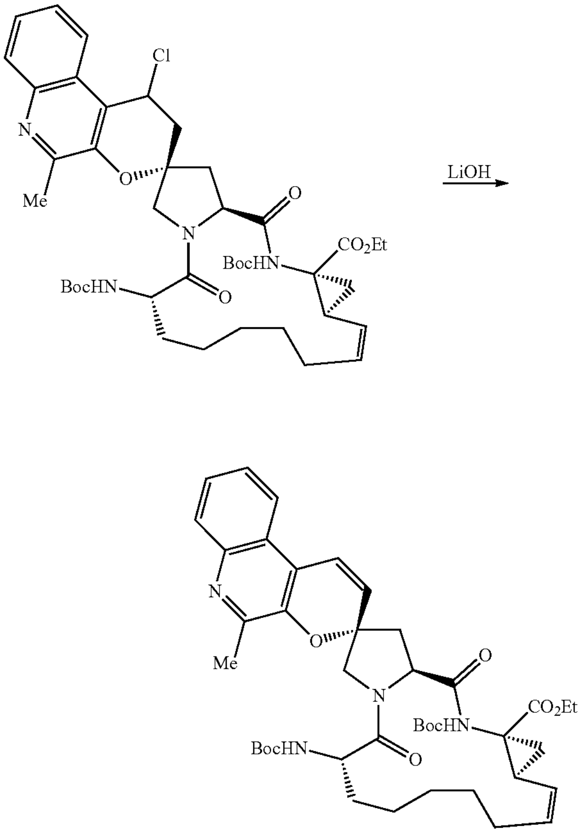

To a solution of the product of Step 5 (70 mg, 0.101 mmol) in THF (2 ml) and MeOH (1 ml) was added LiOH (0.252 ml, 0.503 mmol). The resulting solution was stirred at RT for 15 h. The volatiles were removed in vacuo, and the resulting residue was quenched with 0.45 mL of 1N aq. HCl and diluted with EtOAc and water. The aq. layer was separated and back-extracted with EtOAc. The combined organic extracts were then washed further with water and brine, dried over $Na_2SO_4$, filtered, and the filtrate was concentrated in vacuo to furnish crude product (57 mg, 0.090 mmol, 90% yield).

Step 7

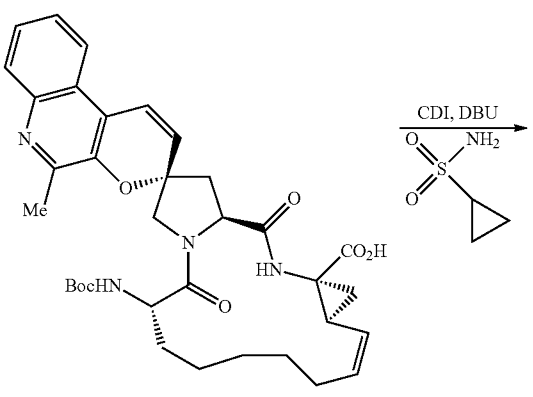

-continued

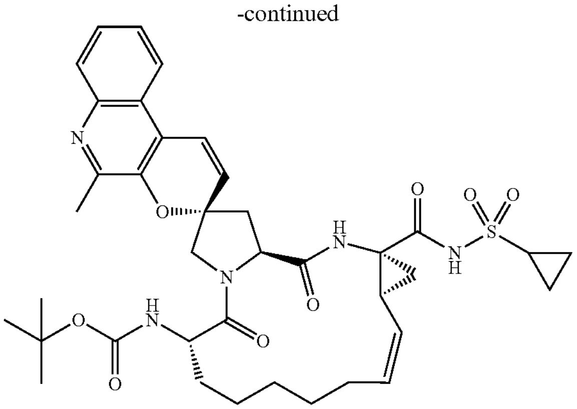

The product of Step 6 (57 mg, 0.090 mmol) was dissolved in THF (1.5 ml) in a sealed tube. To the reaction mixture was added CDI (29.3 mg, 0.181 mmol), and the reaction was heated to 55° C. for 4 h. Then, to this was added cyclopropyl sulfonamide (43.8 mg, 0.361 mmol), and then DBU (0.054 ml, 0.361 mmol). The reaction was resealed, stirred, and heated to 55° C. for overnight. The reaction was quenched with $NH_4Cl$ and extracted twice with DCM. A preparative TLC purification with 10% MeOH/DCM gave I-26 (49 mg, 0.067 mmol, 73.9% yield). MS m/e=734.3 ($MH^+$).

Example 27 tert-Butyl (2R,6S,13aS,14aR,16aS,Z)-10'-chloro-5'-(difluoromethyl)-9'-methoxy-14a-(1-methylcyclopropylsulfonylcarbamoyl)-5,16-dioxo-1',2',3,5,6,7,8,9,10,11, 13a,14,14a,15,16,16a-hexadecahydro-1H-spiro[cyclopropa[e]pyrrolo[1,2-a][1,4]diaza cyclopentadecine-2,3'-pyrano[2,3-c]quinoline]-6-ylcarbamate (I-27)

Step 1

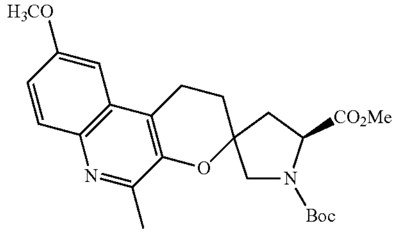 [SMILES: COC(=O)[C@@H]1CC2(CCc3c(c(C)nc4ccc(OC)cc34)O2)CN1C(=O)OC(C)(C)C]

Procedure for the synthesis of the product of Step 1 is the same as the procedure for the synthesis of the products of Example 9, Step 4.

Step 2

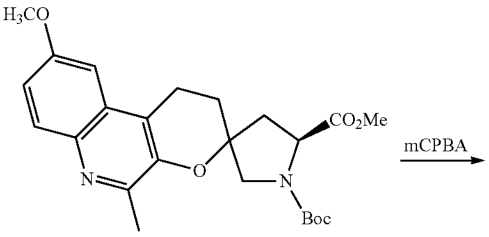

-continued

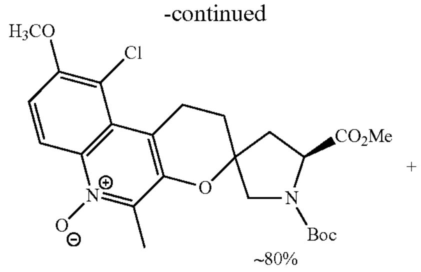

27-2A

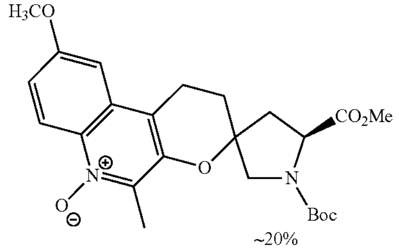

27-2B

The product of Step 1 (0.68 g, 1.537 mmol) was dissolved in chloroform (25 ml) and cooled to 0° C. MCPBA (0.69 g, 3.07 mmol) was added to the mixture, and the resulting mixture was stirred at RT for ~6 h. EtOAc (~25 ml) was added, and the mixture was washed with aq. $NaHCO_3$ (sat.), dried over anhydrous $MgSO_4$, filtered, and the solvent was evaporated under reduced pressure to give product, which was a mixture of compound 27-2A (~80% by LC-MS) and compound 27-2B (~20% by LC-MS), (0.67 g, 1.368 mmol, 89% yield), and was carried forward.

Step 3

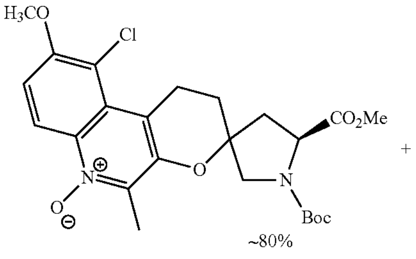

27-2A

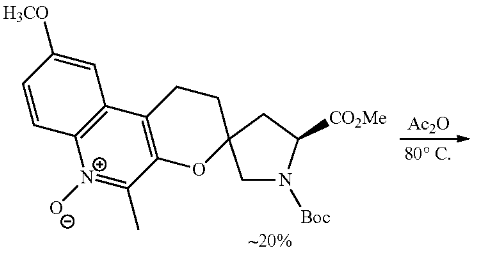

27-2B

-continued

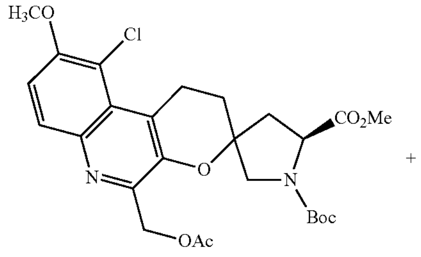

27-3A

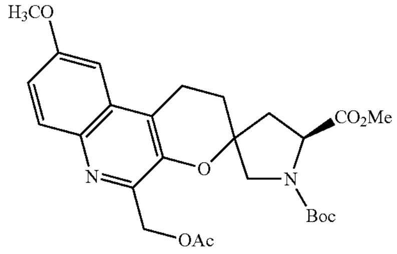

27-3B

The mixture of intermediates 27-2A and 27-2B (0.62 g, 1.258 mmol) was dissolved in acetic anhydride (11.87 ml, 126 mmol) and heated at 80° C. for 2 h. The reaction mixture was concentrated to remove acetic anhydride. The residue was dissolved in EtOAc, washed with aq. $NaHCO_3$ (sat.), dried over anhydrous $MgSO_4$, filtered, concentrated and purified by silica gel column chromatography eluting with (0-80) % EtOAc-DCM, and the product, a mixture of compounds 27-3A and 27-3B, was isolated as yellow oil (0.33 g, 0.62 mmol, 49%).

Step 4

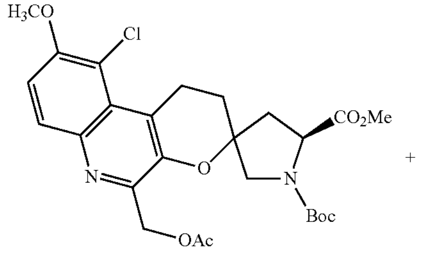

27-3A

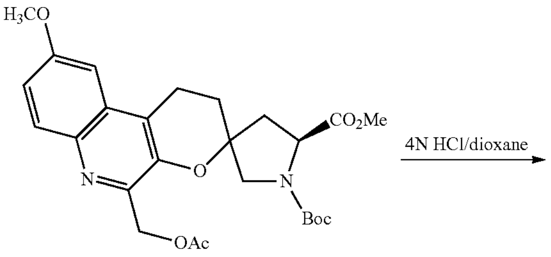

27-3B

-continued
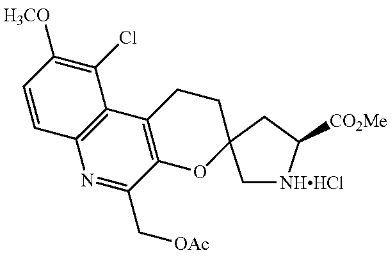
27-4A
+
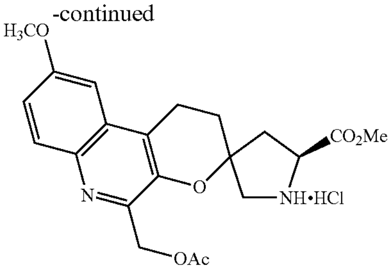
27-4B
A solution of intermediates 27-3A and 27-3B (0.31 g, 0.619 mmol) in 4N HCl in dioxane (10 ml) was stirred at RT for 1 h. The reaction mixture was evaporated to dryness to remove excess acid, co-evaporated with toluene (2×) then with $Et_2O$ (2×) to give the product (0.26 g, 0.619 mmol, 96% yield), a mixture of compounds 27-4A and 27-4B, and used as such.
Step 5
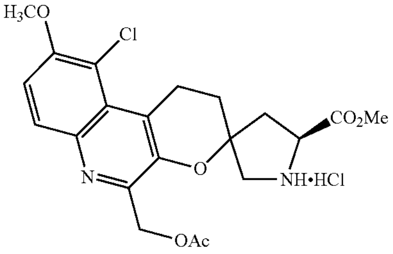
27-4A
+
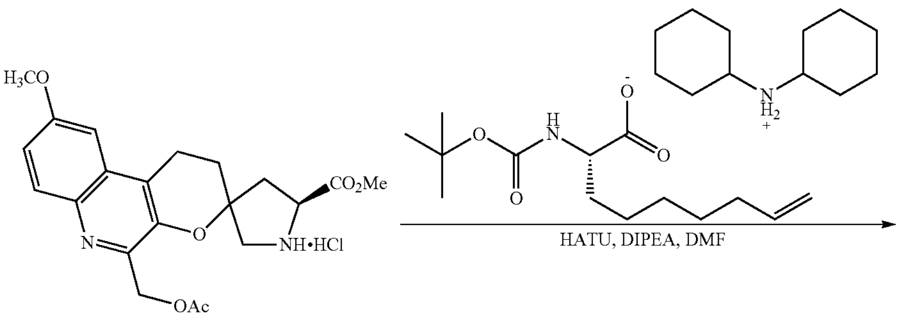
27-4B
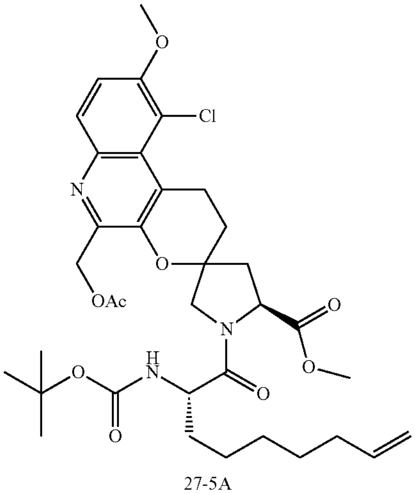
27-5A
+
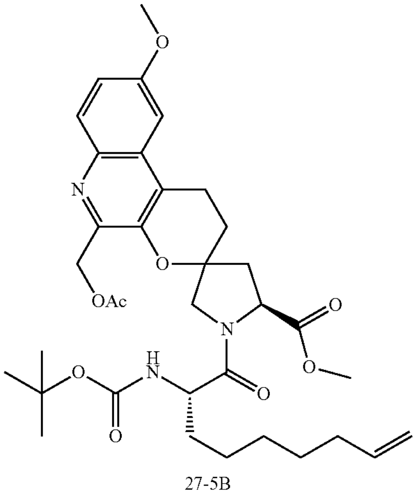
27-5B To a DMF (7 ml) solution of compounds 27-4A and 27-4B (0.25 g, 0.53 mmol), HATU (0.30 g, 0.53 mmol) and (S)-2-(tert-butoxycarbonylamino)non-8-enoic acid (0.36 g, 0.79 mmol) was added DIPEA (0.28 ml, 1.59 mmol) at RT, and the resulting yellow solution was stirred at RT overnight.

LC-MS of the crude reaction mixture showed complete consumption of starting material. The mixture was cooled, diluted with $Et_2O$, washed with water (2×), dried over anhydrous $MgSO_4$, filtered, and the solvent was evaporated under reduced pressure. The crude yellow oil was purified by column chromatography using a silica gel (RS-40) column on an Analogix, eluting with (0-40) % EtOAc-DCM, and the product compounds 27-5A and 27-5B, (0.21 g, 0.31 mmol, 57.5%) was obtained as mixture.

Step 6

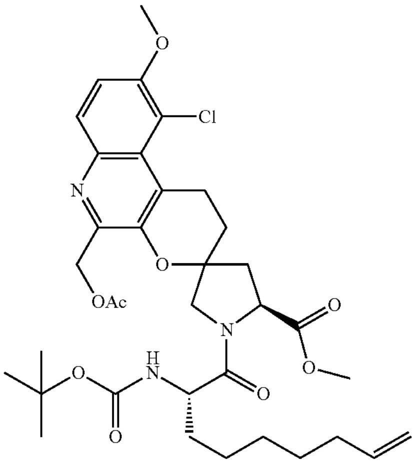

27-5A

+

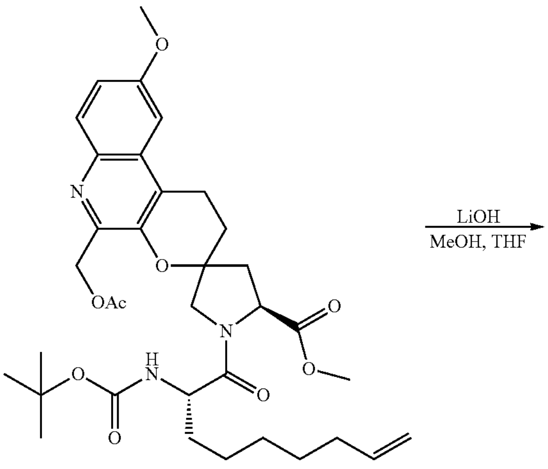

27-5B

-continued

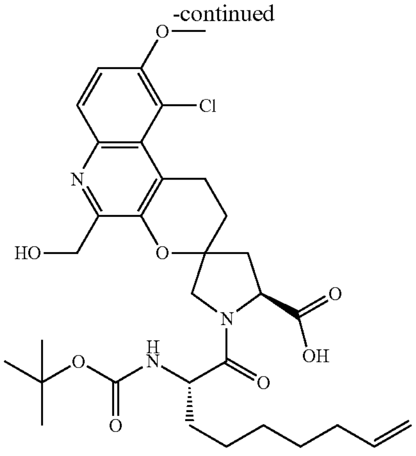

27-6A

+

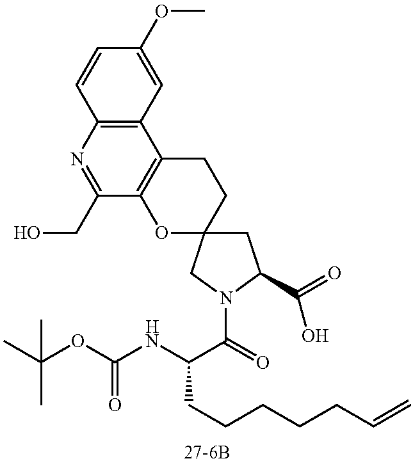 [SMILES: C=CCCCCC[C@H](NC(=O)OC(C)(C)C)C(=O)N1CC2(CCc3c(c(CO)nc4ccc(OC)cc34)O2)C[C@H]1C(=O)O]

27-6B

Intermediates 27-5A and 27-5B (0.21 g, 0.31 mmol) were dissolved in THF (2.5 ml)/MeOH (2.5 ml), LiOH (2M aq. solution, 0.763 ml, 1.526 mmol) was added to the mixture, and the mixture was heated at 60° C. for 1 h. LC-MS showed complete conversion of starting materials. 1M HCl(aq.) (0.320 ml) was added to the reaction mixture, and the reaction mixture was diluted with water (20 ml). The mixture was extracted with EtOAc (2×). The combined organic fractions were dried over anhydrous $MgSO_4$, filtered, and the solvent was evaporated under reduced pressure. The dried mass was co-evaporated with toluene and then with $Et_2O$ to give the product (0.173 g, 0.27 mmol, 90%), mixture of compounds 27-6A and 27-6B.

Step 7

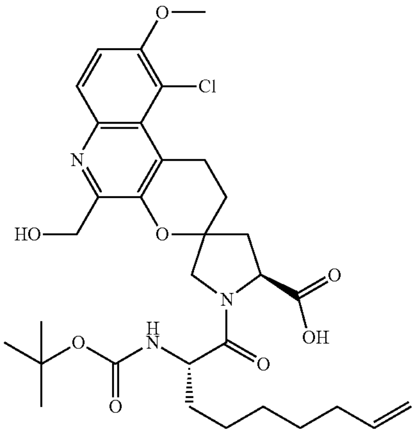

27-6A

+

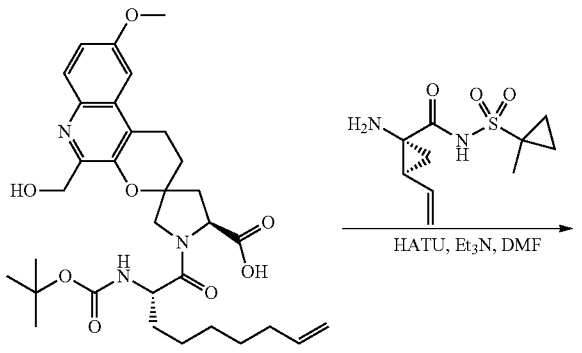

27-6B

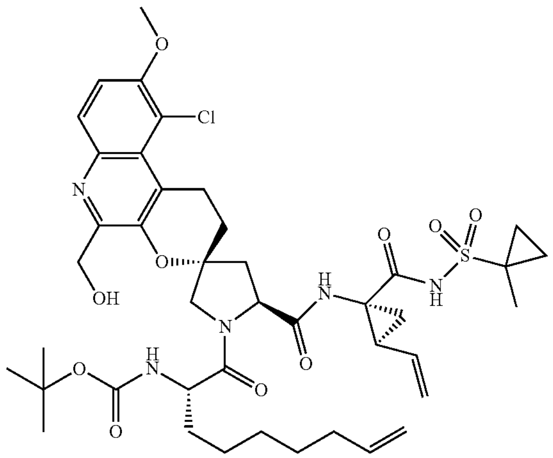

+

27-7A

-continued

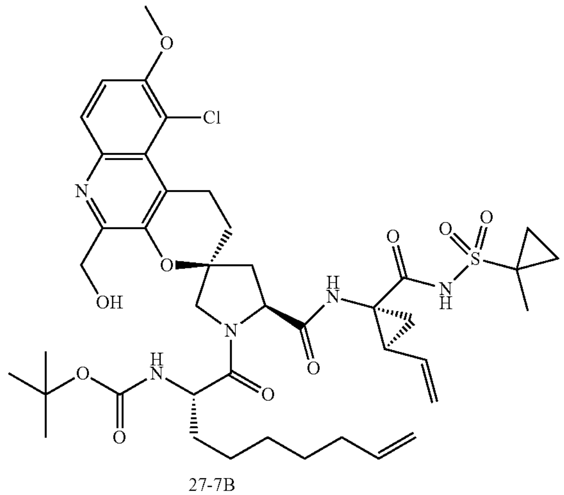 [SMILES: C=CCCCCC[C@H](NC(=O)OC(C)(C)C)C(=O)N1C[C@]2(CCc3c(c(CO)nc4ccc(OC)c(Cl)c34)O2)C[C@H]1C(=O)N[C@]1(C(=O)NS(=O)(=O)C2(C)CC2)C[C@H]1C=C]

27-7B

To a stirred solution of mixtures of intermediates 27-6A and 27-6B (0.173 g, 0.27 mmol), HATU (0.17 g, 0.41 mmol) and (1R,2S)-1-amino-N-(1-methylcyclopropylsulfonyl)-2-vinylcyclopropanecarboxamide (0.10 g, 0.41 mmol) in DMF (5 ml) was added TEA (0.11 ml, 0.82 mmol) at RT. The resulting mixture was stirred at RT overnight.

LC-MS of the crude reaction mixture showed complete consumption of starting material. The mixture was diluted with $Et_2O$, washed with water (2×), and the aq. layer was back extracted with $Et_2O$. The combined organics were dried over anhydrous $MgSO_4$, filtered, and the solvent was evaporated under reduced pressure. The crude yellow oil was purified by preparative TLC using 40% Acetone-60% Hexanes as mobile phase and the products, compound 27-7A (0.08 g, 0.09 mmol, 34.1%) and compound 27-7B (0.06 g, 0.07 mmol, 25.5%) were isolated. Both isomers of des chloro compounds were not isolated as they were minor products and very little in amount.

Step 8

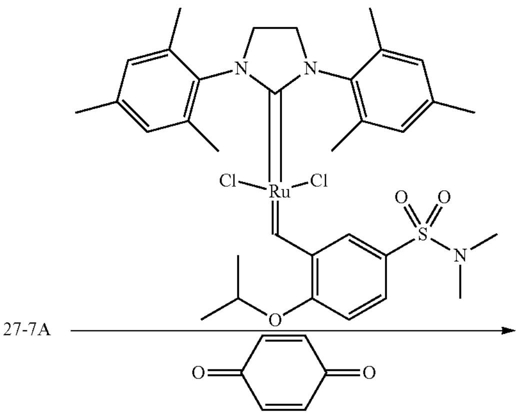

-continued

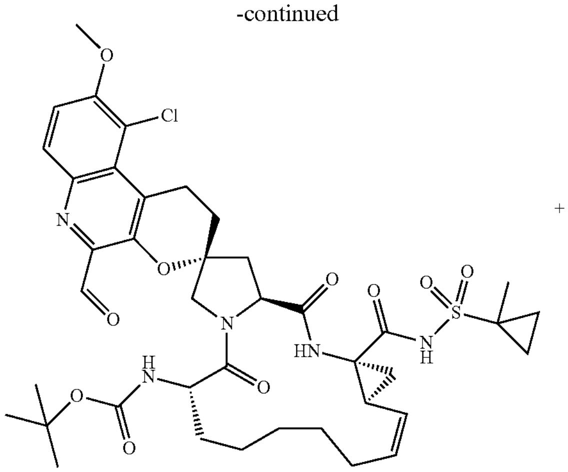

27-8

+

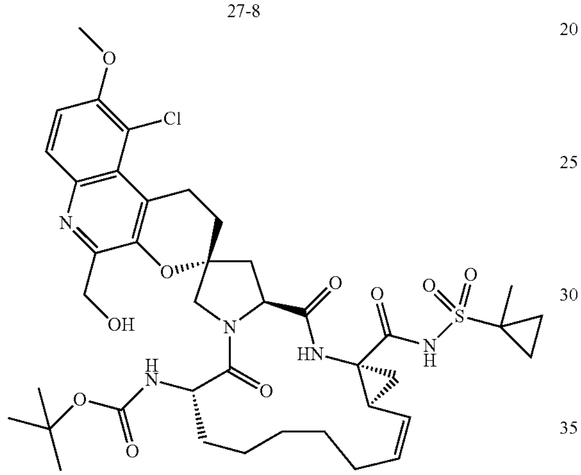

27

Compound 27-7A (0.08 g, 0.09 mmol), Zhan's catalyst (0.017 g, 0.023 mmol), and p-benzoquinone (3.02 mg, 0.028 mmol) were added to a stirred, RT solution of DCE (47 ml). A condenser was added, and the reaction was heated to 65° C. for 3 h. The crude reaction mixture was cooled to RT and quenched with the addition of butyl vinyl ether (0.5 ml). The volatiles were then removed in vacuo, and the resulting dark green/brown residue was directly subjected to purification by way of preparative TLC using 40% Acetone-Hexanes as mobile phase to afford the product as white solid. The product was a mixture of two compounds, which was further purified using silica gel column chromatography (RS 12 g) using (0-75) % EtOAc-DCM as mobile phase and the products, 27-8A (0.01 g, 0.012 mmol, 12.95%) and the compound of I-27 (0.01 g, 0.012 mmol, 12.92%, $M+H^+=831$) were isolated. $^1$H-NMR (400 MHz, $CDCl_3$) δ ppm 10.12 (s, 1H), 7.98-7.92 (m, 1H), 7.36 (t, 1H, 9.6 Hz), 6.99 (s, 1H), 5.75-5.69 (m, 1H), 5.05-4.95 (m, 2H), 4.75-4.60 (m, 3H) 4.48-4.38 (m, 2H), 2.38-2.30 (m, 2H), 2.24-2.11 (m, 2H), Exact mass calculated for $C_{40}H_{52}ClN_5O_{10}S=829.31$, LC-MS $(M+H)^+=830.6$.

Example 28 tert-Butyl [(2R,6S,12Z,13aS,14aR,16aS)-10'-chloro-5'-(difluoromethyl)-9'-methoxy-14a-{[(1-methylcyclopropyl)sulfonyl]carbamoyl}-5,16-dioxo -1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate (I-28)

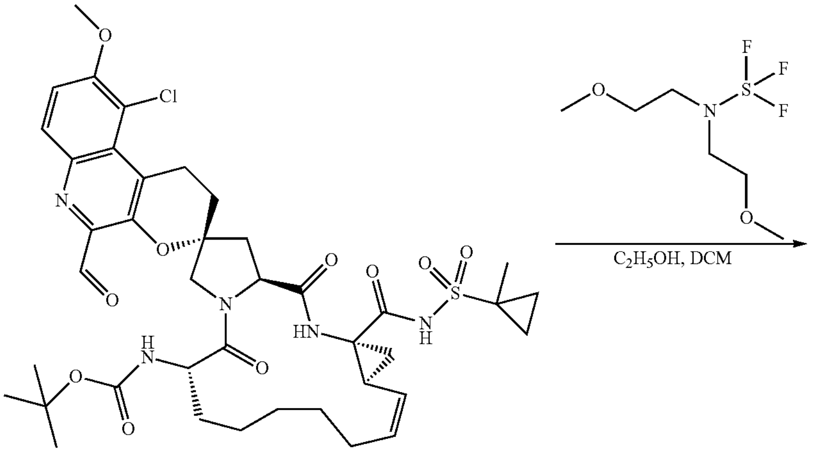

-continued

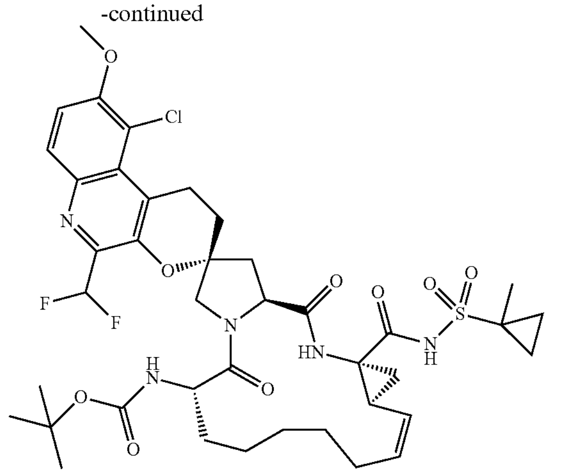

A solution of intermediate 27-8A (Example 27, Step 8; 0.01 g, 0.012 mmol) in $CH_2Cl_2$ (1 ml) was treated with a solution of DeoxoFluor (4.45 μl, 0.024 mmol) in $CH_2Cl_2$ (0.25 ml) at RT and stirred for 2 h. LC-MS showed 19% of product and 74% of starting material. Another Seq. of DeoxoFluor and 0.2 eq. of EtOH were added and stirred for 30 min at RT. LC-MS showed increase in product peak. The reaction mixture was stirred at RT overnight. Sat. $NaHCO_3$ solution (aq.) was added to the mixture and, after $CO_2$ evolution ceased, extracted with DCM and combined organic layers were dried over anhydrous $Na_2SO_4$. The product was purified by preparative TLC using 45% EtOAc -55% DCM as mobile phase and the product, I -28 (0.002 g, 0.002 mmol, 16.6%) was isolated. $^1$H-NMR (400 MHz, $CDCl_3$) δ ppm 10.1 (s, 1H), 8.07 (d, J=9.2 Hz, 2H), 7.40 (d, 1H, 9.6 Hz), 7.03-6.76 (m, 2H), 5.76-5.69 (m, 1H), 4.66-4.61 (m, 1H), 4.48 (d, J=12.4 Hz, 1H), 4.05 (s, 1H), 2.60-2.55 (m, 2H), 2.45-2.21 (m, 4H). Exact mass calculated for $C_{40}H_{50}ClF_2N_5O_9S$=849.3, LC-MS $(M+H)^+$=850.2.

Example 29 tert-butyl (2'R,6'S,13a'S,14a'R,16a'S,Z)-7-cyclopropyl-14a'-(1-methyl cyclopropylsulfonylcarbamoyl)-5',16'-dioxo-3',5',6',7',8',9',10,10',11,11',13a',14',14a',15',16',16a'-hexadecahydro-1'H-spiro[[1,3]dioxolo[4,5-f]pyrano[2,3-c]quinoline-9,2'-cyclopropa[e]pyrrolo[1,2-a][1,4]diazacyclopentadecine]-6'-ylcarbamate (I-29)

Step 1

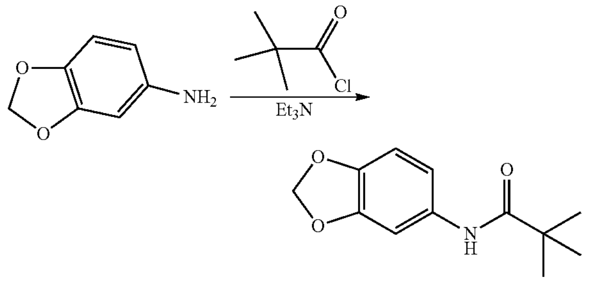

To a solution of 3,4-(methylenedioxy)aniline (16.24 g, 118 mmol) in DCM (180 ml) at 0° C. was added TEA (24.8 ml, 178 mmol) followed by pivaloyl chloride (14.6 ml, 118 mmol), and the mixture was allowed to warm to RT and stirred overnight. The mixture was quenched at RT with sat. aq. $NH_4Cl$ and extracted with DCM. The combined organic fractions were washed with sat. aq. $NaHCO_3$ followed by brine, dried over $Na_2SO_4$, filtered and concentrated in vacuo. The residue was purified by column chromatography over silica gel (eluting with Hexanes/EtOAc 99:1 to 30:70) to give the product of Step 1 (18.31 g, 70% yield) as a light brown solid.

Step 2

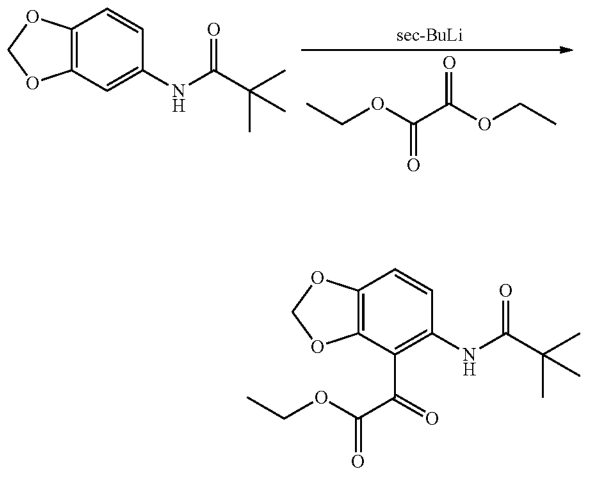

To a solution of the product of Step 1 (15.0 g, 67.8 mmol) in THF (300 ml) at −78° C. was added sec-butyl lithium (107 ml, 149 mmol) slowly, and the mixture was allowed to warm to 0° C. and stirred for 2 h. Diethyl oxalate (12.9 g, 88 mmol) in THF (15 ml) was then added at −78° C. and the reaction was allowed to warm to RT and stirred for 1 h. The mixture was quenched at RT with sat. aq. $NH_4Cl$ and extracted with DCM and EtOAc. The combined organic fractions were washed with sat. brine, dried over $Na_2SO_4$, filtered and concentrated in vacuo. The residue was purified by column chromatography over silica gel (eluting with Hexanes/EtOAc 99:1 to 60:40) to afford the product of Step 2 (11.8 g, 54% yield) as a yellow solid.

Step 3

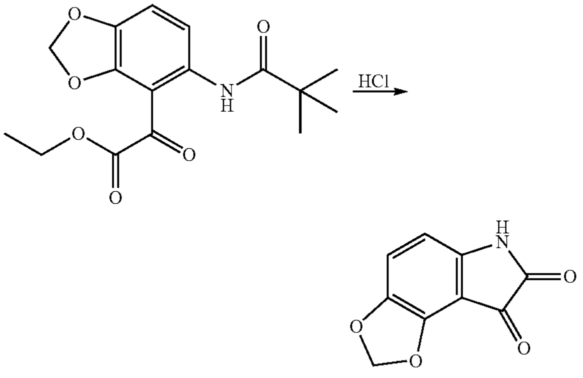

To a solution of the product of Step 2 (14.0 g, 43.6 mmol) in DME (60 ml) was added 12N HCl (50 ml, 43.6 mmol), and the mixture was warmed to 80° C. and stirred for 6 h. The mixture was cooled to RT, diluted with water, concentrated from DME then cooled over ice overnight. The solid was filtered and dried in vacuo to provide the product of Step 3 (6.40 g, 77% yield).

Step 4

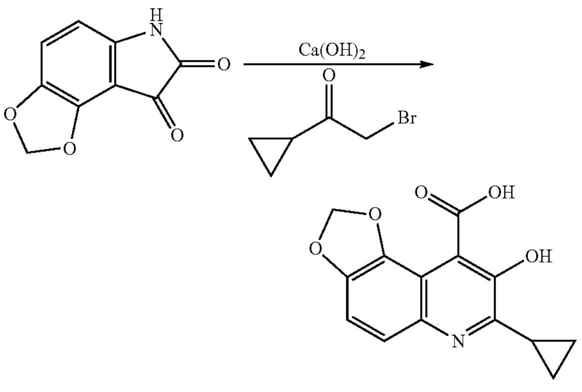

To a solution of the product of Step 3 (6.40 g, 33.5 mmol) in water (150 ml) was added $Ca(OH)_2$ (7.44 g, 100 mmol), and the mixture was warmed to 80° C. and stirred for 1 h. 2-Bromo-1-cyclopropylethan-1-one (13.10 g, 80 mmol) was then added at RT and the reaction was warmed to 80° C. and stirred for 3.5 h. The mixture was cooled to 0° C., ice cold 10% HCl was added slowly, and the reaction was left over ice for 30 min, then the solid was filtered and dried in vacuo to provide the product of Step 4 (7.87 g, 86% yield).

Step 5

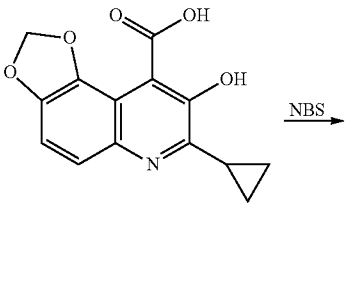

-continued

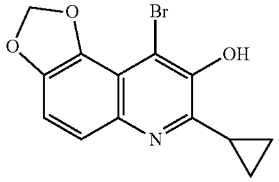

To a solution of the product of Step 4 (7.87 g, 28.8 mmol) in THF (240 ml) at 0° C. was added a solution of NBS (4.87 g, 27.4 mmol) in THF (24 ml) slowly, and the mixture was stirred for 1 h at 0° C. then 9 min at RT. The mixture was poured into sat. brine and extracted with EtOAc. The combined organic fractions were dried over $Na_2SO_4$, filtered and concentrated in vacuo. The residue was purified by column chromatography over silica gel (eluting with DCM/EtOAc 99:1 to 80:20) to give the product of Step 5 (3.26 g, 37% yield).

Step 6

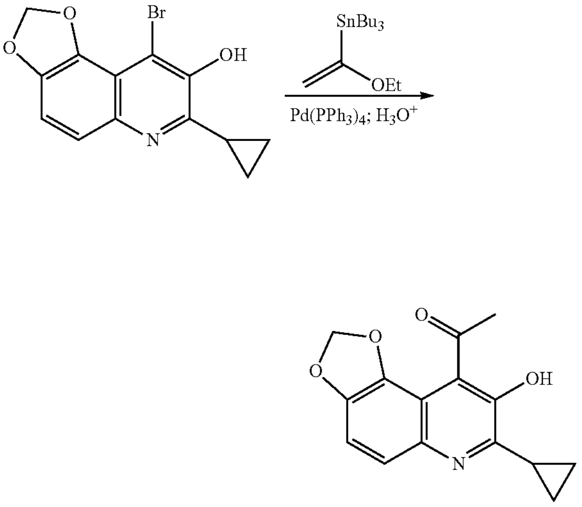

To a solution of the product of Step 5 (2.60 g, 8.44 mmol) and $Pd(PPh_3)$ (975 mg, 0.844 mmol) in 1,4-dioxane (32 ml) was added tributyl(1-ethoxyvinyl)tin (7.12 ml, 21.1 mmol), and the mixture was warmed to 110° C. and stirred for 2 h. More $Pd(PPh_3)_4$ (150 mg) and tributyl(1-ethoxyvinyl)tin (2 ml) were added, and the reaction was stirred at 110° C. for an additional 9 h. The final mixture was quenched at RT with 1N aq. HCl (1 ml) and stirred for 1.5 h. The mixture was poured into sat. aq. $NaHCO_3$ and extracted with EtOAc. The combined organic fractions were washed with sat. brine, dried over $Na_2SO_4$, filtered and concentrated in vacuo. The residue was purified by column chromatography over silica gel (eluting with Hexanes/EtOAc 99:1 to 60:40) to give the product of Step 6 (1.36 g, 59% yield) as a yellow solid.

Step 7

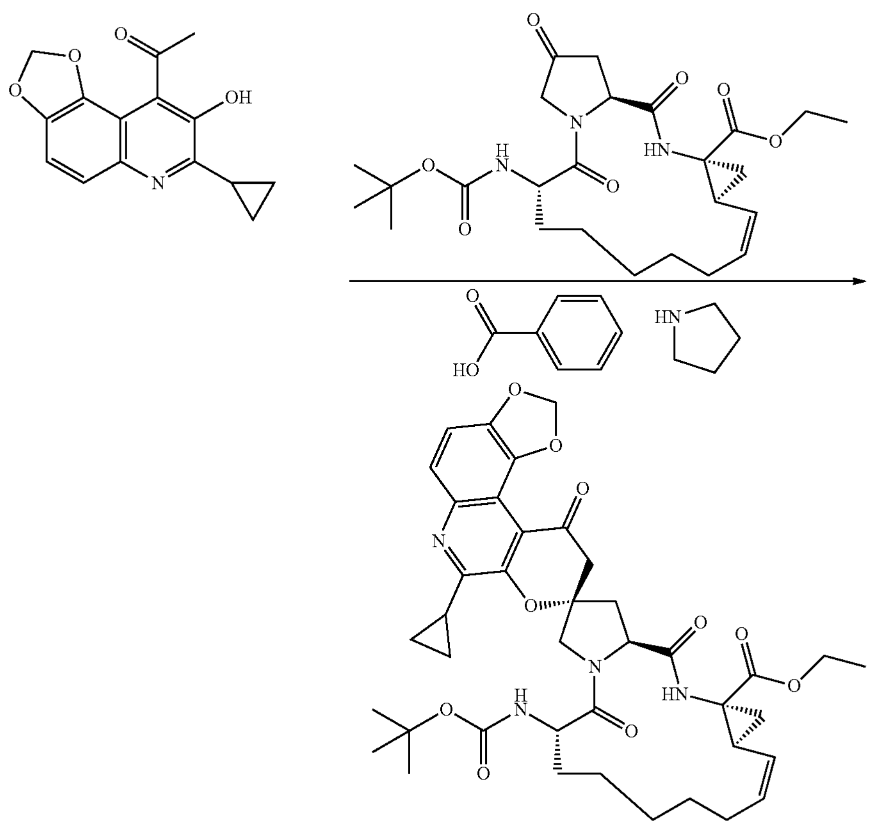

To a solution of the product of Step 6 (293 mg, 1.080 mmol), macrocyclic ketone (531 mg, 1.080 mmol) and benzoic acid (132 mg, 1.080 mmol) in MeOH (9 ml) was added pyrrolidine (0.0345 ml, 0.432 mmol) and 4A molecular sieves (600 mg), and the mixture was warmed to 60° C. and stirred over 72 h. The mixture was quenched at RT with sat. aq. $NaHCO_3$ and brine and extracted with EtOAc. The combined organic fractions were washed with saturated brine and water, dried over $Na_2SO_4$, filtered and concentrated in vacuo. The residue was purified by column chromatography over silica gel (eluting with Hexanes/EtOAc 99:1 to EtOAc) to give, in order of elution, the product of Step 7 (360 mg, 45% yield), as a yellow solid, followed by starting material, the product of Step 6 (60 mg).

Step 8

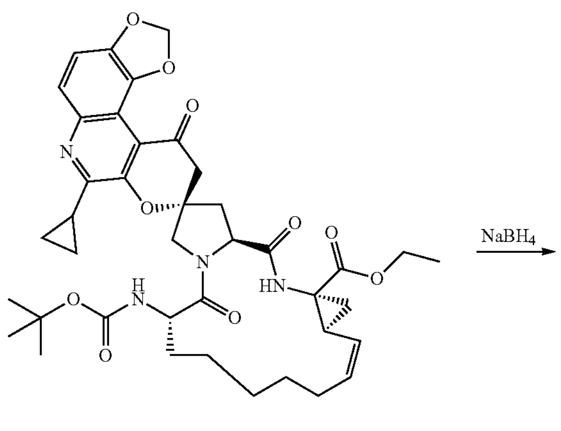

-continued

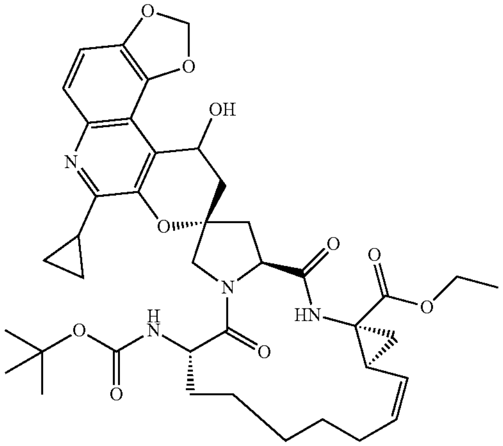

To a solution of the product of Step 7 (330 mg, 0.443 mmol) in THF (3 ml) and MeOH (3 ml) at 0° C. was added $NaBH_4$ (20.1 mg, 0.532 mmol), and the mixture was stirred for 45 min. The mixture was quenched at 0° C. with sat. aq. $NH_4Cl$ and extracted with EtOAc. The combined organic fractions were washed with saturated brine, dried over $Na_2SO_4$, filtered and concentrated in vacuo to give the product of Step 8 (330 mg, 100% yield).

Step 9

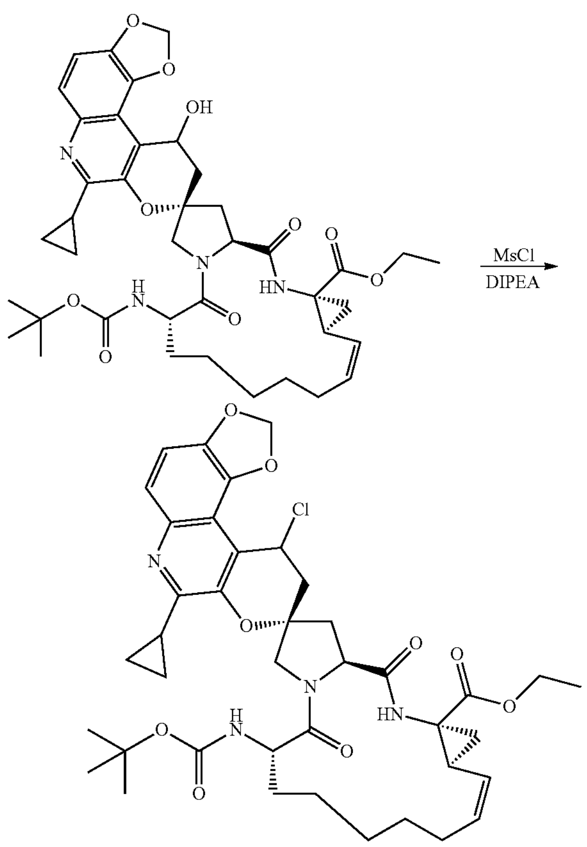

To a solution of the product of Step 8 (330 mg, 0.442 mmol) in DCM (10 ml) was added DIPEA (0.231 ml, 1.326 mmol) followed by MsCl (0.055 ml, 0.707 mmol), and the mixture was stirred for 2 h. More DIPEA (0.231 ml, 1.326 mmol) and MsCl (0.055 ml, 0.707 mmol) were added, and the reaction was stirred for an additional 2 h. LiCl (56.2 mg, 1.326 mmol) followed by DMF (1.0 ml) were then added, and the reaction was stirred overnight. The mixture was quenched at RT with sat. aq. $NH_4Cl$ and extracted with EtOAc. The combined organic fractions were washed with sat. brine, dried over $Na_2SO_4$, filtered and concentrated in vacuo to provide the crude product of Step 9 (340 mg), as crude.

Step 10

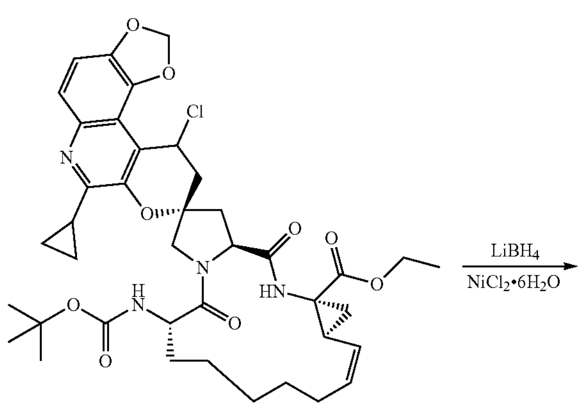

-continued

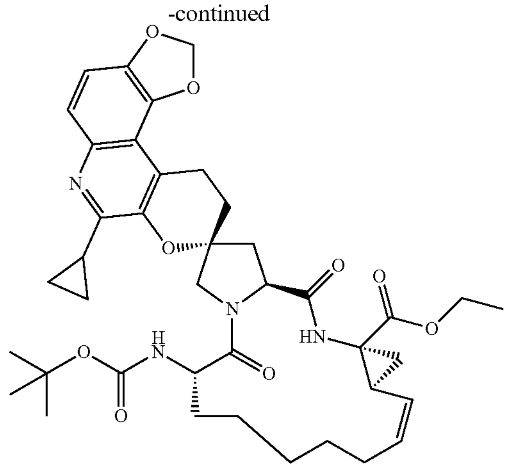

To a solution of the crude product of Step 9 (340 mg, 0.444 mmol) in MeOH (20 ml) at −78° C. was added $NiCl_2.6H_2O$ (106 mg, 0.444 mmol) followed by $LiBH_4$ (0.44 ml, 0.889 mmol) and the mixture was stirred for 1 h. More $LiBH_4$ (0.44 ml, 0.889 mmol) was added at −78° C., and the reaction was stirred for 1 h, and then warmed to 0° C. for 30 min. The final mixture was quenched at 0° C. with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 60:40) to give the product of Step 10 (130 mg, 40% yield) as a white solid.

Step 11

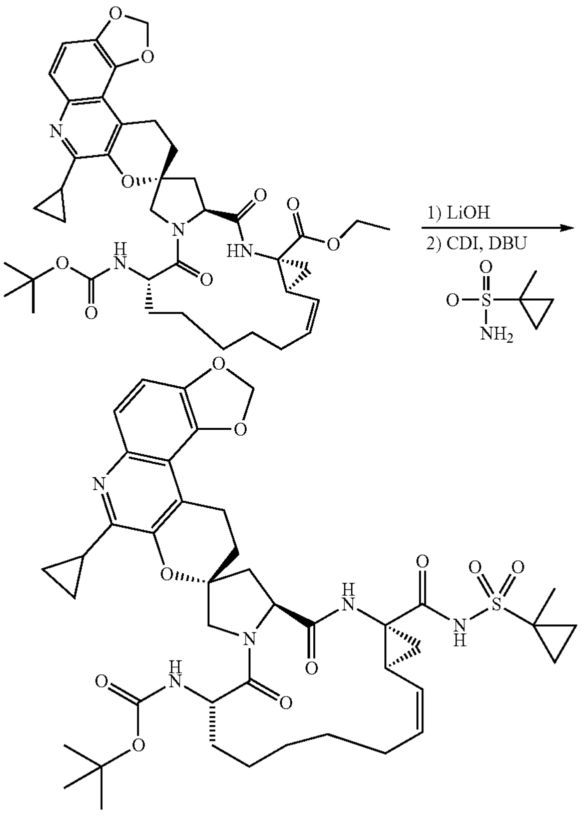

To a solution of the product of Step 10 (120 mg, 0.164 mmol) in THF (3.5 ml), MeOH (3.5 ml) and water (2.5 ml) was added $LiOH.H_2O$ (34.5 mg, 0.821 mmol), and the mixture was warmed to 50° C. and stirred for 5 h. The mixture was quenched at RT with ice-cold 0.2N aq. HCl and extracted with EtOAc. The combined organic fractions were dried over $Na_2SO_4$, filtered and concentrated in vacuo to give an intermediate acid (120 mg, 100% yield). To a solution of this intermediate acid (120 mg, 0.171 mmol) in THF (6 ml) was added carbonyl diimidazole (55.4 mg, 0.341 mmol), and the mixture was warmed to 70° C. and stirred vigorously for 4 h. More carbonyl diimidazole (20 mg) was added, and the reaction was stirred 1 h at 70° C. 1-Methylcyclopropane-1-sulfonamide (92 mg, 0.683 mmol) was then added at RT followed by 1,8-diazabicyclo[5.4.0]undec-7-ene (0.103 ml, 0.683 mmol), and the reaction was warmed to 50° C. and stirred for 9 h. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 50:50) to give I-29 (70 mg, 50% yield) as a white solid. $^1H$-NMR (400 MHz, $CDCl_3$) δ 10.04 (s, 1H), 7.40 (d, J=8.8 Hz, 1H), 7.10 (d, J=8.8 Hz, 1H), 6.76 (s, 1H), 5.71 (m, 1H), 4.95-5.05 (m, 2H), 4.61 (m, 1H), 4.40-4.55 (m, 3H), 4.27 (m, 1H), 4.11 (m, 1H), 3.73 (d, J=10.8 Hz, 1H), 3.25-3.35 (m, 2H), 2.50-2.60 (m, 2H), 2.30-2.45 (m, 3H), 2.15-2.25 (m, 2H), 1.70-1.95 (m, 4H), 1.20-1.65 (m, 8H), 1.47 (s, 3H), 1.32 (s, 9H), 0.77-0.92 (m, 6H); LC-MS ($M^+$) Calc. for $C_{42}H_{53}N_5O_{10}S$: 819.3. Found 820.0.

Example 30 tert-butyl ((2R,6S,13aS,14aR,16aS,Z)-5'-methyl-14a-(((1-methylcyclopropyl) sulfonyl)carbamoyl)-5,16-dioxo-9'-(2,2,2-trifluoroethoxy)-1',2',3,5,6,7,8,9,10,11,13a,14, 14a,15,16,16a-hexadecahydro-1H-spiro[cyclopropa[e]pyrrolo[1,2-a][1,4]diaza cyclopentadecine-2,3'-pyrano[2,3-c]quinolin]-6-yl) carbamate (I-30)

Step 1

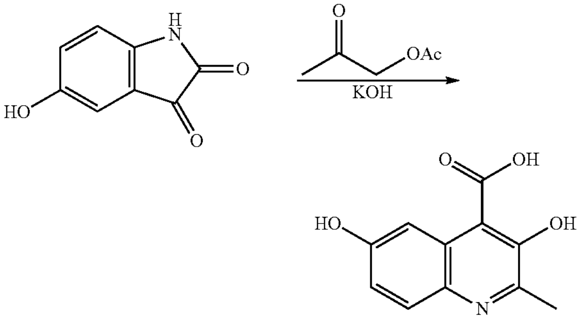

A mixture of 5-hydroxyisatin (9.38 g, 57.5 mmol) and KOH 6N (96 ml, 575 mmol) in water (80 ml) was warmed to 85° C. and stirred for 2 h. Acetoxy-2-propanone (6.21 ml, 57.5 mmol) was then added 3× (3 eq. total), each at 93° C. followed by 1 h stirring at 93° C. The crude was concentrated from EtOH then slowly quenched at RT with 1N aq. HCl until pH ~2, cooled in ice-bath for 15 min. The solid separating out was filtered, rinsed with water and dried under high vacuum to give the product of Step 1 (6.09 g, 48% yield).

Step 2

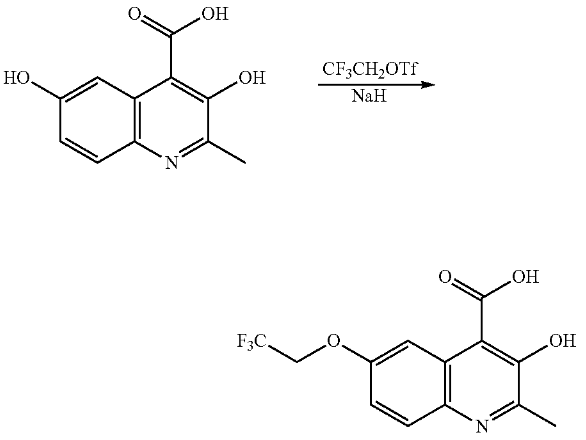

To a solution of the product of Step 1 (3.20 g, 14.6 mmol) in DMF (35 ml) at 0° C. was added sodium hydride 60% in hexanes (1.17 g, 29.2 mmol) portion wise followed by DMSO (5 ml), and the mixture was stirred for 30 min. 2,2,2-Trifluoroethyl trifluoromethanesulfonate (2.42 ml, 16.8 mmol) was then added at 0° C., and the reaction was allowed to warm to RT and stirred for 3 h. The mixture was quenched at 0° C. with 1N HCl until pH ~2, diluted with water then filtered, rinsing with water. The product was dried overnight at 80° C. under high vacuum to give the product of Step 2 (4.55 g) as yellow solid.

Step 3

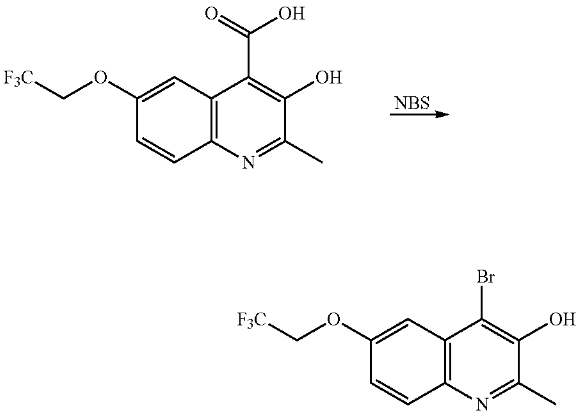

To a solution of the product of Step 2 (4.95 g, 16.4 mmol) in THF (50 ml) at RT was added NBS (3.51 g, 19.7 mmol), and the mixture was stirred for 3 h. The mixture was quenched at RT with saturated brine and extracted with EtOAc. The combined organic fractions were dried over $Na_2SO_4$, filtered and concentrated in vacuo. The reaction was taken up in DCM, and the solid was filtered to provide a first crop of desired compound. The filtrate was concentrated in vacuo and purified by column chromatography over silica gel (eluting with Hexanes/EtOAc 99:1 to 30:70). The resulting purified material was collected with the solid from the first crop to provide the product of Step 3 (2.91 g, 53% yield).

Step 4

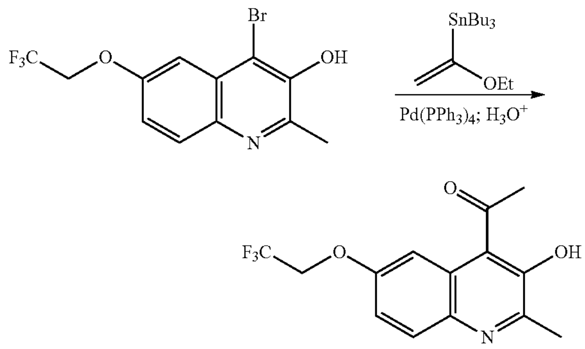

To a solution of the product of Step 3 (3.21 g, 9.55 mmol) and $Pd(PPh_3)_4$ (1.10 g, 0.955 mmol) in dioxane (40 ml) at RT was added tributyl(1-ethoxyvinyl)tin (7.42 ml, 21.97 mmol), and the mixture was warmed to 110° C. and stirred overnight. The mixture was quenched at RT with 1N aq. HCl and stirred for 90 min. The reaction was diluted with sat. aq. $NaHCO_3$ and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to EtOAc) to give the product of Step 4 (1.29 g, 45% yield) as a brown solid.

Step 5

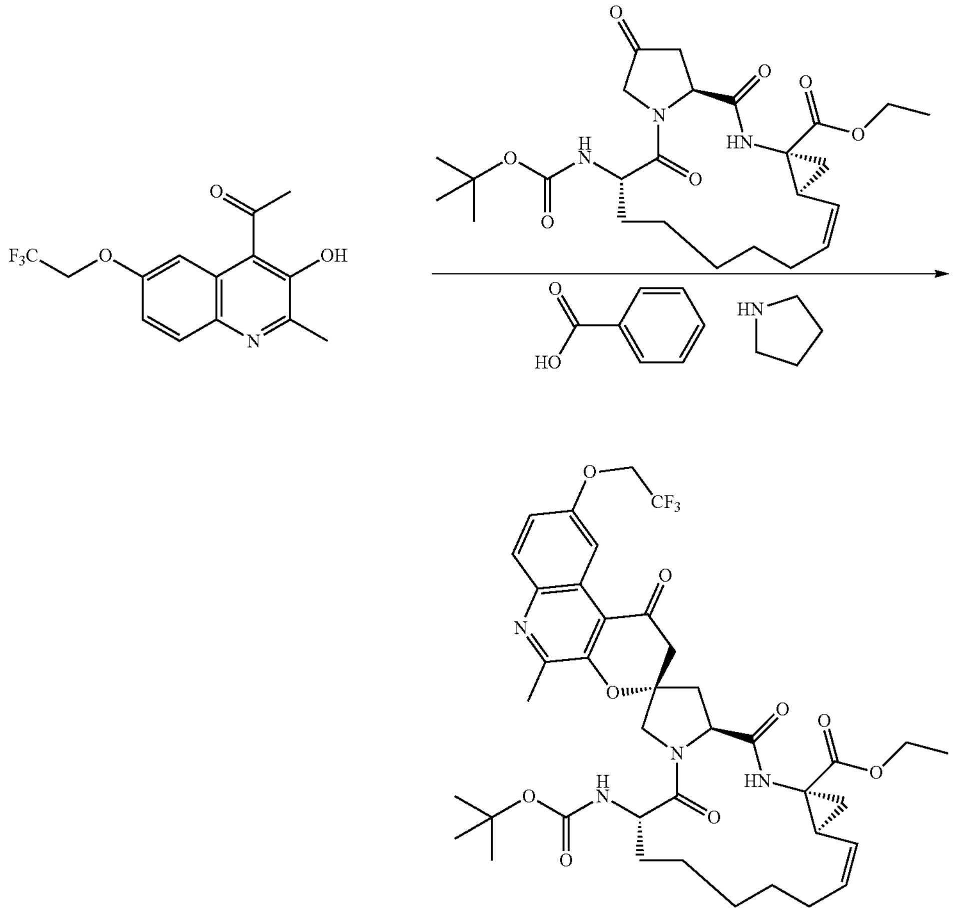

To a solution of the product of Step 4 (500 mg, 1.67 mmol), and macrocyclic ketone (821 mg, 1.671 mmol) and benzoic acid (204 mg, 1.67 mmol) in MeOH (15 ml) at RT was added pyrrolidine (0.053 ml, 0.668 mmol) and 4A molecular sieves (~1 g), and the mixture was warmed to 55° C. and stirred for 72 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give the product of Step 5 (875 mg, 68% yield) as yellow foam.

Step 6

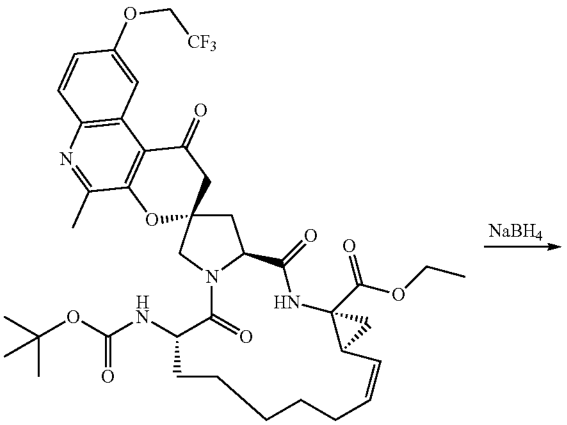

-continued

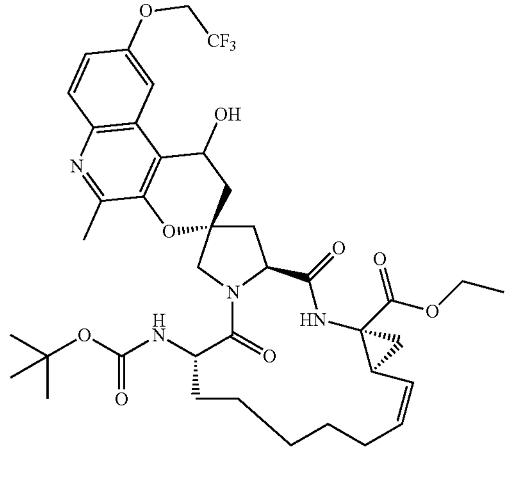

To a solution of the product of Step 5 (875 mg, 1.13 mmol) in THF (6 ml) and MeOH (6 ml) at 0° C. was added $NaBH_4$ (51.4 mg, 1.36 mmol), and the mixture was stirred for 45 min. The mixture was quenched at RT with sat. aq. $NH_4Cl$ and extracted with EtOAc. The combined organic fractions were washed with brine, dried over $Na_2SO_4$, filtered and concentrated in vacuo to afford the product of Step 6(880 mg, 100% yield).

Step 7

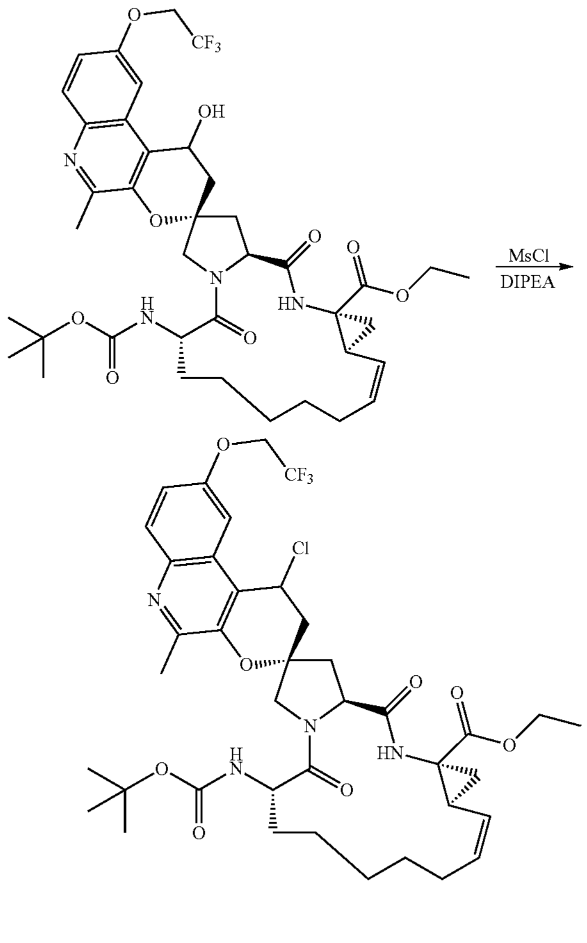

To a solution of the product of Step 6 (880 mg, 1.14 mmol) and 4-dimethylaminopyridine (1.388 mg, 0.011 mmol) in DCM (25 ml) at −10° C. was added DIPEA (0.593 ml, 3.41 mmol), followed by MsCl (0.142 ml, 1.82 mmol) slowly, and the mixture was allowed to warm to RT over 30 min then stirred for 3 h. More DIPEA (0.3 ml) and MsCl (0.070 ml) were then added, and the reaction was stirred for another 5 h. The final mixture was diluted at RT with EtOAc and sat. aq. $NH_4Cl$, extracted with EtOAc, washed with brine then dried over $Na_2SO_4$, filtered and concentrated in vacuo to give the crude product of Step 7 (980 mg).

Step 8

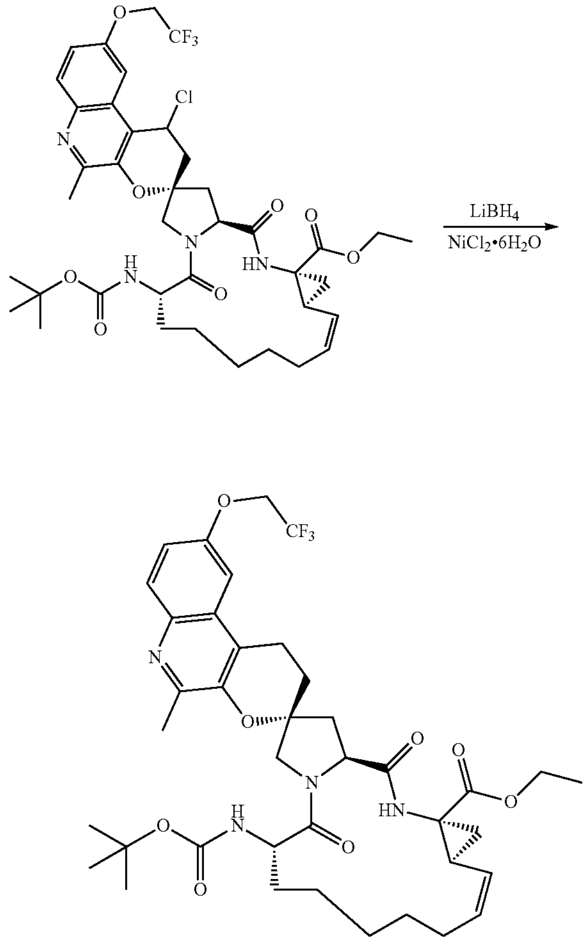

To a solution of the product of Step 7 (660 mg, 0.832 mmol) in MeOH (25 ml) at −78° C. was added $NiCl_2.6H_2O$ (198 mg, 0.832 mmol) then 2N $LiBH_4$ in THF (1.66 ml, 3.33 mmol). The reaction was stirred for 15 min then quenched at −78° C. with sat. aq. $NaHCO_3$. The mixture was extracted with EtOAc, dried over $Na_2SO_4$, filtered and concentrated in vacuo. The residue was purified by column chromatography over silica gel (eluting with Hexanes/EtOAc 99:1 to 20:80) to provide the product of Step 8 (309 mg, 49% yield).

Step 9

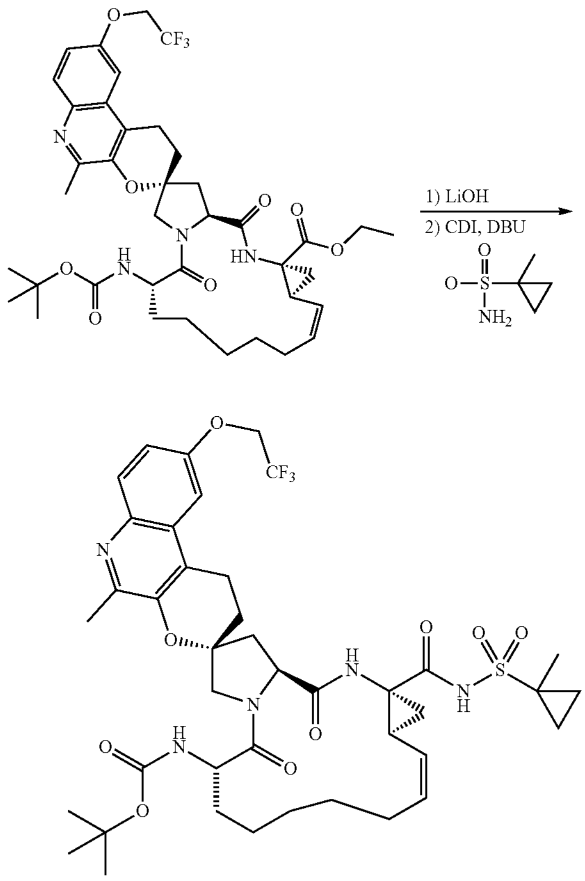

To a solution of the product of Step 8 (361 mg, 0.476 mmol) in THF (10 ml), MeOH (10 ml) and water (7 ml) at RT was added $LiOH.H_2O$ (59.9 mg, 1.427 mmol) and the mixture was warmed to 55° C. and stirred for 6 h. The mixture was quenched at RT with ice-cold 0.2N aq. HCl and extracted with EtOAc. The combined organic fractions were dried over $Na_2SO_4$, filtered and concentrated in vacuo to give an intermediate acid (325 mg, 93% yield). To a solution of this intermediate acid (325 mg, 0.445 mmol) in THF (12 ml) at RT was added carbonyl diimidazole (144 mg, 0.889 mmol), and the mixture was warmed to 70° C. and stirred for 4 h. 1-Methylcyclopropane-1-sulfonamide (240 mg, 1.779 mmol) and DBU (0.268 ml, 1.779 mmol) were then added at RT, and the reaction was warmed to 50° C. and stirred for 3 h. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 20:80) to give I-30 (295 mg, 78% yield) as colorless foam. $^1$H-NMR (400 MHz, $CDCl_3$) δ 10.10 (s, 1H), 7.89 (d, J=9.0 Hz, 1H), 7.22 (d, J=9.0 Hz, 1H), 7.05 (s, 1H), 6.91 (s, 1H), 5.71 (m, 1H), 4.95-5.05 (m, 2H), 4.61 (m, 1H), 4.40-4.55 (m, 4H), 4.17 (m, 1H), 3.70 (d, J=10.8 Hz, 1H), 3.00-3.10 (m, 2H), 2.45-2.60 (m, 2H), 2.47 (s, 3H), 2.25-2.40 (m, 4H), 1.65-1.95 (m, 5H), 1.20-1.50 (m, 8H), 1.46 (m, 3H), 1.30 (s, 9H), 0.80 (br s, 2H).

Example 31 tert-butyl ((2R,6S,13aS,14aR,16aS,Z)-7'-chloro-14a-(((1-methylcyclopropyl) sulfonyl)carbamoyl)-5,16-dioxo-5'-(trifluoromethyl)-1',2',3,5,6,7,8,9,10,11,13a,14,14a,15, 16,16a-hexadecahydro-1H-spiro [cyclopropa[e]pyrrolo[1,2-a][1,4] diazacyclopentadecine -2,3'-pyrano[2,3-c]quinolin]-6-yl)carbamate (I-31)

Step 1

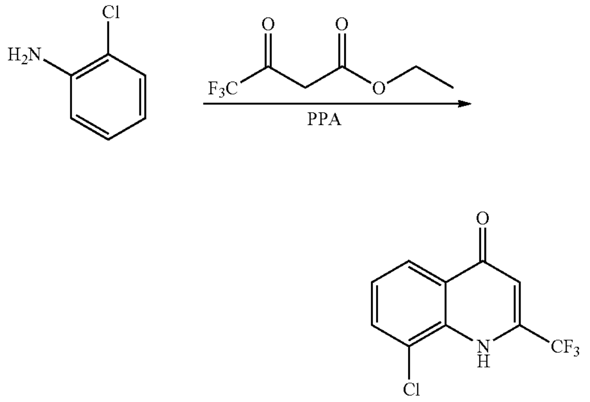

To a well-stirred solution of polyphosphoric acid (70 g) at 100° C. was added ethyl 4,4,4-trifluoroacetoacetate (19.6 ml, 133 mmol) dropwise, and the mixture was stirred for 15 min. 2-Chloroaniline (14 ml, 133 mmol) was then added at 100° C. dropwise, and the reaction was warmed to 150° C. and stirred for 3 h. The slurry was slowly poured at RT over ice-cold water then stirred overnight at RT. The mixture was filtered, and the solid was taken up in DCM/MeOH 1:1, concentrated to ~20 ml, then poured into hexanes (700 ml). The resulting solid was filtered, rinsing with hexanes, and dried in vacuo to give the product of Step 1 (21.35 g, 65% yield).

Step 2

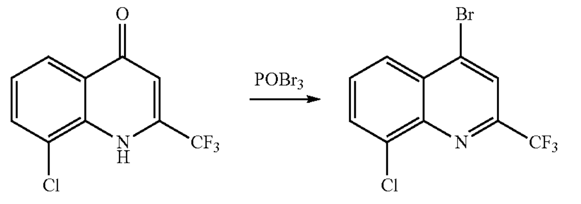 [SMILES: O=c1cc(C(F)(F)F)[nH]c2c(Cl)cccc12 ; "POBr3" ; FC(F)(F)c1cc(Br)c2cccc(Cl)c2n1]

To a solution of the product of Step 1 (10 g, 40.4 mmol) in MeCN (250 ml) at RT was added phosphorus oxybromide (13.32 g, 46.4 mmol), and the mixture was warmed to reflux and stirred for 90 min. The mixture was poured at RT into sat. aq. $NaHCO_3$ and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to 50:50) to provide the product of Step 2 (12.5 g, 100% yield) as a white solid.

Step 3

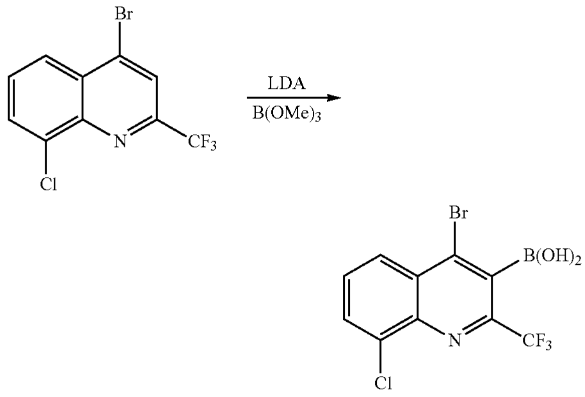

To a solution of DIPA (4.06 ml, 28.7 mmol) in THF (25 ml) at −30° C. was added n-butyl lithium 2.5N in hexanes (11.04 ml, 27.6 mmol), and the mixture was warmed to 0° C. and stirred for 10 min. The product of Step 2 (7.14 g, 23.00 mmol) in THF (20 ml) was then added at −78° C., and the reaction was stirred for 90 min. Trimethylborate (3.85 ml, 34.5 mmol) was then added at −78° C., and the reaction was stirred for 3 h. The mixture was quenched at −78° C. with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 20:80) to give the product of Step 3 (5.47 g, 67% yield) as well as 1.73 g of starting material.

Step 4

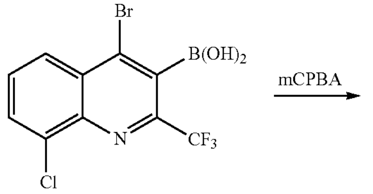

-continued

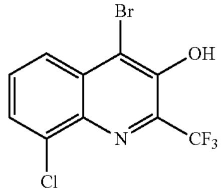

To the product of Step 3 (4.58 g, 12.9 mmol) was added a 0.103N solution of mCPBA in DCM (144 ml, 14.9 mmol), and the reaction was stirred overnight. The reaction was diluted with EtOAc, poured into sat. aq. $NH_4Cl$/5% aq. $Na_2S_2O_3$ 2:1, and extracted with EtOAc. The combined organic fractions were washed with sat. aq. $NH_4Cl$, dried over $Na_2SO_4$, filtered and concentrated in vacuo. The residue was purified by column chromatography over silica gel (eluting with Hexanes/EtOAc 99:1 to 50:50) to provide the product of Step 4 (3.27 g, 77% yield) as yellow solid.

Step 5

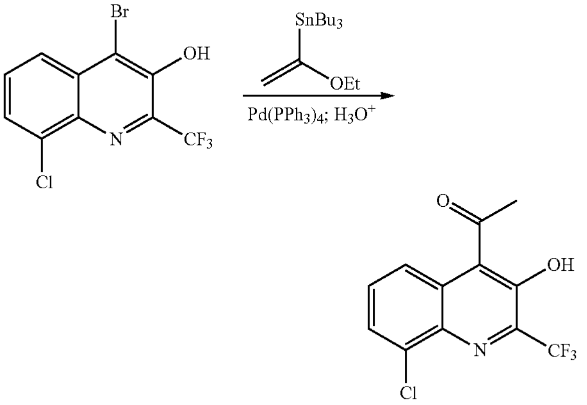

To a solution of the product of Step 4 (6.13 g, 18.8 mmol) and $Pd(PPh_3)_4$ (1.085 g, 0.939 mmol) in dioxane (85 ml) at RT was added tributyl(1-ethoxyvinyl)tin (12.7 ml, 37.6 mmol), and the mixture was warmed to 110° C. and stirred overnight. The mixture was quenched at RT with 1N aq. HCl (60 ml) and stirred for 3 h. The mixture was diluted with water and extracted with EtOAc. The combined organic fractions were washed with brine, dried over $Na_2SO_4$, filtered and concentrated in vacuo. The residue was purified by column chromatography over silica gel (eluting with Hexanes/EtOAc 99:1 to 50:50) to afford the product of Step 5 (4.37 g, 80% yield) as yellow solid.

Step 6

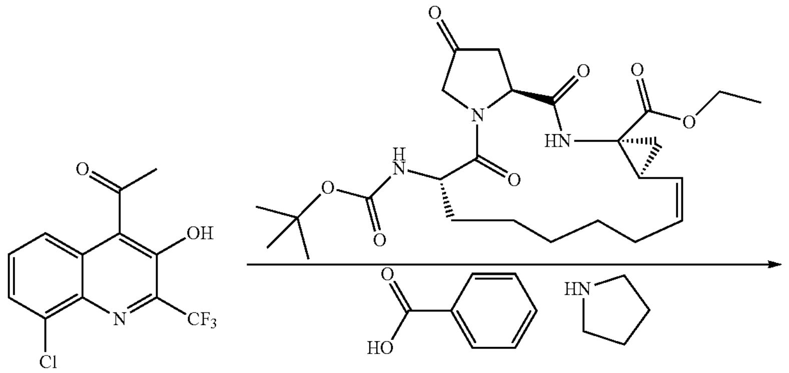

-continued

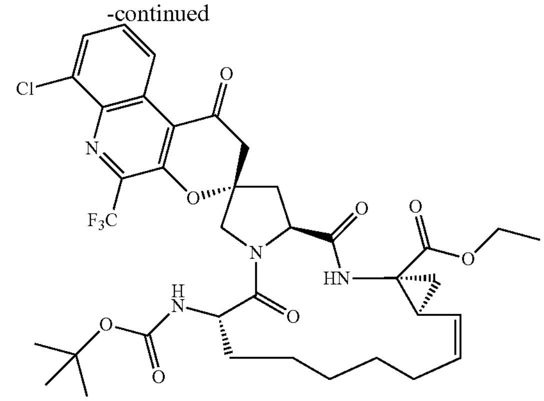

To a solution of the product of Step 5 (450 mg, 1.554 mmol), macrocyclic ketone (764 mg, 1.554 mmol) and benzoic acid (190 mg, 1.554 mmol) in MeOH (12 ml) at RT was added pyrrolidine (0.050 ml, 0.621 mmol) and 4A molecular sieves (~1 g), and the mixture was warmed to 60° C. and stirred for 72 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 40:60) to give the product of Step 6 (799 mg, 67% yield) as yellow foam.

Step 7

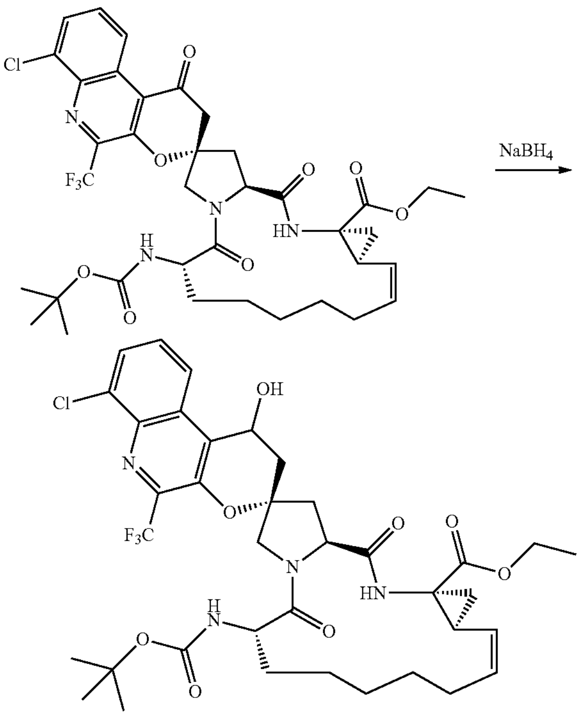

To a solution of the product of Step 6 (799 mg, 1.05 mmol) in THF (6 ml) and MeOH (6 ml) at 0° C. was added $NaBH_4$ (47.5 mg, 1.26 mmol), and the mixture was stirred for 1 h. The mixture was quenched at 0° C. with sat. aq. $NH_4Cl$ and extracted with EtOAc. The combined organic fractions were dried over $Na_2SO_4$, filtered and concentrated in vacuo to provide the product of Step 7 (810 mg, 100% yield) as yellow foam.

Step 8

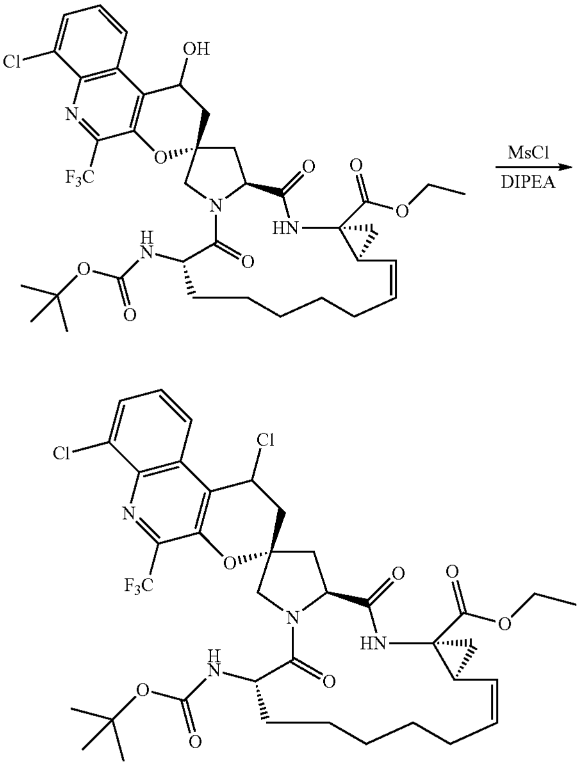

To a solution of the product of Step 7 (222 mg, 0.290 mmol) in DCM (6 ml) at 0° C. was added MsCl (0.045 ml, 0.580 mmol) followed by DIPEA (0.202 ml, 1.16 mmol), and the mixture was allowed to warm to RT and stirred overnight. More MsCl (0.020 ml) and DIPEA (0.070 ml) were added, and the mixture was stirred for 6 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (Isco 24 g, eluting with Hexanes/EtOAc 99:1 to 30:70) to give the product of Step 8 (139 mg, 61% yield).

Step 9

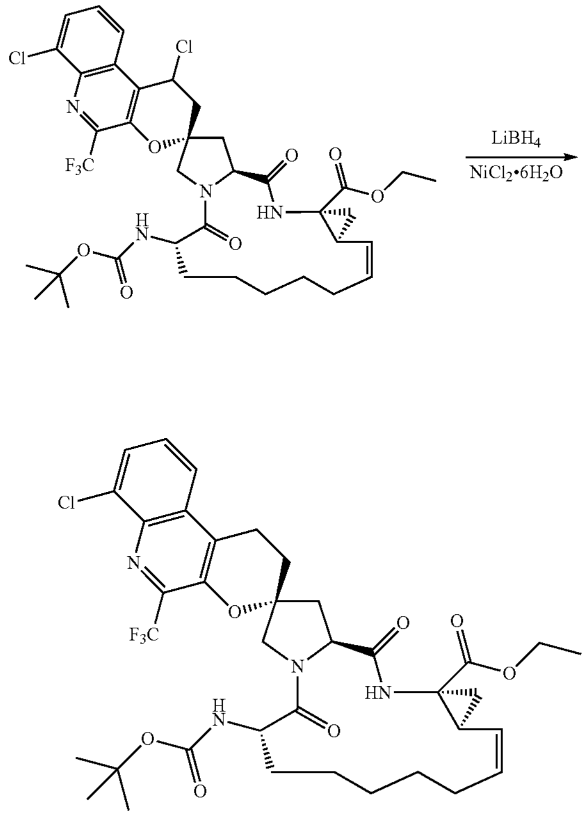

To a solution of the product of Step 8 (139 mg, 0.177 mmol) in MeOH (9 ml) at −78° C. was added $NiCl_2.6H_2O$ (39.2 mg, 0.165 mmol) then 2N $LiBH_4$ in THF (0.266 ml, 0.532 mmol). The reaction was allowed to warm to 0° C. over 1 h then stirred at this temperature for 15 min. The mixture was quenched at 0° C. with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 20:80) to give the product of Step 9 (65.6 mg, 49% yield).

Step 10

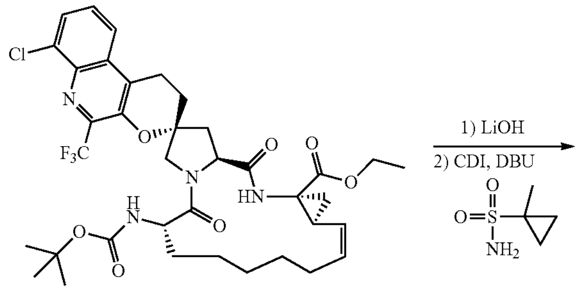

-continued

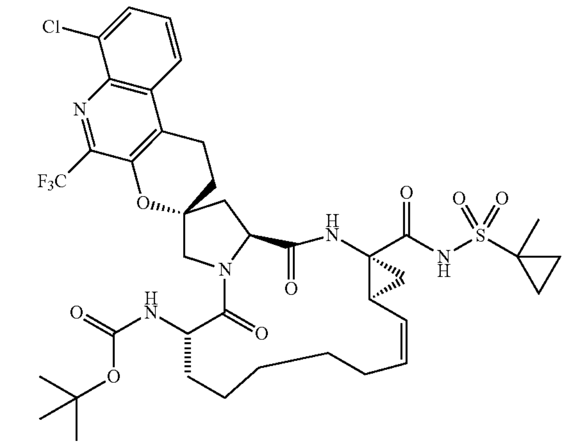

To a solution of the product of Step 9 (65.6 mg, 0.088 mmol) in THF (1.2 ml), MeOH (1.2 ml) and water (3 ml) at RT was added $LiOH.H_2O$ (11.0 mg, 0.263 mmol), and the mixture was stirred at 40° C. overnight. The mixture was concentrated in vacuo then quenched at RT with ice-cold 0.2N aq. HCl and extracted with EtOAc. The combined organic fractions were dried over $Na_2SO_4$, filtered and concentrated in vacuo to give an intermediate acid (63.4 mg, 100% yield). To a solution of this intermediate acid (63.4 mg, 0.088 mmol) in THF (2.5 ml) at RT was added carbonyl diimidazole (28.5 mg, 0.176 mmol), and the mixture was warmed to 70° C. and stirred for 5 h. 1-Methylcyclopropane-1-sulfonamide (47.5 mg, 0.352 mmol) and DBU (0.053 ml, 0.352 mmol) were then added at RT, and the reaction was warmed to 50° C. and stirred for 8 h. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) then preparative TLC over silica gel (eluting with Hexanes/Acetone 6:4) to afford I-31 (7.8 mg, 11% yield) as a white solid. $^1$H-NMR (400 MHz, $CDCl_3$) δ 10.11 (s, 1H), 7.77 (d, J=8.4 Hz, 2H), 7.58 (t, J=8.4 Hz, 1H), 6.84 (s, 1H), 5.72 (m, 1H), 4.95-5.07 (m, 2H), 4.62 (m, 1H), 4.46 (m, 1H), 4.13 (m, 1H), 3.70 (d, J=10.8 Hz, 1H), 3.15-3.35 (m, 2H), 2.45-2.65 (m, 2H), 2.25-2.40 (m, 4H), 1.65-1.95 (m, 5H), 1.20-1.50 (m, 8H), 1.48 (m, 3H), 1.25 (s, 9H), 0.82 (br s, 2H); LC-MS ($M^+$) Calc. for $C_{39}H_{42}ClF_3N_5O_8S$ 837.3. Found 782.0 (M+H-tBu)+.

Example 32 tert-butyl ((1'R,2S,6S,13aS,14aR,16aS,Z)-1'-fluoro-5'-isopropyl-9'-methoxy -14a-(((1-methylcyclopropyl)sulfonyl)carbamoyl)-5,16-dioxo-1',2',3,5,6,7,8,9,10,11,13a,14, 14a,15,16,16a-hexadecahydro-1H-spiro[cyclopropa[e]pyrrolo[1,2-a][1,4]diaza cyclopentadecine-2,3'-pyrano[2,3-c]quinolin]-6-yl) carbamate (I-32)

Step 1

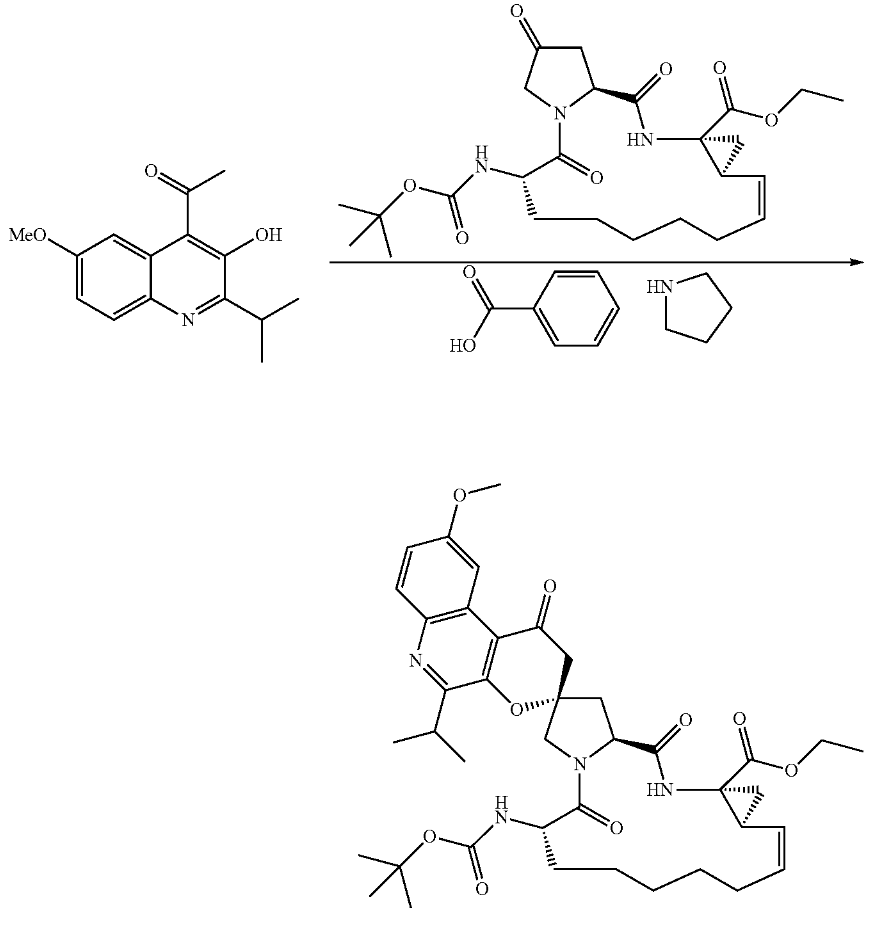

To a solution of the product of Example 2, Step 3 (325 mg, 1.25 mmol), macrocyclic ketone (616 mg, 1.25 mmol) and benzoic acid (153 mg, 1.25 mmol) in MeOH (10 ml) at RT was added pyrrolidine (0.040 ml, 0.50 mmol) and molecular sieves (4A, ~1 g), and the mixture was warmed to 60° C. and stirred for 72 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 40:60) to give the product of Step 1 (686 mg, 75% yield) as yellow foam.

Step 2

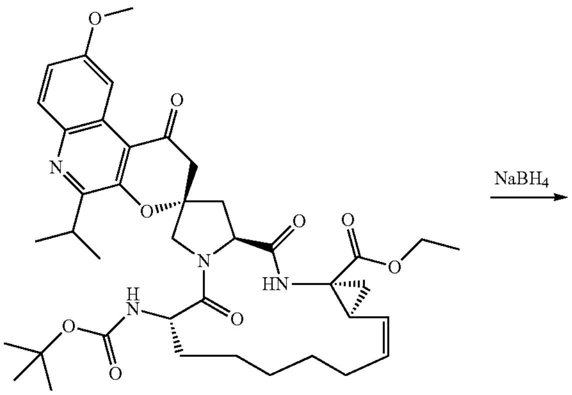

-continued

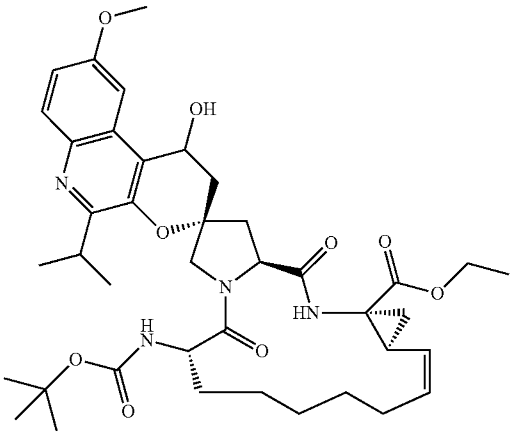

To a solution of the product of Step 1 (686 mg, 0.94 mmol) in THF (5 ml) and MeOH (5 ml) at 0° C. was added $NaBH_4$ (42.5 mg, 1.12 mmol), and the mixture was stirred for 1 h. The mixture was quenched at 0° C. with sat. aq. $NH_4Cl$ and extracted with EtOAc. The combined organic fractions were dried over $Na_2SO_4$, filtered and concentrated in vacuo to provide the product of Step 2 (671 mg, 98% yield) as yellow foam.

Step 3

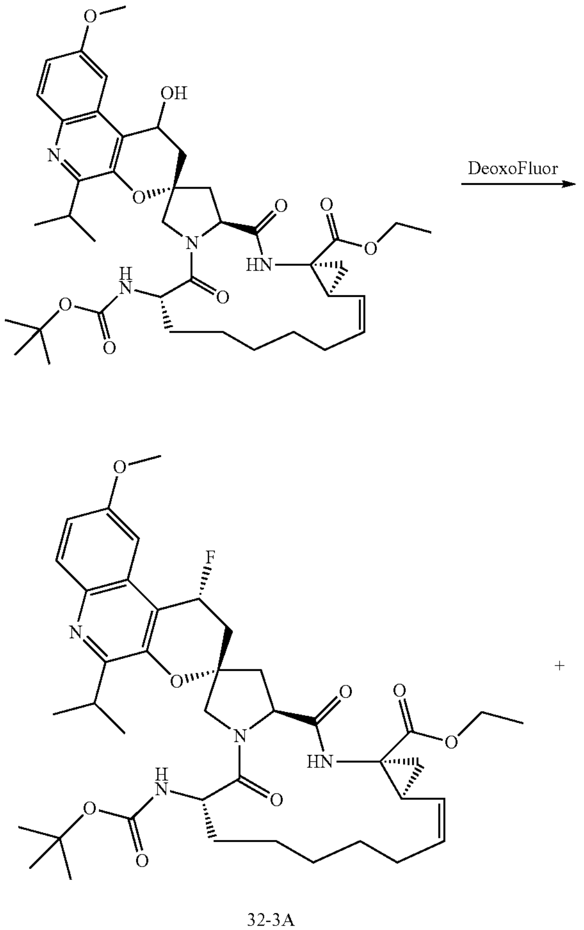

32-3A

+

-continued

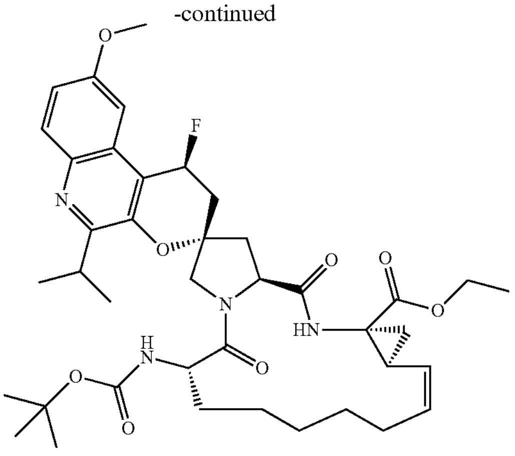

32-3B

To a solution of the product of Step 2 (671 mg, 0.91 mmol) in DCM (9 ml) at 0° C. was added DeoxoFluor (0.20 ml, 1.10 mmol) and EtOH (0.005 ml), and the mixture was allowed to warm to RT and stirred overnight. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to 50:50) to give, in order of elution, intermediate 32-3A (301 mg, 45% yield) followed by intermediate 32-3B (241 mg, 36% yield).

Step 4

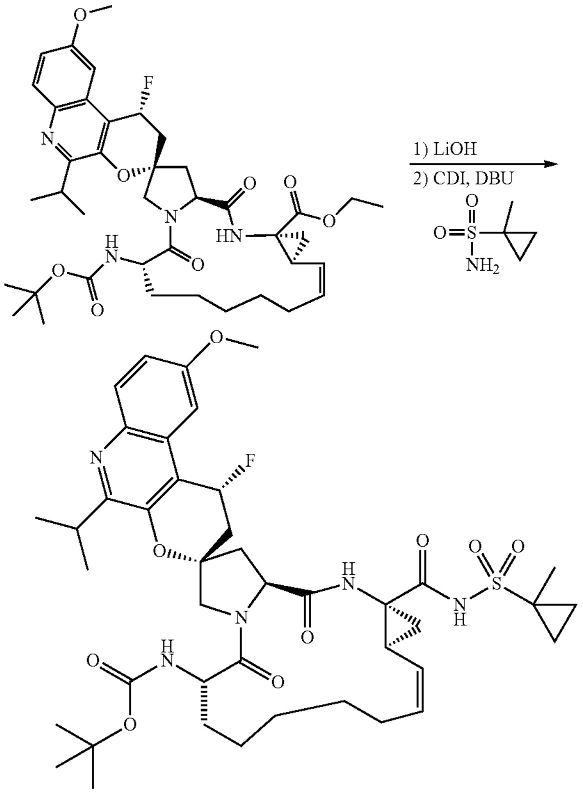

To a solution of intermediate 32-3A from Step 3 (301 mg, 0.408 mmol) in THF (5 ml), MeOH (5 ml) and water (3 ml) at RT was added $LiOH.H_2O$ (51.4 mg, 1.23 mmol), and the mixture was stirred at RT overnight. More $LiOH.H_2O$ (15 mg) was added, and the reaction was stirred another 2 h at RT. The mixture was concentrated in vacuo then quenched at RT with ice-cold 0.2N aq. HCl and extracted with EtOAc. The combined organic fractions were dried over $Na_2SO_4$, filtered and concentrated in vacuo to give an intermediate acid (263 mg, 91% yield). To a solution of this intermediate acid (263 mg, 0.371 mmol) in THF (10 ml) at RT was added carbonyl diimidazole (120 mg, 0.742 mmol), and the mixture was warmed to 70° C. and stirred for 6 h. 1-methylcyclopropane-1-sulfonamide (201 mg, 1.48 mmol) and DBU (0.22 ml, 1.48 mmol) were then added at RT, and the reaction was warmed to 50° C. and stirred for 8 h. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/Acetone 99:1 to 50:50) to afford I-32 (231 mg, 75% yield) as a white solid. $^1$H-NMR (400 MHz, $CDCl_3$) δ 10.02 (s, 1H), 7.90 (d, J=10.0 Hz, 1H), 7.20 (m, 2H), 6.86 (s, 1H), 6.13and 6.00 (br s, 1H), 5.71 (m, 1H), 5.17 (m, 1H), 5.01 (m, 1H), 4.50 (m, 1H), 4.36 (m, 1H), 3.94 (s, 3H), 3.99 (d, J=11.2 Hz, 1H), 3.43 (m, 1H), 2.50-2.75 (m, 2H), 2.44 (m, 1H), 2.30 (m, 1H), 1.72-1.95 (m, 4H), 1.50-1.70 (m, 2H), 1.20-1.50 (m, 8H), 1.43 (s, 3H), 1.39 (s, 9H), 0.80 (br s, 2H); LC-MS ($M^+$) Calc. for $C_{42}H_{56}FN_5O_9S$ 825.38. Found 826.2 $[M+H]^+$.

Example 33 tert-butyl ((2S,6S,13aS,14aR,16aS,Z)-10'-fluoro-2'-methoxy-14a-(((1-methylcyclopropyl)sulfonyl)carbamoyl)-5,16-dioxo-6'-(trifluoromethyl)-3,5,6,7,8,9,9',10,10', 11,13a,14,14a,15,16,16a-hexadecahydro-1H-spiro[cyclopropa[e]pyrrolo[1,2-a][1,4]diazacyclopentadecine-2,8'-pyrano[2,3-c][1,5]naphthyridin]-6-yl)carbamate (I-33)

Step 1

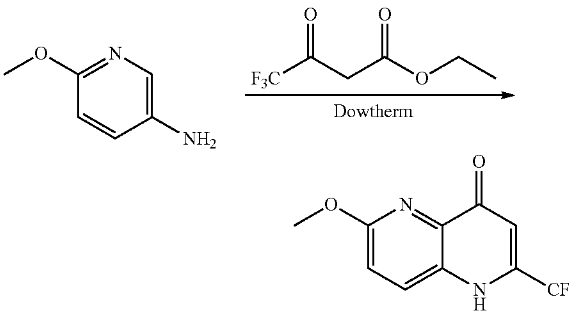

To a solution of 5-amino-2-methoxypyridine (25 g, 201 mmol) in Dowtherm (250 ml) at RT was added ethyl 4,4,4-trifluoroacetoacetate (32.6 ml, 222 mmol), and the mixture was warmed to reflux (250° C.) and stirred for 7 h. The mixture was allowed to cool to RT overnight, then filtered over fritted disk, rinsing with hexanes to provide a crude solid. The filtrate solution was purified by column chromatography over silica gel, eluting with hexanes, to remove Dowtherm. The crude solid was then added to the same column followed by purification through elution from hexanes to hexanes/EtOAc 10:90, to give the product of Step 1 (18.3 g, 37%).

Step 2

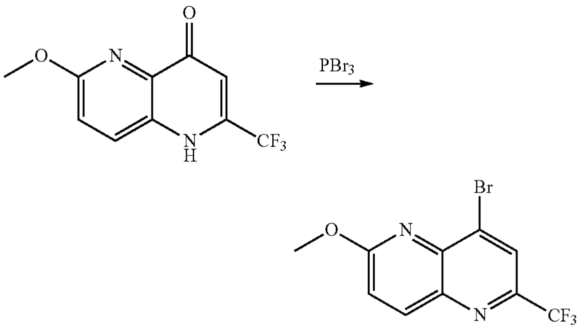

To a solution of the product of Step 1 (13.2 g, 54.1 mmol) in DMF (100 ml) at 0° C. was slowly added $PBr_3$ (6.10 ml, 64.9 mmol), and the mixture was warmed to 40° C. over 1 h then stirred overnight at this temperature. The mixture was quenched at 0° C. with water (50 ml), and $NaHCO_3$ was added slowly until pH ~7. The mixture was filtered over fitted disk, rinsing with water and the resulting solid was dried in vacuo to give the product of Step 2 (12.7 g, 77%) as white solid.

Step 3

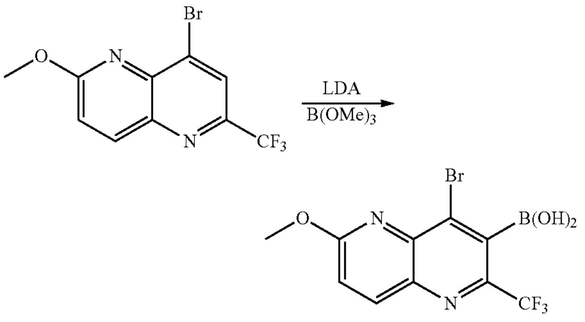

To a solution of the product of Step 2 (15.9 g, 51.8 mmol) in THF (200 ml) at −78° C. was added 1.8M LDA in hexanes (115 ml, 207 mmol) slowly over 30 min, and the mixture was stirred at −78° C. for 2 h. Trimethylborate (46.3 ml, 414 mmol) was added, and the reaction was stirred for 2 h at −78° C., then allowed to warm to RT overnight. The final mixture was poured at 0° C. over ice-cold 1N aq. HCl (200 ml) and extracted with EtOAc. The combined organic fractions were washed with brine, dried over $Na_2SO_4$, filtered and concentrated in vacuo to afford the crude product of Step 3 (22.7 g).

Step 4

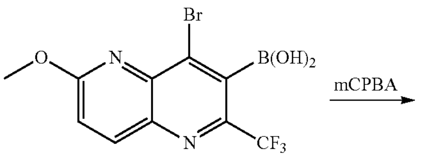

-continued

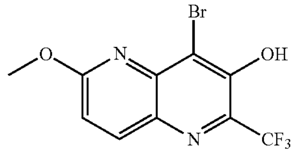

To a solution of the crude product of Step 3 (18.2 g, 51.8 mmol) in MeCN (400 ml) at RT was added 70% mCPBA (13.40 g, 78 mmol), and the mixture was stirred for 15 min. Solid $NaHCO_3$ (6.53 g, 78 mmol) was then added at RT, and the reaction was stirred overnight. The mixture was quenched at RT with water (200 ml), treated with $NaHSO_3$ (3.77 g, 36.2 mmol) and extracted with EtOAc. The combined organic fractions were washed with sat. aq. $NaHCO_3$, dried over $Na_2SO_4$, filtered and concentrated in vacuo to provide crude 1. The combined aq. layers were slowly acidify to pH=4-5 with concentrated HCl, exacted with EtOAc, dried over $Na_2SO_4$, filtered and concentrated in vacuo to provide crude 2. Crudes 1 and 2 were combined and purified by column chromatography over silica gel (eluting with Hexanes/EtOAc 99:1 to Hexanes/EtOAc 20:80 then DCM to DCM/EtOAc 50:50). The purified fractions were diluted with EtOAc, washed with sat. aq. $NaHCO_3$/brine 1:1, dried over $Na_2SO_4$, filtered and concentrated in vacuo to give the product of Step 4 (8.7 g, 51%).

Step 5

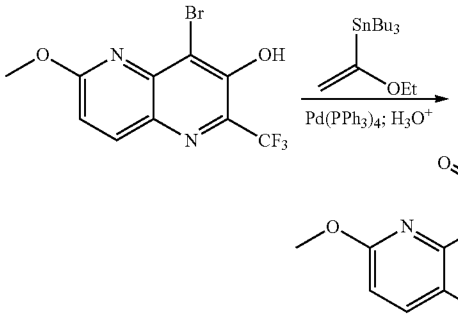

To a solution of the product of Step 4 (3.30 g, 10.2 mmol) and $Pd(PPh_3)_4$ (1.18 g, 1.02 mmol) in 1,4-dioxane (30 ml) at RT was added tributyl(1-ethoxyvinyl)tin (10.4 ml, 30.6 mmol), and the mixture was warmed to 110° C. and stirred overnight. The mixture was quenched at 0° C. with 1N aq. HCl (100 ml) and stirred at RT for 1 h. The mixture was neutralized with sat. aq. $NaHCO_3$ until pH ~7 and extracted with EtOAc. The combined organic fractions were dried over $Na_2SO_4$, filtered and concentrated in vacuo. The residue was purified by column chromatography over silica gel (eluting with Hexanes to Hexanes/EtOAc 50:50) to give the product of Step 5 (2.07 g, 71%).

Step 6

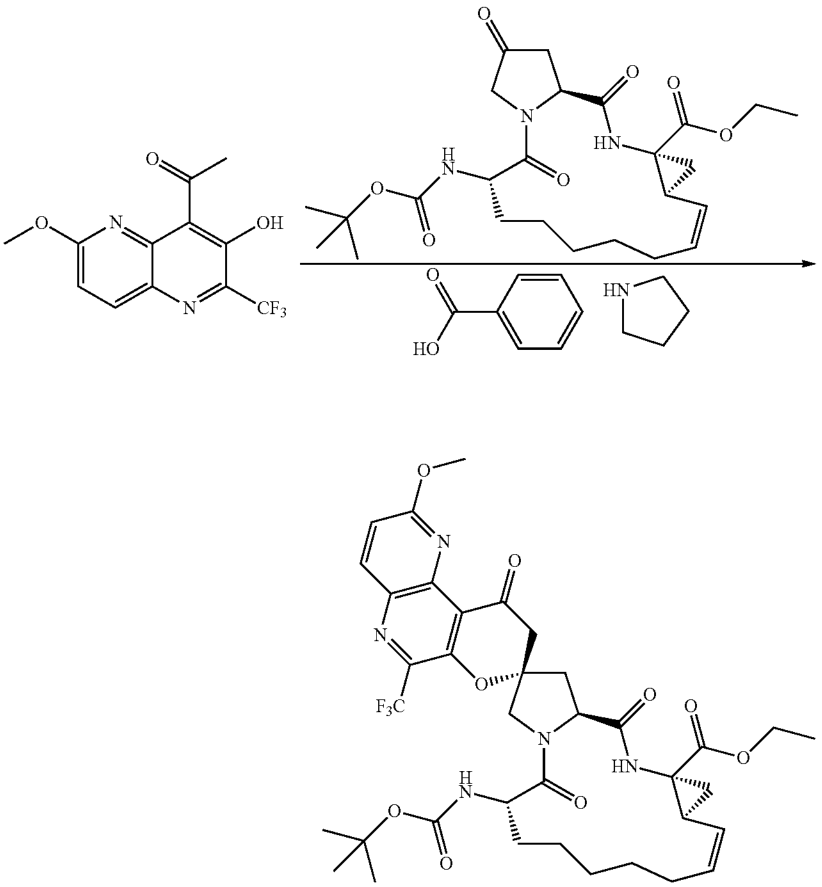

To a solution of the product of Step 5 (520 mg, 1.82 mmol), macrocyclic ketone (893 mg, 1.82 mmol) and benzoic acid (222 mg, 1.82 mmol) in MeOH (12 ml) at RT was added pyrrolidine (0.145 ml, 1.82 mmol) and molecular sieves (4A, ~1 g), and the mixture was warmed to 65° C. and stirred for 48 h. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give, in order of elution, starting material (131 mg) followed by the crude product of Step 6 (664 mg, 48% yield).

Step 7

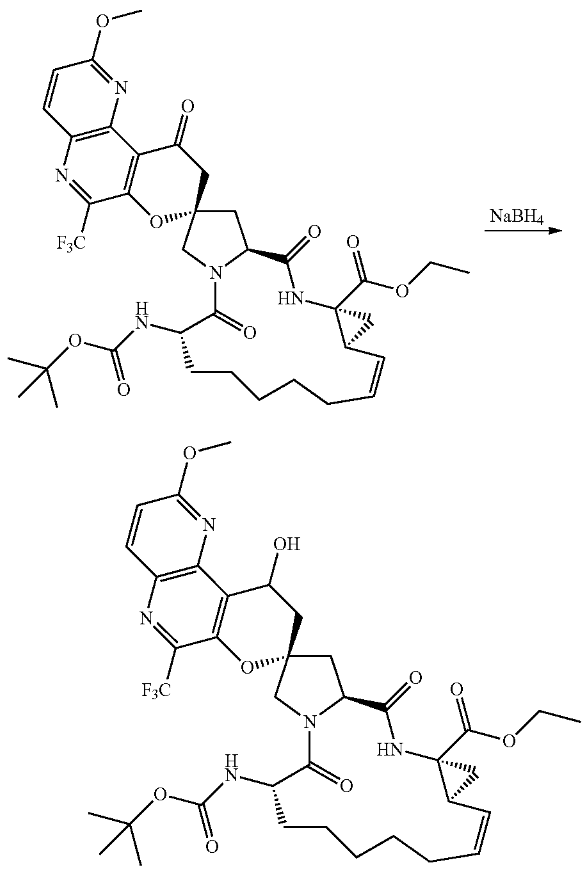

To a solution of the crude product of from Step 6 (664 mg, 0.87 mmol) in THF (5 ml) and MeOH (5 ml) at 0° C. was added $NaBH_4$ (39.7 mg, 1.05 mmol), and the mixture was stirred for 1 h. The mixture was quenched at 0° C. with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give the product of Step 7 (228 mg, 34% yield) as yellow foam.

Step 8

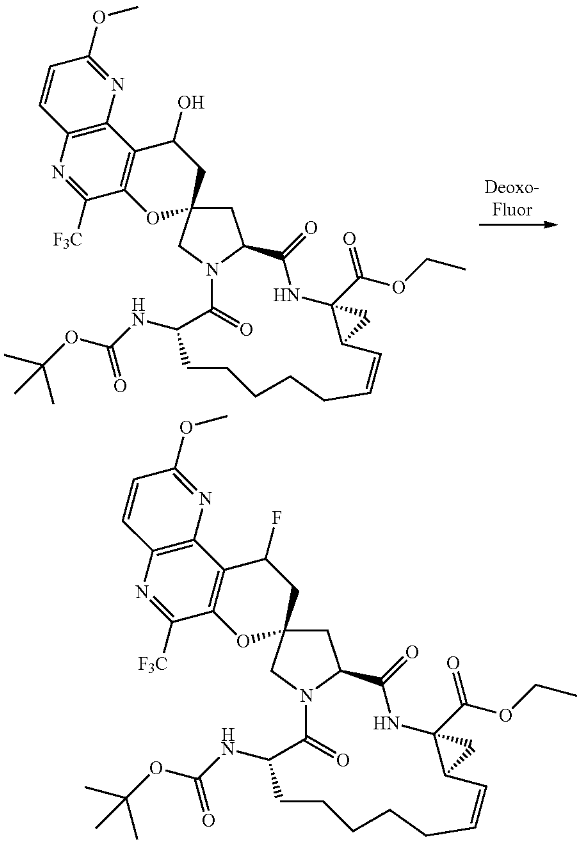

To a solution of the product of Step 7 (228 mg, 0.299 mmol) in DCM (4 ml) at 0° C. was added DeoxoFluor (0.066 ml, 0.359 mmol) and EtOH (0.005 ml), and the mixture was allowed to warm to RT and stirred overnight. The mixture was quenched at RT with sat. aq. $NaHCO_3$ and extracted with EtOAc. The combined organic fractions were dried over $Na_2SO_4$, filtered and concentrated in vacuo. The residue was purified by column chromatography over silica gel (eluting with Hexanes/EtOAc 99:1 to EtOAc) to give the product of Step 8 (66.9 mg, 29% yield) as a ~1:1 mixture of diastereoisomers at the benzylic fluoride.

Step 9

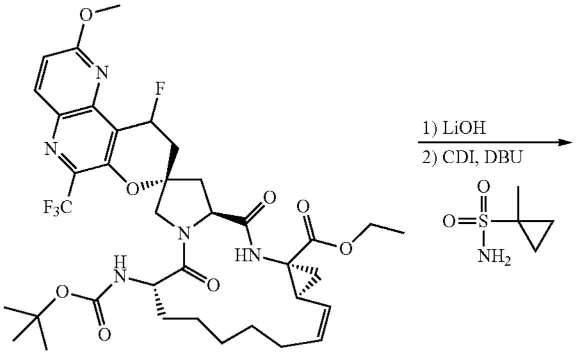

-continued

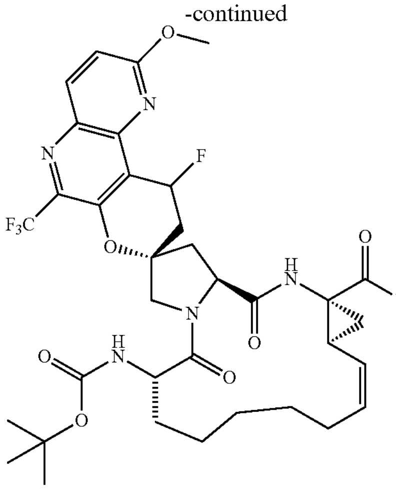

To a solution of the product of Step 8 (66.9 mg, 0.088 mmol) in THF (1.2 ml), MeOH (1.2 ml) and water (0.7 ml) was added $LiOH.H_2O$ (18.38 mg, 0.438 mmol), and the mixture was stirred at RT overnight. The mixture was concentrated in vacuo then quenched at RT with ice-cold 0.2N aq. HCl and extracted with EtOAc. The combined organic fractions were dried over $Na_2SO_4$, filtered and concentrated in vacuo to give an intermediate acid (68.5 mg).

To a solution of this intermediate acid (68.5 mg, 0.093 mmol) in THF (2.5 ml) at RT was added carbonyl diimidazole (30.2 mg, 0.186 mmol), and the mixture was warmed to 70° C. and stirred for 6 h. 1-Methylcyclopropane-1-sulfonamide (50.3 mg, 0.372 mmol) and DBU (0.056 ml, 0.372 mmol) were then added at RT, and the reaction was warmed to 45° C. and stirred overnight. The mixture was quenched at RT with sat. aq. $NH_4Cl$ and extracted with EtOAc. The combined organic fractions were dried over $Na_2SO_4$, filtered and concentrated in vacuo. The residue was purified by column chromatography over silica gel (eluting with Hexanes/acetone 99:1 to 50:50) to give I-33 (33.9 mg, 43% yield) as a ~1:1 mixture of diastereoisomers at the benzylic fluoride, as colorless oil. $^1H$-NMR (400 MHz, $CDCl_3$) δ 10.15 and 10.07 (s, 1H), 8.21 (d, 1H), 7.08 (d, 1H), 6.88 (s, 1H), 6.55 and 6.43 (br d, 1H), 5.70 (m, 1H), 5.26 (d, 1H), 4.95-5.05 (m, 2H), 4.72 (m, 1H), 4.45-4.65 (m, 2H), 4.36 (m, 1H), 4.07 (m, 1H), 3.90 and 3.74 (d, 1H), 2.25-2.75 (m, 5H), 1.60-1.95 (m, 6H), 1.15-1.55 (m, 8H), 1.57 (m, 3H), 1.39 (s, 9H), 0.80 (br s, 2H); LC-MS ($M^+$) Calc. for $C_{39}H_{48}F_4N_6O_9S$ 852.31. Found 853.2.

Example 34 tert-Butyl ((2R,6S,13aR,14aR,16aS)-9'-methoxy-5'-methyl-14a-(((1-methyl cyclopropyl)sulfonyl)carbamoyl)-5,16-dioxo-1',2',3,5,6,7,8,9,10,11,12,13,13a,14,14a,15, 16,16a-octadecahydro-1H-spiro[cyclopropa[e]pyrrolo[1,2-a][1,4]diazacyclopentadecine -2,3'-pyrano[2,3-c]quinolin]-6-yl)carbamate (I-34)

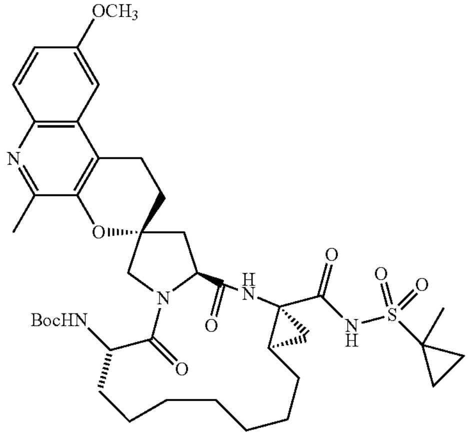 [SMILES: COc1ccc2nc(C)c3c(c2c1)CC[C@]1(C[C@H]2C(=O)N[C@]4(C(=O)NS(=O)(=O)C5(C)CC5)C[C@H]4CCCCCCC[C@H](NC(=O)OC(C)(C)C)C(=O)N2C1)O3]

A suspension of I-9 (260 mg, 0.333 mmol), 10% Pd/C (26 mg) in EtOAc (6 ml) was stirred under a $H_2$ balloon. LC-MS at 4 h indicated no product formation. The mixture was filtered through a CELITE pad, evaporated to dryness and once again stirred with 60 mg of 10% Pd/C in 5 ml of MeOH under $H_2$ balloon for 5 h. The reaction mixture was filtered through a CELITE pad and evaporated to dryness. The crude product was purified by SFC chromatography followed by silica-gel chromatography eluting with 0-40-100% acetone-hexanes to give 54 mg of I-34. LC-MS: m/e=782.2 (MH+).

Example 35

1,1,1-trifluoro-2-methylpropan-2-yl((2R,6S,13aR, 14aR,16aS)-9'-methoxy-5'-methyl-14a-(((1-methylcyclopropyl)sulfonyl)carbamoyl)-5,16-dioxo-1',2',3, 5,6,7,8,9,10, 11,12,13,13a,14,14a,15,16,16a-octadecahydro-1H-spiro[cyclopropa[e]pyrrolo[1,2-a][1,4]diazacyclopentadecine-2,3'-pyrano[2,3-c]quinolin]-6-yl)carbamate (I-35)

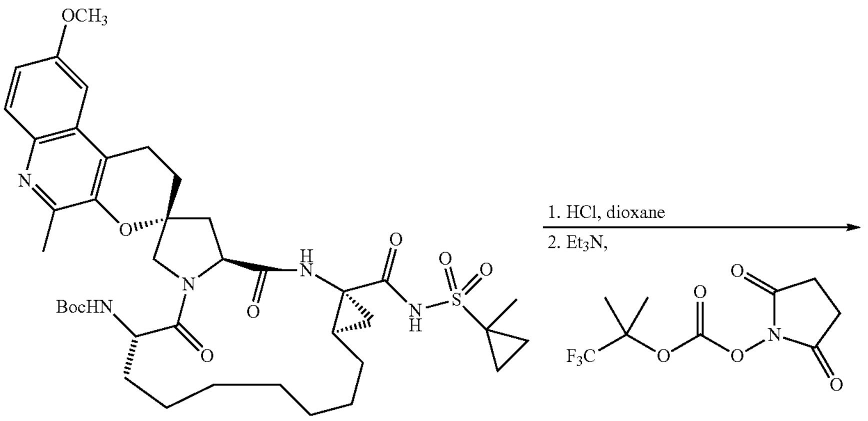

-continued

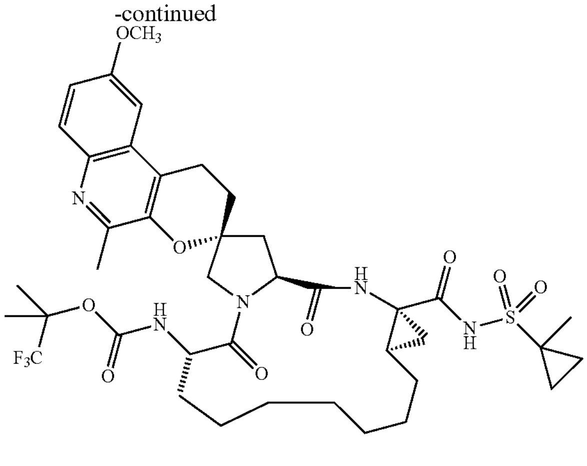

I-34 was converted to I-35 using procedures similar to that of Example 20. LC-MS: m/e=836.2 (MH+).

Example 36

Neopentyl((1'R,2S,6S,13aS,14aR,16aS,Z)-5'-ethyl-1'-fluoro-9'-methoxy-14a -(((1-methylcyclopropyl) sulfonyl)carbamoyl)-5,16-dioxo-1',2',3,5,6,7,8,9,10, 11,13a,14,14a, 15,16,16a-hexadecahydro-1H-spiro [cyclopropa[e]pyrrolo[1,2-a][1,4] diazacyclopentadecine -2,3'-pyrano[2,3-c]quinolin]-6-yl)carbamate (I-36)

Step 1

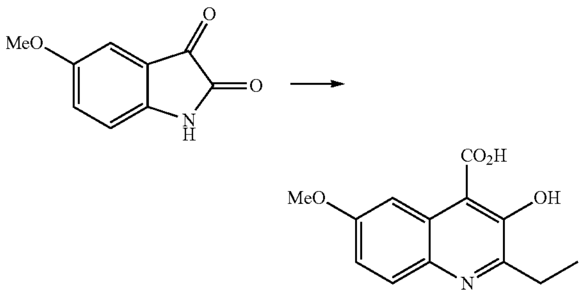

A solution of 5-methoxy isatin (7 g) in 150 ml of water was treated with $Ca(OH)_2$ (6.65 g) and heated at 80° C. for 1 h. The reaction mixture was treated with 2-bromobutanone (11.93 g) and stirred at 80° C. for 6 h. The reaction mixture was cooled to RT and acidified with concentrated HCl until the aq. layer turns acidic. The precipitated solid was filtered dried extensively to give the product of Step 1 (7.4 g, 76%) as a white solid.

Step 2

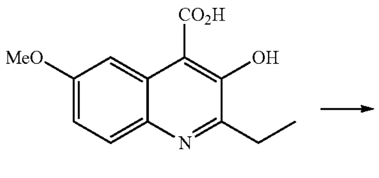

-continued

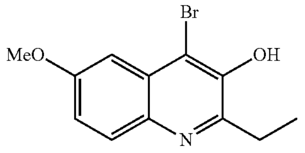

A solution of the product of Step 1 (6.08 g, 24.59 mmol) in THF (60 ml) was treated with NBS (4.38 g, 24.59 mmol) at RT and stirred for 1 h. TLC with 45% EtOAc/Hexanes. The solvent was removed by evaporation, EtOAc was added, and the resulting solution was washed with water and brine, and the solvent was removed to give 5.99 g crude brown solid. After TLC with 25% EtOAc/Hexanes, the crude solid was purified on Analogix with 120 g RediSep column eluting with 0-60% EtOAc/Hexanes. 4.93 g of the product of Step 2 (71%) was isolated as light brown solid.

Step 3

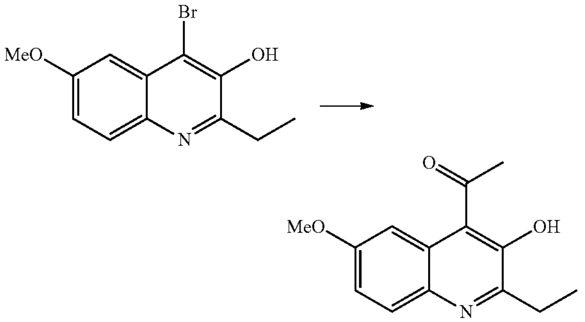

A solution of the product of Step 2 (4.92 g, 17.44 mmol) in dioxane (98 ml) was treated with tributyl(1-ethoxyvinyl)tin (11.78 ml, 34.9 mmol), $Pd(PPh_3)_2Cl_2$ (1.224 g, 1.744 mmol) and heated in an oil bath at 115° C. under $N_2$ atmosphere for 3 h. The reaction mixture was cooled and treated with aq. HCl (1M, 100 ml) and stirred at RT for 1 h. The reaction mixture was made basic with 125 ml sat. $NaHCO_3$ and extracted into EtOAc. After TLC with 5% EtOAc/DCM, the crude solid was purified on Analogix with 220 g redisep column eluting with 0-15% EtOAC/DCM. 3.69 g of the product of Step 3 (86%) was isolated as pale greenish yellow solid.

Step 4

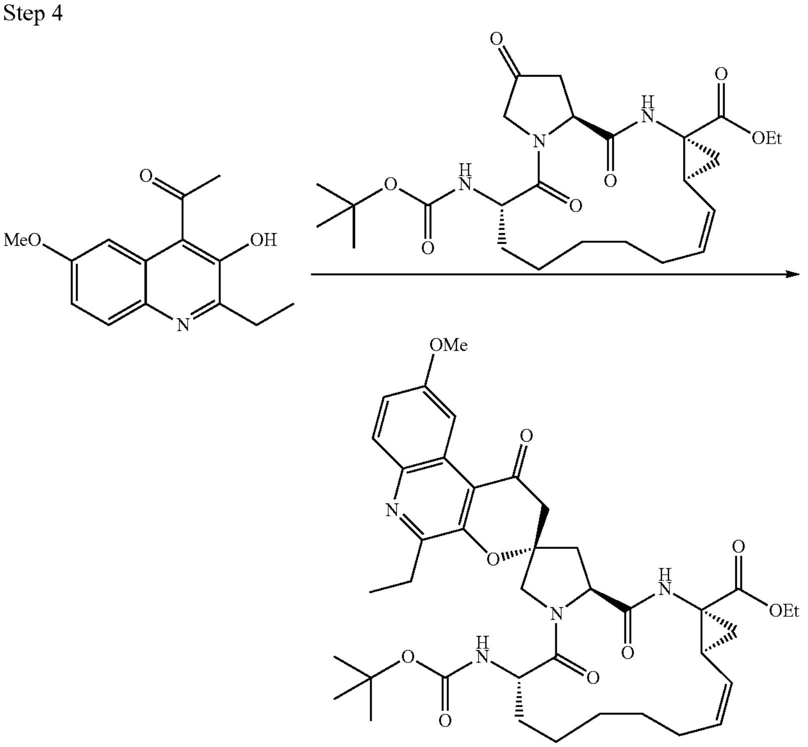

A reaction tube was charged with benzoic acid (149 mg, 1.221 mmol), the product of Step 3 (329 mg, 1.343 mmol) and molecular sieves (600 mg). The tube was sealed, and a solution of ethyl (6S,12Z,13aS,14aR,16aS)-6-[(tert-butoxycarbonyl)amino]-2,5,16-trioxo -1,2,3,6,7,8,9,10,11,13a,14,15,16,16a-tetradecahydrocyclopropa[e]pyrrolo[1,2-a][1,4]diazacyclopentadecine-14a(5H)-carboxylate (600 mg, 1.221 mmol) in MeOH (4882 μl) was added followed by addition of pyrrolidine (40.8 μl, 0.488 mmol). The mixture was stirred (oil bath at 55° C.) overnight. TLC (40% EtOAc in DCM) showed a small amount of starting material left. The mixture was diluted with DCM (50 ml), and the solids were removed by filtration. The filtrate was concentrated in a ROTAVAP, and the residue was dissolved in EtOAc (100 ml). The organic layer was washed with half-saturated $NaHCO_3$ (20 ml), and brine (20 ml), dried over $MgSO_4$, filtered and concentrated in a ROTAVAP. The residue was purified on a gold cap REDISEP (120 g) silica gel column (gradient: 0-40% EtOAc in DCM) to give the product of Step 4 (470 mg, 0.654 mmol, 53.6% yield) as a white powder.

Step 5

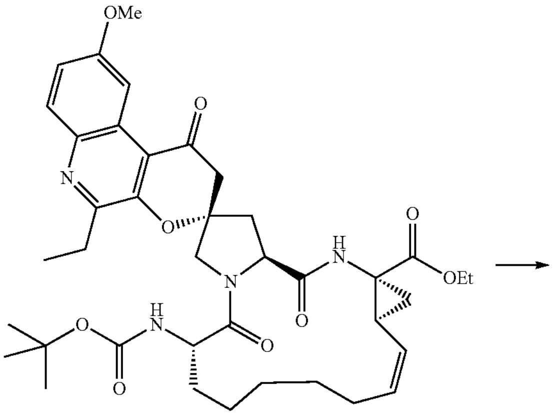

-continued

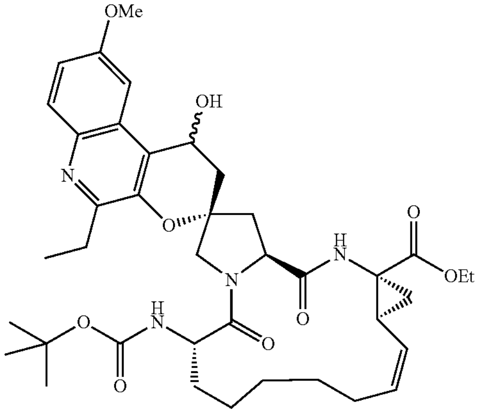

A RB flask was charged with a solution of the product of Step 4 (450 mg, 0.626 mmol) in dry THF (4695 μl) and MeOH (1565 μl). The mixture was cooled in ice-water bath and treated with $NaBH_4$ (26.1 mg, 0.689 mmol). After 30 min, TLC showed complete reaction. The reaction was quenched at 0° C. by addition of aq. sat. $NH_4Cl$ (5 ml) and stirred for 15 min. The mixture was diluted with EtOAc (50 ml) and water (5 ml). Upon separation, the organic layer was washed with aq. half-sat. $NaHCO_3$ (10 ml), and brine (10 ml), dried over $MgSO_4$, filtered and concentrated in a ROTAVAP to give the crude product of Step 5 (455 mg, 0.631 mmol, 101% yield) as a white powder. The crude was used as it is.

Step 6

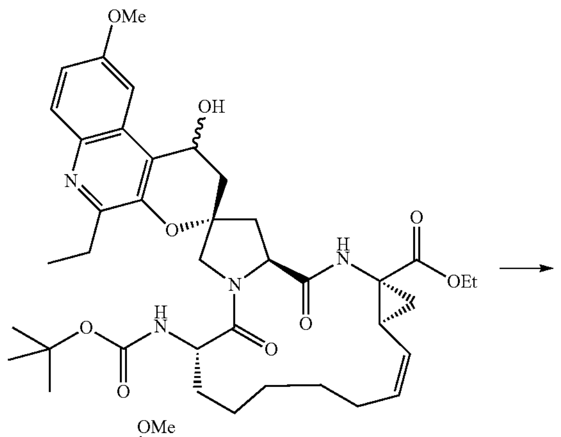

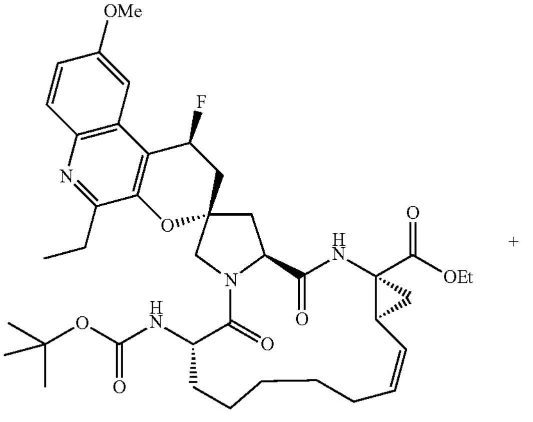

36-6A

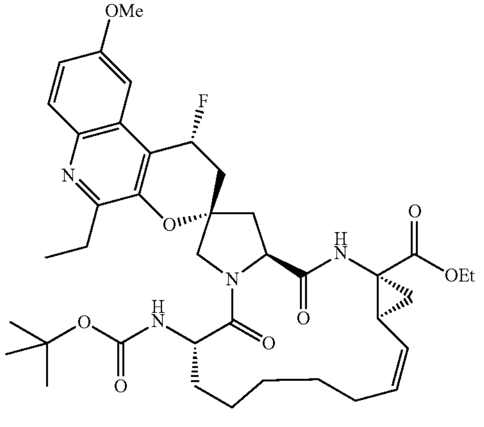

36-6B

A RB flask was charged with a solution of diastereomeric alcohol products of Step 5 (360 mg, 0.499 mmol) in dry DCM (9988 μl). The solution was cooled in ice-water bath and treated with DeoxoFluor (184 μl, 0.999 mmol). LC-MS and TLC showed no starting material after 1 h. The reaction was quenched by careful addition of aq. sat. $NaHCO_3$ (15 ml). The product was extracted into EtOAc (50 ml). The organic layer was dried over $MgSO_4$, filtered and concentrated in a rotavap. The residue was purified on a gold cap Redisep (40 g) silica gel column (gradient: 0 to 60% EtOAc in DCM) to give the corresponding diastereomeric products. 36-6B less polar (110 mg, 0.152 mmol, 30.5% yield); 36-6A more polar (140 mg, 0.194 mmol, 38.8% yield).

Step 7

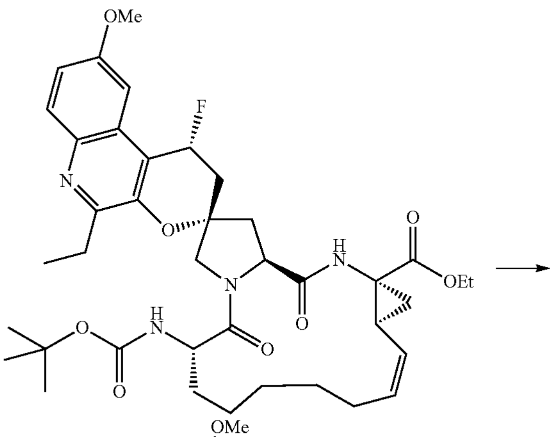

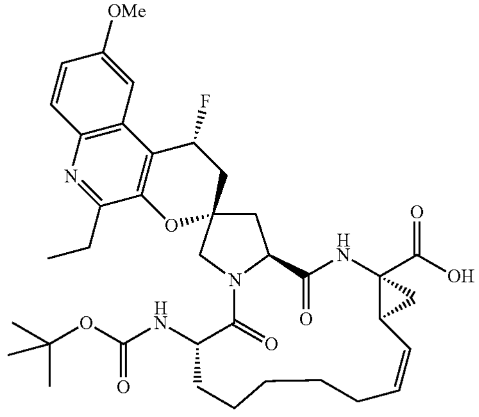

A RB flask was charged with ethyl ester 36-6B (140 mg, 0.194 mmol) and $LiOH.H_2O$ (40.6 mg, 0.968 mmol). THF (3 ml), MeOH (1 ml) and water (1 ml) were added, and the mixture was heated (oil bath at 40° C.) and monitored by LC-MS. After 4 h, the reaction was quenched by addition of aq. 0.5M HCl (10 ml). The product was extracted into EtOAc (2×20 ml). The combined organic layers were washed with brine (5 ml), dried over $MgSO_4$, filtered and concentrated in a rotavap to give the crude product of Step 7 (133 mg, 0.191 mmol, 99% yield) as a white powder. The product was azeotropically dried with toluene (3×5 ml) and used without further purification.

Step 8

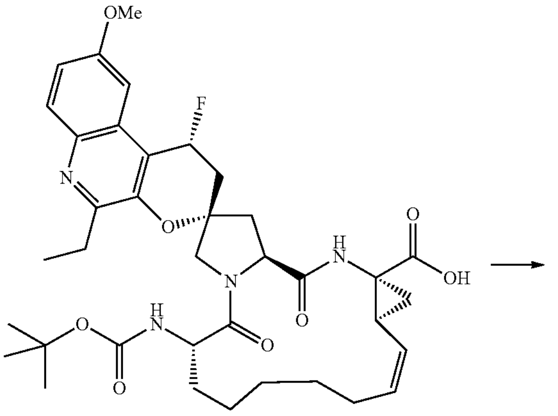

-continued

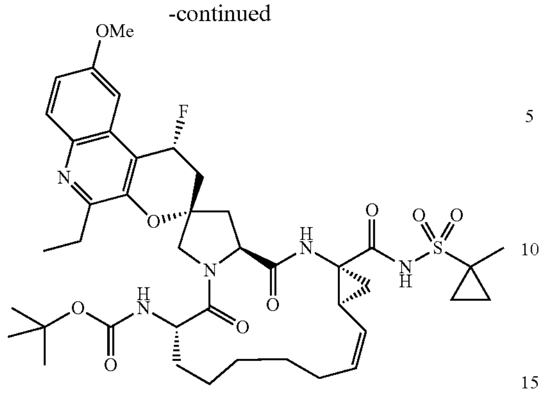

A reaction tube was charged with CDI (56.0 mg, 0.345 mmol) and sealed. A solution of carboxylic acid product of Step 7 (120 mg, 0.173 mmol) in dry THF (1727 μl) was added by syringe. The tube was heated (oil bath at 75° C.) for 3 h. After cooling to RT, a solution of 1-methylcyclopropane-1-sulfonamide (70.0 mg, 0.518 mmol) in dry THF (1 ml) and DBU (77 μl, 0.518 mmol) were successively added. The tube was heated (oil bath at 55° C.) overnight. LC-MS showed very little starting material left. The mixture was diluted with EtOAc (20 ml) and washed with aq. sat. $NH_4Cl$ (2×5 ml) and brine (5 ml), dried over $MgSO_4$, filtered and concentrated in a ROTAVAP. The residue was purified on a gold cap REDISEP (24 g) silica gel column (gradient: 0 to 40% acetone in hexanes) to give the product of Step 8 (94 mg, 0.116 mmol, 67.0% yield) as a white powder.

Step 9

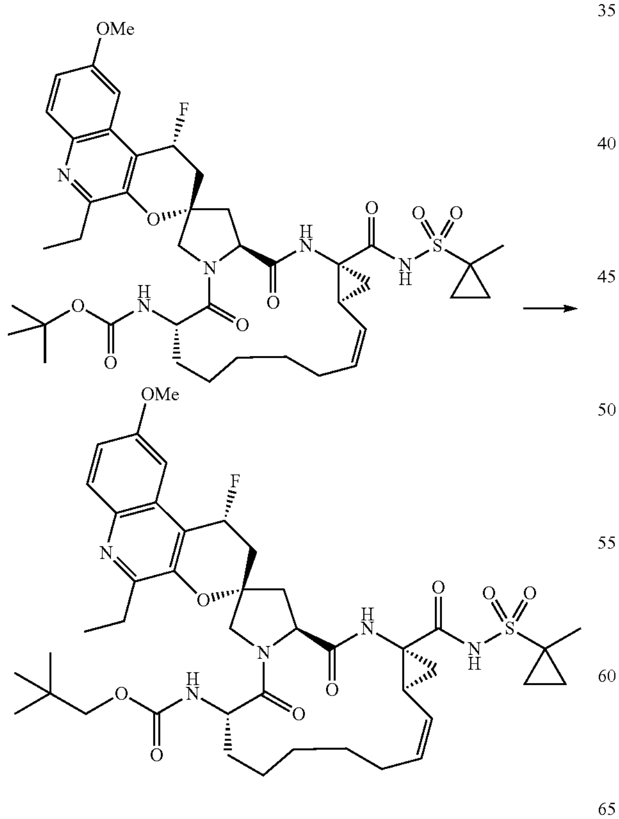

The N-Boc protected product of Step 8 (87 mg, 0.107 mmol) was dissolved in 4M solution in dioxane of HCl (5 ml, 20.00 mmol). The reaction mixture was stirred and monitored by LC-MS. After 2 h, there was no more starting material left. The mixture was concentrated to dryness to give the crude amine hydrochloride (81 mg, 0.108 mmol, 101% yield) as a white powder. No further purification was carried out.

A RB flask was charged with a solution of amine hydrochloride (80 mg, 0.107 mmol) in dry DCM (2 ml) and cooled in an ice-water bath followed by addition of neopentyl chloroformate (0.032 ml, 0.214 mmol) and DIPEA (0.074 ml, 0.428 mmol). The mixture was stirred and monitored by LC-MS. After 2 h, no more starting material was left. The solution was purified on a gold cap REDISEP (12 g) silica gel column (gradient: 0 to 40% acetone in hexanes) to give I-36 (75 mg, 0.091 mmol, 85% yield) as a white powder.

Example 37 tert-butyl ((2R,6S,13aS,14aR,16aS,Z)-5'-(hydroxymethyl)-14a-(((1-methyl cyclopropyl)sulfonyl)carbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-37)

Step 1

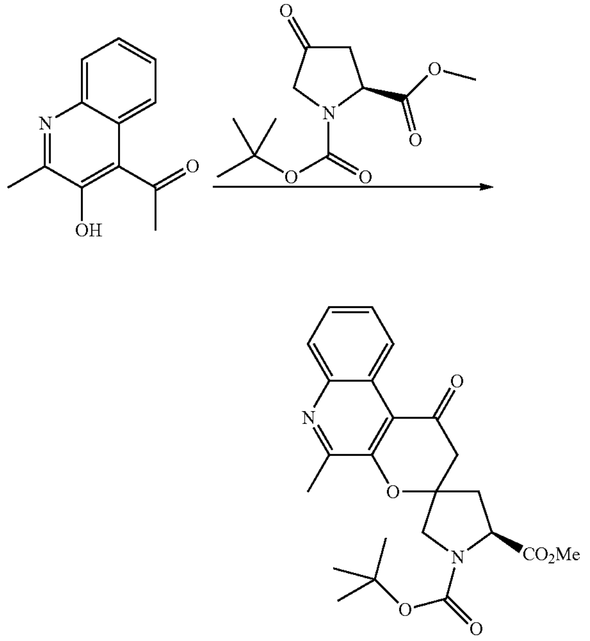

N-Boc-4-oxo-L-proline methyl ester (1209 mg, 4.97 mmol) and 1-(3-hydroxy-2-methylquinolin-4-yl)ethanone (500 mg, 2.485 mmol)dissolved in MeOH (4970 μl), pyrrolidine (82 μl, 0.994 mmol), 3A sieves were added, and the mixture was heated at 105° C. in the microwave for 35 min at very high absorbance. The mixture was cooled to RT and concentrated. The residue was purified by column chromatography on silica gel, eluting with EtOAc/hexane to give the product of Step 1 (1.07 g, 75% yield) as a yellow oil.

Step 2

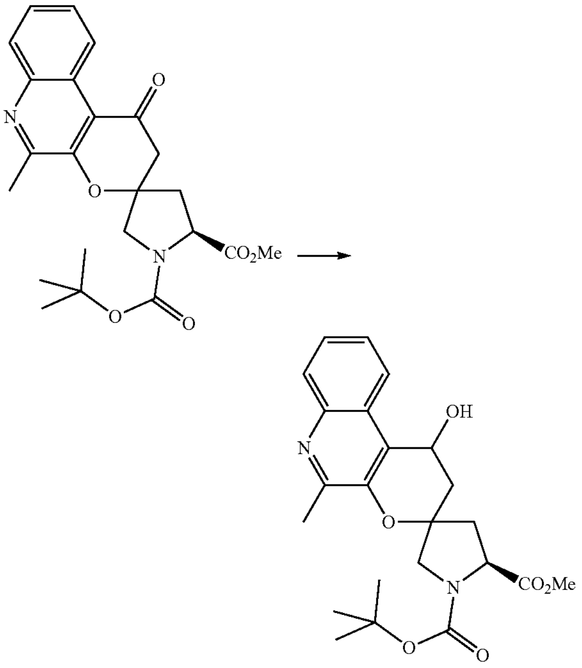

The product of Step 1 (800 mg, 1.876 mmol) was dissolved in MeOH (9379 μl)/THF (9379 μl), cooled to 0° C., $NaBH_4$ (71.0 mg, 1.876 mmol) was added, and the mixture stirred for 15 min. The mixture was concentrated, the residue dissolved in EtOAc (100 ml), and the mixture was washed with aq. $NH_4Cl$ (sat., 3×30 mL), dried ($MgSO_4$), filtered, and the solvent was evaporated under reduced pressure to give the product of Step 2 (700 mg, 1.634 mmol, 87% yield).

Step 3

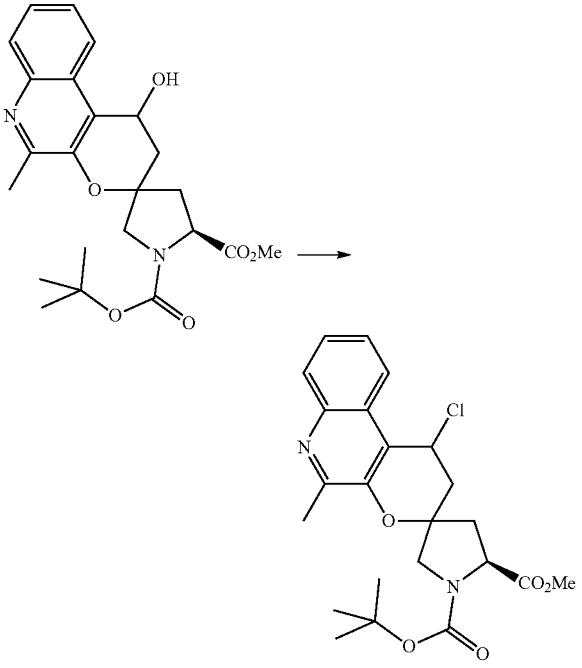

The product of Step 2 (700 mg, 1.634 mmol) was dissolved in DCM (10.900 ml), TEA (0.911 ml, 6.53 mmol), then MsCl (0.255 ml, 3.27 mmol) were added. The mixture was stirred overnight. EtOAc (100 ml) was added, and the mixture was washed with aq. $NH_4Cl$ (sat., 2×50 mL), dried ($MgSO_4$), filtered, and the solvent was evaporated under reduced pressure to give the product of Step 3 (730 mg, 1.633 mmol, 100% yield) as a yellow oil.

Step 4

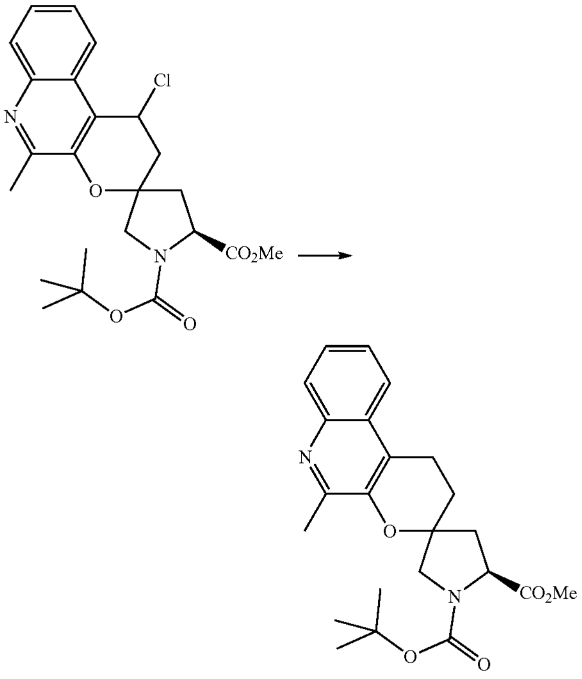

The product of Step 3 (730 mg, 1.633 mmol) was dissolved in EtOAc (16.300 ml), 10% Pd/C (174 mg, 0.163 mmol) was added, and the mixture put under $H_2$ atmosphere (1 atm) and stirred for 1 h. The solid was removed by filtration, additional EtOAc (100 ml) was added to the filtrate, and the mixture was washed with aq. $NaHCO_3$ (sat., 2×50 mL), dried ($MgSO_4$), filtered, and the solvent was evaporated under reduced pressure. The residue was purified by column chromatography on silica gel, eluting with EtOAc/hexane to give the product of Step 4 (510 mg, 1.236 mmol, 76% yield) as a colorless foam.

Step 5

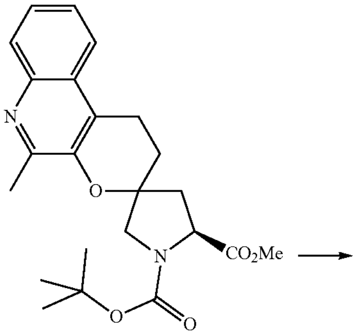

-continued

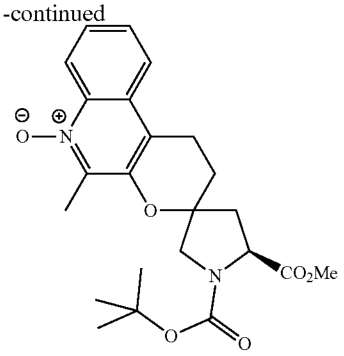

The product of Step 4 (100 mg, 0.242 mmol) was dissolved in chloroform (1.212 mL), mCPBA (109 mg, 0.485 mmol) was added, and the mixture stirred overnight. EtOAc (50 ml) was added, and the mixture was washed with aq. $NaHCO_3$ (sat., 3×30 mL), dried ($MgSO_4$), filtered, and the solvent was evaporated under reduced pressure to give the product of Step 5 (used crude in next step).

Step 6

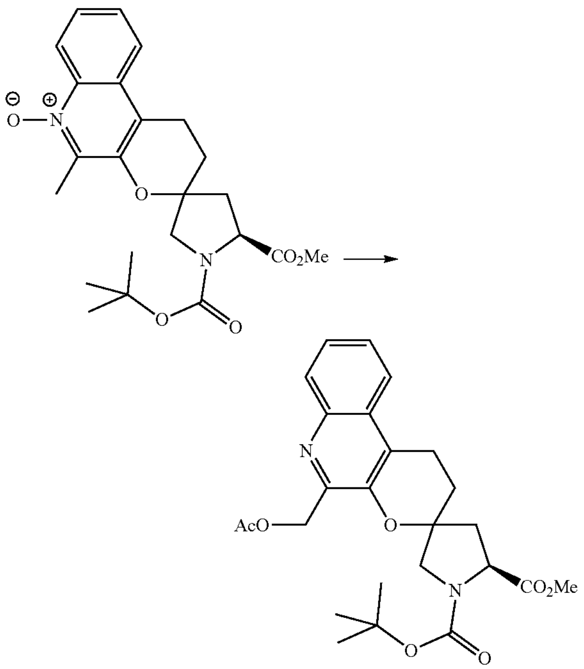

The product of Step 5 (100 mg, 0.233 mmol) was dissolved in acetic anhydride (2202 μl, 23.34 mmol) heated at 80° C. for 2 h, the mixture was then concentrated. The residue was dissolved in EtOAc, washed with $NaHCO_3$ (sat.), dried ($MgSO_4$), and concentrated under reduced pressure. The residue was purified by column chromatography on silica gel, eluting with EtOAc/hexane to give the product of Step 6 (80 mg, 0.170 mmol, 72.9% yield) as colorless oil.

Step 7

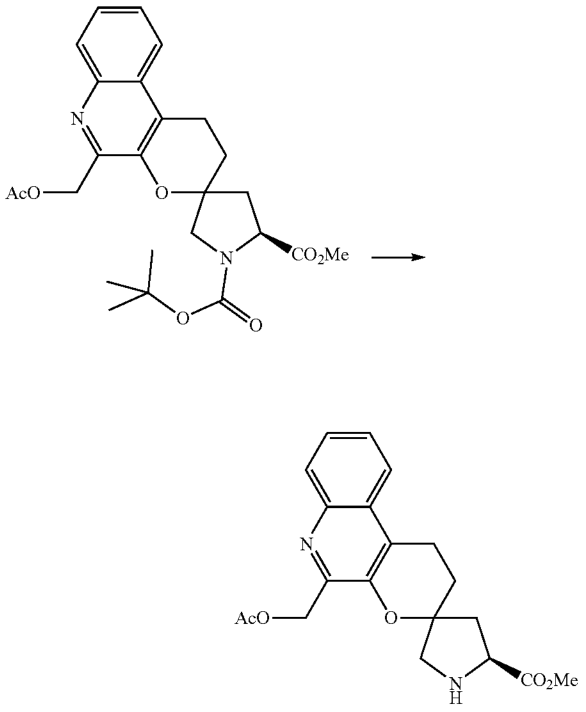

The product of Step 6 (80 mg, 0.170 mmol) was dissolved in HCl in dioxane (2125μl, 8.50 mmol), stirred for 1 h. The mixture was concentrated to give the product of Step 7 (used crude in the next step).

Step 8

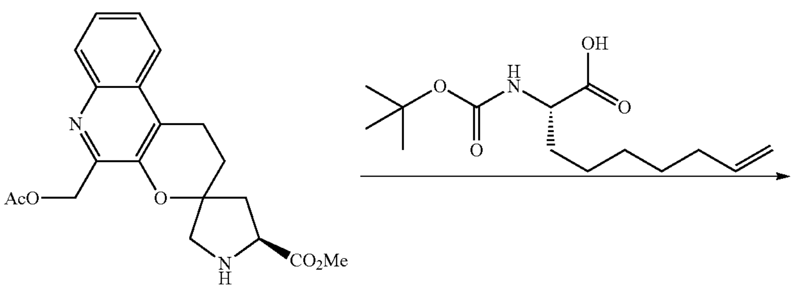

-continued

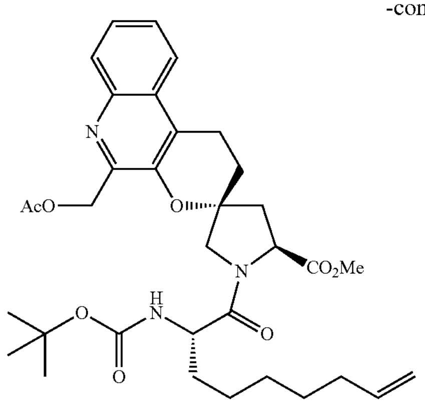

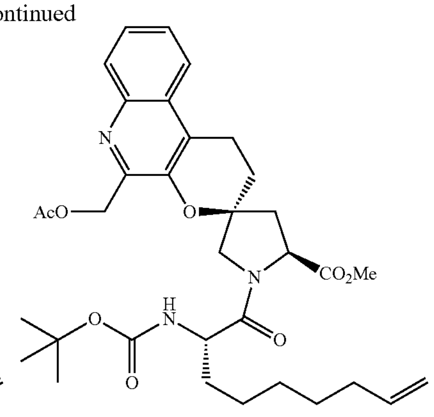

The product of Step 7 (154 mg, 0.340 mmol) was dissolved in DMF (1701 μl), (S)-2-(tert-butoxycarbonylamino)non-8-enoic acid dicyclohexylamine salt (69.2 mg, 0.170 mmol), DIPEA (119 μl, 0.680 mmol), and HATU (129 mg, 0.340 mmol) were added, and the mixture stirred overnight. $Et_2O$ (100 ml) was added, and the mixture was washed with aq. $NH_4Cl$ (sat., 3×30 mL), dried ($MgSO_4$), filtered, and the solvent was evaporated under reduced pressure. The residue was purified by column chromatography on silica gel, eluting with EtOAc/hexane to give in order of elution; product 37-8A (41 mg, 0.066 mmol, 38.6% yield) and product 37-8B (15 mg, 0.024 mmol, 14.14% yield) as colorless oils.

Step 9

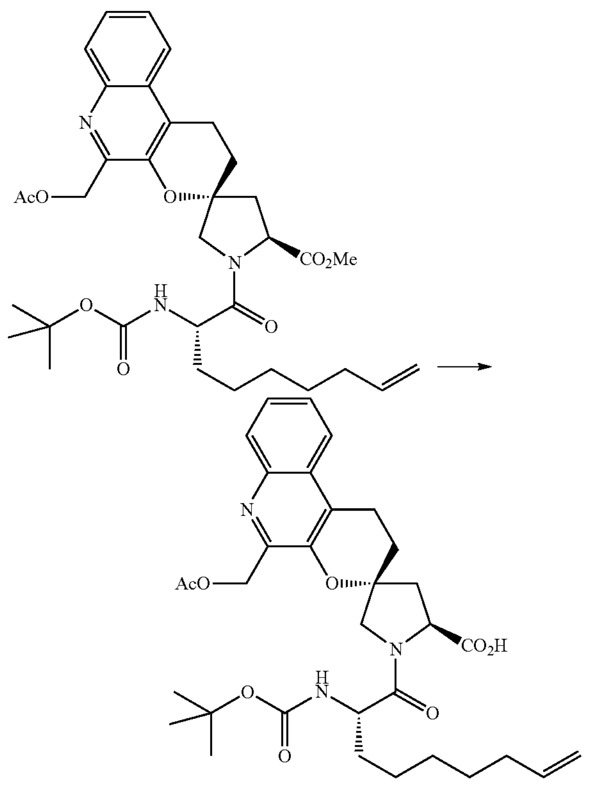

The product of Step 8, 37-8A, (41 mg, 0.066 mmol) was dissolved in THF (506 μl)/MeOH (506 μl), to this LiOH (164 μl, 0.329 mmol) was added, and the mixture heated at 60° C. for 1 h, the mixture was cooled to RT and acidified to pH 4, the mixture was extracted with EtOAc (2×10 mL). The combined organic fractions were dried ($MgSO_4$), filtered, and the solvent was evaporated under reduced pressure to give the product of Step 9 (36 mg, 0.063 mmol, 96% yield).

Step 10

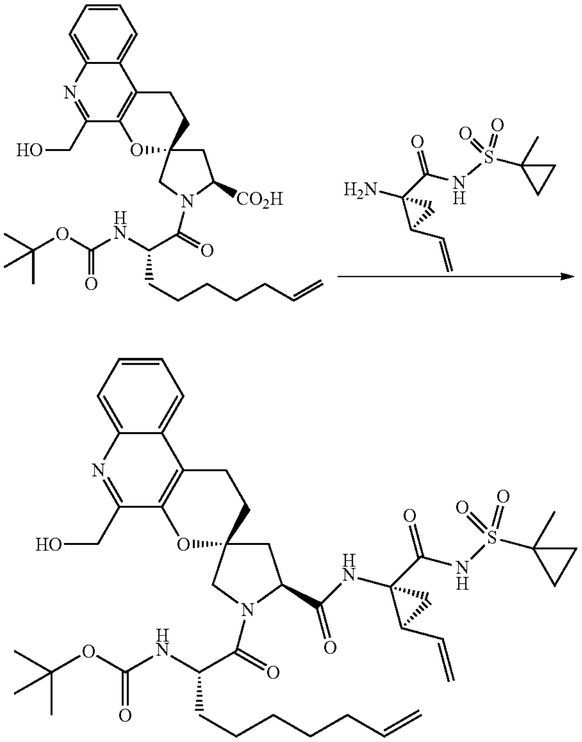

The product of Step 9 (36 mg, 0.063 mmol) was dissolved in DMF (2114 μl), (1R,2S)-1-amino-N-(1-methylcyclopropylsulfonyl)-2-vinylcyclopropanecarboxamide (46.5 mg, 0.190 mmol), DIPEA (22.15 μl, 0.127 mmol), and HATU (48.2 mg, 0.127 mmol) added, and the mixture stirred overnight. EtOAc (50 ml) was added, and the mixture was washed with aq. $NH_4Cl$ (sat., 2×25 mL), dried ($MgSO_4$), filtered, and the solvent was evaporated under reduced pressure. The crude product was purified by column chromatography on silica gel, eluting with EtOAc/hexane to give the product of Step 10 (23 mg, 0.029 mmol, 45.7% yield) as colorless oil.

Step 11

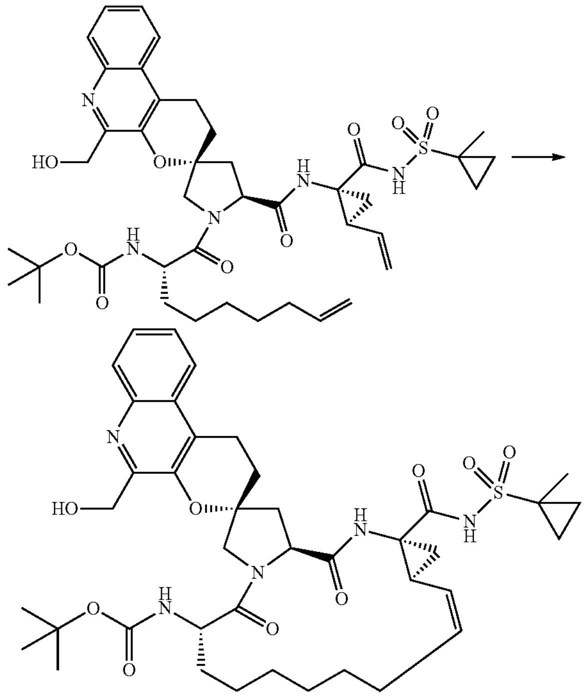

The product of Step 10 (23 mg, 0.029 mmol) was dissolved in DCE (14.500 ml), Zhan's catalyst (5.31 mg, 7.24 μmol) and 1,4-benzoquinone (0.939 mg, 8.69 μmol) were added, the mixture was heated at 65° C. for 2 h. The mixture was cooled to RT; butylvinylether was added, and, after 30 min, the mixture was concentrated under reduced pressure. The residue was purified by column chromatography on silica gel, eluting with EtOAc/hexane to give I-37 (10 mg, 0.013 mmol, 45.1% yield). $^1$H-NMR (400 MHz, $CDCl_3$) δ 8.01 (d, J=8.1 Hz, 1H), 7.81-7.76 (m, 1H), 7.66-7.60 (m, 1H), 7.60-7.52 (m, 2H), 6.95 (m, 1H), 6.02 (m, 1H), 5.83-5.68 (m, 3H), 5.43-5.32 (m, 2H), 5.03-5.49 (m, 5H), 4.75 (m, 1H), 4.62 (m, 1H), 4.47-4.42 (m, 1H), 4.12-4.04 (m, 1H), 3.78-3.62 (m, 4H), 3.19-3.13 (m, 2H), 2.6-0.8 muliplets comprising remaining peaks. MS: m/e=766.2 (100) (MH+).

Example 38 tert-butyl ((2R,6S,13aS,14aR,16aS,Z)-14a-(((1-methylcyclopropyl)sulfonyl) carbamoyl)-5'-(morpholinomethyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-38)

Step 1

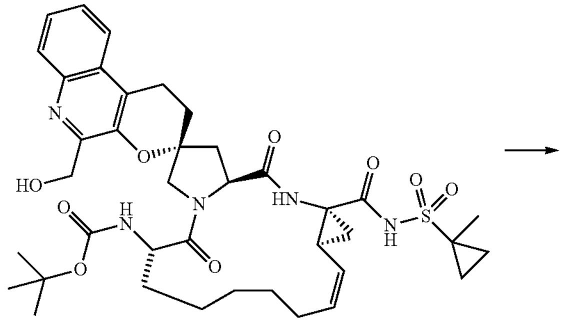

-continued

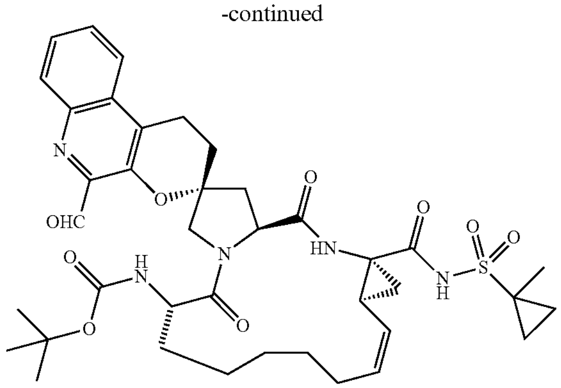

I-37 (80 mg, 0.104 mmol) was dissolved in DCM (1045 μl) cooled to 0° C., $NaHCO_3$ (8.77 mg, 0.104 mmol) then Dess-Martin periodinane (89 mg, 0.209 mmol) were added. The mixture was stirred for 1 h, aq. $NaHCO_3$ (20 ml) was added, and the mixture was extracted with EtOAc (3×20 mL). The combined organic fractions were dried ($MgSO_4$), filtered and the solvent was evaporated under reduced pressure. The residue was purified by column chromatography on silica gel, eluting with EtOAc/hexane to give the product of Step 1 (30 mg, 0.039 mmol, 37.6% yield) as yellow oil.

Step 2

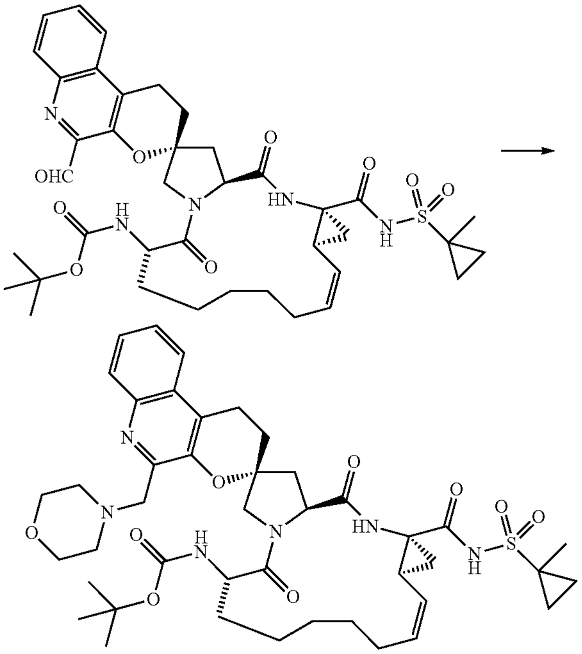

The product of Step 1 (30 mg, 0.039 mmol) was dissolved in DCE (785 μl), morpholine (13.69 μl, 0.157 mmol) was added, and the mixture was cooled to 0° C. Sodium triacetoxyborohydride (33.3 mg, 0.157 mmol) was added, and the mixture was stirred overnight. Aq. $NaHCO_3$ (20 ml) was added, and the mixture was extracted with EtOAc (3×20 mL). The combined organic fractions were dried ($MgSO_4$), filtered, and the solvent was evaporated under reduced pressure. The residue was purified by column chromatography on silica gel, eluting with EtOAc/MeOH to give I-38 (5 mg, 5.99 μmol, 15.25% yield) as colorless solid. $^1$H-NMR (400 MHz, $CDCl_3$) δ 8.03 (d, J=9.3 Hz, 1H), 7.8-7.76 (m, 1H), 7.58-7.51 (m, 2H), 6.73 (m, 1H), 5.72 (q, j+10.5 hz, 1H), 5.07-4.97 (m, 2H), 4.76 (m, 1H), 4.40 (d, J=10.9 Hz, 1H), 4.25 (m, 1H), 3.90 ((d, J=13.1 Hz, 1H), 3.76-3.59 (m, 7H), 3.54 (d, J=12.5 Hz, 1H), 3.49-3.44 (m, 3H), 3.17 (m, 2H), 2.61-2.24 and 1.6-0.8 muliplets comprising remaining peaks. MS: m/e=835 (100) (MH+).

Example 39 tert-Butyl ((2R,6S,13aS,14aR,16aS,Z)-9'-chloro-5'-methyl-14a-(((1-methyl cyclopropyl)sulfonyl)carbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quuinolin]-6-yl)carbamate (I-39)

Step 1

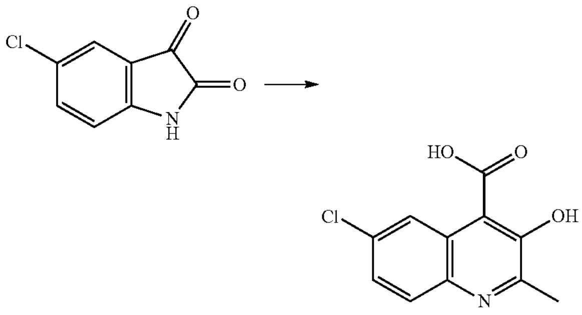

5-Chloroisatin (25 g, 138 mmol) was suspended in water (344 ml), $Ca(OH)_2$ (30.6 g, 413 mmol) was added, and the mixture heated at 80° C. for 1 h. Chloroacetone (27.4 ml, 344 mmol) was added slowly, and the mixture stirred at 80° C. for 1.5 h. The mixture was cooled to 0° C., AcOH (47.3 ml, 826 mmol) added, and the resulting solid collected by filtration, washing with water (2×200 ml), to give the product of Step 1 (32 g, 135 mmol, 98% yield) as yellow solid.

Step 2

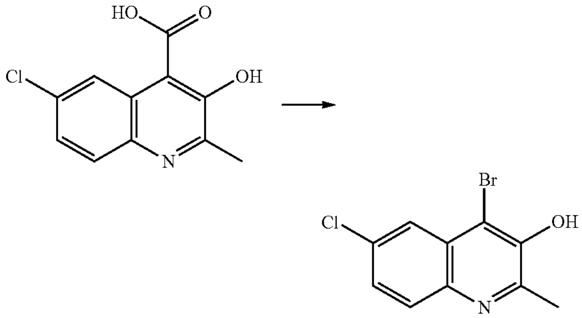

The product of Step 1 (5 g, 21.04 mmol) was suspended in THF (105 ml), NBS (3.74 g, 21.04 mmol) was added, and the mixture stirred for 30 min. The mixture was concentrated under reduced pressure. The residue was triturated with DCM (100 ml), and the solid collected by filtration to give the product of Step 2 (3.682 g, 13.51 mmol, 64.2% yield).

Step 3

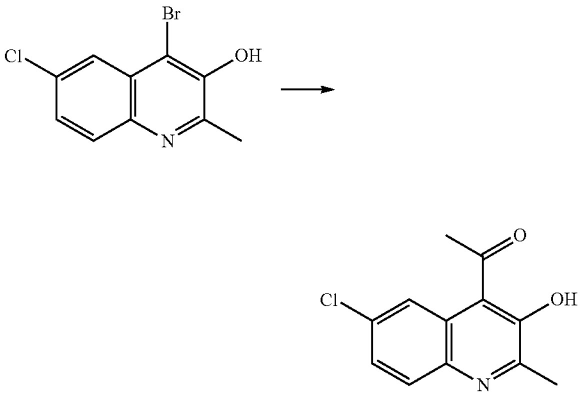

The product of Step 2 (3.682 g, 13.51 mmol) was dissolved in dioxane (54.0 ml), tributyl(1-ethoxyvinyl)tin (9.12 ml, 27.0 mmol) and $Pd(PPh_3)_4$ (0.781 g, 0.676 mmol) added, and the mixture was heated at 107° C. in a sealed tube overnight. After cooling to RT, 1N HCl (54 ml) was added, and the mixture stirred for 30 min. Aq. $NaHCO_3$ was added, and the mixture was extracted with EtOAc (6×150 mL). The combined organic fractions were dried ($MgSO_4$), filtered, and the solvent was evaporated under reduced pressure. The residue was purified by column chromatography on silica gel, eluting with EtOAc/hexane to give the product of Step 3 (2.38 g, 10.10 mmol, 74.7% yield) as a yellow solid.

Step 4

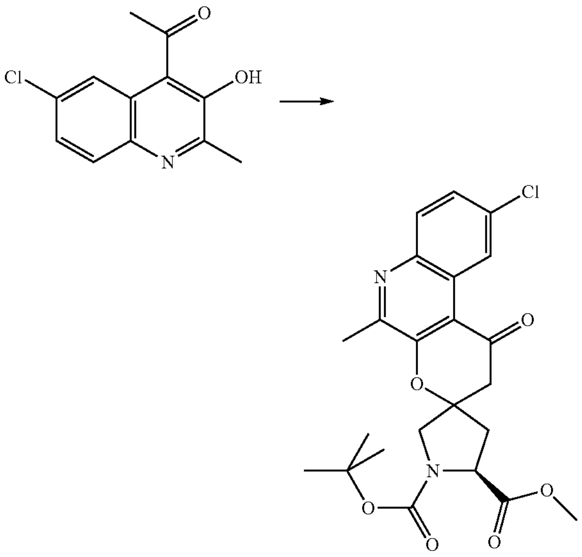

The product of Step 3 (2.38 g, 10.10 mmol) was dissolved in MeOH (67.3 ml), N -Boc-4-oxo-L-proline methyl ester (4.91 g, 20.20 mmol) then pyrrolidine (0.334 ml, 4.04 mmol) was added. The mixture was heated at 105° C. for 1 h. The mixture was cooled to RT and dry-loaded onto silica gel. The residue was purified by column chromatography on silica gel, eluting with EtOAc/hexane to give the product of Step 4 (3.78 g, 8.20 mmol, 81% yield) as a yellow solid.

Step 5

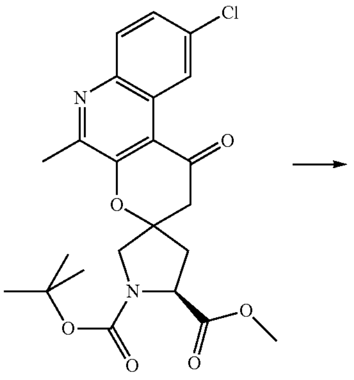

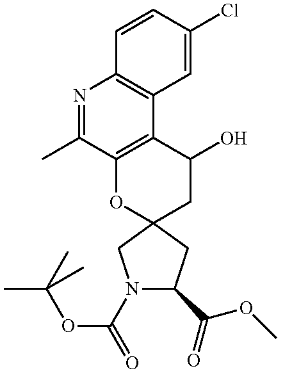

The product of Step 4 (3.78 g, 8.20 mmol) was dissolved in THF (27.3 ml)/MeOH (27.3 ml) and cooled to 0° C. $NaBH_4$ (0.310 g, 8.20 mmol) was added, and the mixture was stirred for 30 min. The mixture was concentrated under reduced pressure, and dissolved in EtOAc/$NaHCO_3$ (sat., 300 ml each). The aqueous layer was extracted with EtOAc (300 ml). The combined organic layers were dried ($MgSO_4$), filtered, and the solvent was evaporated under reduced pressure to give the product of Step 5 (3.8 g, 8.21 mmol, 100% yield), used crude in next step.

Step 6

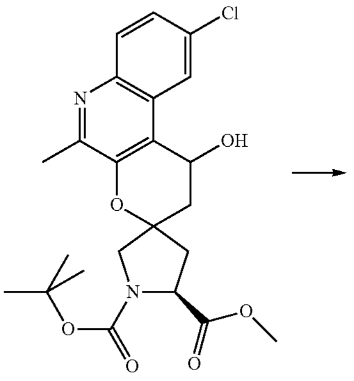

-continued

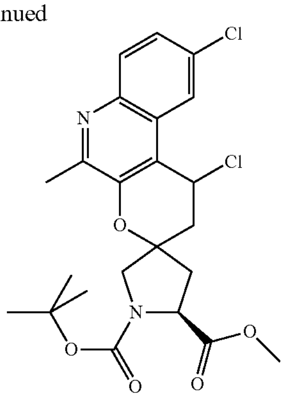

The product of Step 5 (3.8 g, 8.21 mmol) was dissolved in DCM (54.7 ml), cooled to 0° C., TEA (4.58 ml, 32.8 mmol) then MsCl (1.279 ml, 16.42 mmol) were added, and the mixture stirred overnight. DCM (200 ml) was added, and the mixture was washed with aq. $NH_4Cl$ (sat., 2×100 mL), dried ($MgSO_4$), filtered, and the solvent was evaporated under reduced pressure. The residue was purified by column chromatography on silica gel eluting with EtOAc/hexane to give the product of Step 6 (3.22 g, 6.69 mmol, 81% yield) as yellow foam.

Step 7

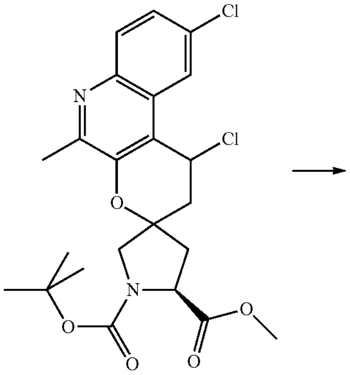

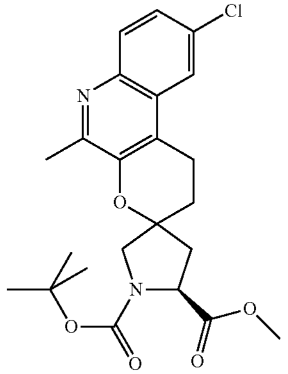

The product of Step 6 (1.56 g, 3.24 mmol) was dissolved in EtOAc (32.4 ml), 10% Pd/C (0.345 g, 0.324 mmol) was added, and the mixture was stirred under 1 atm of $H_2$ for 25 min. The catalyst removed by filtration (washing with MeOH), and the filtrates were concentrated under reduced pressure to give the product of Step 7 (1.45 g, 3.24 mmol, 100% yield).

Step 8
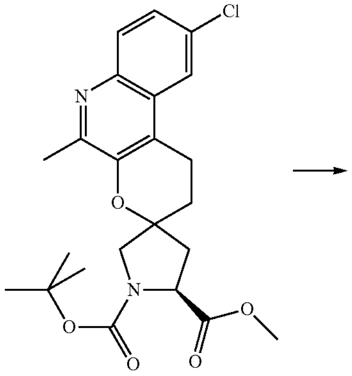
-continued
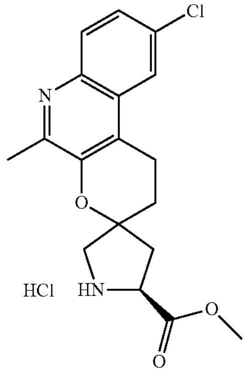
The product of Step 7 (2.91 g, 6.51 mmol) was dissolved in HCl (4M in dioxane) (65.1 ml, 260 mmol) and stirred for 2 h. The mixture was concentrated under reduced pressure to give the product of Step 8 (2.258 g, 6.51 mmol, 100% yield).
Step 9
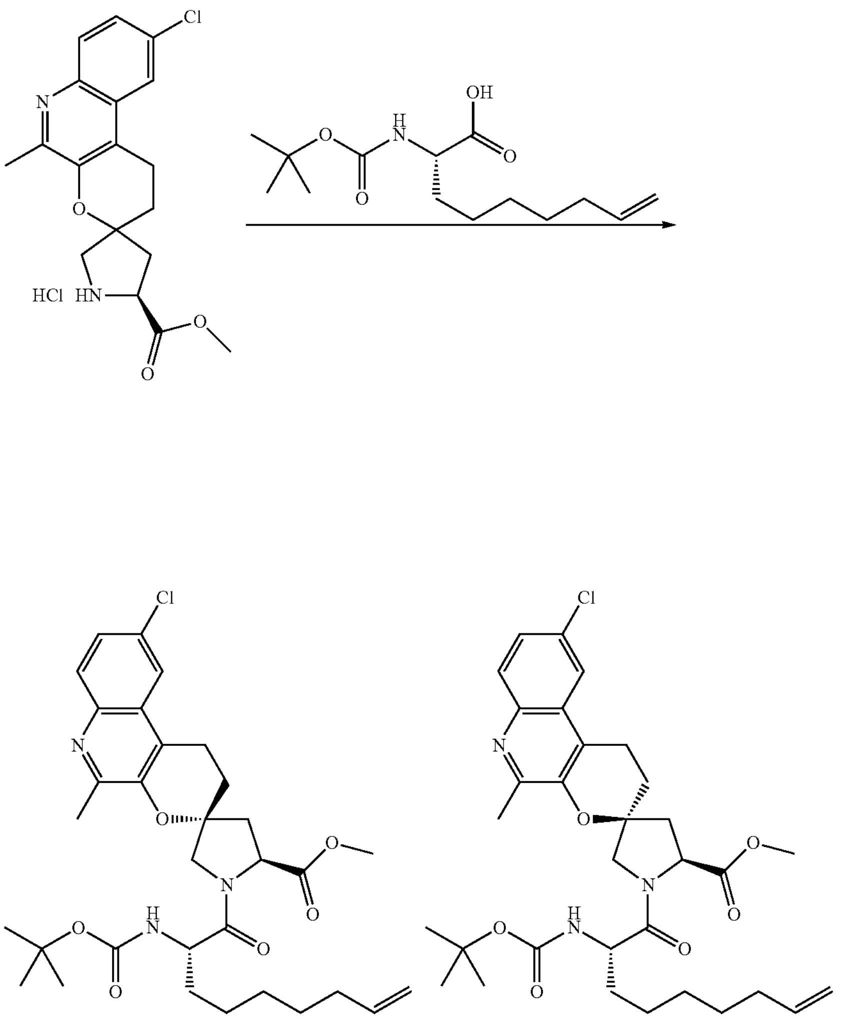
39-9A 39-9B The product of Step 8 (2.258 g, 6.51 mmol) was dissolved in DMF (65.1 ml), (S)-2-((tert-butoxycarbonyl)amino)non-8-enoic acid dicyclohexylamine salt (4.42 g, 9.77 mmol), DIPEA (5.69 ml, 32.6 mmol) and HATU (3.71 g, 9.77 mmol) added, stirred overnight. EtOAc (500 ml) was added, and the mixture was washed with aq. $NH_4Cl$ (sat., 2×200 mL), dried ($MgSO_4$), filtered, and the solvent was evaporated under reduced pressure. The residue was dissolved in ether (400 ml), washed with water (200 ml), dried ($MgSO_4$), and concentrated under reduced pressure. The residue was purified by column chromatography on silica gel, eluting with EtOAc/hexane to give (after re-chromatography of mixed fractions) compound 39-9A (1.4 g, 2.333 mmol, 35.8% yield) and compound 39-9B (0.8 g, 1.333 mmol, 20.47% yield) in order of elution as yellow oils.

Step 10

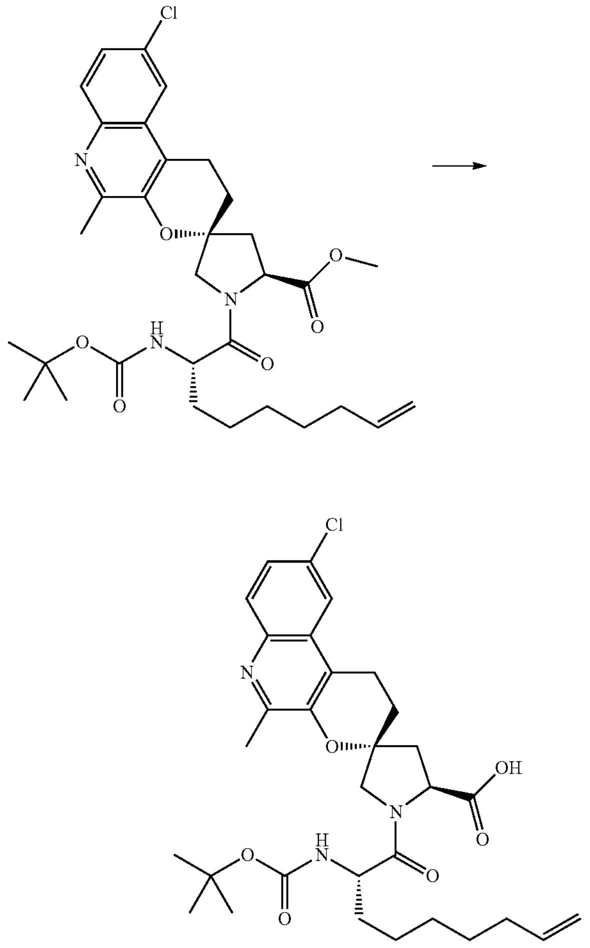

Compound 39-9A (1.4 g, 2.333 mmol) was dissolved in THF (7.78 ml)/MeOH (7.78 ml), LiOH (5.83 ml, 11.66 mmol) was added, and the mixture heated at 60° C. for 30 min. The mixture was cooled to RT, water (50 ml) was added, and the mixture acidified to pH=5 with 1N HCl, the mixture was extracted with EtOAc (2×100 mL). The combined organic fractions were washed with water (1×50 mL), dried ($MgSO_4$), filtered, and the solvent was evaporated under reduced pressure to give the product of Step 10 (1.367 g, 2.332 mmol, 100% yield).

Step 11

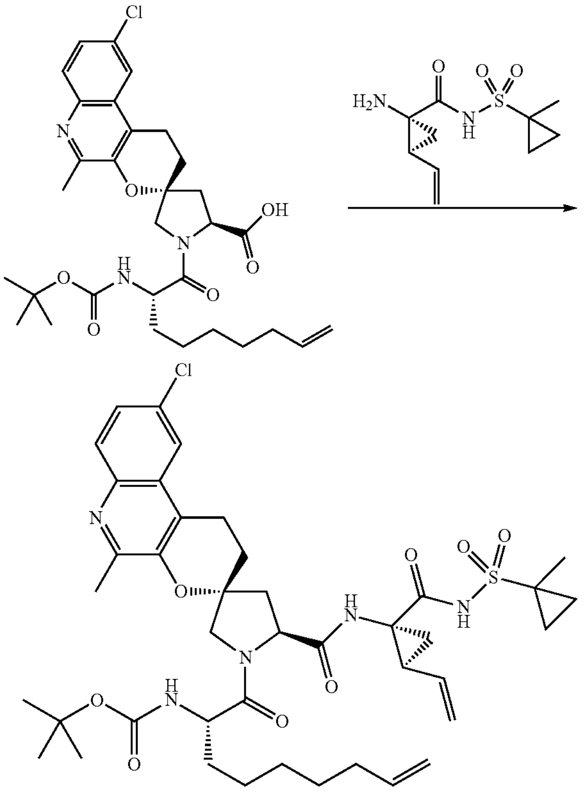

The product of Step 10 (1.367 g, 2.332 mmol) was dissolved in DMF (23.32 ml), (1R,2S)-1-amino-N-(1-methylcyclopropylsulfonyl)-2-vinylcyclopropanecarboxamide (0.855 g, 3.50 mmol), DIPEA (0.815 ml, 4.66 mmol), and HATU (1.330 g, 3.50 mmol) added, stirred overnight. Aq. $NH_4Cl$ (50 ml) was added, and the mixture was extracted with $Et_2O$ (3×50 mL). The combined organic fractions were washed with water (1×50 mL), dried ($MgSO_4$), filtered, and the solvent was evaporated under reduced pressure. The crude product was purified by column chromatography on silica gel, eluting with EtOAc/hexane to give the product of Step 11 (1.337 g, 1.646 mmol, 70.6% yield) as colorless foam.

Step 12

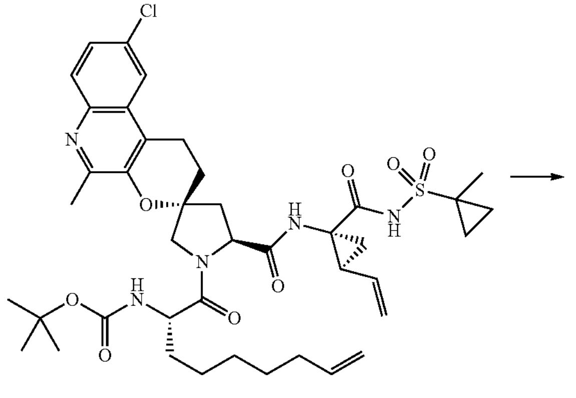

-continued

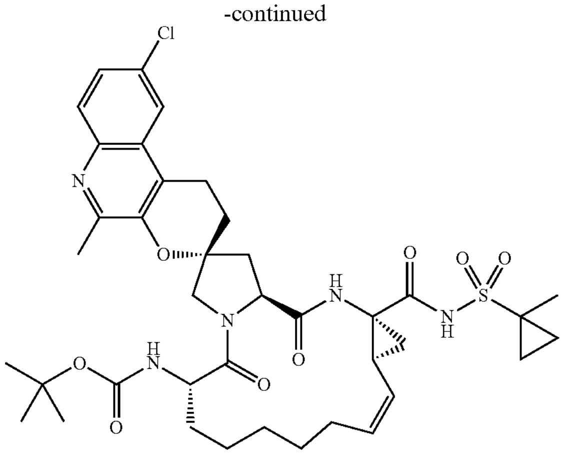

The product of Step 11 (700 mg, 0.862 mmol) was dissolved in DCE (359.00 mL), Zhan's catalyst (158 mg, 0.215 mmol) and 1,4-benzoquinone (27.9 mg, 0.258 mmol) added, and the mixture was heated at 75° C. for 30 min, when TLC showed complete conversion. The mixture was cooled to RT, butyl vinyl ether was added, and the mixture stirred for 30 min, the mixture was then concentrated under reduced pressure. The residue was purified by column chromatography on silica gel, eluting with EtOAc/hexane to give I-39 (484 mg, 0.617 mmol, 71.6% yield) as orange foam. $^{1}$H-NMR (400 MHz, $CDCl_3$) δ 10.06 (m, 1H), 7.86 (d, J=8.8 Hz, 1H), 7.72 (m, 1H), 7.47-7.44 (m, 1H), 6.68 (m, 1H), 5.72 (q, J=10.4 Hz, 1H), 5.29 (m, 3H), 5.01 (t, J=8.33, 1H), 4.94 (d, J=7.3 Hz, 1H), 4.62 (t, J=8.9 Hz, 1H), 4.46 (d, J=11.7 Hz, 1H), 4.17-4.08 (1H, m), 3.68 (d, J=10.6 Hz, 1H), 3.13-3.03 (m, 2H), 1.93 (m, 1H), 1.87-1.73 (m, 3H), 2.61-2.24 and 1.6-0.8 muliplets comprising remaining peaks. MS: m/e=784.2 (100) (MH+).

Example 40

Neopentyl((2R,6S,13aS,14aR,16aS,Z)-9'-chloro-5'-methyl-14a-(((1-methyl cyclopropyl)sulfonyl)carbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-40)

Step 1

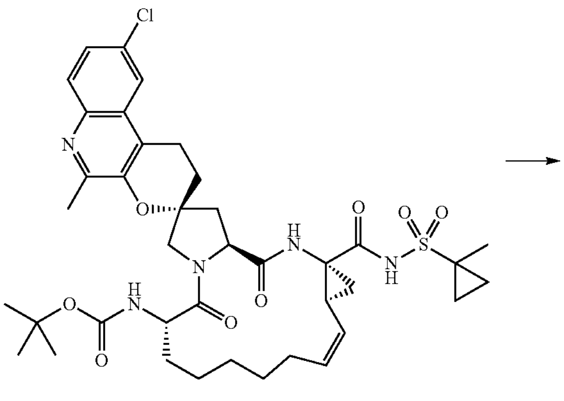

-continued

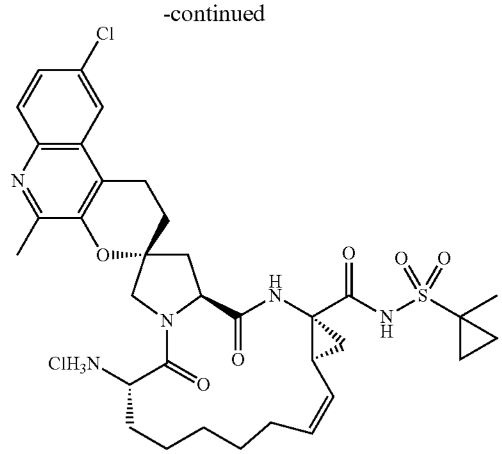

I-39 (440 mg, 0.561 mmol) was dissolved in DCM (5.61 mL), HCl (4M in dioxane, 4.91 mL, 19.63 mmol) was added, and the mixture stirred for 1 h. The mixture was concentrated under reduced pressure to give the product of Step 1 (420 mg, 0.583 mmol, 104% yield) as beige solid.

Step 2

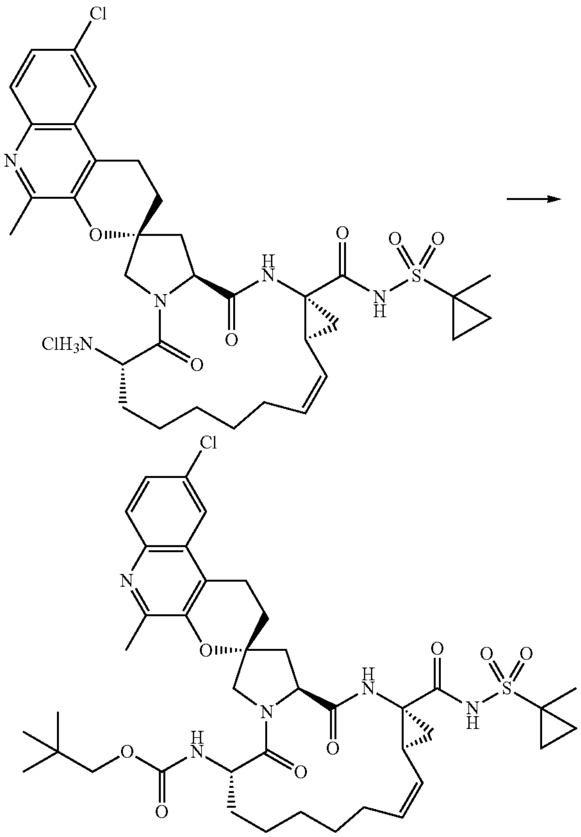

The product from Step 1 (50 mg, 0.069 mmol) was suspended in DCM (694 μl), cooled to 0° C., neopentyl chloroformate (20.90 mg, 0.139 mmol) and TEA (29.0 μl, 0.208 mmol) added, and the mixture stirred at RT for 1 h. TLC showed complete conversion, and the mixture was concentrated under reduced pressure. The residue was purified by column chromatography on silica gel, eluting with EtOAc/hexane to give I-40 (36 mg, 0.045 mmol, 65.0% yield) as a colorless solid. MS: m/e=798.3 (100) (MH+).

Example 41

(1-methylcyclopropyl)methyl((2R,6S,13aS,14aR,16aS,Z)-9'-chloro-5'-methyl -14a-(((1-methylcyclopropyl)sulfonyl)carbamoyl)-5,16-dioxo-1',2',3,5,6,7,8,9,10,11,13a,14, 14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I-41)

Step 1

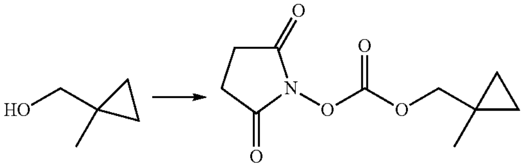

1-Methylcyclopropanemethanol (1.127 ml, 11.61 mmol) was dissolved in MeCN (38.7 ml), N,N'-disuccinimidyl carbonate (3.87 g, 15.09 mmol) then TEA (4.85 ml, 34.8 mmol) added, and the mixture was stirred overnight. The mixture was concentrated to one-third volume, and then treated with aq. $NaHCO_3$ (50 ml). After 5 min, the solution was extracted with EtOAc (3×50 ml), dried ($MgSO_4$), and concentrated to give the product of Step 1 (2.73 g, 12.02 mmol, 103% yield).

Step 2

The product of Step 1 (34.7 mg, 0.153 mmol) and the product of Example 40, Step 1 (50 mg, 0.069 mmol) were dissolved in DCM (694 μl) and cooled to 0° C. TEA (29.0 μl, 0.208 mmol) was added, and the mixture stirred for 1 h. TLC showed complete conversion, and the mixture was concentrated under reduced pressure. The residue was purified by column chromatography on silica gel, eluting with EtOAc/hexane to give I-41 (40 mg, 0.050 mmol, 72.4% yield) as colorless oil. MS: m/e=796.2 (100) (MH+).

Example 42 tert-Butyl (1aR,3aS,3'R,9S,16aS,Z)-5',9'-dimethyl-1a-(1-methylcyclopropyl sulfonylcarbamoyl)-3,8-dioxo-1a,1',2,2',3,3a,4,6,8,9,10,11,12,13,14,16a-hexadecahydro-1H -spiro[cyclopropa[e]pyrrolo[1,2-a][1,4]diazacyclopentadecine-5,3'-pyrano[2,3-c]quinoline]-9-ylcarbamate (I-42)

Step 1

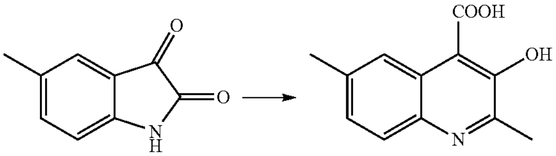

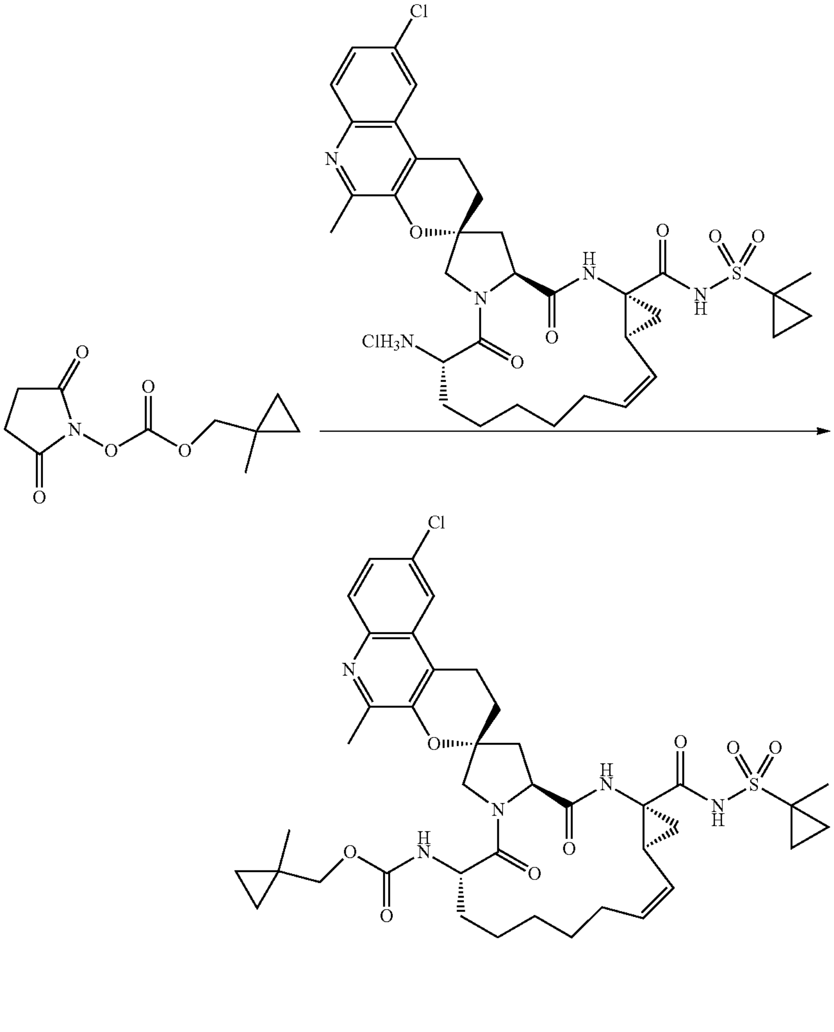

A solution of 5-methylisatin (10.00 g, 62.1 mmol) in water (150 mL) was treated with $Ca(OH)_2$ (13.8 g, 186 mmol) and heated at 80° C. for 1 h. The reaction mixture was then treated with chloroacetone (14.35 g, 12.37 mL) and heated additionally for 6 h. It was cooled to RT and acidified with aq. HCl. The solid separating out was filtered, dried and used as is (yield 12.3 g).

Step 2

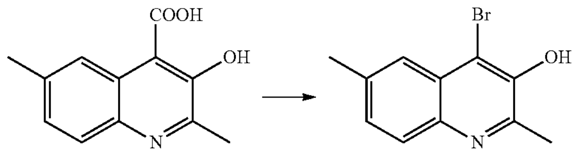

A suspension of the product of Step 1 (7.00 g, 32.2 mmol) in THF (75 mL) was treated with NBS (7.17 g, 40.3 mmol) and stirred at RT for 4 h. The reaction mixture diluted with EtOAc (600 mL) and washed with water (2×300 mL). The combined organic layers were dried ($MgSO_4$), filtered, concentrated in vacuo and purified by silica gel chromatography (EtOAc/Hexanes) to yield bromide product of Step 2 (3.5 g, 43%).

Step 3

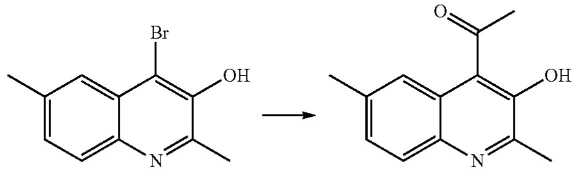

A solution of the bromide product of Step 2 (3.3 g, 13.09 mmol) in dry dioxane (50.0 mL) under $N_2$ was treated with tributyl(1-ethoxyvinyl)stannane (8.84 mL, 9.45 mmol), $Pd(PPh_3)_4$ (1.5 g, 1.3 mmol) and heated at reflux for 4 h. The reaction mixture was cooled to RT and reacted with aq. HCl (1M, 20 mL) and stirred at RT for 45 min. It was neutralized with a solution of sat. aq. $NaHCO_3$ and extracted into EtOAc. The combined organic layers were dried ($MgSO_4$), filtered, concentrated in vacuo and purified by silica gel chromatography to yield desired ketone product of Step 3 (1.4 g, 50%).

Step 4

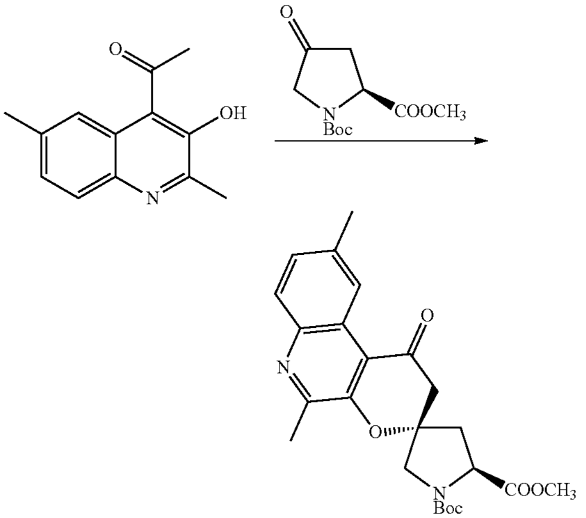

42-4A

-continued

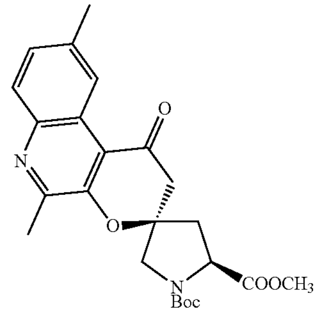

42-4B

A solution of ketone product of Step 3 (700 mg, 3.25 mmol) and 4-oxo-proline (1.5 g, 6.50 mmol) in MeOH (10 mL) was treated with powdered 4A molecular sieves (2.5 g) and pyrrolidine (136 μL, 1.62 mmol) and heated in a microwave at 105° C. for 30 min. The reaction mixture was cooled to RT. A similar scale reaction was repeated, and the crude reactions were combined. The combined reaction mixtures were filtered, concentrated in vacuo and purified by silica gel chromatography (EtOAc/Hexanes) to yield two diasteromers 42-4A (1.3 g) and 42-4B (730 mg).

Step 5

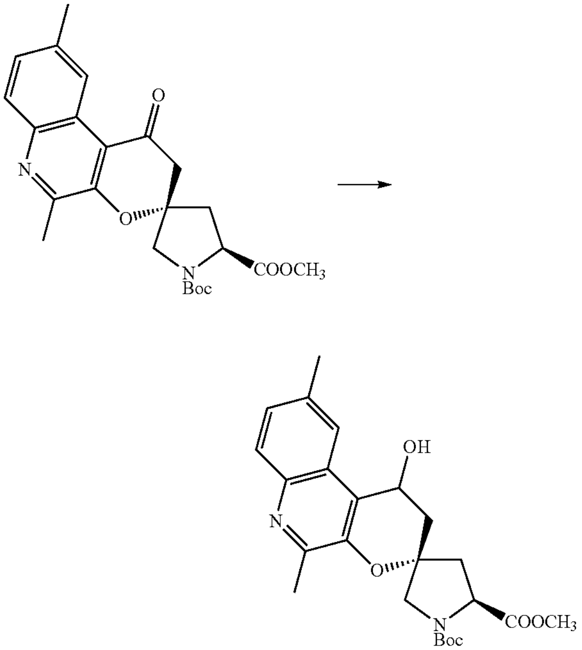

A solution of ketone 42-4A (1.30 g, 2.95 mmol) in MeOH (20 mL) was cooled to 0° C. and treated with $NaBH_4$ (112 mg, 2.95 mmol). The reaction mixture was stirred at RT for 15 min and quenched with a solution of sat. aq. $NaHCO_3$. The reaction mixture was extracted with EtOAc (450 mL). The combined organic layers were dried ($MgSO_4$), filtered, concentrated in vacuo and purified by chromatography ($SiO_2$, EtOAc/Hexanes) to yield the reduced alcohol product of Step 5 (1 g, 77%), colorless foam as a mixture of diasteromers.

Step 6

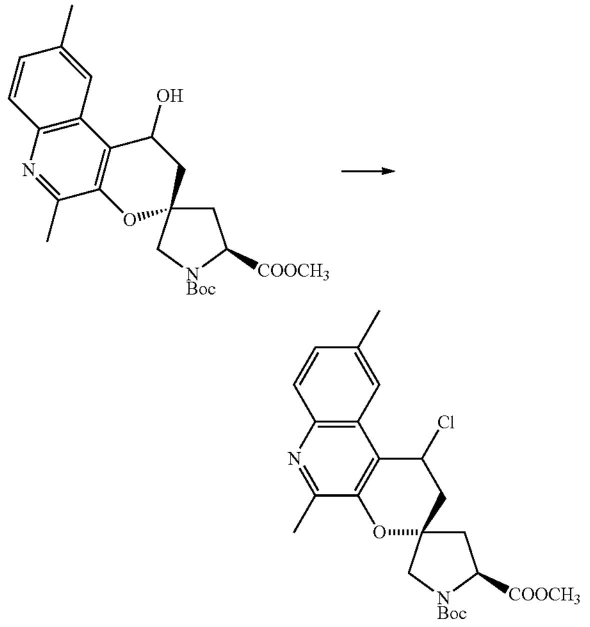

A solution of the product of Step 5 (1.00 g, 2.26 mmol) in DCM (20.0 mL) at 0° C. was treated with TEA (0.813 mL) and MsCl (0.352 mL) and stirred overnight when the ice bath slowly warmed up to RT. The reaction mixture was diluted with a solution of sat. aq. $NaHCO_3$, and the reaction mixture was extracted with EtOAc (300 mL). The combined organic layer were dried ($MgSO_4$), filtered concentrated in vacuo and used in the next step without further purification (1.1 g).

Step 7

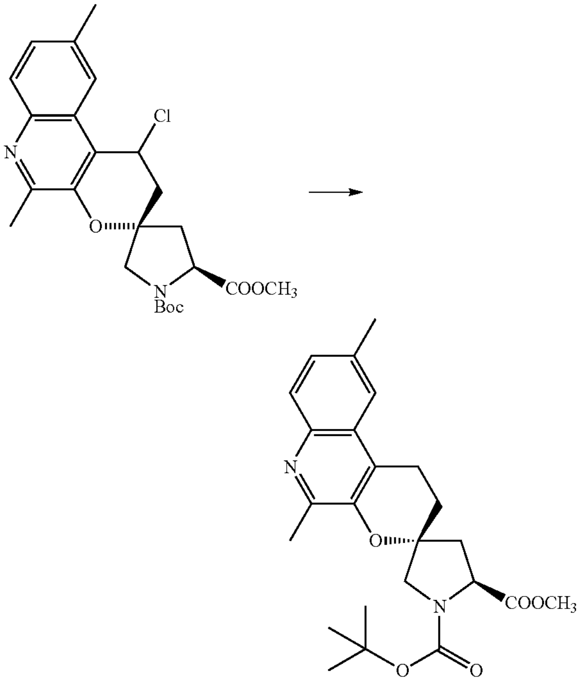

A solution of the product of Step 6 (1.1 g, 2.4 mmol) in EtOAc (40 mL) was treated with Pd/C (10% wt) and hydrogenated with $H_2$ using balloon pressure. The reaction mixture was stirred at RT for 1.5 h and filtered through Celite. The filtrate was concentrated in vacuo and purified by silica gel chromatography ($CH_2Cl_2$/MeOH) to yield reduced product of Step 7 (1.0 g, 98%).

Step 8

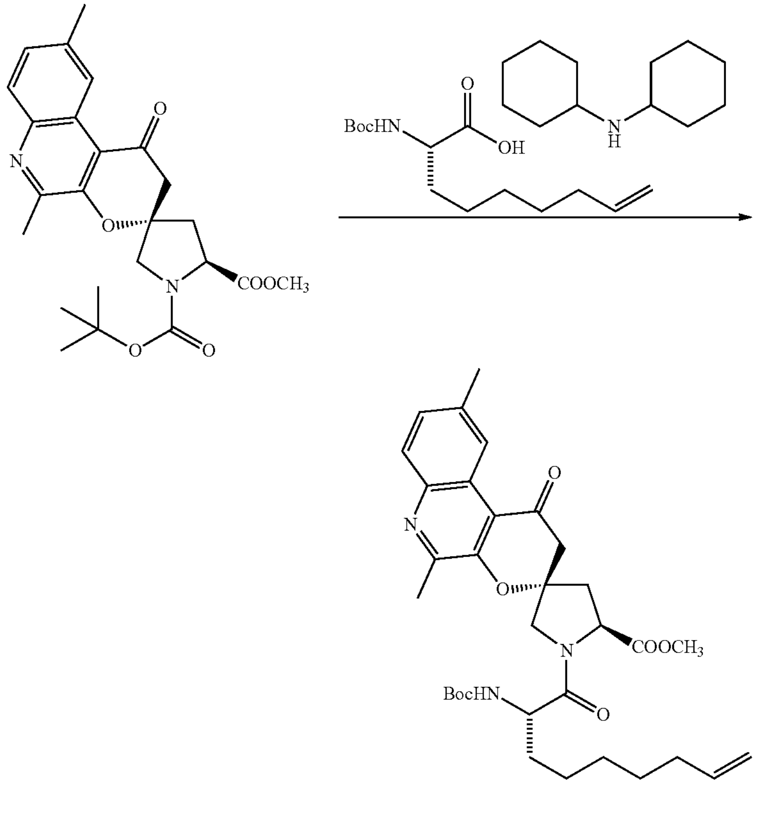

A solution of the product of Step 7 (1.00 g, 2.35 mmol) in DCM (20 mL) was treated with trifluoroacetic acid (20 mL) and stirred at RT for 1 h. The reaction mixture was concentrated in vacuo. The residue was taken in dry dioxane (20 mL) and concentrated in vacuo. The residue was treated with ether, when the amine salt precipitated out, which was filtered, dried and used as is.

A solution of (25)-2-((tert-butoxycarbonyl)amino)non-8-enoic acid (1.165 g, 2.57 mmol), amine salt (1.3 g, 2.34 mmol), HATU (1.34 g, 3.51 mmol) in DMF and DCM (20 mL each) was treated with Hunig's base (1.2 g, 1.6 mL, 9.36 mmol) and stirred at RT for 12 h. The reaction mixture was diluted with EtOAc (300 mL) and washed with water and a solution of sat. aq. $NaHCO_3$. The combined organic layers were dried ($MgSO_4$), filtered, concentrated in vacuo, and purified by silica gel chromatography to yield the product of Step 8 as colorless foam (1.1 g, 81%).

Step 9

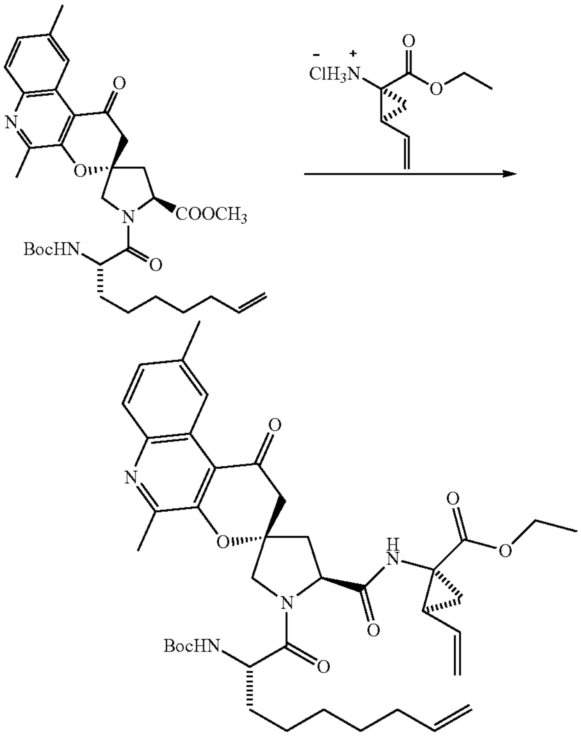

A solution of the product of Step 8 (1.10 g, 1.897 mmol) in MeOH (8.00 mL), water (4.00 mL) and THF (15 mL) was treated with aq. LiOH solution (2M, 2.85 mL) and heated at 60° C. for 1 h. The reaction mixture was cooled to RT and acidified with aq. HCl (1M, 5 mL) and extracted into EtOAc (250 mL). The combined organic layers were dried ($MgSO_4$), filtered, concentrated in vacuo and used as it is.

A solution of acid (1.10 g, 1.95 mmol) in DMF and DCM (5.00 mL each) was treated with (1R,2S)-1-(ethoxycarbonyl)-2-vinylcyclopropanaminium chloride (745 mg, 3.89 mmol), HATU (1.1 g, 2.92 mmol) and Hunig's base (1.70 mL, 9.71 mmol) and stirred at RT for 12 h. The reaction mixture was diluted with aq. $NaHCO_3$ and extracted into EtOAc. The combined organic layers were dried ($MgSO_4$), filtered, concentrated in vacuo and purified by chromatography ($SiO_2$, EtOAc/Hexanes) to yield the coupled product of Step 9 as a colorless foam (1.00 g, 73%).

Step 10

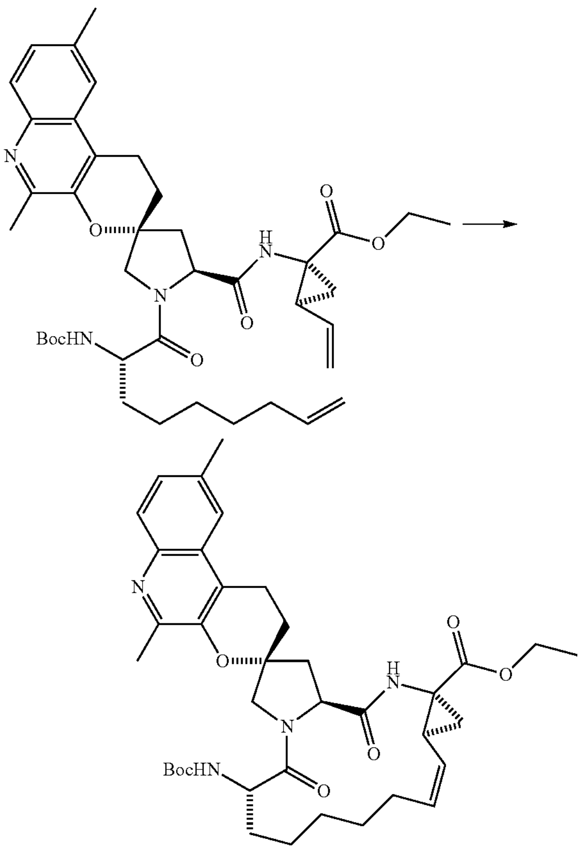

A solution of the diene product of Step 9 (1.00 g, 1.42 mmol) in DCE (400 mL) was degassed and treated with Zhan's catalyst (261 mg, 0.356 mmol), benzoquinone (0.427 mmol, 46 mg) and heated at 65° C. for 3 h. The disappearance of starting material was followed by TLC. On complete consumption of starting material as indicated by TLC, the reaction mixture was quenched with methylvinyl ether (1.00 mL), concentrated in vacuo and purified by silicagel chromatography (Hexanes, EtOAc) to yield the cyclized product of Step 10 (963 mg, 68%).

Step 11

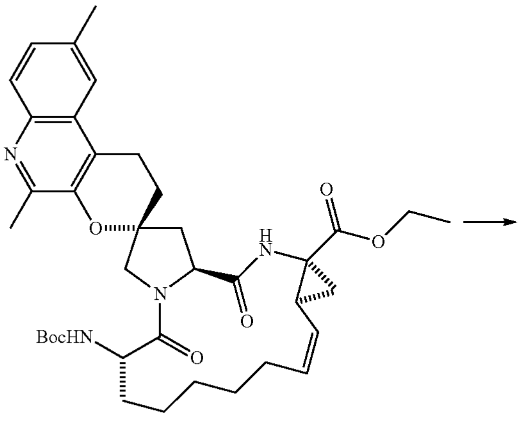

-continued

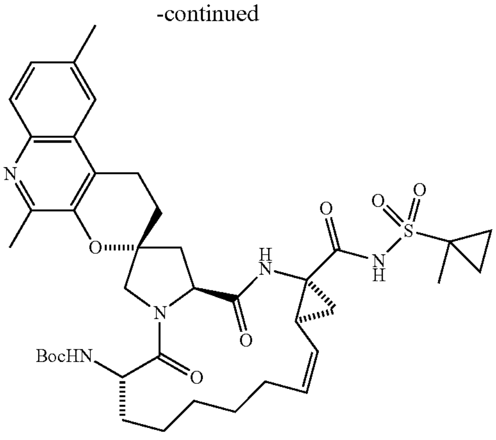

A solution of the cyclized product of Step 10 (650 mg, 0.963 mmol) in MeOH (8.00 mL), water (5.0 mL) and THF (8.0 mL) was treated with aq. LiOH (2.5 mL, 2M, 4.82 mmol) and stirred at RT overnight. The reaction mixture was diluted with aq. HCl to make acidic and extracted into EtOAc (250 mL). The combined organic layers were dried ($MgSO_4$), filtered concentrated in vacuo and used as is.

A solution of acid (100 mg, 0.155 mmol) in THF (3 mL) was treated with carbonyl diimidazole (50 mg, 0.31 mmol) and heated at 70° C. for 2 h. The reaction mixture was cooled to RT and treated with methylcyclopropyl sulfonamide (42 mg) and DBU (46 μl) and heated at 50° C. The reaction was heated at 50° C. for 4 h and once again treated with methylcyclopropylsulfonamide and DBU in the same amounts. The reaction mixture was stirred at RT for 24 h and concentrated in vacuo and purified by silica gel chromatography to yield I-42 as colorless solid (89 mg).

Example 43 tert-Butyl (1aR,3aS,3'R,9S,16aS,Z)-9'-fluoro-5'-methyl-1a-(1-methylcyclopropylsulfonylcarbamoyl)-3, 8-dioxo-1a,1',2,2',3,3a,4,6,8,9,10,11,12,13,14, 16a -hexadecahydro-1H-spiro[cyclopropa[e]pyrrolo [1,2-a][1,4]diazacyclopentadecine-5,3'-pyrano[2,3-c] quinoline]-9-ylcarbamate (I-43)

Step 1

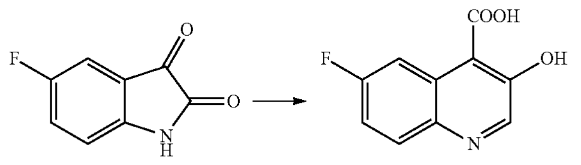 [SMILES: O=C1Nc2ccc(F)cc2C1=O ; O=C(O)c1c(O)cnc2ccc(F)cc12]

A slurry of 5-fluoroisatin (10.1 g, 61.2 mmol) in water (150 ml) was treated with $Ca(OH)_2$ (13.60 g, 184 mmol) and heated at 80° C. for 1 h. The slurry was then treated with chloroacetone (12.18 ml, 153 mmol), when the slurry stopped stirring forming a concrete-like mass. The mass was broken up with a spatula, and more water was added (~200 ml). It was further heated at same temperature for additional 6 h. The reaction mixture was cooled to RT and acidified with aq. HCl (250 ml, 1N). The solid separating out was filtered, washed with water and dried under vacuum to yield the product of Step 1 (11.8 g, 87%) as a pale yellow solid used in the next step without further purification.

Step 2

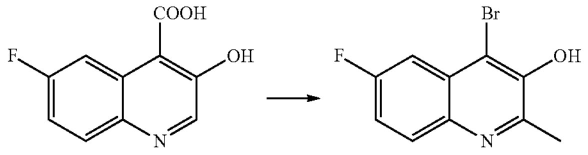

A solution of the product of Step 1 (5.9 g, 26.6 mmol) in DMF (100 ml) was treated with NBS (5.68 g, 31.9 mmol) at RT and stirred for 16 h. The reaction mixture was diluted with EtOAc, and the organic layer was washed with water and brine. The organic layer was concentrated in vacuo to yield a brown solid (6 g). The crude mixture was directly adsorbed on silica gel and purified chromatography (EtOAc/Hexanes) to yield the product of Step 2 (1.05 g) as pale yellow solid.

Step 3

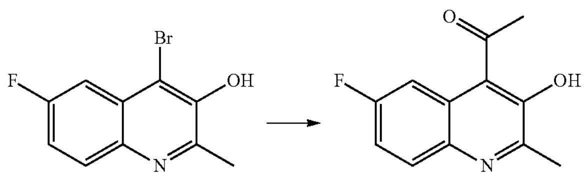 [SMILES: Cc1nc2ccc(F)cc2c(Br)c1O ; CC(=O)c1c(O)c(C)nc2ccc(F)cc12]

A solution of the product of Step 2 (2.4 g, 9.37 mmol) in dioxane (48 mL) was treated with tributyl(1-ethoxyvinyl)tin (6.33 mL, 18.74 mmol), $Pd(PPh_3)_2Cl_2$ (0.658 g, 0.937 mmol) and heated in an oil bath at 115° C. under $N_2$ atmosphere for 3 h. The reaction mixture was cooled to RT, treated with aq. HCl (1M, 48 mL) and stirred at RT for 1 h. The reaction mixture was made basic with a solution of sat. $NaHCO_3$ and extracted into EtOAc. The combined organic layer was dried ($MgSO_4$), filtered, concentrated in vacuo and purified by silica gel chromatography (acetone/Hexanes. 0-25%) to isolate ketone the product of Step 3 (1.49 g) as a pale yellow solid.

Step 4

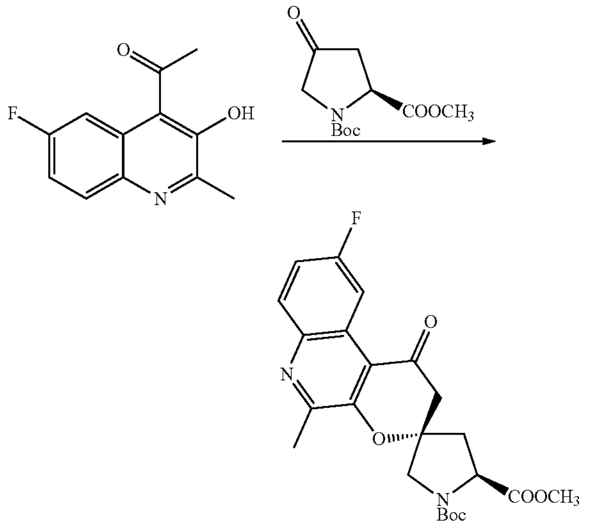

43-4A

-continued

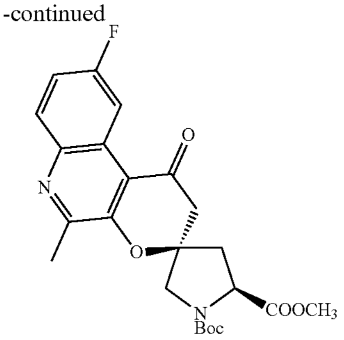

43-4B

A solution of the product of Step 3 (693 mg, 3.16 mmol) in MeOH (14 ml) was treated with 1-tert-butyl-2-methyl(2S)-4-oxopyrrolidine-1,2-dicarboxylate (1.54 g, 6.32 mmol) and pyrrolidine (0.261 ml, 3.16 mmol) in a microwave tube. To this was then added powdered 4A molecular sieves 693 mg, and the reaction was heated to 105° C. in microwave reactor for 35 min. Analysis of TLC (30% EtOAc/Hexanes) indicated complete consumption of starting material and formation of two new products corresponding to 43-4A and 43-4B. The reaction was repeated 3×, and the crude material (7.0 g) were combined and purified by silica gel chromatography to yield an inseparable mixture of 43-4A and 43-4B (3.22 g, 76%).

Step 5

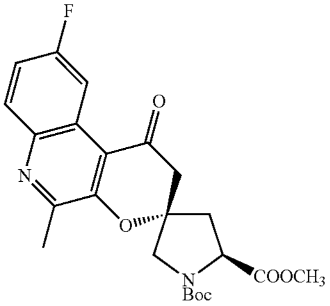

43-4A

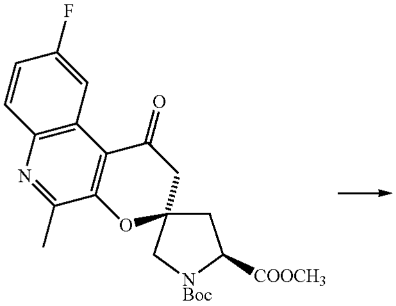

43-4B

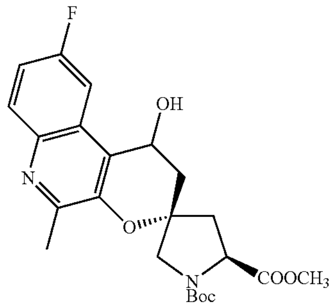

43-5A

-continued

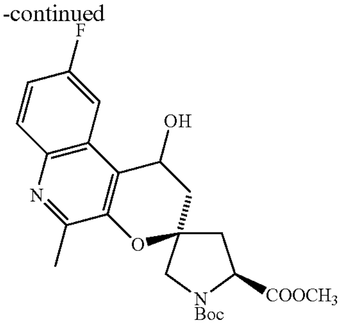

43-5B

A solution of 43-4A and 43-4B (1.96 g, 4.40 mmol) in MeOH (40 ml) was cooled to 0° C. and treated with $NaBH_4$ (166 mg, 4.40 mmol) over 1 min and stirred for 30 min at 0° C. TLC (50% EtOAc/Hexanes) indicated complete consumption of starting material. The reaction was stirred for 45 min total and quenched with sat. aq. $NaHCO_3$ solution. It was extracted with EtOAc, and the combined organic layers were washed with brine, dried ($MgSO_4$), filtered, concentrated in vacuo and purified by silica gel chromatography (EtOAc/Hexanes) to yield 43-5A and 43-5B (1.77 g) as colorless foam.

Step 6

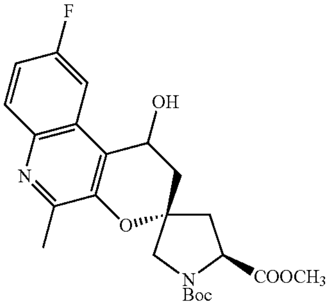

43-5A

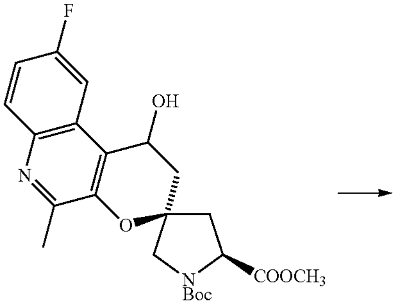

43-5B

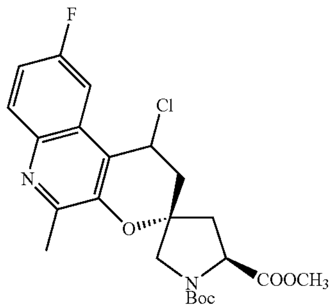

43-6A

-continued

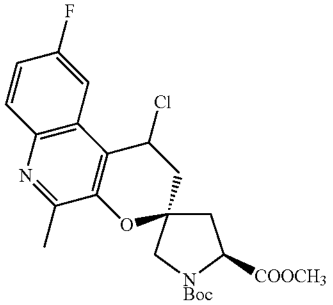

43-6B

A solution of 43-5A and 43-5B (1.77 g, 3.95 mmol) in DCM (35 ml) was cooled in an ice bath and treated with $Et_3N$ (1.652 ml, 11.85 mmol) then MsCl (0.616 ml, 7.90 mmol). The reaction mixture was allowed to slowly warm to RT and stirred overnight. TLC with 50% EtOAc/Hexanes indicated complete consumption of starting material. The reaction mixture was diluted with EtOAc and washed with sat. aq. $NaHCO_3$, water, brine and filtered through anhydrous $Na_2SO_4$. The filtrate was concentrated to dryness and purified by silica gel chromatography to yield chlorides 43-6A and 43-6B (1.74 g, 95%) as a pale yellow solid.

Step 7

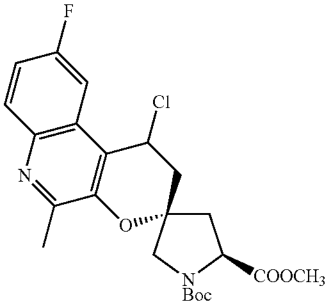

43-6A

-continued

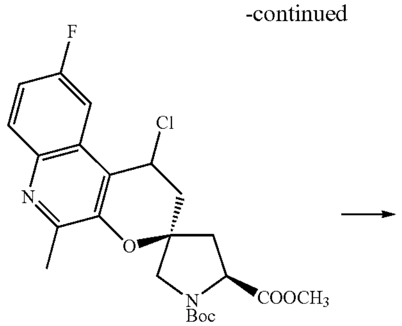

43-6B

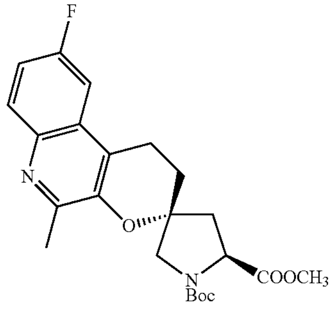

43-7A

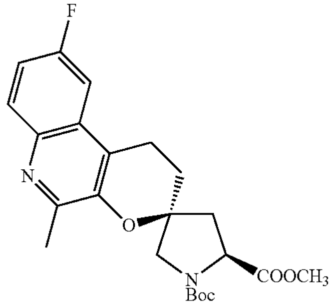

43-7B

A solution of 43-6A and 43-6B (1.74 g, 3.74 mmol) in EtOAc (35 mL) was treated with Pd/C (10%, 199 mg) and hydrogenated with balloon pressure. The reaction mixture was stirred at RT for 2 h. It was diluted with MeOH to dissolve precipitate formed and filtered. The filtered cake was washed with excess MeOH, and the filtrate was concentrated in vacuo to yield reduced products 43-7A and 43-7B (1.75 g) as a colorless solid.

Step 8

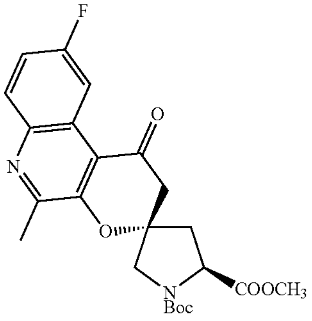

43-7A

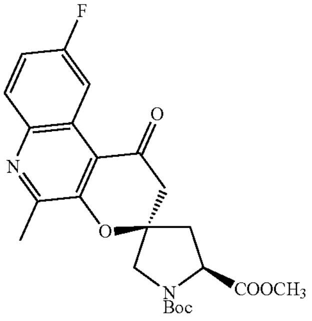

43-7B

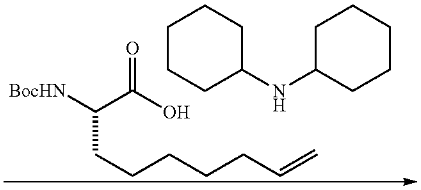

-continued

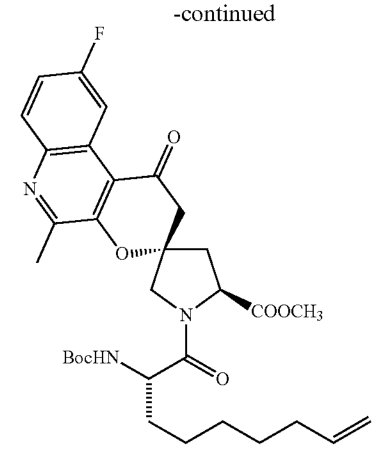

43-8A

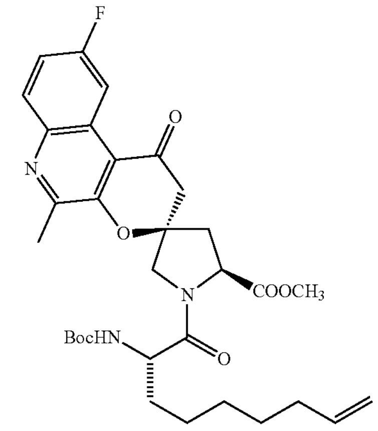

43-8B

A solution of 43-7A and 43-7B (1.74 g, 4.04 mmol) in 4M HCl in dioxane (5 ml) was stirred at RT for 1.25 h. The reaction mixture was concentrated in vacuo to yield amine salts (1.61 g) as orange solid that were used in next reaction without further purification.

A solution of amine salts (1.61 g, 4.87 mmol) in DCM (16 ml) and DMF (16 ml) was treated with DIPEA (2.55 ml, 14.62 mmol), dicyclohexylammonium (S)-2-(tert -butoxycarbonylamino)non-8-enoate (2.65 g, 5.85 mmol) and HATU (2.25 g, 5.85 mmol) and stirred at RT for 16 h. The reaction mixture was diluted with EtOAc (300 mL) and washed with water and a solution of sat. aq. $NaHCO_3$. The combined organic layers were dried ($MgSO_4$), filtered, concentrated in vacuo, and purified by silica gel chromatography to separate the two diastereomers 43-8A and 43-8B yielding desired diastereomer 43-8A (1.42 g) as colorless foam.

Step 9

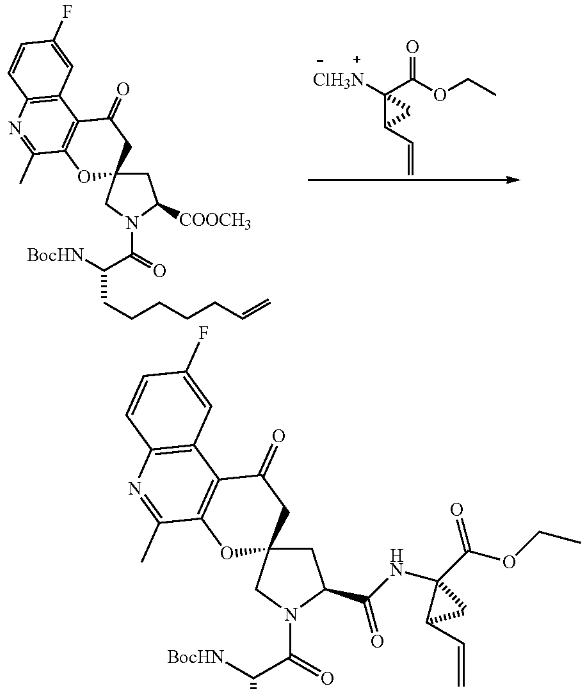

A solution of 43-8A (1.42 g, 2.43 mmol) in MeOH (11 ml) and THF (16.50 ml) was treated with a 2M aq. solution of LiOH (3.64 ml, 7.28 mmol) and heated at 60-65° C. for 1 h. Analysis of TLC (50% EtOAc/Hexanes) indicated all starting material was consumed. The reaction mixture was acidified with 1N HCl (8.0 mL) and extracted with EtOAc. The combined extracts, were washed with brine and filtered through $Na_2SO_4$. The filtrate was concentrated in vacuo to yield carboxylic acid as pale yellow foam (1.46 g).

A solution of acid (1.39 g, 2.43 mmol) in DMF (14 ml) and DCM (14 ml) was treated with DIPEA (2.33 ml, 13.35 mmol), HATU (1.20 g, 3.16 mmol), (1R,2S)-1-(ethoxycarbonyl)-2-vinylcyclopropanaminium chloride (0.93 g, 4.86 mmol) and stirred at RT for 15 h. The reaction mixture was concentrated in vacuo and diluted with EtOAc. The combined organic layers were washed with water, 0.5N aq. HCl, brine and filter through anhydrous $Na_2SO_4$. The filtrate was concentrated in vacuo and purified by silica gel chromatography (EtOAc/Hexanes) to yield the product of Step 9 as a colorless solid (1.6 g).

Step 10

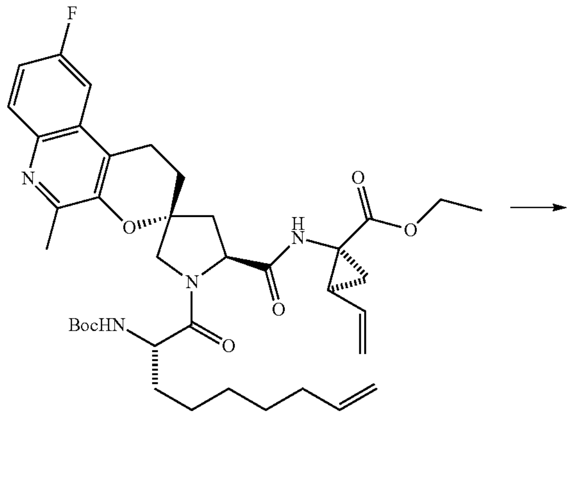

-continued

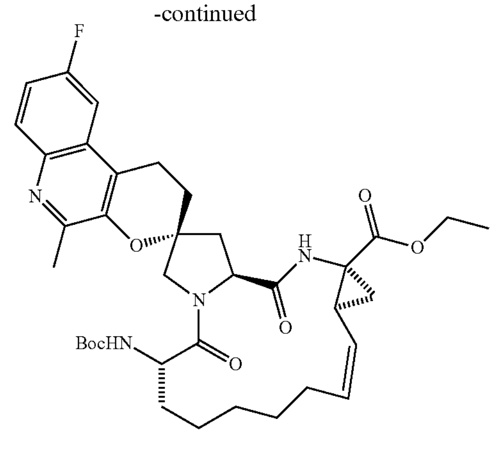

A solution of the product of Step 9 (800 mg, 1.132 mmol) in DCE (400 ml) was degassed, treated with Zhan's catalyst (208 mg, 0.283 mmol), benzoquinone (36.7 mg, 0.340 mmol) and heated at 75° C. for 4 h. The disappearance of starting material was followed by TLC (60% EtOAc/Hexanes). On complete consumption of starting material, the reaction mixture was cooled to RT and quenched with methylvinyl ether and stirred for 10 min. The reaction mixture was concentrated in vacuo and purified by silica gel chromatography to yield the product of Step 10 as a tan colored solid (357 mg, 47%).

Step 11

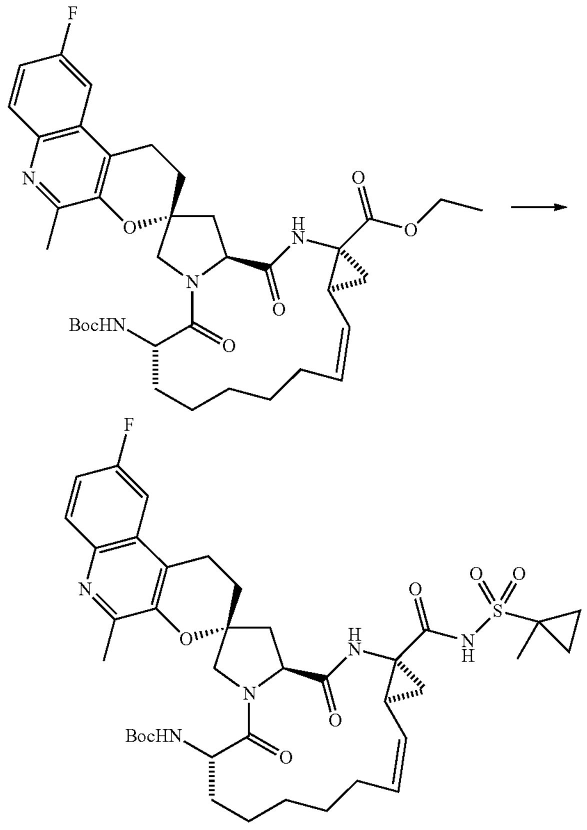

A solution of the product of Step 10 (357 mg, 0.526 mmol) in MeOH (2.0 ml) and THF (3.00 ml) was cooled to 0° C. and treated with a solution of 2M aq. LiOH (1.32 ml, 2.63 mmol). The reaction was allowed to warm to RT and stirred overnight. Analysis of TLC with 60% EtOAc/Hexanes indicated all the starting material was consumed. The reaction mixture was acidified with aqueous 1N HCl (4.00 mL) and concentrated to dryness. The crude mixture was used as is.

A solution of acid (0.342 g, 0.526 mmol) in THF (7 mL) was treated with carbonyl diimidazole (0.171 g, 1.052 mmol) and heated at 70° C. in a sealed tube for 2 h. The reaction mixture was cooled to RT and treated with 1-methylcyclopropane-1-sulfonamide (0.284 g, 2.104 mmol) and DBU (0.315 mL, 2.104 mmol) and further heated at 50° C. for 12 h. The reaction mixture was cooled to RT and diluted with EtOAc. The organic layer was washed with 0.5M aqueous HCl, water, brine and filtered through anhydrous $Na_2SO_4$. The filtered EtOAc layer was concentrated in vacuo, and the residue was purified by silica gel chromatography twice using EtOAc/Hexanes and EtOAc/DCM to yield I-43 as a colorless solid.

Example 44 tert-Butyl (1aR,3aS,3'R,9S,16aS,Z)-5'-methyl-1a-(1-methylcyclopropyl sulfonylcarbamoyl)-3,8-dioxo-7'-(trifluoromethyl)-1a,1',2,2',3,3a,4,6,8,9,10,11,12,13,14,16a -hexadecahydro-1H-spiro[cyclopropa[e]pyrrolo[1,2-a][1,4]diazacyclopentadecine-5,3'-pyrano[2,3-c]quinoline]-9-ylcarbamate (I-44)

Step 1

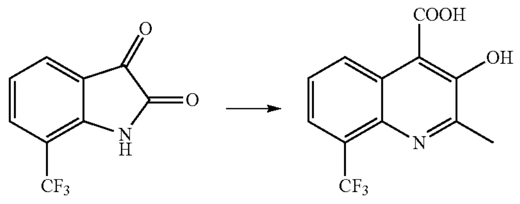 [SMILES: O=C1Nc2c(cccc2C(F)(F)F)C1=O ; Cc1nc2c(C(F)(F)F)cccc2c(C(=O)O)c1O]

A slurry of 7-trifluoroisatin in water was treated with $Ca(OH)_2$ and heated at 80° C. for 1 h. The reaction was then treated with chloroacetone and further heated at 80° C. for 6 h. The reaction mixture was cooled to RT and acidified with aq. HCl (250 ml, 1N). The solid separating out was filtered, washed with water and dried under vacuum to yield the product of Step 1.

Step 2

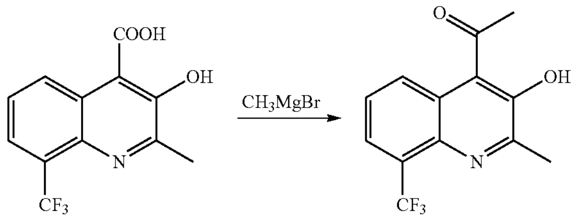

A solution of the product of Step 1 in dry THF was treated with TEA and a solution of MeMgBr in ether. The reaction mixture was heated for 4 h and cooled to 0° C. and quenched with MeOH and aq. $NH_4Cl$ solution. The reaction mixture was diluted with aq. HCl and extracted with EtOAc. The combined organic layers were dried ($MgSO_4$), filtered, concentrated in vacuo and purified by silica gel chromatography to yield the product of Step 2 as a pale yellow solid.

Step 3

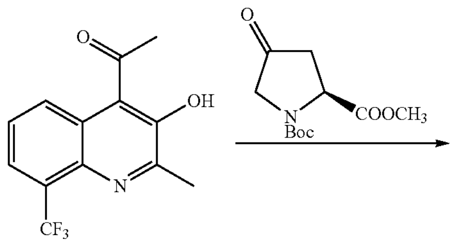

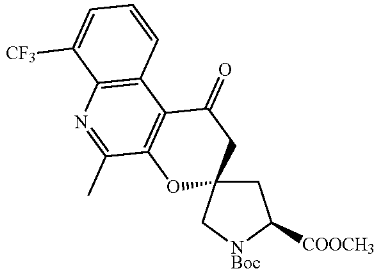

44-3A

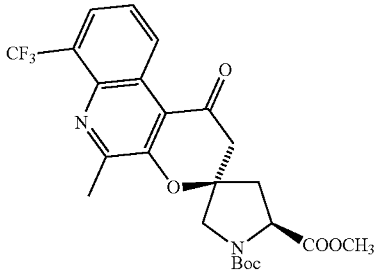

44-3B

A solution of the product of Step 2 (1.11 g, 4.12 mmol) in MeOH (22 ml) was treated with 1-tert-butyl-2-methyl(2S)-4-oxopyrrolidine-1,2-dicarboxylate (2.01 g, 8.25 mmol) and pyrrolidine (0.341 ml, 4.12 mmol) in a sealed tube. To this was added molecular sieves (1.11 g, 4A powder), and the reaction was heated to 105° C. and stirred for 12 h in a sealed tube. The reaction was cooled to RT, and analysis of TLC (EtOAc/Hexanes 2:3) indicated complete consumption of starting material. The reaction mixture was filtered, concentrated in vacuo and purified by silica gel chromatography (Hexanes, EtOAc) to yield condensed products 44-3A and 44-3B as inseparable mixture (2.5 g, 76%).

Step 4

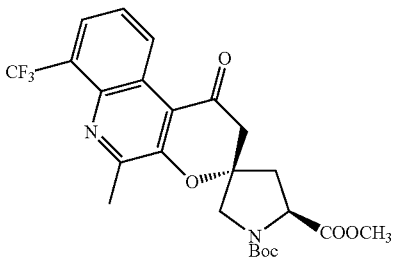

44-3A

-continued

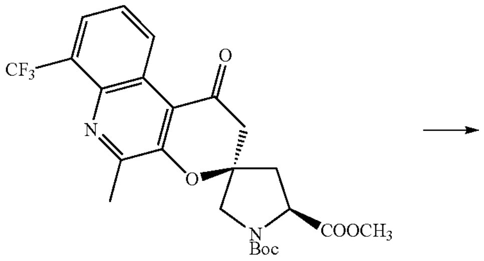

44-3B

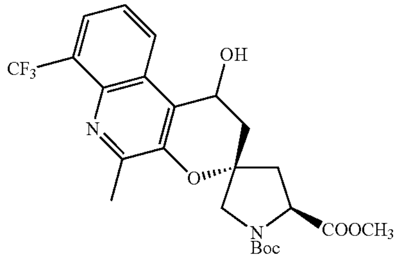

44-4A

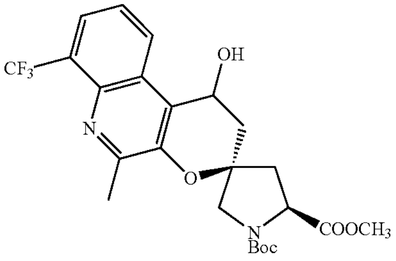

44-4B

A solution of 44-3A and 44-3B (2.24 g, 4.53 mmol) in MeOH (40 ml) was cooled to 0° C. and treated with $NaBH_4$ (0.686 g, 18.12 mmol) over 10 min and stirred for 45 min at 0° C. The reaction was allowed to warm to RT and stirred for an additional 30 min. Analysis of TLC (EtOAc/Hexanes 3:2) indicated complete consumption of starting material. The reaction mixture was concentrated in vacuo, and the residue was taken in EtOAc. The organic layer was washed with 0.5M NaOH solution (2×), water and brine. The combined organic layers were dried ($MgSO_4$), filtered, concentrated in vacuo and purified by silica gel chromatography to yield reduced alcohols 44-4A and 44-4B (1.47 g, 65%).

Step 5

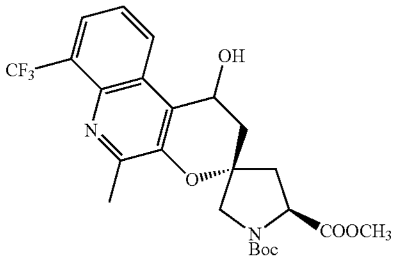

44-4A

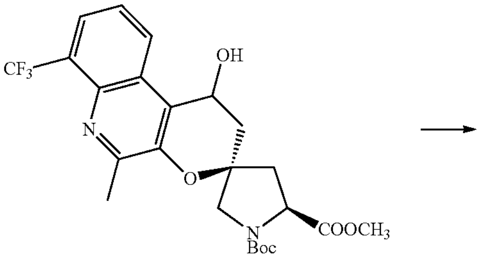

44-4B

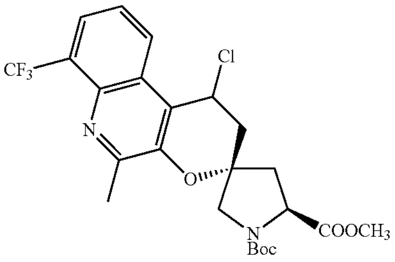

44-5A

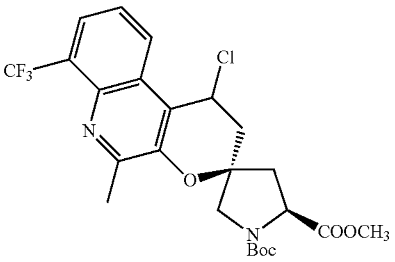

44-5B

A solution of alcohols 44-4A and 44-4B (1.25 g, 2.52 mmol) in DCM (25 ml) was treated with $Et_3N$ (0.877 ml, 6.29 mmol) then MsCl (0.392 ml, 5.04 mmol) and stirred at RT for 5 h. Analysis of reaction mixture using TLC (EtOAc/Hexanes, 35%) indicated complete consumption of starting material. The reaction mixture was diluted with EtOAc and washed with sat. aq. $NaHCO_3$, water, brine and filtered through anhydrous $Na_2SO_4$. The filtrate was concentrated in vacuo and residue purified by silica gel chromatography to yield 44-5A and 44-5B (1.74 g, 95%) as a pale yellow solid.

Step 6

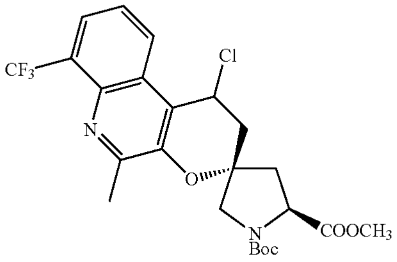

44-5A

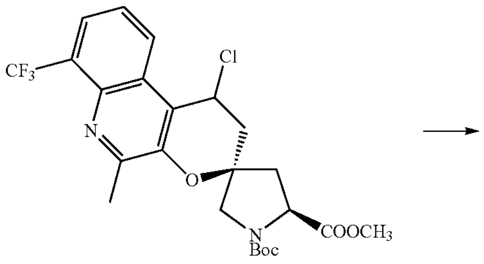

44-5B

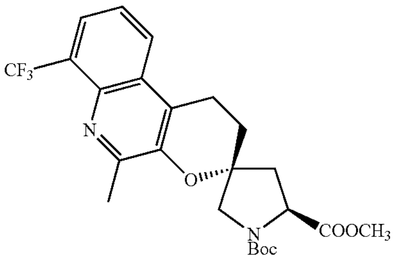

44-6A

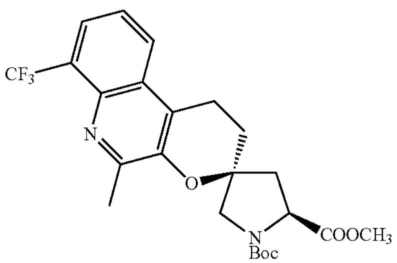

44-6B

A solution of chlorides 44-5A and 44-5B (970 mg, 1.89 mmol) in EtOAc (20 mL) was treated with Pd/C (10% 100 mg) and hydrogenated with balloon pressure at RT for 4 h. On completion of the reaction as indicated by TLC (EtOAc/Hexanes 35%), the reaction mixture was filtered, and the filtrate was concentrated in vacuo to yield 44-6A and 44-6B (850 mg) as off-white foam.

Step 7

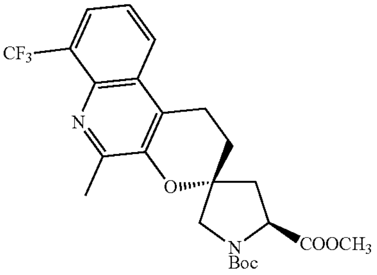

44-6A

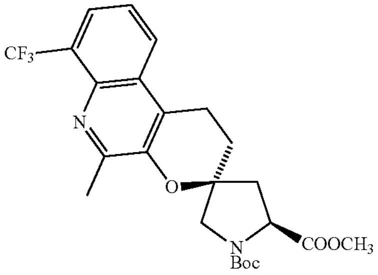

44-6B

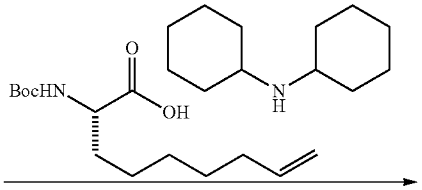

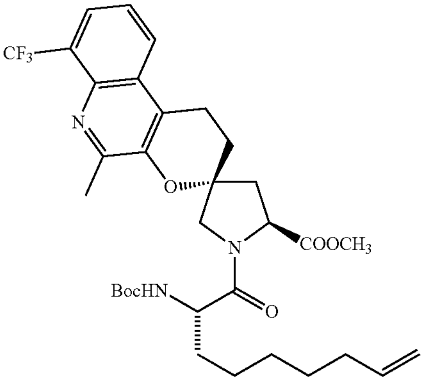

44-7A

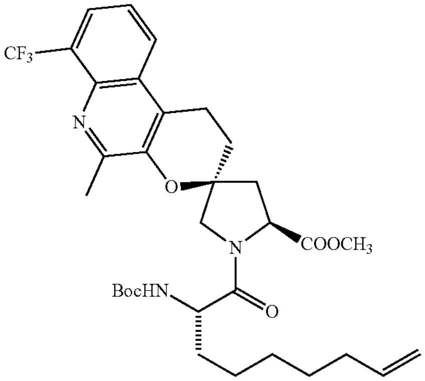

44-7B

A solution of compounds 44-6A and 44-6B (950 mg, 1.977 mmol) in DCM (3.05 ml) was cooled to 0° C. and treated with trifluoroacetic acid (3.05 ml, 39.5 mmol) and allowed to warm to RT. The reaction was stirred for 1 h, when TLC (EtOAc/Hexanes 45%) indicated complete consumption of starting material. The reaction mixture was concentrated in vacuo, and excess TFA was chased out with toluene and then dioxane to give 1.6 g of brownish yellow oil. The mixture was taken in EtOAc and washed with sat. $NaHCO_3$, then 50% water/sat. $NaHCO_3$, brine and dried over $Na_2SO_4$. The EtOAc layer was filtered, and the filtrate was concentrated in vacuo to yield deprotected amine that was used in next reaction without further purification.

A solution of amine salts (730 mg, 1.92 mmol) in DCM (10 ml) and DMF (10 ml) were treated with DIPEA (1.00 ml, 5.76 mmol), dicyclohexylammonium (S)-2-(tert -butoxycarbonylamino)non-8-enoate (1.04 g, 2.30 mmol) and HATU (876 mg, 2.30 mmol) and stirred at RT for 15 h. The reaction mixture was diluted with EtOAc (300 mL) and washed with water and aq. $NaHCO_3$. The combined organic layers were dried ($Na_2SO_4$), filtered, concentrated in vacuo, and purified by silica gel chromatography to separate the two diastereomers 44-7A and 44-7B yielding desired diastereomer 44-7A as a colorless foam (426 mg, 47%).

Step 8

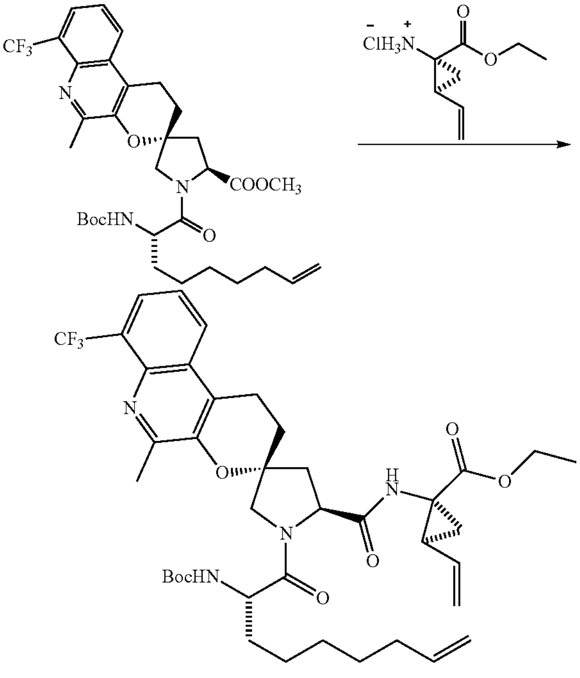

A solution of 44-7A (423 mg, 0.668 mmol) in MeOH (3.38 ml) and THF (5.07 ml) was treated with 2M aq. solution of LiOH (1.00 ml, 2.00 mmol) and heated to 60-65° C. for 1 h. The reaction mixture was acidified with 1N HCl (2.0 mL) and extracted with EtOAc. The combined extracts, were washed with brine and filtered through $Na_2SO_4$. The filtrate was concentrated in vacuo to yield carboxylic acid as a light khaki solid (406 mg).

A solution of acid (403 mg, 0.650 mmol) in DMF (4 ml) and DCM (4 ml) was treated with Hunig's base (0.510 ml, 2.93 mmol), HATU (321 mg, 0.845 mmol), (1R,2S)-1-(ethoxycarbonyl)-2-vinylcyclopropanaminium chloride (249 mg, 1.301 mmol) and stirred at RT for 24 h. The reaction mixture was concentrated in vacuo and diluted with EtOAc. The combined organic layers were washed with water, 0.5N aq. HCl, brine and filter through anhydrous $Na_2SO_4$. The filtrate was concentrated in vacuo and purified by silica gel chromatography to yield the product of Step 8 as a colorless solid (444 mg).

Step 9

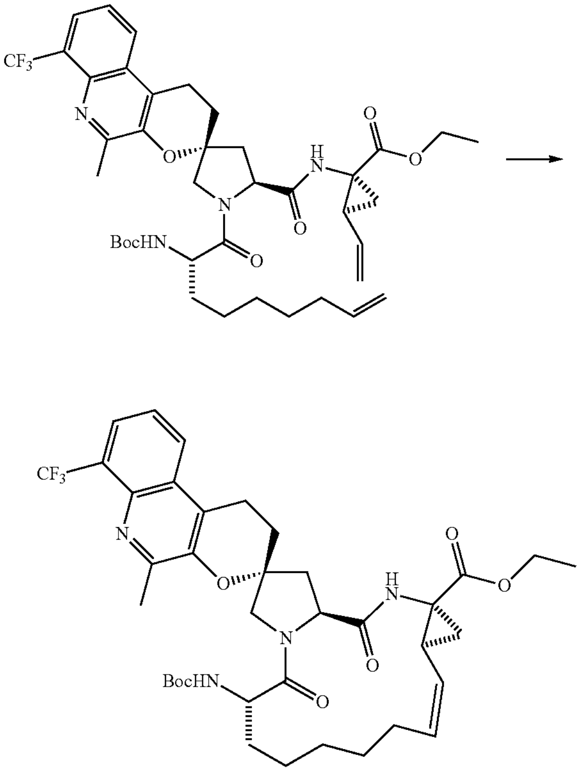

A solution of the product of Step 8 (433 mg, 0.572 mmol) in DCE (170 ml) was degassed, treated with Zhan's catalyst (105 mg, 0.143 mmol), benzoquinone (18.6 mg, 0.172 mmol) and heated at 65° C. for 3 h. The disappearance of starting material was followed by TLC (60% EtOAc/Hexanes). On complete consumption of starting material, the reaction mixture was cooled to RT and quenched with methylvinyl ether. The reaction mixture was concentrated in vacuo and purified by silica gel chromatography to yield the product of Step 9 as a brown colored solid (208 mg, 50%).

Step 10

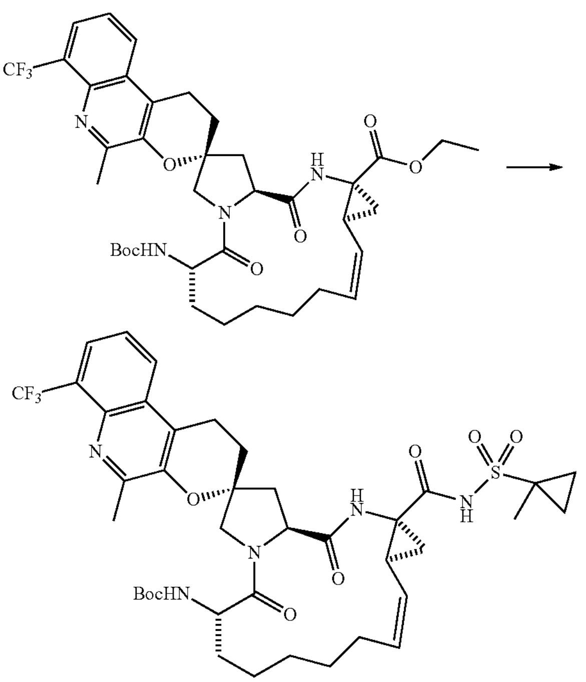

A solution of the product of Step 9 (205 mg, 0.281 mmol) in MeOH (1.6 ml) and THF (2.4 ml) was cooled to 0° C. and treated with 2M aq. solution of LiOH (0.703 ml, 1.406 mmol). The reaction was allowed to warm to RT and stirred overnight. Analysis of TLC with 60% EtOAc/Hexanes indicated all the starting material was consumed. The reaction mixture was acidified with aqueous 0.5N HCl (3.00 mL) and extracted into EtOAc. The combined organic layers were dried, filtered and concentrated in vacuo to yield crude acid (201 mg) as a brown solid.

A solution of acid (75 mg, 0.107 mmol) in THF (2 mL) was treated with carbonyl diimidazole (34.7 mg, 0.214 mmol) and heated at 70° C. for 2 h. The reaction mixture was cooled to RT and treated with 1-methylcyclopropane-1-sulfonamide (57.9 mg, 0.428 mmol) and DBU (0.064 mL, 0.428 mmol) and heated at 50° C. for 12 h. The reaction mixture was cooled to RT and diluted with EtOAc. The organic layer was separated and washed with 0.5M HCl, water, brine and filtered through anhydrous $Na_2SO_4$. The filtered EtOAc layer was concentrated in vacuo and purified by silica gel using EtOAc/Hexanes to yield I-44 (60 mg) as a colorless solid.

Example 45 tert-Butyl (1aR,3aS,3'R,9S,16aS,Z)-7'-fluoro-5'-methyl-1a-(1-methyl cyclopropylsulfonylcarbamoyl)-3,8-dioxo-1a,1',2,2',3,3a,4,6,8,9,10,11,12,13,14,16a -hexadecahydro-1H-spiro[cyclopropa[e]pyrrolo[1,2-a][1,4]diazacyclopentadecine-5,3'-pyrano[2,3-c]quinoline]-9-ylcarbamate (I-45)

Step 1

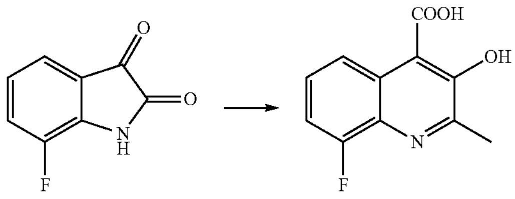 [SMILES: O=C1Nc2c(F)cccc2C1=O ; Cc1nc2c(F)cccc2c(C(=O)O)c1O]

A slurry of 7-fluoroisatin in water was treated with $Ca(OH)_2$ and heated at 80° C. for 1 h. The reaction was then treated with chloroacetone and further heated at 80° C. for 6 h. The reaction mixture was cooled to RT and acidified with aq. HCl (250 ml, 1N). The solid separating out was filtered, washed with water and dried under vacuum to yield the product of Step 1.

Step 2

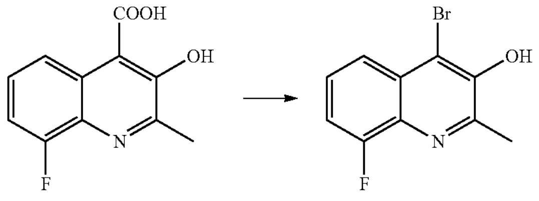 [SMILES: Cc1nc2c(F)cccc2c(C(=O)O)c1O ; Cc1nc2c(F)cccc2c(Br)c1O]

A suspension of the product of Step 1 (7.00 g, 31.6 mmol) in THF (100 mL) was treated with NBS (6.76 g, 38.0 mmol) and stirred at RT for 16 h. The reaction mixture diluted with EtOAc and washed with water. The combined organic layer were dried ($Na_2SO_4$), filtered, concentrated in vacuo and purified by silica gel chromatography (EtOAc/Hexanes) to yield the product of Step 2 (4.5 g, 56%) as a brownish yellow solid.

Step 3

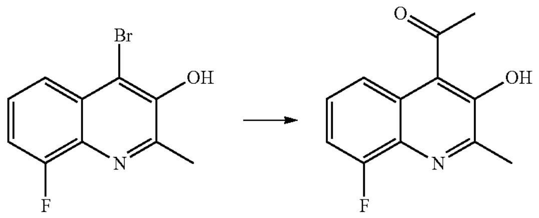 [SMILES: Cc1nc2c(F)cccc2c(Br)c1O ; CC(=O)c1c(O)c(C)nc2c(F)cccc12]

A solution of the product of Step 2 (2.00 g, 7.81 mmol) in dry dioxane (40.0 mL) was treated with tributyl(1-ethoxyvinyl)stannane (5.28 mL, 15.62 mmol), $Pd(PPh_3)_2Cl_2$ (0.548 g, 0.78 mmol) and heated at reflux for 4 h. The reaction mixture was cooled to RT and reacted with 1M aq HCl (40 mL) and stirred at RT for 45 min. The reaction mixture was neutralized with sat. aq. $NaHCO_3$ solution and extracted into EtOAc. The combined organic layers were dried ($Na_2SO_4$), filtered, concentrated in vacuo and purified by silica gel chromatography to yield desired the product of Step 3 (755 mg, 44%).

Step 4

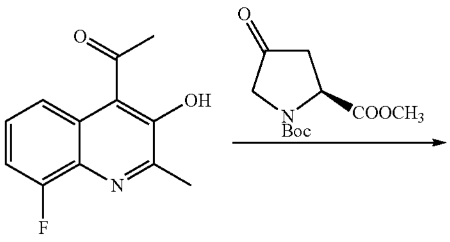

-continued

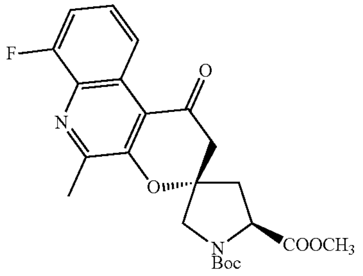

45-4A

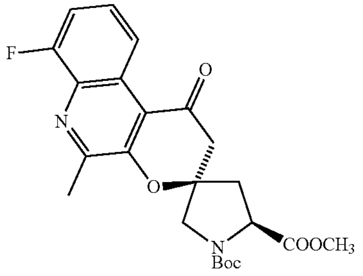

45-4B

A solution of the product of Step 3 (750 mg, 3.42 mmol) in MeOH (15 ml) was treated with (S)-1-tert-butyl 2-methyl 4-oxopyrrolidine-1,2-dicarboxylate (1.66 g, 6.84 mmol) and pyrrolidine (0.283 ml, 3.42 mmol) in a sealed tube. To this was added molecular sieves (750 mg, 4A powder), and the reaction was heated to 105° C. and stirred for 12 h in a sealed tube. The reaction was cooled to RT, and analysis of TLC (EtOAc/Hexanes 30%) indicated complete consumption of starting material. The reaction mixture was filtered, concentrated in vacuo and purified by silica gel chromatography (Hexanes/EtOAc) to yield condensed products 45-4A and 45-4B as inseparable mixture (1.08 g, 71%).

Step 5

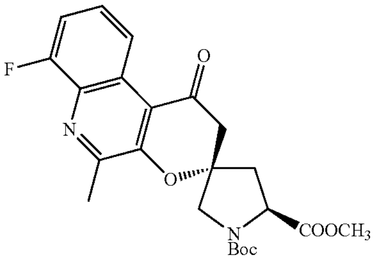

45-4A

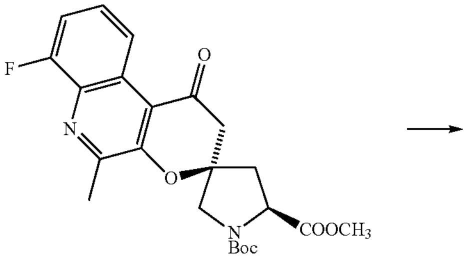

45-4B

-continued

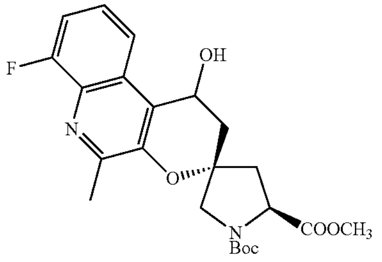

45-5A

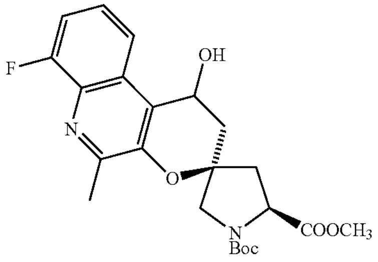

45-5B

A solution of ketones 45-4A and 45-4B (1.08 g, 2.42 mmol) in MeOH (20 ml) was cooled to 0° C. and treated with $NaBH_4$ (92 mg, 2.42 mmol) over 1 min and stirred for 30 min at 0° C. Analysis of TLC (EtOAc/Hexanes 1:1) indicated complete consumption of starting material. The reaction mixture was quenched with sat. aq. $NaHCO_3$, concentrated in vacuo, and residue was taken in EtOAc. The organic layer was washed with water and brine. The combined organic layers were dried, filtered, concentrated in vacuo and purified by silica gel chromatography to yield reduced alcohols 45-5A and 45-5B (878 mg, 81%).

Step 6

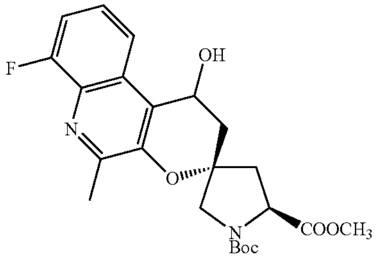

45-5A

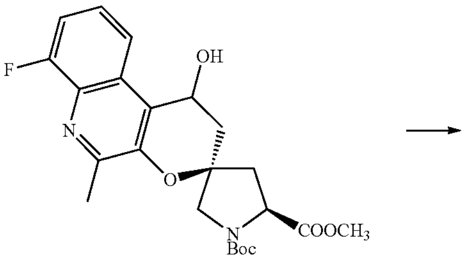

45-5B

-continued

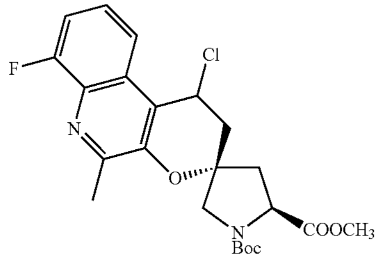

45-6A

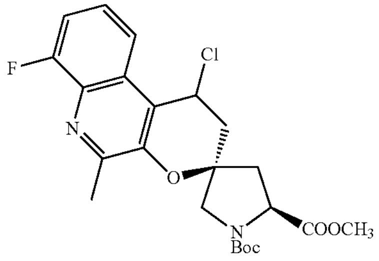

45-6B

A solution of 45-5A and 45-5B (875 mg, 1.96 mmol) in DCM (17 ml) was treated with $Et_3N$ (0.82 ml, 5.88 mmol) then MsCl (0.305 ml, 3.92 mmol) and stirred at RT for 5 h. Analysis of reaction mixture using TLC (EtOAc/Hexanes, 50%) indicated complete consumption of starting material. The reaction mixture was diluted with EtOAc and washed with sat. aq. $NaHCO_3$ solution, water, brine and filtered through anhydrous $Na_2SO_4$. The filtrate was concentrated in vacuo and residue was purified by silica gel chromatography to yield 45-6A and 45-6B (752 mg, 83%) as a pale yellow solid.

Step 7

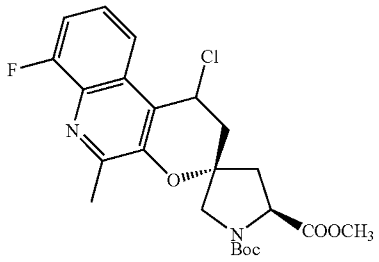

45-6A

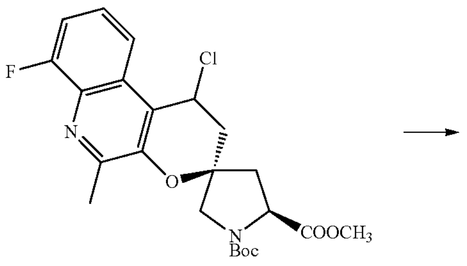

45-6B

-continued

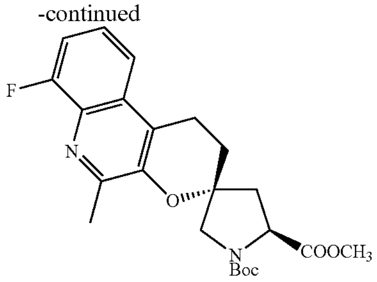

45-7A

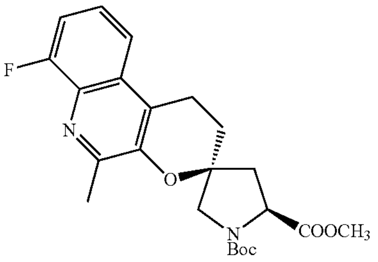

45-7B

A solution of chlorides 45-6A and 45-6B (749 mg, 1.61 mmol) in EtOAc (15 mL) was treated with Pd/C (10% 86 mg) and hydrogenated with balloon pressure RT for 4 h. On completion of the reaction as indicated by TLC (EtOAc/Hexanes 50%), the reaction mixture was diluted with MeOH, filtered, and the filtrate was concentrated in vacuo to yield 45-7A and 45-7B (709 mg) as a yellow orange solid.

Step 8

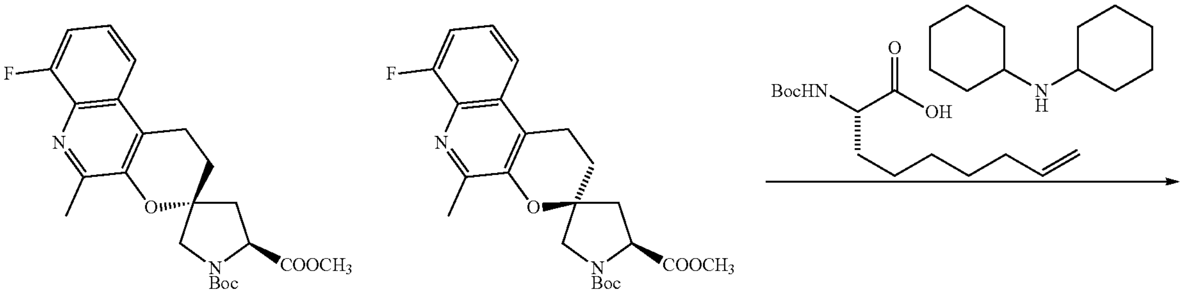

45-7A 45-7B

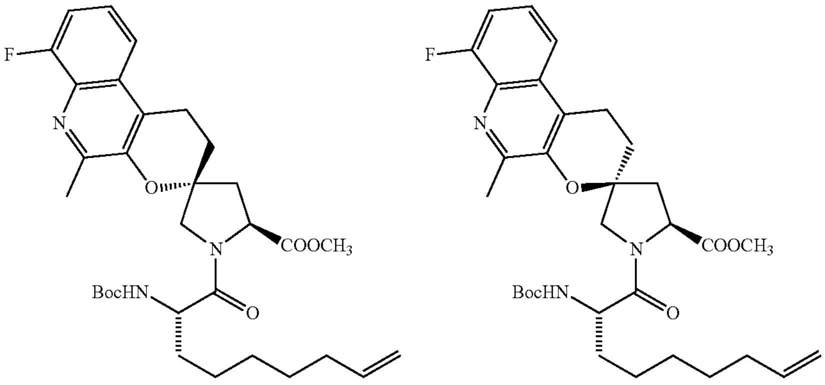

45-8A 45-8B

A solution of compounds 45-7A and 45-7B (943 mg, 2.19 mmol) in DCM (3.38 ml) was cooled to 0° C. and treated with trifluoroacetic acid (3.38 ml, 43.8 mmol) and allowed to warm to RT. The reaction was stirred for 1 h, when TLC (EtOAc/Hexanes 50%) indicated complete consumption of starting material. The reaction mixture was concentrated in vacuo. The mixture was taken in EtOAc and washed with sat. $NaHCO_3$ solution, then 50% water/sat. $NaHCO_3$, brine and dried over $Na_2SO_4$. The reaction mixture was filtered, and the filtrate was concentrated in vacuo to yield deprotected anime (694 mg) that was used in next reaction without further purification.

A solution of amine (691 mg, 2.10 mmol) in DCM (7 ml) and DMF (7 ml) was treated with Hunig's base (1.1 ml, 6.28 mmol), dicyclohexylammonium (S)-2-(tert -butoxycarbonylamino)non-8-enoate (1.14 g, 2.51 mmol) and HATU (954 mg, 2.51 mmol) and stirred at RT for 20 h. The reaction mixture was diluted with EtOAc (300 mL) and washed with water and aq. $NaHCO_3$. The combined organic layers were dried ($Na_2SO_4$), filtered, concentrated in vacuo, and purified by silica gel chromatography to separate the two diastereomers 45-8A and 45-8B yielding desired diastereomer 45-8A as a colorless foam (505 mg, 41%).

Step 9

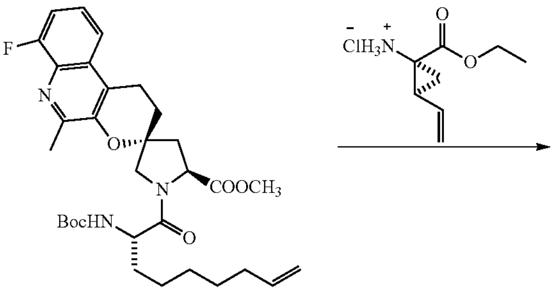

-continued

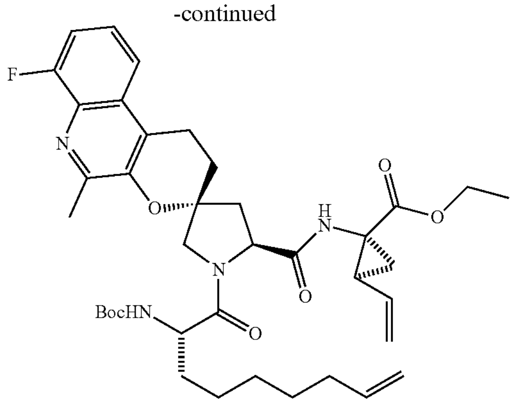

A solution of 45-8A (503 mg, 0.862 mmol) in MeOH (3.5 ml) and THF (5.25 ml) was treated with 2M aq. solution of LiOH (1.30 ml, 2.59 mmol) and heated at 60-65° C. for 1 h. The reaction mixture was acidified with 1N HCl (3.0 mL) and extracted with EtOAc. The combined extracts were washed with brine and filtered through $Na_2SO_4$. The filtrate was concentrated in vacuo to yield carboxylic acid as white foam (491 mg).

A solution of acid (484 mg, 0.850 mmol) in DMF (4 ml) and DCM (4 ml) was treated with Hunig's base (0.666 ml, 3.82 mmol), HATU (420 mg, 1.11 mmol), (1R,2S)-1-(ethoxycarbonyl)-2-vinylcyclopropanaminium chloride (326 mg, 1.70 mmol) and stirred at RT for 15 h. The reaction mixture was concentrated in vacuo and diluted with EtOAc. The combined organic layers were washed with water, 0.5N aq. HCl, brine and filtered through anhydrous $Na_2SO_4$. The filtrate was concentrated in vacuo and purified by silica gel chromatography to yield the product of Step 9 as colorless solid (580 mg).

Step 10

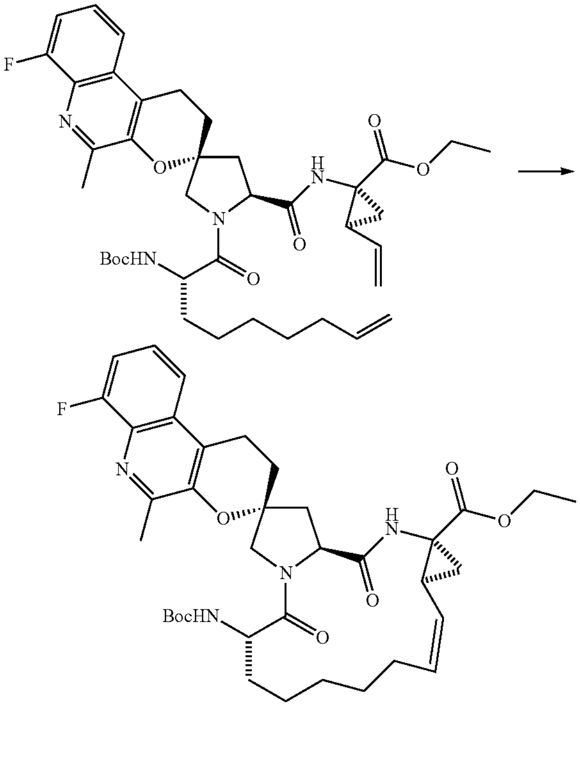

A solution of the product of Step 9 (577 mg, 0.816 mmol) in DCE (180 ml) was degassed, treated with Zhan's catalyst (150 mg, 0.204 mmol), benzoquinone (26.5 mg, 0.245 mmol) and heated at 65° C. for 1 h. The disappearance of starting material was followed by TLC (60% EtOAc/Hexanes). On complete consumption of starting material, the reaction mixture was cooled to RT and quenched with methylvinyl ether (2.0 mL). The reaction mixture was concentrated in vacuo and purified by silica gel chromatography to yield the product of Step 10 as a brown colored solid (263 mg, 48%).

Step 11

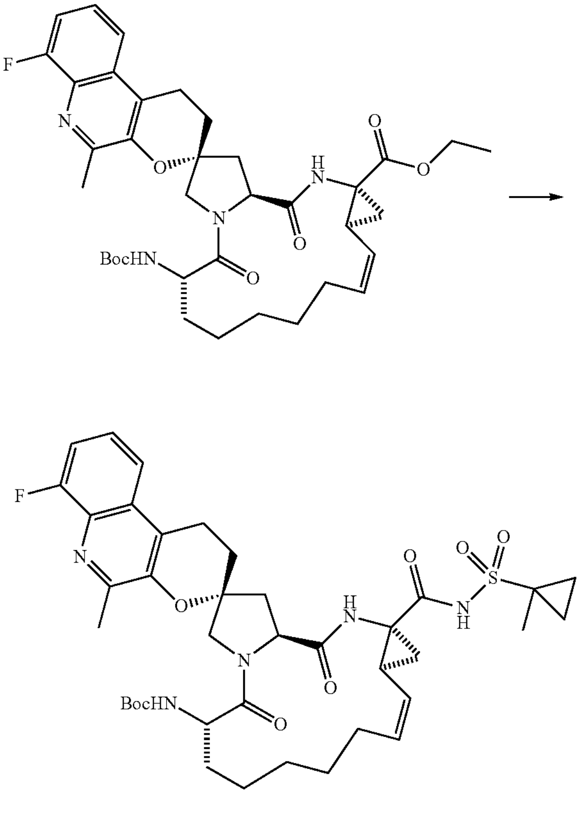

A solution of the product of Step 10 (262 mg, 0.386 mmol) in MeOH (2.0 ml) and THF (3.0 ml) was cooled to 0° C. and treated with 2M aq. solution of LiOH (0.965 ml, 1.93 mmol).

The reaction was allowed to warm to RT and stirred for 22 h. Analysis of TLC with 60% EtOAc/Hexanes indicated all the starting material was consumed. The reaction mixture was acidified with aqueous 0.5N HCl (3.00 mL) and extracted into EtOAc. The combined organic layers were dried, filtered and concentrated in vacuo to yield crude acid (229 mg) as grayish brown solid.

A solution of acid (100 mg, 0.154 mmol) in THF (2 mL) was treated with carbonyl diimidazole (49.8 mg, 0.307 mmol) and heated at 70° C. for 2 h. The reaction mixture was cooled to RT and treated with 1-methylcyclopropane-1-sulfonamide (83 mg, 0.615 mmol) and DBU (92 μl, 0.615 mmol) and heated at 50° C. for 12 h. The reaction mixture was cooled to RT and diluted with EtOAc. The organic layer was separated and washed with 0.5M HCl, water, brine and filtered through anhydrous $Na_2SO_4$. The filtered EtOAc layer was concentrated in vacuo and purified by silica gel using EtOAc/Hexanes to yield I-45 (134 mg).

Example 46 tert-Butyl (1aR,3aS,3'R,9S,16aS,Z)-5'-cyclobutyl-9'-methoxy-1a-(1-methylcyclopropylsulfonylcarbamoyl)-3,8-dioxo-1a,1',2,2',3,3a,4,6,8,9,10,11,12,13,14,16a -hexadecahydro-1H-spiro[cyclopropa[e]pyrrolo[1,2-a][1,4]diazacyclopentadecine-5,3'-pyrano[2,3-c]quinoline]-9-ylcarbamate (I-46)

Step 1

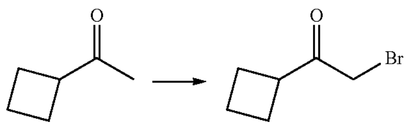

A solution of 1-cyclobutylethanone (5.0 g, 50.1 mmol) in MeOH (50 mL) was treated with bromine (10.0 g, 62.6 mmol) at 0° C. and stirred 1 h at RT. The reaction mixture was extracted in ether (150 mL) washed with aq. $Na_2S_2O_3$. The combined organic layer were dried ($MgSO_4$), filtered, concentrated in vacuo and distilled under reduced pressure to yield the product of Step 1 as colorless oil (5.6 g, 51%) that turns brown on standing.

Step 2

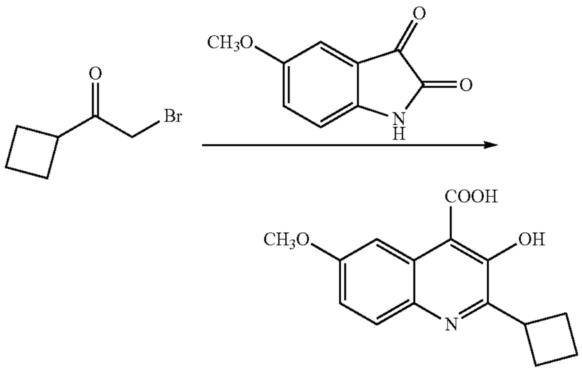

A solution of 5-methoxy-1H-indole-2,3-dione (2.5 g, 14.11 mmol) in water (20.0 mL) was treated with $Ca(OH)_2$ (3.14 g, 42.3 mmol) and heated at 80° C. for 1 h. The reaction mixture was treated with the product of Step 1 (5.00 g, 28.2 mmol) and heated at reflux for additional 8 h. The reaction mixture was cooled and treated with aq. HCl to precipitate the desired product of Step 2 (3.86 g, 99%), which was filtered and used without further purification.

Step 3

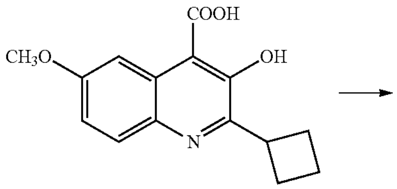

-continued

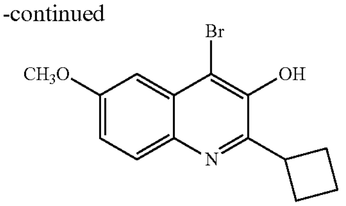

A suspension of the product of Step 2 (3.8 g, 13.9 mmol) in THF (40 mL) and dioxane (50 mL) was treated with NBS (3.13 g, 13.90 mmol) and stirred at RT for 1 h. The reaction mixture was diluted with EtOAc (300 mL) and washed with water. The combined organic layer were dried ($MgSO_4$), filtered, concentrated in vacuo and purified by silica gel chromatography (EtOAc/Hexanes) to yield the product of Step 3 (1.7 g, 40%).

Step 4

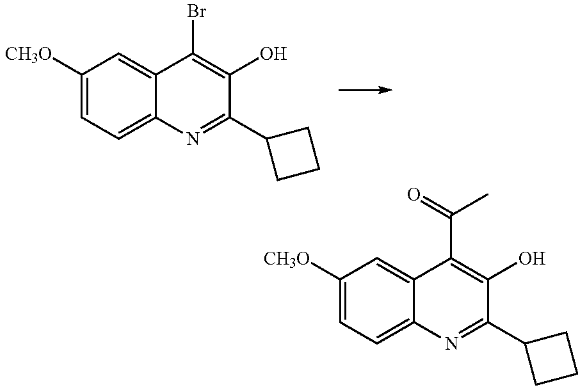

A solution of the product of Step 3 (1.6 g, 5.19 mmol) in dry dioxane (30.0 mL) was treated with tributyl(1-ethoxyvinyl) stannane (4.51 g, 12.98 mmol), $Pd(PPh_3)_2Cl_2$ (0.342 g, 0.779 mmol) and heated at reflux for 4 h. The reaction mixture was cooled to RT and reacted with aq. HCl (30 mL) and stirred at RT for 45 min. The reaction mixture was neutralized with sat. aq. $NaHCO_3$ and extracted into EtOAc. The combined organic layers were dried ($MgSO_4$), filtered, concentrated in vacuo and purified by silica gel chromatography to yield desired product of Step 4 (800 mg, 57%).

Step 5

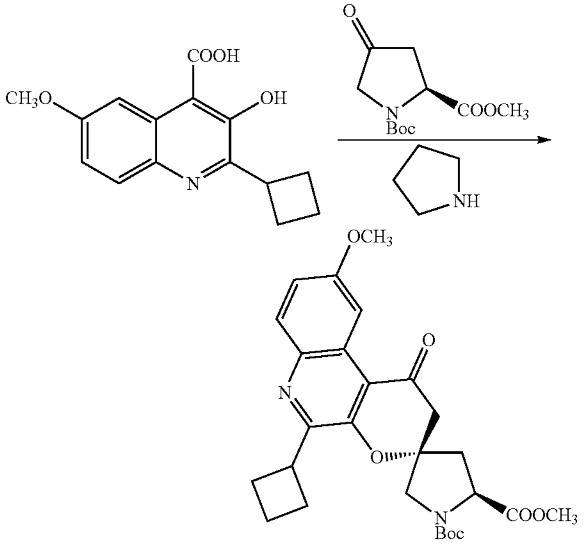

46-5A

-continued

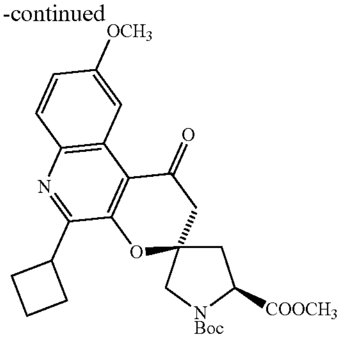

46-5B

A solution of the product of Step 4 (800 mg, 2.95 mmol) and Boc-4-oxo-proline methyl ester (1.44 g, 5.90 mmol) in MeOH (10 mL) was treated with powdered 4A molecular sieves (2.0 g) and pyrrolidine (120 μl, 1.17 mmol) and heated in a microwave at 105° C. for 30 min. The reaction mixture was cooled to RT. The reaction mixture was filtered, concentrated in vacuo and purified by silica gel chromatography using EtOAc/Hexanes to yield cyclized products 46-5A and 46-5B as inseparable mixture of diasteromers (total yield, 674 mg).

Step 6

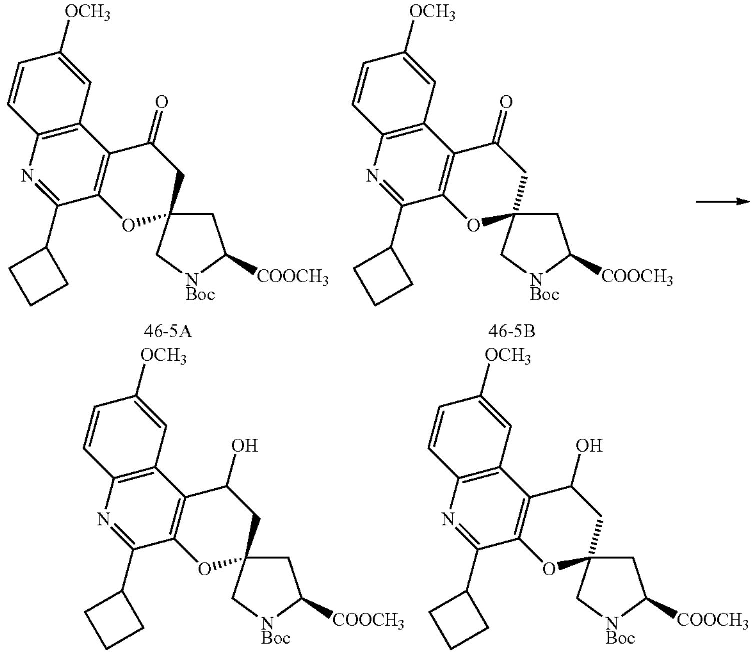

46-5A 46-5B 46-6A 46-6B

A solution of 46-5A and 46-5B (674 mg, 1.36 mmol) were dissolved in MeOH (10 mL) and cooled to 0° C. To this mixture was added $NaBH_4$ (51.4 mg, 1.36 mmol) and stirred at 0° C. for 20 min. The reaction mixture was diluted with aq. $NaHCO_3$ and was extracted into EtOAc (250 mL). The combined organic layer were dried ($MgSO_4$), filtered, concentrated in vacuo and purified by silica gel chromatography using EtOAc/Hexanes to yield reduced products 46-6A and 46-6B as mixture (556 mg, 82%).

Step 7

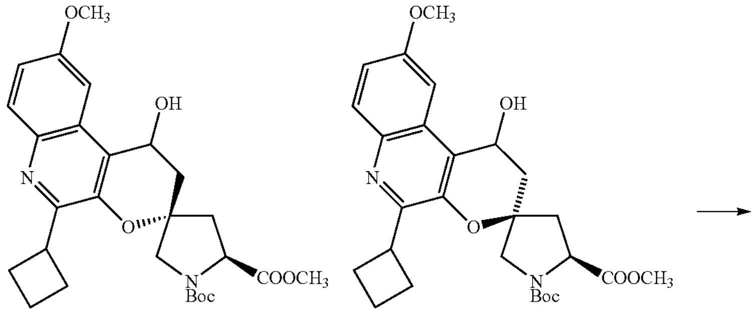

46-6A 46-6B

-continued

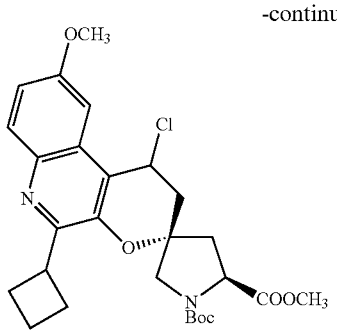

46-7A

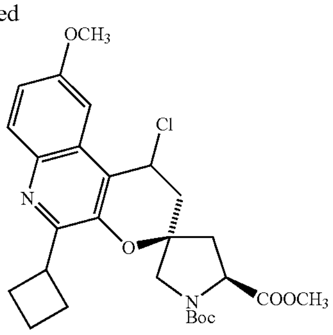

46-7B

A solution of 46-6A and 46-6B (556 mg, 1.12 mmol) in DCM (10 mL) was cooled to 0° C. and treated with $Et_3N$ (0.403 mL, 282 mg) and MsCl (0.267 mL, 255 mg) and stirred overnight when the ice bath slowly warmed-up to RT. The ice bath was removed, and the reaction mixture was allowed to stir at RT. The reaction mixture was quenched with aq. $NaHCO_3$, and extracted into EtOAc. The combined organic layer was dried, ($MgSO_4$), filtered, and concentrated in vacuo. The residue containing 46-7A and 46-7B was used as is (crude yield 610 mg).

Step 8

A solution of 46-7A and 46-7B (crude 610 mg) were taken in EtOAc (25 mL) and treated with Pd/C (10%, 126 mg) and hydrogenated for 0.5 h at 1 atm. On completion of the reaction as indicated by TLC, the reaction mixture was filtered through a plug of CELITE. The solid cake was washed with DCM and concentrated in vacuo. The crude mixture was purified by silica gel chromatography (DCM, MeOH) to yield reduced products 46-8A and 46-8B (580 mg).

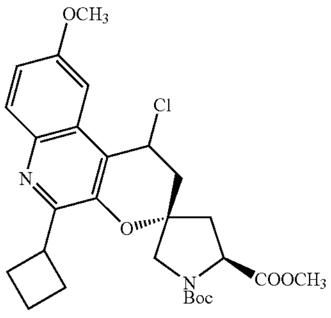

46-7A

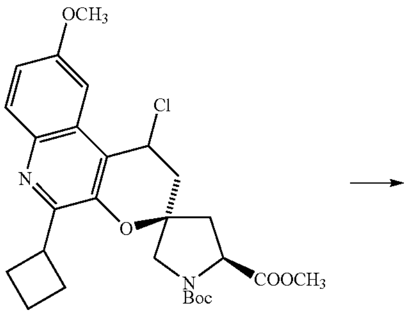

46-7B

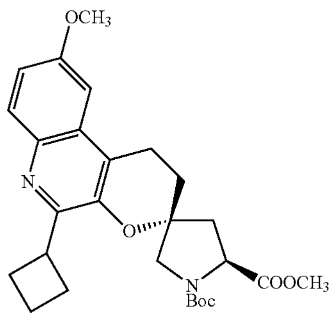

46-8A

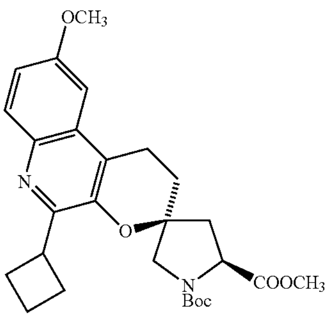

46-8B

Step 9
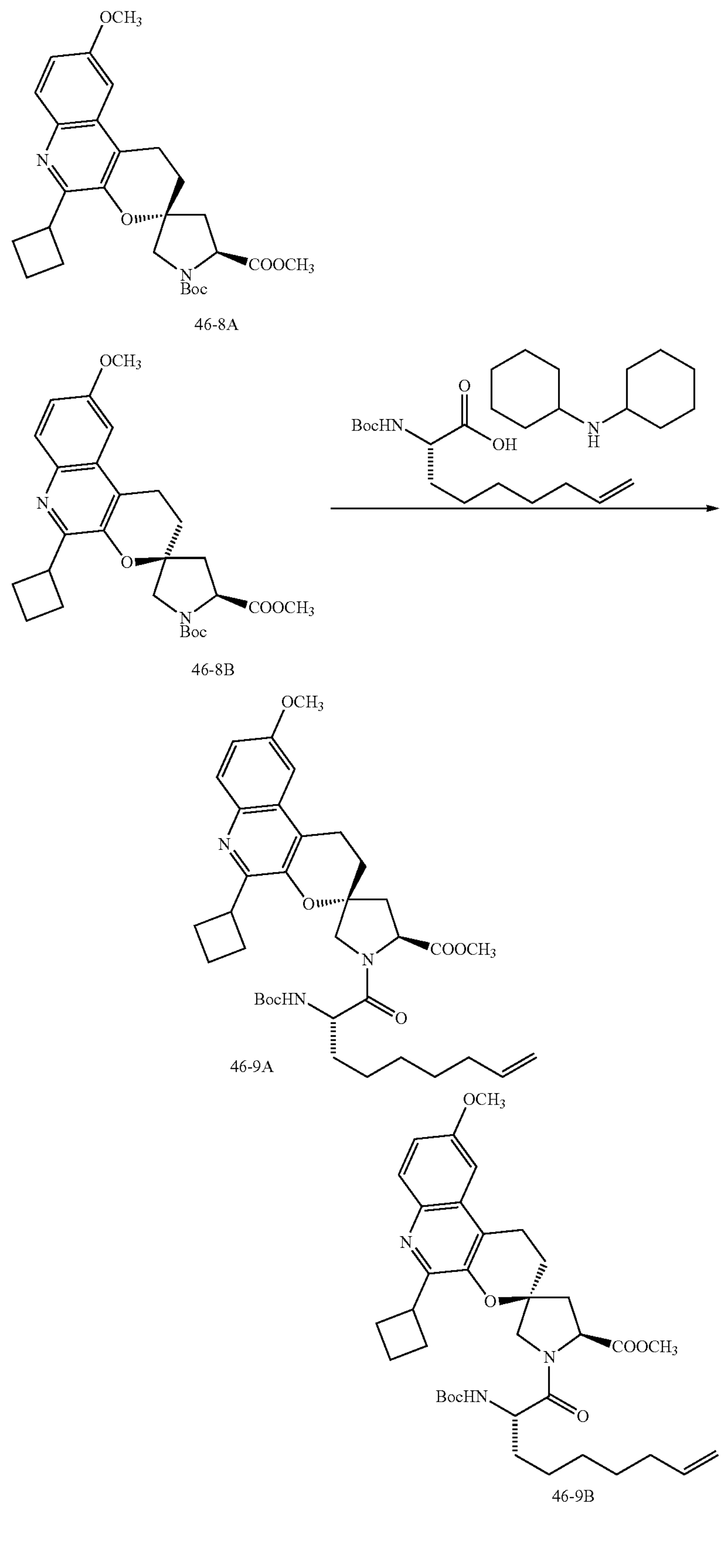
46-8A
46-8B
46-9A
46-9B

A solution of Boc-protected compounds 46-8A and 46-8B (600 g, 1.24 mmol) in 4M HCl in dioxane (15 mL) was stirred at RT for 1 h. The reaction mixture was concentrated in vacuo. The residue obtained was used without further purification.

A solution of acid (773 mg, 1.71 mmol), amine salt (550 mg, 1.31 mmol), HATU (749 mg, 1.97 mmol) in DMF and DCM (5 mL each) was treated with Hunig's base (679 mg, 5.25 mmol) and stirred at RT for 12 h. The reaction mixture was diluted with EtOAc (250 mL) and washed with water and aq. $NaHCO_3$. The combined organic layers were dried ($MgSO_4$), filtered, concentrated in vacuo, and purified by silica gel chromatography to separate two diasteromers 46-9A (400 mg) and 46-9B (201 mg) as colorless foam.

Step 10

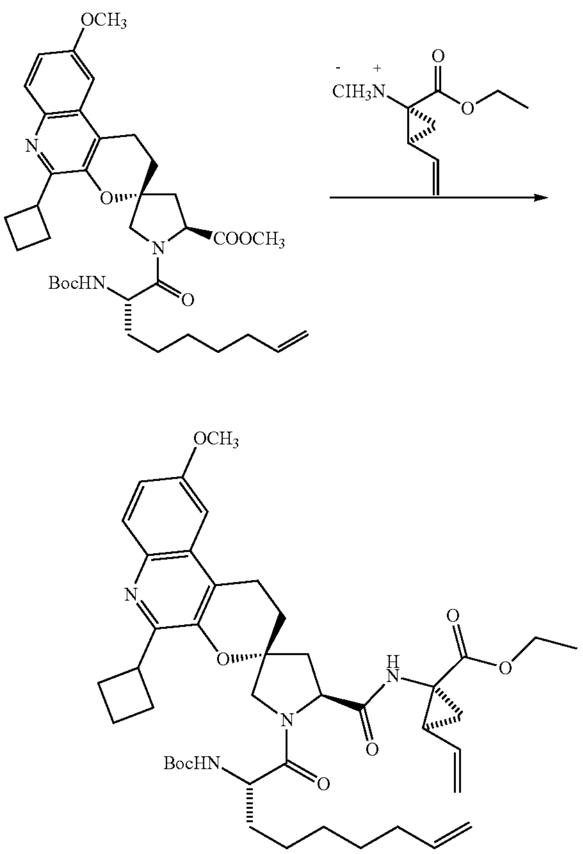

A solution of 46-9A (400 mg, 0.629 mmol) in MeOH, water, and THF (5.0 mL each) was treated with LiOH and stirred at 70° C. for 1 h. The reaction mixture was acidified with aq. HCl (1M) and extracted into EtOAc (250 mL). The organic layers were dried ($MgSO_4$), filtered concentrated in vacuo and used as is.

A solution of acid (300 g, 0.482 mmol) in DMF and DCM (5.00 mL each) was treated with amine salt (139 mg, 0.724 mmol), HATU (275 mg, 0.724 mmol) and Hunigs base (249 mg, 1.93 mmol) and stirred at RT for 12 h. The reaction mixture was diluted with aq. $NaHCO_3$ and extracted into EtOAc. The combined organic layers were dried ($MgSO_4$), filtered concentrated in vacuo and purified by chromatography ($SiO_2$, EtOAc/Hexanes) to yield coupled product of Step 10 as a colorless foam (340 mg, 93%).

Step 11

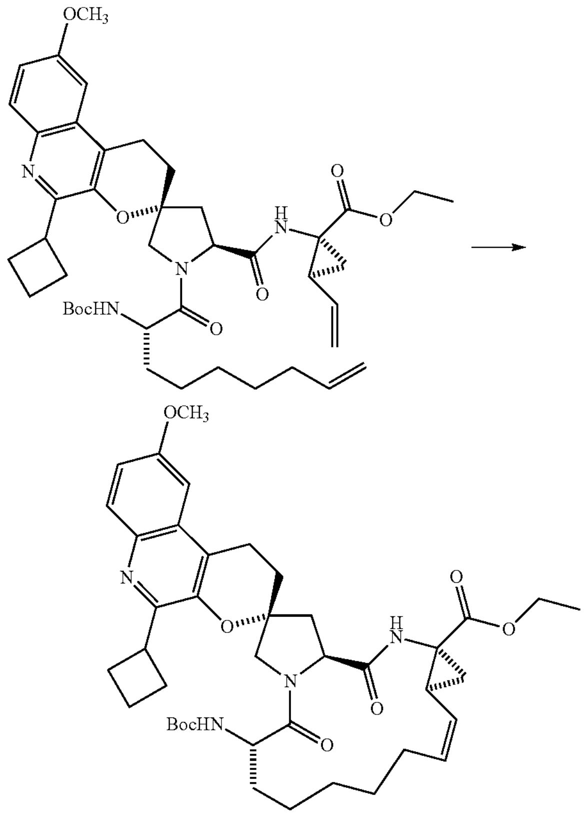

A solution of the product of Step 10 (340 mg, 0.45 mmol) in DCE (100 mL) was degassed and treated with Zhan's catalyst (82 mg, 0.112 mmol) and benzoquinone (14.5 mg, 0.134 mmol) and heated at 70° C. for 2.2 h. The disappearance of starting material was followed by TLC. On complete consumption of starting material as indicated by TLC, the reaction mixture was quenched with methylvinyl ether (1.00 mL), concentrated in vacuo and purified by silica gel chromatography (Hexanes, EtOAc) to yield the product of Step 11 cyclized product. (233 mg, 72%).

Step 12

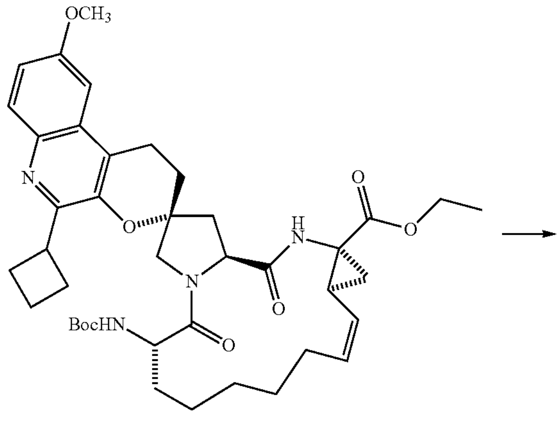

-continued

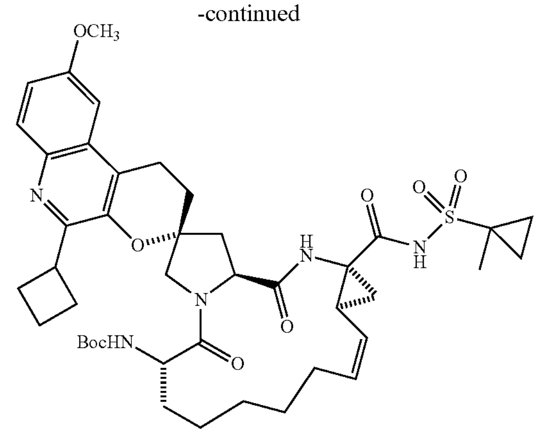

A solution of the product of Step 11 (230 mg, 0.315 mmol) in MeOH (3.0 ml), THF (3.0 ml) and water (3.00 mL) was treated with LiOH (38 mg, 1.57 mmol). The reaction mixture was stirred at RT overnight. Analysis of TLC (EtOAc/Hexanes, 60%) indicated all the starting material was consumed. The reaction mixture was acidified with 1M HCl (2.00 mL) and extracted into EtOAc. The combined organic layers were dried ($MgSO_4$), filtered and concentrated in vacuo to yield crude acid (313 mg).

A solution of acid (220 mg, 0.313 mmol) in THF (4 mL) was treated with carbonyl diimidazole (102 mg, 0.626 mmol) and heated at 70° C. for 2 h. The reaction mixture was cooled to RT and treated with 1-methylcyclopropane-1-sulfonamide (169 mg, 1.25 mmol) and DBU (191 mg, 1.25 mmol) and heated at 70° C. for 12 h. The reaction mixture was cooled to RT and diluted with EtOAc and treated with 1 mL of AcOH. The organic layer was separated and washed with water, brine, dried ($MgSO_4$) and filtered. The filtered EtOAc layer was concentrated in vacuo and purified by silica gel using EtOAc/Hexanes to yield I-46 (213 mg, 68%).

Example 47 tert-Butyl ((2R,6S,13aS,14aR,16aS,Z)-5'-methyl-14a-(((1-methylcyclopropyl) sulfonyl)carbamoyl)-5,16-dioxo-1',2',3,5,6,7,8,9,10,11,13a,14,14a,15,16,16a-hexadecahydro -1H-spiro[cyclopropa[e]pyrrolo[1,2-a][1,4]diazacyclopentadecine-2,3'-pyrano[2,3-c]quinolin]-6-yl)carbamate (I-47)

Step 1

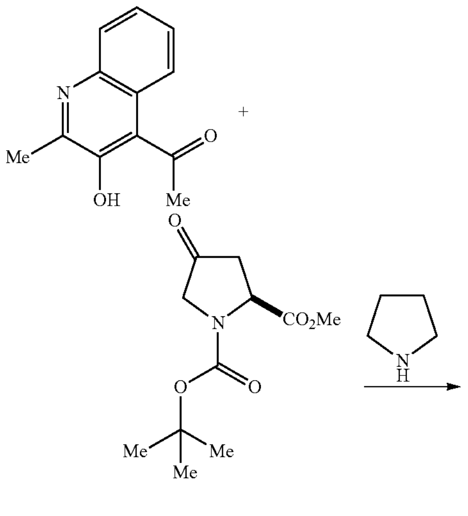

-continued

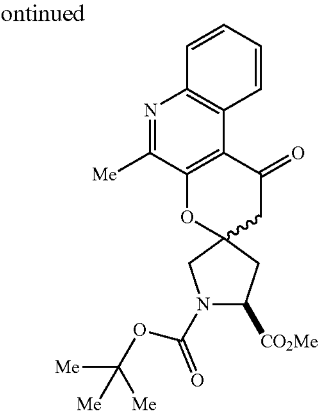

Boc-γ-keto-L-proline methyl ester (9.67 g, 39.8 mmol), 2-methyl-3-hydroxy-4-acylquinoline (5 g, 24.85 mmol) and pyrrolidine (0.822 ml, 9.94 mmol) were combined in MeOH (62.1 ml) in a sealed tube. To this was added dry molecular sieves, and the mixture was heated at 105° C. for 60 min. The mixture was filtered and concentrated. The residue was purified by column chromatography on silica gel eluting with EtOAc/isohexane (0-80%) to give a mixture of the product of Step 1 (10.22 g, 23.96 mmol, 96% yield) as a yellow solid.

Step 2

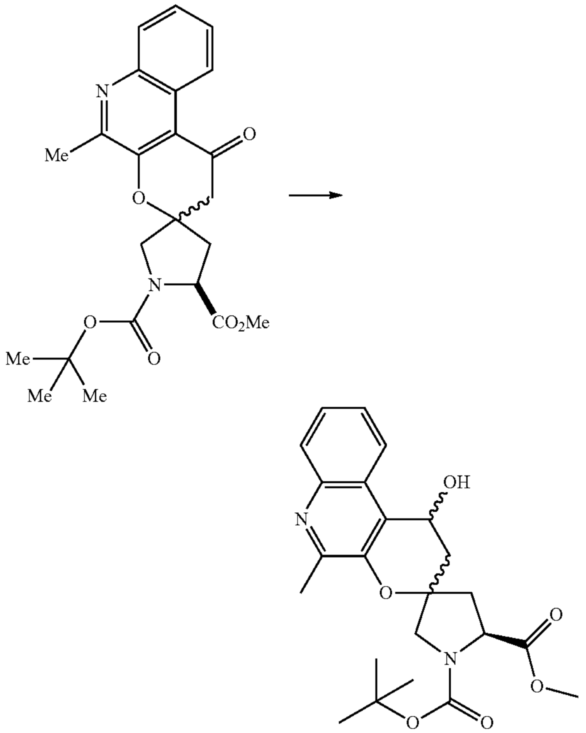

The product of Step 1 (10.22 g, 23.96 mmol) was dissolved in THF (59.9 ml) and MeOH (59.9 ml). The mixture was cooled to 0° C. $NaBH_4$ (0.92 g, 24.32 mmol) was added portionwise, and the mixture was stirred for 15 min at 0° C. The reaction was then stirred at RT for 1 h. The mixture was quenched and stirred with aq. $NH_4Cl$ (100 ml) and EtOAc (200 ml) at 0° C. for 30 min. The aq. layer was separated and extracted with EtOAc (100 ml). The combined organic fractions were washed with brine (50 ml), dried ($MgSO_4$), filtered, and the solvent was evaporated under reduced pressure. The residue was purified by column chromatography on silica gel eluting with EtOAc/DCM (0-80%) to give the product of Step 2 (13.07 g, 27.8 mmol, 116% yield) as an off-white solid.

Step 3

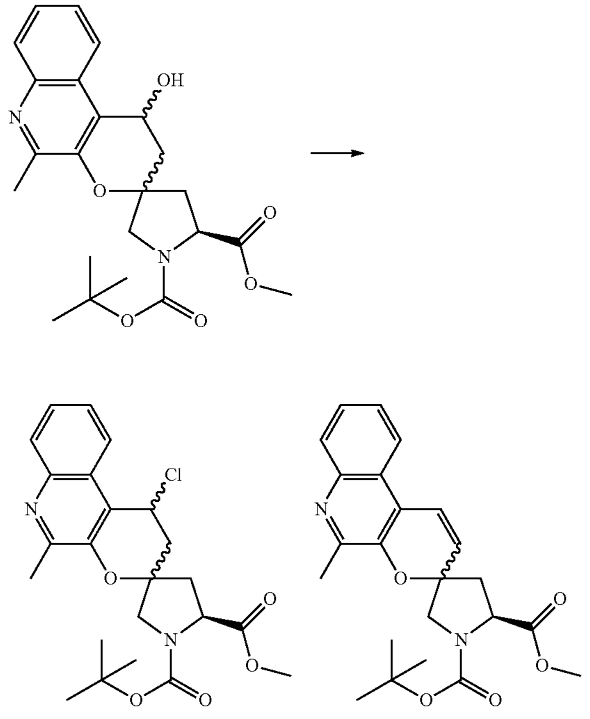

47-3A 47-3B

MsCl (3.54 ml, 45.8 mmol) was added to a mixture of the product of Step 2 13.07 g, 30.5 mmol) and TEA (8.48 ml, 61.0 mmol) in DCM (200 ml) at RT, and the resulting solution was stirred overnight at RT.

Aq. $NH_4Cl$ (sat., 100 mL) was added, and the mixture was extracted with DCM (100 mL). The organic fraction was separated, and the solvent was evaporated under reduced pressure. The residue was purified by column chromatography on silica gel eluting with EtOAc/hexanes (0% to 100%) to give compound 47-3A (8.37 g, 18.73 mmol, 61.4% yield) as a light-yellow solid along with small amounts 47-3B.

Step 4

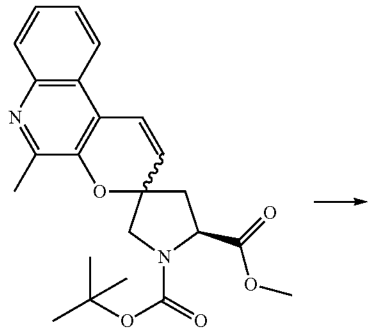

-continued

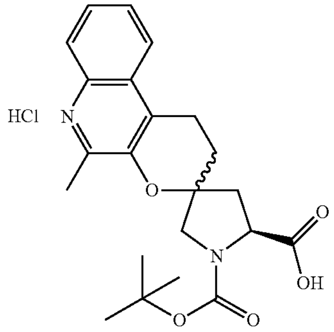

A solution of compound 47-3B (8.37 g, 18.73 mmol) in EtOAc (187 ml) was hydrogenated over Pd/C (0.997 g, 0.936 mmol) at RT under an $H_2$ balloon overnight. The mixture was filtered. The insolubles were washed with EtOAc and MeOH. The filtrates were evaporated under reduced pressure to give the product of Step 4 (8.19 g, 18.24 mmol, 97% yield) as yellow solids.

Step 5

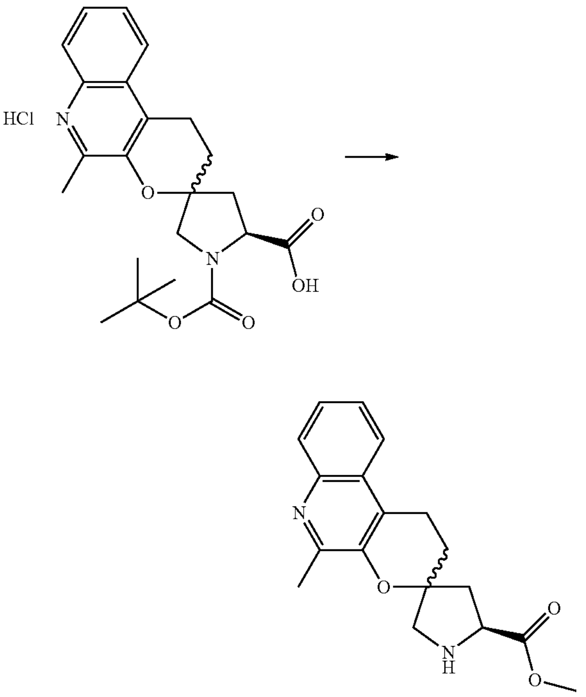

TFA (61.2 mL, 794 mmol) was added to a solution of the product of Step 4 (8.19 g, 19.86 mmol) in DCM (120 mL) at RT and stirred for 2 h. The solution was concentrated. The residue was diluted with DCM and washed with aq. $NaHCO_3$. The aq. layer was separated and extracted with DCM. The organic layers were combined, dried ($MgSO_4$), filtered and the solvent was evaporated under reduced pressure to give the product of Step 5 (5.4 g, 17.29 mmol, 87% yield) as yellow foam.

Step 6

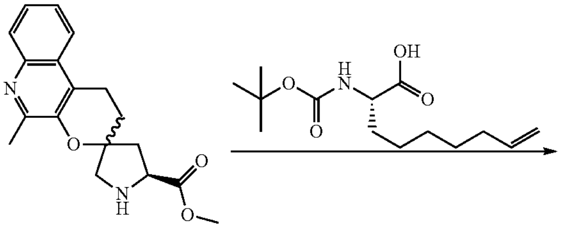

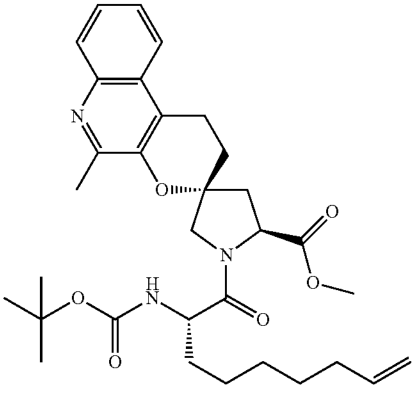

47-6A

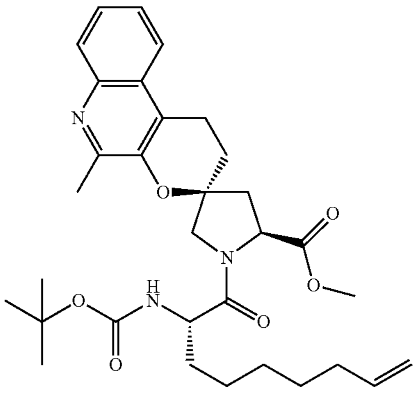

47-6B

The product of Step 5 (5.4 g, 17.29 mmol), the dihexyl amine salt of (S)-2-(tert -butoxycarbonylamino)non-8-enoic acid (11.74 g, 25.9 mmol), and HATU (13.15 g, 34.6 mmol) were dissolved in DMF (200 ml). To this solution was added DIEA (5.71 ml, 34.6 mmol). The reaction was stirred at RT overnight. The mixture was diluted with water and extracted with $Et_2O$. The combined organics were washed with brine (250 mL), dried ($MgSO_4$), filtered, and the solvent was evaporated under reduced pressure. The residue was purified by column chromatography on silica gel eluting with EtOAc/isohexane (0-100%) to give first compound 47-6A (3.44 g, 6.08 mmol, 35.2% yield) as off-white foam and then compound 47-6B (3.18 g, 5.62 mmol, 32.5% yield) as tan foam.

Step 7

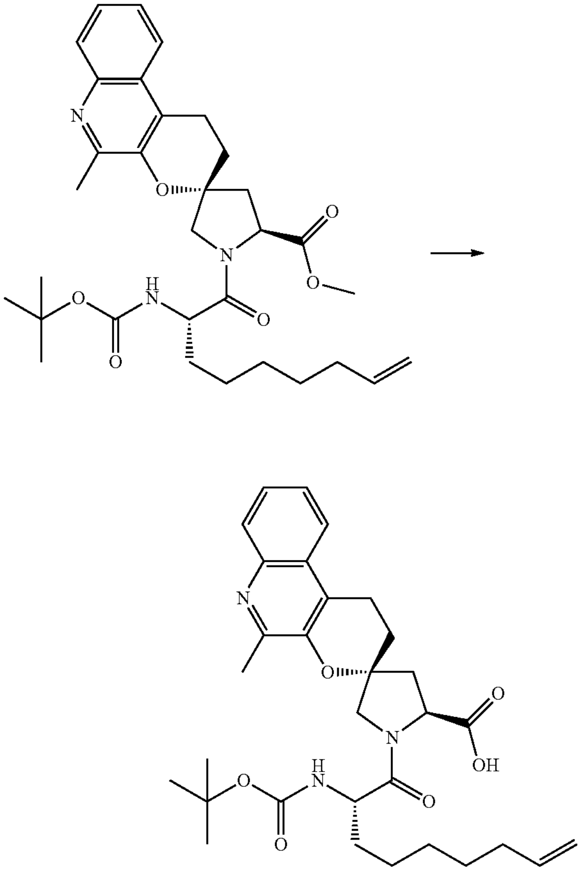

Compound 47-6A (1.71 g, 3.02 mmol) was dissolved in THF (15.00 mL) and MeOH (15 mL). NaOH (10% aq., 15 mL, 41.3 mmol) was added and stirred at RT for 2.5 h. The mixture was diluted with brine, acidified with 10% HCl (15.01 ml) to pH 3-5, and extracted with EtOAc. The aq. layer was extracted with EtOAc. The combined organic layers were washed with brine, dried ($MgSO_4$), filtered, and concentrated to give the product of Step 7 (1.68 g).

Step 8

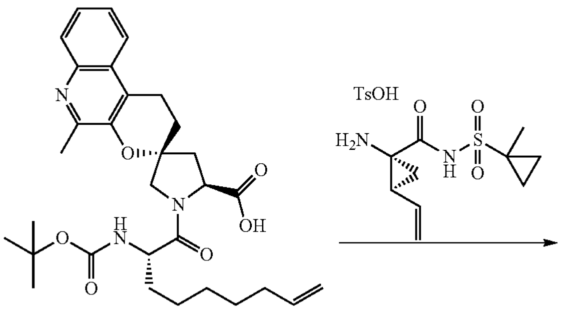

-continued

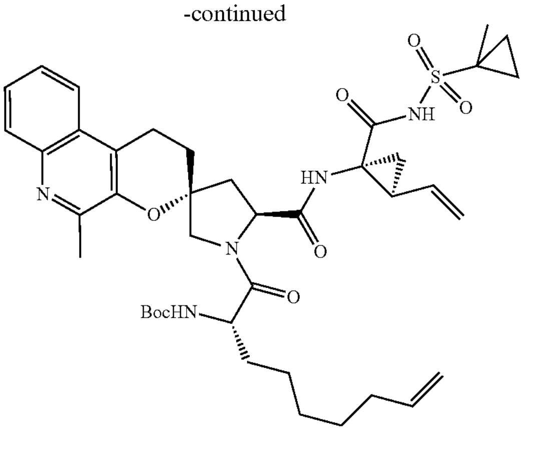

A mixture of the product of Step 7 (1.68 g, 3.05 mmol), (1R,2S)-1-amino-N-(1-methylcyclopropylsulfonyl)-2-vinylcyclopropanecarboxamide 4-methylbenzenesulfonate (1.903 g, 4.57 mmol), HATU (1.853 g, 4.87 mmol), and TEA (1.698 ml, 12.18 mmol) in DMF (30.5 ml) was stirred for 4 h at RT. The mixture was diluted with EtOAc (300 ml), washed with water and brine, dried over $MgSO_4$, filtered, and concentrated. The residue was purified by column chromatography on silica gel eluting with MeOH-DCM 0-6% to give the product of Step 8 (2.36 g, 3.03 mmol, 100% yield) as off-white foam.

Step 9

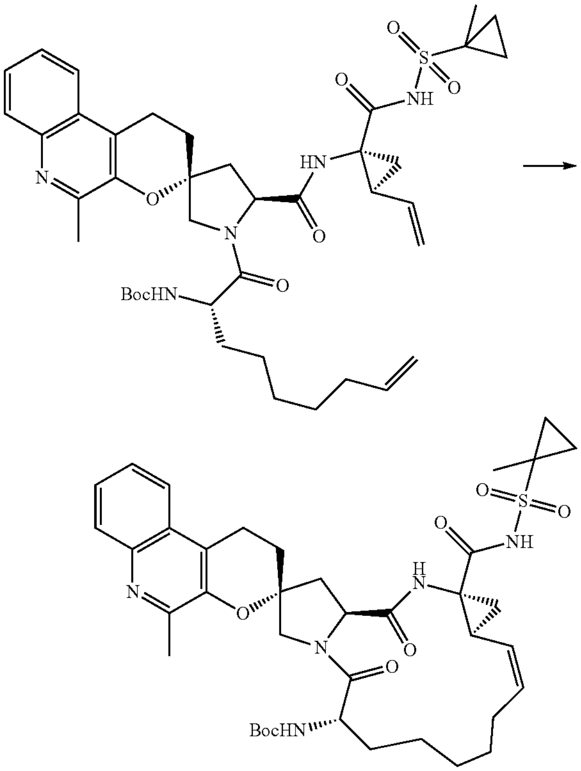

A solution of the product of Step 8 (0.99 g, 1.273 mmol), Zhan's catalyst (0.196 g, 0.267 mmol), and p-benzoquinone (0.055 g, 0.509 mmol) in DCE (509 ml) was heated at 65° C. for 7 h. The solution was cooled to RT, quenched with butyl vinyl ether (5 mL) and stirred for 15 min. Then it was washed with aq. $NH_4Cl$ (sat.), dried ($MgSO_4$), filtered, and concentrated. The residue was purified by column chromatography on silica gel eluting with 0-60% acetone/hexanes to give the product of Step 9 (600 mg, 0.800 mmol, 62.9% yield) as a brown resin. LC-MS $MH^+$: 750.

Step 10

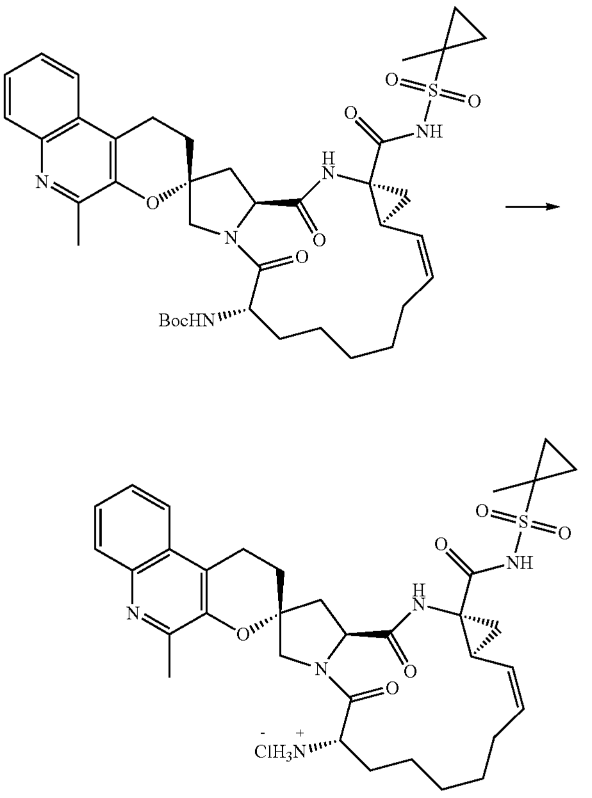

To a flask containing the product of Step 9 (600 mg, 0.800 mmol) was added HCl in dioxane (20 ml, 80 mmol), and the mixture was stirred at RT for 1.5 h. The mixture was triturated with 100 ml hexane and allowed to settle. The clear solvent was decanted. The residue was evaporated 3× with toluene to give the crude product of Step 10 (627 mg, 0.914 mmol, 114% yield) as a tan solid. This material was used for next step reaction without further purification.

Step 11

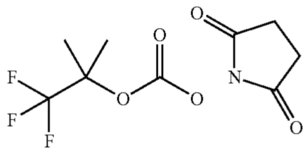

To a mixture of 2-trifluoromethyl-2-propanol (1.84 g, 14.36 mmol) and N,N'-disuccinimidyl carbonate (5.52 g, 21.55 mmol) in MeCN (71.8 ml) was added TEA (6.01 ml, 43.1 mmol). The resulting solution was stirred overnight at RT. The solution was diluted with EtOAc, washed with brine, dried, and evaporated to dryness to give the product of Step 11 (2.17 g, 8.06 mmol, 56.1% yield) as a tan solid.

Step 12

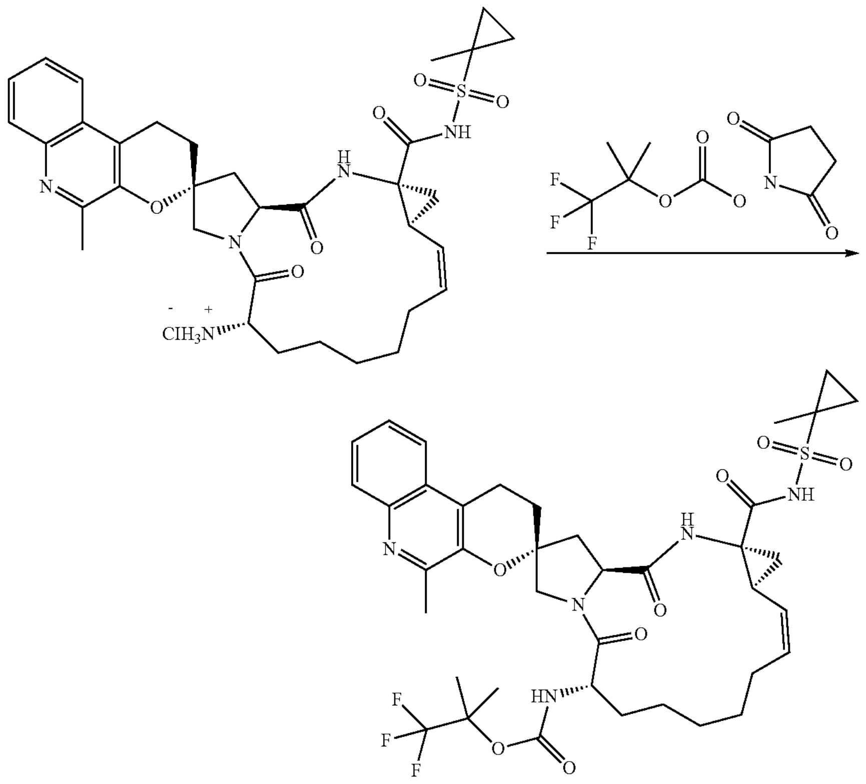

To a suspension of the product of Step 10 (59 mg, 0.086 mmol) and the product of Step 11 (93 mg, 0.344 mmol) in DCM (1.5 ml) was added TEA (0.060 ml, 0.430 mmol). The mixture was stirred at RT overnight. It was diluted with DCM, washed with aq. $NH_4Cl$, concentrated, and separated by preparative TLC with 5% MeOH/DCM to give I-47 (24.7 mg, 35.7%) as a white solid. LC-MS $MH^+$: 804.

Similar protocols were used for preparing derivatives of the product of Step 10 as amides and sulfonamides by the treatment with acid chlorides and sulfonyl chlorides. Alternatively, the product of Step 10 may be coupled with acids to yield amides using standard peptide coupling agents. Similarly, treatment of amine salts with TEA and isocyanates allows formation of ureas that may be purified in a similar manner.

Example 48

Neopentyl((2R,6S,13aS,14aR,16aS,Z)-9'-methoxy-14a-(((1-methyl cyclopropyl)sulfonyl)carbamoyl)-5,16-dioxo-5'-(2,2,2-trifluoroethyl)-1',2',3,5,6,7,8,9,10,11,13a,14,14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I-48)

Step 1

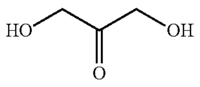

-continued

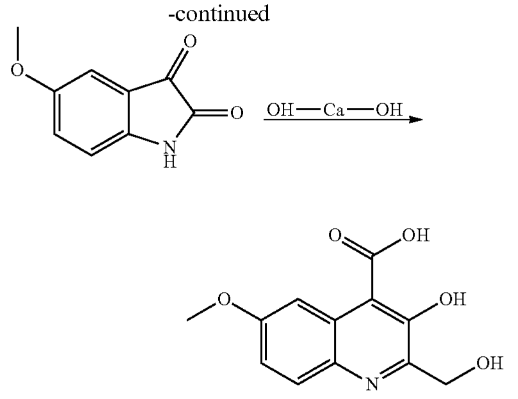

To 5-methoxyisatin (30 g, 169 mmol) in water (1000 ml) was added $Ca(OH)_2$ (37.6 g, 508 mmol), and the mixture was heated to 80° C. while stirring under $N_2$ for 1 h. 1,3-Dihydroxyacetone (30.5 g, 339 mmol) was then added, and the mixture was stirred fro another 3 h. After allowing the mixture to cool to about 50° C., 80 ml of concentrated aq. HCl was added, and the mixture was stirred overnight. The mixture was cooled in a freezer to near 0° C., then the solid collected by vacuum filtration. The solid was dried in a vacuum oven at 70° C. for 7 h, then at RT over 2 d. The product of Step 1 (41.15 g, 165 mmol, 98% yield) was obtained as a reddish brown solid.

Step 2

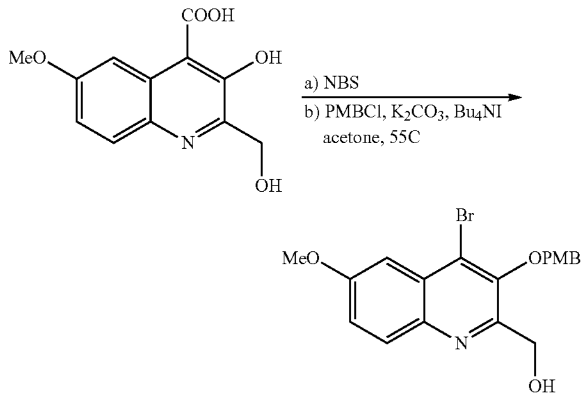

NBS (23.40 g, 131 mmol) was added in portions to a stirred, cooled −10° C. mixture of the product of Step 1 (32.77 g, 131 mmol) in THF over 1.5 h. The mixture was stirred for 1 h at −10° C. under $N_2$. The reaction mixture was poured onto aq. $Na_2S_2O_3$ and extracted (3×) with EtOAc. The combined extracts were washed with brine, dried with $MgSO_4$, filtered and evaporated to dryness. The crude product was dry-loaded onto silica gel and purified in two batches (EtOAc/hexanes, 0-60%). 17.9 g of bromide was obtained (47.9% yield).

The product of bromide (10.79 g, 38 mmol), $K_2CO_3$ (15.75 g, 114 mmol) and $Bu_4NI$ (4.21 g, 11.39 mmol) were slurried in acetone (108 mL). PMB-Cl(6.21 mL, 45.6 mmol) was added, and the mixture was heated at 55° C. for 1 h. The reaction was then cooled, poured into water (100 mL) and EtOAc (400 mL), and the layers were separated. The organic layers was washed with brine (100 mL), dried over $MgSO_4$ and concentrated to an orange solid. The material was purified on silica gel using a gradient of 0-30% EtOAc in hexane to give 11.5 g of the product of Step 2 in 75% yield.

Step 3

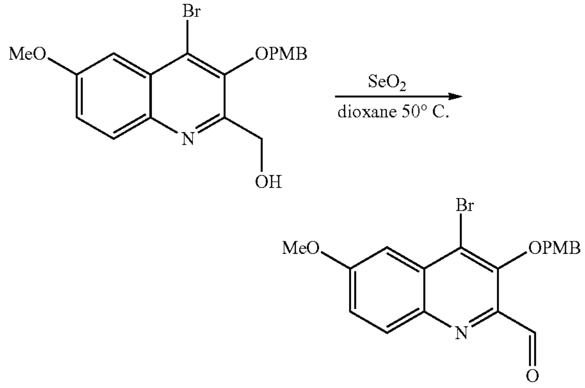

The product of Step 2 (6.0 g, 14.84 mmol) was dissolved in dioxane (95 mL), $SeO_2$ (1.65 g, 14.84 mmol) was added, and the slurry was heated to 50° C. for 1 h. After cooling, the inorganic solids were filtered off and washed with EtOAc. The filtrate was concentrated to yield 5.0 g pure product of Step 3 in 84% yield.

Step 4

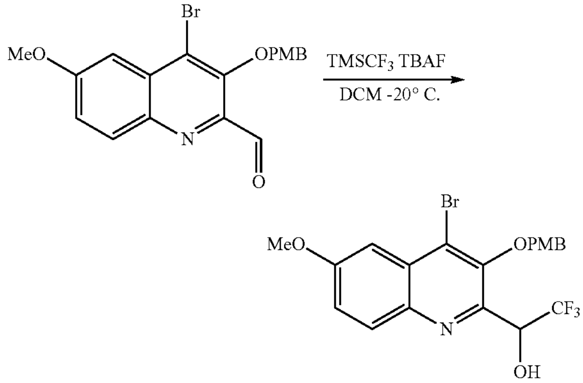

To a solution of the product of Step 3 (3.2 g, 7.95 mmol) in DCM (60 mL) was added CsF (1.2 g, 19.5 mmol) and molecular sieves (1 g, 4A). The mixture was cooled to −20° C. and aged 20 min. $TMSCF_3$ (4.0 mL, 7.95 mmol, 2.0M THF) was added, and after no reaction was observed, additional $TMSCF_3$ (2.0 mL, 4.0 mmol, 2.0M THF) and TBAF (4.0 mL, 4.0 mmol, 1.0M THF) were added concurrently dropwise, resulting in complete conversion to product. The mixture was warmed to RT and filtered, washing with DCM. The filtrate was washed with saturated $NH_4Cl$ and purified on silica gel using a gradient of 0-40% EtOAc in hexane to give 3.3 g desired product of Step 4 in 88% yield.

Step 5

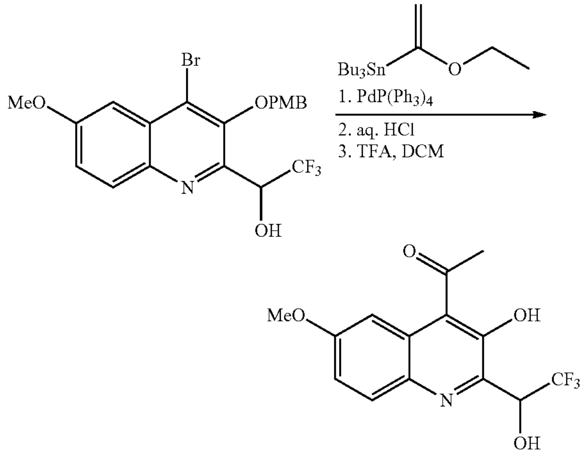

A flask containing a solution of the product of Step 4 (2.8 g, 593 mmol) and tributyl(1-ethoxyvinyl)tin (4.28 g, 11.86 mmol) in dioxane (56 mL) was 3× evacuated and backfilled with $N_2$ to remove oxygen. $Pd(P(Ph)_3)_4$ (685 mg, 0.593 mmol) was added, and the degas sequence was repeated. The reaction was heated at 105° C. for 16 h, giving complete conversion to the enol intermediate. The reaction was then cooled to RT and aged with aq. HCl (20 mL, 2N) for 4 h to unmask the ketone. The mixture was then poured into sat. $NaHCO_3$ (50 mL) and EtOAc (50 mL), the aq. was separated, and the organic was washed with brine, dried over $MgSO_4$ and concentrated to an oil, which contained both PMB- and des-PMB product. Tin reagent was removed by a silica column using 0-25% EtOAc in hexane, and the resulting solid was slurried in DCM and aged with TFA (0.914 mL, 11.86 mmol) for 1 h. After flushing 3× with DCM, $NaHCO_3$ was added to obtain pH ~5. The organic was dried over $MgSO_4$ and purified by silica column using 0-40% EtOAc in hexane to give 1.2 g of the product of Step 5 in 64% yield.

Step 6

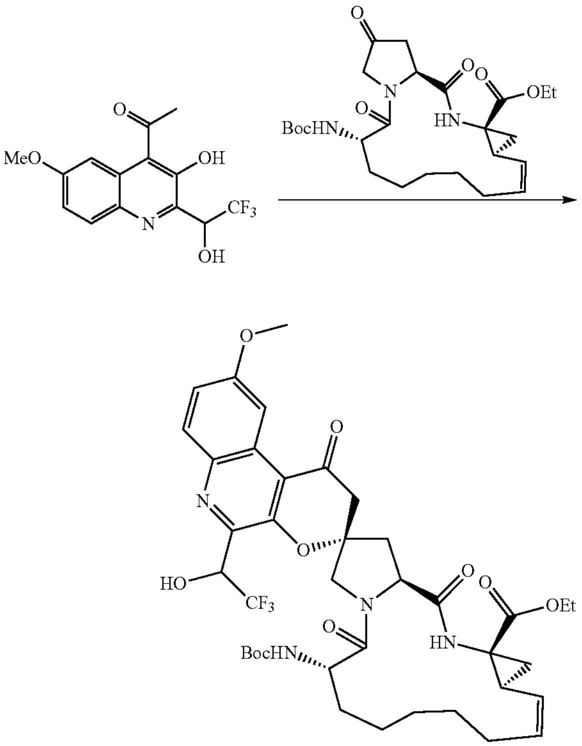 [SMILES: COc1ccc2nc(C(O)C(F)(F)F)c(O)c(C(C)=O)c2c1 ; CCOC(=O)[C@@]12C[C@H]1/C=C\CCCCC[C@H](NC(=O)OC(C)(C)C)C(=O)N1CC(=O)C[C@H]1C(=O)N2 ; CCOC(=O)[C@@]12C[C@H]1/C=C\CCCCC[C@H](NC(=O)OC(C)(C)C)C(=O)N1C[C@@]3(CC(=O)c4c(c(C(O)C(F)(F)F)nc5ccc(OC)cc45)O3)C[C@H]1C(=O)N2]

The product of Step 5 (1.2 g, 3.81 mmol), macrocyclic ketone (1.87 g, 3.81 mmol), benzoic acid (0.456 g, 3.81 mmol), pyrrolidine (160 μl, 1.90 mmol) and molecular sieves (1.7 g, 4A) were combined in MeOH (24 mL) and heated to 70° C. for 19 h. The mixture was filtered over SOLKA FLOC and washed with MeOH. The filtrate was concentrated, dissolved in EtOAc, washed with $NaHCO_3$ and then brine, and concentrated to a brown foam that was purified on silica using 10-80% EtOAc in hexane to afford 1.24 g of the product of Step 6 in 41% yield.

Step 7

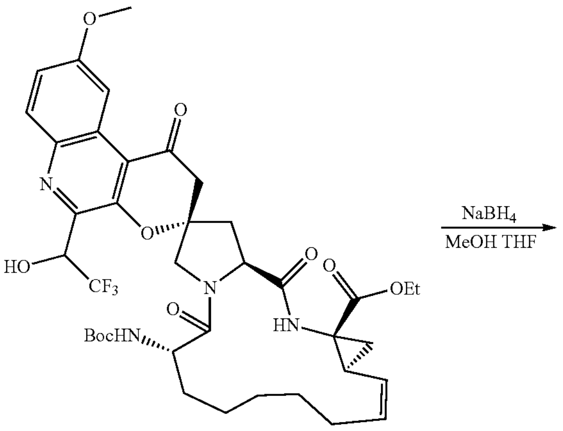

-continued

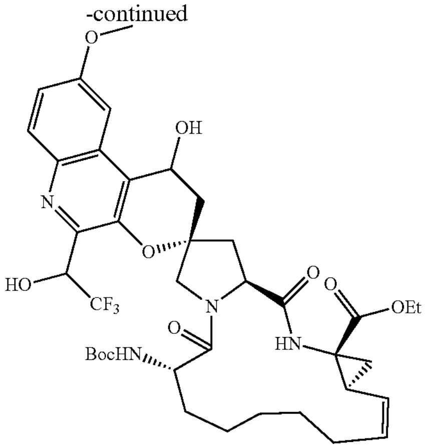

The product of Step 6 (1.24 g, 1.57 mmol) was dissolved in THF (10 mL) and MeOH (5 mL) and cooled to 0° C. $NaBH_4$ (65 mg, 1.73 mmol) was added in portions over 3 min, effecting vigorous gas evolution. After 15 min, the reaction was determined complete and sat. $NH_4Cl$ (10 mL) was slowly added. After a 5 min age, the reaction was poured into EtOAc (40 mL) and water (10 mL). The organic layer was dried over $MgSO_4$ and concentrated to 1.21 g of the product of Step 7 in 97% yield.

Step 8

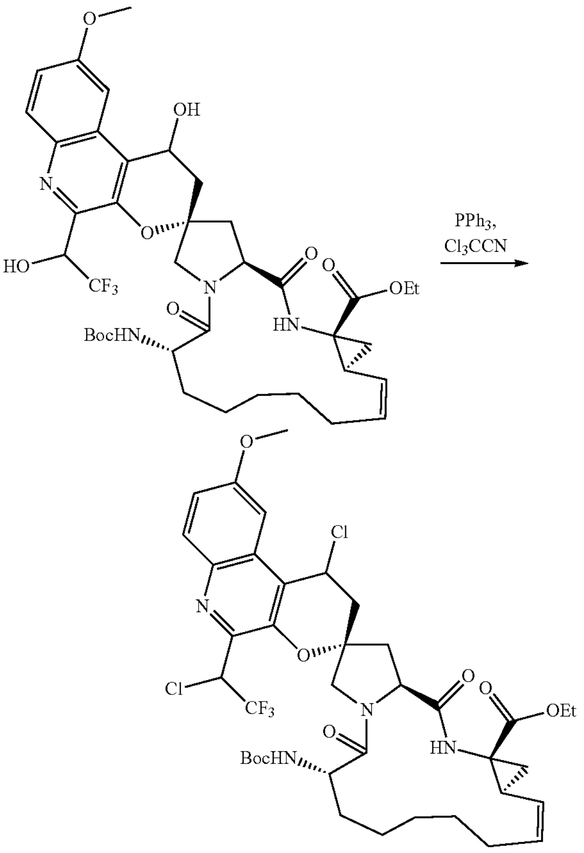

To a solution of the product of Step 7 (1.21 g, 1.53 mmol) in THF (12 mL) was added $Cl_3CCN$ (0.54 mL, 5.35 mmol) and then $PPh_3$ (1.40 g, 5.35 mmol) in portions with an exotherm to 30° C. The resulting mixture was heated at 60° C. for several hours. After cooling, the mixture was filtered and washed with THF. The filtrate was concentrated and purified by silica gel chromatography using 5-60% EtOAc/hexane to give 600 mg of the product of Step 8 in 47% yield.

Step 9

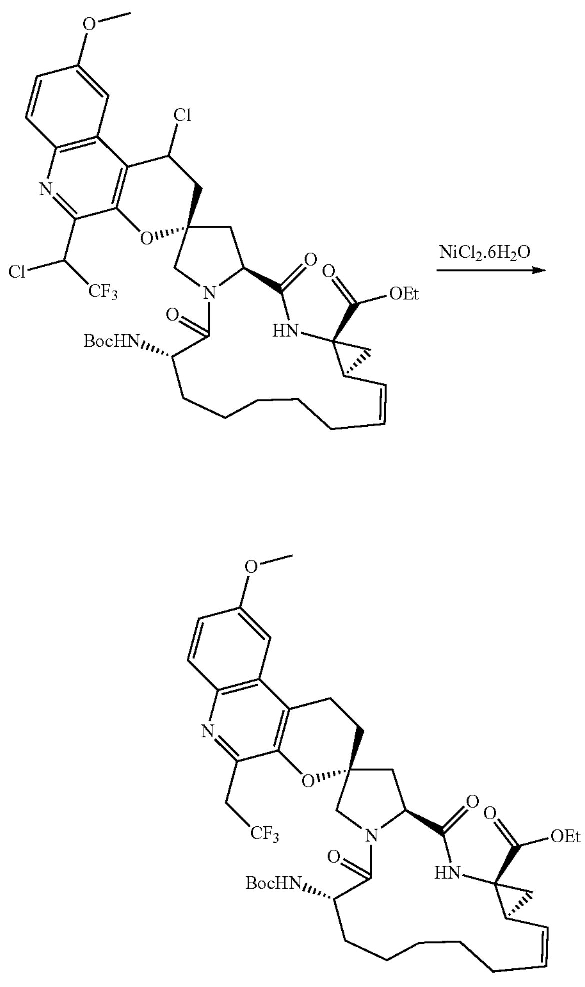

The product of Step 8 (600 mg 0.725 mmol) was dissolved in MeOH (12 mL) and degassed with subsurface $N_2$ spurge for 15 min. $NiCl_2.6H_2O$ (517 mg, 2.17 mmol) was added, and after it dissolved, the reaction was cooled to −78° C. $NaBH_4$ (110 mg, 2.90 mmol) was added, and the mixture was stirred for 1 h. After quenching with $NaHCO_3$, the reaction was poured into EtOAc and water, adding brine to clear the emulsion. The layers were separated, and the aq. layer was extracted once with EtOAc. The combined organic was washed with brine, dried over $MgSO_4$ and concentrated to 520 mg solid, which was purified on silica with 5-60% EtOAc/hexane to yield 330 mg of the product of Step 9 in 60% yield.

Step 10

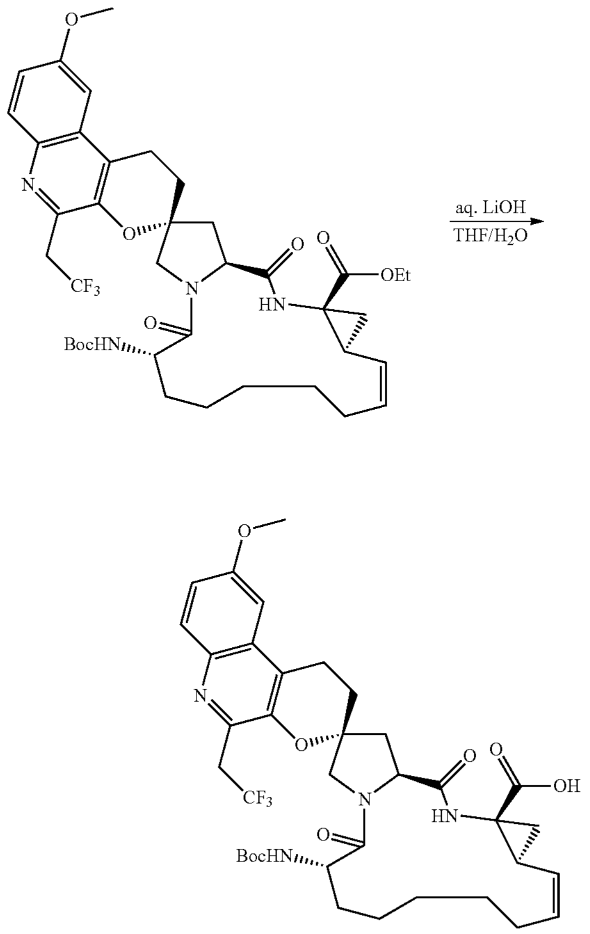 [SMILES: CCOC(=O)[C@@]12C[C@H]1/C=C\CCCCC[C@H](NC(=O)OC(C)(C)C)C(=O)N1C[C@@]3(CCc4c(c(CC(F)(F)F)nc5ccc(OC)cc45)O3)C[C@H]1C(=O)N2 ; COc1ccc2nc(CC(F)(F)F)c3c(c2c1)CC[C@]1(C[C@H]2C(=O)N[C@]4(C(=O)O)C[C@H]4/C=C\CCCCC[C@H](NC(=O)OC(C)(C)C)C(=O)N2C1)O3]

A solution of the product of Step 9 (330 mg, 0.435 mmol) in THF (3 mL), MeOH (1.5 mL) and water (1.5 mL) was treated with LiOH and heated at 45° C. for 1 h, and then cooled, and acidified to pH 4 with HCl (0.8 mL, 2N) and poured into EtOAc and water. The aq. layer was extracted with EtOAc, and the combined organics were washed twice with brine, dried over $MgSO_4$ and azeotroped with toluene to give 280 mg of the product of Step 10 in 88% yield.

Step 11

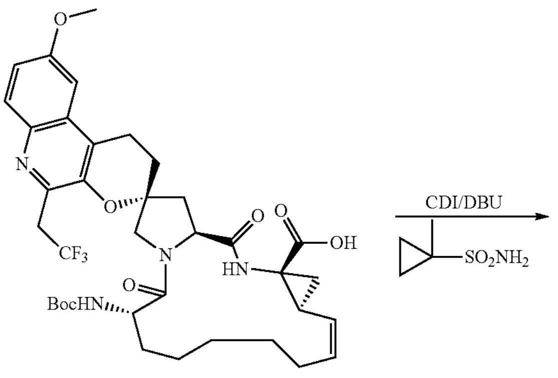

-continued

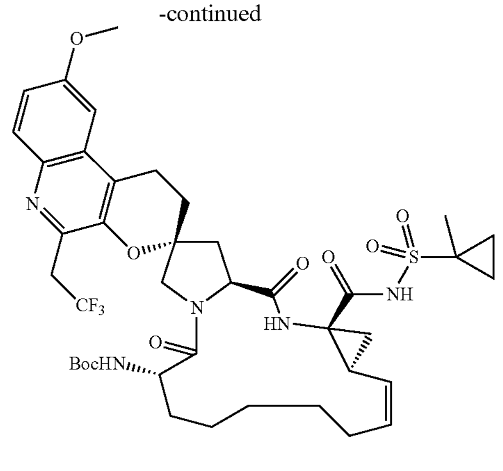

A solution of the product of Step 10 (220 mg, 0.301 mmol) and CDI (98 mg, 0.602 mmol) in THF (2 mL) was heated at 70° C. for 2 h. 1-Methylcyclopropane-1-sulfonamide (122 mg, 0.903 mmol) and DBU (136 μl, 0.903 mmol) were then added, and the reaction was aged at 50° C. for 45 min. The reaction was cooled and poured into EtOAc and $NH_4Cl$. The layers were separated, and the organic was washed with brine, dried over $MgSO_4$, concentrated and purified on silica with 0-10% MeOH/DCM to obtain 200 mg of the product of Step 11 in 78% yield.

Step 12

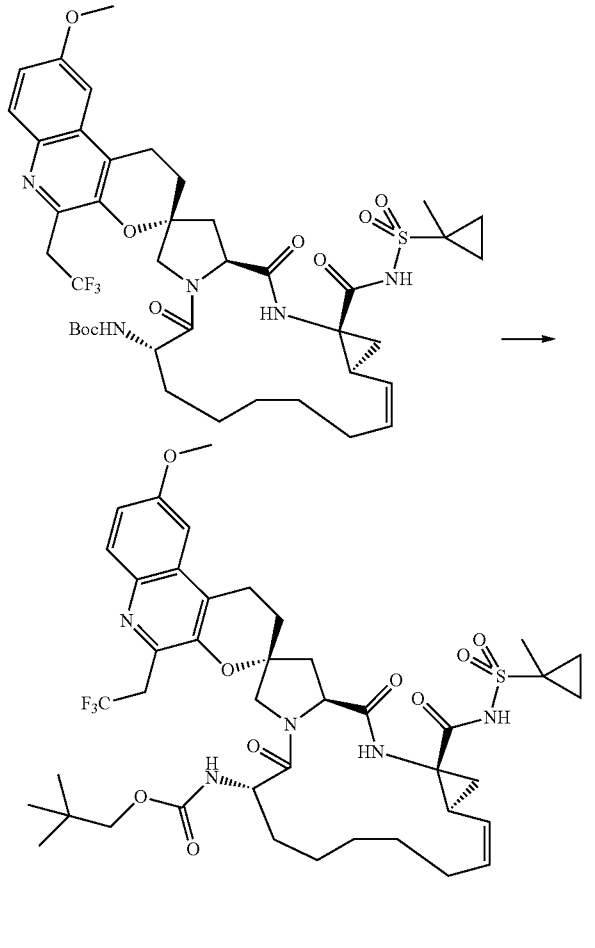

The product of Step 11 (192 mg, 0.226 mmol) was stirred for 45 min in a dioxane solution of HCl (5 mL, 20 mmol, 4N), at which point the solvent was removed and the solid was dried under vacuum to give 178 mg deprotected amine salt in 100% yield.

The amine salt (42 mg, 0.054 mmol) in DCM (1 mL) was cooled to 0° C., and neopentyl chloroformate (16 μl, 0.107 mmol) was added, followed by DiPEA (28 μl, 0.161 mmol). The reaction was stirred for 20 min and then purified directly on silica column with a gradient of 0-60% acetone in hexane to give 24 mg of I-48 in 52% yield. Mass spec. observed mass 862.71 (M+1) $^1$H NMR δ (ppm)(Acetone-$d_6$): 10.58 (1 H, s), 8.52 (1 H, s), 7.86 (1 H, d, J=8.93 Hz), 7.24 (2 H, s), 6.37 (1 H, s), 5.71 (1 H, d, J=10.05 Hz), 5.02 (1 H, t, J=9.21 Hz), 4.74 (1 H, m), 4.53 (1 H, d, J=10.80 Hz), 4.14 (1 H, m), 3.99 (4 H, m), 3.95-3.79 (2 H, m), 3.69-3.63 (2 H, m), 3.60-3.51 (2 H, m), 3.29-3.14 (3 H, m), 2.84-2.81 (8 H, m), 2.65-2.61 (bm), 2.57-2.52 (m), 2.43-2.34 (bm), 2.11 (bm), 1.89 (3 H, bs), 1.74-1.22 (bm), 0.87 (12 H, m).

Example 49 tert-Butyl ((2R,6S,13AS,14AR,16AS,Z)-9'-methoxy-14a-(((1-(methoxymethyl) cyclopropyl)sulfonyl) carbamoyl)-5,16-dioxo-5'-(trifluoromethyl)-1',2',3,5,6,7,8,9,10,11, 13A,14,14A,15,16,16A-hexadecahydro-1H-spiro[cyclopropa[e]pyrrolo[1,2-A][1,4]diazacyclopentadecine-2,3'-pyrano[2,3-c]quinolin]-6-yl)carbamate (I-49)

Step 1

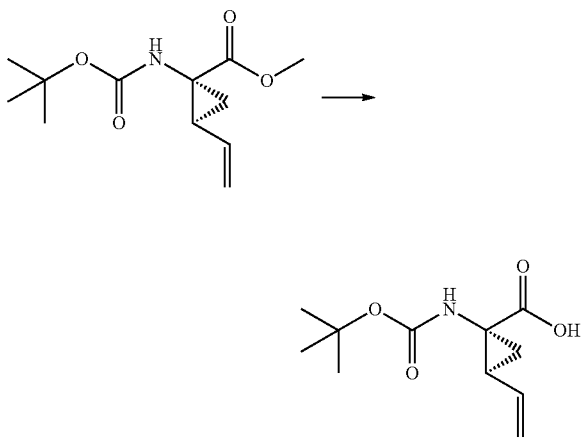 [SMILES: C=C[C@@H]1C[C@]1(NC(=O)OC(C)(C)C)C(=O)OC ; C=C[C@@H]1C[C@]1(NC(=O)OC(C)(C)C)C(=O)O]

To a THF solution (58.8 mL) of (1R,2S)-ethyl 1-((tert-butoxycarbonyl)amino)-2-vinylcyclopropanecarboxylate (3.0 g, 11.76 mmol) was added a solution of $LiOH.H_2O$ (2.465 g, 58.8 mmol) in water (58.8 mL) over a period of 10 min. The resultant mixture was heated at 65° C. for 16 h, then was concentrated to half its volume and the pH adjusted to 2-3 with 1M (aq.) HCl. The mixture was extracted with DCM (3×100 mL) and the combined organic extracts dried over $MgSO_4$, filtered, and concentrated in vacuo to afford 2.7 g of the product of Step 1, which was used without further purification.

Step 2

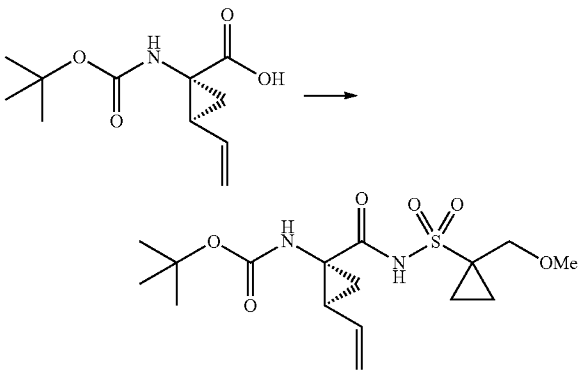

To a THF solution (22 mL) of the product from Step 1 was added N,N'-carbonyldiimidazole (1.070 g, 6.60 mmol), and the resultant mixture heated at 85° C. for 2 h. The mixture was cooled to ambient temperature, and a THF solution (11 mL) of 1-(methoxymethyl)cyclopropane-1-sulfonamide (1.454 g, 8.80 mmol) was added, followed by 1,8-diazabicyclo[5.4.0]undec-7-ene (1.316 mL, 8.80 mmol). The resultant mixture was heated at 75° C. for 16 h, then 1M (aq.) HCl (10 mL) and $H_2O$ (50 mL) was added. The product was extracted with EtOAc (200 mL), and the organic extract washed sequentially with 1M HCl/$H_2O$ (1:2, 50 mL) and brine (50 mL), dried over $MgSO_4$, filtered, and concentrated in vacuo. The residue was purified by silica gel column chromatography using a gradient of 0-30% EtOAc/$CH_2Cl_2$ as eluent to afford 1.13 g of the indicated product of Step 2.

Step 3

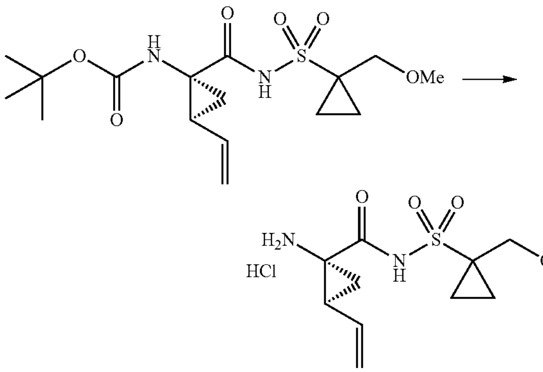

To the product from Step 2 (1.1 g, 2.94 mmol) was added 4M HCl in dioxane (10 mL, 40 mmol), and the resultant mixture stirred for 1 h. The mixture was concentrated in vacuo to afford 920 mg of the product of Step 3, which was used without further purification.

Step 4

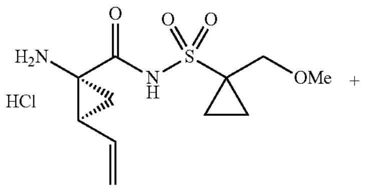

-continued

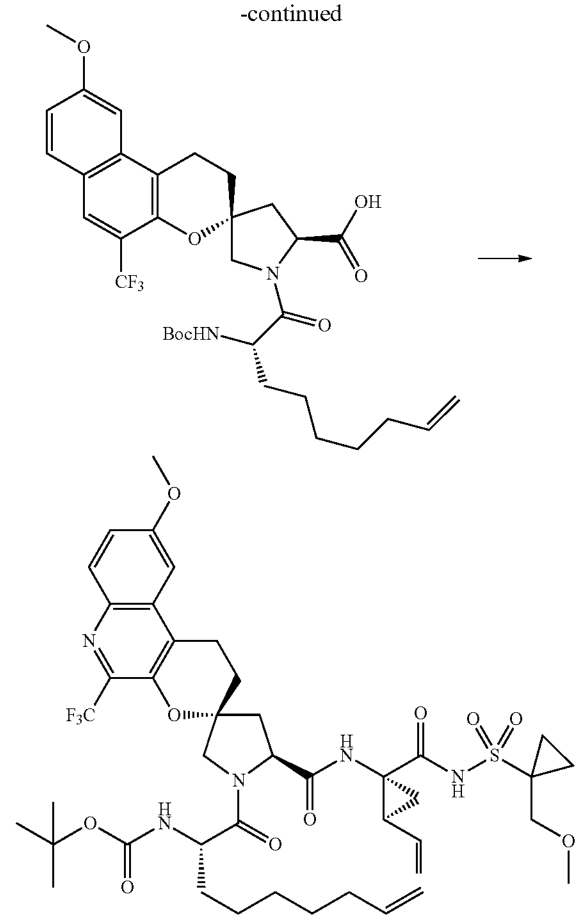

To a DMF solution (10 mL) of acid obtained similarly to the product of Example 4, Step 11 (805 mg, 1.266 mmol) was added the product from Step 3 (590 mg, 1.9 mmol), HATU (722 mg, 1.9 mmol), and TEA (0.53 mL, 3.8 mmol). The resultant mixture was stirred at ambient temperature for 14 h, diluted with EtOAc, and the organic layer washed sequentially with $H_2O$ (3×) and brine (1×), dried over $MgSO_4$, filtered, and concentrated in vacuo. The residue was purified by silica gel column chromatography using a gradient of 0-100% EtOAc/Hexanes as eluent to obtain 1.123 g of the product of Step 4. m/z=892.4 (M+H).

Step 5

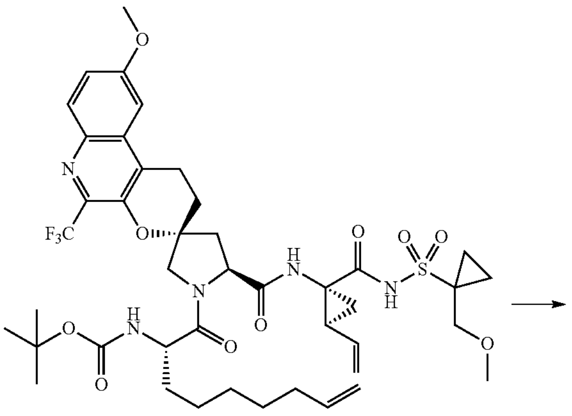

-continued

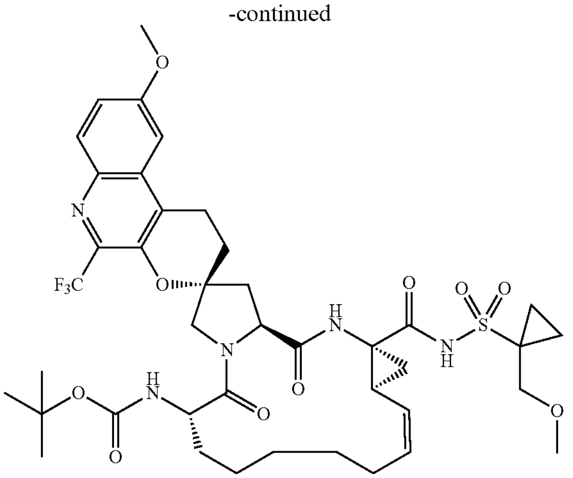

To a DCE solution (434 mL) of the product from Step 4 (1.123 g, 1.259 mmol) was added 1,4-benzoquinone (40.8 mg, 0.378 mmol) and Zhan's catalyst (23.1 mg, 0.315 mmol). The mixture was evacuated/flushed with $N_2$ 5× and heated at 75° C. under a stream of $N_2$ for 3.5 h then at 80° C. for 30 min. The mixture was cooled to ambient temperature and quenched by the addition of 0.4 mL of butyl vinyl ether. After stirring at ambient temperature for 20 min, the mixture was concentrated in vacuo and purified by silica gel column chromatography using a gradient of 0-50% Acetone/Hexanes as eluent. The product was further purified by SFC chromatography to provide 359 mg of I-49. $^1$H NMR δ (ppm)($CHCl_3$-d): 10.08 (1 H, br s), 8.04 (1 H, d, J=9.22 Hz), 7.36-7.26 (1 H, m), 7.04 (1 H, s), 6.85 (1 H, s), 5.74 (1 H, d, J=10.07 Hz), 5.21 (1 H, d, J=8.44 Hz), 5.06 (1 H, s), 4.64 (1 H, s), 4.44 (1 H, d, J=10.88 Hz), 4.25 (1 H, s), 4.00 (3 H, s), 3.76 (2 H, t, J=13.86 Hz), 3.71-3.61 (1 H, m), 3.36 (3 H, s), 3.26-3.10 (2 H, m), 2.57 (2 H, t, J=9.09 Hz), 2.48 (1 H, t, J=11.62 Hz), 2.38 (2 H, m), 1.96-1.83 (4 H, m), 1.77 (1 H, d, J=11.98 Hz), 1.68 (1 H, m), 1.61-1.43 (4 H, m), 1.30 (12 H, s), 1.08 (2 H, s), 0.93-0.83 (2 H, m). m/z=864.4 (M+H).

Example 50 tert-Butyl ((2R,6S,13aS,14aR,16aS,Z)-14a-(((1-methylcyclopropyl)sulfonyl) carbamoyl)-9'-(3-morpholinopropoxy)-5,16-dioxo-5'-(trifluoromethyl)-1',2',3,5,6,7,8,9, 10,11,13a,14,14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I-50)

Step 1

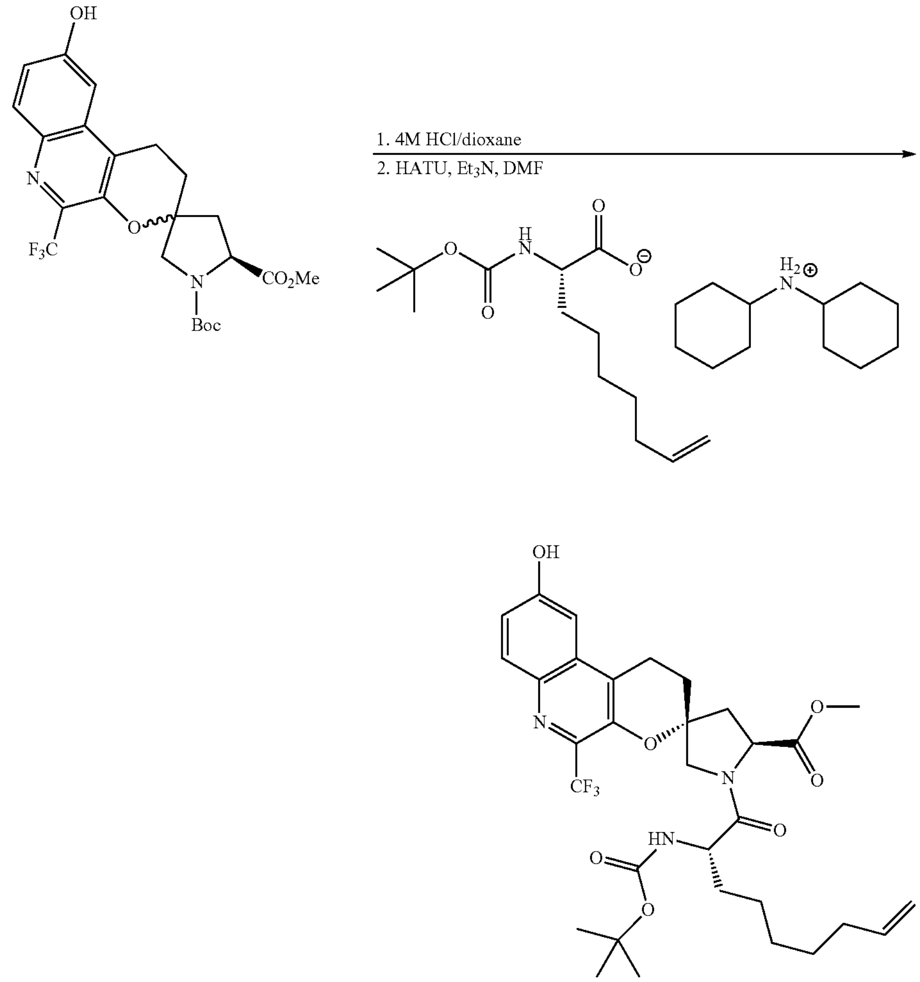

A solution of the product of Example 7, Step 7 (520 mg, 1.078 mmol) and 4M HCl in dioxane (4 mL, 16.00 mmol) was stirred at RT for 2 h. The volatiles were removed under reduced pressure, and the residue was azeotroped 3× with toluene. The solid thus obtained was used without purification.

The solid thus obtained was taken in DMF (10.75 mL) and treated with TEA (0.451 mL, 3.24 mmol), dicyclohexylammonium (S)-2-(tert-butoxycarbonylamino)non-8-enoate (973 mg, 2.149 mmol) followed by HATU (817 mg, 2.149 mmol) at RT. The reaction was stirred at RT for 2 h, at which stage LC-MS showed complete consumption of the starting material. The reaction was quenched with aq. $NaHCO_3$ and extracted with EtOAc. The organics were dried ($MgSO_4$), concentrated and purified by silica gel column chromatography (0-60-100% EtOAc in hexane) to provide the indicated product of Step 1 and its diastereomer.

Step 2

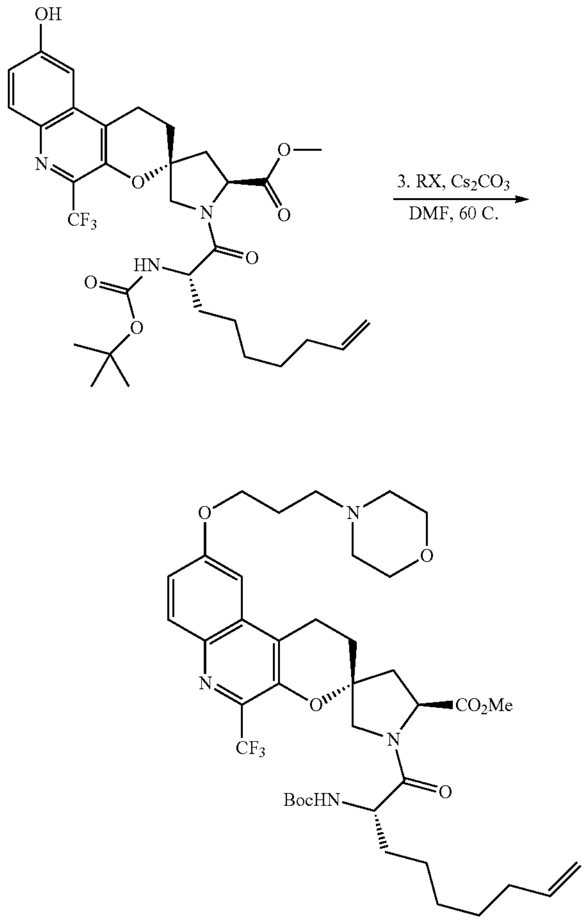

The product of Step 2 was prepared from the product of Step 1 by the procedure described in Example 7, Step 8, in which the 4-(2-bromoethyl)morpholine HBr salt was replaced with 4-(3-chloropropyl)morpholine hydrochloride.

Step 3

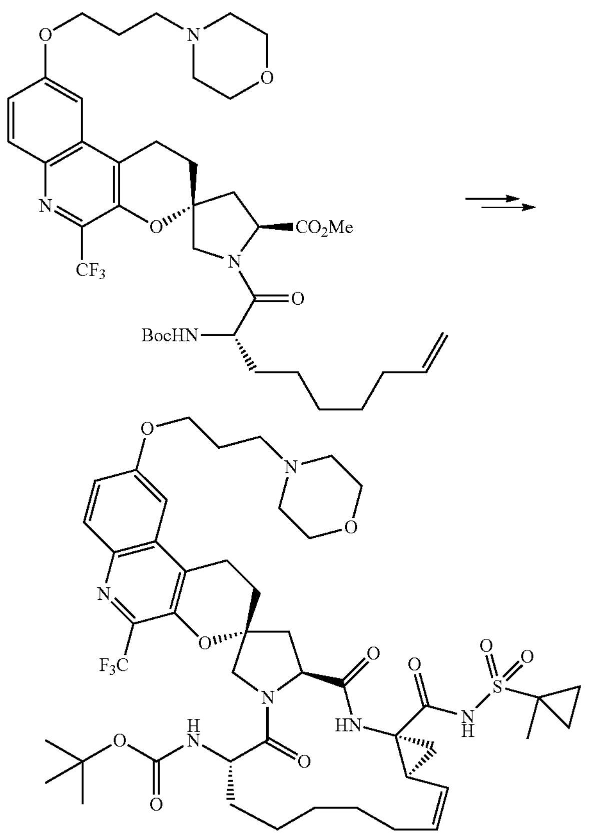

The product of Step 2 was converted to I-50 by the procedures described in Example 7, Steps 9-11.

Example 51 tert-Butyl ((2R,6S,13aS,14aR,16aS,Z)-9'-(3-methoxypropoxy)-14a-(((1-methyl cyclopropyl)sulfonyl) carbamoyl)-5,16-dioxo-5'-(trifluoromethyl)-1',2',3,5, 6,7,8,9,10,11,13a, 14,14a,15,16,16a-hexadecahydro-1H-spiro[cyclopropa[e]pyrrolo[1,2-a][1,4] diazacyclopentadecine-2,3'-pyrano[2,3-c]quinolin]-6-yl)carbamate (I-51)

Step 1

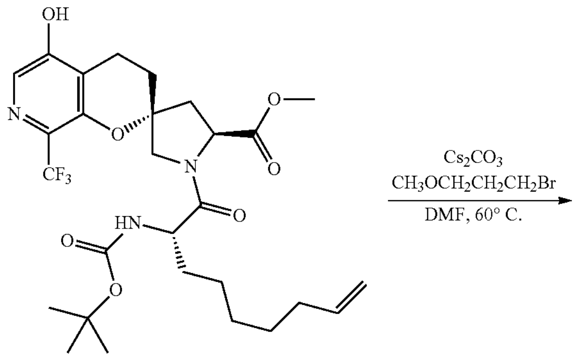

-continued

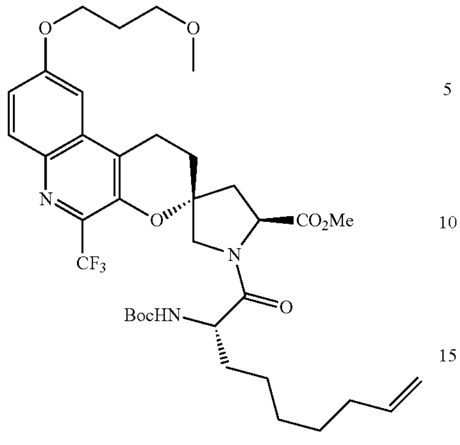

The product of Step 1 was prepared from the product of Example 50, Step 1 by the procedure described in Example 50, Step 2, in which 4-(3-chloropropyl)morpholine hydrochloride was replaced with 1-bromo-3-methoxy propane.

Step 2

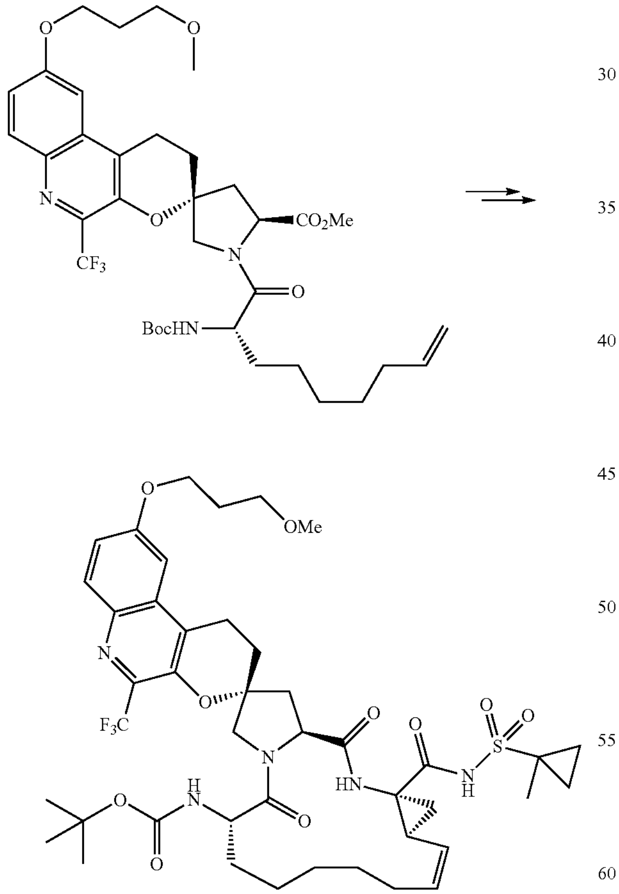

The product of Step 1 was converted to I-51 using the procedures described in Example 7, Steps 9-11.

Example 52 tert-Butyl ((1'R,2S,6S,13aS,14aR,16aS,Z)-9'-methoxy-14a-(((1-methylcyclopropyl)sulfonyl)carbamoyl)-1'-((((1-methylcyclopropyl)sulfonyl) carbamoyl)oxy)-5,16-dioxo-5'-(trifluoromethyl)-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-52); and Example 53 tert-Butyl ((1'R,2S,6S,13aS,14aR,16aS,Z)-9'-methoxy-14a-(((1-methylcyclopropyl)sulfonyl)carbamoyl)-1'-((((1-methylcyclopropyl)sulfonyl) carbamoyl)oxy)-5,16-dioxo-5'-(trifluoromethyl)-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-53)

Step 1

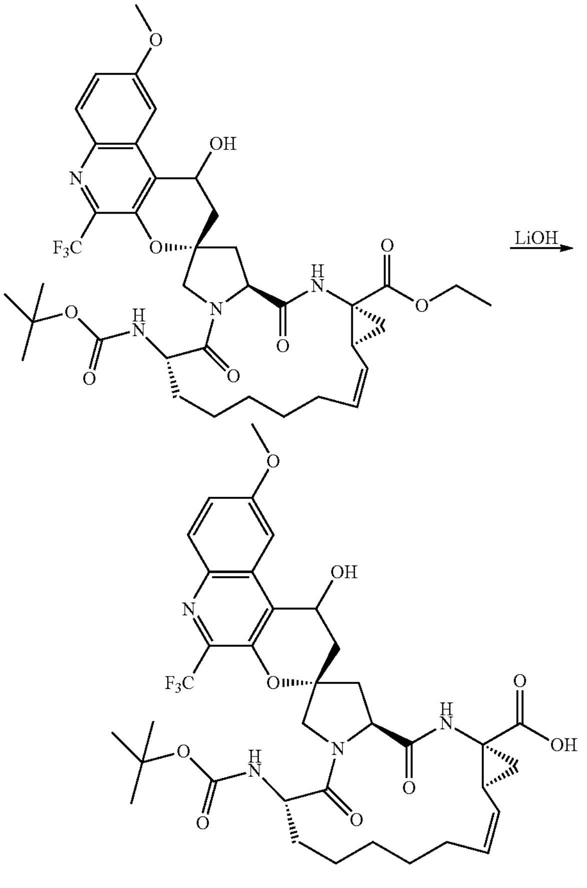

To a solution of the product of Example 5, alternate procedure Step 5 (380 mg, 0.499 mmol) in THF (4.5 ml), MeOH (2.0 ml) and $H_2O$ (2.0 ml) was added the LiOH (72 mg, 3.0 mmol) at RT. It was stirred at RT for 5.5 h. The LC-MS shows the hydrolysis was completed. The reaction mixture was cooled to 0° C., and acidified to pH=2~3 with 1N HCl, and diluted with EtOAc (30 ml). The layers were separated and the aq. layer was extracted again with EtOAc (15 ml×2). The organic layers were combined and washed with brine, dried over $MgSO_4$, filtered, and concentrated in vacuo to give (2S,6S,13aS,14aR,16aS,Z)-6-((tert -butoxycarbonyl)amino)-1'- hydroxy-9'-methoxy-5,16-dioxo-5'-(trifluoromethyl) -1',2',3,5,6,7,8,9,10,11,13a,14,14a,15,16,16a-hexadecahydro-1H-spiro[cyclopropa[e]pyrrolo[1,2-a][1,4]diazacyclopentadecine-2,3'-pyrano[2,3-c]quinoline]-14a-carboxylic acid (the product of Step 1) as a white solid. The product was azeotroped with toluene (2×10 ml) and kept under vacuum overnight. This product was carried on to next step without further purification. m/z=733.3 (M+1).

Step 2

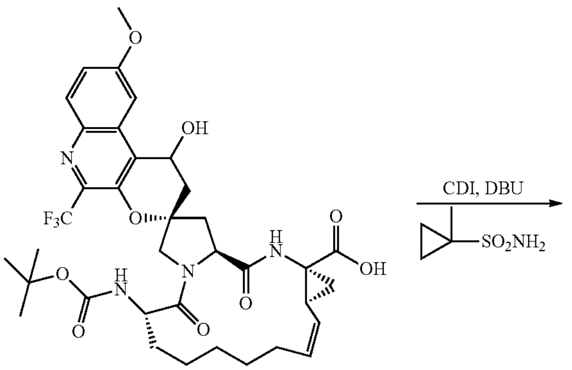

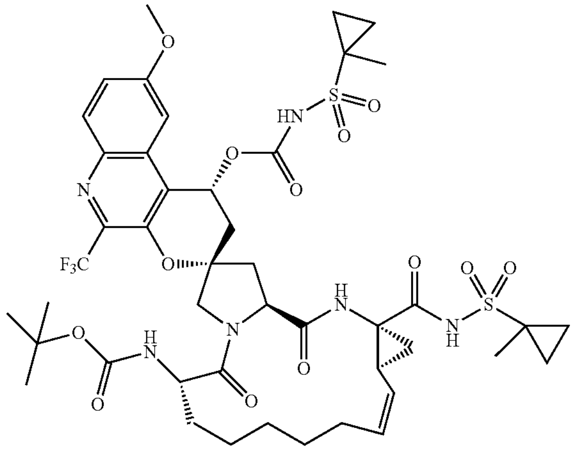

I-52

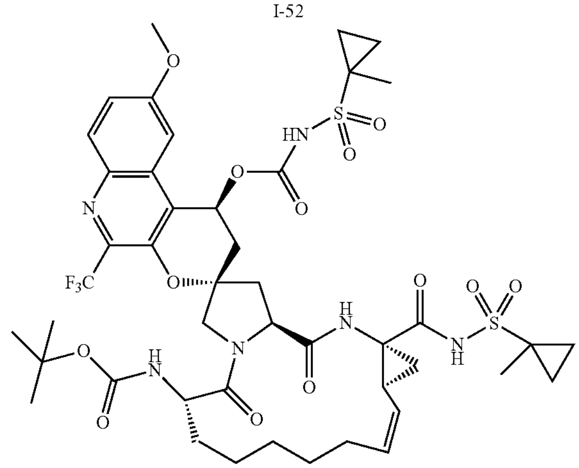

I-53

A solution of the product of Step 1 (380 mg, 0.519 mmol) and CDI (160 mg, 0.985 mmol) in THF (4.5 ml) was stirred in an oil-bath at 70° C. for 3 h, then cooled to RT. To this reaction mixture was added 1-methylcyclopropane-1-sulfonamide (175 mg, 1.296 mmol) and DBU in THF (1M) (1.296 ml, 1.296 mmol), and the mixture was stirred in an oil-bath at 46° C. for 2.2 h. The LC-MS indicates that the major is desired product. The reaction mixture was diluted with EtOAc (40 ml), washed with aq. $NH_4Cl$(2×6 ml), brine, dried over $MgSO_4$, filtered, concentrated. The residue was purified by column chromatography on silica gel (40 g, gold column), eluting with 100% hexane for 200 ml, gradient to 40% of acetone to give the mixture of the compounds of Examples 52 and 53, which were separated by Gilson (the column is C18, 19×150 mm; eluting with MeCN/water+0.1% fomic acid (gradient 40% of MeCN to 100% MeCN). Freeze drying gave I-52 and I-53 as white solids.

Example 52: $^1$H NMR δ (ppm)($CDCl_3$): 10.01 (1 H, s), 8.02 (1 H, d, J=9.25 Hz), 7.30 (1 H, s), 7.09 (1 H, s), 6.90 (1 H, s), 6.49 (1 H, s), 5.73 (1 H, q, J=8.85 Hz), 5.15 (1 H, s), 5.00 (1 H, t, J=9.39 Hz), 4.62 (1 H, d, J=11.10 Hz), 4.49 (1 H, s), 4.32 (1 H, s), 3.96 (3 H, s), 3.87 (1 H, d, J=11.65 Hz), 2.66 (3 H, d, J=14.80 Hz), 2.47 (2 H, d, J=15.75 Hz), 2.34 (1 H, t, J=12.26 Hz), 2.17 (2 H, d, J=19.79 Hz), 1.86 (2 H, s), 1.81 (1 H, s), 1.71 (1 H, s), 1.41 (11 H, s), 1.38-1.24 (9 H, m), 0.86 (4 H, s), 0.61 (1 H, s), 0.40 (1 H, s). m/z=1011.2 [M+1].

Example 53: $^1$H NMR δ (ppm)($CDCl_3$): 10.22 (1 H, s), 8.95 (1 H, s), 8.05 (1 H, t, J=9.20 Hz), 7.37-7.27 (2 H, m), 7.08 (1 H, s), 7.03 (1 H, s), 6.65 (1 H, s), 5.75 (1 H, q, J=8.87 Hz), 5.16 (1 H, d, J=8.85 Hz), 5.07 (1 H, t, J=9.37 Hz), 4.69 (1 H, t, J=8.07 Hz), 4.52 (1 H, d, J=12.45 Hz), 4.24 (1 H, t, J=10.01 Hz), 3.98 (3 H, s), 3.83 (1 H, d, J=12.29 Hz), 2.75-2.66 (3 H, m), 2.70-2.54 (3 H, m), 2.49 (1 H, q, J=8.83 Hz), 1.98 (1 H, t, J=7.01 Hz), 1.89 (1 H, s), 1.85 (3 H, d, J=12.90 Hz), 1.27 (4 H, d, J=15.05 Hz), 1.06 (9 H, s), 1.01 (1 H, s), 0.96-0.75 (4 H, m). m/z=1011.2 [M+1].

Example 54 tert-Butyl [(1'R,2S,6S,12Z,13aS,14aR,16aS)-1'-hydroxy-9'-methoxy-14a-{[(1-methylcyclopropyl)sulfonyl]carbamoyl}-5,16-dioxo-5'-(trifluoromethyl) -1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate (I-54); and

Example 55 tert-Butyl [(1'S,2S,6S,12Z,13aS,14aR,16aS)-1'-hydroxy-9'-methoxy-14a-{[(1-methylcyclopropyl)sulfonyl]carbamoyl}-5,16-dioxo-5'-(trifluoromethyl) -1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate (I-55)

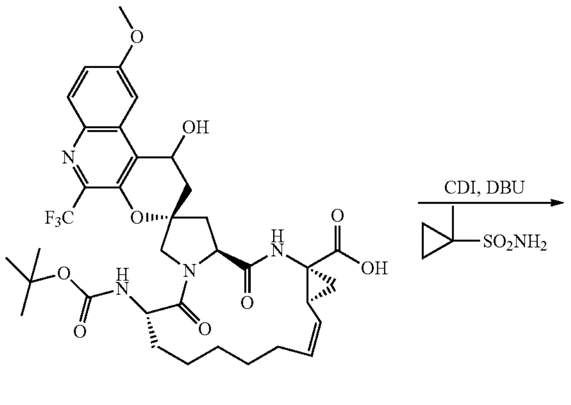

-continued

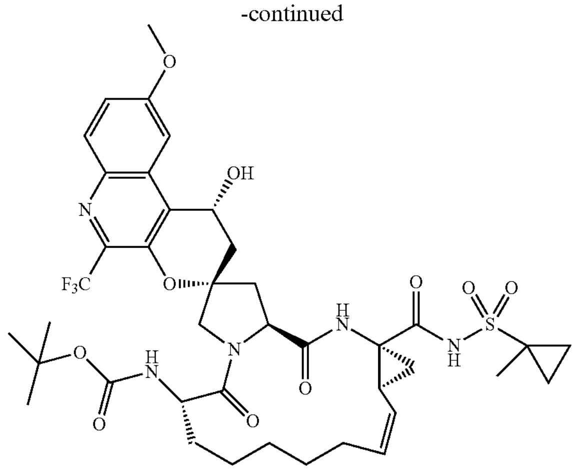

I-54

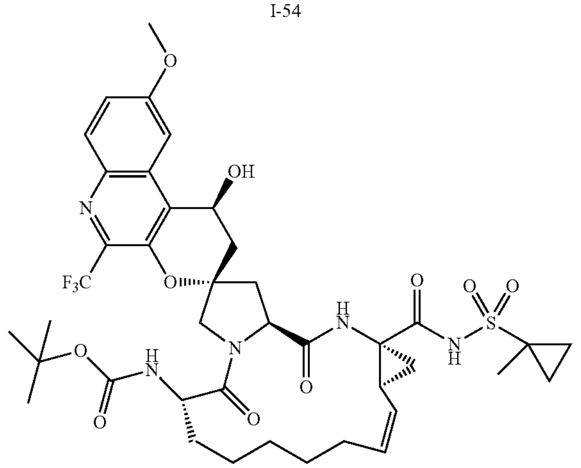

I-55

A solution of the product of Examples 52 and 53, Step 1 (250 mg, 0.341 mmol) and CDI (83 mg, 0.512 mmol) in THF (4.5 ml) was stirred in an oil-bath kept at 70° C. for 3 h, then cooled to RT. To this was added 1-methylcyclopropane-1-sulfonamide (92 mg, 0.682 mmol) and DBU in THF (1M) (0.853 ml, 0.853 mmol), and the mixture was stirred in an oil-bath kept at 46° C. for 2.2 h. The reaction mixture was diluted with EtOAc (40 ml), washed with aq. $NH_4Cl$ (2×4 ml), brine, dried over $MgSO_4$, filtered, concentrated. The residue was purified by column chromatography on silica gel (40 g, gold column, dry loading), eluting with 100% hexane for 400 ml, gradient to 60% of acetone to give the mixture of I-54 and I-55 along with a mixture of bis-sulfonamides. The mixture of I-54 and I-55 were separated by HPLC(C18, 19×150 mm; eluting with MeCN/water+0.1% fomic acid (gradient 50% of MeCN to 100% MeCN).

Example 54: $^1$H NMR (500 MHz, $CDCl_3$) δ (ppm): 10.31-10.18 (1 H, m), 8.04 (1 H, d, J=9.20 Hz), 7.38 (1 H, s), 7.32 (2 H, t, J=10.07 Hz), 5.71 (1 H, d, J=9.91 Hz), 5.37 (1 H, s), 5.23 (1 H, d, J=8.49 Hz), 4.98 (1 H, t, J=9.48 Hz), 4.50 (2 H, d, J=11.01 Hz), 4.36 (1 H, s), 4.15 (1 H, q, J=7.20 Hz), 4.01 (3 H, s), 3.89-3.76 (1 H, m), 2.72 (2 H, s), 2.57 (6 H, s), 2.51-2.37 (4 H, m), 2.07 (1 H, s), 1.93-1.82 (3 H, m), 1.72 (1 H, d, J=11.63 Hz), 1.41-1.22 (6 H, m), 1.03 (1 H, s), 0.80 (2 H, s), 0.10 (1 H, s). m/z=850.3 [M+1].

Example 55: $^1$H NMR (500 MHz, $CDCl_3$) δ (ppm): 10.23 (1 H, s), 8.03 (1 H, d, J =9.16 Hz), 7.30 (3 H, d, J=4.81 Hz), 7.09 (1 H, s), 5.76 (1 H, q, J=8.88 Hz), 5.40 (1 H, s), 5.34 (1

H, d, J=8.56 Hz), 5.05 (1 H, t, J=9.36 Hz), 4.70 (1 H, t, J=8.17 Hz), 4.56 (1 H, d, J =12.07 Hz), 4.24-4.11 (2 H, m), 3.98 (3 H, s), 3.86 (1 H, d, J=12.06 Hz), 2.79 (4 H, s), 2.69-2.54 (4 H, m), 2.50 (2 H, s), 2.37 (1 H, q, J=8.64 Hz), 2.08 (1 H, s), 1.95 (1 H, t, J=6.99 Hz), 1.91-1.81 (4 H, m), 1.37 (2 H, s), 1.38-1.26 (8 H, m), 1.21 (9 H, s), 0.98-0.81 (4 H, m), 0.10 (1 H, s). m/z=850.3 [M+1].

Example 56 tert-Butyl ((1'R,2S,6S,13aS,14aR,16aS,Z)-1'-fluoro-9'-methoxy-5'-methyl-14a -(((1-methylcyclopropyl) sulfonyl)carbamoyl)-5,16-dioxo-1',2',3,5,6,7,8,9,10, 11,13a,14,14a, 15,16,16a-hexadecahydro-1H-spiro [cyclopropa[e]pyrrolo[1,2-a][1,4] diazacyclopentadecine -2,3'-pyrano[2,3-c]quinolin]-6-yl)carbamate (I-56)

Step 1

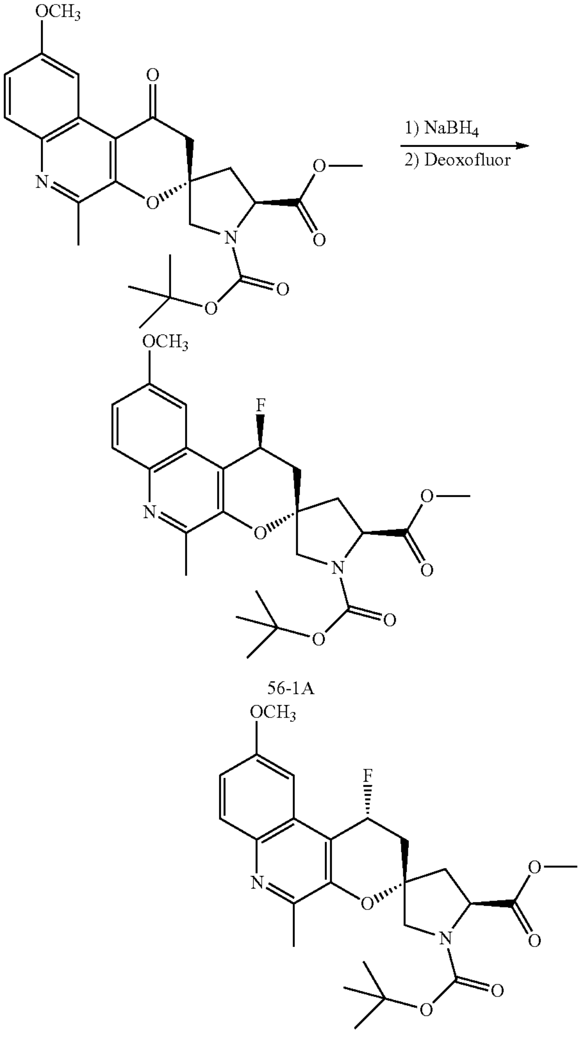

56-1A 56-1B

To a solution of compound 9-4A prepared by Example 9, Steps 1-4 (1.5 g, 3.29 mmol) in MeOH (10 ml) and THF (10 ml) at 0° C. was added $NaBH_4$ (0.124 g, 3.29 mmol). The mixture was stirred at 0° C. for 10 min then quenched by the addition of aq. $NH_4Cl$. The slurry was extracted 3× with EtOAc, and the combined organic layer was washed with brine, dried over $MgSO_4$, filtered and evaporated to dryness to give a mixture of diastereomeric alcohols. The crude products were azeotroped with toluene and used as such.

To a solution of the crude mixture (1508 mg, 3.29 mmol) in DCM (20 ml) at 0° C. was added DeoxoFluor (0.607 ml, 3.29 mmol). The ice-bath was removed, and the mixture was stirred at RT for 2.5 h. The reaction mixture was stirred with aq. $NaHCO_3$, and the organic layer was separated. The aq. phase was extracted 2× with DCM. The combined organic layer was washed with brine, dried over $MgSO_4$, filtered, concentrated and purified by chromatography eluting with 0-40% EtOAc-hexanes to give 560 mg of 56-1A and 450 mg of 56-1B. LC-MS m/e =461.2 (MH+) for 56-1A. LC-MS m/e=461.2 (MH+) for 56-1B.

Step 2

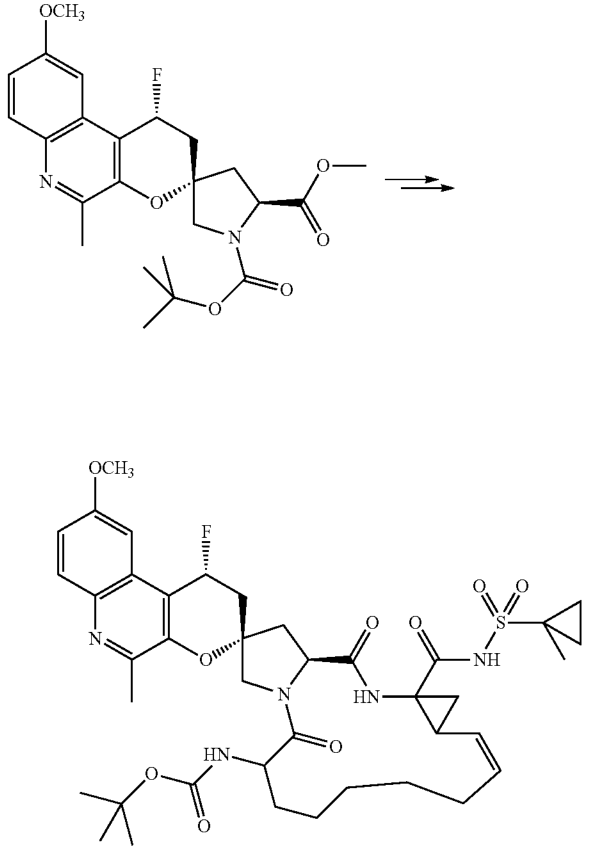

Compound 56-1B was converted to I-56 using a procedure similar to the procedures of Example 9. $^1$H NMR (400 MHz, acetone-$d_6$) 10.47 (s, 1H), 8.30 (s, 1H), 7.82 (d, J =8.8 Hz, 1H), 7.37 (s, 1H), 7.20 (d, J=9.2 Hz, 1H), 6.36 (s, 1H), 6.23 (s, 1H), 6.18 (d, J=8.0 Hz, 1H), 5.72 (q, J=8.2 Hz, 1H), 5.00 (t, J=9.2 Hz, 1H), 4.72 (d, J=10.8 Hz, 1H), 4.63-4.59 (m, 1H), 4.26 (t, J=8.0 Hz, 1H), 4.00 (d, J=10.8 Hz, 1H), 3.96 (s, 3H), 3.75 (s, 3H), 2.94-2.55 (m), 2.45 (s, 3H), 2.28-2.22 (m), 2.07-1.88 (m), 1.72-1.68 (m, 1H), 1.61-1.30 (m,), 0.87 (m, 2H). MS m/e=798.2 (MH$^+$).

Example 57

(2R,6S,13aS,14aR,16aS,Z)-9'-methoxy-5'-methyl-N-((1-methylcyclopropyl) sulfonyl)-5,16-dioxo-6-(pyrimidin-2-ylamino)-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-14a-carboxamide (I-57)

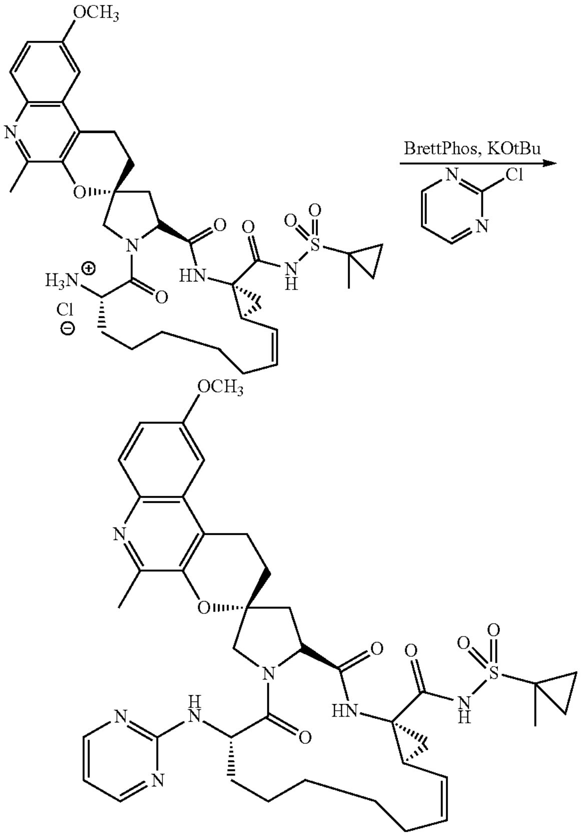

To a solution of (2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a -hexadecahydrospiro[cyclopropa[e]pyrrolo[1,2-α][1,4]diazacyclopentadecine-2,3'-pyrano[2,3-c]quinolin]-6-aminium chloride (obtained by treatment of I-9 with 4M HCl in dioxane for 30 min and concentration in vacuo; 50 mg, 0.070 mmol) in dioxane (500 μl) was added chloro[2-(dicyclohexylphosphino)-3,6-dimethoxy-2'-4'-6'-tri-1-propyl-1,1'-biphenyl][2-(2-aminoethyl)phenyl]palladium(II) (BrettPhos indoline precatalyst, 11.15 mg, 0.014 mmol) sodium tert-butoxide (18.78 mg, 0.195 mmol) and 2 chloroquinoline (16 mg, 0.144 mmol), and the mixture heated to 80° C. while stirring under $N_2$ overnight. The reaction mixture was filtered then purified by preparative HPLC Reverse phase (C-18), eluting with acetonitrile/water+0.1% formic acid, to yield I-57 (7.4 mg, 9.76 μmol, 13.99% yield) as a off white solid.

Example 58 tert-Butyl ((2R,6S,13aS,14aR,16aS,Z)-9'-hydroxy-5'-methyl-14a-(((1-methyl cyclopropyl)sulfonyl) carbamoyl)-5,16-dioxo-1',2',3,5,6,7,8,9,10,11,13a, 14,14a,15,16,16a -hexadecahydro-1H-spiro [cyclopropa[e]pyrrolo[1,2-a][1,4] diazacyclopentadecine-2,3'-pyrano[2,3-c]quinolin]-6-yl)carbamate (I-58)

Step 1

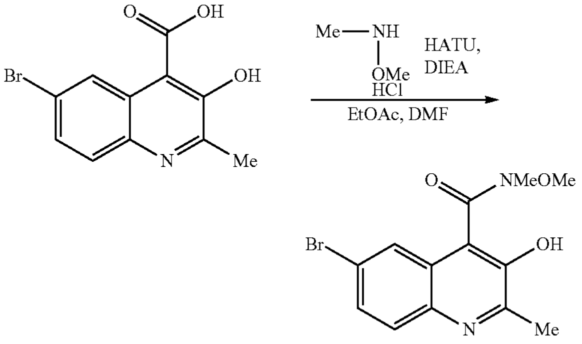

To a mixture of 6-bromo-3-hydroxy-2-methylquinoline-4-carboxylic acid (5.27 g, 18.68 mmol; prepared from 5-bromoindoline-2,3-dione using the procedure described in Step 1 for the synthesis of Example 1). N,O-dimethyl hydroxylamine hydrochloride (2.369 g, 24.29 mmol) and Hunig's base (6.04 g, 46.7 mmol) in EtOAc (72 ml) and DMF (8.00 ml) was added HATU (10.66 g, 28.0 mmol) at RT. The reaction was heated to 50° C. and stirred 16 h. LC-MS indicated complete conversion to a product with desired mass. The reaction was quenched with water and extracted several times with EtOAc. The organics were washed with water and brine, dried ($Na_2SO_4$) and concentrated. Purification by silica gel column chromatography (ISCO 220 g column, 0-30% acetone in hexane) provided the desired compound (4.25 g, 13.07 mmol, 70.0% yield) as a yellow solid.

Step 2

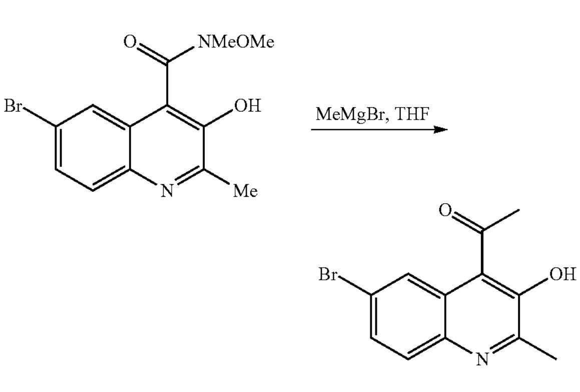

To a solution of the product obtained from Step 1 (4.2 g, 12.92 mmol) in THF (120 ml) at 0° C. was added MeMgBr (12.92 ml, 38.8 mmol; 3M in ether), and the reaction was stirred overnight after gradually allowing it to come to RT. LC-MS indicated approximately 75% conversion to the desired product. After cooling, the reaction to 0° C., 1.0 eq. of MeMgBr was added; no change after 2 h. The reaction was carefully quenched with sat. aq. $NH_4Cl$ solution and extracted with EtOAc. The combined organic fractions were, dried ($MgSO_4$), filtered, concentrated under vacuo and purified by column chromatography (0-50% EtOAc in hexane) to provide 1-(6-bromo-3-hydroxy-2-methylquinolin-4-yl)ethanone (2.5 g, 8.92 mmol, 69.1% yield) as a yellow solid.

Step 3

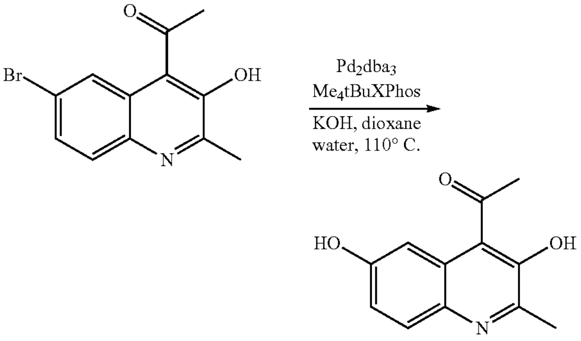

In a sealed tube were placed 1-(6-bromo-3-hydroxy-2-methylquinolin-4-yl)ethanone (2.0 g, 7.14 mmol, obtained from Step 2), KOH (1.202 g, 21.42 mmol), $Pd_2(dba)_3$ (0.327 g, 0.357 mmol), $Me_4$tBuXPhos [CAS: 857356-94-6; bis(1,1,dimethylethyl[3,4,5,6-tetramethyl-2',4',6'-tris(1-methylethyl)[1,1'-biphenyl]-2-yl]phosphine (0.343 g, 0.714 mmol), dioxane (20 ml) and degassed water (20 ml). The reaction was heated at 110° C. for 2 h, at which stage LC-MS indicated complete conversion to the desired product. After cooling to RT, the reaction was transferred into a beaker and carefully acidified with 1N HCl, stirred for 5 min and then carefully basified by addition of solid $NaHCO_3$ (effervesence observed—slow addition is crucial). The mixture was then extracted several times with EtOAc until all the product was in the organic fractions. The combined organics were washed with brine, dried over $Na_2SO_4$ and concentrated. Purification by column chromatography (0-40% acetone in hexane) provided the product of Step 3 (1.0 g, 64.5% yield).

Step 4

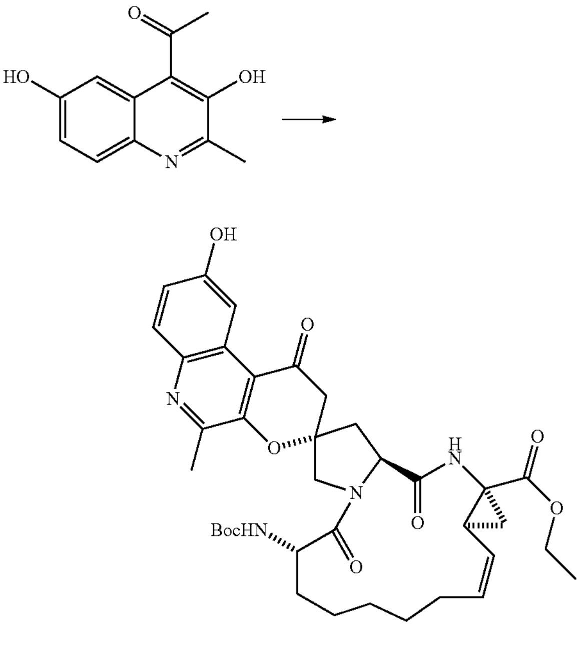

The product of Step 4 was prepared from the product of Step 3 using the procedures described in Example 30, Step 5.

Step 5

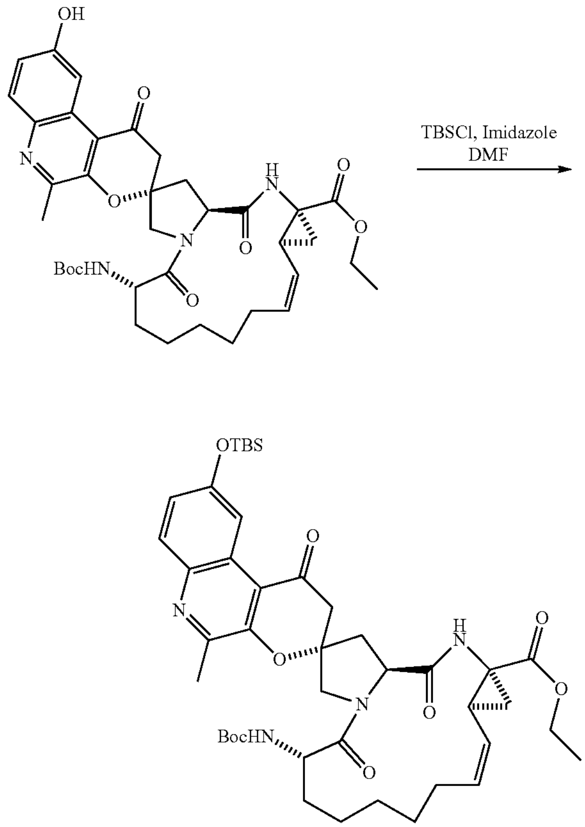

To a solution of the product of Step 4 (230 mg, 0.333 mmol) in DMF (3330 μl) was added imidazole (68.0 mg, 0.999 mmol) followed by tert-butyldimethylchlorosilane (100 mg, 0.666 mmol). The reaction was stirred overnight under $N_2$ at RT and then diluted with EtOAc and washed with water and brine. The combined organic fractions were dried ($MgSO_4$), concentrated and purified by column chromatography (0-100% EtOAc in hexane) to provide the product of Step 5 (250 mg, 0.311 mmol, 93% yield).

Step 6

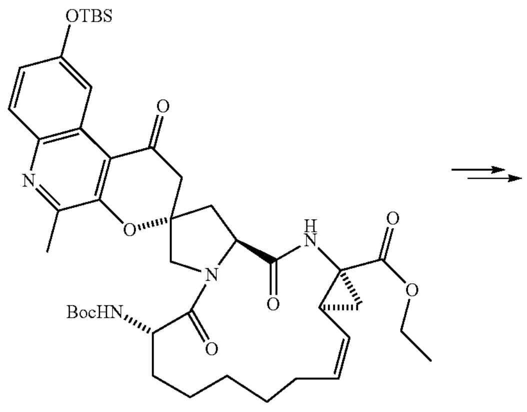

-continued

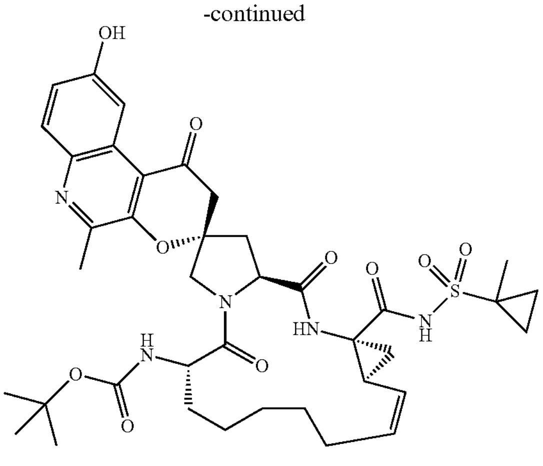

The product of Step 5 was converted into I-58 using the procedures described in Example 30, Steps 6-9.

Example 59 tert-Butyl ((2R,6S,13aS,14aR,16aS,Z)-9'-cyano-5'-methyl-14a-(((1-methyl cyclopropyl)sulfonyl)carbamoyl)-5,16-dioxo-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinolin]-6-yl)carbamate (I-59)

Step 1

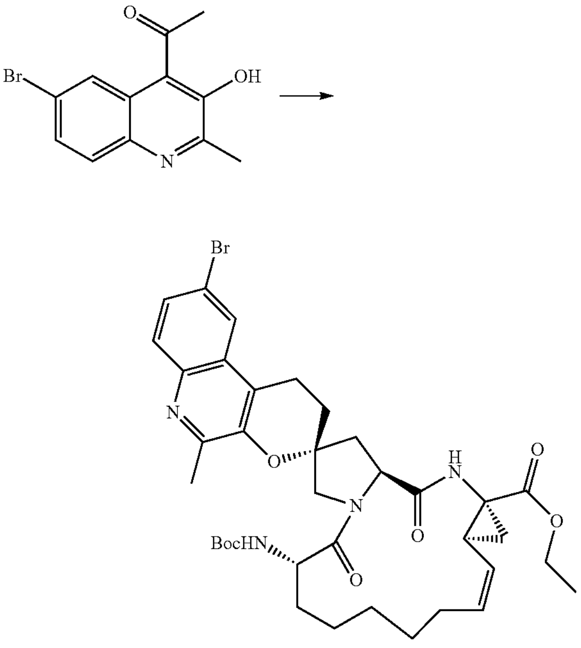 [SMILES: CC(=O)c1c(O)c(C)nc2ccc(Br)cc12 ; CCOC(=O)[C@@]12C[C@H]1/C=C\CCCCC[C@H](NC(=O)OC(C)(C)C)C(=O)N1C[C@@]3(CCc4c(c(C)nc5ccc(Br)cc45)O3)C[C@H]1C(=O)N2]

The product of Step 1 was prepared from i-(6-bromo-3-hydroxy-2-methylquinolin-4-yl)ethanone using the procedures described in Example 30, Steps 5-8

Step 2

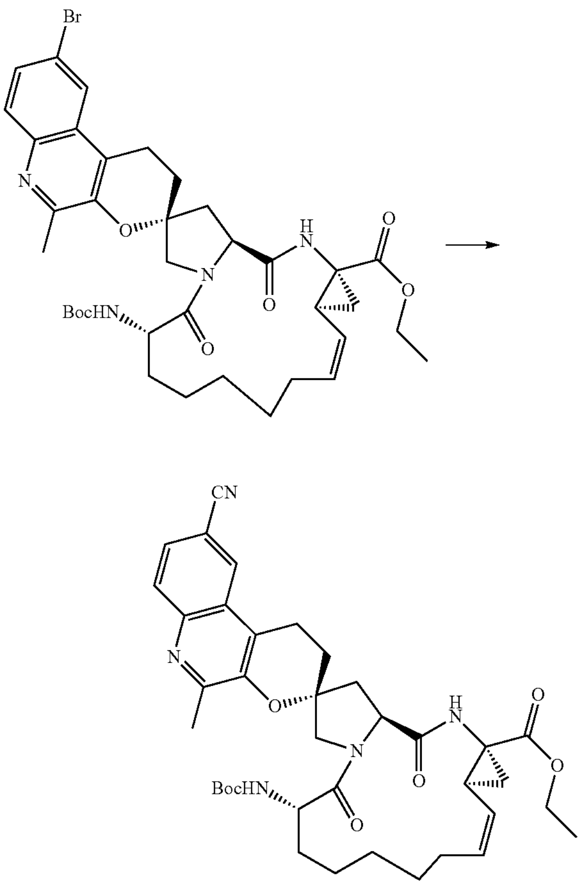

To a solution of the product of Step 1 (47 mg, 0.064 mmol) in DMF (1 mL) was added zinc cyanide (9.70 mg, 0.083 mmol) followed by $Pd(Ph_3P)_4$ (11.01 mg, 9.53 μmol). The reaction was stirred at 100° C. for 16 h, cooled to RT and then diluted with EtOAc and washed with water and brine. The combined organic fractions were dried ($MgSO_4$), concentrated and purified by column chromatography (0-100% EtOAc in hexane) to provide the product of Step 2 (37 mg, 0.054 mmol, 85% yield).

Step 3

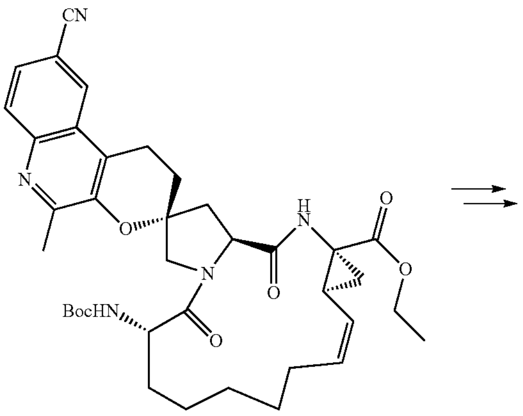

-continued

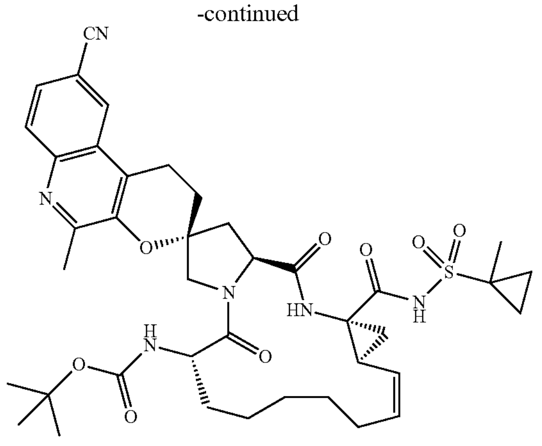

The product of Step 2 was converted into I-59 using the procedures described in Example 30, Step 9.

Example 60 tert-Butyl ((2R,6S,13aS,14aR,16aS,Z)-9'-(2-hydroxyethoxy)-14a-(((1-methyl cyclopropyl)sulfonyl) carbamoyl)-5,16-dioxo-5'-(trifluoromethyl)-1',2',3,5, 6,7,8,9,10,11,13a, 14,14a,15,16,16a-hexadecahydro-1H-spiro[cyclopropa[e]pyrrolo[1,2-a][1,4] diazacyclopentadecine-2,3'-pyrano[2,3-c]quinolin]-6-yl)carbamate (I-60)

Step 1

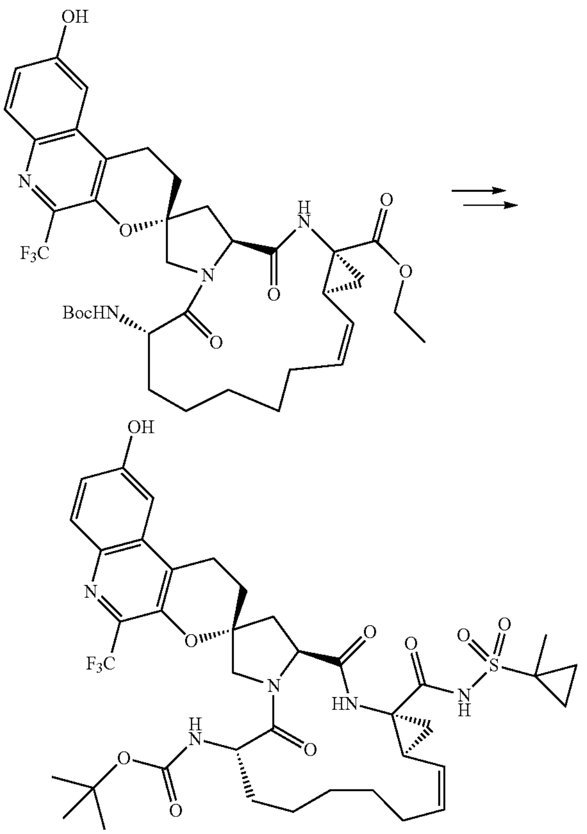

The product of Example 50, Step 1 was converted into the product of Step 1 by using the procedures described in Example 30, Step 9.

Step 2

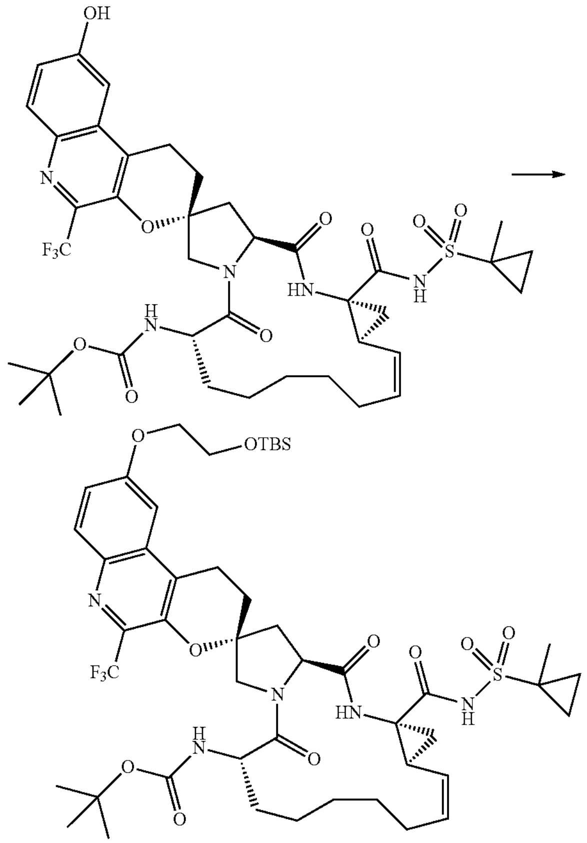

To a solution of the product of Step 1 (205 mg, 0.250 mmol) in DMF (2.500 mL) was added (2-bromoethoxy)(tert-butyl)dimethylsilane (90 mg, 0.375 mmol) followed by $Cs_2CO_3$ (163 mg, 0.500 mmol) at RT. The reaction was stirred at 65° C. for 8 h and then allowed to cool to RT. After diluting with EtOAc, the reaction was washed with water and brine. The organic fraction was dried ($Na_2SO_4$), filtered, concentrated and purified (ISCO, 24 g silica gel column, 0-60% EtOAc in hexane) to provide the product of Step 2 (180 mg, 0.184 mmol, 73.6% yield).

Step 3

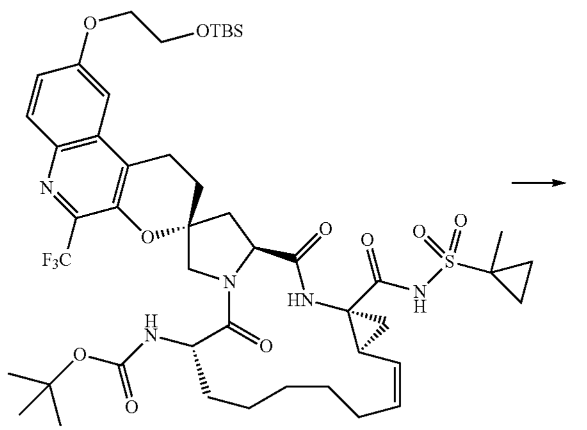

-continued

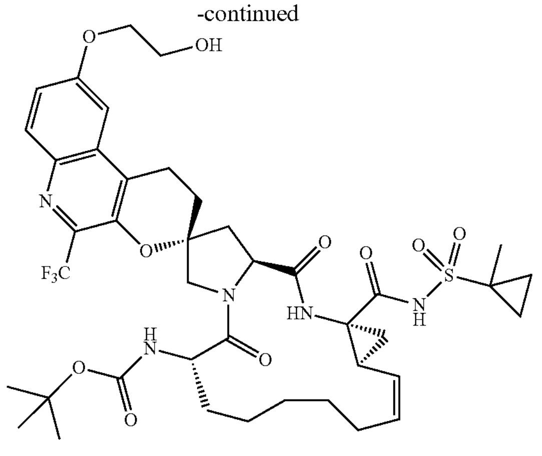

To a solution of the product of Step 2 (175 mg, 0.179 mmol) in THF (4 mL) was added TBAF (0.53 mL, 0.537 mmol) at RT. The reaction was stirred under an atmosphere of $N_2$ for 1 h, at which stage LC-MS indicated complete conversion to the desired product. The reaction was quenched with sat. aq. $NH_4Cl$ solution and washed with EtOAc. The organic fractions were combined, dried ($Na_2SO_4$), filtered and concentrated to give an oily residue, which was purified by silica gel chromatography (24 g Redisep column, 0-80% acetone in hexane) to provide I-60 (145 mg, 0.168 mmol, 94% yield) as a white solid.

Example 61

(2R,6S,12Z,13aS,14aR,16aS)-5'-methyl-N-[(1-methylcyclopropyl)sulfonyl]-5,16-dioxo-6-[(pyrrolidin-1-ylcarbonyl)amino]-1,1',2',6,7,8,9,10,11,13a,14,15,16,16a -tetradecahydrospiro[cyclopropa[e]pyrrolo[1,2-a][1,4]diazacyclopentadecine-2,3'-pyrano[2,3-c]quinoline]-14a(5H)-carboxamide (I-61)

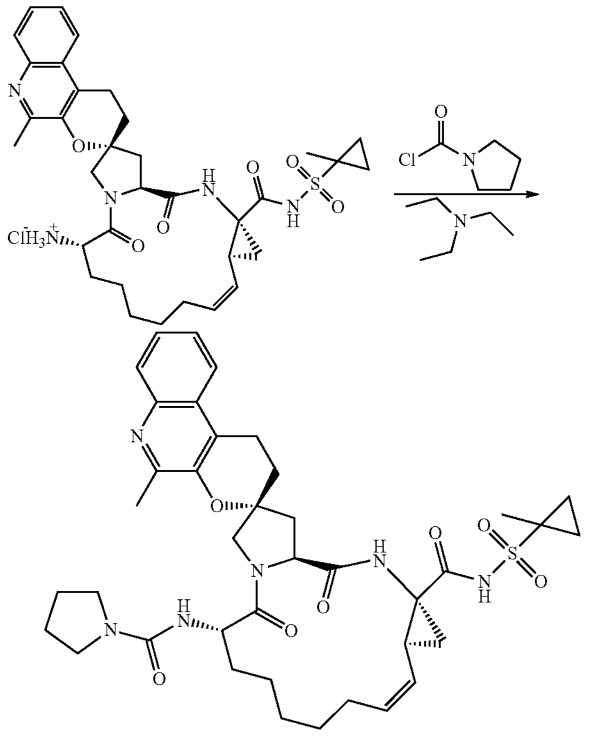

To a suspension of the product of Example 47, Step 10 (11 mg, 0.016 mmol) in DCM (0.5 ml) were added $Et_3N$ (0.011 ml, 0.080 mmol) and 1-pyrrolidinecarbonyl chloride (5.31 μl, 0.048 mmol). The mixture was stirred at RT overnight. It was diluted with DCM, washed with aq. $NH_4Cl$, concentrated and separated by preparative thin layer chromatography with 5% MeOH/DCM to give I-61 (10 mg, 0.013 mmol, 84% yield) as a white solid. LC-MS $MH^+$: 747.

Example 62 tert-Butyl ((2S,6S,13aS,14aR,16aS,Z)-9'-methoxy-1-methyl-14a-(((1-methyl cyclopropyl)sulfonyl)carbamoyl)-5,16-dioxo-5'-(trifluoromethyl)-3,5,6,7,8,9,10,11,13a, 14,14a,15,16,16a-tetradecahydro-1H-spiro[cyclopropa[e]pyrrolo[1,2-a][1,4]diaza cyclopentadecine-2,3'-pyrano[2,3-c]quinolin]-6-yl) carbamate (I-62);

Example 63 tert-Butyl ((1'R,2S,6S,13aS,14aR,16aS,Z)-1'-fluoro-9'-methoxy-1-methyl-14a -(((1-methylcyclopropyl) sulfonyl)carbamoyl)-5,16-dioxo-5'-(trifluoromethyl)-1',2',3,5,6,7,8, 9,1011,13a,14,14a,15,16,16a-hexadecahydro-1H-spiro[cyclopropa[e]pyrrolo[1,2-a][1,4]diazacyclopentadecine-2,3'-pyrano[2,3-c] quinolin]-6-yl)carbamate (I-63); and Example 64 tert-Butyl ((1'S,2S,6S,13aS,14aR,16aS,Z)-1'-fluoro-9'-methoxy-1-methyl-14a -(((1-methylcyclopropyl) sulfonyl)carbamoyl)-5,16-dioxo-5'-(trifluoromethyl)-1',2',3,5,6,7,8, 9,10,11,13a,14,14a,15,16,16a-hexadecahydro-1H-spiro[cyclopropa[e]pyrrolo[1,2-a][1,4]diazacyclopentadecine-2,3'-pyrano[2,3-c] quinolin]-6-yl)carbamate (I-64)

Step 1

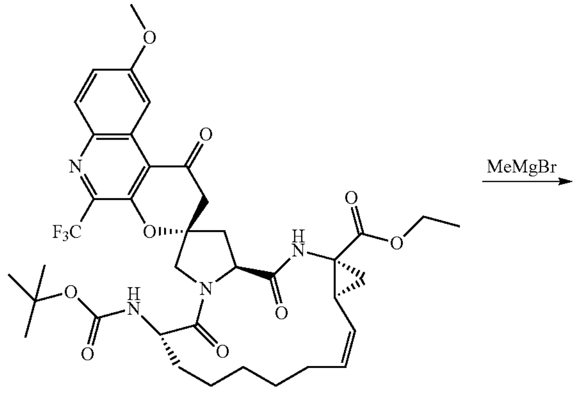

-continued

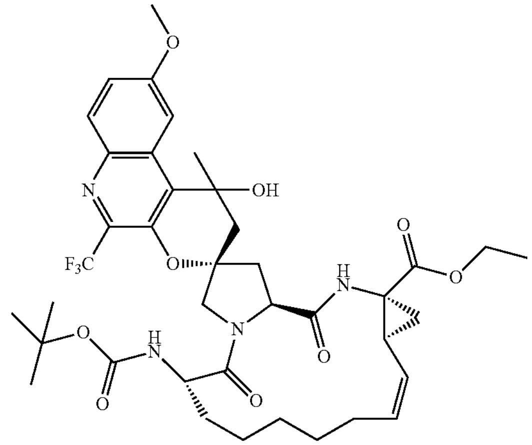

To the solution of (2S,6S,13aS,14aR,16aS,Z)-ethyl 6-((tert-butoxycarbonyl) amino)-9'-methoxy-1',5,16-trioxo-5'-(trifluoromethyl)-1',2',3,5,6,7,8,9,10,11,13a,14,14a,15, 16,16a-hexadecahydro-1H-spiro[cyclopropa[e]pyrrolo[1,2-a][1,4]diazacyclopentadecine-2,3'-pyrano[2,3-c]quinoline]-14a-carboxylate (2923 mg, 3.85 mmol) in THF (26 ml) was added 1.4M of MeMgBr solution in THF (11.01 ml, 15.41 mmol) at −25° C. and stirred at −25° C. for 20 min. TLC and LC-MS indicated that the major was product (about 50%) and starting material. Then the reaction was quenched with 1N HCl to pH=5-6 (about 12 ml 1N HCl), and diluted with EtOAc (40 ml). The layers were separated, and the aq. layer was extracted again with EtOAc (25 ml×2). The organic layers were combined and washed with brine, dried over $MgSO_4$, filtered, and concentrated in vacuo. The residue was purified by column chromatography on silica gel (120 g, gold column), eluting with 100% hexane for 400 ml, gradient to 35% of acetone to give 1430 mg of starting material and 1130 mg of (2S,6S,13aS,14aR,16aS,Z)-ethyl 6-((tert -butoxycarbonyl)amino)-1'-hydroxy-9'-methoxy-1'-methyl-5,16-dioxo-5'-(trifluoromethyl)-1',2',3,5,6,7,8,9,10,11,13a,14,14a, 15,16,16a-hexadecahydro-1H-spiro[cyclopropa[e]pyrrolo [1,2-a][1,4]diazacyclopentadecine-2,3'-pyrano[2,3-c] quinoline]-14a-carboxylate as a light yellow solid. m/z=775.4 (M+1)

Step 2

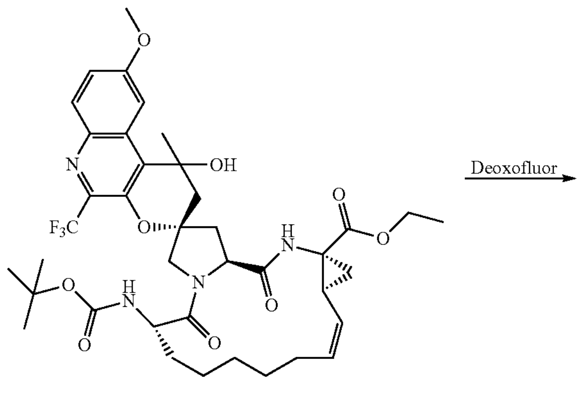

-continued

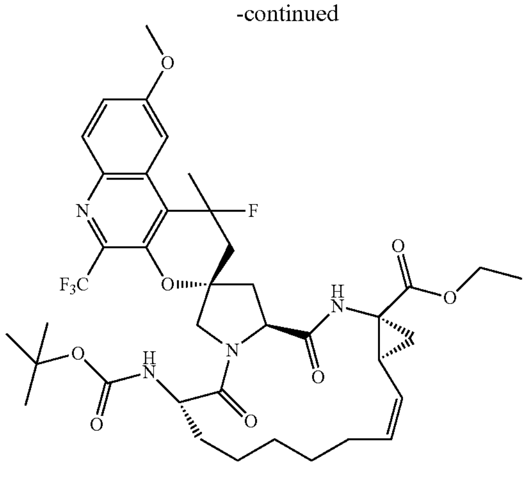

62-2A

+

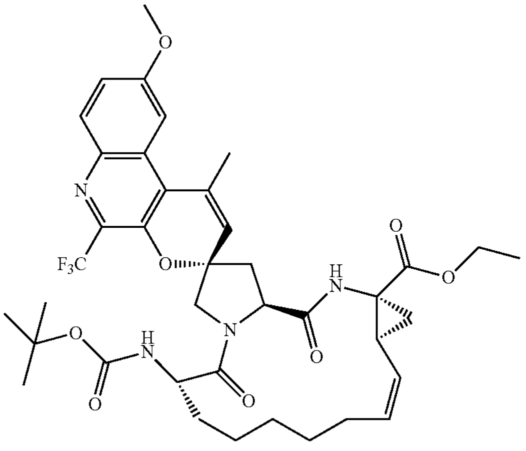

62-2B

To a solution of the product of Step 1 (731 mg, 0.143 mmol) in DCM (18 ml) at 0° C. was added DeoxoFluor (0.209 ml, 1.132 mmol) and EtOH (0.013 ml), and the mixture was stirred at 0° C. for 30 min. The reaction was quenched with aq. $NaHCO_3$ (15 ml). The layers were separated, and the aq. layer was extracted again with DCM (3×30 ml). The combined organic layer were dried over $MgSO_4$, filtered, evaporated to dryness under reduced pressure. The residue was purified by column chromatography using silica gel column (80 g, gold column), eluting with 100% hexane for 400 ml, gradient to 60% of EtOAc to give the mixture of (2S,6S,13aS,14aR,16aS,Z)-ethyl 6-((tert-butoxycarbonyl)amino)-1'-fluoro-9'-methoxy-1'-methyl-5,16-dioxo-5'-(trifluoromethyl)-1',2',3,5,6,7,8,9,10,11,13a,14,14a,15,16,16a -hexadecahydro-1H-spiro[cyclopropa[e]pyrrolo[1,2-a][1,4]diazacyclopentadecine-2,3'-pyrano[2,3-c]quinoline]-14a-carboxylate (m/z=777.3 (M+1)) and (2S,6S,13aS,14aR,16aS,Z) -ethyl 6-((tert-butoxycarbonyl)amino)-9'-methoxy-1'-methyl-5,16-dioxo-5'-(trifluoromethyl) -3,5,6,7,8,9,10,11,13a,14,14a,15,16,16a-tetradecahydro-1H-spiro[cyclopropa[e]pyrrolo[1,2-a][1,4]diazacyclopentadecine-2,3'-pyrano[2,3-c]quinoline]-14a-carboxylate (m/z=757.3 (M+1)) as a white solid (the LC-MS indicate the ratio about 62-2A/62-2B=4/1).

Step 3

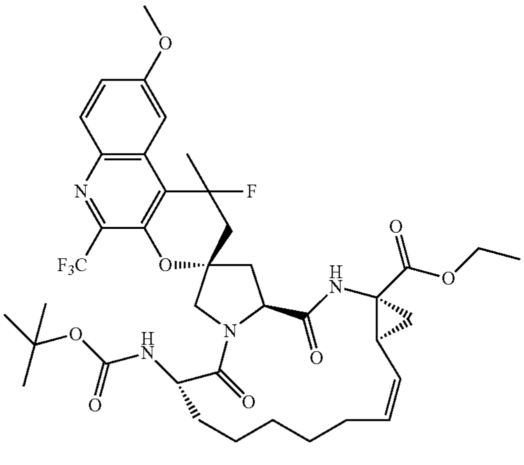

62-2A

+

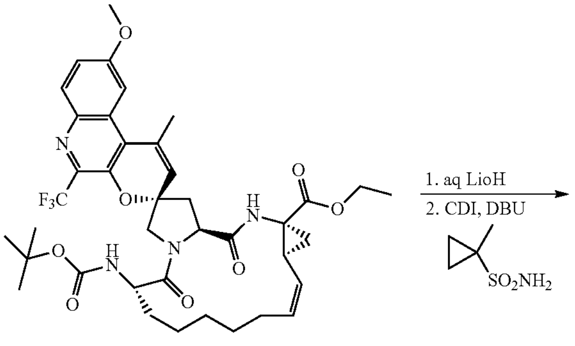

62-2B

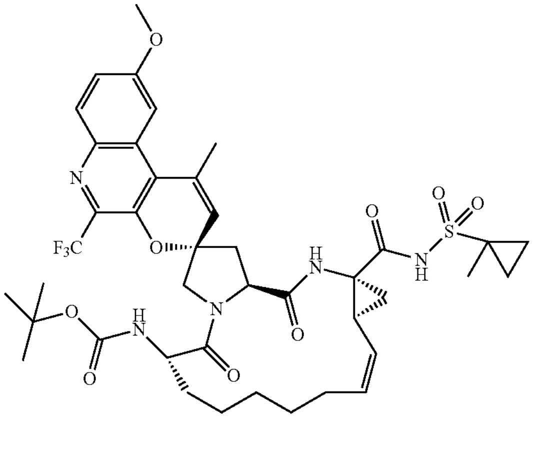

+

I-62

-continued

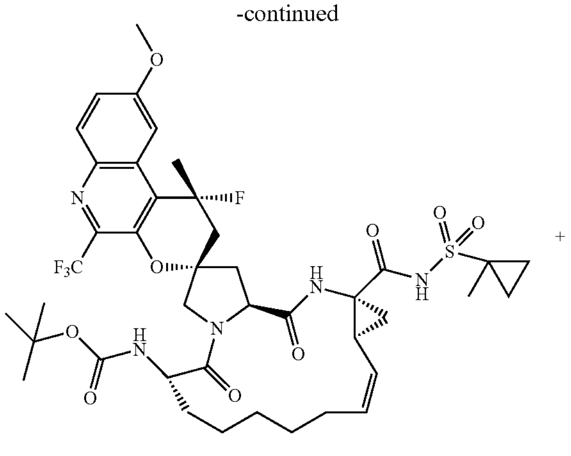

I-63

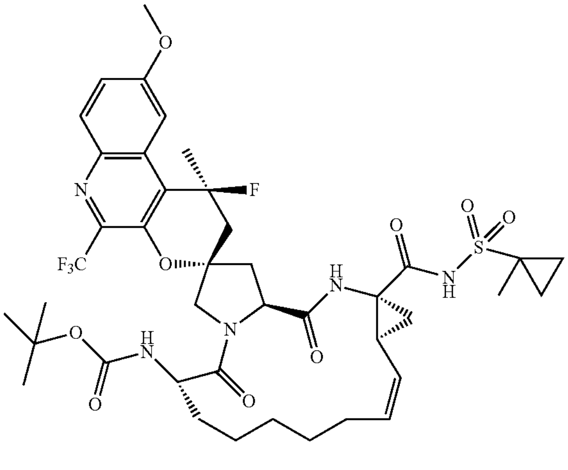

I-64

The reaction mixture of 62-2A and 62-2B (275 mg, which about 80% of 62-2A and 20% of 62-2B) was suspended in THF (4.5 ml), MeOH (1.5 ml) and $H_2O$ (1.1 ml) and the LiOH (56.0 mg, 2.336 mmol) was added. It was stirred at RT for 7.5 h. The LC-MS shows the hydrolysis was complete. It was acidified to pH=2~3 with 1N HCl solution (about 1.9 ml of 1N HCl) at 0° C., and diluted with EtOAc (30 ml). The layers were separated, and the aq. layer was extracted again with EtOAc (30 ml×1). The organic layers were combined and washed with brine (4×6 ml), dried over $MgSO_4$, filtered, and concentrated in vacuo. The concentrated layer was azeotroped with toluene (2×) and kept under vacuum overnight to give 256 mg of the mixture of acids which were used without purification.

A reaction mixture of (2S,6S,13aS,14aR,16aS,Z)-6-((tert-butoxycarbonyl)amino) -1'-fluoro-9'-methoxy-1'-methyl-5,16-dioxo-5'-(trifluoromethyl)-1',2',3,5,6,7,8,9,10,11,13a,14,14a,15,16,16a-hexadecahydro-1H-spiro[cyclopropa[e]pyrrolo[1,2-a][1,4]diazacyclopentadecine -2,3'-pyrano[2,3-c]quinoline]-14a-carboxylic acid and (2S,6S,13aS,14aR,16aS,Z)-6-((tert -butoxycarbonyl)amino)-9'-methoxy-1'-methyl-5,16-dioxo-5'-(trifluoromethyl)-3,5,6,7,8,9, 10,11,13a,14,14a,15,16,16a-tetradecahydro-1H-spiro[cyclopropa[e]pyrrolo[1,2-a][1,4]diazacyclopentadecine-2,3'-pyrano[2,3-c]quinoline]-14a-carboxylic acid (269 mg), CDI (114 mg, 0.704 mmol) in THF (4.5 ml) was stirred in an oil-bath at 70° C. for 3 h, then it was cooled to RT. To this reaction mixture was added 1-methylcyclopropane-1-sulfonamide (95 mg, 0.704 mmol) and DBU in THF (1M) (0.932 ml, 0.932 mmol), and the mixture was stirred in an oil-bath at 46° C. for 2.2 h. The reaction mixture was diluted with EtOAc (40 ml), washed with aq. $NH_4Cl$(2×4 ml), brine, dried over $MgSO_4$, filtered, concentrated. The residue was purified by column chromatography on silica gel (40 g, gold column), eluting with 100% hexane for 200 ml, gradient to 40% of acetone to give mixture of fluorides, which were separated by supercritical fluid chromatography to yield:

Example 62: $^1$H NMR δ (ppm)($CHCl_3$): 10.13 (1 H, s), 8.05 (1 H, d, J=9.23 Hz), 7.49 (1 H, s), 7.37-7.26 (2 H, m), 6.95 (1 H, s), 5.91 (1 H, s), 5.75 (1 H, q, J=8.80 Hz, 5.24 (1 H, s), 5.04 (1 H, t, J=9.29 Hz), 4.61 (2 H, t, J=13.23 Hz), 4.21 (1 H, s), 3.99 (3 H, s), 3.64 (1 H, d, J=11.38 Hz), 2.80 (1 H, d, J=12.09 Hz), 2.61 (1 H, s), 2.55 (3 H, s), 2.48 (1 H, d, J=12.05 Hz), 2.39 (1 H, q, J=8.72 Hz), 1.94 (3 H, s), 1.91-1.73 (4 H, m), 1.41 (1 H, s), 1.30 (18 H, d, J=13.55 Hz), 1.18 (1 H, s), 1.12 (3 H, s), 0.95-0.80 (5 H, m). m/z=846.3 (M+1).

Example 63: $^1$H NMR δ (ppm)($CHCl_3$): 10.01 (1 H, s), 8.07 (1 H, d, J=9.18 Hz), 7.60 (1 H, s), 7.35 (1 H, d, J=9.21 Hz), 7.30 (1 H, s), 6.85 (1 H, s), 5.72 (1 H, q, J=8.82 Hz), 5.30 (1 H, d, J=8.60 Hz), 5.00 (1 H, t, J=9.35 Hz), 4.62 (1 H, d, J=10.99 Hz), 4.47 (1 H, t, J=8.33 Hz), 4.35 (1 H, t, J=9.61 Hz), 4.01 (3 H, s), 3.85 (1 H, d, J=11.10 Hz), 2.82 (1 H, dd, J=21.99, 14.86 Hz), 2.66 (1 H, s), 2.66-2.55 (3 H, m), 2.55-2.40 (1 H, m), 2.37 (1 H, q, J=8.72 Hz), 2.08 (1 H, s), 2.08-1.98 (2 H, m), 1.93-1.82 (4 H, m), 1.83-1.73 (4 H, m), 1.39 (9 H, s), 1.33 (5 H, s), 1.29 (3 H, s), 0.96-0.77 (4 H, m). m/z=866.2 [M+1].

Example 64: $^1$H NMR δ (ppm)($CHCl_3$): 10.17 (1 H, s), 8.11-8.02 (1 H, m), 7.60 (1 H, s), 7.38-7.26 (2 H, m), 7.05 (1 H, s), 5.75 (1 H, q, J=8.88 Hz), 5.08-5.00 (2 H, m), 4.68 (1 H, t, J=8.43 Hz), 4.62-4.39 (4 H, m), 4.01 (4 H, s), 3.72 (1 H, d, J=11.84 Hz), 2.84-2.51 (6 H, m), 2.41-2.29 (1 H, m), 2.13-1.98 (4 H, m), 1.95 (2 H, t, J=7.37 Hz), 1.91-1.69 (7 H, m), 1.38 (3 H, d, J=18.32 Hz), 1.31 (9 H, s), 1.24 (1 H, d, J=7.55 Hz), 1.19 (9 H, s), 0.96-0.83 (6 H, m). m/z=866.2 [M+1].

Example 65 tert-Butyl((1'S,2R,6S,13aS,14aR,16aS,Z)-9'-methoxy-14a-(((1-methyl cyclopropyl)sulfonyl)carbamoyl)-1'-morpholino-5,16-dioxo-5'-(trifluoromethyl) -1',2',3,5,6,7,8,9,10,11,13a,14,14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I -65); and

Example 66 tert-Butyl((1'R,2R,6S,13aS,14aR,16aS,Z)-9'-methoxy-14a-(((1-methyl cyclopropyl)sulfonyl)carbamoyl)-1'-morpholino-5,16-dioxo-5'-(trifluoromethyl) -1',2',3,5,6,7,8,9,10,11,13a,14,14a,15,16,16a-hexadecahydro-1H-spiro[cyclopropa[e]pyrrolo[1,2-α][1,4]diazacyclopentadecine-2,3'-pyrano[2,3-c]quinolin]-6-yl)carbamate (I-66)

Step 1

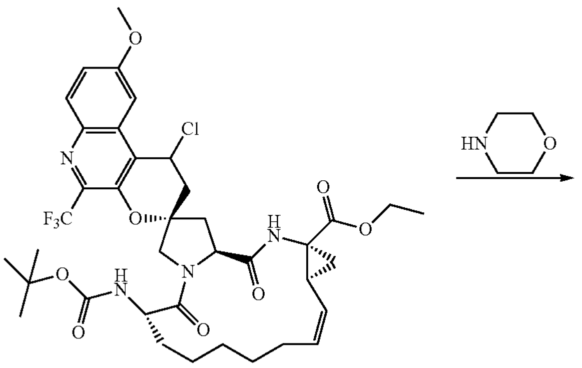

-continued

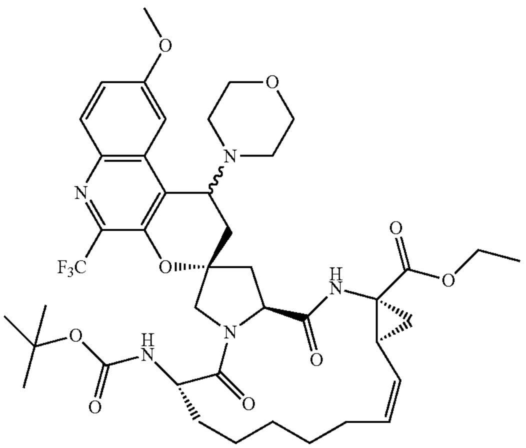

The reaction mixture of ethyl (2S,6S,12Z,13aS,14aR,16aS)-6-[(tert -butoxycarbonyl)amino]-1'-chloro-9'-methoxy-5,16-dioxo-5'-(trifluoromethyl)-1,1',2',6,7,8,9,10,11,13a,14,15,16,16a-tetradecahydrospiro[cyclopropa[e]pyrrolo[1,2-α][1,4]diazacyclopentadecine-2,3'-pyrano[2,3-c]quinoline]-14a(5H)-carboxylate (176 mg, 0.226 mmol) and sodium iodide (67.7 mg, 0.452 mmol) in 1.00 ml of morpholine in a microwave vial was stirred for 24 h at RT. The LC-MS indicated the reaction almost complete. It was evaporated under reduced pressure to remove excess morpholine, diluted with EtOAc (15 ml) and water (5 ml). The layers were separated, and the aq. layer was extracted again with EtOAc (15 ml×2). The organic layers were combined and washed with brine (3 ml), dried over $MgSO_4$, filtered, and the solvent was evaporated under reduced pressure. The residue was purified by column chromatography on silica gel (24 g, gold column, dry loading), eluting with 100% hexane for 300 ml, gradient to 40% of EtOAc to yield the product of Step 1 (m/z=830.3 (M+1)), as a light yellow solid.

Step 2

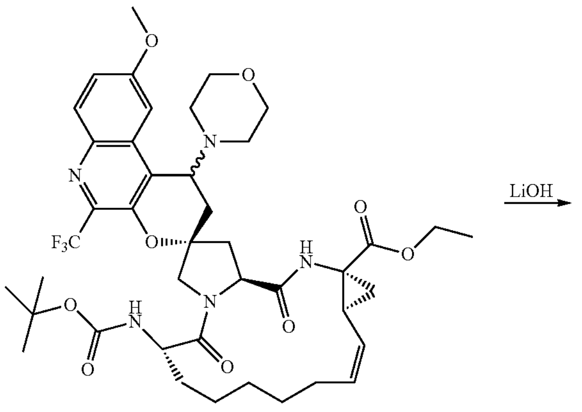

-continued

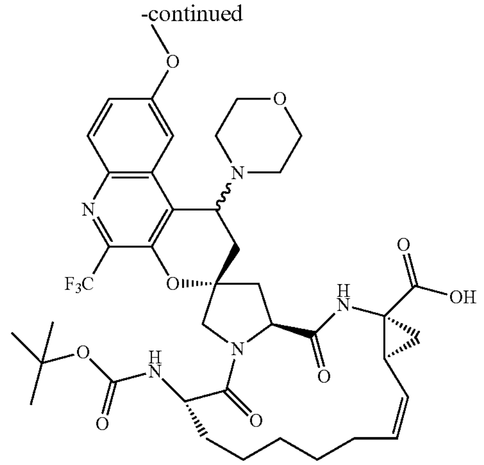

To the reaction mixture of the product of Step 1 (110 mg, 0.133 mmol) in THF (2.0 ml), MeOH (1.0 ml) and $H_2O$ (0.7 ml) was added the LiOH (38.1 mg, 1.591 mmol) at RT. It was stirred at RT for 5.5 h. The LC-MS shows the hydrolysis was complete. It was acidified to pH=2~3 with 1N HCl solution (about 1.2 ml of 1N HCl) at 0° C., and diluted with EtOAc (30 ml). The layers were separated, and the aq. layer was extracted again with EtOAc (10 ml×1). The organic layers were combined and washed with brine (4×3 ml), dried over $MgSO_4$, filtered, and was evaporated under reduced pressure. The resulting concentrate was azeotroped with toluene (2×) and kept under vacuum overnight to give 104 mg of the product of Step 2 (m/z=802.08 (M+1), as a white solid that was used without further purification.

Step 3

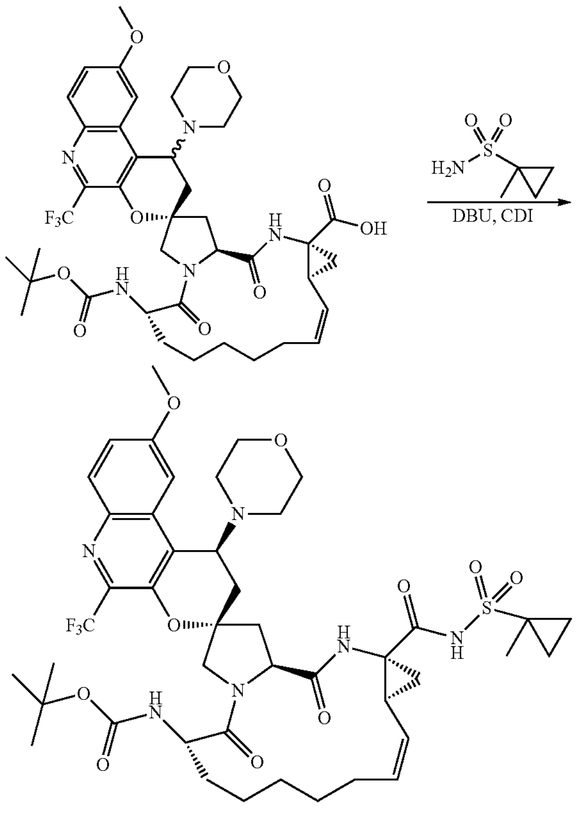

I-65

-continued

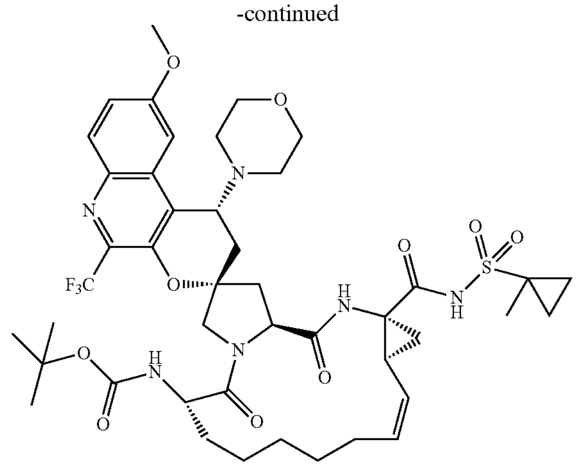

I-66

A solution of the product of Step 2 (98 mg, 0.122 mmol) and CDI (41.6 mg, 0.257 mmol) in THF (2.0 ml) was stirred in an oil-bath kept at 70° C. for 3 h, then cooled to RT. To this reaction mixture was added 1-methylcyclopropane-1-sulfonamide (49.6 mg, 0.367 mmol) and DBU in THF (1M) (0.428 ml, 0.428 mmol), and the mixture was stirred in an oil-bath kept at 50° C. for 2.5 h. LC-MS indicated that the reaction almost completed. The reaction mixture was diluted with EtOAc (30 ml), washed with aq. $NH_4Cl$(2×4 ml), brine, dried over $MgSO_4$, filtered, and concentrated. The residue was purified by column chromatography on silica gel (12 g, gold column, dry loading), eluting with 100% hexane for 200 ml, gradient to 45% of acetone/hexanes to tert-butyl ((2R,6S,13aS,14aR,16aS,Z)-9'-methoxy-14a-(((1-methylcyclopropyl)sulfonyl) carbamoyl)-1'-morpholino-5,16-dioxo-5'-(trifluoromethyl)-1',2',3,5,6,7,8,9,10,11,13a,14,14a, 15,16,16a-hexadecahydro-1H-spiro[cyclopropa[e]pyrrolo[1,2-a][1,4] diazacyclopentadecine-2,3'-pyrano[2,3-c]quinolin]-6-yl) carbamate (m/z=919.80 (M+1)), as a white solid.

The isomeric mixture of tert-butyl ((2R,6S,13aS,14aR, 16aS,Z)-9'-methoxy-14a -(((1-methylcyclopropyl)sulfonyl) carbamoyl)-1'-morpholino-5,16-dioxo-5'-(trifluoromethyl)-1',2',3,5,6,7,8,9,10,11,13a,14,14a,15,16,16a-hexadecahydro-1H-spiro[cyclopropa[e]pyrrolo[1,2-a][1,4] diazacyclopentadecine-2,3'-pyrano[2,3-c]quinolin]-6-yl) carbamate was separated and purified with 50% MeOH (0.2% diethylamine)/$CO_2$, 70 ml/min, 100 bar, on an IC column (30×250 mm) to obtain I-65 and I-66.

Example 65: $^1$H NMR δ (ppm)($CHCl_3$): $^1$H NMR δ (ppm) ($CHCl_3$-d): 10.10 (1 H, s), 8.02 (1 H, d, J=9.14 Hz), 7.83 (1 H, s), 7.35-7.27 (3 H, m), 6.97 (1 H, s), 5.73 (1 H, q, J=8.87 Hz), 5.28 (1 H, d, J=8.96 Hz), 5.01 (1 H, t, J=9.31 Hz), 4.78 (1 H, d, J=11.39 Hz), 4.63 (1 H, s), 4.54-4.44 (2 H, m), 4.35 (1 H, t, J=10.01 Hz), 4.02 (4 H, s), 3.90 (1 H, t, J=11.39 Hz), 3.73 (4 H, s), 3.68 (4 H, s), 3.51 (1 H, q, J=7.12 Hz), 3.44 (1 H, q, J=7.13 Hz), 3.08-3.00 (3 H, m), 2.70-2.33 (12 H, m), 2.28 (1 H, dd, J=13.77, 5.73 Hz), 1.95-1.81 (5 H, m), 1.76 (7 H, t, J=22.15 Hz), 1.33 (12 H, s), 1.32-1.20 (7 H, m), 0.99 (1 H, d, J=6.65 Hz), 0.94-0.75 (7 H, m), 0.09 (1 H, s). m/z=919.70 [M+1].

Example 66: $^1$H NMR δ (ppm)($CHCl_3$): $^1$H NMR δ (ppm) ($CHCl_3$-d): 10.10 (1 H, s), 8.02 (1 H, d, J=9.14 Hz), 7.83 (1 H, s), 7.35-7.27 (3 H, m), 6.97 (1 H, s), 5.73 (1 H, q, J=8.87 Hz), 5.28 (1 H, d, J=8.96 Hz), 5.01 (1 H, t, J=9.31 Hz), 4.78 (1 H, d, J=11.39 Hz), 4.63 (1 H, s), 4.54-4.44 (2 H, m), 4.35 (1 H, t, J=10.01 Hz), 4.02 (4 H, s), 3.90 (1 H, t, J=11.39 Hz), 3.73 (4 H, s), 3.68 (4 H, s), 3.51 (1 H, q, J=7.12 Hz), 3.44 (1 H, q, J=7.13 Hz), 3.08-3.00 (3 H, m), 2.70-2.33 (12 H, m), 2.28 (1 H, dd, J=13.77, 5.73 Hz), 1.95-1.81 (5 H, m), 1.76 (7 H, t, J=22.15 Hz), 1.33 (12 H, s), 1.32-1.20 (7 H, m), 0.99 (1 H, d, J=6.65 Hz), 0.94-0.75 (7 H, m), 0.09 (1 H, s). m/z=919.70 [M+1].

Example 67 tert-Butyl ((2R,6S,13aS,14aR,16aS,Z)-14a-(((1-methylcyclopropyl)sulfonyl) carbamoyl)-5,16-dioxo-9'(2-(piperidin-1-yl)ethoxy)-5'-(trifluoromethyl)-1',2',3,5,6,7,8, 9,10,11,13a,14,14a,15,16,16a-hexadecahydro-1H-spiro[cyclopropa[e]pyrrolo[1,2-a][1,4]diazacyclopentadecine-2,3'-pyrano[2,3-c]quinolin]-6-yl)carbamate (I-67)

Step 1

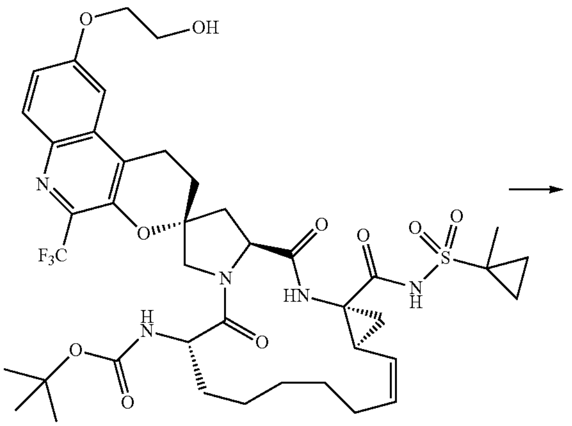

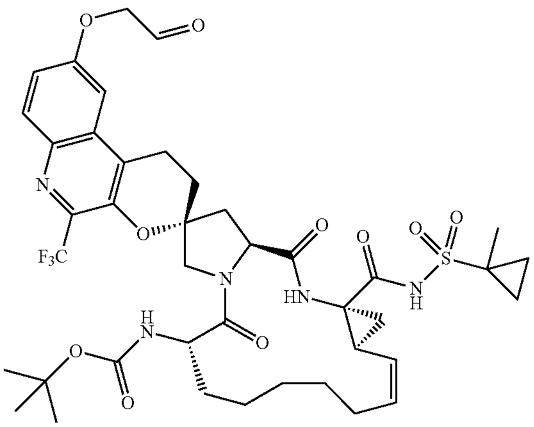

To a solution of the compound of Example 60 (145 mg, 0.168 mmol) in $CH_2Cl_2$ (3.357 mL) was added Dess-Martin periodinane (85 mg, 0.201 mmol) at RT. The reaction was stirred 2 h, at which stage LC-MS indicated complete consumption of the starting material (a new peak corresponding to the mass of the product dihydrate was observed by LC-MS). The reaction was quenched with 10% aq. $Na_2S_2O_3$ solution and sat. aq. $NaHCO_3$ solution and stirred for 15 min at RT. After separating the organic fraction, the aq. layer was washed twice with $CH_2Cl_2$. The combined organic fractions were washed with sat. aq. $NaHCO_3$ followed by brine. The organic fraction was dried ($Na_2SO_4$), filtered, concentrated to give the product of Step 1 (142 mg, 0.165 mmol, 98% yield) as a white solid, which was used without purification.

Step 2

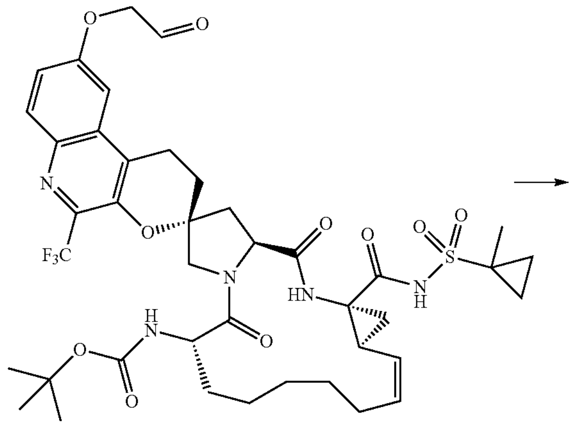

-continued

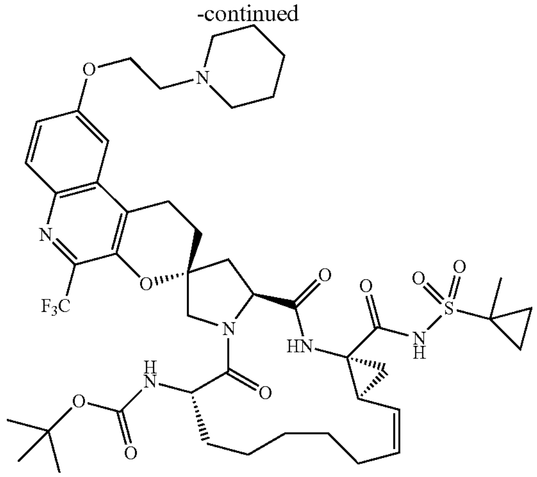

To a solution of the product of Step 1 (50 mg, 0.058 mmol) in DCE (2.5 mL) was added piperidine (0.029 mL, 0.290 mmol) at RT. The reaction was stirred for 15 min and then was treated with 0.05 mL AcOH followed by sodium triacetoxyborohydride (24.59 mg, 0.116 mmol) at RT. The reaction was stirred at RT for 16 h and then diluted with $CH_2Cl_2$ and washed twice with sat. aq. $NaHCO_3$ followed by brine. The organic fraction was dried ($Na_2SO_4$), filtered, concentrated and purified by silica gel column chromatography (0-60-100% acetone in hexane) to provide I-67 (20 mg, 0.021 mmol, 37.0% yield).

Examples 68-526

Table 1 illustrates additional HCV protease inhibitors. Reference to "Proc." indicates the Example describing the general procedure employed to produce the compound. The procedure was modified as needed. By using the appropriate procedures or combination of procedures and the appropriate intermediates, the compounds of Examples 68-526 were prepared, as shown in Table 1 below. All compounds prepared from racemic intermediates were separated from resulting diastereomers using reverse or normal phase column chromatography following macrocycle formation or after the final step.

TABLE 1

| Compounds of Examples 68-526 | | | | |
|---|---|---|---|---|
| Ex. No. | Structure | Name | Proc. | LR-MS (M + H) |
| 68 | 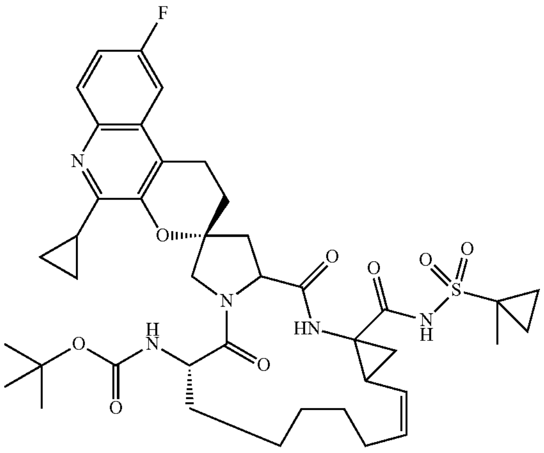 I-68 | tert-butyl [(2R,6S,12Z)-5'-cyclopropyl-9'-fluoro-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 794 |
| 69 | 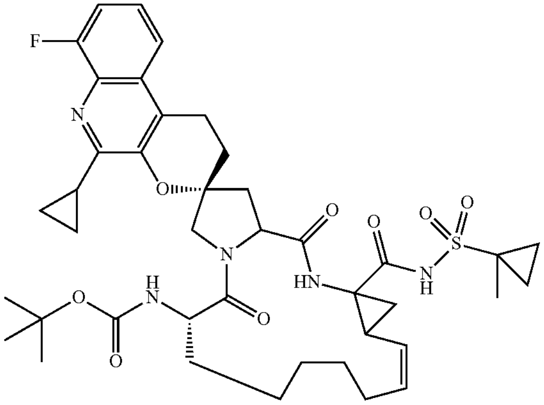 I-69 | tert-butyl [(2R,6S,12Z)-5'-cyclopropyl-7'-fluoro-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 794 |

TABLE 1-continued

| Compounds of Examples 68-526 | | | | |
|---|---|---|---|---|
| Ex. No. | Structure | Name | Proc. | LR-MS (M + H) |
| 70 | 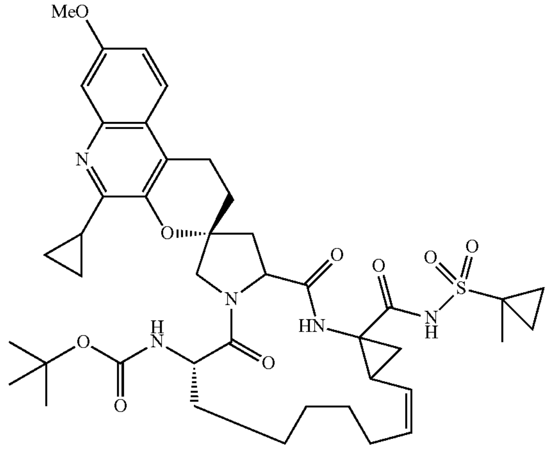 I-70 | tert-butyl [(2R,6S,12Z)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 806 |
| 71 | 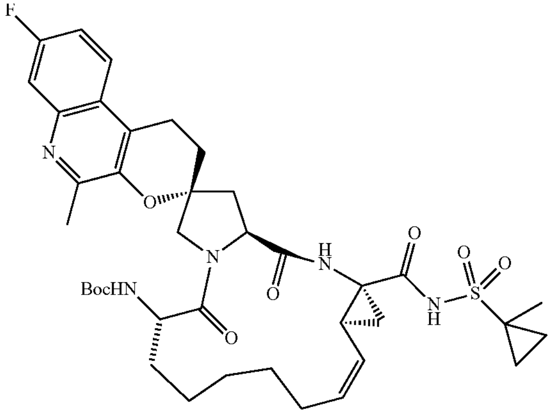 I-71 | tert-butyl [(2R,6S,12Z,13aS,14aR,16aS)-8'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 768.2 |

TABLE 1-continued

| Compounds of Examples 68-526 | | | | |
|---|---|---|---|---|
| Ex. No. | Structure | Name | Proc. | LR-MS (M + H) |
| 72 | 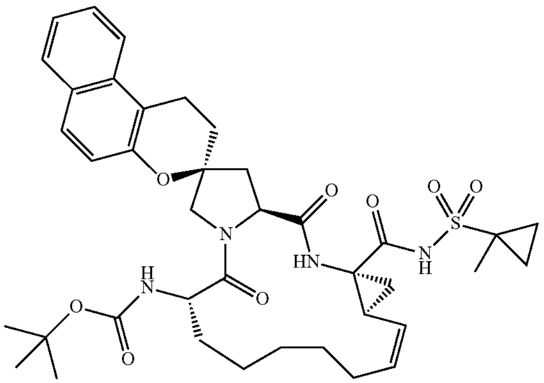 I-72 | tert-butyl [(3S,6'S,12'Z,13a'S,14a'R,16a'S)-14a'-{[(1-methylcyclopropyl)sulfonyl]carbamoyl}-5',16'-dioxo-1,1',2,5',6',7',8',9',10',11',13a',14',14a',15',16',16a'-hexadecahydrospiro[benzo[f]chromene-3,2'-cyclopropa[e]pyrrolo[1,2-a][1,4]diazacyclopentadecin]-6'-yl]carbamate | 9 | 773.2 |
| 73 | 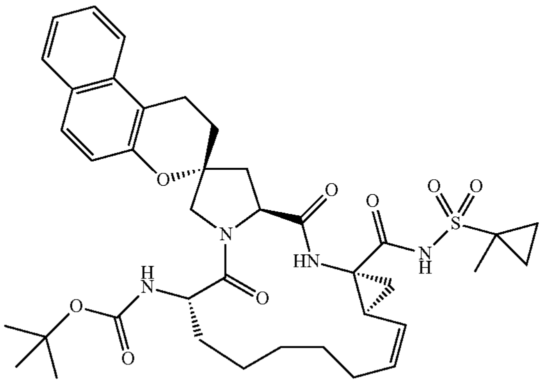 I-73 | tert-butyl [(3R,6'S,12'Z,13a'S,14a'R,16a'S)-14a'-{[(1-methylcyclopropyl)sulfonyl]carbamoyl}-5',16'-dioxo-1,1',2,5',6',7',8',9',10',11',13a',14',14a',15',16',16a'-hexadecahydrospiro[benzo[f]chromene-3,2'-cyclopropa[e]pyrrolo[1,2-a][1,4]diazacyclopentadecin]-6'-yl]carbamate | 9 | 773.2 |

TABLE 1-continued

| Compounds of Examples 68-526 | | | | |
|---|---|---|---|---|
| Ex. No. | Structure | Name | Proc. | LR-MS (M + H) |
| 74 | 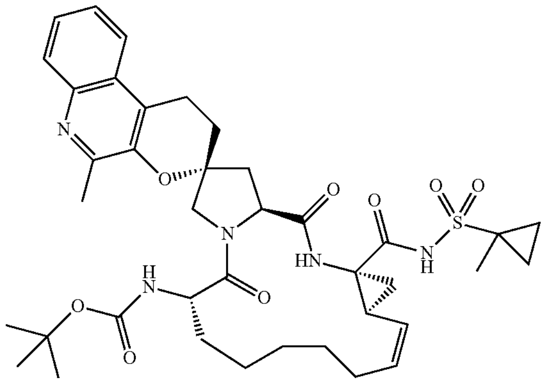 I-74 | tert-butyl [(2R,6S,12Z,13aS,14aR,16aS)-5'-methyl-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 750.3 |
| 75 | 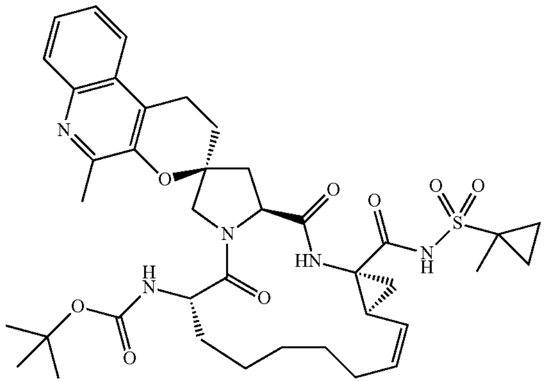 I-75 | tert-butyl [(2S,6S,12Z,13aS,14aR,16a5)-5'-methyl-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 750.3 |

TABLE 1-continued

| Compounds of Examples 68-526 | | | | |
|---|---|---|---|---|
| Ex. No. | Structure | Name | Proc. | LR-MS (M + H) |
| 76 | 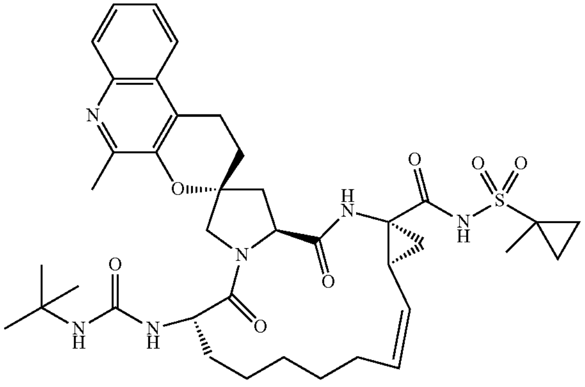 I-76 | (2R,6S,12Z,13aS,14aR,16aS)-6-[(tert-butylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 749.2 |
| 77 | 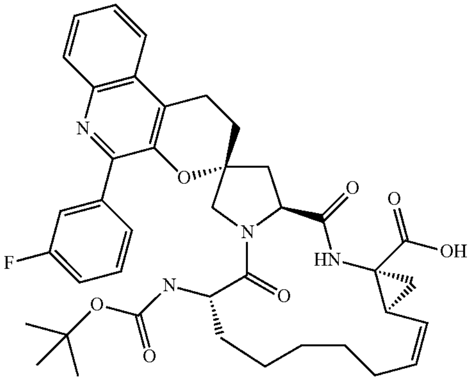 I-77 | (2R,6S,12Z,13aS,14aR,16aS)-6-[(tert-butoxycarbonyl)amino]-5'-(3-fluorophenyl)-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxylic acid | 13 | 713.4 |

TABLE 1-continued

Compounds of Examples 68-526

| Ex. No. | Structure | Name | Proc. | LR-MS (M + H) |
|---|---|---|---|---|
| 78 | 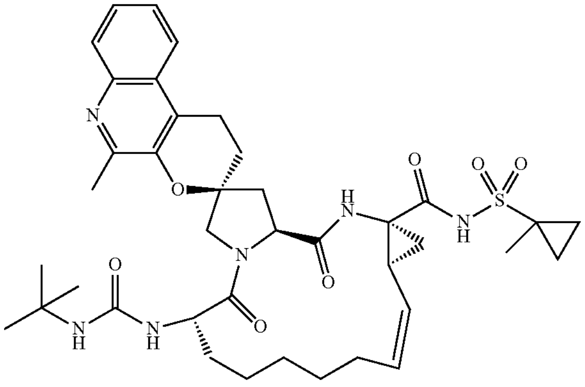 I-78 | (2S,6S,12Z,13aS,14aR,16aS)-6-[(tert-butylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 23 | 749.4 |
| 79 | 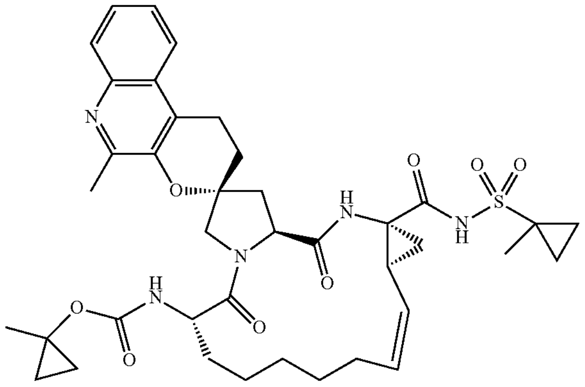 I-79 | 1-methylcyclopropyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 748.4 |

TABLE 1-continued

| Compounds of Examples 68-526 | | | | |
|---|---|---|---|---|
| Ex. No. | Structure | Name | Proc. | LR-MS (M + H) |
| 80 | 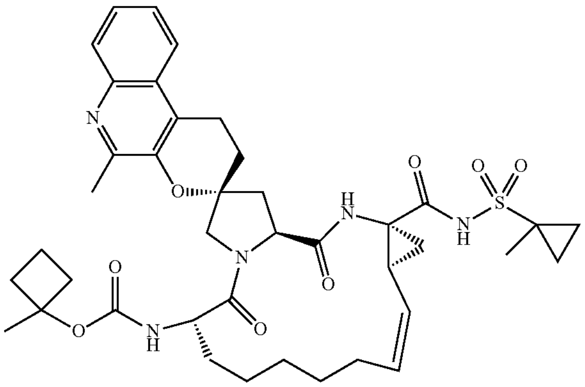 I-80 | 1-methylcyclobutyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 35 | 762.4 |
| 81 | 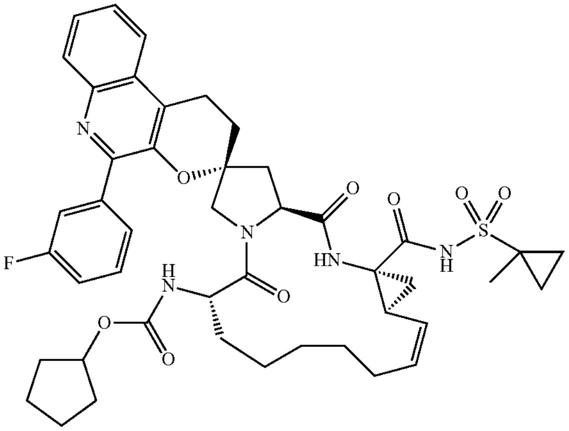 I-81 | cyclopentyl [(2R,6S,12Z,13aS,14aR,16aS)-5'-(3-fluorophenyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 13 | 842.4 |

TABLE 1-continued

| Compounds of Examples 68-526 | | | | |
|---|---|---|---|---|
| Ex. No. | Structure | Name | Proc. | LR-MS (M + H) |
| 82 | 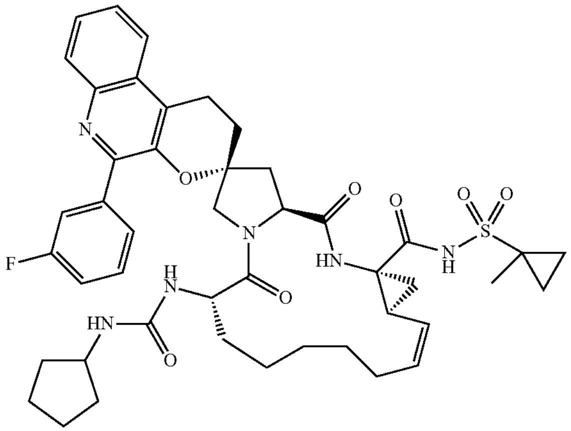 I-82 | (2R,6S,12Z,13aS,14aR,16aS)-6-[(cyclopentylcarbamoyl)amino]-5'-(3-fluorophenyl)-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 13 | 841.2 |
| 83 | 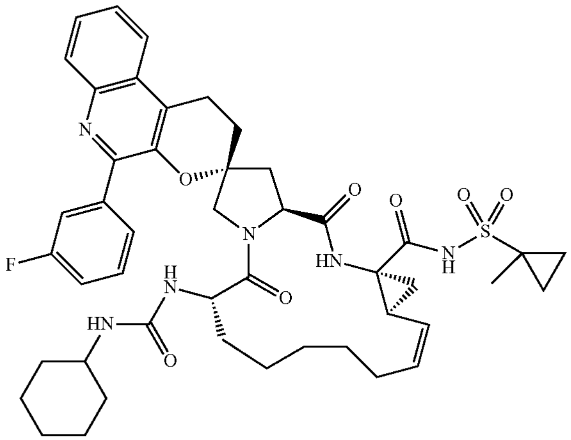 I-81 | (2R,6S,12Z,13aS,14aR,16aS)-6-[(cyclohexylcarbamoyl)amino]-5'-(3-fluorophenyl)-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 13 | 855.2 |

TABLE 1-continued

Compounds of Examples 68-526

| Ex. No. | Structure | Name | Proc. | LR-MS (M + H) |
|---|---|---|---|---|
| 84 | 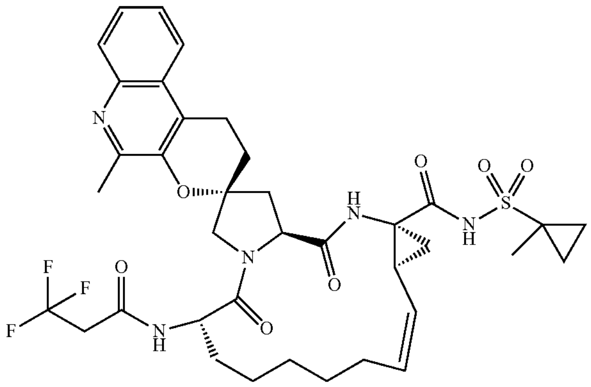 I-84 | (2R,6S,12Z,13aS,14aR,16aS)-5'-methyl-N-[(1-methylcyclopropyl)sulfonyl]-5,16-dioxo-6-[(3,3,3-trifluoropropanoyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 24 | 760.4 |
| 85 | 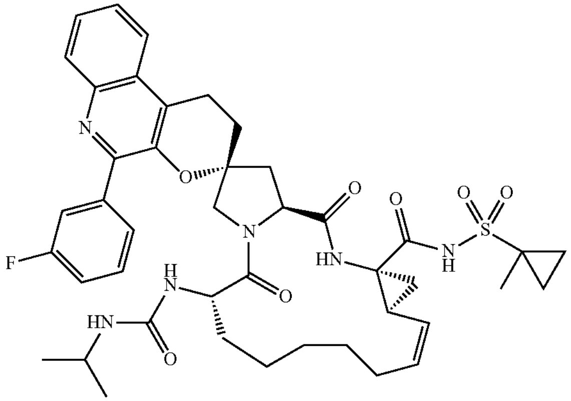 I-85 | (2R,6S,12Z,13aS,14aR,16aS)-5'-(3-fluorophenyl)-N-[(1-methylcyclopropyl)sulfonyl]-5,16-dioxo-6-[(propan-2-ylcarbamoyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5R)-carboxamide | 13 | 815.2 |

TABLE 1-continued

| Compounds of Examples 68-526 | | | | |
| --- | --- | --- | --- | --- |
| Ex. No. | Structure | Name | Proc. | LR-MS (M + H) |
| 86 | 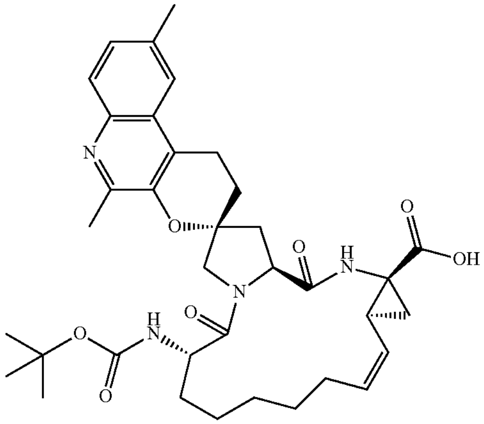 I-86 | (2R,6S,12Z,13aS,14aR,16aS)-6-[(tert-butoxycarbonyl)amino]-5',9'-dimethyl-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxylic acid | 42 | 647.5 |
| 87 | 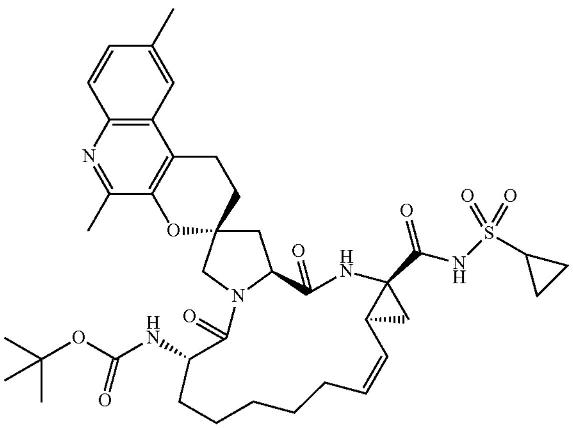 I-87 | tert-butyl {(2R,6S,12Z,13aS,14aR,16aS)-14a-[(cyclopropylsulfonyl)carbamoyl]-5',9'-dimethyl-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 42 | 750.5 |

TABLE 1-continued

| Compounds of Examples 68-526 | | | | |
|---|---|---|---|---|
| Ex. No. | Structure | Name | Proc. | LR-MS (M + H) |
| 88 | 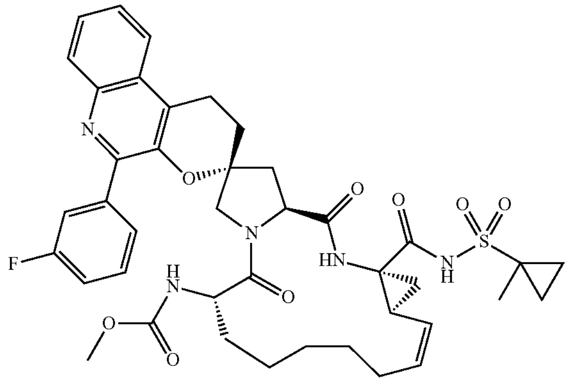 I-88 | methyl [(2R,6S,12Z,13aS,14aR,16aS)-5'-(3-fluorophenyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 13 | 788.4 |
| 89 | 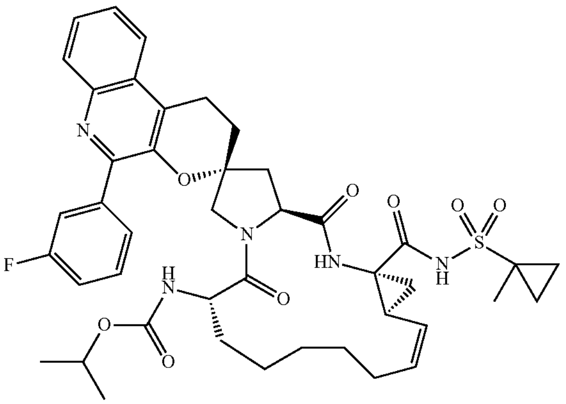 I-89 | propan-2-yl [(2R,6S,12Z,13aS,14aR,16aS)-5'-(3-fluorophenyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 13 | 817.2 |

TABLE 1-continued

Compounds of Examples 68-526

| Ex. No. | Structure | Name | Proc. | LR-MS (M + H) |
|---|---|---|---|---|
| 90 | 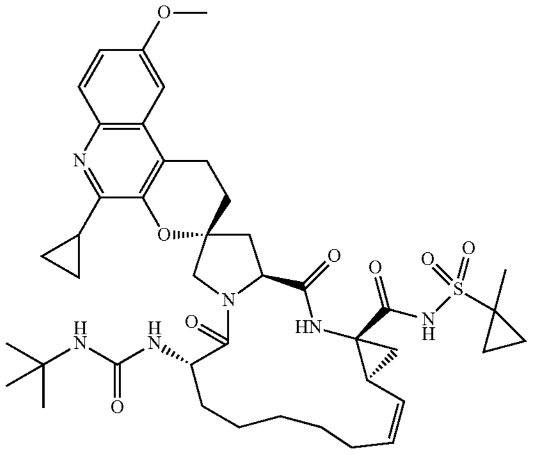 I-90 | (2R,6S,12Z,13aS,14aR,16aS)-6-[(tert-butylcarbamoyl)amino]-5'-cyclopropyl-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 16 | 805.4 |
| 91 | 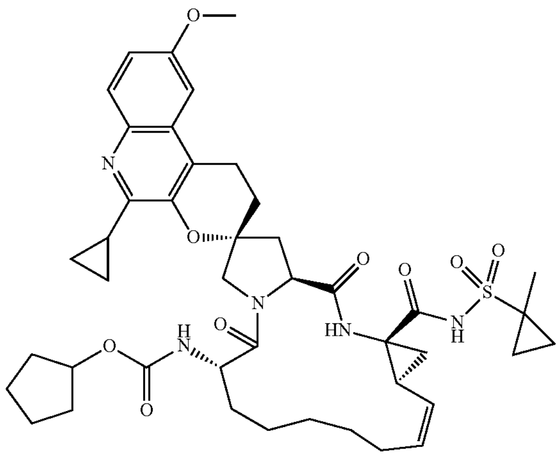 I-91 | cyclopentyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 818.5 |

TABLE 1-continued

| Compounds of Examples 68-526 | | | | |
|---|---|---|---|---|
| Ex. No. | Structure | Name | Proc. | LR-MS (M + H) |
| 92 | 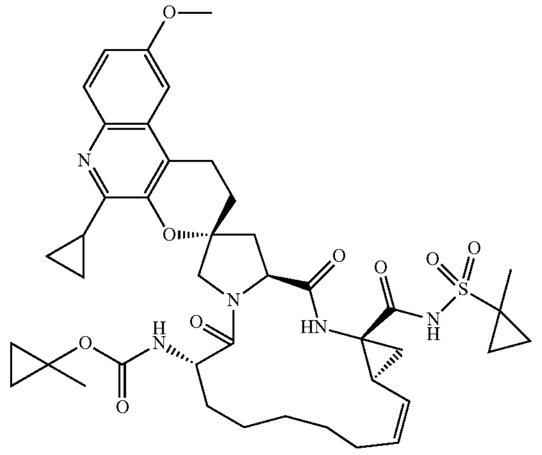 I-92 | 1-methylcyclopropyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 804.4 |
| 93 | 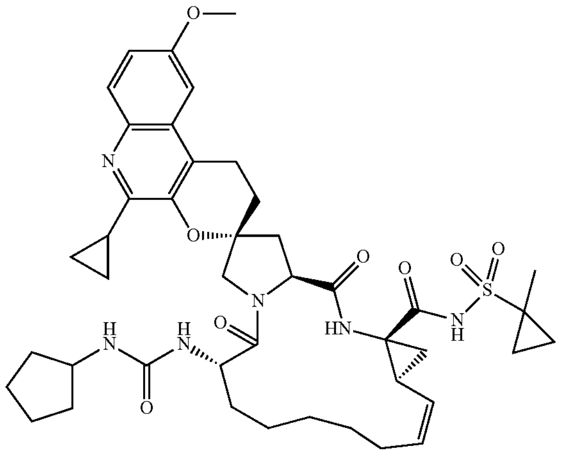 I-93 | (2R,6S,12Z,13aS,14aR,16aS)-6-[(cyclopentylcarbamoyl)amino]-5'-cyclopropyl-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 16 | 817.4 |

TABLE 1-continued

Compounds of Examples 68-526

| Ex. No. | Structure | Name | Proc. | LR-MS (M + H) |
|---|---|---|---|---|
| 94 | 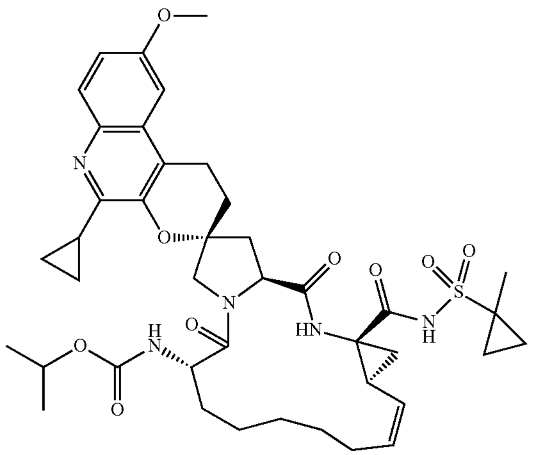 I-94 | propan-2-yl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16, 528 | 792.4 |
| 95 | 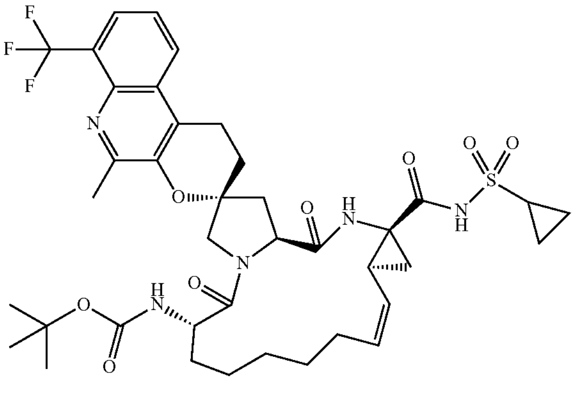 I-95 | tert-butyl [(2R,6S,12Z,13aS,14aR,16aS)-14a-[(cyclopropylsulfonyl)carbamoyl]-5'-methyl-5,16-dioxo-7'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 804.2 |

TABLE 1-continued

Compounds of Examples 68-526

| Ex. No. | Structure | Name | Proc. | LR-MS (M + H) |
|---|---|---|---|---|
| 96 | 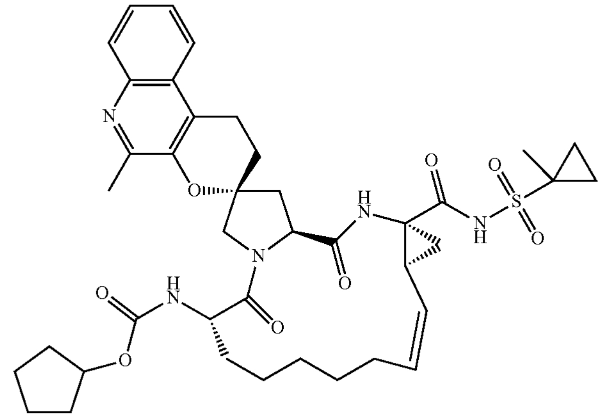 I-96 | cyclopentyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 761.8 |
| 97 | 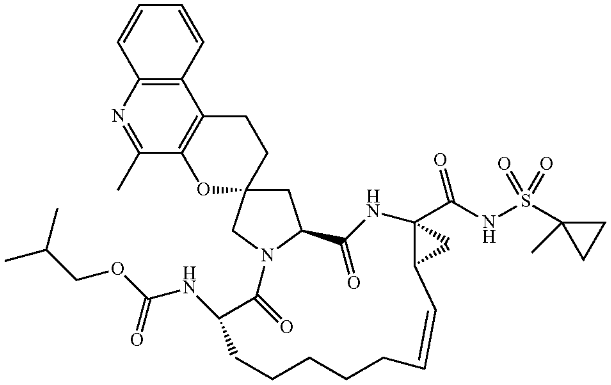 I-97 | 2-methylpropyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 750.4 |

TABLE 1-continued

| Compounds of Examples 68-526 | | | | |
|---|---|---|---|---|
| Ex. No. | Structure | Name | Proc. | LR-MS (M + H) |
| 98 | 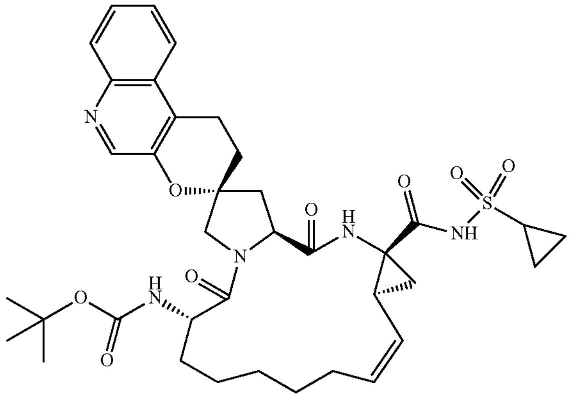 I-98 | tert-butyl {(2R,6S,12Z,13aS,14aR,16aS)-14a-[(cyclopropylsulfonyl)carbamoyl]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 9 | 766.4 |
| 99 | 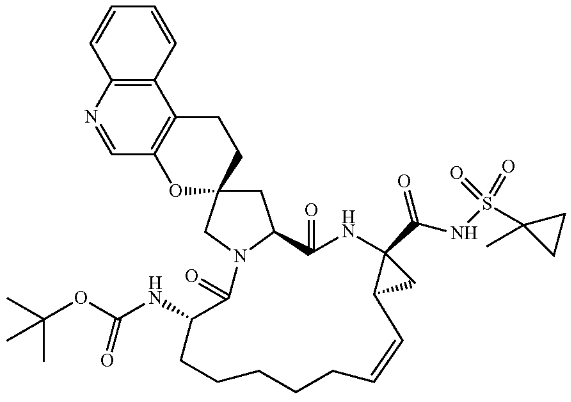 I-99 | tert-butyl [(2R,6S,12Z,13aS,14aR,16aS)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 736.4 |

TABLE 1-continued

| Compounds of Examples 68-526 | | | | |
|---|---|---|---|---|
| Ex. No. | Structure | Name | Proc. | LR-MS (M + H) |
| 100 | 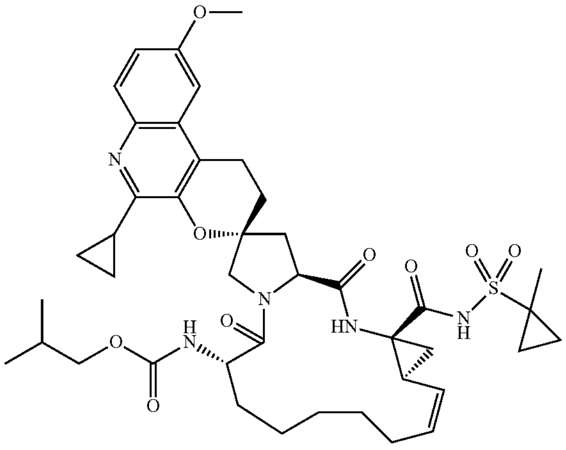 I-100 | 2-methylpropyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 806.2 |
| 101 | 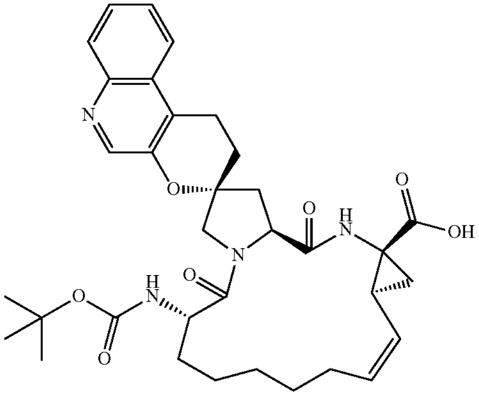 I-101 | (2R,6S,12Z,13aS,14aR,16aS)-6-[(tert-butoxycarbonyl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxylic acid | 9 | — |

TABLE 1-continued

| Compounds of Examples 68-526 | | | | |
|---|---|---|---|---|
| Ex. No. | Structure | Name | Proc. | LR-MS (M + H) |
| 102 | 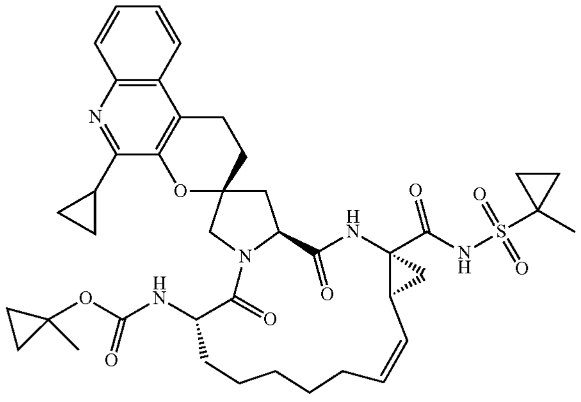 I-102 | 1-methylcyclopropyl [(2R,6S,12Z,13aS,14aR,16aS)-5'-cyclopropyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 773.8 |
| 103 | 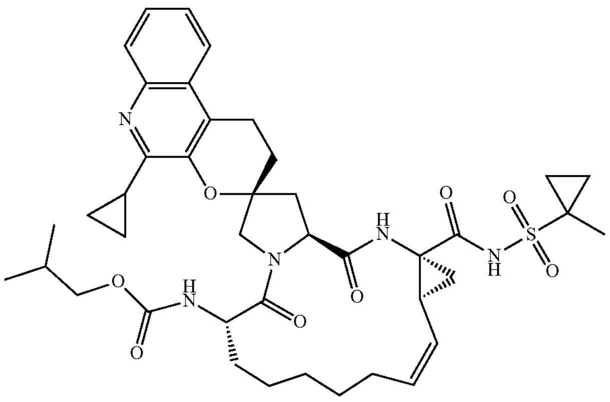 I-103 | 2-methylpropyl [(2R,6S,12Z,13aS,14aR,16aS)-5'-cyclopropyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 775.6 |

TABLE 1-continued

| Compounds of Examples 68-526 | | | | |
|---|---|---|---|---|
| Ex. No. | Structure | Name | Proc. | LR-MS (M + H) |
| 104 | 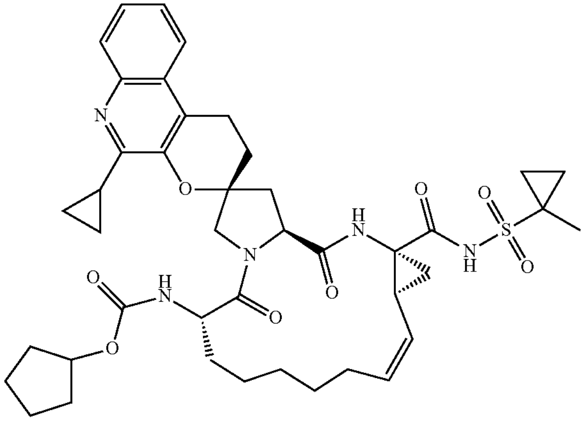 I-104 | cyclopentyl [(2R,6S,12Z,13aS,14aR,16aS)-5'-cyclopropyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4 | 787.8 |
| 105 | 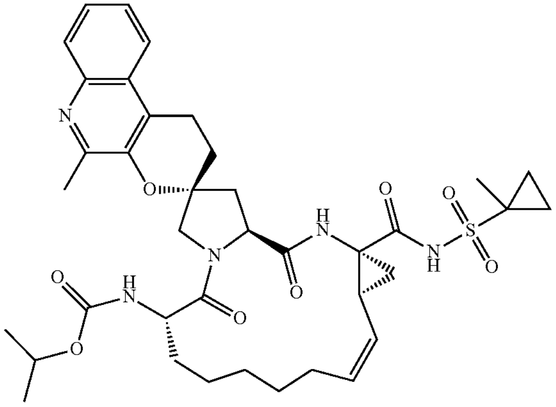 I-105 | propan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 6 | 736.2 |

TABLE 1-continued

| Compounds of Examples 68-526 | | | | |
|---|---|---|---|---|
| Ex. No. | Structure | Name | Proc. | LR-MS (M + H) |
| 106 | 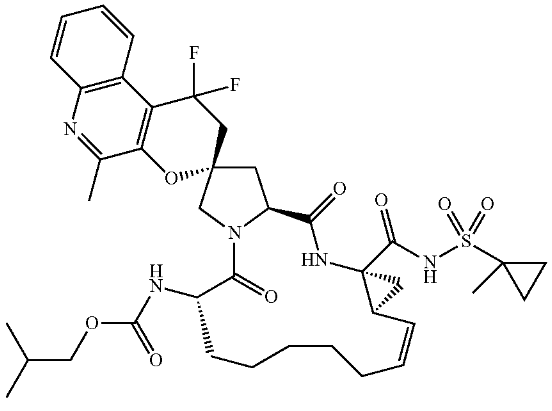 I-106 | 2-methylpropyl [(2S,6S,12Z,13aS,14aR,16aS)-1',1'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19, 21 | 786.2 |
| 107 | 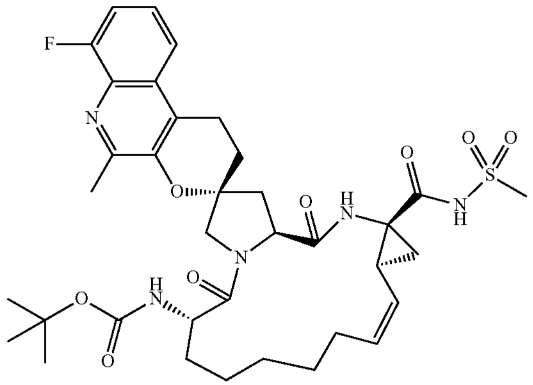 I-107 | tert-butyl {(2R,6S,12Z,13aS,14aR,16aS)-14a-[(cyclopropylsulfonyl)carbamoyl]-7'-fluoro-5'-methyl-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 45 | 753.8 |

TABLE 1-continued

| Compounds of Examples 68-526 | | | | |
|---|---|---|---|---|
| Ex. No. | Structure | Name | Proc. | LR-MS (M + H) |
| 108 | 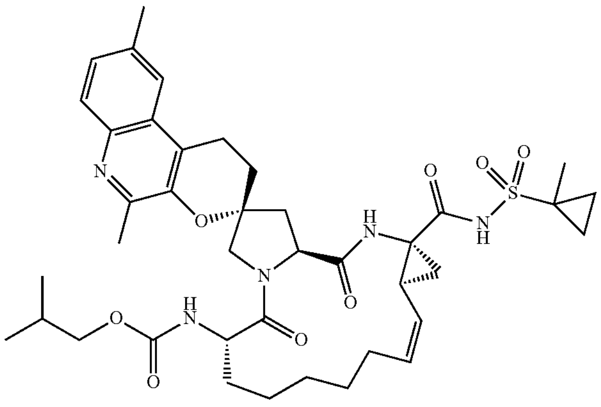 I-108 | 2-methylpropyl [(2R,6S,12Z,13aS,14aR,16aS)-5',9'-dimethyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 42 | 764.5 |
| 109 | 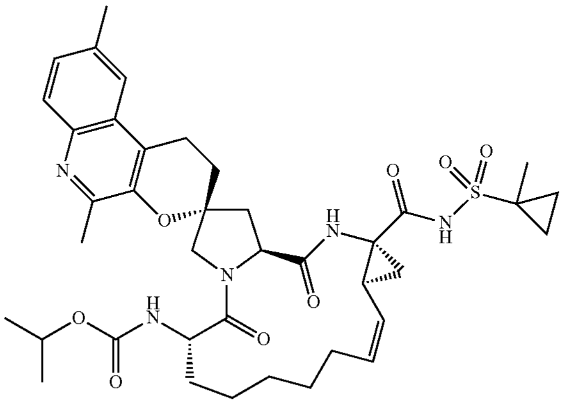 I-109 | propan-2-yl [(2R,6S,12Z,13aS,14aR,16aS)-5',9'-dimethyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 42 | 750.5 |

TABLE 1-continued

| Compounds of Examples 68-526 | | | | |
|---|---|---|---|---|
| Ex. No. | Structure | Name | Proc. | LR-MS (M + H) |
| 110 | 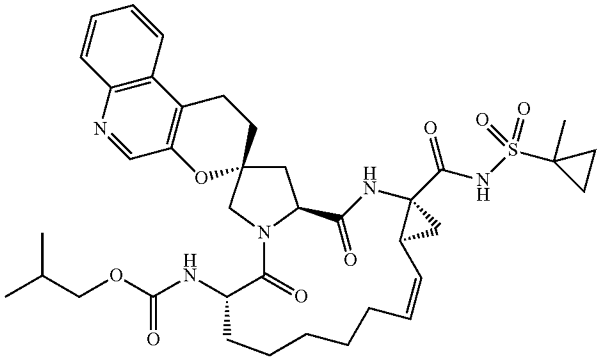 I-110 | 2-methylpropyl [(2R,6S,12Z,13aS,14aR,16aS)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | — |
| 111 | 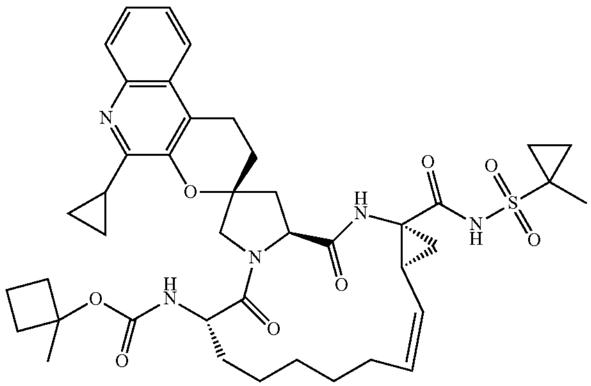 I-111 | 1-methylcyclobutyl [(2R,6S,12Z,13aS,14aR,16aS)-5'-cyclopropyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 787.8 |

TABLE 1-continued

| Compounds of Examples 68-526 | | | | |
|---|---|---|---|---|
| Ex. No. | Structure | Name | Proc. | LR-MS (M + H) |
| 112 | 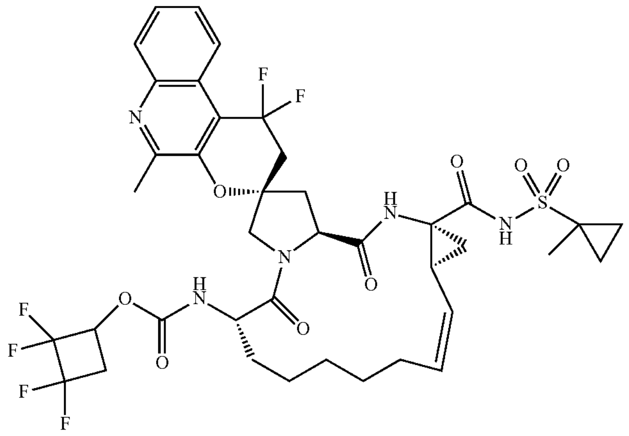 I-112 | 2,2,3,3-tetrafluorocyclobutyl [(2S,6S,12Z,13aS,14aR,16aS)-1',1'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19, 35 | 856.2 |
| 113 | 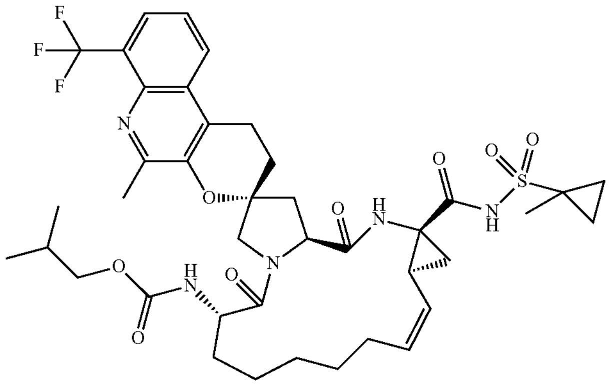 I-113 | 2-methylpropyl [(2R,6S,12Z,13aS,14aR,16aS)-5'-methyl-14a-{[(1-methylcyclopropyl)sulfonyl]carbamoyl}-5,16-dioxo-7'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 818.2 |

TABLE 1-continued

Compounds of Examples 68-526

| Ex. No. | Structure | Name | Proc. | LR-MS (M + H) |
|---|---|---|---|---|
| 114 | 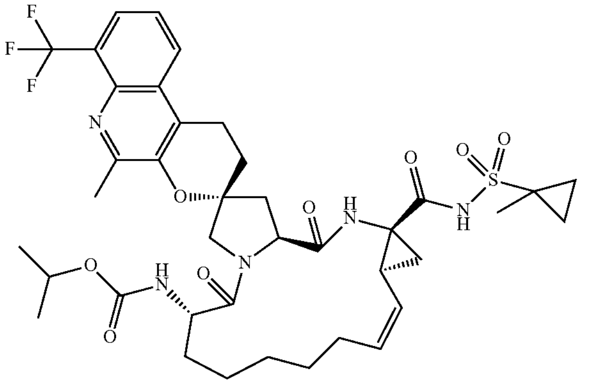 I-114 | propan-2-yl [(2R,6S,12Z,13aS,14aR,16aS)-5'-methyl-14a-{[(1-methylcyclopropyl)sulfonyl]carbamoyl}-5,16-dioxo-7'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 804.2 |
| 115 | 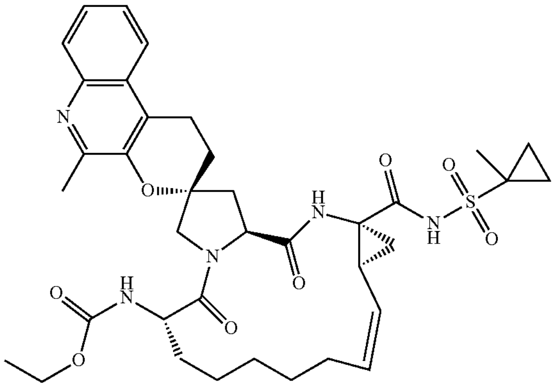 I-115 | ethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 722.4 |

TABLE 1-continued

| Compounds of Examples 68-526 | | | | |
|---|---|---|---|---|
| Ex. No. | Structure | Name | Proc. | LR-MS (M + H) |
| 116 | 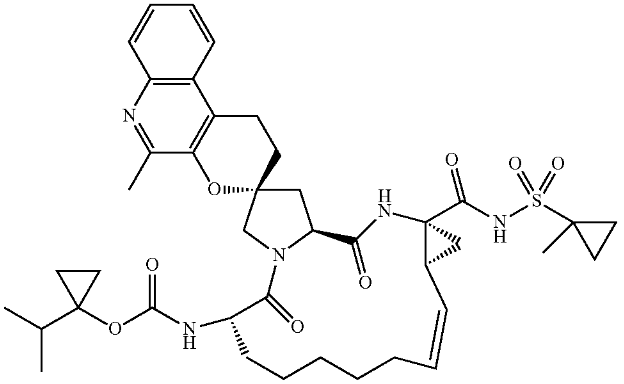 I-116 | 1-(propan-2-yl)cyclopropyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 776.4 |
| 117 | 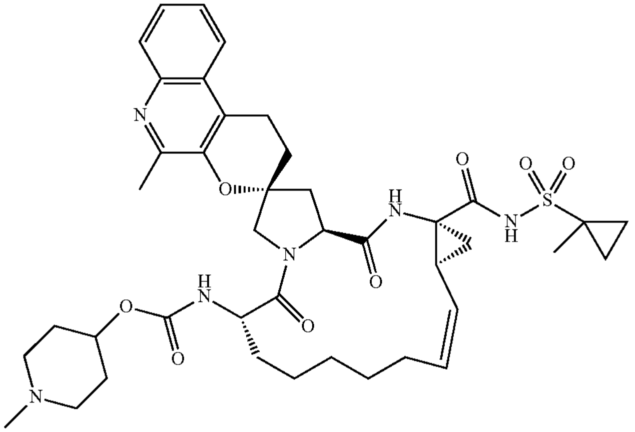 I-117 | 1-methylpiperidin-4-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 790.8 |

TABLE 1-continued

| Compounds of Examples 68-526 | | | | |
|---|---|---|---|---|
| Ex. No. | Structure | Name | Proc. | LR-MS (M + H) |
| 118 | 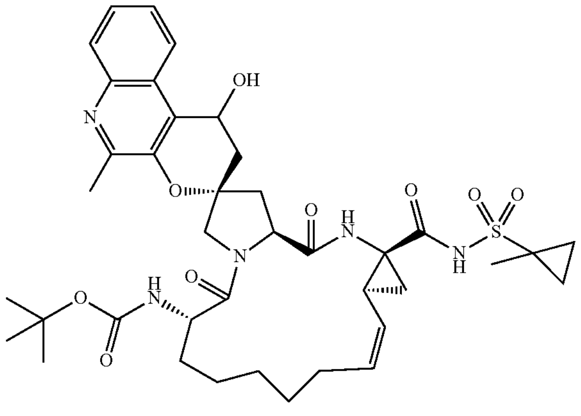 I-118 | tert-butyl [(2S,6S,12Z,13aS,14aR,16aS)-1'-hydroxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 766.5 |
| 119 | 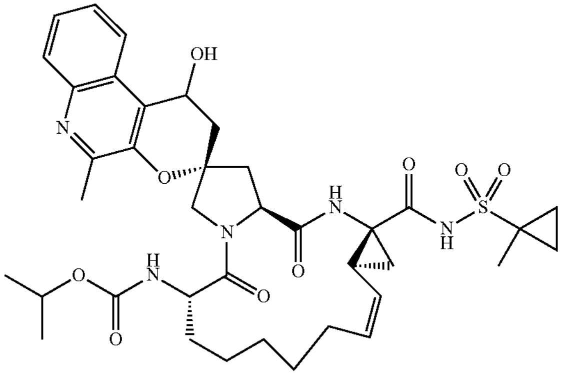 I-119 | propan-2-yl [(2S,6S,12Z,14aR,16aS)-1'-hydroxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 752.5 |

TABLE 1-continued

| Compounds of Examples 68-526 | | | | |
|---|---|---|---|---|
| Ex. No. | Structure | Name | Proc. | LR-MS (M + H) |
| 120 | 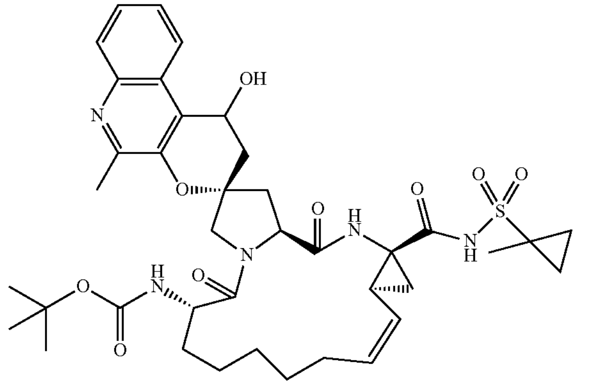 I-120 | tert-butyl [(2S,6S,12Z,13aS,14aR,16aS)-1'-hydroxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 766.5 |
| 121 | 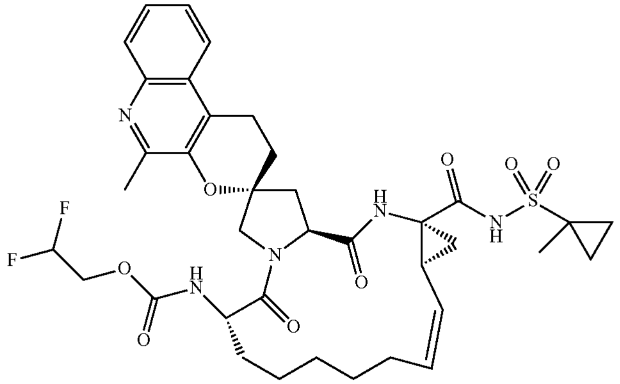 I-121 | 2,2-difluoroethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 757.7 |

TABLE 1-continued
| Compounds of Examples 68-526 | | | | |
|---|---|---|---|---|
| Ex. No. | Structure | Name | Proc. | LR-MS (M + H) |
| 122 | 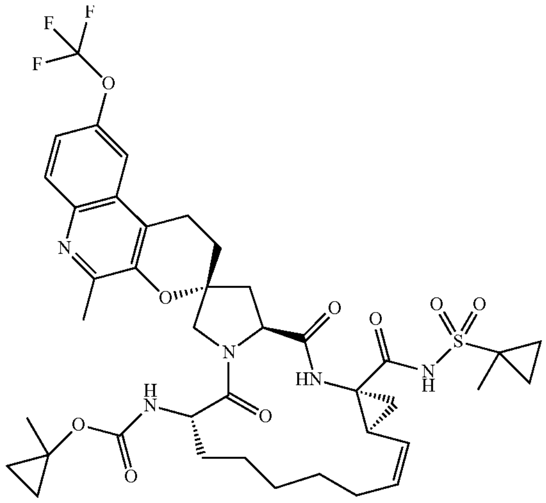 I-122 | 1-methylcyclopropyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 832.2 |

TABLE 1-continued
| Compounds of Examples 68-526 | | | | |
|---|---|---|---|---|
| Ex. No. | Structure | Name | Proc. | LR-MS (M + H) |
| 123 | 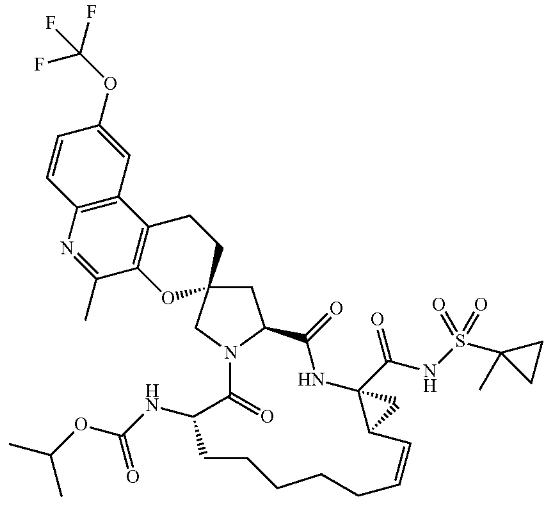 I-123 | propan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 820.2 |

TABLE 1-continued
| Compounds of Examples 68-526 | | | | |
|---|---|---|---|---|
| Ex. No. | Structure | Name | Proc. | LR-MS (M + H) |
| 124 | 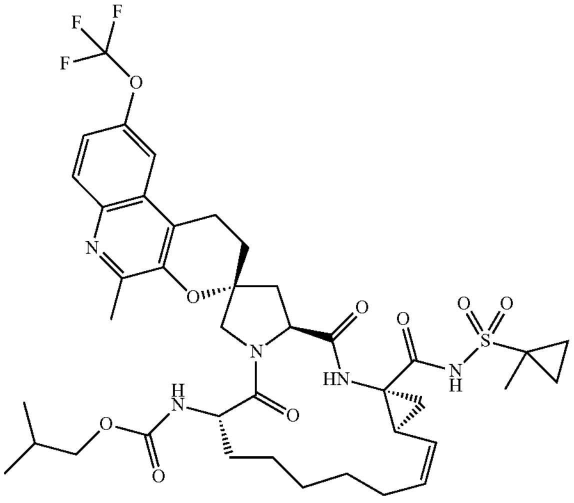 I-124 | 2-methylpropyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 528 | 834.2 |

TABLE 1-continued

| Compounds of Examples 68-526 | | | | |
|---|---|---|---|---|
| Ex. No. | Structure | Name | Proc. | LR-MS (M + H) |
| 125 | 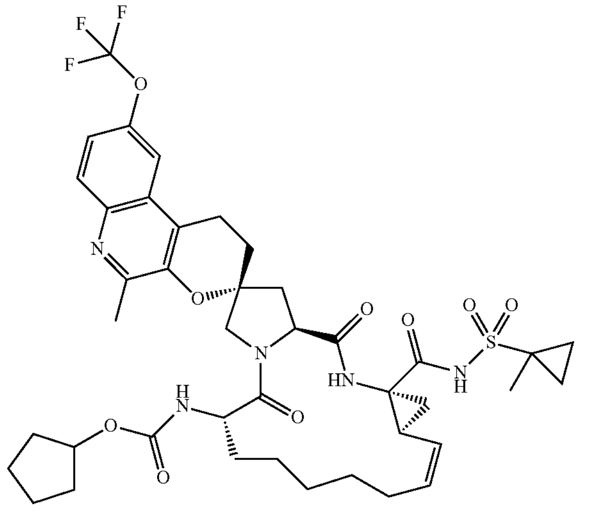 I-125 | cyclopentyl [(2R,6S,12Z,13aS,14aR,16a5)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 846.2 |
| 126 | 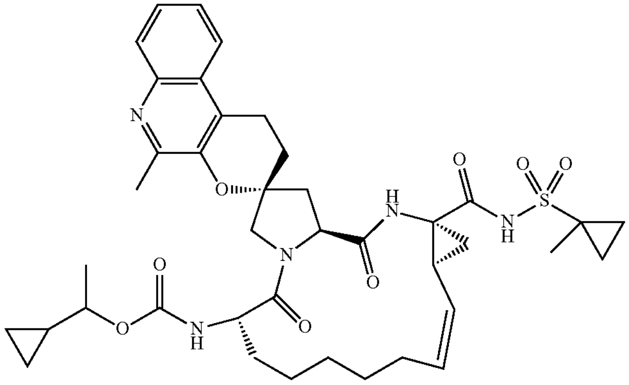 I-126 | 1-cyclopropylethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 761.7 |

TABLE 1-continued

| Compounds of Examples 68-526 | | | | |
|---|---|---|---|---|
| Ex. No. | Structure | Name | Proc. | LR-MS (M + H) |
| 127 | 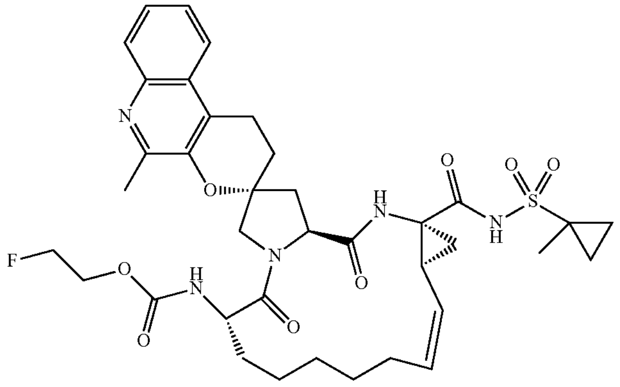 I-127 | 2-fluoroethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 739.7 |
| 128 | 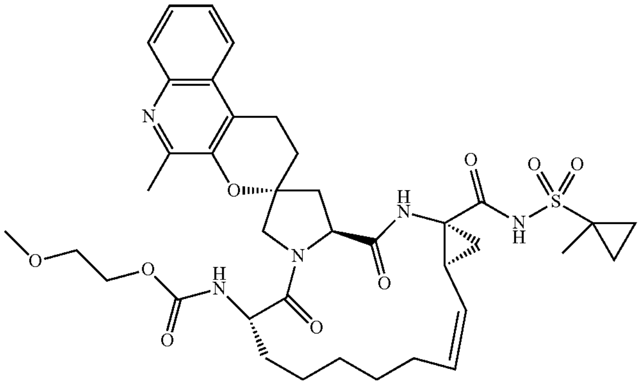 I-128 | 2-methoxyethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 751.8 |

TABLE 1-continued

| Compounds of Examples 68-526 | | | | |
|---|---|---|---|---|
| Ex. No. | Structure | Name | Proc. | LR-MS (M + H) |
| 129 | 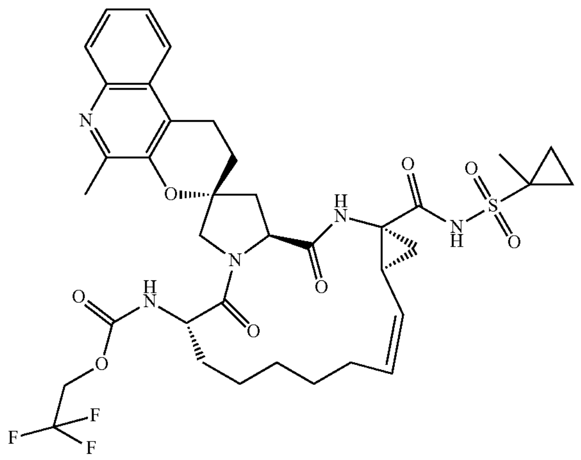 I-129 | 2,2,2-trifluoroethyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 6 | 776.2 |
| 130 | 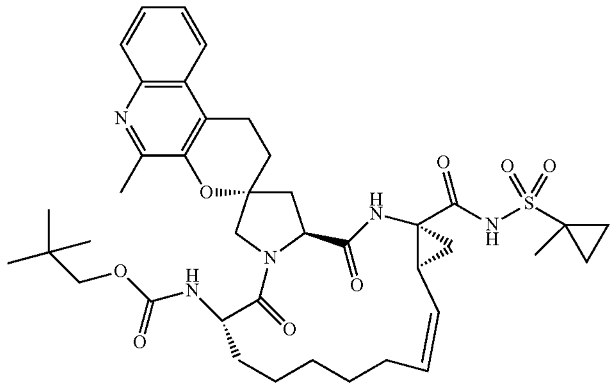 I-130 | 2,2-dimethylpropyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 763.8 |

TABLE 1-continued

| Compounds of Examples 68-526 | | | | |
|---|---|---|---|---|
| Ex. No. | Structure | Name | Proc. | LR-MS (M + H) |
| 131 | 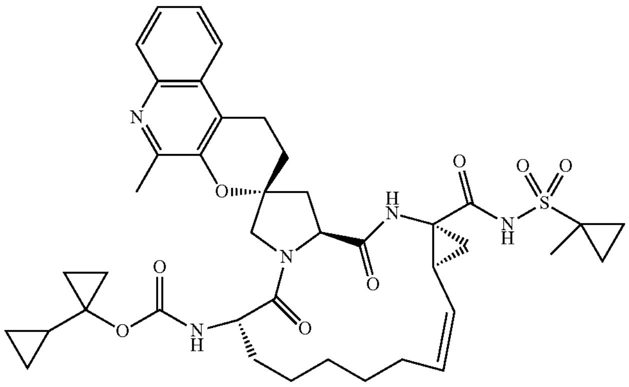 I-131 | 1,1'-bi(cyclopropyl)-1-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 773.7 |
| 132 | 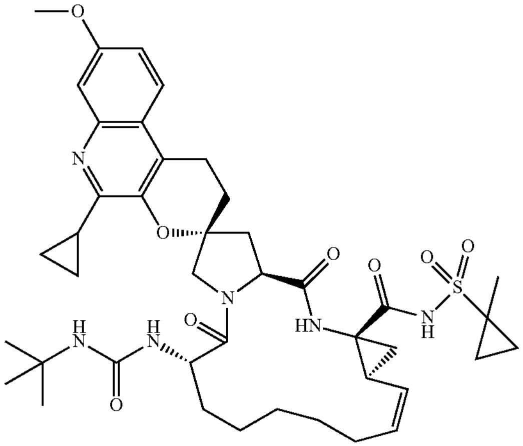 I-132 | (2R,6S,12Z,13aS,14aR,16aS)-6-[(tert-butylcarbamoyl)amino]-5'-cyclopropyl-8'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 16 | 805.2 |

TABLE 1-continued

| Ex. No. | Structure | Name | Proc. | LR-MS (M + H) |
|---|---|---|---|---|
| | Compounds of Examples 68-526 | | | |
| 133 | 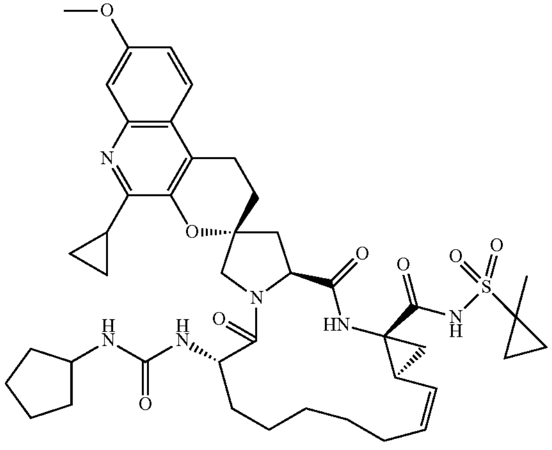 I-133 | (2R,6S,12Z,13aS,14aR,16aS)-6-[(cyclopentylcarbamoyl)amino]-5'-cyclopropyl-8'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 16 | 817.2 |
| 134 | 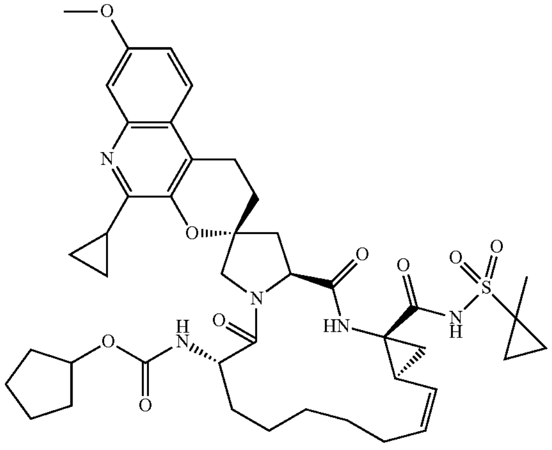 I-134 | cyclopentyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 818.4 (K+ salt) |

TABLE 1-continued

| Compounds of Examples 68-526 | | | | |
|---|---|---|---|---|
| Ex. No. | Structure | Name | Proc. | LR-MS (M + H) |
| 135 | 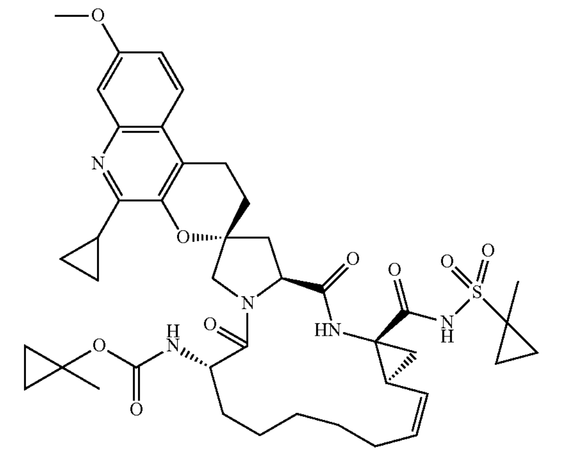 I-135 | 1-methylcyclopropyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 804.4 (K+ salt) |
| 136 | 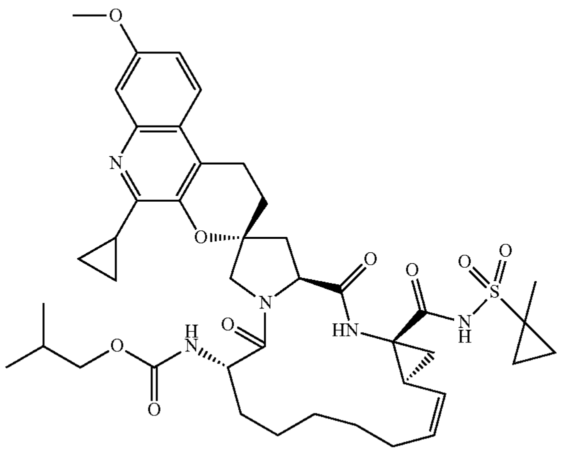 I-136 | 2-methylpropyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 806.2 (K+ salt) |

TABLE 1-continued

| Compounds of Examples 68-526 | | | | |
|---|---|---|---|---|
| Ex. No. | Structure | Name | Proc. | LR-MS (M + H) |
| 137 | 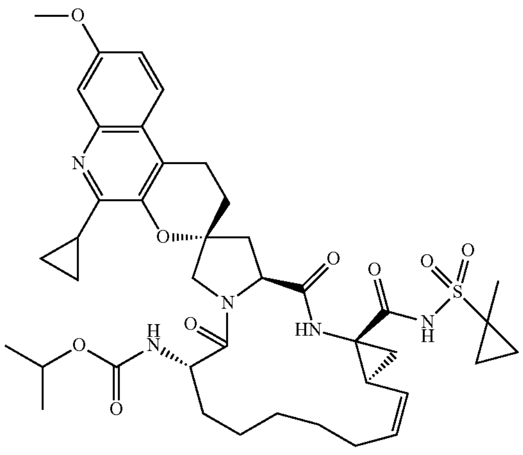 I-137 | propan-2-yl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 791.6 |
| 138 | 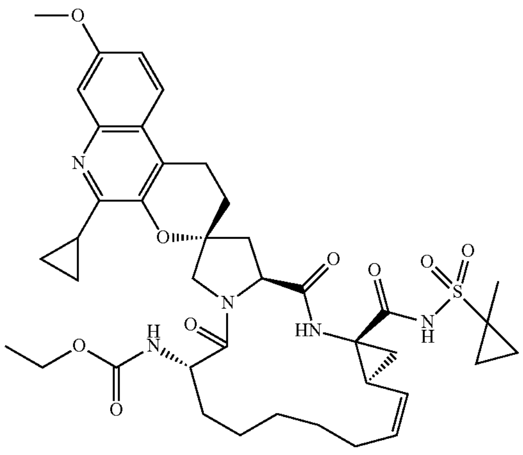 I-138 | ethyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 777.7 |

TABLE 1-continued

| Compounds of Examples 68-526 | | | | |
|---|---|---|---|---|
| Ex. No. | Structure | Name | Proc. | LR-MS (M + H) |
| 139 | 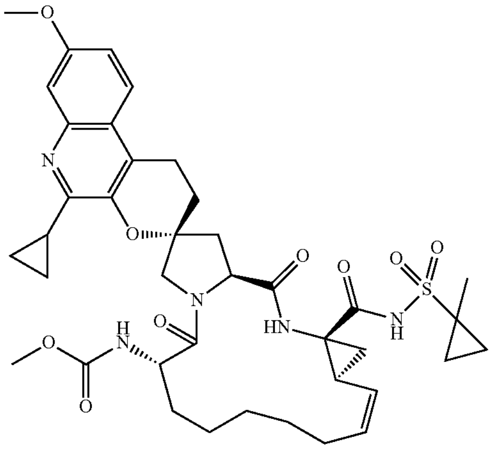 I-139 | methyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 763.7 |
| 140 | 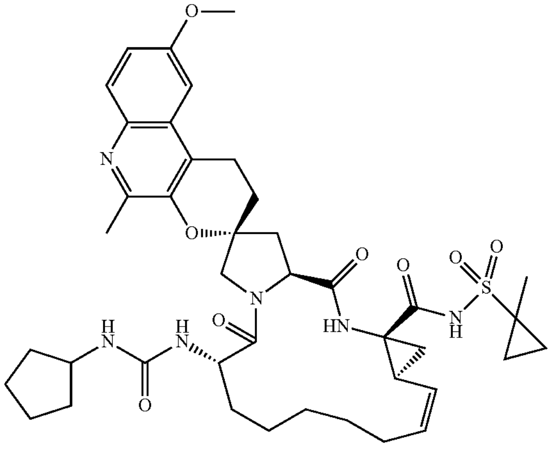 I-140 | cyclopentyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 792.2 (K+ salt) |

TABLE 1-continued

| Compounds of Examples 68-526 | | | | |
|---|---|---|---|---|
| Ex. No. | Structure | Name | Proc. | LR-MS (M + H) |
| 141 | 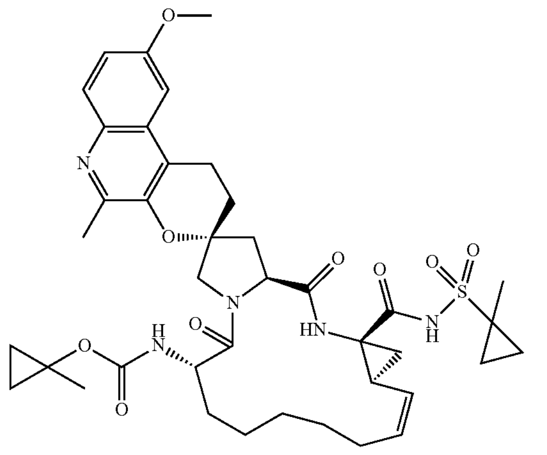 I-141 | 1-methylcyclopropyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 778.2 |
| 142 | 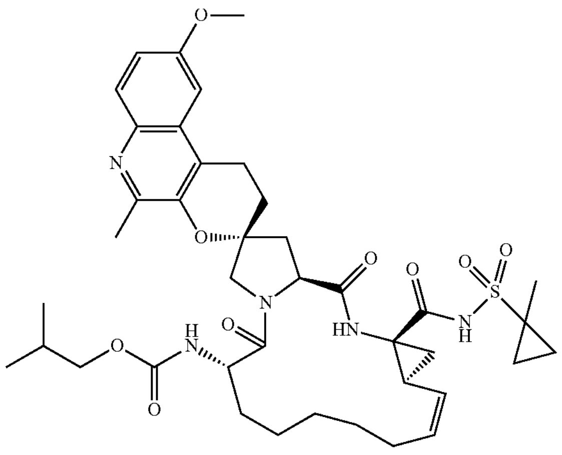 I-142 | 2-methylpropyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 780.2 |

TABLE 1-continued

| Compounds of Examples 68-526 | | | | |
|---|---|---|---|---|
| Ex. No. | Structure | Name | Proc. | LR-MS (M + H) |
| 143 | 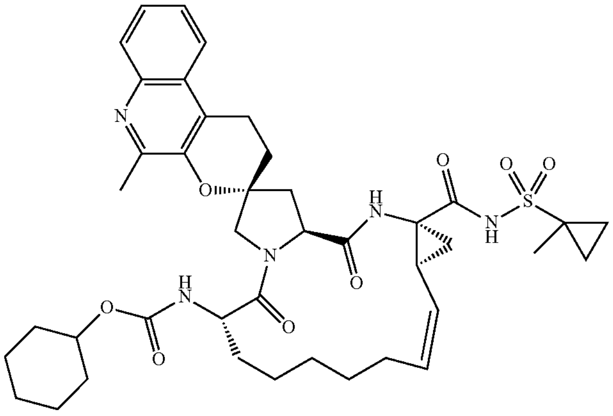 I-143 | cyclohexyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 776.6 (K+ salt) |
| 144 | 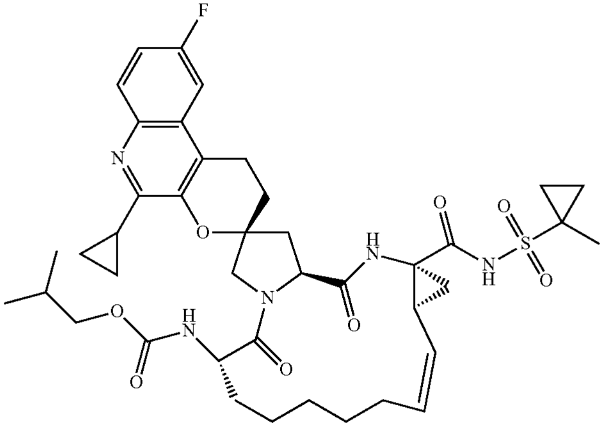 I-144 | 2-methylpropyl [(2R,6S,12Z,13aS,14aR,16aS)-5'-cyclopropyl-9'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 793.7 |

TABLE 1-continued

| Compounds of Examples 68-526 | | | | |
|---|---|---|---|---|
| Ex. No. | Structure | Name | Proc. | LR-MS (M + H) |
| 145 | 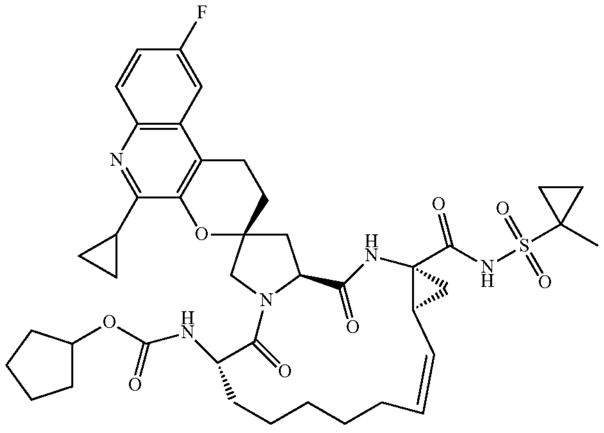 I-145 | cyclopentyl [(2R,6S,12Z,13aS,14aR,16aS)-5'-cyclopropyl-9'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 805.7 |
| 146 | 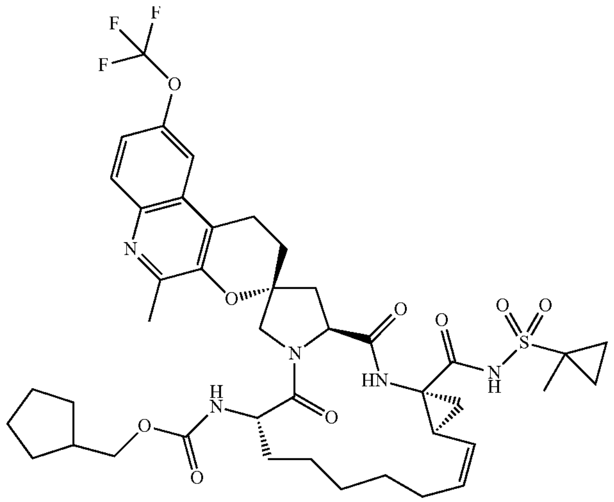 I-146 | cyclopentylmethyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 860.2 |

TABLE 1-continued

| Compounds of Examples 68-526 | | | | |
|---|---|---|---|---|
| Ex. No. | Structure | Name | Proc. | LR-MS (M + H) |
| 147 | 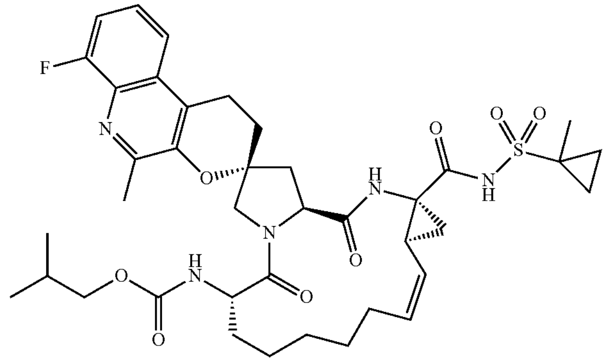 I-147 | 2-methylpropyl [(2R,6S,12Z,13aS,14aR,16aS)-7'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 45 | 768.2 |
| 148 | 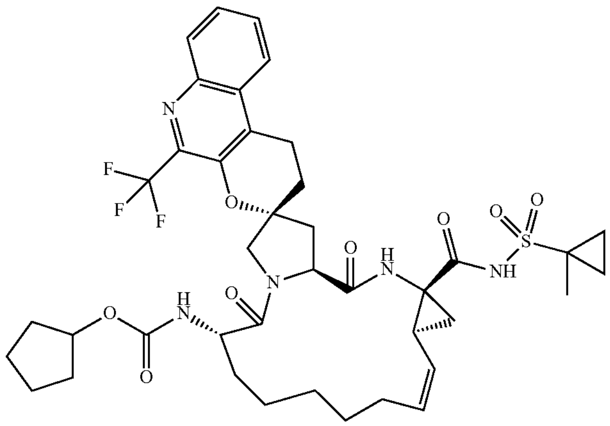 I-148 | cyclopentyl [(2R,6S,12Z,13aS,14aR,16aS)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4, 35 | 816.6 (K+ salt) |

TABLE 1-continued

| Compounds of Examples 68-526 | | | | |
|---|---|---|---|---|
| Ex. No. | Structure | Name | Proc. | LR-MS (M + H) |
| 149 | 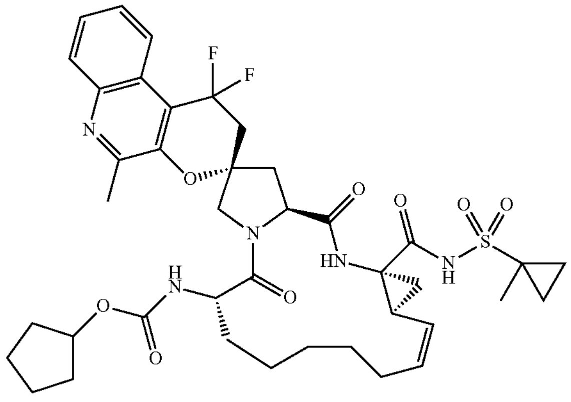 I-149 | cyclopentyl [(2S,6S,12Z,13aS,14aR,16aS)-1',1'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20, 35 | 798.6 |
| 150 | 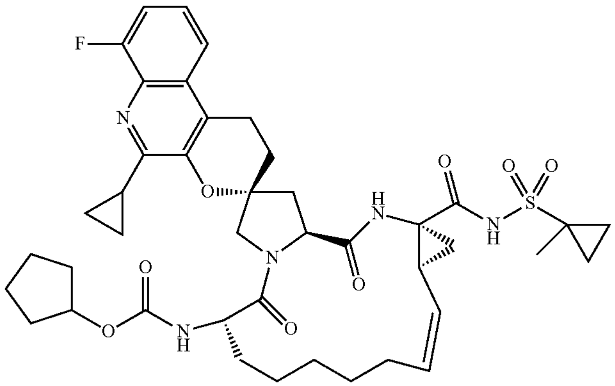 I-150 | cyclopentyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 805.6 |

TABLE 1-continued

| Compounds of Examples 68-526 | | | | |
|---|---|---|---|---|
| Ex. No. | Structure | Name | Proc. | LR-MS (M + H) |
| 151 | 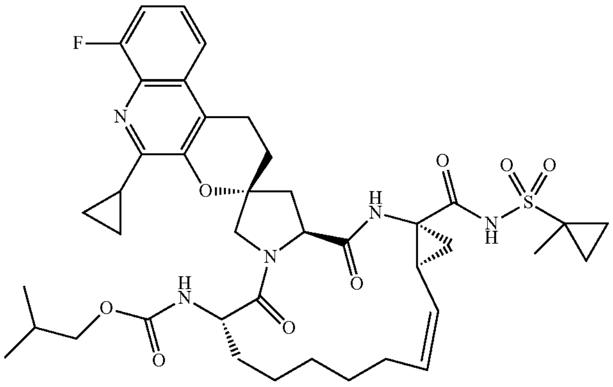 I-151 | 2-methylpropyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 794.4 (K+ salt) |
| 152 | 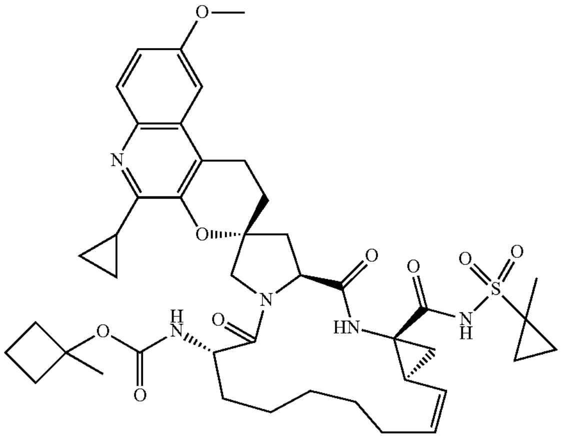 I-152 | 1-methylcyclobutyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 817.6 (K+ salt) |

TABLE 1-continued

| Compounds of Examples 68-526 | | | | |
|---|---|---|---|---|
| Ex. No. | Structure | Name | Proc. | LR-MS (M + H) |
| 153 | 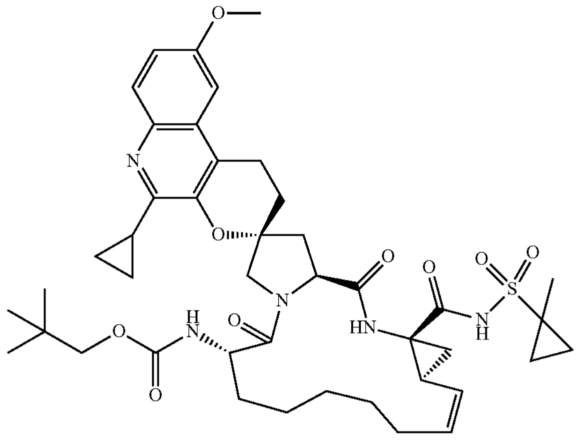 I-153 | 2,2-dimethylpropyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 819.6 (K+ salt) |
| 154 | 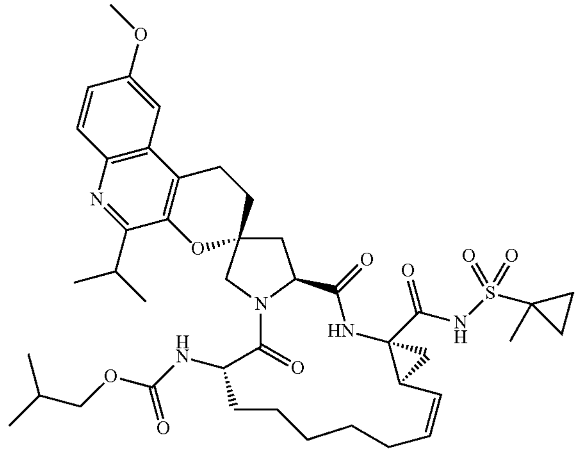 I-154 | 2-methylpropyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 808.2 |

TABLE 1-continued

| Compounds of Examples 68-526 | | | | |
|---|---|---|---|---|
| Ex. No. | Structure | Name | Proc. | LR-MS (M + H) |
| 155 | 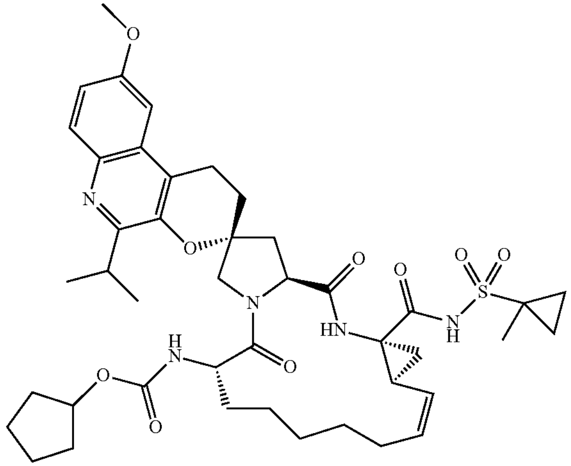 I-155 | cyclopentyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 820.2 |
| 156 | 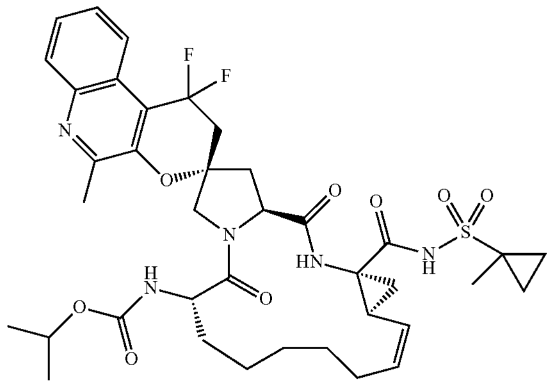 I-156 | propan-2-yl [(2S,6S,12Z,13aS,14aR,16aS)-1',1'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20, 35 | 772.6 |

TABLE 1-continued

| Compounds of Examples 68-526 | | | | |
|---|---|---|---|---|
| Ex. No. | Structure | Name | Proc. | LR-MS (M + H) |
| 157 | 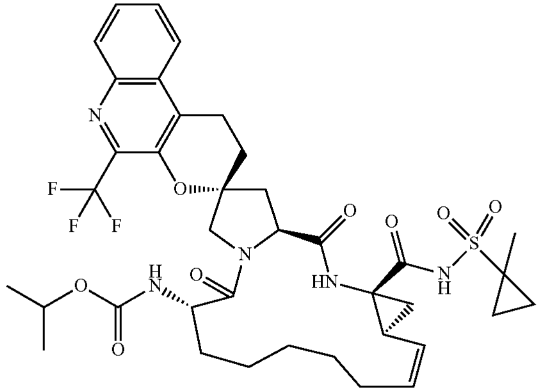 I-157 | propan-2-yl [(2R,6S,12Z,13aS,14aR,16aS)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4, 35 | 790.4 |
| 158 | 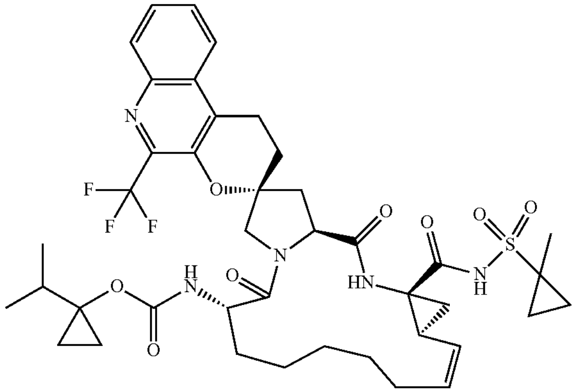 I-158 | 1-(propan-2-yl)cyclopropyl [(2R,6S,12Z,13aS,14aR,16aS)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4, 35 | 830.4 |

TABLE 1-continued

| Compounds of Examples 68-526 | | | | |
|---|---|---|---|---|
| Ex. No. | Structure | Name | Proc. | LR-MS (M + H) |
| 159 | 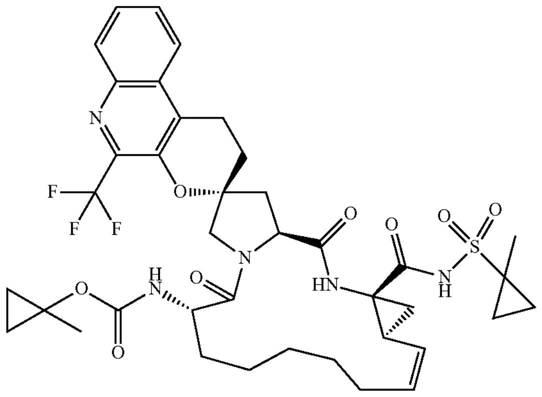 I-159 | 1-methylcyclopropyl [(2R,6S,12Z,13aS,14aR,16aS)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4, 35 | 802.4 |
| 160 | 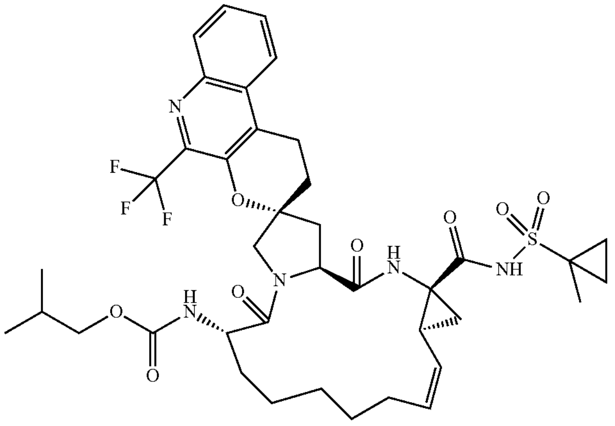 I-160 | 2-methylpropyl [(2R,6S,12Z,13aS,14aR,16aS)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 4, 35 | 804.4 (K+ salt) |

TABLE 1-continued

| Compounds of Examples 68-526 | | | | |
|---|---|---|---|---|
| Ex. No. | Structure | Name | Proc. | LR-MS (M + H) |
| 161 | 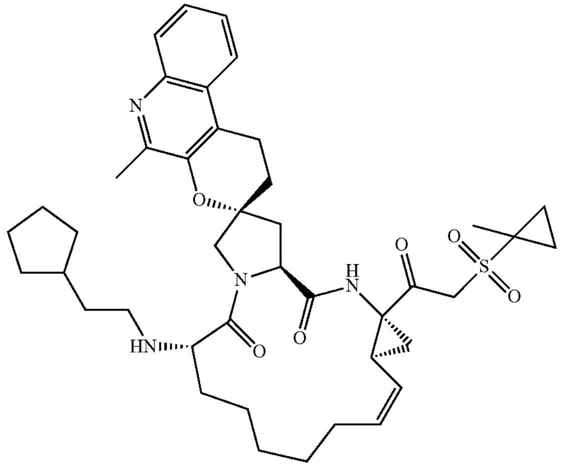 I-161 | (2R,6S,12Z,13aS,14aR,16aS)-6-[(2-cyclopentylethyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 745.5 |
| 162 | 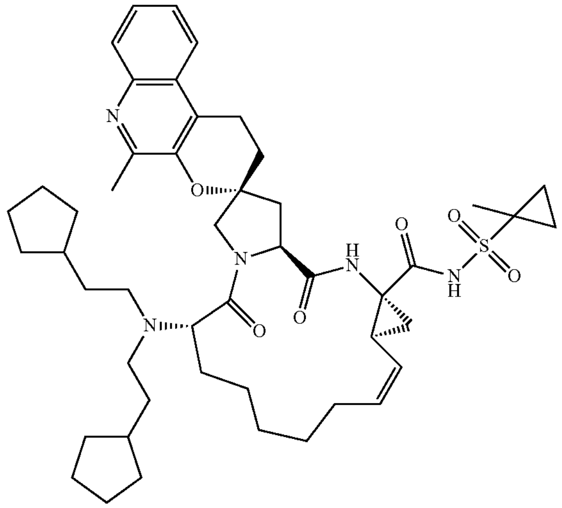 I-162 | (2R,6S,12Z,13aS,14aR,16aS)-6-[bis(2-cyclopentylethyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 841.5 |

TABLE 1-continued

| Compounds of Examples 68-526 | | | | |
|---|---|---|---|---|
| Ex. No. | Structure | Name | Proc. | LR-MS (M + H) |
| 163 | 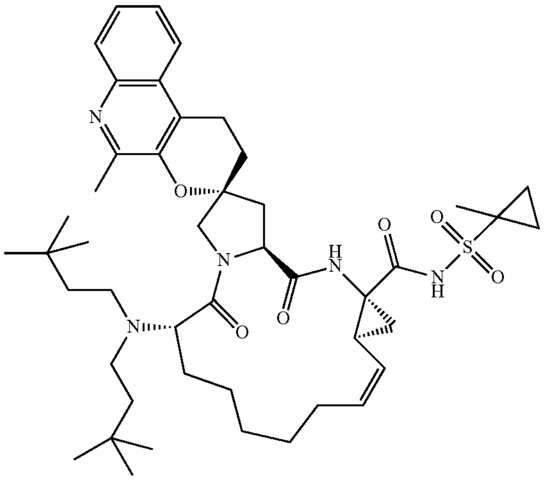 [SMILES: Cc1nc2ccccc2c2c1O[C@]1(CC2)C[C@H]2C(=O)N[C@]3(C(=O)NS(=O)(=O)C4(C)CC4)C[C@H]3/C=C\CCCCC[C@H](NCCC(C)(C)C)C(=O)N2C1] I-163 | (2R,6S,12Z,13aS,14aR,16aS)-6-[bis(3,3-dimethylbutyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 817.5 |
| 164 | 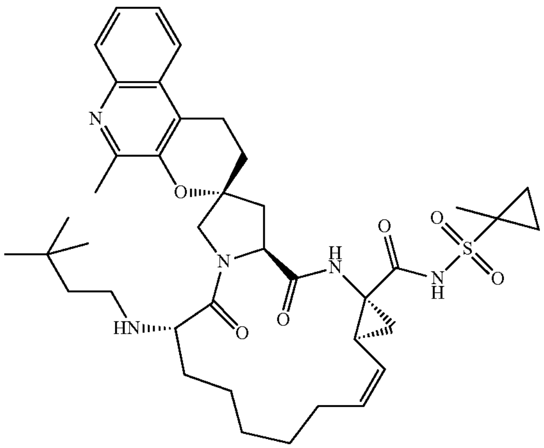 I-164 | (2R,6S,12Z,13aS,14aR,16aS)-6-[(3,3-dimethylbutyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 733.5 |

TABLE 1-continued

| Ex. No. | Structure | Name | Proc. | LR-MS (M + H) |
|---|---|---|---|---|
| Compounds of Examples 68-526 | | | | |
| 165 | 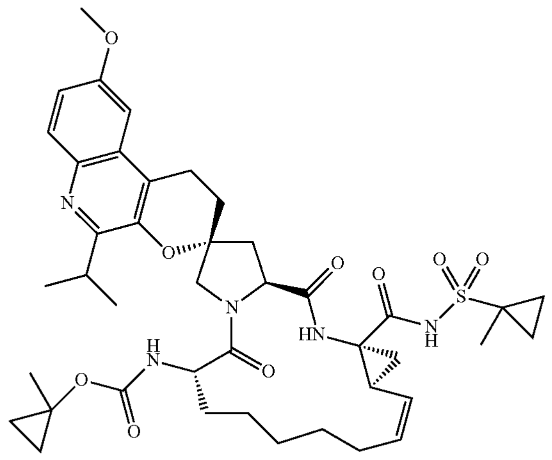 I-165 | 1-methylcyclopropyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 806.2 |
| 166 | 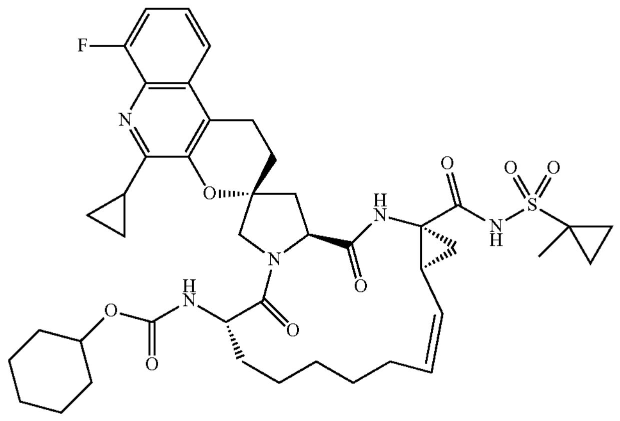 I-166 | cyclohexyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 820.4 |

TABLE 1-continued

| Compounds of Examples 68-526 | | | | |
|---|---|---|---|---|
| Ex. No. | Structure | Name | Proc. | LR-MS (M + H) |
| 167 | 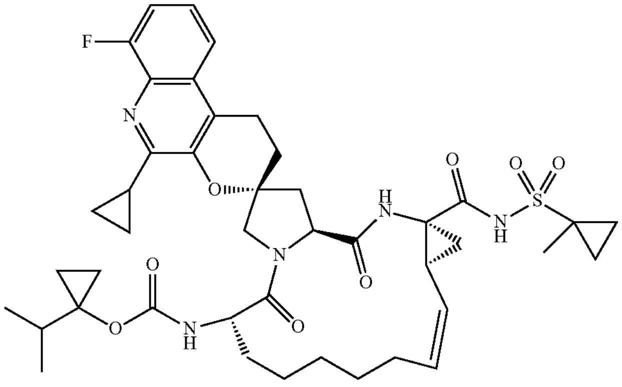 I-167 | 1-(propan-2-yl)cyclopropyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 820.4 |
| 168 | 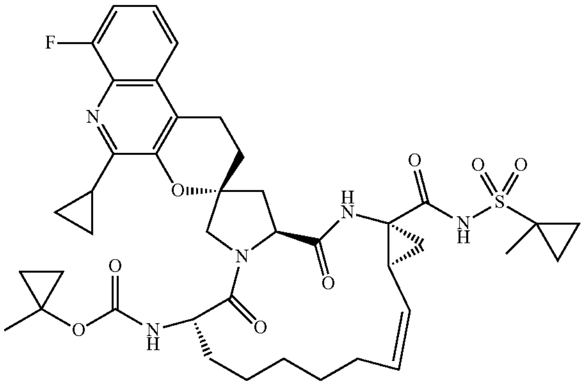 I-168 | 1-methylcyclopropyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 792.4 |

TABLE 1-continued

| Ex. No. | Structure | Name | Proc. | LR-MS (M + H) |
|---|---|---|---|---|
| Compounds of Examples 68-526 | | | | |
| 169 | 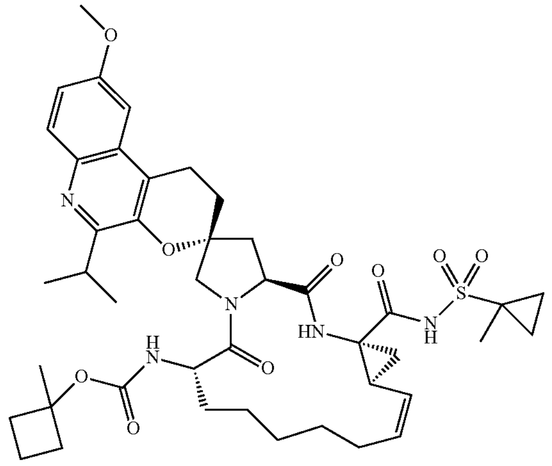 I-169 | 1-methylcyclobutyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 820.2 |
| 170 | 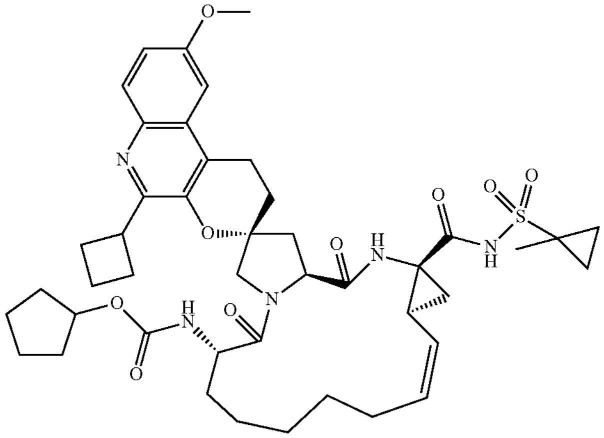 I-170 | cyclopentyl [(2R,6S,12Z,13aS,14aR,16aS)-5'-cyclobutyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 46 | 832.6 |

TABLE 1-continued

| Ex. No. | Structure | Name | Proc. | LR-MS (M + H) |
|---|---|---|---|---|
| Compounds of Examples 68-526 | | | | |
| 171 | 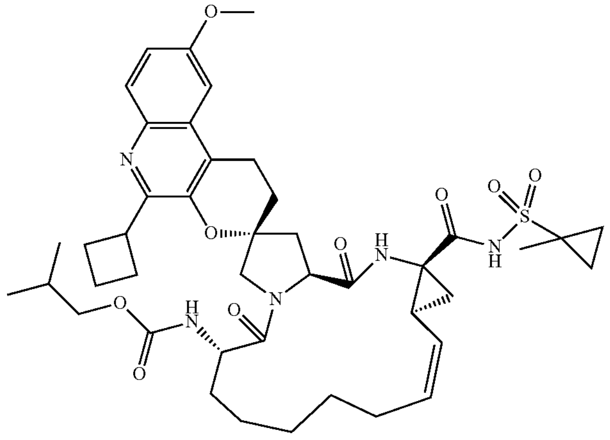 I-171 | 2-methylpropyl [(2R,6S,12Z,13aS,14aR,16aS)-5'-cyclobutyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 46 | 820.6 |
| 172 | 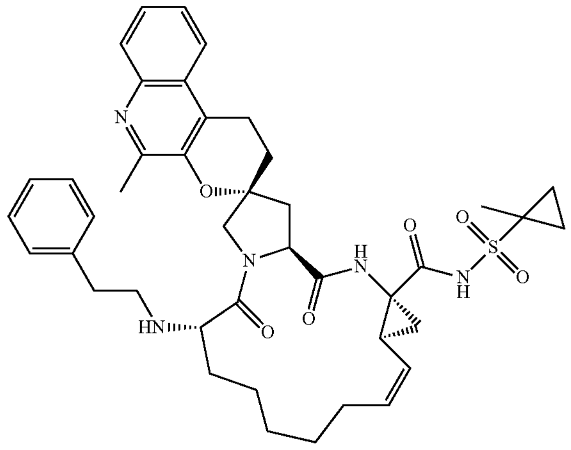 I-172 | (2R,6S,12Z,13aS,14aR,16aS)-5'-methyl-N-[(1-methylcyclopropyl)sulfonyl]-5,16-dioxo-6-[(2-phenylethyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 753.5 |

TABLE 1-continued
| Compounds of Examples 68-526 | | | | |
|---|---|---|---|---|
| Ex. No. | Structure | Name | Proc. | LR-MS (M + H) |
| 173 | 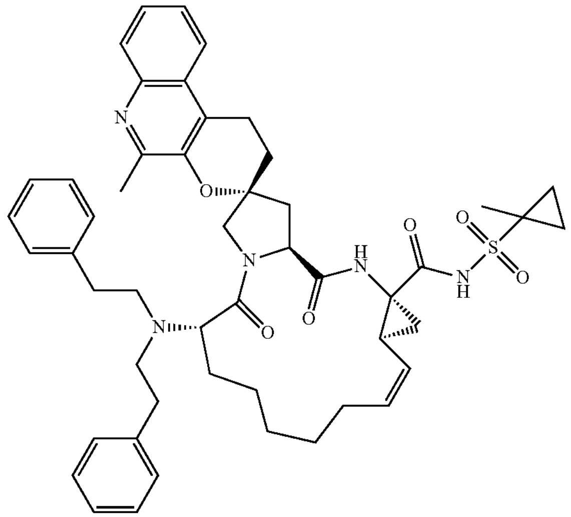 I-173 | (2R,6S,12Z,13aS,14aR,16aS)-6-[bis(2-phenylethyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 857.5 |

TABLE 1-continued

Compounds of Examples 68-526

| Ex. No. | Structure | Name | Proc. | LR-MS (M + H) |
|---|---|---|---|---|
| 174 | 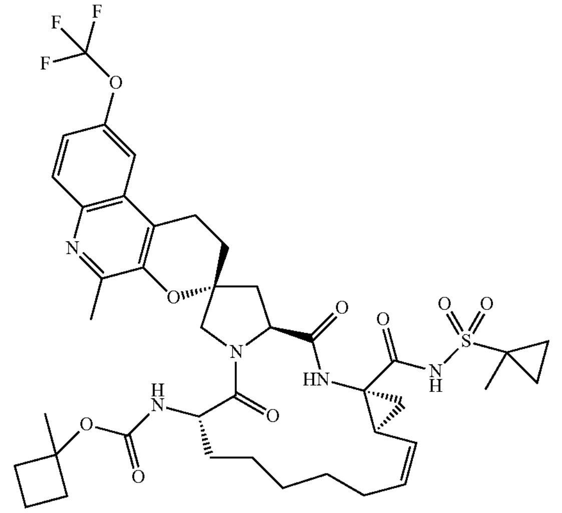 I-174 | 1-methylcyclobutyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 846.2 |
| 175 | 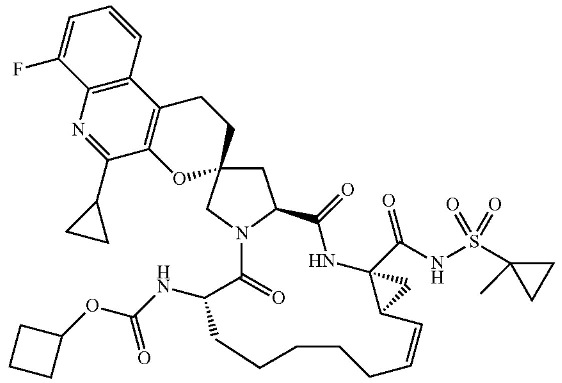 I-175 | cyclobutyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 792.4 |

TABLE 1-continued

| Compounds of Examples 68-526 | | | | |
|---|---|---|---|---|
| Ex. No. | Structure | Name | Proc. | LR-MS (M + H) |
| 176 | 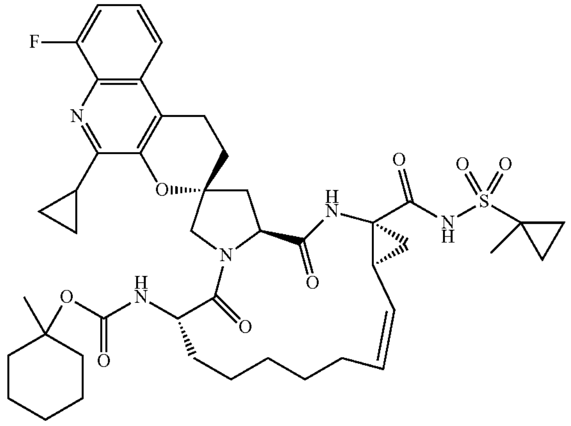 I-176 | 1-methylcyclohexyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 834.4 |
| 177 | 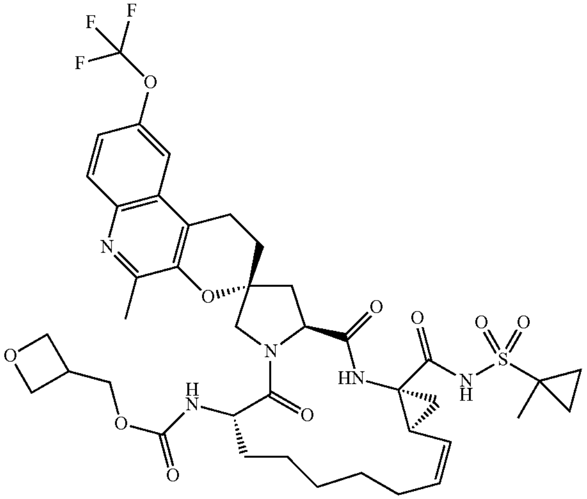 I-177 | oxetan-3-ylmethyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 848.2 |

TABLE 1-continued

| Compounds of Examples 68-526 | | | | |
|---|---|---|---|---|
| Ex. No. | Structure | Name | Proc. | LR-MS (M + H) |
| 178 | 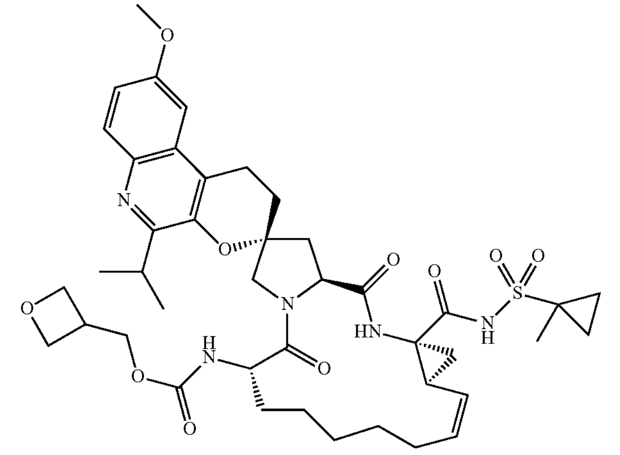 I-178 | oxetan-3-ylmethyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 822.2 |
| 179 | 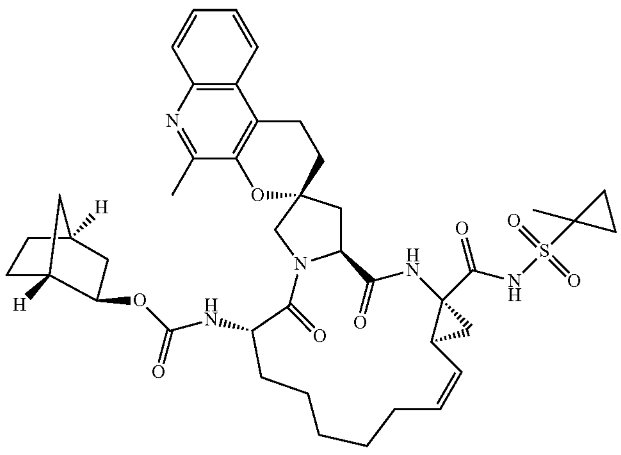 I-162 | (1R,2R,4S)-bicyclo[2.2.1]hept-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 787.5 |

TABLE 1-continued

| Compounds of Examples 68-526 | | | | |
|---|---|---|---|---|
| Ex. No. | Structure | Name | Proc. | LR-MS (M + H) |
| 180 | 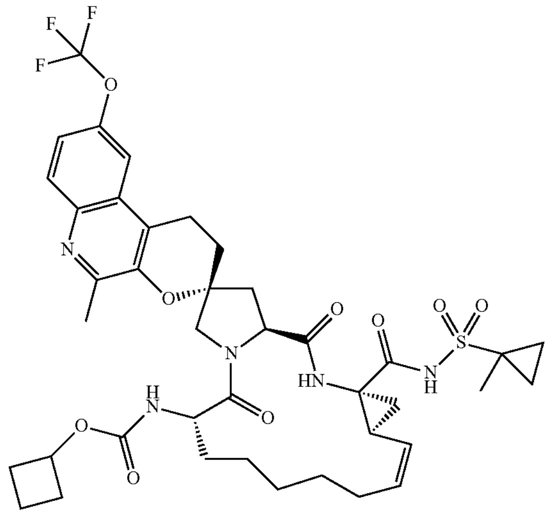 I-180 | cyclobutyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 832.2 |
| 181 | 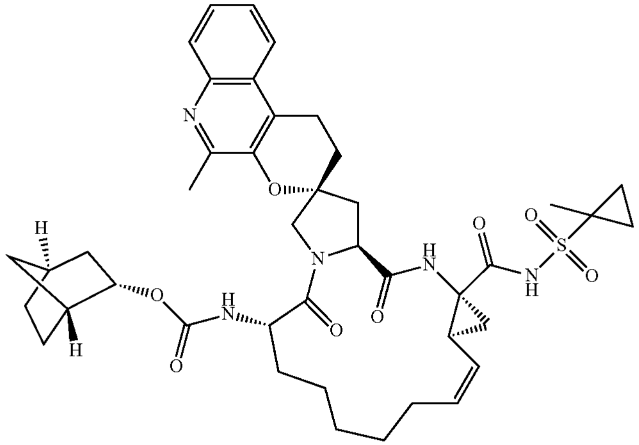 I-181 | (1R,2S,4S)-bicyclo[2.2.1]hept-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 787.5 |

TABLE 1-continued

| Compounds of Examples 68-526 | | | | |
|---|---|---|---|---|
| Ex. No. | Structure | Name | Proc. | LR-MS (M + H) |
| 182 | 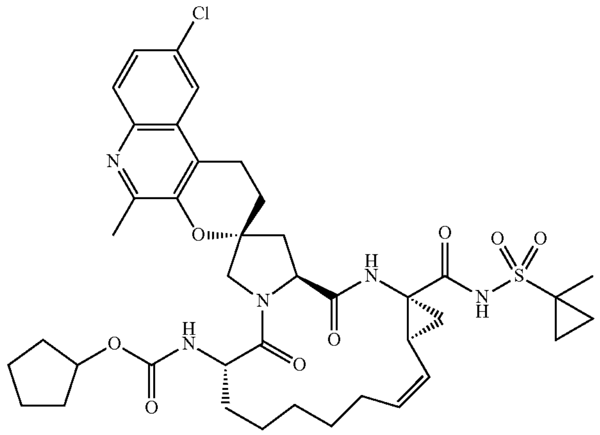 I-182 | cyclopentyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 796.3 (K+ salt) |
| 183 | 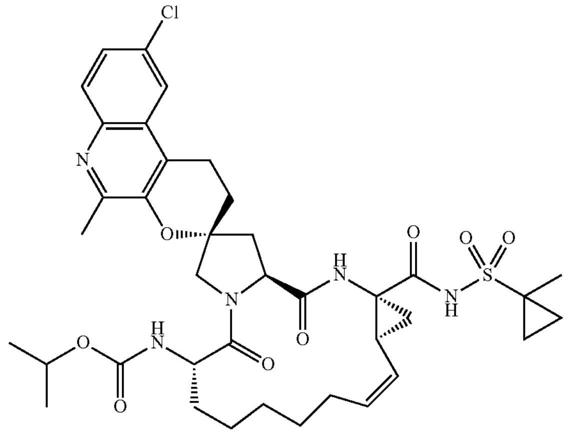 I-183 | propan-2-yl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 770.2 (K+ salt) |

TABLE 1-continued

Compounds of Examples 68-526

| Ex. No. | Structure | Name | Proc. | LR-MS (M + H) |
| --- | --- | --- | --- | --- |
| 184 | 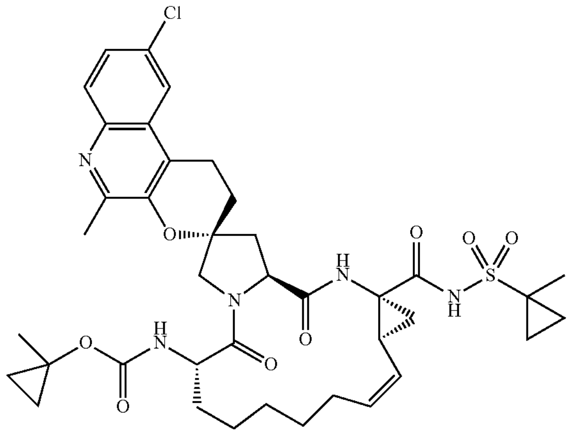 I-184 | 1-methylcyclopropyl [(2R,6S,12Z,13aS,14aR,16aS)-9'-chloro-5'-methyl-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 782.2 (K+ salt) |
| 185 | 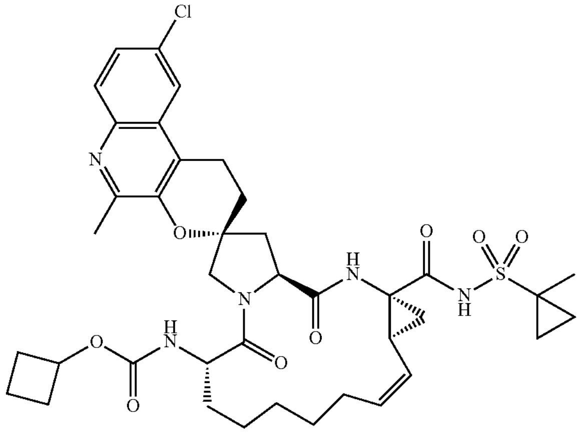 I-185 | cyclobutyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 782.2 (K+ salt) |

TABLE 1-continued

| Compounds of Examples 68-526 | | | | |
|---|---|---|---|---|
| Ex. No. | Structure | Name | Proc. | LR-MS (M + H) |
| 186 | 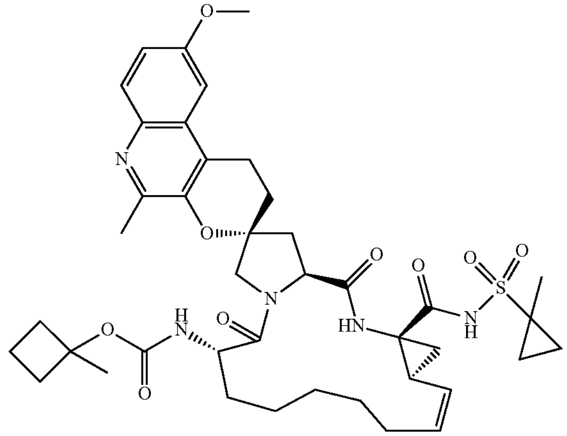 I-186 | 1-methylcyclobutyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 792.4 (K+ salt) |
| 187 | 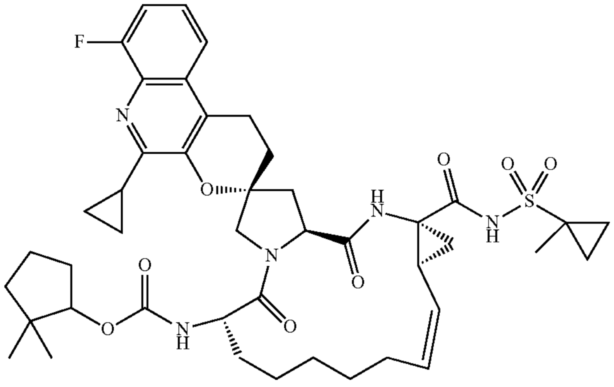 I-187 | 2,2-dimethylcyclopentyl [(2R,6S,12Z,13aS,14aR,16aS)-5'-cyclopropyl-7'-fluoro-14a-{[(1-methylcyclopropyl)sulfonyl] carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 834 |

TABLE 1-continued

| Compounds of Examples 68-526 | | | | |
|---|---|---|---|---|
| Ex. No. | Structure | Name | Proc. | LR-MS (M + H) |
| 188 | 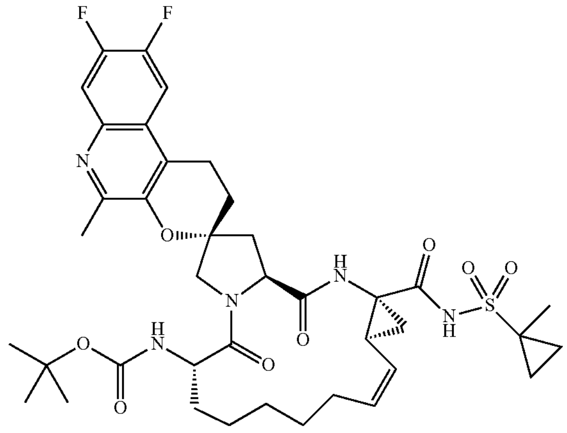 I-188 | tert-butyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 786.2 |
| 189 | 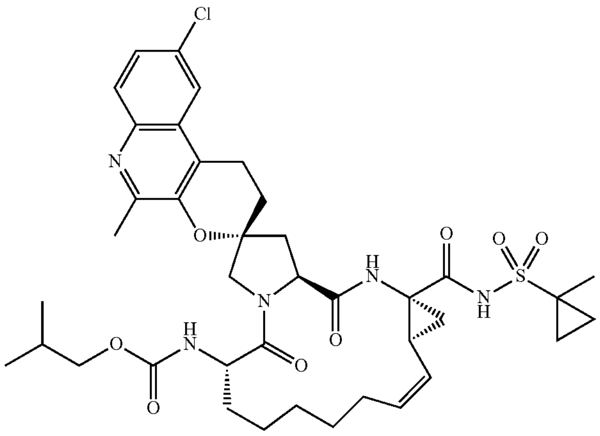 I-189 | 2-methylpropyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39, 528 | 784.2 (K+ salt) |

TABLE 1-continued

| Compounds of Examples 68-526 | | | | |
|---|---|---|---|---|
| Ex. No. | Structure | Name | Proc. | LR-MS (M + H) |
| 190 | 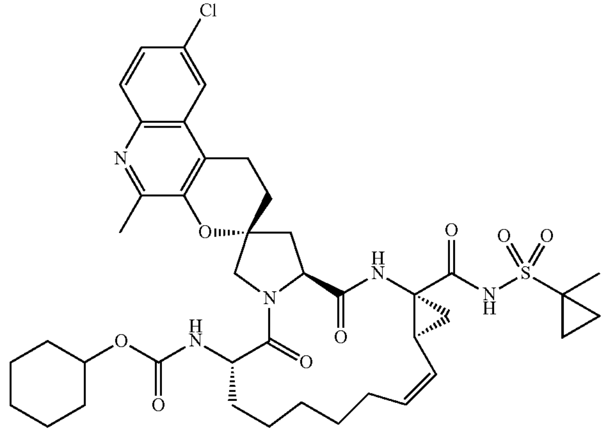 I-190 | cyclohexyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 810.2 (K+ salt) |
| 191 | 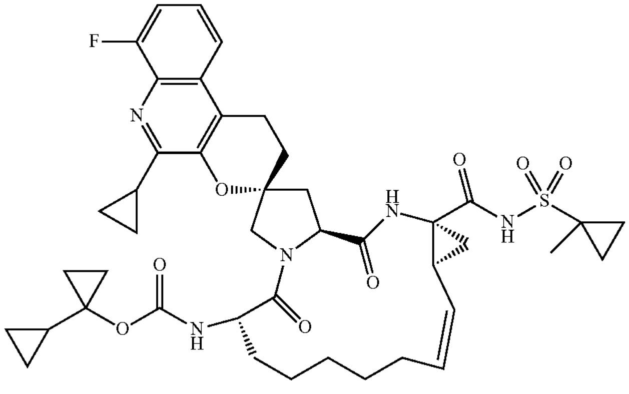 I-191 | 1,1'-bi(cyclopropyl)-1-yl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 818 |

TABLE 1-continued

| Compounds of Examples 68-526 | | | | |
|---|---|---|---|---|
| Ex. No. | Structure | Name | Proc. | LR-MS (M + H) |
| 192 | 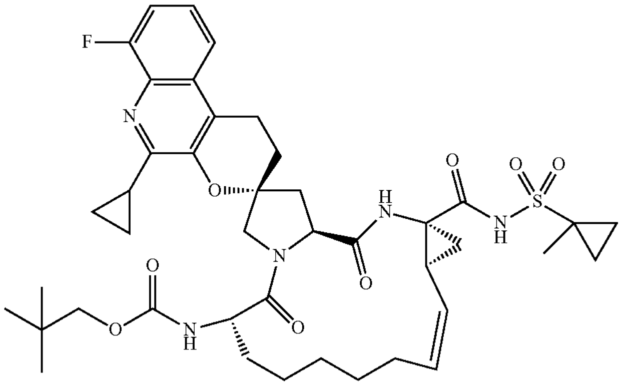 I-192 | 2,2-dimethylpropyl [(2R,6S,12Z,13aS,14aR,16aS)-5'-cyclopropyl-7'-fluoro-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 45 | 808 |
| 193 | 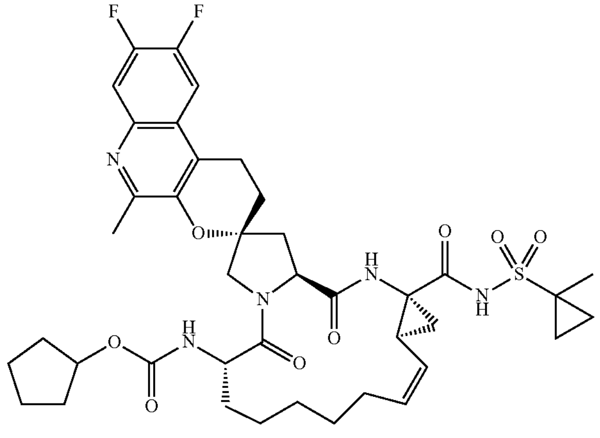 I-193 | cyclopentyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 799.2 (K+ salt) |

TABLE 1-continued

| Compounds of Examples 68-526 | | | | |
|---|---|---|---|---|
| Ex. No. | Structure | Name | Proc. | LR-MS (M + H) |
| 194 | 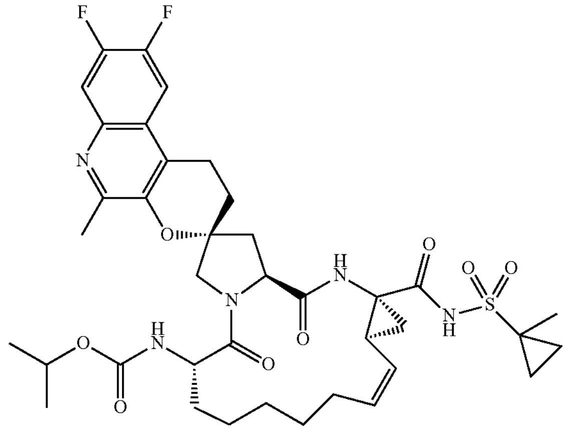 I-194 | propan-2-yl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 772.2 (K+ salt) |
| 195 | 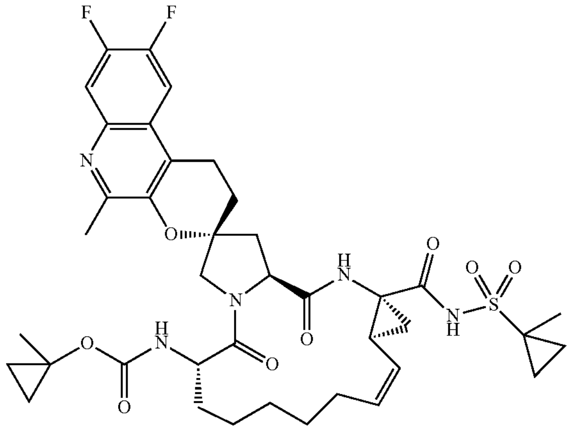 I-195 | 1-methylcyclopropyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 784.2 (K+ salt) |

TABLE 1-continued

| Compounds of Examples 68-526 | | | | |
|---|---|---|---|---|
| Ex. No. | Structure | Name | Proc. | LR-MS (M + H) |
| 196 | 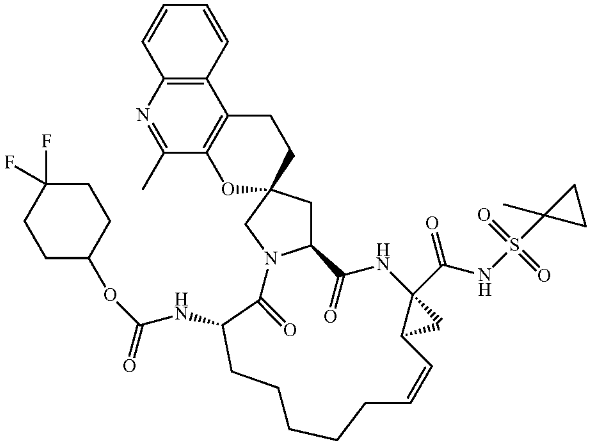 I-196 | 4,4-difluorocyclohexyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 812.5 |
| 197 | 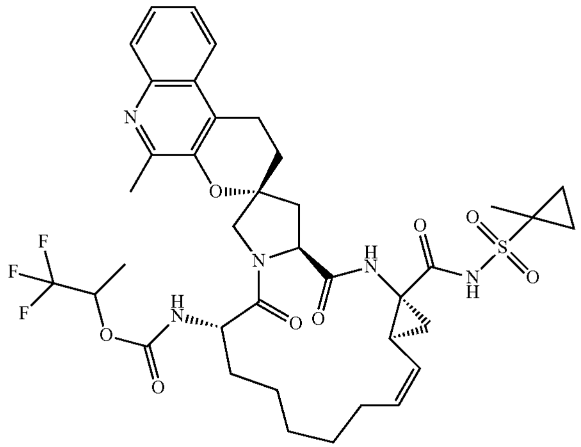 I-197 | 1,1,1-trifluoropropan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 790.3 |

TABLE 1-continued

| Compounds of Examples 68-526 | | | | |
|---|---|---|---|---|
| Ex. No. | Structure | Name | Proc. | LR-MS (M + H) |
| 198 | 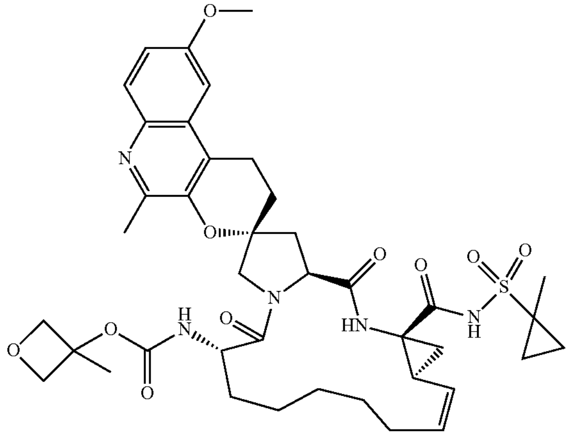 I-198 | 3-methyloxetan-3-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 794.2 |
| 199 | 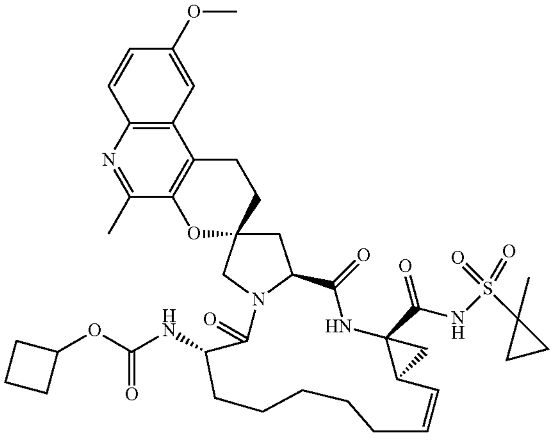 I-199 | cyclobutyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 778.2 (K+ salt ) |

TABLE 1-continued

Compounds of Examples 68-526

| Ex. No. | Structure | Name | Proc. | LR-MS (M + H) |
|---|---|---|---|---|
| 200 | 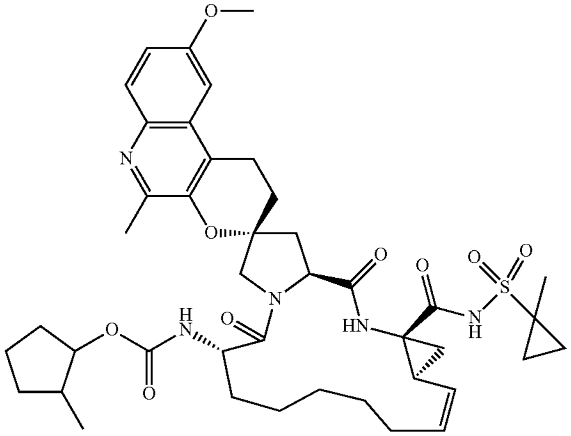 I-200 | 2-methylcyclopentyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 806.2 (K+ salt) |
| 201 | 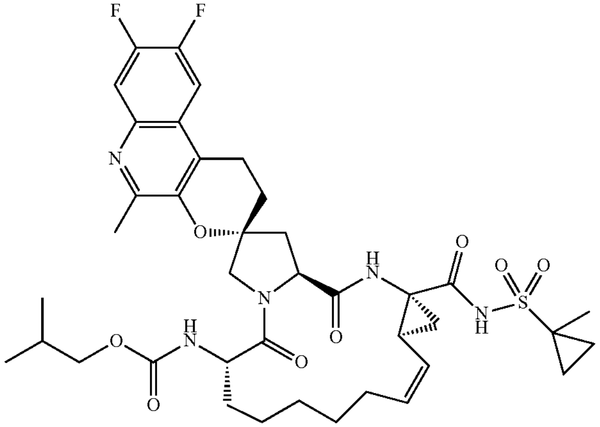 I-201 | 2-methylpropyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 786.2 (K+ salt) |

TABLE 1-continued

| Compounds of Examples 68-526 | | | | |
|---|---|---|---|---|
| Ex. No. | Structure | Name | Proc. | LR-MS (M + H) |
| 202 | 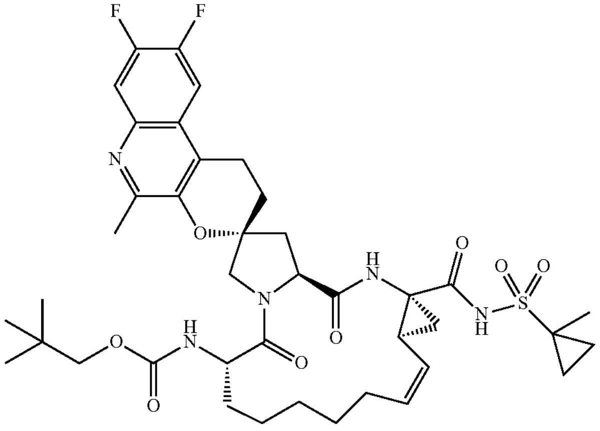 I-202 | 2,2-dimethylpropyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 800.2 (K+ salt) |
| 203 | 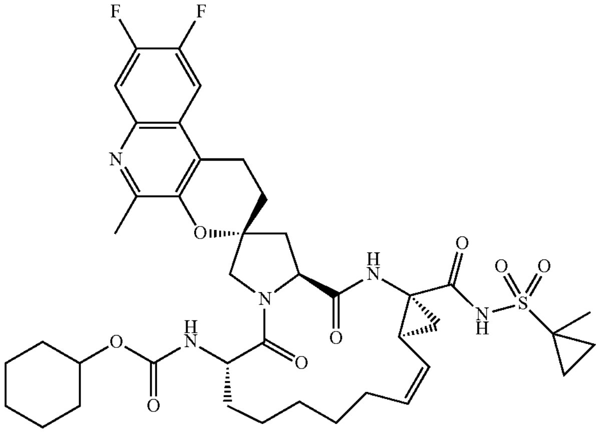 I-203 | cyclohexyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 812.2 (K+ salt) |

TABLE 1-continued

| Compounds of Examples 68-526 | | | | |
|---|---|---|---|---|
| Ex. No. | Structure | Name | Proc. | LR-MS (M + H) |
| 204 | 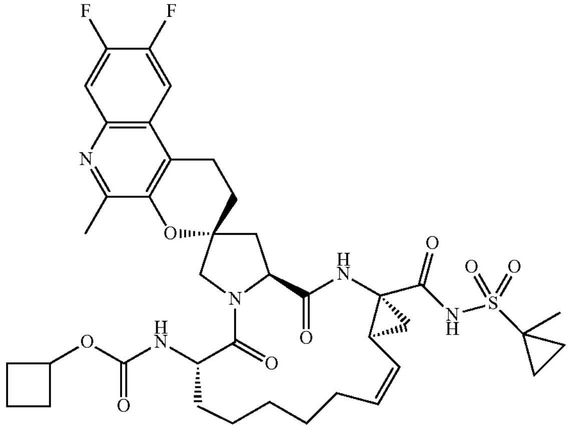 I-204 | cyclobutyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 784.2 (K+ salt) |
| 205 | 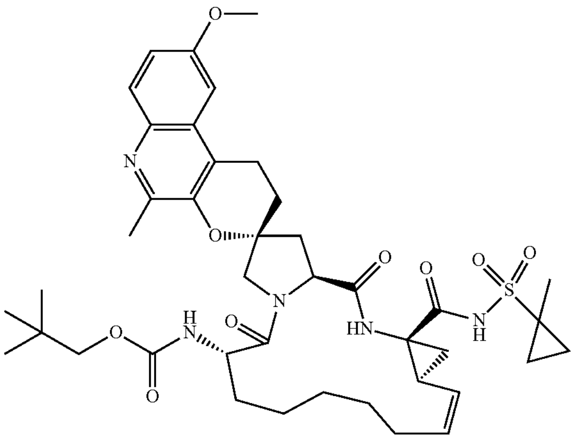 I-205 | 2,2-dimethylpropyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 794.2 (K+ salt) |

TABLE 1-continued

| Compounds of Examples 68-526 | | | | |
|---|---|---|---|---|
| Ex. No. | Structure | Name | Proc. | LR-MS (M + H) |
| 206 | 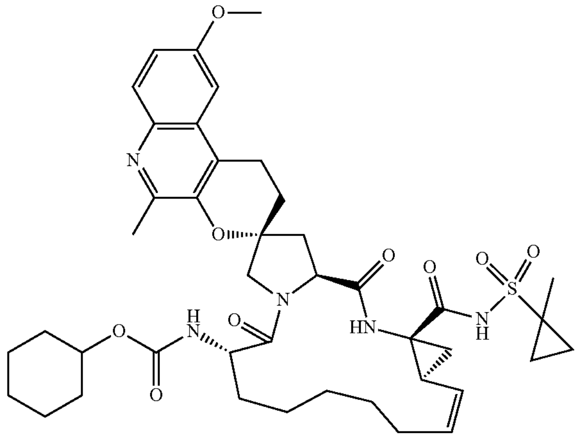 I-206 | cyclohexyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 806.2 (K+ salt) |
| 207 | 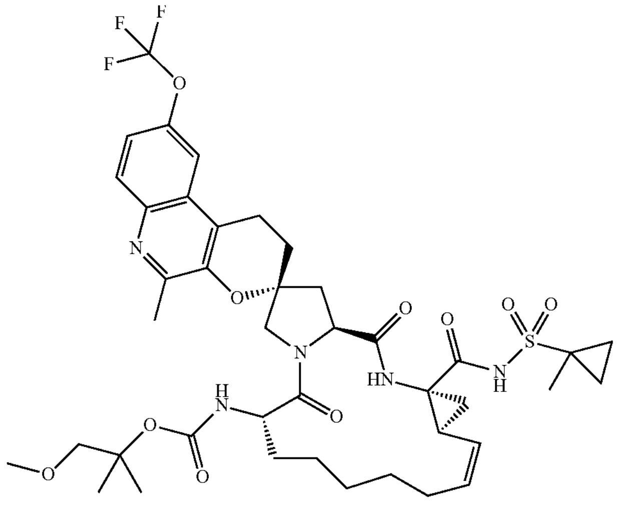 I-207 | 1-methoxy-2-methylpropan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 864.2 |

TABLE 1-continued

| Compounds of Examples 68-526 | | | | |
|---|---|---|---|---|
| Ex. No. | Structure | Name | Proc. | LR-MS (M + H) |
| 208 | 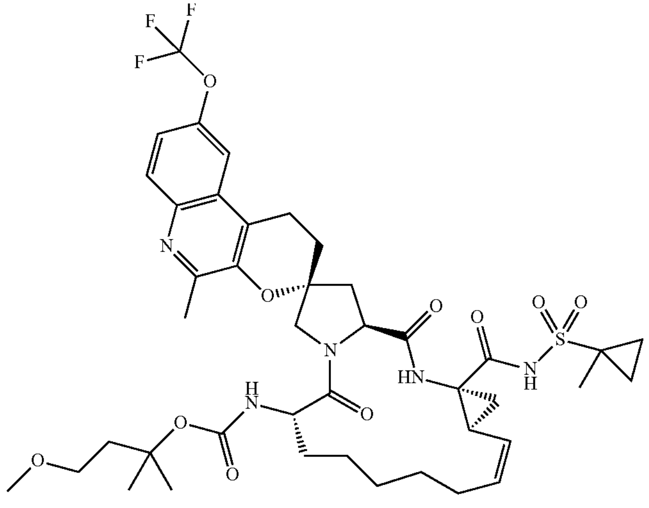 I-208 | 4-methoxy-2-methylbutan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 878.2 |
| 209 | 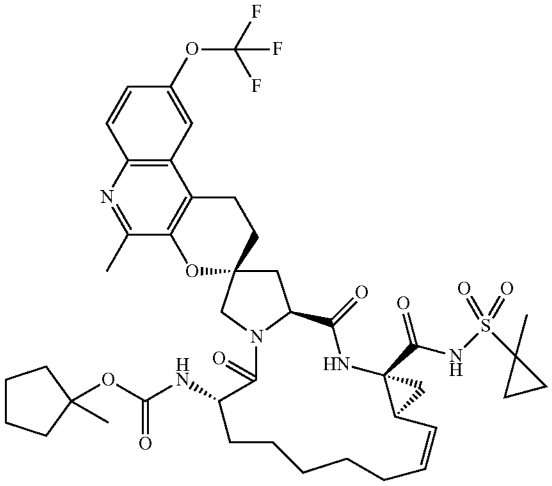 I-209 | 1-methylcyclopentyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 860.2 |

TABLE 1-continued

| Compounds of Examples 68-526 | | | | |
|---|---|---|---|---|
| Ex. No. | Structure | Name | Proc. | LR-MS (M + H) |
| 210 | 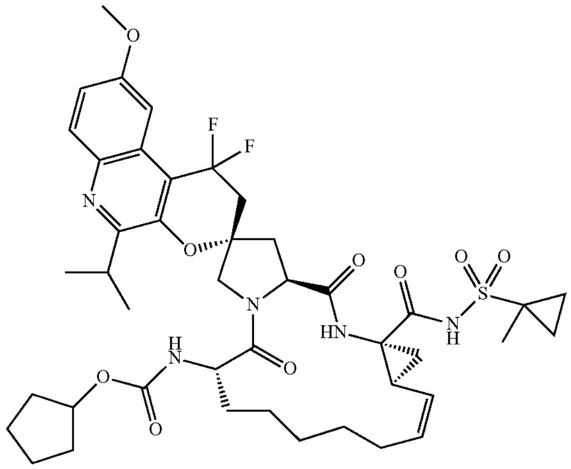 I-210 | cyclopentyl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 3 | 856.2 |
| 211 | 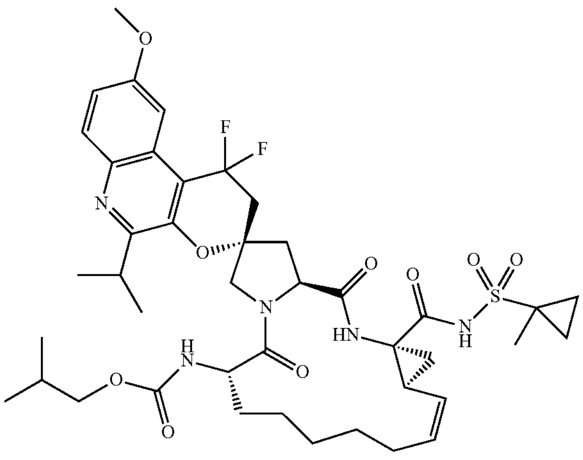 I-211 | 2-methylpropyl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 3 | 844.2 |

TABLE 1-continued

| Compounds of Examples 68-526 | | | | |
|---|---|---|---|---|
| Ex. No. | Structure | Name | Proc. | LR-MS (M + H) |
| 212 | 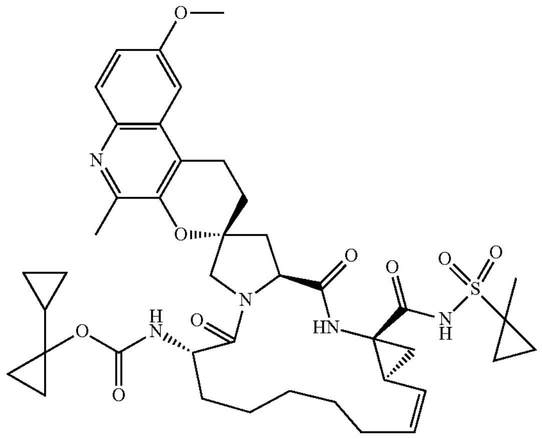 I-212 | 1,1'-bi(cyclopropyl)-1-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazcyclopentadecine-2,3'-pyrano[2,3-c]quinolin]-6-yl]carbamate | 9 | 804.2 (K+ salt) |
| 213 | 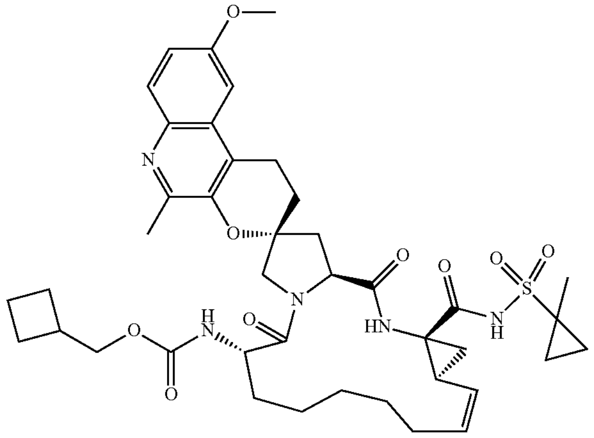 I-213 | cyclobutylmethyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 792.2 (K+ salt) |

TABLE 1-continued

| Compounds of Examples 68-526 | | | | |
|---|---|---|---|---|
| Ex. No. | Structure | Name | Proc. | LR-MS (M + H) |
| 214 | 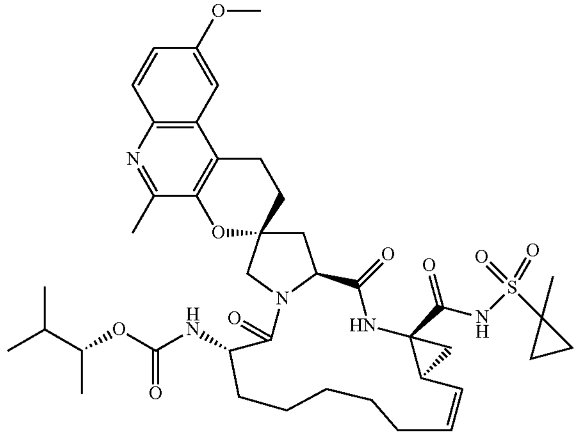 I-214 | (2R)-3-methylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 794.2 (K+ salt) |
| 215 | 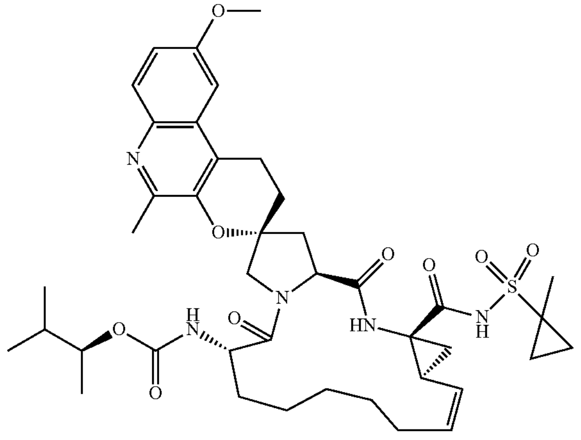 I-215 | (2S)-3-methylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 794.2 (K+ salt) |

TABLE 1-continued

| Compounds of Examples 68-526 | | | | |
|---|---|---|---|---|
| Ex. No. | Structure | Name | Proc. | LR-MS (M + H) |
| 216 | 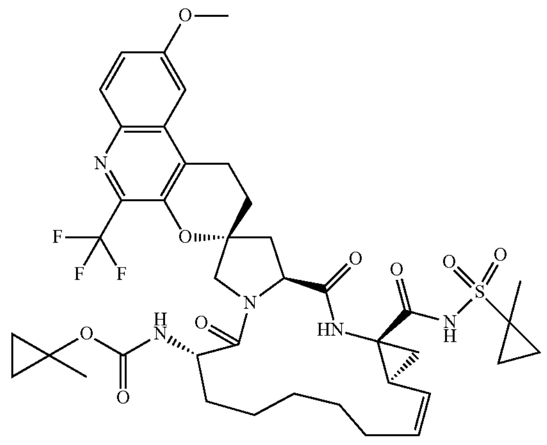 I-216 | 1-methylcyclopropyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 832.2 |
| 217 | 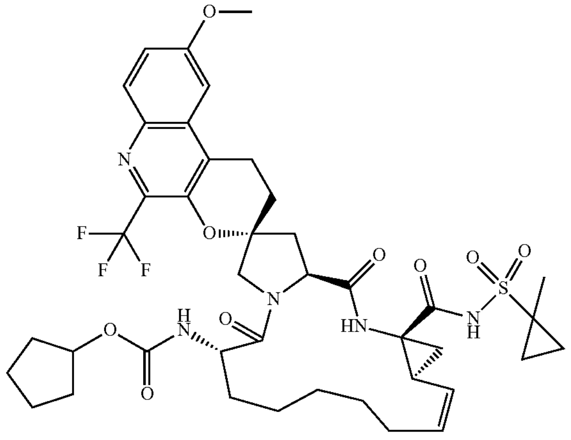 I-217 | cyclopentyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 846.3 |

TABLE 1-continued

Compounds of Examples 68-526

| Ex. No. | Structure | Name | Proc. | LR-MS (M + H) |
|---|---|---|---|---|
| 218 | 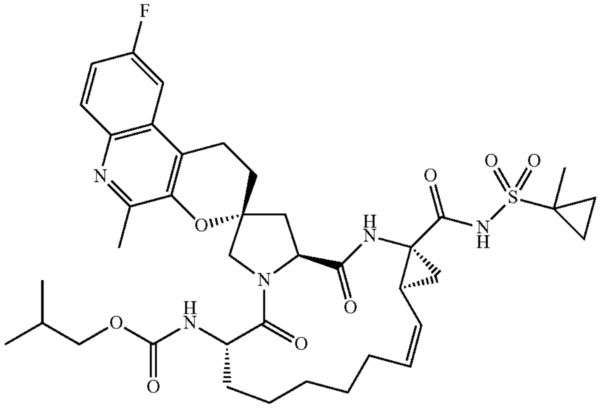 I-218 | 2-methylpropyl [(2R,6S,12Z,13aS,14aR,16aS)-9'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 768.2 |
| 219 | 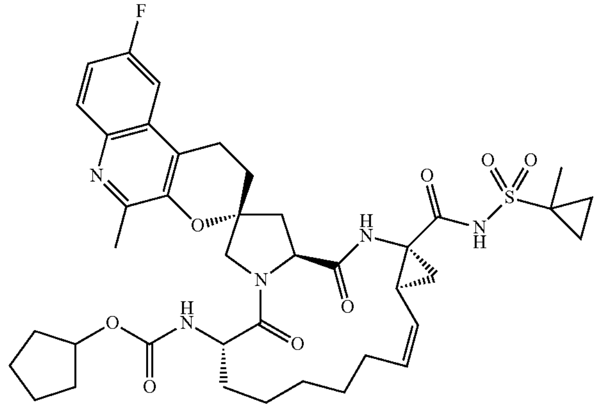 I-219 | cyclopentyl [(2R,6S,12Z,13aS,14aR,16aS)-9'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 780.2 |

TABLE 1-continued

| Compounds of Examples 68-526 | | | | |
|---|---|---|---|---|
| Ex. No. | Structure | Name | Proc. | LR-MS (M + H) |
| 220 | 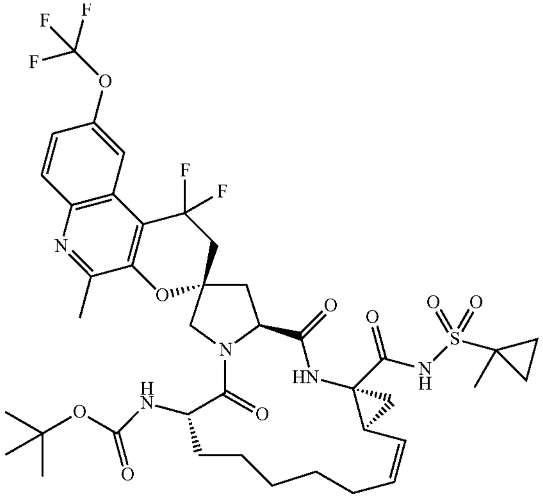 I-220 | tert-butyl [(2S,6S,12Z,13aS,14aR,16aS)-1',1'-difluoro-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 870.2 |
| 221 | 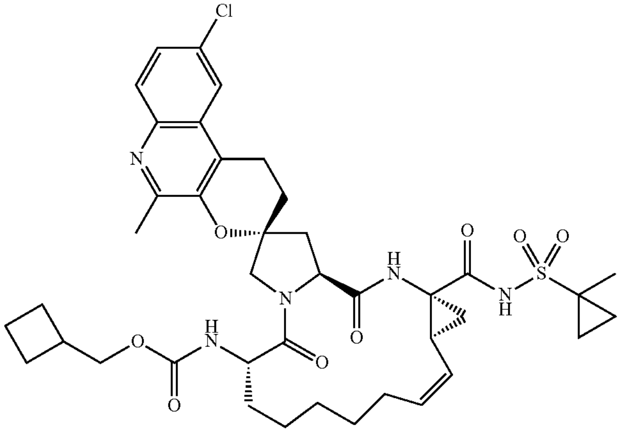 I-221 | cyclobutylmethyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 796.2 |

TABLE 1-continued

| Compounds of Examples 68-526 | | | | |
|---|---|---|---|---|
| Ex. No. | Structure | Name | Proc. | LR-MS (M + H) |
| 222 | 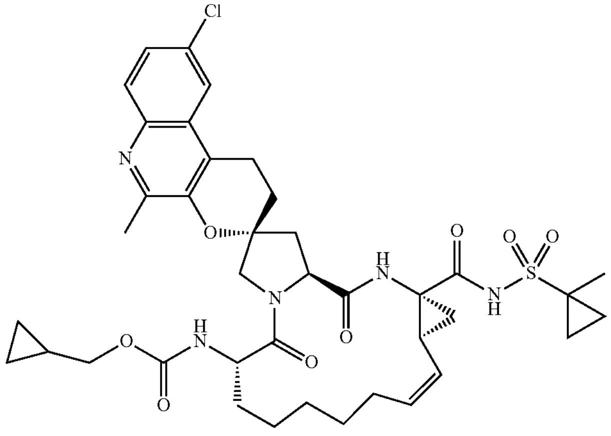 I-222 | cyclopropylmethyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 782.2 (K+ salt) |
| 223 | 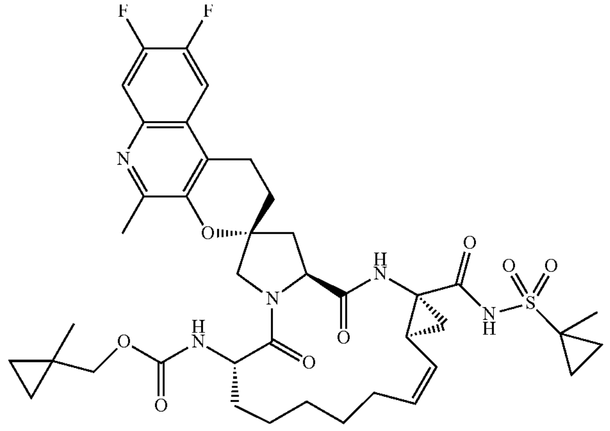 I-223 | (1-methylcyclopropyl)methyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 798.2 |

TABLE 1-continued

| Compounds of Examples 68-526 | | | | |
|---|---|---|---|---|
| Ex. No. | Structure | Name | Proc. | LR-MS (M + H) |
| 224 | 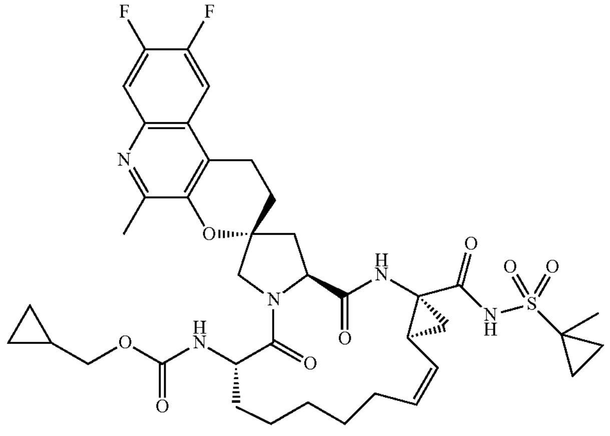 I-224 | cyclopropylmethyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 784.2 |
| 225 | 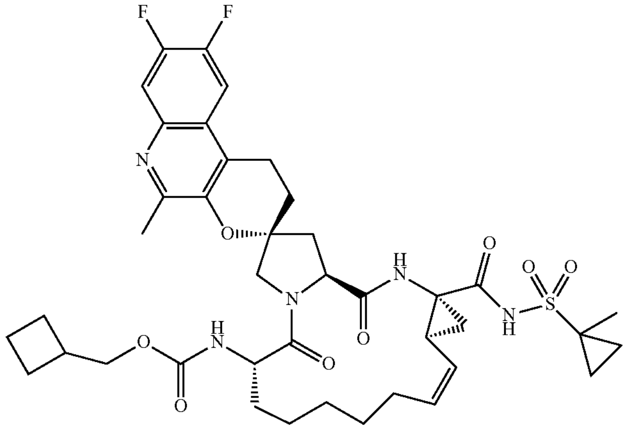 I-225 | cyclobutylmethyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 798.2 |

TABLE 1-continued
| Compounds of Examples 68-526 | | | | |
|---|---|---|---|---|
| Ex. No. | Structure | Name | Proc. | LR-MS (M + H) |
| 226 | 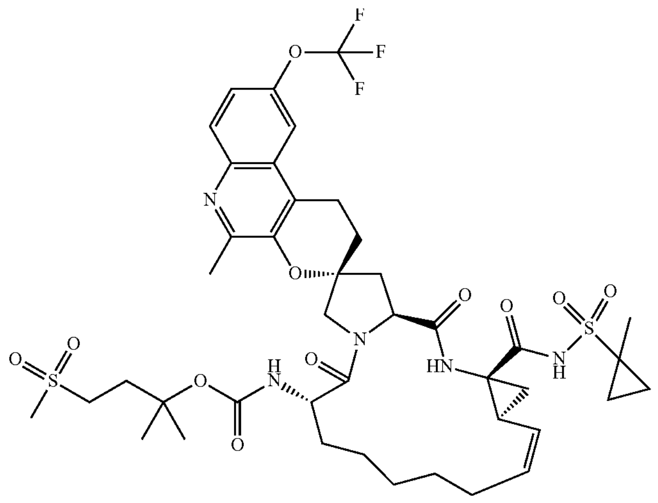 I-226 | 2-methyl-4-(methylsulfonyl)butan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 926.2 (K+ salt) |

TABLE 1-continued

| Compounds of Examples 68-526 | | | | |
|---|---|---|---|---|
| Ex. No. | Structure | Name | Proc. | LR-MS (M + H) |
| 227 | 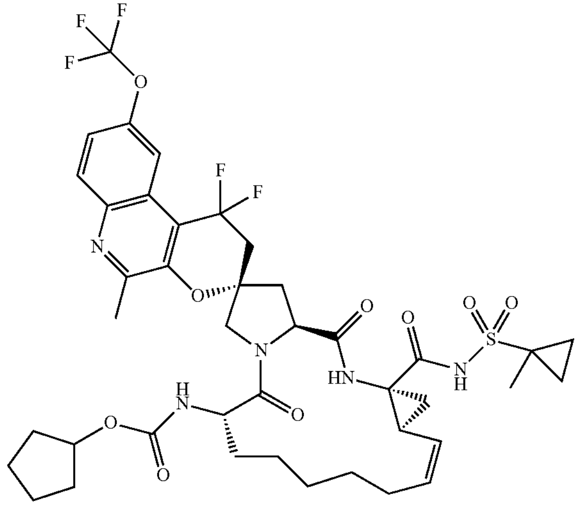 I-227 | cyclopentyl [(2S,6S,12Z,13aS,14aR,16aS)-1',1'-difluoro-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 882.2 (K+ salt) |
| 228 | 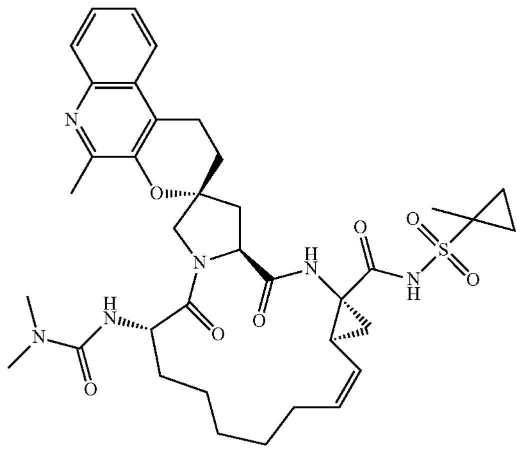 I-228 | (2R,6S,12Z,13aS,14aR,16aS)-6-[(dimethylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 61 | 721.4 |

TABLE 1-continued

| Compounds of Examples 68-526 | | | | |
|---|---|---|---|---|
| Ex. No. | Structure | Name | Proc. | LR-MS (M + H) |
| 229 | 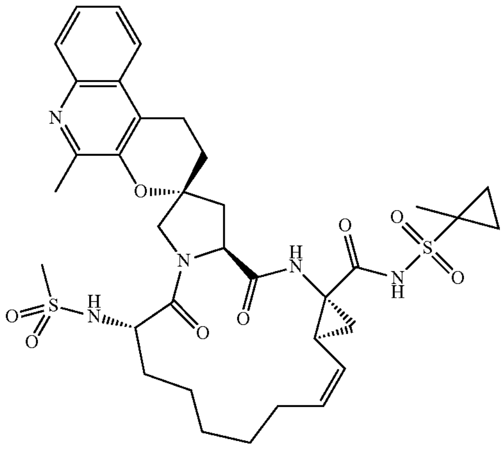 I-229 | (2R,6S,12Z,13aS,14aR,16aS)-5'-methyl-N-[(1-methylcyclopropyl)sulfonyl]-6-[(methylsulfonyl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 728.4 |
| 230 | 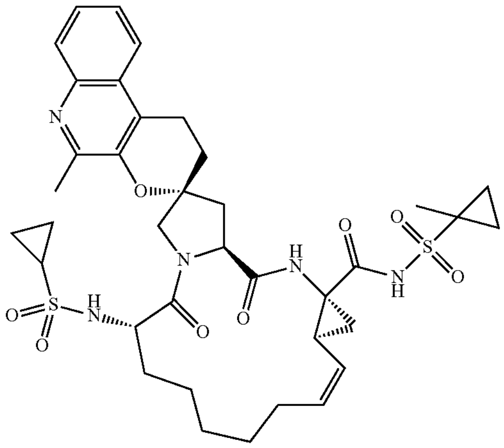 I-230 | (2R,6S,12Z,13aS,14aR,16aS)-6-[(cyclopropylsulfonyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | — |

TABLE 1-continued

| Compounds of Examples 68-526 | | | | |
|---|---|---|---|---|
| Ex. No. | Structure | Name | Proc. | LR-MS (M + H) |
| 231 | 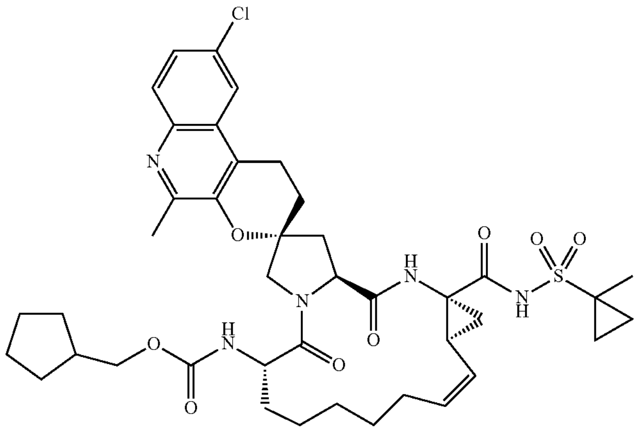 I-231 | cyclopentylmethyl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 810.2 |
| 232 | 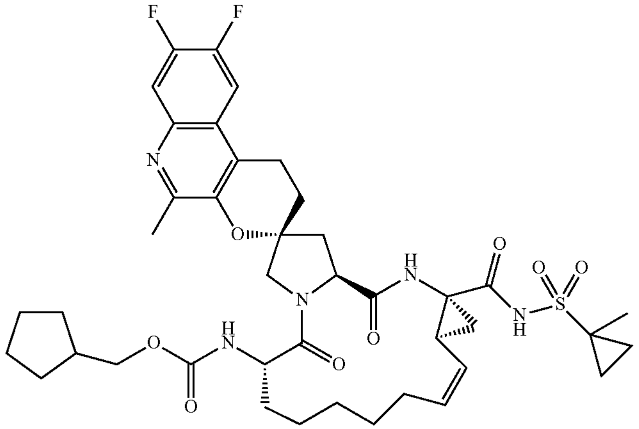 I-232 | cyclopentylmethyl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 812.2 |

TABLE 1-continued

| Compounds of Examples 68-526 | | | | |
|---|---|---|---|---|
| Ex. No. | Structure | Name | Proc. | LR-MS (M + H) |
| 233 | 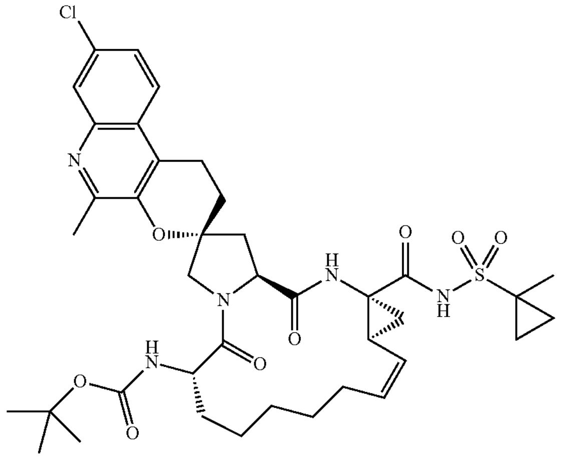 I-233 | tert-butyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 784.2 |
| 234 | 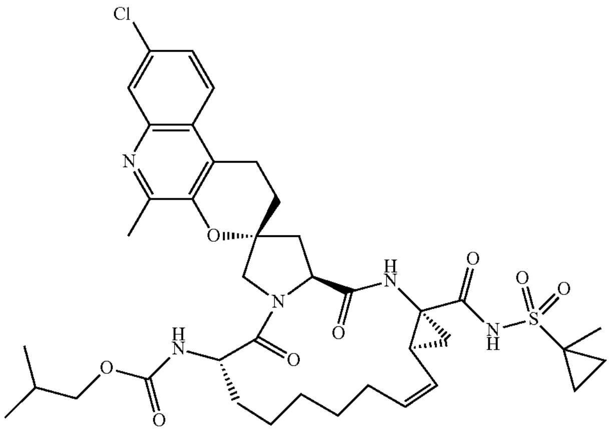 I-234 | 2-methylpropyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 784.2 (K+ salt) |

TABLE 1-continued

| Compounds of Examples 68-526 | | | | |
|---|---|---|---|---|
| Ex. No. | Structure | Name | Proc. | LR-MS (M + H) |
| 235 | 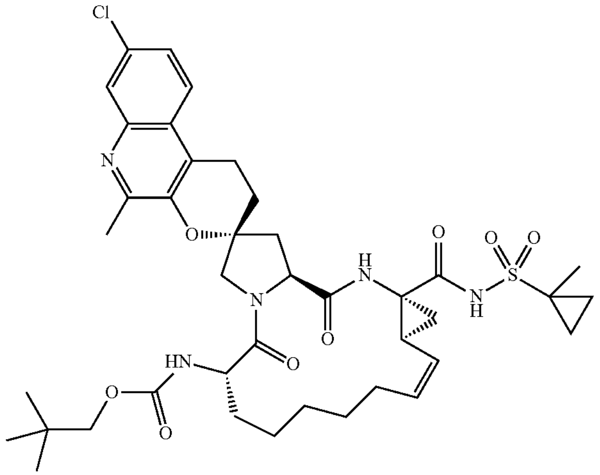 I-235 | 2,2-dimethylpropyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 798.2 (K+ salt) |
| 236 | 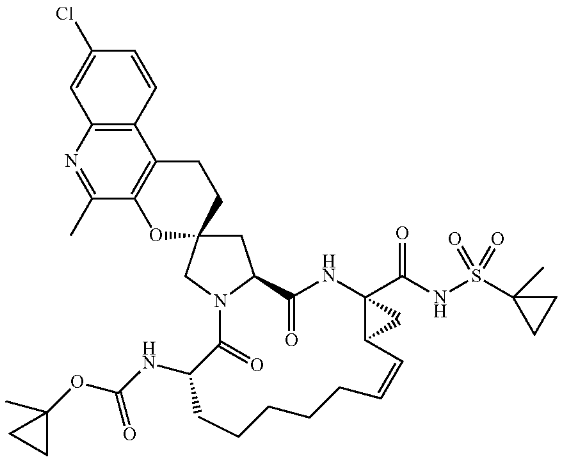 I-236 | 1-methylcyclopropyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 782.2 (K+ salt) |

TABLE 1-continued

| Compounds of Examples 68-526 | | | | |
|---|---|---|---|---|
| Ex. No. | Structure | Name | Proc. | LR-MS (M + H) |
| 237 | 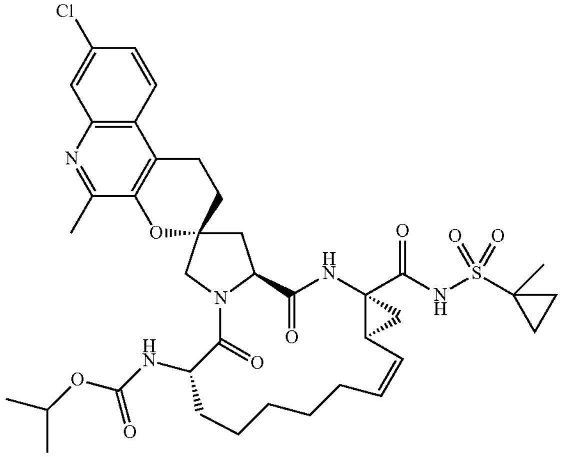 I-237 | propan-2-yl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 770.2 |
| 238 | 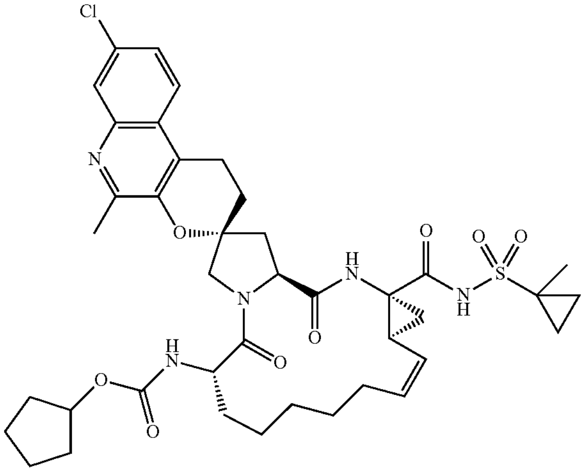 I-238 | cyclopentyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 796.2 |

TABLE 1-continued

| Compounds of Examples 68-526 | | | | |
|---|---|---|---|---|
| Ex. No. | Structure | Name | Proc. | LR-MS (M + H) |
| 239 | 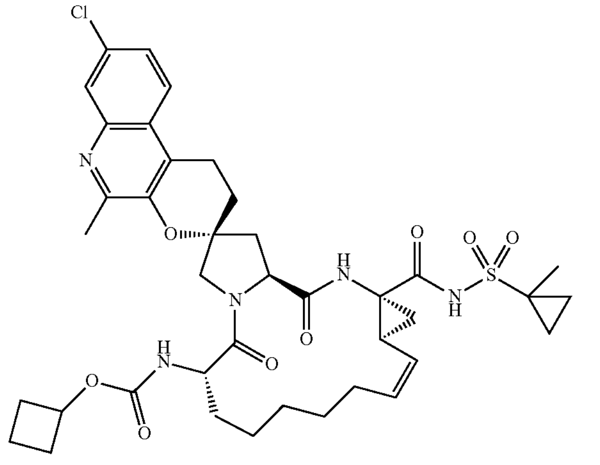 I-239 | cyclobutyl [(2R,6S,12Z,13aS,14aR,16aS)-8'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 782.2 |
| 240 | 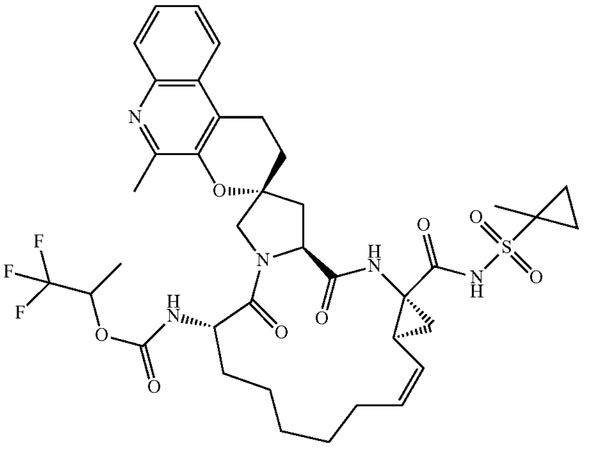 I-240 | 1,1,1-trifluoropropan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 790.5 |

TABLE 1-continued

| Compounds of Examples 68-526 | | | | |
|---|---|---|---|---|
| Ex. No. | Structure | Name | Proc. | LR-MS (M + H) |
| 241 | 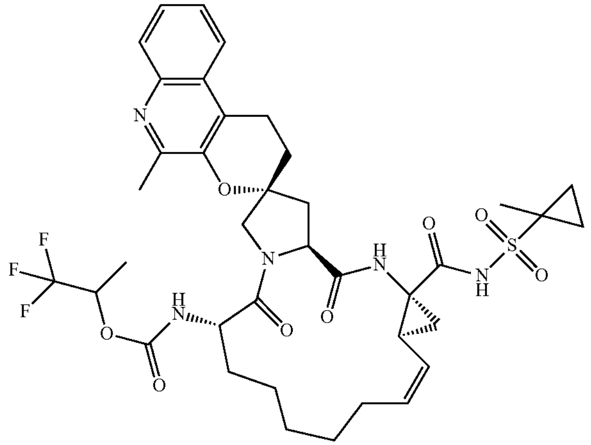 I-241 | 1,1,1-trifluoropropan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 790.5 |
| 242 | 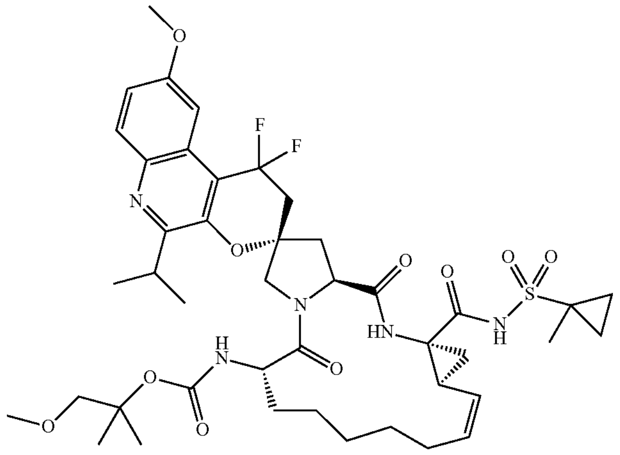 I-242 | 1-methoxy-2-methylpropan-2-yl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 3 | 874.2 |

TABLE 1-continued

| Compounds of Examples 68-526 | | | | |
|---|---|---|---|---|
| Ex. No. | Structure | Name | Proc. | LR-MS (M + H) |
| 243 | 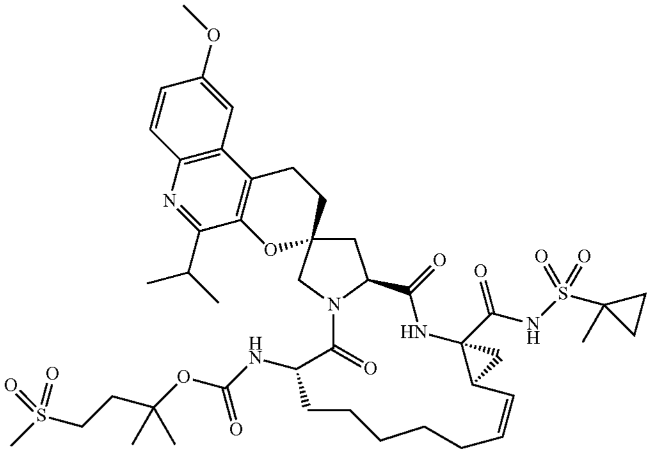 I-243 | 2-methyl-4-(methylsulfonyl)butan-2-yl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 900.2 (K+ salt) |
| 244 | 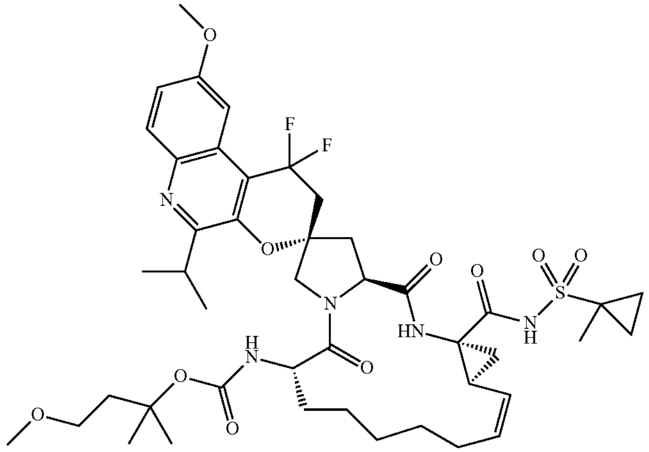 I-244 | 4-methoxy-2-methylbutan-2-yl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 888.2 |

TABLE 1-continued

| Compounds of Examples 68-526 | | | | |
|---|---|---|---|---|
| Ex. No. | Structure | Name | Proc. | LR-MS (M + H) |
| 245 | 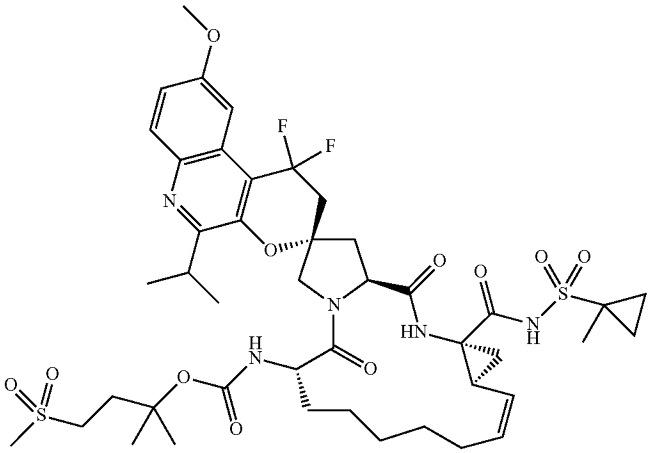 I-245 | 2-methyl-4-(methylsulfonyl)butan-2-yl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 936.2 (K+ salt) |
| 246 | 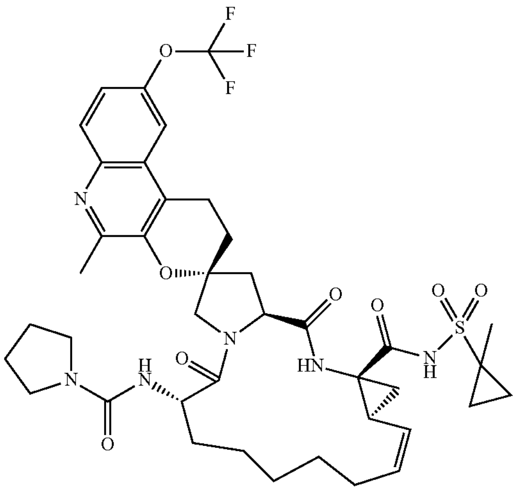 I-246 | (2R,6S,12Z,13aS,14aR,16aS)-5'-methyl-N-[(1-methylcyclopropyl)sulfonyl]-5,16-dioxo-6-[(pyrrolidin-1-ylcarbonyl)amino]-9'-(trifluoromethoxy)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 1 | 830.7 |

TABLE 1-continued

Compounds of Examples 68-526

| Ex. No. | Structure | Name | Proc. | LR-MS (M + H) |
|---|---|---|---|---|
| 247 | 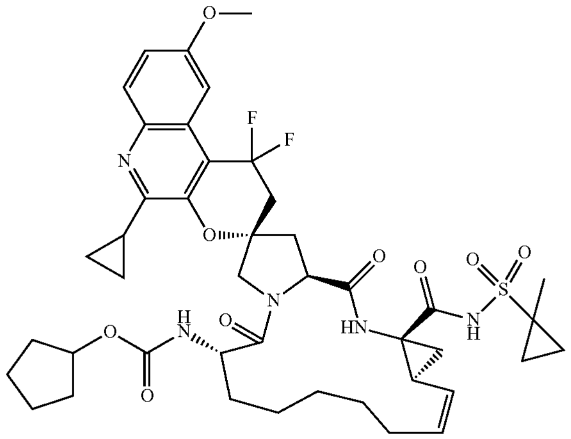 I-247 | cyclopentyl [(2S,6S,12Z,13aS,14aR,16aS)-5'-cyclopropyl-1',1'-difluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19 | 854.2 |
| 248 | 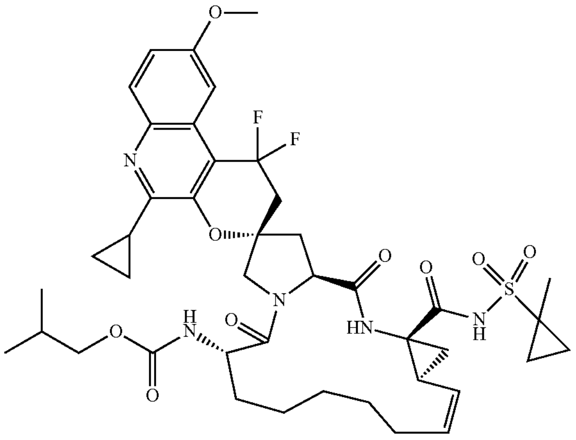 I-248 | 2-methylpropyl [(2S,6S,12Z,13aS,14aR,16aS)-5'-cyclopropyl-1',1'-difluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19 | 842.2 (K+ salt) |

TABLE 1-continued

Compounds of Examples 68-526

| Ex. No. | Structure | Name | Proc. | LR-MS (M + H) |
|---|---|---|---|---|
| 249 | 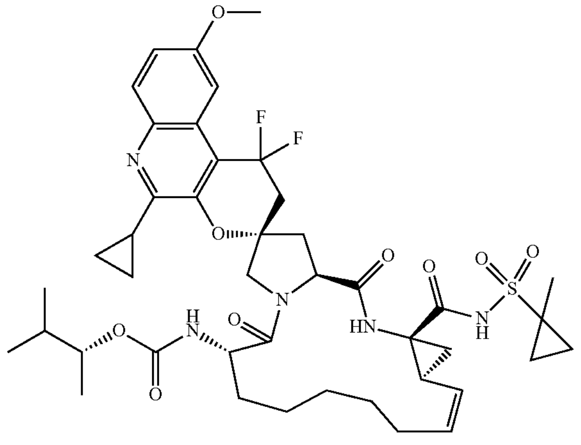 I-249 | (2R)-3-methylbutan-2-yl [(2S,6S,12Z,13aS,14aR,16aS)-5'-cyclopropyl-1',1'-difluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19 | 856.2 (K+ salt) |
| 250 | 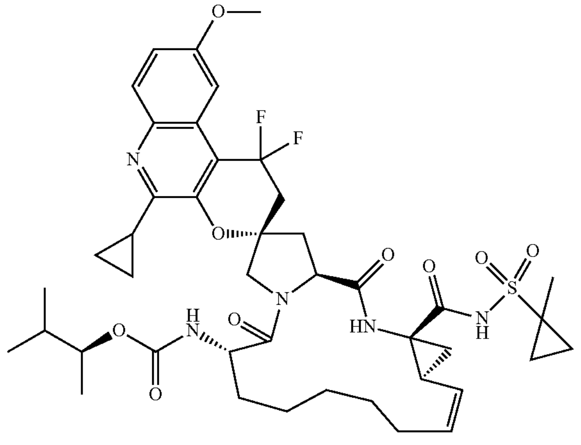 I-250 | (2S)-3-methylbutan-2-yl [(2S,6S,12Z,13aS,14aR,16aS)-5'-cyclopropyl-1',1'-difluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 19 | 856.2 |

TABLE 1-continued

| Compounds of Examples 68-526 | | | | |
|---|---|---|---|---|
| Ex. No. | Structure | Name | Proc. | LR-MS (M + H) |
| 251 | 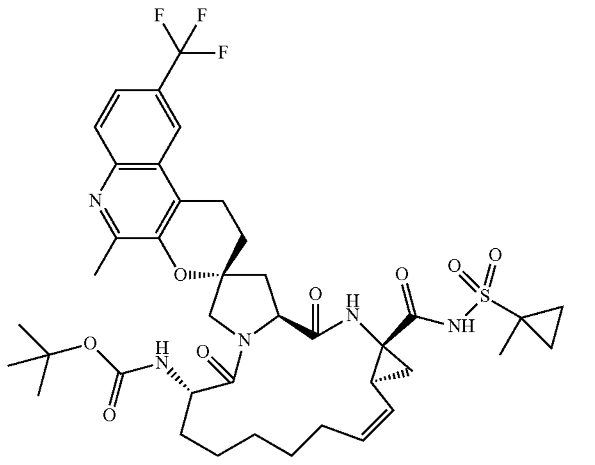 I-251 | tert-butyl [(2R,6S,12Z,13aS,14aR,16aS)-5'-methyl-14a-{[(1-methylcyclopropyl)sulfonyl]carbamoyl}-5,16-dioxo-9'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 817.4 |
| 252 | 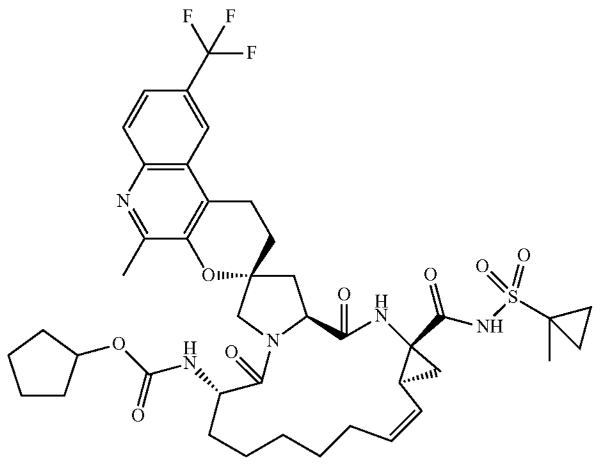 I-252 | cyclopentyl [(2R,6S,12Z,13aS,14aR,16aS)-5'-methyl-14a-{[(1-methylcyclopropyl)sulfonyl]carbamoyl}-5,16-dioxo-9'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | — |

TABLE 1-continued

| Compounds of Examples 68-526 | | | | |
|---|---|---|---|---|
| Ex. No. | Structure | Name | Proc. | LR-MS (M + H) |
| 253 | 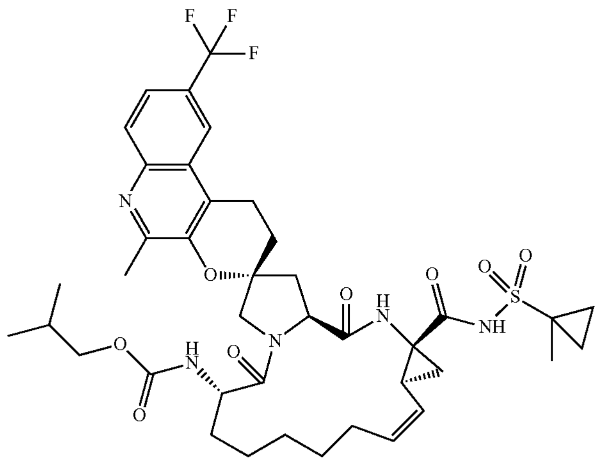 I-253 | 2-methylpropyl [(2R,6S,12Z,13aS,14aR,16aS)-5'-methyl-14a-{[(1-methylcyclopropyl)sulfonyl]carbamoyl}-5,16-dioxo-9'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 818.5 |
| 254 | 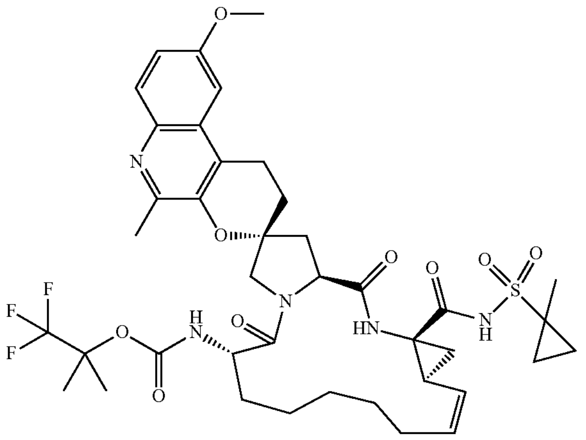 I-254 | 1,1,1-trifluoro-2-methylpropan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 834.2 (K+ salt) |

TABLE 1-continued

| Compounds of Examples 68-526 | | | | |
|---|---|---|---|---|
| Ex. No. | Structure | Name | Proc. | LR-MS (M + H) |
| 255 | 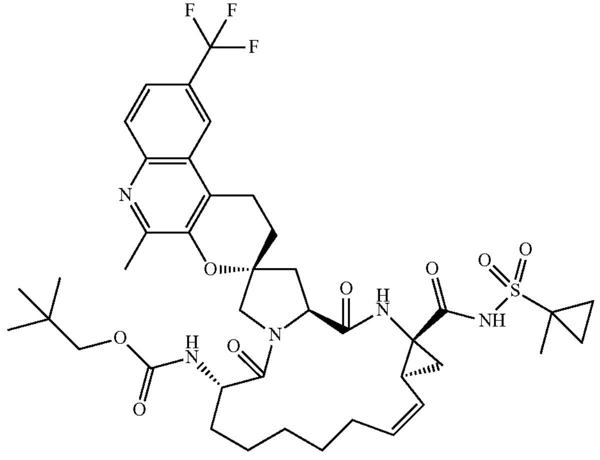 I-255 | 2,2-dimethylpropyl [(2R,6S,12Z,13aS,14aR,16aS)-5'-methyl-14a-{[(1-methylcyclopropyl)sulfonyl]carbamoyl}-5,16-dioxo-9'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 832.5 |
| 256 | 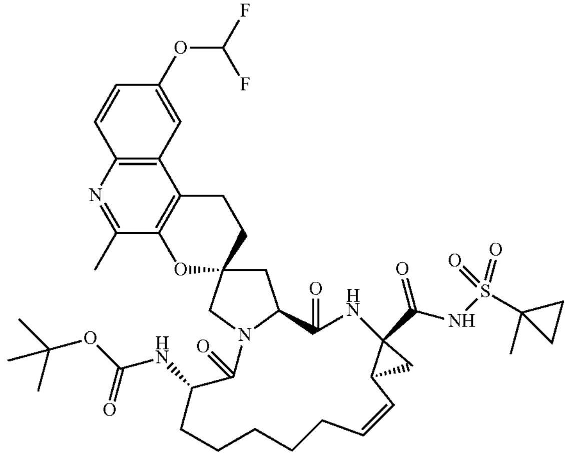 I-256 | tert-butyl [(2R,6S,12Z,13aS,14aR,16aS)-9'-(difluoromethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 816.5 |

TABLE 1-continued

| Compounds of Examples 68-526 | | | | |
|---|---|---|---|---|
| Ex. No. | Structure | Name | Proc. | LR-MS (M + H) |
| 257 | 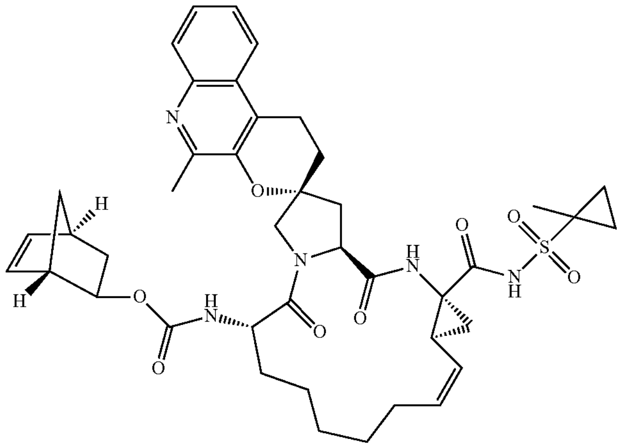 I-257 | (1S,4S)-bicyclo[2.2.1]hept-5-en-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 786.4 |
| 258 | 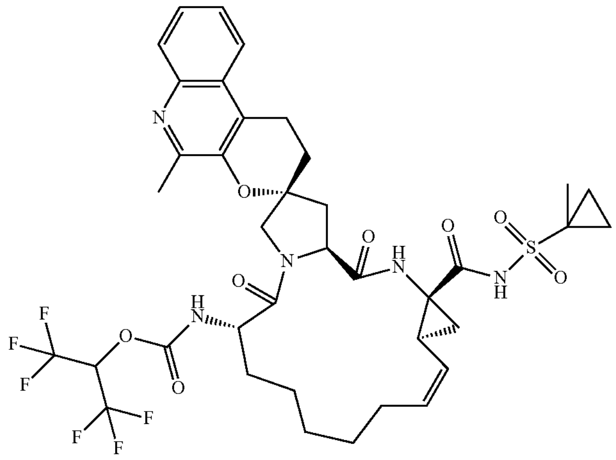 I-258 | 1,1,1,3,3,3-hexafluoropropan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | — |

TABLE 1-continued

| Compounds of Examples 68-526 | | | | |
|---|---|---|---|---|
| Ex. No. | Structure | Name | Proc. | LR-MS (M + H) |
| 259 | 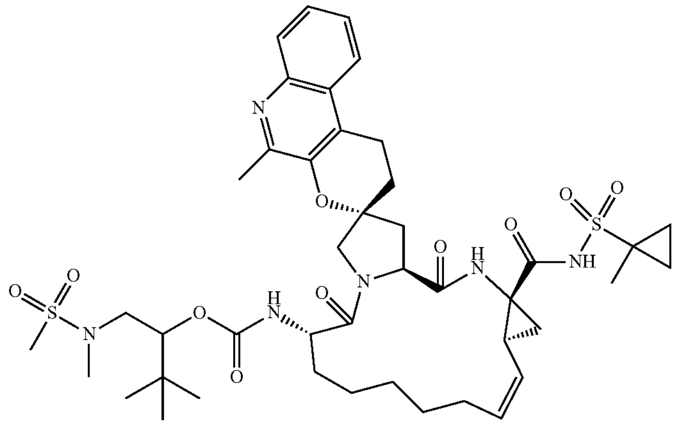 I-259 | 3,3-dimethyl-1-[methyl(methylsulfonyl)amino]butan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 885.4 |
| 260 | 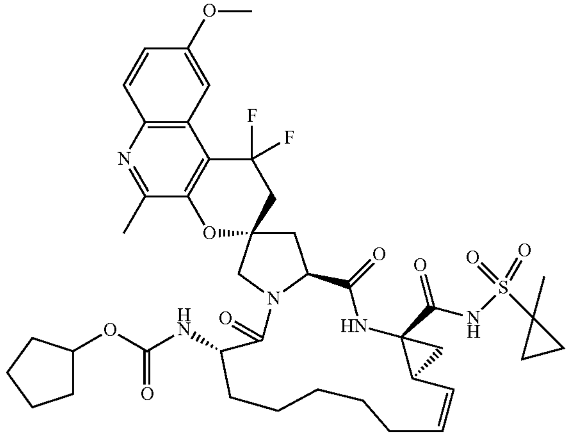 I-260 | cyclopentyl [(2S,6S,12Z,13aS,14aR,16aS)-1',1'-difluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20 | 828.2 |

TABLE 1-continued

| Compounds of Examples 68-526 | | | | |
|---|---|---|---|---|
| Ex. No. | Structure | Name | Proc. | LR-MS (M + H) |
| 261 | 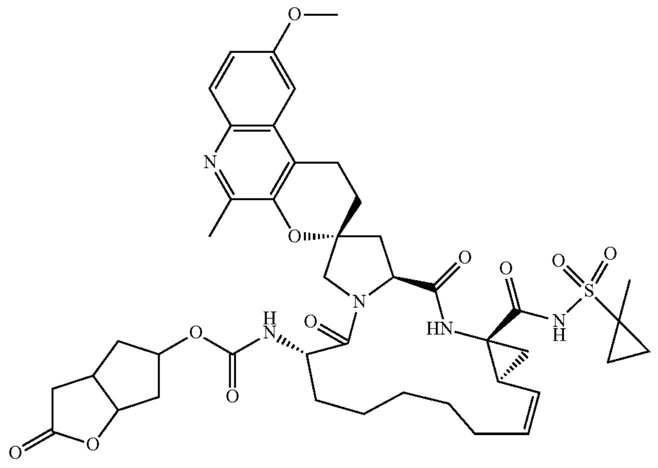 I-261 | 2-oxohexahydro-2H-cyclopenta[b]furan-5-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 848.2 |
| 262 | 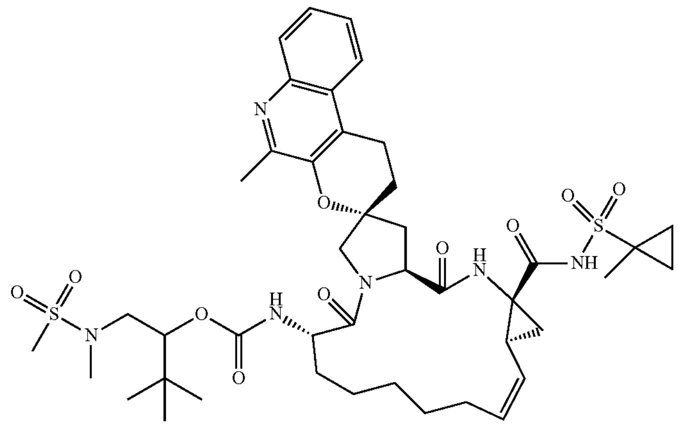 I-262 | 3,3-dimethyl-1-[methyl(methylsulfonyl)amino]butan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 35 | 885.4 |

TABLE 1-continued

| Compounds of Examples 68-526 | | | | |
|---|---|---|---|---|
| Ex. No. | Structure | Name | Proc. | LR-MS (M + H) |
| 263 | 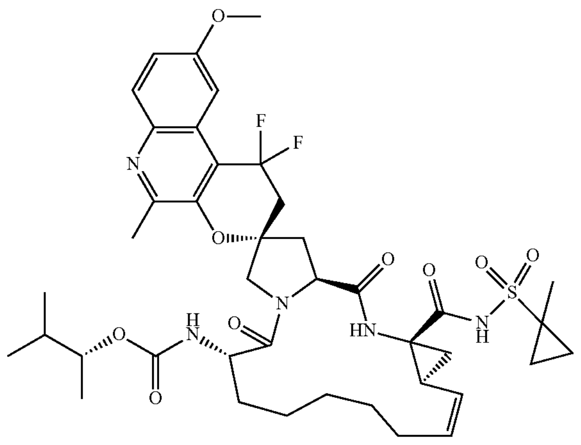 I-263 | (2R)-3-methylbutan-2-yl [(2S,6S,12Z,13aS,14aR,16aS)-1',1'-difluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20 | 830.2 (K+ salt) |
| 264 | 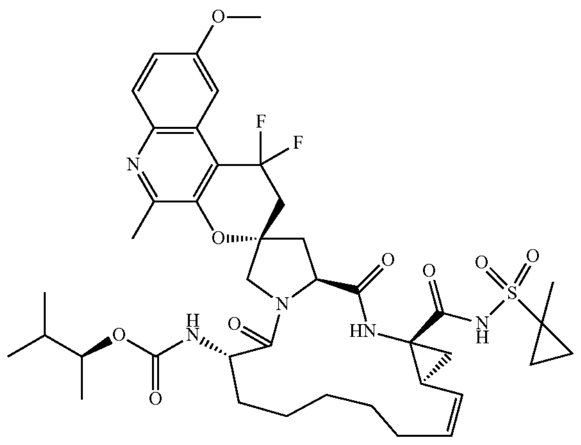 I-264 | (2S)-3-methylbutan-2-yl [(2S,6S,12Z,13aS,14aR,16aS)-1',1'-difluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20 | 830.2 (K+ salt) |

TABLE 1-continued

Compounds of Examples 68-526

| Ex. No. | Structure | Name | Proc. | LR-MS (M + H) |
|---|---|---|---|---|
| 265 | 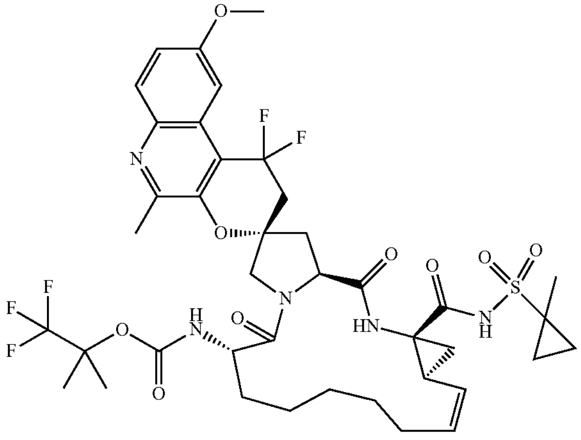 I-265 | 1,1,1-trifluoro-2-methylpropan-2-yl [(2S,6S,12Z,13aS,14aR,16aS)-1',1'-difluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20 | 870.2 (K+ salt) |
| 266 | 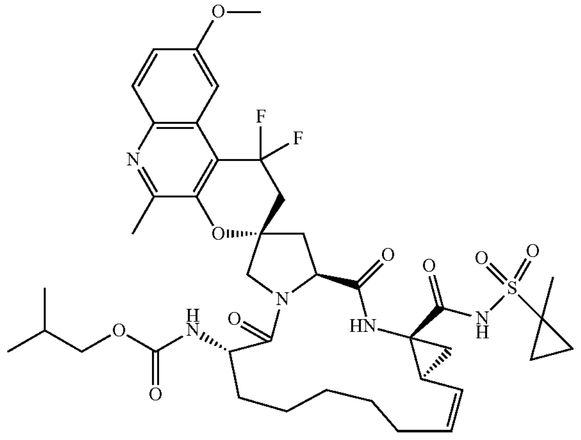 I-266 | 2-methylpropyl [(2S,6S,12Z,13aS,14aR,16aS)-1',1'-difluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 20 | 816.2 (K+ salt) |

TABLE 1-continued

| Compounds of Examples 68-526 | | | | |
|---|---|---|---|---|
| Ex. No. | Structure | Name | Proc. | LR-MS (M + H) |
| 267 | 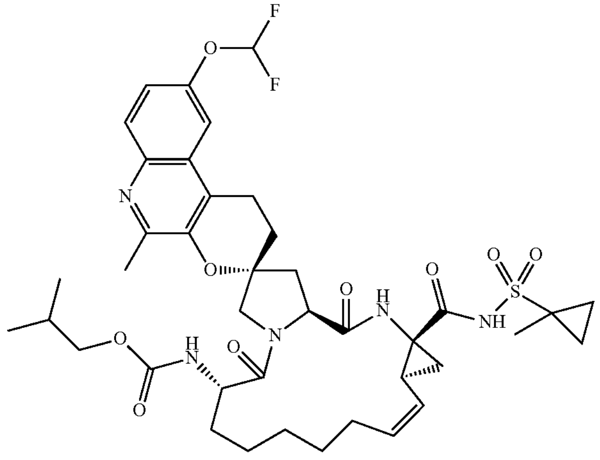 I-267 | 2-methylpropyl [(2R,6S,12Z,13aS,14aR,16aS)-9'-(difluoromethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 816.4 |
| 268 | 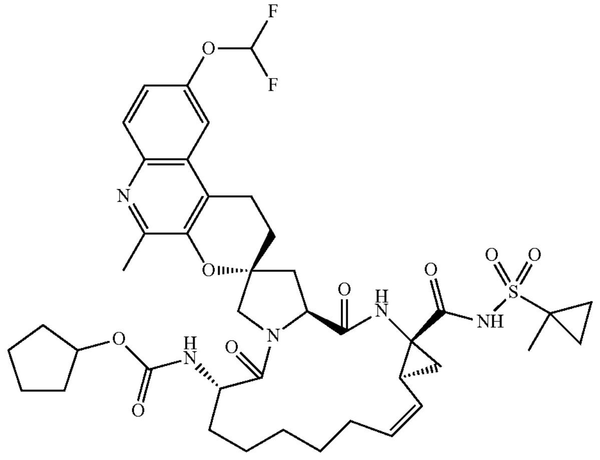 I-268 | cyclopentyl [(2R,6S,12Z,13aS,14aR,16aS)-9'-(difluoromethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | — |

TABLE 1-continued
| Compounds of Examples 68-526 | | | | |
|---|---|---|---|---|
| Ex. No. | Structure | Name | Proc. | LR-MS (M + H) |
| 269 | 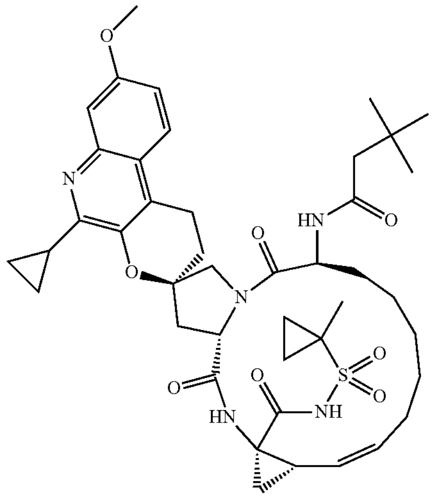 I-269 | (2R,6S,12Z,13aS,14aR,16aS)-5'-cyclopropyl-6-[(3,3-dimethylbutanoyl)amino]-8'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 9 | 804.61 (HCOOH salt) |

TABLE 1-continued

| Compounds of Examples 68-526 | | | | |
|---|---|---|---|---|
| Ex. No. | Structure | Name | Proc. | LR-MS (M + H) |
| 270 | 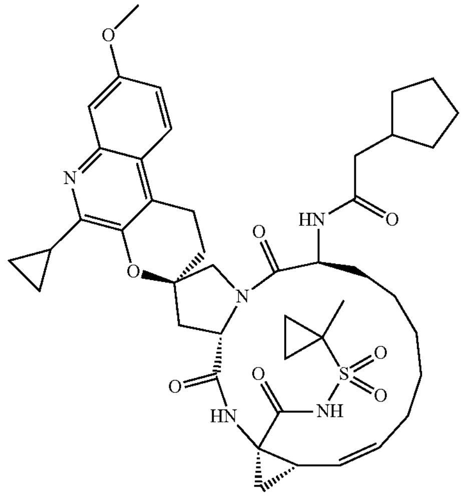 I-270 | (2R,6S,12Z,13aS,14aR,16aS)-6-[(cyclopentylacetyl)amino]-5'-cyclopropyl-8'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 9 | — |
| 271 | 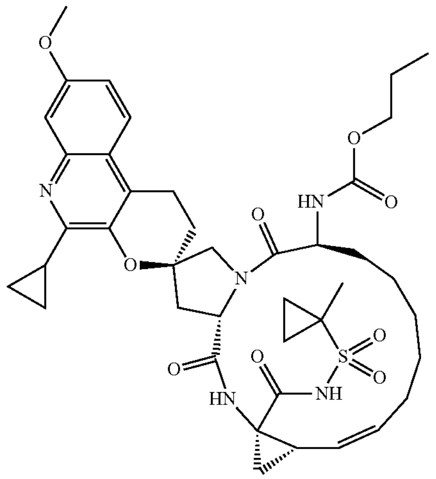 I-271 | propyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 792.55 (HCOOH salt) |

TABLE 1-continued
| Compounds of Examples 68-526 | | | | |
|---|---|---|---|---|
| Ex. No. | Structure | Name | Proc. | LR-MS (M + H) |
| 272 | 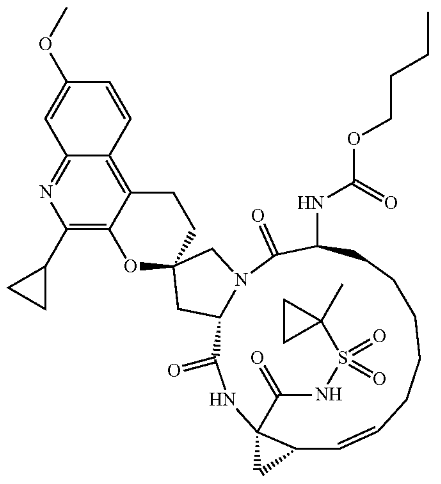<br>I-272 | butyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 806.56<br>(HCOOH salt) |

TABLE 1-continued

Compounds of Examples 68-526

| Ex. No. | Structure | Name | Proc. | LR-MS (M + H) |
|---|---|---|---|---|
| 273 | 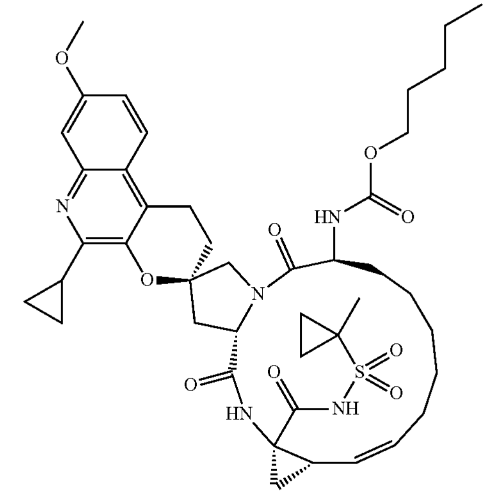 I-273 | pentyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 820.58 (HCOOH salt) |
| 274 | 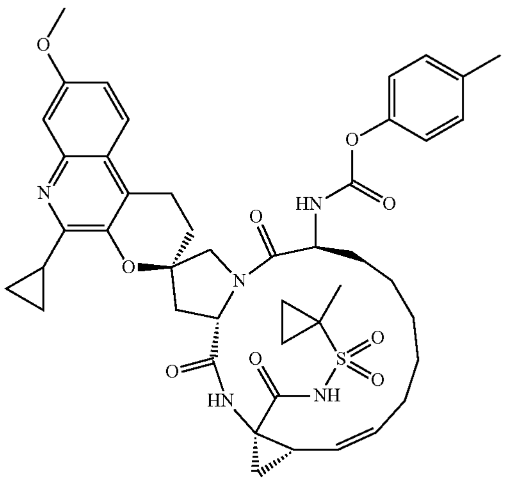 I-274 | 4-methylphenyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 840.59 (HCOOH salt) |

TABLE 1-continued

| Compounds of Examples 68-526 | | | | |
|---|---|---|---|---|
| Ex. No. | Structure | Name | Proc. | LR-MS (M + H) |
| 275 | 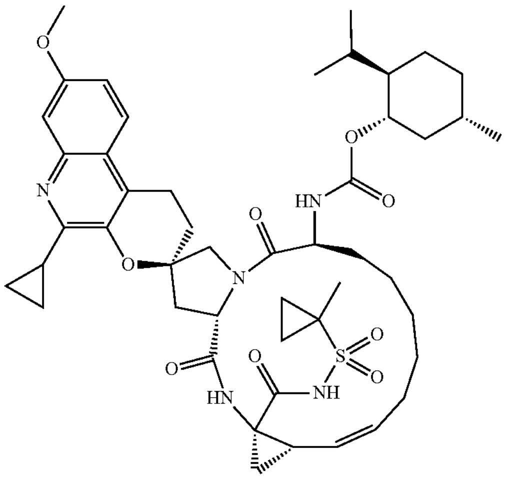 I-275 | (1S,2R,5S)-5-methyl-2-(propan-2-yl)cyclohexyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 888.67 (HCOOH salt) |
| 276 | 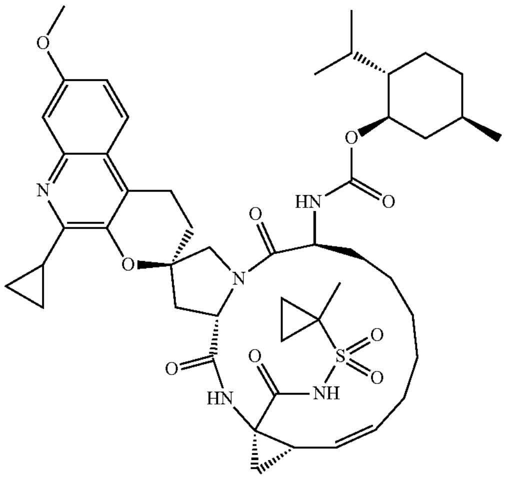 I-276 | (1R,2S,5R)-5-methyl-2-(propan-2-yl)cyclohexyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 888.7 (HCOOH salt) |

TABLE 1-continued

| Compounds of Examples 68-526 | | | | |
|---|---|---|---|---|
| Ex. No. | Structure | Name | Proc. | LR-MS (M + H) |
| 277 | 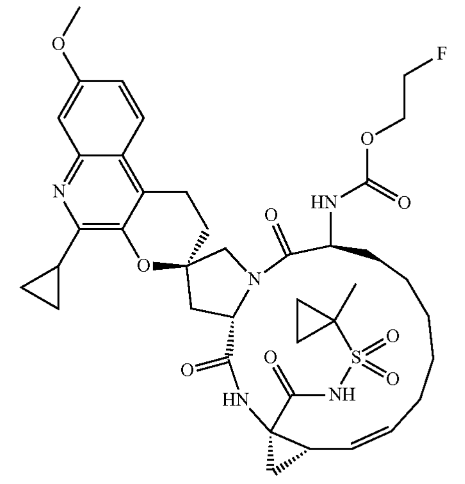 I-277 | 2-fluoroethyl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 796.51 (HCOOH salt) |
| 278 | 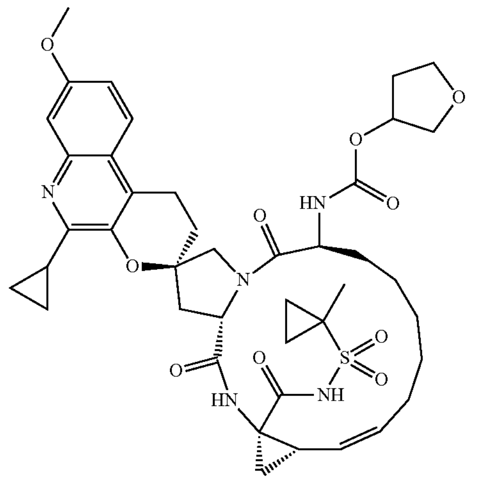 I-278 | tetrahydrofuran-3-yl [(2R,6S,12Z,13aS,14aR,16aS)-5'-cyclopropyl-8'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 820.53 (HCOOH salt) |

TABLE 1-continued

| Compounds of Examples 68-526 | | | | |
|---|---|---|---|---|
| Ex. No. | Structure | Name | Proc. | LR-MS (M + H) |
| 279 | 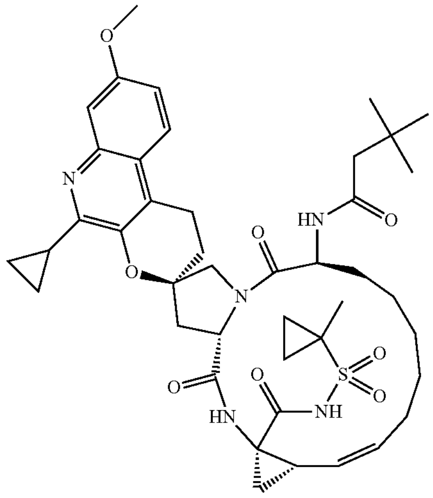 I-279 | (2R,6S,12Z,13aS,14aR,16aS)-5'-cyclopropyl-6-[(3,3-dimethylbutanoyl)amino]-8'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 9 | 820.59 (HCOOH salt) |
| 280 | 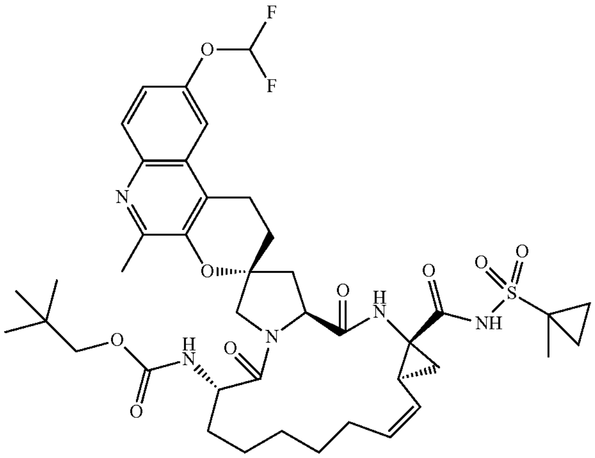 I-280 | 2,2-dimethylpropyl [(2R,6S,12Z,13aS,14aR,16aS)-9'-(difluoromethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 830.5 |

TABLE 1-continued

| Compounds of Examples 68-526 | | | | |
|---|---|---|---|---|
| Ex. No. | Structure | Name | Proc. | LR-MS (M + H) |
| 281 | 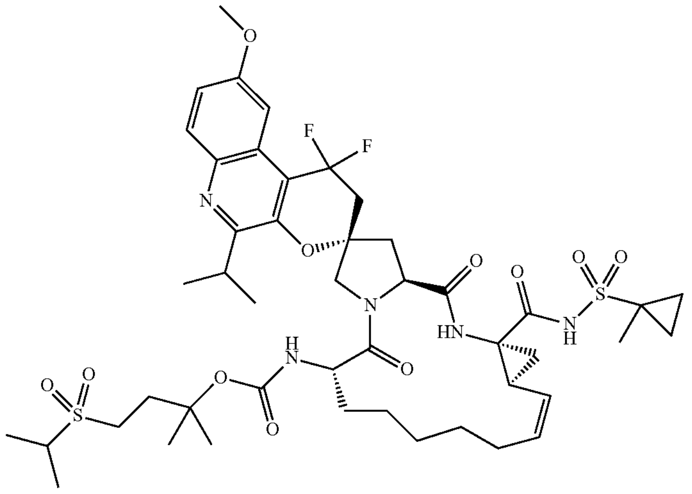 I-281 | 2-methyl-4-(propan-2-ylsulfonyl)butan-2-yl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 963.6 |
| 282 | 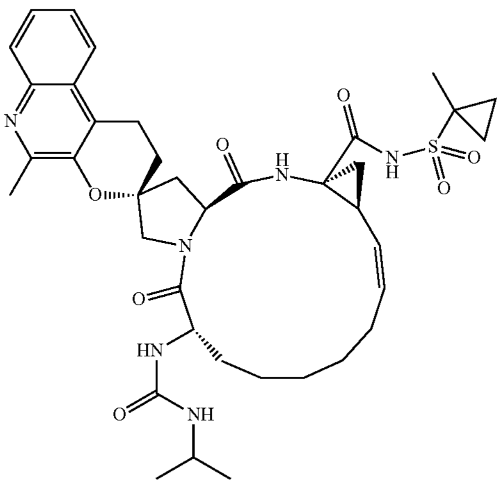 I-282 | (2R,6S,12Z,13aS,14aR,16aS)-5'-methyl-N-[(1-methylcyclopropyl)sulfonyl]-5,16-dioxo-6-[(propan-2-ylcarbamoyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 735.47 (HCOOH salt) |

TABLE 1-continued
| Compounds of Examples 68-526 | | | | |
|---|---|---|---|---|
| Ex. No. | Structure | Name | Proc. | LR-MS (M + H) |
| 283 | 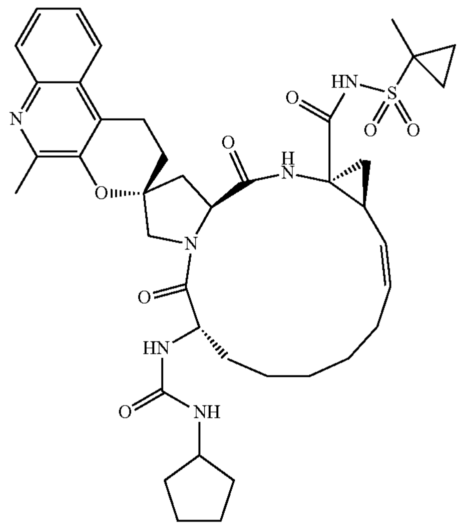 I-283 | (2R,6S,12Z,13aS,14aR,16aS)-6-[(cyclopentylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 761.51 (HCOOH salt) |

TABLE 1-continued
| Compounds of Examples 68-526 | | | | |
|---|---|---|---|---|
| Ex. No. | Structure | Name | Proc. | LR-MS (M + H) |
| 284 | 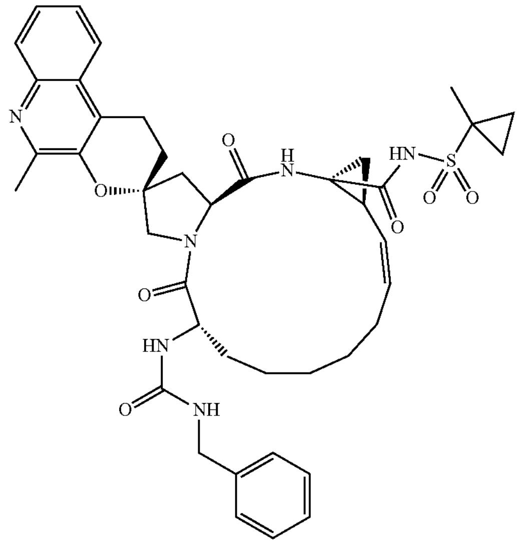 I-284 | (2R,6S,12Z,13aS,14aR,16aS)-6-[(benzylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 783.47 (HCOOH salt) |

TABLE 1-continued
| Compounds of Examples 68-526 | | | | |
|---|---|---|---|---|
| Ex. No. | Structure | Name | Proc. | LR-MS (M + H) |
| 285 | 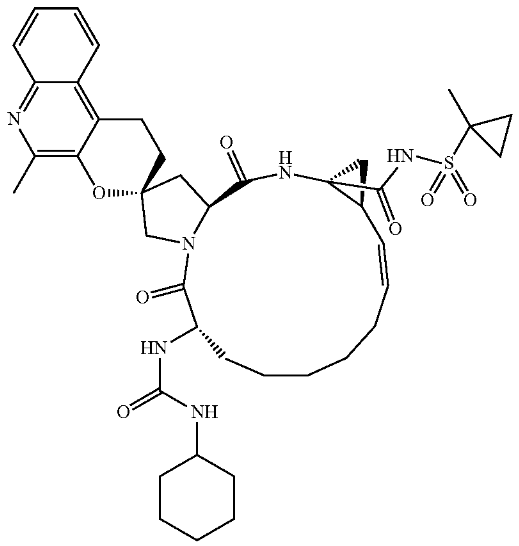 I-285 | (2R,6S,12Z,13aS,14aR,16aS)-6-[(cyclohexylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 775.5 (HCOOH salt) |

TABLE 1-continued
| Compounds of Examples 68-526 | | | | |
|---|---|---|---|---|
| Ex. No. | Structure | Name | Proc. | LR-MS (M + H) |
| 286 | 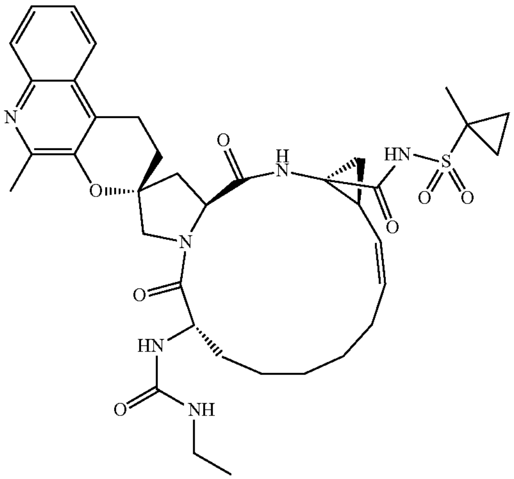 I-286 | (2R,6S,12Z,13aS,14aR,16aS)-6-[(ethylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 721.43 |

TABLE 1-continued
| Compounds of Examples 68-526 | | | | |
|---|---|---|---|---|
| Ex. No. | Structure | Name | Proc. | LR-MS (M + H) |
| 287 | 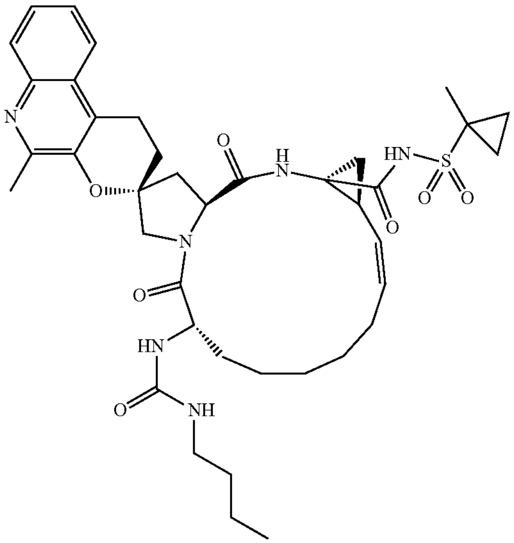 I-287 | (2R,6S,12Z,13aS,14aR,16aS)-6-[(butylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 749.48 (HCOOH salt) |

TABLE 1-continued
| Compounds of Examples 68-526 | | | | |
|---|---|---|---|---|
| Ex. No. | Structure | Name | Proc. | LR-MS (M + H) |
| 288 | 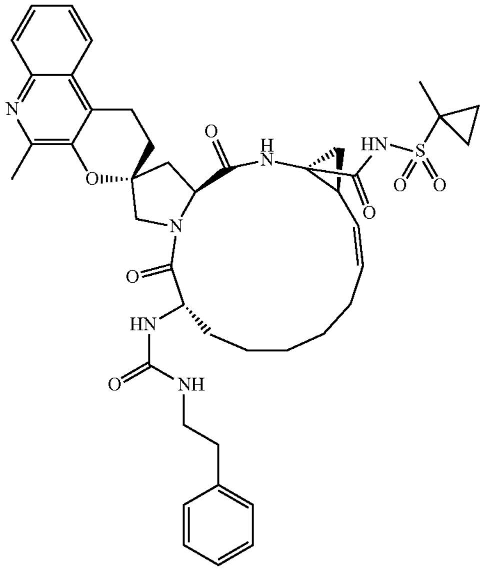 I-288 | (2R,6S,12Z,13aS,14aR,16aS)-5'-methyl-N-[(1-methylcyclopropyl)sulfonyl]-5,16-dioxo-6-{[(2-phenylethyl)carbamoyl]amino}-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 797.51 (HCOOH salt) |

TABLE 1-continued
| Compounds of Examples 68-526 | | | | |
|---|---|---|---|---|
| Ex. No. | Structure | Name | Proc. | LR-MS (M + H) |
| 289 | 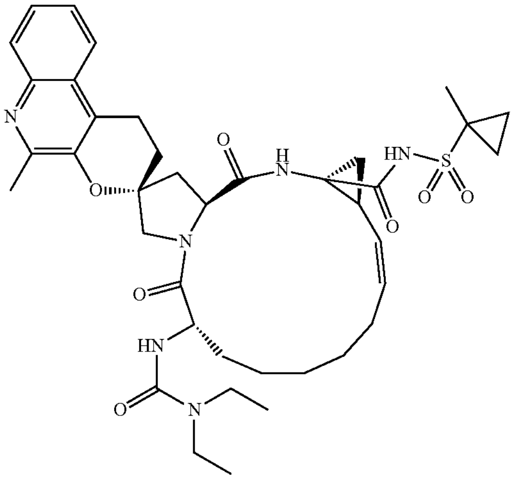 I-289 | (2R,6S,12Z,13aS,14aR,16aS)-6-[(diethylcarbamoyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 61 | 49.5 (HCOOH salt) |

TABLE 1-continued

Compounds of Examples 68-526

| Ex. No. | Structure | Name | Proc. | LR-MS (M + H) |
|---|---|---|---|---|
| 290 | 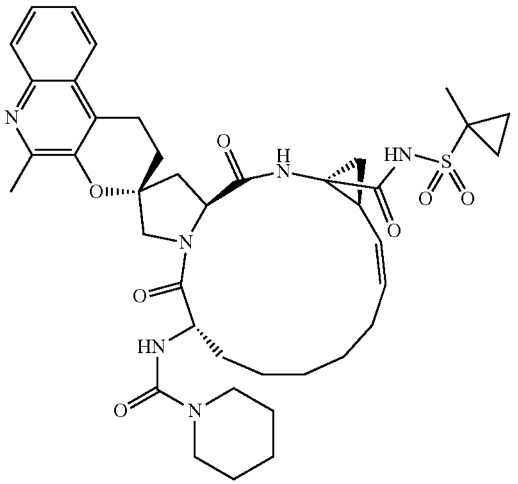 I-290 | (2R,6S,12Z,13aS,14aR,16aS)-5'-methyl-N-[(1-methylcyclopropyl)sulfonyl]-5,16-dioxo-6-[(piperidin-1-ylcarbonyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 61 | 761.51 (HCOOH salt) |
| 291 | 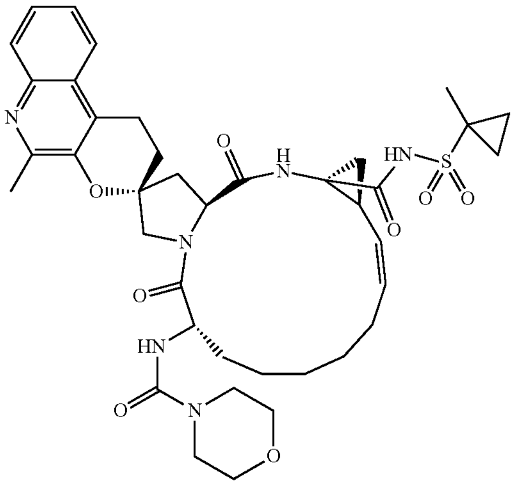 I-291 | (2R,6S,12Z,13aS,14aR,16aS)-5'-methyl-N-[(1-methylcyclopropyl)sulfonyl]-6-[(morpholin-4-ylcarbonyl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5R)-carboxamide | 61 | 763.47 (HCOOH salt) |

TABLE 1-continued
| Compounds of Examples 68-526 | | | | |
|---|---|---|---|---|
| Ex. No. | Structure | Name | Proc. | LR-MS (M + H) |
| 292 | 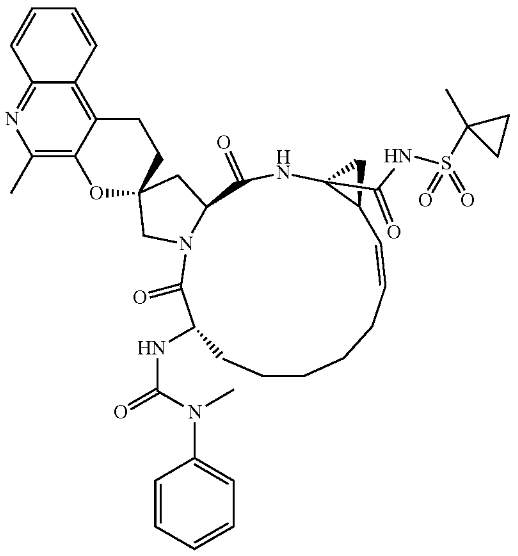 I-292 | (2R,6S,12Z,13aS,14aR,16aS)-5'-methyl-N-[(1-methylcyclopropyl)sulfonyl]-6-{[methyl(phenyl)carbamoyl]amino}-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 61 | 783.46 (HCOOH salt) |

TABLE 1-continued

| Ex. No. | Structure | Name | Proc. | LR-MS (M + H) |
|---|---|---|---|---|
| Compounds of Examples 68-526 | | | | |
| 293 | 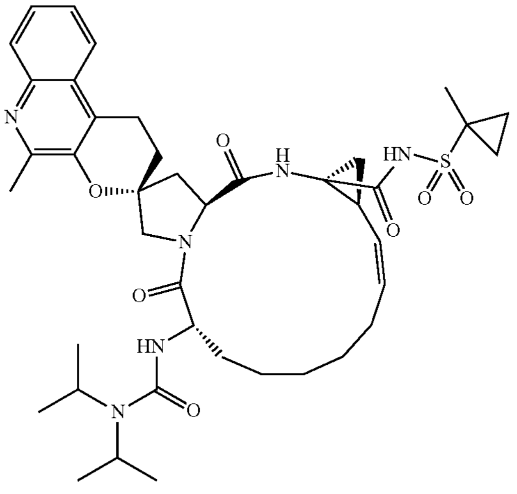 I-293 | (2R,6S,12Z,13aS,14aR,16aS)-6-{[di(propan-2-yl)carbamoyl]amino}-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 61 | 777.51 (HCOOH salt) |
| 294 | 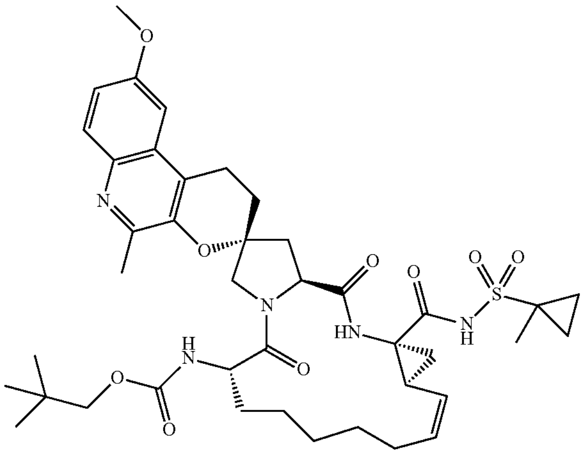 I-294 | 2,2-dimethylpropyl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 821.8 |

TABLE 1-continued

| Compounds of Examples 68-526 | | | | |
|---|---|---|---|---|
| Ex. No. | Structure | Name | Proc. | LR-MS (M + H) |
| 295 | 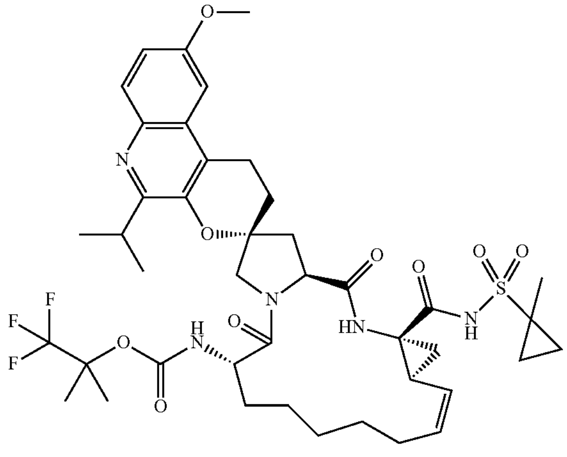 I-295 | 1,1,1-trifluoro-2-methylpropan-2-yl [(2R,6S,12Z,13aS,14aR,16aS)-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 861.7 |
| 296 | 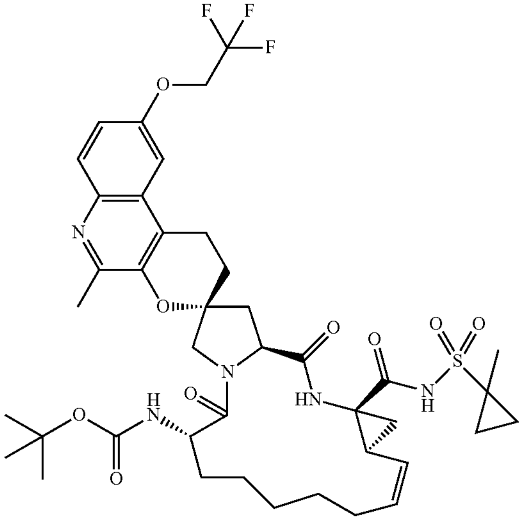 I-296 | tert-butyl [(2R,6S,12Z,13aS,14aR,16aS)-5'-methyl-14a-{[(1-methylcyclopropyl)sulfonyl]carbamoyl}-5,16-dioxo-9'-(2,2,2-trifluoroethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 847.7 |

TABLE 1-continued

| Compounds of Examples 68-526 | | | | |
|---|---|---|---|---|
| Ex. No. | Structure | Name | Proc. | LR-MS (M + H) |
| 297 | 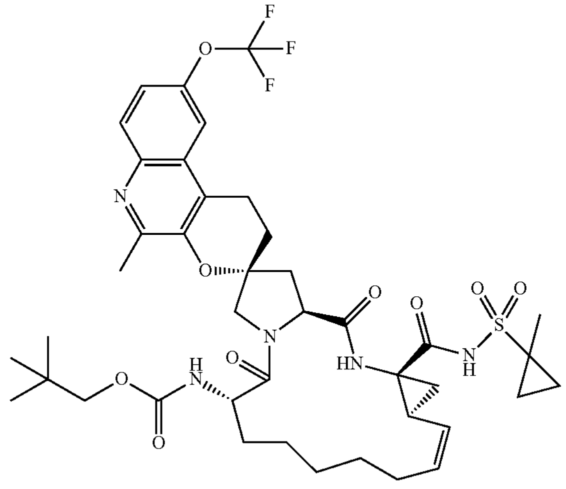 I-297 | 2,2-dimethylpropyl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 847.8 |
| 298 | 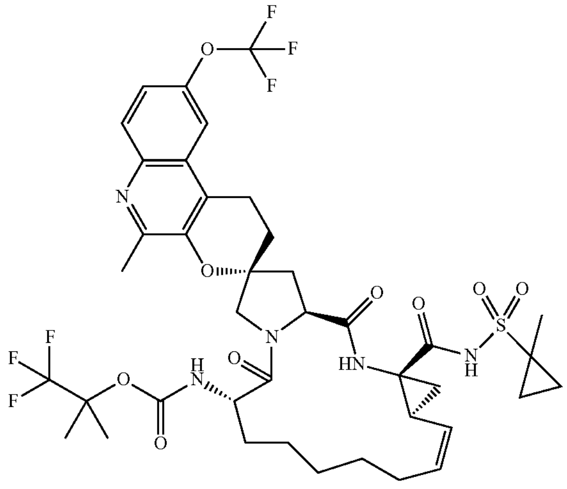 I-298 | 1,1,1-trifluoro-2-methylpropan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 887.6 |

TABLE 1-continued

Compounds of Examples 68-526

| Ex. No. | Structure | Name | Proc. | LR-MS (M + H) |
|---|---|---|---|---|
| 299 | 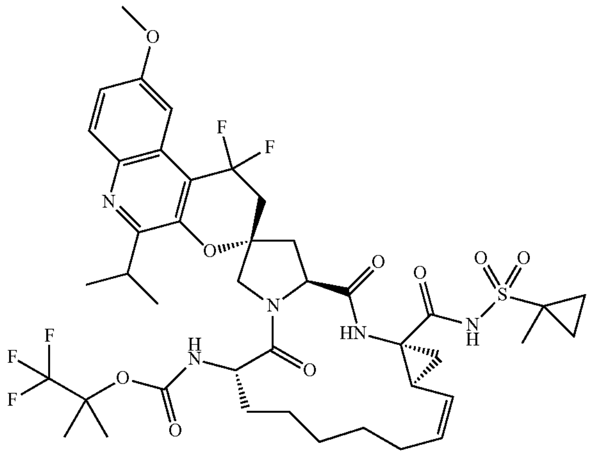 I-299 | 1,1,1-trifluoro-2-methylpropan-2-yl [(2S,6S,12Z,13aS,14aR,16aS)-1',1'-difluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2 | 897.6 (K+ salt) |
| 300 | 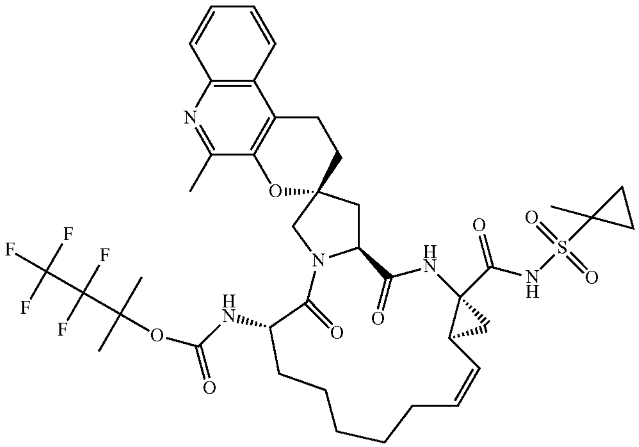 I-300 | 3,3,4,4,4-pentafluoro-2-methylbutan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 854.5 |

TABLE 1-continued
| Compounds of Examples 68-526 | | | | |
|---|---|---|---|---|
| Ex. No. | Structure | Name | Proc. | LR-MS (M + H) |
| 301 | 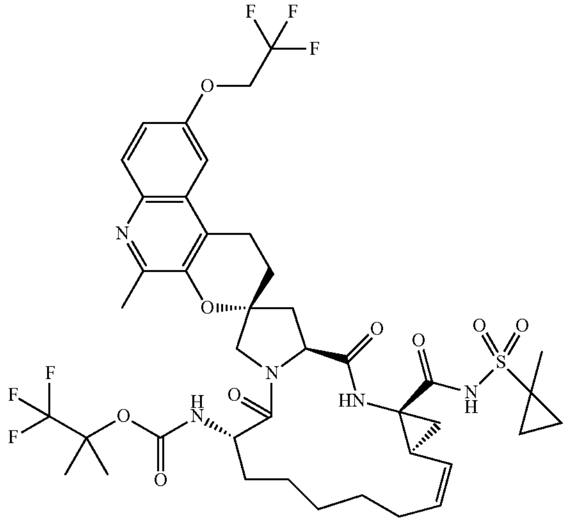 I-301 | 1,1,1-trifluoro-2-methylpropan-2-yl [(2R,6S,12Z,13aS,14aR,16aS)-5'-methyl-14a-{[(1-methylcyclopropyl)sulfonyl]carbamoyl}-5,16-dioxo-9'-(2,2,2-trifluoroethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 901.6 |

TABLE 1-continued
| Compounds of Examples 68-526 | | | | |
|---|---|---|---|---|
| Ex. No. | Structure | Name | Proc. | LR-MS (M + H) |
| 302 | 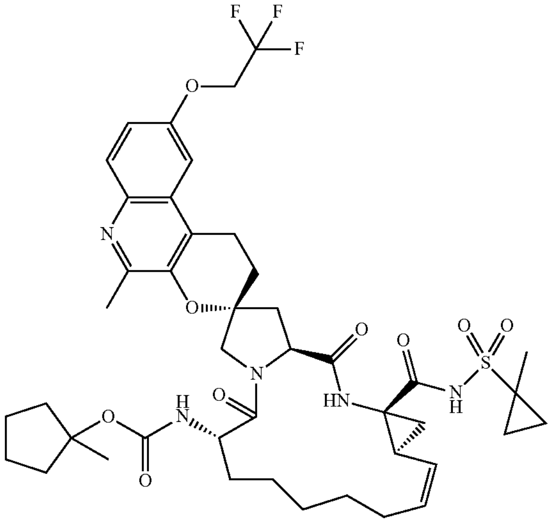 I-302 | 1-methylcyclopentyl [(2R,6S,12Z,13aS,14aR,16aS)-5'-methyl-14a-{[(1-methylcyclopropyl)sulfonyl]carbamoyl}-5,16-dioxo-9'-(2,2,2-trifluoroethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 873.6 |

TABLE 1-continued

| Compounds of Examples 68-526 | | | | |
|---|---|---|---|---|
| Ex. No. | Structure | Name | Proc. | LR-MS (M + H) |
| 303 | 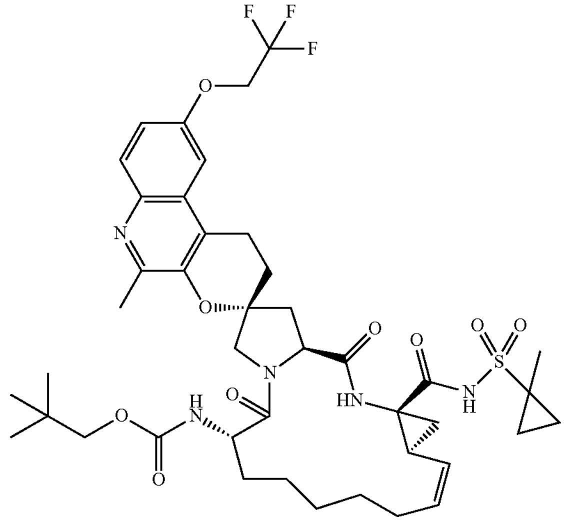 I-303 | 2,2-dimethylpropyl [(2R,6S,12Z,13aS,14aR,16aS)-5'-methyl-14a-{[(1-methylcyclopropyl)sulfonyl]carbamoyl}-5,16-dioxo-9'-(2,2,2-trifluoroethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 861.7 |
| 304 | 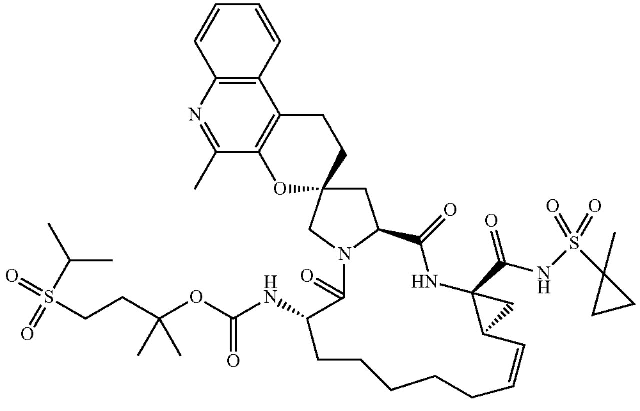 I-304 | 2-methyl-4-(propan-2-ylsulfonyl)butan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 869.7 |

TABLE 1-continued

| Compounds of Examples 68-526 | | | | |
|---|---|---|---|---|
| Ex. No. | Structure | Name | Proc. | LR-MS (M + H) |
| 305 | 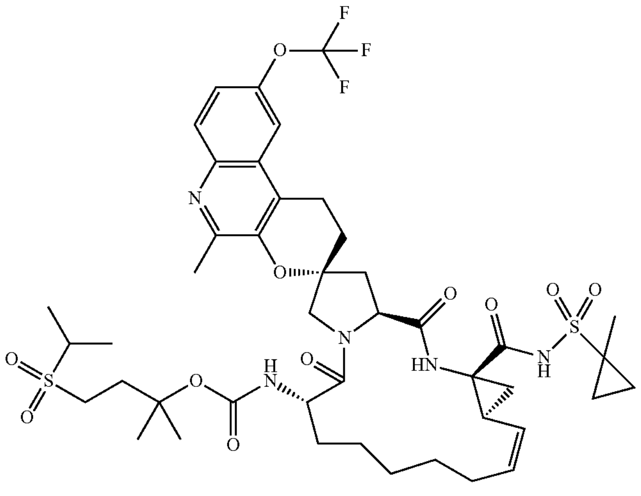 I-305 | 2-methyl-4-(propan-2-ylsulfonyl)butan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 954.6 |
| 306 | 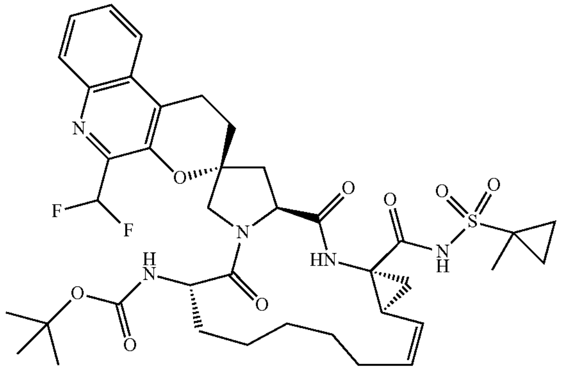 I-306 | tert-butyl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 786.2 |

TABLE 1-continued
| Compounds of Examples 68-526 | | | | |
|---|---|---|---|---|
| Ex. No. | Structure | Name | Proc. | LR-MS (M + H) |
| 307 | 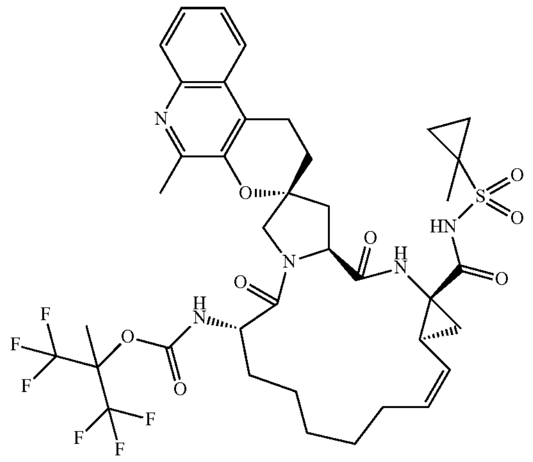 I-307 | 1,1,1,3,3,3-hexafluoro-2-methylpropan-2-yl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | — |

TABLE 1-continued

| Compounds of Examples 68-526 | | | | |
|---|---|---|---|---|
| Ex. No. | Structure | Name | Proc. | LR-MS (M + H) |
| 308 | 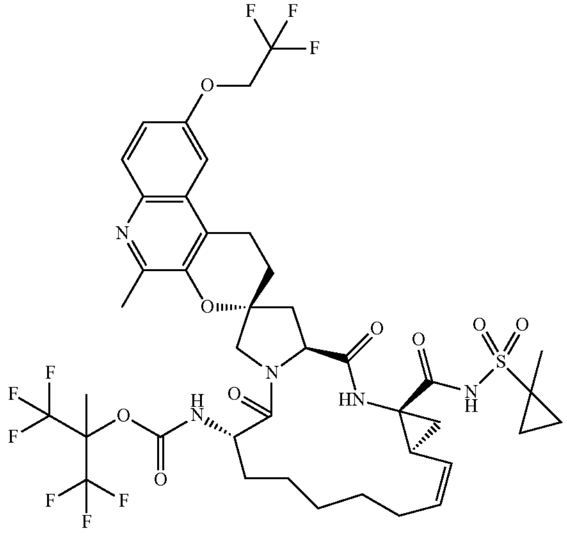 I-308 | 1,1,1,3,3,3-hexafluoro-2-methylpropan-2-yl [(2R,6S,12Z,13aS,14aR,16aS)-5'-methyl-14a-{[(1-methylcyclopropyl)sulfonyl]carbamoyl}-5,16-dioxo-9'-(2,2,2-trifluoroethoxy)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 955.5 |
| 309 | 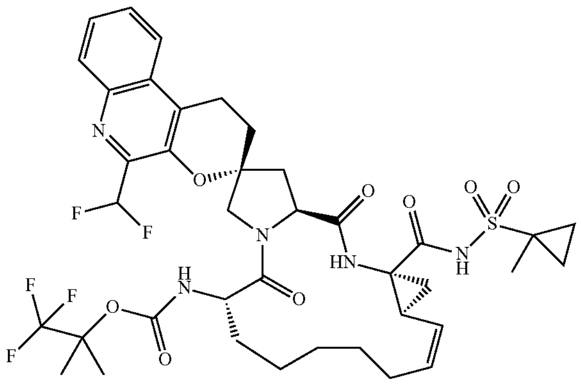 I-309 | 1,1,1-trifluoro-2-methylpropan-2-yl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10, 35 | 840 |

TABLE 1-continued

| Compounds of Examples 68-526 | | | | |
|---|---|---|---|---|
| Ex. No. | Structure | Name | Proc. | LR-MS (M + H) |
| 310 | 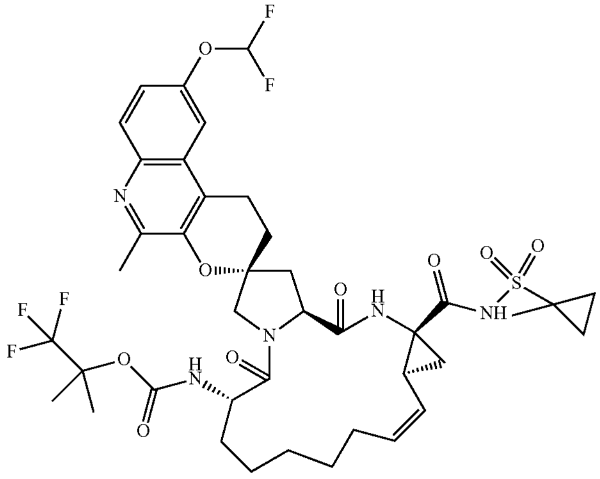 I-310 | 1,1,1-trifluoro-2-methylpropan-2-yl [(2R,6S,12Z,13aS,14aR,16aS)-9'-(difluoromethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | — |
| 311 | 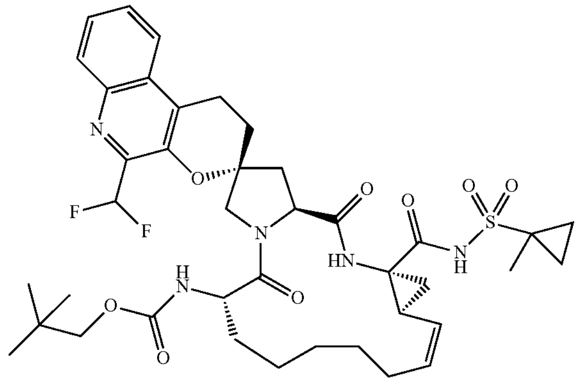 I-311 | 2,2-dimethylpropyl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10, 35 | 800.2 |

TABLE 1-continued

| Compounds of Examples 68-526 | | | | |
|---|---|---|---|---|
| Ex. No. | Structure | Name | Proc. | LR-MS (M + H) |
| 312 | 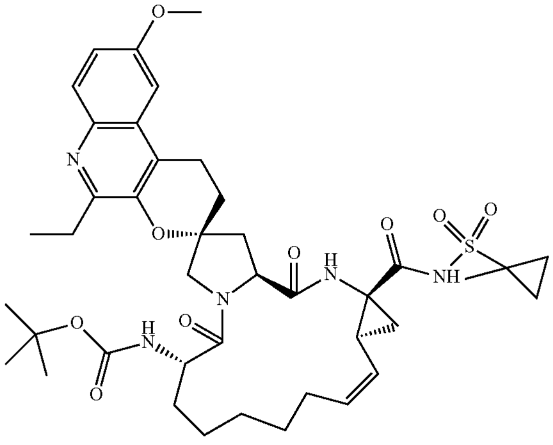 I-312 | tert-butyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | — |
| 313 | 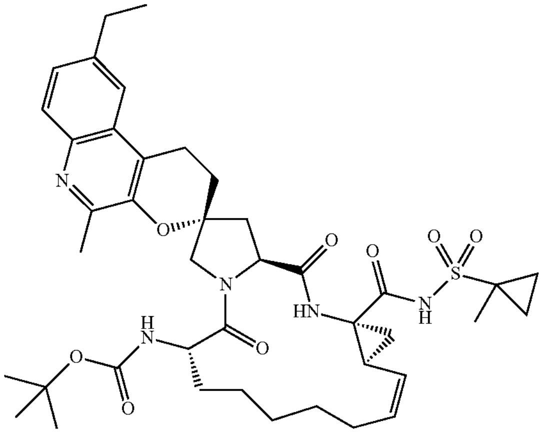 I-313 | tert-butyl [(2R,6S,12Z,13aS,14aR,16aS)-9'-ethyl-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 778.2 |

TABLE 1-continued

| Compounds of Examples 68-526 | | | | |
|---|---|---|---|---|
| Ex. No. | Structure | Name | Proc. | LR-MS (M + H) |
| 314 | 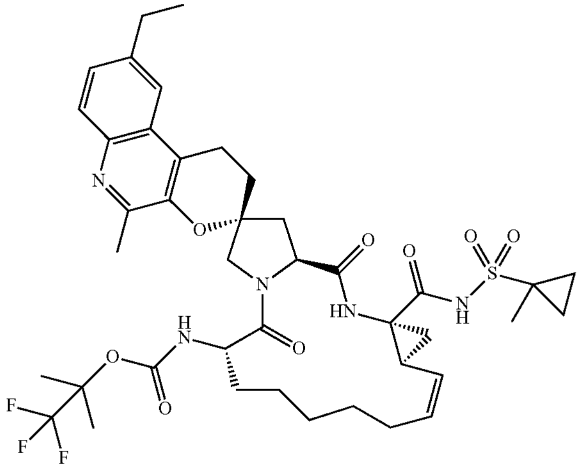 I-314 | 1,1,1-trifluoro-2-methylpropan-2-yl [(2R,6S,12Z,13aS,14aR,16aS)-9'-ethyl-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 832.2 |
| 315 | 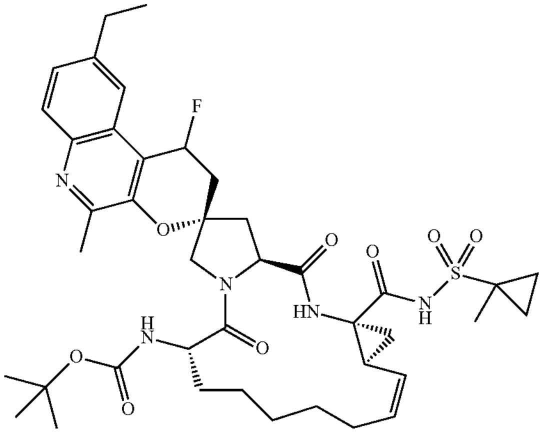 I-315 | tert-butyl [(2S,6S,12Z,13aS,14aR,16aS)-9'-ethyl-1'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 796.2 |

TABLE 1-continued

| Compounds of Examples 68-526 | | | | |
|---|---|---|---|---|
| Ex. No. | Structure | Name | Proc. | LR-MS (M + H) |
| 316 | 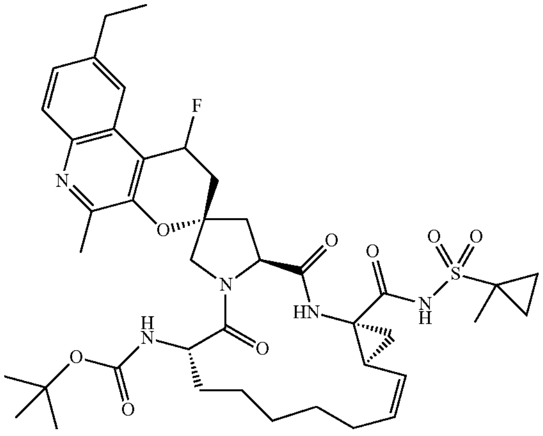 I-316 | tert-butyl [(2S,6S,12Z,13aS,14aR,16aS)-9'-ethyl-1'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 796.2 |
| 317 | 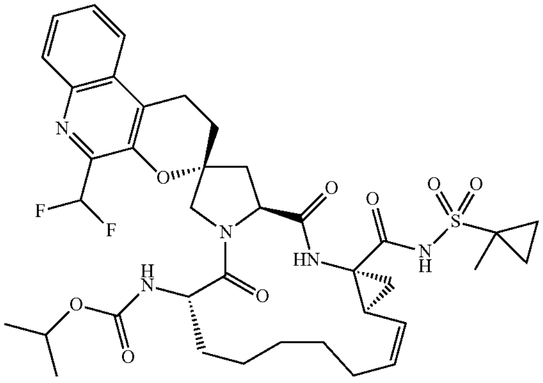 I-317 | propan-2-yl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10, 35 | 772.1 |

TABLE 1-continued

| Compounds of Examples 68-526 | | | | |
|---|---|---|---|---|
| Ex. No. | Structure | Name | Proc. | LR-MS (M + H) |
| 318 | 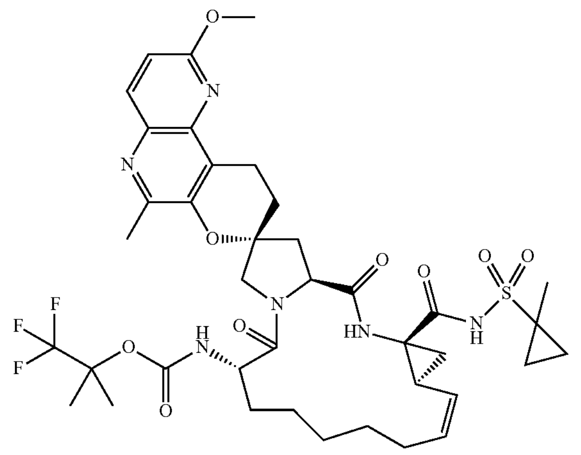 I-318 | 1,1,1-trifluoro-2-methylpropan-2-yl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 835.2 |
| 319 | 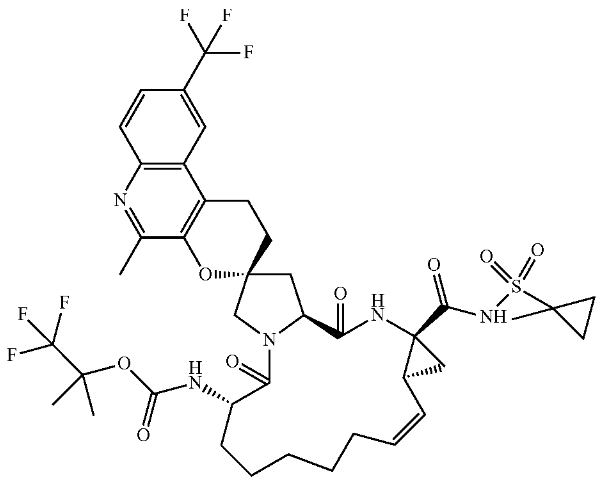 I-319 | 1,1,1-trifluoro-2-methylpropan-2-yl [(2R,6S,12Z,13aS,14aR,16aS)-5'-methyl-14a-{[(1-methylcyclopropyl)sulfonyl]carbamoyl}-5,16-dioxo-9'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 888.5 |

TABLE 1-continued

| Compounds of Examples 68-526 | | | | |
|---|---|---|---|---|
| Ex. No. | Structure | Name | Proc. | LR-MS (M + H) |
| 320 | 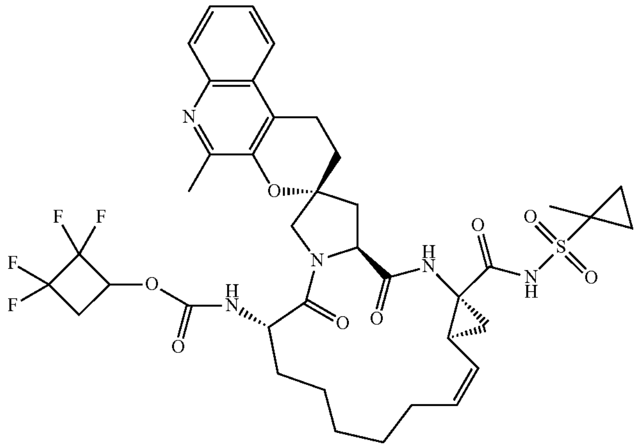 I-320 | 2,2,3,3-tetrafluorocyclobutyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 820.4 |
| 321 | 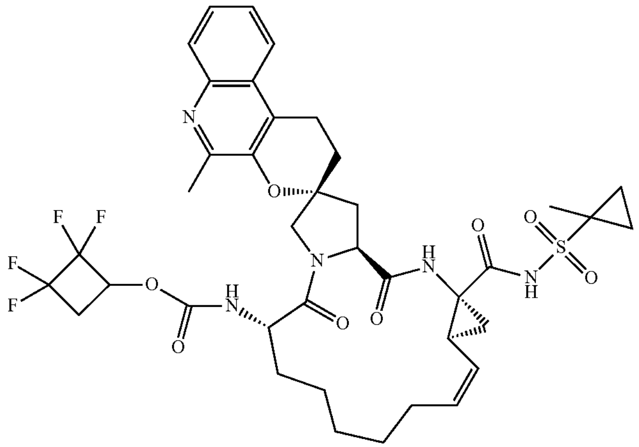 I-321 | 2,2,3,3-tetrafluorocyclobutyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 820.4 |

TABLE 1-continued

| Compounds of Examples 68-526 | | | | |
|---|---|---|---|---|
| Ex. No. | Structure | Name | Proc. | LR-MS (M + H) |
| 322 | 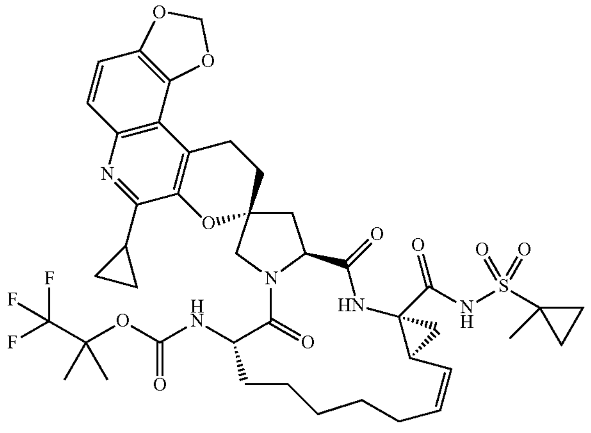 I-322 | 1,1,1-trifluoro-2-methylpropan-2-yl [(2R,6S,12Z,13aS,14aR,16aS)-7'-cyclopropyl-14a-{[(1-methylcyclopropyl)sulfonyl]carbamoyl}-5,16-dioxo-1,5,6,7,8,9,10,10',11,11',13a,14,14a,15,16,16a-hexadecahydrospiro[cyclopropa[e]pyrrolo[1,2-a][1,4]diazacyclopentadecine-2,9'-[1,3]dioxolo[4,5-f]pyrano[2,3-c]quinolin]-6-yl]carbamate | 29 | 873.6 |
| 323 | 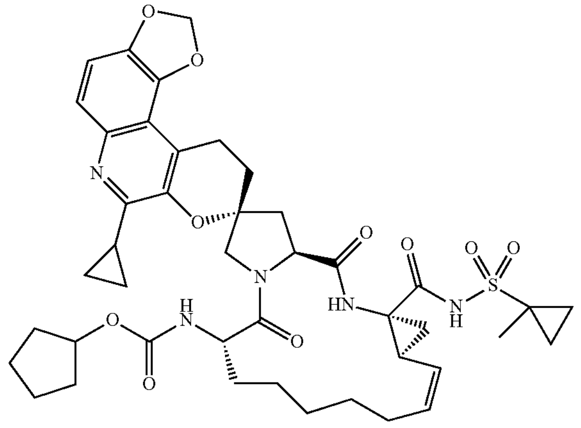 I-323 | cyclopentyl [(2R,6S,12Z,13aS,14aR,16aS)-7'-cyclopropyl-14a-{[(1-methylcyclopropyl)sulfonyl]carbamoyl}-5,16-dioxo-1,5,6,7,8,9,10,10',11,11',13a,14,14a,15,16,16a-hexadecahydrospiro[cyclopropa[e]pyrrolo[1,2-a][1,4]diazacyclopentadecine-2,9'-[1,3]dioxolo[4,5-f]pyrano[2,3-c]quinolin]-6-yl]carbamate | 29 | 831.7 |

TABLE 1-continued

Compounds of Examples 68-526

| Ex. No. | Structure | Name | Proc. | LR-MS (M + H) |
|---|---|---|---|---|
| 324 | 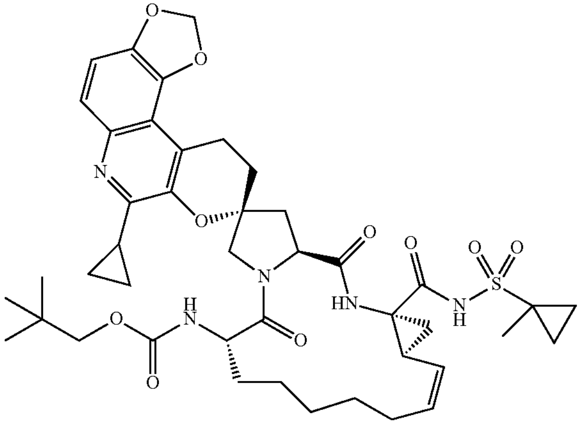 I-324 | 2,2-dimethylpropyl [(2R,6S,12Z,13aS,14aR,16aS)-7'-cyclopropyl-14a-{[(1-methylcyclopropyl)sulfonyl]carbamoyl}-5,16-dioxo-1,5,6,7,8,9,10,10',11,11',13a,14,14a,15,16,16a-hexadecahydrospiro[cyclopropa[e]pyrrolo[1,2-a][1,4]diazacyclopentadecine-2,9'-[1,3]dioxolo[4,5-f]pyrano[2,3-c]quinolin]-6-yl]carbamate | 29 | 833.6 |
| 325 | 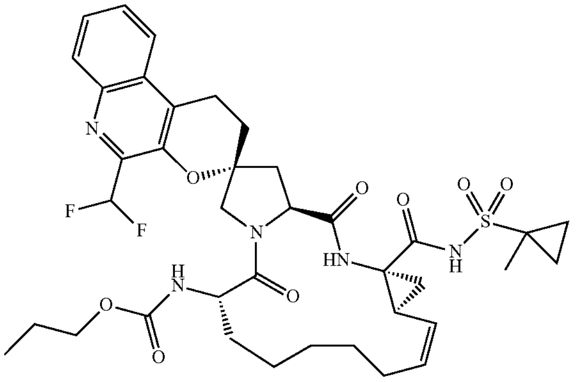 I-325 | propyl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10, 35 | 772.2 |

TABLE 1-continued

| Compounds of Examples 68-526 | | | | |
|---|---|---|---|---|
| Ex. No. | Structure | Name | Proc. | LR-MS (M + H) |
| 326 | 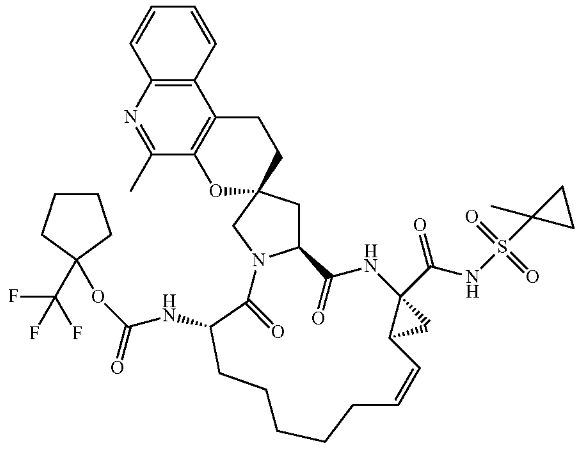 I-326 | 1-(trifluoromethyl)cyclopentyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 830.5 |
| 327 | 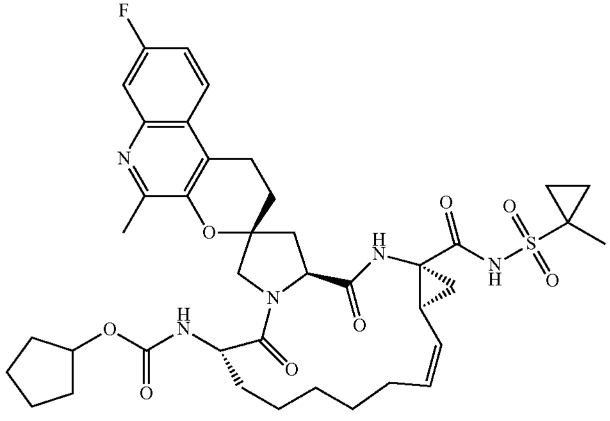 I-327 | cyclopentyl [(2R,6S,12Z,13aS,14aR,16aS)-8'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 780.2 (K+ salt) |

TABLE 1-continued

| Compounds of Examples 68-526 | | | | |
|---|---|---|---|---|
| Ex. No. | Structure | Name | Proc. | LR-MS (M + H) |
| 328 | 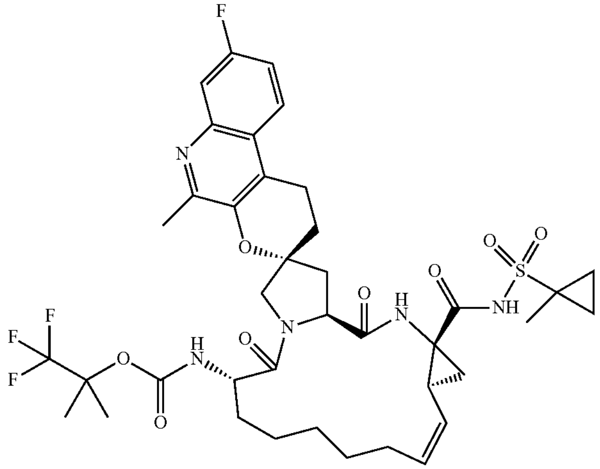 I-328 | 1,1,1-trifluoro-2-methylpropan-2-yl [(2R, 6S,12Z,13aS,14aR,16aS)-8'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 822.5 |
| 329 | 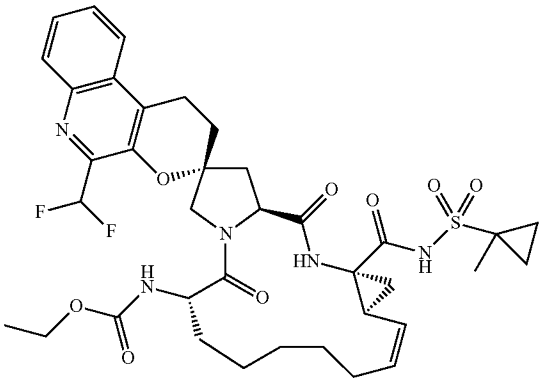 I-329 | ethyl [(2R,6S,12Z,13aS,14aR,16aS)-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10, 35 | 758.2 |

TABLE 1-continued

| Compounds of Examples 68-526 | | | | |
|---|---|---|---|---|
| Ex. No. | Structure | Name | Proc. | LR-MS (M + H) |
| 330 | 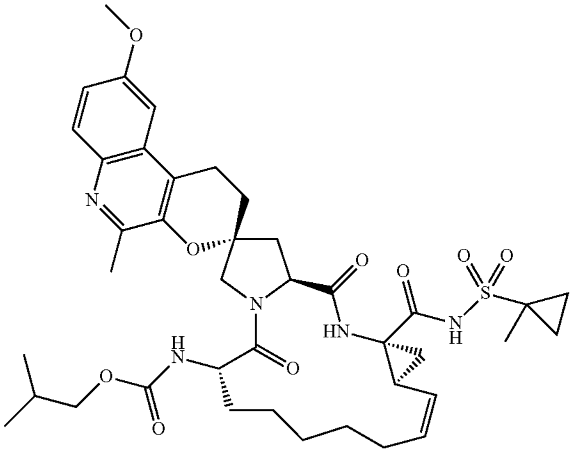 I-330 | 2-methylpropyl [(2R,6S,12Z,13aS,14aR,16aS)-9'-ethyl-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 30 | 778.2 |
| 331 | 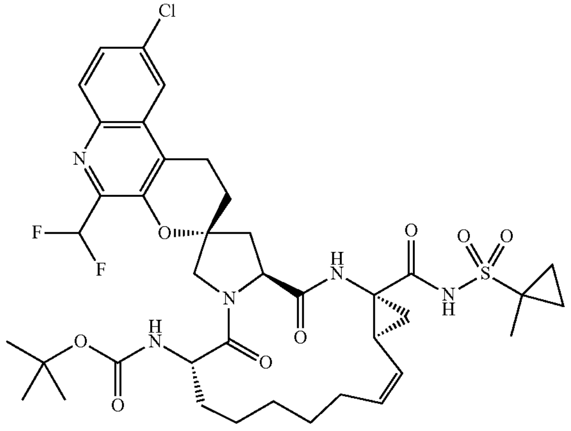 I-331 | tert-butyl [(2R,6S,12Z,13aS,14aR,16aS)-9'-chloro-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 764 |

TABLE 1-continued

| Compounds of Examples 68-526 | | | | |
|---|---|---|---|---|
| Ex. No. | Structure | Name | Proc. | LR-MS (M + H) |
| 332 | 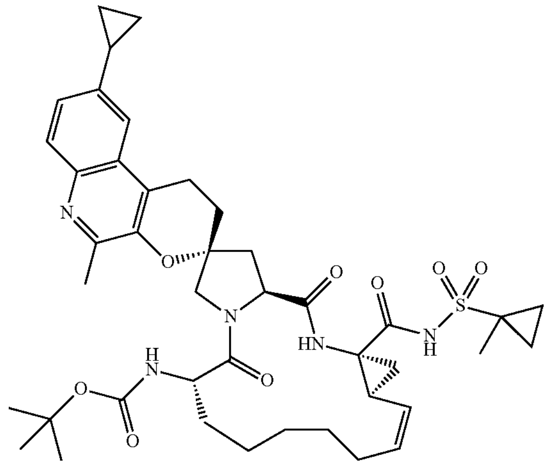 I-332 | tert-butyl [(2R,6S,12Z,13aS,14aR,16aS)-9'-cyclopropyl-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1 | 790.2 |
| 333 | 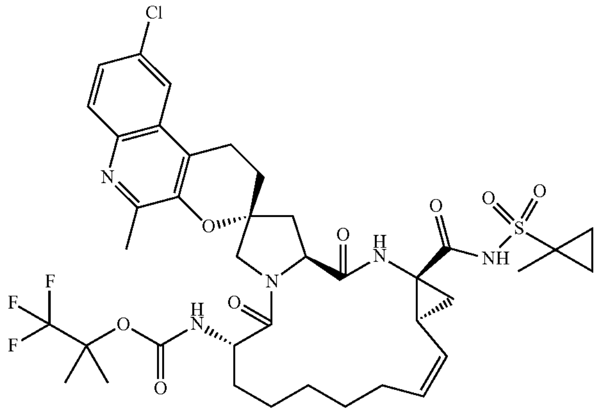 I-333 | 1,1,1-trifluoro-2-methylpropan-2-yl [(2R,6S,12Z,13aS,14aR,16aS)-9'-chloro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 39 | 838 |

TABLE 1-continued

| Compounds of Examples 68-526 | | | | |
|---|---|---|---|---|
| Ex. No. | Structure | Name | Proc. | LR-MS (M + H) |
| 334 | 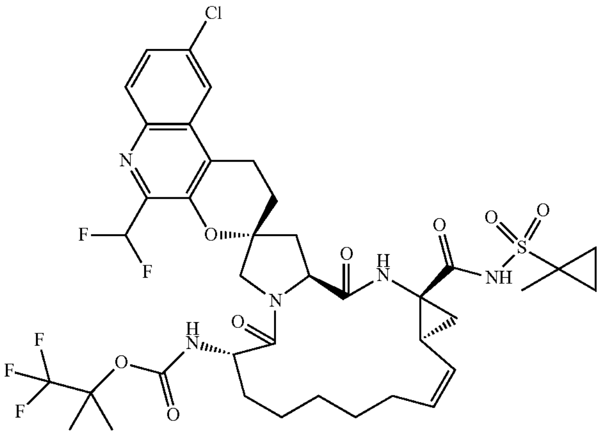 I-334 | 1,1,1-trifluoro-2-methylpropan-2-yl [(2R,6S,12Z,13aS,14aR,16aS)-9'-chloro-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 874.2 |
| 335 | 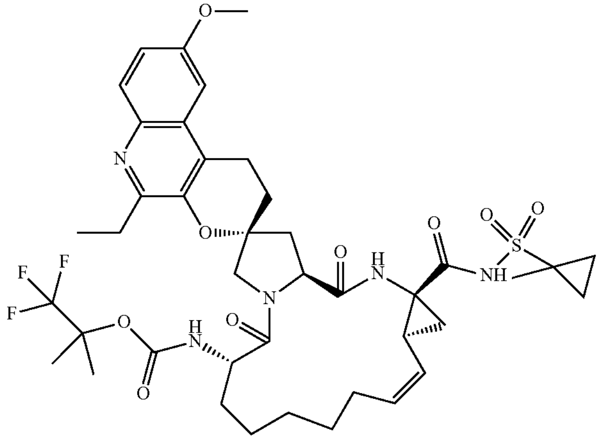 I-335 | 1,1,1-trifluoro-2-methylpropan-2-yl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 848.0 |

TABLE 1-continued

| Compounds of Examples 68-526 | | | | |
|---|---|---|---|---|
| Ex. No. | Structure | Name | Proc. | LR-MS (M + H) |
| 336 | 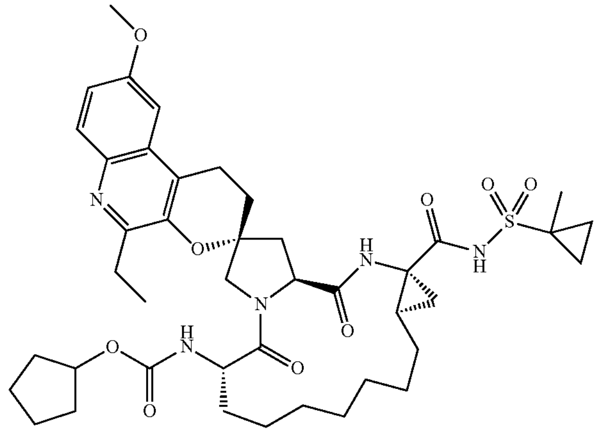 I-336 | cyclopentyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 806.5 |
| 337 | 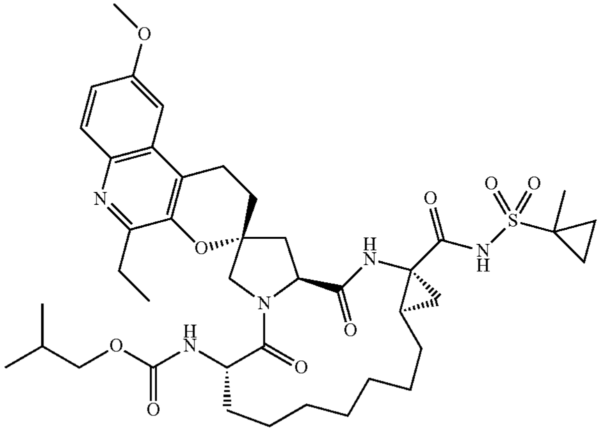 I-337 | 2-methylpropyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 794 |

TABLE 1-continued

| Compounds of Examples 68-526 | | | | |
|---|---|---|---|---|
| Ex. No. | Structure | Name | Proc. | LR-MS (M + H) |
| 338 | 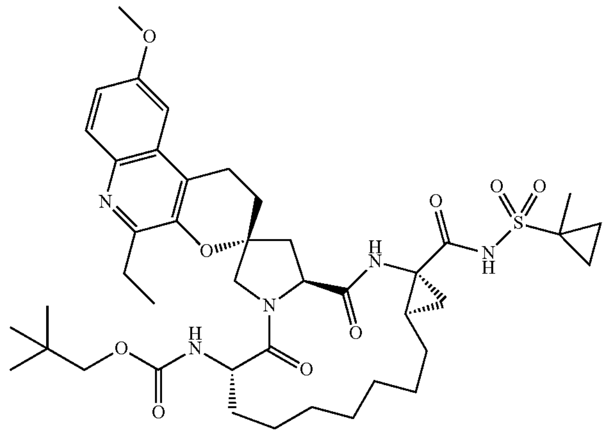 I-338 | 2,2-dimethylpropyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 808.38 |
| 339 | 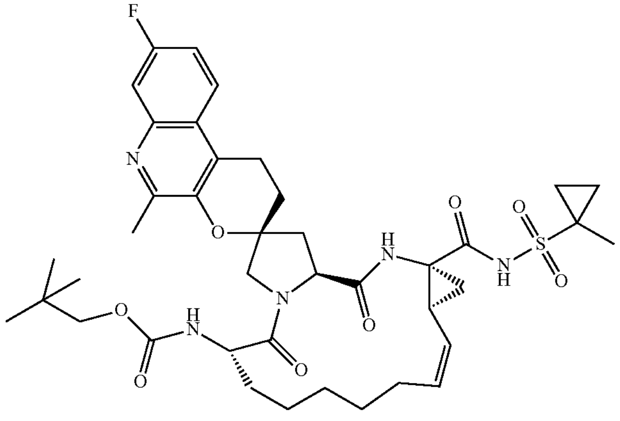 I-339 | 2,2-dimethylpropyl [(2R,6S,12Z,13aS,14aR,16aS)-8'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 782.2 |

TABLE 1-continued

| Compounds of Examples 68-526 | | | | |
|---|---|---|---|---|
| Ex. No. | Structure | Name | Proc. | LR-MS (M + H) |
| 340 | 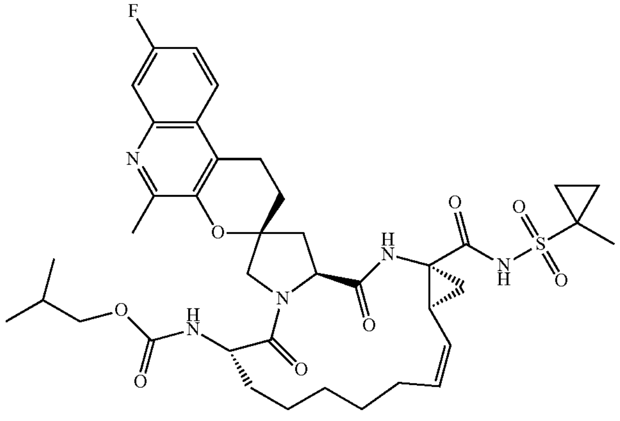 I-340 | 2-methylpropyl [(2R,6S,12Z,13aS,14aR,16aS)-8'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 48 | 768.1 |
| 341 | 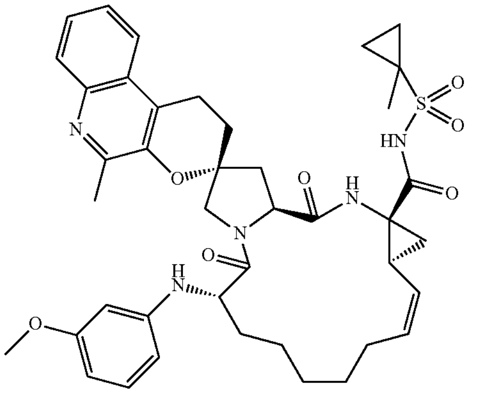 I-341 | (2R,6S,12Z,13aS,14aR,16aS)-6-[(3-methoxyphenyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5R)-carboxamide | 57 | 756.4 |

TABLE 1-continued

| Compounds of Examples 68-526 | | | | |
|---|---|---|---|---|
| Ex. No. | Structure | Name | Proc. | LR-MS (M + H) |
| 342 | 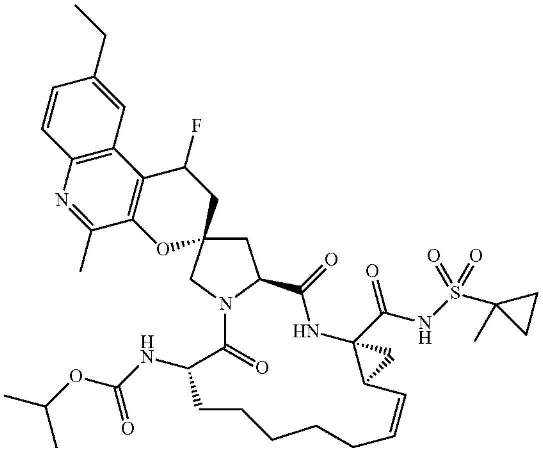 I-342 | propan-2-yl [(2S,6S,12Z,13aS,14aR,16aS)-9'-ethyl-1'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 796.6 |
| 343 | 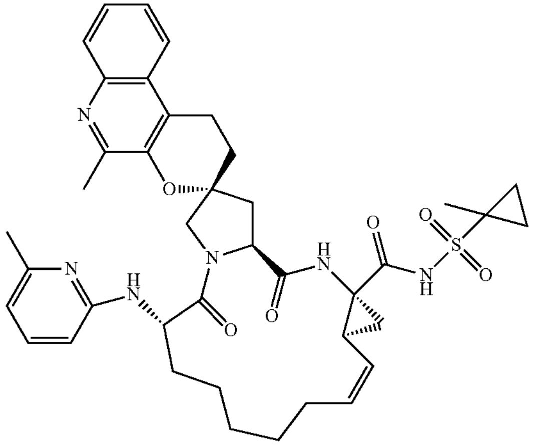 I-343 | (2R,6S,12Z,13aS,14aR,16aS)-5'-methyl-N-[(1-methylcyclopropyl)sulfonyl]-6-[(6-methylpyridin-2-yl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 741.4 |

TABLE 1-continued

| Ex. No. | Structure | Name | Proc. | LR-MS (M + H) |
|---|---|---|---|---|
| | Compounds of Examples 68-526 | | | |
| 344 | 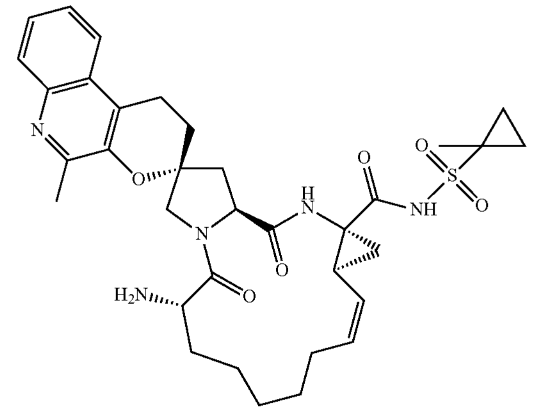 I-344 | (2R,6S,12Z,13aS,14aR,16aS)-6-amino-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 650.4 |
| 345 | 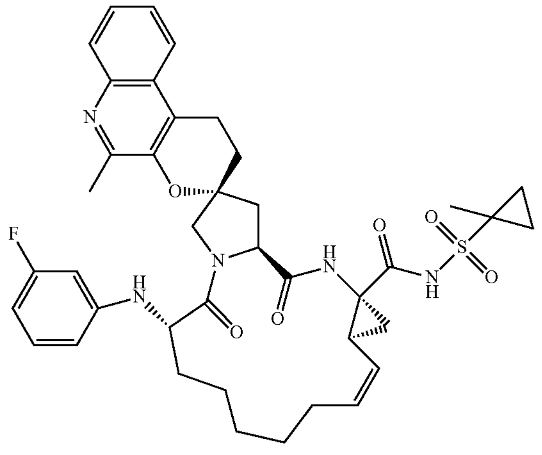 I-345 | (2R,6S,12Z,13aS,14aR,16aS)-6-[(3-fluorophenyl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 744 |

TABLE 1-continued

Compounds of Examples 68-526

| Ex. No. | Structure | Name | Proc. | LR-MS (M + H) |
| --- | --- | --- | --- | --- |
| 346 | 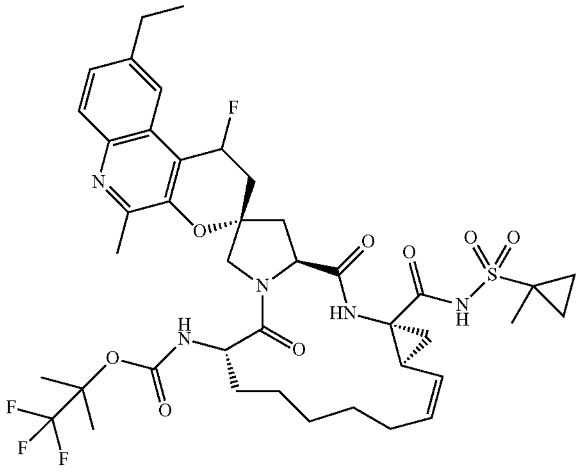 I-346 | 1,1,1-trifluoro-2-methylpropan-2-yl [(2S,6S,12Z,13aS,14aR,16aS)-9'-ethyl-1'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 850.1 |
| 347 | 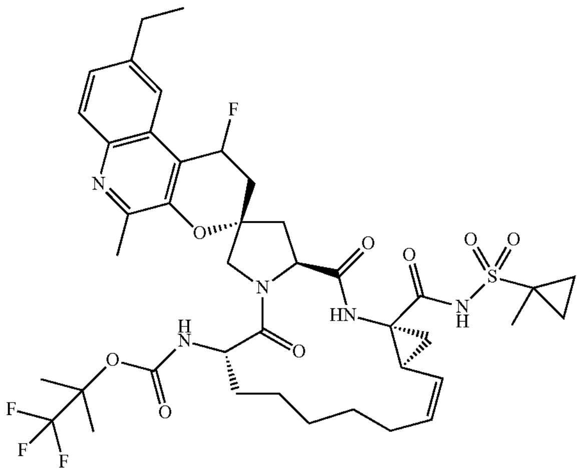 I-347 | 1,1,1-trifluoro-2-methylpropan-2-yl [(2S,6S,12Z,13aS,14aR,16aS)-9'-ethyl-1'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 850.1 |

TABLE 1-continued

| Compounds of Examples 68-526 | | | | |
|---|---|---|---|---|
| Ex. No. | Structure | Name | Proc. | LR-MS (M + H) |
| 348 | 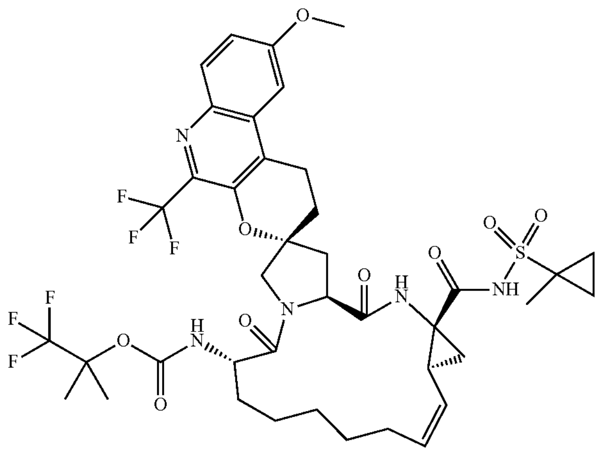 I-348 | 1,1,1-trifluoro-2-methylpropan-2-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 888 (K+ salt) |
| 349 | 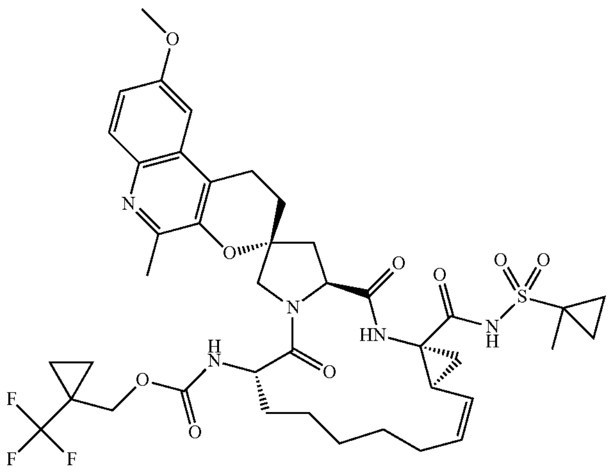 I-349 | [1-(trifluoromethyl)cyclopropyl]methyl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 846 (K+ salt) |

TABLE 1-continued

| Compounds of Examples 68-526 | | | | |
|---|---|---|---|---|
| Ex. No. | Structure | Name | Proc. | LR-MS (M + H) |
| 350 | 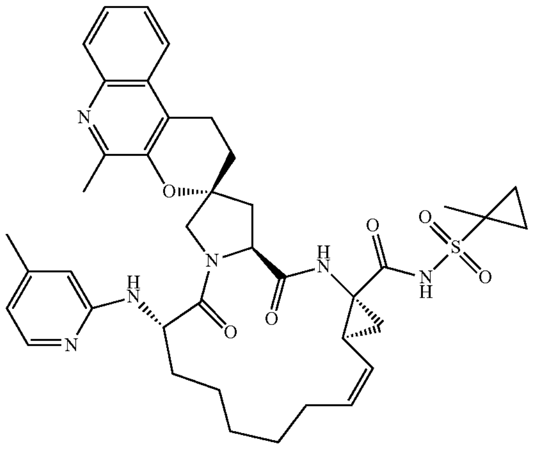 I-350 | (2R,6S,12Z,13aS,14aR,16aS)-5'-methyl-N-[(1-methylcyclopropyl)sulfonyl]-6-[(4-methylpyridin-2-yl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 740.4 |
| 351 | 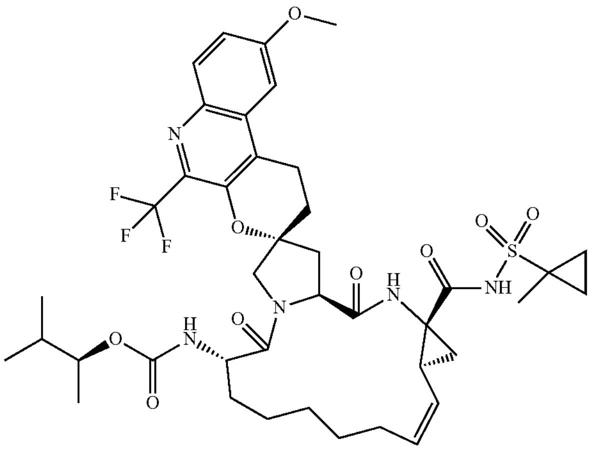 I-351 | (2S)-3-methylbutan-2-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 848.2 (K+ salt) |

TABLE 1-continued

Compounds of Examples 68-526

| Ex. No. | Structure | Name | Proc. | LR-MS (M + H) |
|---|---|---|---|---|
| 352 | 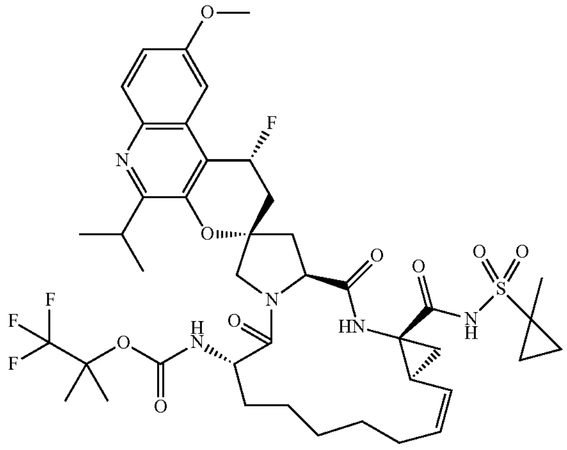 I-352 | 1,1,1-trifluoro-2-methylpropan-2-yl [(1'R,2S,6S,12Z,13aS,14aR,16aS)-1'-fluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2, 56 | 880.2 (K+ salt) |
| 353 | 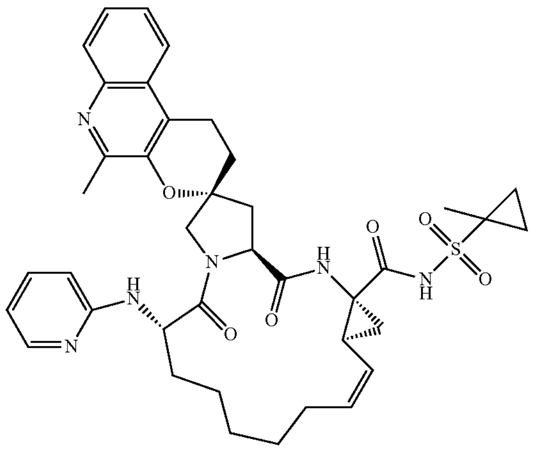 I-353 | (2R,6S,12Z,13aS,14aR,16aS)-5'-methyl-N-[(1-methylcyclopropyl)sulfonyl]-5,16-dioxo-6-(pyridin-2-ylamino)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5R)-carboxamide | 57 | 727.3 |

TABLE 1-continued

| Compounds of Examples 68-526 | | | | |
|---|---|---|---|---|
| Ex. No. | Structure | Name | Proc. | LR-MS (M + H) |
| 354 | 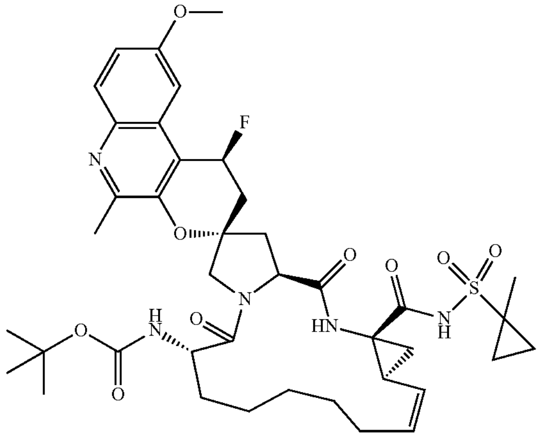 I-354 | tert-butyl [(1'S,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 798.2 |
| 355 | 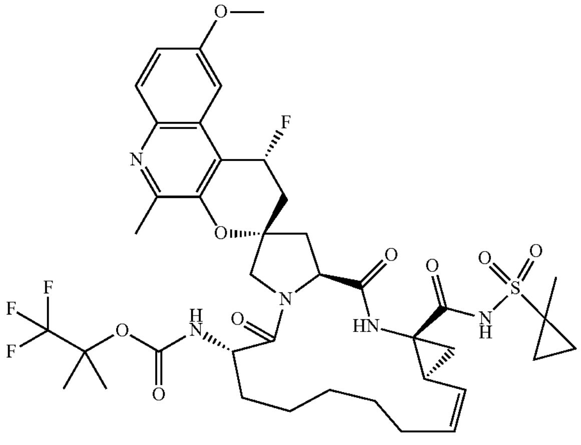 I-355 | 1,1,1-trifluoro-2-methylpropan-2-yl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 853.2 (K+ salt) |

TABLE 1-continued

| Compounds of Examples 68-526 | | | | |
|---|---|---|---|---|
| Ex. No. | Structure | Name | Proc. | LR-MS (M + H) |
| 356 | 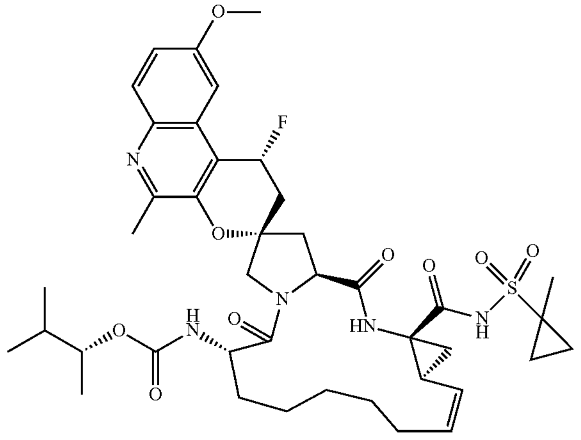 I-356 | (2R)-3-methylbutan-2-yl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 812.2 (K+ salt) |
| 357 | 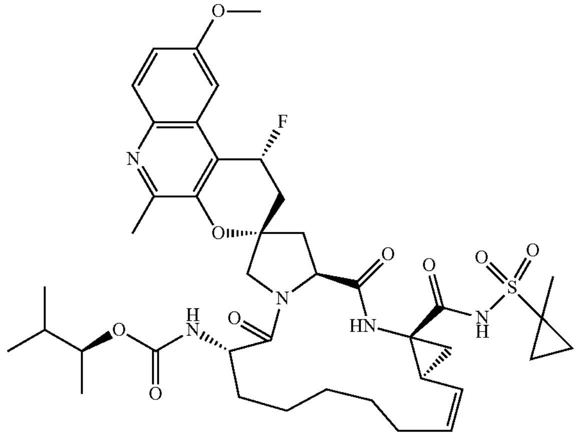 I-357 | (2S)-3-methylbutan-2-yl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 812.2 (K+ salt) |

TABLE 1-continued

| Compounds of Examples 68-526 | | | | |
|---|---|---|---|---|
| Ex. No. | Structure | Name | Proc. | LR-MS (M + H) |
| 358 | 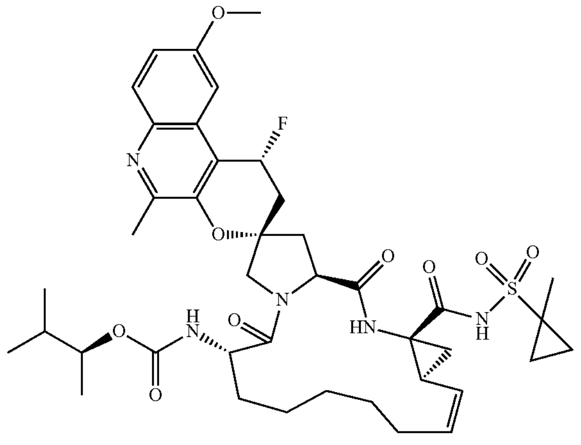 I-358 | (2S)-3-methylbutan-2-yl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 57 | 812.5 |
| 359 | 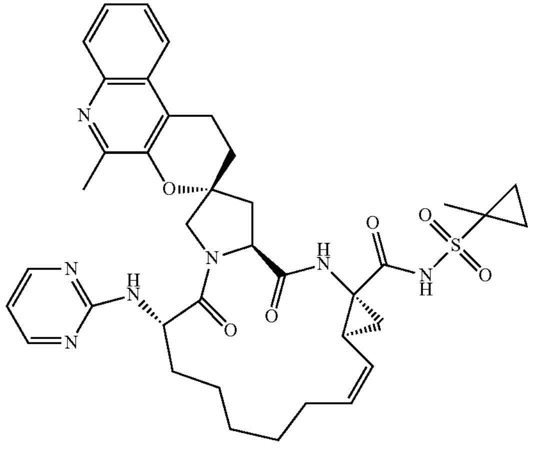 I-359 | (2R,6S,12Z,13aS,14aR,16aS)-5'-methyl-N-[(1-methylcyclopropyl)sulfonyl]-5,16-dioxo-6-(pyrimidin-2-ylamino)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 56, 528 | 727.4 |

TABLE 1-continued

| Ex. No. | Structure | Name | Proc. | LR-MS (M + H) |
|---|---|---|---|---|
| | Compounds of Examples 68-526 | | | |
| 360 | 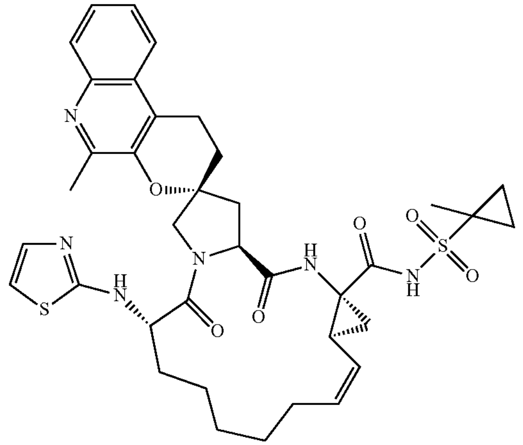 I-360 | (2R,6S,12Z,13aS,14aR,16aS)-5'-methyl-N-[(1-methylcyclopropyl)sulfonyl]-5,16-dioxo-6-(1,3-thiazol-2-ylamino)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 733.4 |
| 361 | 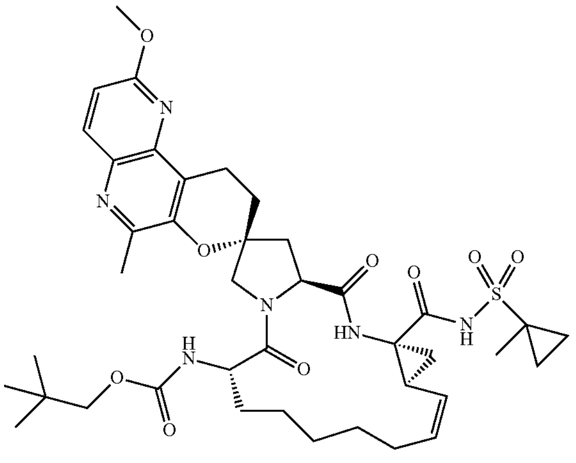 I-361 | 2,2-dimethylpropyl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 795.2 |

TABLE 1-continued

| Compounds of Examples 68-526 | | | | |
|---|---|---|---|---|
| Ex. No. | Structure | Name | Proc. | LR-MS (M + H) |
| 362 | 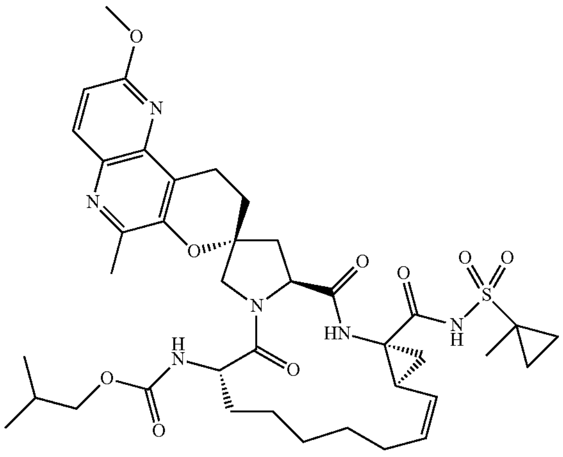 I-362 | 2-methylpropyl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 781.2 |
| 363 | 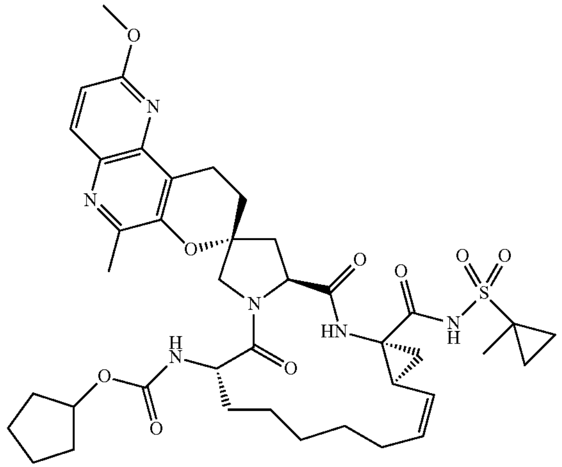 I-363 | cyclopentyl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 793.2 |

TABLE 1-continued

| Compounds of Examples 68-526 | | | | |
|---|---|---|---|---|
| Ex. No. | Structure | Name | Proc. | LR-MS (M + H) |
| 364 | 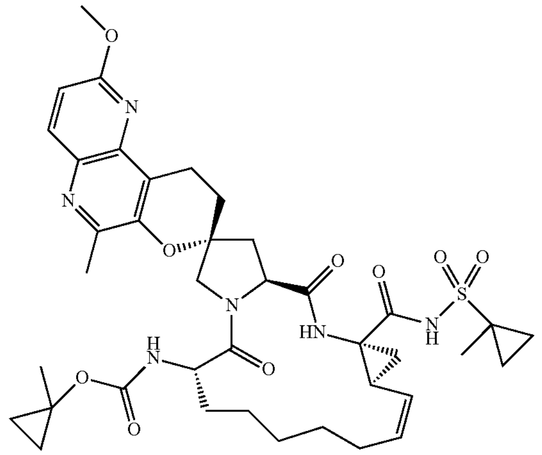 I-364 | 1-methylcyclopropyl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 779.2 |
| 365 | 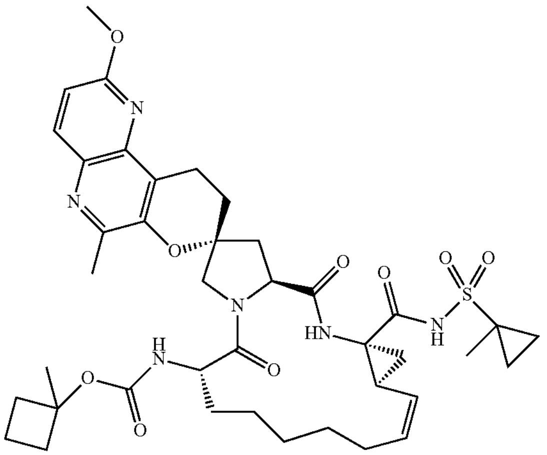 I-365 | 1-methylcyclobutyl [(2R,6S,12Z,13aS,14aR,16aS)-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 11 | 793.2 |

TABLE 1-continued

| Compounds of Examples 68-526 | | | | |
|---|---|---|---|---|
| Ex. No. | Structure | Name | Proc. | LR-MS (M + H) |
| 366 | 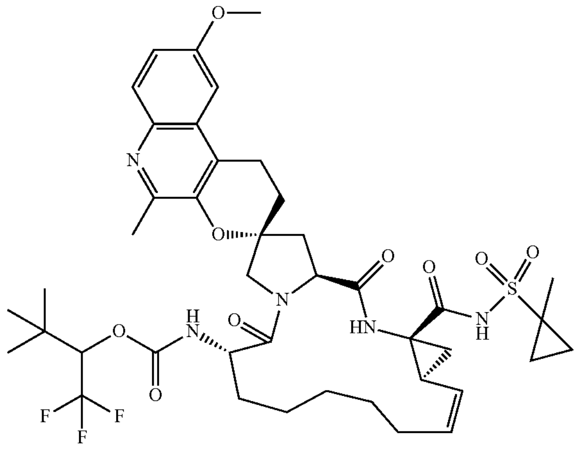 I-366 | 1,1,1-trifluoro-3,3-dimethylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 862 |
| 367 | 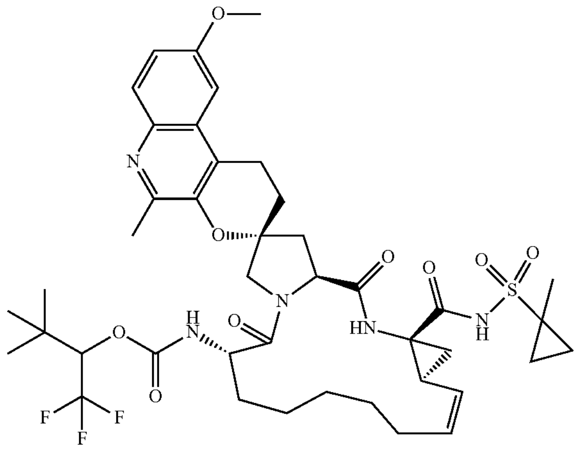 I-367 | 1,1,1-trifluoro-3,3-dimethylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 862.2 |

TABLE 1-continued

Compounds of Examples 68-526

| Ex. No. | Structure | Name | Proc. | LR-MS (M + H) |
|---|---|---|---|---|
| 368 | 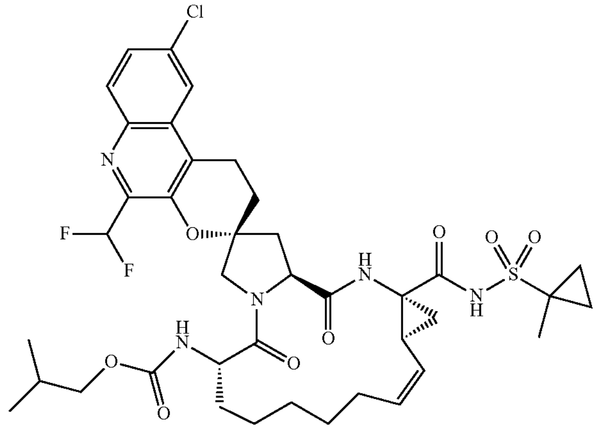 I-368 | 2-methylpropyl [(2R,6S,12Z,13aS,14aR,16aS)-9'-chloro-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 820 |
| 369 | 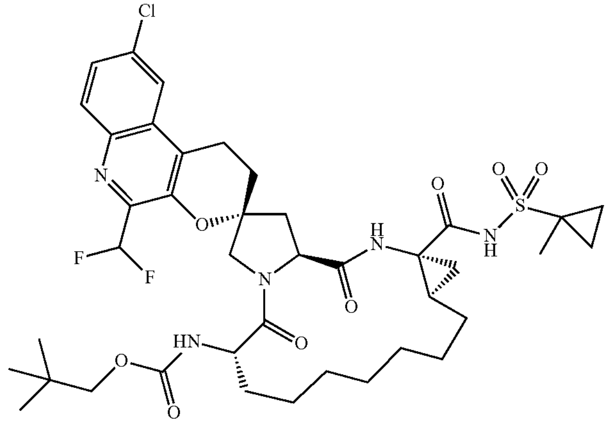 I-369 | 2,2-dimethylpropyl [(2R,6S,12Z,13aS,14aR,16aS)-9'-chloro-5'-(difluoromethyl)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 834 |

TABLE 1-continued

| Compounds of Examples 68-526 | | | | |
|---|---|---|---|---|
| Ex. No. | Structure | Name | Proc. | LR-MS (M + H) |
| 370 | 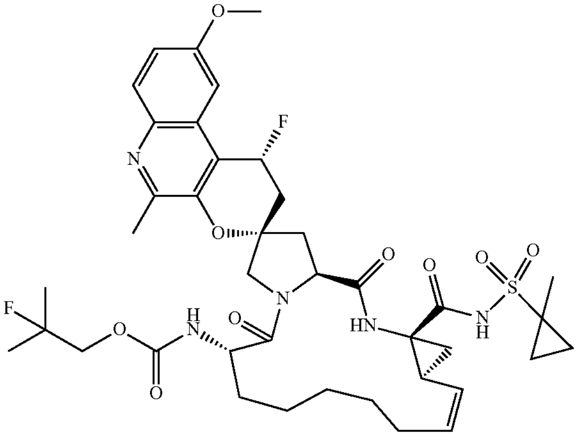 I-370 | 2-fluoro-2-methylpropyl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 816 (K+ salt) |
| 371 | 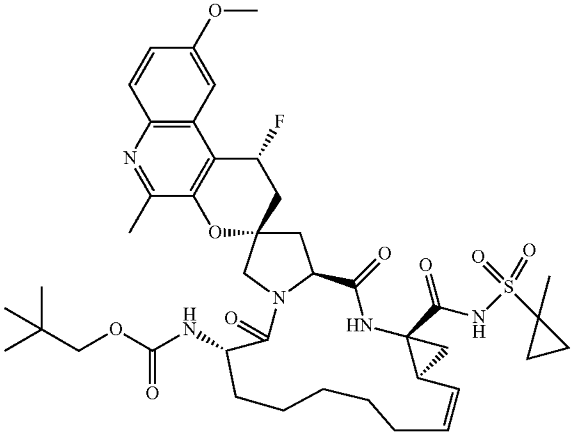 I-371 | 2,2-dimethylpropyl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 812.2 (K+ salt) |

TABLE 1-continued

| Compounds of Examples 68-526 | | | | |
|---|---|---|---|---|
| Ex. No. | Structure | Name | Proc. | LR-MS (M + H) |
| 372 | 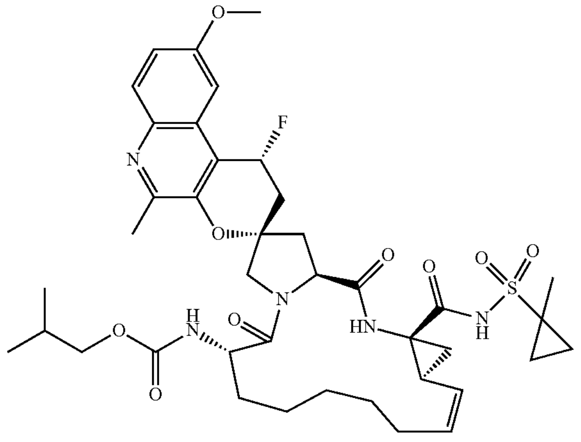 I-372 | 2-methylpropyl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 798.2 (K+ salt) |
| 373 | 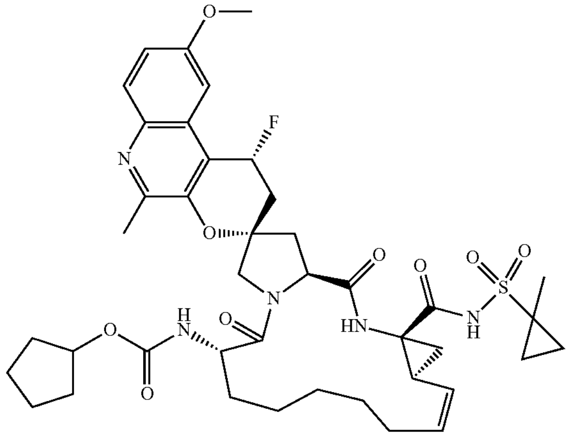 I-373 | cyclopentyl [(1'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56 | 810.2 (K+ salt) |

TABLE 1-continued

| Compounds of Examples 68-526 | | | | |
|---|---|---|---|---|
| Ex. No. | Structure | Name | Proc. | LR-MS (M + H) |
| 374 | 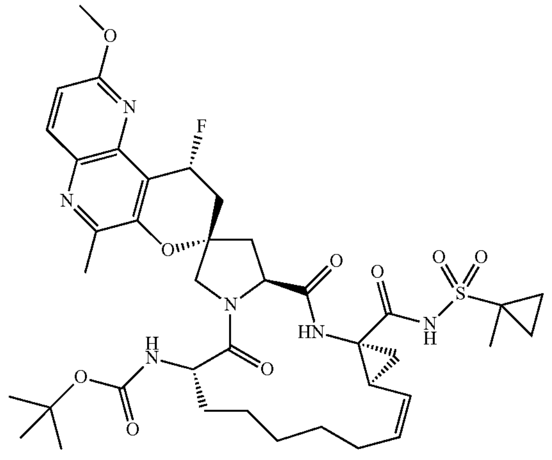 I-374 | tert-butyl [(2S,6S,10'R,12Z,13aS,14aR,16aS)-10'-fluoro-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 33 | 799.2 |
| 375 | 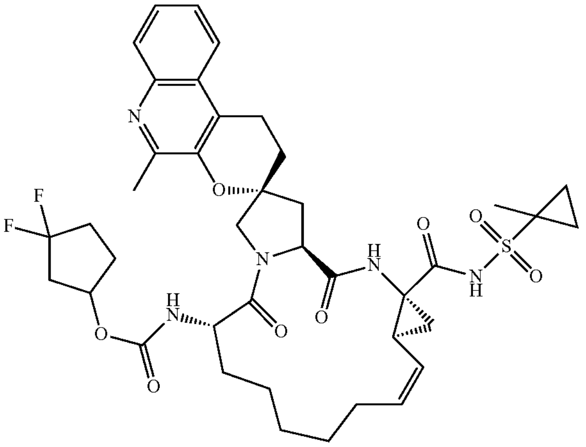 I-375 | 3,3-difluorocyclopentyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 798.5 |

TABLE 1-continued

| Compounds of Examples 68-526 | | | | |
|---|---|---|---|---|
| Ex. No. | Structure | Name | Proc. | LR-MS (M + H) |
| 376 | 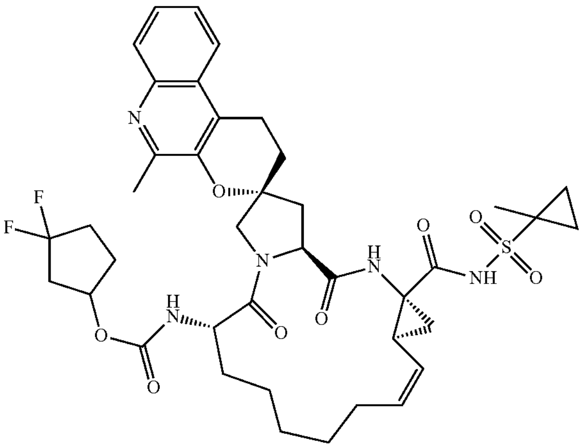 I-376 | 3,3-difluorocyclopentyl [(2R,6S,12Z,13aS,14aR,16aS)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 798.5 |
| 377 | 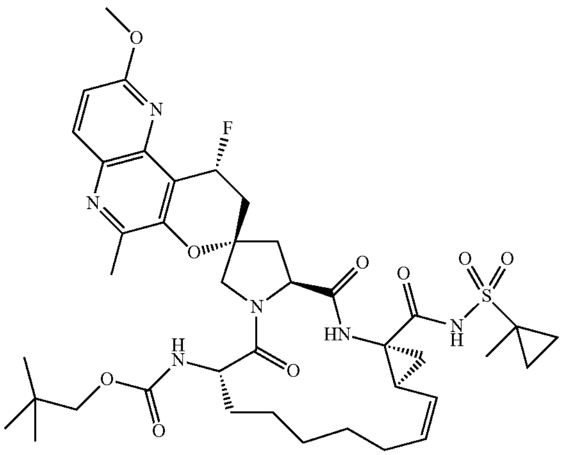 I-377 | 2,2-dimethylpropyl [(2S,6S,10'R,12Z,13aS,14aR,16aS)-10'-fluoro-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 33 | 813.2 |

TABLE 1-continued

| Compounds of Examples 68-526 | | | | |
|---|---|---|---|---|
| Ex. No. | Structure | Name | Proc. | LR-MS (M + H) |
| 378 | 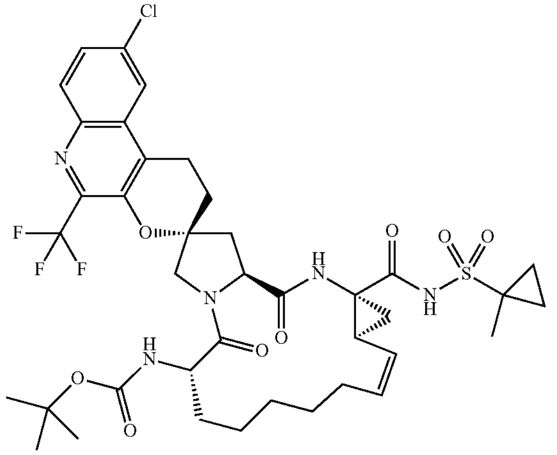 I-378 | tert-butyl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 782 |
| 379 | 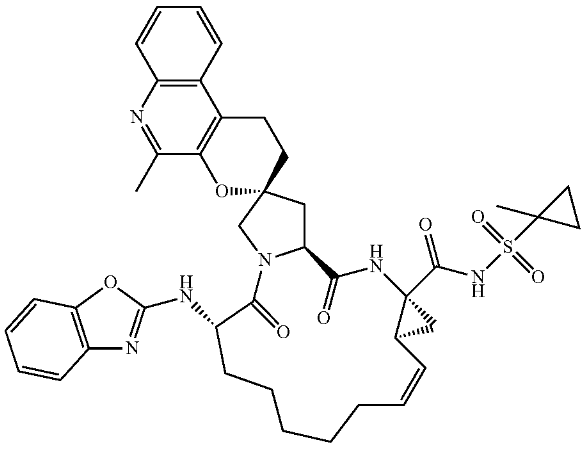 I-379 | (2R,6S,12Z,13aS,14aR,16aS)-6-(1,3-benzoxazol-2-ylamino)-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 766.4 |

TABLE 1-continued

Compounds of Examples 68-526

| Ex. No. | Structure | Name | Proc. | LR-MS (M + H) |
|---|---|---|---|---|
| 380 | 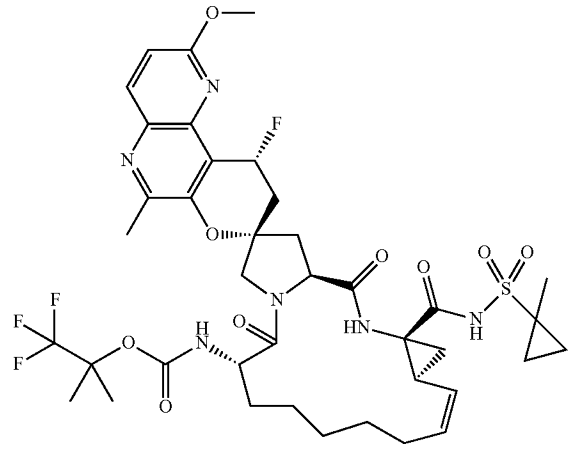 I-380 | 1,1,1-trifluoro-2-methylpropan-2-yl [(2S,6S,10'R,12Z,13aS,14aR,16aS)-10'-fluoro-2'-methoxy-6'-methyl-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 33 | 853.2 (K+ salt) |
| 381 | 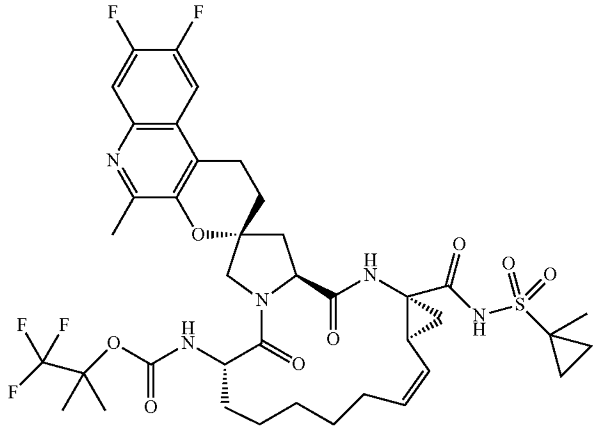 I-381 | 1,1,1-trifluoro-2-methylpropan-2-yl [(2R,6S,12Z,13aS,14aR,16aS)-8',9'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 44 | 840 |

TABLE 1-continued

| Compounds of Examples 68-526 | | | | |
|---|---|---|---|---|
| Ex. No. | Structure | Name | Proc. | LR-MS (M + H) |
| 382 | 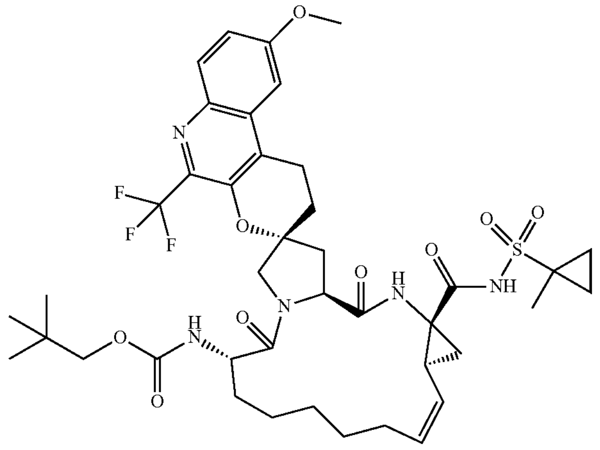 I-382 | 2,2-dimethylpropyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 848 (K+ salt) |
| 383 | 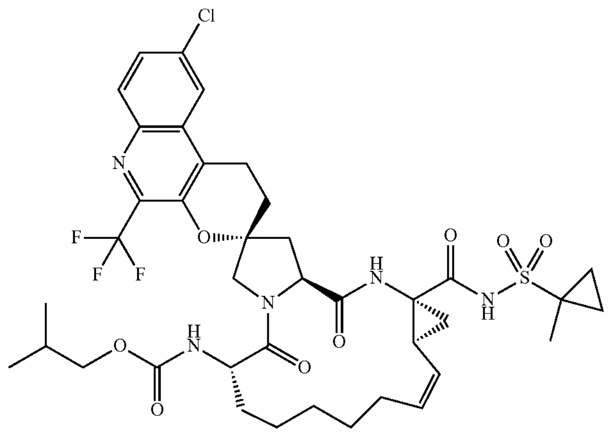 I-383 | 2-methylpropyl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 839 |

TABLE 1-continued

| Compounds of Examples 68-526 | | | | |
|---|---|---|---|---|
| Ex. No. | Structure | Name | Proc. | LR-MS (M + H) |
| 384 | 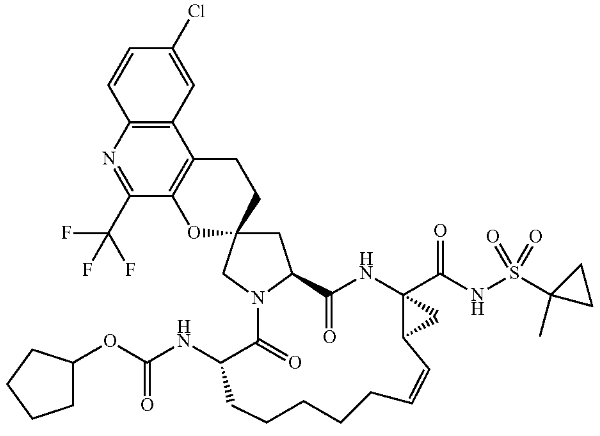 I-384 | cyclopentyl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 850 |
| 385 | 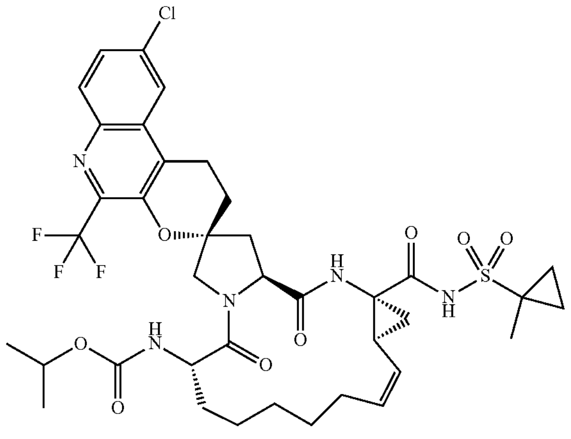 I-385 | propan-2-yl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 824 |

TABLE 1-continued

| Compounds of Examples 68-526 | | | | |
|---|---|---|---|---|
| Ex. No. | Structure | Name | Proc. | LR-MS (M + H) |
| 386 | 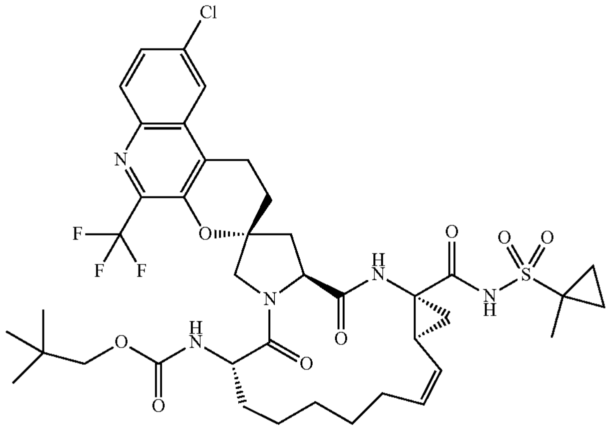 I-386 | 2,2-dimethylpropyl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 852 |
| 387 | 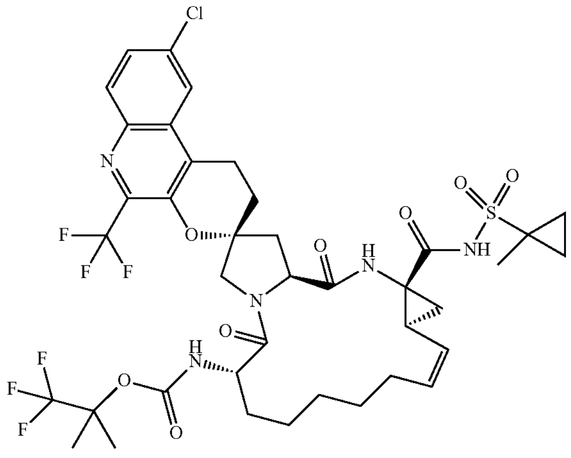 I-387 | 1,1,1-trifluoro-2-methylpropan-2-yl [(2R,6S,12Z,13aS,14aR,16aS)-9'-chloro-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5 | 891.8 |

TABLE 1-continued

| Compounds of Examples 68-526 | | | | |
|---|---|---|---|---|
| Ex. No. | Structure | Name | Proc. | LR-MS (M + H) |
| 388 | 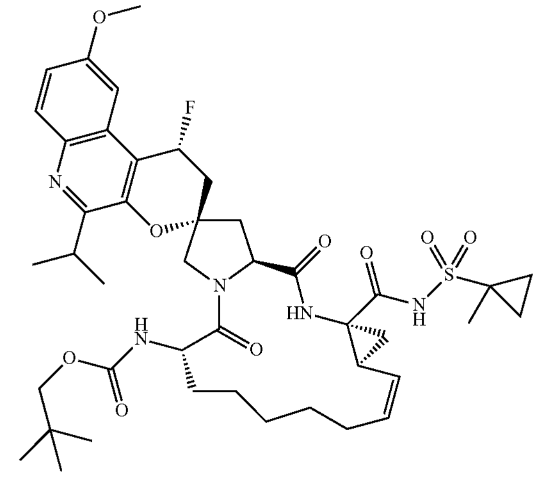 I-388 | 2,2-dimethylpropyl [(1'R,2S,6S,12Z,13aS,14aR,16aS)-1'-fluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 840.2 |
| 389 | 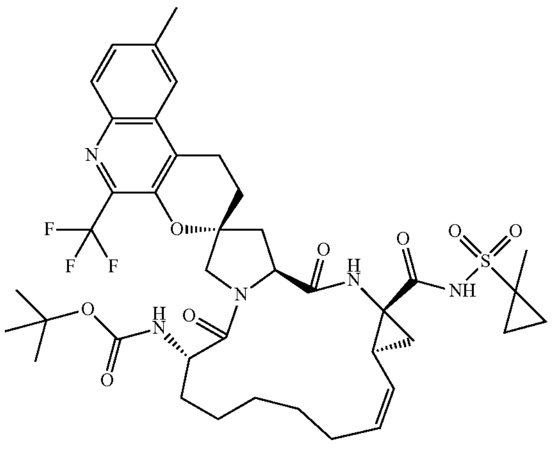 I-389 | tert-butyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 841.1 |

TABLE 1-continued

| Compounds of Examples 68-526 | | | | |
|---|---|---|---|---|
| Ex. No. | Structure | Name | Proc. | LR-MS (M + H) |
| 390 | 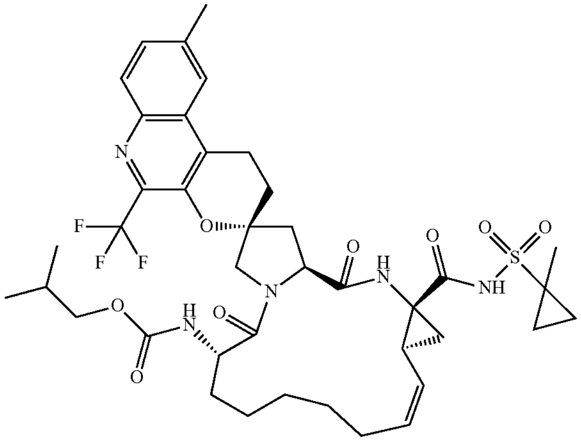 I-390 | 2-methylpropyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 818.2 |
| 391 | 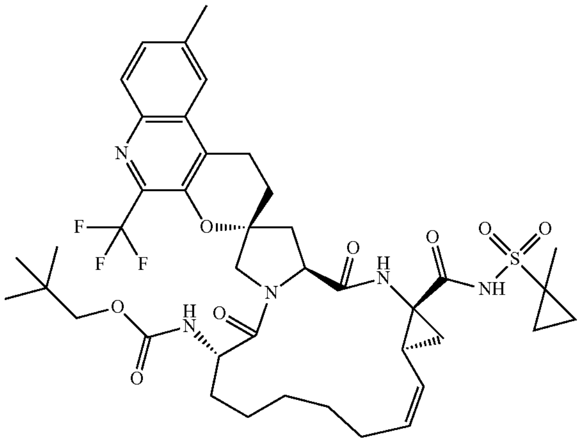 I-391 | 2,2-dimethylpropyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 832.2 |

TABLE 1-continued

| Compounds of Examples 68-526 | | | | |
|---|---|---|---|---|
| Ex. No. | Structure | Name | Proc. | LR-MS (M + H) |
| 392 | 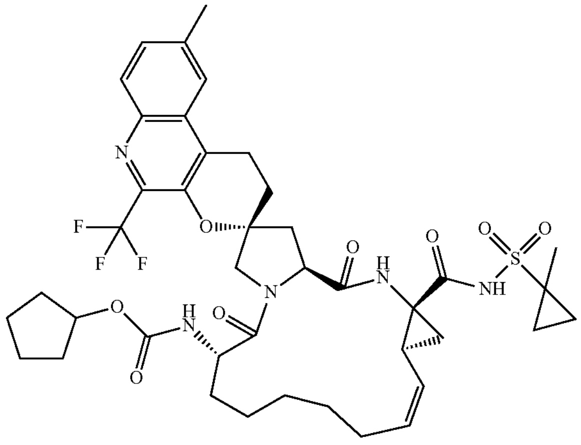 I-392 | cyclopentyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 830.2 |
| 393 | 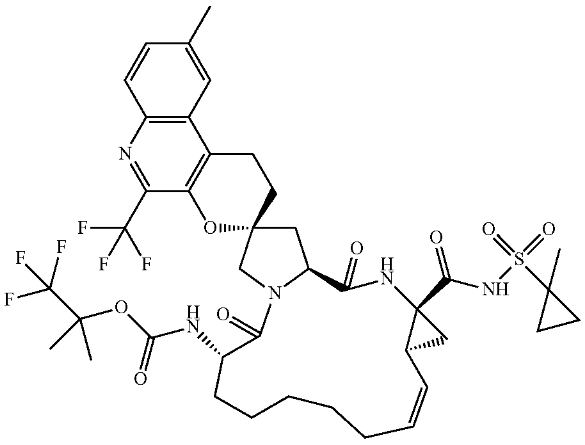 I-393 | 1,1,1-trifluoro-2-methylpropan-2-yl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 872.1 |

TABLE 1-continued

| Compounds of Examples 68-526 | | | | |
|---|---|---|---|---|
| Ex. No. | Structure | Name | Proc. | LR-MS (M + H) |
| 394 | 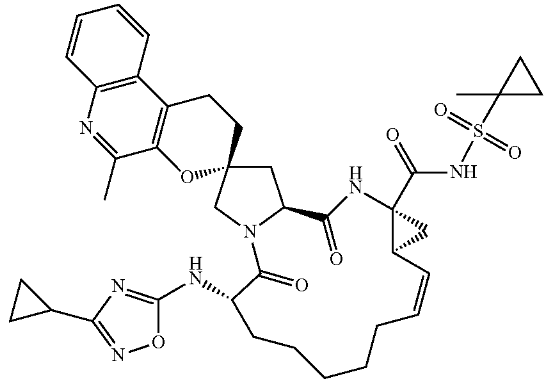 I-394 | (2R,6S,12Z,13aS,14aR,16aS)-6-[(3-cyclopropyl-1,2,4-oxadiazol-5-yl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 758 |
| 395 | 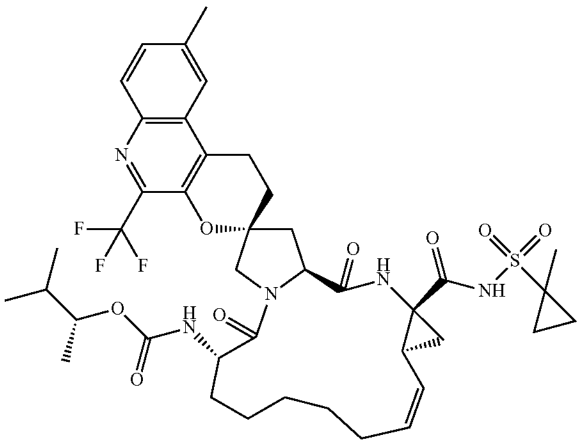 I-395 | (2R)-3-methylbutan-2-yl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 832.2 |

TABLE 1-continued

| Compounds of Examples 68-526 | | | | |
|---|---|---|---|---|
| Ex. No. | Structure | Name | Proc. | LR-MS (M + H) |
| 396 | 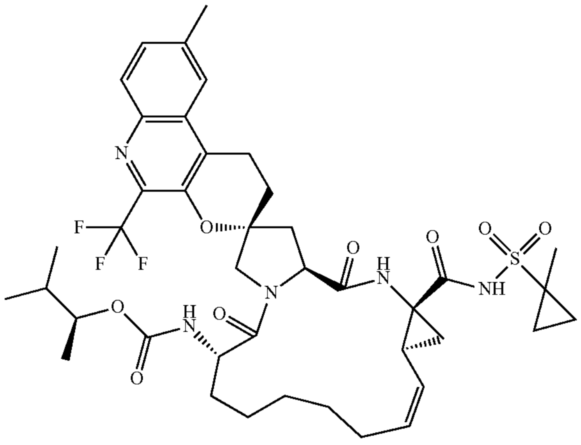 I-396 | (2S)-3-methylbutan-2-yl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 832.2 |
| 397 | 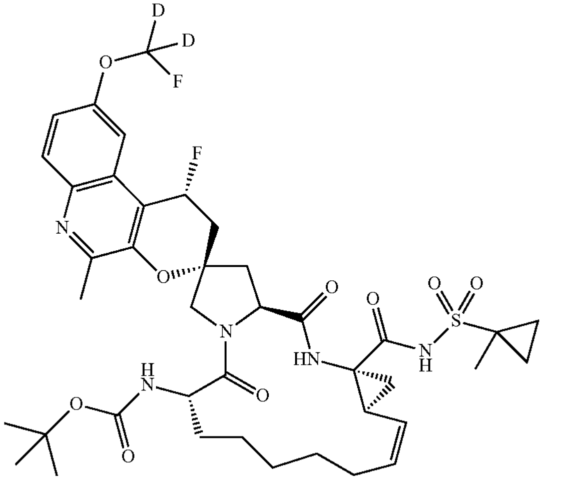 I-397 | tert-butyl [(1'R,2S,6S,12Z,13aS,14aR,16aS)-1'-fluoro-9'-{[fluoro($^2H_2$)methyl]oxy}-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 58, 7, 50, 32 | 818.2 |

TABLE 1-continued

| Compounds of Examples 68-526 | | | | |
|---|---|---|---|---|
| Ex. No. | Structure | Name | Proc. | LR-MS (M + H) |
| 398 | 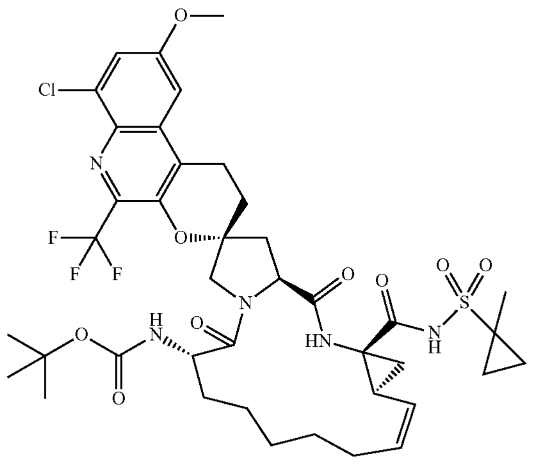 I-398 | tert-butyl [(2R,6S,12Z,13aS,14aR,16aS)-7'-chloro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 6 | 812 |
| 399 | 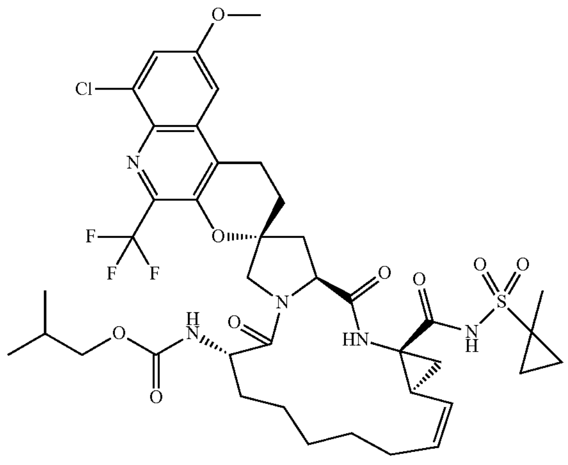 I-399 | 2-methylpropyl [(2R,6S,12Z,13aS,14aR,16aS)-7'-chloro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 6 | 868 |

TABLE 1-continued

| Compounds of Examples 68-526 | | | | |
|---|---|---|---|---|
| Ex. No. | Structure | Name | Proc. | LR-MS (M + H) |
| 400 | 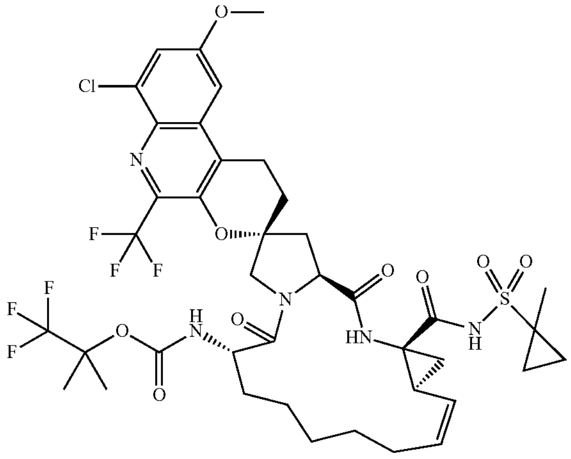 I-400 | 1,1,1-trifluoro-2-methylpropan-2-yl [(2R,6S,12Z,13aS,14aR,16aS)-7'-chloro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 6 | 922 |
| 401 | 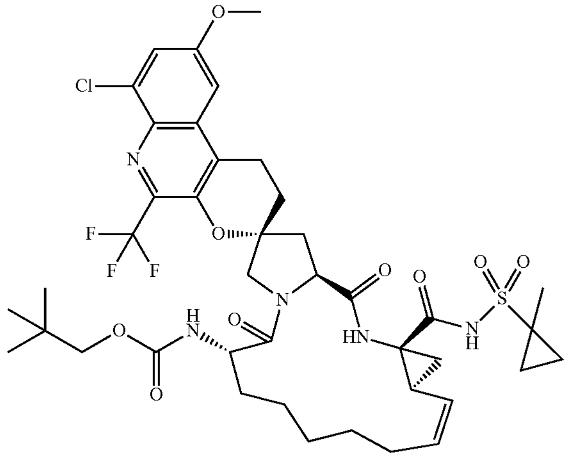 I-401 | 2,2-dimethylpropyl [(2R,6S,12Z,13aS,14aR,16aS)-7'-chloro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 6 | 882 |

TABLE 1-continued

| Compounds of Examples 68-526 | | | | |
|---|---|---|---|---|
| Ex. No. | Structure | Name | Proc. | LR-MS (M + H) |
| 402 | 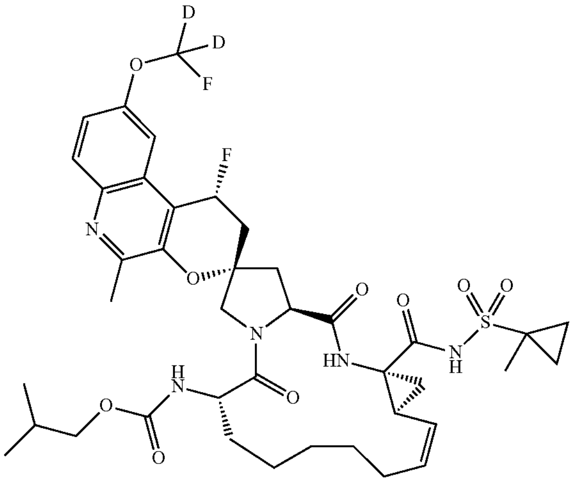 I-402 | 2-methylpropyl [(1'R,2S,6S,12Z,13aS,14aR,16aS)-1'-fluoro-9'-{[fluoro($^2H_2$)methyl]oxy}-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56, 7, 50, 32 | 818.2 (K+ salt) |
| 403 | 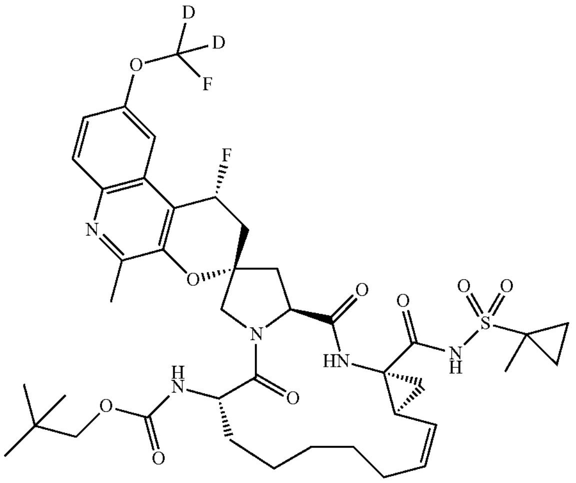 I-403 | 2,2-dimethylpropyl [(1'R,2S,6S,12Z,13aS,14aR,16aS)-1'-fluoro-9'-{[fluoro($^2H_2$)methyl]oxy}-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 58, 7, 50, 32 | 832.2 (K+ salt) |

TABLE 1-continued

| Compounds of Examples 68-526 | | | | |
|---|---|---|---|---|
| Ex. No. | Structure | Name | Proc. | LR-MS (M + H) |
| 404 | 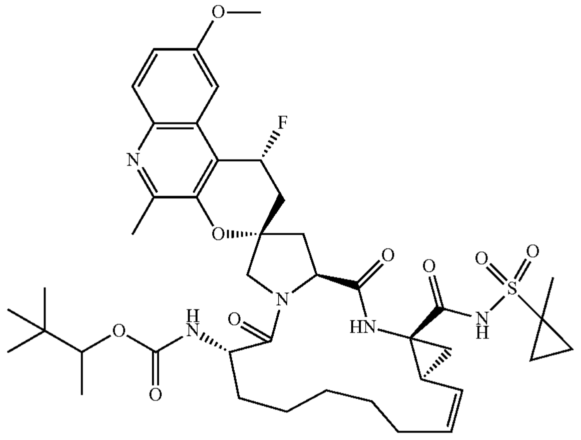 I-404 | 3,3-dimethylbutan-2-yl [(l'R,2S,6S,12Z,13aS,14aR,16aS)-1'-fluoro-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 58, 7 | 826.2 |
| 405 | 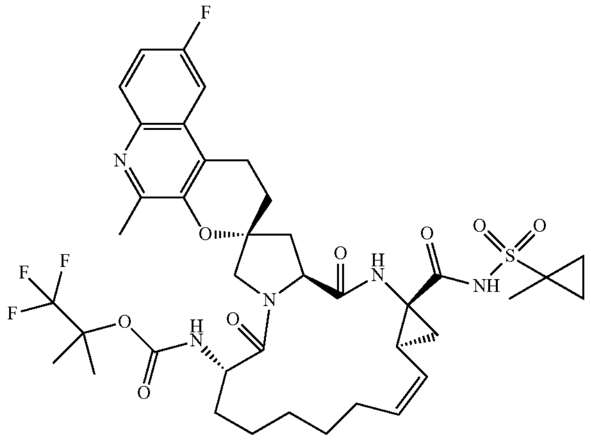 I-405 | 1,1,1-trifluoro-2-methylpropan-2-yl [(2R,6S,12Z,13aS,14aR,16aS)-9'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 822.0 |

TABLE 1-continued

| Compounds of Examples 68-526 | | | | |
|---|---|---|---|---|
| Ex. No. | Structure | Name | Proc. | LR-MS (M + H) |
| 406 | 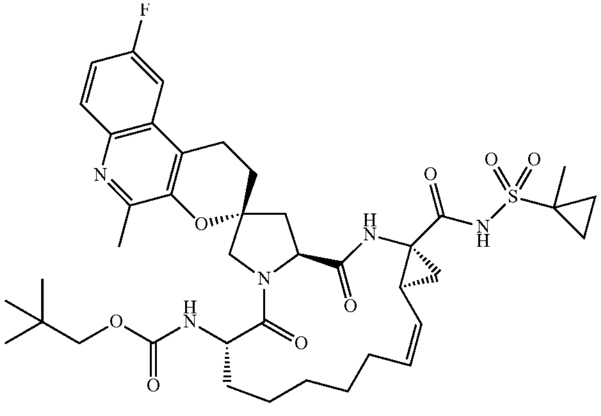 I-406 | 2,2-dimethylpropyl [(2R,6S,12Z,13aS,14aR,16aS)-9'-fluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 43 | 782.0 |
| 407 | 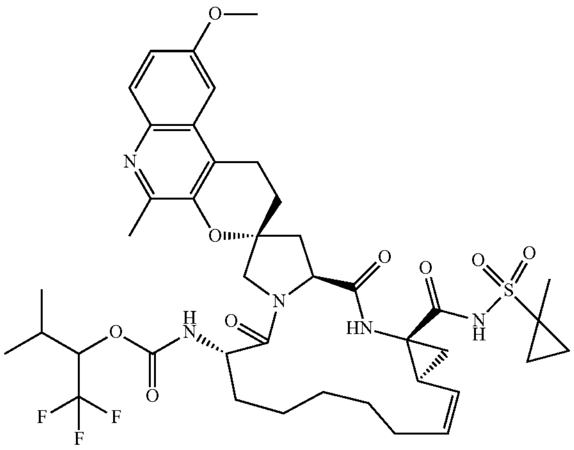 I-407 | 1,1,1-trifluoro-3-methylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 848 (K+ salt) |

TABLE 1-continued

| Compounds of Examples 68-526 | | | | |
|---|---|---|---|---|
| Ex. No. | Structure | Name | Proc. | LR-MS (M + H) |
| 408 | 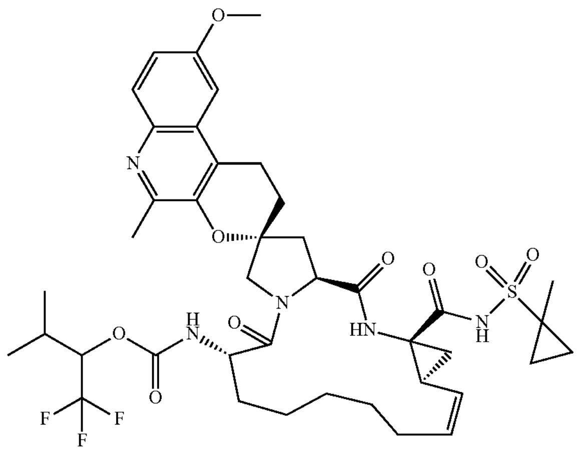 I-408 | 1,1,1-trifluoro-3-methylbutan-2-yl [(2R,6S,12Z,13aS,14aR,16aS)-9'-methoxy-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 9 | 848 (K+ salt) |
| 409 | 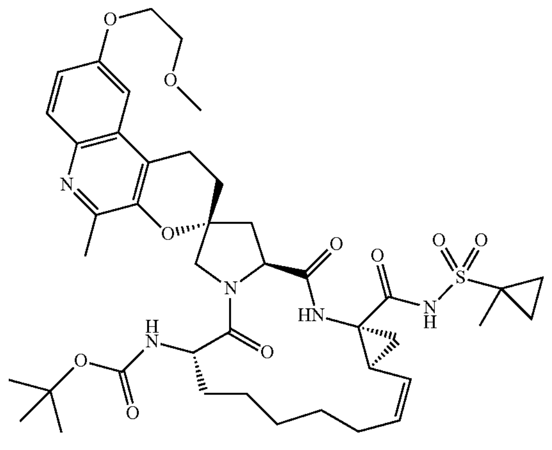 I-409 | tert-butyl [(2R,6S,12Z,13aS,14aR,16aS)-9'-(2-methoxyethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50, 51 | 824.2 |

TABLE 1-continued

| Compounds of Examples 68-526 | | | | |
|---|---|---|---|---|
| Ex. No. | Structure | Name | Proc. | LR-MS (M + H) |
| 410 | 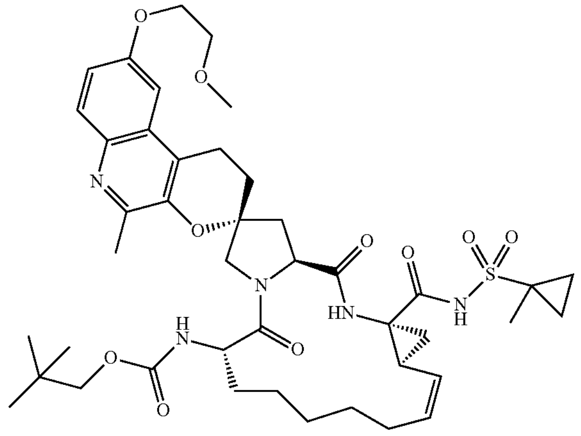 I-410 | 2,2-dimethylpropyl [(2R,6S,12Z,13aS,14aR,16aS)-9'-(2-methoxyethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50, 51, 6 | 838.2 |
| 411 | 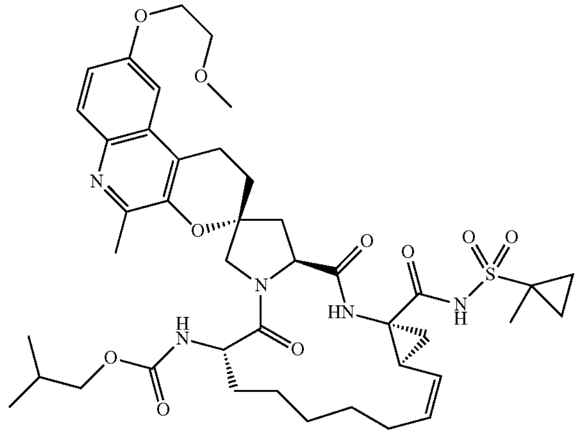 I-411 | 2-methylpropyl [(2R,6S,12Z,13aS,14aR,16aS)-9'-(2-methoxyethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50, 51, 6 | 824.2 |

TABLE 1-continued

| Compounds of Examples 68-526 | | | | |
|---|---|---|---|---|
| Ex. No. | Structure | Name | Proc. | LR-MS (M + H) |
| 412 | 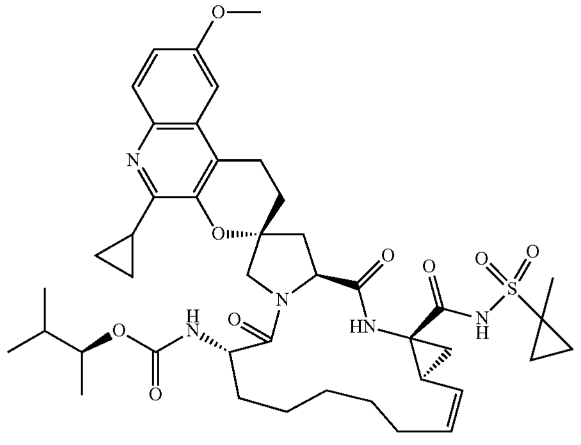 I-412 | (2S)-3-methylbutan-2-yl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 820.2 (K+ salt) |
| 413 | 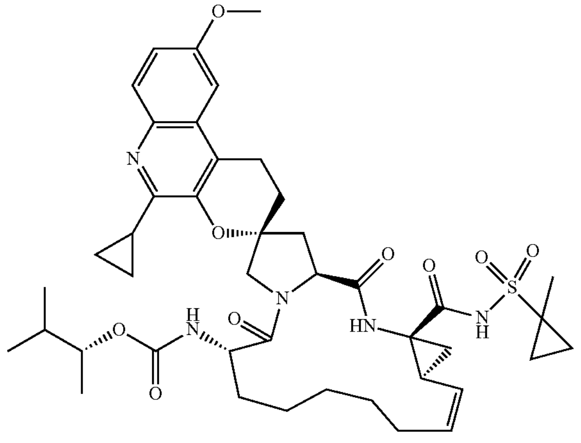 I-413 | (2R)-3-methylbutan-2-yl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 820.2 (K+ salt) |

TABLE 1-continued

Compounds of Examples 68-526

| Ex. No. | Structure | Name | Proc. | LR-MS (M + H) |
|---|---|---|---|---|
| 414 | 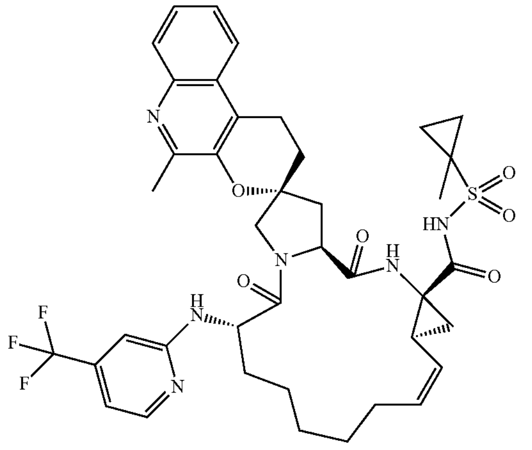 I-414 | (2R,6S,12Z,13aS,14aR,16aS)-5'-methyl-N-[(1-methylcyclopropyl)sulfonyl]-5,16-dioxo-6-{[4-(trifluoromethyl)pyridin-2-yl]amino}-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 794.4 |
| 415 | 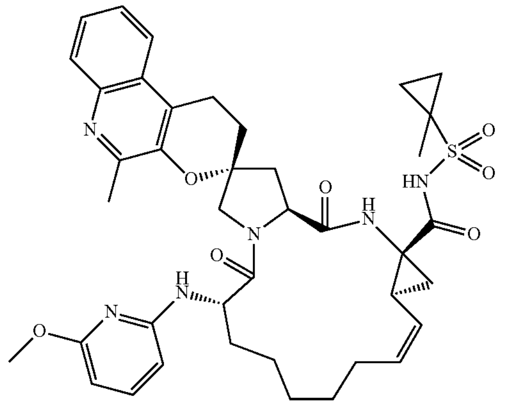 I-415 | (2R,6S,12Z,13aS,14aR,16aS)-6-[(6-methoxypyridin-2-yl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 756.4 |

TABLE 1-continued

| Compounds of Examples 68-526 | | | | |
|---|---|---|---|---|
| Ex. No. | Structure | Name | Proc. | LR-MS (M + H) |
| 416 | 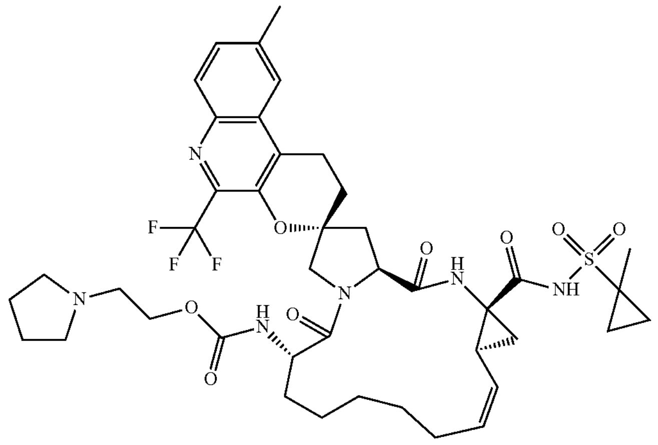 I-416 | 2-(pyrrolidin-1-yl)ethyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 859.2 |
| 417 | 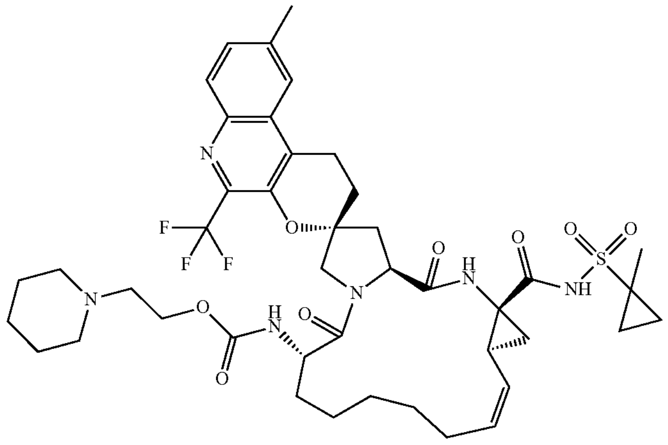 I-417 | 2-(piperidin-1-yl)ethyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 873.2 |

TABLE 1-continued

| Compounds of Examples 68-526 | | | | |
|---|---|---|---|---|
| Ex. No. | Structure | Name | Proc. | LR-MS (M + H) |
| 418 | 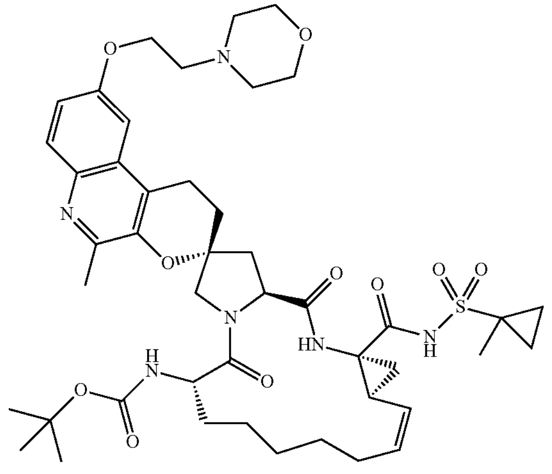 I-418 | tert-butyl {(2R,6S,12Z,13aS,14aR,16aS)-5'-methyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 58, 50 | 879.3 |
| 419 | 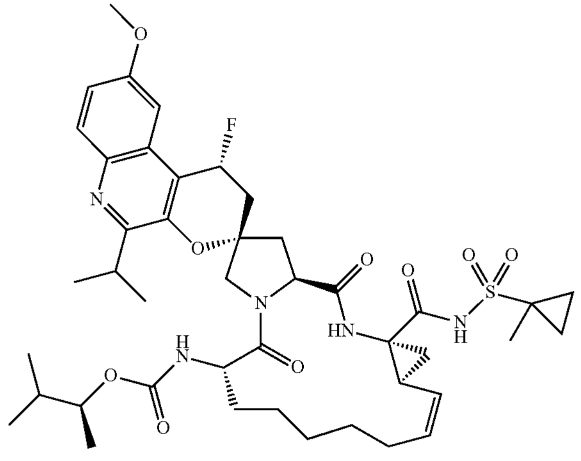 I-419 | (2S)-3-methylbutan-2-yl [(1'R,2S,6S,12Z,13aS,14aR,16aS)-1'-fluoro-9'-methoxy-14a-{[(1-methylcyclopropyl)sulfonyl]carbamoyl}-5,16-dioxo-5'-(propan-2-yl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 3 | 840.2 (K+ salt) |

TABLE 1-continued

| Compounds of Examples 68-526 | | | | |
|---|---|---|---|---|
| Ex. No. | Structure | Name | Proc. | LR-MS (M + H) |
| 420 | 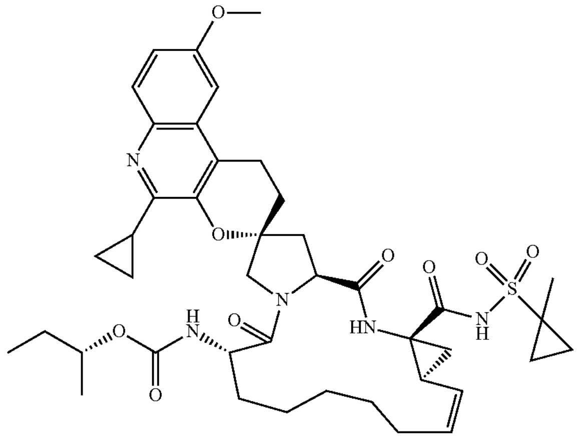 I-420 | (2R)-butan-2-yl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 806.2 (K+ salt) |
| 421 | 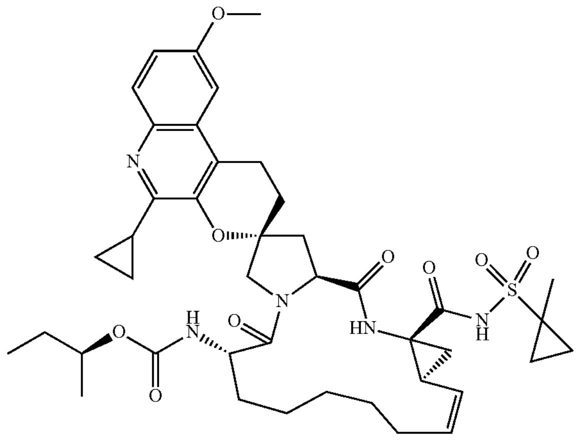 I-421 | (2S)-butan-2-yl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 16 | 806.3 |

TABLE 1-continued

| Compounds of Examples 68-526 | | | | |
|---|---|---|---|---|
| Ex. No. | Structure | Name | Proc. | LR-MS (M + H) |
| 422 | 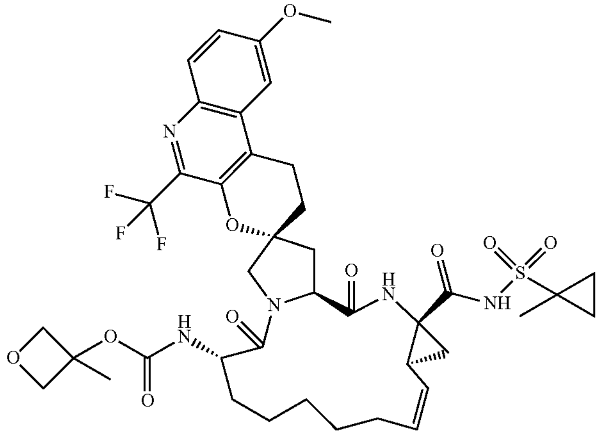 I-422 | 3-methyloxetan-3-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 848.2 (K+ salt) |
| 423 | 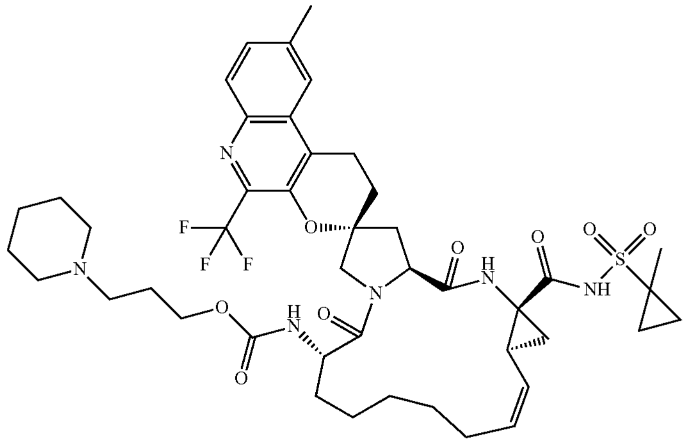 I-423 | 3-(piperidin-1-yl)propyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 887.2 |

TABLE 1-continued

| Compounds of Examples 68-526 | | | | |
|---|---|---|---|---|
| Ex. No. | Structure | Name | Proc. | LR-MS (M + H) |
| 424 | 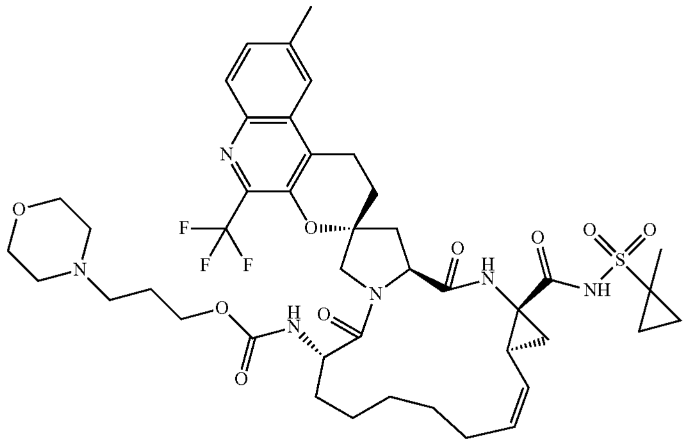 I-424 | 3-(morpholin-4-yl)propyl [(2R,6S,12Z,13aS,14aR,16aS)-9'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 31 | 889.2 |
| 425 | 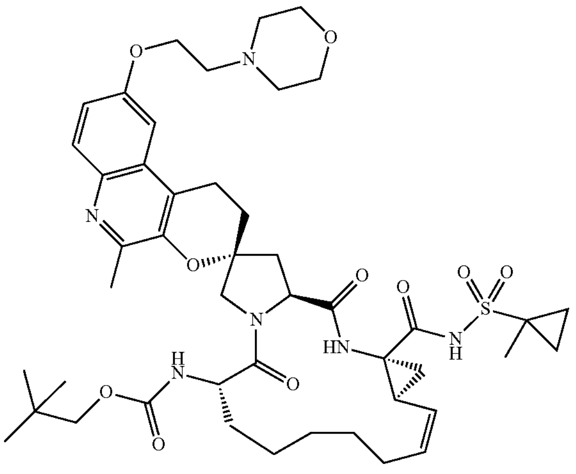 I-425 | 2,2-dimethylpropyl {(2R,6S,12Z,13aS,14aR,16aS)-5'-methyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 58, 50 | 893.2 |

TABLE 1-continued

| Compounds of Examples 68-526 | | | | |
|---|---|---|---|---|
| Ex. No. | Structure | Name | Proc. | LR-MS (M + H) |
| 426 | 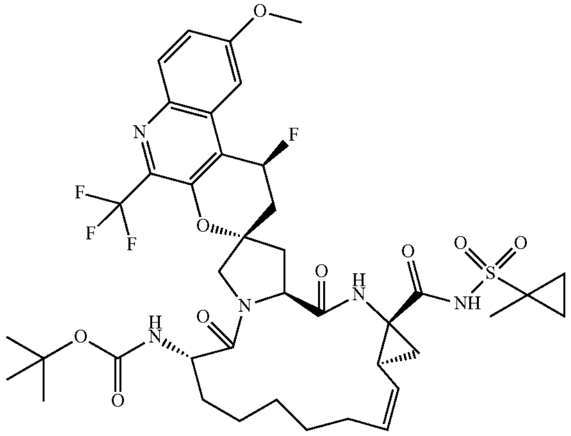 I-426 | tert-butyl [(l'S,2S,6S,12Z,13aS,14aR,16aS)-1'-fluoro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 874.4 |
| 427 | 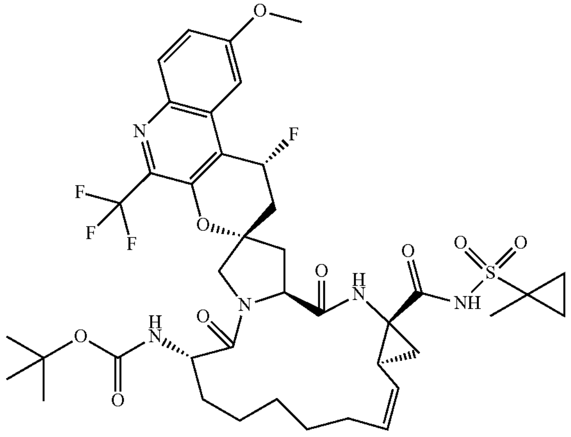 I-427 | tert-butyl [(l'R,2S,6S,12Z,13aS,14aR,16aS)-1'-fluoro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 852.29 |

TABLE 1-continued

| Compounds of Examples 68-526 | | | | |
|---|---|---|---|---|
| Ex. No. | Structure | Name | Proc. | LR-MS (M + H) |
| 428 | 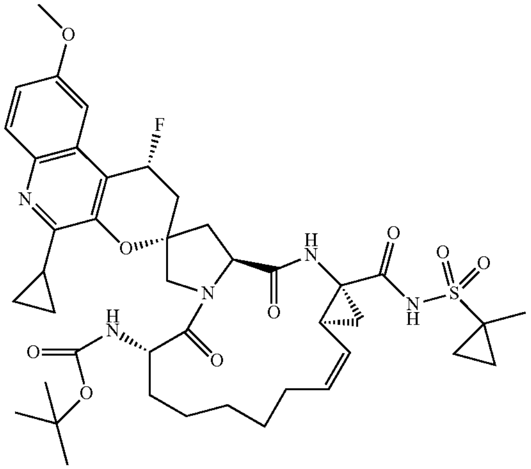 I-428 | tert-butyl [(l'R,2S,6S,12Z,13aS,14aR,16aS)-5'-cyclopropyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 32 | 824.2 |
| 429 | 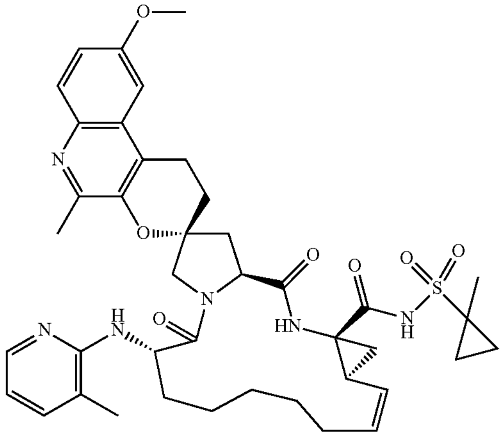 I-429 | (2R,6S,12Z,13aS,14aR,16aS)-9'-methoxy-5'-methyl-N-[(1-methylcyclopropyl)sulfonyl]-6-[(3-methylpyridin-2-yl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 771.2 |

TABLE 1-continued

| Compounds of Examples 68-526 | | | | |
|---|---|---|---|---|
| Ex. No. | Structure | Name | Proc. | LR-MS (M + H) |
| 430 | 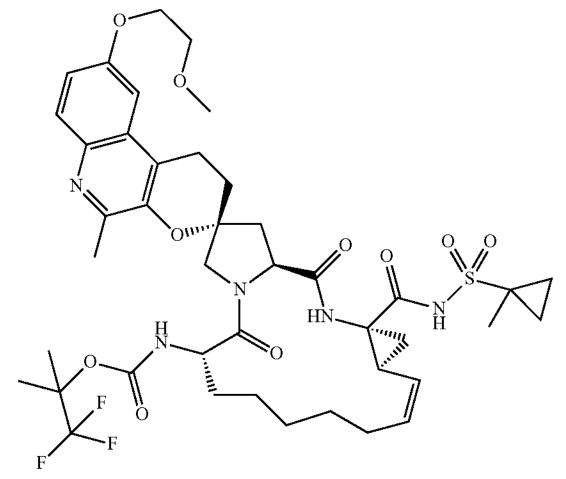 [SMILES: COCCOc1ccc2nc(C)c3c(c2c1)CC[C@]1(C[C@H]2C(=O)N[C@]4(C(=O)NS(=O)(=O)C5(C)CC5)C[C@H]4/C=C\CCCCC[C@H](NC(=O)OC(C)(C)C)C(=O)N2C1)O3] I-430 | 1,1,1-trifluoro-2-methylpropan-2-yl [(2R,6S,12Z,13aS,14aR,16aS)-9'-(2-methoxyethoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50, 51, 35 | 878.1 |
| 431 | 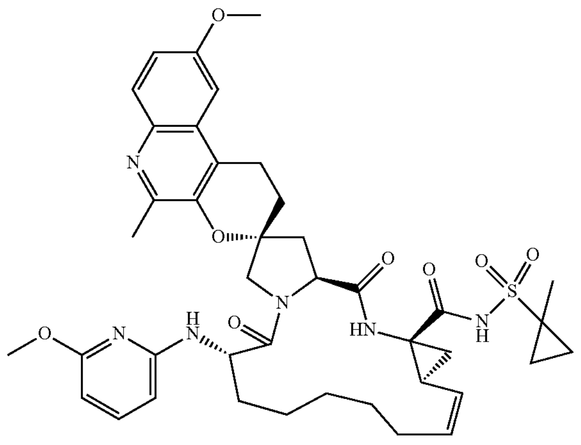 I-431 | (2R,6S,12Z,13aS,14aR,16aS)-9'-methoxy-6-[(6-methoxypyridin-2-yl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 787.2 |

TABLE 1-continued

| Compounds of Examples 68-526 | | | | |
|---|---|---|---|---|
| Ex. No. | Structure | Name | Proc. | LR-MS (M + H) |
| 432 | 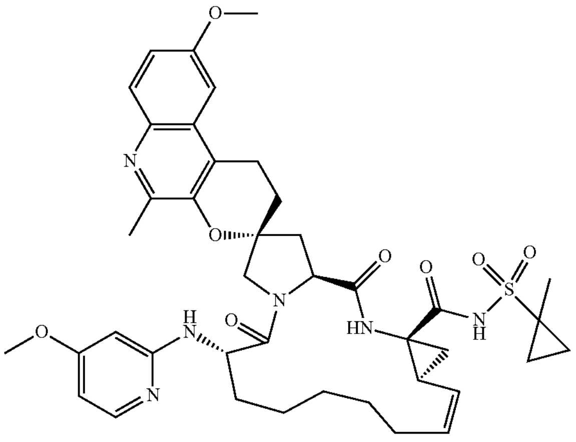 I-432 | (2R,6S,12Z,13aS,14aR,16aS)-9'-methoxy-6-[(4-methoxypyridin-2-yl)amino]-5'-methyl-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 787.2 |
| 433 | 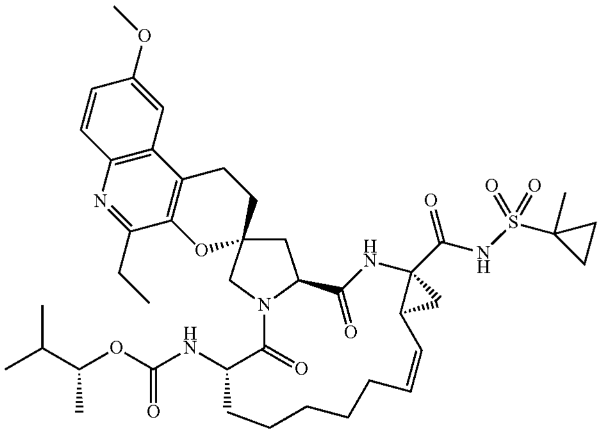 I-433 | (2R)-3-methylbutan-2-yl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2, 31 | 808.4 |

TABLE 1-continued

| Ex. No. | Structure | Name | Proc. | LR-MS (M + H) |
|---|---|---|---|---|
| Compounds of Examples 68-526 | | | | |
| 434 | 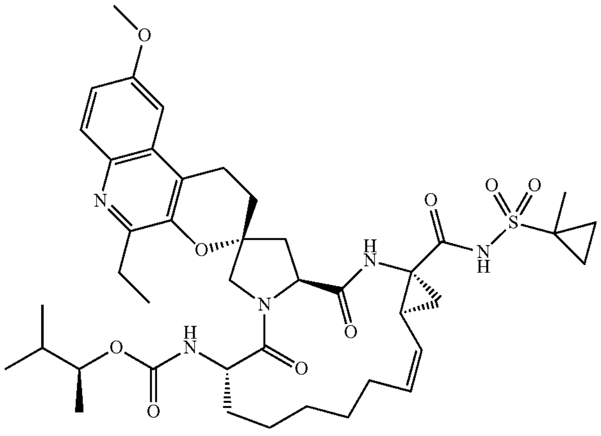 I-434 | (2S)-3-methylbutan-2-yl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2, 31 | 808.2 |
| 435 | 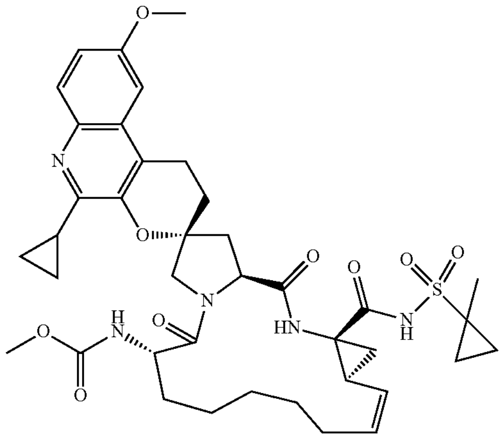 I-435 | methyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 764.2 (K+ salt) |

TABLE 1-continued

| Compounds of Examples 68-526 | | | | |
|---|---|---|---|---|
| Ex. No. | Structure | Name | Proc. | LR-MS (M + H) |
| 436 | 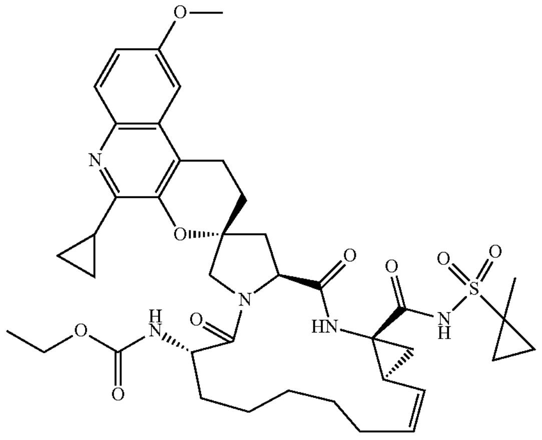 I-436 | ethyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 778.2 (K+ salt) |
| 437 | 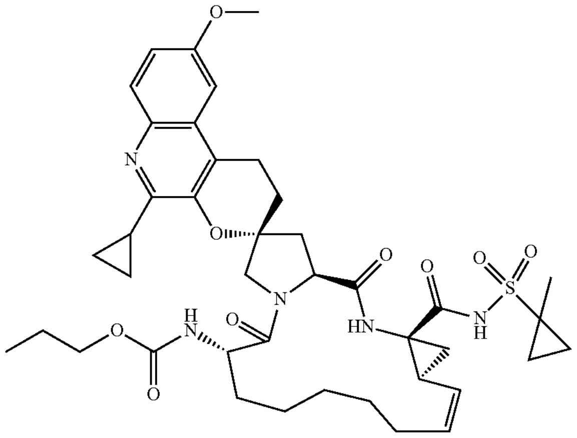 I-437 | propyl [(2R,6S,12Z,13aS,14aR,16aS)-5'-cyclopropyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 792.2 (K+ salt) |

TABLE 1-continued

| Compounds of Examples 68-526 | | | | |
|---|---|---|---|---|
| Ex. No. | Structure | Name | Proc. | LR-MS (M + H) |
| 438 | 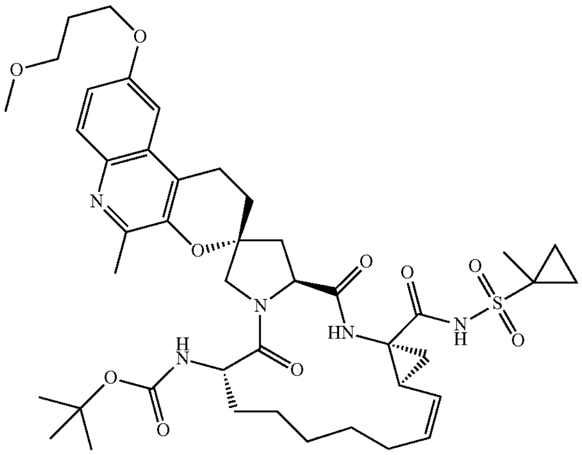 I-438 | tert-butyl [(2R,6S,12Z,13aS,14aR,16aS)-9'-(3-methoxypropoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50 51 | 838.4 |
| 439 | 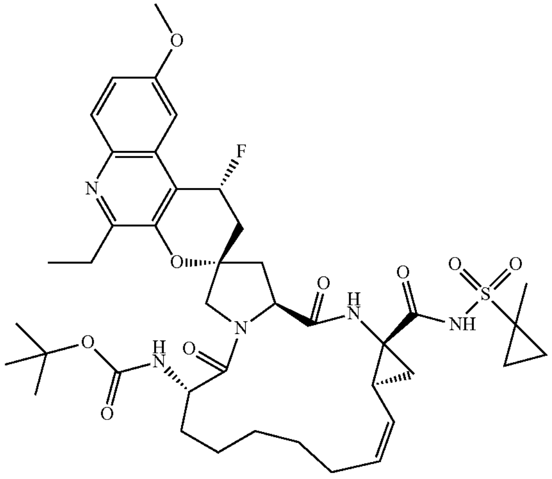 I-439 | tert-butyl [(1'R,2S,6S,12Z,13aS,14aR,16aS)-5'-ethyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 36 | 812.2 |

TABLE 1-continued

| Compounds of Examples 68-526 | | | | |
|---|---|---|---|---|
| Ex. No. | Structure | Name | Proc. | LR-MS (M + H) |
| 440 | 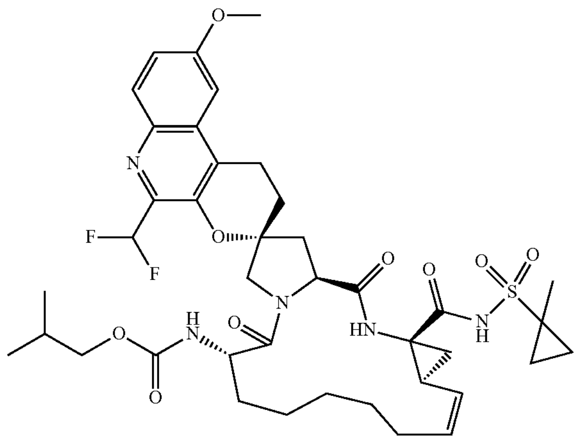 I-440 | 2-methylpropyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 816.2 (K+ salt) |
| 441 | 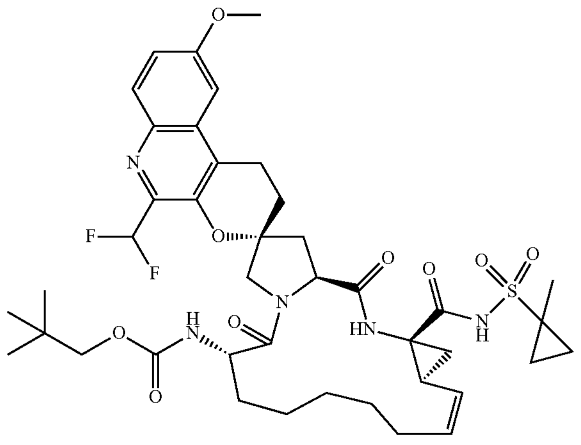 I-441 | 2,2-dimethylpropyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 830.5 |

TABLE 1-continued

| Ex. No. | Structure | Name | Proc. | LR-MS (M + H) |
|---|---|---|---|---|
| | Compounds of Examples 68-526 | | | |
| 442 | 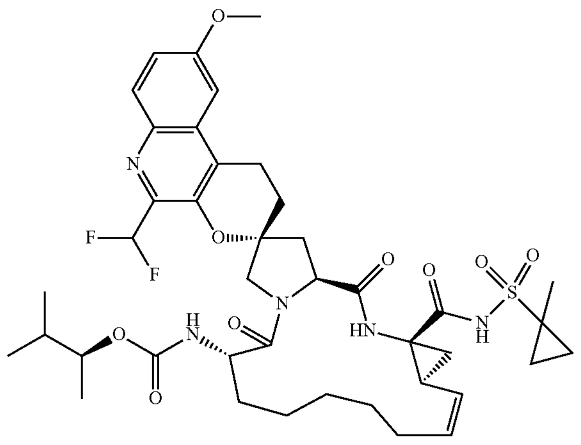 I-442 | (2S)-3-methylbutan-2-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 830.2 (K+ salt) |
| 443 | 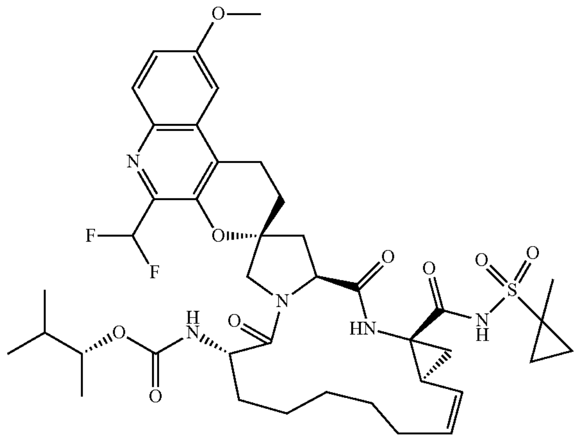 I-443 | (2R)-3-methylbutan-2-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 830.2 (K+ salt) |

TABLE 1-continued

| Compounds of Examples 68-526 | | | | |
|---|---|---|---|---|
| Ex. No. | Structure | Name | Proc. | LR-MS (M + H) |
| 444 | 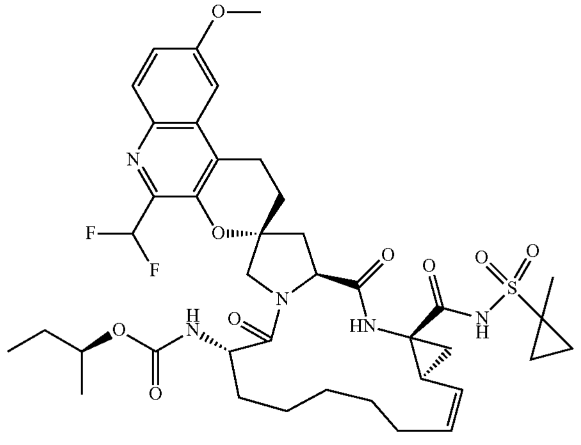 I-444 | (2S)-butan-2-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 816.2 (K+ salt) |
| 445 | 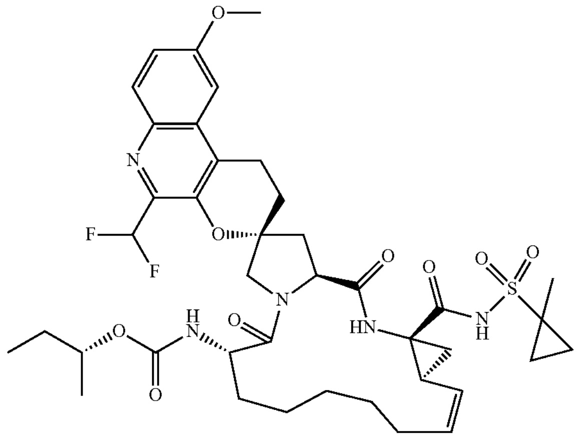 I-445 | (2R)-butan-2-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 816.2 (K+ salt) |

TABLE 1-continued

| Compounds of Examples 68-526 | | | | |
|---|---|---|---|---|
| Ex. No. | Structure | Name | Proc. | LR-MS (M + H) |
| 446 | 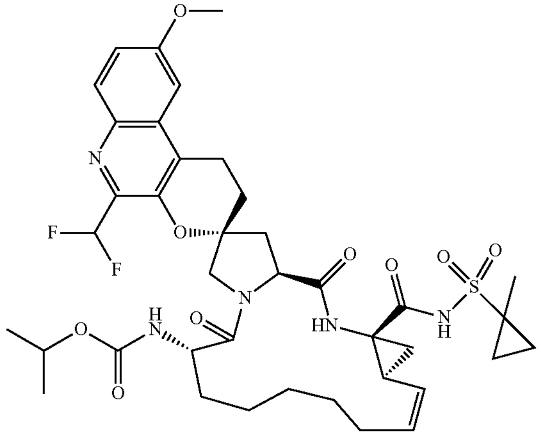 I-446 | propan-2-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 802.2 |
| 447 | 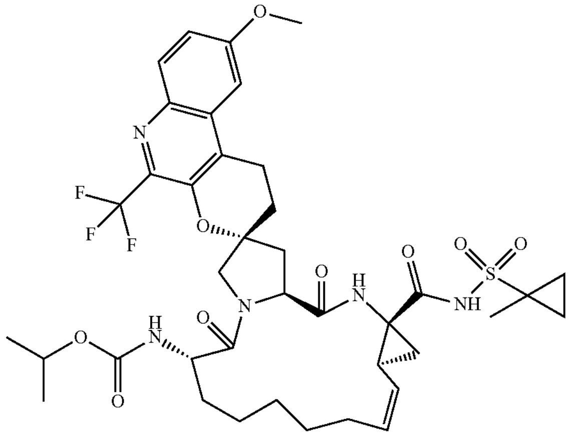 I-447 | propan-2-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 820.8 |

TABLE 1-continued

| Compounds of Examples 68-526 | | | | |
|---|---|---|---|---|
| Ex. No. | Structure | Name | Proc. | LR-MS (M + H) |
| 448 | 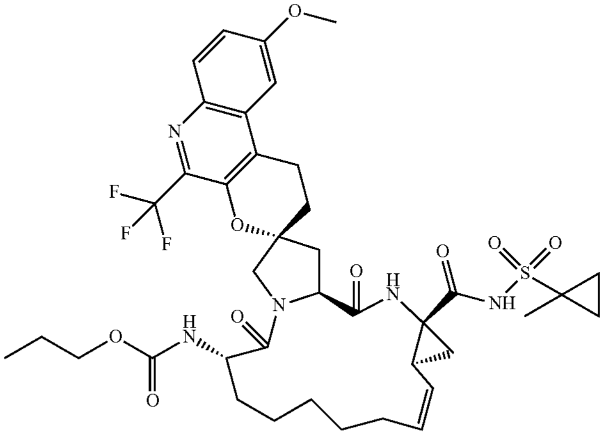 I-448 | propyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 820.3 |
| 449 | 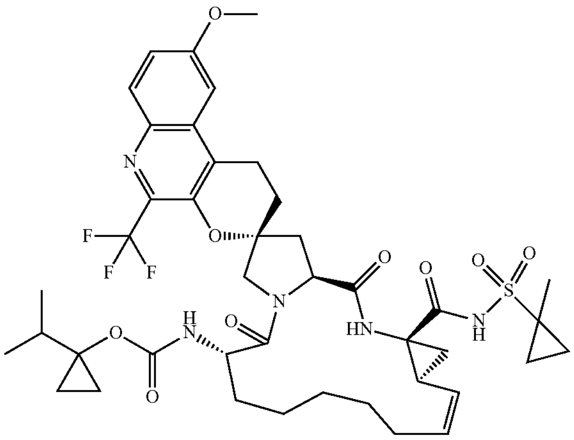 I-449 | 1-(propan-2-yl)cyclopropyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 860.34 |

TABLE 1-continued

| Compounds of Examples 68-526 | | | | |
|---|---|---|---|---|
| Ex. No. | Structure | Name | Proc. | LR-MS (M + H) |
| 450 | 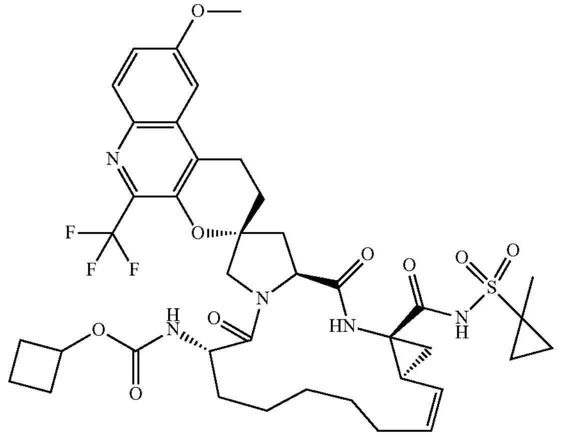 I-450 | cyclobutyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 832.3 |
| 451 | 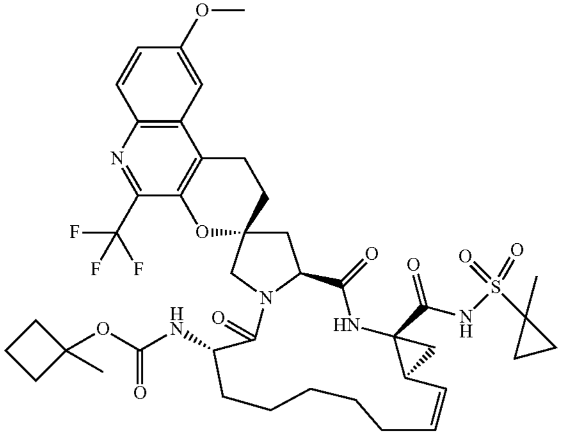 I-451 | 1-methylcyclobutyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 846.5 |

TABLE 1-continued

| Compounds of Examples 68-526 | | | | |
|---|---|---|---|---|
| Ex. No. | Structure | Name | Proc. | LR-MS (M + H) |
| 452 | 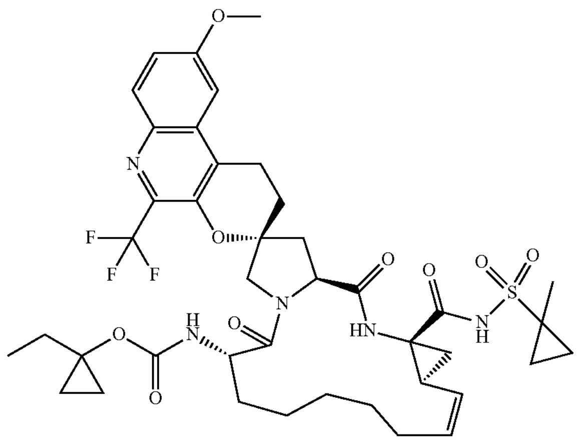 I-452 | 1-ethylcyclopropyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 846.6 |
| 453 | 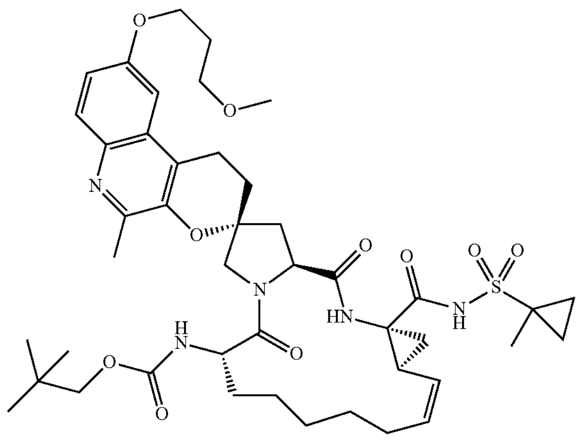 I-453 | 2,2-dimethylpropyl [(2R,6S,12Z,13aS,14aR,16aS)-9'-(3-methoxypropoxy)-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 1, 7, 50, 51, 6 | 852.4 |

TABLE 1-continued

| Compounds of Examples 68-526 | | | | |
|---|---|---|---|---|
| Ex. No. | Structure | Name | Proc. | LR-MS (M + H) |
| 454 | 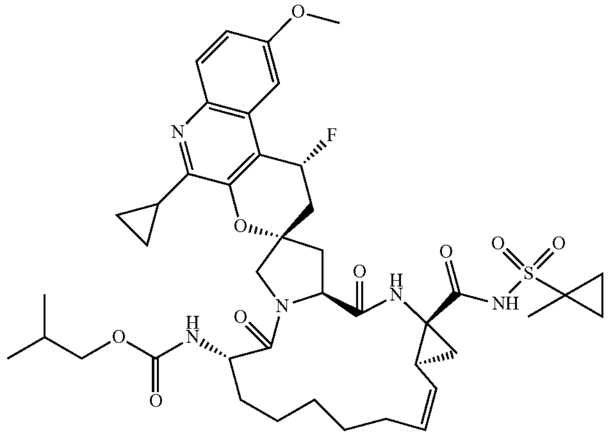 I-454 | 2-methylpropyl [(1'R,2S,6S,12Z,13aS,14aR,16aS)-5'-cyclopropyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 824.2 (K+ salt) |
| 455 | 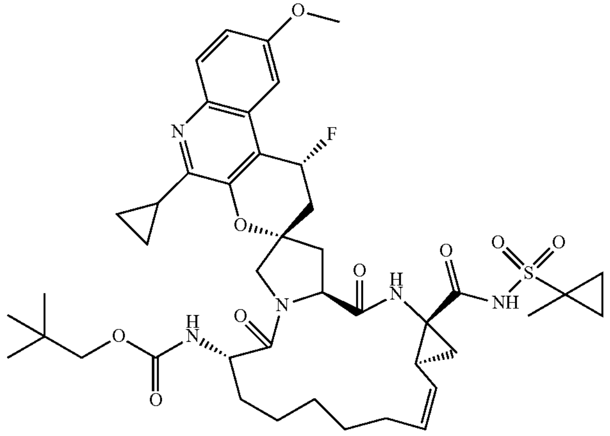 I-455 | 2,2-dimethylpropyl [(1'R,2S,6S,12Z,13aS,14aR,16aS)-5'-cyclopropyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 838.2 (K+ salt) |

TABLE 1-continued

| Compounds of Examples 68-526 | | | | |
|---|---|---|---|---|
| Ex. No. | Structure | Name | Proc. | LR-MS (M + H) |
| 456 | 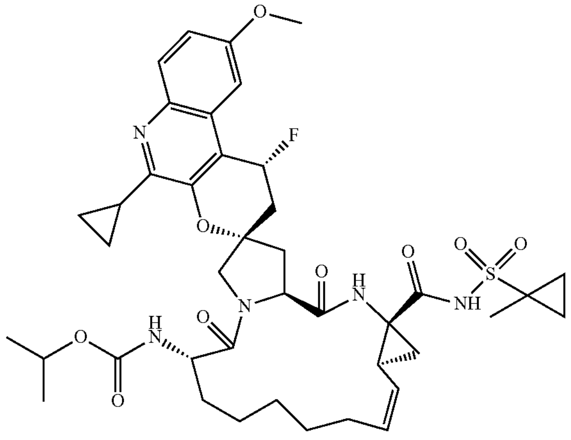 I-456 | propan-2-yl [(1'R,2S,6S,12Z,13aS,14aR,16aS)-5'-cyclopropyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 810.2 (K+ salt) |
| 457 | 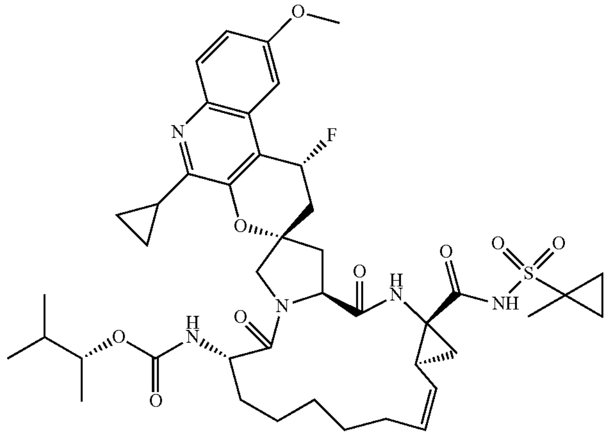 I-457 | (2R)-3-methylbutan-2-yl [(1'R,2S,6S,12Z,13aS,14aR,16aS)-5'-cyclopropyl-1'-fluoro-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 17 | 838.2 (K+ salt) |

TABLE 1-continued

| Compounds of Examples 68-526 | | | | |
|---|---|---|---|---|
| Ex. No. | Structure | Name | Proc. | LR-MS (M + H) |
| 458 | 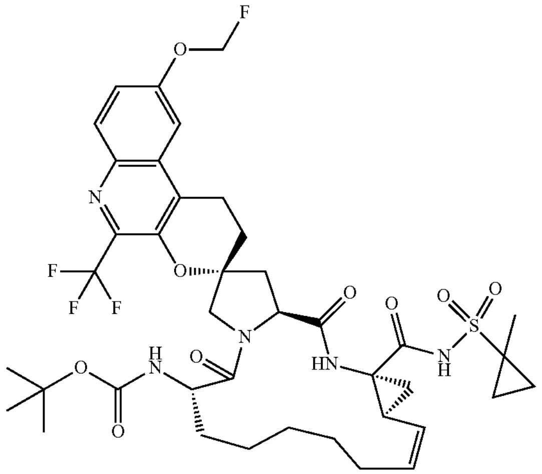 I-458 | tert-butyl [(2R,6S,12Z,13aS,14aR,16aS)-9'-(fluoromethoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7 | 852.4 |
| 459 | 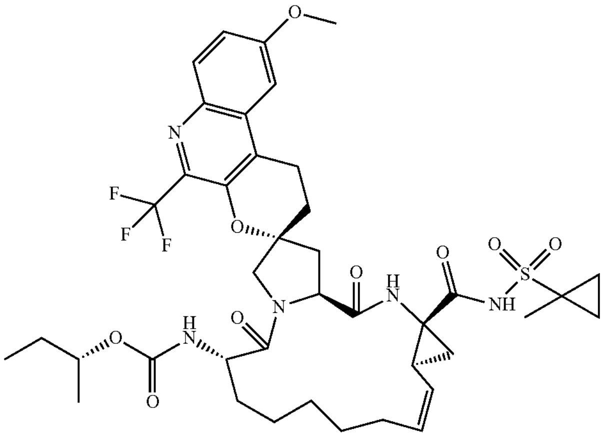 I-459 | (2R)-butan-2-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 834.8 (K+ salt) |

TABLE 1-continued

| Compounds of Examples 68-526 | | | | |
|---|---|---|---|---|
| Ex. No. | Structure | Name | Proc. | LR-MS (M + H) |
| 460 | 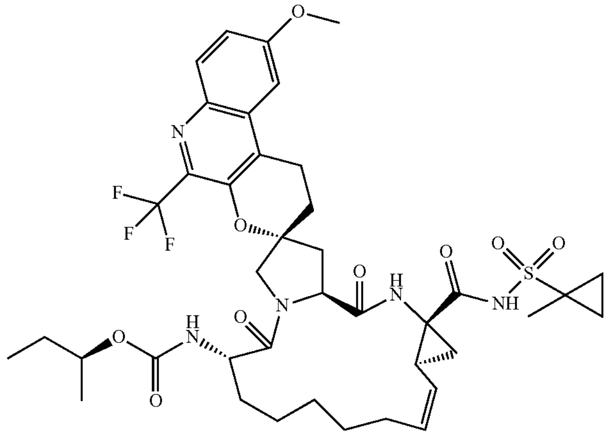 I-460 | (2S)-butan-2-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 834.8 (K+ salt) |
| 461 | 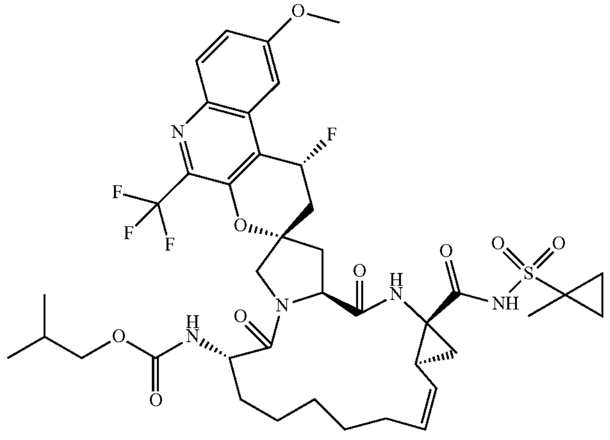 I-461 | 2-methylpropyl [(1'R,2S,6S,12Z,13aS,14aR,16aS)-1'-fluoro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 3, 35 | 852.26 |

TABLE 1-continued

| Compounds of Examples 68-526 | | | | |
|---|---|---|---|---|
| Ex. No. | Structure | Name | Proc. | LR-MS (M + H) |
| 462 | 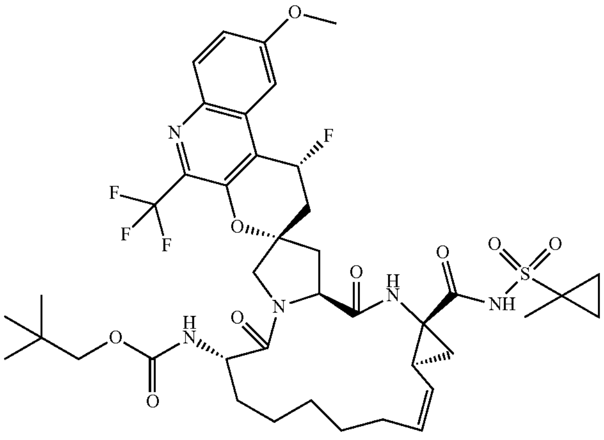 I-462 | 2,2-dimethylpropyl [(1'R,2S,6S,12Z,13aS,14aR,16aS)-1'-fluoro-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 866 |
| 463 | 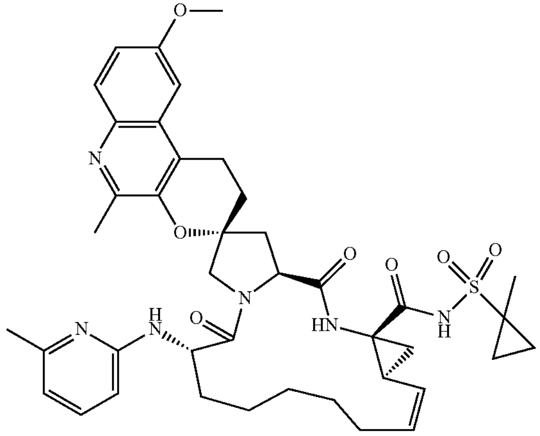 I-463 | (2R,6S,12Z,13aS,14aR,16aS)-9'-methoxy-5'-methyl-N-[(1-methylcyclopropyl)sulfonyl]-6-[(6-methylpyridin-2-yl)amino]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 57 | 771.3 |

TABLE 1-continued

Compounds of Examples 68-526

| Ex. No. | Structure | Name | Proc. | LR-MS (M + H) |
|---|---|---|---|---|
| 464 | 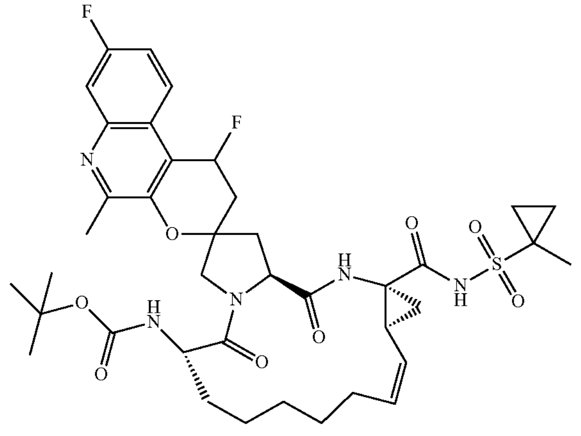 I-464 | tert-butyl [(6S,12Z,13aS,14aR,16aS)-1',8'-difluoro-5'-methyl-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 25 | 786.2 |
| 465 | 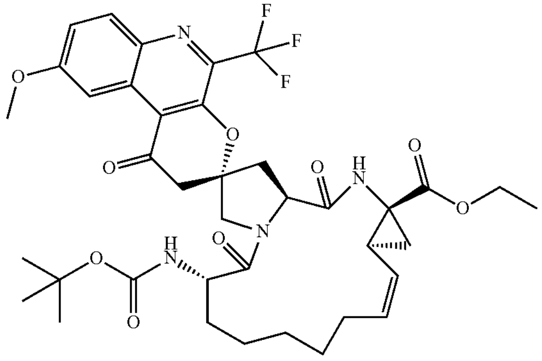 I-465 | ethyl (2S,6S,12Z,13aS,14aR,16aS)-6-[(tert-butoxycarbonyl)amino]-9'-methoxy-1',5,16-trioxo-5'-(trifluoromethyl)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxylate | 5 | — |

TABLE 1-continued

| Compounds of Examples 68-526 | | | | |
|---|---|---|---|---|
| Ex. No. | Structure | Name | Proc. | LR-MS (M + H) |
| 466 | 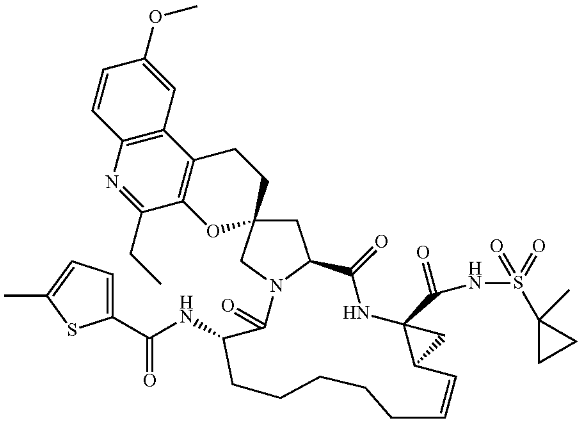 I-466 | (2R,6S,12Z,13aS,14aR,16aS)-5'-ethyl-9'-methoxy-N-[(1-methylcyclopropyl)sulfonyl]-6-{[(5-methylthiophen-2-yl)carbonyl]amino}-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 818.35 |
| 467 | 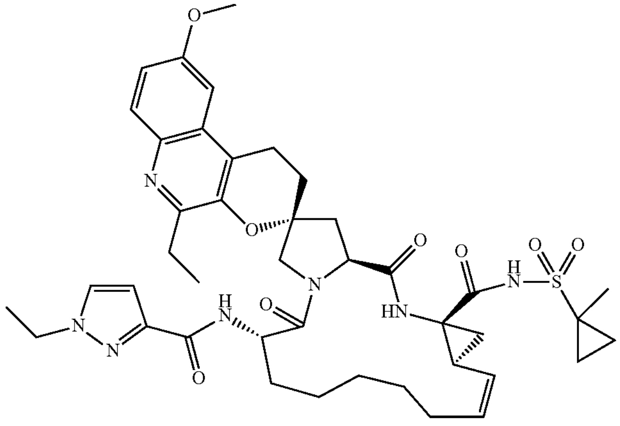 I-467 | (2R,6S,12Z,13aS,14aR,16aS)-5'-ethyl-6-{[(1-ethyl-1H-pyrazol-3-yl)carbonyl]amino}-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 816.34 |

TABLE 1-continued

| Compounds of Examples 68-526 | | | | |
|---|---|---|---|---|
| Ex. No. | Structure | Name | Proc. | LR-MS (M + H) |
| 468 | 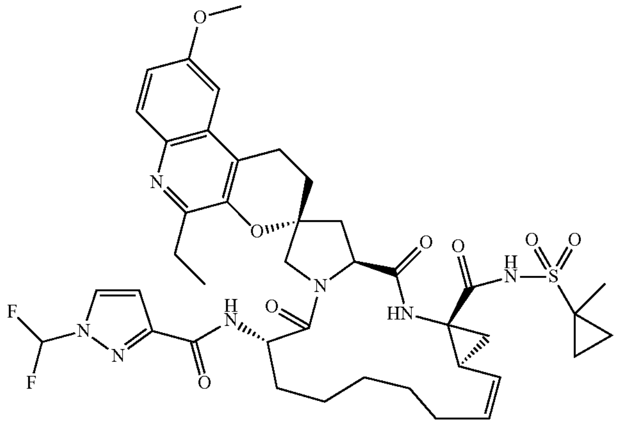 I-468 | (2R,6S,12Z,13aS,14aR,16aS)-6-({[1-(difluoromethyl)-1H-pyrazol-3-yl]carbonyl}amino)-5'-ethyl-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 838.03 |
| 469 | 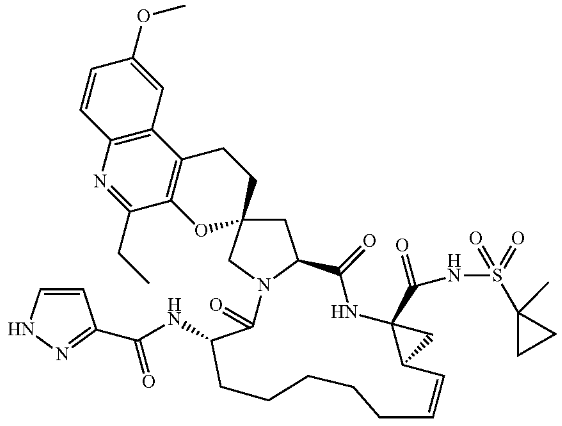 I-469 | (2R,6S,12Z,13aS,14aR,16aS)-5'-ethyl-9'-methoxy-N-[(1-methylcyclopropyl)sulfonyl]-5,16-dioxo-6-[(1H-pyrazol-3-ylcarbonyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 788.06 |

TABLE 1-continued
| Compounds of Examples 68-526 | | | | |
|---|---|---|---|---|
| Ex. No. | Structure | Name | Proc. | LR-MS (M + H) |
| 470 | 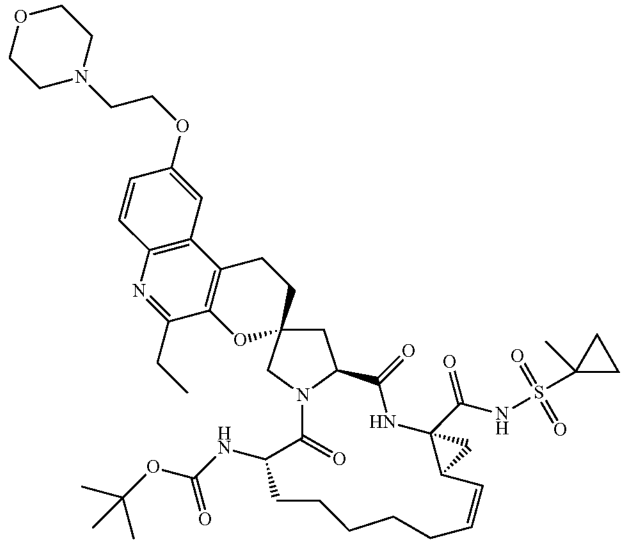 I-470 | tert-butyl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51 | 893.29 |

TABLE 1-continued

| Compounds of Examples 68-526 | | | | |
|---|---|---|---|---|
| Ex. No. | Structure | Name | Proc. | LR-MS (M + H) |
| 471 | 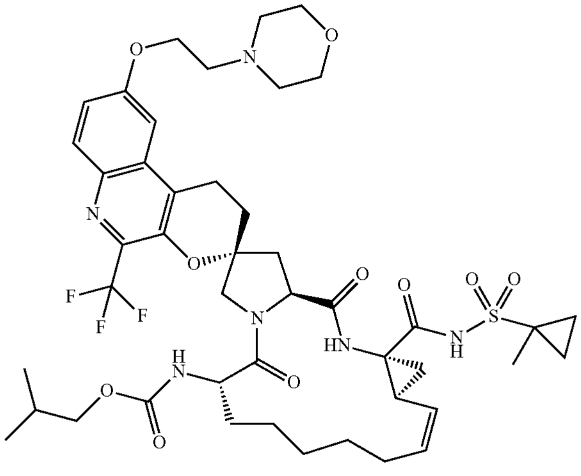 I-471 | 2-methylpropyl [(2R,6S,12Z,13aS,14aR,16aS)-14a-{[(1-methylcyclopropyl)sulfonyl]carbamoyl}-9'-[2-(morpholin-4-yl)ethoxy]-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7 | 933.59 (HCl salt) |
| 472 | 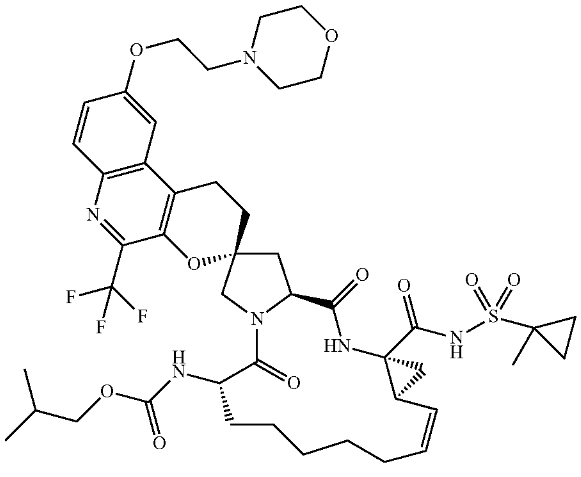 I-472 | 2,2-dimethylpropyl [(2R,6S,12Z,13aS,14aR,16aS)-14a-{[(1-methylcyclopropyl)sulfonyl]carbamoyl}-9'-[2-(morpholin-4-yl)ethoxy]-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7 | 947.42 (HCl salt) |

TABLE 1-continued
| Compounds of Examples 68-526 | | | | |
|---|---|---|---|---|
| Ex. No. | Structure | Name | Proc. | LR-MS (M + H) |
| 473 | 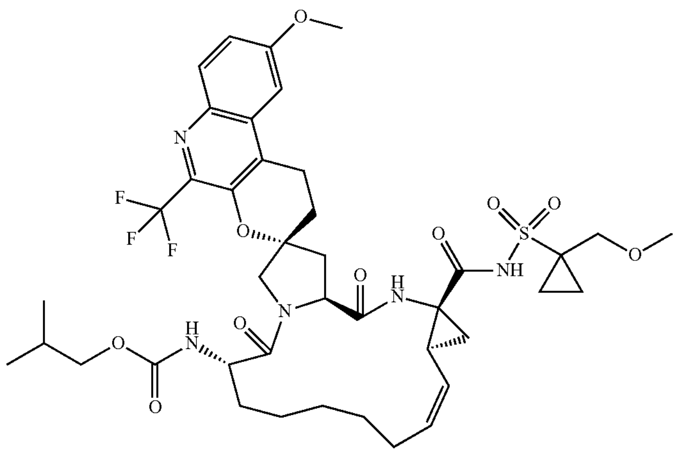 I-473 | 2-methylpropyl [(2R,6S,12Z,13aS,14aR,16aS)-9'-methoxy-14a-({[1-(methoxymethyl)cyclopropyl]sulfonyl}carbamoyl)-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47, 6 | 864.3 |

TABLE 1-continued
| Compounds of Examples 68-526 | | | | |
|---|---|---|---|---|
| Ex. No. | Structure | Name | Proc. | LR-MS (M + H) |
| 474 | 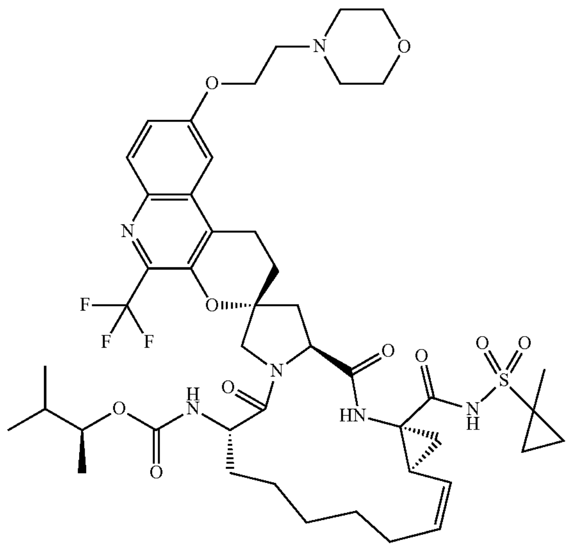 I-474 | (2S)-3-methylbutan-2-yl [(2R,6S,12Z,13aS,14aR,16aS)-14a-{[(1-methylcyclopropyl)sulfonyl]carbamoyl}-9'-[2-(morpholin-4-yl)ethoxy]-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7 | 947.48 |

TABLE 1-continued

| Compounds of Examples 68-526 | | | | |
|---|---|---|---|---|
| Ex. No. | Structure | Name | Proc. | LR-MS (M + H) |
| 475 | 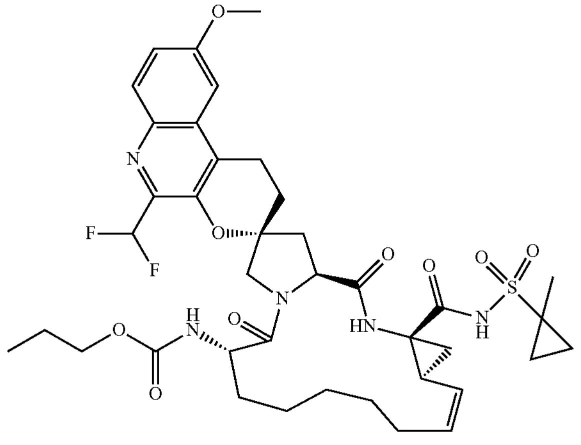 I-475 | propyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 802.41 (K+ salt) |
| 476 | 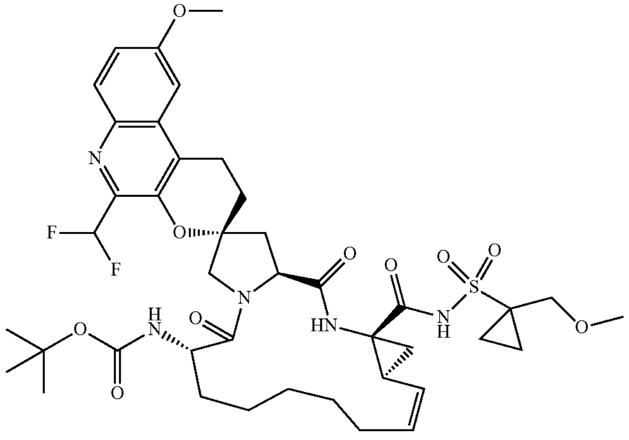 I-476 | tert-butyl [(2R,6S,12Z,13aS,14aR,16aS)-5'-(difluoromethyl)-9'-methoxy-14a-({[1-(methoxymethyl)cyclopropyl]sulfonyl}carbamoyl)-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 846.33 |

TABLE 1-continued

| Compounds of Examples 68-526 | | | | |
|---|---|---|---|---|
| Ex. No. | Structure | Name | Proc. | LR-MS (M + H) |
| 477 | 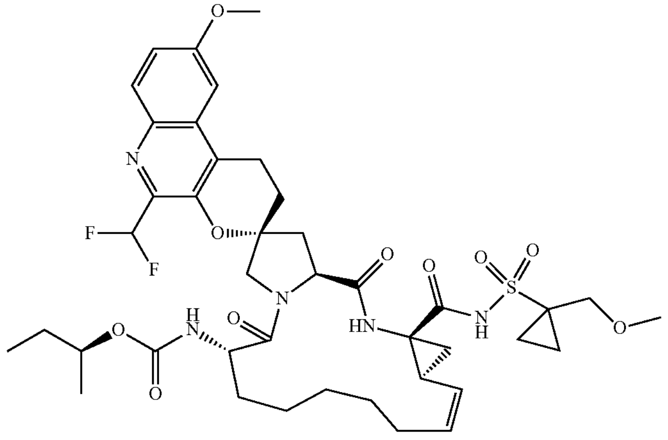 I-477 | (2S)-butan-2-yl [(2R,6S,12Z,13aS,14aR,16aS)-5'-(difluoromethyl)-9'-methoxy-14a-({[1-(methoxymethyl)cyclopropyl]sulfonyl}carbamoyl)-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 846.38 (K+ salt) |
| 478 | 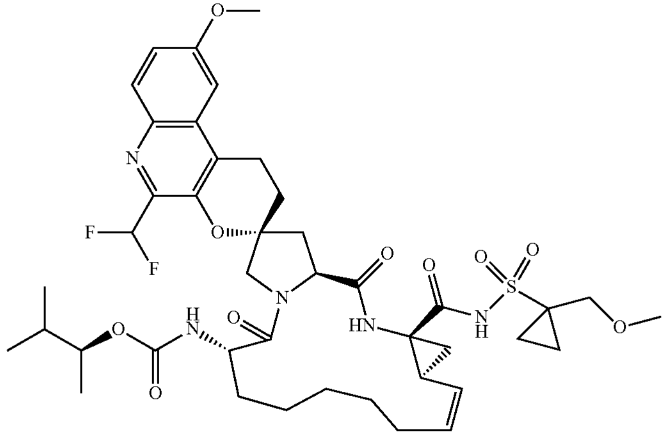 I-478 | (2S)-3-methylbutan-2-yl [(2R,6S,12Z,13aS,14aR,16aS)-5'-(difluoromethyl)-9'-methoxy-14a-({[1-(methoxymethyl)cyclopropyl]sulfonyl}carbamoyl)-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 860.38 |

TABLE 1-continued

| Compounds of Examples 68-526 | | | | |
|---|---|---|---|---|
| Ex. No. | Structure | Name | Proc. | LR-MS (M + H) |
| 479 | 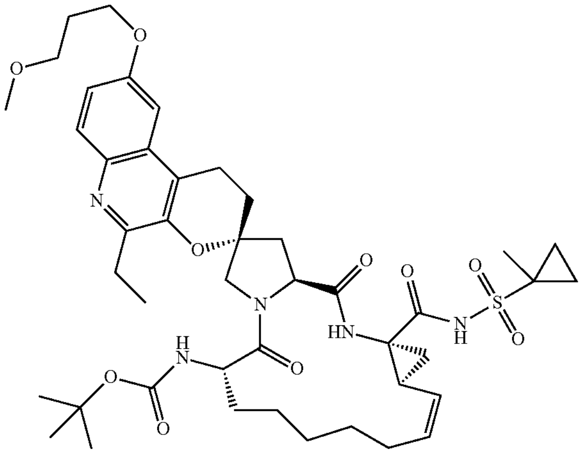 I-479 | tert-butyl [(2R,6S,12Z,13aS,14aR,16aS)-5'-ethyl-9'-(3-methoxypropoxy)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56, 30, 51 | 852.25 |
| 480 | 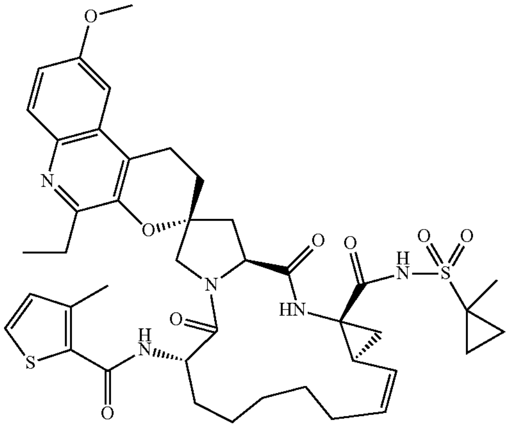 I-480 | (2R,6S,12Z,13aS,14aR,16aS)-5'-ethyl-9'-methoxy-N-[(1-methylcyclopropyl)sulfonyl]-6-{[(3-methylthiophen-2-yl)carbonyl]amino}-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 818.27 |

TABLE 1-continued

| Compounds of Examples 68-526 | | | | |
|---|---|---|---|---|
| Ex. No. | Structure | Name | Proc. | LR-MS (M + H) |
| 481 | 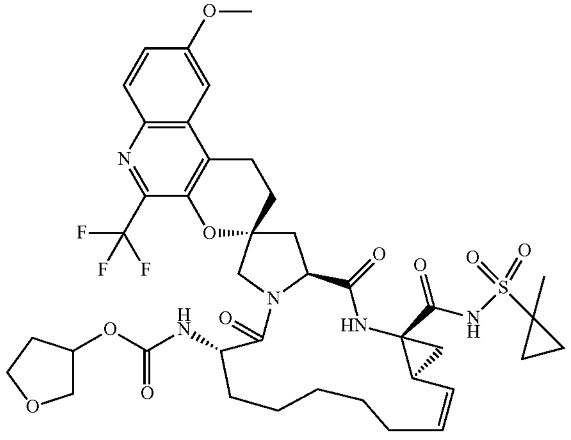 I-481 | tetrahydrofuran-3-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 35 | 848.27 (K+ salt) |
| 482 | 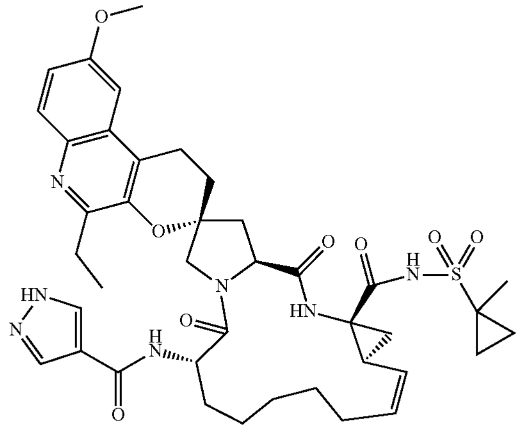 I-482 | (2R,6S,12Z,13aS,14aR,16aS)-5'-ethyl-9'-methoxy-N-[(1-methylcyclopropyl)sulfonyl]-5,16-dioxo-6-[(1H-pyrazol-4-ylcarbonyl)amino]-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 788.24 |

TABLE 1-continued

| Compounds of Examples 68-526 | | | | |
|---|---|---|---|---|
| Ex. No. | Structure | Name | Proc. | LR-MS (M + H) |
| 483 | 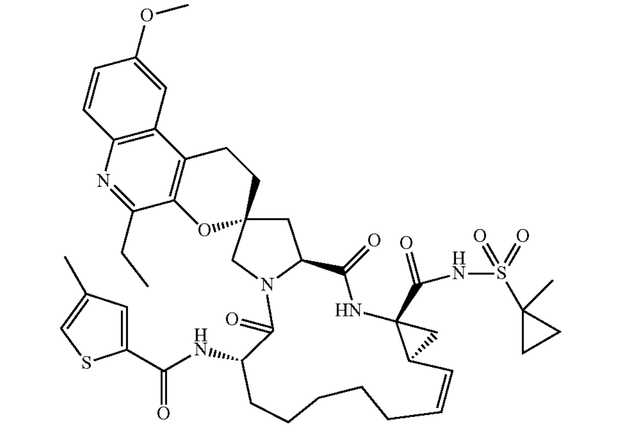 I-483 | (2R,6S,12Z,13aS,14aR,16aS)-5'-ethyl-9'-methoxy-N-[(1-methylcyclopropyl)sulfonyl]-6-{[(4-methylthiophen-2-yl)carbonyl]amino}-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 818.27 |
| 484 | 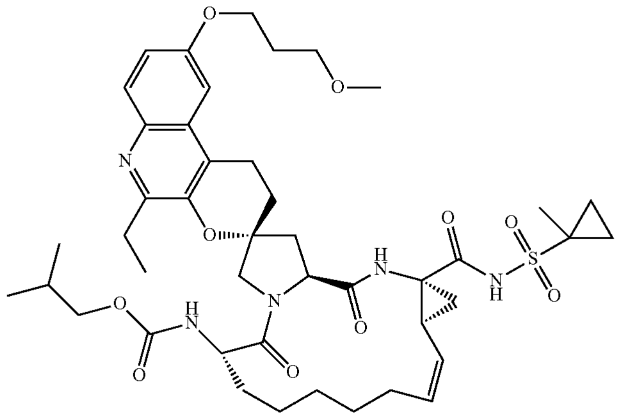 I-484 | 2-methylpropyl [(2R,6S,12Z,13aS,14aR,16aS)-5'-ethyl-9'-(3-methoxypropoxy)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56, 30, 51, 6 | 852.5 (K+ salt) |

TABLE 1-continued

| Compounds of Examples 68-526 | | | | |
|---|---|---|---|---|
| Ex. No. | Structure | Name | Proc. | LR-MS (M + H) |
| 485 | 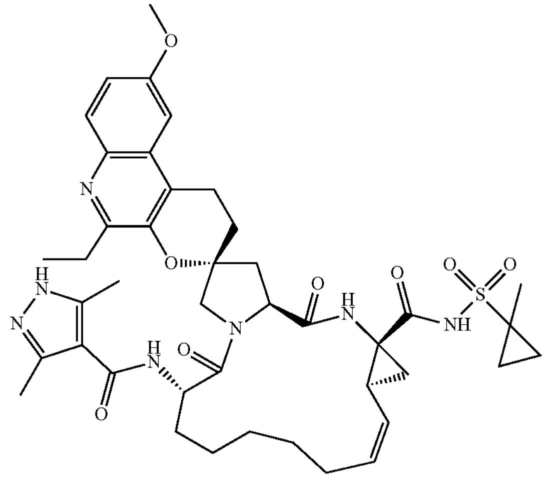 I-485 | (2R,6S,12Z,13aS,14aR,16aS)-6-{[(3,5-dimethyl-1H-pyrazol-4-yl)carbonyl]amino}-5'-ethyl-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 2, 47 | 816.4 |
| 486 | 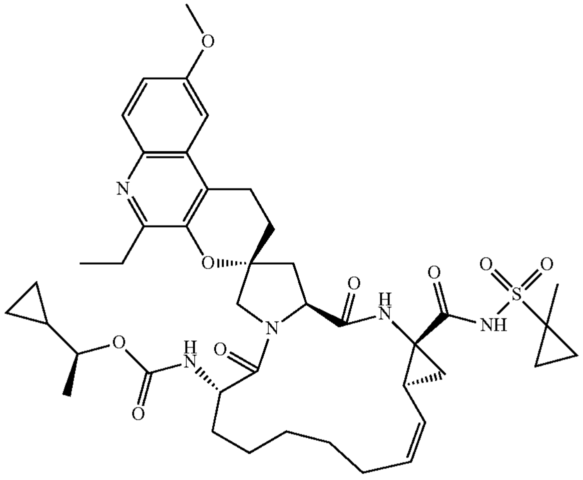 I-486 | (1S)-1-cyclopropylethyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 2, 47 | 806.4 |

TABLE 1-continued

| Compounds of Examples 68-526 | | | | |
|---|---|---|---|---|
| Ex. No. | Structure | Name | Proc. | LR-MS (M + H) |
| 487 | 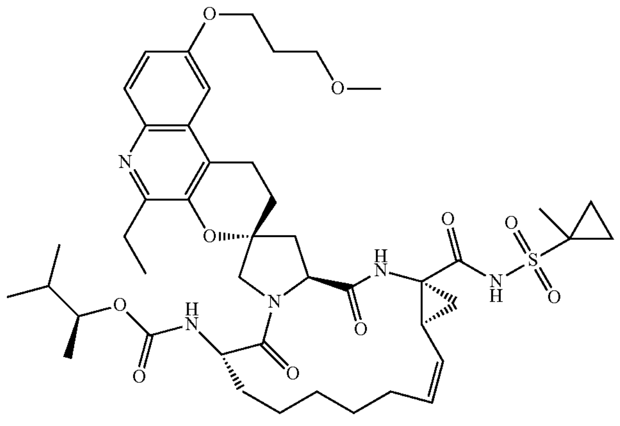 I-487 | (2S)-3-methylbutan-2-yl [(2R,6S,12Z,13aS,14aR,16aS)-5'-ethyl-9'-(3-methoxypropoxy)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56, 30, 51, 35 | 866.5 (K+ salt) |
| 488 | 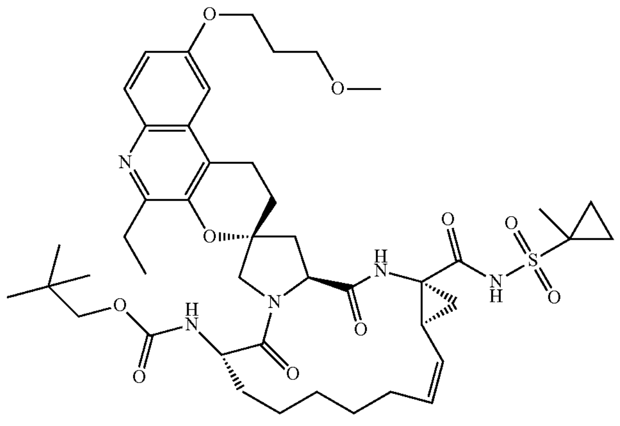 I-488 | 2,2-dimethylpropyl [(2R,6S,12Z,13aS,14aR,16aS)-5'-ethyl-9'-(3-methoxypropoxy)-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 56, 30, 51, 6 | 866.5 (K+ salt) |

TABLE 1-continued

| Compounds of Examples 68-526 | | | | |
|---|---|---|---|---|
| Ex. No. | Structure | Name | Proc. | LR-MS (M + H) |
| 489 | 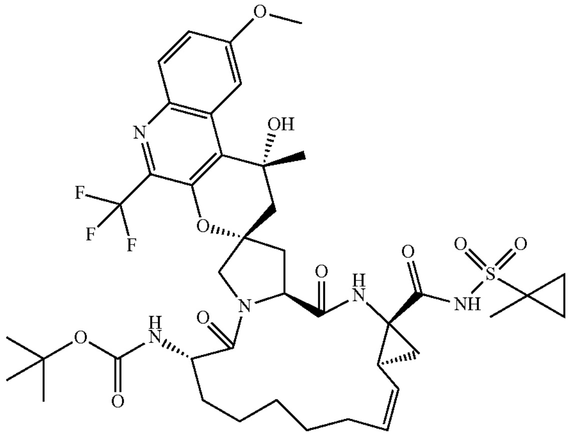 I-489 | tert-butyl [(1'R,2S,6S,12Z,13aS,14aR,16aS)-1'-hydroxy-9'-methoxy-1'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 62 | 865.3 |
| 490 | 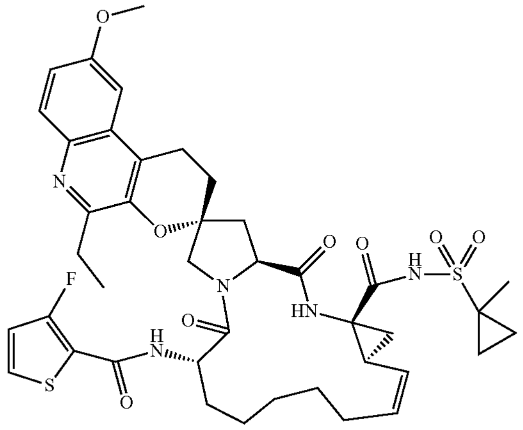 I-490 | (2R,6S,12Z,13aS,14aR,16aS)-5'-ethyl-6-{[(3-fluorothiophen-2-yl)carbonyl]amino}-9'-methoxy-N-[(1-methylcyclopropyl)sulfonyl]-5,16-dioxo-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 47 | 822.23 |

TABLE 1-continued
| Compounds of Examples 68-526 | | | | |
|---|---|---|---|---|
| Ex. No. | Structure | Name | Proc. | LR-MS (M + H) |
| 491 | 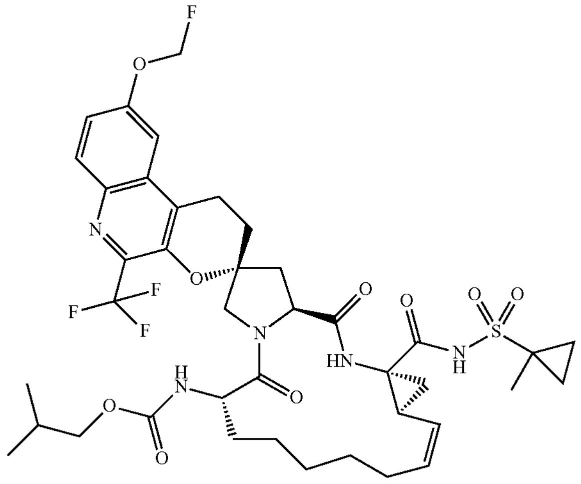 I-491 | 2-methylpropyl [(2R,6S,12Z,13aS,14aR,16aS)-9'-(fluoromethoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7, 50, 6 | 852.4 (K+ salt) |

TABLE 1-continued
| Compounds of Examples 68-526 | | | | |
|---|---|---|---|---|
| Ex. No. | Structure | Name | Proc. | LR-MS (M + H) |
| 492 | 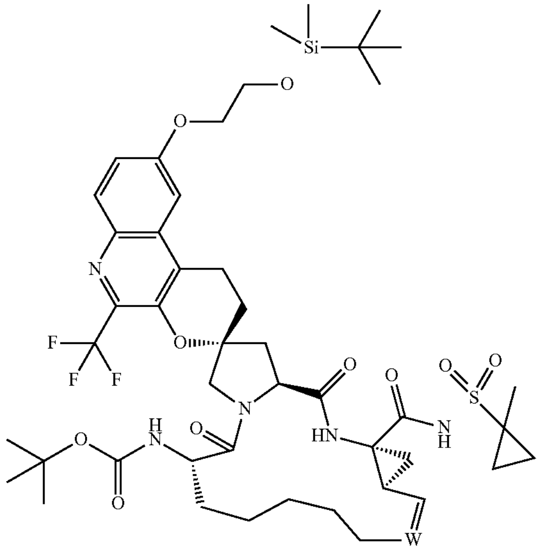 I-492 | tert-butyl [(2R,6S,12Z,13aS,14aR,16aS)-9'-(2-{[tert-butyl(dimethyl)silyl]oxy}ethoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 60 | 978.4 |

TABLE 1-continued

| Compounds of Examples 68-526 | | | | |
|---|---|---|---|---|
| Ex. No. | Structure | Name | Proc. | LR-MS (M + H) |
| 493 | 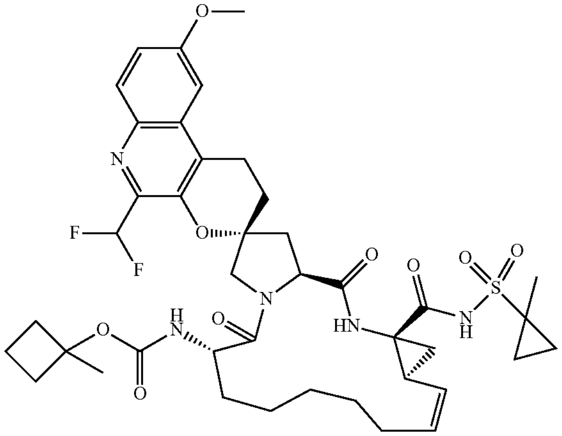 I-493 | 1-methylcyclobutyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 828.33 (K+ salt) |
| 494 | 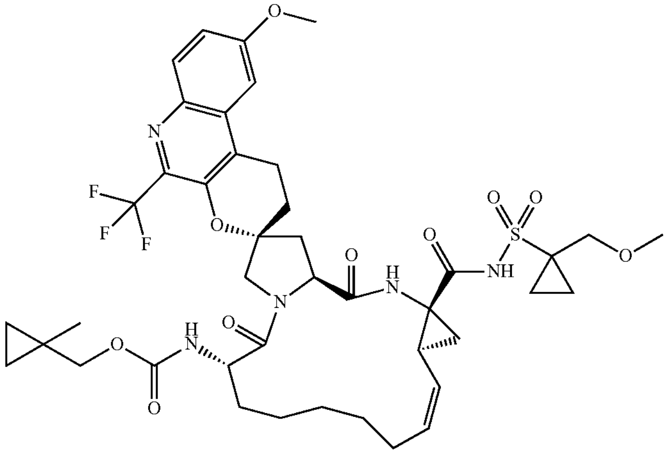 I-494 | (1-methylcyclopropyl)methyl [(2R,6S,12Z,13aS,14aR,16aS)-9'-methoxy-14a-({[1-(methoxymethyl)cyclopropyl] sulfonyl}carbamoyl)-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 49, 41 | 876.4 |

TABLE 1-continued

| Ex. No. | Structure | Name | Proc. | LR-MS (M + H) |
|---|---|---|---|---|
| Compounds of Examples 68-526 | | | | |
| 495 | 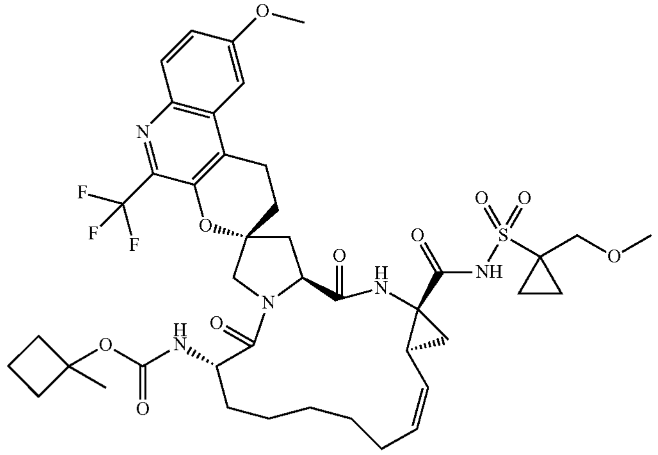 I-495 | 1-methylcyclobutyl [(2R,6S,12Z,13aS,14aR,16aS)-9'-methoxy-14a-({[1-(methoxymethyl)cyclopropyl]sulfonyl}carbamoyl)-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 49, 41 | 876.4 |
| 496 | 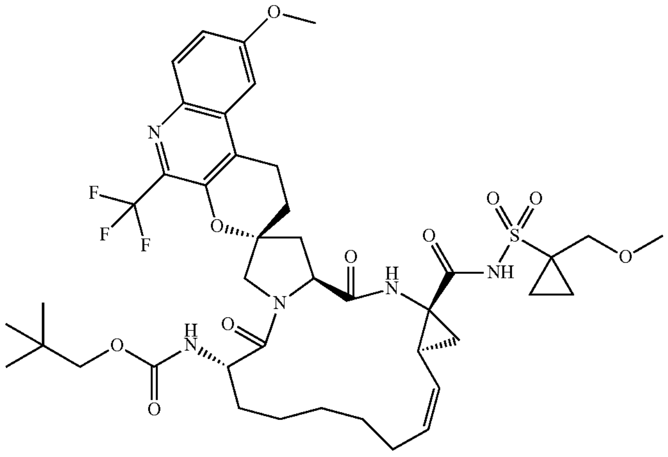 I-496 | 2,2-dimethylpropyl [(2R,65,12Z,13aS,14aR,16aS)-9'-methoxy-14a-({[1-(methoxymethyl)cyclopropyl]sulfonyl}carbamoyl)-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 49, 41 | 878.4 |

TABLE 1-continued

Compounds of Examples 68-526

| Ex. No. | Structure | Name | Proc. | LR-MS (M + H) |
|---|---|---|---|---|
| 497 | 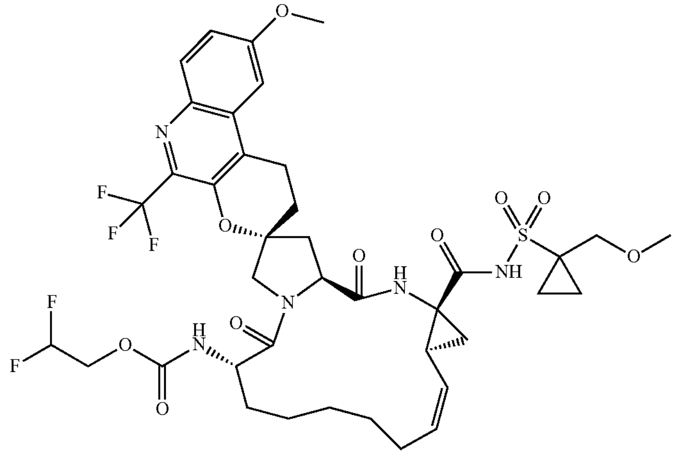 I-497 | 2,2-difluoroethyl [(2R,6S,12Z,13aS,14aR,16aS)-9'-methoxy-14a-({[1-(methoxymethyl)cyclopropyl]sulfonyl}carbamoyl)-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 49, 41 | 872.3 |
| 498 | 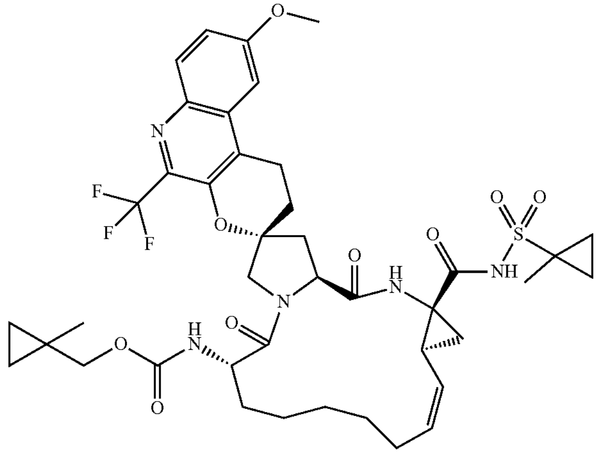 I-498 | (1-methylcyclopropyl)methyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 41 | 846.3 (K+ salt) |

TABLE 1-continued

| Compounds of Examples 68-526 | | | | |
|---|---|---|---|---|
| Ex. No. | Structure | Name | Proc. | LR-MS (M + H) |
| 499 | 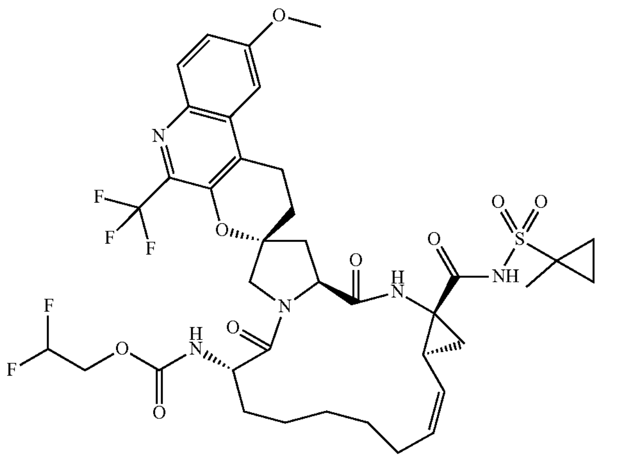 I-499 | 2,2-difluoroethyl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 41 | 842.3 (K+ salt) |
| 500 | 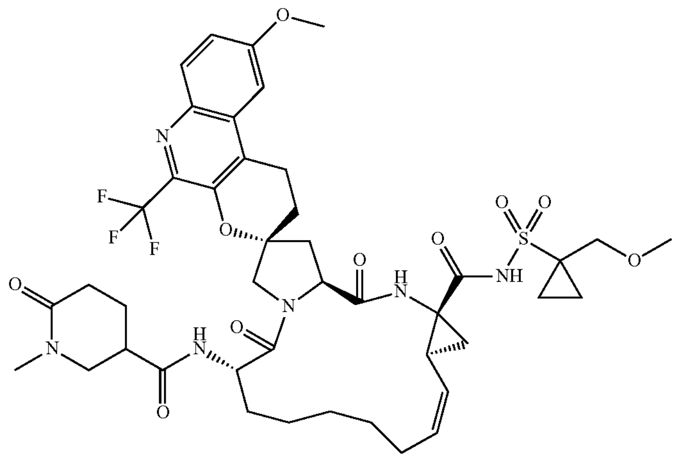 I-500 | (2R,6S,12Z,13aS,14aR,16aS)-9'-methoxy-N-{[1-(methoxymethyl)cyclopropyl]sulfonyl}-6-{[(1-methyl-6-oxopiperidin-3-yl)carbonyl]amino}-5,16-dioxo-5'-(trifluoromethyl)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 49 | 903.3 |

TABLE 1-continued
| Compounds of Examples 68-526 | | | | |
|---|---|---|---|---|
| Ex. No. | Structure | Name | Proc. | LR-MS (M + H) |
| 501 | 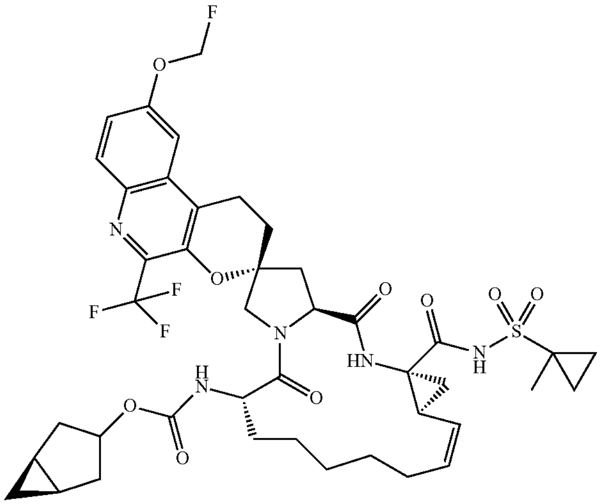 I-501 | (1R,5S)-bicyclo[3.1.0]hex-3-yl [(2R,6S,12Z,13aS,14aR,16aS)-9'-(fluoromethoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7, 50, 35 | 876.28 (K+ salt) |

TABLE 1-continued

| Compounds of Examples 68-526 | | | | |
|---|---|---|---|---|
| Ex. No. | Structure | Name | Proc. | LR-MS (M + H) |
| 502 | 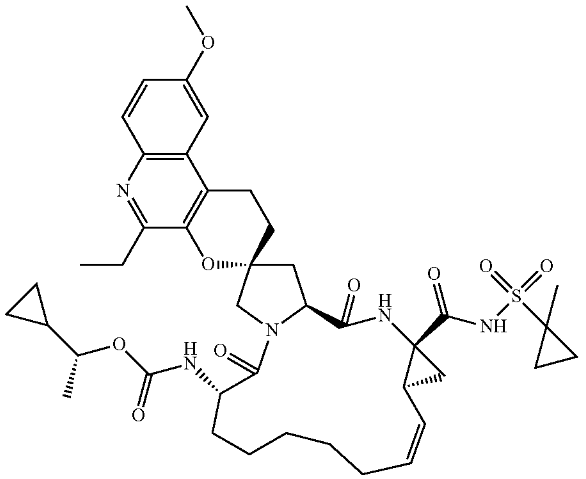 I-502 | (1R)-1-cyclopropylethyl [(2R,6S,12Z,13aS,14aR,16aS)-5'-ethyl-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 47 | 806.4 |
| 503 | 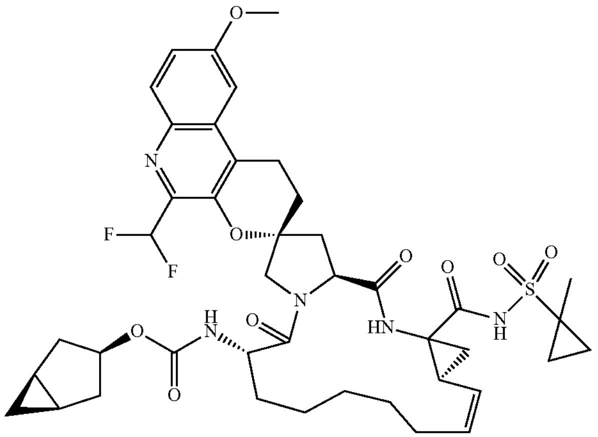 I-503 | (1R,3r,5S)-bicyclo[3.1.0]hex-3-yl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 840.28 (K+ salt) |

TABLE 1-continued

| Compounds of Examples 68-526 | | | | |
|---|---|---|---|---|
| Ex. No. | Structure | Name | Proc. | LR-MS (M + H) |
| 504 | 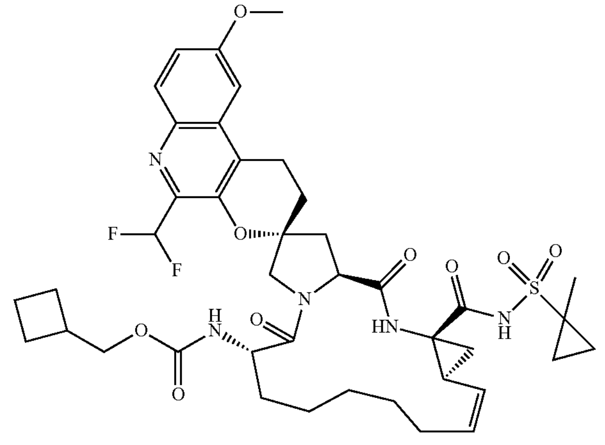 I-504 | cyclobutylmethyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 828.29 (K+ salt ) |
| 505 | 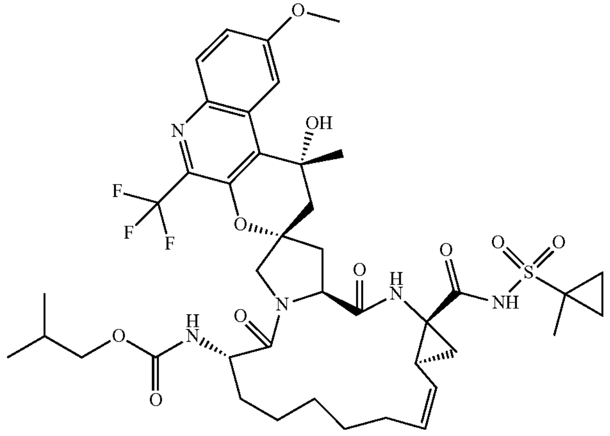 I-505 | 2-methylpropyl [(1'R,2S,6S,12Z,13aS,14aR,16aS)-1'-hydroxy-9'-methoxy-1'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 62, | 865.2 |

TABLE 1-continued

| Compounds of Examples 68-526 | | | | |
|---|---|---|---|---|
| Ex. No. | Structure | Name | Proc. | LR-MS (M + H) |
| 506 | 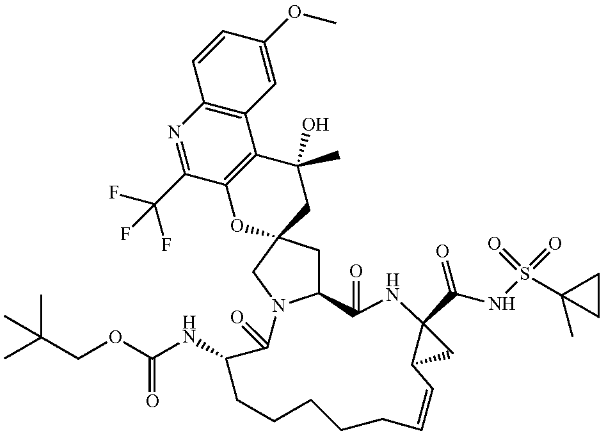 I-506 | 2,2-dimethylpropyl [(1'R,2S,6S,12Z,13aS,14aR,16aS)-1'-hydroxy-9'-methoxy-1'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 62 | 879.3 |
| 507 | 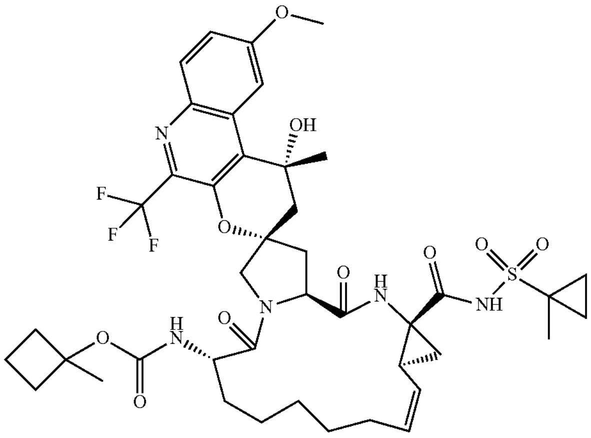 I-507 | 1-methylcyclobutyl [(1'R,2S,6S,12Z,13aS,14aR,16aS)-1'-hydroxy-9'-methoxy-1'-methyl-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 62 | 876.2 |

TABLE 1-continued

| Ex. No. | Structure | Name | Proc. | LR-MS (M + H) |
|---|---|---|---|---|
| | Compounds of Examples 68-526 | | | |
| 508 | 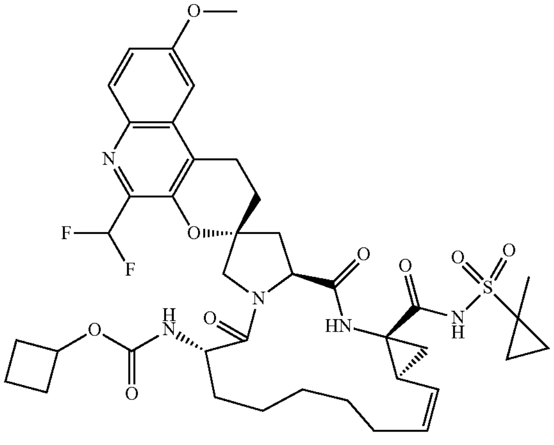 I-508 | cyclobutyl [(2R,6S,12Z,13aS,14aR,16aS)-5'-(difluoromethyl)-9'-methoxy-14a-{[(1-methylcyclopropyl)sulfonyl]carbamoyl}-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 10 | 814.31 (K+ salt) |
| 509 | 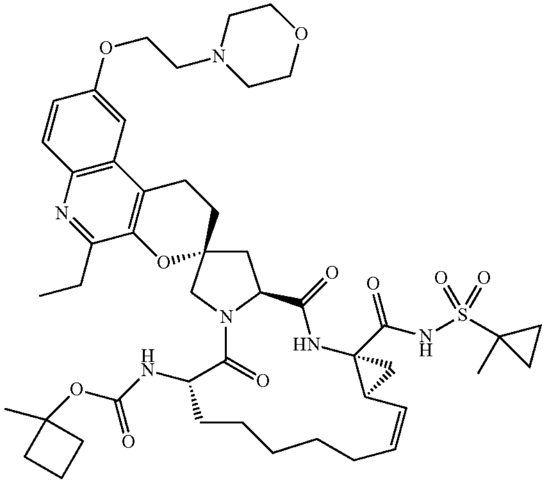 I-509 | 1-methylcyclobutyl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 528 | 905.36 (K+ salt) |

TABLE 1-continued

| Compounds of Examples 68-526 | | | | |
|---|---|---|---|---|
| Ex. No. | Structure | Name | Proc. | LR-MS (M + H) |
| 510 | 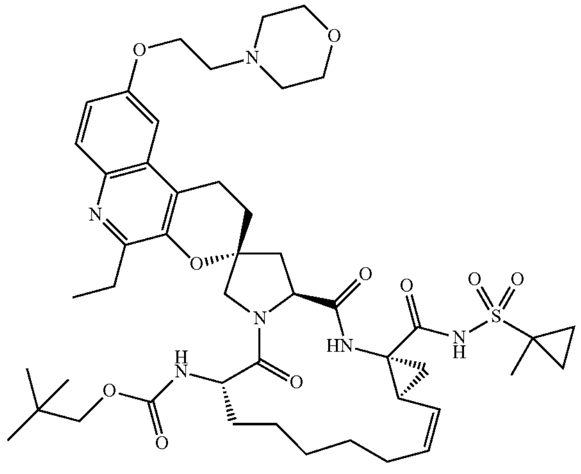 I-510 | 2,2-dimethylpropyl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 6 | 907.58 (K+ salt) |
| 511 | 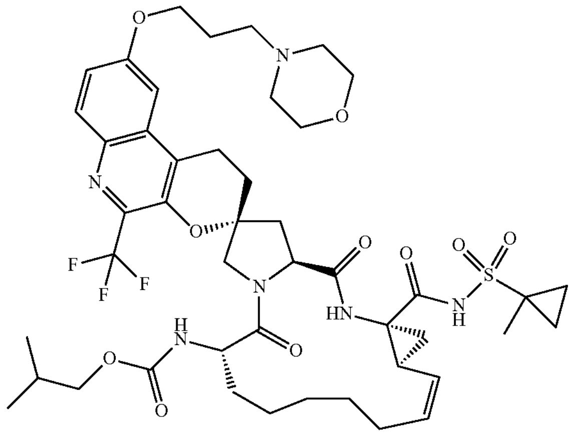 I-511 | 2-methylpropyl [(2R,6S,12Z,13aS,14aR,16aS)-14a-{[(1-methylcyclopropyl)sulfonyl]carbamoyl}-9'-[3-(morpholin-4-yl)propoxy]-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 7, 50 | 947.32 |

TABLE 1-continued

| Compounds of Examples 68-526 | | | | |
|---|---|---|---|---|
| Ex. No. | Structure | Name | Proc. | LR-MS (M + H) |
| 512 | 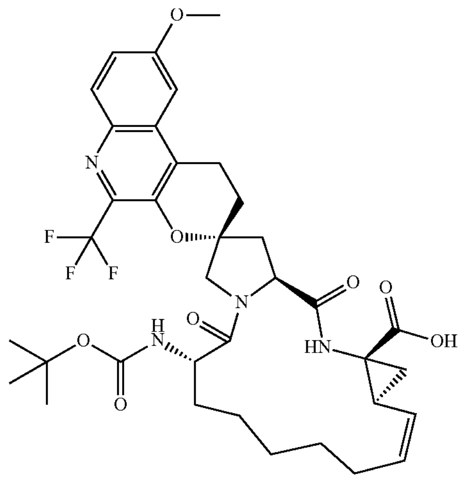 I-512 | (2R,6S,12Z,13aS,14aR,16aS)-6-[(tert-butoxycarbonyl)amino]-9'-methoxy-5,16-dioxo-5'-(trifluoromethyl)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxylic acid | 5 | 716.2 |
| 513 | 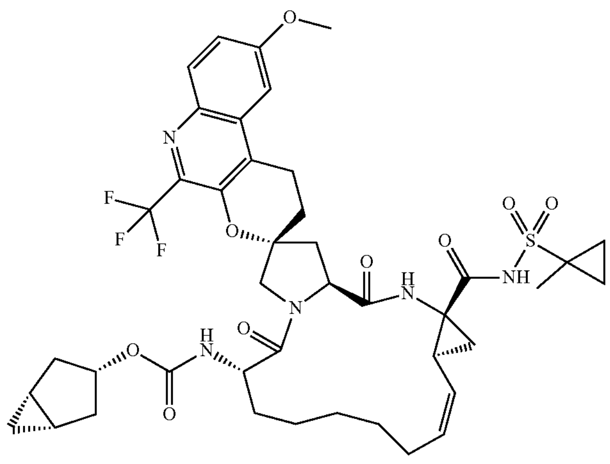 I-513 | (1R,3r,5S)-bicyclo[3.1.0]hex-3-yl [(2R,6S,12Z,13aS,14aR,16aS)-9'-methoxy-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 5, 41 | 858.3 |

TABLE 1-continued

| Compounds of Examples 68-526 | | | | |
|---|---|---|---|---|
| Ex. No. | Structure | Name | Proc. | LR-MS (M + H) |
| 514 | 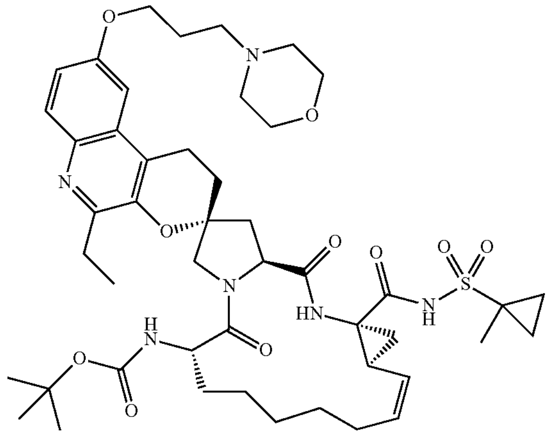 I-514 | tert-butyl {(2R,6S,12Z,13aS,14aR,16aS)-5'-ethyl-14a-{[(1-methylcyclopropyl)sulfonyl]carbamoyl}-9'-[3-(morpholin-4-yl)propoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 6 | 907.4 |
| 515 | 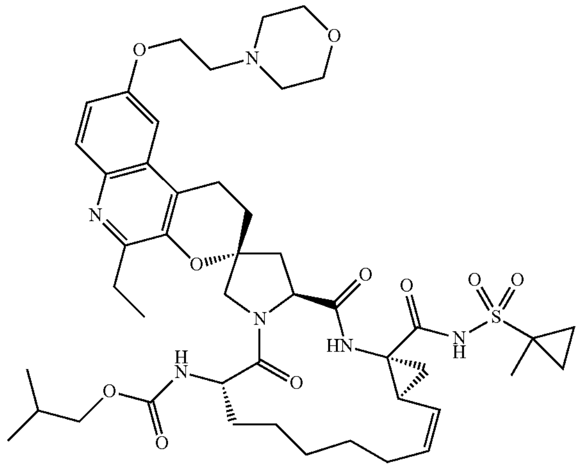 I-515 | 2-methylpropyl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 6 | 893.39 (HCl salt) |

TABLE 1-continued
Compounds of Examples 68-526
| Ex. No. | Structure | Name | Proc. | LR-MS (M + H) |
|---|---|---|---|---|
| 516 | 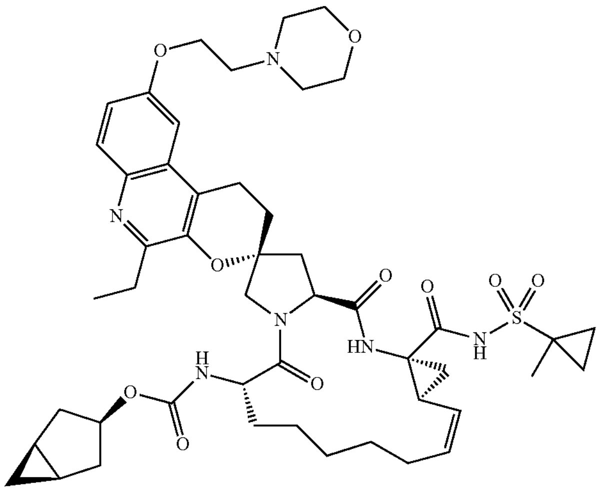 I-516 | (1R,3r,5S)-bicyclo[3.1.0]hex-3-yl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 6 | 917.46 (HCl salt) |

TABLE 1-continued
| Compounds of Examples 68-526 | | | | |
|---|---|---|---|---|
| Ex. No. | Structure | Name | Proc. | LR-MS (M + H) |
| 517 | 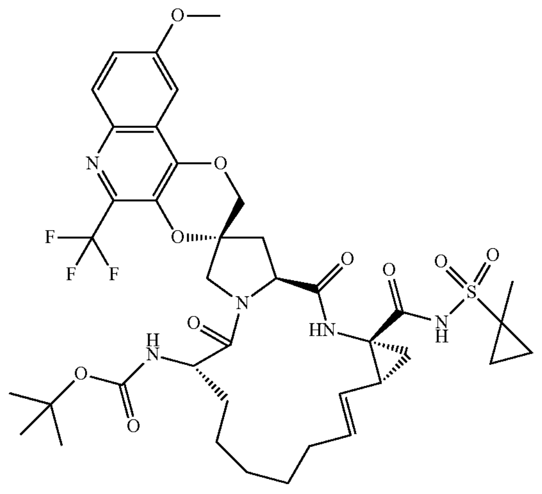 I-517 | tert-butyl [(2R,6S,12E,13aR,14aR,16aS)-9'-methoxy-14a-{[(1-methylcyclopropyl)sulfonyl]carbamoyl}-5,16-dioxo-5'-(trifluoromethyl)-1,5,6,7,8,9,10,11,13a,14,14a,15,16,16a-tetradecahydrospiro[cyclopropa[e]pyrrolo[1,2-a][1,4]diazacyclopentadecine-2,3'-[1,4]dioxino[2,3-c]quinolin]-6-yl]carbamate | 8 | 836.5 |

TABLE 1-continued
| Compounds of Examples 68-526 | | | | |
|---|---|---|---|---|
| Ex. No. | Structure | Name | Proc. | LR-MS (M + H) |
| 518 | 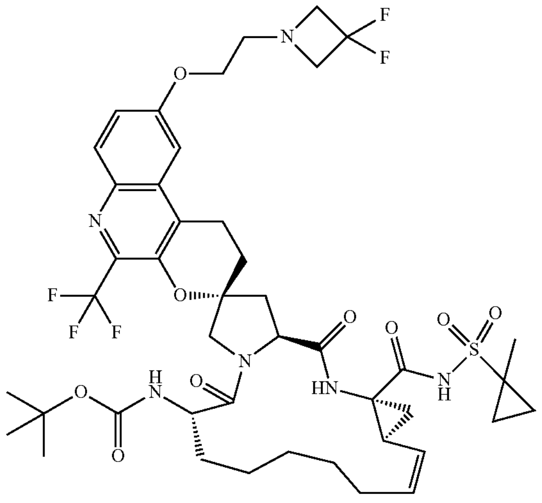 I-518 | tert-butyl [(2R,6S,12Z,13aS,14aR,16aS)-9'-[2-(3,3-difluoroazetidin-1-yl)ethoxy]-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 67 | 939.4 |

TABLE 1-continued

Compounds of Examples 68-526

| Ex. No. | Structure | Name | Proc. | LR-MS (M + H) |
|---|---|---|---|---|
| 519 | 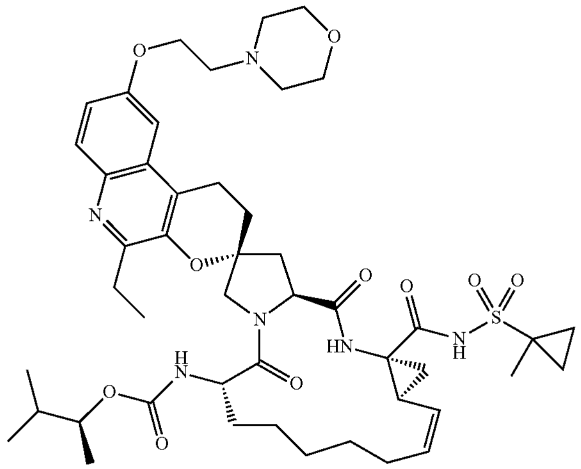 I-519 | (2S)-3-methylbutan-2-yl {(2R,6S,12Z,13aS,14aR,16aS)-5'-ethyl-14a-{[(1-methylcyclopropyl)sulfonyl]carbamoyl}-9'-[2-(morpholin-4-yl)ethoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 35 | 907.6 (HCl salt) |
| 520 | 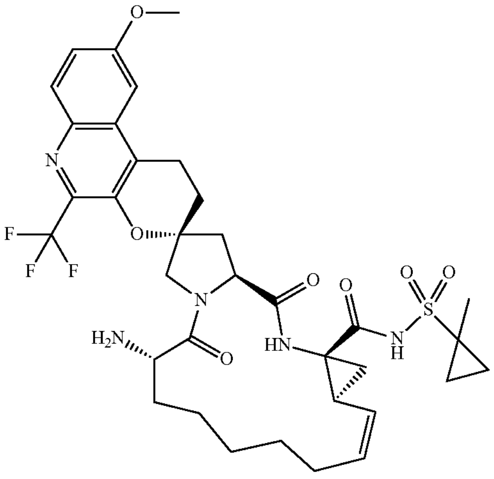 I-520 | (2R,6S,12Z,13aS,14aR,16aS)-6-amino-9'-methoxy-N-[(1-methylcyclopropyl)sulfonyl]-5,16-dioxo-5'-(trifluoromethyl)-1,1',2',6,7,8,9,10,11,13a,14,15,16,16a-tetradecahydrospiro[cyclopropa[e]pyrrolo[1,2-a][1,4]diazacyclopentadecine-2,3'-pyrano[2,3-c]quinoline]-14a(5H)-carboxamide | 6 | — |

TABLE 1-continued

| Compounds of Examples 68-526 | | | | |
|---|---|---|---|---|
| Ex. No. | Structure | Name | Proc. | LR-MS (M + H) |
| 521 | 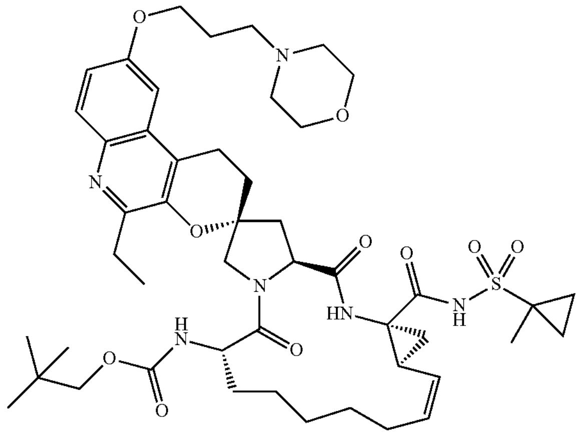 I-521 | 2,2-dimethylpropyl {(2R,6S,12Z,13aS,14aR,16aS)-5'-ethyl-14a-{[(1-methylcyclopropyl)sulfonyl]carbamoyl}-9'-[3-(morpholin-4-yl)propoxy]-5,16-dioxo-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl}carbamate | 56, 30, 51, 35 | 921.68 (HCl salt) |
| 522 | 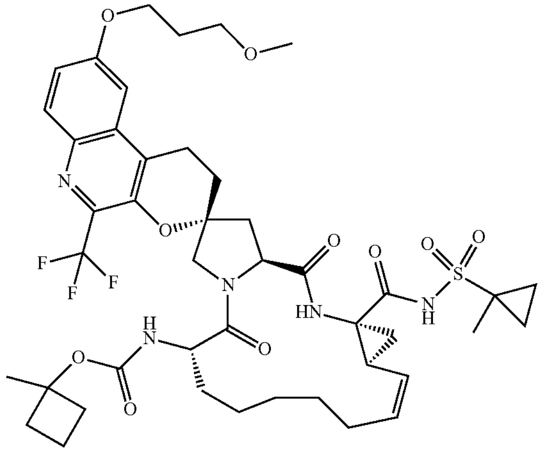 I-522 | 1-methylcyclobutyl [(2R,6S,12Z,13aS,14aR,16aS)-9'-(3-methoxypropoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 51 | 904.4 (K+ salt) |

TABLE 1-continued

| Compounds of Examples 68-526 | | | | |
|---|---|---|---|---|
| Ex. No. | Structure | Name | Proc. | LR-MS (M + H) |
| 523 | 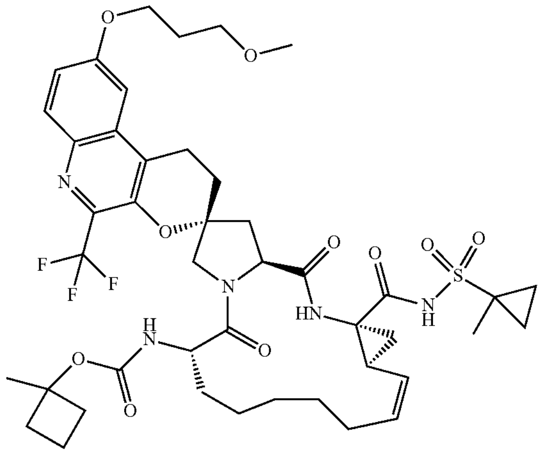 I-523 | 1-methylcyclobutyl [(2R,6S,12Z,13aS,14aR,16aS)-9'-(3-methoxypropoxy)-14a-{[(1-methylcyclopropyl)sulfonyl]carbamoyl}-5,16-dioxo-5'-(trifluoromethyl)-1,1',2',5,6,7,8,9,10,11,13a,14,14a,15,16,16a-hexadecahydrospiro[cyclopropa[e]pyrrolo[1,2-a][1,4]diazacyclopentadecine-2,3'-pyrano[2,3-c]quinolin]-6-yl]carbamate | 51 | 892.38 (K+ salt) |
| 524 | 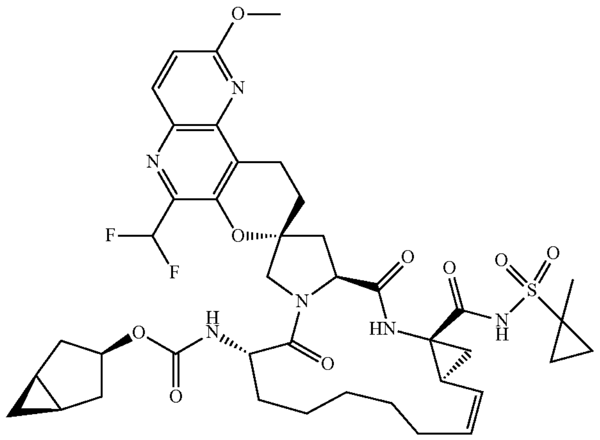 I-524 | (1R,3r,5S)-bicyclo[3.1.0]hex-3-yl [(2R,6S,12Z,13aS,14aR,16aS)-6'-(difluoromethyl)-2'-methoxy-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 12 | 841.45 |

TABLE 1-continued

| Compounds of Examples 68-526 | | | | |
|---|---|---|---|---|
| Ex. No. | Structure | Name | Proc. | LR-MS (M + H) |
| 525 | 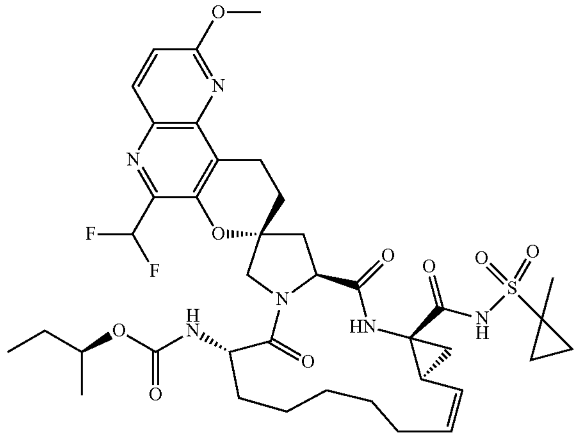 I-525 | (2S)-butan-2-yl [(2R,6S,12Z,13aS,14aR,16aS)-6'-(difluoromethyl)-2'-methoxy-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 12 | 817.46 |
| 526 | 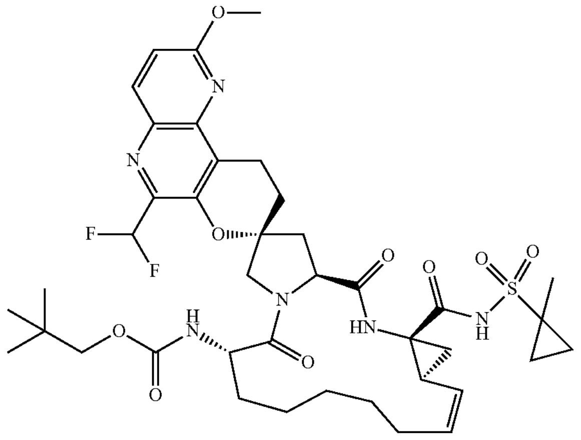 I-526 | 2,2-dimethylpropyl [(2R,6S,12Z,13aS,14aR,16aS)-6'-(difluoromethyl)-2'-methoxy-14a-{[(1-methylcyclopropyl)sulfonyl]carbamoyl}-5,16-dioxo-1,5,6,7,8,9,9',10,10',11,13a,14,14a,15,16,16a-hexadecahydrospiro[cyclopropa[e]pyrrolo[1,2-a][1,4]diazacyclopentadecine-2,8'-pyrano[2,3-c][1,5]naphthyridin]-6-yl]carbamate | 12 | 831.46 |

Example 527

(I-527)

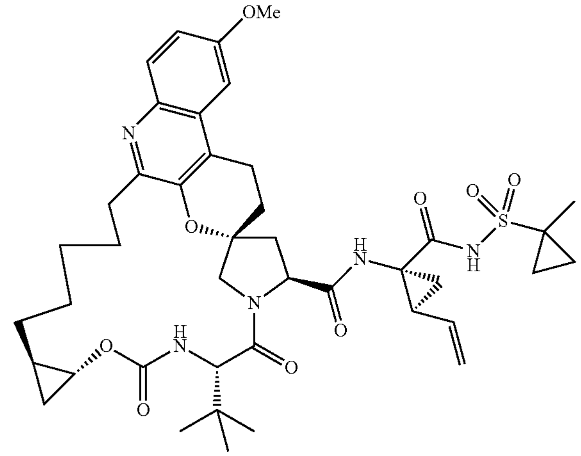

Experimental Procedures:

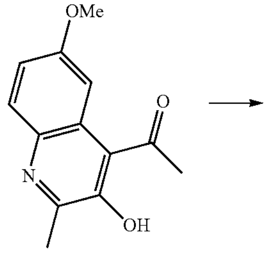

527-01

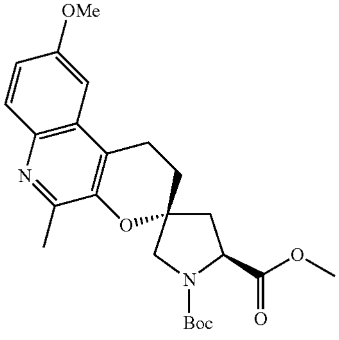

527-02

2-Methyl-3-hydroxy-4-acetyl-6-methoxyquinoline (527-01) was synthetically manipulated following previously described procedures to obtain the required spirocyclic intermediate 527-02.

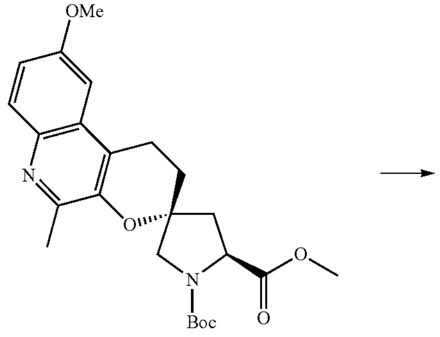

527-02

-continued

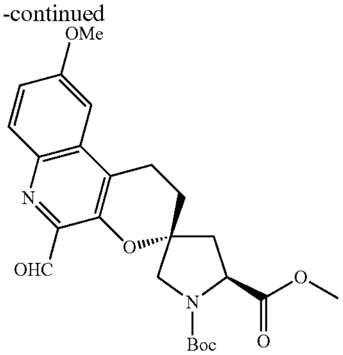

527-03

The 2-methylquinoline intermediate 527-02 was synthetically manipulated using previously described procedures to obtain the required 2-formylquinoline intermediate 527-03.

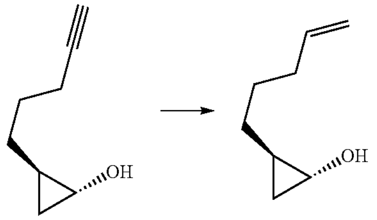

527-04 527-05

A solution of (1R,2R)-2-(pent-4-yn-1-yl)cyclopropanol (527-04) (2 g, 16.11 mmol) in methanol (64.4 ml) was treated with quinoline (1.908 ml, 16.11 mmol) and Lindlar Catalyst (0.428 g, 0.201 mmol). The mixture was hydrogenated at room temp (ballon pressure). After 2 h TLC showed a complete reaction. The solids were removed by filtration and the filtrate was concentrated to almost dryness in rotavap. The residue was taken into ether (100 mL) and washed with aq 1M HCl (2×25 mL) and brine (20 mL), dried over magnesium sulfate, filtered and concentrated in rotavap. The residue was adsorbed on silica gel and purified on a gold cap Redisep (80 g) silica gel column using dichloromethane to elute the column. The product 527-05 (740 mg, 5.75 mmol, 35.7% yield) was obtained as a colorless oil.

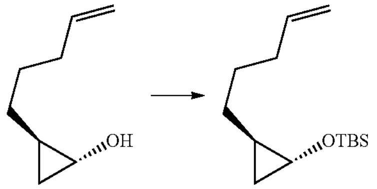

527-05 527-06

A round-bottom flask was charged with a solution of alcohol 527-05 (470 mg, 3.72 mmol) in dry 2-methyl-THF (1.49 ml). The solution was cooled in ice-water bath and treated with 2,6-lutidine (1084 μl, 9.31 mmol), imidazole (63.4 mg, 0.931 mmol) and tert-butyldimethylsilyl trifluoromethanesulfonate (898 μl, 3.91 mmol). The cooling bath was removed after 10 min and the mixture was stirred at room temp overnight. The mixture was diluted with ethyl ether (50 mL). The organic layer was washed with aq 1M HCl (2×20 mL), aq saturated sodium bicarbonate (20 mL) and brine (20 mL), dried over magnesium sulfate, filtered and concentrated in rotavap to give the crude product 527-06 (920 mg, 3.83 mmol, 103% yield) as a colorless oil. No further purification was carried out.

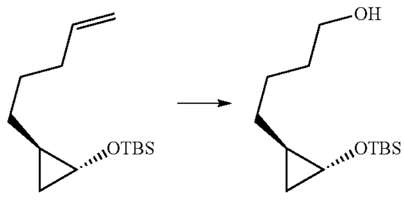

527-06 527-07

A round-bottom flask was charged with a solution of alkene 527-06 (900 mg, 3.74 mmol) in acetone (1.87 ml) and Water (1.87 ml). More Acetone (18.7 mL) was added followed by potassium osmate(VI)dihydrate (69.0 mg, 0.187 mmol). After 5 min sodium periodate (4003 mg, 18.71 mmol) was added. A thick slurry was formed after 5 min and stirring was continued for 3 h. TLC (20% ethyl acetate in hexanes) showed no more alkene was left. The solids were removed by filtration. The filter cake was washed with acetone (20 mL). The filtrate was cooled in ice-water bath. 5% Aq sodium thiosulfate (40 mL) was slowly added. Stirring was continued for 10 min. The mixture was extracted with ethyl acetate (2×20 mL). The combined organic extracts were washed with 5% aq sodium thiosulfate (20 mL) and brine (20 mL), dried over magnesium sulfate, filtered and concentrated to almost dryness. The residual acetone was co-evaporated with toluene (2×10 mL) to give the crude aldehyde intermediate as a colorless oil which was used without further purification. The aldehyde intermediate was dissolved in 2-methyl-THF (20 mL) and methanol (2 mL). The solution was cooled in ice water bath and treated with sodium borohydride (212 mg, 5.61 mmol). Stirring was continued for 30 min. The mixture was treated with aq saturated ammonium chloride (20 mL) and stirred for 10 min. Water (20 mL) was added and the mixture was extracted with ethyl acetate (50 mL). The aq layer was acidified with aq 1M HCl (pH 1) and extracted with ethyl acetate (50 mL). The combined organic extracts were washed with brine (20 mL), dried over magnesium sulfate, filtered and concentrated in rotavap. The residue was adsorbed on silica gel and purified on a gold cap Redisep (80 g) silica gel column (gradient: 0 to 100% ethyl acetate in hexanes) to give the product 527-07 (570 mg, 2.332 mmol, 62.3% yield) as a colorless oil.

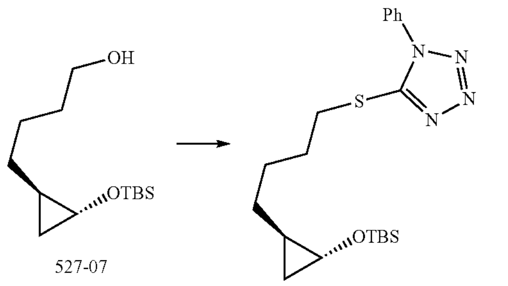

527-07 527-08

A round-bottom flask was charged with alcohol 527-07 (0.57 g, 2.332 mmol), triphenylphosphine (0.917 g, 3.50 mmol) and 1-phenyl-1 h-tetrazole-5-thiol (0.499 g, 2.80 mmol). Dry 2-methylTHF (23.32 ml) was added at 0° C. follow by slow addition of DIAD (0.5270 ml, 3.50 mmol). The mixture was gradually warmed to room temp and stirred for 3 h. The mixture was diluted with ethyl acetate (80 mL) and washed with half-saturated sodium bicarbonate (2×25 mL), water (25 mL) and brine (20 mL), dried over magnesium sulfate, filtered and concentrated in rotavap. The residue was adsorbed on silica gel and purified on a gold cap Redisep (120 g) silica gel column (gradient: 0 to 30% ethyl acetate in hexanes) to give the product 527-08 (830 mg, 2.051 mmol, 88% yield) as a colorless oil.

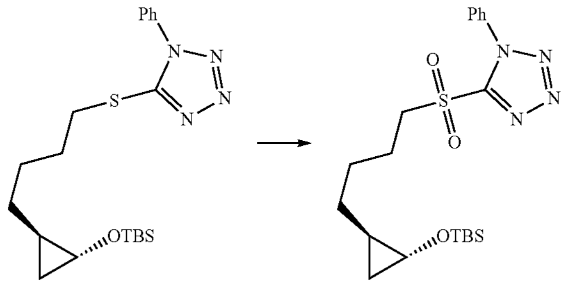

527-08 527-09

A round-bottom flask was charged with a solution of sulfide 527-08 (0.825 g, 2.039 mmol) in $CH_2Cl_2$ (20.39 ml). The solution was cooled in ice-water bath and treated with 75% m-CPBA (1.876 g, 8.16 mmol). The cooling bath was removed after 10 min and the mixture was stirred at room temp. After 6 h LCMS showed complete conversion. The reaction mixture was cooled and quenched with 10% aq sodium thiosulfate (20 mL), stirred for 5 min followed by addition of aq saturated sodium bicarbonate (20 mL). The mixture was stirred for 5 min and extracted with ethyl acetate (2×40 mL). The combined organic layers were washed with 10% aq potassium carbonate (2×15 mL) and brine (15 mL), dried over magnesium sulfate, filtered and concentrated in rotavap. The residue was adsorbed on silica gel and purified on a Redisep (80 g) silica gel column (gradient: 0 to 25% ethyl acetate in hexanes) to give the product 527-09 (810 mg, 1.855 mmol, 91% yield) a colorless oil.

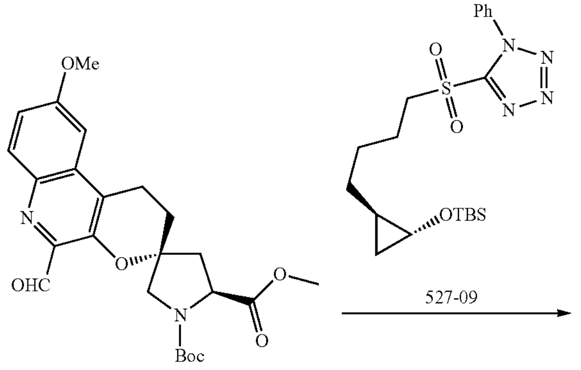

527-03

527-09

-continued

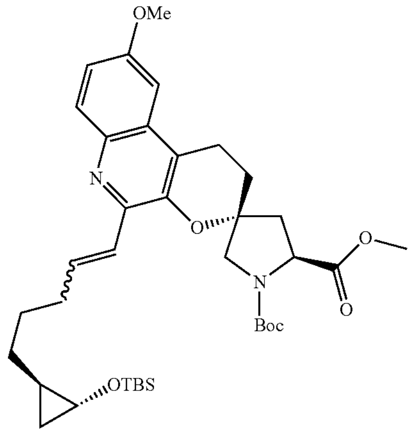

527-10

-continued

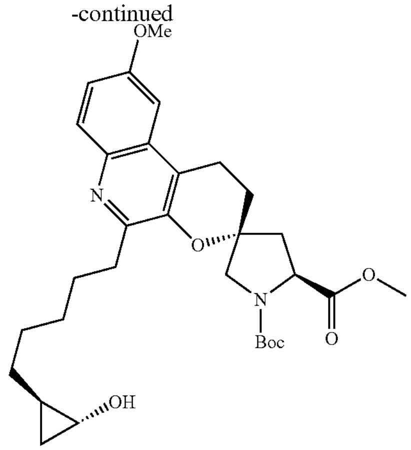

527-11

A solution of sulfone 527-09 (800 mg, 1.831 mmol) in dry 2-methyl-THF (6104 μl) was cooled in acetone-dry ice bath and treated with 1M potassium hexamethyldisilazide (1831 μl, 1.831 mmol). The resulting yellow solution was stirred for 45 min followed by addition of aldehyde 527-03 (697 mg, 1.526 mmol) in dry 2-methylTHF (1 mL). The mixture was gradually warmed to room temp and stirred overnight. The reaction was quenched by addition of water (5 mL) and stirred for 5 min. Aq 1M HCl (1 mL) was added and the product was extracted into ethyl acetate (20 mL). Upon separation the organic layer was washed with brine (5 mL), dried over magnesium sulfate, filtered and concentrated in rotavap. The residue was adsorbed on silica gel and purified on a Redisep (12 g) silica gel column (gradient: 0 to 70% ethyl acetate in hexanes) to give the product 527-10 (610 mg, 0.915 mmol, 59.9% yield) as a colorless oil.

A round-bottom flask was charged with a solution of 527-10 (0.57 g, 0.855 mmol) in 2-methyl-THF (8.55 ml). 10% palladium on carbon (30 mg, 0.028 mmol) was added and the mixture was hydrogenated at room temp (ballon pressure). After 3 h LCMS showed complete hydrogenation of the double bond. The solids were removed by filtration (celite) and the filtrate was treated with 1M TBAF (1.709 ml, 1.709 mmol) at room temp. At 1 h LCMS showed no more of the silylether present. The mixture was diluted with ethyl acetate (80 mL) and washed with aq saturated sodium bicarbonate (20 mL), and brine (20 mL), dried over magnesium sulfate, filtered and concentrated in rotavap. The residue was adsorbed on silica gel and purified on a gold cap Redisep (80 g) silica gel column (gradient: 0 to 60% acetone in hexanes) to give the product 527-11 (420 mg, 0.757 mmol, 89% yield) as a colorless foam.

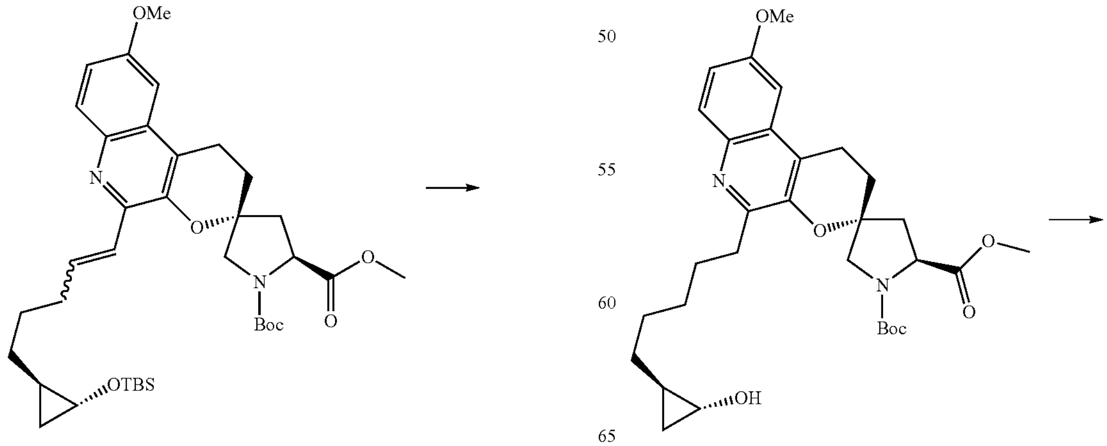

527-10 527-11

-continued

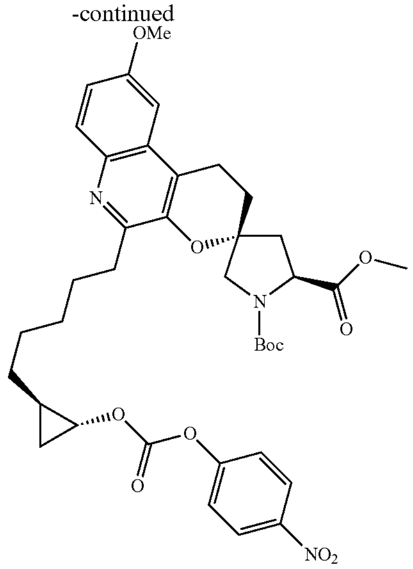

527-12

-continued

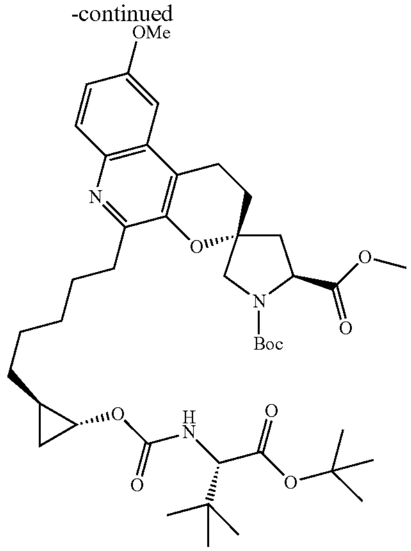

527-13

A reaction tube was charged with 527-11 (0.42 g, 0.757 mmol) and 4-nitrophenyl chloroformate (0.382 g, 1.893 mmol). Acetonitrile (3.03 ml) was added to dissolve solids followed by addition of pyridine (0.306 ml, 3.79 mmol). The reaction mixture was stirred at room temperature until no more starting material was left. LCMS showed no more starting material left after 2 h. The mixture was diluted with ethyl acetate (300 mL) and washed with aq 0.5M HCl (2×30 mL). The organic layer was washed with aq saturated sodium bicarbonate (30 mL), brine (30 mL), dried over magnesium sulfate, filtered and concentrated in rotavap. The residue was adsorbed on silica gel and purified on a gold cap Redisep (80 g) silica gel column (gradient: 0 to 60% ethyl acetate in hexanes) to give the product 527-12 (469 mg, 0.652 mmol, 86% yield) as a colorless foam.

A round-bottom flask was charged with mixed carbonate 527-12 (230 mg, 0.320 mmol) and amine hydrochloride (S)-tert-butyl 2-amino-3,3-dimethylbutanoate hydrochloride (107 mg, 0.479 mmol). The mixture was dissolved in dry acetonitrile (3195 μl) followed by addition of Hunig's Base (223 μl, 1.278 mmol). The mixture was stirred overnight. A solution of DMAP (7.81 mg, 0.064 mmol) in THF (0.3 mL) was added and the mixture was stirred overnight. LCMS showed about 20% starting material left and the mixture was kept at 5° C. over weekend. LCMS showed about 7% starting material left. The mixture was diluted with ethyl acetate (30 mL) and washed with 0.5M HCl (5 mL), aq saturated sodium bicarbonate (5 mL) and brine (5 mL), dried over magnesium sulfate, filtered and concentrated in rotavap. The residue was adsorbed on silica gel and purified on a gold cap Redisep (40 g) silica gel column (gradient: 0 to 50% acetone in hexanes) to give the product 527-13 (185 mg, 0.241 mmol, 75% yield) as a colorless foam.

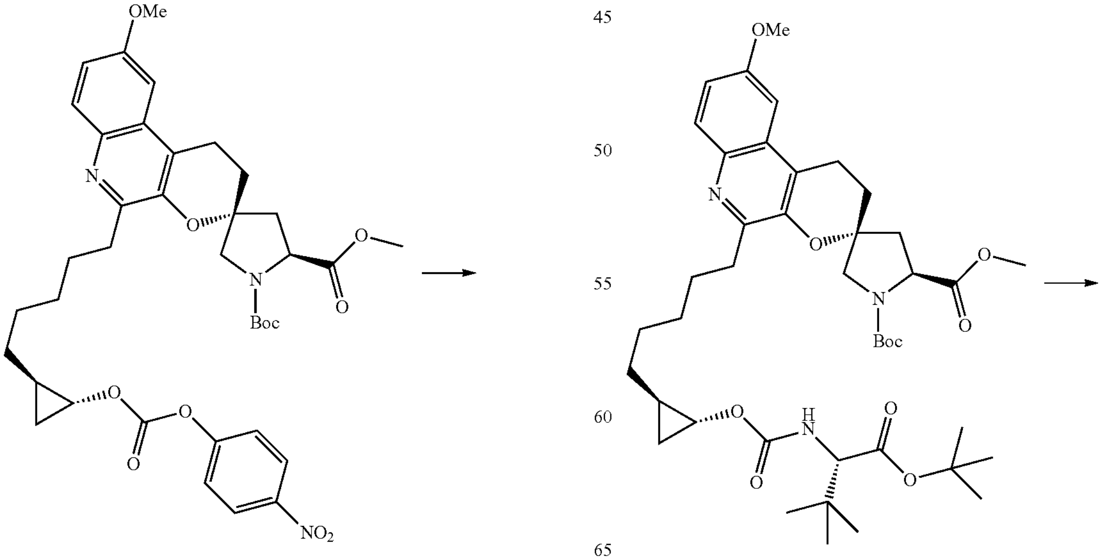

527-12 527-13

-continued

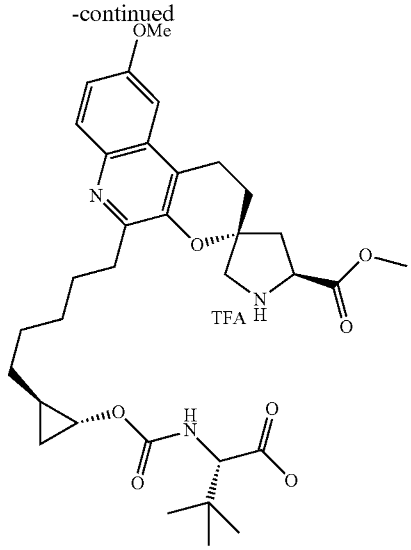

527-14

-continued

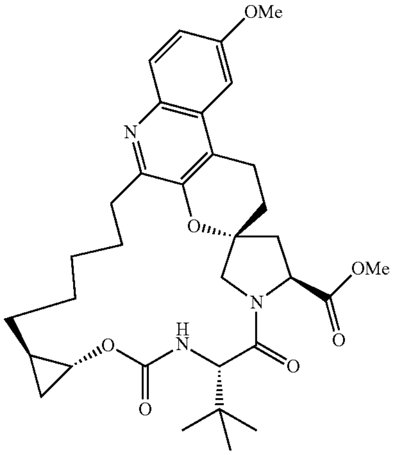

527-15

The intermediate 527-13 (0.18 g, 0.234 mmol) was dissolved in $CH_2Cl_2$ (3 ml) and treated with TFA (3 mL). The resulting solution was stirred at room temp until complete deprotection of the N-Boc and t-butylester moieties was attained. After 4 h LCMS showed complete reaction. The mixture was concentrated in rotavap to give the product 527-14 (175 mg, 0.241 mmol, 103% yield) as a slightly yellow oil. The product was dried azeotropically with toluene (2×3 mL). No further purification was carried out.

A round-bottom flask was charged with HATU (0.178 g, 0.4527 mmol) and dry DMF (2.342 ml). The resulting solution was cooled in an ice-water bath and Hunig's Base (0.205 ml, 1.171 mmol) was added followed by slow addition of a solution of amino acid 527-14 (0.17 g, 0.234 mmol) in dry DMF (7.03 ml) over 15 min (syringe pump). The reaction was stirred overnight (temp from 0 to 25° C.). The reaction mixture was concentrated to almost dryness in rotavap (high vacuum pump) and the residue was diluted with ethyl acetate (30 mL). The mixture was washed with aq 0.5M HCl (5 mL), half-saturated sodium bicarbonate (2×5 mL) and brine (5 mL). The organic layer was dried over magnesium sulfate, filtered and concentrated in rotavap. The residue was adsorbed on silica gel and purified on a gold cap Redisep (40 g) silica gel column (gradient: 0 to 50% acetone in hexanes) to give the product 527-15 (124 mg, 0.209 mmol, 89% yield) as a white powder.

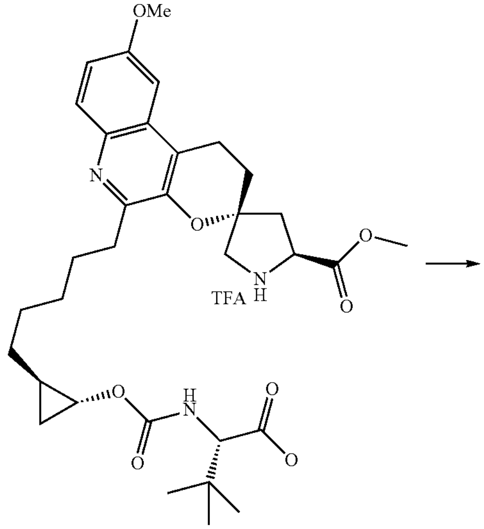

527-14

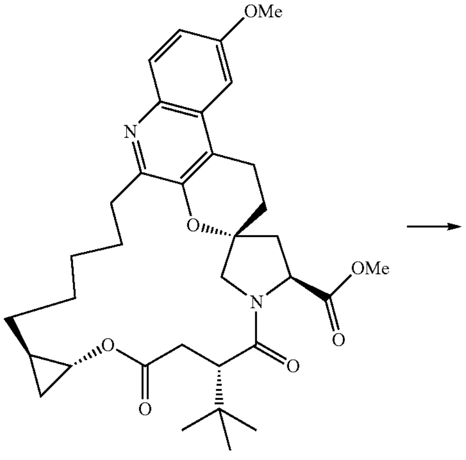

527-15

-continued

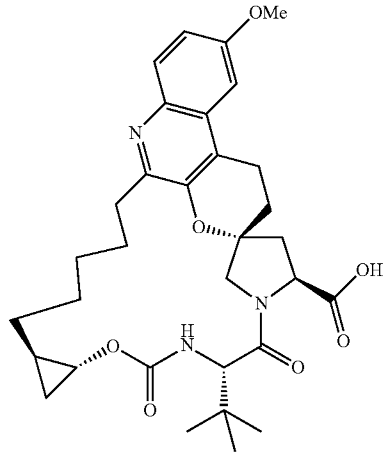

527-16

A round-bottom flask was charged with methyl ester 527-15 (120 mg, 0.202 mmol) and lithium hydroxide (24.20 mg, 1.011 mmol). 2-Methyl-THF (3 ml), MeOH (0.5 ml) and Water (0.5 ml) were added and the mixture was stirred at room temp. LCMS at 3 h showed complete reaction. The reaction was treated with dichloromethane (10 mL) and water (10 ml). Aq 1M HCl was added until acidic pH (aprox 1.5 mL). Layers were separated. Aq layer was extracted with dichloromethane (10 mL) and ethyl acetate (10 mL). The combined organic extracts were washed with brine (5 mL), dried over magnesium sulfate, filtered and concentrated to give the product 527-16 (111 mg, 0.191 mmol, 95% yield) as a white powder. No further purification was carried out for the product.

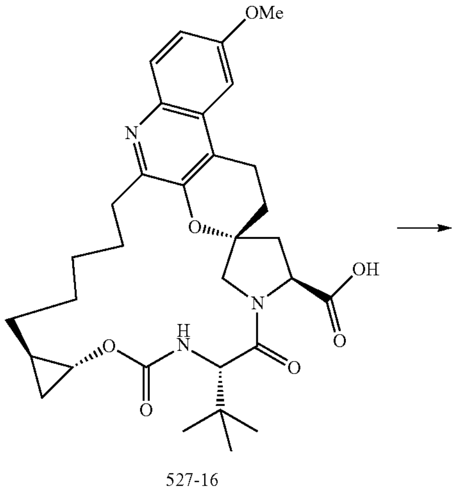

527-16

-continued

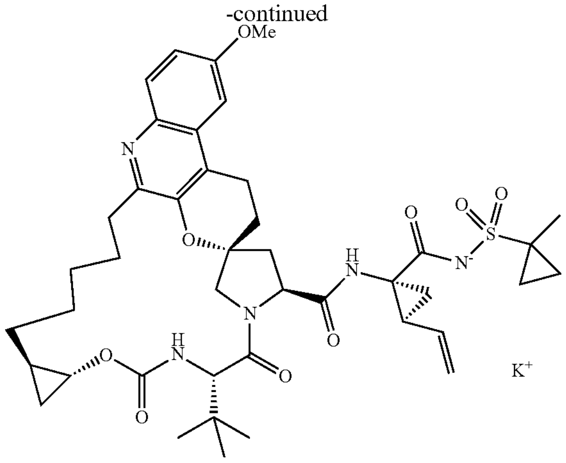

527

A round bottom flask was charged with acid 527-16 (40 mg, 0.069 mmol), (1R,2S)-1-amino-N-((1-methylcyclopropyl)sulfonyl)-2-vinylcyclopropanecarboxamide 4-methylbenzenesulfonate (57.5 mg, 0.138 mmol) and HATU (52.5 mg, 0.138 mmol). The mixture was dissolved in dry DMF (0.5 ml) followed by addition of Hunig's Base (60.3 μl, 0.345 mmol). The mixture was stirred overnight. The DMF was removed in rotavap using high-vacuum and the residue was treated with ethyl acetate (15 mL). The organic layer was washed with aq 0.5M HCl (3 mL), half-saturated sodium bicarbonate (2×3 mL) and brine (3 mL), dried over magnesium sulfate, filtered and concentrated in rotavap. The residue was adsorbed on silica gel and purified on a gold cap Redisep (12 g) silica gel column (gradient: 0 to 60% acetone in hexanes) to give the product 527 (45 mg, 0.056 mmol, 81% yield) as a white powder. The product 527 (45 mg, 0.056 mmol, 81% yield) was dissolved in acetonitrile (3 mL) and cooled in ice-water bath. A 0.5M soln of potassium hydroxide (112 μl, 0.56 mmol) was added and the mixture was stirred for 5 min. The mixture was concentrated to dryness in rotavap and dried under vacuum to give the potassium salt of 527 (47.3 mg, 0.056 mmol, 81% yield) as a white powder.

Example 528

Additional Synthesis

Additional examples of synthesizing different compounds are provided below. These example further illustrate different synthesis techniques that can employed for compounds described herein.

Synthesis of I-94

Step 1

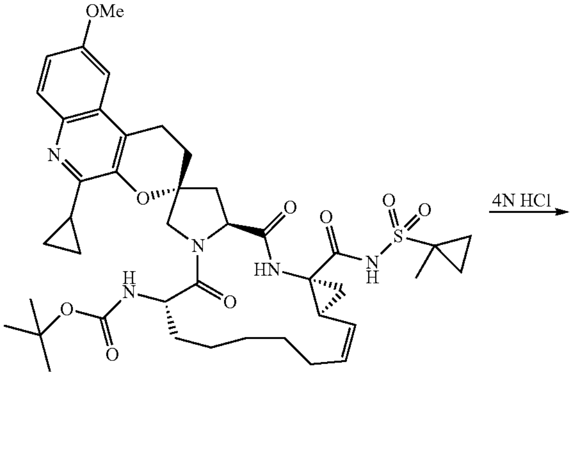

-continued

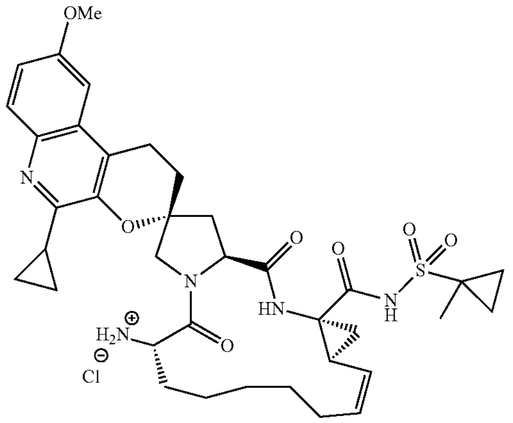

A solution of I-16 (200 mg, 0.248 mmol) in 3 ml of 4 \N HCl in dioxane was stirred at rt for 2 hr, and concentrated. The residue was evaporated twice with toluene and twice with ether to give the crude product of step 1 as a hydrochloride salt. MS m/e=706.4 ($MH^+$).

Step 2

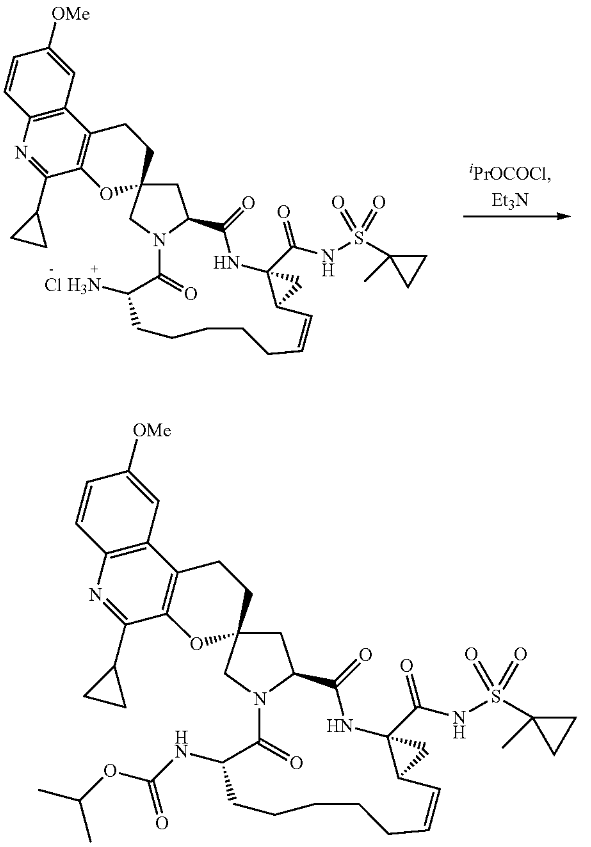

A solution of product of step 1 (20 mg, 0.027 mmol), $Et_3N$ (0.011 ml, 0.081 mmol) and isopropyl chloroformate (7.40 μl, 0.054 mmol) in 1 mL dichloromethane was stirred at rt for 2 hr, diluted with EtOAc, washed 2× with water, brine, concentrated and purified by preparative TLC eluting with 5% MeOH-DCM to give I-94 MS m/e=792.4 (MH+).

Synthesis of I-124

Step 1

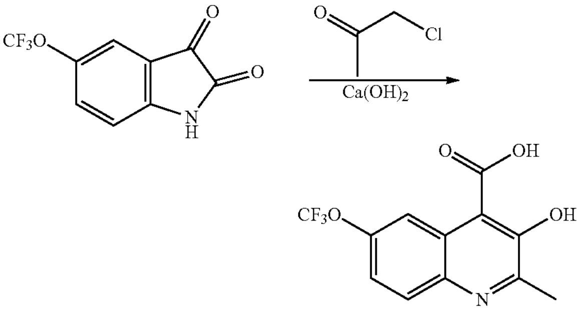

To a mixture of $Ca(OH)_2$ (38.5 g, 519 mmol) and 5-trifluoroisatin (40 g, 173 mmol) at room temperature was added water (150 ml) and the mixture was allowed to warm to 80° C. and stirred for 1 h. It was removed from bath and chloroacetone (34.5 ml, 433 mmol) was then added cautiously (very exothermic) and the reaction was left at room temperature for a while, then allowed to warm to 80° C. and stirred for 5 hr. 1N HCl was added adjusting the pH =2. The solid separating out was filtered and dried over house vacuum. It was dried at 50° C. under vacuum pump for several hours until no water was present to yield product of step 1 (yield 95%)

Step 2

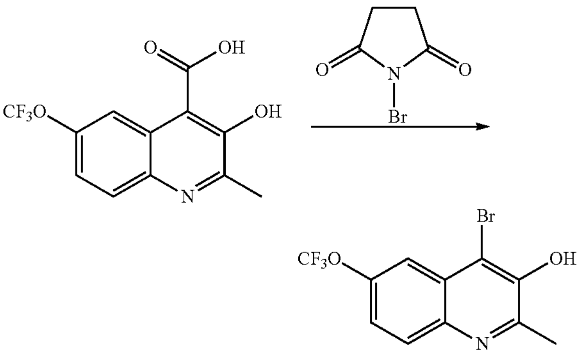

The product of step 1 (40 g, 139 mmol) in THF (1000 ml) at room temperature was treated with NBS (29.7 g, 167 mmol) and the mixture was stirred for 4 h. The mixture was quenched at room temperature with saturated brine and extracted with EtOAc. The combined organic fractions were dried over $Na_2SO_4$, filtered, and concentrated in vacuo. The residue was purified by column chromatography several times over silica gel (Isco 330 g, eluting with $CH_2Cl_2$/EtOAc) to give bromide as a red solid in a combined yield of 56%

Step 3

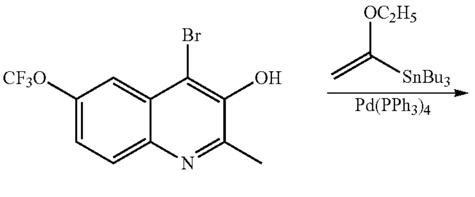

-continued

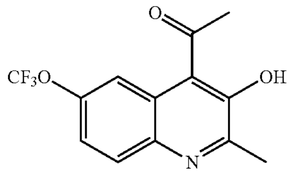

The product of step 2 (20 g, 62.1 mmol) and $Pd(PPh_3)_4$ (7.18 g, 6.21 mmol) in dioxane (240 ml) at room temperature was added tributyl(1-ethoxyvinyl)tin (52.4 ml, 155 mmol) and the mixture was allowed to warm to 110° C. and stirred for 3 h. The mixture was treated with 240 ml of 1N HCl and stirred for 90 min at room temperature. The mixture was quenched at room temperature with saturated aqueous NaHCO3 and extracted with EtOAc. The combined organic fractions were washed with saturated brine, dried over $Na_2SO_4$, filtered and concentrated in vacuo. The crude mixture was taken in hexanes and washed with acetonitrile. The hexane layer was concentrated in vacuo and the crude residue was purified by silica gel chromatography twice to yield 3.4 g product of step 3 as a yellow solid Step 4

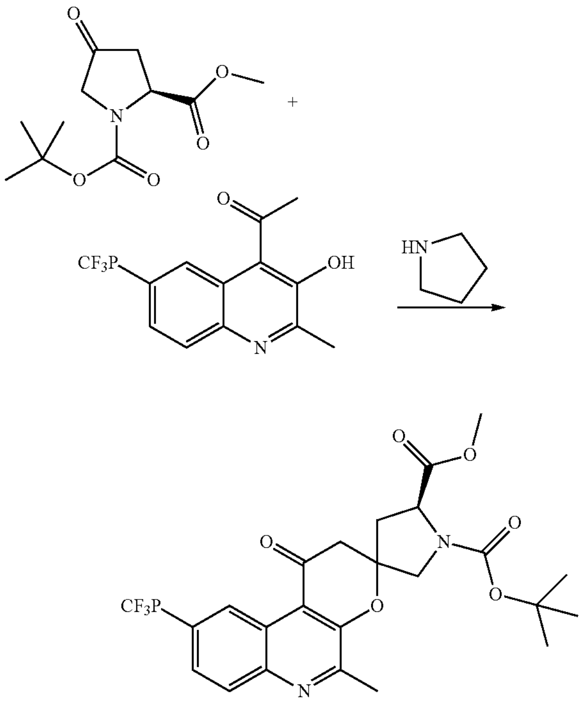

To a solution of ketone of step 3 (2.0 g, 7.01 mmol) in MeOH (30 ml) at room temperature was added BOC-4-Oxo-Pro-OMe (3.41 g, 14.02 mmol), pyrrolidine (0.580 ml, 7.01 mmol), followed by molecular sieves (4A powder, 2.0 g) and the mixture was warmed to 105° C. using microwave-high absorbance and stirred for 30 min. The mixture was filtered washing the cake with MeOH. The filtrate was concentrated in vacuo and the residue was purified by column chromatography over silica gel (Isco 120 g, eluting with Hexanes/EtOAc) to yield 2.73 g (76%) of product of step 4 as a yellow solid as a mixture of diastereomers.

Step 5

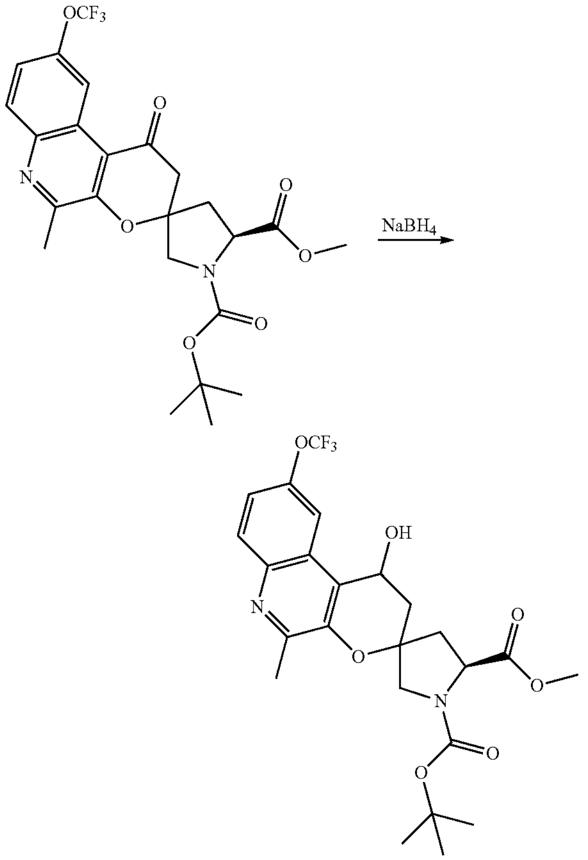

To a solution of diatereomeric products from step 4 (2.2 g, 4.31 mmol) in THF (20 ml) and MeOH (20 ml) at 0° C. was added $NaBH_4$ (0.196 g, 5.17 mmol) and stirred at that temperature for 30 min. On complete consumption of the starting material, the mixture was quenched at 0° C. with saturated aqueous $NH_4Cl$ solution and extracted with EtOAc. The combined organic fractions were washed with brine, dried over $Na_2SO_4$, filtered and concentrated in vacuo to yield a colorless solid in 100% yield.

Step 6

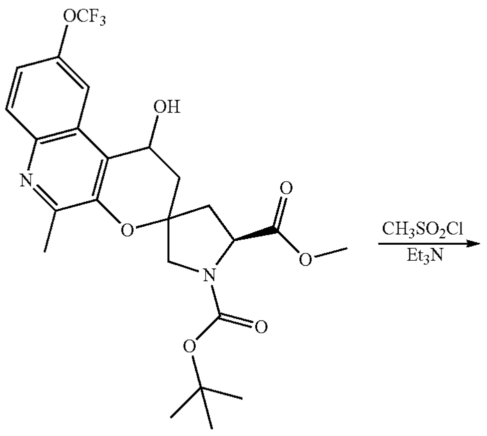

-continued

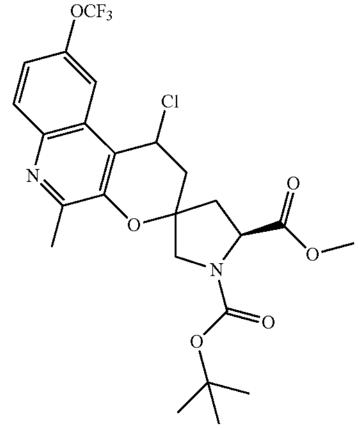

To a solution of product of step 6 (2.2 g, 4.29 mmol) in $CH_2Cl_2$ (40 ml) at 0° C. was added $Et_3N$ (2.094 ml, 15.03 mmol) followed by $CH_3SO_2Cl$ (0.667 ml, 8.59 mmol) and the mixture was allowed to warm to room temperature stirring overnight. Analysis of reaction mixture with LCMS indicated presence of unreacted starting material. It was cooled to 0° C. and additional $Et_3N$ (1 eq., 0.6 ml, 4.29 mmol) and $CH_3SO_2Cl$ (0.5 eq., 2.14 mmol, 0.16 ml) was added and the reaction was stirred at room temperature for 2 hrs. The reaction mixture was quenched at room temperature with saturated aqueous sodium bicarbonate and extracted with $CH_2Cl_2$. The combined organic fractions were dried over $Na_2SO_4$, filtered and concentrated in vacuo. The residue was purified by column chromatography over silica gel (Isco 120 g, eluting with Hexanes/EtOAc) to give chloride as a yellow oil. (2.2 g, 90%)

Step 7

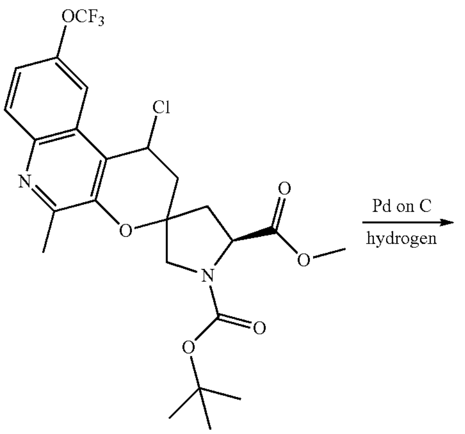

-continued

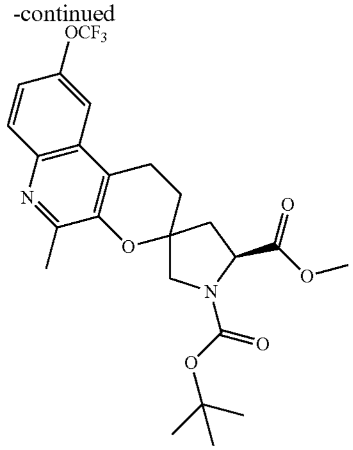

To a solution of product of step 6 (2.44 g, 4.60 mmol) in EtOAc (100 ml) at room temperature was added 5% palladium on carbon (0.489 g, 0.460 mmol) and the mixture was degassed and backfilled with hydrogen balloon at room temperature and stirred for 3 h. On complete consumption of starting material as indicated by TLC and LC-MS, the mixture was filtered over Celite, washing the cake with EtOAc and MeOH. The residue was purified by column chromatography over silica gel (Isco 120 g, eluting with MeOH/DCM) to give reduced product as yellow foam in 92% yield.

Step 8

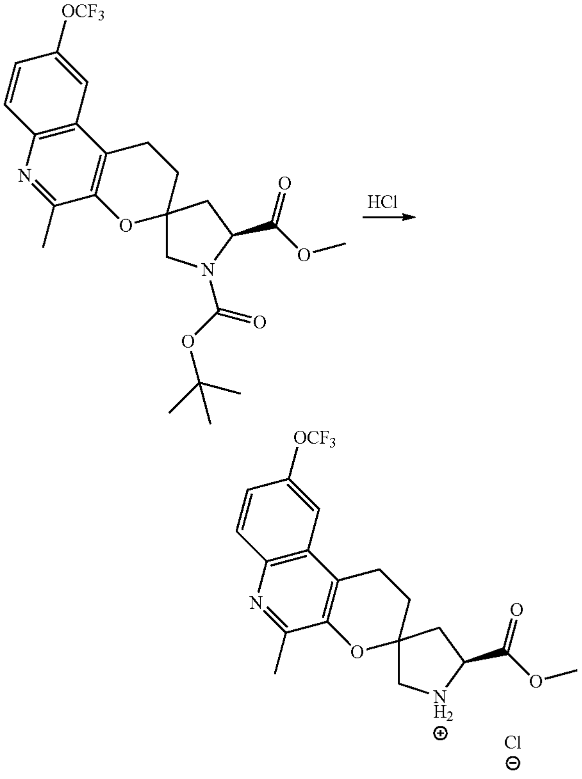

To a solution of product of step 7 (1.1 g, 2.216 mmol) was added 4 N HCl in dioxane (22.16 ml, 89 mmol) at RT and the mixture was stirred for 2 h. The reaction mixture was concentrated. The crude mixture was coevaporated with toluene 3-4 times until dry of all solvents. (Yield=100%)

Step 9

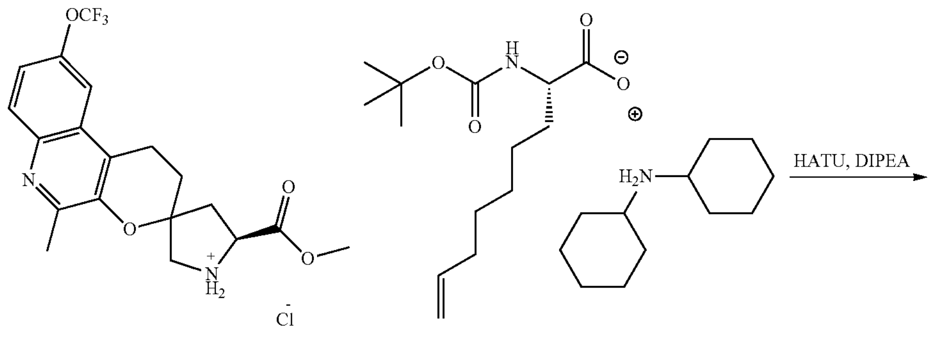

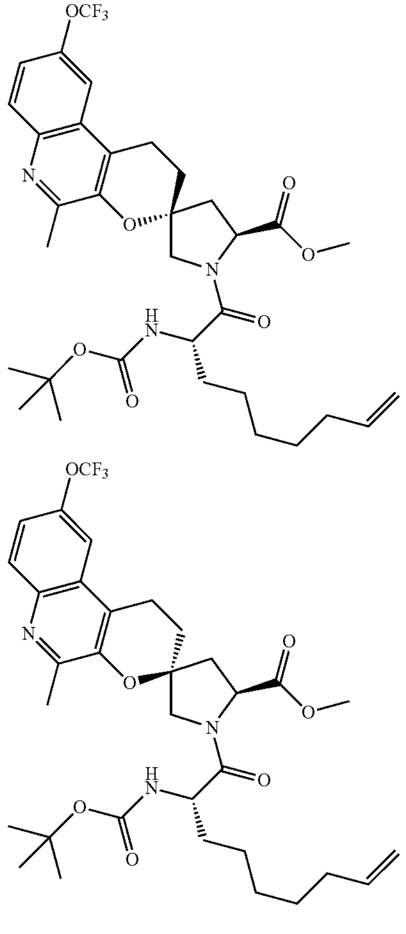

To a solution of product of step 8 (1.0 g, 2.52 mmol), acid salt (1.713 g, 3.78 mmol) and HATU (1.439 g, 3.78 mmol) in DMF (20 ml) at room temperature was added DIPEA (1.716 ml, 10.09 mmol) and the mixture was stirred at room temperature overnight. The reaction was cloudy and not homogenous. Additional 5 ml DMF, 20 ml DCM and 0.4 ml Hunigs base and allow stirring at room temperature overnight. The mixture was diluted at room temperature with water and extracted with EtOAc. The combined organic fractions were washed with brine, dried over $Na_2SO_4$, filtered and concentrated in vacuo. The residue was purified by column chromatography over silica gel via a slow gradient (Isco 120 g, eluting with Hexanes/EtOAc) to give two diasteromers of coupled of product in 40 and 32%

Step 10

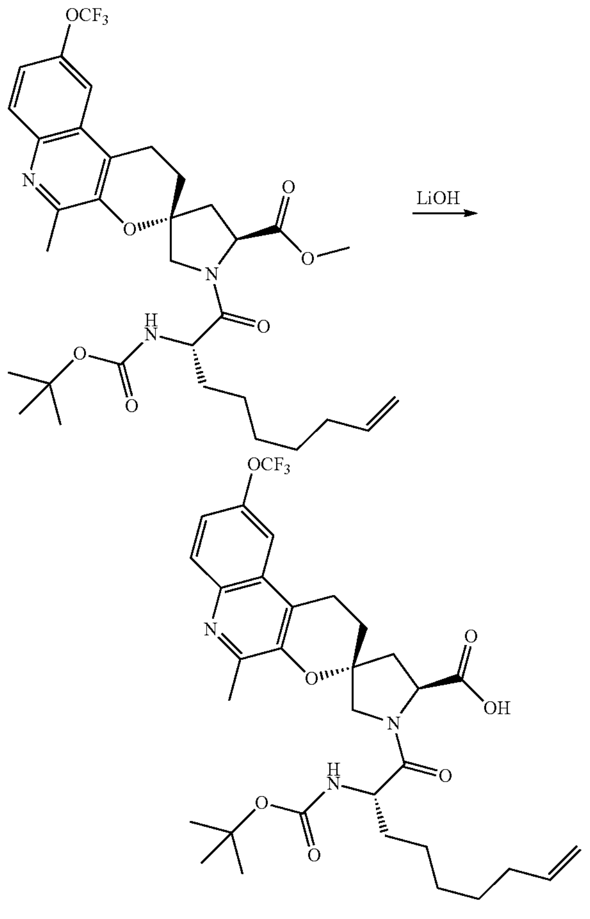

To a solution of nonpolar diasteromer from step 9 (660 mg, 1.016 mmol) in THF (12 ml), MeOH (12.00 ml) and $H_2O$ (8 ml) at RT was added LiOH (73.0 mg, 3.05 mmol) and the mixture was allowed to warm to 50° C. and stirred for 2 h. LCMS of the reaction mixture indicated complete consumption of starting material. The mixture was quenched at room temperature by concentrating MeOH and THF then adding a solution of 0.5 M aqueous HCl until pH=2. The mostly aqueous solution was then extracted with EtOAc several times. The combined organic layers were dried with $Na_2SO_4$, filtered and concentrated in vacuo. The crude was used as it is in next step (Yield=99%)

Step 11

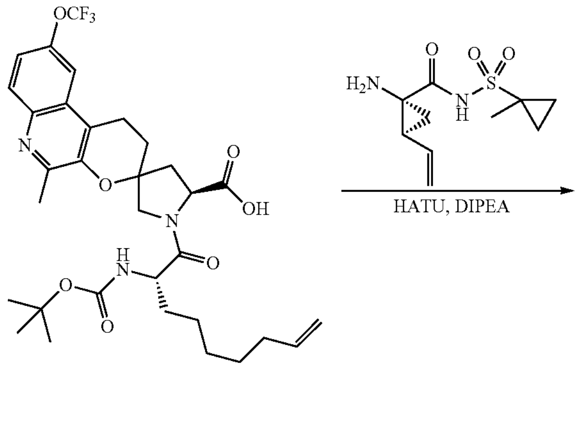

-continued

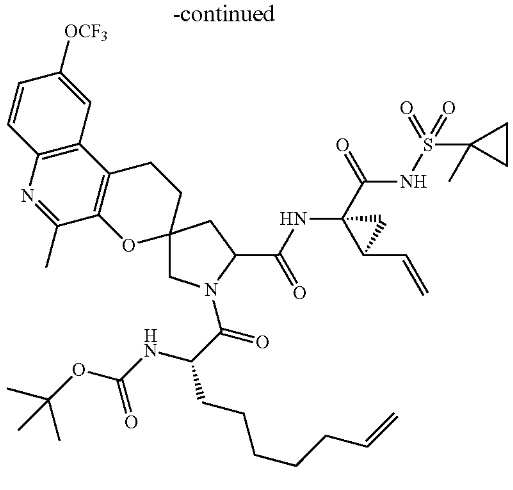

To a solution of product of step 10 (640 mg, 1.007 mmol) and amine (369 mg, 1.510 mmol) in DMF (10 ml) at room temperature was added HATU (574 mg, 1.510 mmol) followed by Hunigs base (0.514 ml, 3.02 mmol) and the mixture was stirred at RT overnight. The mixture was diluted with water and extracted with EtOAc. The combined organic fractions were washed with brine, dried over $Na_2SO_4$, filtered and concentrated in vacuo. The residue was purified by column chromatography over silica gel (Isco 80 g, eluting with Hexanes/EtOAc) to give in order product in 89% yield.

Step 11

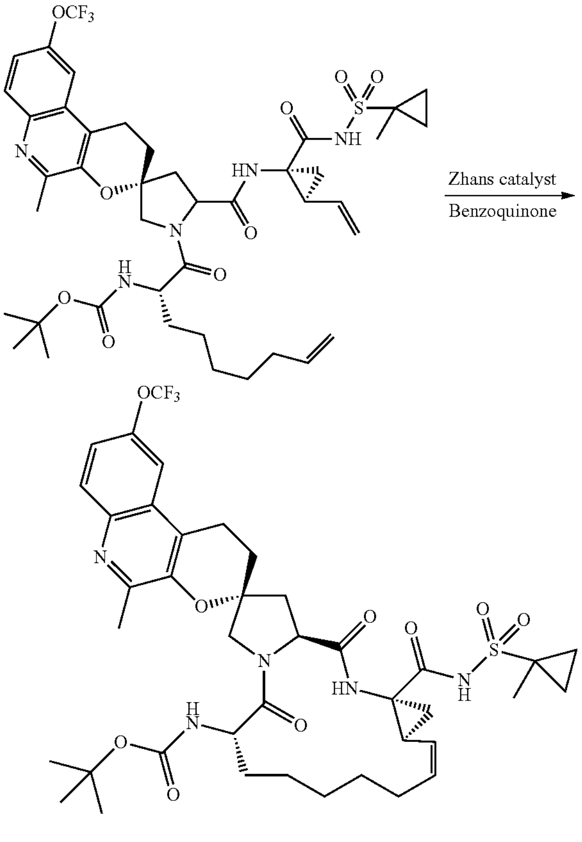

To a solution of product of step 10 (300 mg, 0.348 mmol), 1,3-bis(2,4,6-trimethylphenyl)-4,5-dihydroimidazol-2-ylidene[2-(i-propoxy)-5-(n,n -dimethylaminosulfonyl)phenyl]methyleneruthenium(ii)dichloride (63.8 mg, 0.087 mmol) and 1,4-benzoquinone (11.29 mg, 0.104 mmol) in DCE (150 ml) at room temperature was degassed, put under nitrogen, then warmed to 70° C. and stirred 3 h. LCMS indicated ~10% SM remaining, allow to stir additional hour at 70° C. The mixture was quenched at room temperature with 1 ml butyl vinyl ether and concentrated to dryness. The residue was purified by column chromatography over silica gel (Isco 40 g, eluting with Hexanes/EtOAc) to give in order of elution product containing 10% of uncyclized starting material. It was treated with 51 mg Zhan's catalyst and 10 mg 1,4-Benxoquinone and heat to 70° C. for 2 hrs. LCMS indicated all SM consumed. The mixture was quenched at room temperature with 1 ml butyl vinyl ether and concentrated to dryness. The residue was combined with 0316331-0051-02 (~80 mg additional material) and purified by column chromatography over silica gel (Isco 80 g, eluting with Hexanes/EtOAc) to give product in 71%

Step 12

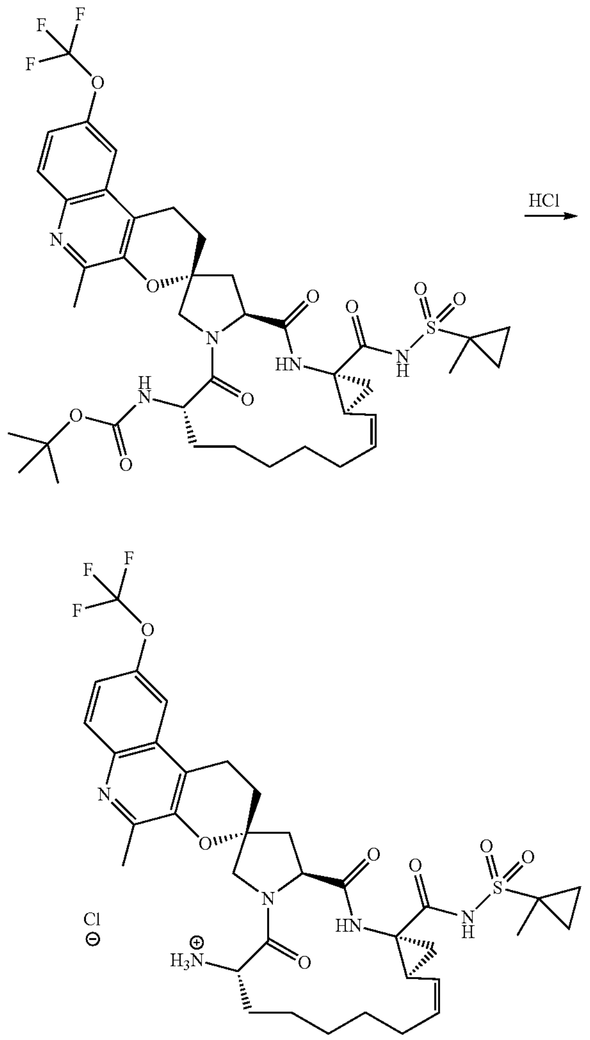

A solution of product of step 11 (200 mg, 0.240 mmol) in 4M HCl in dioxane (10 ml, 40.0 mmol) was stirred at RT for 2 h. LCMS indicated complete consumption of starting material. The reaction mixture was concentrated to dryness to yield amine salt at 100%

Step 13

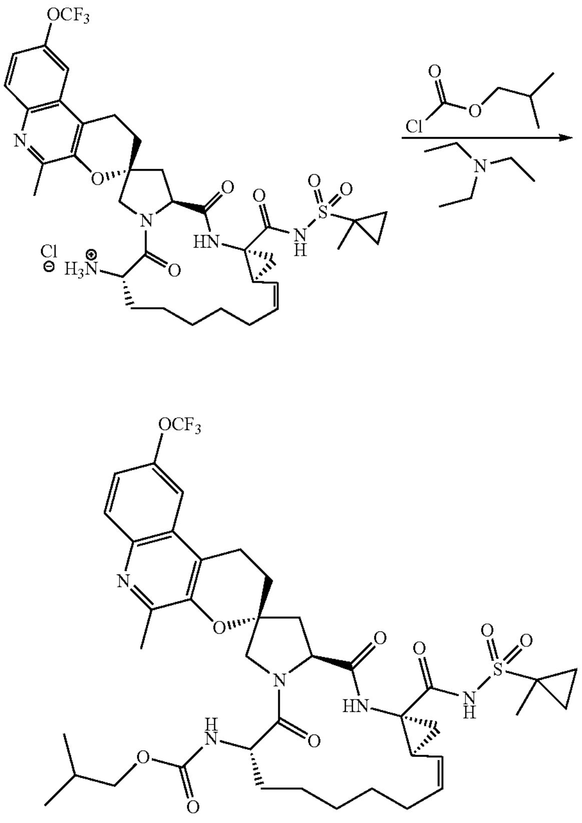

To a solution of product of step 12 (15 mg, 0.019 mmol) in DCM (2 ml) at room temperature was added triethylamine (10.86 μl, 0.078 mmol) followed by isobutyl chloroformate (5.07 μl, 0.039 mmol) and the mixture was stirred for 1 h under nitrogen. LCMS indicated reaction was complete. The mixture was quenched at room temperature with water and extracted with $CH_2Cl_2$ and dried over $Na_2SO_4$, filtered and concentrated in vacuo. The residue was purified by column chromatography over silica gel (Isco 4 g, eluting with $CH_2Cl_2$/MeOH) to give as a yellow solid in 48% yield.

Synthesis of I-189

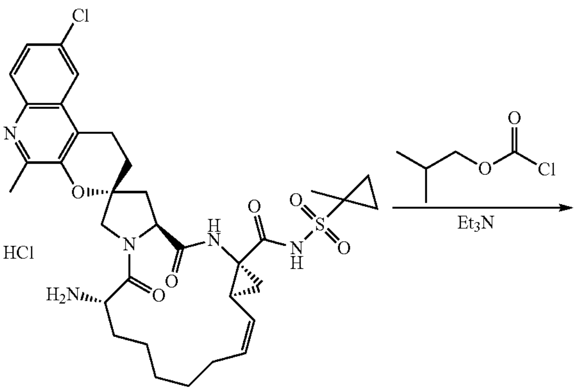

-continued

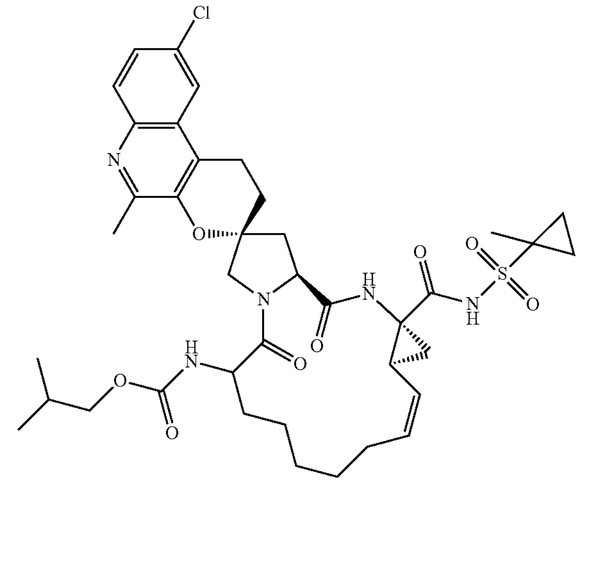

The product of Example 40 step 1 was converted to I-189 following procedure in Example 40 step 2 where the neopentyl chloroformate was replaced with isobutyl chloroformate.

Synthesis of I-161

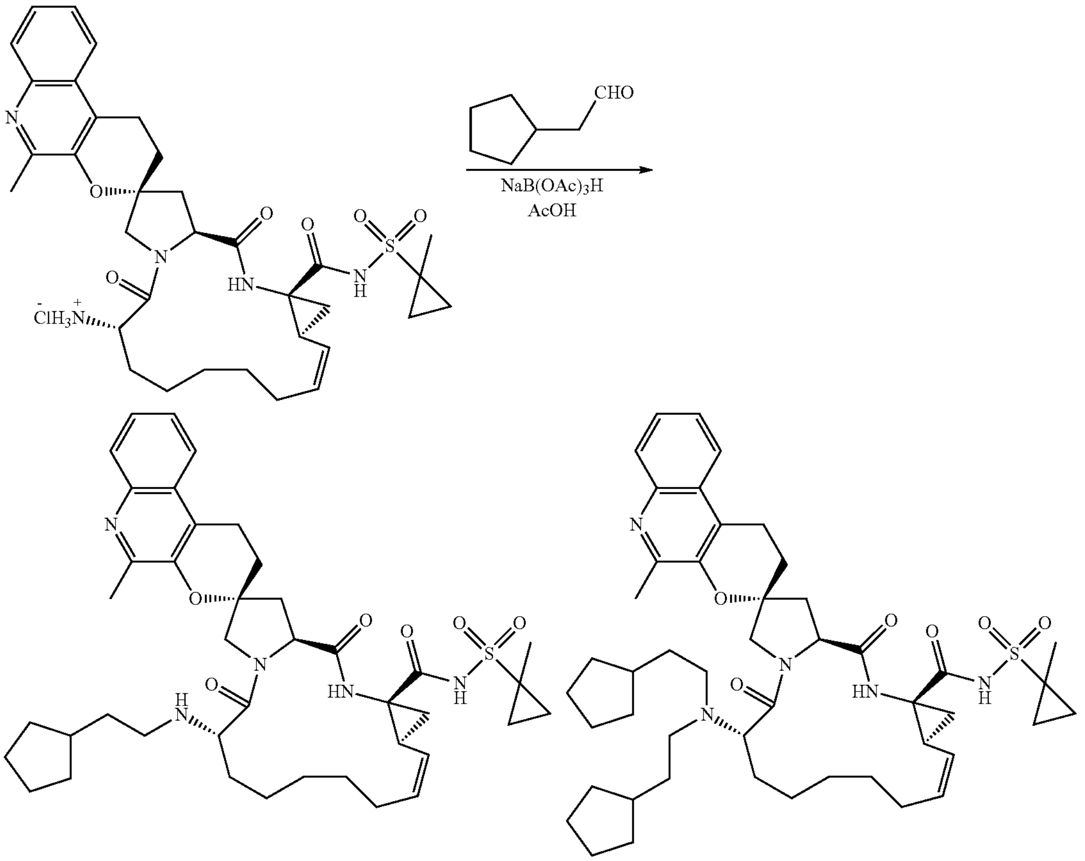

To a solution of product of Example 47, Step 10 (33 mg, 0.048 mmol) in DCE (1202 μl), cyclopentyl acetaldehyde (16.18 mg, 0.144 mmol) (3 drops) were added and the mixture cooled to 0° C. AcOH (2.75 μl, 0.048 mmol) (1 drop) and $NaB(OAc)_3H$ (40 mg, 0.189 mmol) were added and the mixture stirred at 0° C. for a couple of minutes and at rt for 18 h. The reaction mixture was treated with aqueous sodium hydrogen carbonate (2 ml) and stirred for 1 h at rt. It was extracted with dichloromethane. The combined organic fractions were combined and the solvent was evaporated under reduced pressure. The crude mixture was purified by preparative TLC, eluting with 5% MeOH/DCM to give I-161 (12.5 mg, 0.017 mmol, 34.8% yield) as a white solid and I-162 (14.2 mg, 0.017 mmol, 35.1% yield) as a white solid.

Synthesis of I-359

Step 1

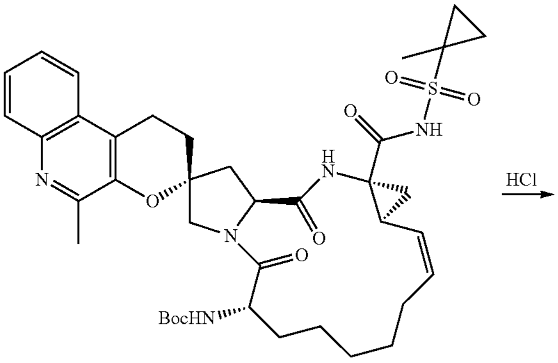

-continued

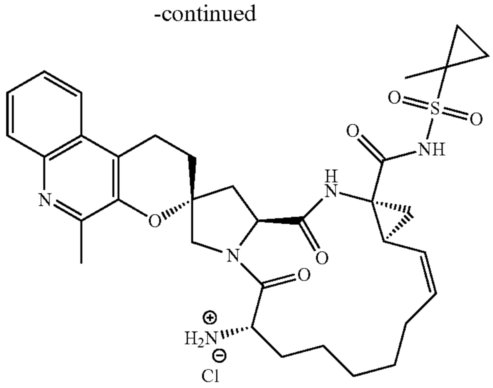

To a flask containing product of example 47, step 9 (1280 mg, 1.707 mmol) was added 4N solution of HCl in dioxane (40 mL, 160 mmol) and the mixture was stirred at rt for 2 h. The precipitate was triturated with 300 ml of hexanes and the clear layer was decanted. This was repeated twice and the resultant residue was evaporated with dichloromethane followed by hexanes (3 times) to give product of step 1 as a tan solid. (1.21 g, 1.763 mmol, 103% yield). MS m/e=650.2 (MH+)

Step 2

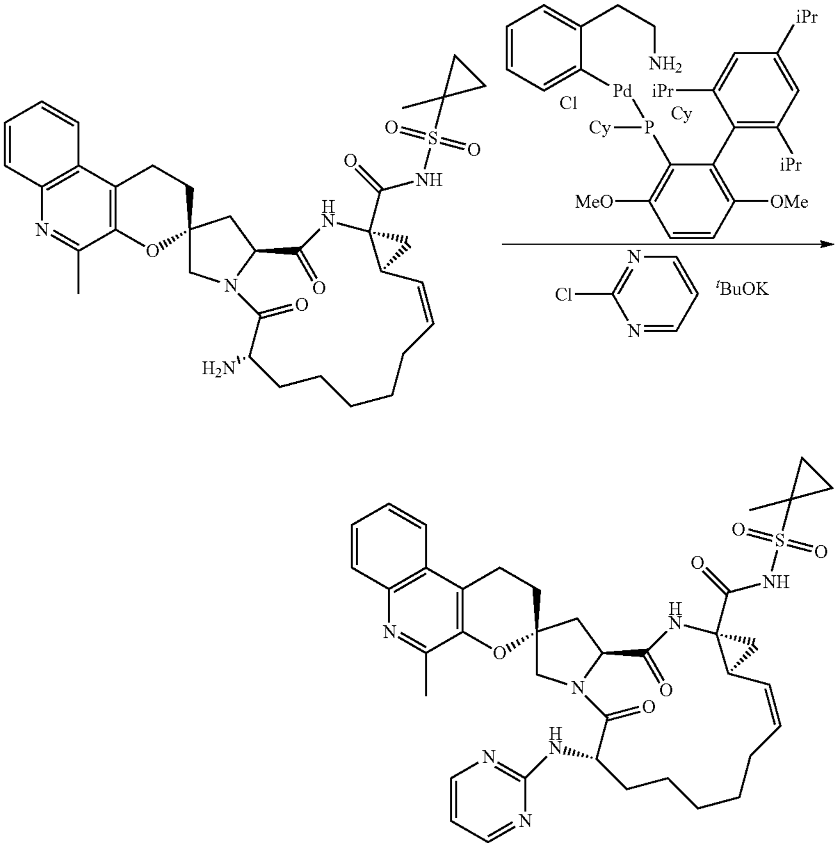

In a microwave vial product of step 1 (22 mg, 0.032 mmol) and potassium tert -butoxide (9.24 mg, 0.096 mmol) were combined, followed by the addition of dioxane (214 μl), 2-chloropyrimidine (25.7 mg, 0.224 mmol), and BrettPhos indoline precatalyst (2.56 mg, 3.21 μmol). This mixture was then purged with nitrogen and sealed. This mixture was heated at 80° C. for 2 h. The mixture was cooled to rt, diluted with ethyl acetate, washed with aqueous ammonium chloride (saturated), and the solvent was evaporated under reduced pressure. The residue was purified by thin-layer chromatography on silica gel, eluting with $CH_2Cl_2$/MeOH 95/5 to give I-359 (5.0 mg, 6.87 μmol, 21.43% yield) as a white solid. MS m/e=728.3 ($MH^+$).

Synthesis of I-509

Step 1

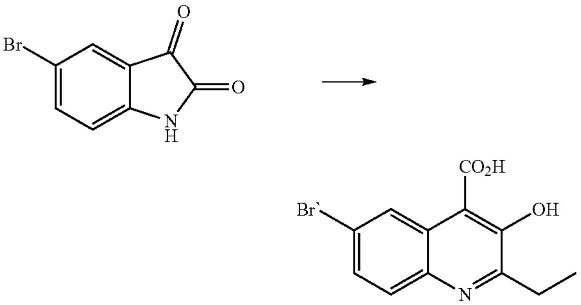

5-Bromoindoline-2,3-dione was converted to 6-bromo-2-ethyl-3-hydroxyquinoline-4-carboxylic acid using the procedure described for the synthesis of Example 1, step 1.

Step 2

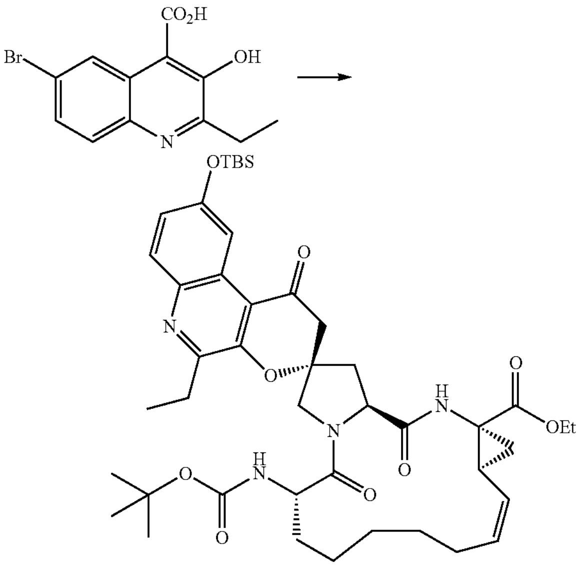

The product of step 1 was converted to macrocyclic ketone using the procedures described for the synthesis of Example 58, steps 3-6.

Step 3

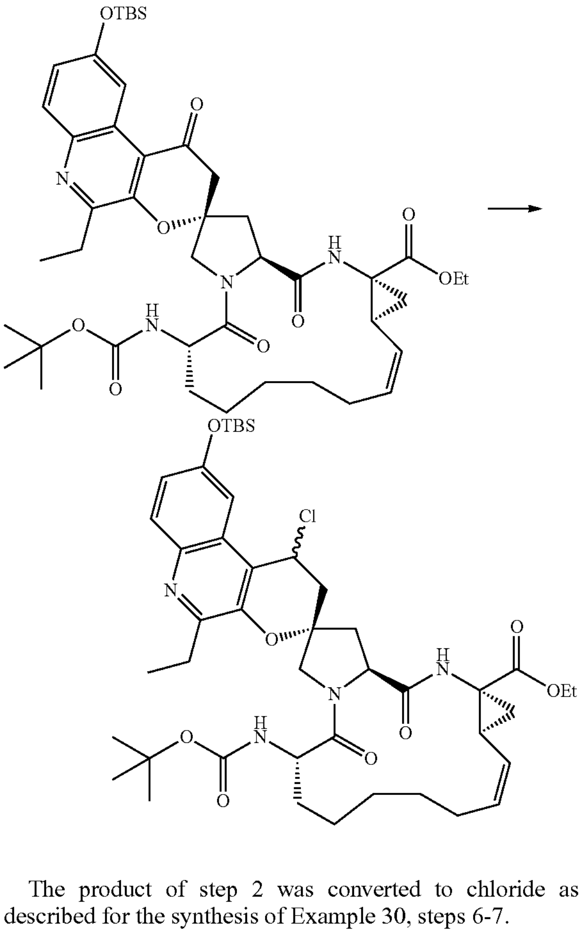

The product of step 2 was converted to chloride as described for the synthesis of Example 30, steps 6-7.

Step 4

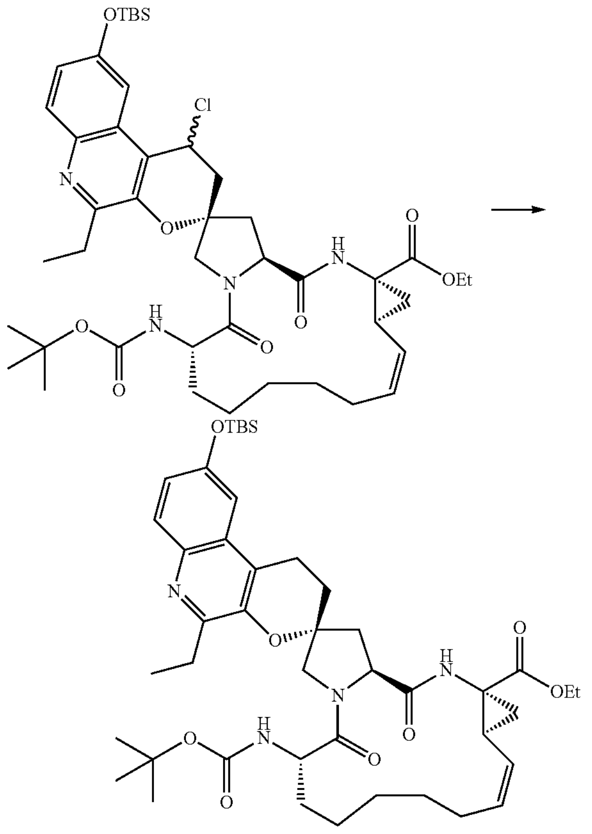

To a solution of product of step 3 (1.2 g, 1.429 mmol) in THF (9.53 ml) and MeOH (20 ml) was added $Et_3N$ (0.571 ml, 4.29 mmol) followed by Lindlar catalyst ($Pd/CaCO_3$; 0.12 g, 0.59 mmol). The reaction was hydrogenated (1 atm, $H_2$ balloon) at room temperature for 2 h at which stage LCMS indicated incomplete conversion. An additional 0.12 g of Lindlar catalyst was added and the reaction was stirred under $H_2$ balloon for an additional 6 h. The reaction was filtered through celite, rinsed with dichloromethane, and concentrated. The crude yellow solid was purified by column chromatography (0-100% ethyl acetate-hexanes) to provide dechlorinated product (800 mg, 0.994 mmol, 69.5% yield) as white solid.

Step 5

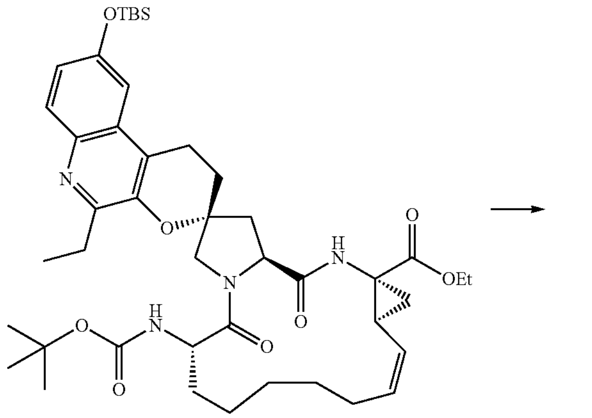

-continued

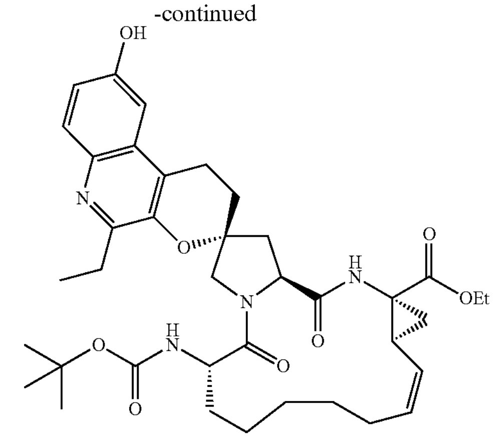

To a solution of product of step 4 (1.4 g, 1.739 mmol) in THF (17 ml) was added TBAF (1M in THF; 3.48 ml, 3.48 mmol) at room temperature. After stirring for 1.5 h the reaction was quenched with water and extracted with ethyl acetate (×3). The organics were combined, dried with sodium sulfate, and concentrated. The crude residue was purified by column chromatography (0-50% acetone-hexanes) to provide deprotected macrocycle (1.1 g, 1.592 mmol, 92% yield) as a white solid.

Step 6

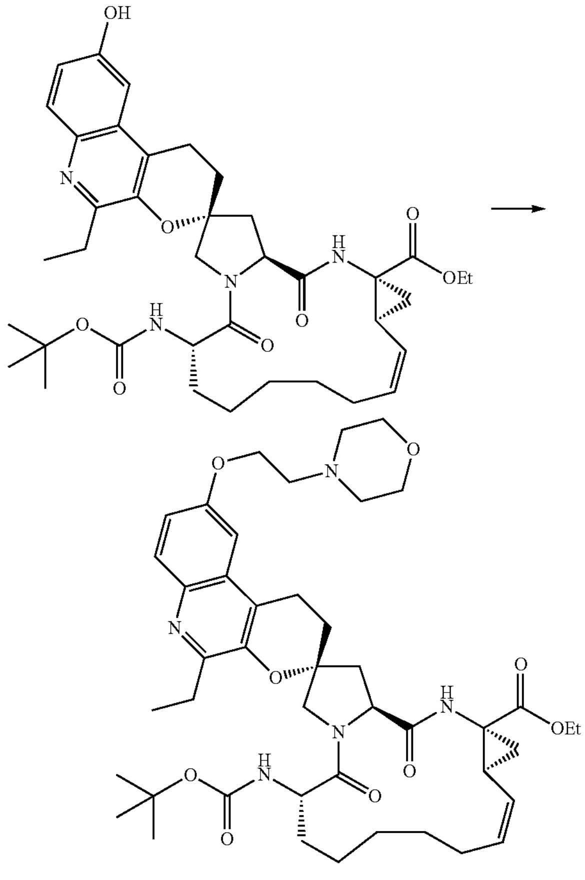

A mixture of deprotected macrocycle (0.50 g, 0.724 mmol), 4-(2-bromoethyl)morpholine hydrobromide and $Cs_2CO_3$ in DMF (14.5 ml) was stirred at 60° C. 4 h. The reaction was quenched with 2M aq. LiCl solution and extracted with ethyl acetate (×3). The organics were combined, dried over sodium sulfate, and concentrated. The crude material was purified by column chromatography (0-5% MeOH in $CH_2Cl_2$) to yield alkylated product (450 mg, 0.560 mmol, 77% yield) as a white solid.

Step 7

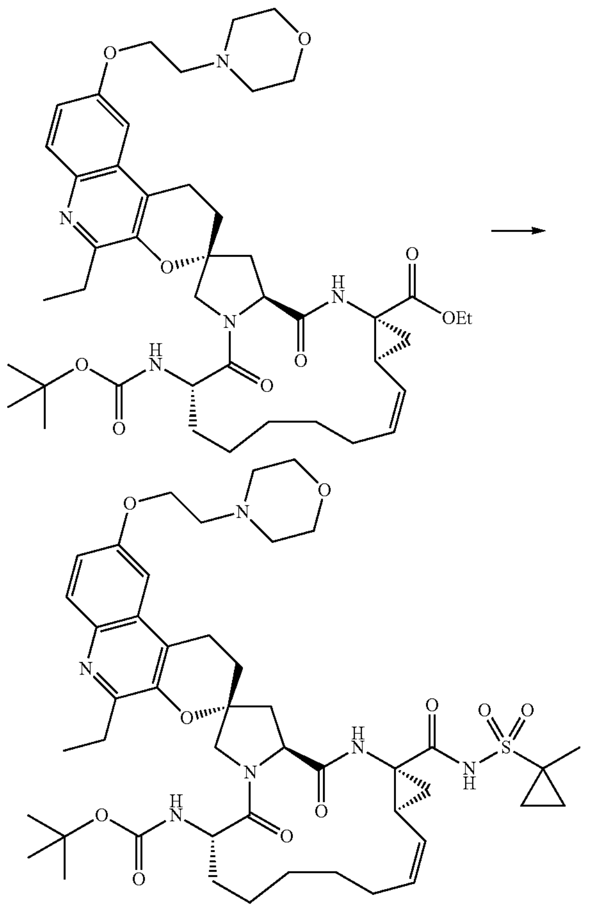

The product of step 6 was converted to acyl sulfoanamide product using the procedure described for the synthesis of Example 12, Step 8.

Step 8

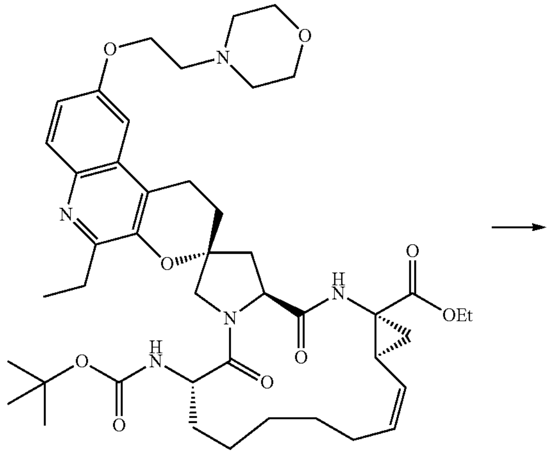

-continued

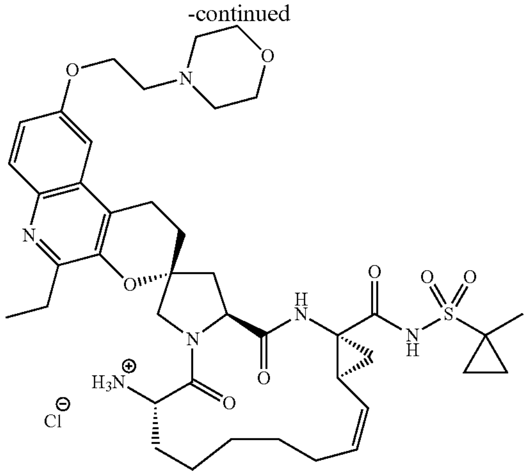

The product of step 7 converted to amine salt using 4 M HCl in dioxane using the procedure described for the synthesis of Example 47, step 10.

Step 9

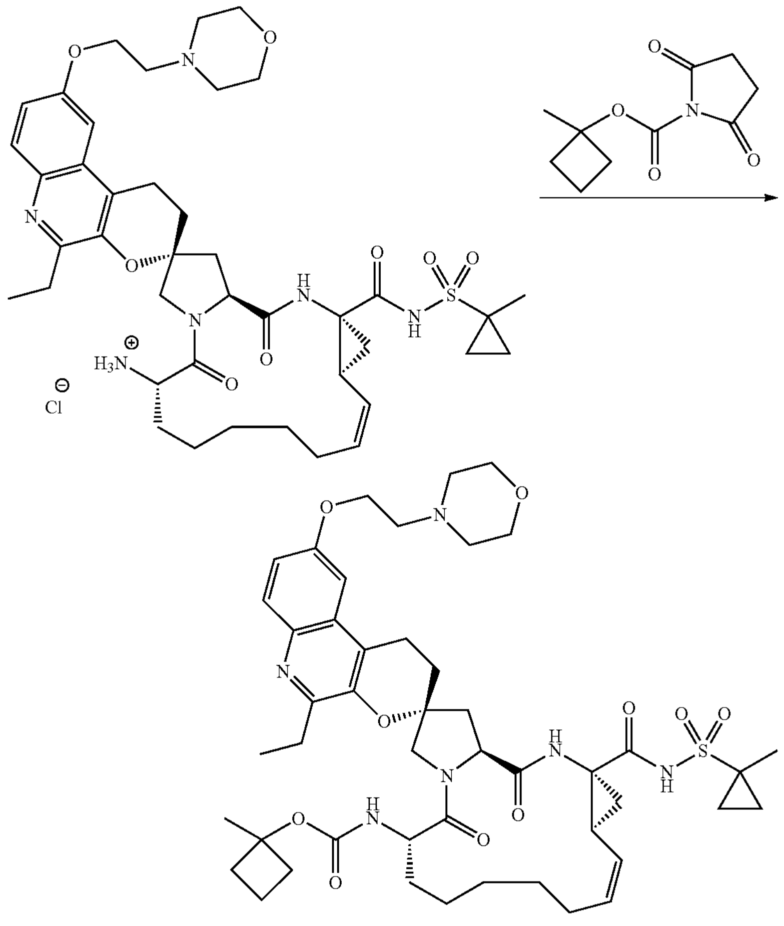

The amine salt from step 8 was converted to Example I-509 by following the procedure described for the synthesis of Example 47 step 12.

Example 529

HCV NS3 Inhibitory Activity of Exemplary Compounds

Compounds described herein can be evaluated for different activities such as the ability to inhibit HCV NS3 activity, HCV replicon activity, and HCV replication activity using techniques well-known in the art (See, for example, Steven S. Carroll et al., *Inhibition of Hepatitis C Virus RNA Replication by 2'-Modified Nucleoside Analogs,* 278(14) J. Biological Chemistry 11979 (2003)).

Measuring Compound Inhibitory Potency (Genotype 1b Replicon EC50 (nM))

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C,* 110 J. Virological Methods 201 (2003); Steven S. Carroll et al., *Inhibition of Hepatitis C Virus RNA Replication by 2'-Modified Nucleoside Analogs,* 278(14) J. Biological Chemistry 11979 (2003). However, the underlying principles are common to all of these determinations, and are outlined below.

Stable neomycin phosphotransferase encoding replicon-harboring cell lines were used, so all cell lines were maintained under G418 selection prior to the assay. In some cases the cell lines encoded a luciferase:$Neo^r$ fusion and could be assayed either directly by determination of RNA copy number, or indirectly through measurement of the luciferase activity.

To initiate an assay, replicon cells were plated in the presence of a dilution series of test compound in the absence of G418. Typically, the assays were performed in a 96-well plate format for manual operation, or a 384 well plate in an automated assay. Replicon cells and compound were incubated for 24-48 hours, depending on the assay. At the end of the assay, cells are washed free of media and compound and then lysed. For direct quantitation, RNA levels were measured by $^{32}$P-probe hybridization and protection, or in a TAQMAN based assay and normalized to cellular cyclophilin A RNA levels. In some cases, luciferase activity was measured using a conventional luciferase assay. In all cases EC50 determinations were calculated as a percent of a DMSO control by fitting the data to a four parameter fit function.

Measuring NS3/4A Inhibitory Activity (Ki) Against Genotype 1b, Against A156T Mutants and Against Genotype 3a One assay for measuring inhibitory activity is HCV NS3 protease time-resolved fluorescence (TRF) assay as described below and in Mao et al., *Anal. Biochem.* 373:1-8, 2008 and International Patent Application Publication WO 2006/102087. A NS3 protease assay can be performed, for example, in a final volume of 20 μl assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 30 min. The reaction is initiated by adding the TRF peptide substrate (final concentration 25 nM). NS3 mediated hydrolysis of the substrate was run for 2.5 hours at room temperature. Product fluorescence is detected using A Pherastar Plus plate reader (BMG) or Envision (Perkin Elmer Life and Analytical Sciences with excitation at 340 nm and emission at 615 nm using the appropriate delay time optimized for the europium fluorescence probe. Testing concentrations of different enzyme forms are selected to result in a signal to background ratio (S/B) of 10-30. $IC_{50}$ values are derived using a standard four-parameter fit to the data. $K_i$ values are derived from $IC_{50}$ values using the following formula, $$IC_{50}=K_i(1+[S]/K_M), \quad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996); Mao et al., *Analytical Biochemistry* 373: 1-8, 2008.

The assay described above was run against genotype 1b at a concentration of 0.2 nM, against A156T mutant strains at a concentration of 0.4 nM, and against genotype 3a at a concentration of 0.025 nM.

Table 2 provides inhibitory data for the listed Exemplary compounds, obtained in accordance with the procedures above.

TABLE 2

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 1 | 1.47 | 0.013 | — | — |
| 2 | 1.187 | 0.012 | — | — |
| 3 | 2.898 | 0.004 | — | — |
| 4 | 0.813 | 0.009 | — | — |
| 5 | 1.362 | 0.015 | — | — |
| 6 | 1.226 | 0.016 | 0.53 | 0.5908 |
| 7 | 0.4335 | 0.020 | — | — |
| 8 | — | 0.011 | — | — |
| 9 | — | 0.006 ($K^+$ salt) | — | — |
| 10 | 1.113 ($K^+$ salt) | 0.013 ($K^+$ salt) | — | — |
| 11 | 2.705 | 0.007 | — | — |
| 12 | — | 0.007 | — | — |
| 13 | 4.23 | — | — | — |
| 14 | 6.5 | — | — | — |
| 15 | 9.36 | — | — | — |
| 16 | 0.69 | 0.009 | — | — |
| 17 | — | — | — | — |
| 18 | 0.77 | — | — | — |
| 19 | 1.984 ($K^+$ salt) | 0.018 ($K^+$ salt) | — | — |
| 20 | 1.777 ($K^+$ salt) | 0.009 ($K^+$ salt) | — | — |
| 21 | 0.81 | — | — | — |
| 22 | 4.14 | — | — | — |
| 23 | 9.13 | — | — | — |
| 24 | 5.92 | — | — | — |
| 25 | 1.11 | 0.016 | — | — |
| 26 | 1.34 | 0.013 | — | — |
| 27 | 10.61 | 0.011 | — | — |
| 28 | 14.72 | 0.016 | — | — |
| 29 | 0.608 | 0.021 | — | — |
| 30 | 2.546 | 0.009 | — | — |
| 31 | 1.56 | 0.020 | — | — |
| 32 | — | 0.024 | — | — |
| 33 | 1.651 | 0.042 | — | — |
| 34 | 1.79 | 0.013 | — | — |
| 35 | 1.69 | 0.016 | — | — |
| 36 | 1.202 | 0.009 | — | — |
| 37 | 11.29 | 0.036 | — | — |

TABLE 2-continued

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 38 | 22.1 | 0.058 | — | — |
| 39 | 0.59 | 0.004 | — | — |
| 40 | 5.329 ($K^+$ salt) | 0.005 ($K^+$ salt) | — | — |
| 41 | 16.16 ($K^+$ salt) | 0.007 ($K^+$ salt) | — | — |
| 42 | 2.59 | 0.008 | — | — |
| 43 | 1.249 | 0.005 | — | — |
| 44 | 1.60 | 0.104 | — | — |
| 45 | 1.098 | 0.011 | — | — |
| 46 | 0.4 ($K^+$ salt) | 0.020 ($K^+$ salt) | — | — |
| 47 | 3.719 | 0.011 | — | — |
| 48 | 1.10 | 0.006 | — | — |
| 49 | 9.131 | 0.014 | — | — |
| 50 | 0.2836 | 0.010 | 0.09646 | 0.07863 |
| 51 | 0.2456 ($K^+$ salt) | 0.011 ($K^+$ salt) | — | — |
| 52 | 1.774 | 0.004 | — | — |
| 53 | 15.91 | 0.056 | — | — |
| 54 | 1.182 | 0.012 | — | — |
| 55 | 0.5775 | 0.007 | — | — |
| 56 | 1.661 ($K^+$ salt) | 0.008 ($K^+$ salt) | — | — |
| 57 | 9.226 | 0.137 | — | — |
| 58 | 47.6 | 0.006 | — | — |
| 59 | 3.45 | 0.019 | — | — |
| 60 | 1.23 | 0.009 | — | — |
| 61 | 12.19 | 0.015 | — | — |
| 62 | 0.26 | 0.016 | — | — |
| 63 | 0.2455 | 0.007 | — | — |
| 64 | — | 0.046 | — | — |
| 65 | 0.148 | 0.011 | — | — |
| 66 | 0.148 | 0.011 | — | — |
| 67 | — | 0.021 | — | — |
| 68 | 0.98 | 0.016 | — | — |
| 69 | 0.82 ($K^+$ salt) | 0.012 ($K^+$ salt) | — | — |
| 70 | 1.39 ($K^+$ salt) | 0.028 ($K^+$ salt) | — | — |
| 71 | 0.628 ($K^+$ salt) | 0.023 ($K^+$ salt) | — | — |
| 72 | 24.2 | 0.665 | — | — |
| 73 | 1.71 | 0.12 | — | — |
| 74 | 2.48 | 0.008 | 0.5718 | 0.1239 |
| 75 | 7.36 | 0.022 | — | — |
| 76 | 11.87 | — | — | — |
| 77 | >100 | — | — | — |
| 78 | 85 | — | — | 3.112 |
| 79 | 1.687 | — | — | 0.1514 |
| 80 | 1.47 | — | — | — |
| 81 | 1.33 | — | — | — |
| 82 | 4.25 | — | — | — |
| 83 | 3.71 | — | — | — |
| 84 | 7.79 | — | — | — |
| 85 | 1.314 | 0.013 | — | — |
| 86 | >100 | — | — | — |
| 87 | 5.87 | 0.01 | — | — |
| 88 | 0.582 | 0.202 | — | — |
| 89 | 2.85 | | — | — |
| 90 | 1.15 | 0.006 | — | — |
| 91 | 0.46 | 0.009 | — | — |
| 92 | 0.44 | 0.01 | — | — |
| 93 | 3.40 | 0.007 | — | — |
| 94 | 0.61 | 0.003 | — | — |
| 95 | 5.24 | 0.993 | — | — |
| 96 | 0.796 | 0.01 | — | — |
| 97 | 1.94 | 0.016 | — | — |
| 98 | 9.72 | 0.057 | — | — |
| 99 | 4.53 | 0.033 | — | — |
| 100 | 2.079 | 0.011 | — | — |
| 101 | >100 | 38.22 | — | — |
| 102 | 1.58 | 0.004 | — | — |
| 103 | 1.51 | 0.012 | — | — |
| 104 | 1.39 | 0.013 | — | — |
| 105 | 1.423 | 0.013 | — | — |
| 106 | 3.21 | 0.048 | — | — |
| 107 | 3.485 | 0.014 | — | — |
| 108 | 1.23 | 0.007 | — | — |
| 109 | 0.944 | 0.011 | — | — |
| 110 | 47.71 | 0.806 | — | — |
| 111 | 0.685 | 0.011 | — | — |
| 112 | 32.04 | 0.226 | — | — |

TABLE 2-continued

| Inhibitory Activity Data for Compounds of the Examples | | | | |
|---|---|---|---|---|
| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
| 113 | 3.954 | 0.298 | — | — |
| 114 | 3.53 | 0.308 | — | — |
| 115 | 6.86 | 0.017 | — | — |
| 116 | 0.312 | 0.008 | — | — |
| 117 | — | 0.056 | — | — |
| 118 | 47.3 | 0.027 | — | — |
| 119 | ~78.5 | 0.031 | — | — |
| 120 | 19.03 | 0.032 | — | — |
| 121 | 6.46 | 0.025 | — | — |
| 122 | 1.98 | 0.019 | — | — |
| 123 | 2.07 | 0.017 | — | — |
| 124 | 2.49 | 0.016 | — | — |
| 125 | 3.71 | 0.016 | — | — |
| 126 | 2.61 | 0.029 | — | — |
| 127 | 0.394 | 0.031 | — | — |
| 128 | 2.011 | 0.044 | — | — |
| 129 | 2.11 | 0.011 | — | — |
| 130 | 1.934 | 0.01 | — | — |
| 131 | 1.282 | 0.003 | — | — |
| 132 | 1.412 | 0.002 | — | — |
| 133 | 17.36 | 0.007 | — | — |
| 134 | 2.84 (K+ salt) | 0.014 (K+ salt) | — | — |
| 135 | 2.818 (K+ salt) | 0.037 (K+ salt) | — | — |
| 136 | 2.122 (K+ salt) | 0.019 (K+ salt) | — | — |
| 137 | 1.707 | 0.025 | — | — |
| 138 | 2.507 | 0.043 | — | — |
| 139 | 8.09 | 0.127 | — | — |
| 140 | 1.027 (K+ salt) | 0.004 (K+ salt) | — | — |
| 141 | 1.47 | 0.003 | — | — |
| 142 | 1.14 | 0.004 | — | — |
| 143 | 1.18 (K+ salt) | 0.009 (K+ salt) | — | — |
| 144 | 1.024 | 0.007 | — | — |
| 145 | 1.161 | 0.006 | — | — |
| 146 | 11.79 | 0.03 | — | — |
| 147 | 1.051 | 0.01 | — | — |
| 148 | 0.195 (K+ salt) | 0.011 (K+ salt) | — | — |
| 149 | 0.195 | 0.022 | — | — |
| 150 | 0.195 | 0.013 | — | — |
| 151 | 1.774 (K+ salt) | 0.014 (K+ salt) | — | — |
| 152 | 0.7287 (K+ salt) | 0.014 (K+ salt) | — | — |
| 153 | 1.863 (K+ salt) | 0.014 (K+ salt) | — | — |
| 154 | 1.002 | 0.014 | — | — |
| 155 | 1.174 | 0.015 | — | — |
| 156 | — | — | — | — |
| 157 | 1.715 | 0.020 | — | — |
| 158 | 1.174 | 0.020 | — | — |
| 159 | 1.188 | 0.013 | — | — |
| 160 | 1.822 (K+ salt) | 0.026 (K+ salt) | — | — |
| 161 | 3.021 | 0.138 | — | — |
| 162 | 71.97 | 6.380 | — | — |
| 163 | >100 | 6.211 | — | — |
| 164 | 2.713 | 0.132 | — | — |
| 165 | 1.389 | 0.005 | — | — |
| 166 | 2.399 | 0.019 | — | — |
| 167 | 1.877 | 0.020 | — | — |
| 168 | 3.733 | 0.013 | — | — |
| 169 | 1.531 | 0.019 | — | — |
| 170 | 2.648 | 0.013 | — | — |
| 171 | 1.619 | 0.013 | — | — |
| 172 | 7.987 | 0.240 | — | — |
| 173 | >100 | 6.266 | — | — |
| 174 | 2.331 | 0.007 | — | — |
| 175 | 1.671 | 0.028 | — | — |
| 176 | 2.258 | 0.026 | — | — |
| 177 | 21.92 | 0.011 | — | — |
| 178 | 11.07 | 0.007 | — | — |
| 179 | 0.2 | 0.012 | — | — |
| 180 | 1.715 | 0.012 | — | — |
| 181 | 0.39 | 0.017 | — | — |
| 182 | 1.7 (K+ salt) | 0.009 (K+ salt) | — | — |
| 183 | 1.626 (K+ salt) | 0.008 (K+ salt) | — | — |
| 184 | 4.225 (K+ salt) | 0.004 (K+ salt) | — | — |
| 185 | 4.139 (K+ salt) | 0.005 (K+ salt) | — | — |
| 186 | — | 0.009 (K+ salt) | — | — |
| 187 | 8.333 | 0.023 | — | — |

TABLE 2-continued

| Inhibitory Activity Data for Compounds of the Examples | | | | |
|---|---|---|---|---|
| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
| 188 | 3.848 | 0.006 | — | — |
| 189 | 6.415 (K+ salt) | 0.002 (K+ salt) | 0.394 (K+ salt) | 0.062 (K+ salt) |
| 190 | 13.15 (K+ salt) | 0.009 (K+ salt) | — | — |
| 191 | 3.587 | 0.012 | — | — |
| 192 | 9.609 | 0.019 | — | — |
| 193 | 31.06 (K+ salt) | 0.007 (K+ salt) | — | — |
| 194 | 8.284 (K+ salt) | 0.007 (K+ salt) | 0.9943 (K+ salt) | 0.05409 (K+ salt) |
| 195 | 8.668 (K+ salt) | 0.010 (K+ salt) | 1.729 (K+ salt) | 0.1342 (K+ salt) |
| 196 | 5.525 | 0.003 | — | — |
| 197 | 9.868 | 0.004 | — | — |
| 198 | 9.186 | 0.006 | 0.5611 | 0.1036 |
| 199 | 1.001 (K+ salt) | 0.003 (K+ salt) | 0.287 (K+ salt) | 0.04619 (K+ salt) |
| 200 | 0.3688 (K+ salt) | 0.005 (K+ salt) | — | — |
| 201 | 0.9099 (K+ salt) | 0.007 (K+ salt) | — | — |
| 202 | 1.43 (K+ salt) | 0.009 (K+ salt) | — | — |
| 203 | — | 0.015 (K+ salt) | — | — |
| 204 | — | 0.015 (K+ salt) | — | — |
| 205 | 0.6473 (K+ salt) | 0.005 (K+ salt) | — | — |
| 206 | 0.8082 (K+ salt) | 0.005 (K+ salt) | — | — |
| 207 | 1.081 | 0.007 | — | — |
| 208 | 2.047 | 0.009 | — | — |
| 209 | — | 0.030 | — | — |
| 210 | 2.376 | 0.008 | — | — |
| 211 | 3.543 | 0.006 | — | — |
| 212 | — | 0.003 (K+ salt) | — | — |
| 213 | — | 0.004 (K+ salt) | — | — |
| 214 | — | 0.005 (K+ salt) | — | — |
| 215 | — | 0.005 (K+ salt) | — | — |
| 216 | 6.43 | 0.013 | — | — |
| 217 | 10.35 | 0.024 | — | — |
| 218 | 2.154 | 0.005 | — | — |
| 219 | 1.196 | 0.004 | — | — |
| 220 | — | 0.033 | — | — |
| 221 | 11.57 | 0.008 | — | — |
| 222 | 4.777 (K+ salt) | 0.009 (K+ salt) | — | — |
| 223 | 11.05 | 0.013 | — | — |
| 224 | 6.728 | 0.019 | — | — |
| 225 | 12.54 | 0.031 | — | — |
| 226 | 17.98 (K+ salt) | 0.021 (K+ salt) | — | — |
| 227 | 28.43 (K+ salt) | 0.043 (K+ salt) | — | — |
| 228 | 6.627 | 0.025 | — | — |
| 229 | 14.64 | 0.122 | — | — |
| 230 | 57.83 | 0.265 | — | — |
| 231 | 4.773 | 0.024 | — | — |
| 232 | 12.91 | 0.085 | — | — |
| 233 | 1.511 | 0.051 | — | — |
| 234 | 4.48 (K+ salt) | 0.025 (K+ salt) | — | — |
| 235 | 4.308 (K+ salt) | 0.027 (K+ salt) | — | — |
| 236 | 7.237 (K+ salt) | 0.056 (K+ salt) | — | — |
| 237 | 5.721 | 0.040 | — | — |
| 238 | 7.722 | 0.020 | — | — |
| 239 | 5.164 | 0.068 | — | — |
| 240 | 2.646 | 0.010 | — | — |
| 241 | 2.895 | 0.012 | — | — |
| 242 | 3.376 | 0.022 | — | — |
| 243 | 43.04 (K+ salt) | 0.012 (K+ salt) | — | — |
| 244 | 2.889 | 0.008 | — | — |
| 245 | 13.41 (K+ salt) | 0.025 (K+ salt) | — | — |
| 246 | 17.38 | 0.004 | — | — |
| 247 | — | 0.013 | — | — |
| 248 | 14.74 (K+ salt) | 0.026 (K+ salt) | — | — |
| 249 | 14.6 (K+ salt) | 0.020 (K+ salt) | — | — |
| 250 | 6.498 | 0.024 | — | — |
| 251 | 14.32 | 0.021 | — | — |
| 252 | 44.36 | 0.010 | — | — |
| 253 | — | 0.014 | — | — |
| 254 | 1.578 (K+ salt) | 0.010 (K+ salt) | — | — |
| 255 | 50.9 | 0.015 | 2.863 | 0.6788 |
| 256 | 3.075 | 0.005 | — | — |
| 257 | 3.253 | 0.018 | — | — |
| 258 | 717 | 0.022 | — | — |
| 259 | 24.02 | 0.007 | — | — |
| 260 | 5.224 | 0.006 | — | — |
| 261 | 192.5 | 0.008 | — | — |
| 262 | 38.9 | 0.037 | — | — |

TABLE 2-continued

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 263 | 5.296 (K+ salt) | 0.007 (K+ salt) | — | — |
| 264 | 4.298 (K+ salt) | 0.013 (K+ salt) | — | — |
| 265 | 3.349 (K+ salt) | 0.007 (K+ salt) | — | — |
| 266 | 4.473 (K+ salt) | 0.014 (K+ salt) | 2.101 (K+ salt) | 0.3836 (K+ salt) |
| 267 | 3.563 (K+ salt) | 0.006 (K+ salt) | — | — |
| 268 | 4.032 (K+ salt) | 0.003 (K+ salt) | — | — |
| 269 | 11.91 (HCOOH salt) | 0.337 (HCOOH salt) | — | — |
| 270 | 24.25 (HCOOH salt) | 0.044 (HCOOH salt) | — | — |
| 271 | 5.898 (HCOOH salt) | 0.031 (HCOOH salt) | — | — |
| 272 | 11.19 (HCOOH salt) | 0.116 (HCOOH salt) | — | — |
| 273 | 163.4 (HCOOH salt) | 1.128 (HCOOH salt) | — | — |
| 274 | 28.28 (HCOOH salt) | 0.832 (HCOOH salt) | — | — |
| 275 | 39.46 (HCOOH salt) | 11.340 (HCOOH salt) | — | — |
| 276 | 103.6 (HCOOH salt) | 3.970 (HCOOH salt) | — | — |
| 277 | 81.62 (HCOOH salt) | 1.050 (HCOOH salt) | — | — |
| 278 | 12.45 (HCOOH salt) | 0.027 (HCOOH salt) | — | — |
| 279 | 22.27 (HCOOH salt) | 0.051 (HCOOH salt) | — | — |
| 280 | 2.844 | 0.005 | — | — |
| 281 | 10.75 | 0.060 | — | — |
| 282 | 43.63 (HCOOH salt) | 0.018 (HCOOH salt) | — | — |
| 283 | 19.01 (HCOOH salt) | 0.012 (HCOOH salt) | — | — |
| 284 | 58.74 (HCOOH salt) | 0.038 (HCOOH salt) | — | — |
| 285 | 10.26 (HCOOH salt) | 0.002 (HCOOH salt) | — | — |
| 286 | 118.6 | 0.015 | — | — |
| 287 | 23.04 (HCOOH salt) | 0.013 (HCOOH salt) | — | — |
| 288 | 614.1 (HCOOH salt) | 0.131 (HCOOH salt) | — | — |
| 289 | 6.998 (HCOOH salt) | 0.023 (HCOOH salt) | — | — |
| 290 | 7.018 (HCOOH salt) | 0.017 (HCOOH salt) | — | — |
| 291 | 84.56 (HCOOH salt) | 0.032 (HCOOH salt) | — | — |
| 292 | 27.41 (HCOOH salt) | 0.077 (HCOOH salt) | — | — |
| 293 | 4.873 (HCOOH salt) | 0.021 (HCOOH salt) | — | — |
| 294 | 4.245 | 0.016 | — | — |
| 295 | 2.364 | 0.024 | — | — |
| 296 | 2.546 | 0.009 | — | — |
| 297 | 6.059 | 0.009 | — | — |
| 298 | 6.313 | 0.017 | — | — |
| 299 | 6.37 (K+ salt) | 0.020 (K+ salt) | — | — |
| 300 | 3.118 | 0.021 | — | — |
| 301 | 3.464 | 0.013 | — | — |
| 302 | 4.189 | 0.006 | — | — |
| 303 | 5.793 | 0.012 | — | — |
| 304 | 99.6 | 0.027 | — | — |
| 305 | 35.16 | 0.029 | — | — |
| 306 | 1.87 | 0.015 | — | — |
| 307 | 1080 | 0.019 | — | — |
| 308 | 416 | 0.006 | — | — |
| 309 | 1.94 | 0.010 | — | — |
| 310 | 5.655 (K+ salt) | 0.008 (K+ salt) | — | — |
| 311 | 1.23 | 0.008 | — | — |
| 312 | 3.56 | 0.009 | — | — |
| 313 | 2.87 | 0.016 | — | — |
| 314 | 8.74 | 0.013 | — | — |
| 315 | 294 | 1.294 | — | — |

TABLE 2-continued

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 316 | 2.63 | 0.008 | — | — |
| 317 | 3.25 | 0.023 | — | — |
| 318 | 4.99 | 0.013 | — | — |
| 319 | 17.8 (K+ salt) | 0.044 (K+ salt) | — | — |
| 320 | 4.44 | 0.013 | — | — |
| 321 | 7.16 | 0.030 | — | — |
| 322 | 6.92 | 0.073 | — | — |
| 323 | 11.36 | 0.012 | — | — |
| 324 | 3.62 | 0.022 | — | — |
| 325 | 3.23 | 0.013 | — | — |
| 326 | 1.11 | 0.023 | — | — |
| 327 | 3.61 (K+ salt) | 0.026 (K+ salt) | — | — |
| 328 | 47 (K+ salt) | 0.348 (K+ salt) | — | — |
| 329 | 12.2 | 0.032 | — | — |
| 330 | 3.58 | 0.016 | — | — |
| 331 | 6.715 | 0.010 | — | — |
| 332 | 2.69 | 0.017 | — | — |
| 333 | 10.27 | 0.010 | — | — |
| 334 | 5.59 | 0.019 | — | — |
| 335 | 2.603 | 0.017 | — | — |
| 336 | 3.455 | 0.008 | — | — |
| 337 | 2.37 | 0.009 | — | — |
| 338 | 1.533 | 0.009 | — | — |
| 339 | 1.92 | 0.019 | — | — |
| 340 | 3.23 | 0.030 | — | — |
| 341 | 1.04 | 0.172 | — | — |
| 342 | — | — | — | — |
| 343 | 5.86 | 0.050 | — | — |
| 344 | 662 | 0.685 | — | — |
| 345 | 6.59 | 0.428 | — | — |
| 346 | 4.23 | 0.012 | — | — |
| 347 | 3060 | 0.981 | — | — |
| 348 | 9.23 (K+ salt) | 0.046 (K+ salt) | — | — |
| 349 | 4.55 (K+ salt) | 0.012 (K+ salt) | — | — |
| 350 | 2.84 | 0.035 | — | — |
| 351 | 2.195 (K+ salt) | 0.029 (K+ salt) | — | — |
| 352 | 1.448 (K+ salt) | 0.042 (K+ salt) | — | — |
| 353 | 39.5 | 0.111 | — | — |
| 354 | 103 | 0.169 | — | — |
| 355 | 3.77 (K+ salt) | 0.020 (K+ salt) | — | — |
| 356 | 3.73 (K+ salt) | 0.012 (K+ salt) | — | — |
| 357 | 2.91 (K+ salt) | 0.010 (K+ salt) | — | — |
| 358 | 42.8 (K+ salt) | 0.172 (K+ salt) | — | — |
| 359 | 205 | 0.400 | — | — |
| 360 | 140 | 0.143 | — | — |
| 361 | 4.43 | 0.012 | 0.4333 | 0.2409 |
| 362 | 4.07 | 0.008 | — | — |
| 363 | 8.16 | 0.011 | — | — |
| 364 | 5.46 | 0.012 | — | — |
| 365 | 4.93 | 0.020 | — | — |
| 366 | 6.46 | 0.023 | — | — |
| 367 | 3.61 | 0.030 | — | — |
| 368 | 9.68 | 0.017 | — | — |
| 369 | 15.1 | 0.018 | 1.18 | 1.155 |
| 370 | 8.56 (K+ salt) | 0.009 (K+ salt) | 0.149 (K+ salt) | 0.037 (K+ salt) |
| 371 | 1.27 (K+ salt) | 0.015 (K+ salt) | — | — |
| 372 | 2.12 (K+ salt) | 0.010 (K+ salt) | — | — |
| 373 | 2.67 (K+ salt) | 0.011 (K+ salt) | — | — |
| 374 | 2.29 | 0.012 | — | — |
| 375 | 6.38 | 0.018 | — | — |
| 376 | 2.69 | 0.013 | — | — |
| 377 | 2.52 | 0.018 | — | — |
| 378 | 3.59 | 0.020 | — | — |
| 379 | 1.36 | 0.104 | — | — |
| 380 | 5.62 (K+ salt) | 0.021 (K+ salt) | — | — |
| 381 | 6.74 | 0.040 | — | — |
| 382 | 3.61 (K+ salt) | 0.028 (K+ salt) | 1.09 (K+ salt) | 2.339 (K+ salt) |
| 383 | 38.3 | 0.024 | — | — |
| 384 | 19.8 | 0.023 | — | — |
| 385 | 6.79 | 0.017 | — | — |
| 386 | 49.6 | 0.029 | — | — |
| 387 | 20.1 | 0.038 | — | — |
| 388 | 1.31 | 0.028 | — | — |
| 389 | 2.609 | 0.011 | — | — |
| 390 | 15.5 | 0.015 | — | — |

TABLE 2-continued

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 391 | — | 0.026 | — | — |
| 392 | — | 0.014 | — | — |
| 393 | — | 0.026 | — | — |
| 394 | — | 0.057 | — | — |
| 395 | — | 0.014 | — | — |
| 396 | — | 0.009 | — | — |
| 397 | — | 0.006 | — | — |
| 398 | — | 0.025 | 2.347 | 0.4965 |
| 399 | — | 0.027 | 6.454 | 1.452 |
| 400 | — | 0.052 | — | — |
| 401 | — | 0.057 | — | — |
| 402 | 2.27 (K+ salt) | 0.011 (K+ salt) | — | — |
| 403 | 1.92 (K+ salt) | 0.013 (K+ salt) | — | — |
| 404 | 1.23 | 0.018 | — | — |
| 405 | 0.813 | 0.021 | — | — |
| 406 | 1 | 0.013 | — | — |
| 407 | 1.5 (K+ salt) | 0.019 (K+ salt) | — | — |
| 408 | 1.23 (K+ salt) | 0.023 (K+ salt) | — | — |
| 409 | 4.73 | 0.020 | — | — |
| 410 | 3.1 | 0.011 | — | — |
| 411 | 5.77 | 0.064 | — | — |
| 412 | 1.423 (K+ salt) | 0.038 (K+ salt) | — | — |
| 413 | 2.53 (K+ salt) | 0.021 (K+ salt) | — | — |
| 414 | 5.16 | 0.047 | — | — |
| 415 | 16.3 | 0.118 | — | — |
| 416 | 272 | 0.164 | — | — |
| 417 | 45.3 | 0.094 | — | — |
| 418 | 6.24 | 0.008 | — | — |
| 419 | 1.75 (K+ salt) | 0.038 (K+ salt) | — | — |
| 420 | 1.251 (K+ salt) | 0.011 (K+ salt) | — | — |
| 421 | 1.72 | 0.024 | — | — |
| 422 | 3.143 (K+ salt) | 0.008 (K+ salt) | — | — |
| 423 | 18.97 | 0.048 | — | — |
| 424 | 15.05 | 0.033 | — | — |
| 425 | 3.292 | 0.024 | — | — |
| 426 | 21.36 | 0.603 | — | — |
| 427 | 1.462 | 0.015 | — | — |
| 428 | 2.213 | 0.020 | — | — |
| 429 | 4.278 | 0.194 | — | — |
| 430 | 5.041 | 0.026 | — | — |
| 431 | 9.124 | 0.209 | — | — |
| 432 | 7.496 | 0.091 | — | — |
| 433 | 2.167 | 0.012 | — | — |
| 434 | 1.777 | 0.012 | — | — |
| 435 | 3.08 (K+ salt) | 0.069 (K+ salt) | — | — |
| 436 | 1.177 (K+ salt) | 0.029 (K+ salt) | — | — |
| 437 | 1.001 (K+ salt) | 0.016 (K+ salt) | — | — |
| 438 | 3.496 | 0.023 | — | — |
| 439 | 1.549 | 0.009 | — | — |
| 440 | 1.984 (K+ salt) | 0.016 (K+ salt) | — | — |
| 441 | 1.53 (K+ salt) | 0.016 (K+ salt) | — | — |
| 442 | 1.675 (K+ salt) | 0.024 (K+ salt) | — | — |
| 443 | 1.792 (K+ salt) | 0.025 (K+ salt) | — | — |
| 444 | 1.31 (K+ salt) | 0.014 (K+ salt) | — | — |
| 445 | 1.141 (K+ salt) | 0.014 (K+ salt) | — | — |
| 446 | 1.165 | 0.013 | — | — |
| 447 | 1.37 | 0.019 | — | — |
| 448 | 2.689 | 0.006 | — | — |
| 449 | 1.387 | 0.007 | — | — |
| 450 | 1.694 | 0.019 | — | — |
| 451 | 1.857 | 0.006 | 0.5042 | 0.3382 |
| 452 | 2.401 | 0.030 | — | — |
| 453 | 1.78 | 0.017 | — | — |
| 454 | 1.379 (K+ salt) | 0.024 (K+ salt) | — | — |
| 455 | 1.549 (K+ salt) | 0.040 (K+ salt) | — | — |
| 456 | 1.412 (K+ salt) | 0.021 (K+ salt) | — | — |
| 457 | 1.168 (K+ salt) | 0.068 (K+ salt) | — | — |
| 458 | 1.426 | 0.015 | — | — |
| 459 | 4.404 (K+ salt) | 0.049 (K+ salt) | 2.31 (K+ salt) | 2.649 (K+ salt) |
| 460 | 2.993 (K+ salt) | 0.034 (K+ salt) | 1.777 (K+ salt) | 2.74 (K+ salt) |
| 461 | 3.29 | 0.029 | 0.6239 | 0.4347 |
| 462 | 5.752 | 0.036 | — | — |
| 463 | 2.156 | 0.057 | — | — |
| 464 | 14.97 | 1.030 | — | — |
| 465 | — | — | — | — |

TABLE 2-continued

Inhibitory Activity Data for Compounds of the Examples

| Ex. No. | $EC_{50}$ [gt-1b] (nM) | $IC_{50}$ [gt-1b] (nM) | $IC_{50}$ [gt-3] (nM) | $IC_{50}$ [gt-1b A156T] (nM) |
|---|---|---|---|---|
| 466 | 1.622 | 0.041 | — | — |
| 467 | 4.705 | 0.028 | — | — |
| 468 | 7.154 | 0.031 | — | — |
| 469 | 48.78 | 0.016 | — | — |
| 470 | 5.743 | 0.011 | — | — |
| 471 | 3.06 (HCl salt) | 0.021 (HCl salt) | — | — |
| 472 | 3.433 (HCl salt) | 0.020 (HCl salt) | — | — |
| 473 | 2.269 | 0.031 | — | — |
| 474 | 1.728 | 0.033 | — | — |
| 475 | 2.392 (K+ salt) | 0.005 (K+ salt) | — | — |
| 476 | 4.349 | 0.012 | — | — |
| 477 | 5.051 (K+ salt) | 0.019 (K+ salt) | — | — |
| 478 | 5.799 | 0.016 | — | — |
| 479 | 1.049 | 0.005 | — | — |
| 480 | 0.2661 | 0.006 | — | — |
| 481 | 1.306 (K+ salt) | 0.006 (K+ salt) | 0.225 (K+ salt) | 0.436 (K+ salt) |
| 482 | 68.57 | 0.008 | 0.4178 | 0.101 |
| 483 | 0.4378 | 0.008 | 0.6668 | 0.09686 |
| 484 | 0.3568 (K+ salt) | 0.003 (K+ salt) | 0.628 (K+ salt) | 0.1642 (K+ salt) |
| 485 | 0.3059 | 0.005 | — | — |
| 486 | 15.23 | 0.010 | — | — |
| 487 | 0.3426 (K+ salt) | 0.005 (K+ salt) | — | — |
| 488 | 0.4121 (K+ salt) | 0.004 (K+ salt) | 0.4857 (K+ salt) | 0.1361 (K+ salt) |
| 489 | 4.22 | 0.016 | — | — |
| 490 | 0.4639 | 0.017 | — | — |
| 491 | 2.526 (K+ salt) | 0.003 (K+ salt) | — | — |
| 492 | 1.391 | 0.044 | — | — |
| 493 | 0.2834 (K+ salt) | 0.003 (K+ salt) | — | — |
| 494 | 1.73 | 0.018 | — | — |
| 495 | 1.448 | 0.007 | — | — |
| 496 | 6.931 | 0.027 | — | — |
| 497 | 1.938 | 0.014 | — | — |
| 498 | 0.6073 (K+ salt) | 0.009 (K+ salt) | — | — |
| 499 | 0.4332 (K+ salt) | 0.004 (K+ salt) | — | — |
| 500 | 435.3 | 0.014 | — | — |
| 501 | 3.704 (K+ salt) | 0.004 (K+ salt) | 0.2058 (K+ salt) | 0.6 (K+ salt) |
| 502 | 0.2899 | 0.004 | 0.4801 | 0.1212 |
| 503 | — | 0.007 (K+ salt) | — | — |
| 504 | — | 0.010 (K+ salt) | — | — |
| 505 | — | 0.016 | — | — |
| 506 | — | 0.015 | — | — |
| 507 | — | 0.025 | 4.448 | 2.367 |
| 508 | — | 0.004 (K+ salt) | — | — |
| 509 | — | 0.006 (K+ salt) | — | — |
| 510 | — | 0.004 (K+ salt) | — | — |
| 511 | 0.7818 | 0.008 | 0.2582 | 0.2349 |
| 512 | — | — | — | — |
| 513 | 1.418 | 0.010 | — | — |
| 514 | 0.6677 | 0.012 | 0.2242 | 0.06813 |
| 515 | 0.5035 (HCl salt) | 0.005 (HCl salt) | 0.292 (HCl salt) | 0.05752 (HCl salt) |
| 516 | 1.094 (HCl salt) | 0.010 (HCl salt) | — | — |
| 517 | 8.869 | 11.220 | — | — |
| 518 | 0.7263 | 0.012 | — | — |
| 519 | 0.5413 (HCl salt) | 0.009 (HCl salt) | — | — |
| 520 | — | — | — | — |
| 521 | — | 0.004 (HCl salt) | — | — |
| 522 | — | 0.005 (K+ salt) | 0.3113 (K+ salt) | 0.2806 (K+ salt) |
| 523 | — | 0.009 (K+ salt) | — | — |
| 524 | — | 0.003 | 0.1092 | 0.182 |
| 525 | 1.156 | 0.004 | — | — |
| 526 | 2.591 | 0.005 | — | — |
| 527 | | 0.026 | 0.679 | |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound of Formula II:

(II)

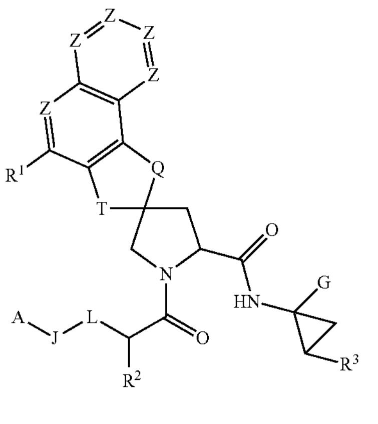

or a pharmaceutically acceptable salt thereof, wherein each Z is independently either N or C—$R^4$;

A is a selected from the group consisting of a) $C_1$-$C_8$ alkyl, $C_2$-$C_8$ alkenyl, $C_2$-$C_8$ alkynyl, $C_3$-$C_8$ cycloalkyl, $C_6$-$C_8$ bridged cycloalkyl, or $C_6$-$C_8$ bridged cycloalkenyl, b) substituted $C_1$-$C_8$ alkyl, substituted $C_2$-$C_8$ alkenyl, substituted $C_2$-$C_8$ alkynyl, substituted $C_3$-$C_8$ cycloalkyl, substituted $C_6$-$C_8$ bridged cycloalkyl, or substituted $C_6$-$C_8$ bridged cycloalkenyl, each of which is substituted with 0, 1, 2, 3 or 4 independently selected $R^A$, and 0 or 1 $R^B$, provided that at least one $R^A$ substituent other than H, or an $R^B$ substituent is present;

c) $C_1$-$C_8$ haloalkyl, $C_3$-$C_8$ halocycloalkyl, or $C_1$-$C_8$ haloalkyl substituted with $R^B$, d) Aryl, and e) Het;

J is selected from the group consisting of a direct bond,

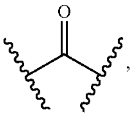, 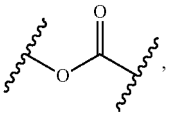, 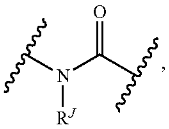, and

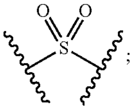;

$R^J$ is selected from the group consisting of hydrogen and $C_1$-$C_6$ alkyl;

L is NH;

G is selected from the group consisting of

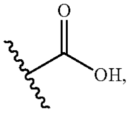 and 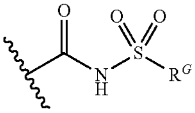

wherein $R^G$ is selected from the group consisting of $C_3$-$C_6$ cycloalkyl, $C_3$-$C_6$ cycloalkyl-$C_1$-$C_5$ alkyl, or $C_3$-$C_6$ cycloalkyl-$C_1$-$C_5$ alkyl substituted with $C_1$-$C_6$ alkoxy;

each $R^1$ is selected from the group consisting of hydrogen, $C_1$-$C_9$ alkyl, $C_1$-$C_6$ alkyl-$R^B$, $C_1$-$C_9$ hydroxylalkyl, $C_3$-$C_8$ cycloalky, $C_1$-$C_4$ haloalkyl, Aryl, and Het;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, Het, and Aryl;

$R^3$ is selected from the group consisting of $C_1$-$C_9$ alkyl, $C_2$-$C_9$ alkenyl, and $C_2$-$C_9$ alkynyl;

T is selected from the group consisting of O, $(CH_2)_{q2}$, NH, $SO_2$ and S, wherein $q_2$ is 1 or 2;

Q is —$(CR^A{}_2)_2$ or —O—$CH_2$—;

each $R^4$ is independently selected from the group consisting of: hydrogen, halogen, OH, $C_1$-$C_6$ alkyl, $C_1$-$C_6$ haloalkyl, $C_1$-$C_6$ alkoxy, $C_1$-$C_6$ haloalkoxy, $C_1$-$C_6$—alkyl-$R^B$, $C_1$-$C_6$ haloalkyl-$R^B$, $C_1$-$C_6$ alkoxy-$R^B$, $C_1$-$C_6$ haloalkoxy —$R^B$, $C_3$-$C_8$ cycloalkyl, $C_3$-$C_8$ cycloalkyl-$C_1$-$C_9$ alkyl, $C_1$-$C_6$ hydroxyalkyl, O—$C_1$-$C_6$ hydroxyalkyl, O—$C_1$-$C_6$ alkyl-$R^B$, CN, O—($C_1$-$C_5$ alkyl)-O—($C_1$-$C_3$ alkyl), O—($C_1$-$C_5$ alkyl)-O—($C_1$-$C_3$ alkyl)-$R^B$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-$S(O)_2$—($C_0$-$C_3$ alkyl)-($C_3$-$C_8$ cycloalkyl), Het, Aryl, and

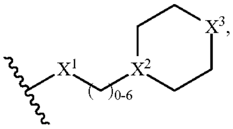, wherein $X^1$ is either $CH_2$, NH, O, or S; $X^2$ is either CH or N; and $X^3$ is either NH, $CH_2$, O, or S;

provided that two $R^4$ groups can join together to form methylene dioxy;

each Aryl is independently phenyl optionally substituted with 1 or 2 $R^C$ substituents;

each Het is independently either (a) 4-, 5- or 6-membered saturated or unsaturated monocyclic ring with 1 or 2 heteroatom ring atoms independently selected from the group consisting of N, O and S; or (b) 8-, 9- or 10-membered saturated or unsaturated bicyclic ring with 1, 2, or 3 heteroatom ring atoms independently selected from the group consisting of N, O and S, provided that said Het is optionally substituted with 1 or 2 $R^C$ substituents;

each $R^A$ is independently selected from the group consisting of: H, F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), $C_6$-$C_8$ bridged cycloalkyl, $C_3$-$C_8$ cycloalkyl, $C_1$-$C_6$ haloalkoxy, $C_3$-$C_8$ halocycloalkyl, SH, S($C_1$-$C_6$ alkyl), $NH_2$, NH($C_1$-$C_6$ alkyl), N($C_1$-$C_6$ alkyl)$_2$, C(O)($C_1$-$C_6$ alkyl), C(O)($C_3$-$C_8$ cycloalkyl), $CONH_2$, $SO_2NH_2$, $NO_2$, CN, $CF_3$, $CHF_2$, $CH_2F$, $OCHF_2$, $OCF_3$, $OCH_2F$, $SO_2$($C_1$-$C_6$ alkyl), S(O)($C_1$-$C_6$ alkyl), —($C_1$-$C_6$ alkyl)S(O)($C_1$-$C_6$ alkyl), $SO_2$($C_3$-$C_6$ cycloalkyl), —($C_1$-$C_6$ alkyl)$S(O)_2$($C_1$-$C_6$ alkyl), —($C_1$-$C_6$ alkyl)N($C_1$-$C_6$ alkyl)$SO_2$($C_1$-$C_6$ alkyl), N($C_1$-$C_6$ alkyl)$SO_2$($C_1$-$C_6$ alkyl), $SO_2N$($C_1$-$C_6$ alkyl)$_2$, —($C_1$-$C_6$ alkyl)$SO_2N$($C_1$-$C_6$ alkyl)$_2$, NHCOO($C_1$-$C_6$ alkyl), NHCO($C_1$-$C_6$ alkyl), NHCONH($C_1$-$C_6$ alkyl), $CO_2$($C_1$-$C_6$ alkyl), C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), —($C_0$-$C_5$ alkyl)-S(O)$_2$—($C_0$-$C_5$ alkyl)-($C_3$-$C_8$ cycloalkyl), Aryl, and Het; provided that two $R^A$ groups present on adjacent carbon atoms can together with the adjacent carbon atoms form a $C_3$-$C_6$ cycloalkyl;

each $R^B$ is independently either Het or Aryl;

each $R^C$ is independently either halogen, $C_1$-$C_6$ alkyl, $C_1$-$C_6$ alkoxy, $C_3$-$C_6$ cycloalkyl or $C_1$-$C_6$ haloalkyl;

alternatively, with respect to A and $R^1$, A is either $C_1$-$C_4$ alkyl, $C_2$-$C_4$ alkenyl, $C_2$-$C_4$ alkynyl, or $C_3$-$C_8$ cycloalkyl, each of which is substituted with $R^{A1}$, and $R^{A1}$ in combination with $R^1$ forms a $C_3$-$C_8$ alkylene, a $C_3$-$C_8$ alkenylene, or a $C_3$-$C_8$ alkynylene;

alternatively, with respect to A and $R^2$, A is either $C_1$-$C_4$ alkyl, $C_2$-$C_4$ alkenyl, $C_2$-$C_4$ alkynyl, or $C_3$-$C_8$ cycloalkyl, each of which is substituted with $R^{A1}$, and $R^{A1}$ in combination with $R^2$ form a $C_3$-$C_8$ alkylene, a $C_3$-$C_8$ alkenylene, or a $C_3$-$C_8$ alkynylene;

alternatively, with respect to $R^2$ and $R^3$, $R^2$ and $R^3$ form a $C_3$-$C_8$ alkylene, $C_3$-$C_8$ alkenylene, or $C_3$-$C_8$ alkynylene.

2. The compound according to claim 1, wherein Q is selected from the group consisting of —$(CH_2)_2$—,

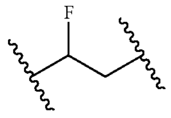 and 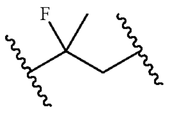

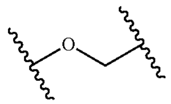 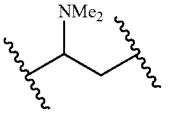 and

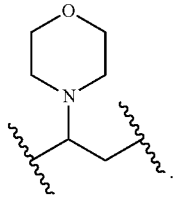.

3. The compound according to claim 1, wherein G is

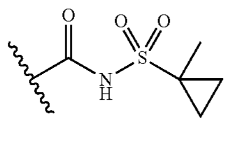 or 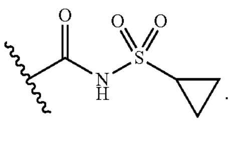.

4. The compound according to claim 1, wherein $R^1$ is hydrogen, $C_1$-$C_6$ alkyl, $C_3$-$C_8$ cycloalkyl, $C_1$-$C_4$ haloalkyl, Aryl, or Het.

5. The compound according to claim 1, wherein said compound of Formula II is a compound of Formula IIa:

(IIa)

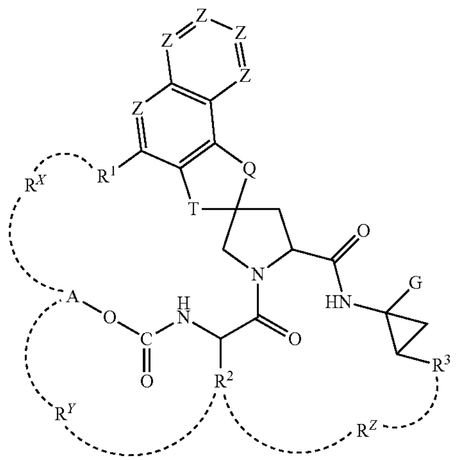

or a pharmaceutically acceptable salt thereof, wherein each Z is independently either N or C—$R^4$;

A is a selected from the group consisting of:

a) $C_1$-$C_6$ alkyl, $C_2$-$C_6$ alkenyl, $C_2$-$C_6$ alkynyl, $C_3$-$C_6$ cycloalkyl, $C_6$-$C_8$ bridged cycloalkyl, or $C_6$-$C_8$ bridged cycloalkenyl, b) substituted $C_1$-$C_8$ alkyl, substituted $C_2$-$C_8$ alkenyl, substituted $C_2$-$C_8$ alkynyl, substituted $C_3$-$C_8$ cycloalkyl, substituted $C_6$-$C_8$ bridged cycloalkyl, or substituted $C_6$-$C_8$ bridged cycloalkenyl, each of which is substituted with 0, 1, 2, 3 or 4 $R^A$, and 0 or 1 $R^B$, provided that at least one $R^A$ or $R^B$ substituent is present, c) $C_1$-$C_8$ haloalkyl, $C_3$-$C_8$ halocycloalkyl, or $C_1$-$C_8$ haloalkyl substituted with $R^B$, d) Aryl, and e) Het;

Q is selected from the group consisting of —$(CH_2)_2$—,

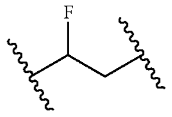 and 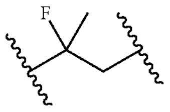

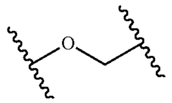 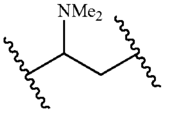 and

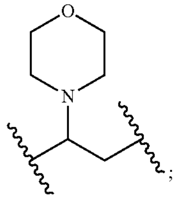;

T is selected from the group consisting of O, —$(CH_2)_{q2}$—, NH, $SO_2$ and S, wherein $q_2$ is 1 or 2;

G is

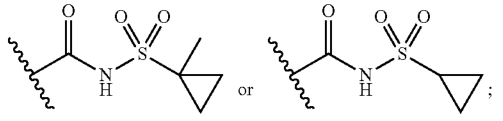 [SMILES: *C(=O)NS(=O)(=O)C1(C)CC1 ; *C(=O)NS(=O)(=O)C1CC1]

$R^1$ is hydrogen, $C_1$-$C_6$ alkyl, $C_3$-$C_8$ cycloalkyl, $C_1$-$C_4$ haloalkyl, $C_1$-$C_6$ alkyl-$R^B$, Aryl, or Het;

$R^2$ is selected from the group consisting of $C_1$-$C_9$ alkyl, $C_2$-$C_9$ alkenyl, $C_2$-$C_9$ alkynyl, $C_3$-$C_8$ cycloalkyl, Het, and Aryl;

$R^3$ is selected from the group consisting of $C_1$-$C_9$ alkyl, $C_2$-$C_9$ alkenyl, and $C_2$-$C_9$ alkynyl;

each $R^4$ is independently selected from the group consisting of: hydrogen, halogen, OH, $C_1$-$C_6$ alkyl, $C_1$-$C_4$ haloalkyl, $C_1$-$C_6$ alkoxy, $C_1$-$C_6$ haloalkoxy, $C_1$-$C_6$ alkyl-$R^B$, $C_1$-$C_6$ haloalkyl-$R^B$, $C_1$-$C_6$ alkoxy-$R^B$, $C_1$-$C_6$ haloalkoxy —$R^B$, $C_3$-$C_8$ cycloalkyl, $C_3$-$C_8$ cycloalkyl-$C_1$-$C_9$ alkyl, $C_1$-$C_6$ hydroxyalkyl, O—$C_1$-$C_6$ hydroxyalkyl, O—$C_1$-$C_6$ alkyl-$R^B$, CN, O—($C_1$-$C_5$ alkyl)-O—($C_1$-$C_3$ alkyl), O—($C_1$-$C_5$ alkyl)-O—($C_1$-$C_3$ alkyl)-$R^B$, —($C_0$-$C_3$ alkyl)-O—($C_0$-$C_3$ alkyl)-($C_3$-$C_8$ cycloalkyl), —($C_0$-$C_3$ alkyl)-S—($C_0$-$C_3$ alkyl)-($C_3$-$C_8$ cycloalkyl), —($C_0$-$C_3$ alkyl)-S(O)$_2$—($C_0$-$C_3$ alkyl)-($C_3$-$C_8$ cycloalkyl), Het, Aryl, and

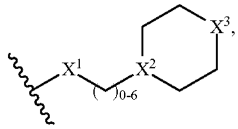

wherein $X^1$ is either $CH_2$, NH, O, or S; $X^2$ is either CH or N; and $X^3$ is either NH, $CH_2$, O, or S;

provided that two $R^4$ groups can join together form methylene dioxy;

each $R^A$ is independently selected from the group consisting of: F, Cl, Br, I, OH, $C_1$-$C_6$ alkyl, $C_1$-$C_6$ haloalkyl, $C_1$-$C_6$ alkoxy, $C_1$-$C_6$ alkyl($NH_2$), $C_6$-$C_8$ bridged cycloalkyl, $C_3$-$C_8$ cycloalkyl, $C_1$-$C_6$ haloalkoxy, $C_3$-$C_8$ halocycloalkyl, SH, S($C_1$-$C_6$ alkyl), $NH_2$, NH($C_1$-$C_6$ alkyl), N($C_1$-$C_6$ alkyl)$_2$, C(O)($C_1$-$C_6$ alkyl), C(O)($C_3$-$C_8$ cycloalkyl), $CONH_2$, $SO_2NH_2$, $NO_2$, CN, $CF_3$, $CHF_2$, $CH_2F$, $OCHF_2$, $OCF_3$, $OCH_2F$, $SO_2$($C_1$-$C_6$ alkyl), S(O)($C_1$-$C_6$ alkyl), —($C_1$-$C_6$ alkyl)S(O)($C_1$-$C_6$ alkyl), $SO_2$($C_3$-$C_6$ cycloalkyl), —($C_1$-$C_6$ alkyl)S(O)$_2$($C_1$-$C_6$ alkyl), —($C_1$-$C_6$ alkyl)N($C_1$-$C_6$ alkyl)$SO_2$($C_1$-$C_6$ alkyl), N($C_1$-$C_6$ alkyl)$SO_2$($C_1$-$C_6$ alkyl), $SO_2$N($C_1$-$C_6$ alkyl)$_2$, —($C_1$-$C_6$ alkyl)$SO_2$N($C_1$-$C_6$ alkyl)$_2$, NHCOO($C_1$-$C_6$ alkyl), NHCO($C_1$-$C_6$ alkyl), NHCONH($C_1$-$C_6$ alkyl), $CO_2$($C_1$-$C_6$ alkyl), C(O)N($C_1$-$C_6$ alkyl)$_2$, —($C_0$-$C_5$ alkyl)-($C_3$-$C_8$ cycloalkyl), —($C_0$-$C_5$ alkyl)-O—($C_0$-$C_5$ alkyl)-($C_3$-$C_8$ cycloalkyl), —($C_0$-$C_5$ alkyl)-S—($C_0$-$C_5$ alkyl)-($C_3$-$C_8$ cycloalkyl), —($C_0$-$C_5$ alkyl)-S(O)$_2$—($C_0$-$C_5$ alkyl)-($C_3$-$C_8$ cycloalkyl), Aryl, and Het; provided that two $R^A$ groups present on adjacent carbon atoms can together with the adjacent carbon atoms form a $C_3$-$C_6$cycloalkyl;

each $R^B$ is independently either phenyl or a 5- or 6-membered saturated or unsaturated monocyclic ring with 1, or 2 heteroatom ring atoms independently selected from the group consisting of N, O and S, $R^B$ may be substituted with 1 or 2 independently selected $R^C$;

each $R^C$ is independently either halo, $C_1$-$C_6$ alkyl, $C_1$-$C_6$ alkoxy, $C_3$-$C_6$ cycloalkyl or, $C_1$-$C_6$ haloalkyl;

each Aryl is independently phenyl optionally substituted with 1 or 2 independently selected $R^C$;

each Het is independently a 4-, 5- or 6-membered saturated or unsaturated monocyclic rings with 1 or 2 heteroatom ring atoms independently selected from the group consisting of N, O and S; provided that said Het is optionally substituted with 1 or 2 independently selected $R^C$ substituents;

$R^X$ if present, is a $C_3$-$C_8$ alkylene, $C_3$-$C_8$ alkenylene, or $C_3$-$C_8$ alkynylene, formed between A and $R^1$, $R^Y$ if present, is a $C_3$-$C_8$ alkylene, $C_3$-$C_8$ alkenylene, $C_3$-$C_8$ alkynylene, formed between A and $R^2$, $R^Z$ if present, is a $C_3$-$C_8$ alkylene, $C_3$-$C_8$ alkenylene, or $C_3$-$C_8$ alkynylene, formed between $R^2$ and $R^3$, provided that either (a) $R^X$ is present, $R^Y$ is not present and $R^Z$ is not present; (b) $R^Y$ is present, $R^X$ is not present and $R^Z$ is not present; (c) $R^Z$ is present, $R^X$ is not presen and $R^Y$ is not present; or (d) $R^X$ and $R^Z$ are present, and $R^Y$ is not present.

6. The compound according to claim 5, wherein T is O.

7. The compound according to claim 5, wherein A is a selected from the group consisting of a) $C_1$-$C_6$ alkyl, $C_3$-$C_8$ cycloalkyl, or $C_6$-$C_8$ bridged cycloalkyl, b) substituted $C_1$-$C_6$ alkyl, substituted $C_3$-$C_8$ cycloalkyl, or substituted $C_6$-$C_8$ bridged cycloalkyl, each of which contains 0 or 1 $R^A$ and 0 or 1 $R^B$, provided that at least one $R^A$ substituent other than H, or an $R^B$ substituent is present;

c) Aryl; and d) Het.

8. The compound according to claim 5, wherein $R^1$ is $CF_3$, $CH_2CF_3$, $CHF_2$, $CH_3$, or cyclopropyl.

9. The compound according to claim 5, wherein each $R^4$ is independently selected from the group consisting of: hydrogen, F, Cl, OH, $C_1$-$C_6$ alkyl, $C_1$-$C_2$ haloalkyl, $C_1$-$C_6$ alkoxy, $C_1$-$C_4$ haloalkoxy, $C_1$-$C_6$ alkyl-$R^B$, $C_3$-$C_8$ cycloalkyl, Het, Aryl and

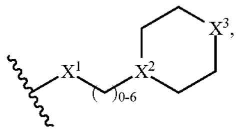

wherein $X^1$ is either $CH_2$, NH, O, or S; $X^2$ is either CH or N; and $X^3$ is either NH, $CH_2$, O, or S.

10. The compound according to claim 9, wherein each $R^4$ is independently selected from the group consisting of H, F, Cl, OH, $C_1$-$C_5$ alkyl, $CF_3$, $CH_2$—$CF_3$, and $CF_2$—$CH_3$.

11. The compound according to claim 5, wherein said compound of Formula IIa is a compound of Formula IIb:

(Formula IIb)

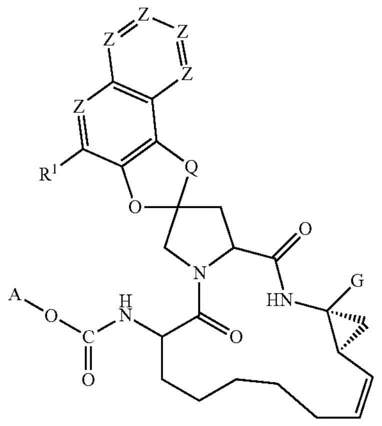

or a pharmaceutically acceptable salt thereof, wherein each Z is independently either N or C—$R^4$;

A is a selected from the group consisting of a) $C_1$-$C_6$ alkyl, $C_3$-$C_6$ cycloalkyl, or $C_6$-$C_8$ bridged cycloalkyl, b) substituted $C_1$-$C_6$ alkyl, substituted $C_3$-$C_8$ cycloalkyl, or substituted $C_6$-$C_8$ bridged cycloalkyl, each of which contains 0 or 1 $R^A$ and 0 or 1 $R^B$, provided that at least one $R^A$ or $R^B$ substituent is present;

c) Aryl; and d) Het;

Q is selected from the group consisting of selected from —$(CH_2)_2$—,

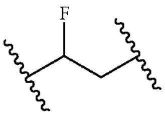
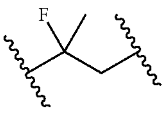
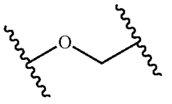

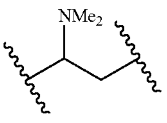
and
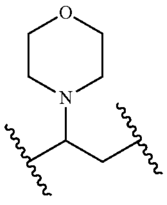
;

G is

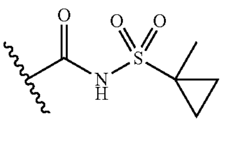
or
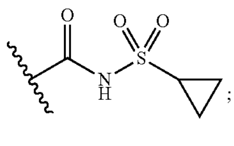
;

$R^1$ is either hydrogen, $C_1$-$C_6$ alkyl, $C_3$-$C_8$ cycloalkyl, $C_1$-$C_4$ haloalkyl, Aryl, or Het;

each $R^4$ is independently selected from the group consisting of:

hydrogen, F, Cl, OH, $C_1$-$C_6$ alkyl, $C_1$-$C_2$ haloalkyl, $C_1$-$C_6$ alkoxy, $C_1$-$C_4$ haloalkoxy, $C_1$-$C_6$ alkyl-$R^B$, $C_3$-$C_8$ cycloalkyl, Het, Aryl and

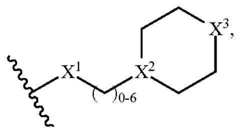

wherein $X^1$ is either $CH_2$, NH, O, or S; $X^2$ is either CH or N; and $X^3$ is either NH, $CH_2$, O, or S;

each Aryl is independently phenyl optionally substituted with 1 or 2 independently selected $R^C$;

each Het is independently a 4-, 5- or 6-membered saturated or unsaturated monocyclic ring with 1 or 2 heteroatom ring atoms independently selected from the group consisting of N, O and S; provided that said Het is optionally substituted with 1 or 2 independently selected $R^C$;

each $R^A$ is independently selected from the group consisting of: F, Cl, OH, $C_1$-$C_6$ alkyl, $C_1$-$C_6$ haloalkyl, $C_1$-$C_6$ alkoxy, $C_3$-$C_8$ halocycloalkyl, and $C_1$-$C_6$ haloalkoxy;

each $R^B$ is independently either phenyl or 5- or 6-membered saturated or unsaturated monocyclic ring with 1, or 2 heteroatom ring atoms independently selected from the group consisting of N, O and S, $R^B$ may be substituted with 1 or 2 independently selected $R^C$; and each $R^C$ is independently either halo, $C_1$-$C_6$ alkyl, $C_1$-$C_6$ alkoxy, $C_3$-$C_6$ cycloalkyl or $C_1$-$C_6$ haloalkyl.

12. The compound according to claim 11, wherein $R^1$ is $CF_3$, $CH_2CF_3$, $CHF_2$, $CH_3$, or cyclopropyl.

13. The compound according to claim 11, wherein each $R^4$ is independently selected from the group consisting of $CF_3$, $CH_2$—$CF_3$, and $CF_2$—$CH_3$.

14. The compound according to claim 5 wherein

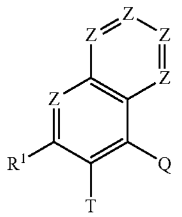

is selected from the group consisting of:

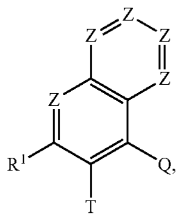
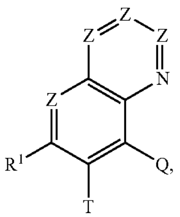
and

-continued

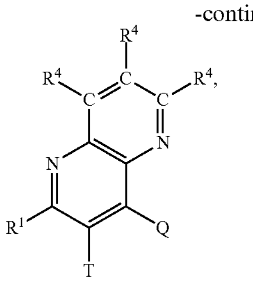

wherein each Z is independently either N or C—$R^4$, each $R^4$ is independently selected from the group consisting of:

hydrogen, F, Cl, OH, $C_1$-$C_6$ alkyl, $C_1$-$C_2$ haloalkyl, $C_1$-$C_6$ alkoxy, $C_1$-$C_4$ haloalkoxy, $C_1$-$C_6$ alkyl-$R^B$, $C_3$-$C_8$ cycloalkyl, Het, Aryl, and

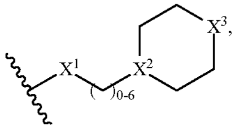

wherein $X^1$ is either $CH_2$, NH, O, or S; $X^2$ is either CH or N; and $X^3$ is either NH, $CH_2$, O, or S;

each Aryl is independently phenyl optionally substituted with 1 or 2 independently selected $R^C$;

each Het is independently a 4-, 5- or 6-membered saturated or unsaturated monocyclic ring with 1 or 2 heteroatom ring atoms independently selected from the group consisting of N, O and S; provided that said Het is optionally substituted with 1 or 2 independently selected $R^C$;

each $R^A$ is independently selected from the group consisting of F, Cl, OH, $C_1$-$C_6$ alkyl, $C_1$-$C_6$ haloalkyl, $C_1$-$C_6$ alkoxy, $C_3$-$C_8$ halocycloalkyl, and $C_1$-$C_6$ haloalkoxy;

each $R^B$ is independently either phenyl or a 5- or 6-membered saturated or unsaturated monocyclic ring with 1, or 2 heteroatom ring atoms independently selected from the group consisting of N, O and S, wherein $R^B$ may be substituted with 1 or 2 independently selected $R^C$; and each $R^C$ is independently either halo, $C_1$-$C_6$ alkyl, $C_1$-$C_6$ alkoxy, $C_3$-$C_6$ cycloalkyl or $C_1$-$C_6$ haloalkyl.

15. A compound which is selected from the group consisting of:

I-1

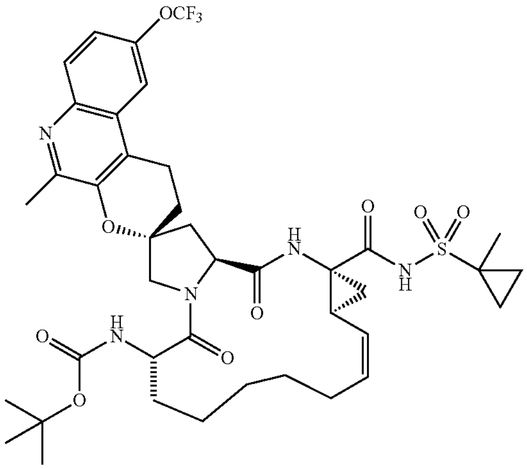

-continued

I-2

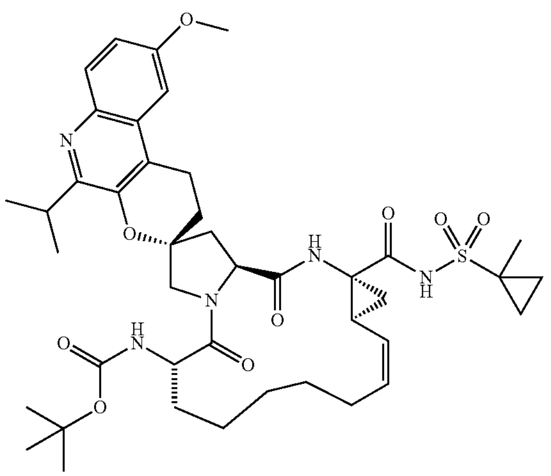

I-3

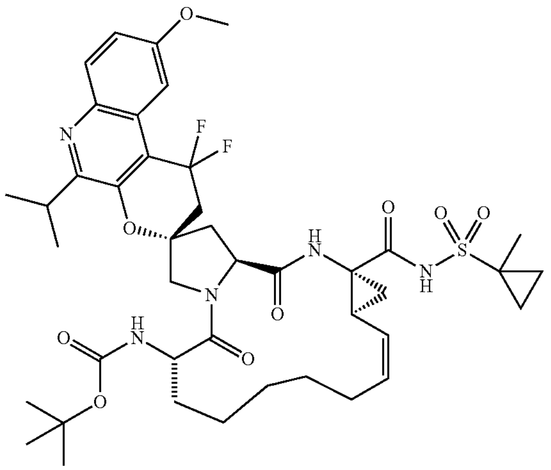

I-4

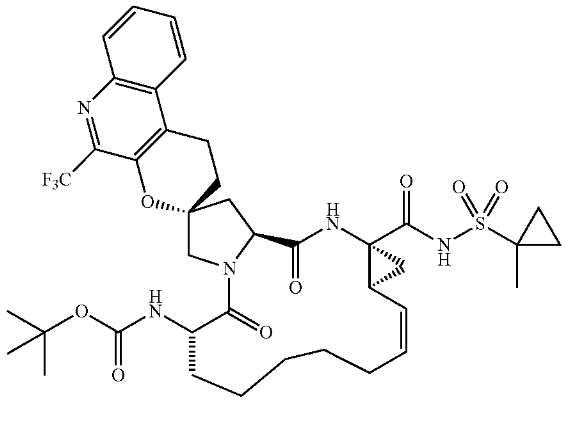

-continued
I-5
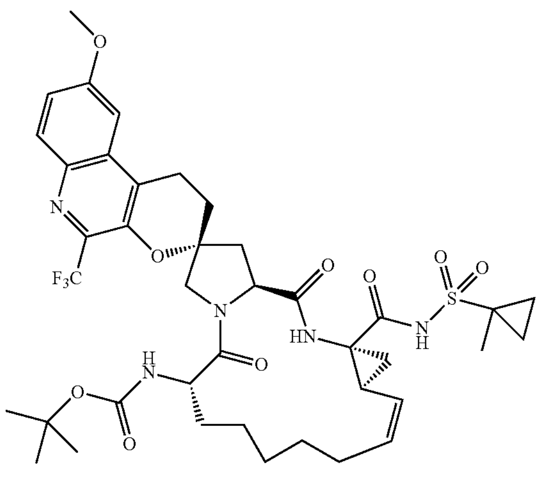
I-6
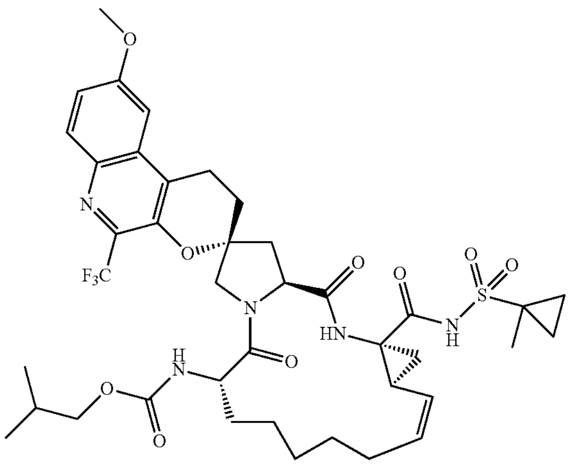
I-7
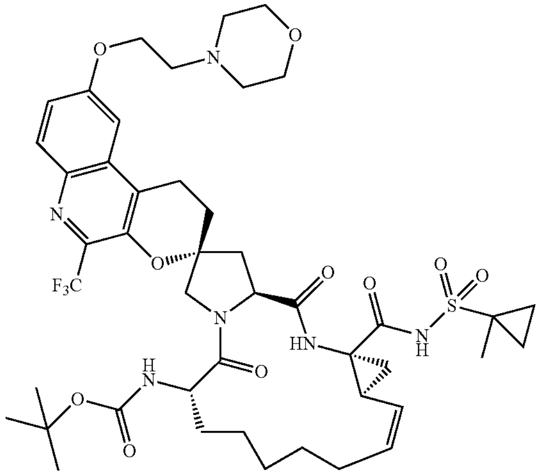
-continued
I-8
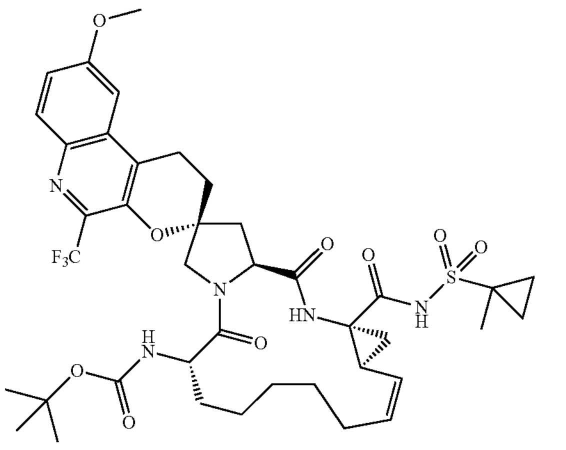
I-9
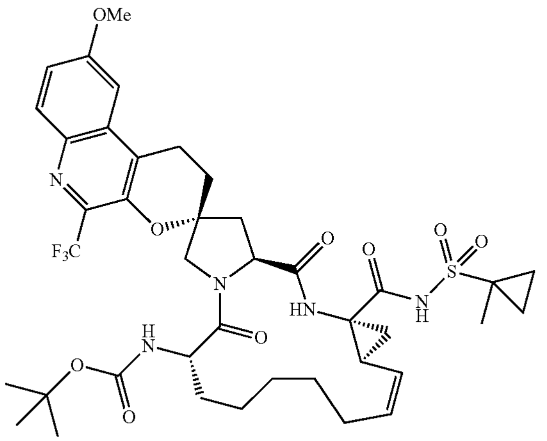
I-10
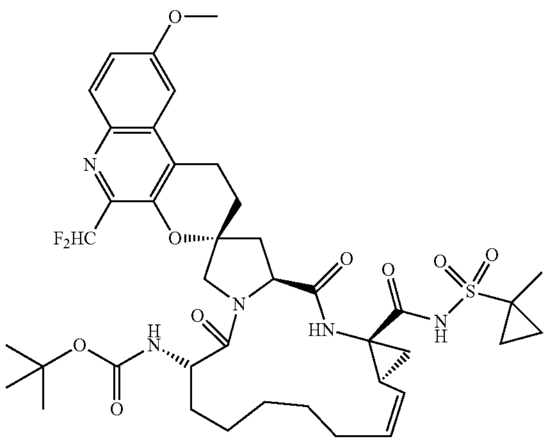

-continued
I-11
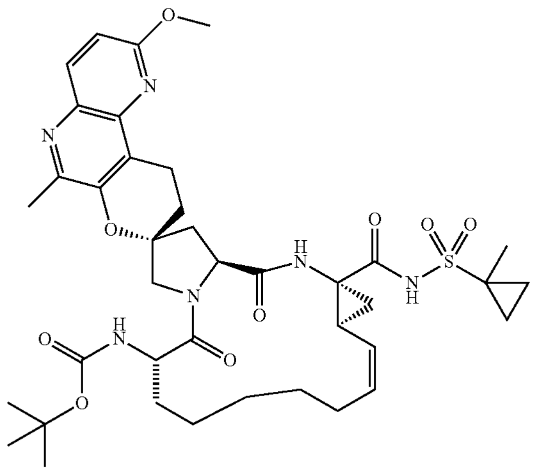
I-12
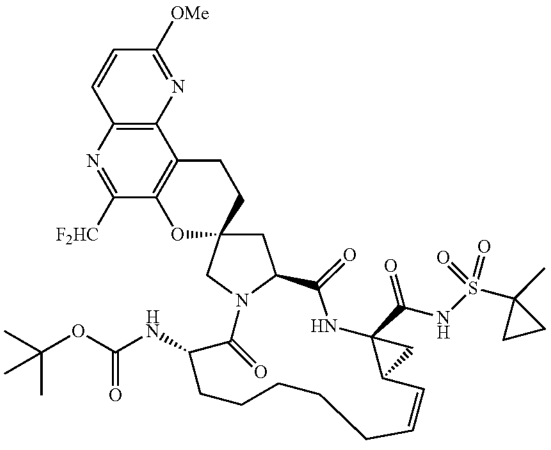
I-13
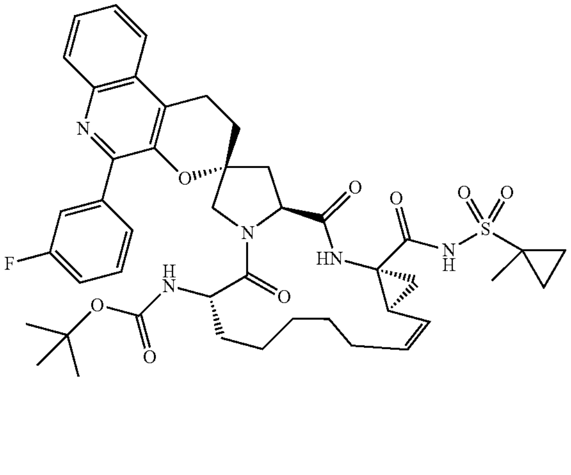
-continued
I-14
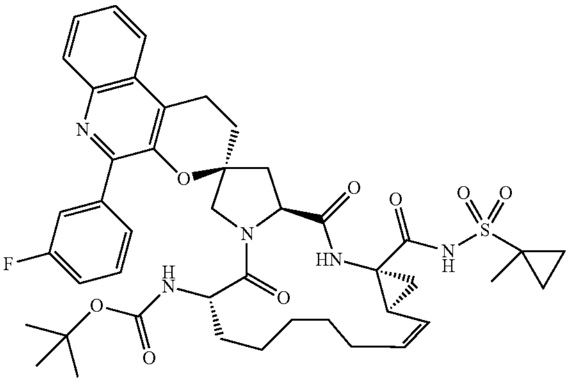
I-15
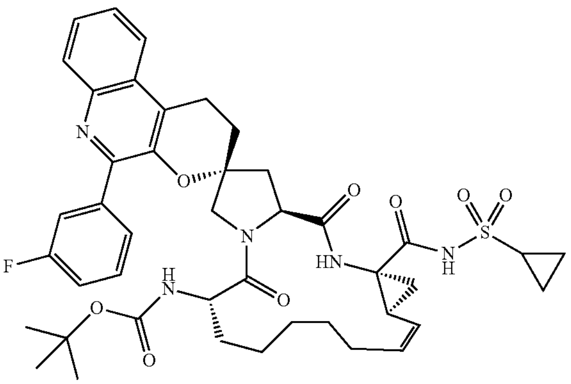
I-16
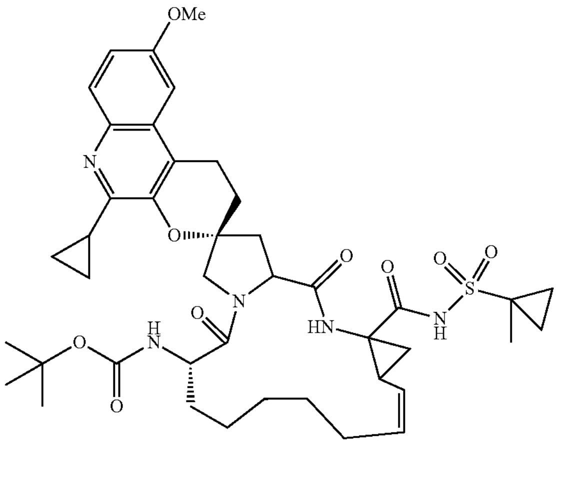

I-17
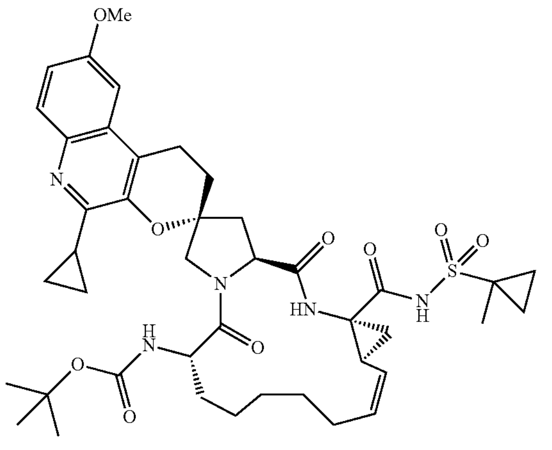
I-18
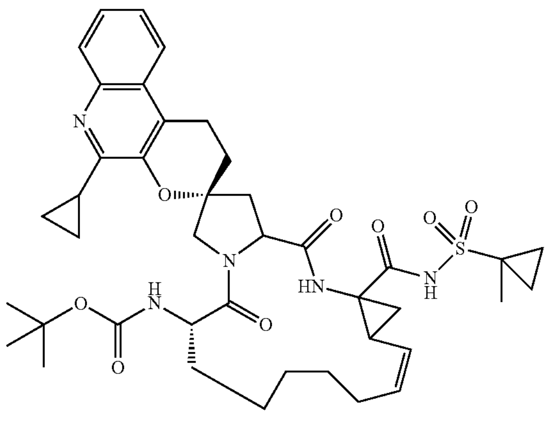
I-19
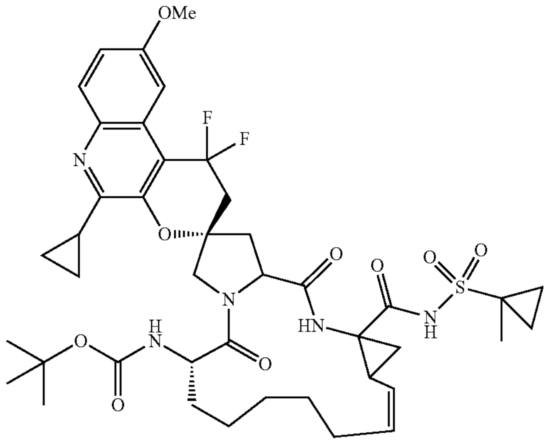
I-20
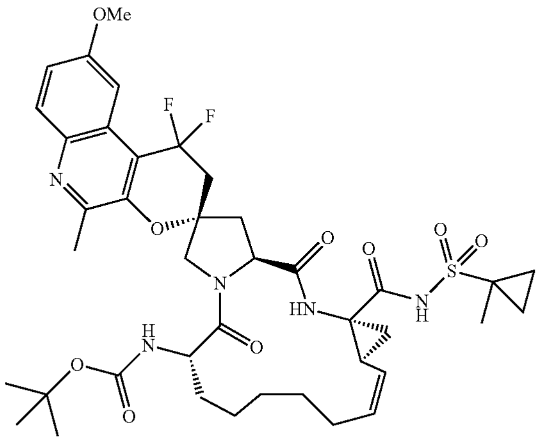
I-21
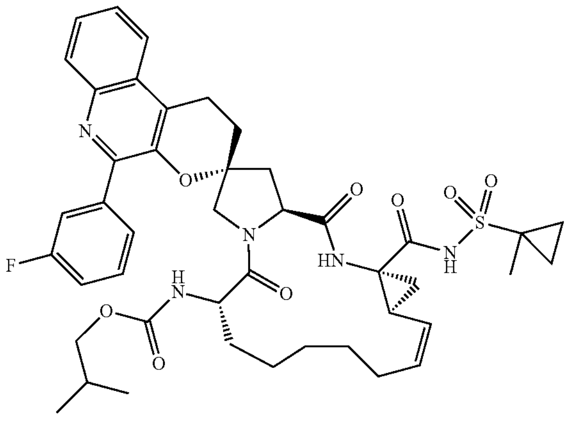
I-22
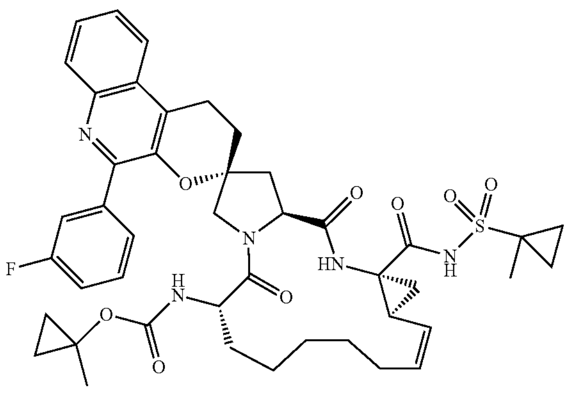

-continued
I-23
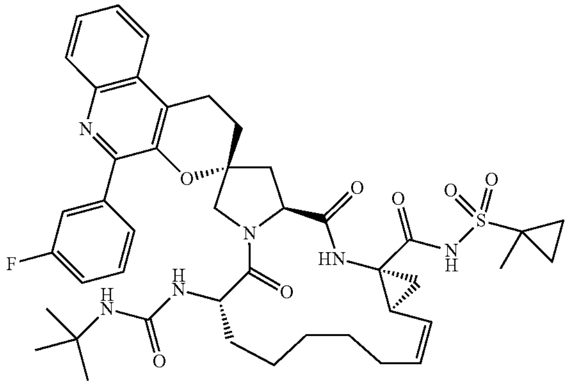
I-24
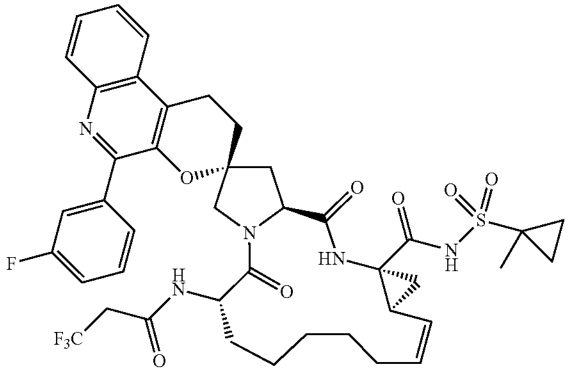
I-25
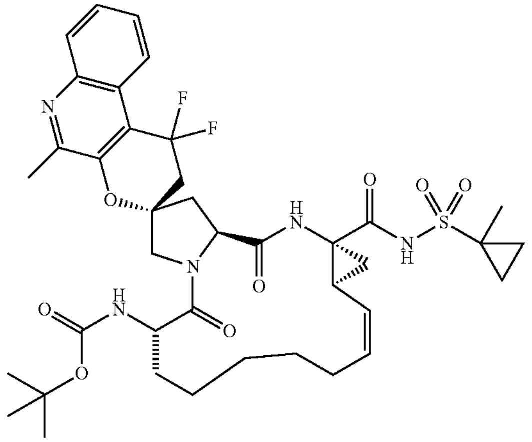
-continued
I-26
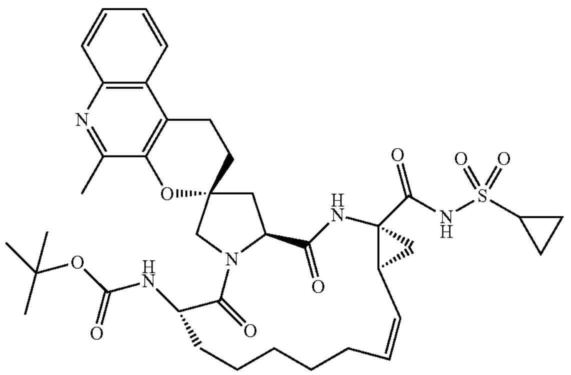
I-27
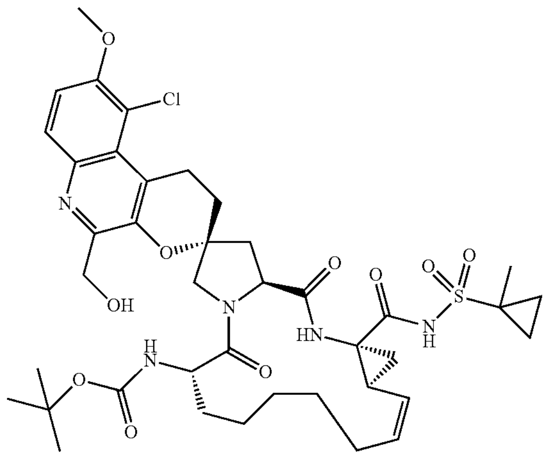
I-28
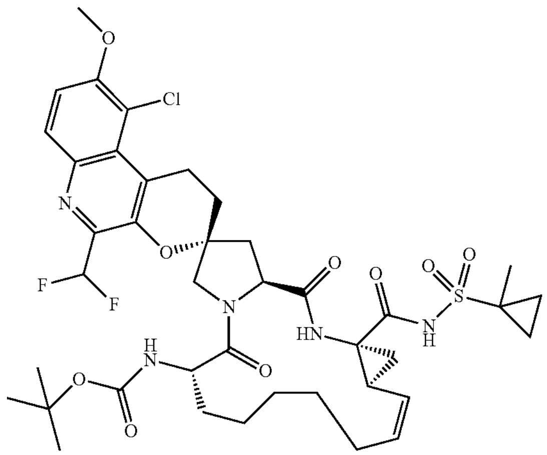

-continued
I-29
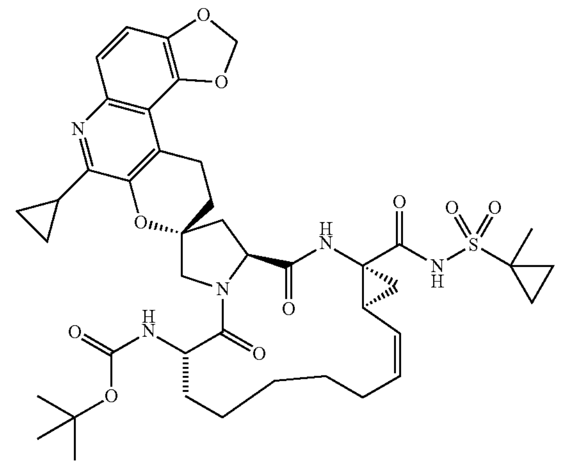
I-30
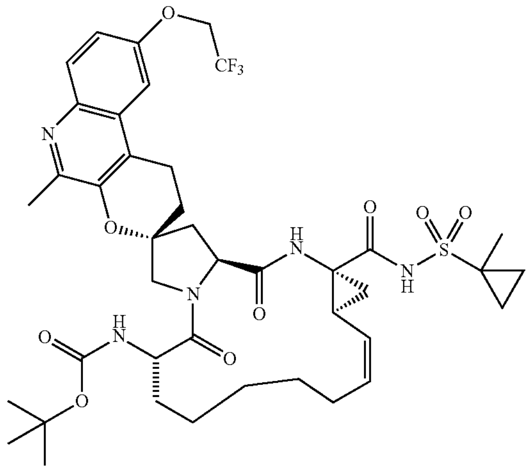
I-31
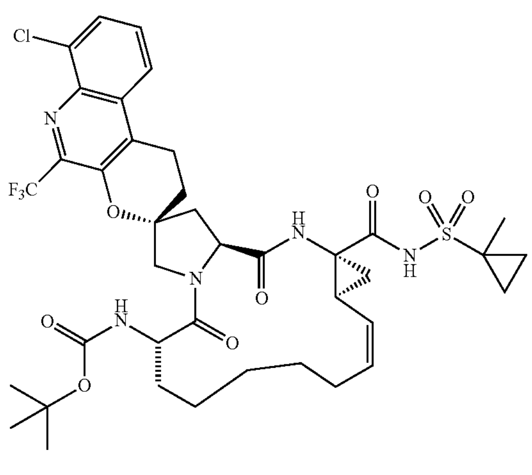
-continued
I-32
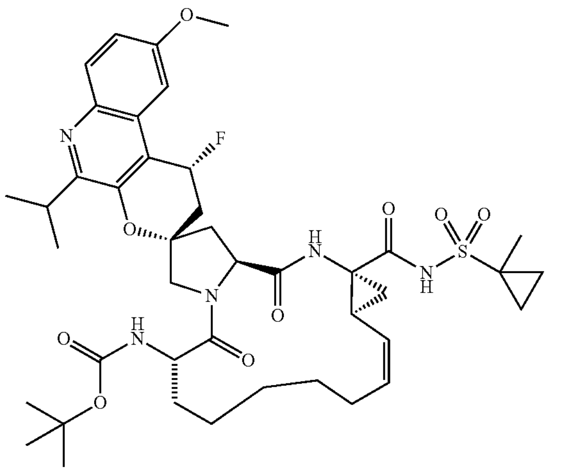
I-33
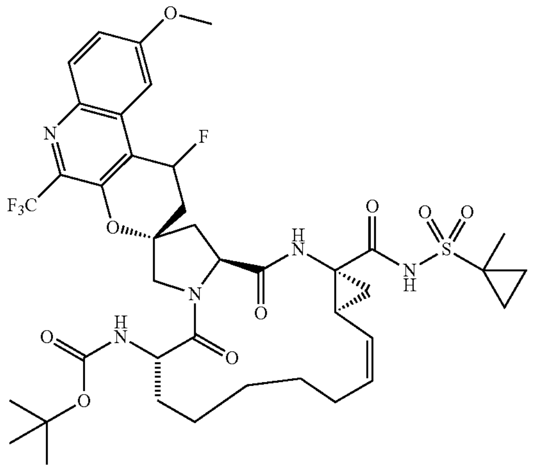
I-34
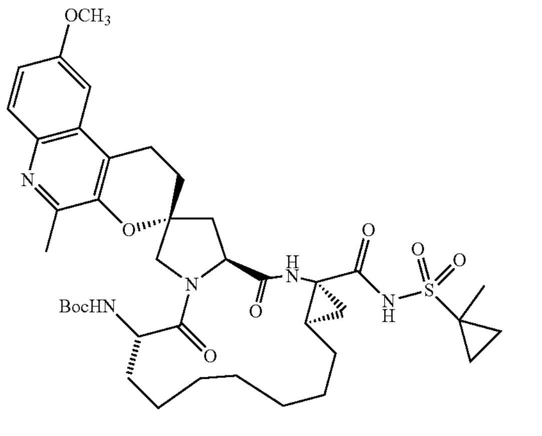

I-35
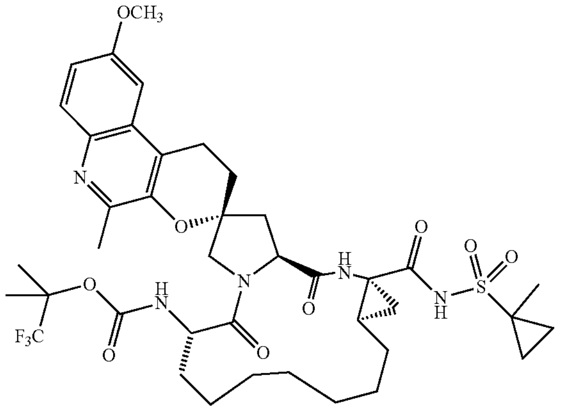
I-36
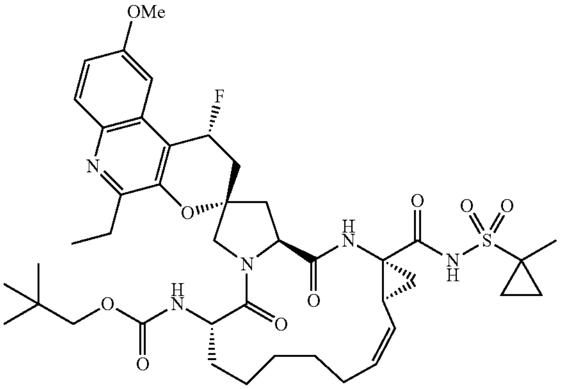
I-37
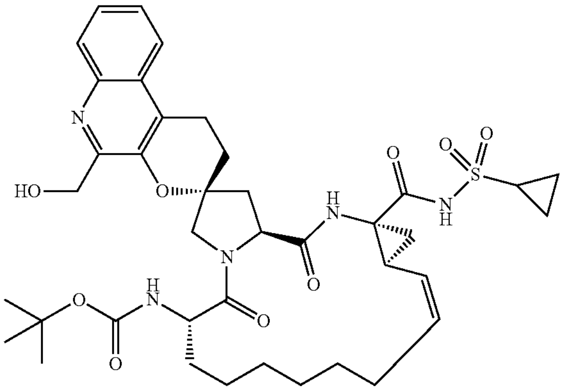
I-38
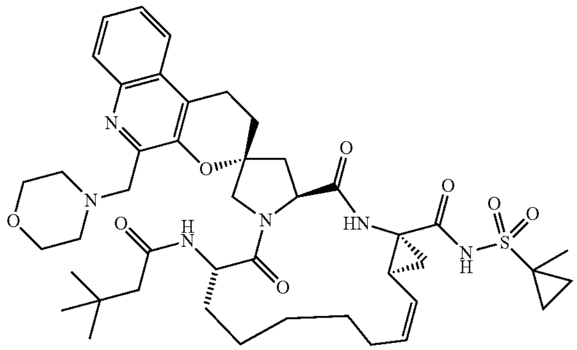
I-39
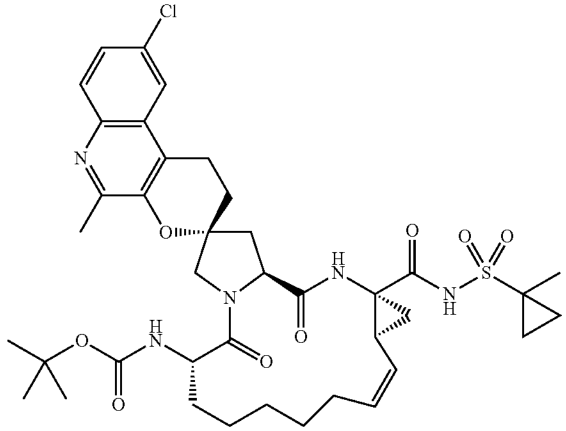
I-40
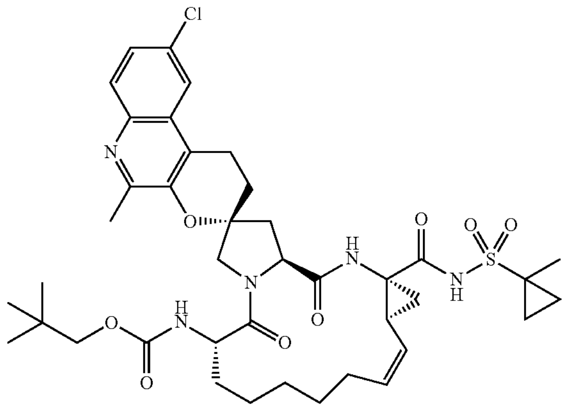
I-41
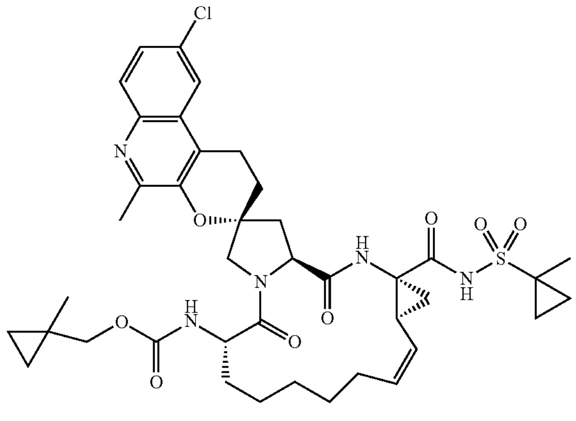

-continued
I-42
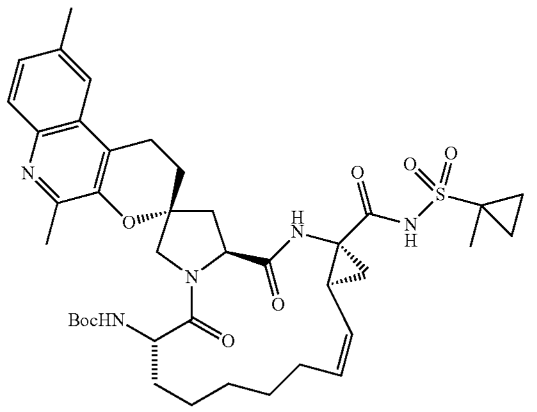
I-43
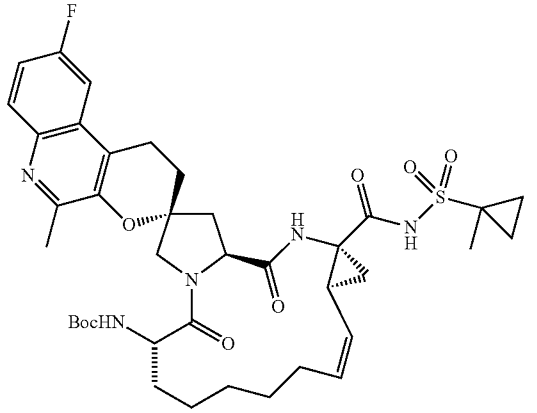
I-44
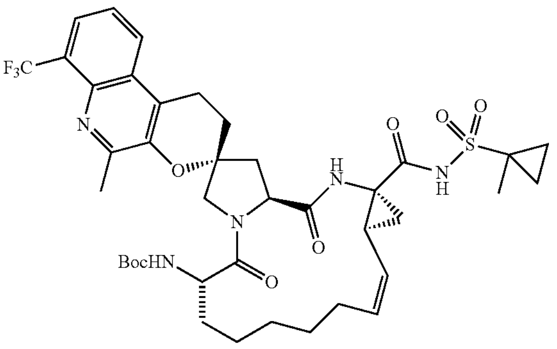
I-45
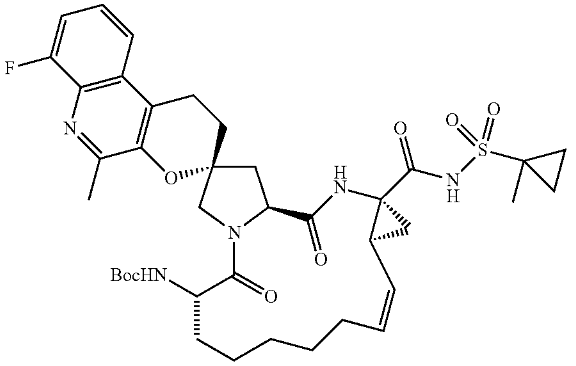
-continued
I-46
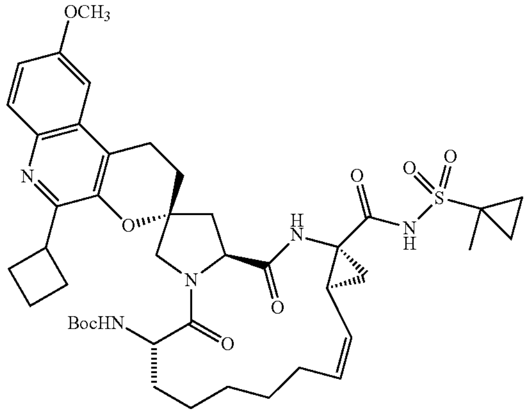
I-47
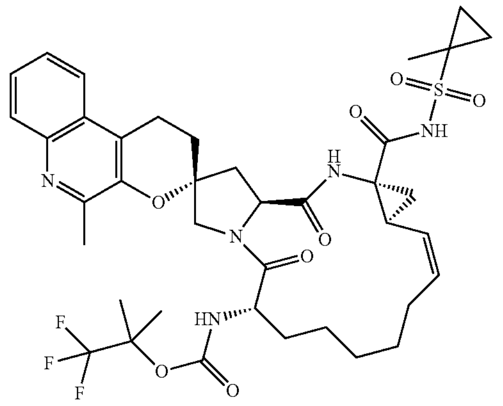
I-48
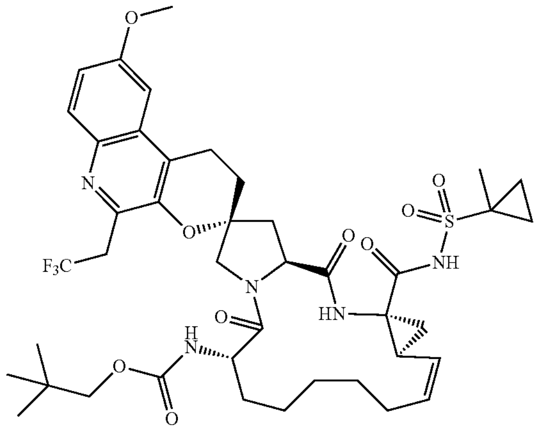

-continued
I-49
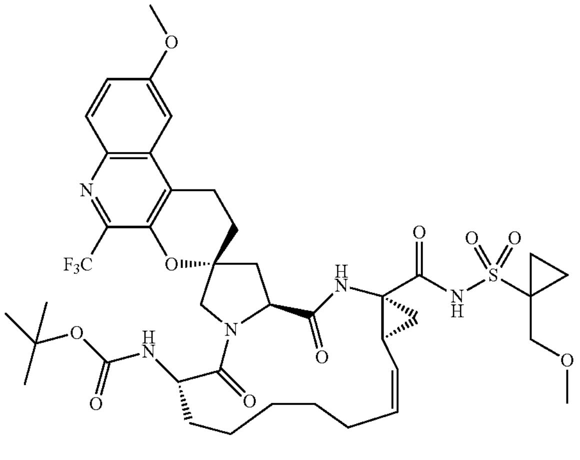
I-50
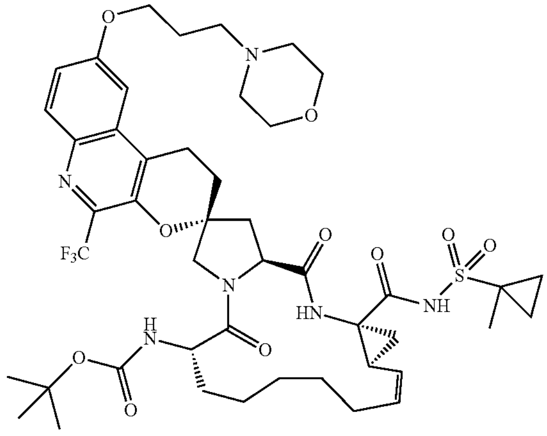
I-51
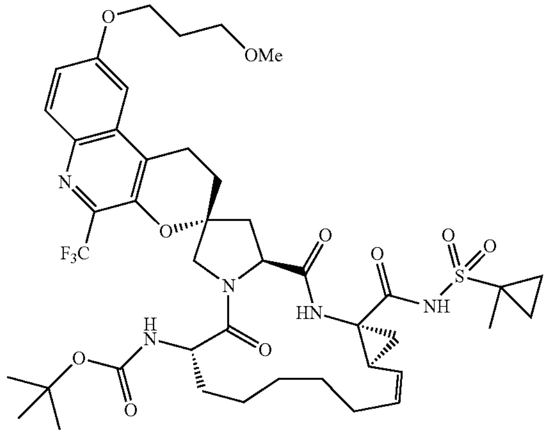
-continued
I-54
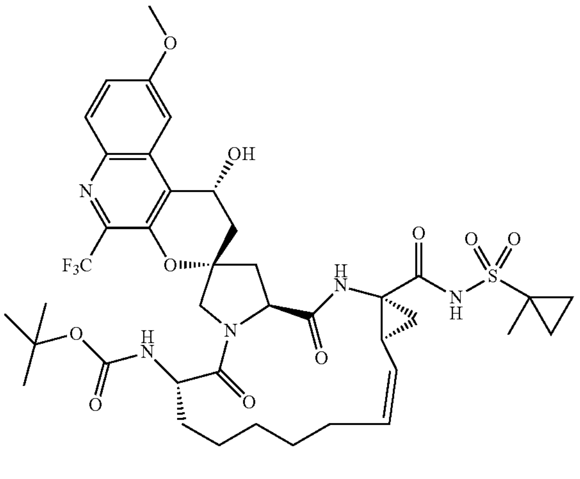
I-55
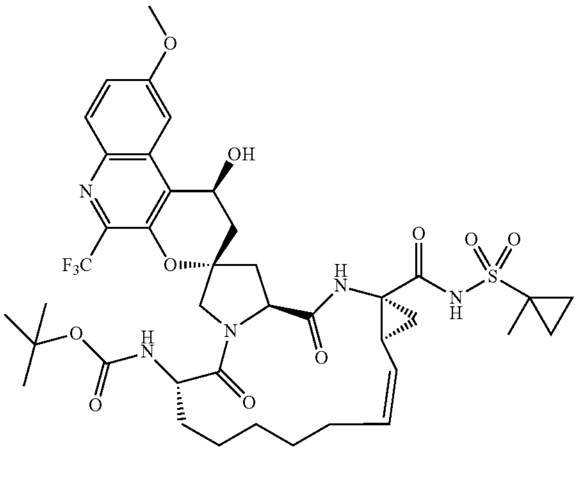
I-56
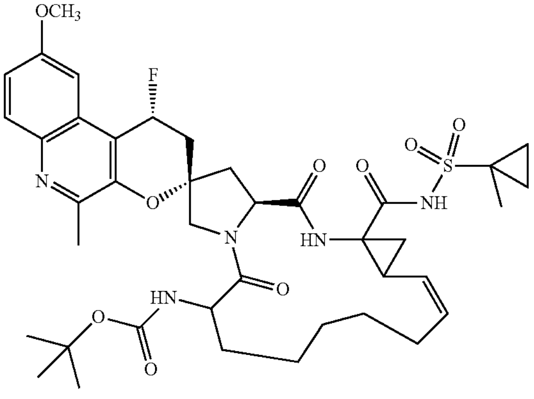

-continued
I-57
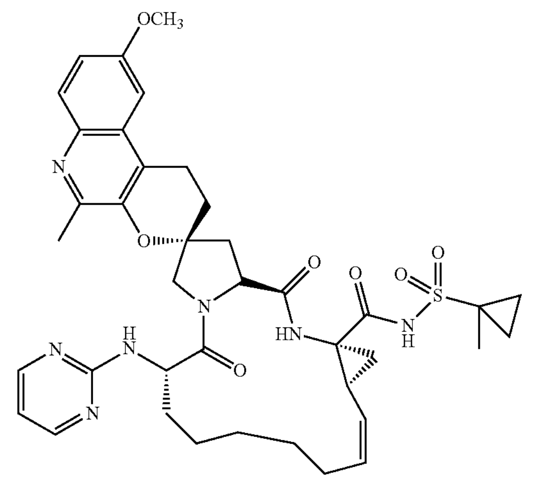
I-58
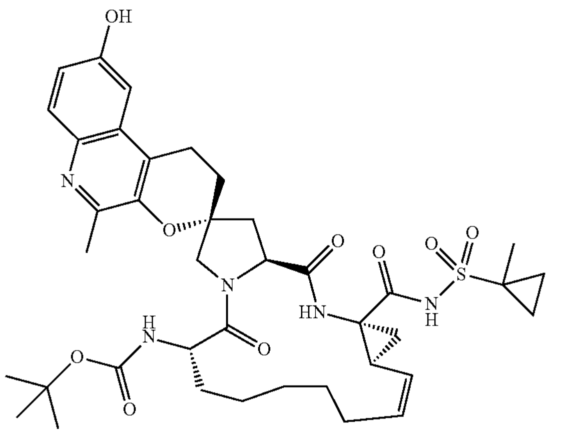
I-59
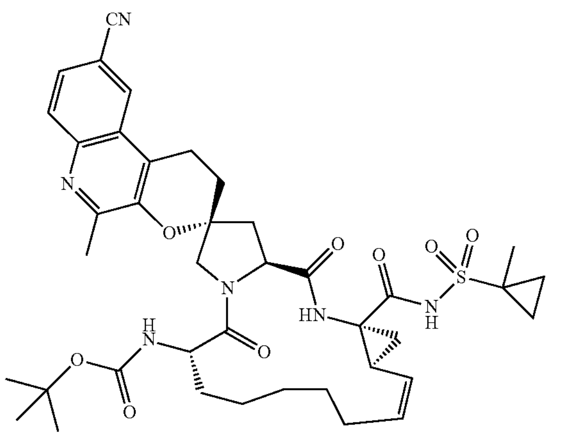
-continued
I-60
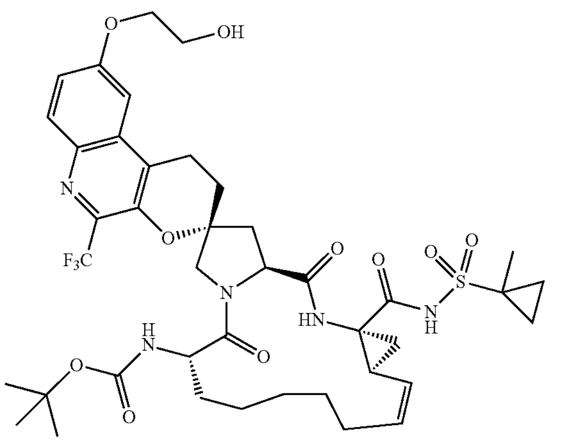
I-61
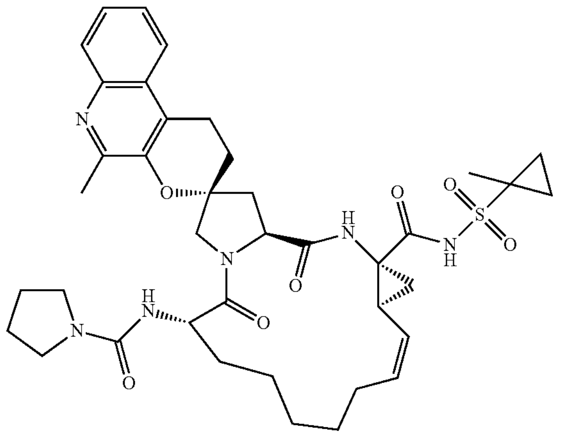
I-62
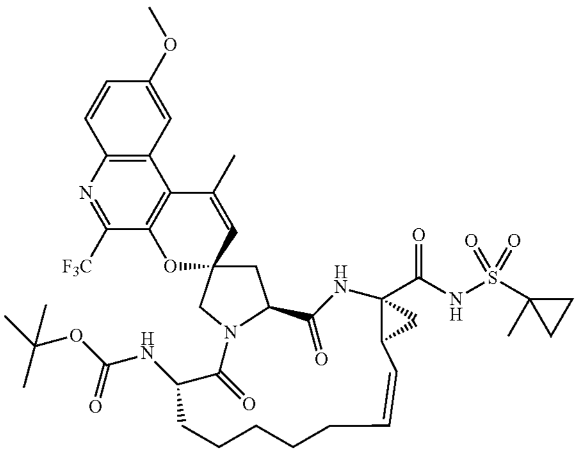

I-63
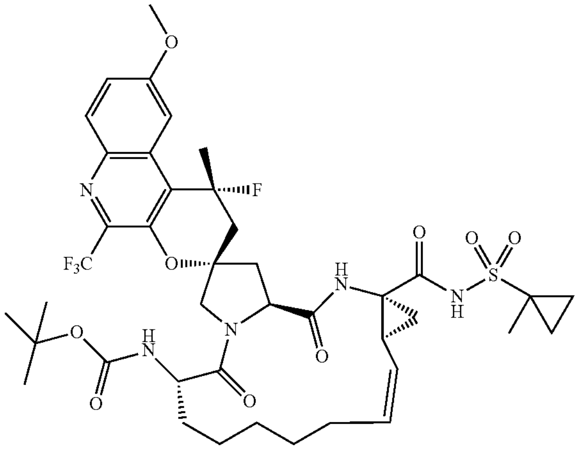
I-64
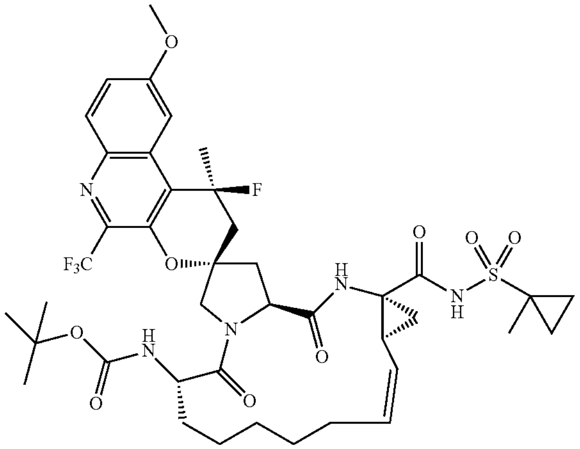
I-65
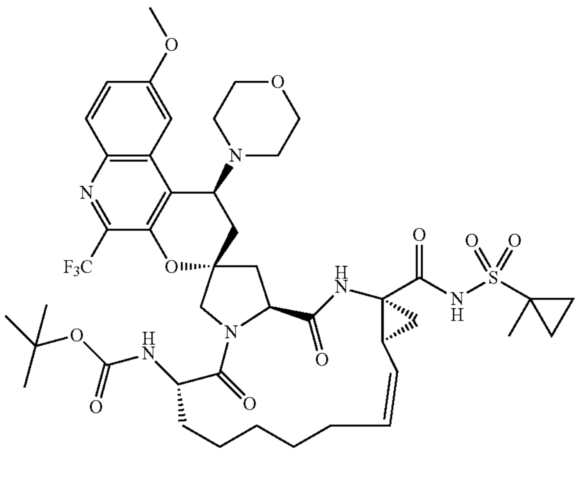
I-66
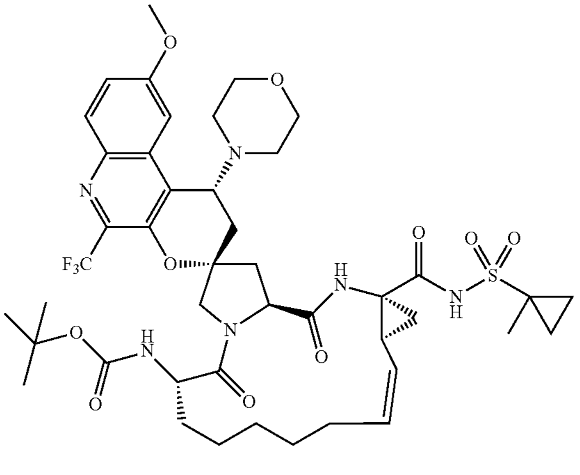
I-67
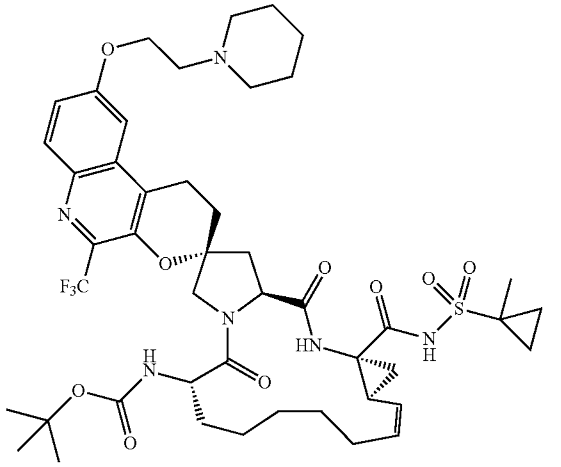
I-68
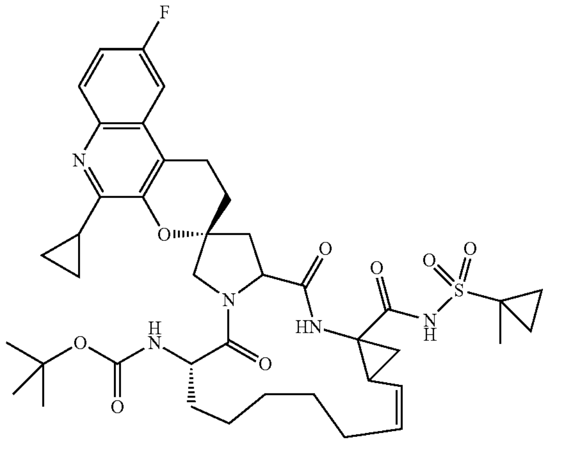

-continued
I-69
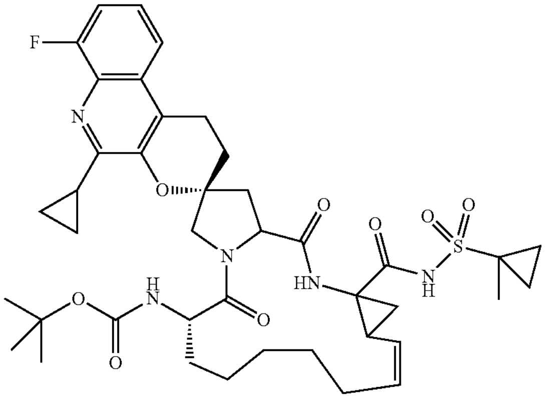
I-70
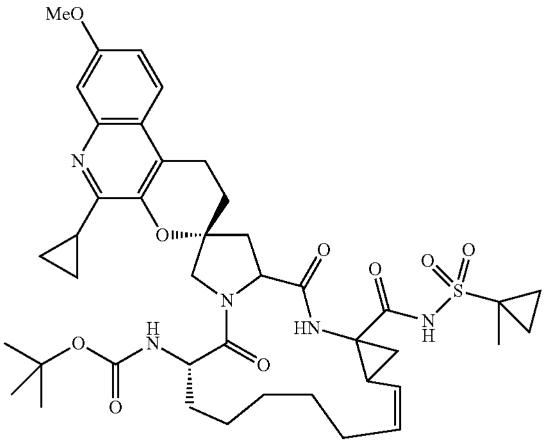
I-71
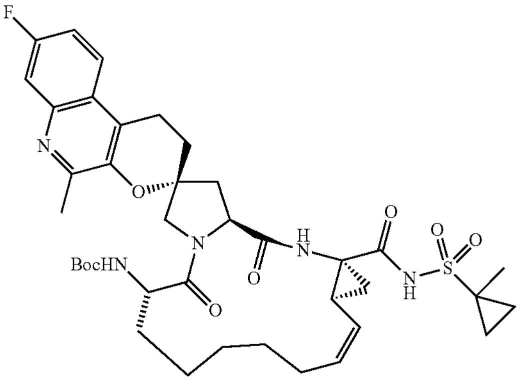
-continued
I-72
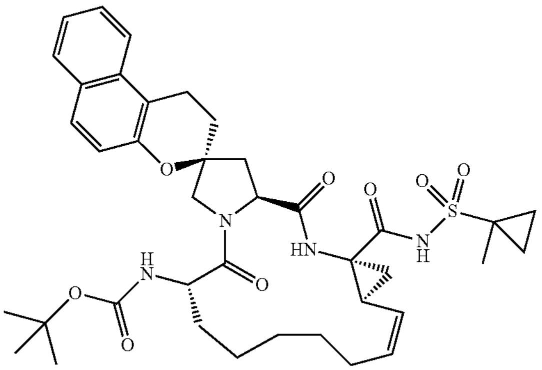
I-73
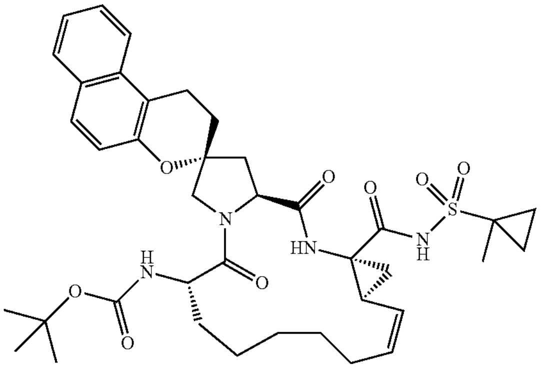
I-74
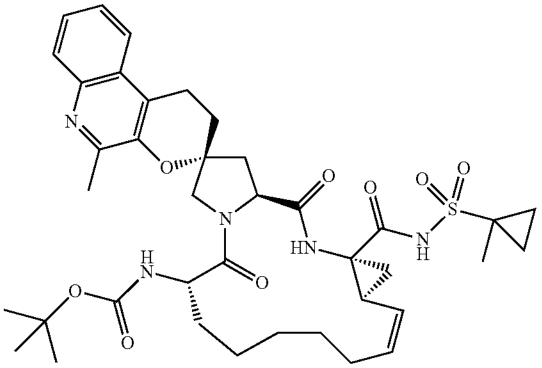
I-75
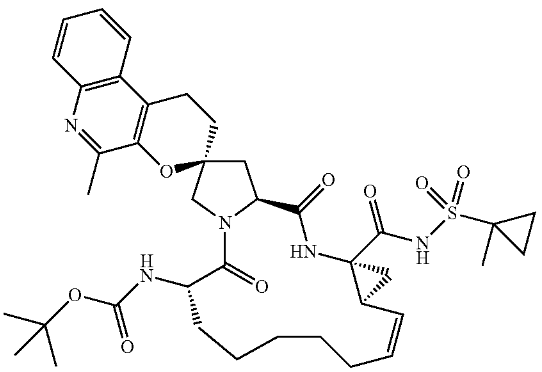

-continued
I-76
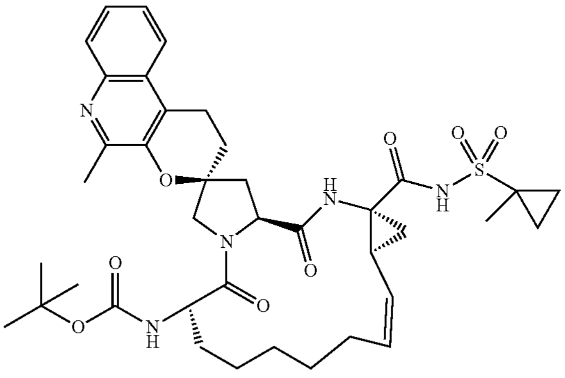
I-77
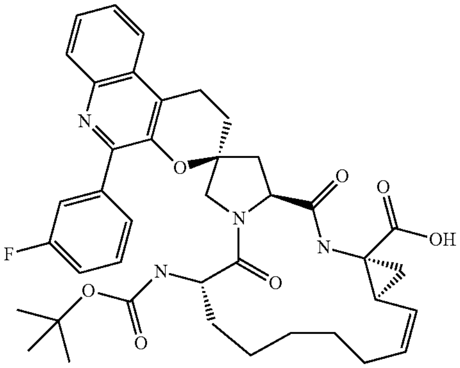
I-78
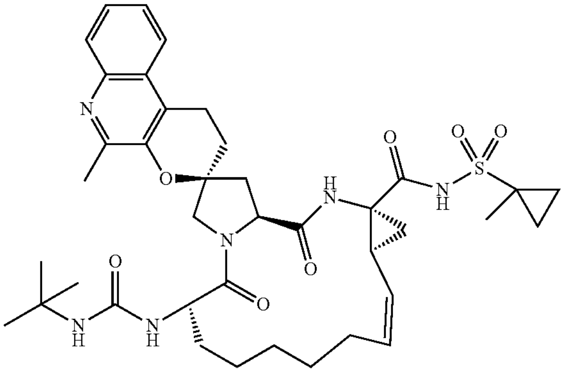
I-79
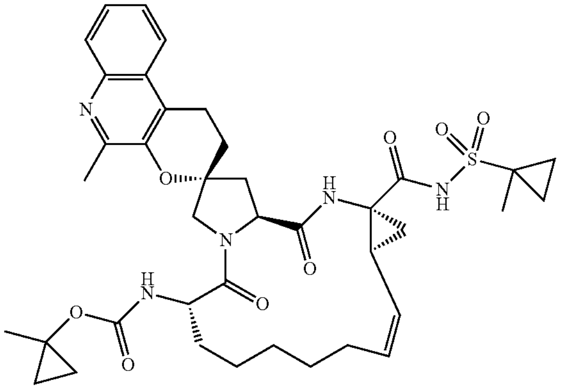
-continued
I-80
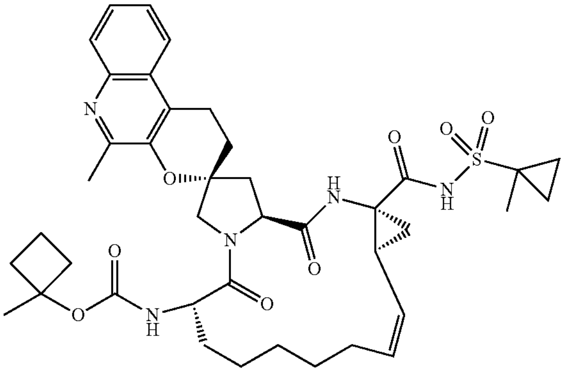
I-81
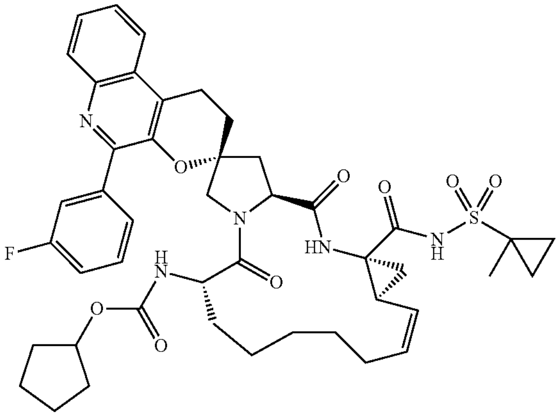
I-82
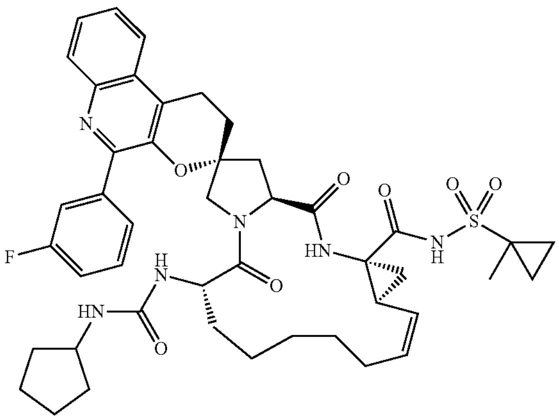

-continued
I-83
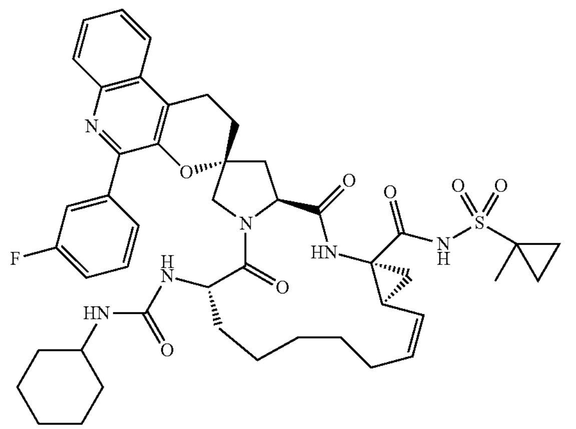
I-84
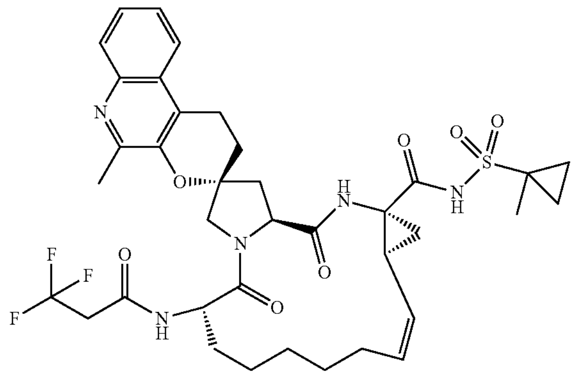
I-85
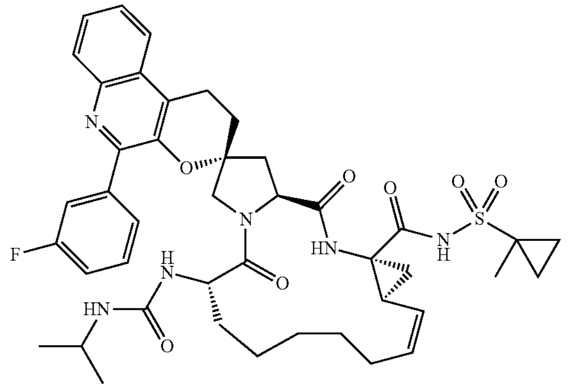
I-86
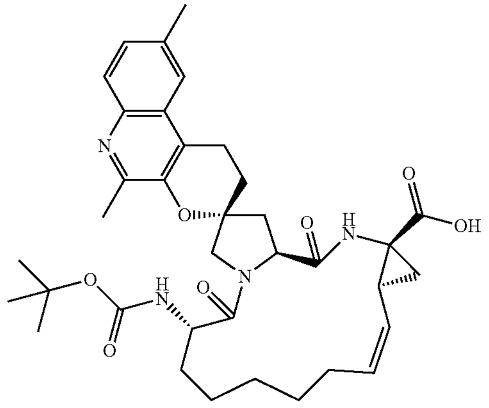
-continued
I-87
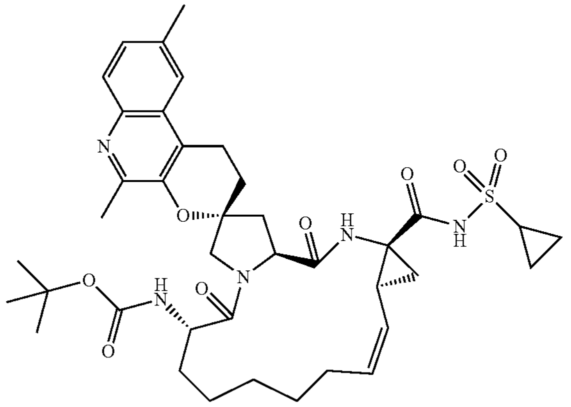
I-88
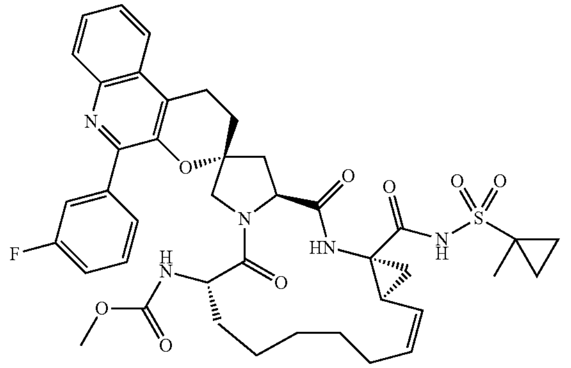
I-89
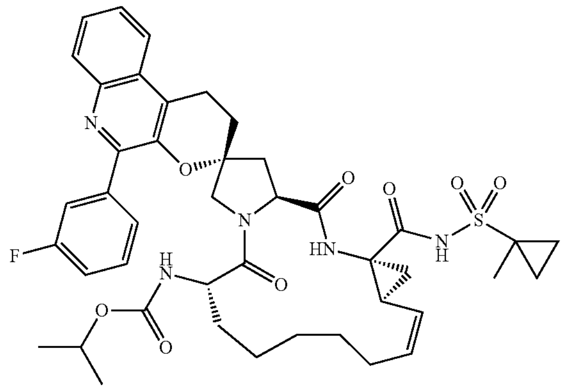

-continued
I-90
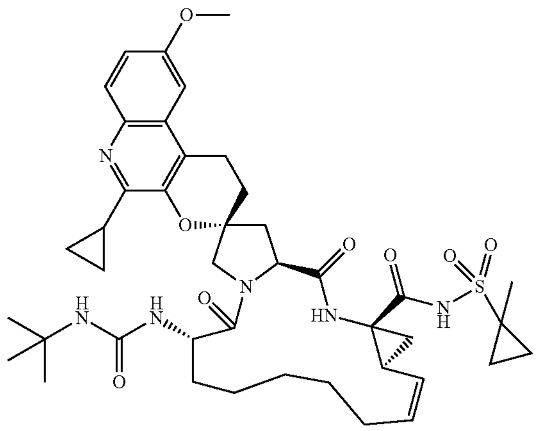
I-91
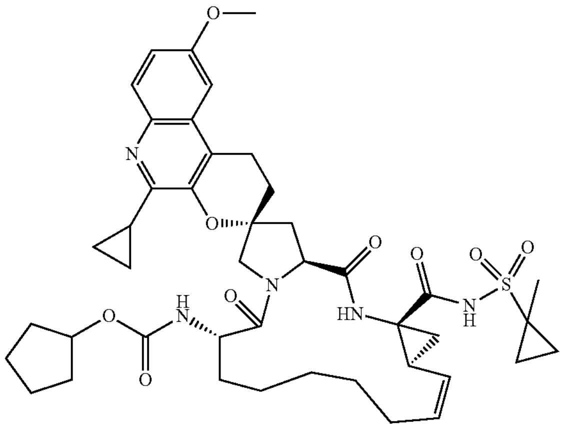
I-92
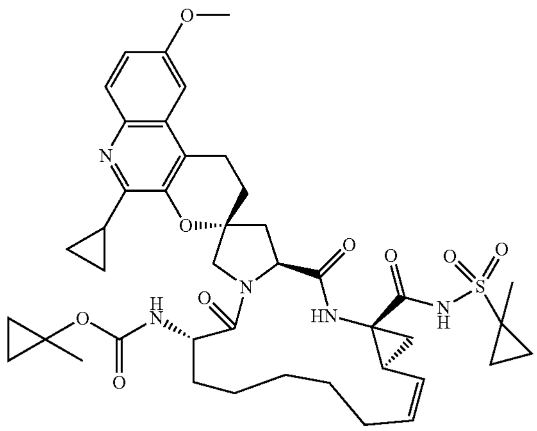
-continued
I-93
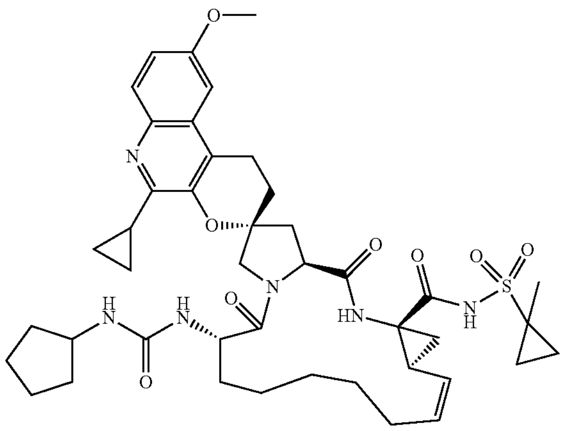
I-94
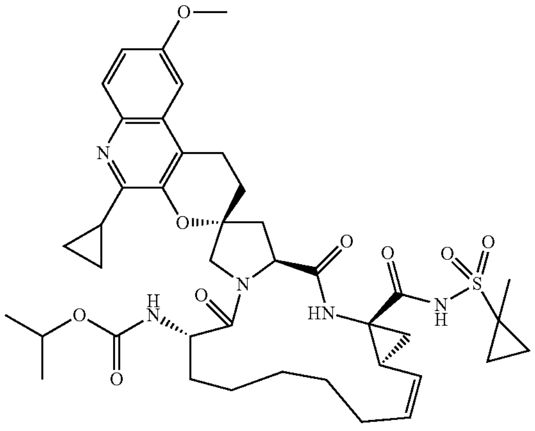
I-95
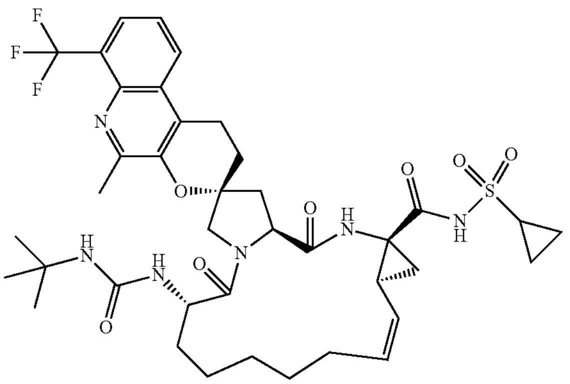

-continued
I-96
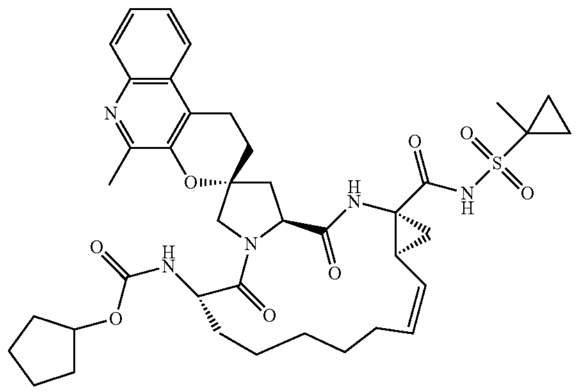
I-97
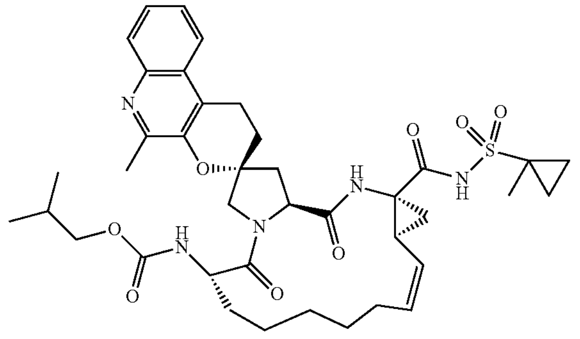
I-98
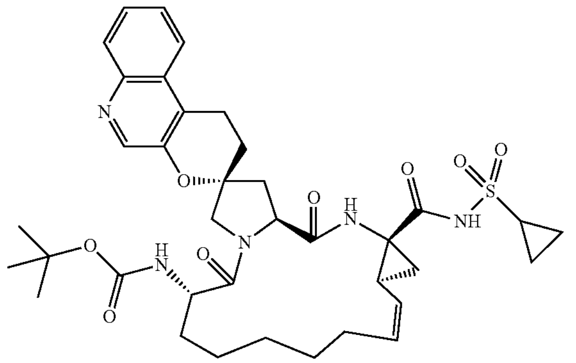
I-99
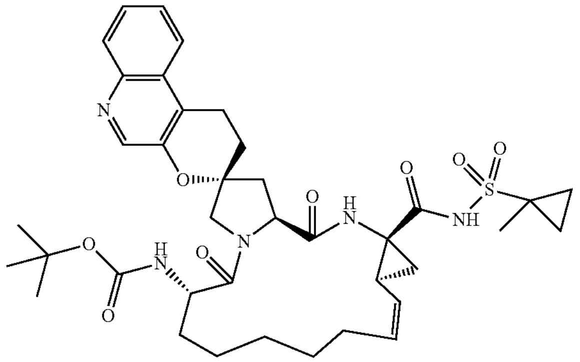
-continued
I-100
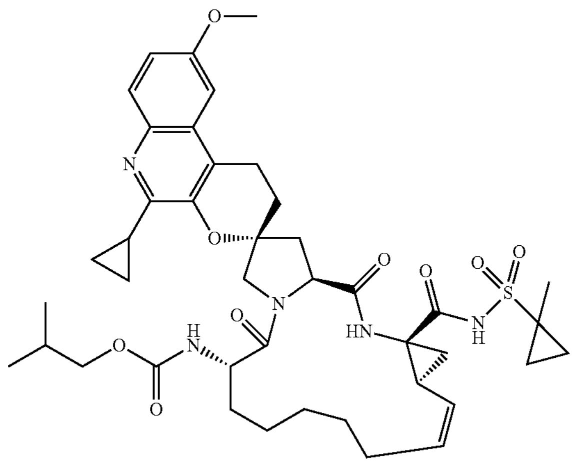
I-101
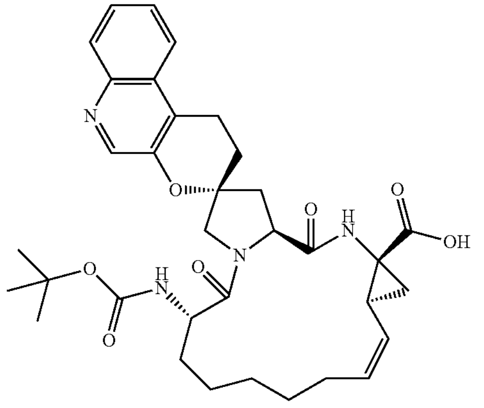
I-102
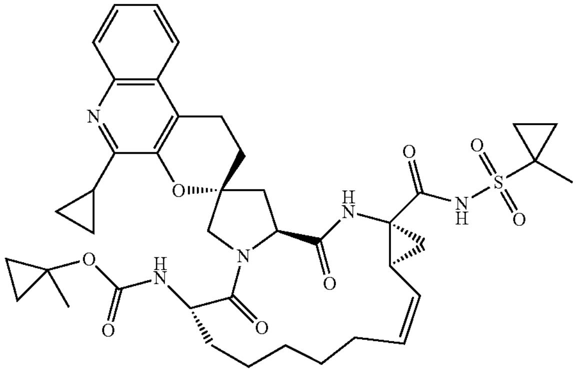
I-103
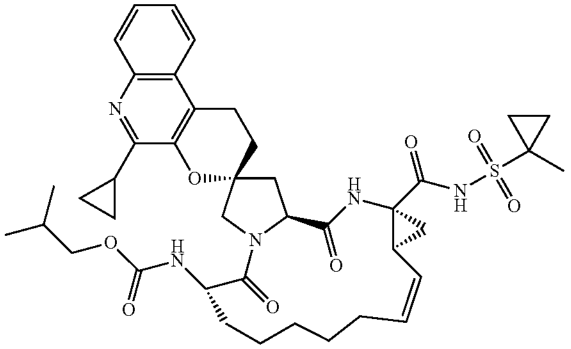

I-104
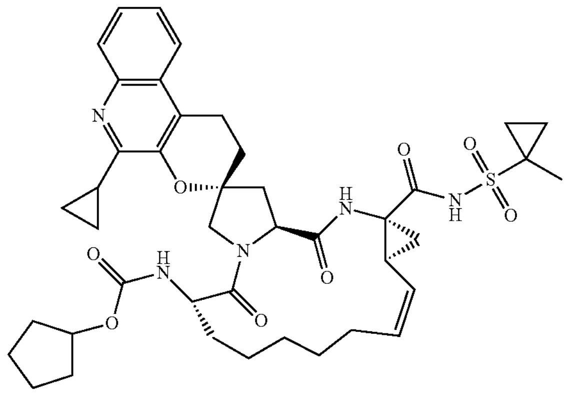
I-105
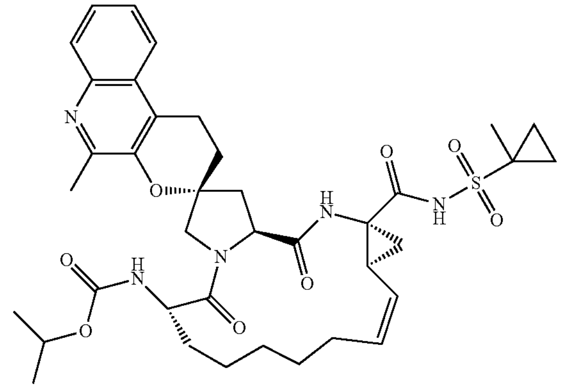
I-106
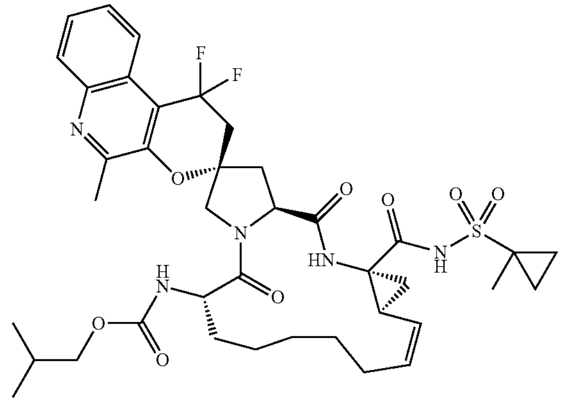
I-107
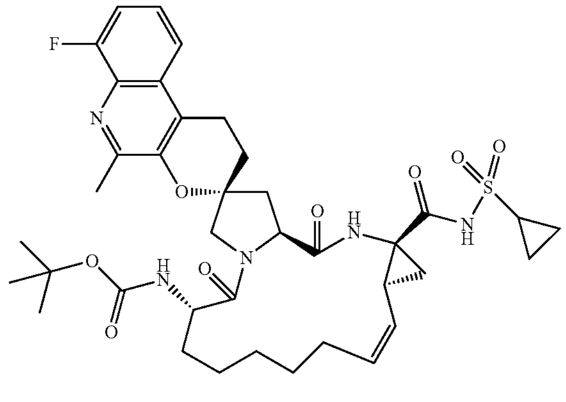
I-108
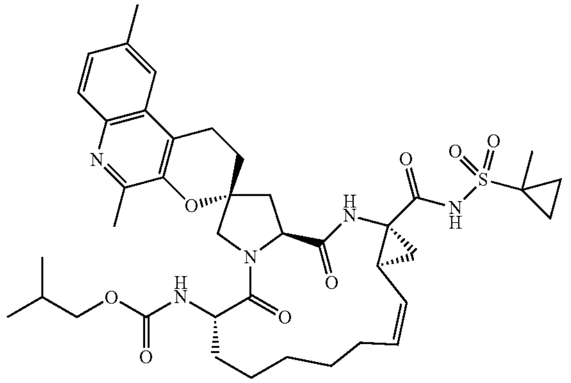
I-109
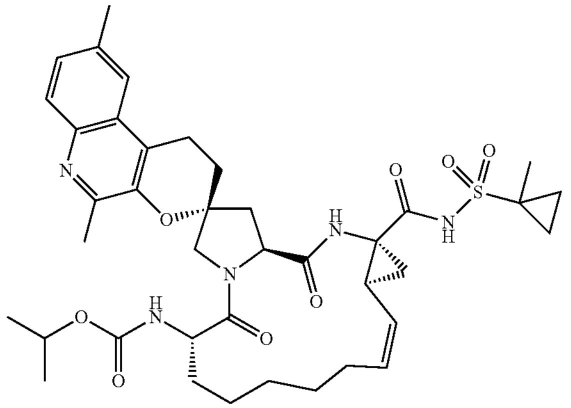
I-110
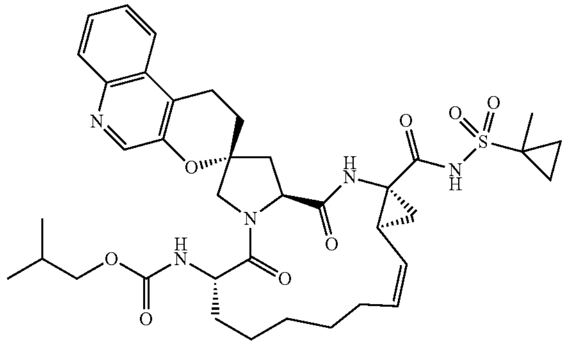
I-111
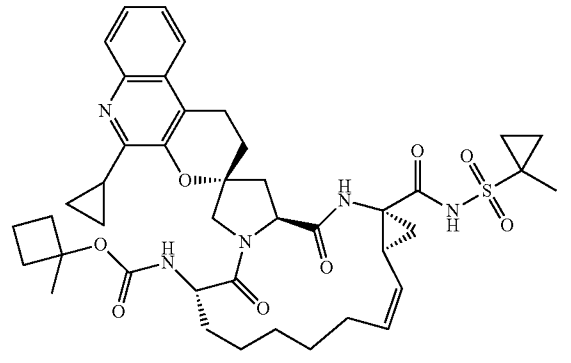

-continued
I-112
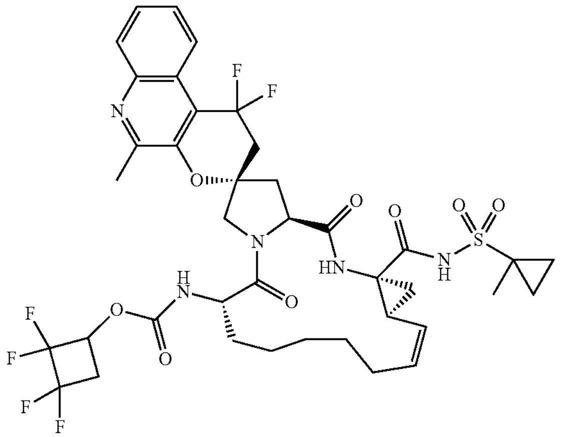
I-113
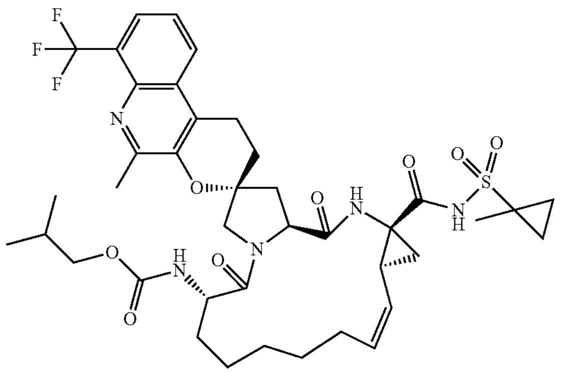
I-114
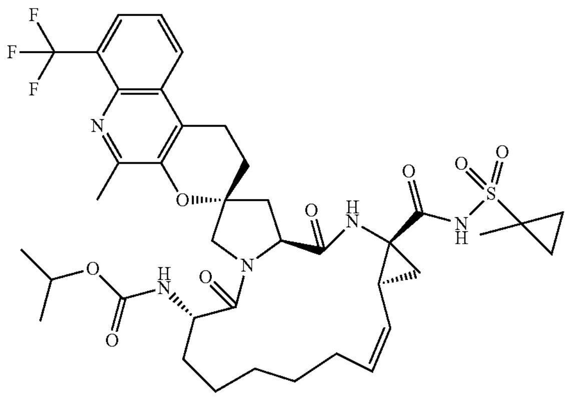
I-115
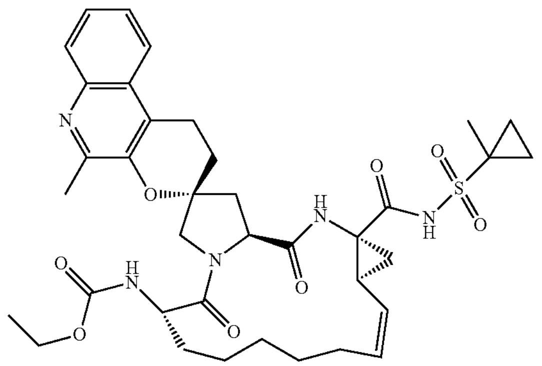
-continued
I-116
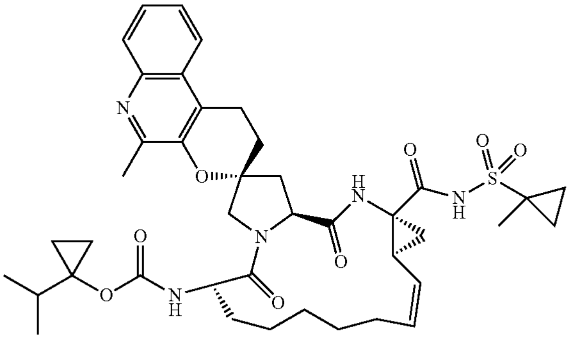
I-117
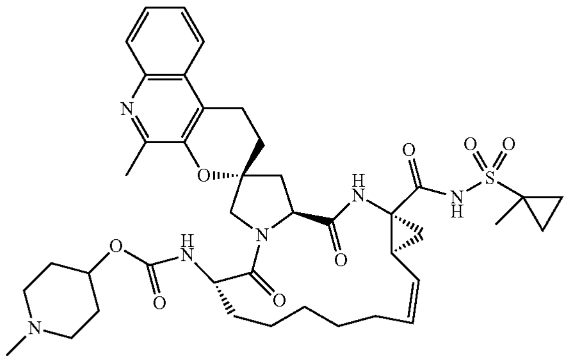
I-118/I-120
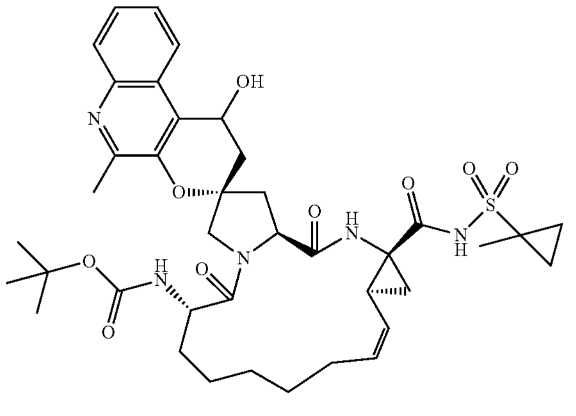
I-119
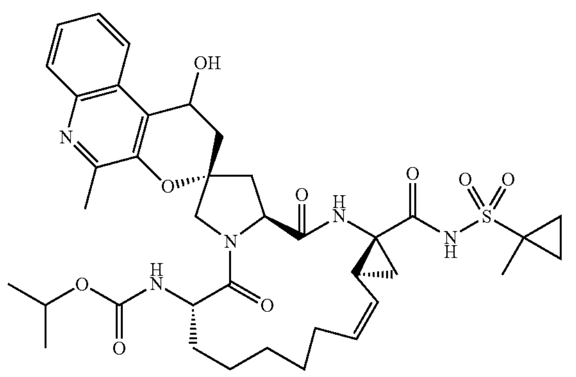

-continued
I-121
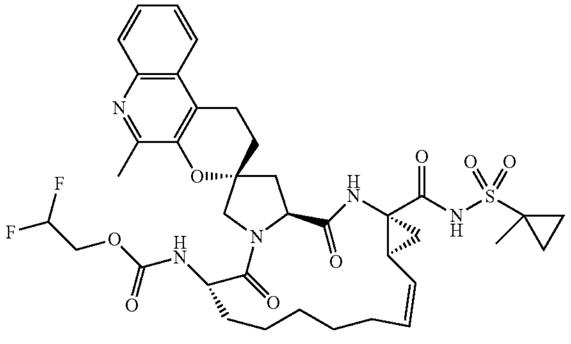
I-122
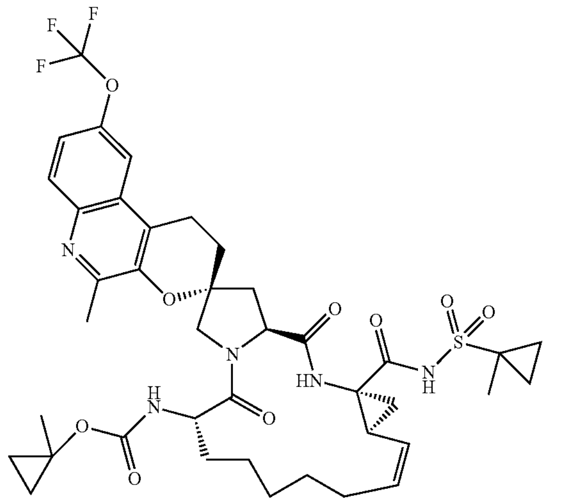
I-123
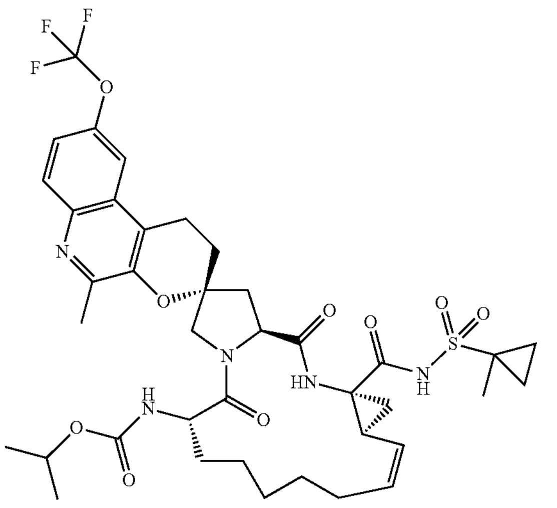
-continued
I-124
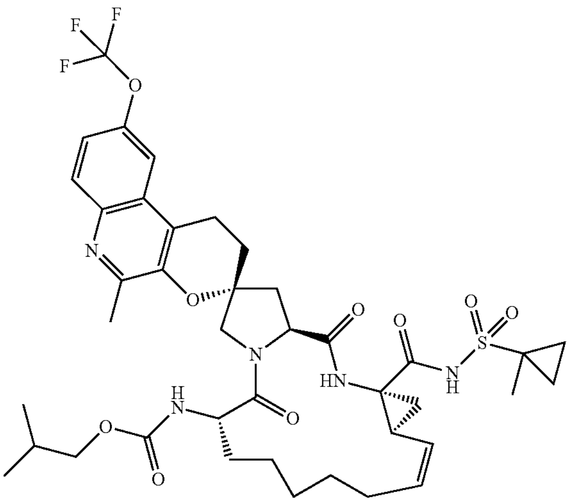
I-125
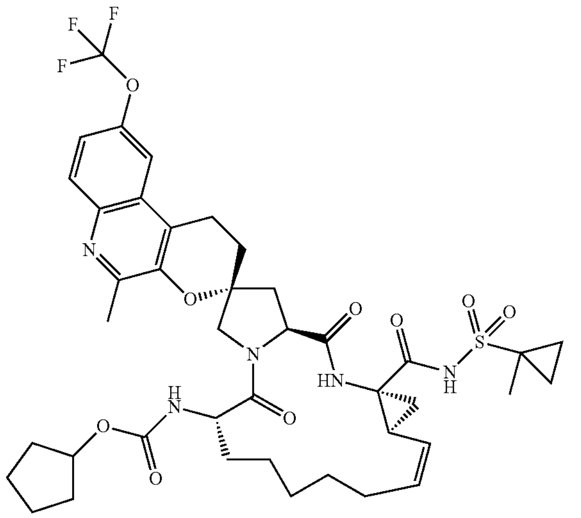
I-126
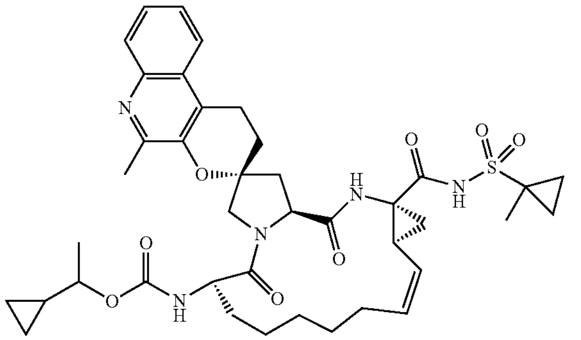

-continued
I-127
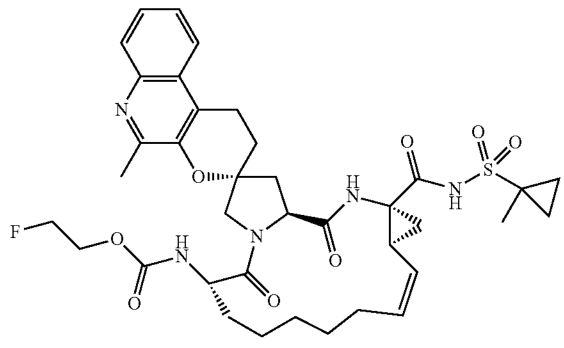
I-128
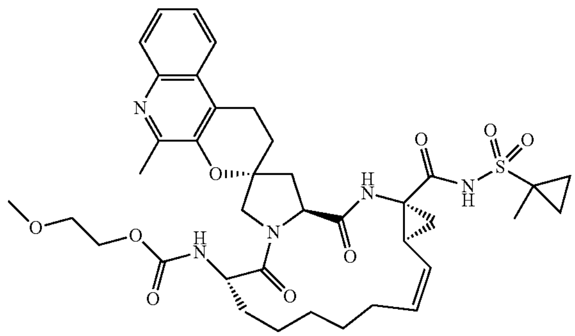
I-129
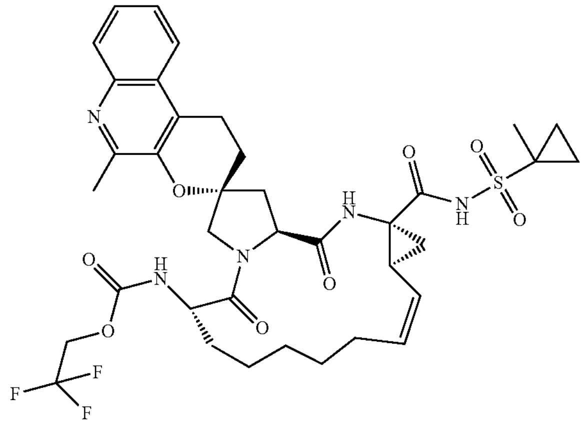
I-130
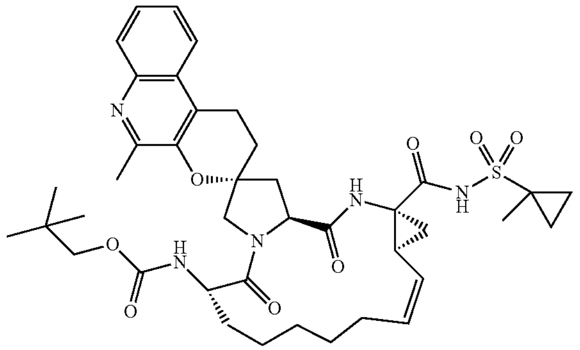
-continued
I-131
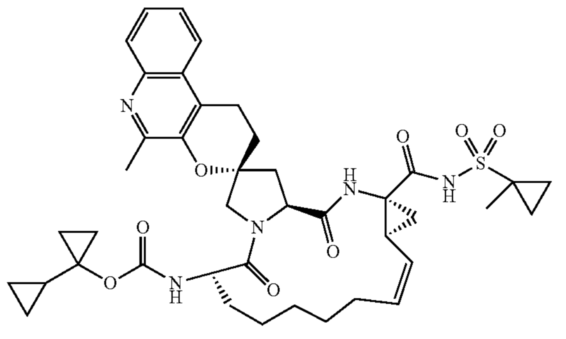
I-132
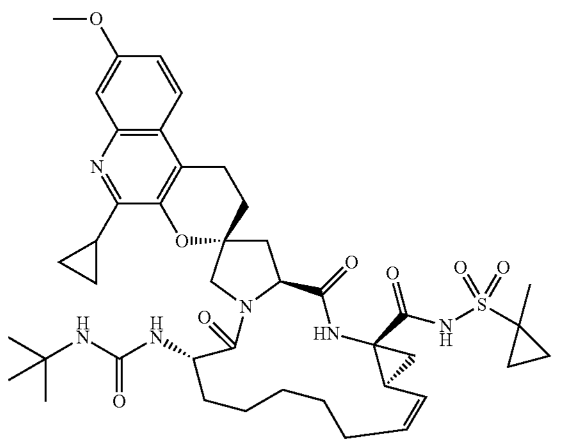
I-133
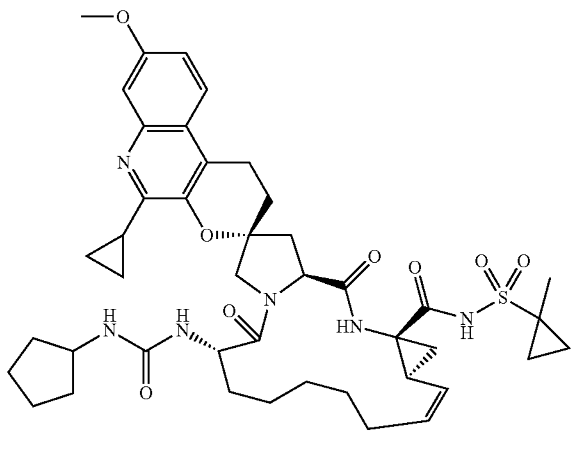

-continued
I-134
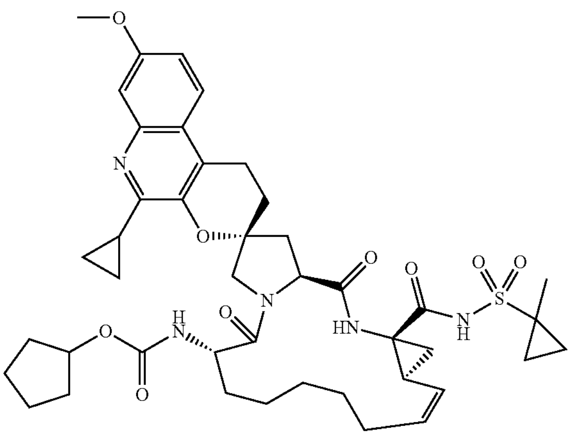
I-135
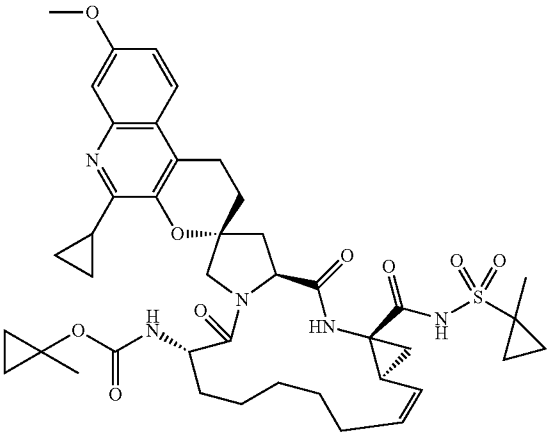
I-136
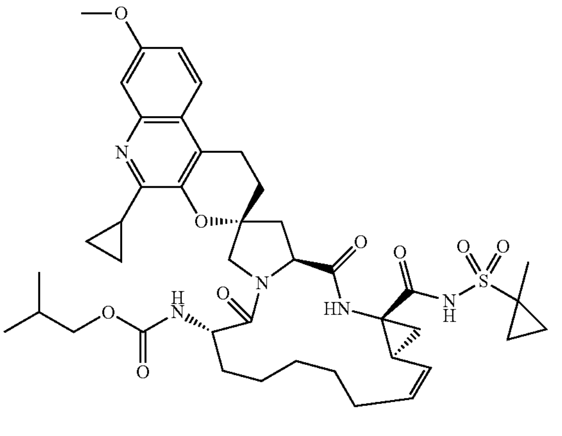
-continued
I-137
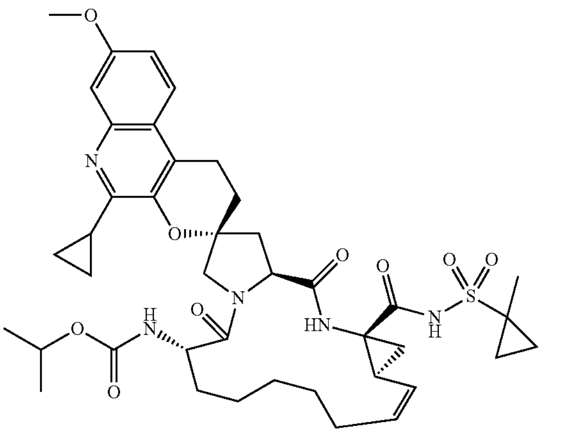
I-138
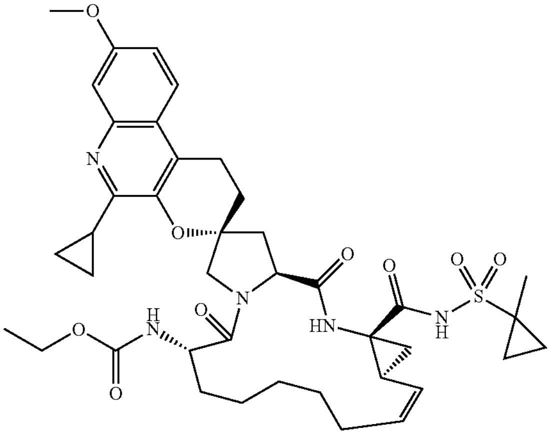
I-139
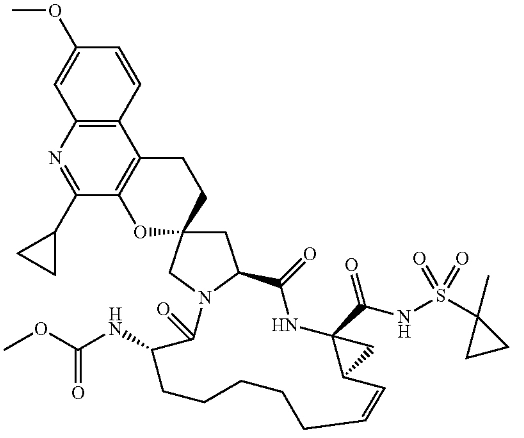

-continued
I-140
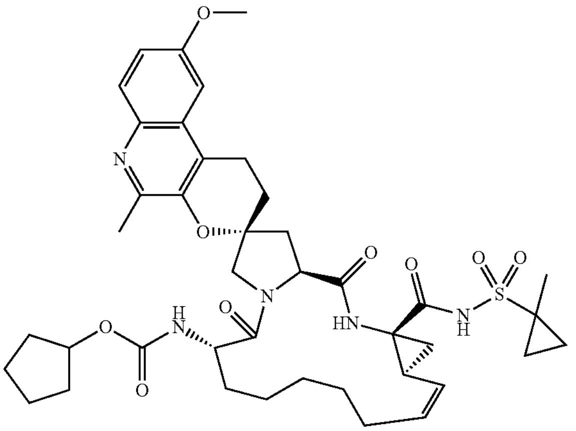
I-141
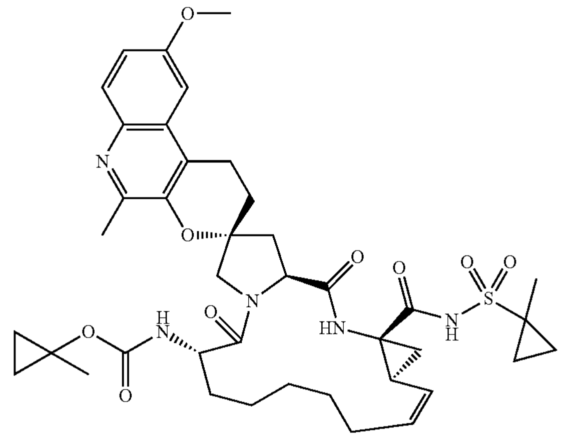
I-142
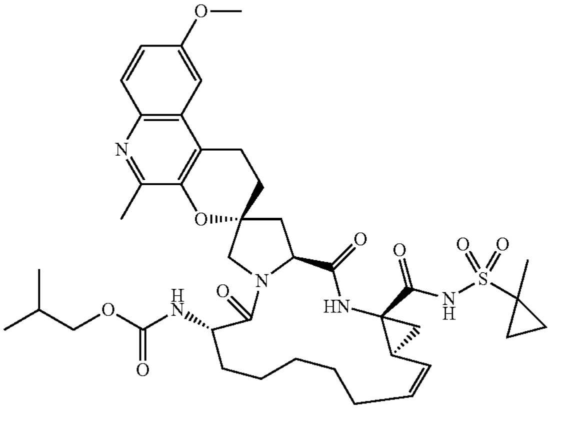
-continued
I-143
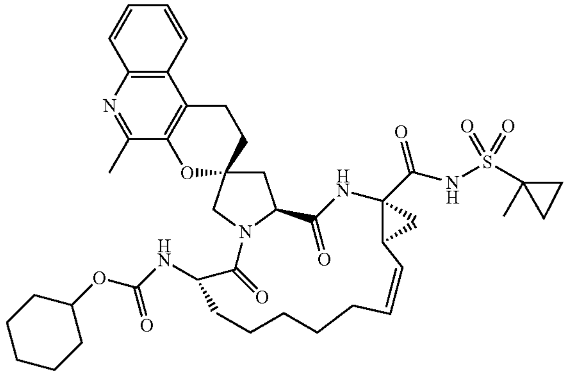
I-144
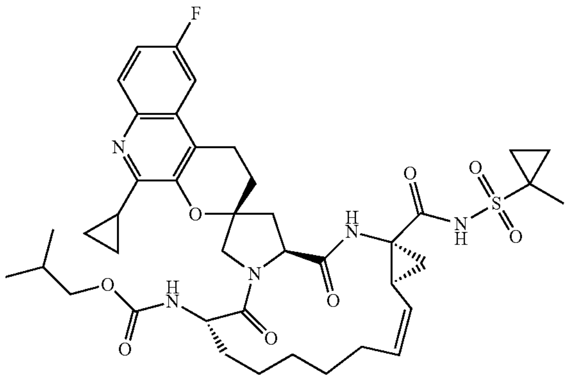
I-145
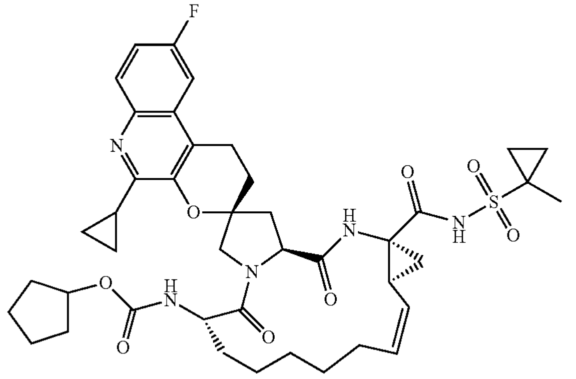

-continued
I-146
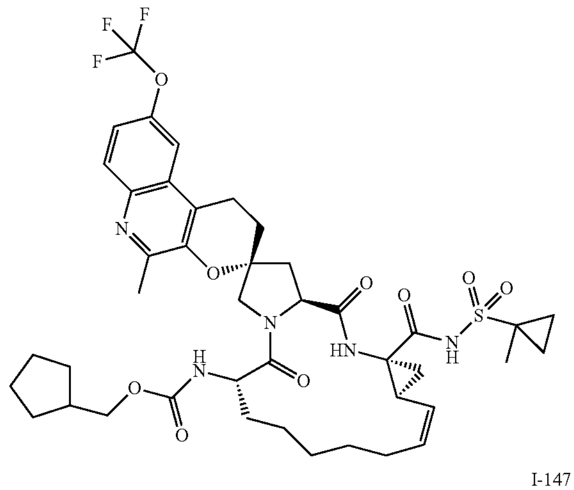
I-147
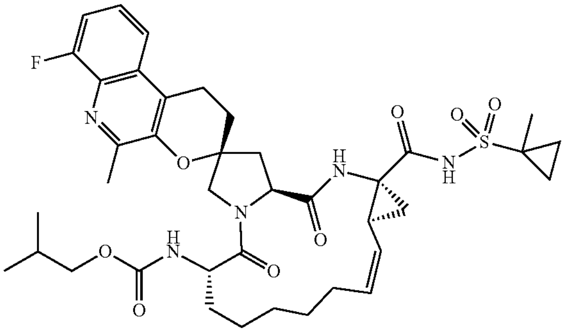
I-148
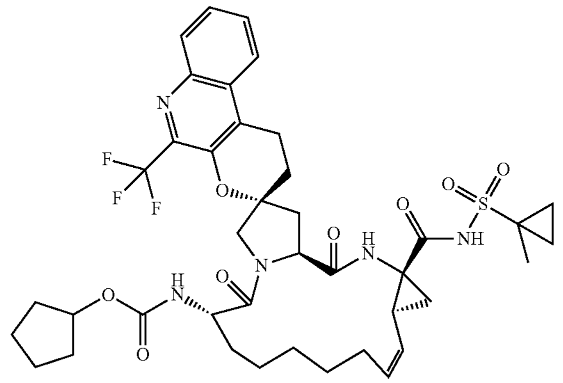
I-149
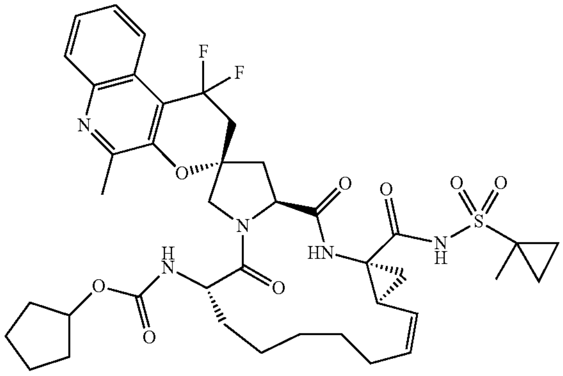
-continued
I-150
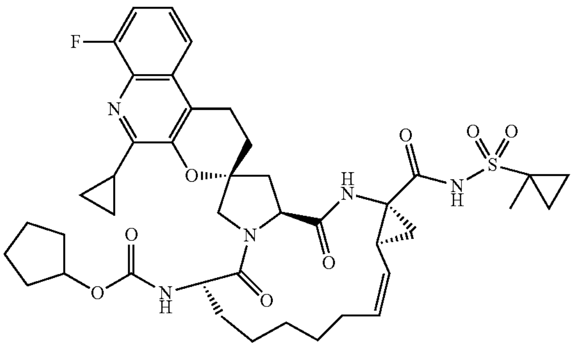
I-151
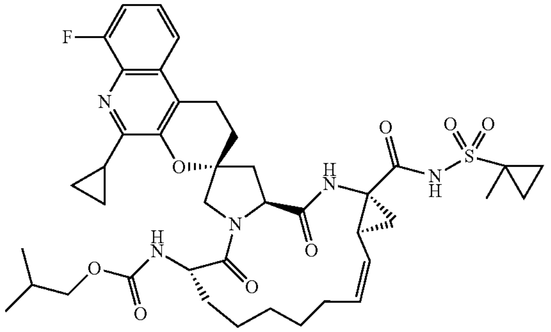
I-152
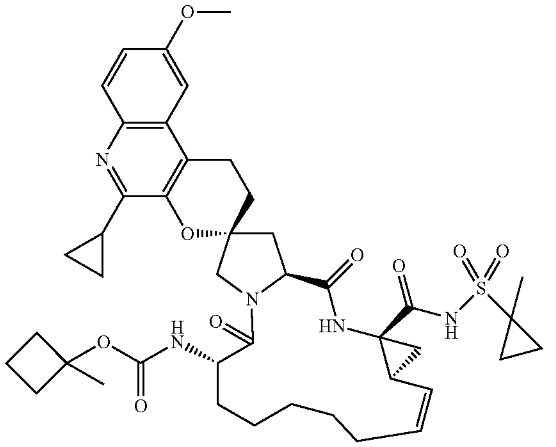
I-153
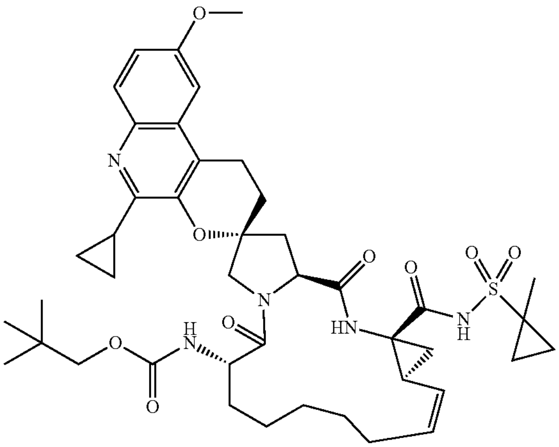

-continued
I-154
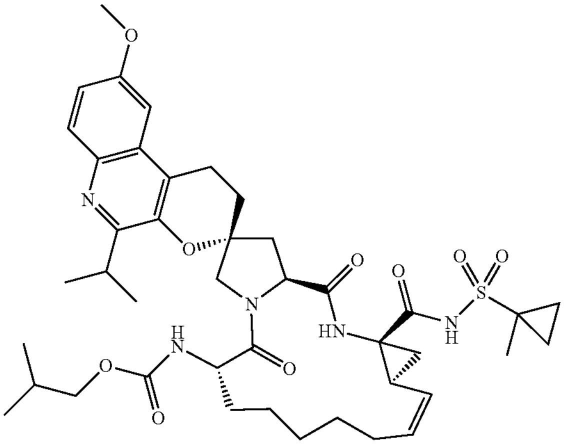
I-155
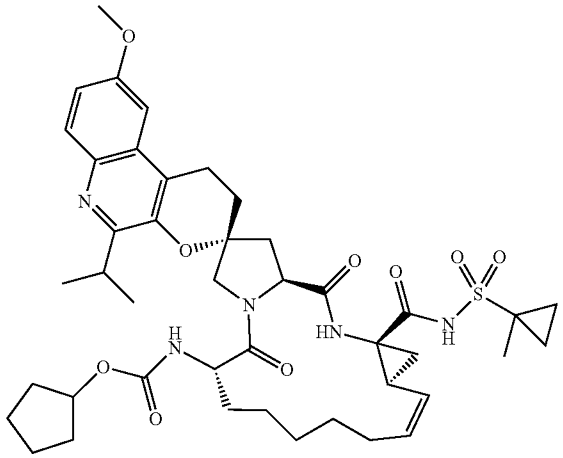
I-156
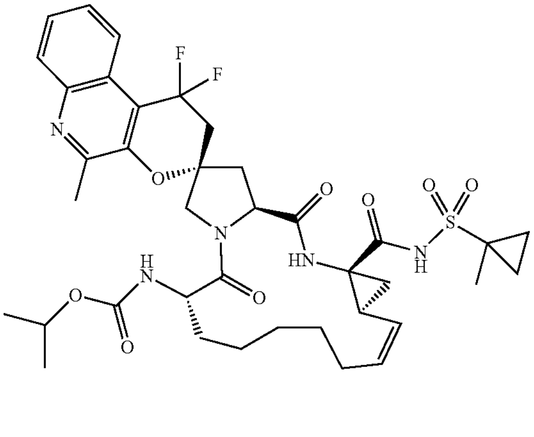
-continued
I-157
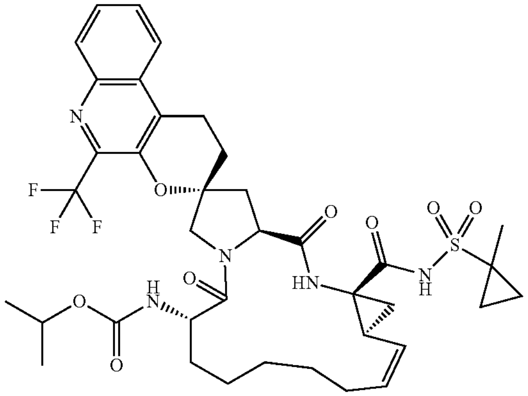
I-158
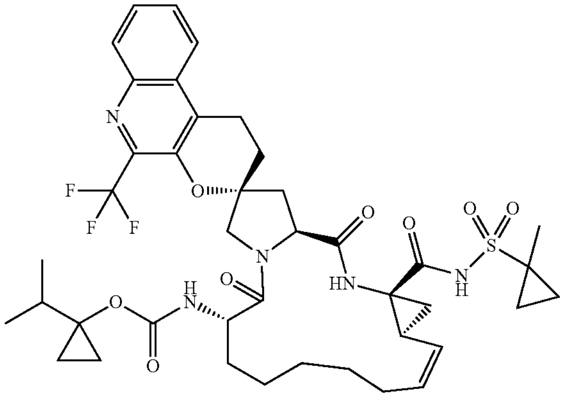
I-159
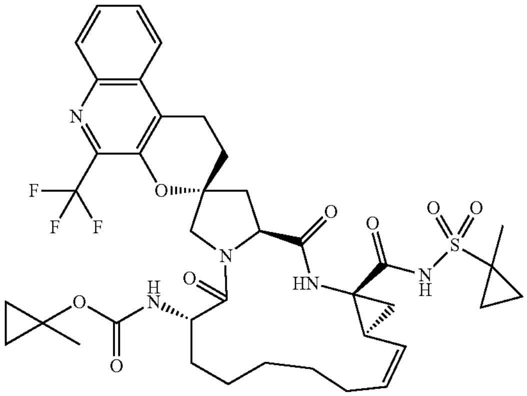
I-160
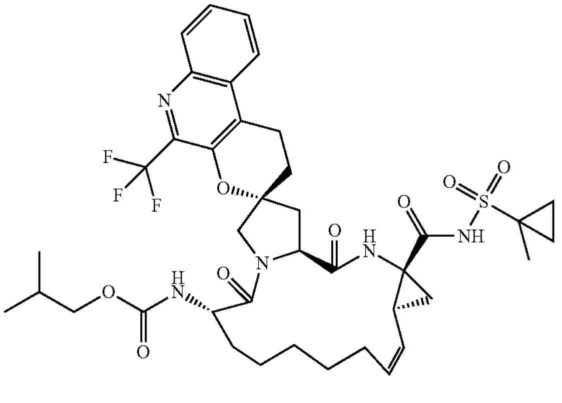

-continued
I-161
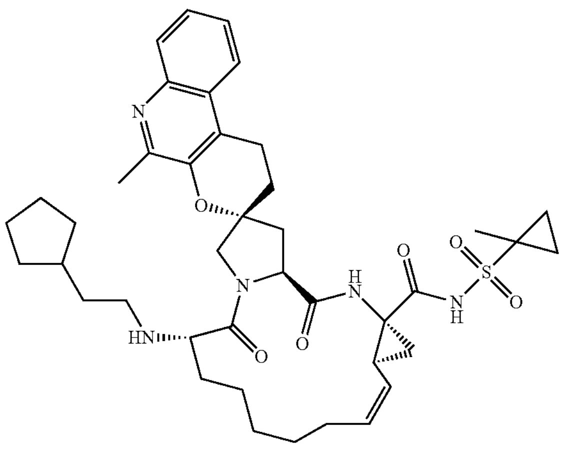
I-164
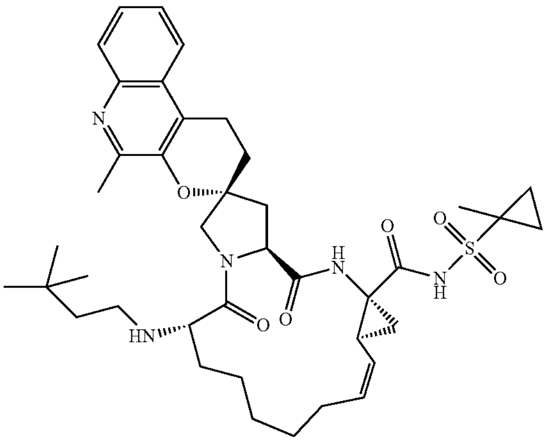
I-165
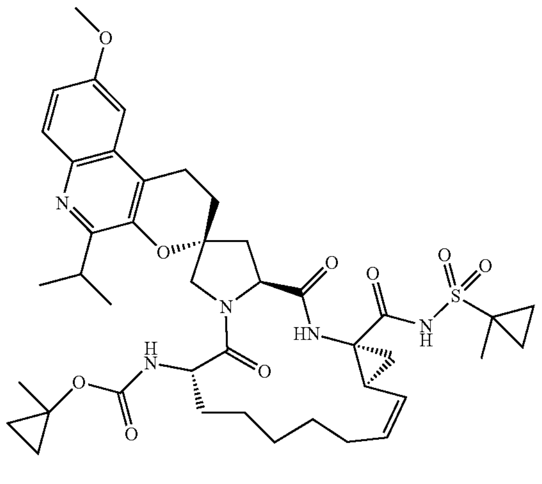
-continued
I-166
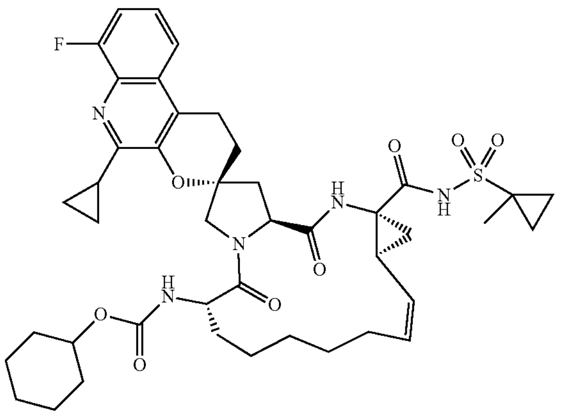
I-167
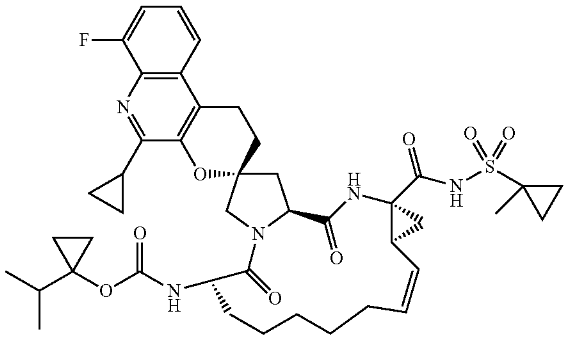
I-168
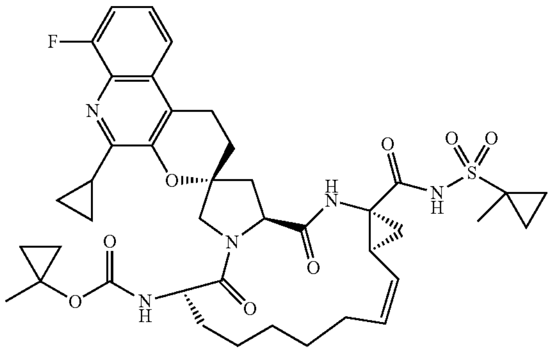
I-169
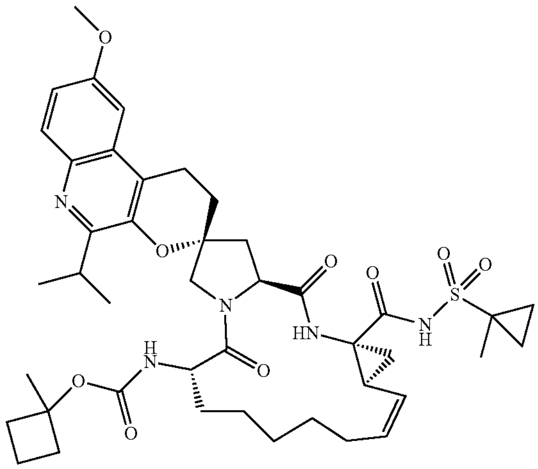

-continued
I-170
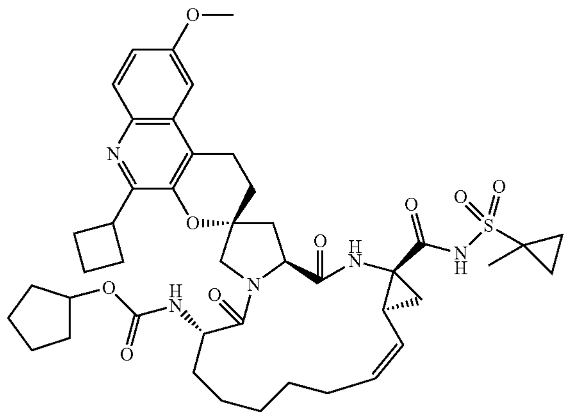
I-171
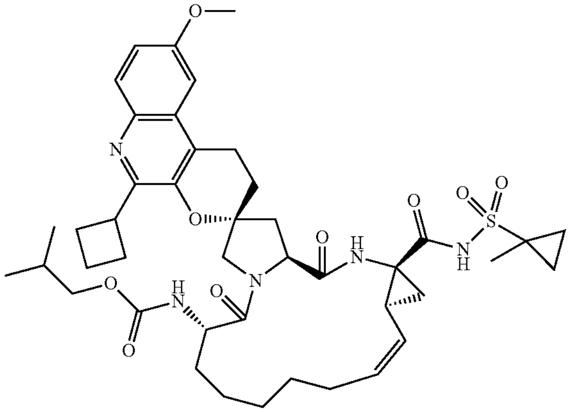
I-172
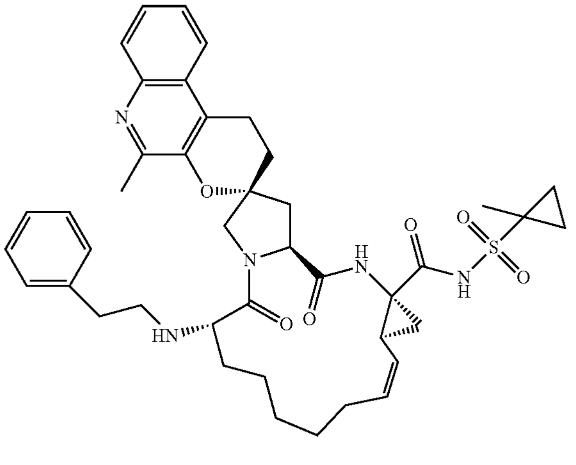
-continued
I-174
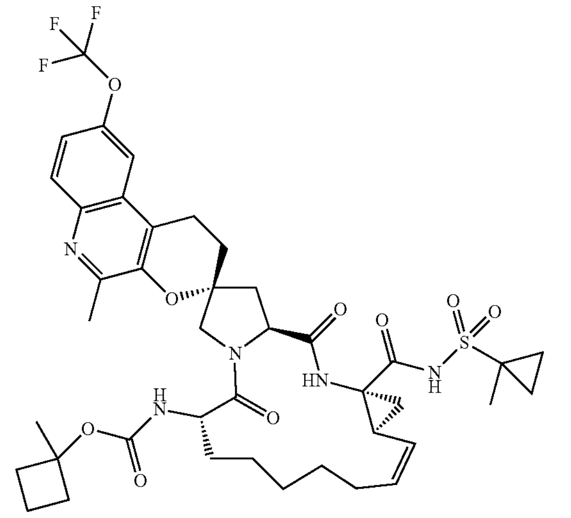
I-175
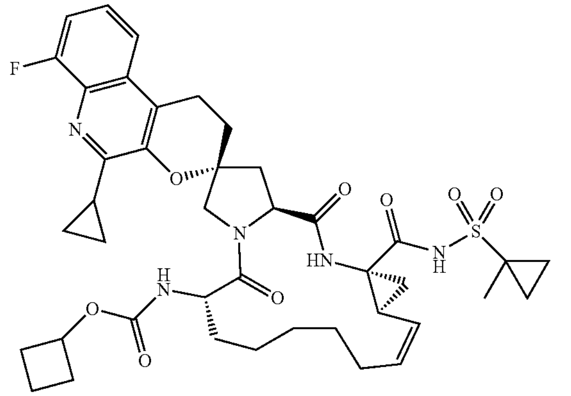
I-176
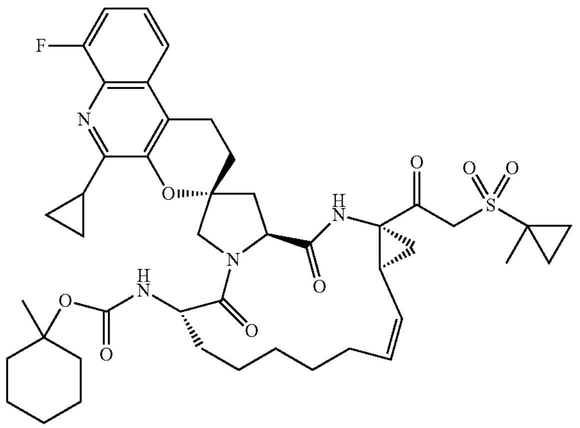

I-177
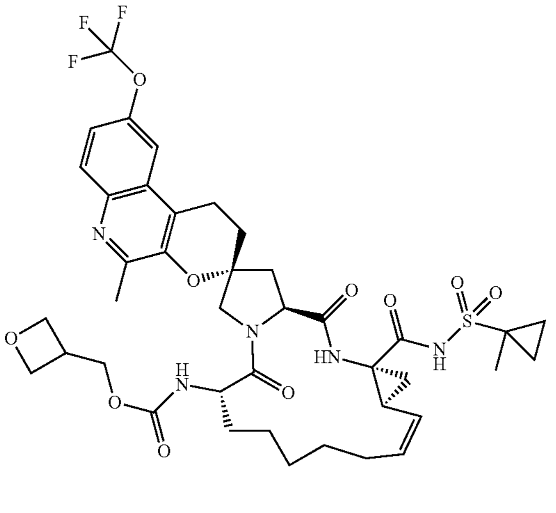
I-178
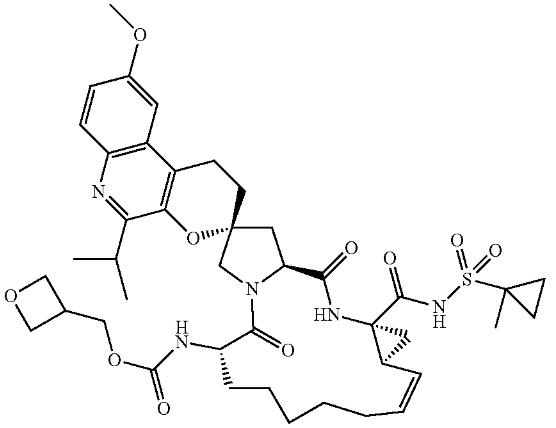
I-179
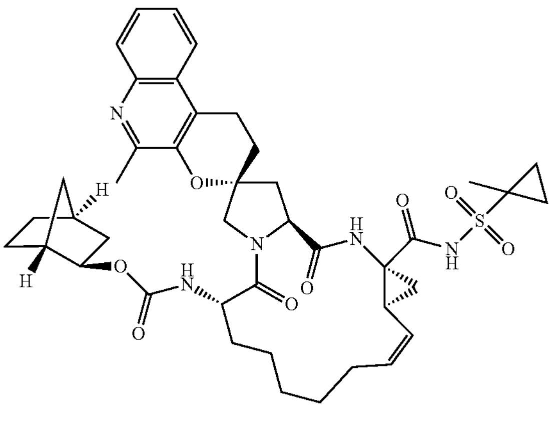
I-180
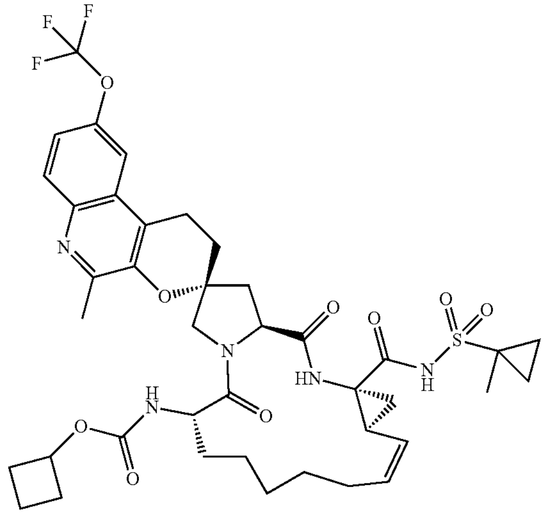
I-181
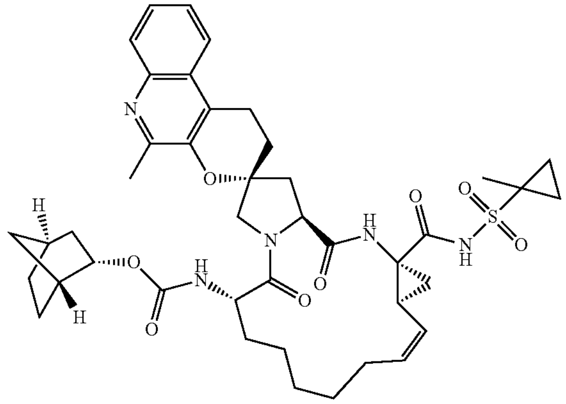
I-182
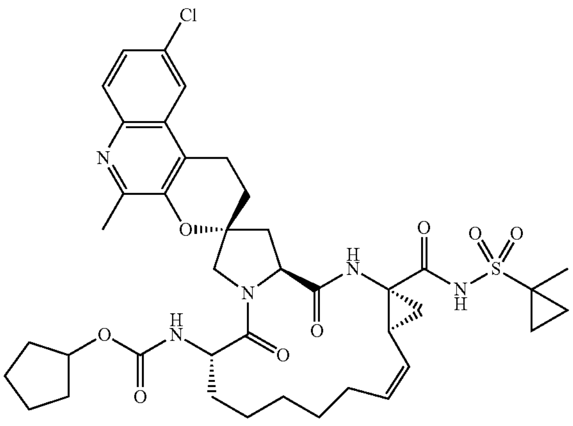

-continued
I-183
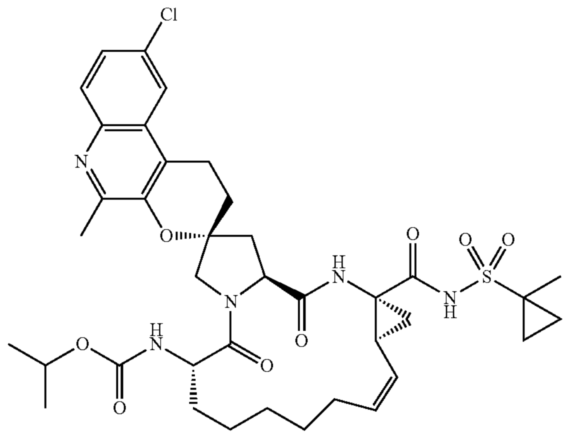
I-184
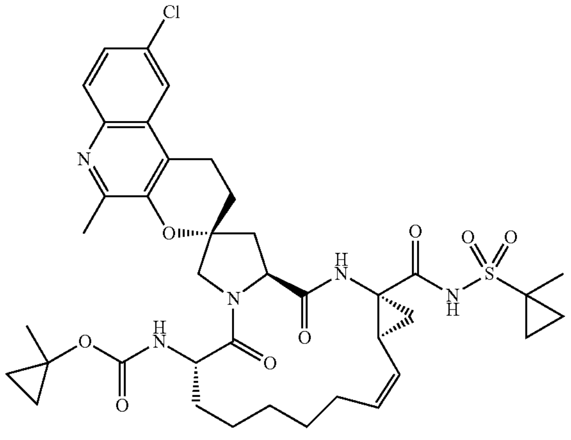
I-185
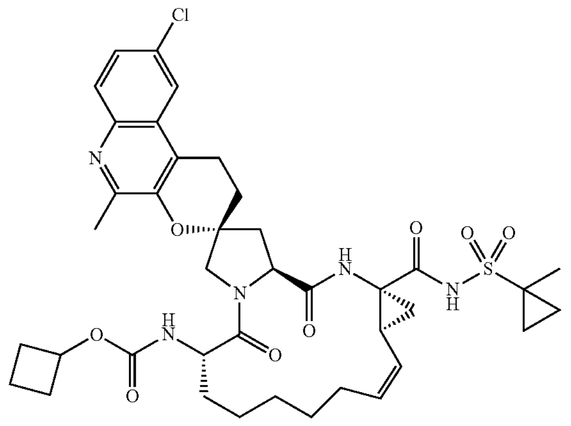
-continued
I-186
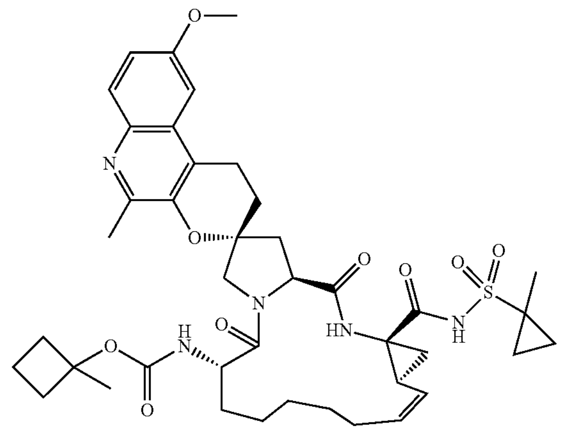
I-187
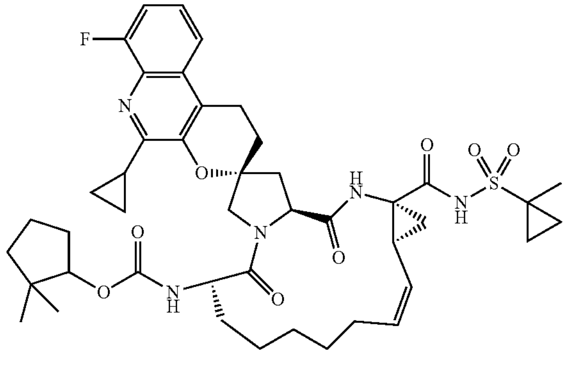
I-188
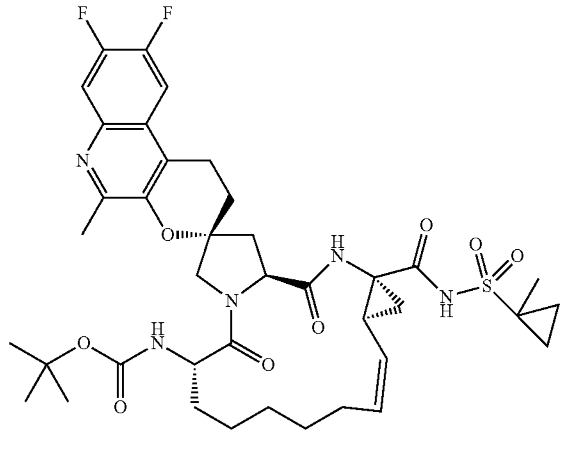

-continued
I-189
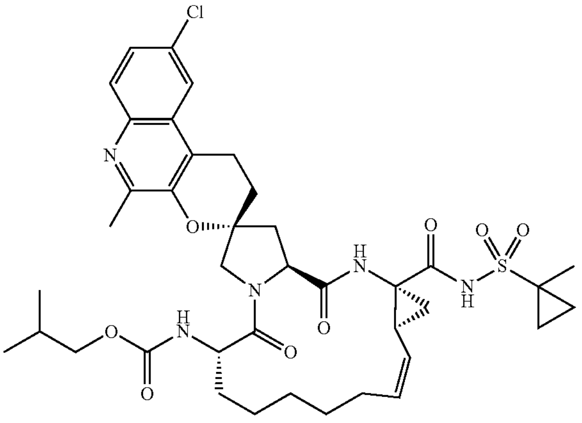
I-190
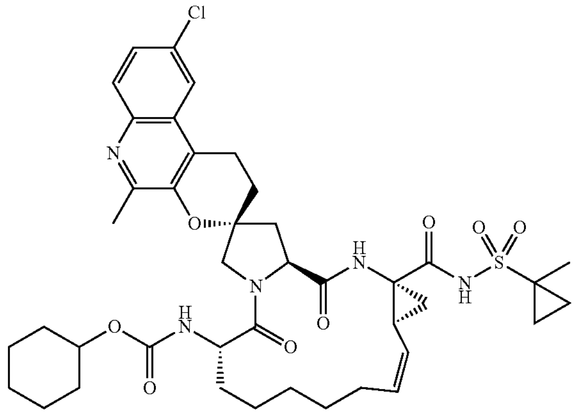
I-191
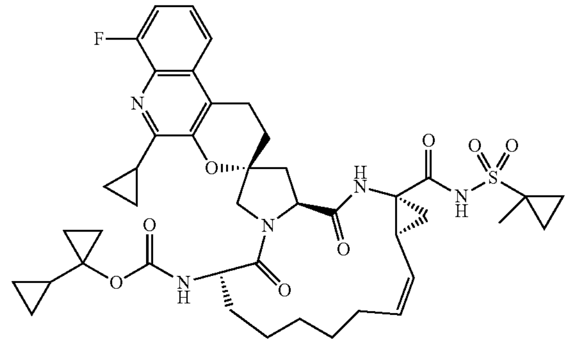
I-192
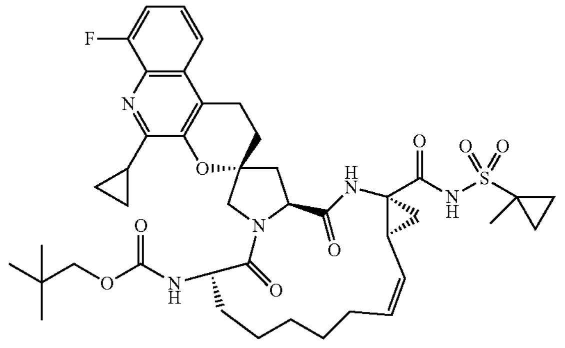
-continued
I-193
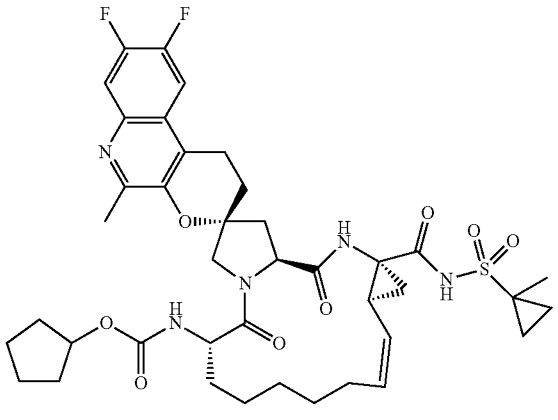
I-194
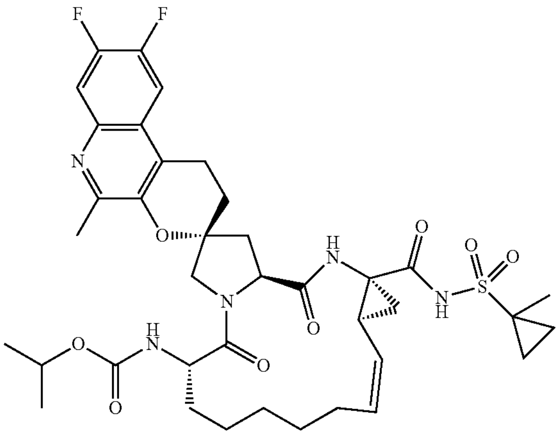
I-195
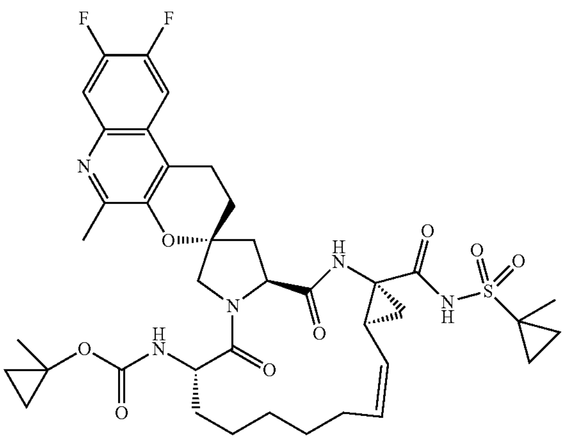

-continued
I-196
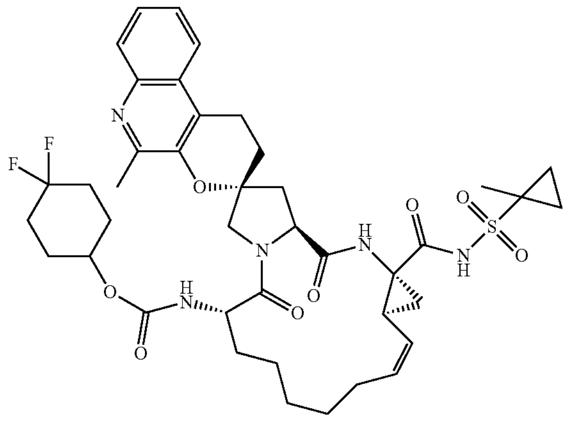
I-197
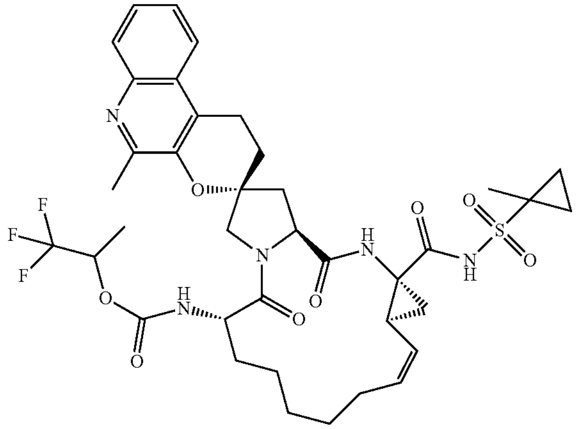
I-198
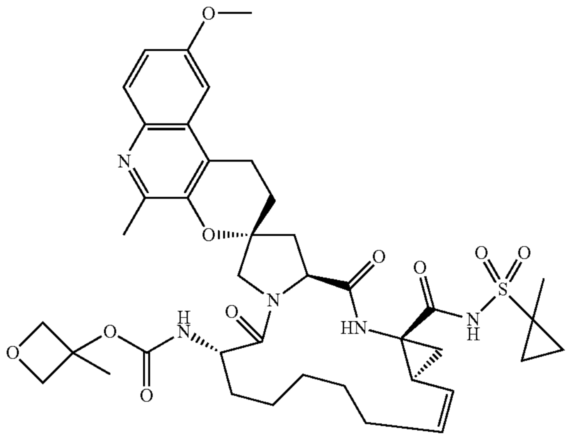
-continued
I-199
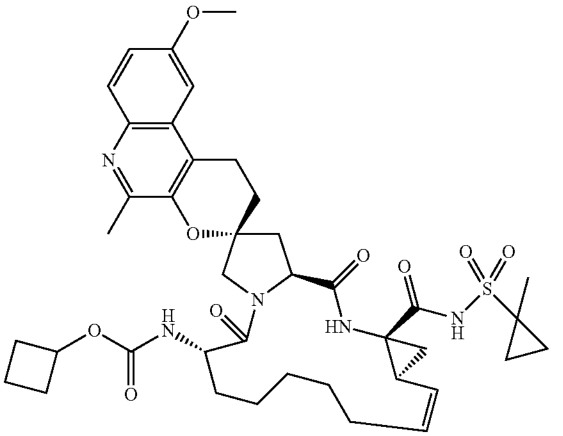
I-200
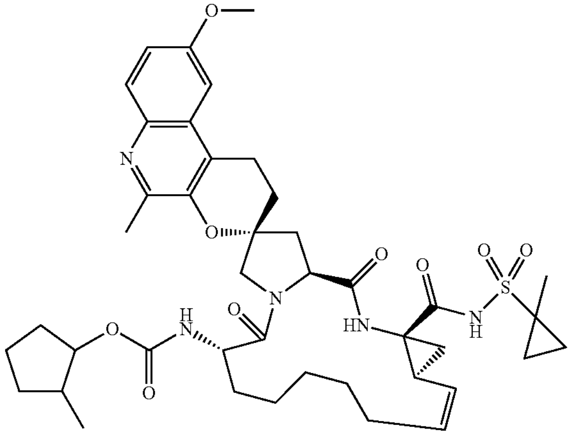
I-201
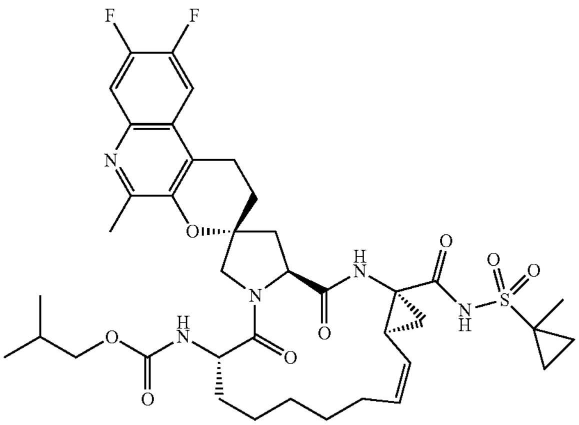

-continued
I-202
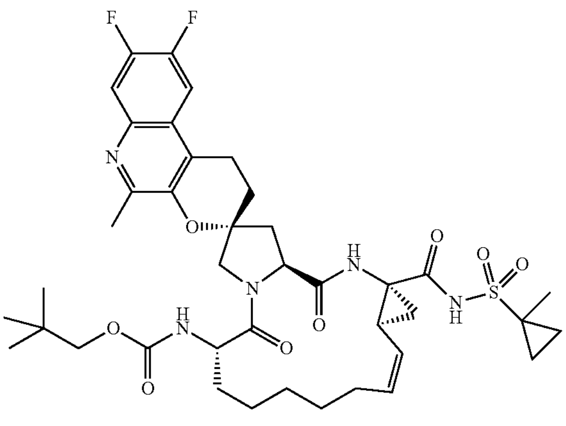
I-203
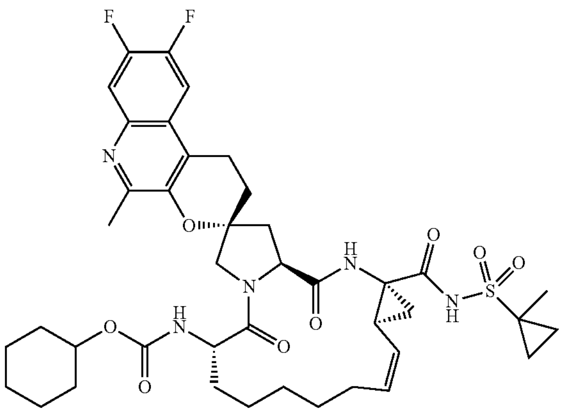
I-204
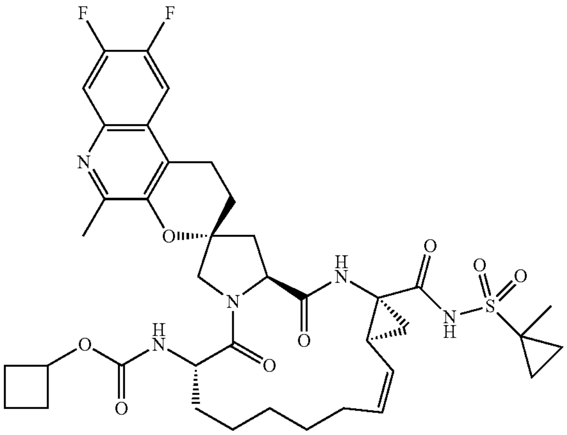
-continued
I-205
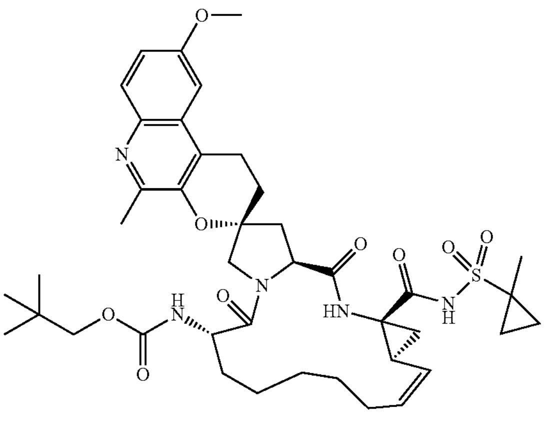
I-206
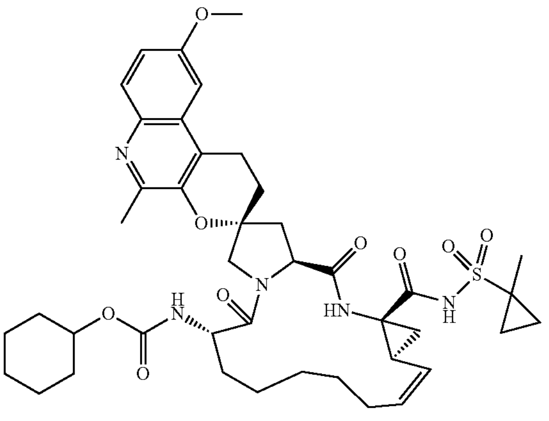
I-207
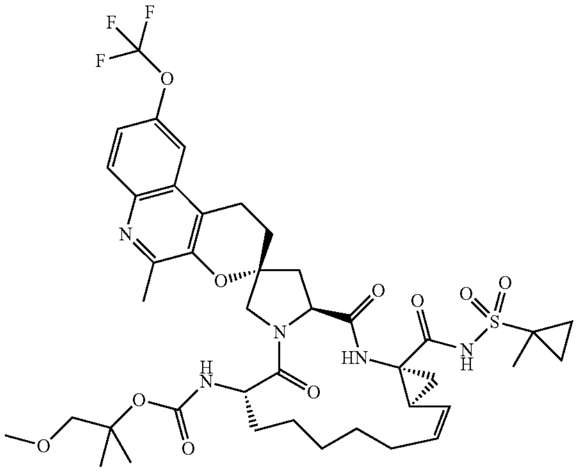

-continued
I-208
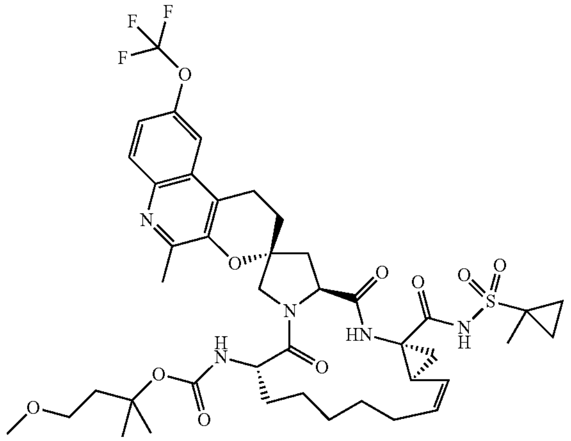
I-209
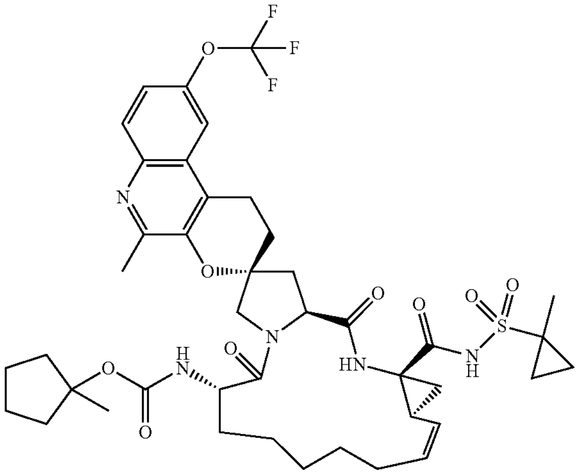
I-210
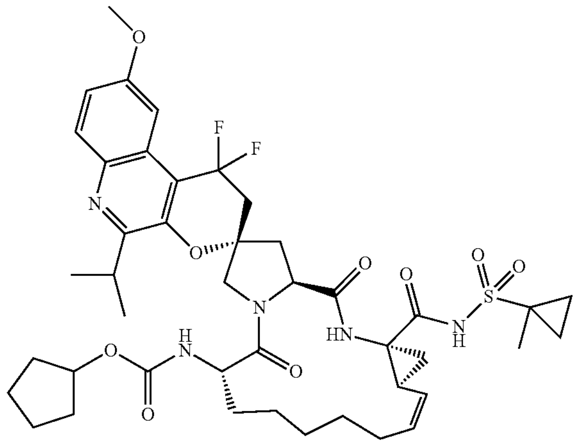
-continued
I-211
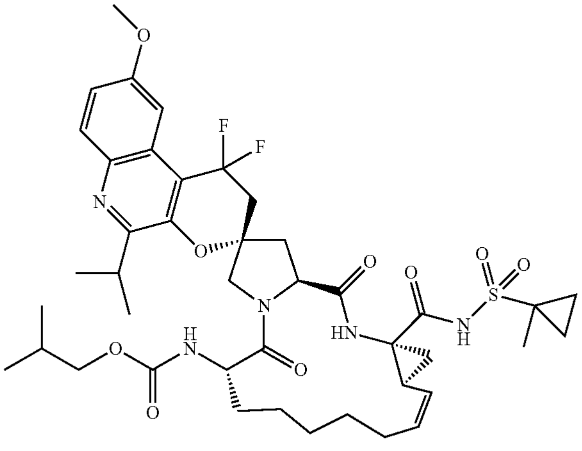
I-212
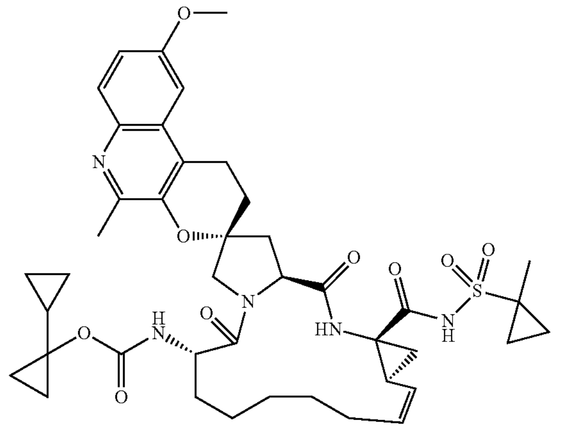
I-213
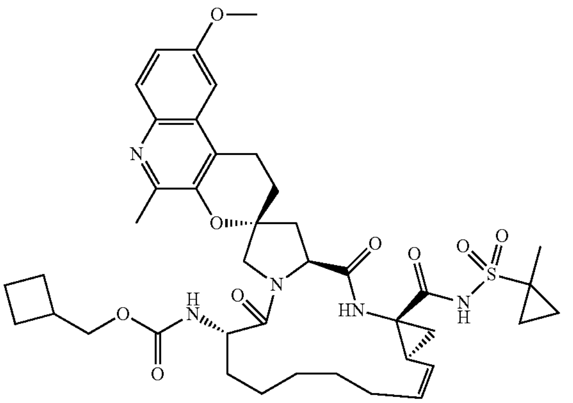

-continued
I-214
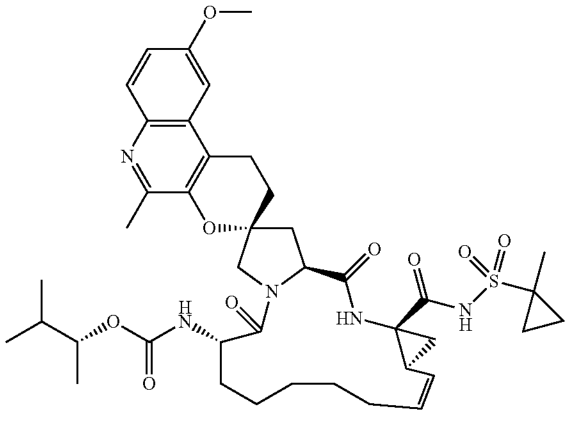
I-215
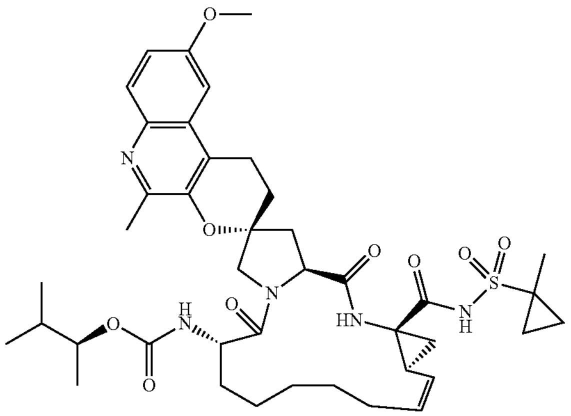
I-216
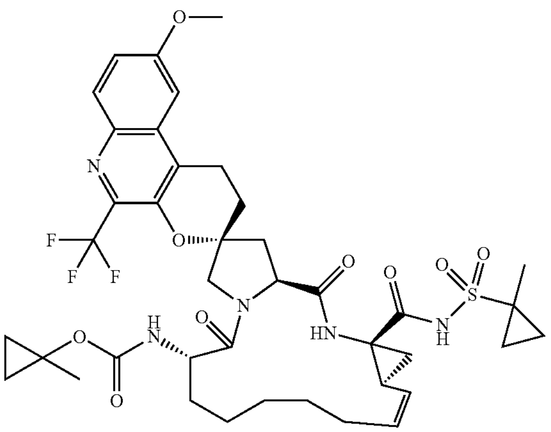
-continued
I-217
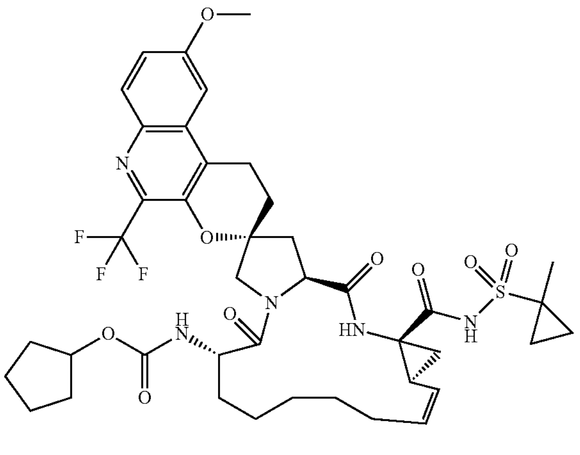
I-218
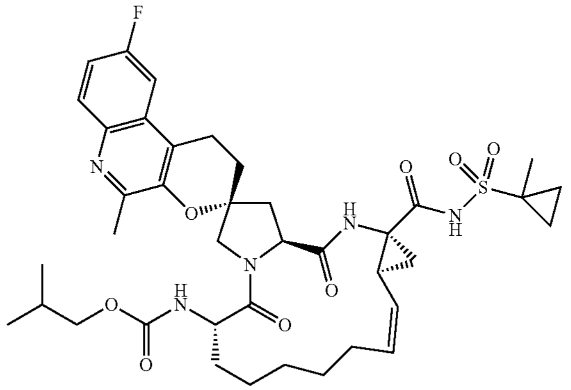
I-219
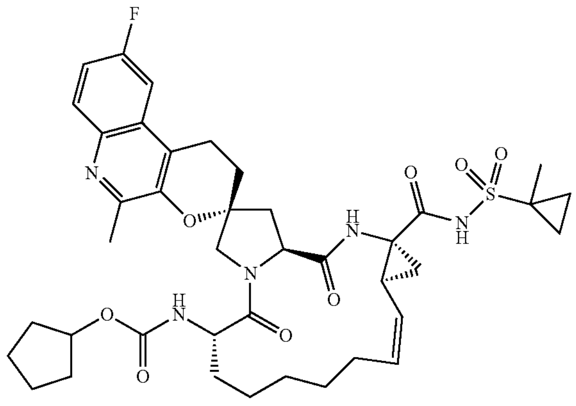

I-220
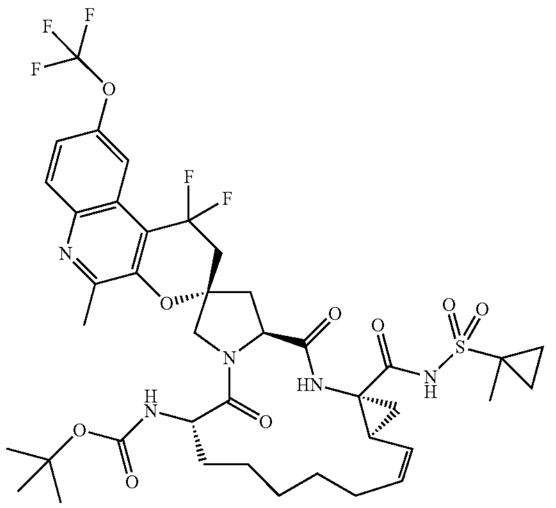
I-221
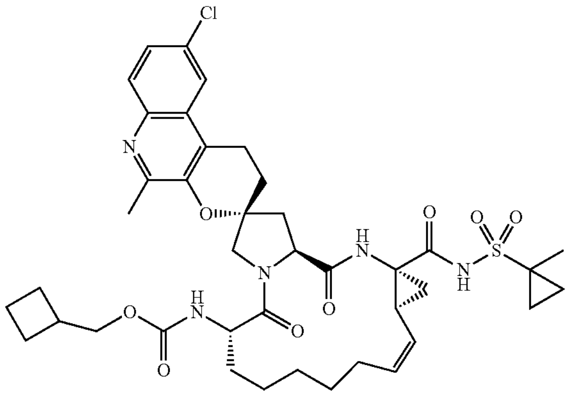
I-222
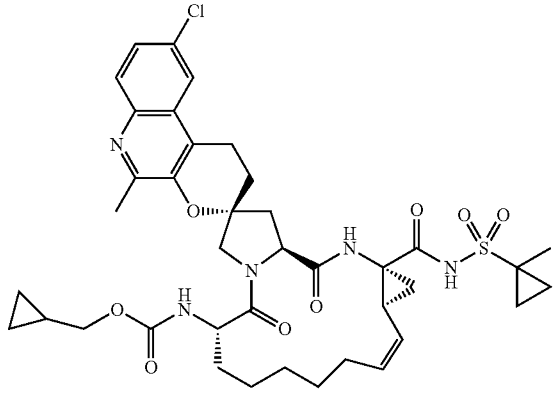
I-223
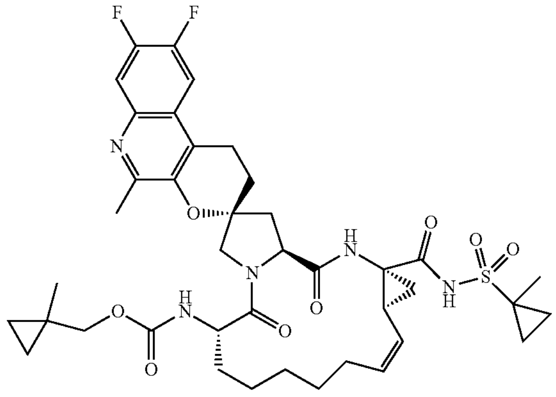
I-224
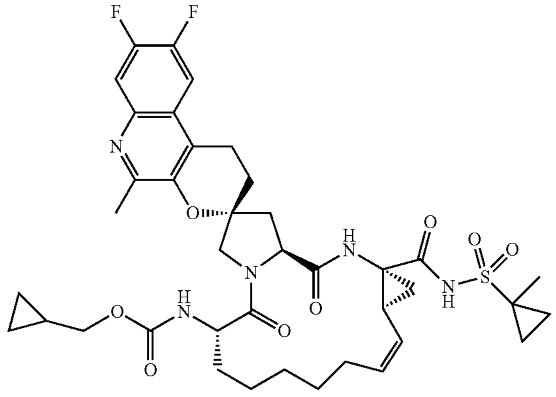
I-225
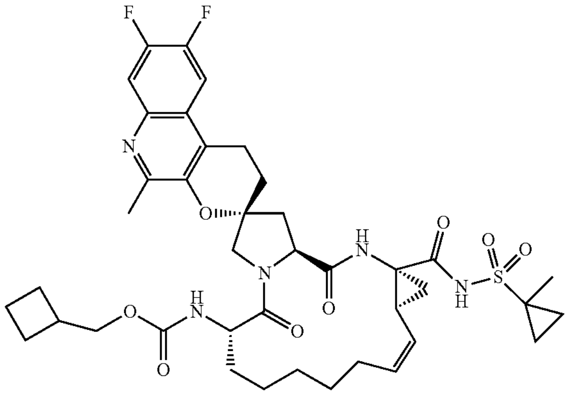

I-226
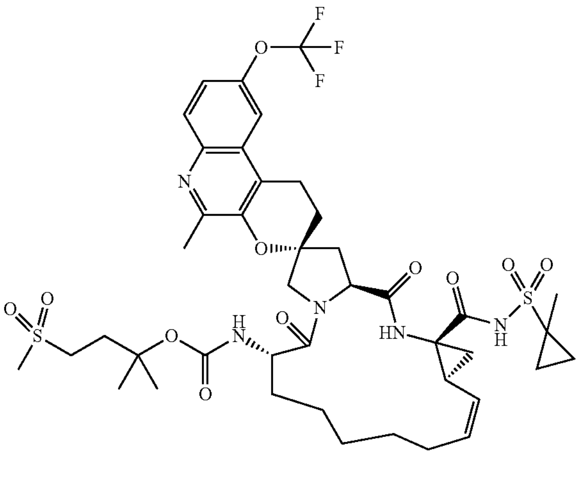
I-227
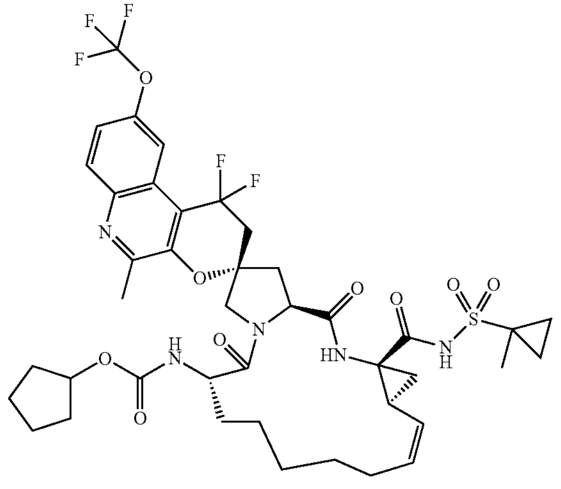
I-228
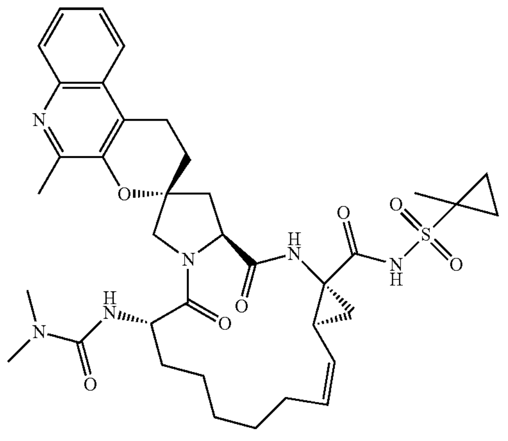
I-229
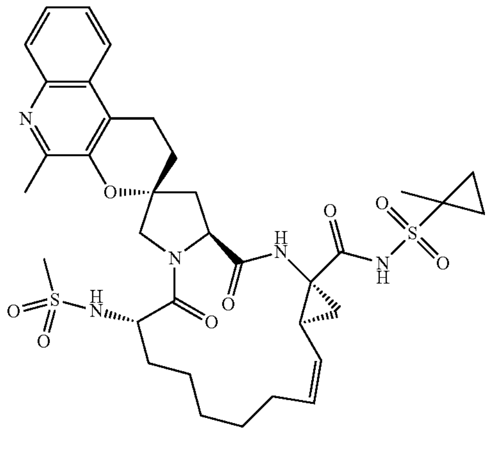
I-230
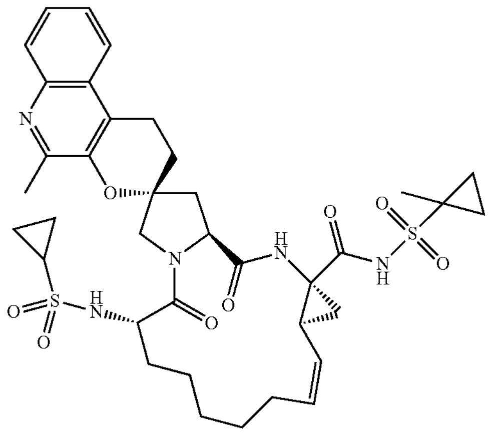
I-231
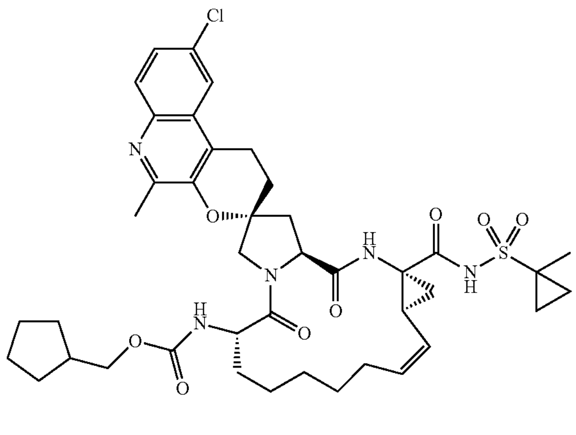

-continued
I-232
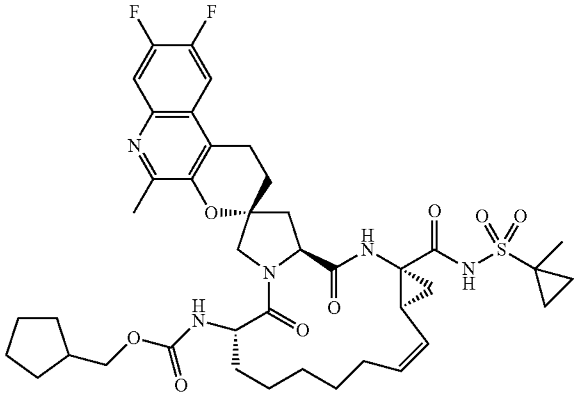
I-233
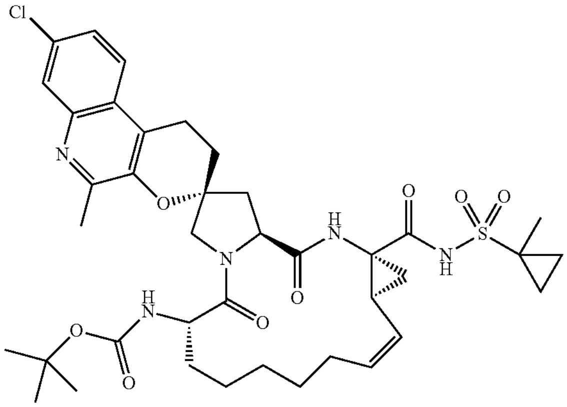
I-234
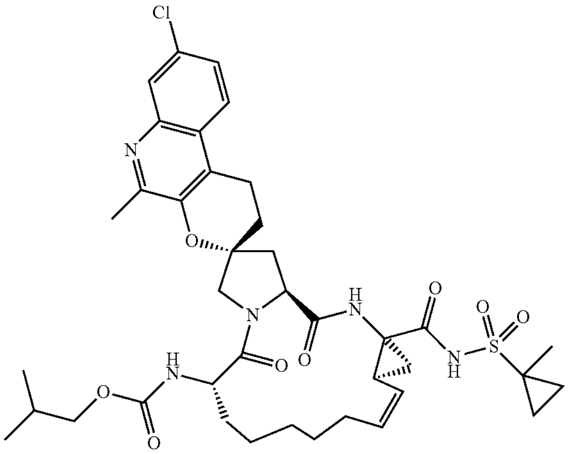
-continued
I-235
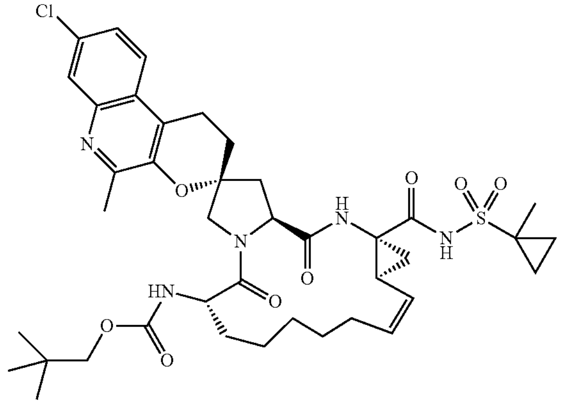
I-236
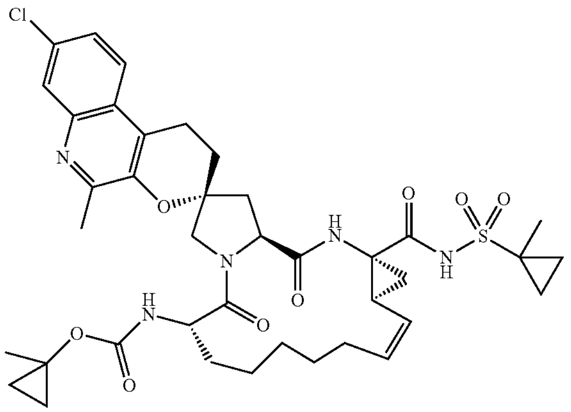
I-237
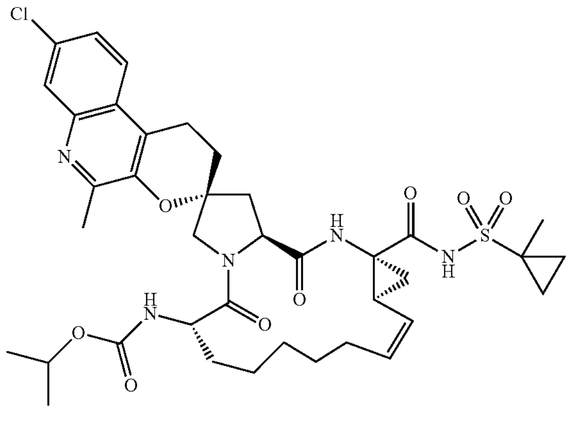

-continued
I-238
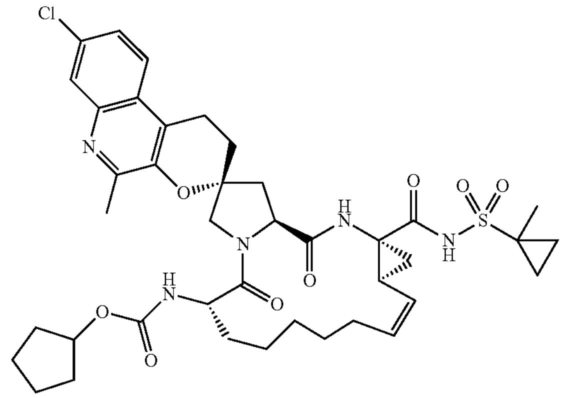
I-239
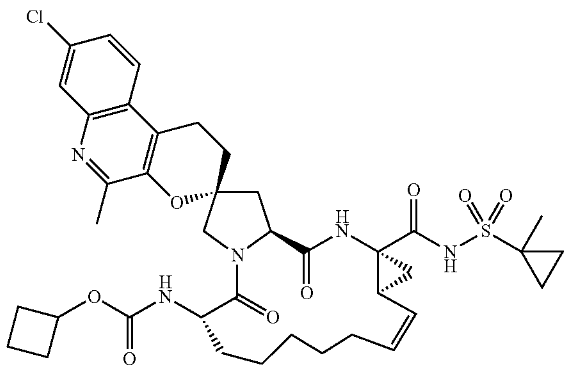
I-240
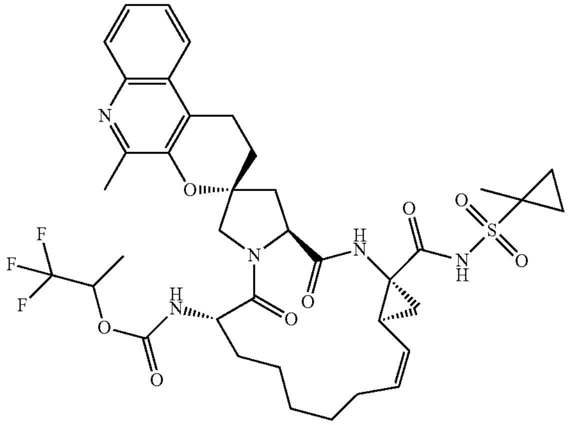
-continued
I-241
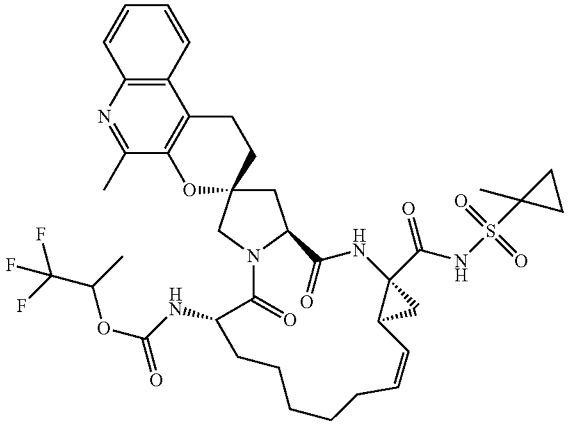
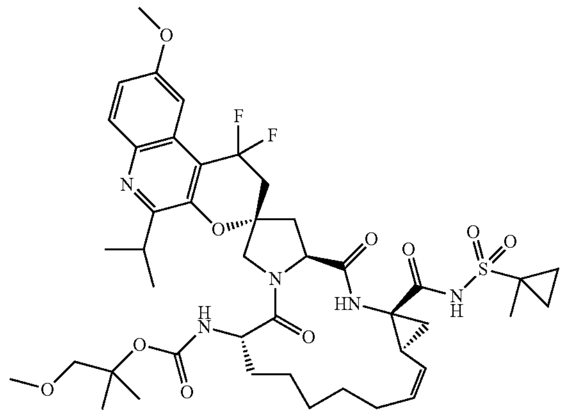
I-243
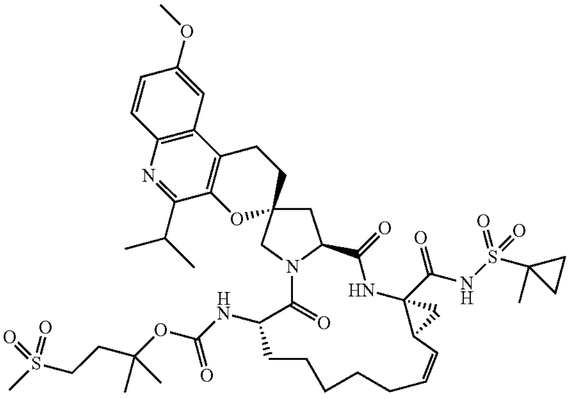

-continued
I-244
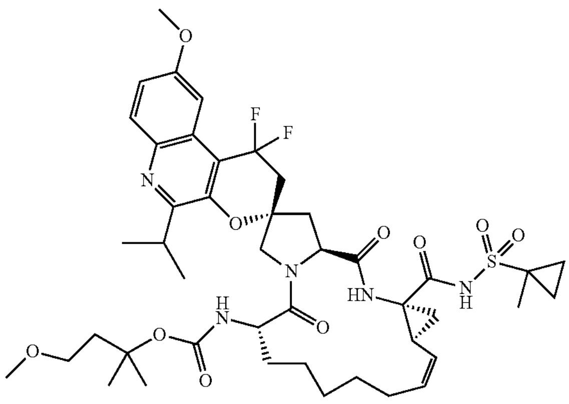
I-245
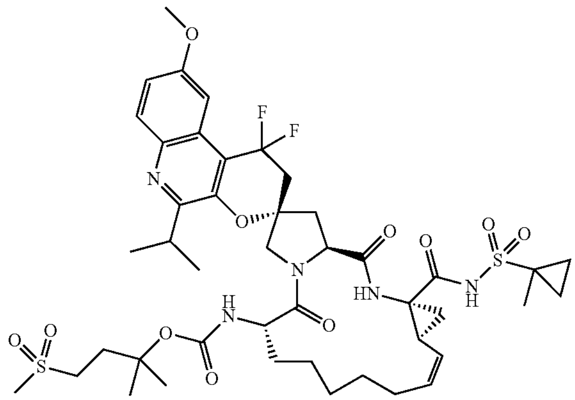
I-246
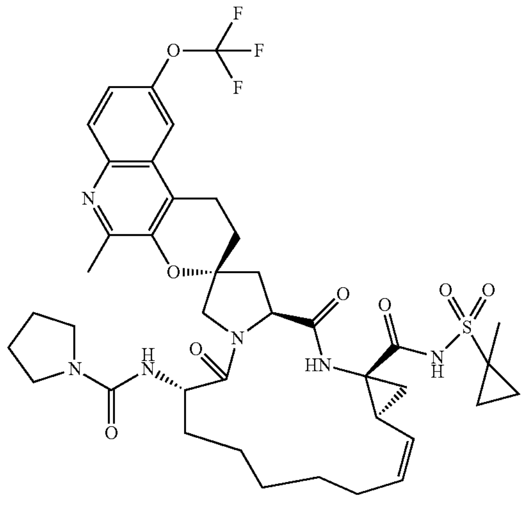
-continued
I-247
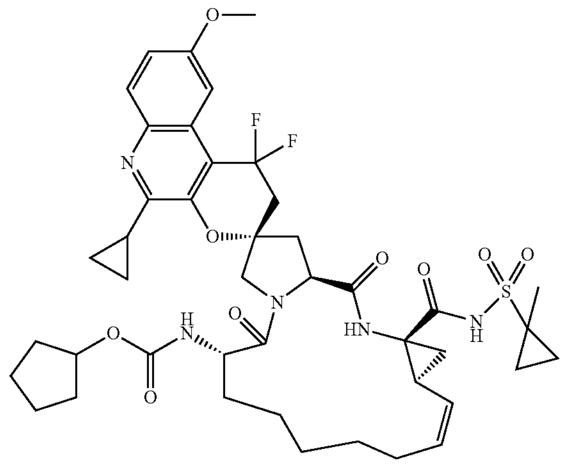
I-248
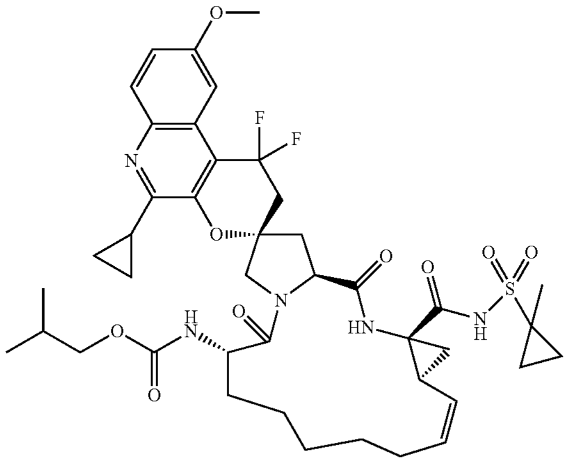
I-249
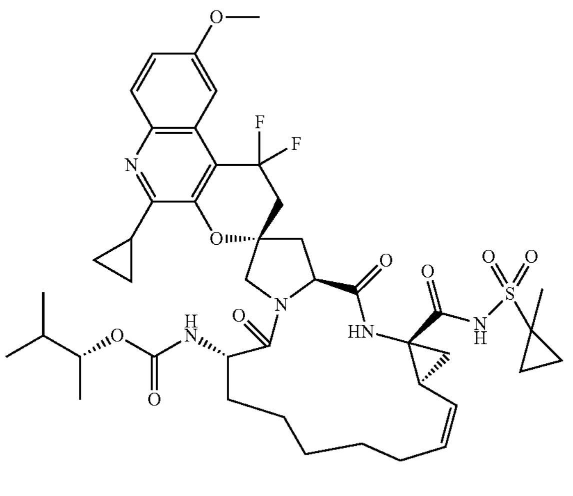

-continued
I-250
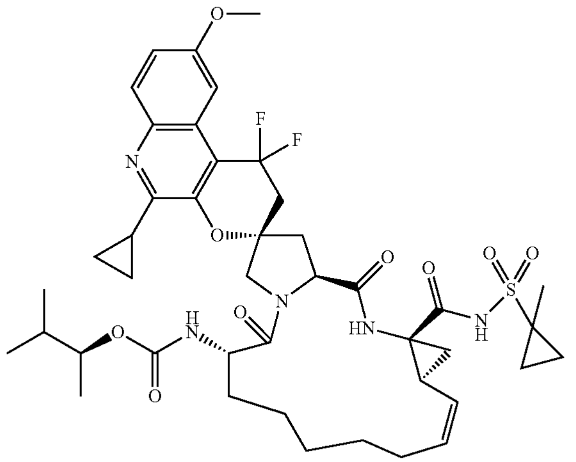
I-251
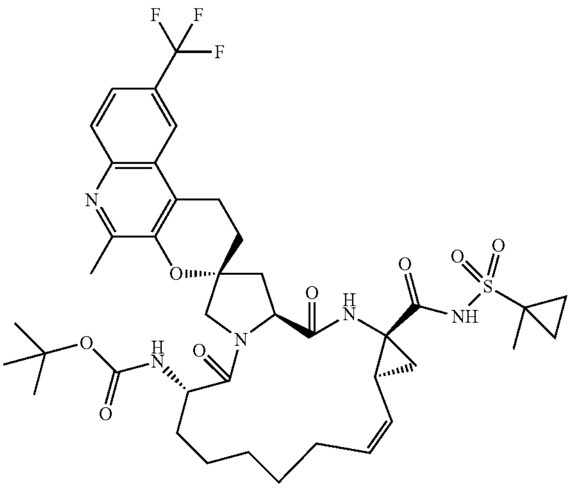
I-252
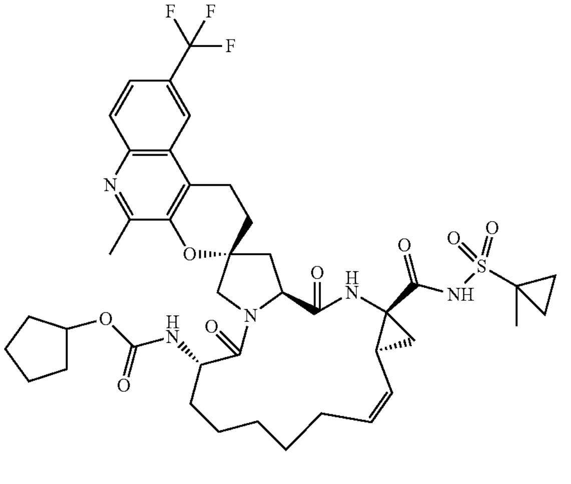
-continued
I-253
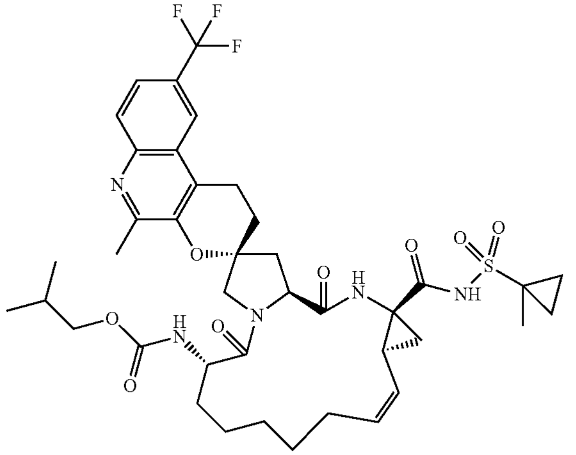
I-254
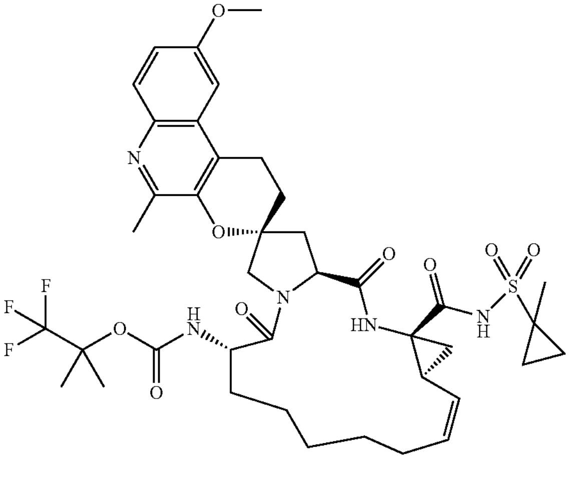
I-255
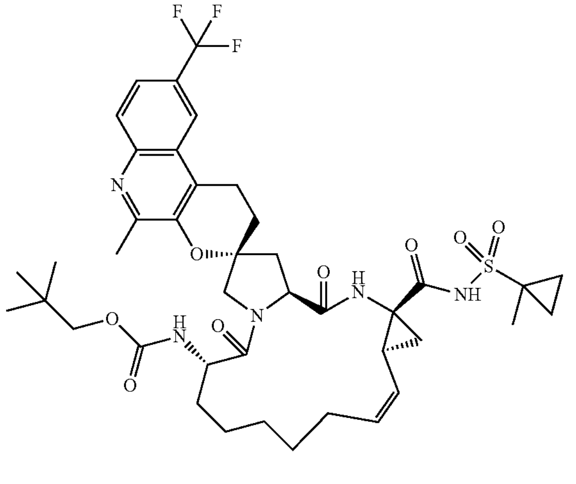

-continued
I-256
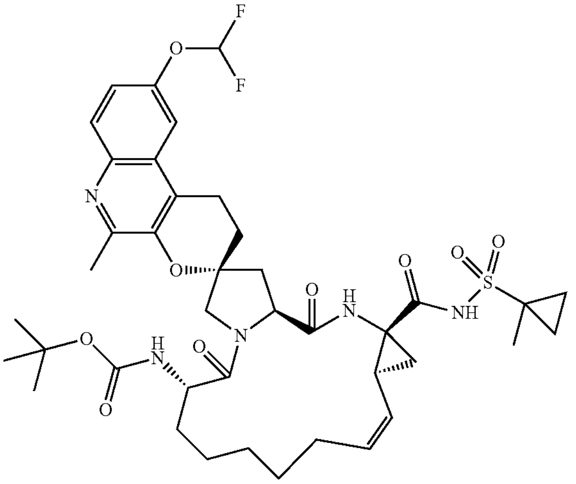
I-257
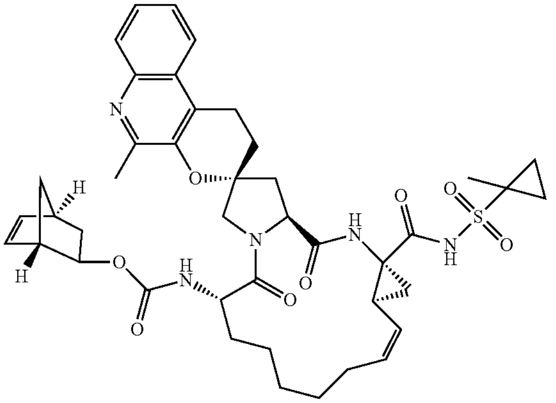
I-258
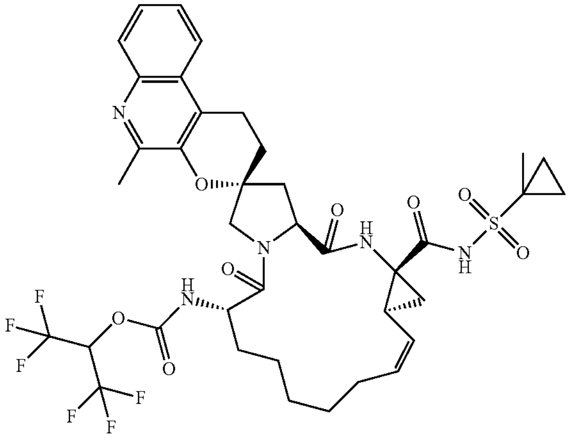
-continued
I-259
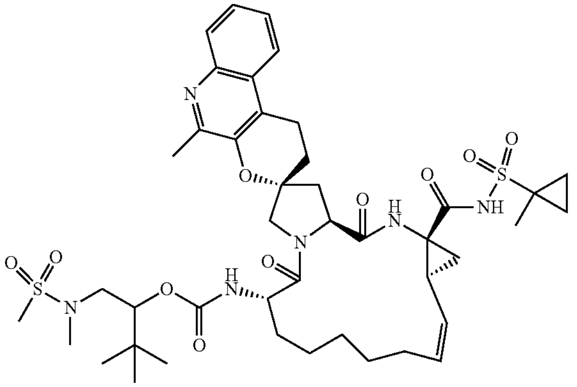
I-260
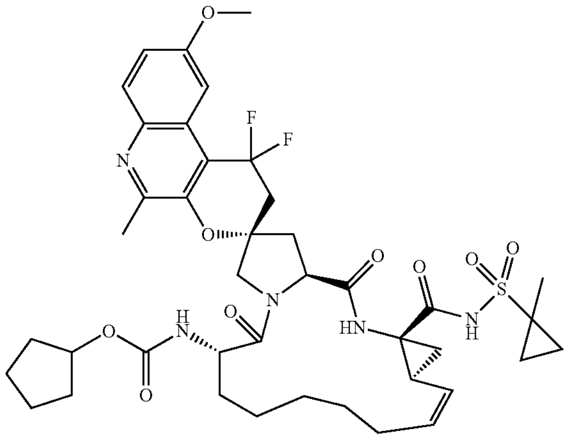
I-262
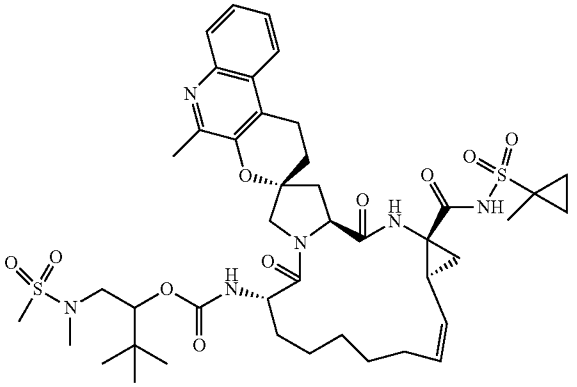

-continued
I-263
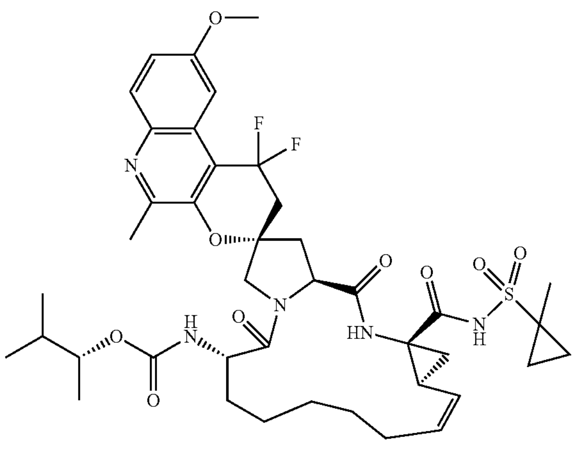
I-264
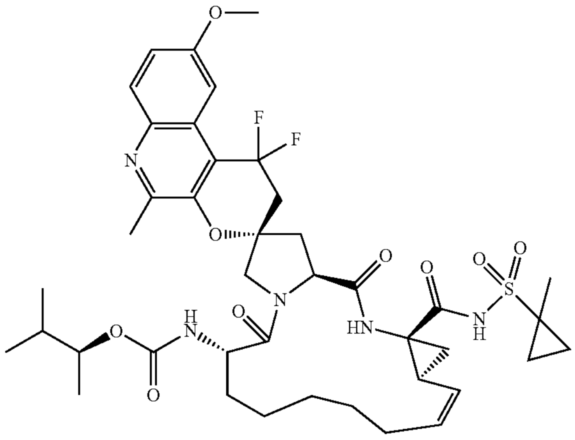
I-265
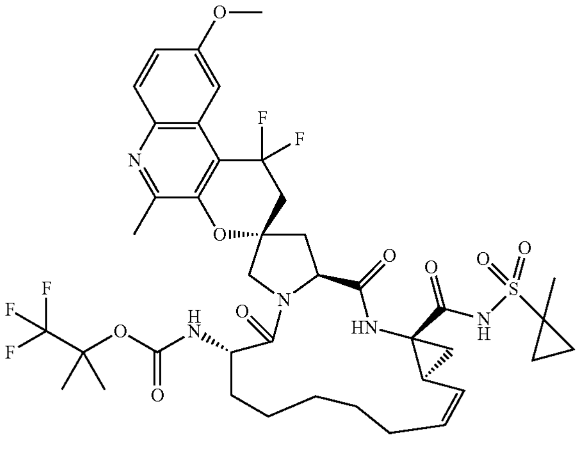
-continued
I-266
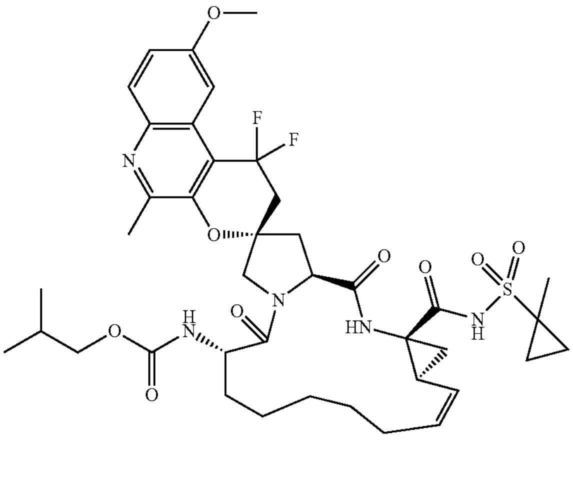
I-267
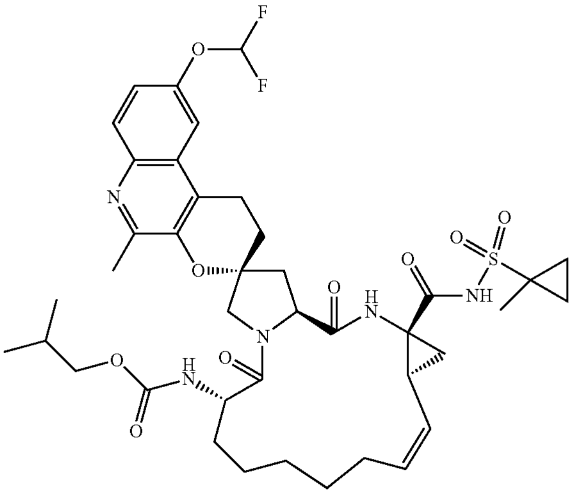
I-268
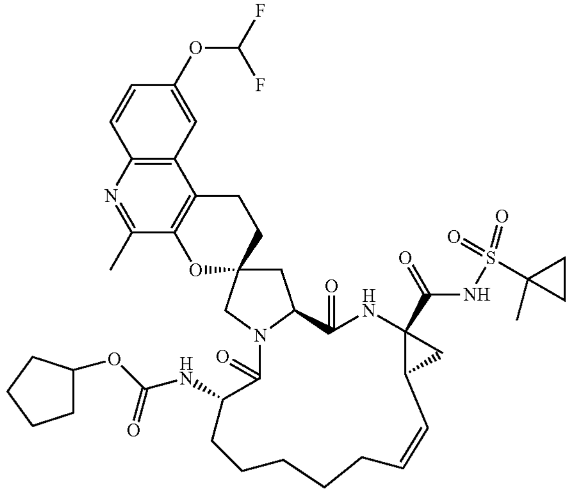

-continued
I-269
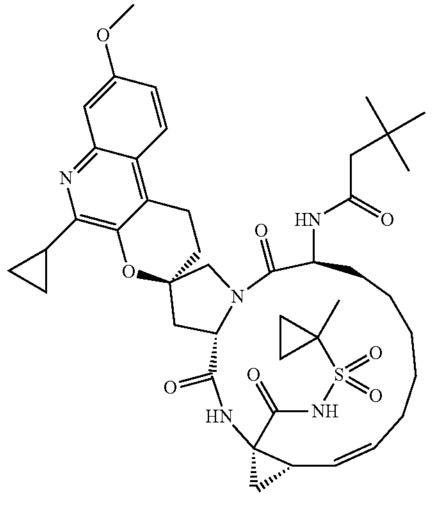
I-270
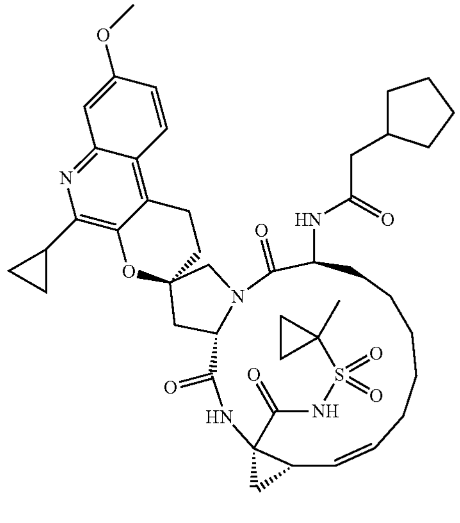
I-271
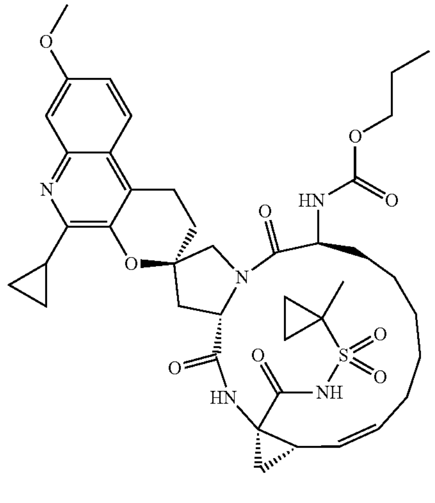
-continued
I-272
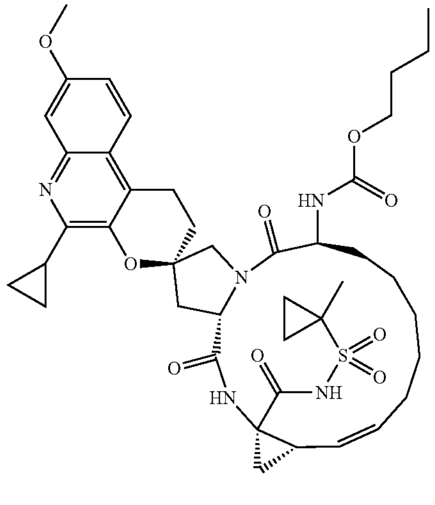
I-273
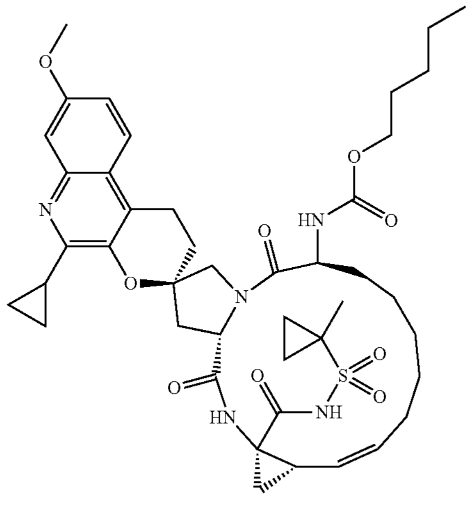
I-274
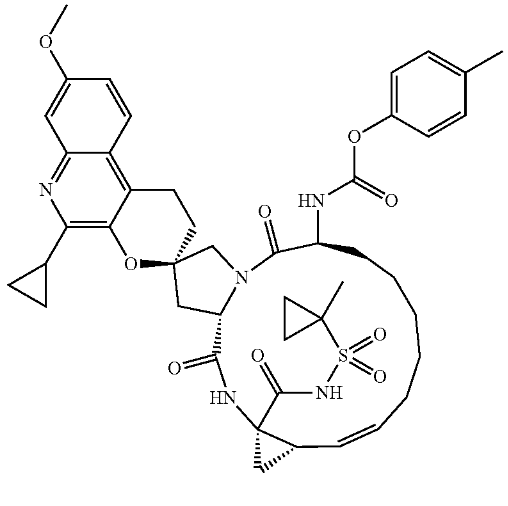

-continued
I-275
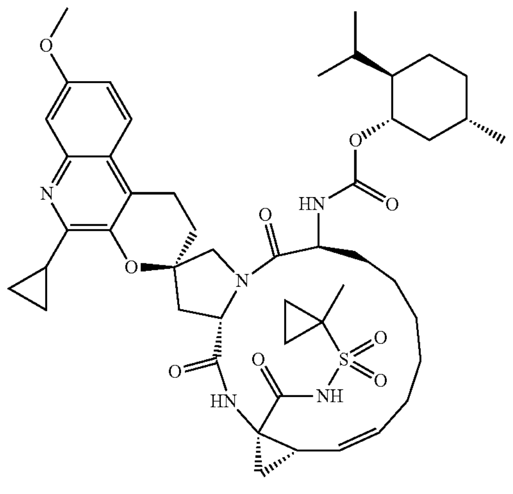
I-276
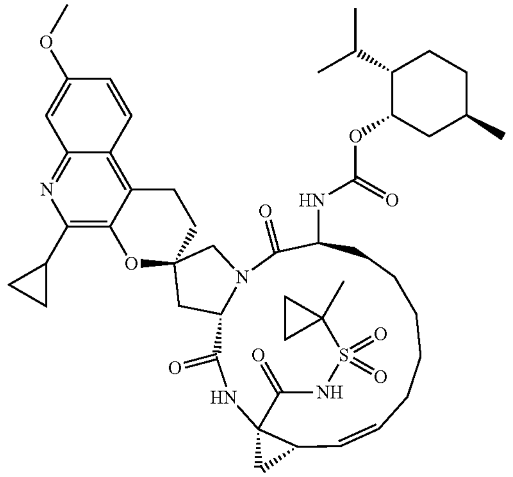
I-277
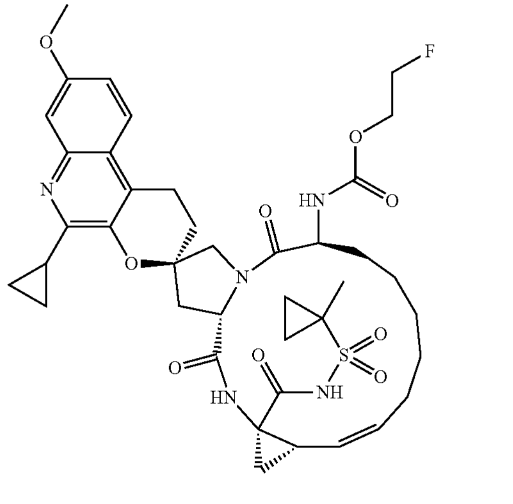
-continued
I-278
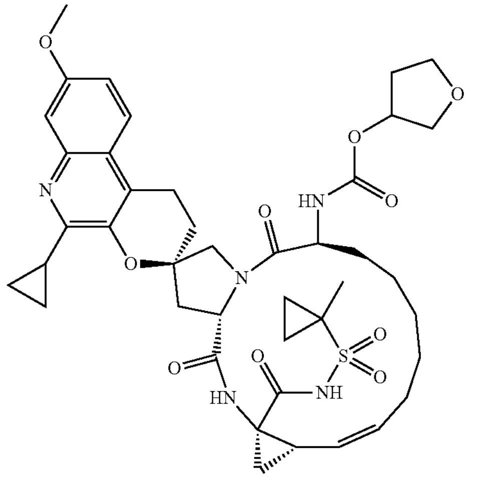
I-279
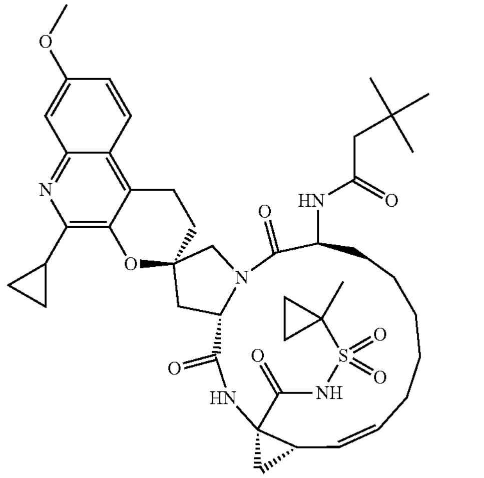
I-280
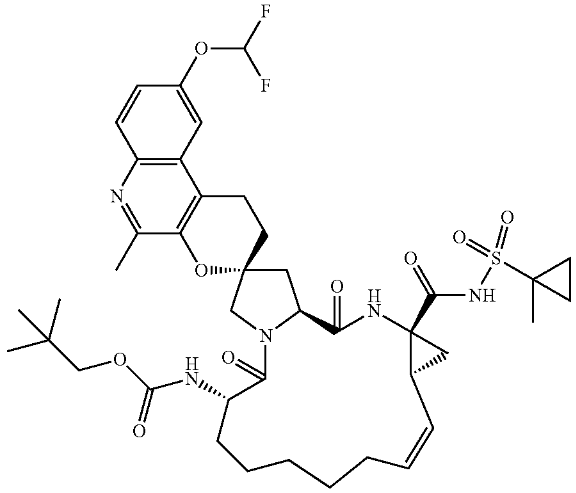

-continued
I-281
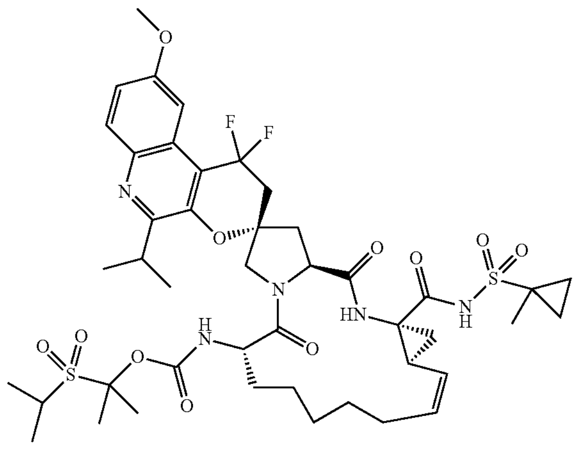
I-282
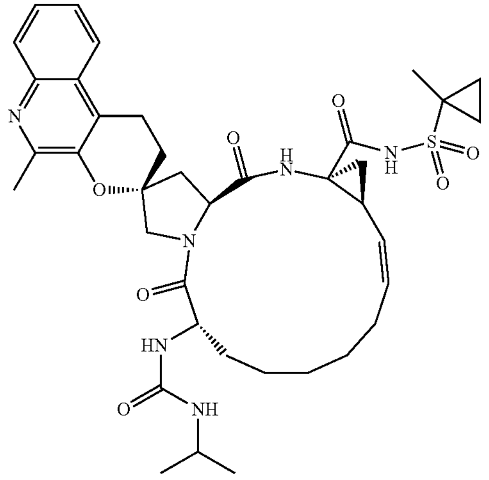
I-283
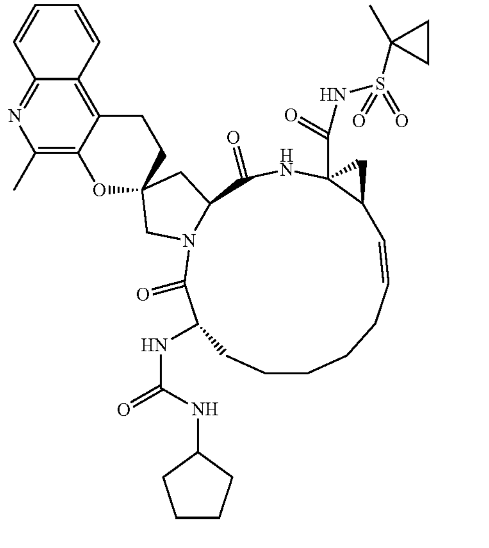
-continued
I-284
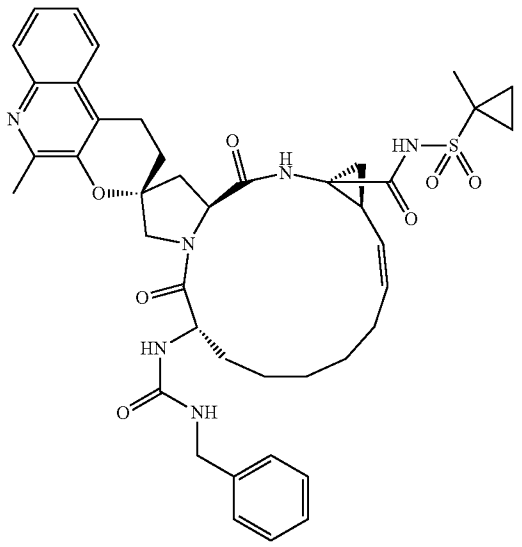
I-285
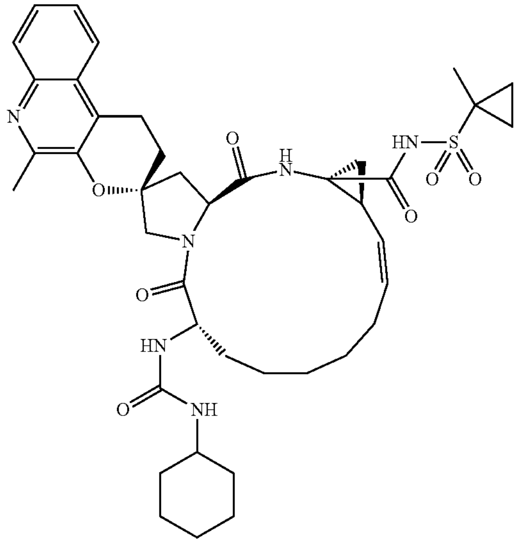
I-286
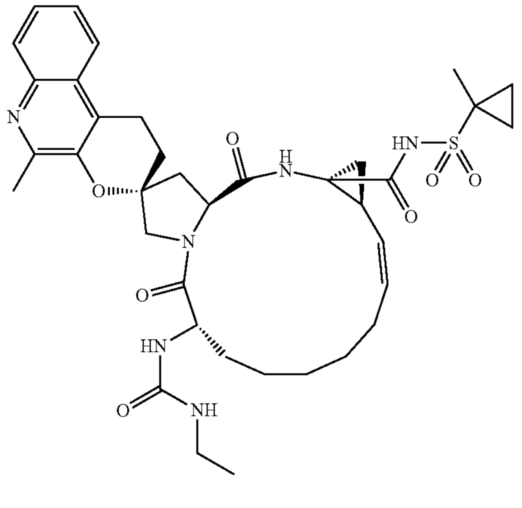

I-287
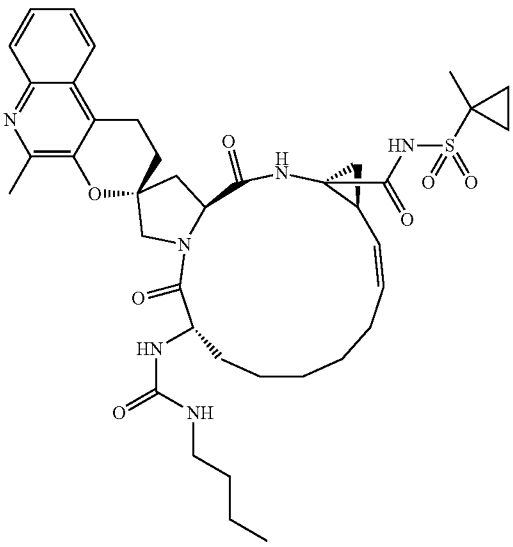
I-288
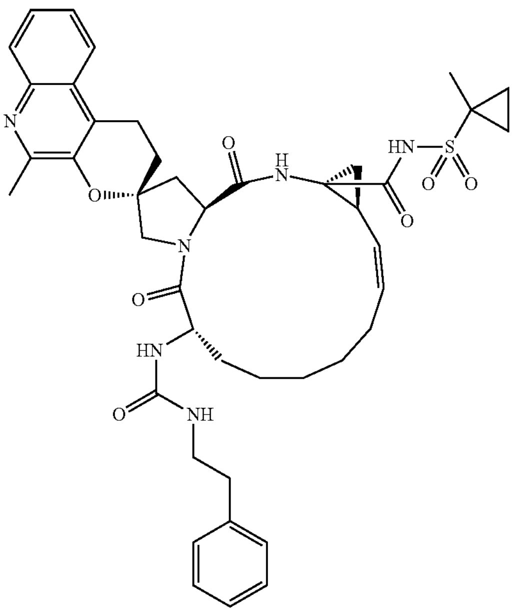
I-289
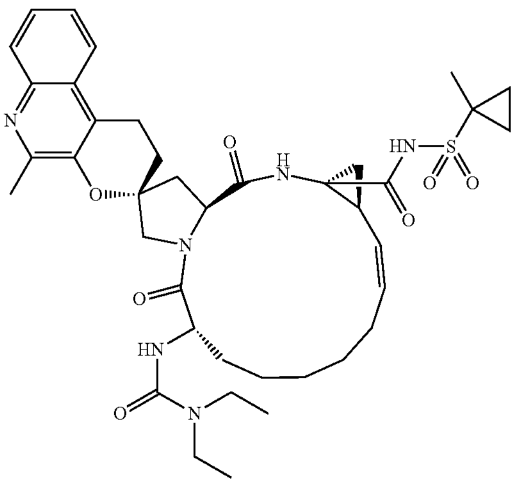
I-290
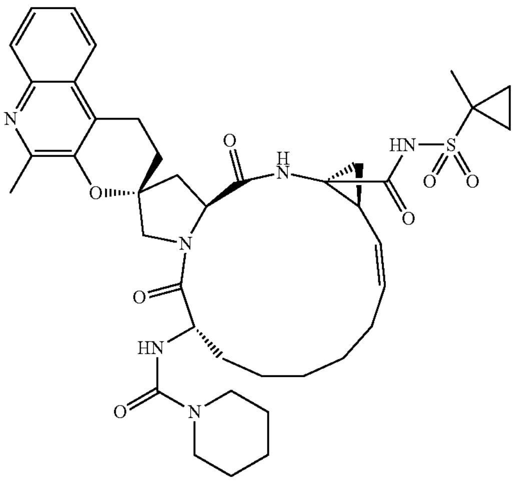
I-291
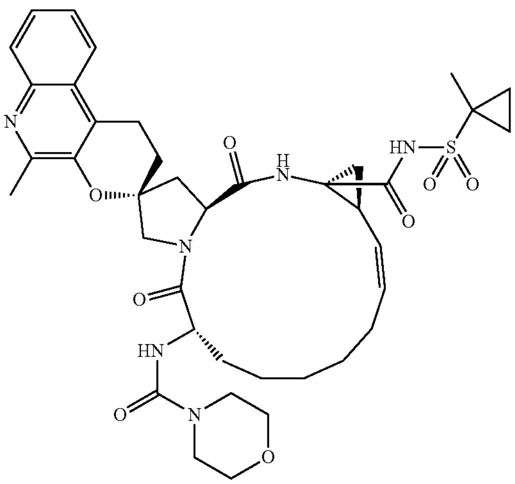

-continued
I-292
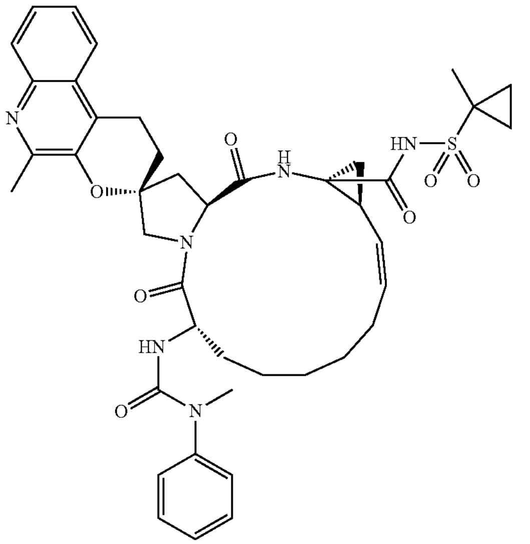
I-293
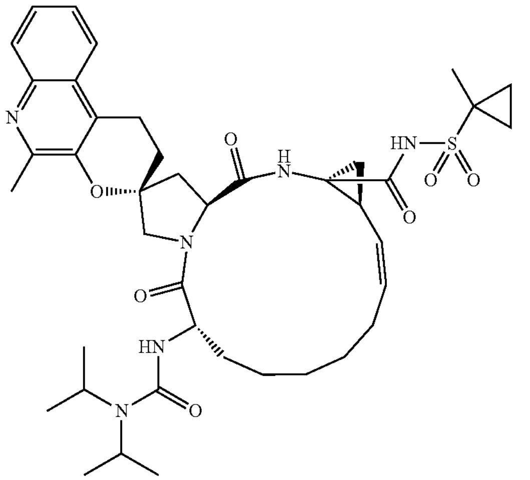
I-294
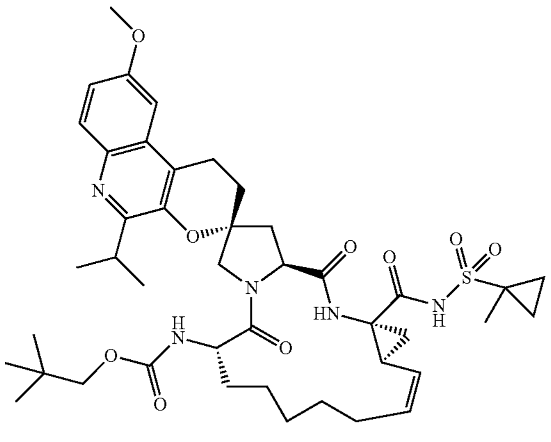
-continued
I-295
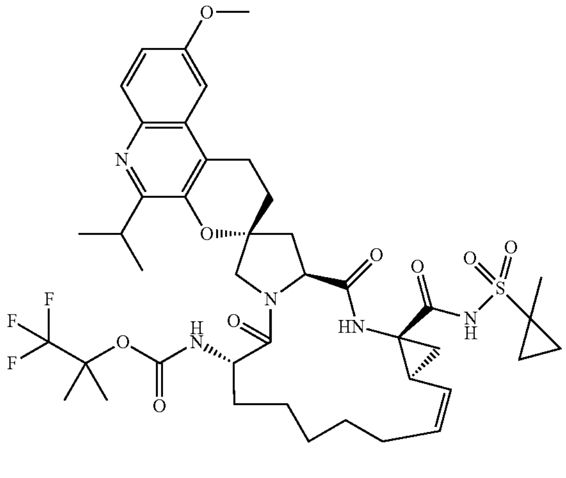
I-296
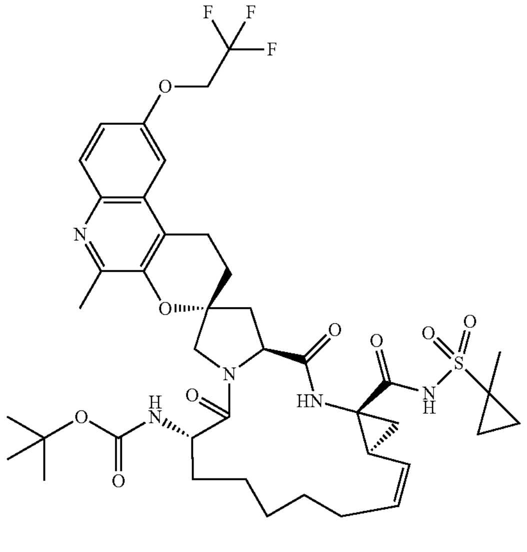
I-297
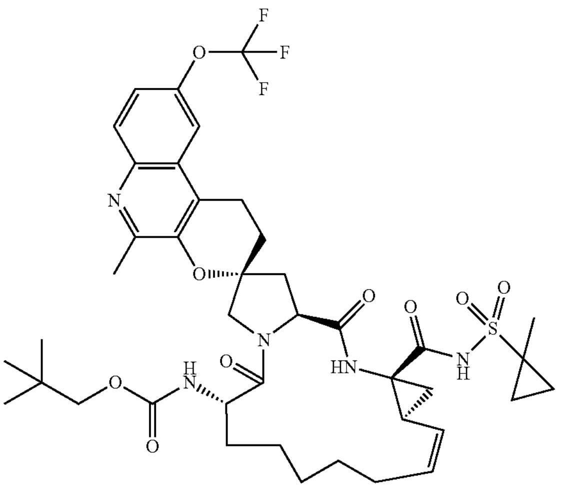

-continued
I-298
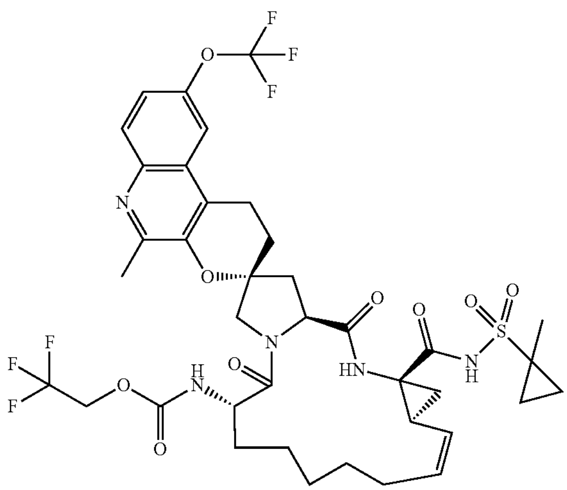
I-299
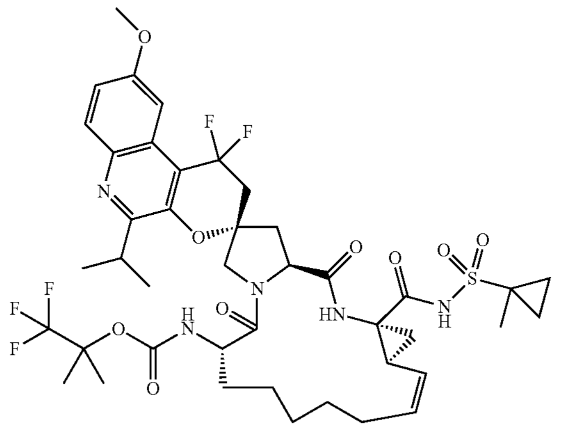
I-300
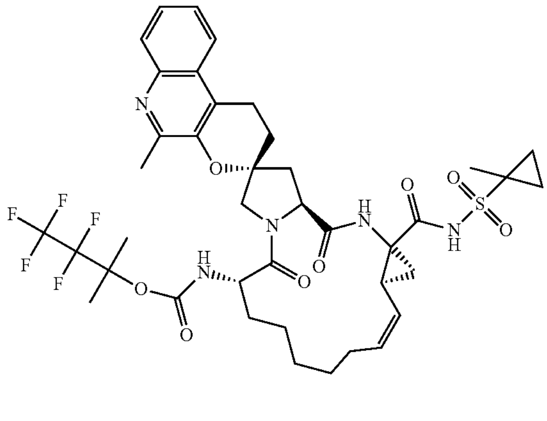
-continued
I-301
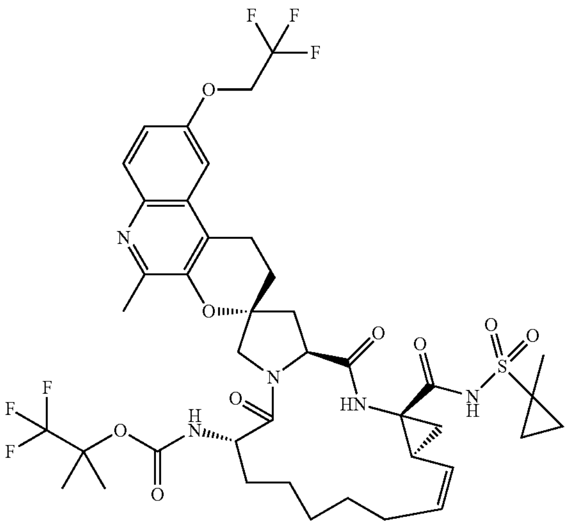
I-302
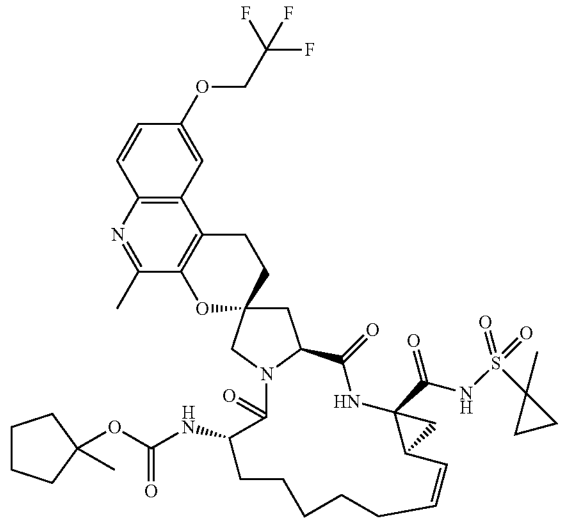
I-303
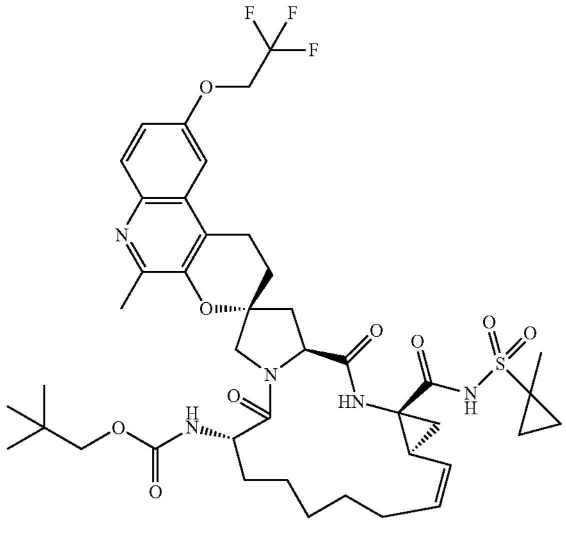

-continued
I-304
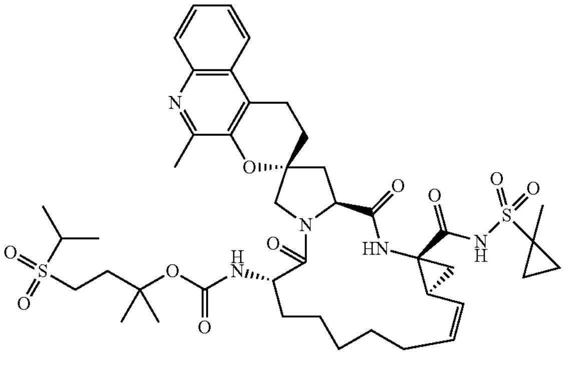
I-305
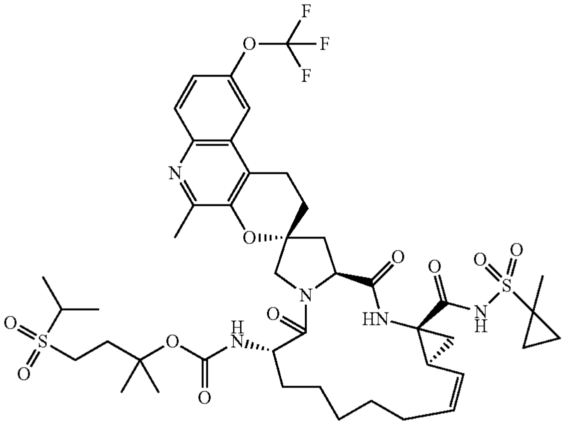
I-306
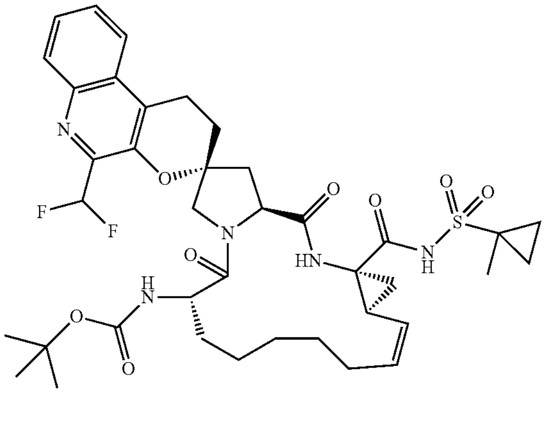
-continued
I-307
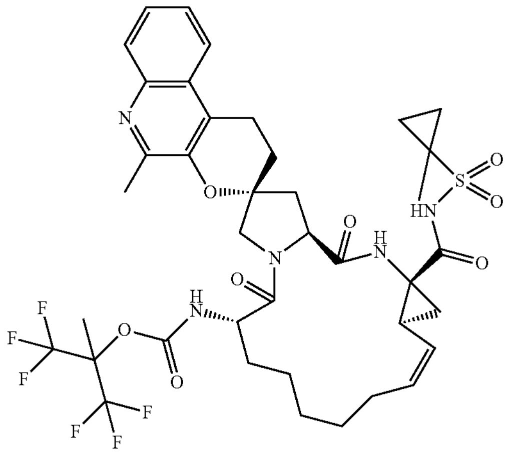
I-308
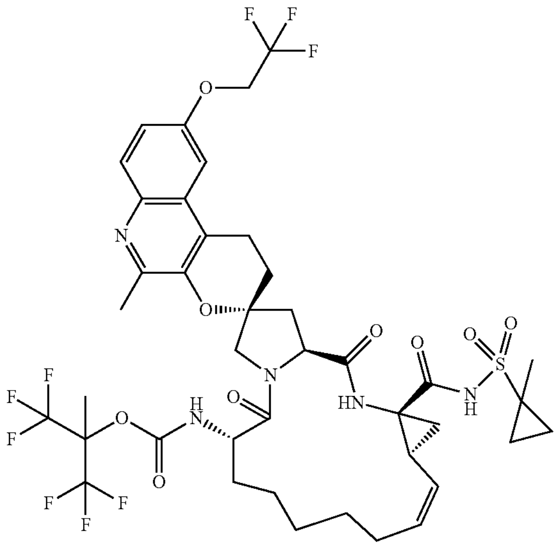
I-309
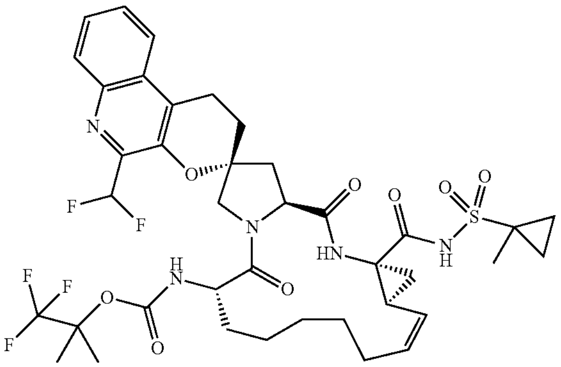

-continued
I-310
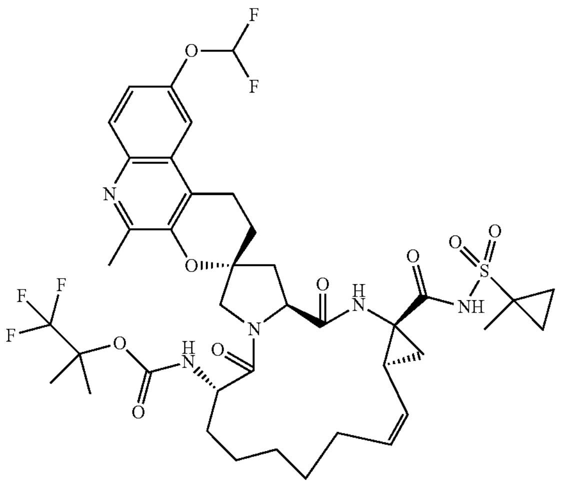
I-311
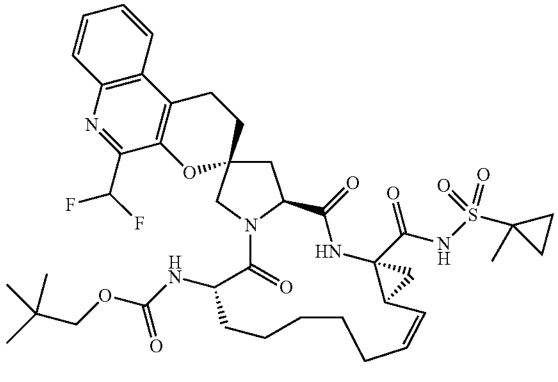
I-312
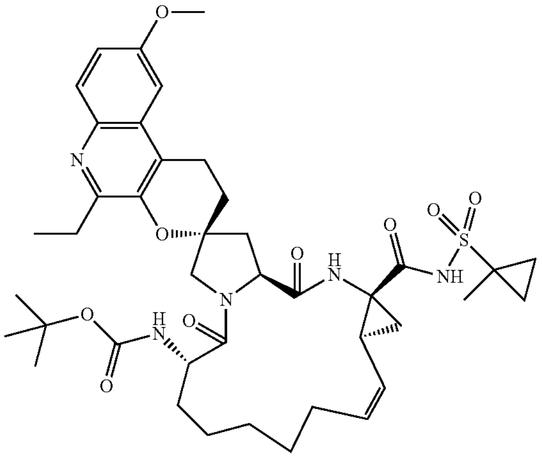
-continued
I-313
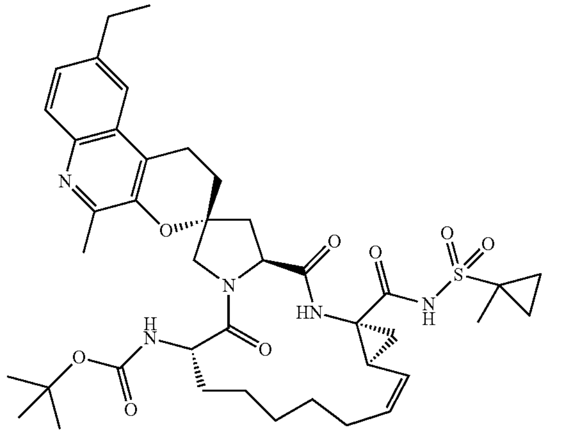
I-314
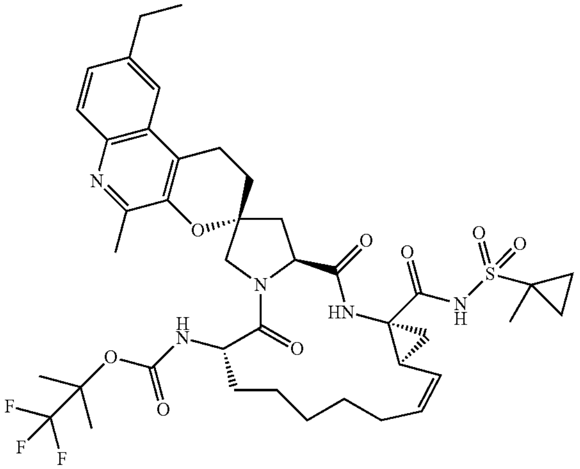
I-315
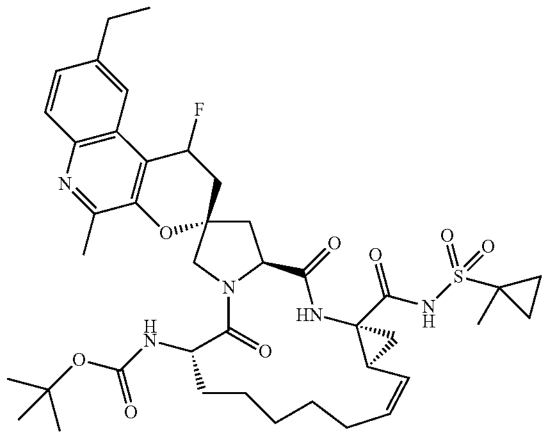

-continued
I-316
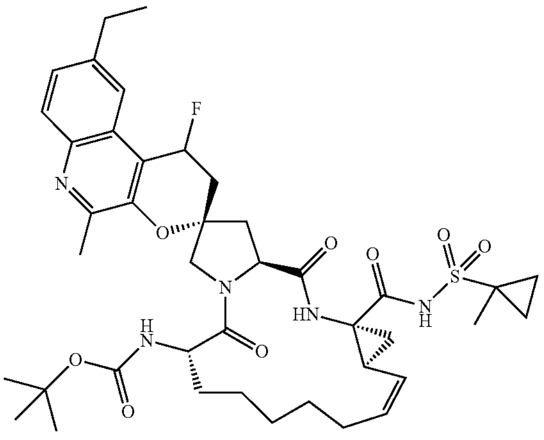
I-317
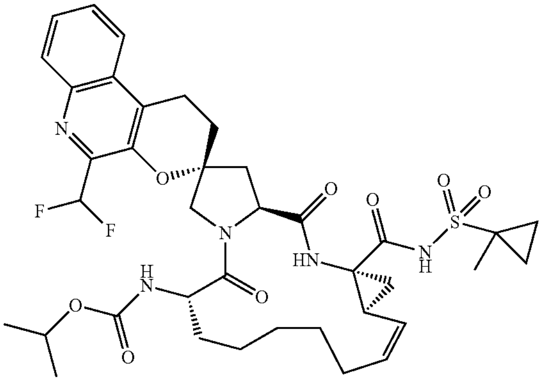
I-318
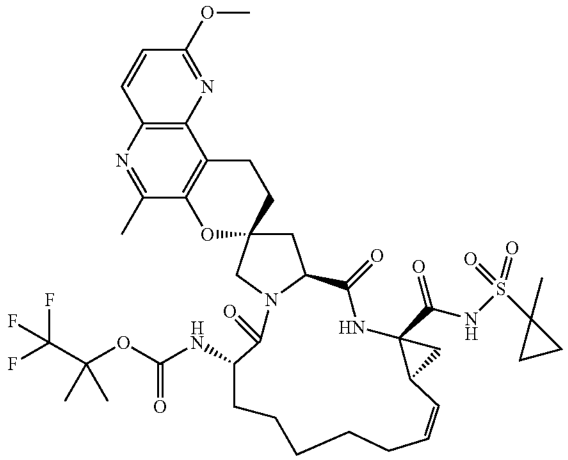
-continued
I-319
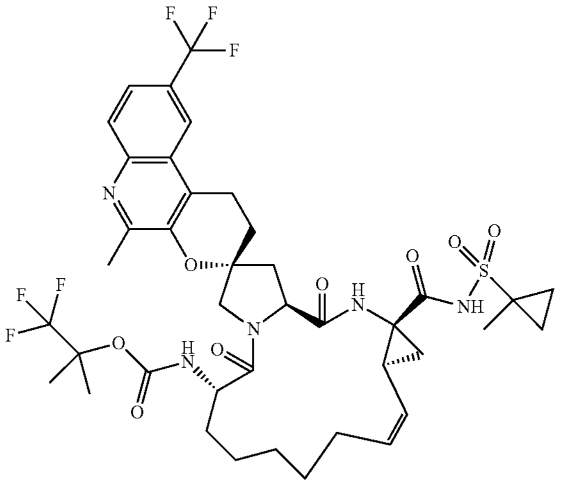
I-320
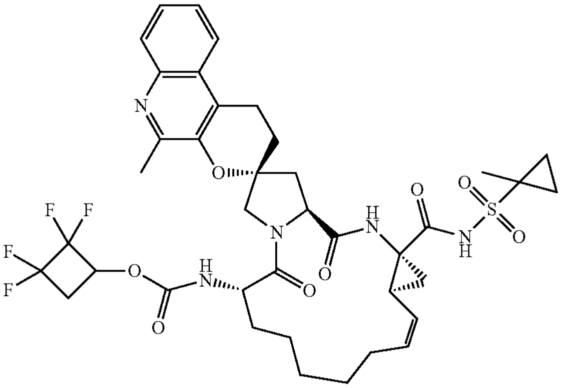
I-321
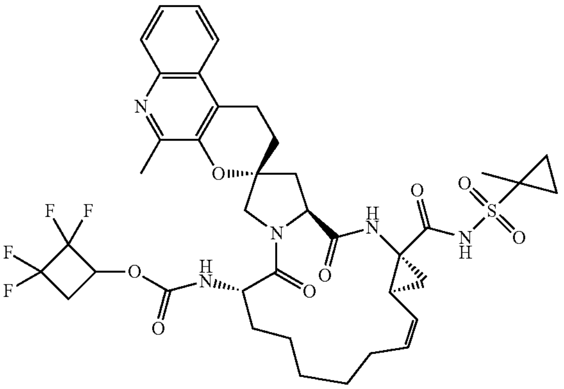

-continued
I-322
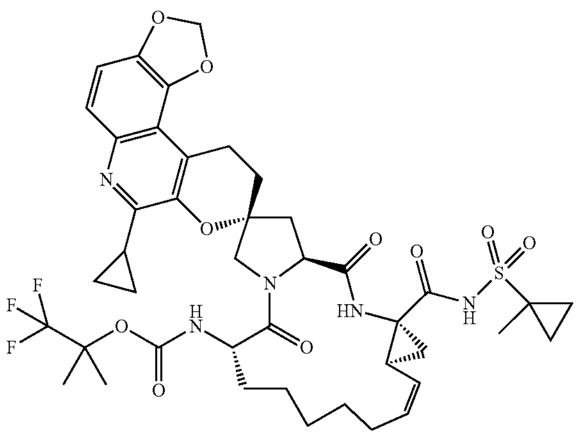
I-323
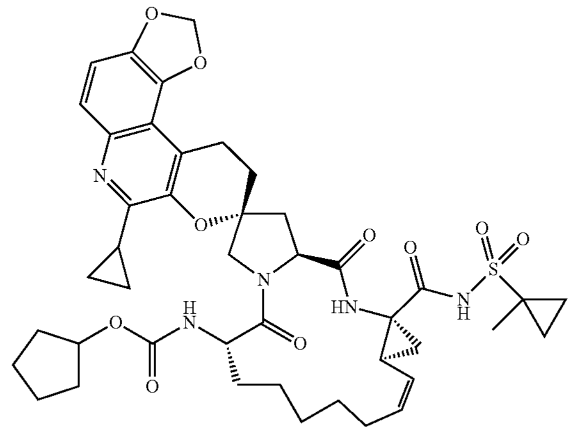
I-324
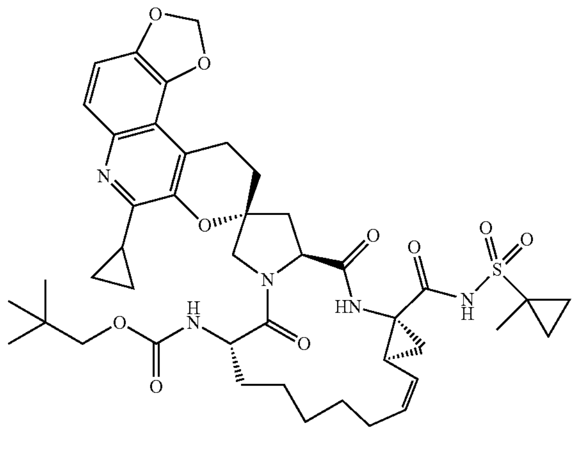
-continued
I-325
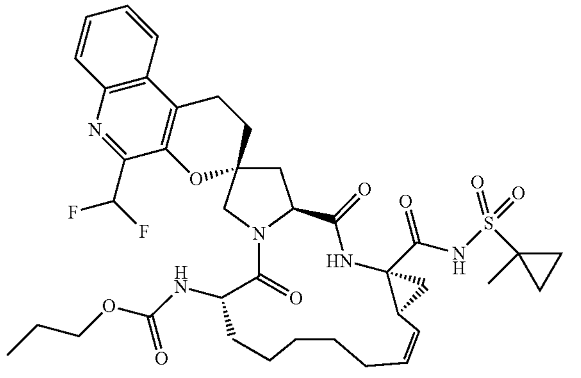
I-326
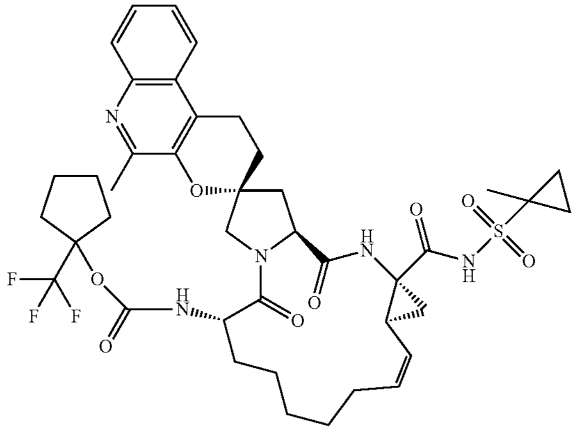
I-327
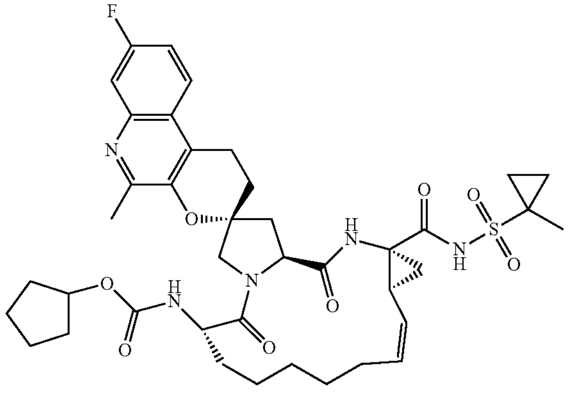

-continued
I-328
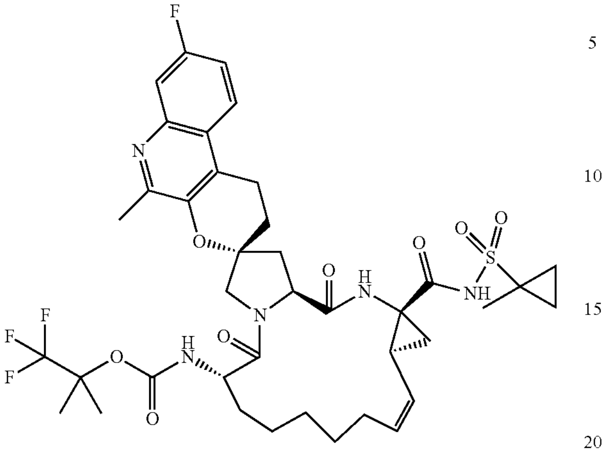
I-329
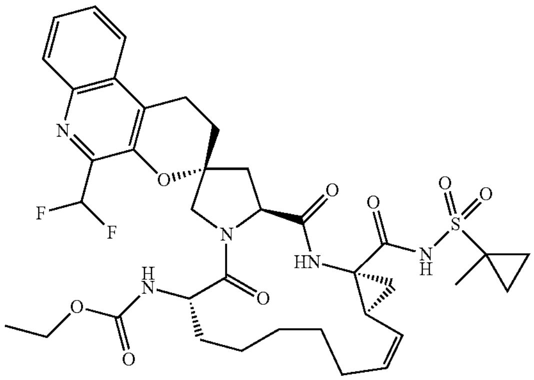
I-330
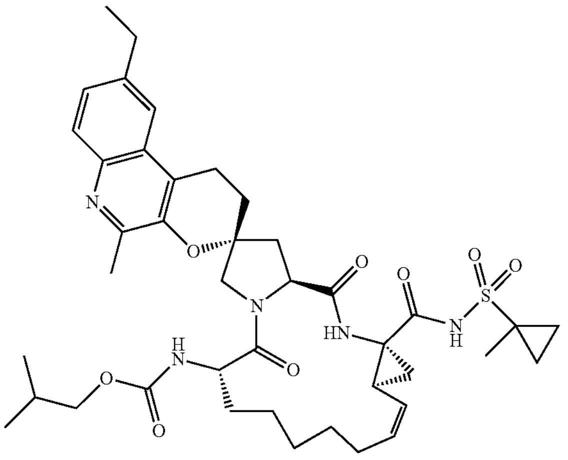
-continued
I-331
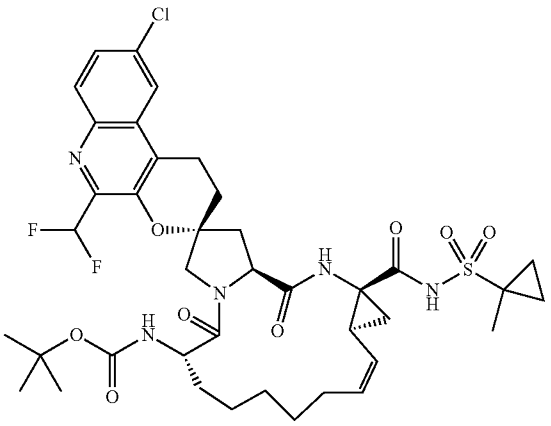
I-332
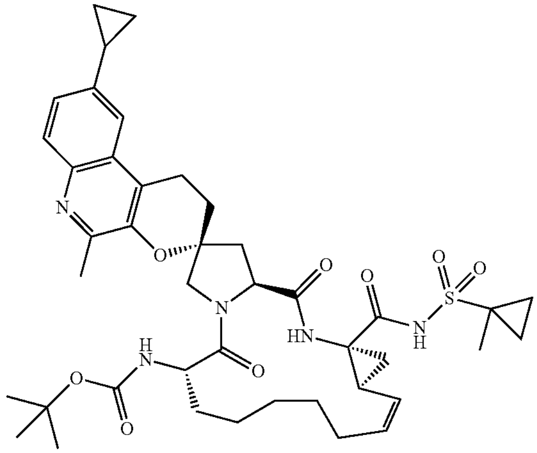
I-333
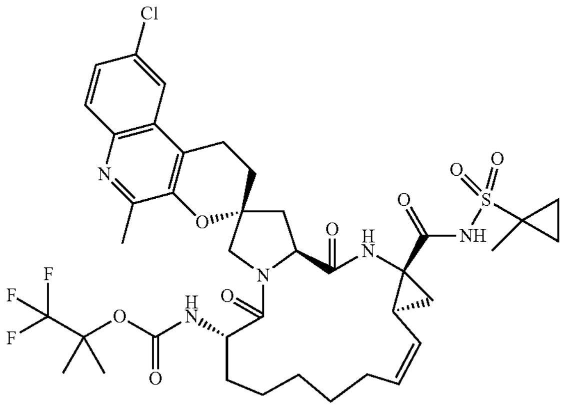

-continued
I-334
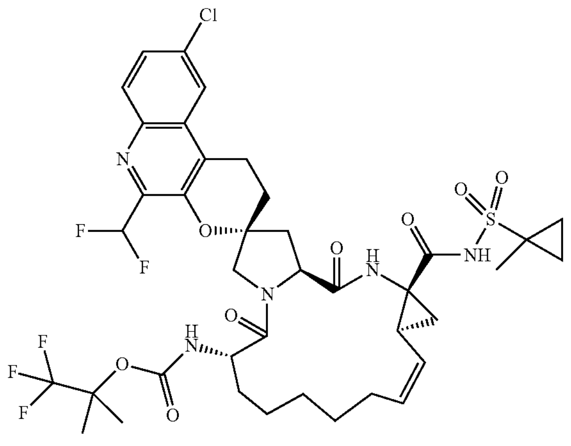
I-335
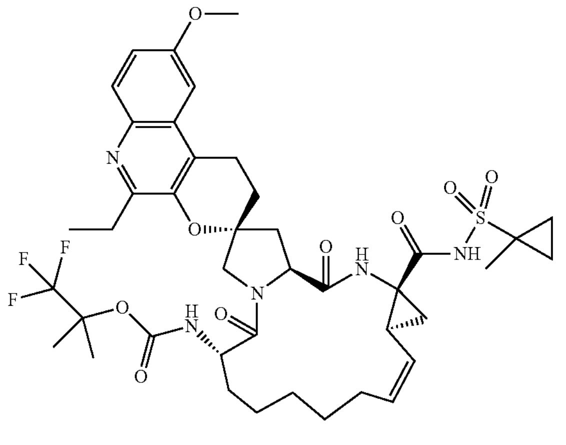
I-336
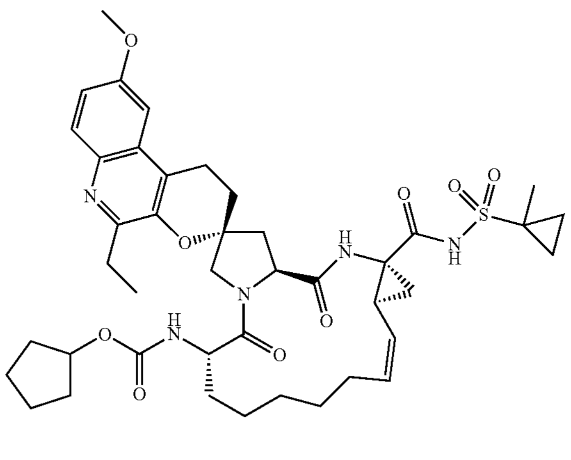
-continued
I-337
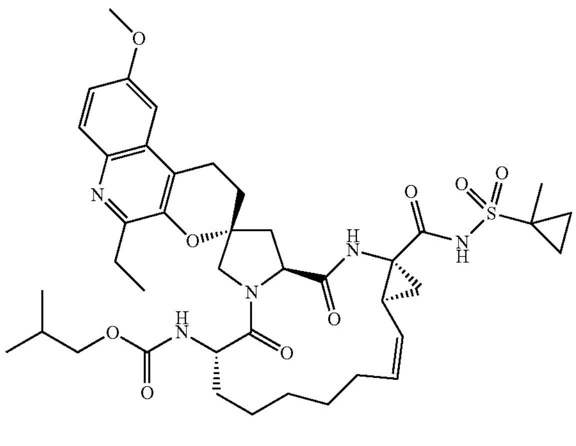
I-338
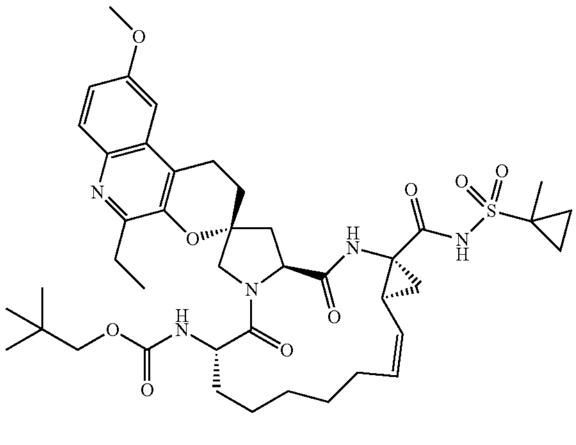
I-339
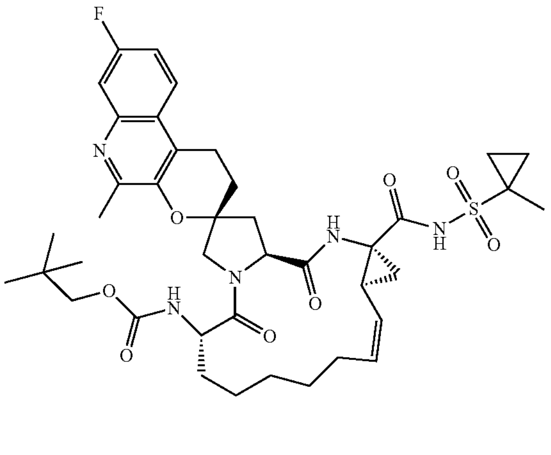

-continued
I-340
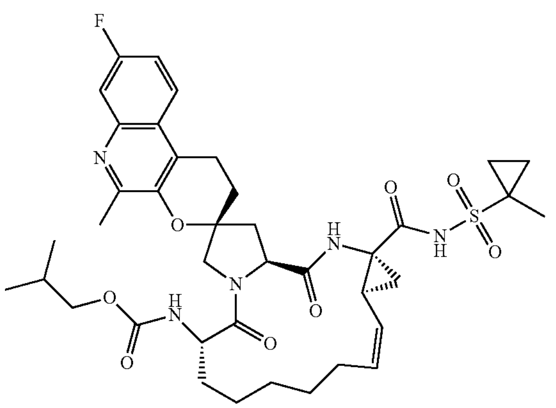
I-341
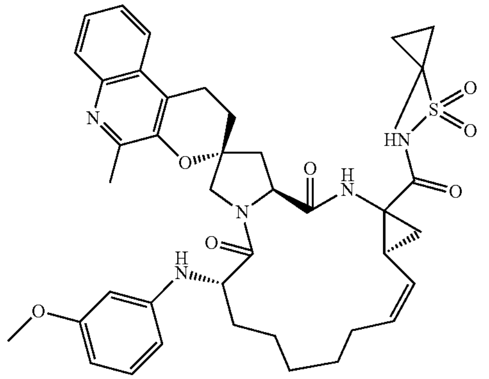
I-342
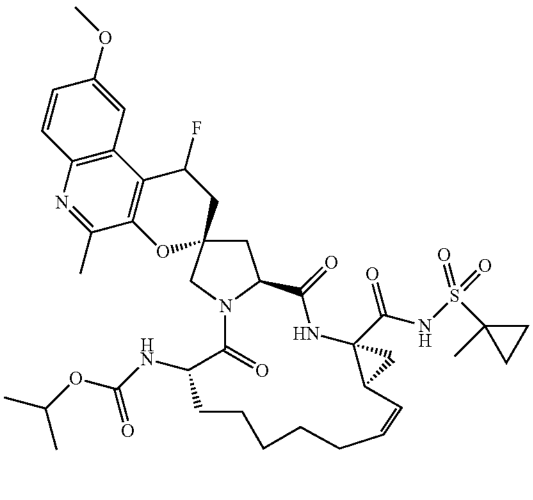
-continued
I-343
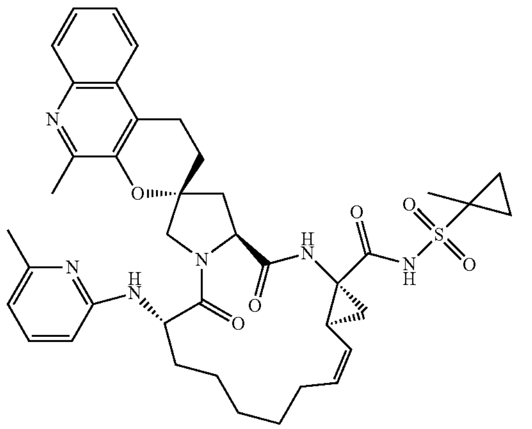
I-345
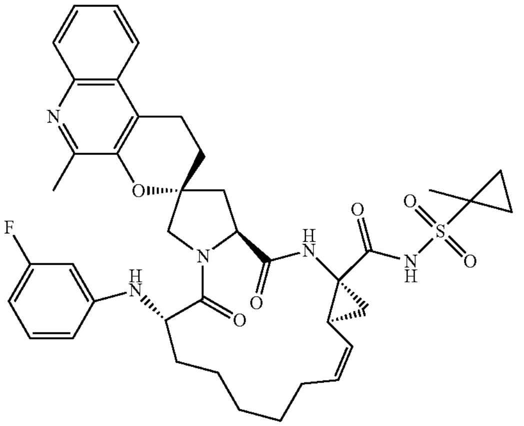
I-346
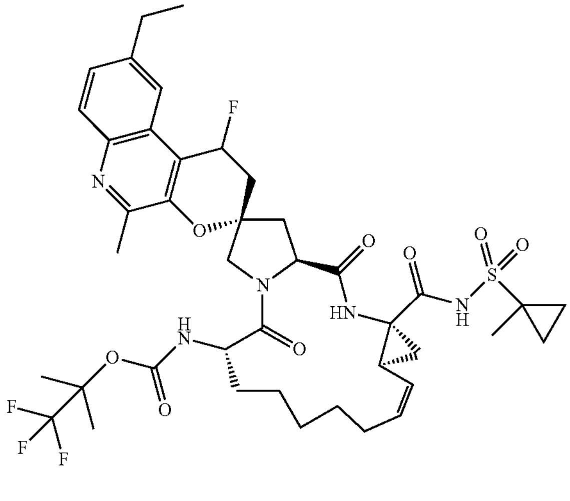

-continued
I-347
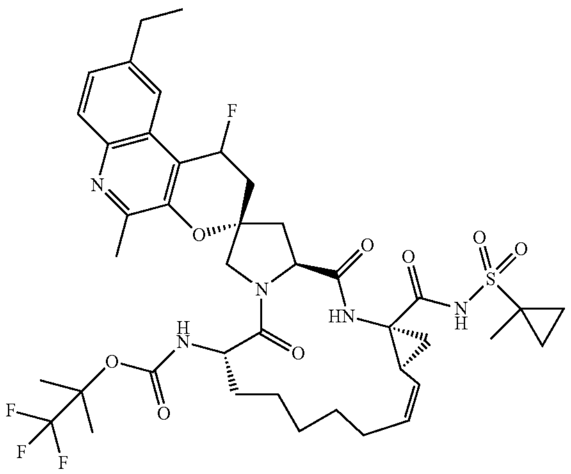
I-348
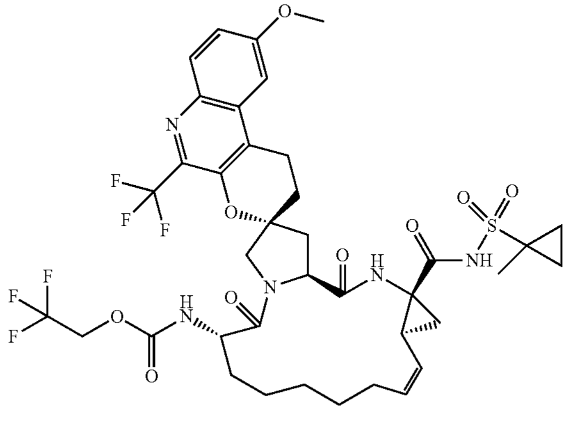
I-349
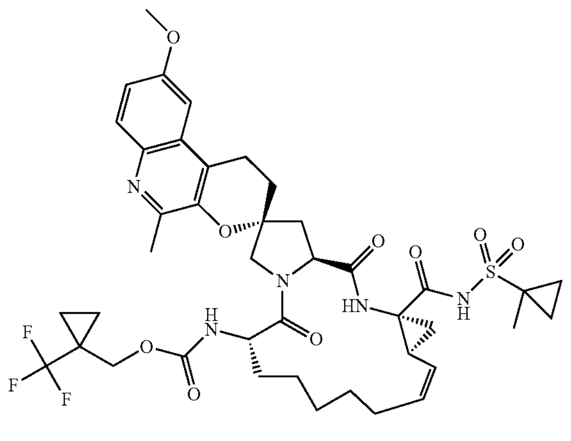
-continued
I-350
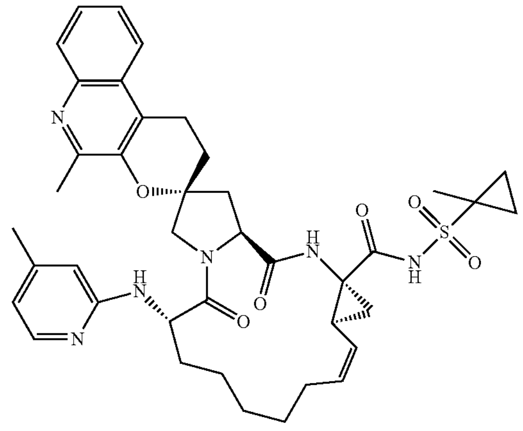
I-351
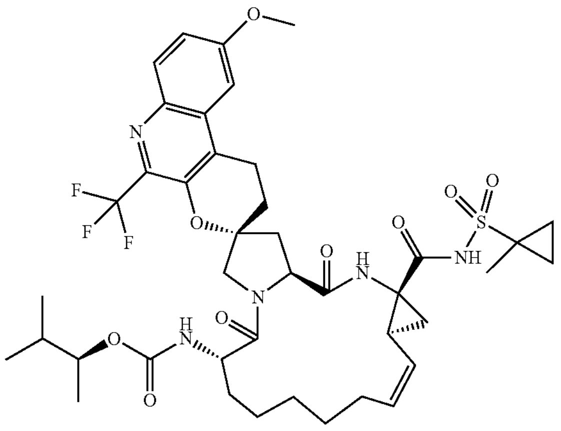
I-352
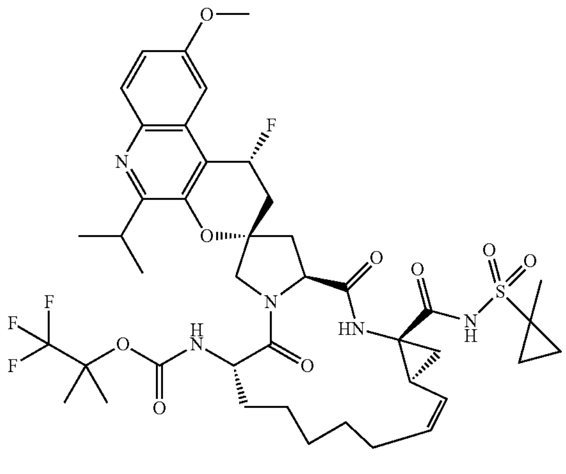

-continued
I-353
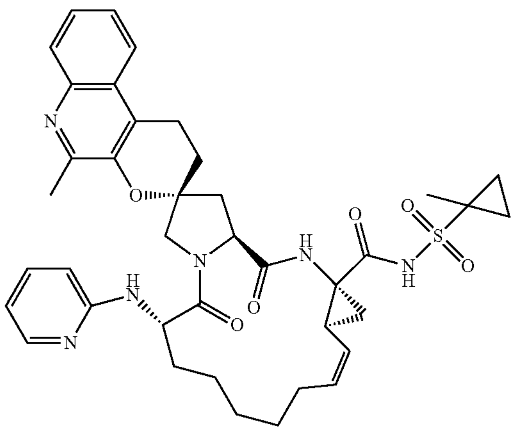
I-354
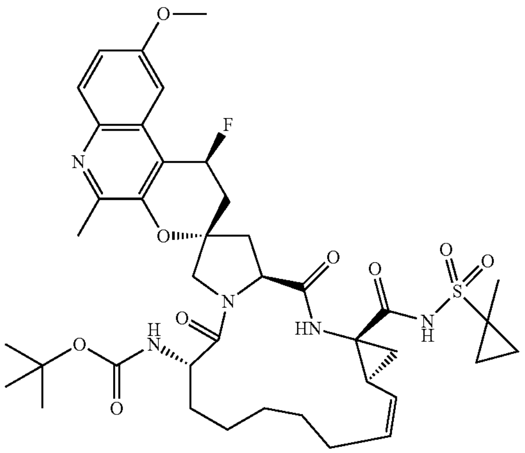
I-355
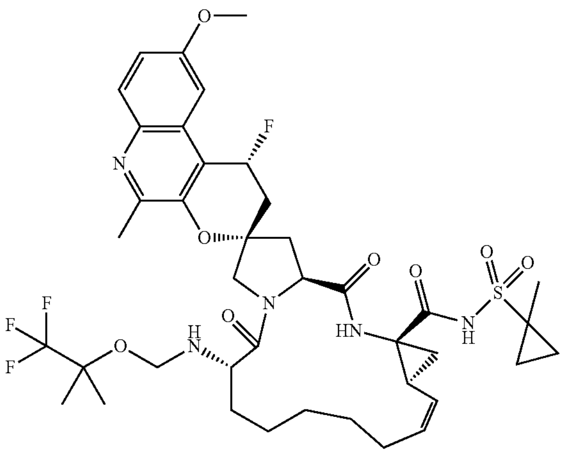
-continued
I-356
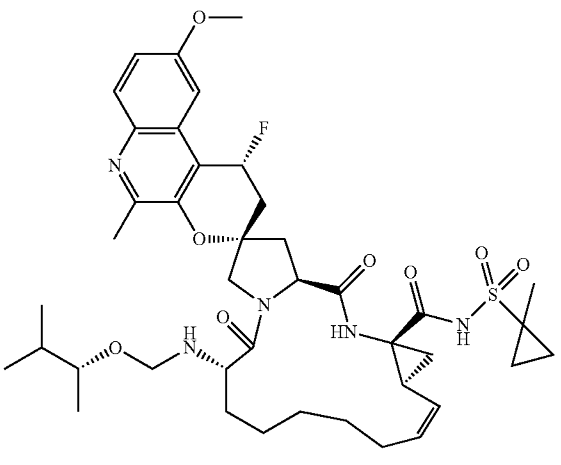
I-357
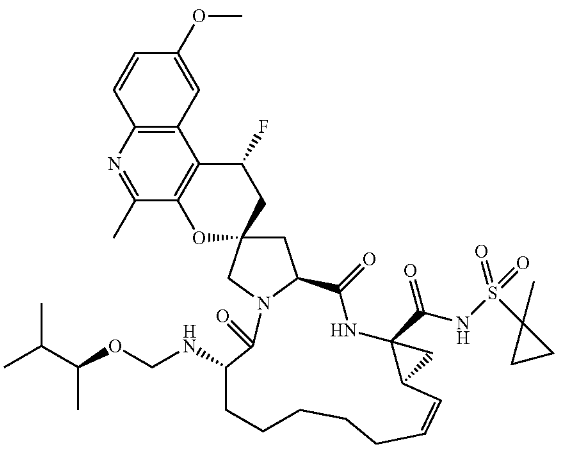
I-358
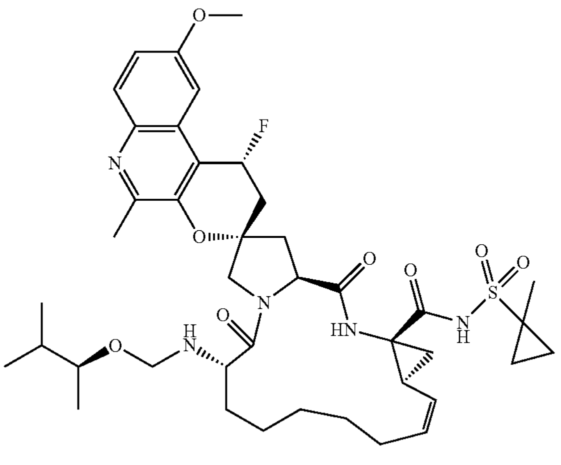

-continued
I-359
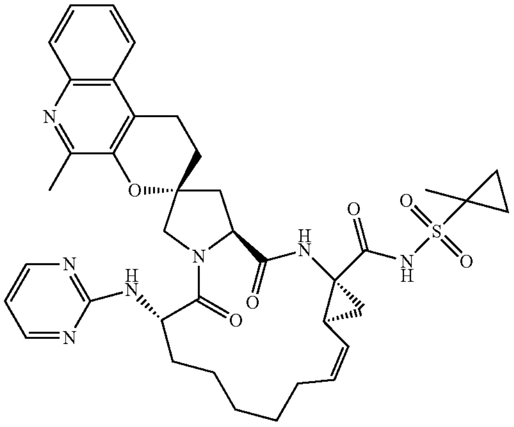
I-360
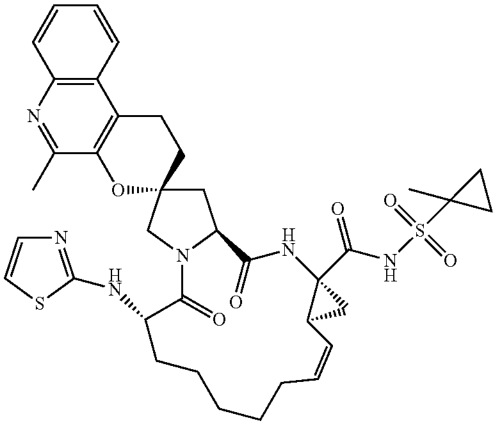
I-361
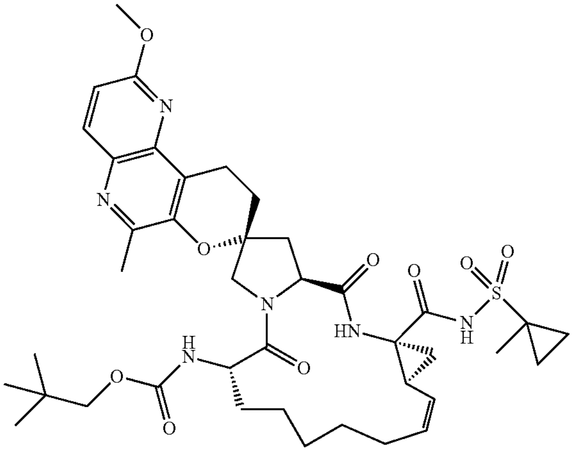
-continued
I-362
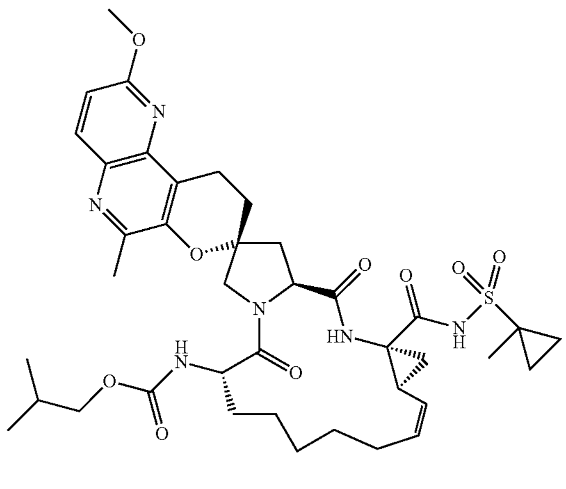
I-363
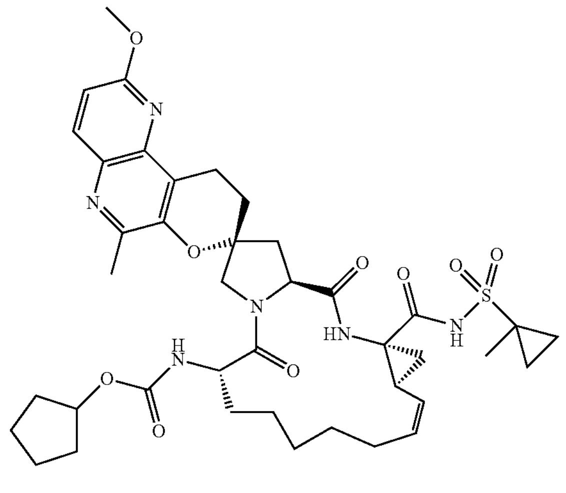
I-364
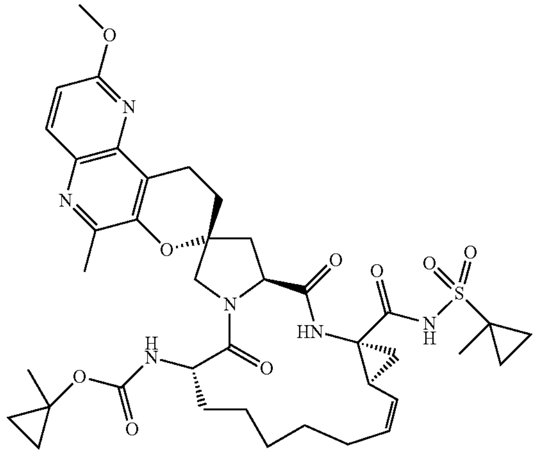

-continued
I-365
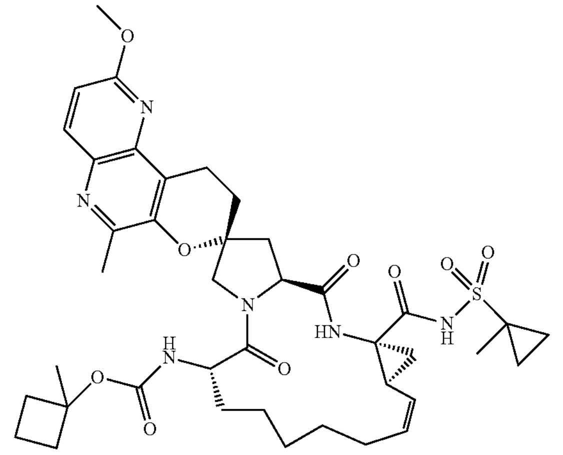
I-366
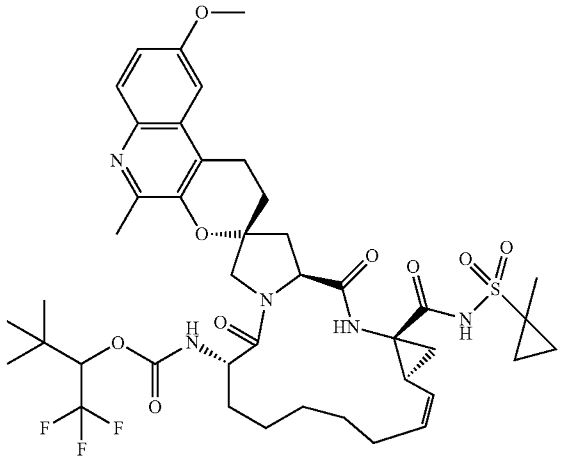
I-367
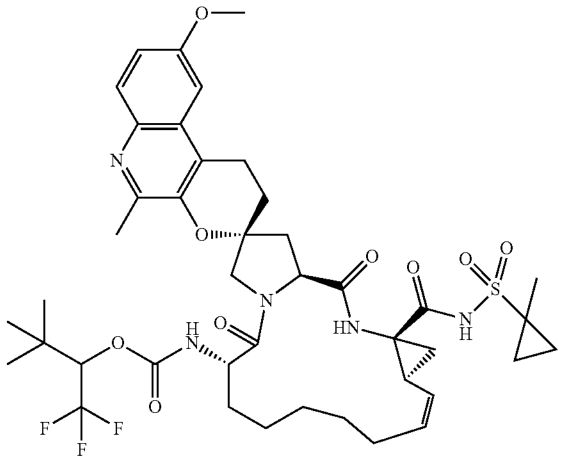
-continued
I-368
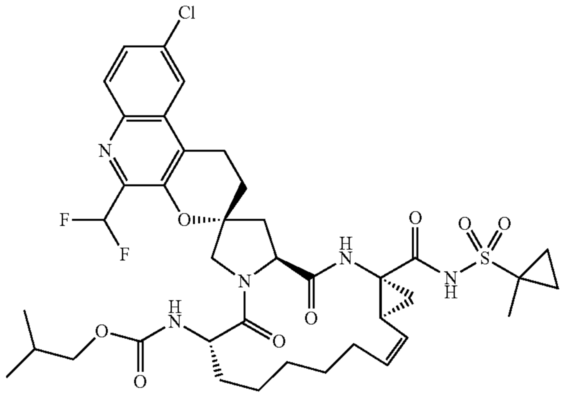
I-369
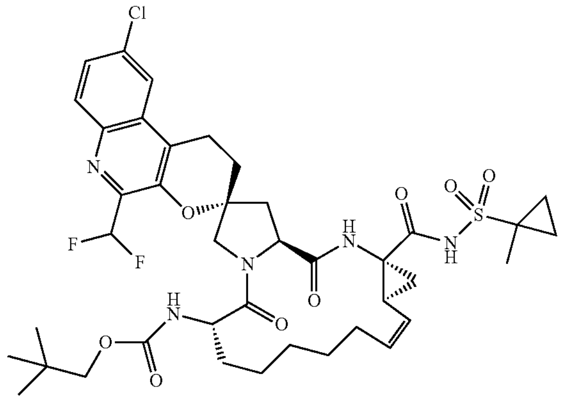
I-370
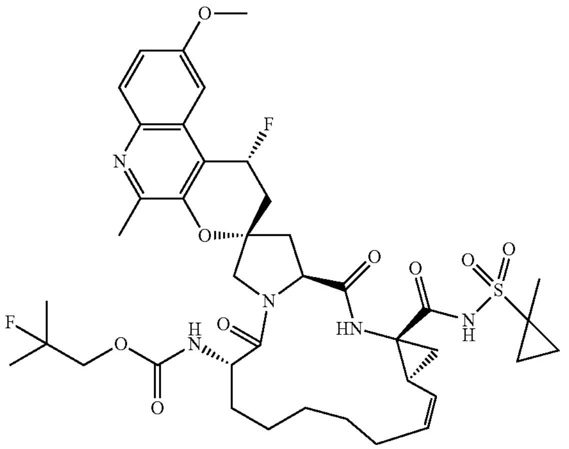

-continued
I-371
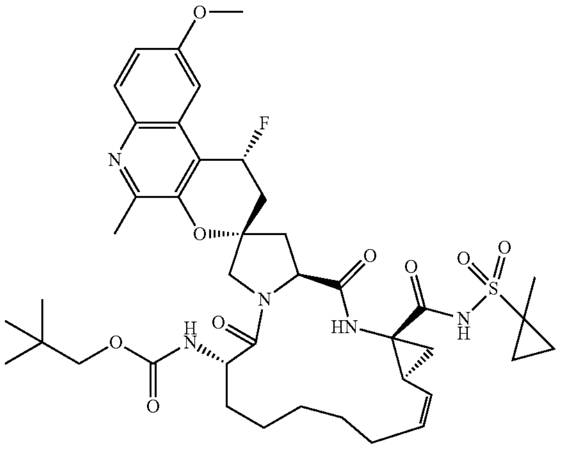
I-372
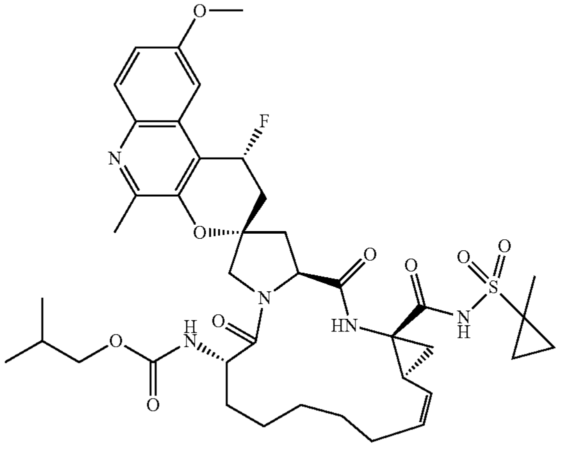
I-373
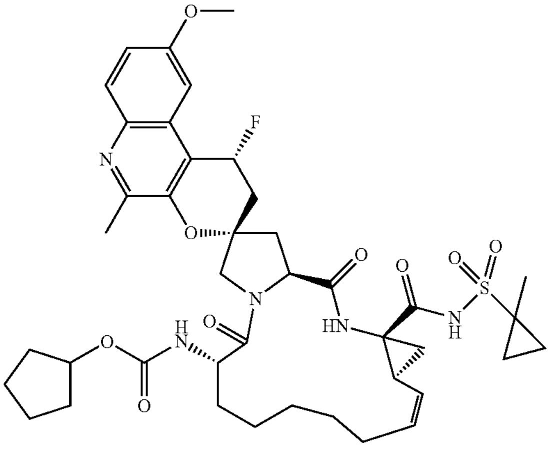
-continued
I-374
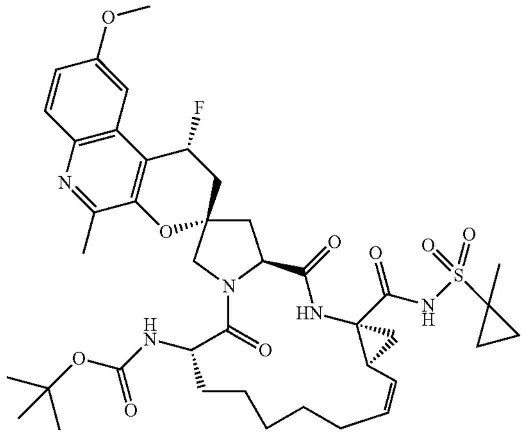
I-375
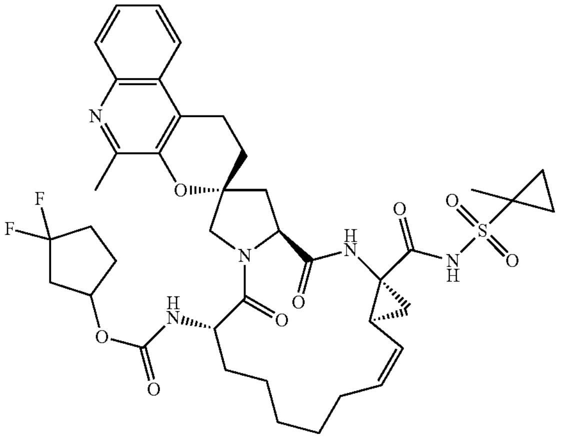
I-376
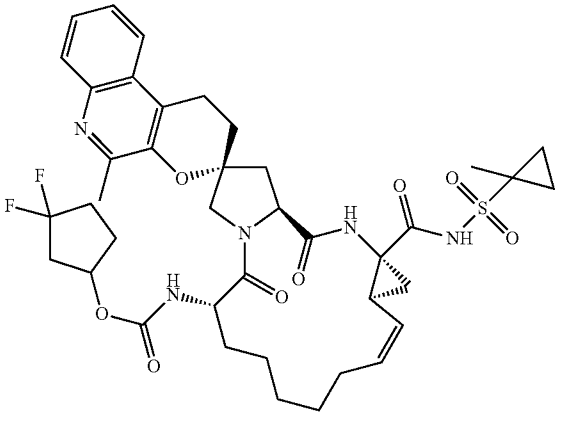

-continued
I-377
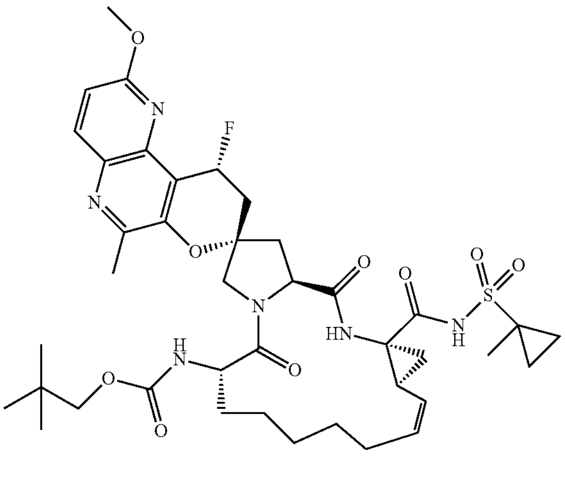
I-378
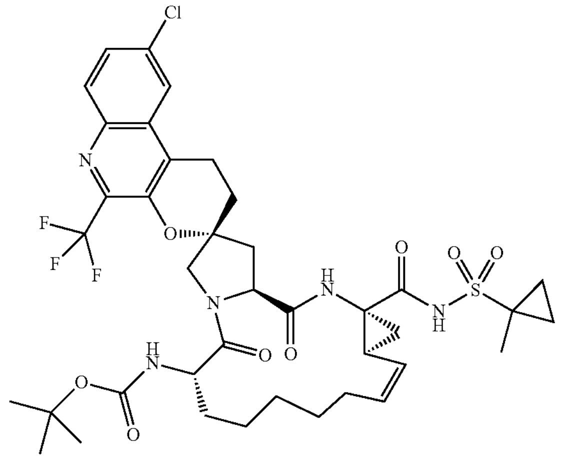
I-379
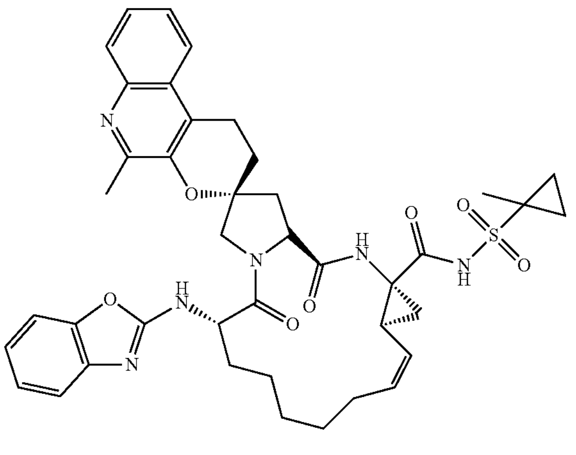
-continued
I-380
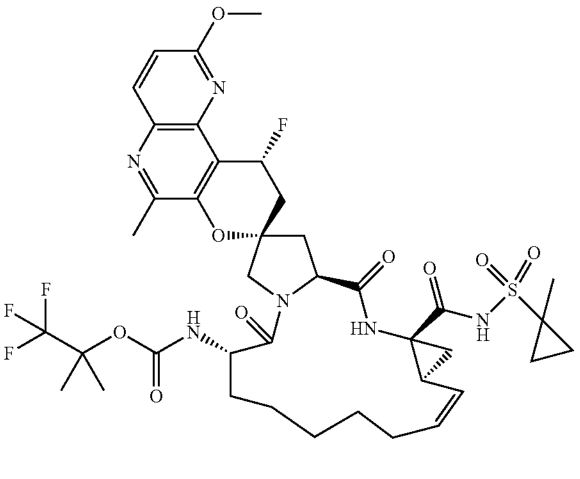
I-381
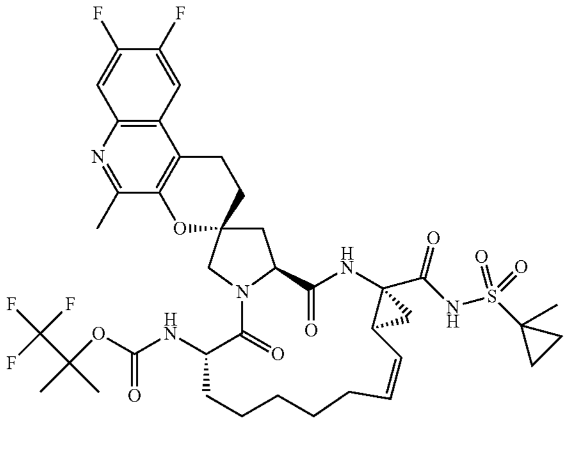
I-382
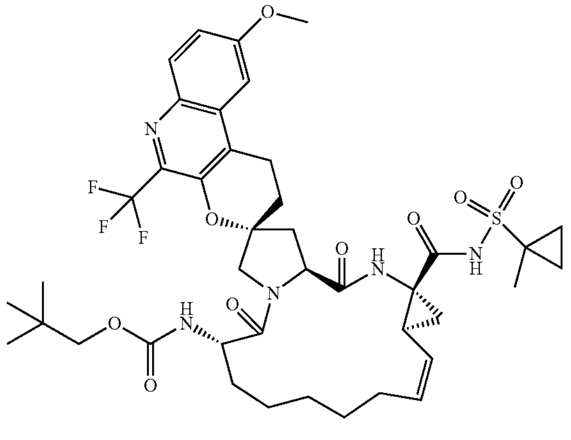

I-383
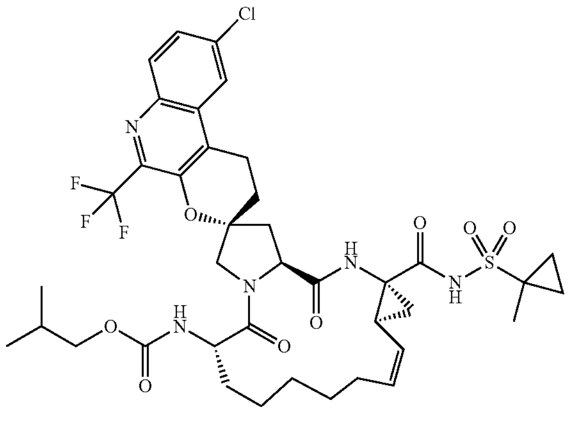
I-384
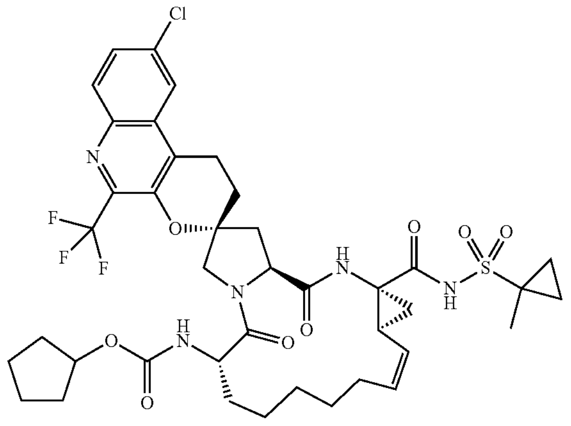
I-385
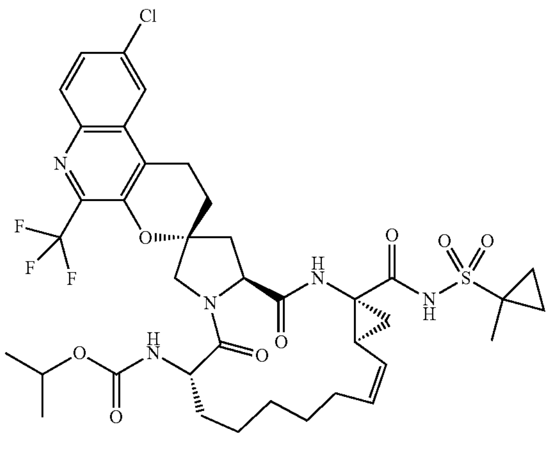
I-386
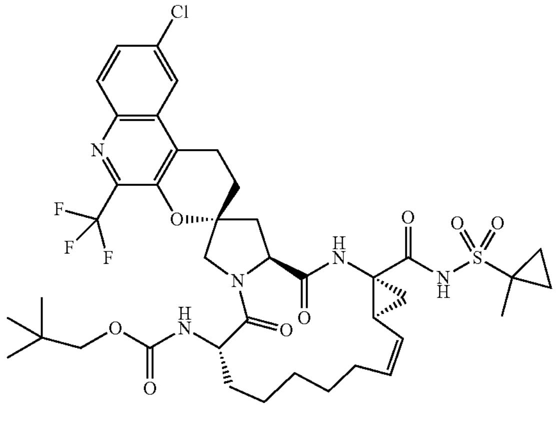
I-387
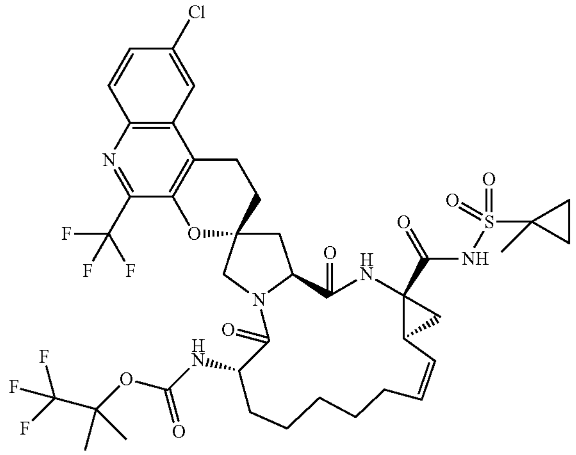
I-388
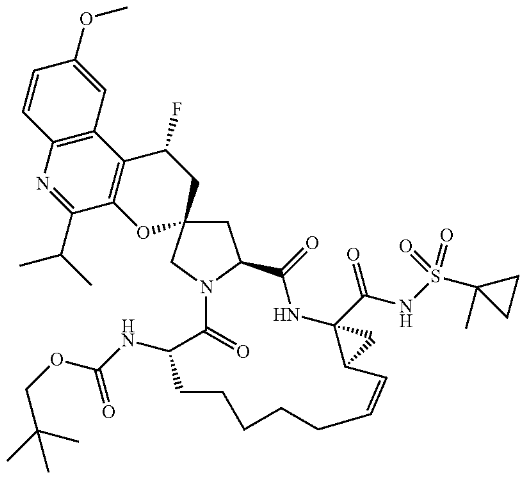

I-389
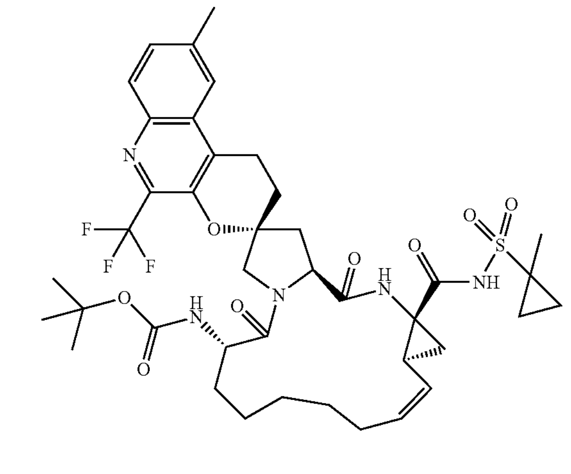
I-390
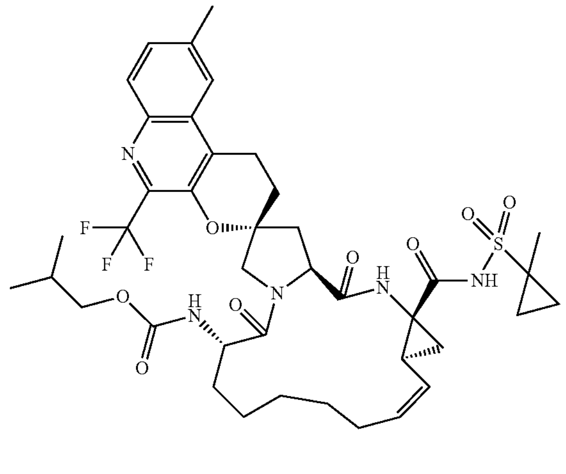
I-391
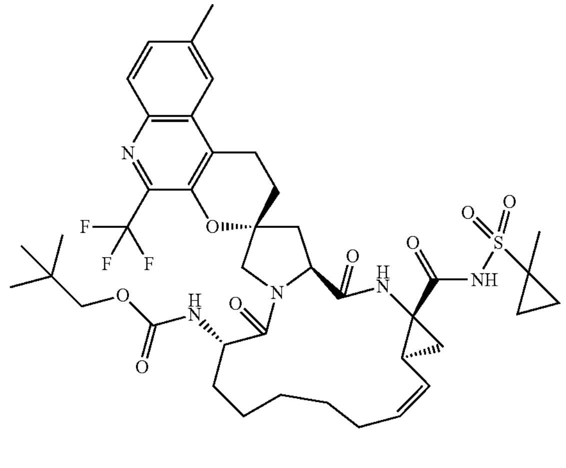
I-392
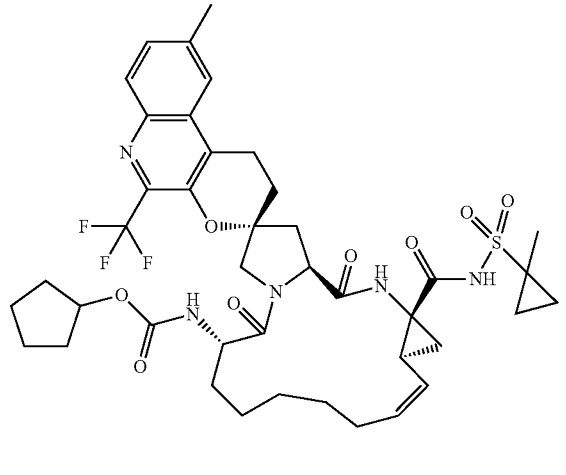
I-393
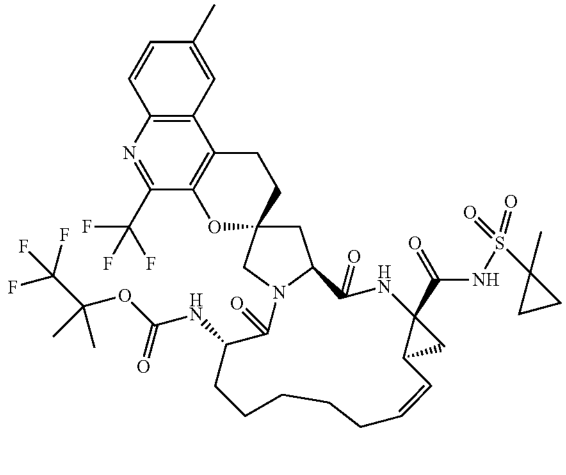
I-394
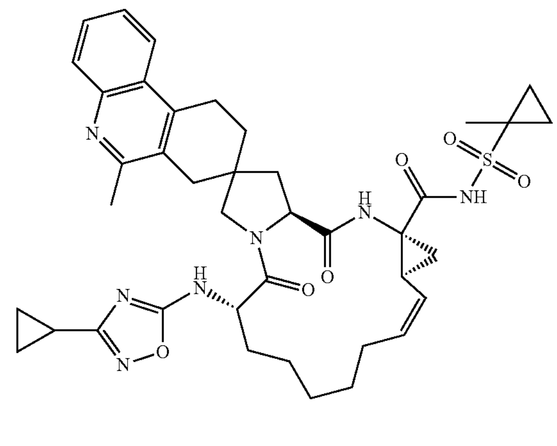

I-395
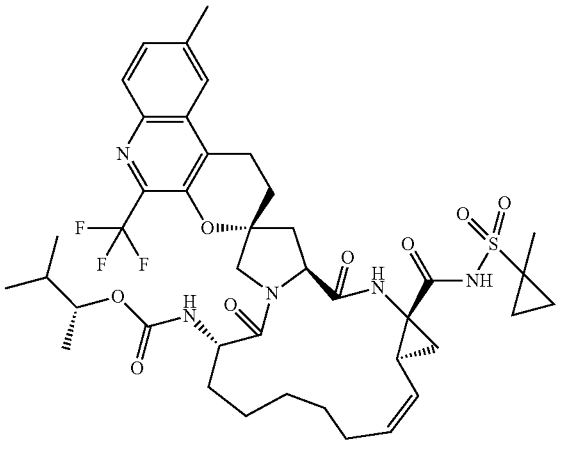
I-396
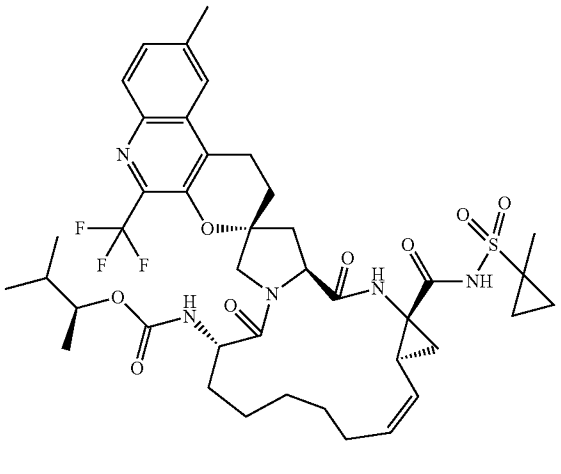
I-397
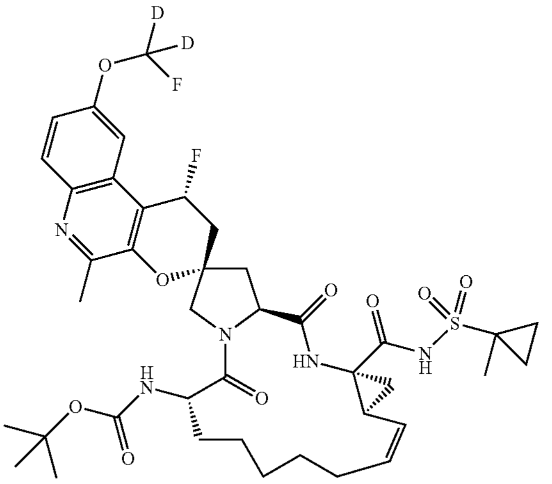
I-398
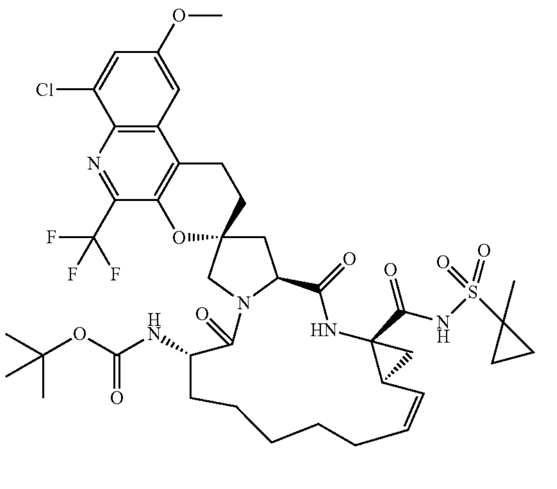
I-399
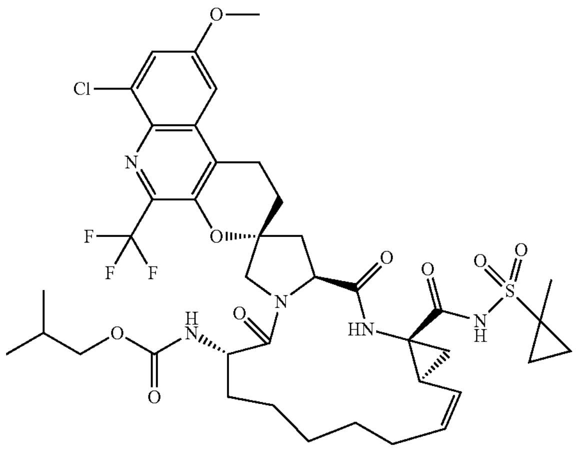
I-400
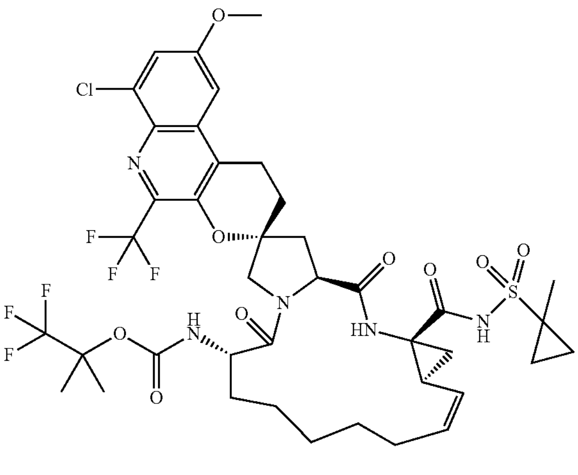

-continued
I-401
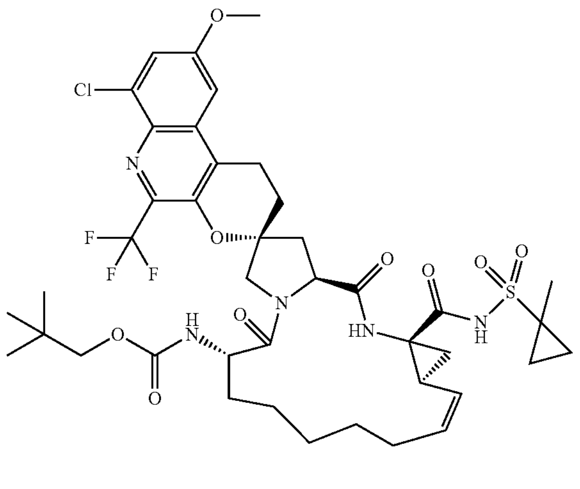
I-402
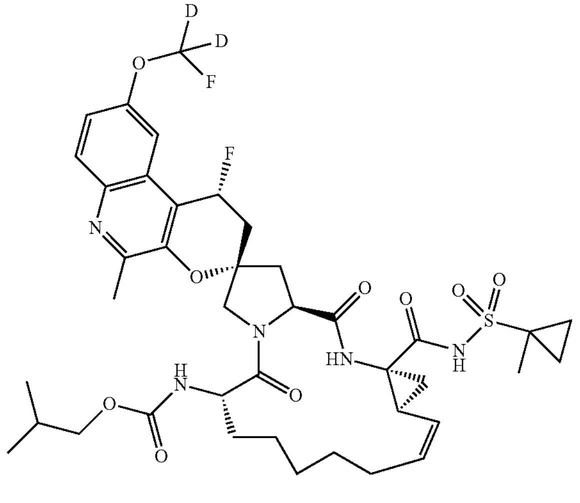
I-403
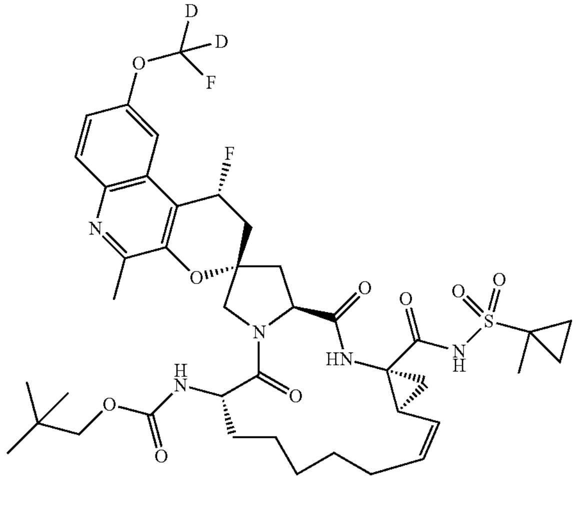
-continued
I-404
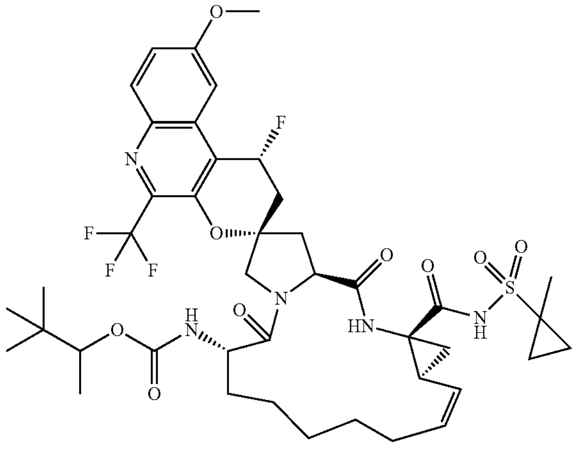
I-405
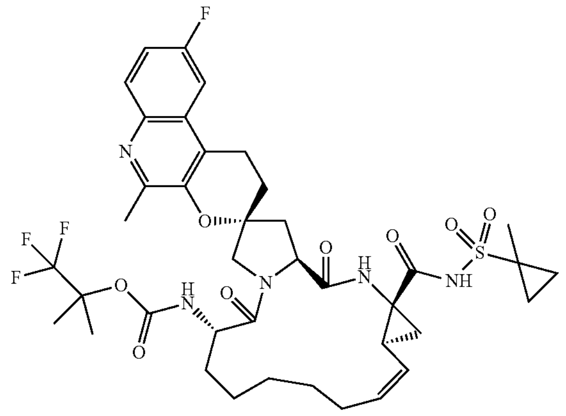
I-406
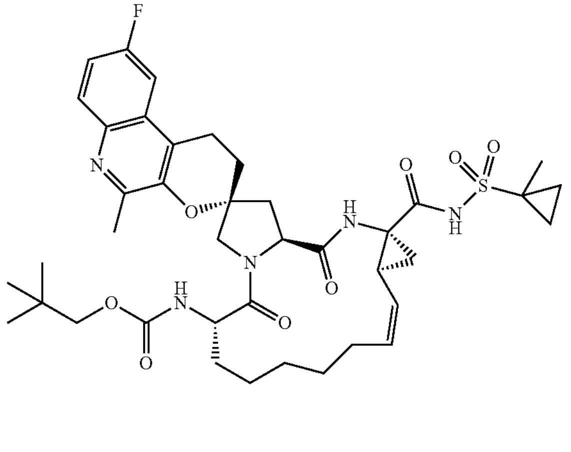

-continued
I-407
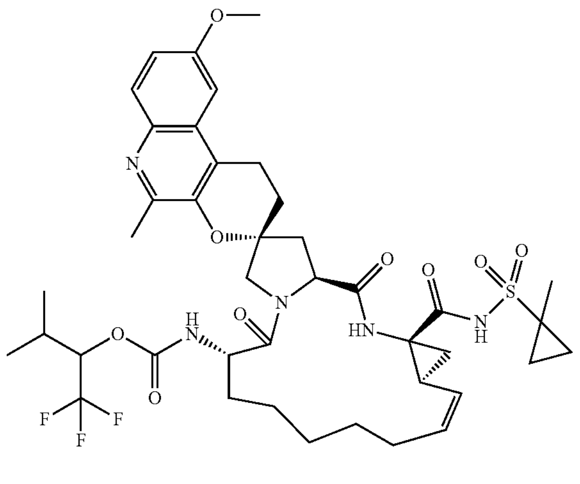
I-408
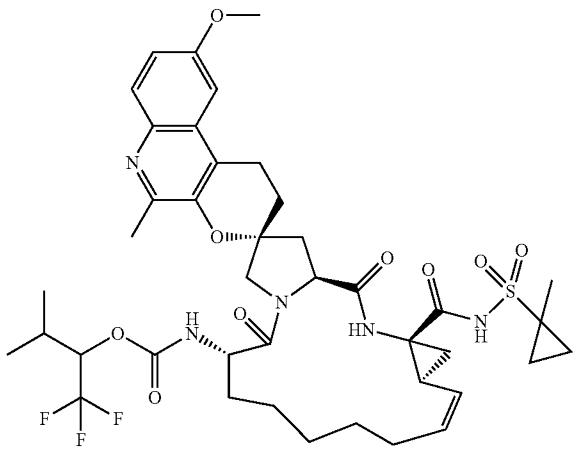
I-409
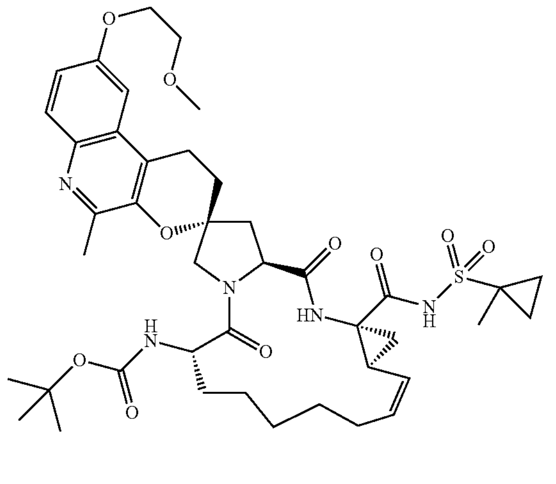
-continued
I-410
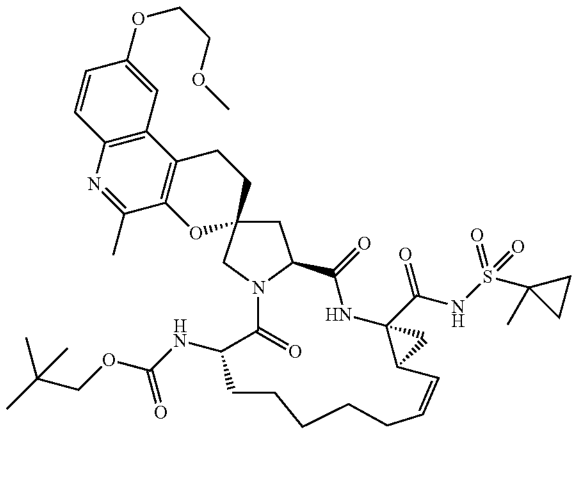
I-411
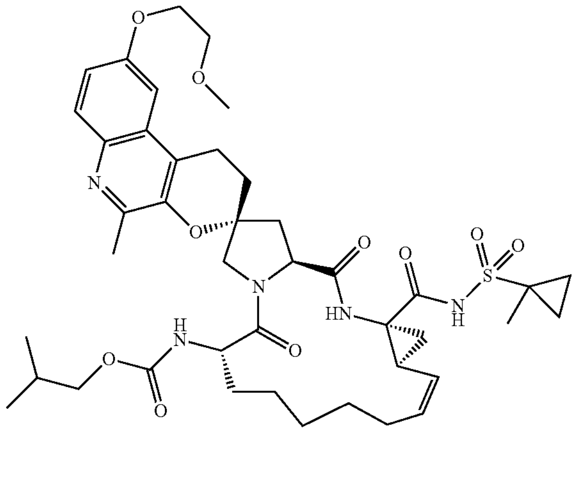
I-412
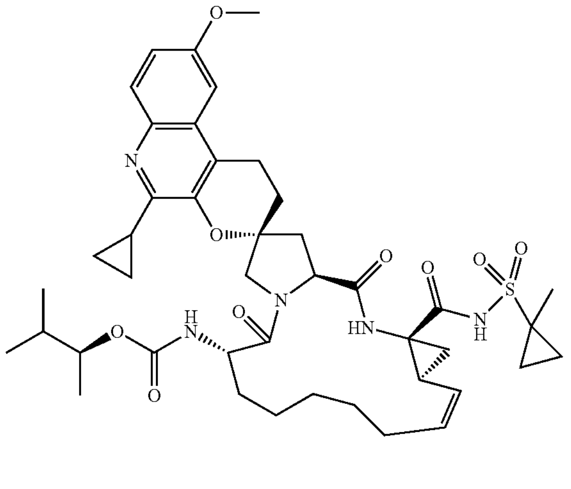

-continued
I-413
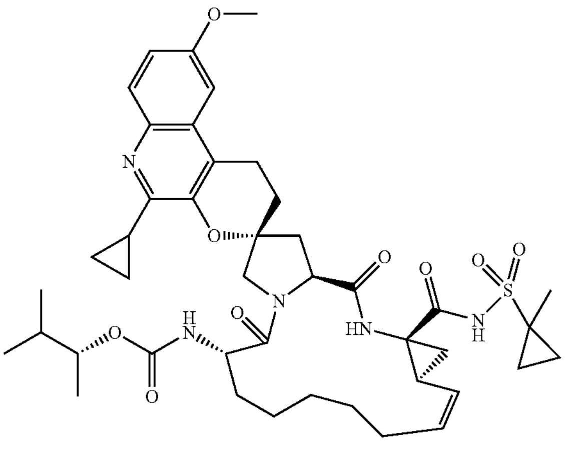
I-414
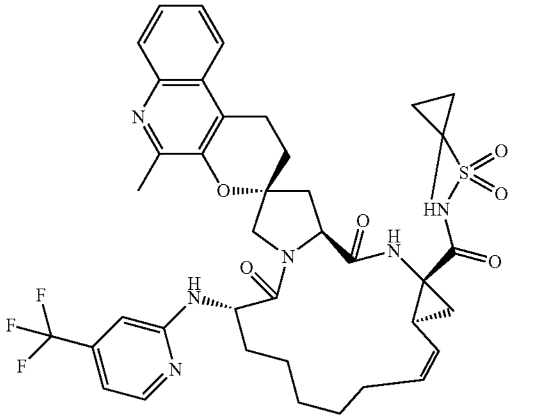
I-415
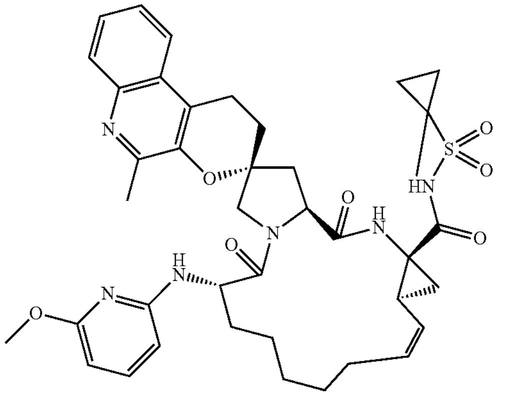
-continued
I-416
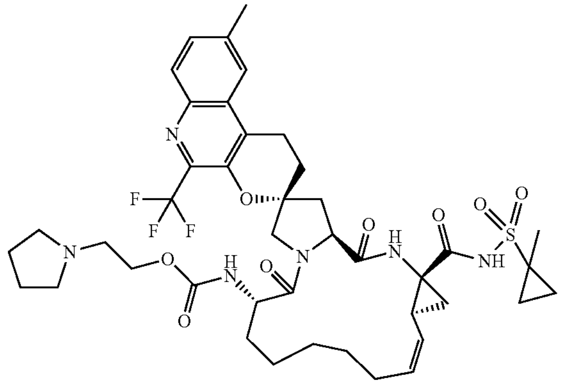
I-417
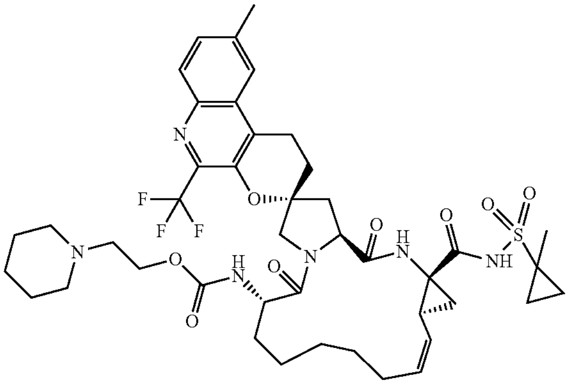
I-418
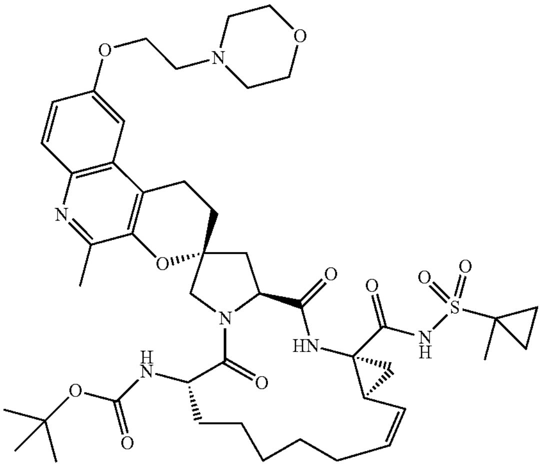

-continued
I-419
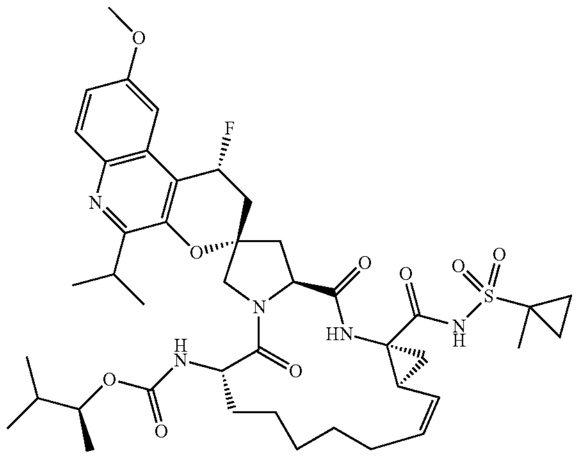
I-420
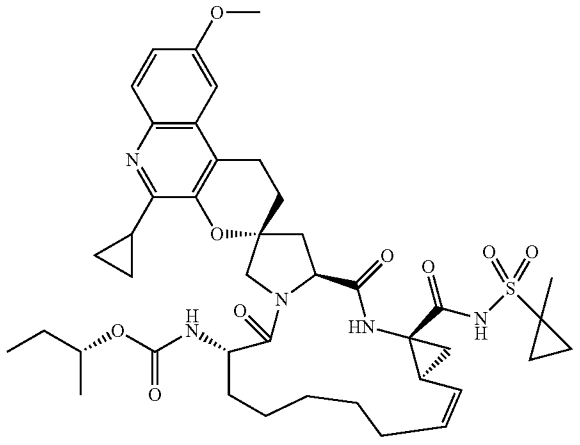
I-421
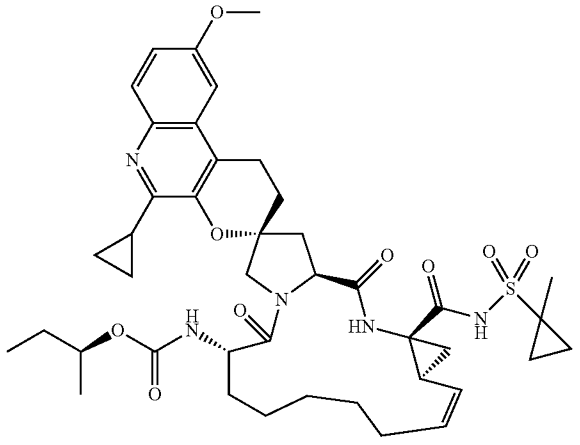
-continued
I-422
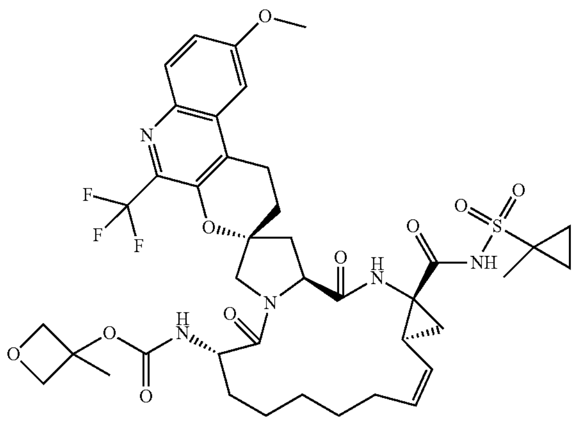
I-423
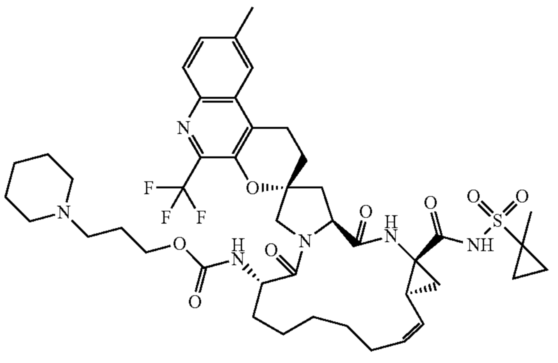
I-424
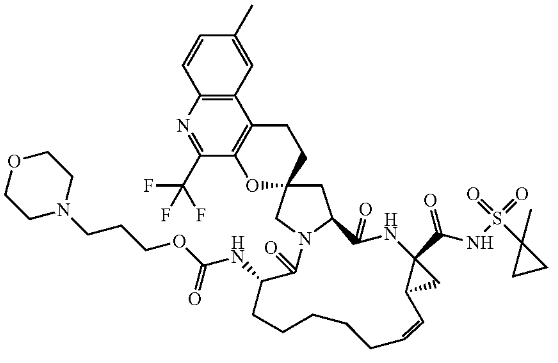

-continued
I-425
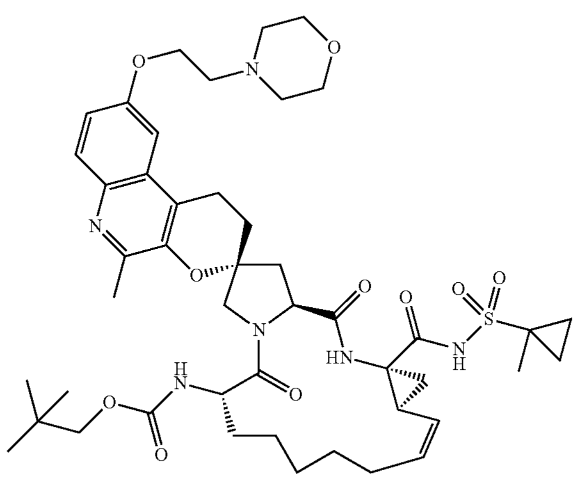
I-426
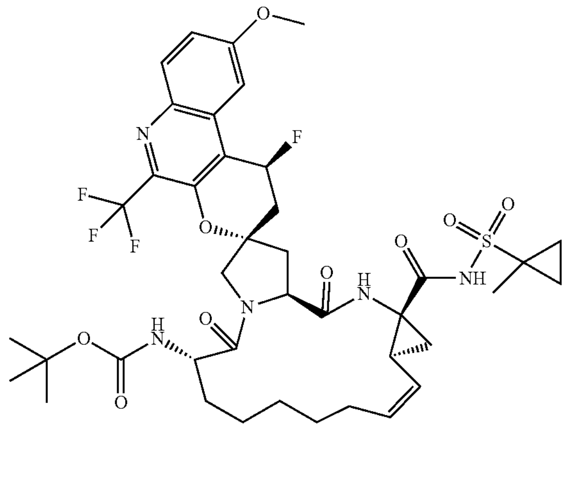
I-427
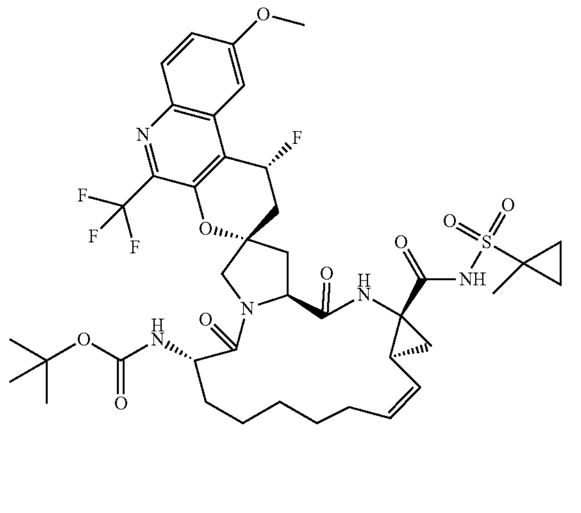
-continued
I-428
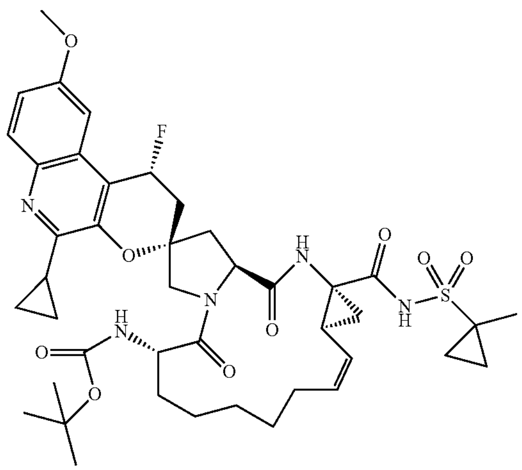
I-429
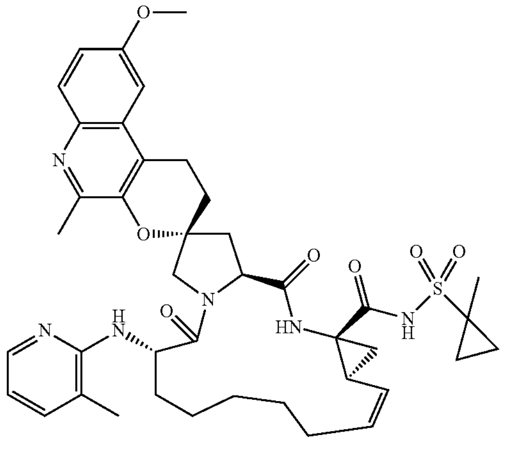
I-430
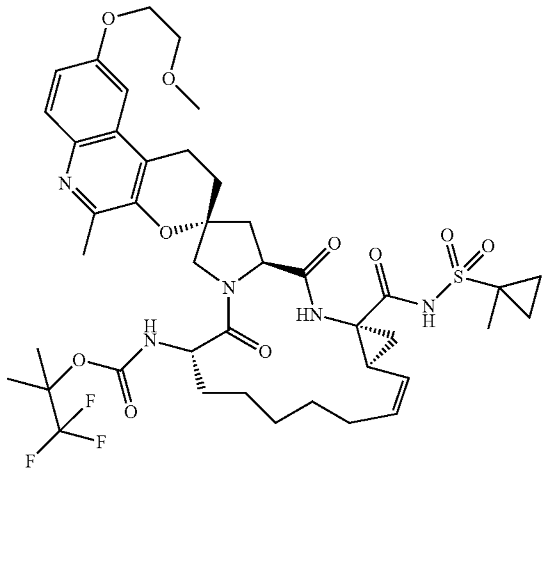

-continued
I-431
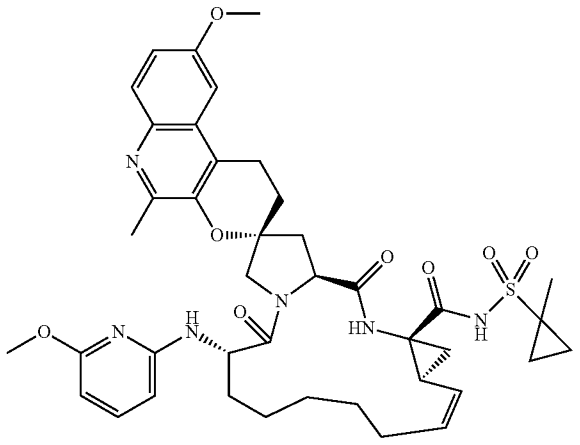
I-432
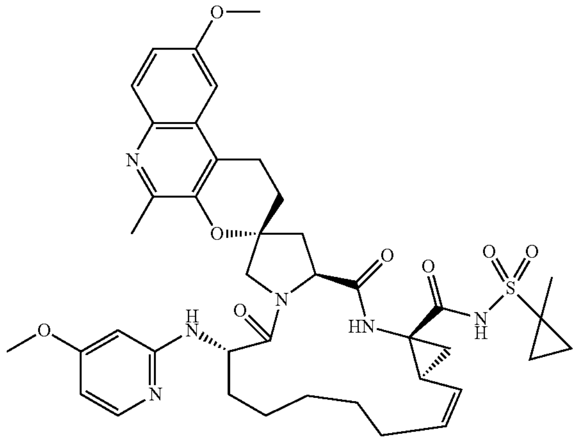
I-433
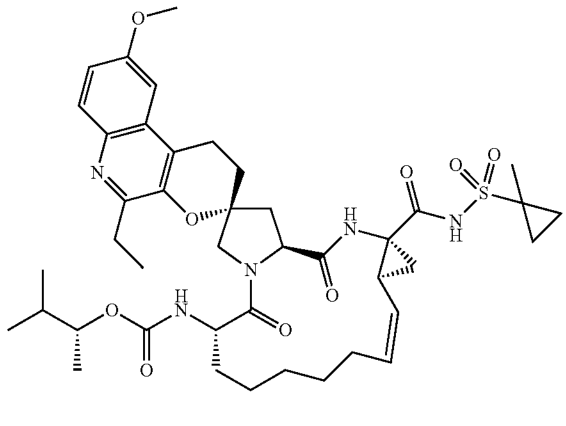
-continued
I-434
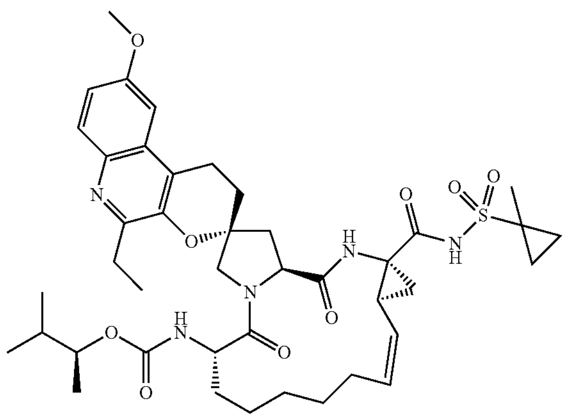
I-435
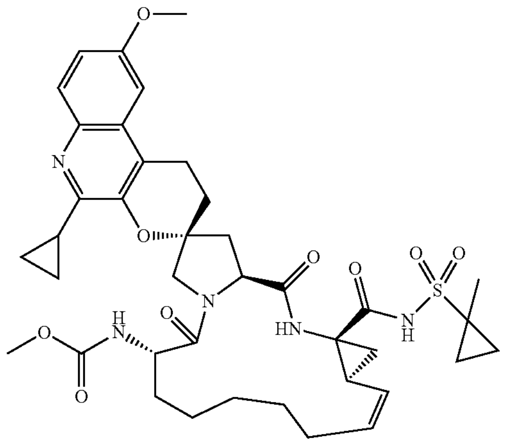
I-436
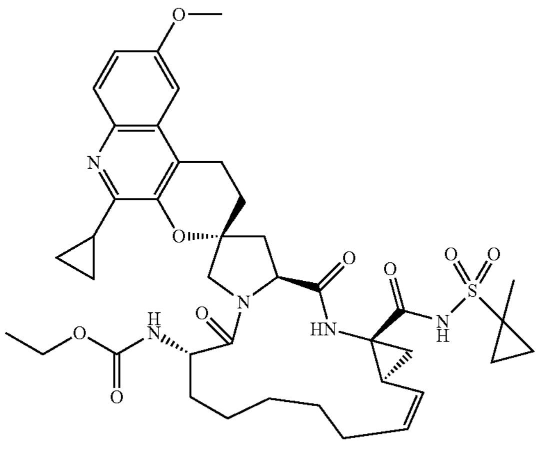

I-437
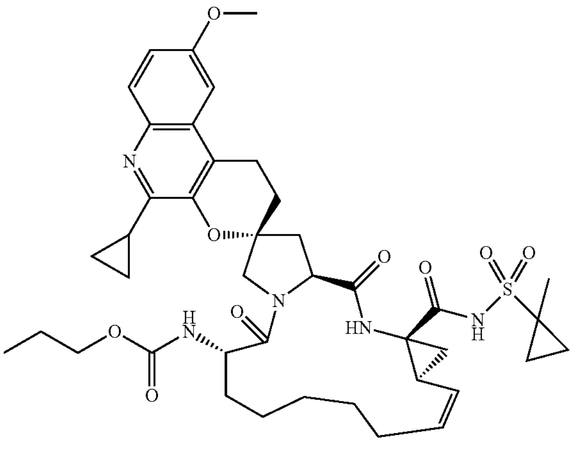
I-438
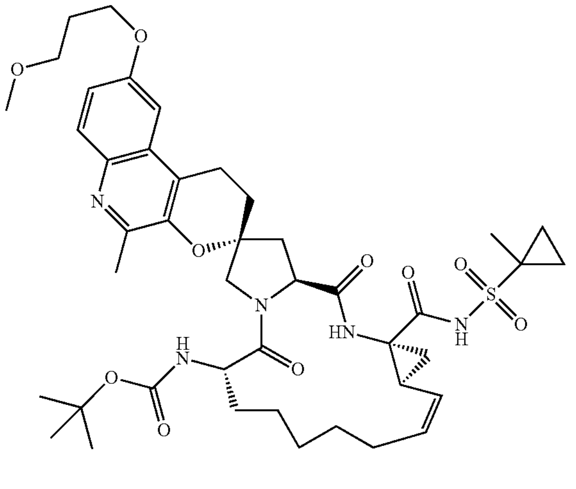
I-439
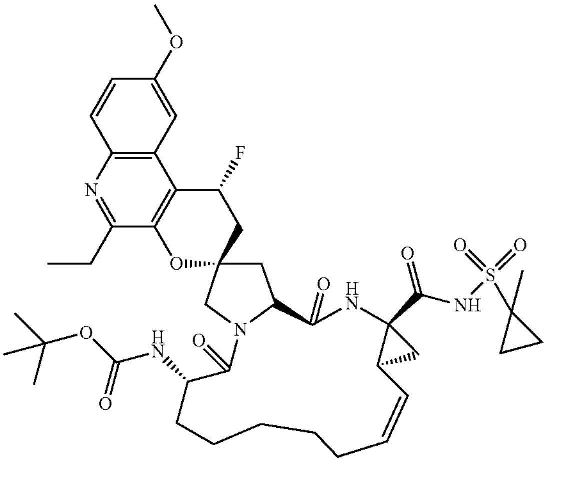
I-440
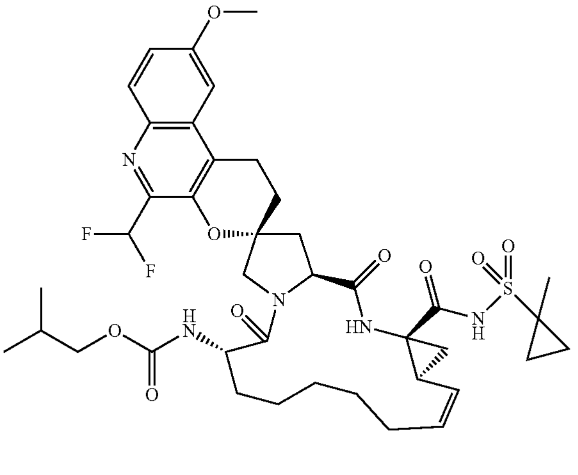
I-441
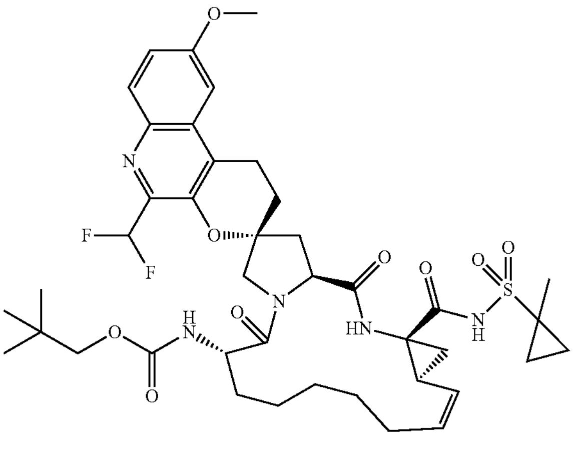
I-442
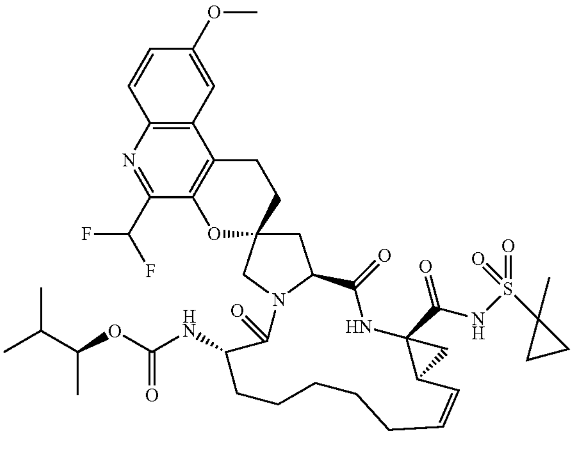

-continued
I-443
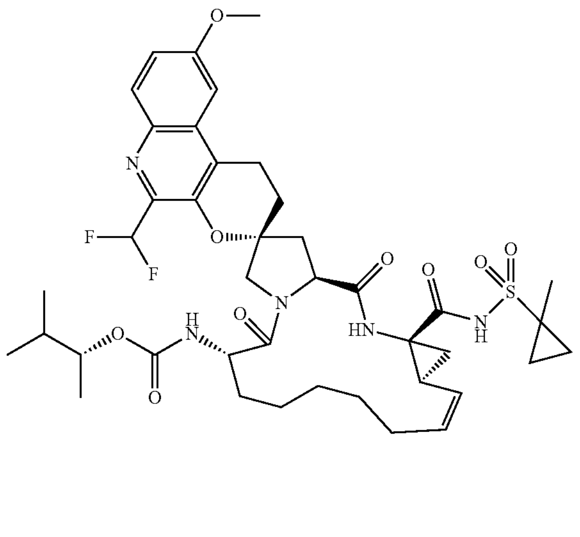
I-444
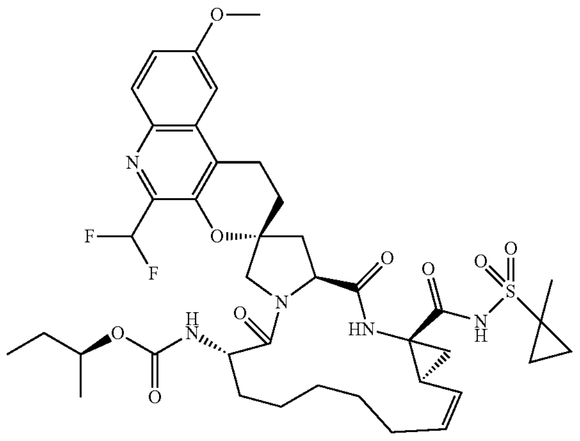
I-445
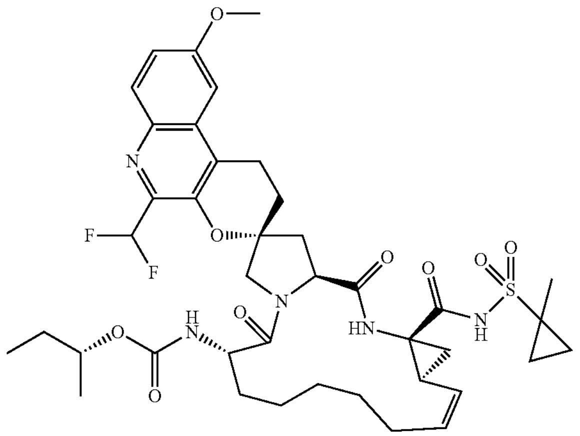
-continued
I-446
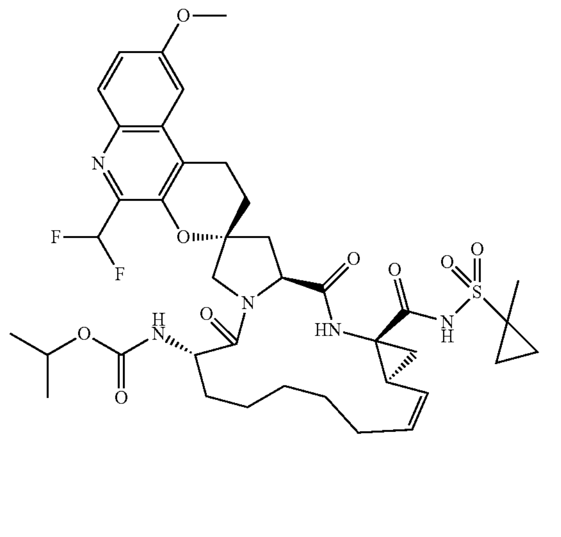
I-447
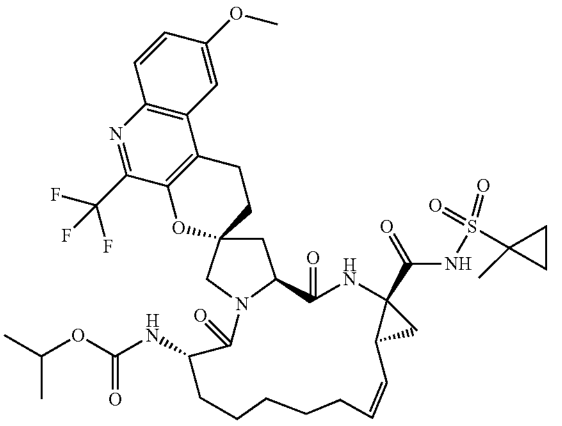
I-448
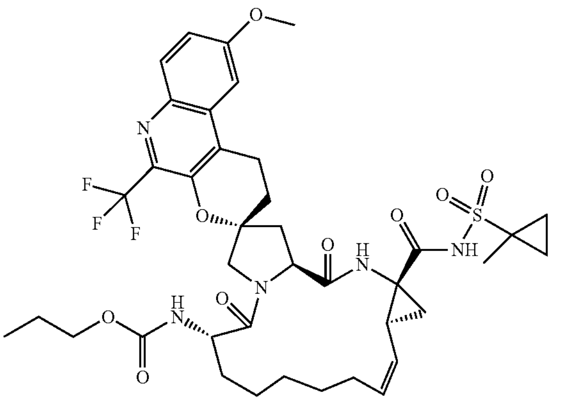

-continued
I-449
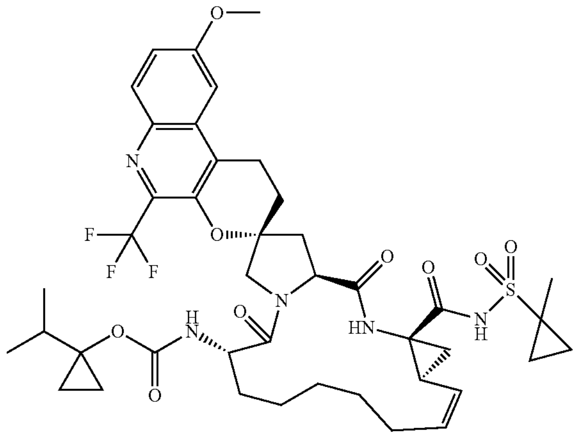
I-450
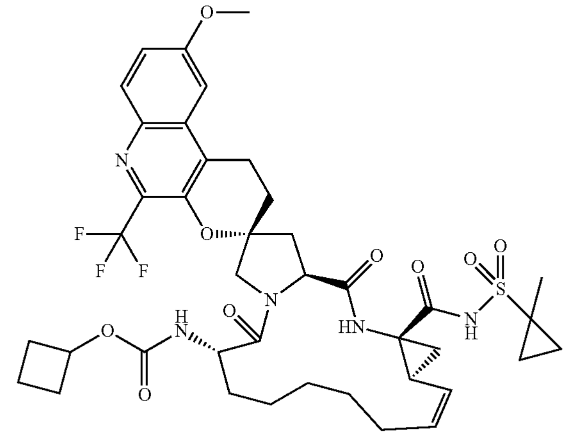
I-451
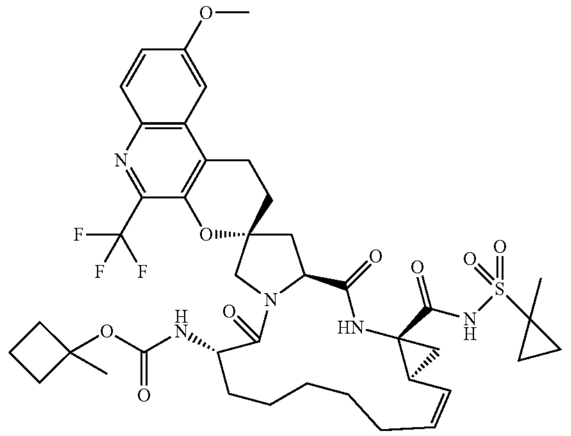
-continued
I-452
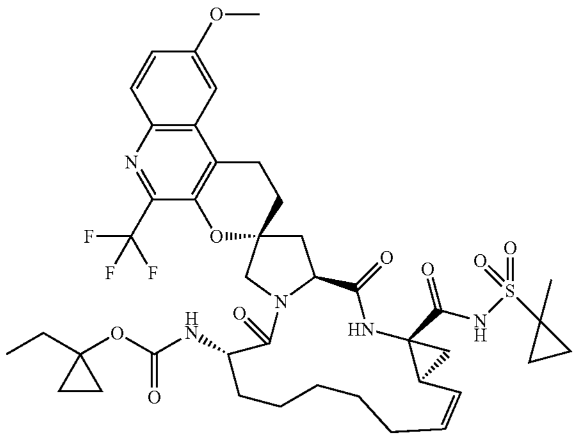
I-453
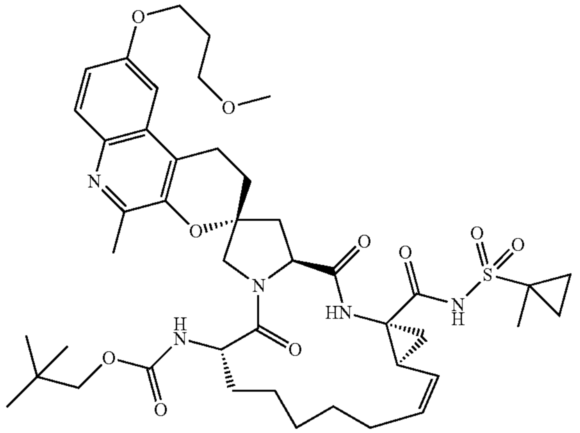
I-454
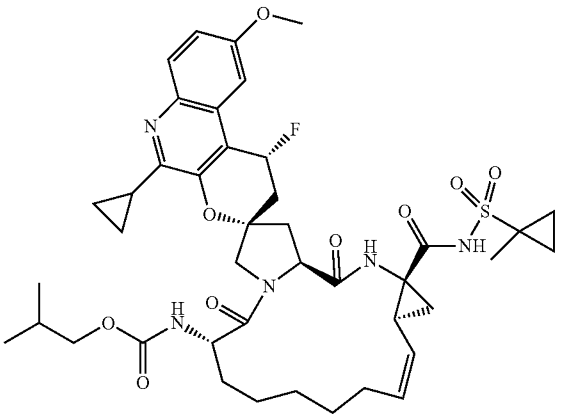

I-455
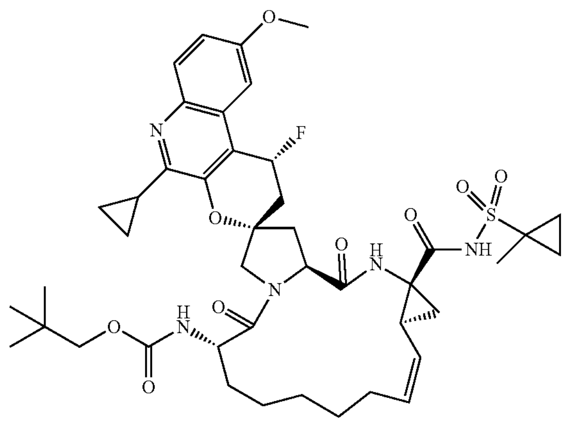
I-456
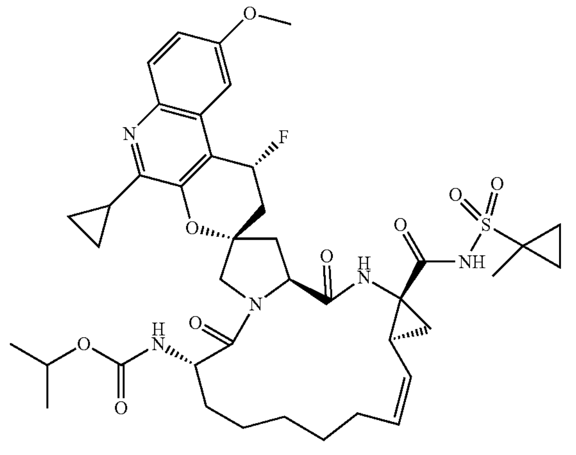
I-457
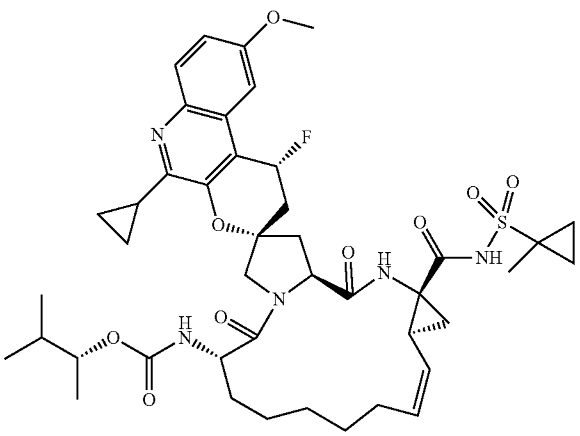
I-458
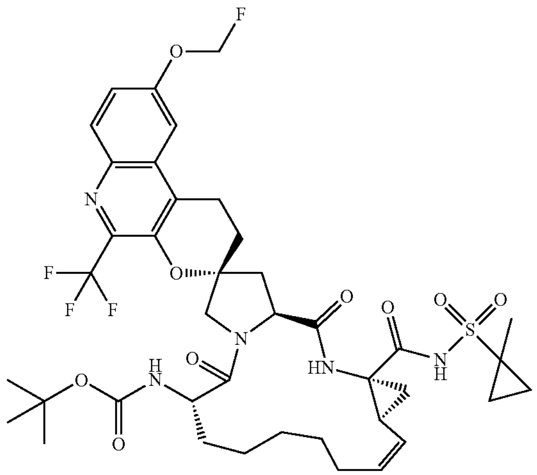
I-459
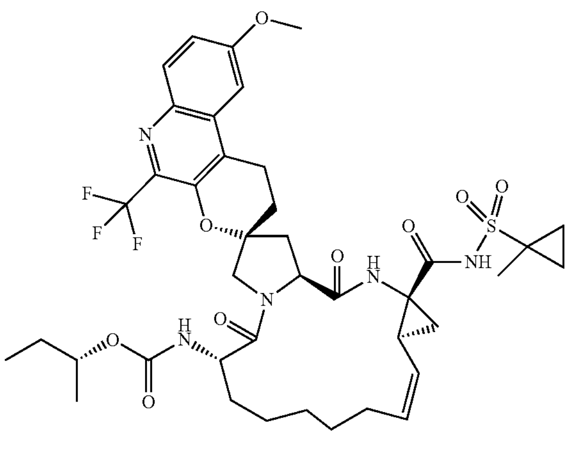
I-460
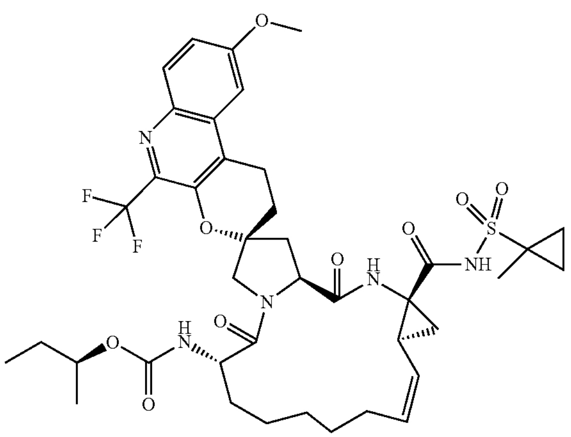

I-461
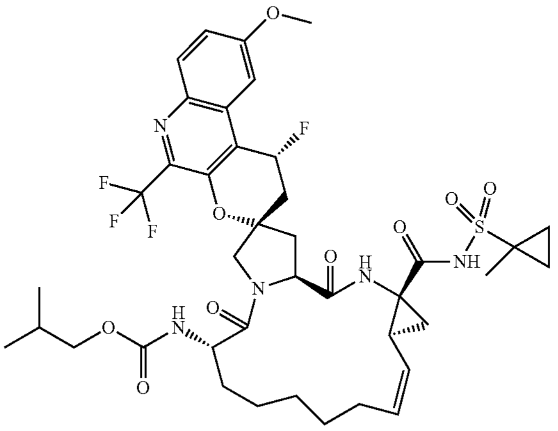
I-464
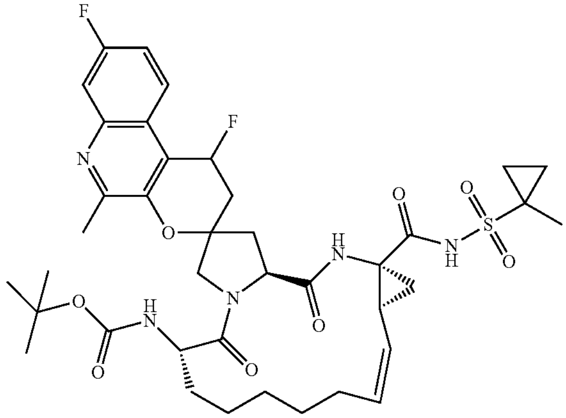
I-462
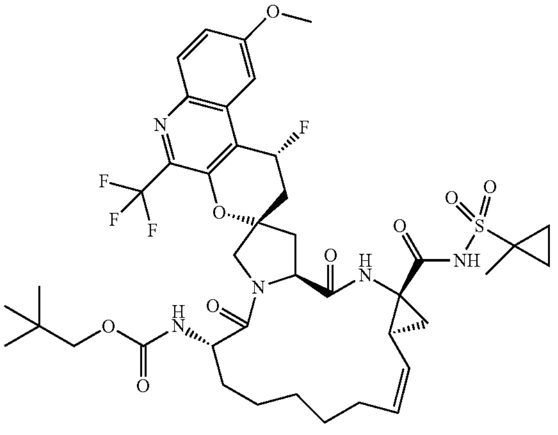
I-466
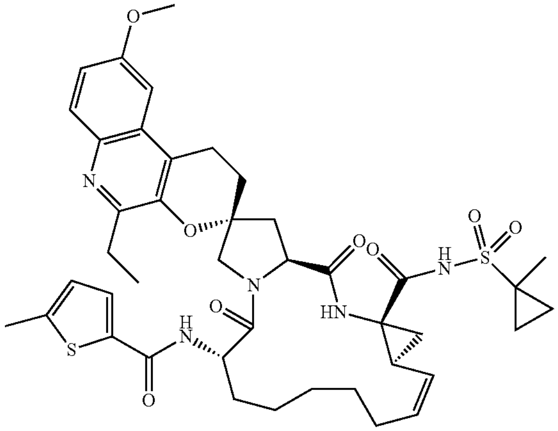
I-463
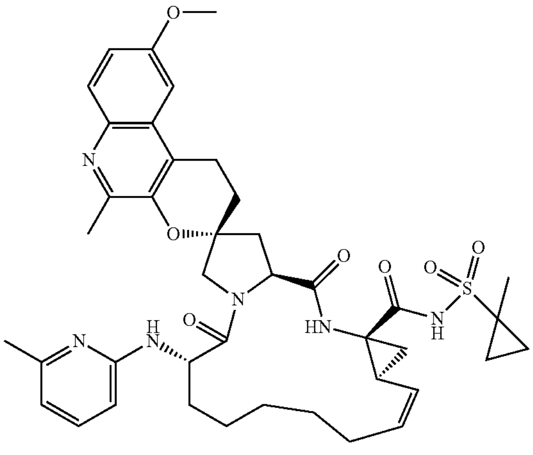
I-467
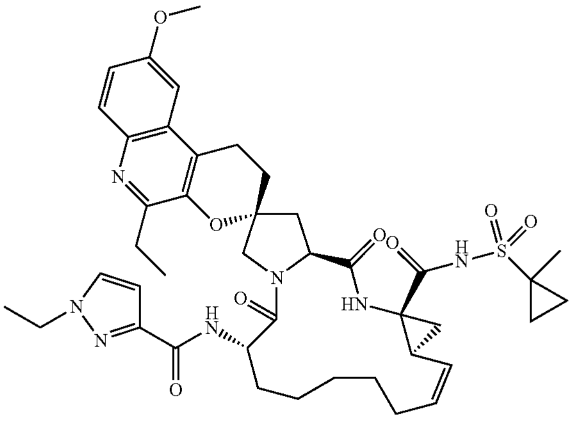

I-468
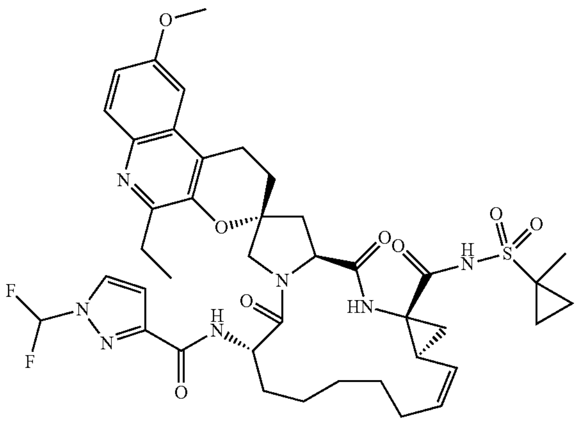
I-469
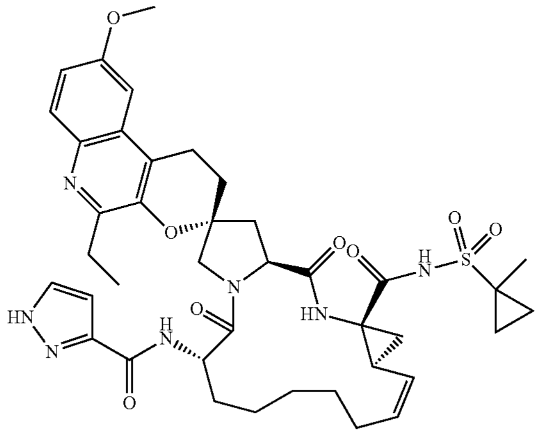
I-470
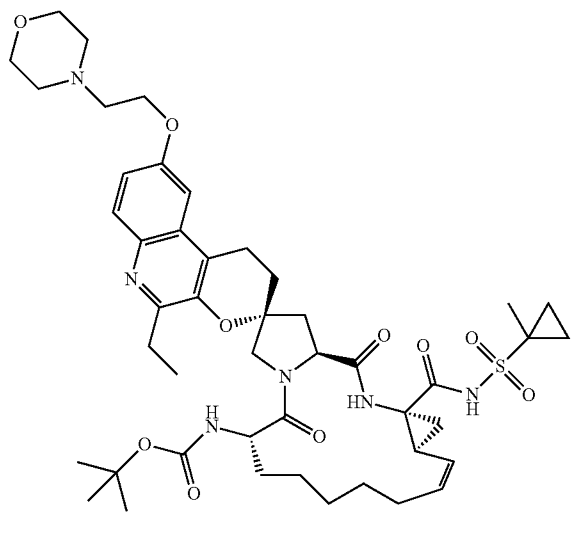
I-471
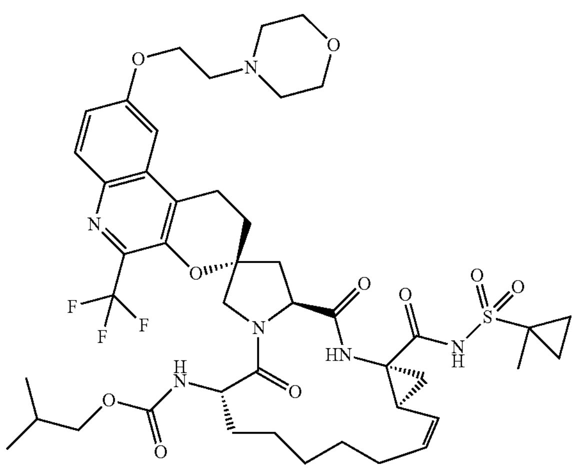
I-472
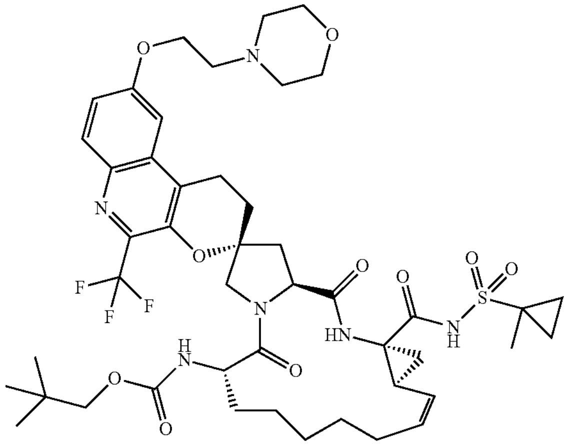
I-473
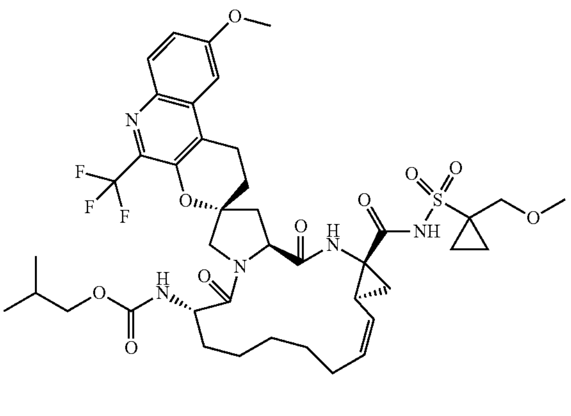

I-474
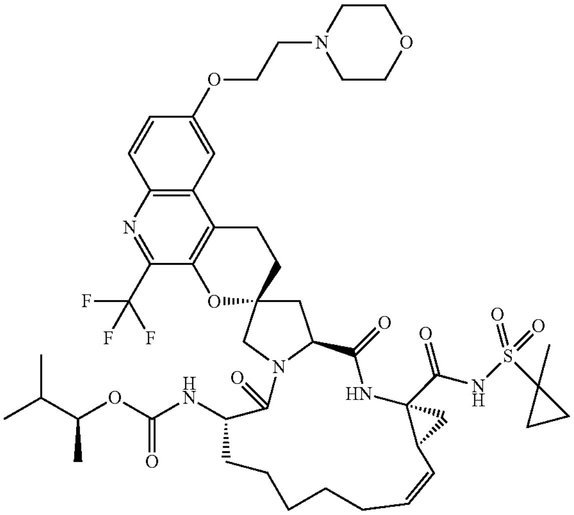
I-475
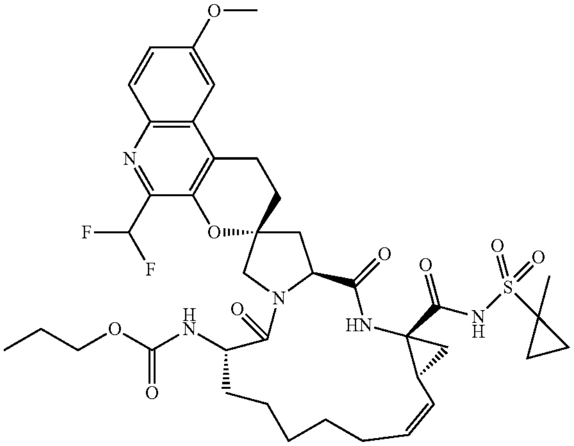
I-476
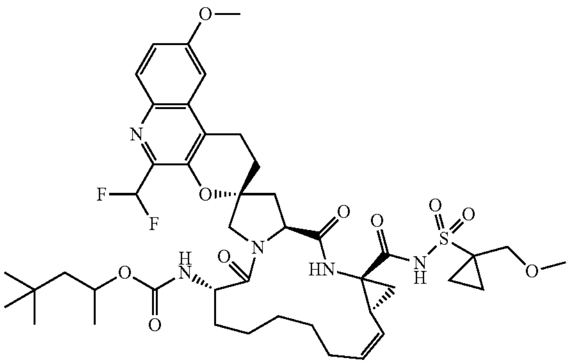
I-477
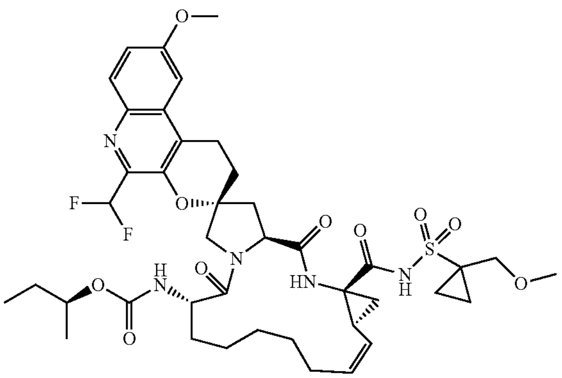
I-478
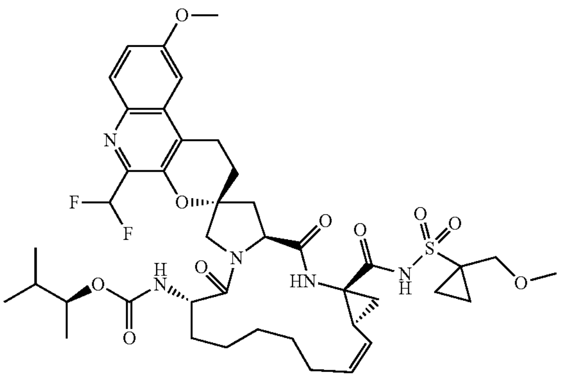
I-479
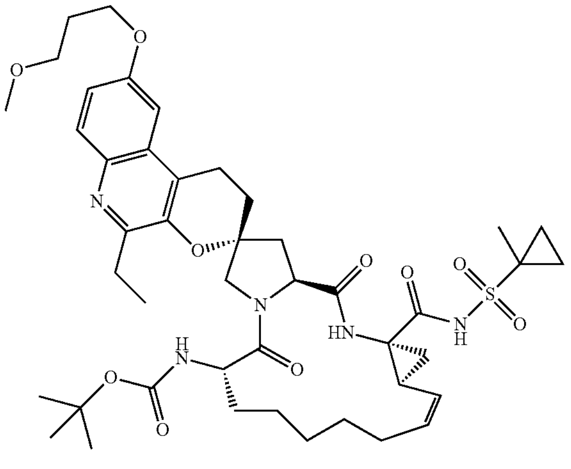

-continued
I-480
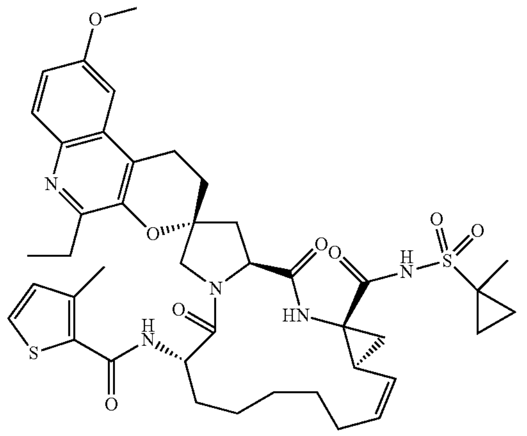
I-481
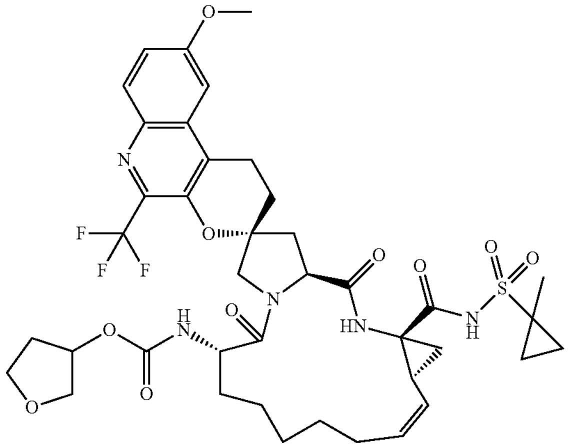
I-482
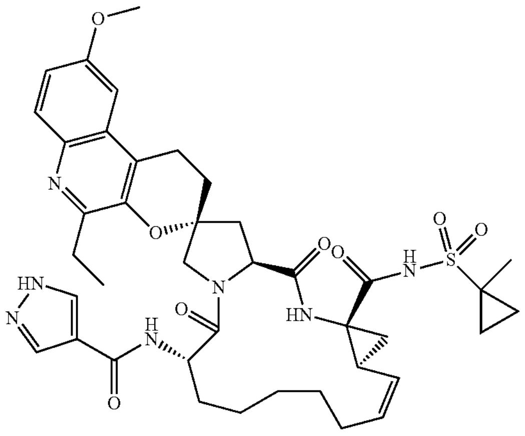
-continued
I-483
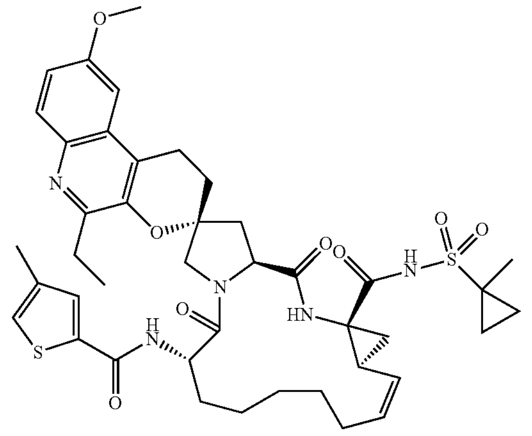
I-484
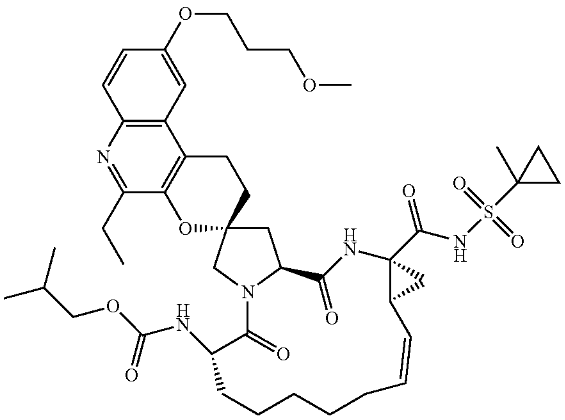
I-485
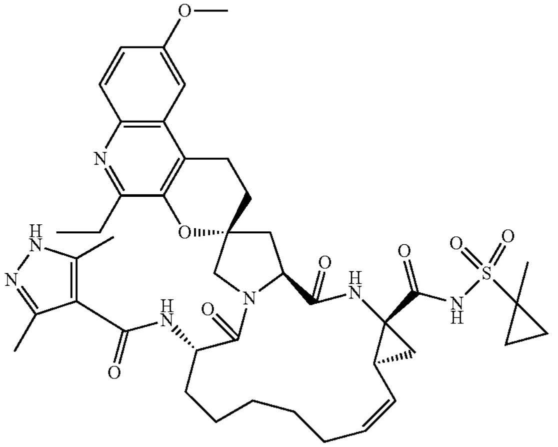

-continued
I-486
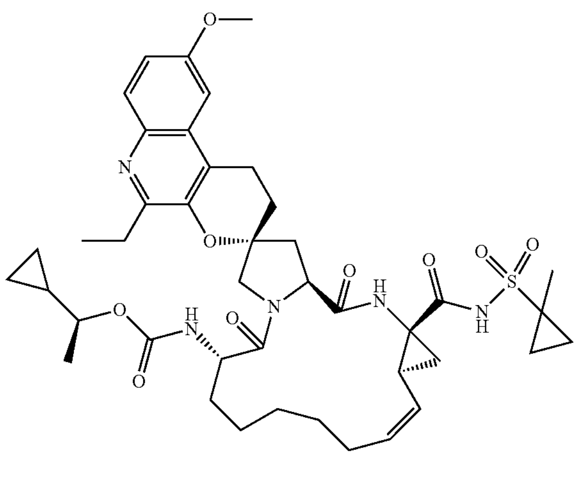
I-487
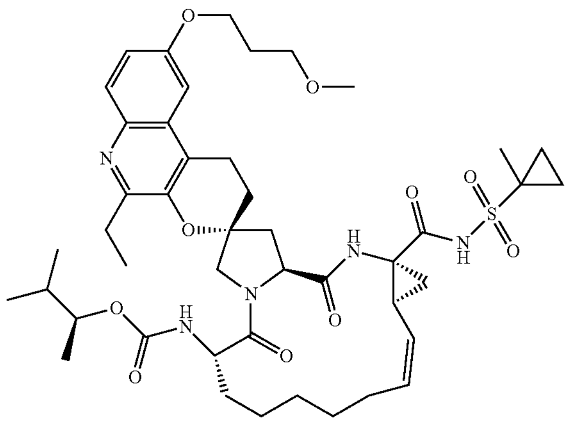
I-488
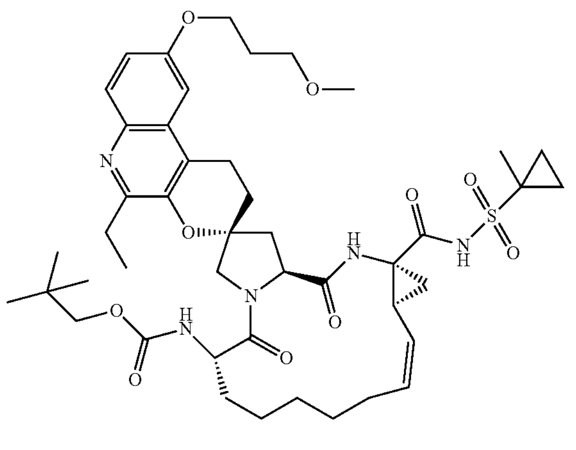
-continued
I-489
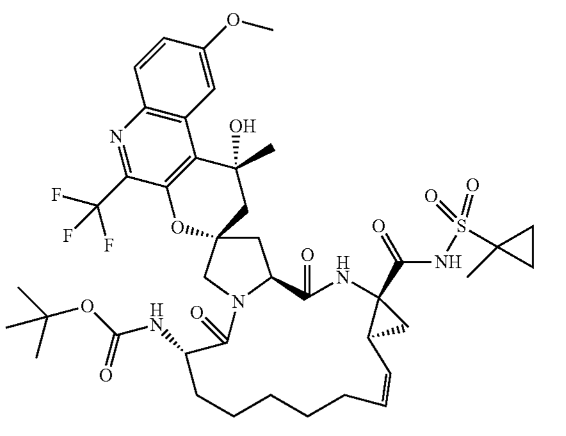
I-490
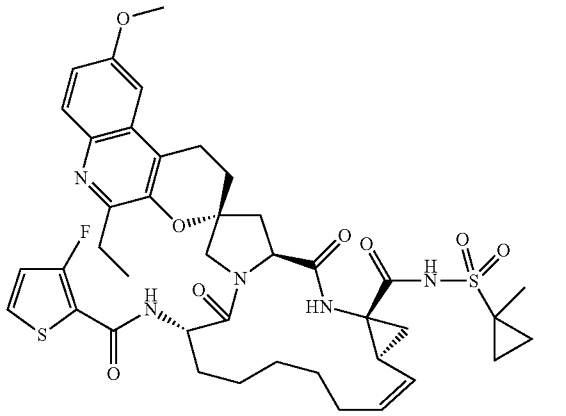
I-491
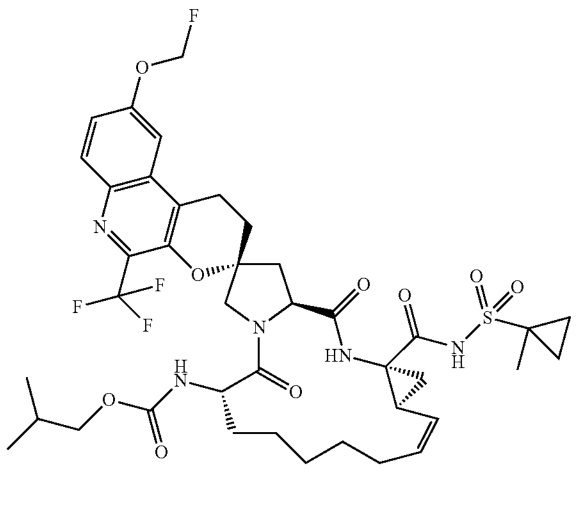

-continued
I-493
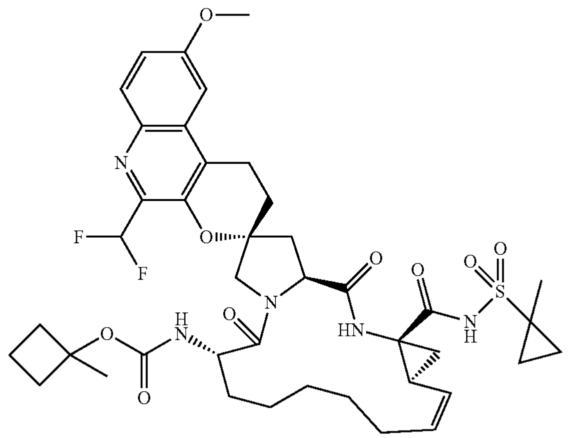
I-494
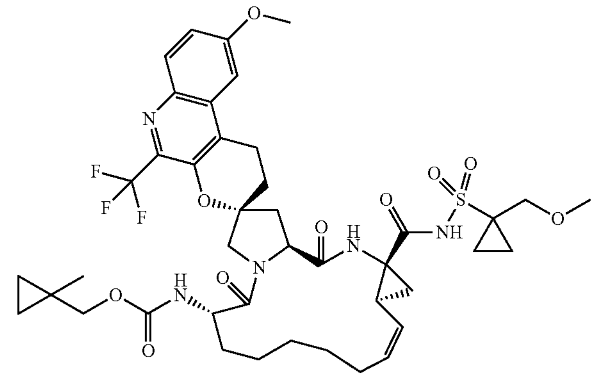
I-495
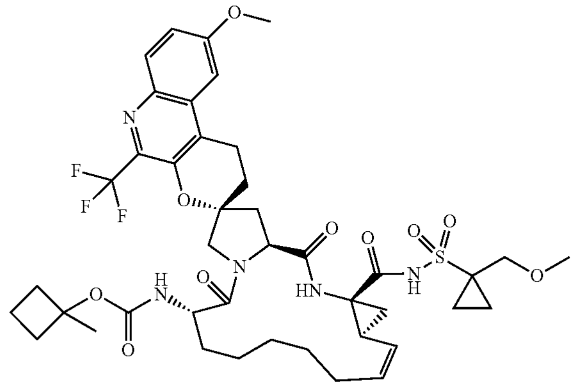
I-496
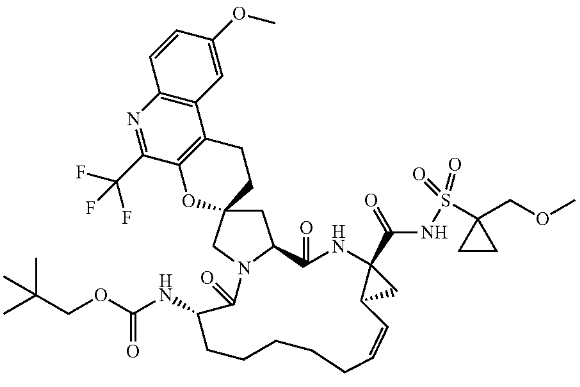
-continued
I-497
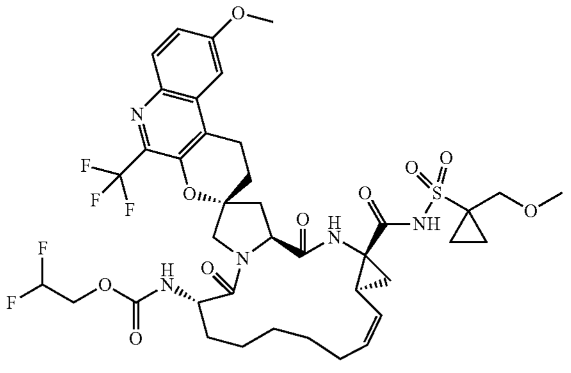
I-498
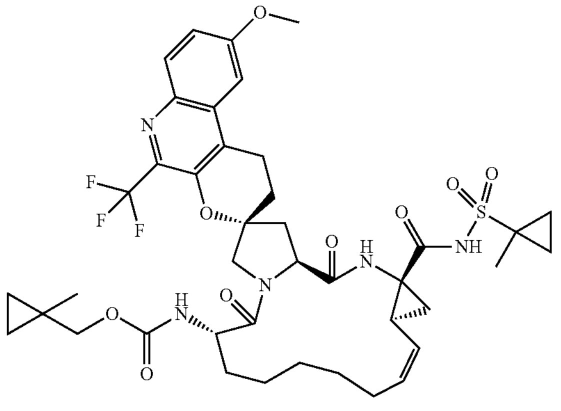
I-499
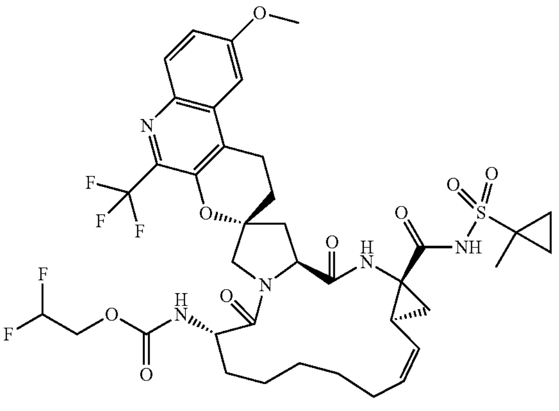

-continued
I-501
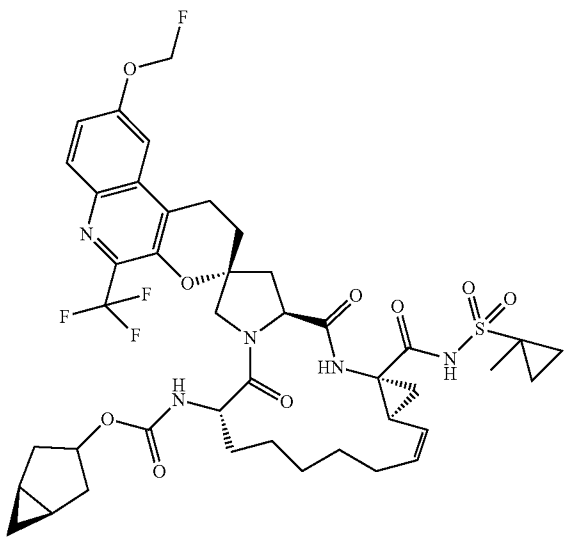
I-502
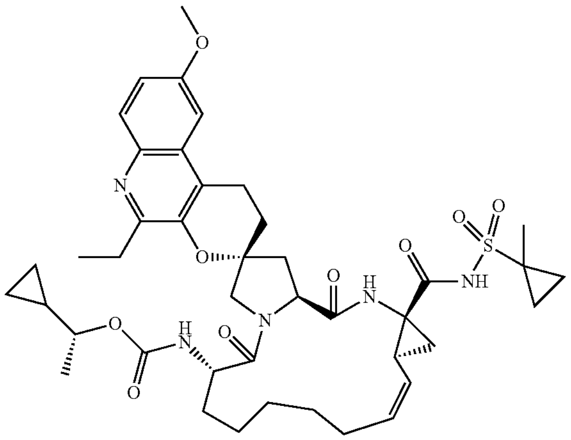
I-503
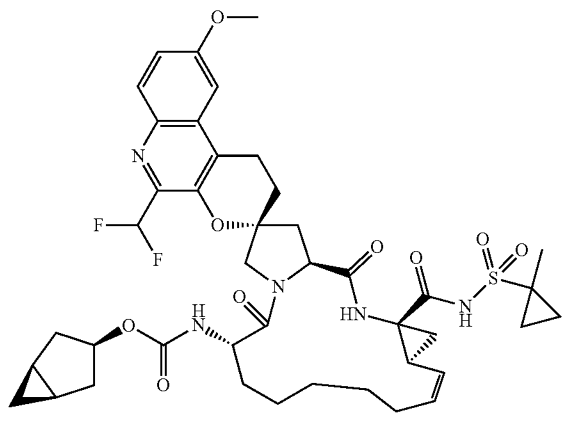
-continued
I-504
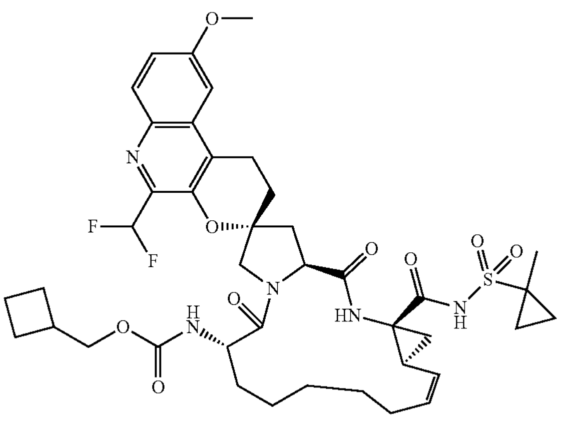
I-505
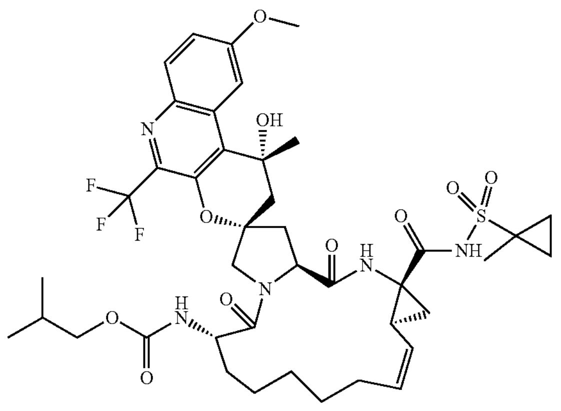
I-506
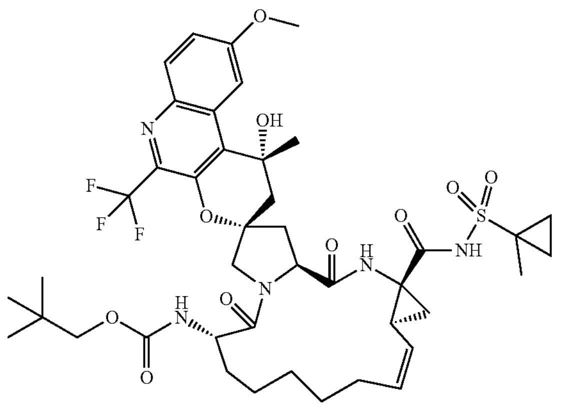

-continued
I-507
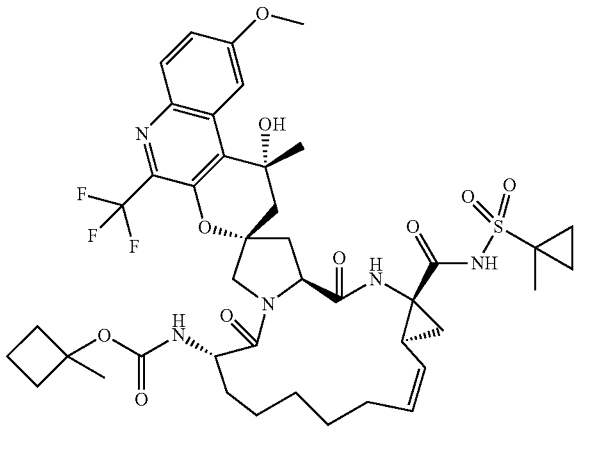
I-508
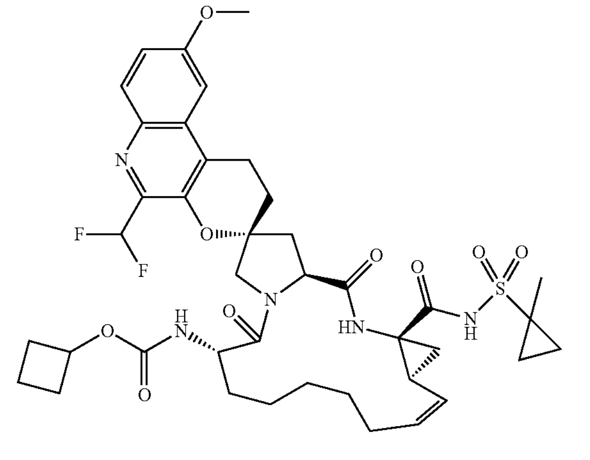
I-509
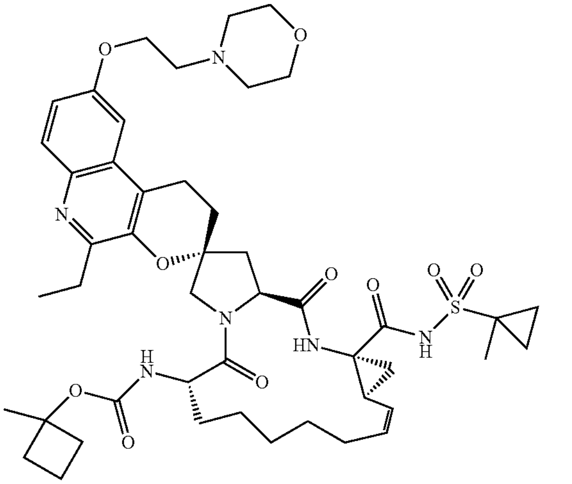
-continued
I-510
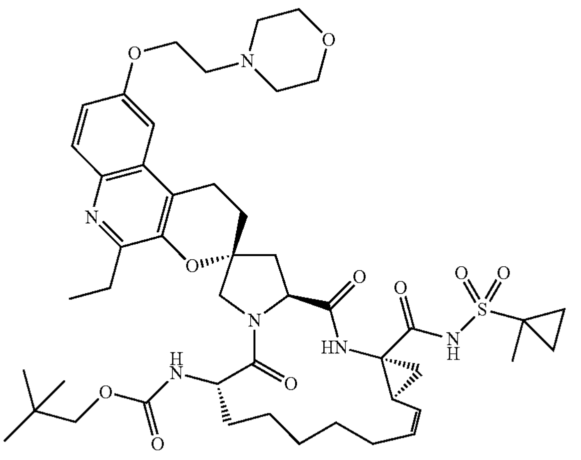
I-511
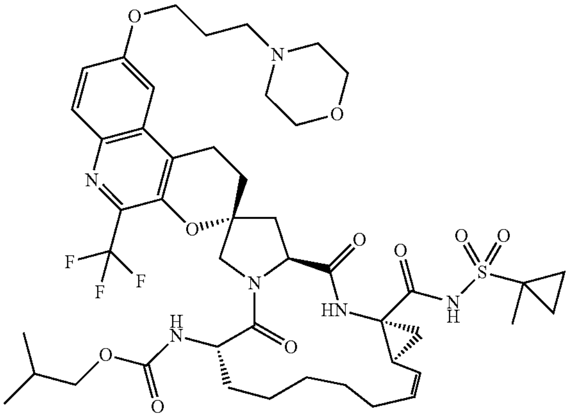
I-512
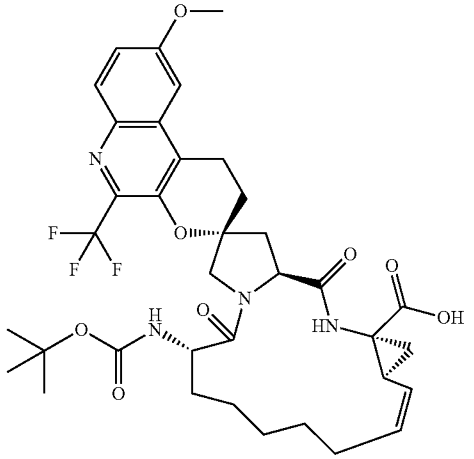

-continued
I-513
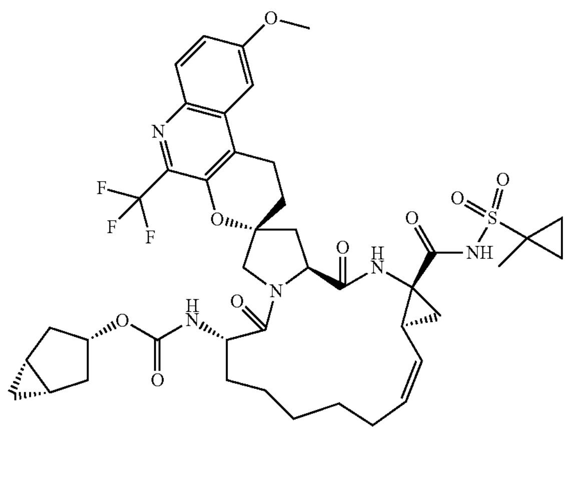
I-514
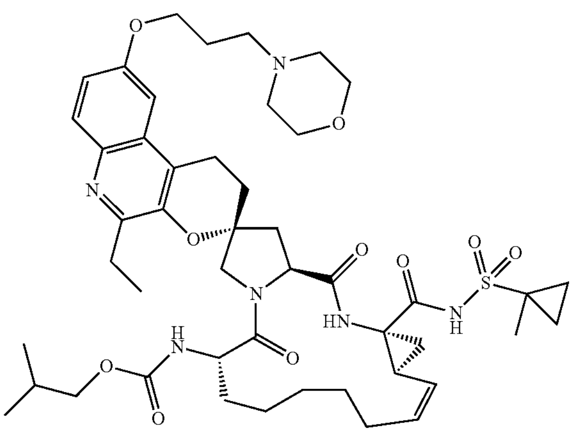
I-515
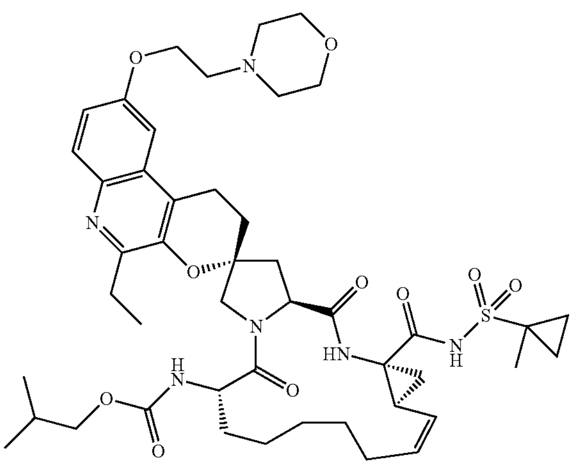
-continued
I-516
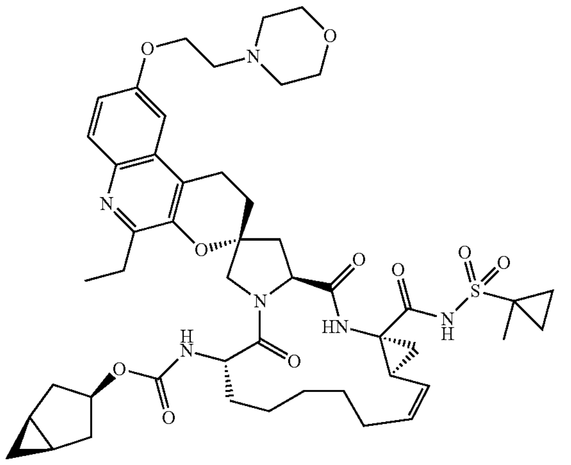
I-517
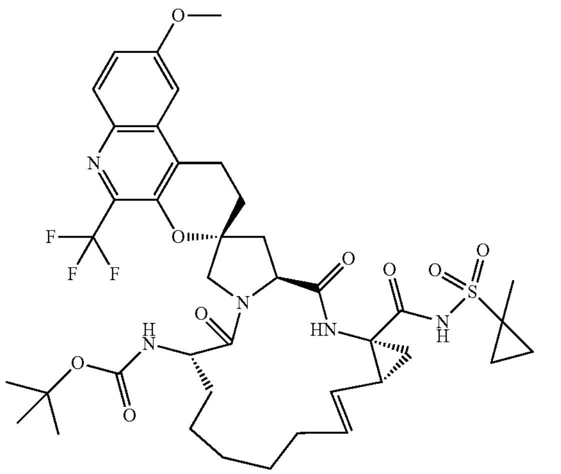
I-518
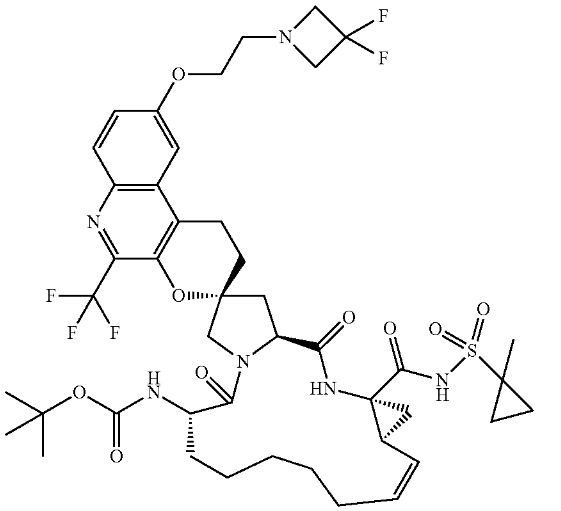

I-519
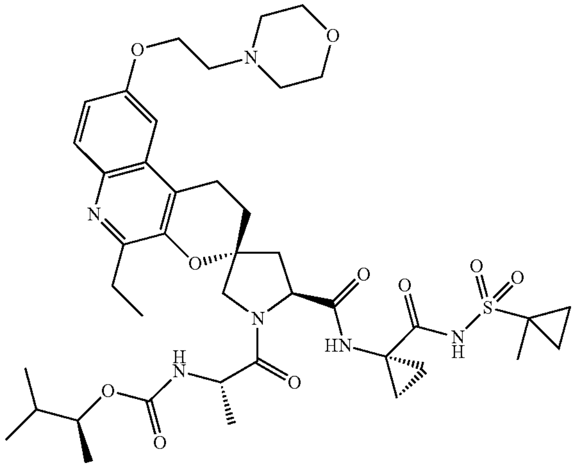
I-520
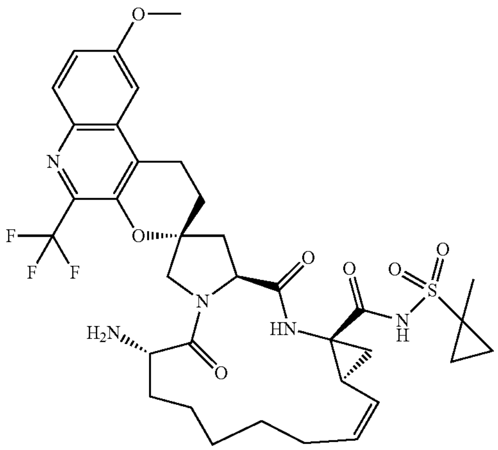
I-521
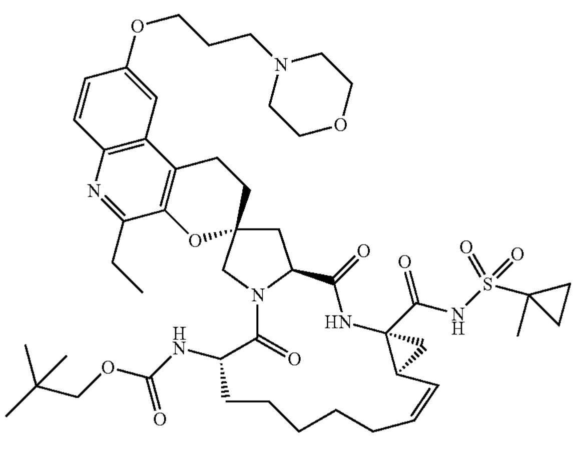
I-522
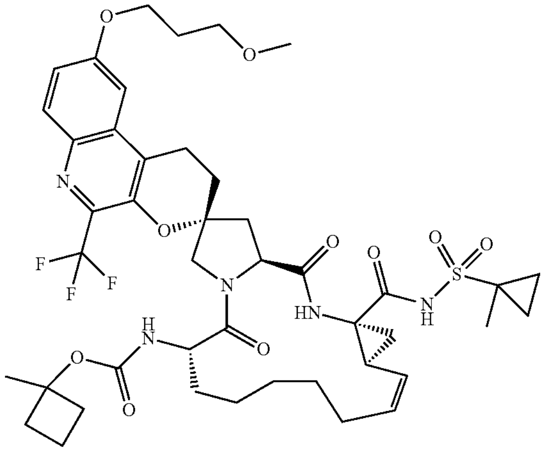
I-523
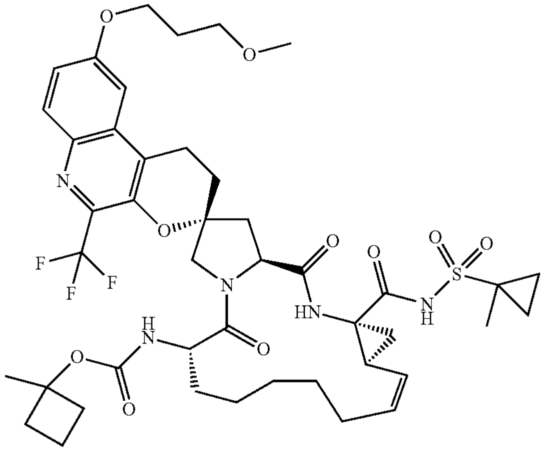
I-524
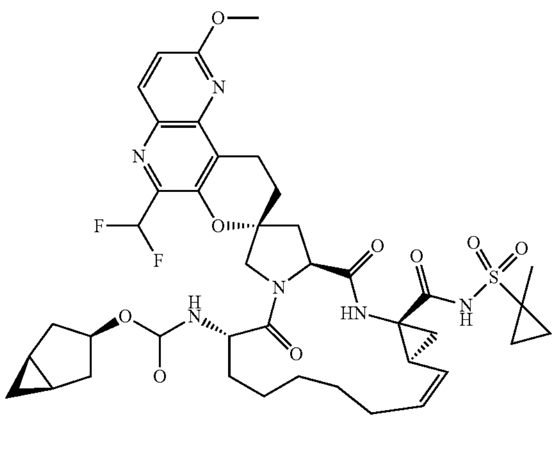

-continued
I-525
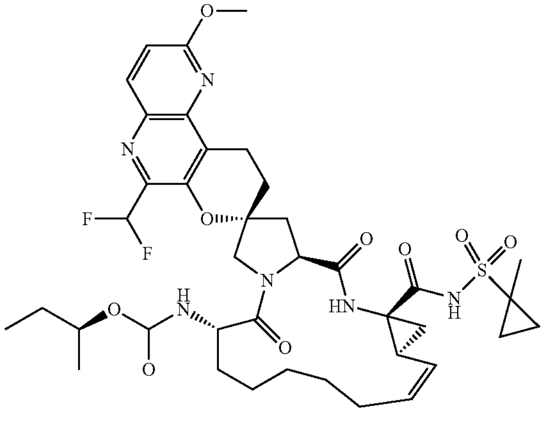
I-526
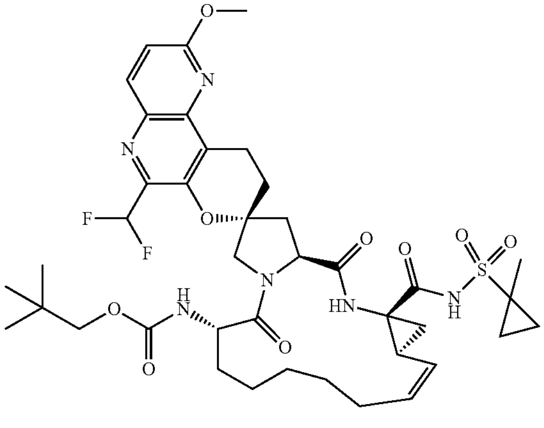
I-527
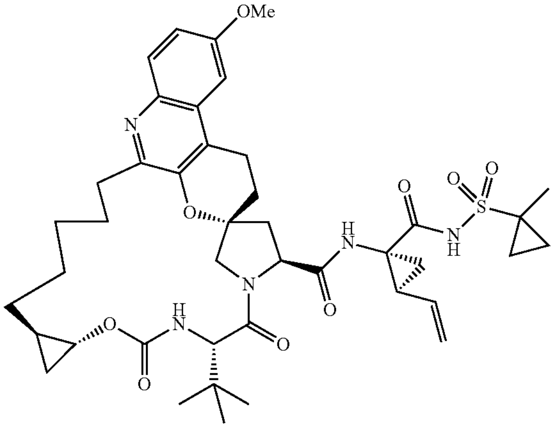
and pharmaceutically acceptable salts thereof.
16. The compound according to claim 1, wherein the compound is selected from the group consisting of:
I-5
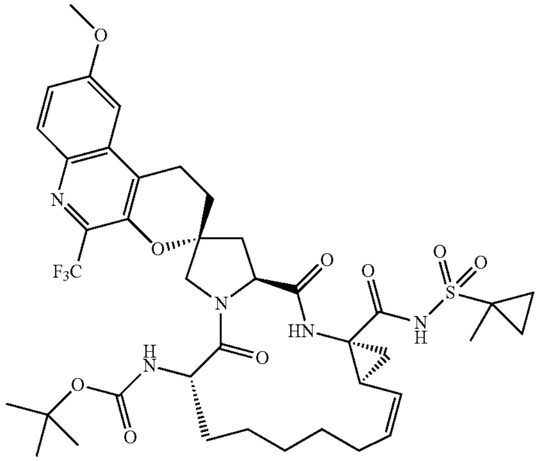
I-6
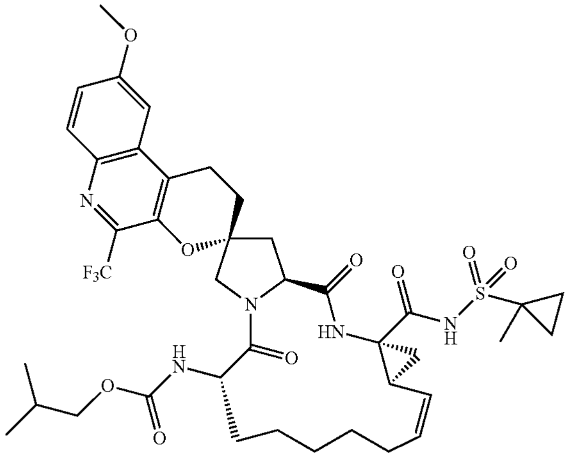
I-12
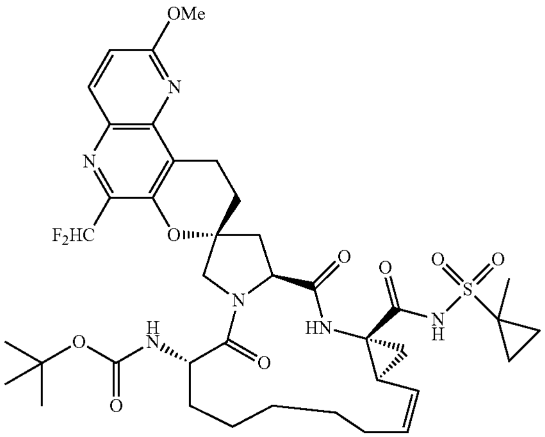

I-13
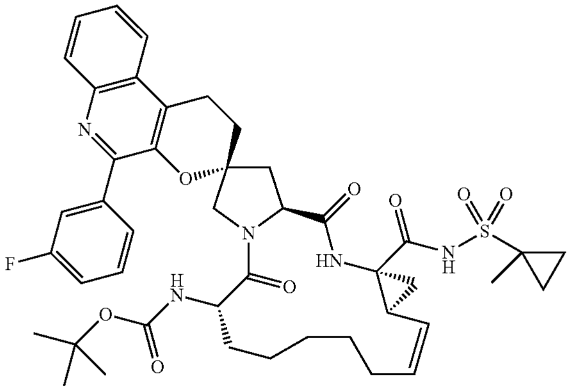
I-16
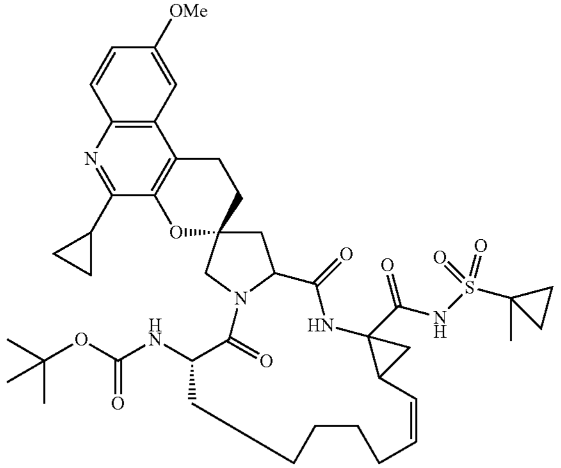
I-33
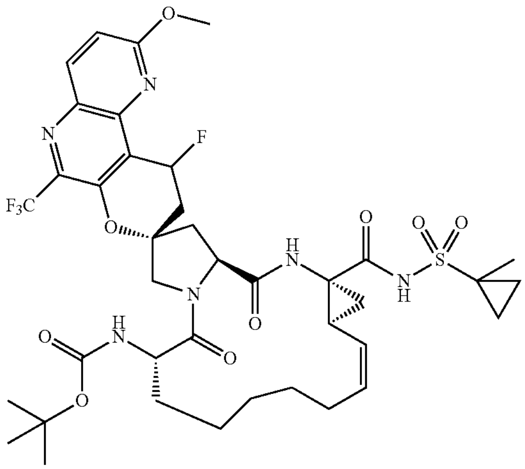
I-50
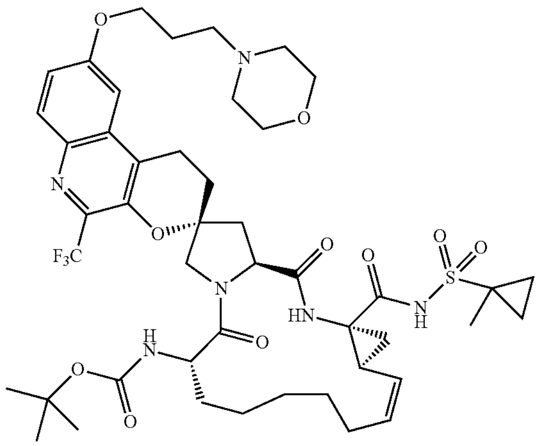
I-63
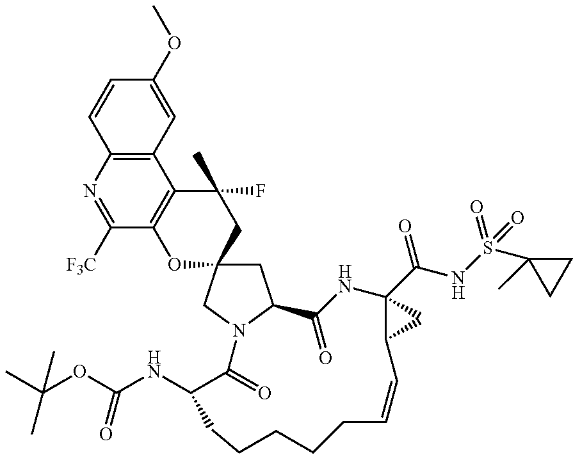
I-66
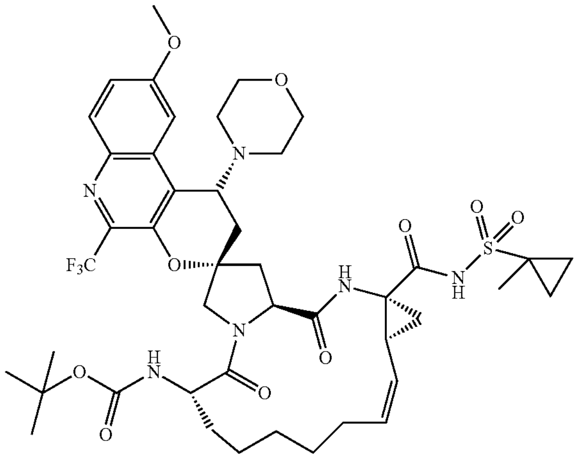

-continued

I-94

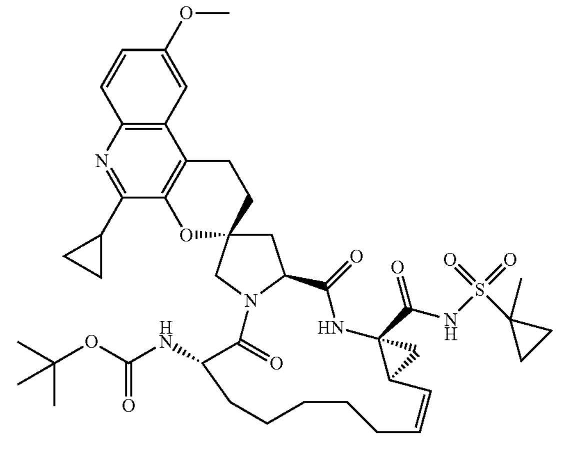

I-124

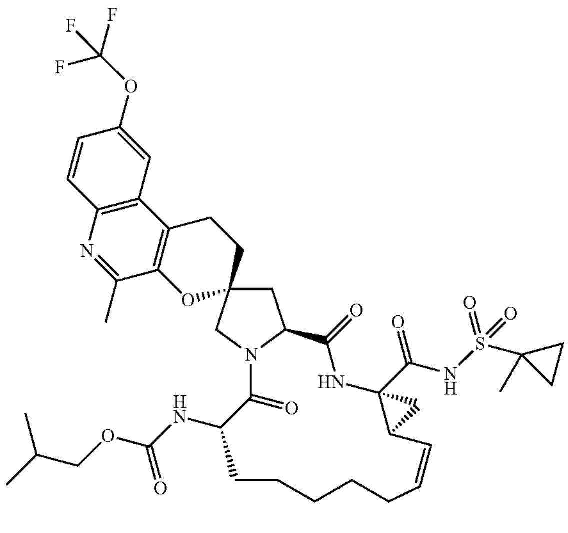

I-161

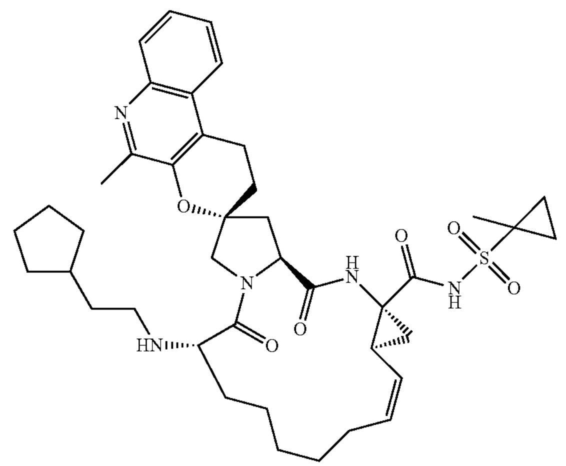

-continued

I-189

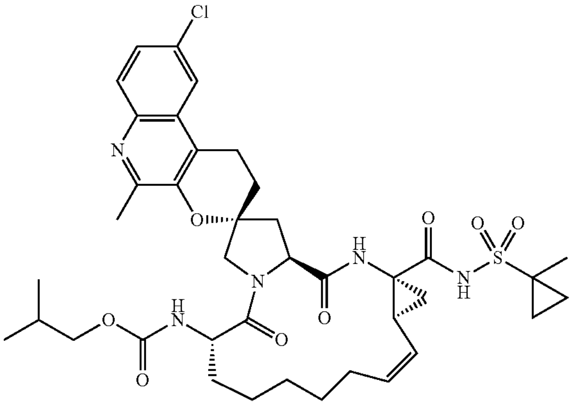

I-359

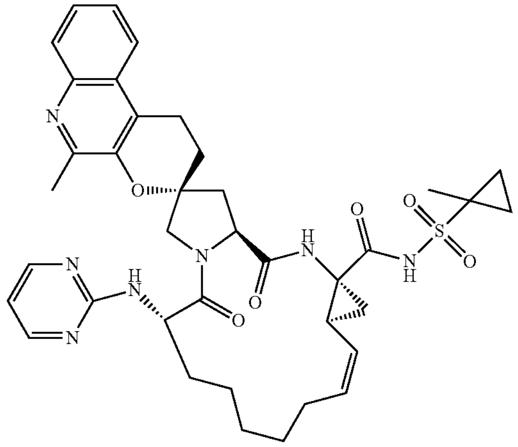

I-509

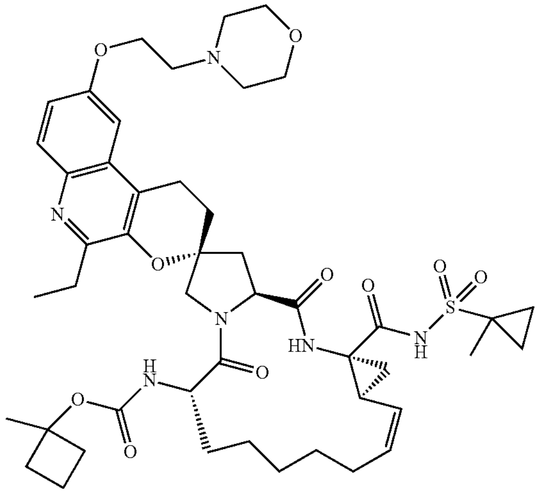

or a pharmaceutically acceptable salt thereof.

17. A pharmaceutical composition comprising an effective amount of the compound of claim 1 and a pharmaceutically acceptable carrier.

18. The pharmaceutical composition according to claim 17, further comprising a second therapeutic agent selected from the group consisting of HCV antiviral agents, immunomodulators, and anti-infective agents.

19. The pharmaceutical composition according to claim 18, further comprising a second therapeutic agent selected from the group consisting of HCV protease inhibitors, inhibitors of HCV NS4A, inhibitors of HCV NS4B, inhibitors of HCV NS5A and inhibitors of HCV NS5B.

20. A method for treating HCV in patient comprising the step of administering to said patient a therapeutically effective amount of the compound of claim 1.

21. A compound which is a pharmaceutically acceptable salt of

I-6

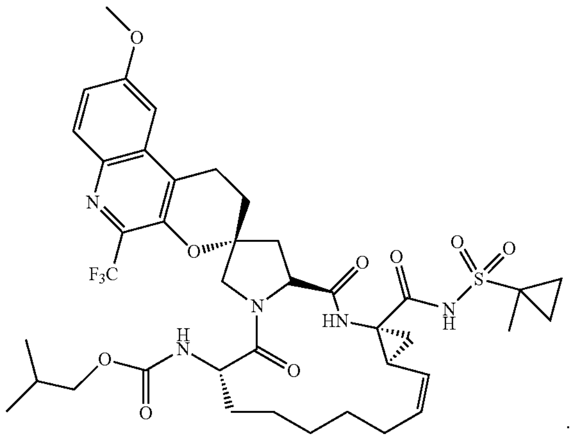

.

22. A compound which is

I-6

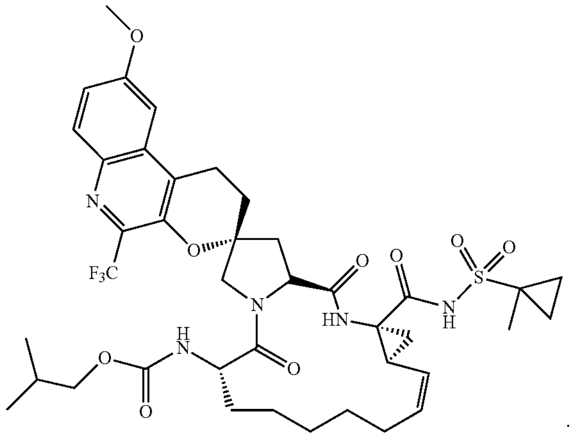

.

23. The compound according to claim 21, which is the sodium or potassium salt of

I-6

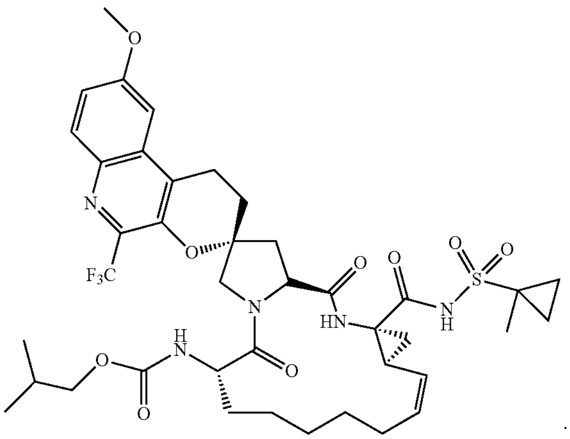

.

24. A pharmaceutical composition comprising an effective amount of the compound of claim 21 and a pharmaceutically acceptable carrier.

25. A pharmaceutical composition comprising an effective amount of the compound of claim 22 and a pharmaceutically acceptable carrier.

26. A method for treating HCV in patient comprising the step of administering to said patient a therapeutically effective amount of the compound of claim 21.

27. A method for treating HCV in patient comprising the step of administering to said patient a therapeutically effective amount of the compound of claim 22.

* * * * *